(12) United States Patent
Li et al.

(10) Patent No.: US 10,020,455 B2
(45) Date of Patent: Jul. 10, 2018

(54) TETRADENTATE PLATINUM AND PALLADIUM COMPLEX EMITTERS CONTAINING PHENYL-PYRAZOLE AND ITS ANALOGUES

(71) Applicant: ARIZONA BOARD OF REGENTS ON BEHALF OF ARIZONA STATE UNIVERSITY, Scottsdale, AZ (US)

(72) Inventors: Jian Li, Tempe, AZ (US); Guijie Li, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/591,188

(22) Filed: Jan. 7, 2015

(65) Prior Publication Data

US 2015/0194616 A1 Jul. 9, 2015

Related U.S. Application Data

(60) Provisional application No. 61/924,462, filed on Jan. 7, 2014.

(51) Int. Cl.
| | |
|---|---|
| *C07F 15/00* | (2006.01) |
| *H01L 51/50* | (2006.01) |
| *H01L 51/00* | (2006.01) |
| *C09K 11/06* | (2006.01) |

(52) U.S. Cl.
CPC ........ *H01L 51/0087* (2013.01); *C07F 15/006* (2013.01); *C07F 15/0086* (2013.01); *C09K 11/06* (2013.01); *H01L 51/0084* (2013.01); *C09K 2211/1029* (2013.01); *C09K 2211/1033* (2013.01); *C09K 2211/1037* (2013.01); *C09K 2211/1044* (2013.01); *C09K 2211/1048* (2013.01); *C09K 2211/1051* (2013.01); *C09K 2211/1059* (2013.01); *C09K 2211/1062* (2013.01); *C09K 2211/1066* (2013.01); *C09K 2211/1077* (2013.01); *C09K 2211/1081* (2013.01); *C09K 2211/1088* (2013.01); *C09K 2211/1092* (2013.01); *C09K 2211/1096* (2013.01); *C09K 2211/185* (2013.01); *H01L 51/5016* (2013.01)

(58) Field of Classification Search
CPC ................................. C07F 15/00; H01L 51/50
USPC ................................................ 546/2; 313/504
See application file for complete search history.

(56) References Cited

U.S. PATENT DOCUMENTS

| | | |
|---|---|---|
| 4,769,292 A | 9/1988 | Tang et al. |
| 5,707,745 A | 1/1998 | Forrest et al. |
| 5,844,363 A | 12/1998 | Gu et al. |
| 6,200,695 B1 | 3/2001 | Arai et al. |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan |
| 7,279,704 B2 | 10/2007 | Walters et al. |
| 7,332,232 B2 | 2/2008 | Ma et al. |
| 7,442,797 B2 | 10/2008 | Itoh et al. |

(Continued)

FOREIGN PATENT DOCUMENTS

| | | |
|---|---|---|
| CN | 1777663 | 5/2006 |
| CN | 1894269 | 1/2007 |

(Continued)

OTHER PUBLICATIONS

Wong; Challenges in organometallic research—Great opportunity for solar cells and OLEDs, Journal of Organometallic Chemistry, 2009, 694, 2644-2647.

(Continued)

*Primary Examiner* — Charanjit Aulakh
(74) *Attorney, Agent, or Firm* — Fish & Richardson P.C.

(57) ABSTRACT

A phosphorescent emitter or delayed fluorescent and phosphorescent emitters represented by Formula 1 or Formula II, where M is platinum or palladium.

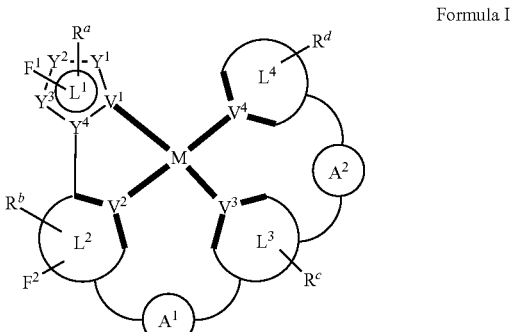

Formula I

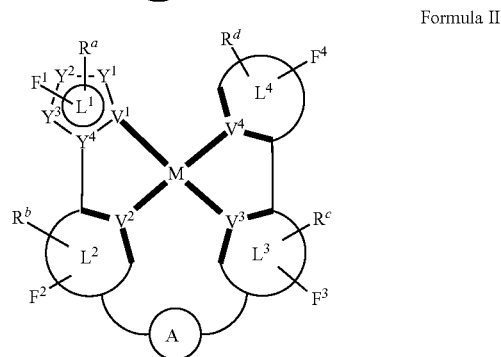

Formula II

20 Claims, 15 Drawing Sheets

(56) References Cited

U.S. PATENT DOCUMENTS

| | | |
|---|---|---|
| 7,501,190 B2 | 3/2009 | Ise |
| 7,655,322 B2 | 2/2010 | Forrest et al. |
| 7,854,513 B2 | 12/2010 | Quach |
| 7,947,383 B2 | 5/2011 | Ise et al. |
| 8,389,725 B2 | 3/2013 | Li |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Li et al. |
| 9,059,412 B2 | 6/2015 | Zeng et al. |
| 9,224,963 B2 | 12/2015 | Li et al. |
| 9,238,668 B2 | 1/2016 | Li et al. |
| 9,312,505 B2 | 4/2016 | Brooks |
| 9,324,957 B2 | 4/2016 | Li et al. |
| 9,382,273 B2 | 7/2016 | Li |
| 9,385,329 B2* | 7/2016 | Li .................. C09K 11/06 |
| 9,425,415 B2 | 8/2016 | Li |
| 9,461,254 B2 | 10/2016 | Tsai et al. |
| 9,550,801 B2 | 1/2017 | Li |
| 9,617,291 B2 | 4/2017 | Li et al. |
| 9,673,409 B2 | 6/2017 | Li et al. |
| 9,698,359 B2 | 7/2017 | Li et al. |
| 9,711,739 B2 | 7/2017 | Li |
| 9,711,742 B2 | 7/2017 | Li et al. |
| 9,755,163 B2 | 9/2017 | Li et al. |
| 9,818,959 B2 | 11/2017 | Li et al. |
| 2002/0068190 A1 | 6/2002 | Tsuboyama et al. |
| 2003/0062519 A1 | 4/2003 | Yamazaki |
| 2003/0186077 A1 | 10/2003 | Chen |
| 2005/0170207 A1 | 8/2005 | Ma et al. |
| 2005/0260446 A1 | 11/2005 | Mackenzie et al. |
| 2006/0073359 A1 | 4/2006 | Ise et al. |
| 2006/0094875 A1 | 5/2006 | Itoh et al. |
| 2006/0182992 A1 | 8/2006 | Nii et al. |
| 2006/0202197 A1 | 9/2006 | Nakayama et al. |
| 2006/0210831 A1 | 9/2006 | Sano et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0171111 A1 | 7/2010 | Takada et al. |
| 2010/0171418 A1 | 7/2010 | Kinoshita |
| 2011/0049496 A1 | 3/2011 | Fukuzaki |
| 2012/0095232 A1 | 4/2012 | Li et al. |
| 2012/0181528 A1 | 7/2012 | Takada et al. |
| 2012/0215001 A1 | 8/2012 | Li et al. |
| 2012/0223634 A1 | 9/2012 | Xia et al. |
| 2012/0273736 A1 | 11/2012 | James et al. |
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0191206 A1 | 7/2014 | Cho |
| 2014/0203248 A1 | 7/2014 | Zhou |
| 2014/0326960 A1 | 11/2014 | Kim et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0207086 A1 | 7/2015 | Li et al. |
| 2015/0228914 A1 | 8/2015 | Li et al. |
| 2015/0274762 A1 | 10/2015 | Li et al. |
| 2015/0287938 A1 | 10/2015 | Li et al. |
| 2015/0349279 A1 | 12/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133862 A1 | 5/2016 | Li et al. |
| 2016/0197291 A1 | 7/2016 | Li |
| 2016/0285015 A1 | 9/2016 | Li |
| 2016/0359120 A1 | 12/2016 | Li |
| 2016/0359125 A1 | 12/2016 | Li |
| 2017/0005278 A1 | 1/2017 | Li |
| 2017/0012224 A1 | 1/2017 | Li |
| 2017/0040555 A1 | 2/2017 | Li et al. |
| 2017/0047533 A1 | 2/2017 | Li |
| 2017/0066792 A1 | 3/2017 | Li et al. |
| 2017/0069855 A1 | 3/2017 | Li |
| 2017/0267923 A1 | 9/2017 | Li |
| 2017/0271611 A1 | 9/2017 | Li et al. |
| 2017/0301871 A1 | 10/2017 | Li et al. |
| 2017/0305881 A1 | 10/2017 | Li et al. |
| 2017/0331056 A1 | 11/2017 | Li et al. |
| 2017/0373260 A1 | 12/2017 | Li et al. |

FOREIGN PATENT DOCUMENTS

| | | | |
|---|---|---|---|
| CN | 101142223 | A | 3/2008 |
| CN | 101667626 | A | 3/2010 |
| CN | 102449108 | A | 5/2012 |
| CN | 102892860 | A | 1/2013 |
| CN | 102971396 | A | 3/2013 |
| CN | 104232076 | A | 12/2014 |
| CN | 104693243 | A | 6/2015 |
| CN | 105367605 | A1 | 3/2016 |
| CN | 105418591 | A1 | 3/2016 |
| EP | 1808052 | | 7/2007 |
| EP | 1874893 | | 1/2008 |
| EP | 1874894 | | 1/2008 |
| EP | 1919928 | | 5/2008 |
| EP | 2036907 | | 3/2009 |
| EP | 2096690 | A2 | 9/2009 |
| EP | 2417217 | | 2/2012 |
| EP | 2112213 | | 7/2012 |
| EP | 2711999 | | 3/2014 |
| JP | 2005267557 | A | 9/2005 |
| JP | 2005310733 | A | 11/2005 |
| JP | 2006047240 | A | 2/2006 |
| JP | 2006232784 | A | 9/2006 |
| JP | 2006242080 | A | 9/2006 |
| JP | 2006242081 | A | 9/2006 |
| JP | 2006256999 | A | 9/2006 |
| JP | 2006257238 | A | 9/2006 |
| JP | 2006261623 | A | 9/2006 |
| JP | 2006290988 | | 10/2006 |
| JP | 2006313796 | A | 11/2006 |
| JP | 2006332622 | A | 12/2006 |
| JP | 2006351638 | A | 12/2006 |
| JP | 2007019462 | A | 1/2007 |
| JP | 2007042875 | A | 2/2007 |
| JP | 2007053132 | | 3/2007 |
| JP | 2007066581 | A | 3/2007 |
| JP | 2007073620 | A | 3/2007 |
| JP | 2007073845 | A | 3/2007 |

(56) References Cited

FOREIGN PATENT DOCUMENTS

| | | |
|---|---|---|
| JP | 2007073900 A | 3/2007 |
| JP | 2007080593 A | 3/2007 |
| JP | 2007080677 A | 3/2007 |
| JP | 2007088105 A | 4/2007 |
| JP | 2007088164 | 4/2007 |
| JP | 2007096259 A | 4/2007 |
| JP | 2007110067 A | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 A | 5/2008 |
| JP | 2008109103 A | 5/2008 |
| JP | 2008160087 A | 7/2008 |
| JP | 2008198801 A | 8/2008 |
| JP | 2008270729 A | 11/2008 |
| JP | 2008270736 A | 11/2008 |
| JP | 2009016184 A | 1/2009 |
| JP | 2009016579 A | 1/2009 |
| JP | 2009032977 A | 2/2009 |
| JP | 2009032988 A | 2/2009 |
| JP | 2009266943 A | 11/2009 |
| JP | 2009267171 | 11/2009 |
| JP | 2009267244 | 11/2009 |
| JP | 2009272339 A | 11/2009 |
| JP | 2009283891 | 12/2009 |
| JP | 2010135689 | 6/2010 |
| JP | 2012222255 A | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| TW | 201710277 | 3/2017 |
| WO | WO2000070655 | 11/2000 |
| WO | WO2004003108 A1 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 A1 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 A2 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 A1 | 1/2014 |
| WO | WO2014031977 | 2/2014 |
| WO | WO2014031977 A1 | 2/2014 |
| WO | WO2014047616 | 3/2014 |
| WO | WO2014109814 | 7/2014 |
| WO | WO2015027060 | 2/2015 |
| WO | WO2015131158 A1 | 9/2015 |
| WO | WO2016025921 A1 | 2/2016 |
| WO | WO2016029137 A1 | 2/2016 |
| WO | WO2016029186 A1 | 2/2016 |
| WO | WO2016197019 A1 | 12/2016 |

OTHER PUBLICATIONS

JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Barry O'Brien et al.: White organic light emitting diodes using Pt-based red, green and blue phosphorescent dopants. Proc. SPIE, vol. 8829, pp. 1-6, Aug. 25, 2013.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)$_3$ and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.

(56) References Cited

OTHER PUBLICATIONS

Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O^N^C^N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O^N^C^N ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Murakami; JP 2007258550, English machine translation from EPO, Oct. 4, 2007. 80 pages.
Murakami; JP 2007324309, English machine translation from EPO, Dec. 13, 2007, 89 pages.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.

\* cited by examiner

TETRADENTATE PLATINUM AND PALLADIUM COMPLEX EMITTERS CONTAINING PHENYL-PYRAZOLE AND ITS ANALOGUES

CROSS-REFERENCE TO RELATED APPLICATION

This application claims priority to U.S. Ser. No. 61/924,462 entitled "DELAYED FLUORESCENT EMITTERS CONTAINING PHENYL-PYRAZOLE AND ITS ANALOGUES," filed on Jan. 7, 2014, which is incorporated by reference herein in its entirety.

TECHNICAL FIELD

The present disclosure relates to multidentate platinum and palladium compounds suitable for phosphorescent emitters and delayed fluorescent and phosphorescent emitters in display and lighting applications, and specifically to delayed fluorescent and phosphorescent or phosphorescent tetradentate metal complexes having modified emission spectra.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, or devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency, improvements in the stability of devices, as well as improvements in processing ability.

Despite significant advances in research devoted to optical and electro-optical materials, for example, red and green phosphorescent organometallic materials are commercial, and they have been used as phosphors in organic light emitting diodes (OLEDs), lighting and advanced displays. Many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is very high compared with that of the red and green phosphors, which means that the lowest triplet excited state energy of host materials for the blue devices should be even higher. Thus, one of the problems is that there are limited host materials to be used for the blue devices. Accordingly, a need exists for new materials which exhibit improved performance in optical emitting and absorbing applications.

SUMMARY

The present disclosure provides a materials design route to reduce the energy gap between the lowest triplet excited state and the lowest singlet excited state of the metal compounds to afford delayed fluorescent materials which can be an approach to solve the problems of the blue emitters.

The present disclosure relates to platinum and palladium compounds suitable as emitters in organic light emitting diodes (OLEDs), display and lighting applications.

Disclosed herein are compounds of Formula I and Formula II:

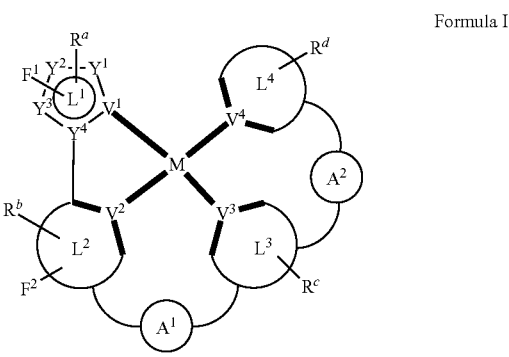

Formula I

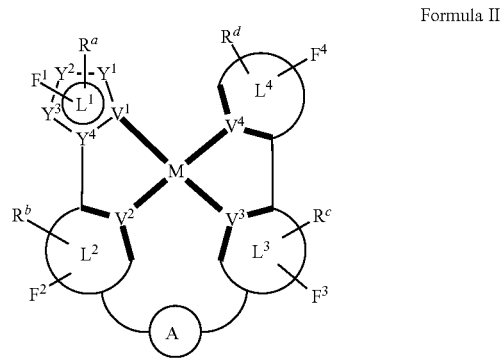

Formula II wherein M is platinum or palladium,
wherein $L^1$ is a five-membered heterocyclyl, heteroaryl, carbene, or N-heterocyclic carbene,
wherein each of $L^2$, $L^3$, and $L^4$ is independently a substituted or an unsubstituted aryl, cycloalkyl, cycloalkenyl, heteroaryl, heterocyclyl, carbene, or N-heterocyclic carbene,
wherein each of $F^1$, $F^2$, $F^3$, and $F^4$ is independently present or absent, wherein at least one of, $F^1$, $F^2$, $F^3$, and $F^4$ is present, and each of $F^1$, $F^2$, $F^3$, and $F^4$ present is a fluorescent luminophore,
wherein each of $A^1$, $A^2$, and A is independently $CH_2$, $CR^1R^2$, $C=O$, $CH_2$, $SiR^1R^2$, $GeH_2$, $GeR^1R^2$, NH, $NR^3$, PH, $PR^3$, $R^3P=O$, $AsR^3$, $R^3As=O$, O, S, $S=O$, $SO_2$, Se, $Se=O$, $SeO_2$, BH, $BR^3$, $R^3Bi=O$, BiH, or $BiR^3$,
wherein each of $V^1$, $V^2$, $V^3$, and $V^4$ is coordinated with M and is independently N, C, P, B, or Si,
wherein each of $Y^1$, $Y^2$, $Y^3$, and $Y^4$ is independently C, N, O, S, $S=O$, $SO_2$, Se, $Se=O$, $SeO_2$, $PR^3$, $R^3P=O$, $AsR^3$, $R^3As=O$, or $BR^3$,
wherein $R^a$ is present or absent, wherein $R^b$ is present or absent, wherein $R^c$ is present or absent, wherein $R^d$ is present or absent, and if present each of $R^a$, $R^b$, $R^c$, and $R^d$ independently represents mono-, di-, or tri-substitutions, and wherein each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Also disclosed herein are compositions comprising one or more compounds disclosed herein.

Also disclosed herein are devices, such as OLEDs, comprising one or more compounds or compositions disclosed herein.

DETAILED DESCRIPTION

Figure 1:
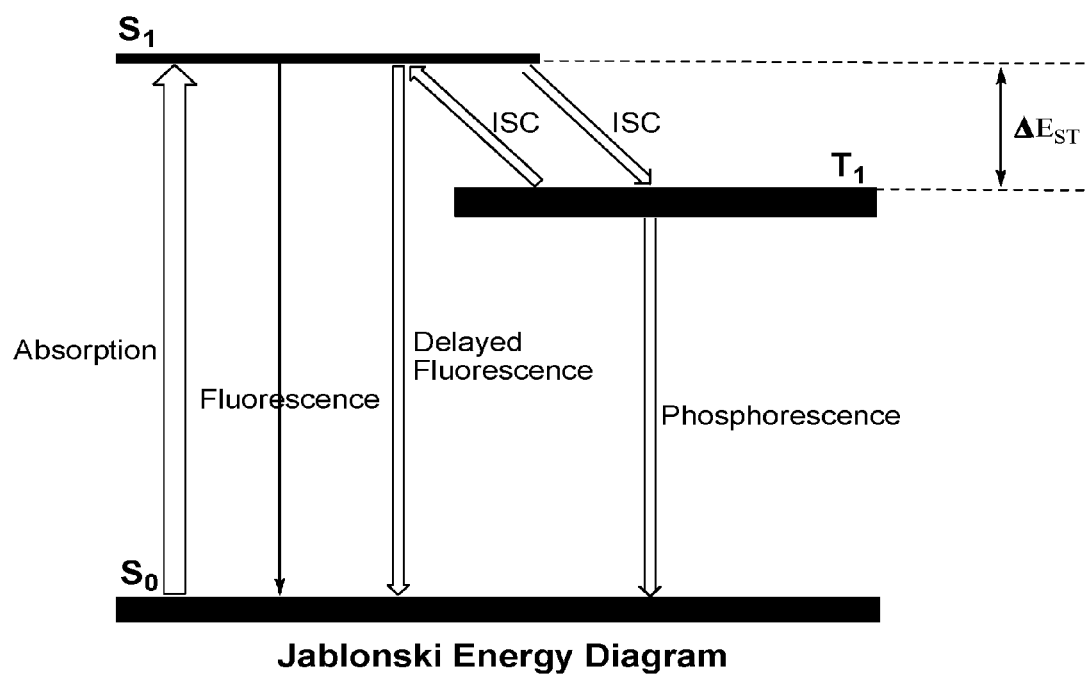
FIG. 1 shows a Jablonski Energy Diagram, which shows the emission pathways of fluorescence, phosphorescence, and delayed fluorescence. The energy difference between the lowest triplet excited state ($T_1$) and the lowest singlet excited state ($S_1$) is $\Delta E_{ST}$. When $\Delta E_{ST}$ becomes small enough, efficient intersystem crossing (ISC) from lowest triplet excited state ($T_1$) to lowest singlet excited state ($S_1$) can occur. In such situations, the excitons undergo non-radiative relaxation via ISC from $T_1$ to $S_1$, and then further relaxation from $S_1$ to $S_0$, commonly known as delayed fluorescence.

The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" and "optionally" mean that the subsequently described event or circumstance can or cannot occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom or group connects two atoms such as, for example, a N atom and a C atom. A linking atom or group is in one aspect disclosed as X, Y, or Z herein. The linking atom or group can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$- or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COO CH$_2$CH$_3$)]$_n$—CH$_3$, and —[CH$_2$CH(COO$^t$Bu)]$_n$—CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

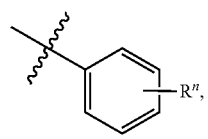

which is understood to be equivalent to a formula:

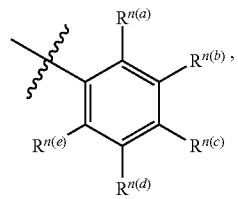

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

1. Compounds

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. Excitons decay from triplet excited states to ground state to generate luminescence, which is phosphorescence. Because the strong spin-orbit coupling of the heavy metal atom enhances intersystem crossing (ISC) very efficiently between singlet and triplet excited states, phosphorescent metal complexes, such as platinum complexes, have demonstrated their potential to harvest both the singlet and triplet excitons to achieve 100% internal quantum efficiency. Thus phosphorescent metal complexes are good dopants in the emissive layer of organic light emitting devices (OLEDs). Much achievement has been made in the past decade to lead to the lucrative commercialization of the technology, for example, OLEDs have been used in advanced displays in smart phones, televisions, and digital cameras.

However, to date, blue electroluminescent devices remain the most challenging area of this technology, due at least in part to instability of the blue devices. It is generally understood that the choice of host materials is a factor in the stability of the blue devices. But the lowest triplet excited state ($T_1$) energy of the blue phosphors is high, which generally means that the lowest triplet excited state ($T_1$) energy of host materials for the blue devices should be even higher. This leads to difficulty in the development of the host materials for the blue devices.

This disclosure provides a materials design route by introducing fluorescent luminophore(s) to the ligand of the metal complexes. Thereby chemical structures of the fluorescent luminophores and the ligands may be modified, and also the metal may be changed to adjust the singlet states energy and the triplet states energy of the metal complexes, which all may affect the optical properties of the complexes, for example, emission and absorption spectra. Accordingly, the energy gap ($\Delta E_{ST}$) between the lowest triplet excited state ($T_1$) and the lowest singlet excited state ($S_1$) may be also adjusted. When the $\Delta E_{ST}$ becomes small enough, intersystem crossing (ISC) from the lowest triplet excited state ($T_1$) to the lowest singlet excited state ($S_1$) may occur efficiently, such that the excitons undergo non-radiative relaxation via ISC from $T_1$ to $S_1$, then relax from $S_1$ to $S_0$, which leads to delayed fluorescence, as depicted in the Jablonski Energy Diagram in FIG. 1. Through this pathway, higher energy excitons may be obtained from lower excited state (from $T_1 \rightarrow S_1$), which means more host materials may be available for the dopants. This approach offers a solution to problems associated with blue devices.

For example, when fluorescent luminophore fluorene in PtON1b was changed to biphenyl in PtON1a, triplet excited state ($T_1$) energy was increased (1240/476=2.605 eV nm in PtON1b and 1240/472=2.627 eV in PtON1a). However, the singlet excited state ($S_1$) energy was still nearly the same, so the energy gap ($\Delta E_{ST}$) decreased, as can been seen in FIGS. 2 and 8. Thus, the complex undergoes intersystem crossing (ISC) more efficiently, resulting in a larger ($S_1 \rightarrow S_0$) delayed fluorescent peak in PtON1a.

The metal complexes described herein can be tailored or tuned to a specific application that desires a particular emission or absorption characteristic. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can be generally exhibit different optical properties, including emission and absorption spectra. The color of the metal complexes can be tuned by modifying the conjugated groups on the fluorescent luminophores and ligands.

The emission of these complexes can be tuned, for example, from the ultraviolet to near-infrared, by, for example, modifying the ligand or fluorescent luminophore structure. A fluorescent luminophore is a group of atoms in an organic molecule, which can absorb energy to generate singlet excited state(s), the singlet exciton(s) produce(s) decay rapidly to yield prompt luminescence. In another aspect, the complexes can provide emission over a majority of the visible spectrum. In a specific example, the complexes can emit light over a range of from about 400 nm to about 700 nm. In another aspect, the complexes have improved stability and efficiency over traditional emission complexes. In yet another aspect, the complexes can be useful as luminescent labels in, for example, bio-applications, anti-cancer agents, emitters in organic light emitting diodes (OLED), or a combination thereof. In another aspect, the complexes can be useful in light emitting devices, such as, for example, compact fluorescent lamps (CFL), light emitting diodes (LED), incandescent lamps, and combinations thereof.

Disclosed herein are compounds or compound complexes comprising platinum and palladium. The terms compound or compound complex are used interchangeably herein. In one aspect, the compounds discloses herein have a neutral charge.

The compounds disclosed herein, can exhibit desirable properties and have emission and/or absorption spectra that can be tuned via the selection of appropriate ligands. In another aspect, the present invention can exclude any one or more of the compounds, structures, or portions thereof, specifically recited herein.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are platinum and palladium complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLEDs), luminescent devices and displays, and other light emitting devices.

In another aspect, the compounds can provide improved efficiency, improved operational lifetimes, or both in lighting devices, such as, for example, organic light emitting devices, as compared to conventional materials.

These compounds can be made using a variety of methods, including, but not limited to those recited in the examples provided herein.

The compounds disclosed herein can be delayed fluorescent emitters, delayed phosphorescent emitters, or both. In one aspect, the compounds disclosed herein can be a delayed fluorescent emitter. In another aspect, the compounds disclosed herein can be a phosphorescent emitter. In yet another aspect, the compounds disclosed herein can be a delayed fluorescent emitter and a phosphorescent emitter.

Disclosed herein are compounds of Formula I and Formula II:

Formula I

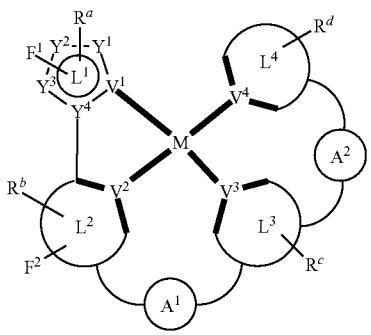

Formula II

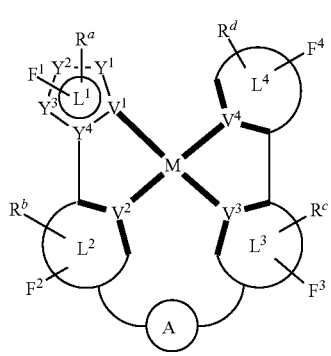

Formula III


Formula IV


Formula V

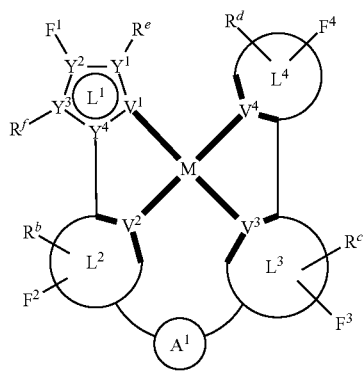

wherein M is platinum or palladium, wherein $L^1$ is a five-membered heterocyclyl, heteroaryl, carbene, or N-heterocyclic carbene, wherein each of $L^2$, $L^3$, and $L^4$ is independently a substituted or an unsubstituted aryl, cycloalkyl, cycloalkenyl, heteroaryl, heterocyclyl, carbene, or N-heterocyclic carbene, wherein each of $F^1$, $F^2$, $F^3$, and $F^4$ is independently present or absent, wherein at least one of $F^1$, $F^2$, $F^3$, and $F^4$ is present, and each of $F^1$, $F^2$, $F^3$, and $F^4$ present is a fluorescent luminophore, wherein each of $A^1$, $A^2$, and A is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, wherein each of $V^1$, $V^2$, $V^3$, and $V^4$ is coordinated with M and is independently N, C, P, B, or Si, wherein each of $Y^1$, $Y^2$, $Y^3$, and $Y^4$ is independently C, N, O, S, S=O, $SO_2$, Se, Se=O, $SeO_2$, $PR^3$, $R^3P$=O, $AsR^3$, $R^3As$=O, or $BR^3$, wherein $R^a$ is present or absent, wherein $R^b$ is present or absent, wherein $R^c$ is present or absent, wherein $R^d$ is present or absent, and if present each of $R^a$, $R^b$, $R^c$, and $R^d$ independently represents mono-, di-, or tri-substitutions, and wherein each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, the wherein the compound is represented by the structure of Formula III, Formula IV, Formula V, or Formula VI:

Formula VI

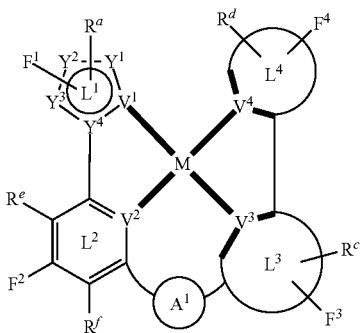

wherein each of $R^e$ and $R^f$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In another aspect, the compound can have the structure of Formula VII or Formula VIII:

Formula VII

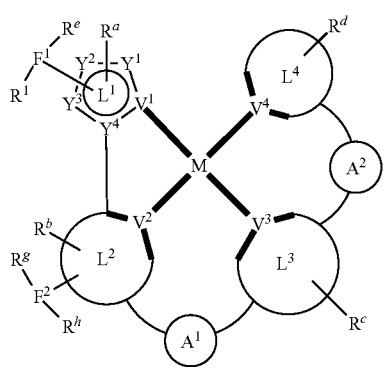

Formula VIII

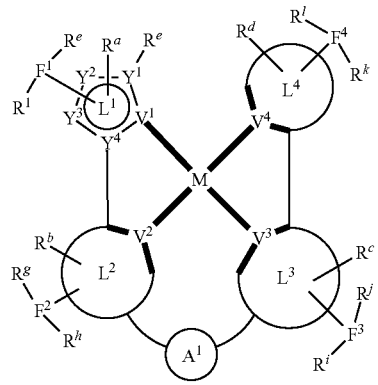

wherein $R^e$ and $R^f$ are on the ortho-positions of the bond between $F^1$ and $L^1$,
wherein $R^g$ and $R^h$ are on the ortho-positions of the bond between $F^2$ and $L^2$,
wherein $R^i$ and $R^j$ are on the ortho-positions of the bond between $F^3$ and $L^3$,
wherein $R^k$ and $R^l$ are on the ortho-positions of the bond between $F^4$ and $L^4$,
wherein each of $R^e$, $R^f$, $R^g$, $R^h$, $R^i$, $R^j$, $R^k$, and $R^l$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In yet another aspect, the compound can have any one of Formulas A1-A23:

A-1

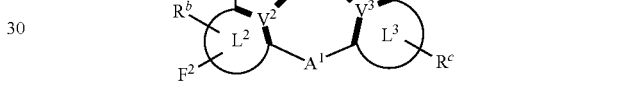

A-2

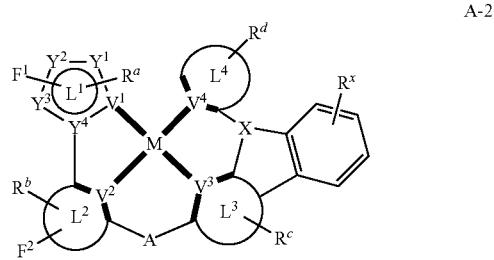

A-3

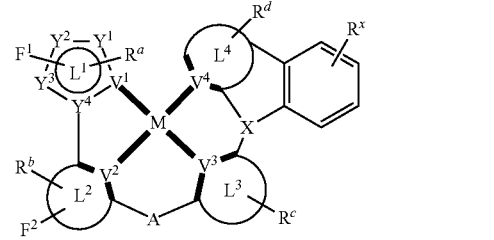

A-4

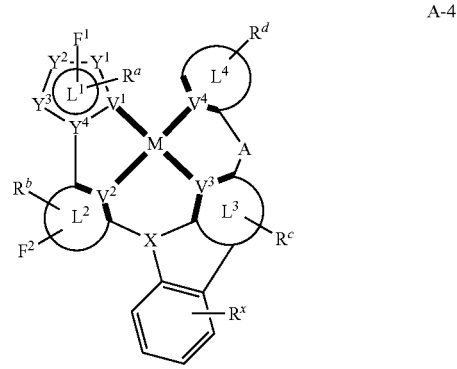

A-5
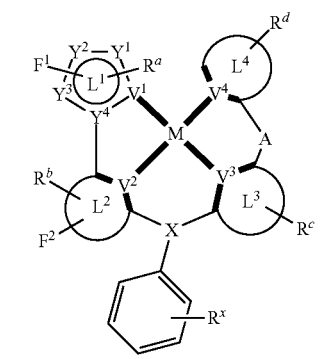
A-6
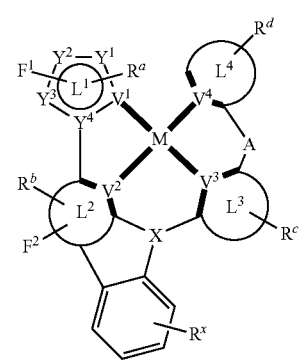
A-7
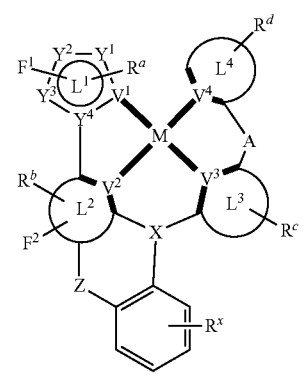
A-8
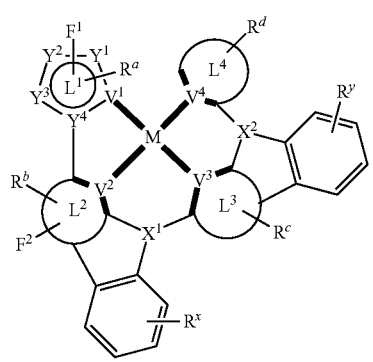
A-9
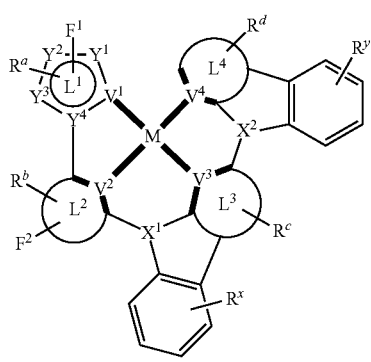
A-10
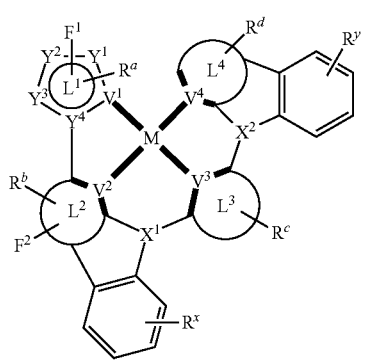
A-11
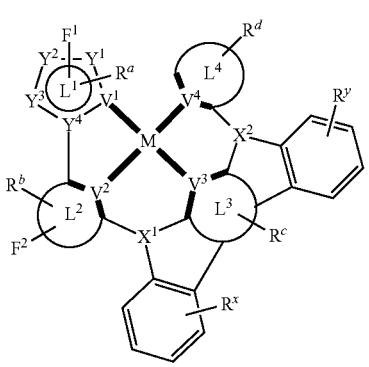
A-12
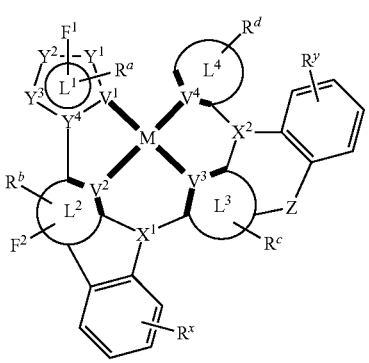

A-13
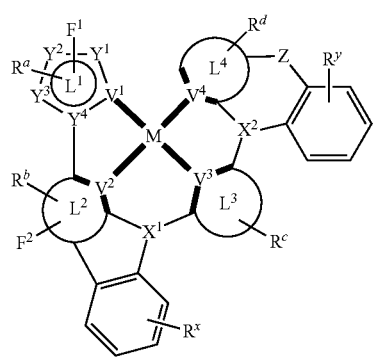
A-14
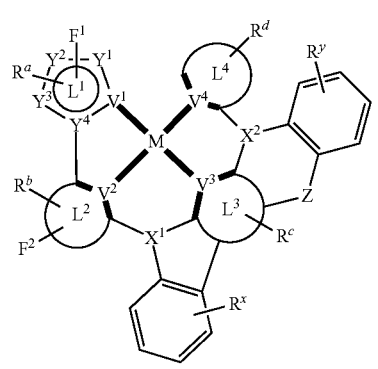
A-15
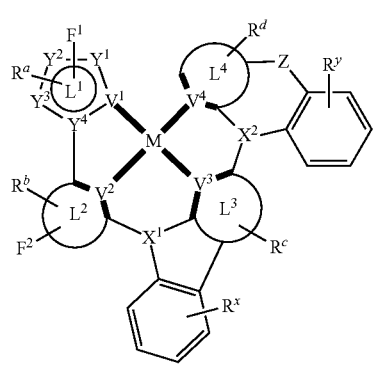
A-16
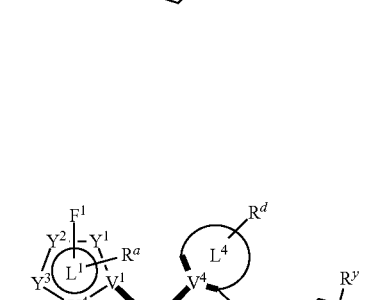
A-17
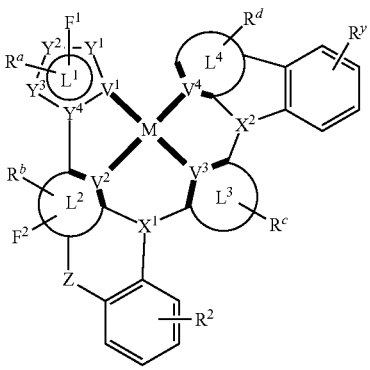
A-18
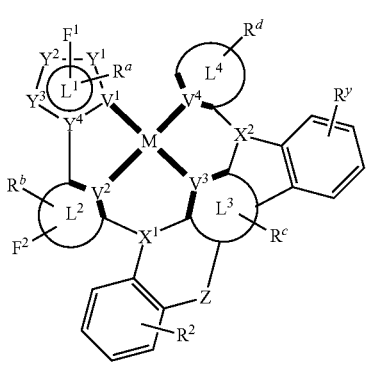
A-19
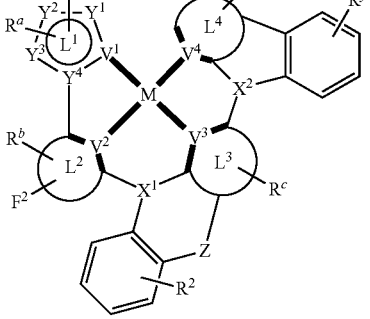
A-20
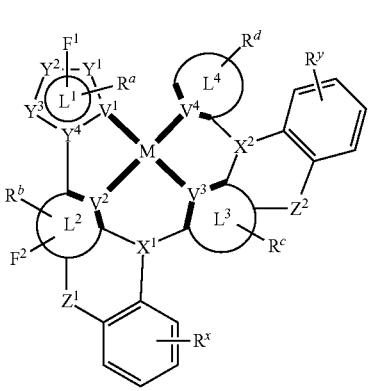

-continued

A-21
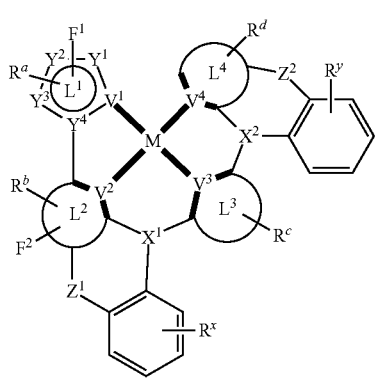

A-22
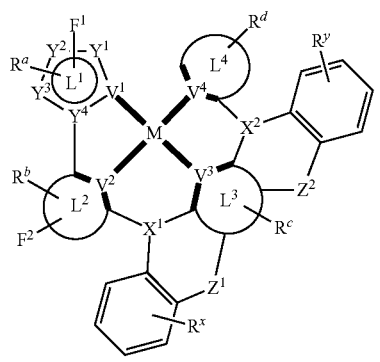

A-23
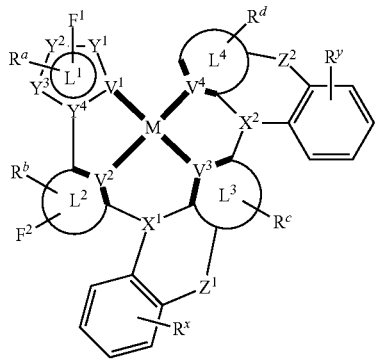

wherein each of X, X¹, and X² is independently selected from N, P, P=O, As, As=O, CR¹, CH, SiR¹, SiH, GeR¹, GeH, B, Bi, and Bi=O, wherein each of Z, Z¹, and Z² is independently a linking atom or group, wherein $R^x$ is present or absent, wherein $R^y$ is present or absent, and if present each of $R^x$ and $R^y$ independently represents mono-, di-, or tri-substitutions, and wherein each of $R^x$ and $R^y$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In yet another aspect, the compound can have any one of the structures of Formula A-24 or asymmetrical Formulas A-25 through A-36:

A-24
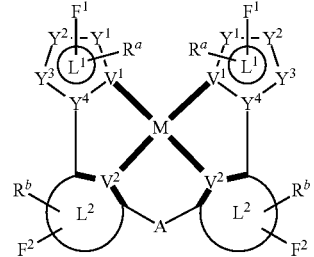

A-25
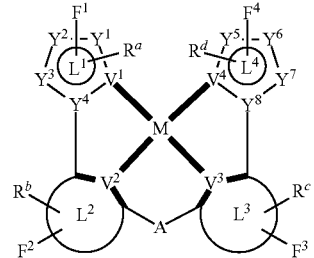

A-26
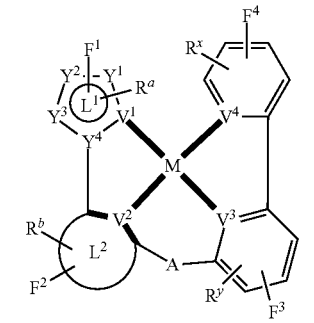

A-27
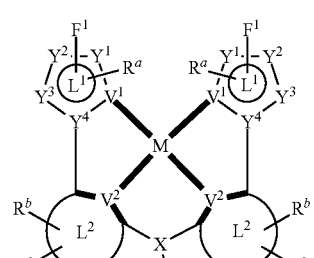

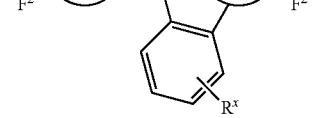

A-28
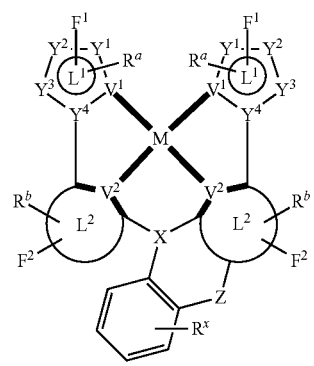

A-29
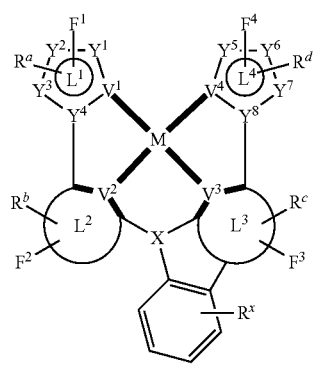
A-30
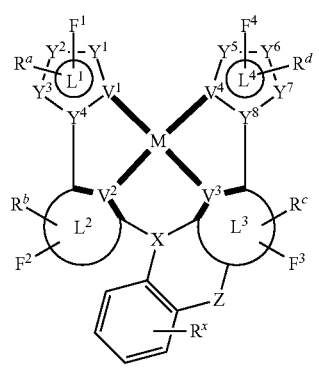
A-31
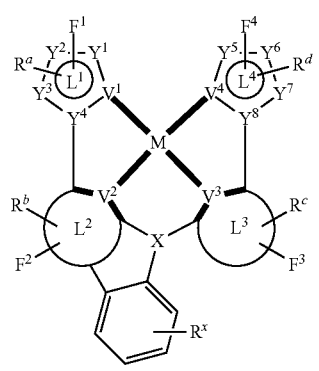
A-32
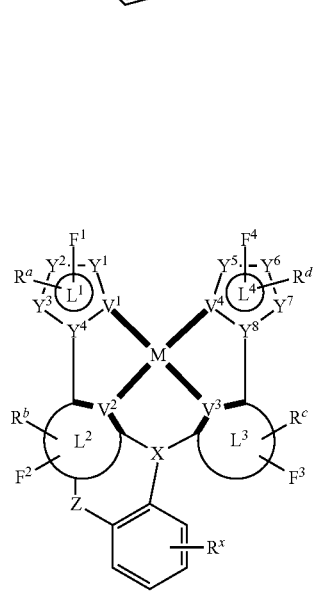
A-33
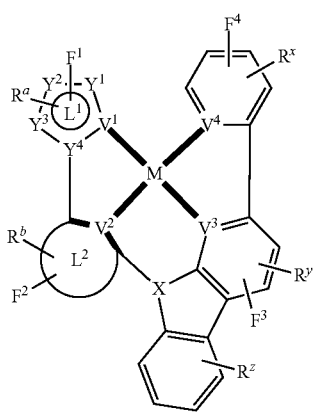
A-34
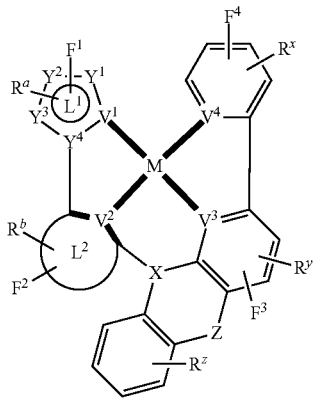
A-35
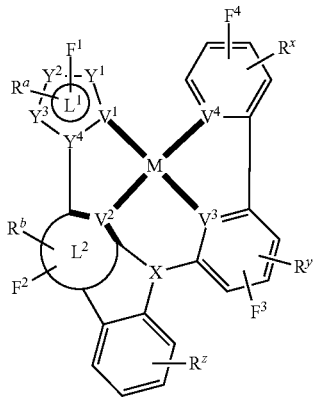
A-36
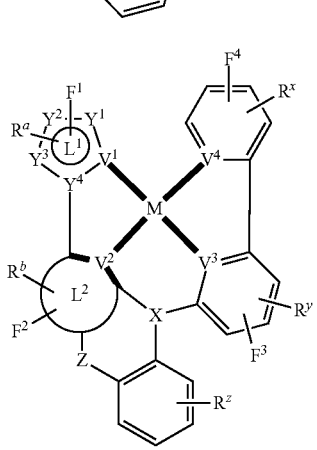

wherein each of $Y^5$, $Y^6$, $Y^7$, and $Y^8$ is independently C, N, O, S, S=O, $SO_2$, Se, Se=O, $SeO_2$, $PR^3$, $R^3P$=O, $AsR^3$, $R^3As$=O or $BR^3$, wherein X is selected from N, P, P=O, As, As=O, $CR^1$, CH, $SiR^1$, SiH, $GeR^1$, GeH, B, Bi, and Bi=O, wherein Z is a linking atom or group, wherein $R^x$ is present or absent, wherein $R^y$ is present or absent, wherein $R^z$ is present or absent, and if present each of $R^x$, $R^y$, and $R^z$ independently represents mono-, di-, or tri-substitutions, and wherein each of $R^x$, $R^y$, and $R^z$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

A. M Groups

In one aspect, M is Pt.

In another aspect, M is Pd.

B. A Groups

In one aspect, each of $A^1$, $A^2$, and A is independently $CH_2$, $CR^1R^2$, C=O, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$.

In another aspect, each of $A^1$, $A^2$, and A is independently O, S, or $CH_2$.

C. Z Groups

In one aspect, for any of the formulas disclosed herein, each of

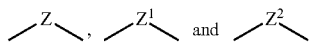,  and 

(also denoted as Z, $Z^1$, and $Z^2$ herein) is independently one of the following structures:

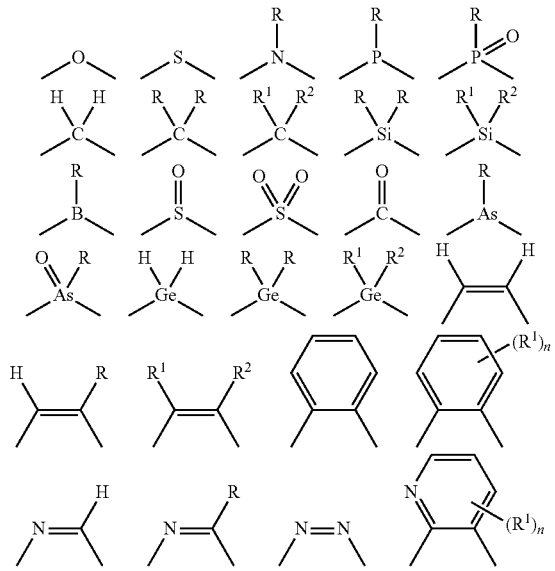

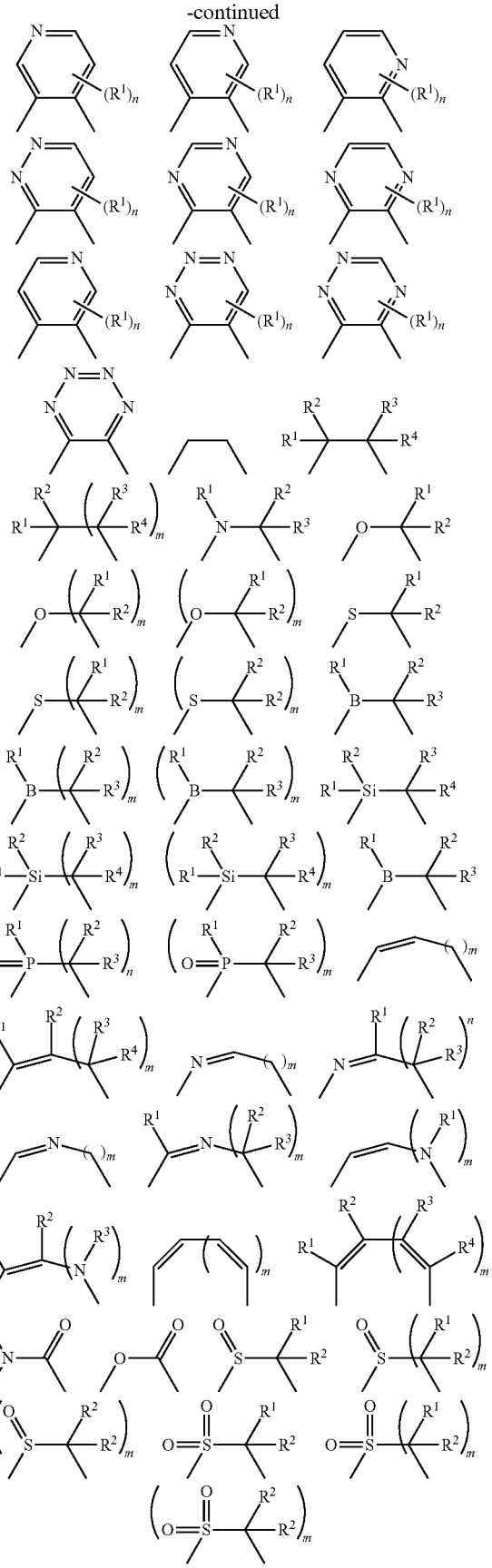

wherein n is an integer from 0 to 4, wherein m is an integer from 1 to 3, wherein each of R, $R^1$, $R^2$, $R^3$, and $R^4$ is independently hydrogen, deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, n is 0. In another aspect, n is 1. In yet another aspect, n is 2. In yet another aspect, n is 3. In yet another aspect, n is 4.

In one aspect, m is 1. In another aspect, m is 2. In yet another aspect, m is 3.

In one aspect, each of R, $R^1$, $R^2$, $R^3$, and $R^4$ is independently hydrogen, halogen, hydroxyl, thiol, or independently substituted or unsubstituted aryl, cycloalkyl, cycloalkenyl, heterocyclyl, heteroaryl, alkyl, alkenyl, alkynyl, or amino D. L Groups In one aspect, $L^1$ is a five-membered heterocyclyl, heteroaryl, carbene, or N-heterocyclic carbene.

In one aspect, $L^2$ is aryl, cycloalkyl, cycloalkenyl, heteroaryl, heterocyclyl, carbene, or N-heterocyclic carbene. In one example, $L^2$ is aryl, cycloalkyl, cycloalkenyl, heteroaryl, or N-heterocyclyl. In another example, $L^2$ is aryl or heteroaryl. In yet another example, $L^2$ is aryl. In one aspect, $L^2$ has the structure

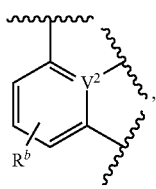

for example,

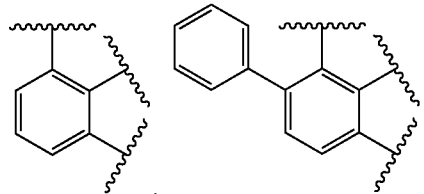

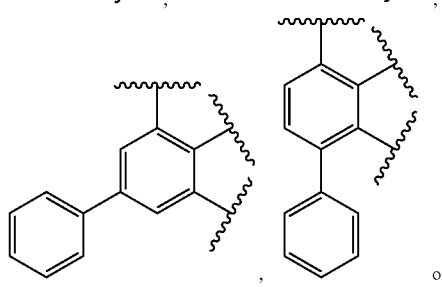

or

,

In another aspect, $L^2$ has the structure

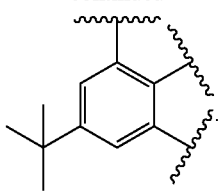

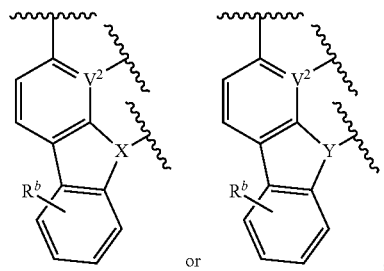

or

, for example.

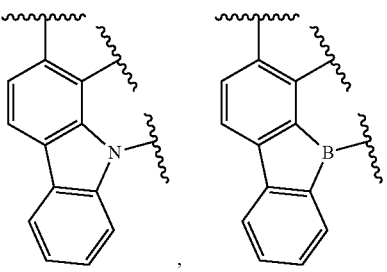

,

,

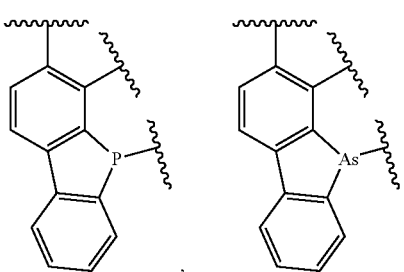

,

,

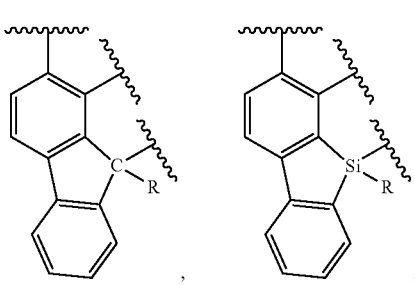

,

,

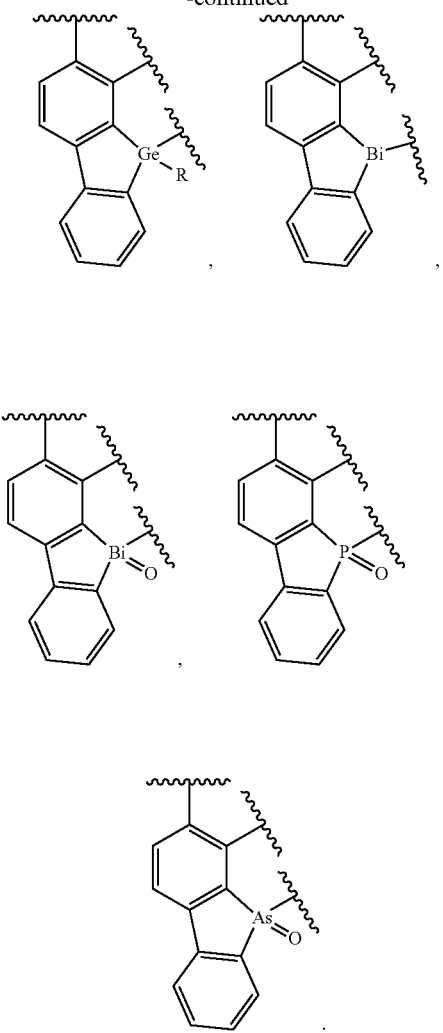
In another aspect, L² has the structure
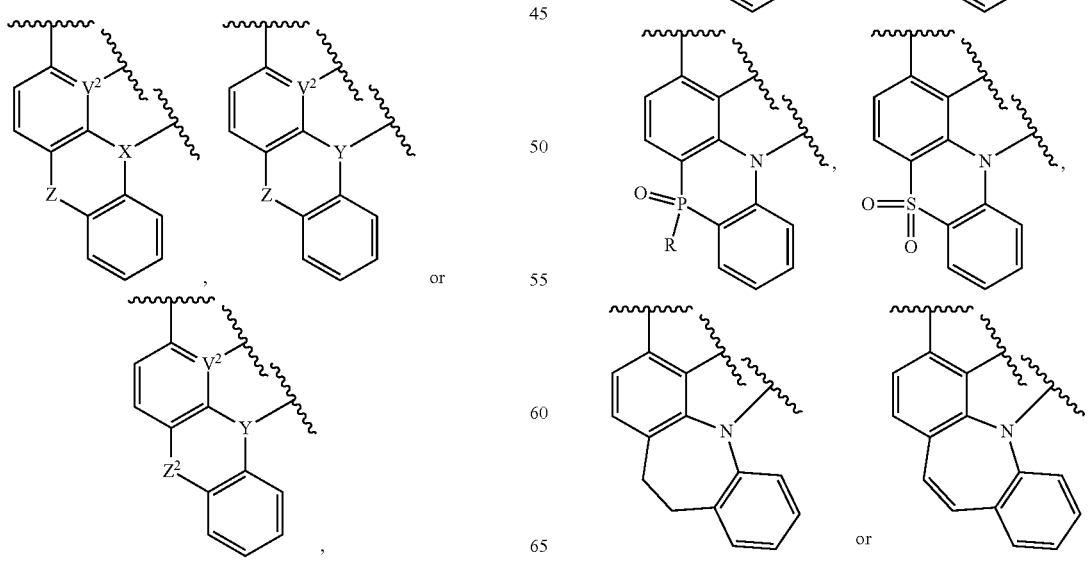
for example,
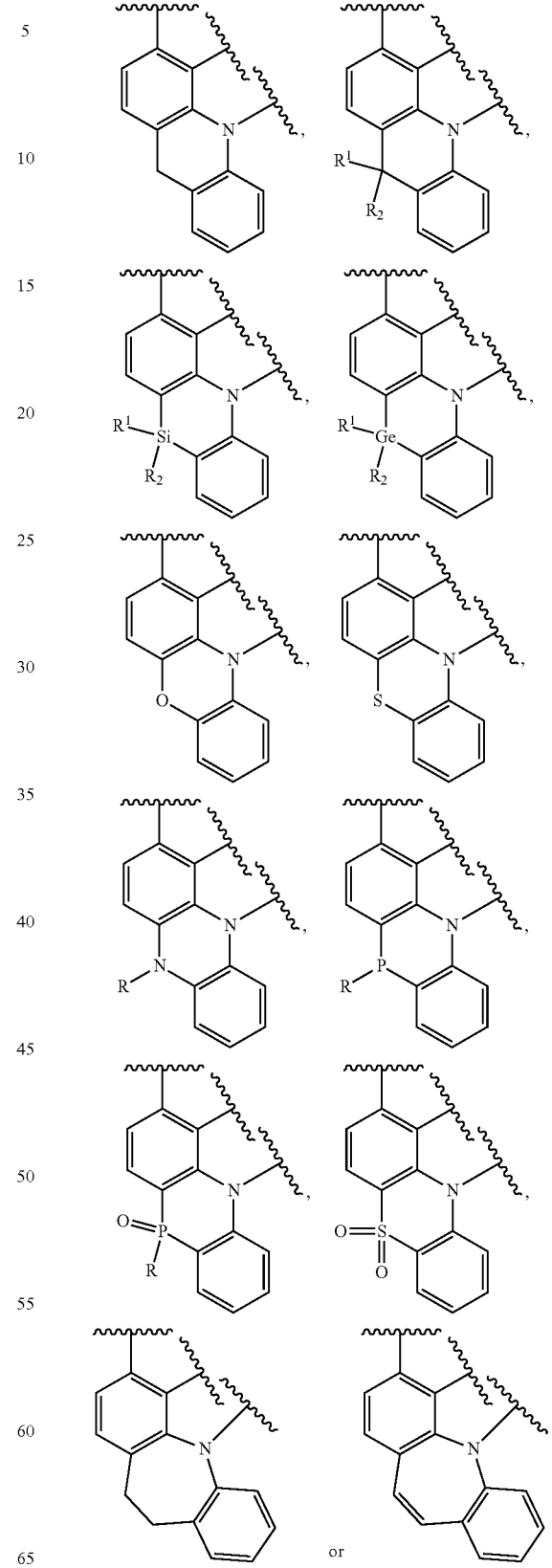

In another aspect, L² has the structure

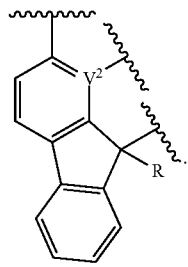

wherein each R, R¹ and R² is independently hydrogen, alkyl, alkenyl, alkynyl, aryl, cycloalkyl, cycloalkenyl, heteroaryl, heterocyclyl, halogen, hydroxyl, amino, or thiol. In one aspect, V² is N, C, P, B, or Si. In one example, V² is N or C. Wherein each of V¹ and V² is coordinated with M and is independently N, C, P, B, or Si. Wherein X is selected from N, P, P=O, As, As=O, CR¹, CH, SiR¹, SiH, GeR¹, GeH, B, Bi, and Bi=O. Y is C, N, O, S, S=O, SO₂, Se, Se=O, SeO₂, PR³, R³P=O, AsR³, R³As=O, or BR³. Each of Z, Z¹, and Z² is independently a linking atom or group.

In one aspect, L³ is aryl, cycloalkyl, cycloalkenyl, heteroaryl, heterocyclyl, carbene, or N-heterocyclic carbene. In one example, L³ is aryl, cycloalkyl, cycloalkenyl, heteroaryl, or heterocyclyl. In another example, L³ is aryl or heteroaryl. In yet another example, L³ is aryl. In one aspect, L³ has the structure

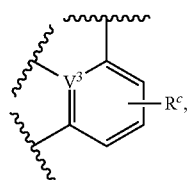

for example,

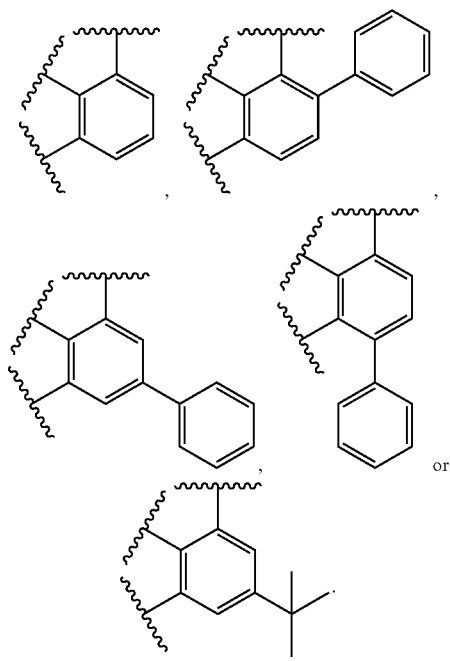

In another aspect, L³ has the structure

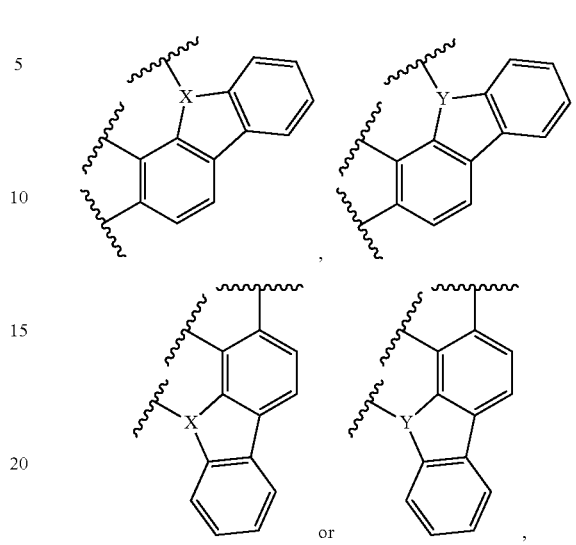

for example,

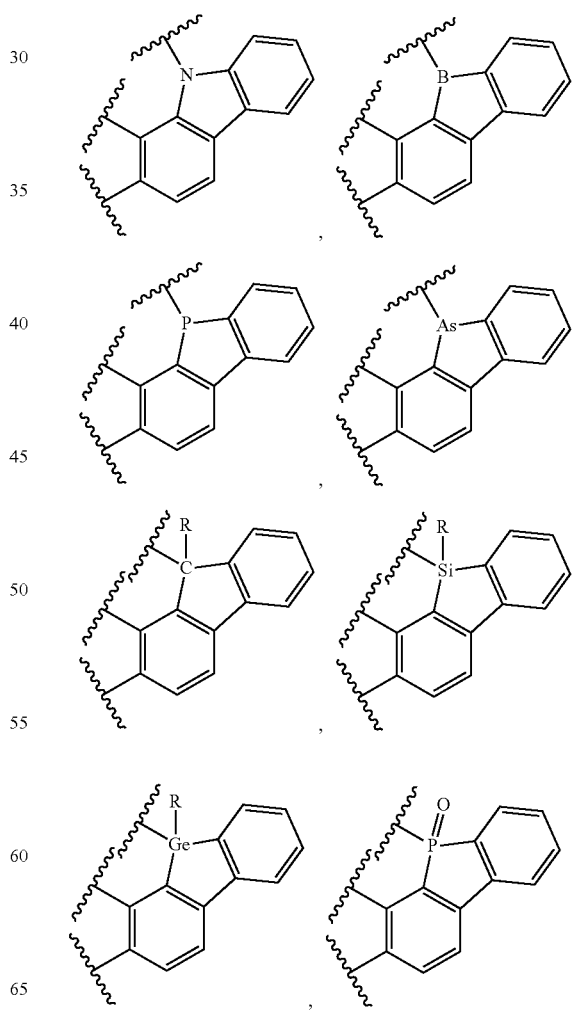

-continued

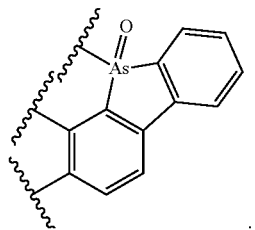

In another aspect, L³ has the structure

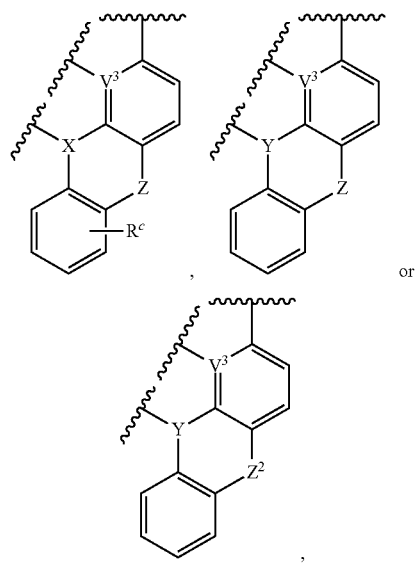

for example,

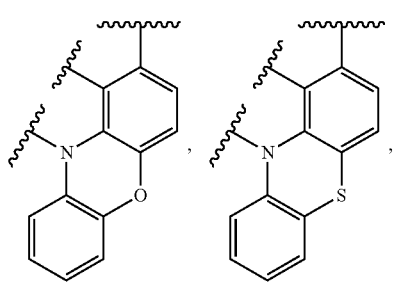

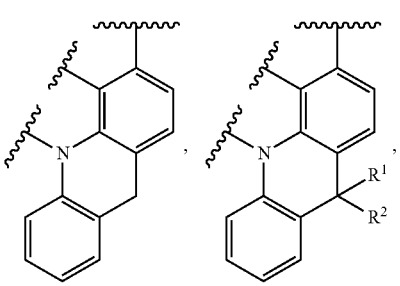

-continued

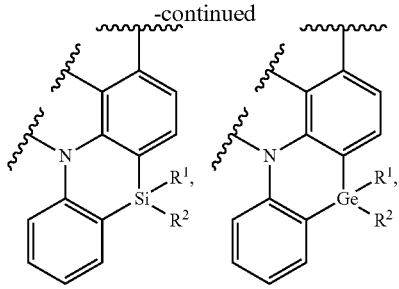

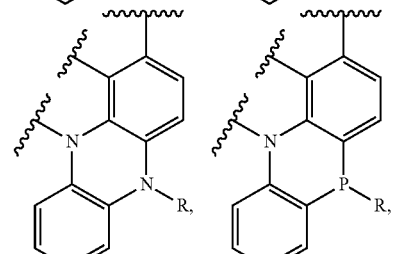

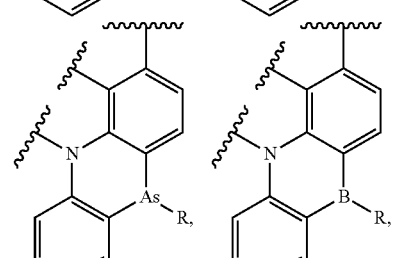

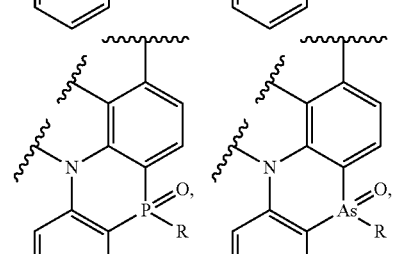

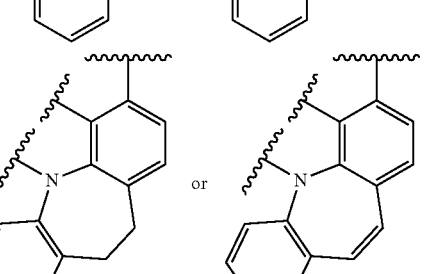

wherein each R, R¹ and R² is independently hydrogen, alkyl, alkenyl, alkynyl, aryl, cycloalkyl, cycloalkenyl, heteroaryl, heterocyclyl, halogen, hydroxyl, amino, or thiol. In one aspect, V³ is N, C, P, B, or Si. In one example, V³ is N or C. Each of V¹ and V² is coordinated with M and is independently N, C, P, B, or Si. X is selected from N, P, P═O, As, As═O, CR¹, CH, SiR¹, SiH, GeR¹, GeH, B, Bi, and Bi═O. Y is C, N, O, S, S═O, SO₂, Se, Se═O, SeO₂, PR³, R³P═O, AsR³, R³As═O, or BR³. Each of Z, Z¹, and Z² is independently a linking atom or group.

In one aspect, L⁴ is aryl, cycloalkyl, cycloalkenyl, heteroaryl, heterocyclyl, carbene, or N-heterocyclic carbene. In one example, L⁴ is aryl, cycloalkyl, cycloalkenyl, heteroaryl, or heterocyclyl. In another example, L⁴ is aryl or heteroaryl. In yet another example, L⁴ is heteroaryl. In yet another example, $L^4$ is heterocyclyl. It is understood that $V^4$ can be a part of $L^4$ and is intended to be included the description of $L^4$ above. In one aspect, $L^4$ has the structure

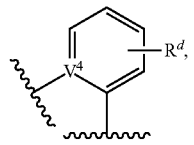

for example,

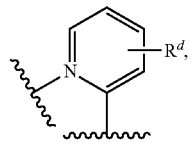

In yet another aspect, $L^4$ can has structure

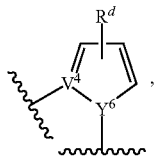

for example,

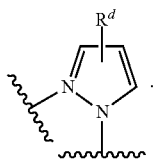

In yet another aspect, $L^4$ has the structure

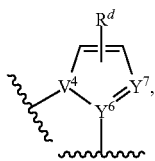

for example,

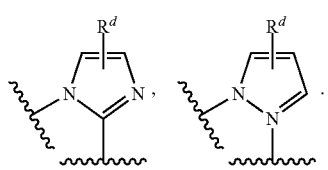

In yet another aspect, $L^4$ has the structure

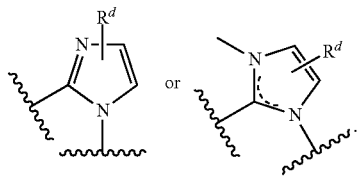

In yet another aspect, $L^4$ has the structure

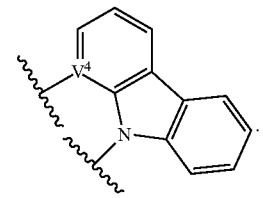

In one aspect, $V^4$ is N, C, P, B, or Si. In one example, $V^4$ is N or C. Each of $Y^6$, and $Y^7$ is independently C, N, O, S, S=O, $SO_2$, Se, Se=O, $SeO_2$, $PR^3$, $R^3P$=O, $AsR^3$, $R^3As$=O or $BR^3$.

In one aspect, for any of the formulas disclosed herein, five-membered heterocylyl

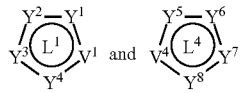

may represent one or more of the following structures:

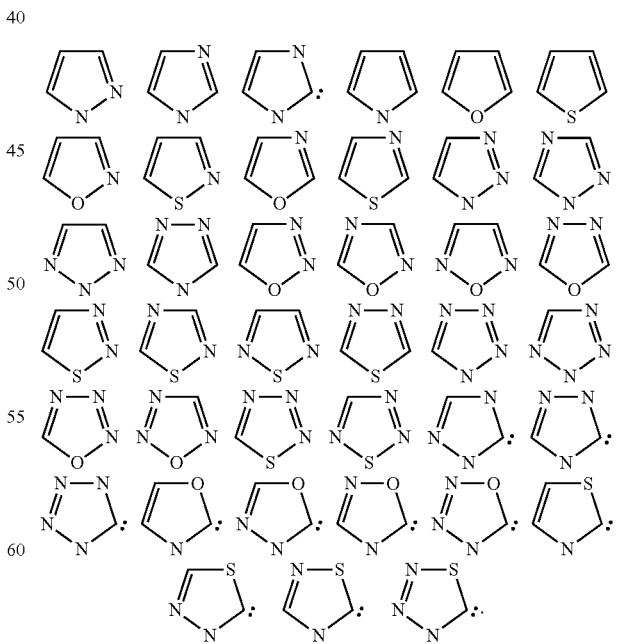

It is understood that one or more of $R^a$, $R^b$, $R^c$, and $R^d$ as described herein may be bonded to

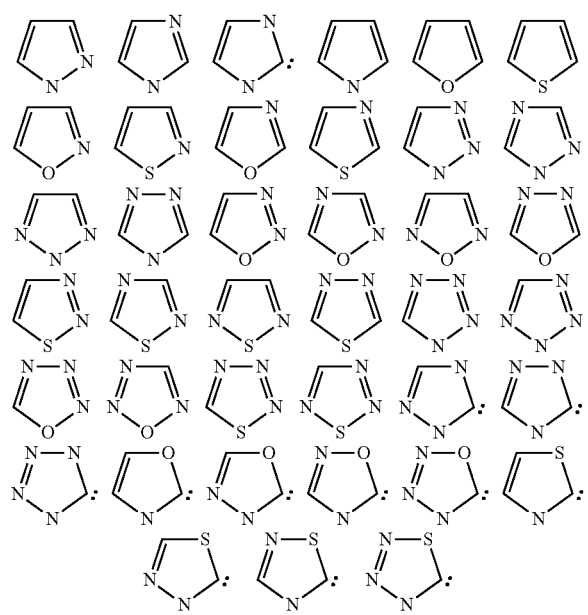
as permitted by valency.
In one aspect,
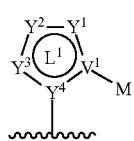
has the structure
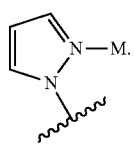
In one aspect, for any of the formulas illustrated in this disclosure, each of
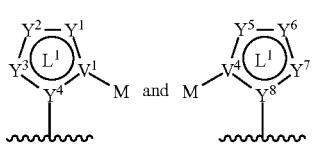
independently has one of the following structures:
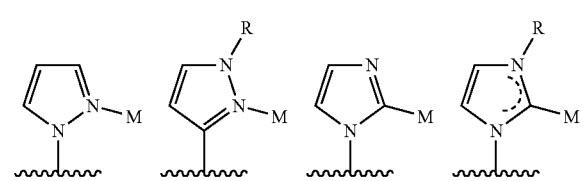
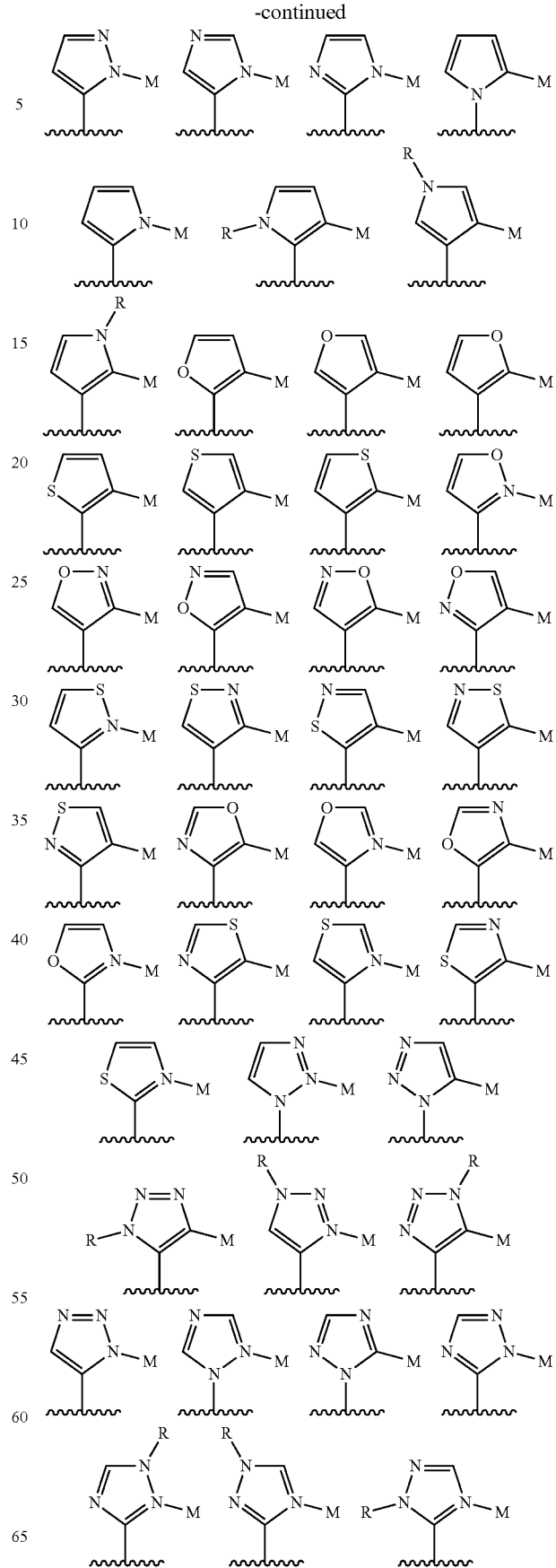

-continued

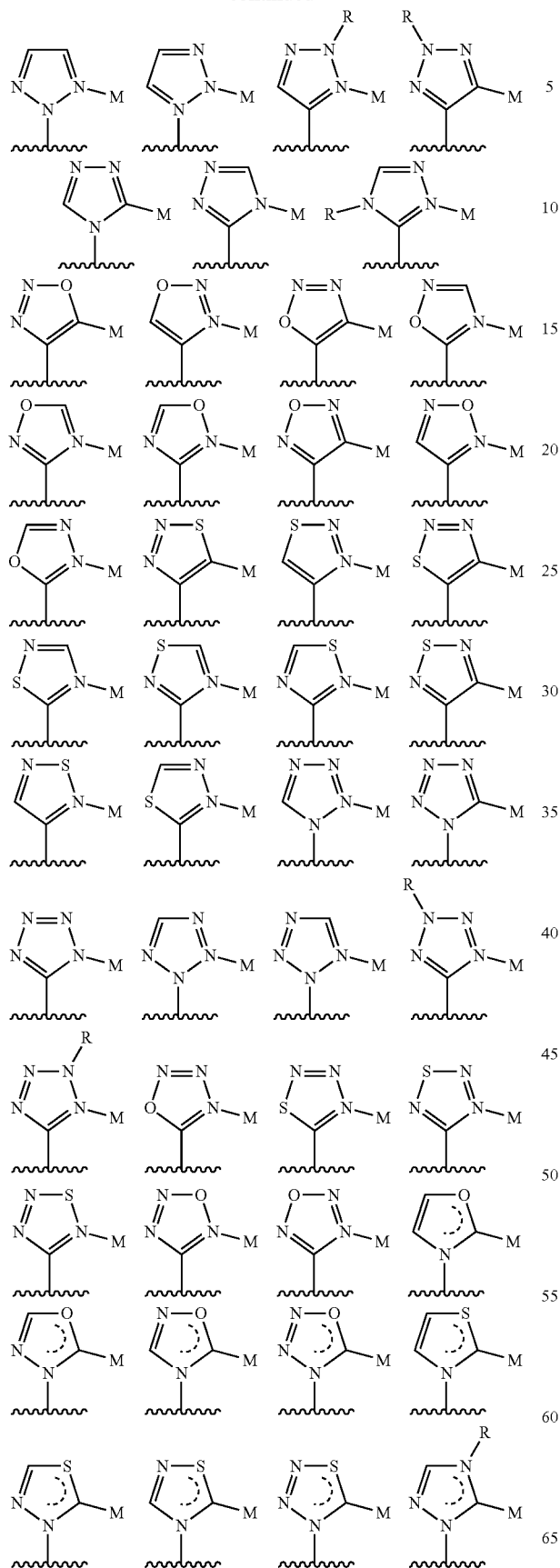

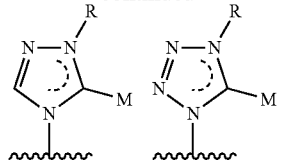

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect,

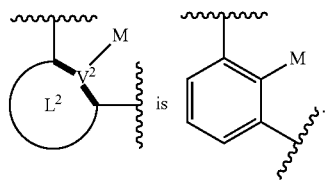

In one aspect,

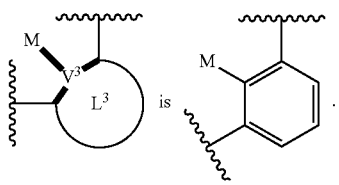

In another aspect,

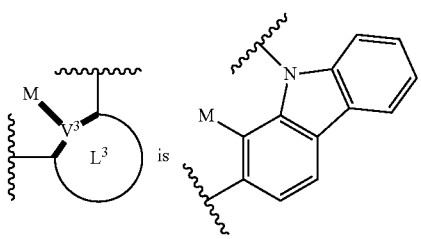

In one aspect, for any of the formulas disclosed herein, each of

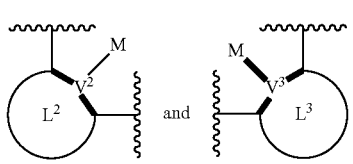

is independently one of the following structures:
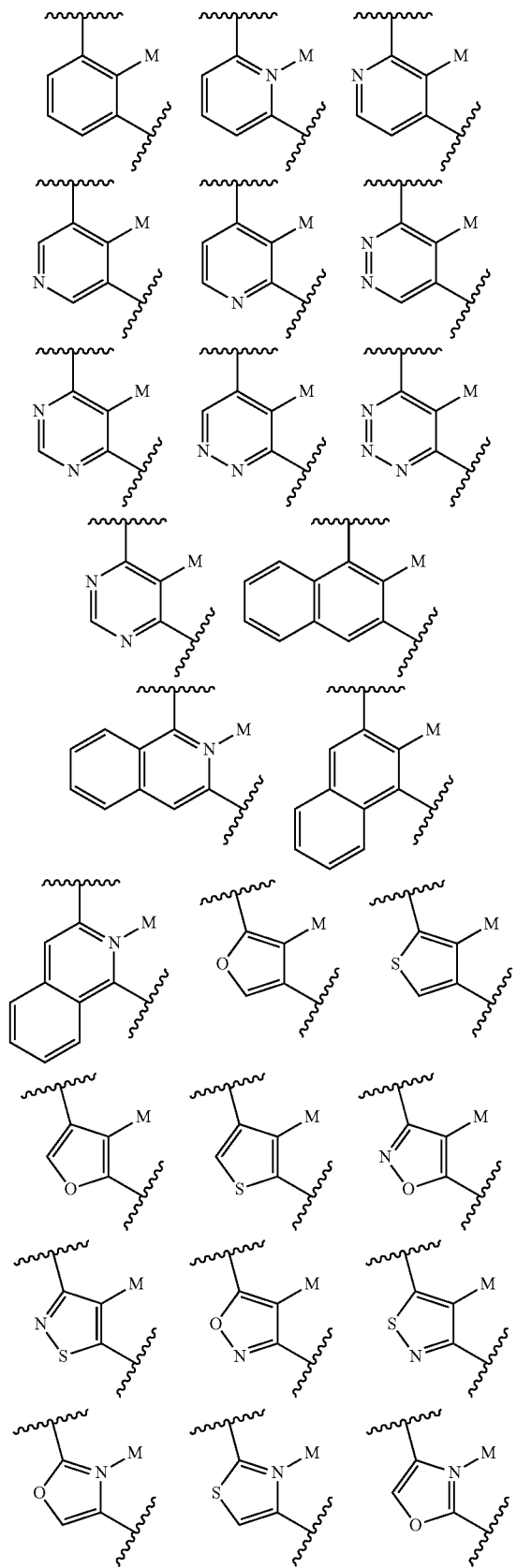
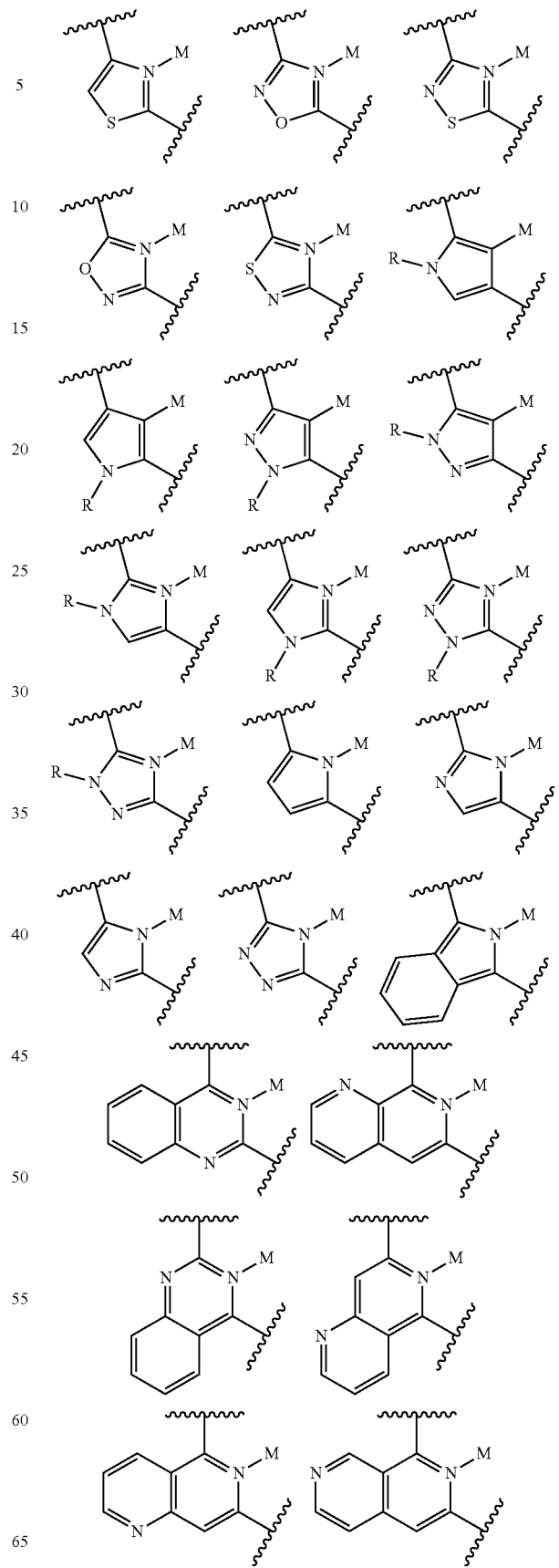

-continued

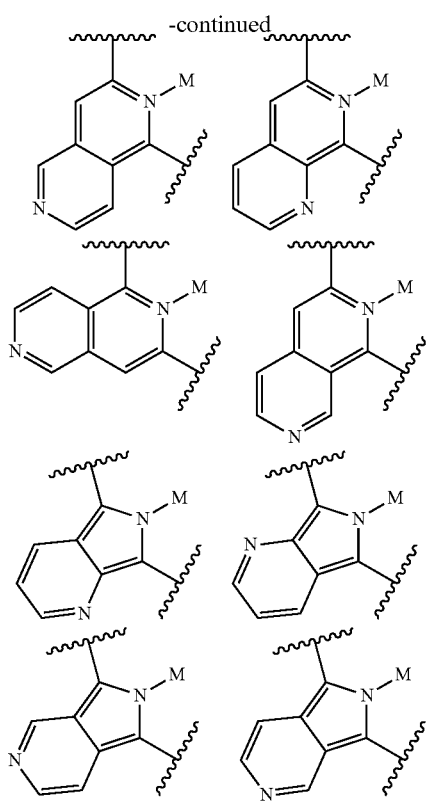

wherein R is hydrogen, deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In one aspect, for any of the formulas illustrated in this disclosure, each of

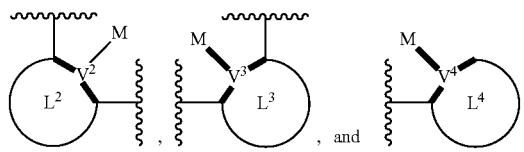

is independently one of the following structures:

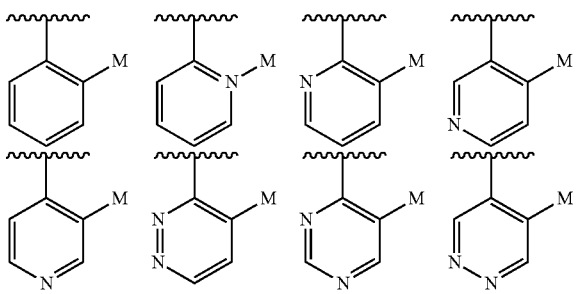

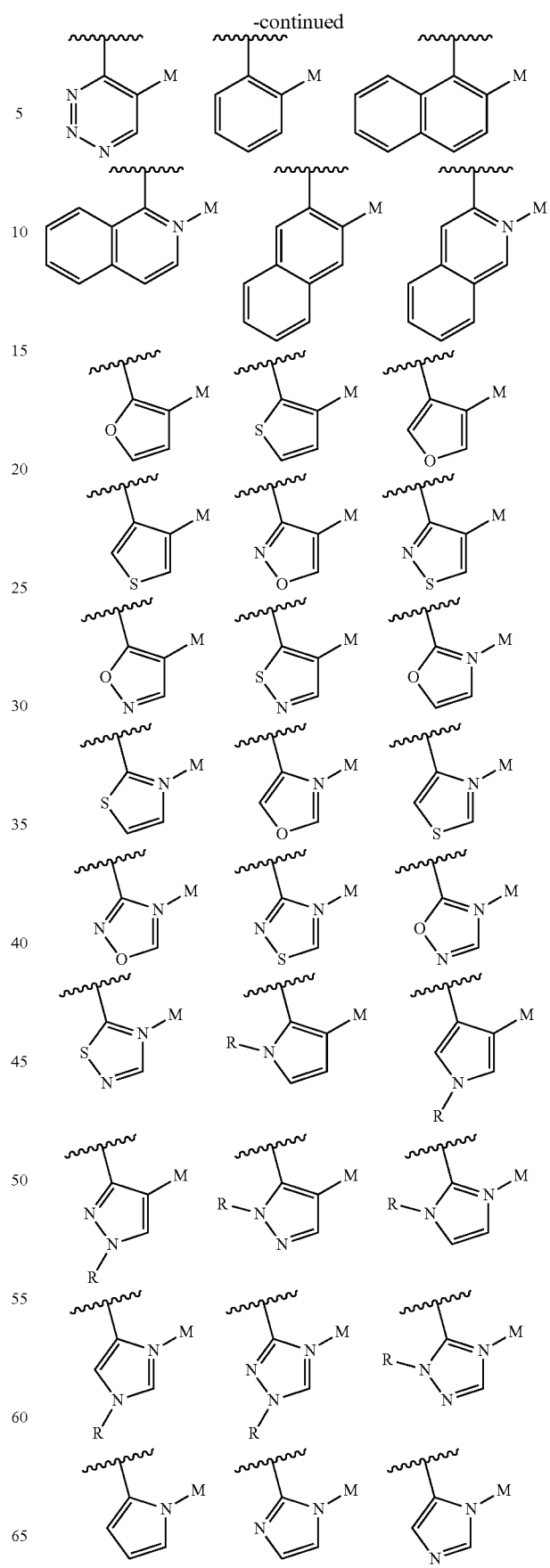

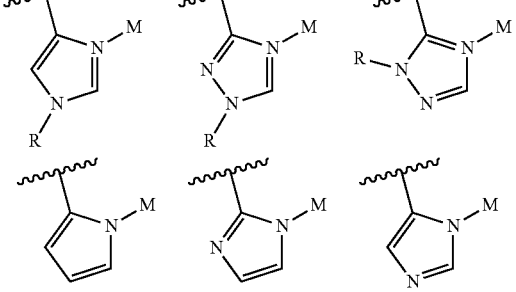

-continued

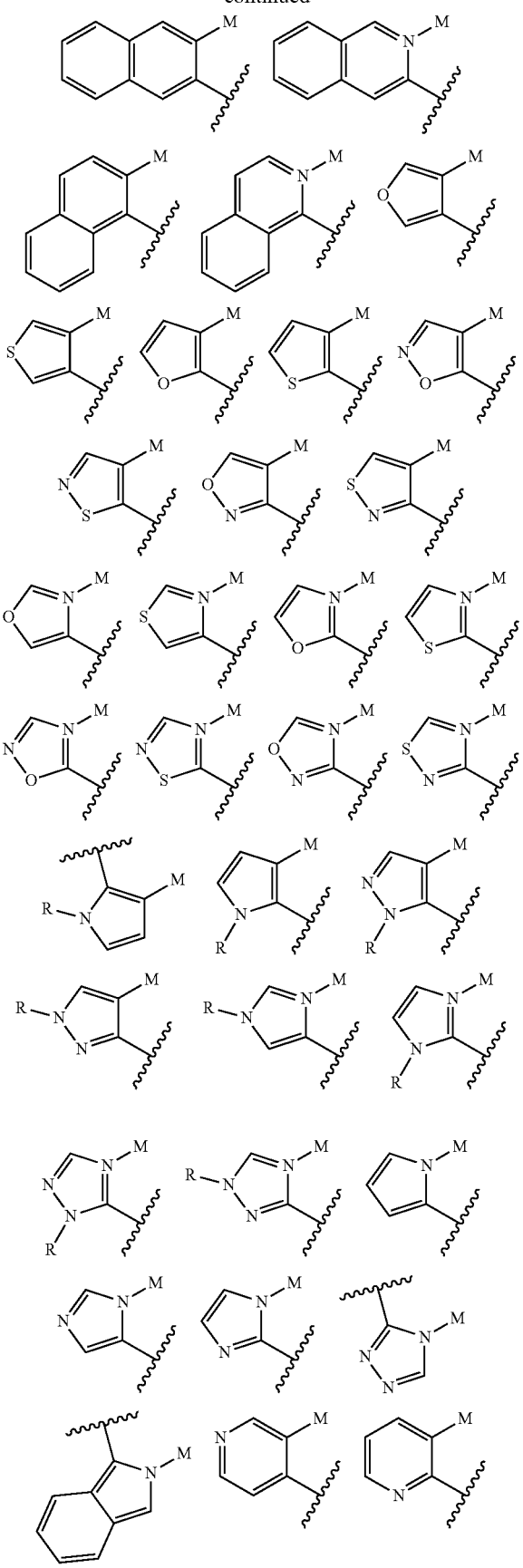
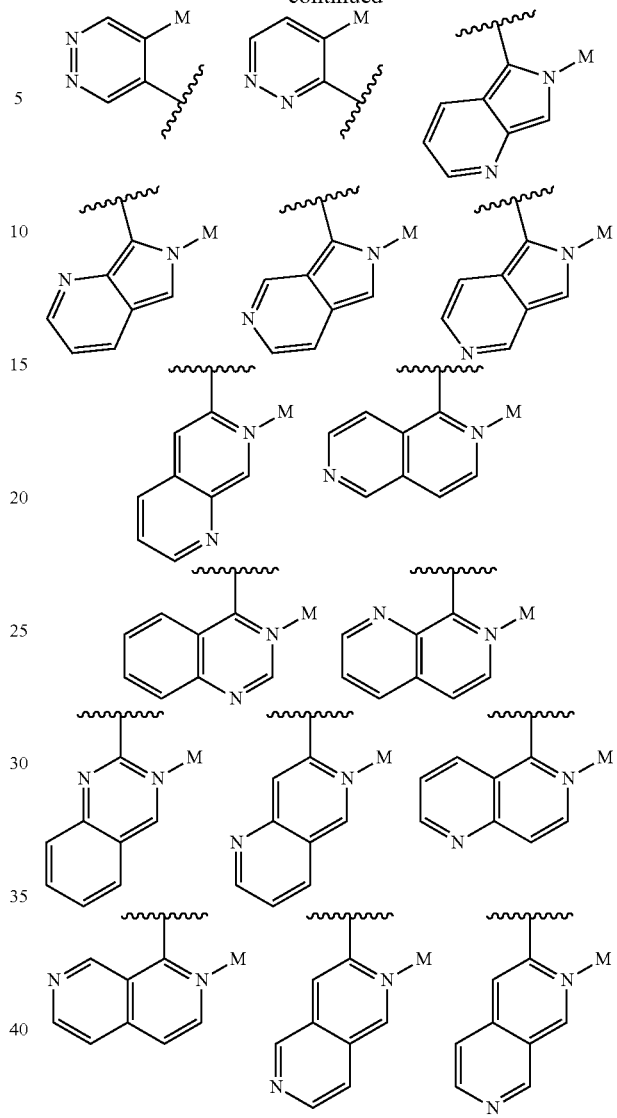

wherein R hydrogen, deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

E. Fluorescent Luminophore Groups

In one aspect, any one more of $F^1$, $F^2$, $F^3$, and $F^4$ is present. In another aspect, $F^1$ is present and $F^2$, $F^3$, and $F^4$ are absent.

In one aspect, each fluorescent luminophore is independently selected from aromatic hydrocarbons and their derivatives, polyphenyl hydrocarbons, hydrocarbons with condensed aromatic nuclei, naphthalene, anthracene, phenanthrene, chrysene, pyrene, triphenylene, perylene, acenapthene, tetracene, pentacene, tetraphene, coronene, fluorene, biphenyl, p-terphenyl, o-diphenylbenzene, m-diphenylbenzene, p-quaterphenyl, benzo[α]tetracene, benzo

[k]tetraphene, indeno[1,2,3-cd]fluoranthene, tetrabenzo[de, hi,op,st]pentacene, arylethylene, arylacetylene and their derivatives, diarylethylenes, diarylpolyenes, diaryl-substituted vinylbenzenes, distyrylbenzenes, trivinylbenzenes, arylacetylenes, stilbene and functional substitution products of stilbene.

In another aspect, each fluorescent luminophore is independently selected from substituted or unsubstituted five-, six- or seven-membered heterocyclic compounds, furan, thiophene, pyrrole and their derivatives, aryl-substituted oxazoles, 1,3,4-oxadiazoles, 1,3,4-thiadiazoles, aryl-substituted 2-pyrazolines and pyrazoles, benzazoles, 2H-benzotriazole and its substitution products, heterocycles with one, two or three nitrogen atoms, oxygen-containing heterocycles, coumarins and their derivatives, miscellaneous dyes, acridine dyes, xanthene dyes, oxazines, and thiazines.

In yet another aspect, for any of the formulas disclosed herein, each of $F^1$, $F^2$, $F^3$, and $F^4$, if present, is independently one of the following:

1. Aromatic Hydrocarbons and their Derivatives

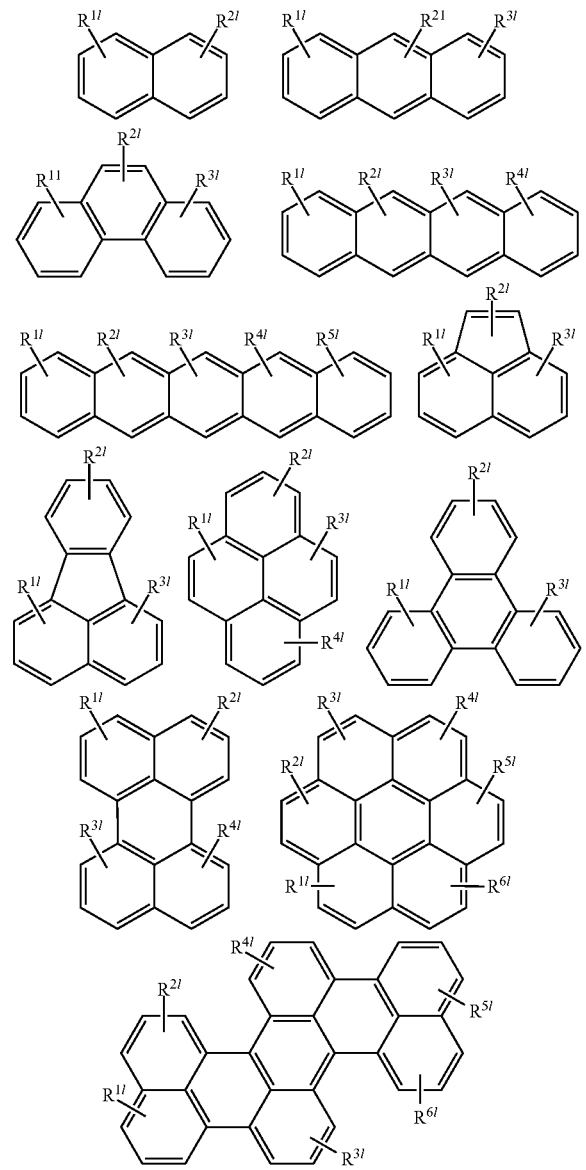

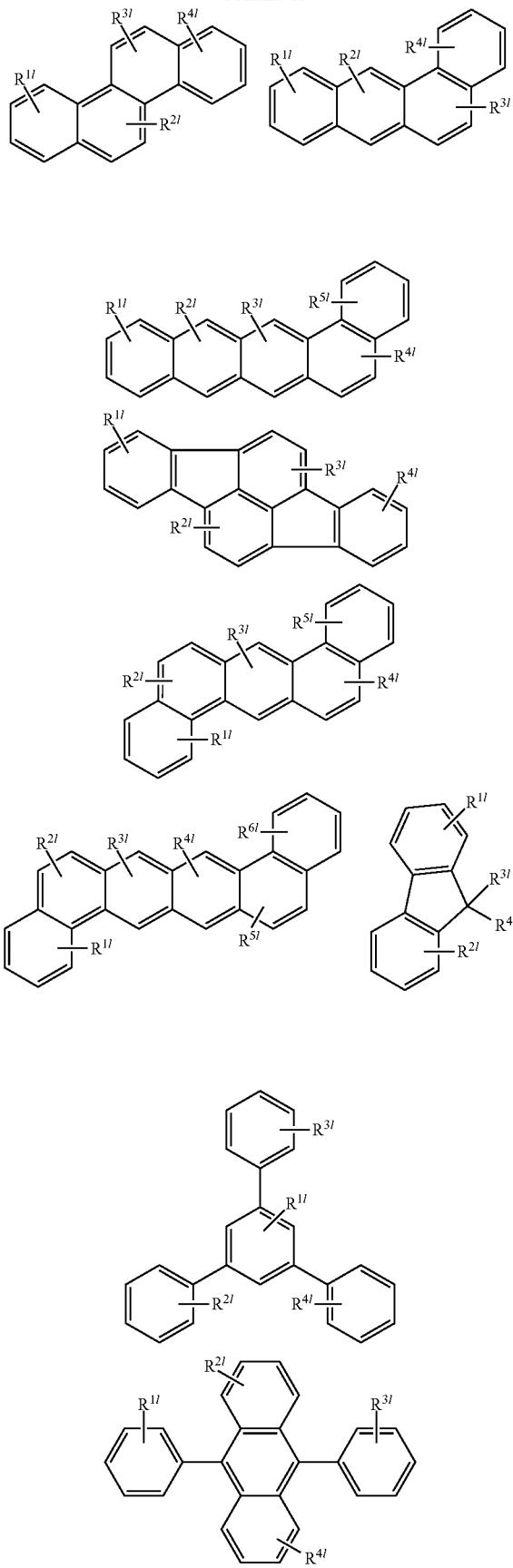

-continued
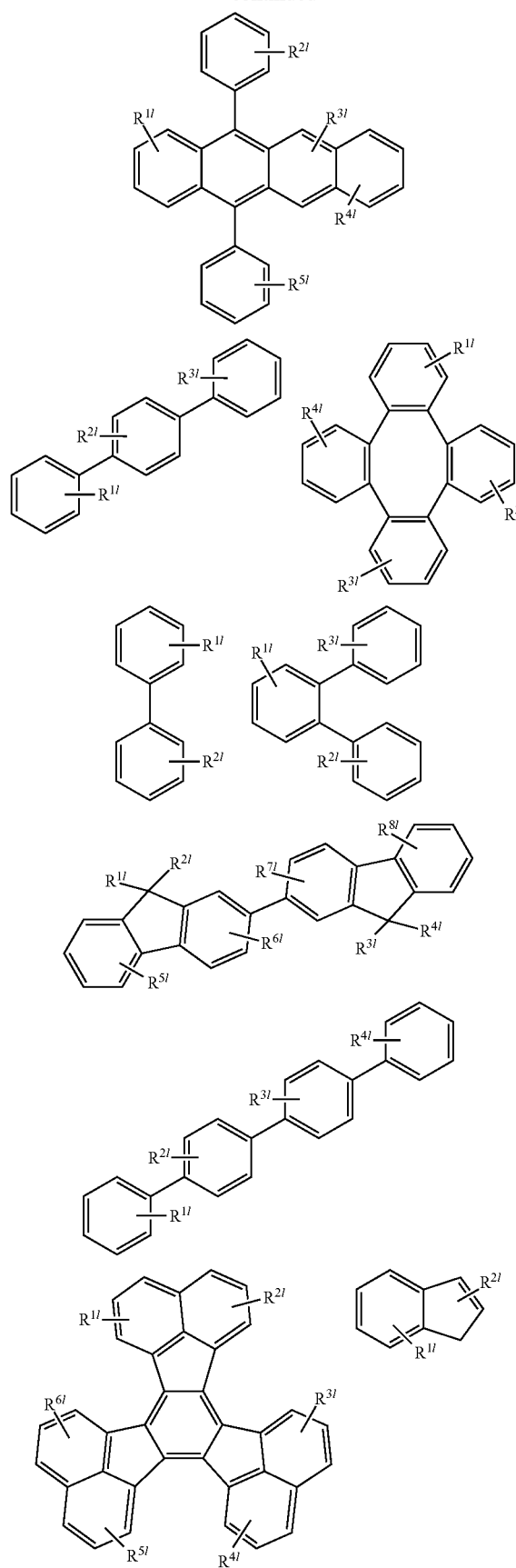
-continued
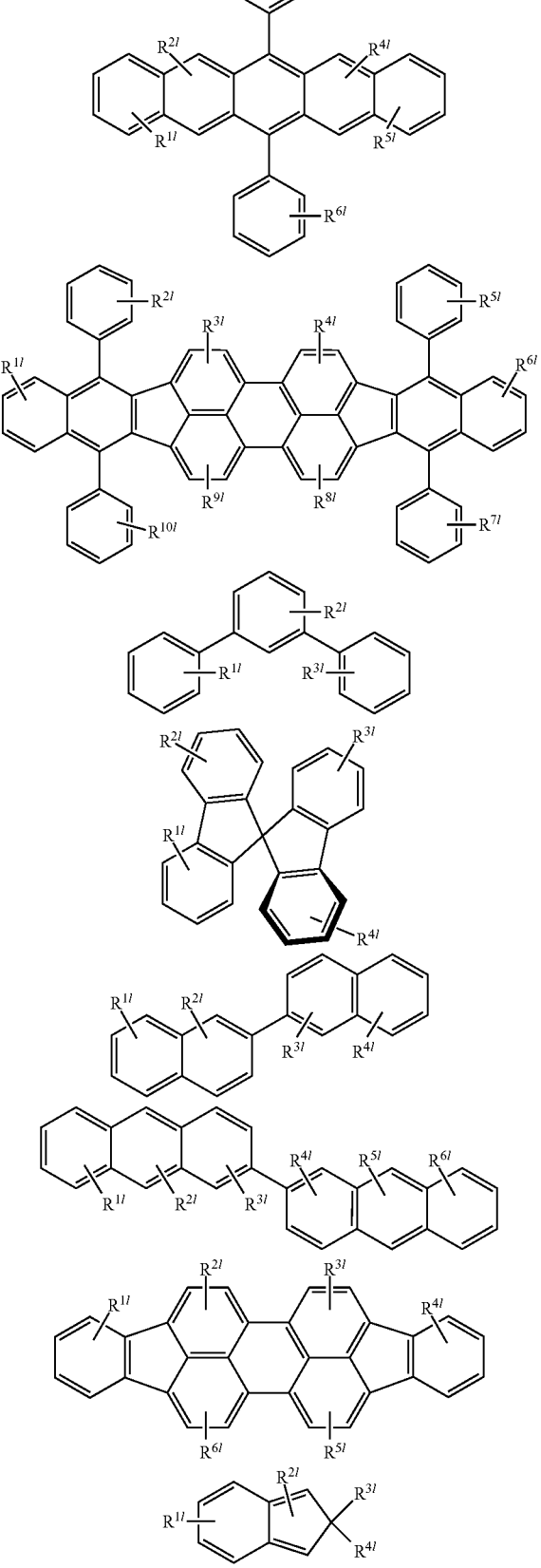

-continued
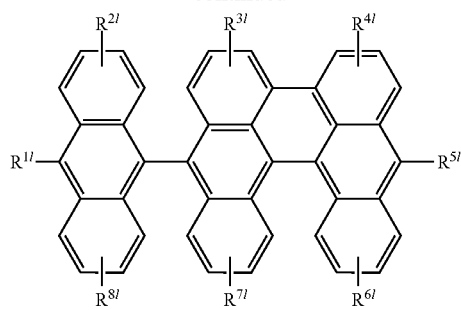
2. Arylethylene, Arylacetylene and their Derivatives
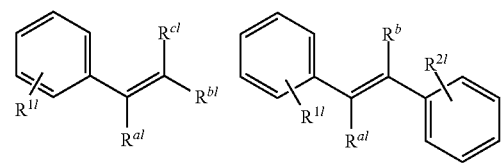
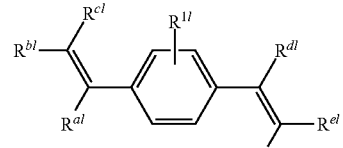
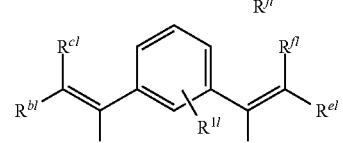
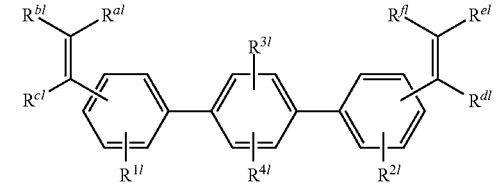
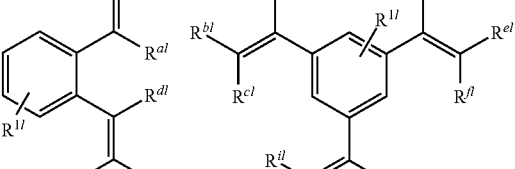
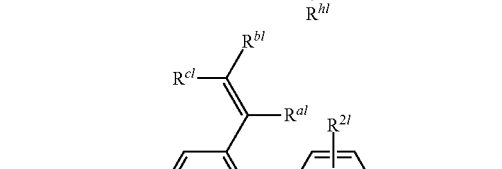
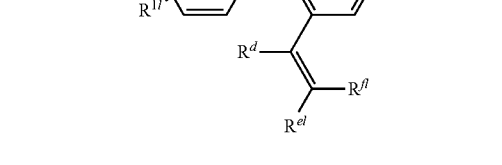
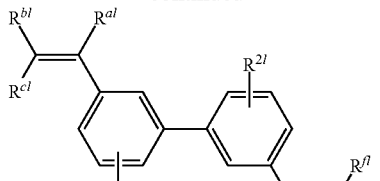
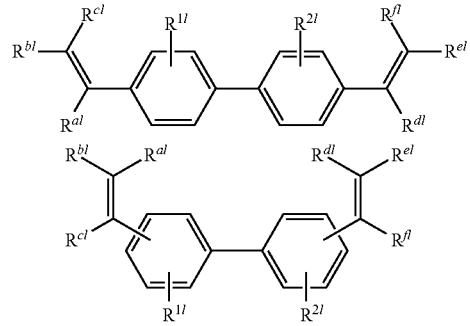
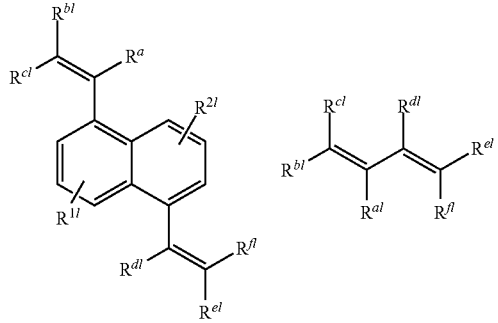
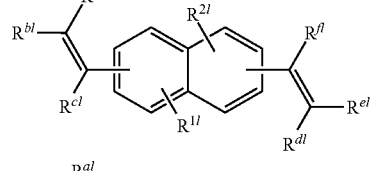
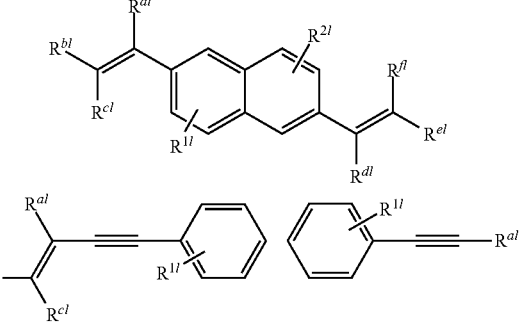
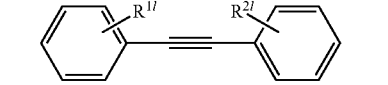
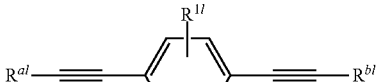
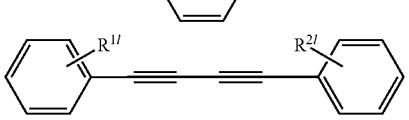

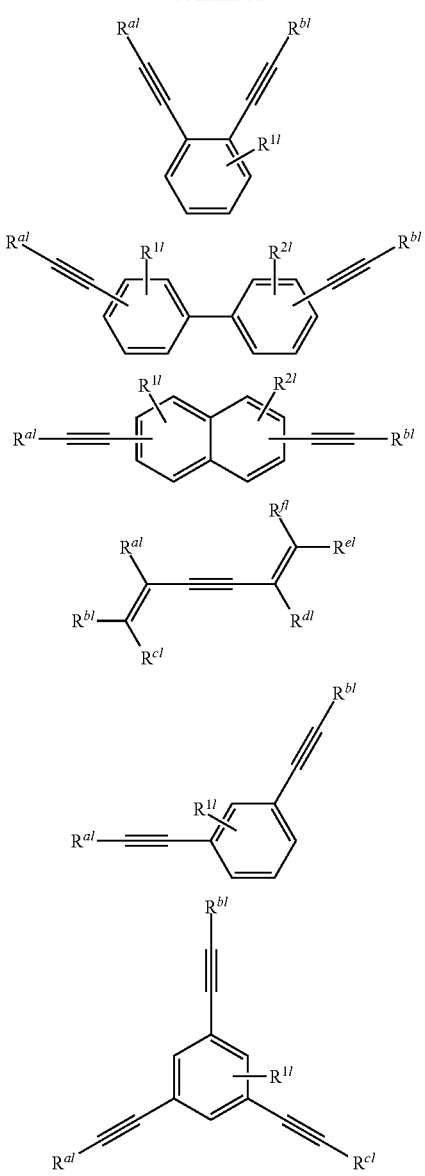
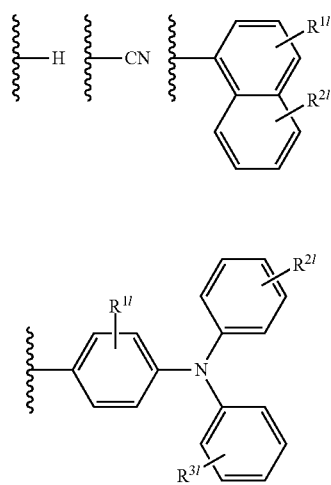
where each of $R^{al}$, $R^{bl}$, $R^{cl}$, $R^{dl}$, $R^{el}$, $R^{fl}$, $R^{gl}$, $R^{hl}$ and $R^{il}$ can be one of the following structure:
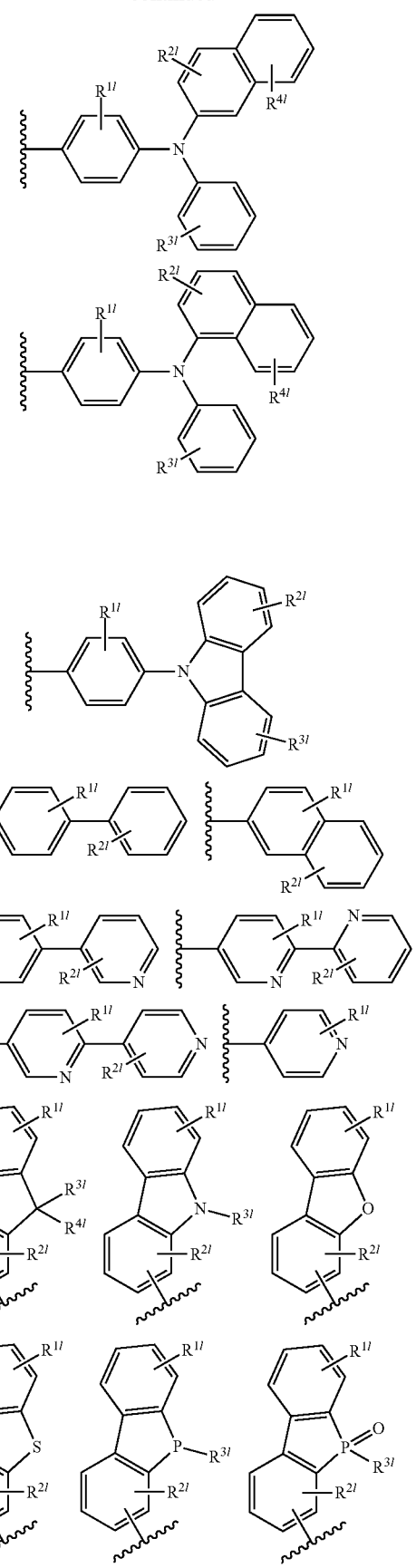

-continued
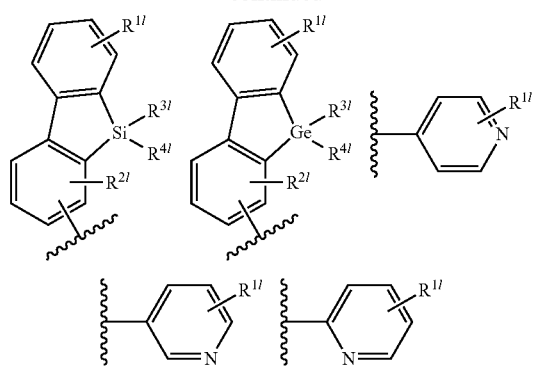
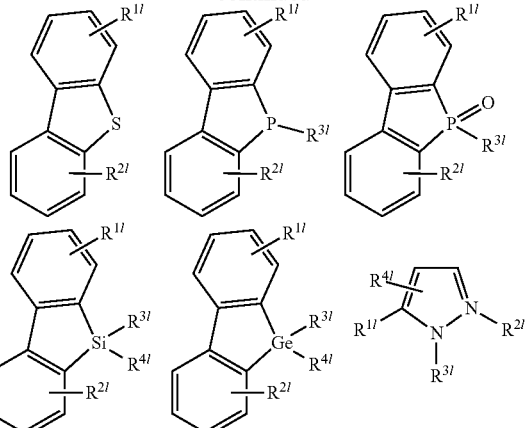
3. Heterocyclic Compounds and their Derivatives
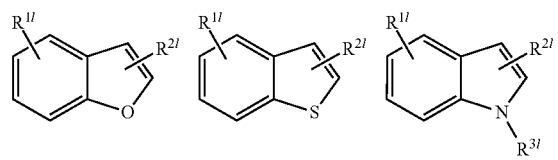
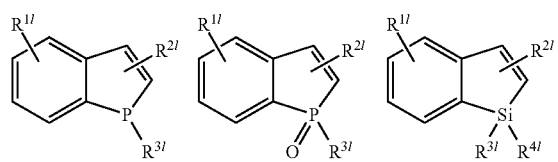
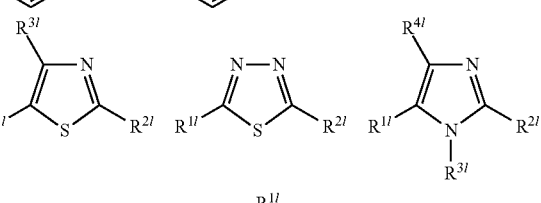
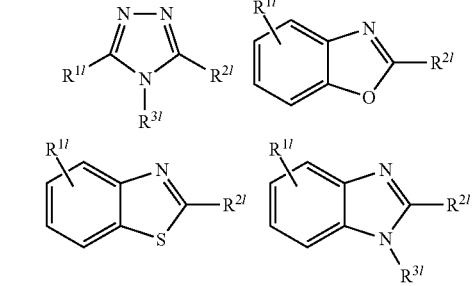
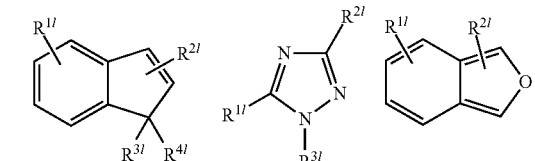
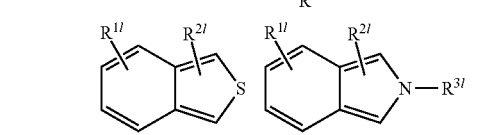
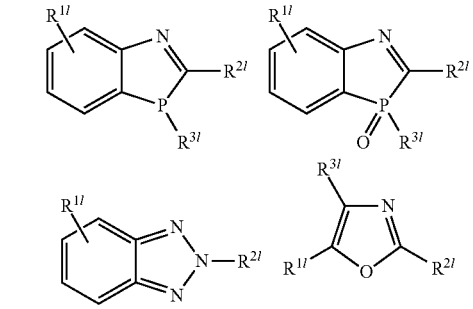
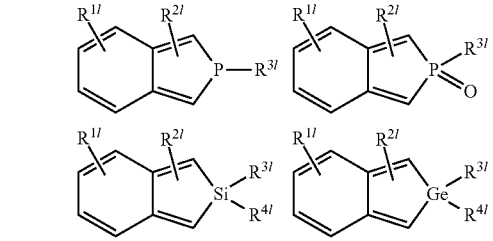
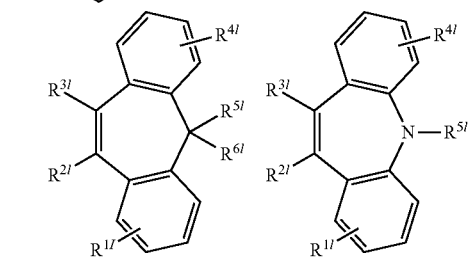
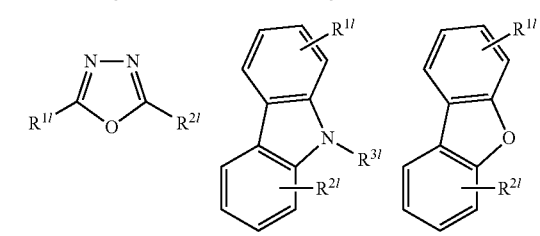
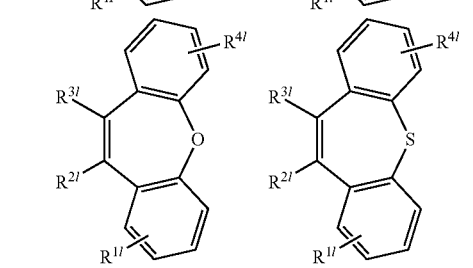

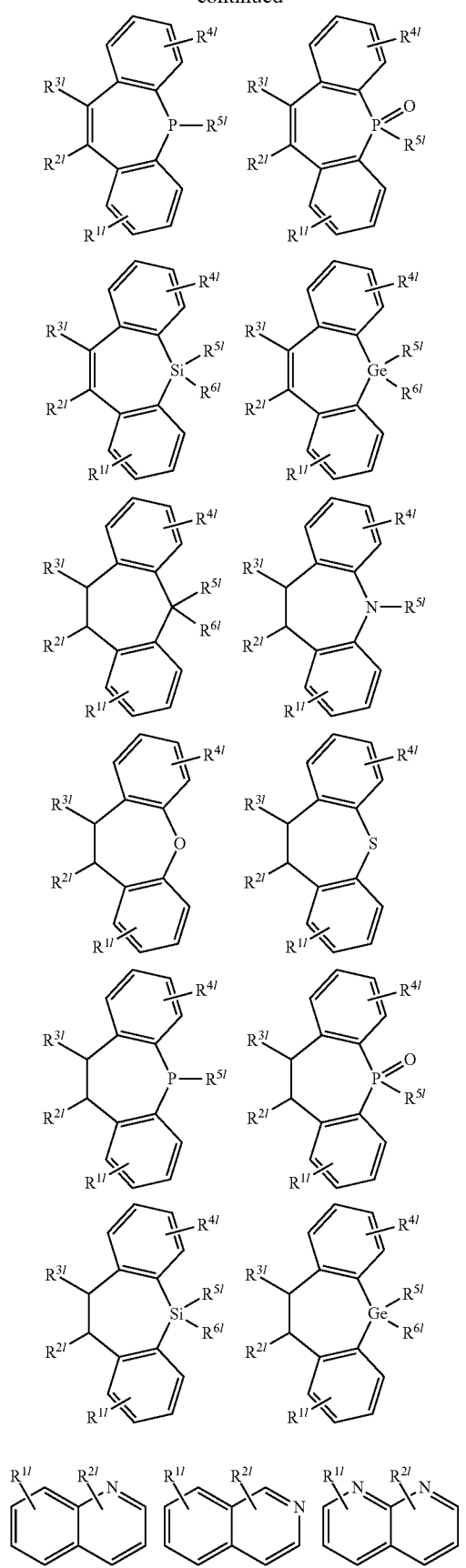
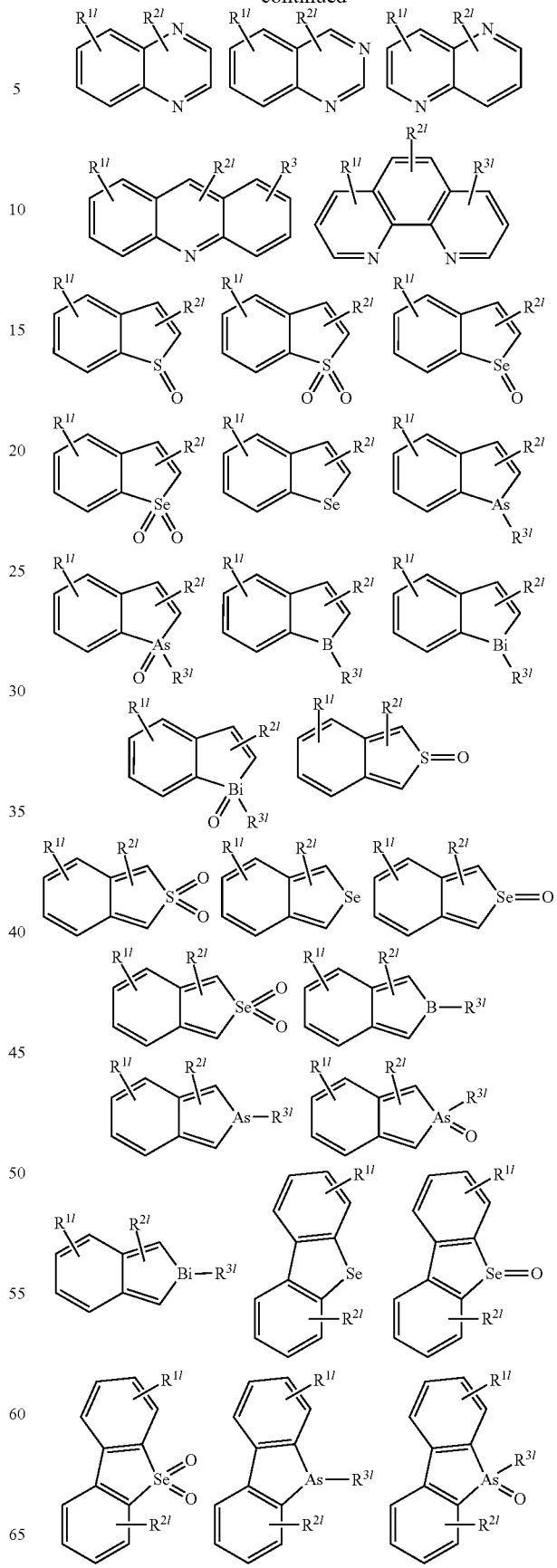

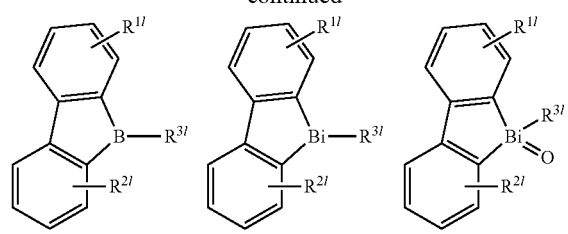
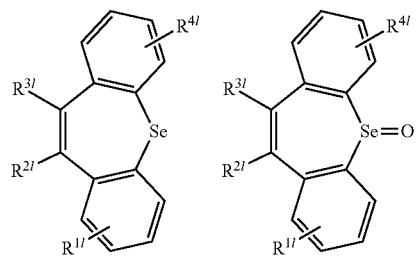
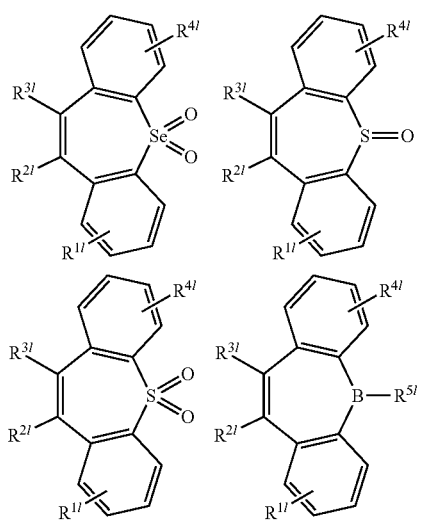
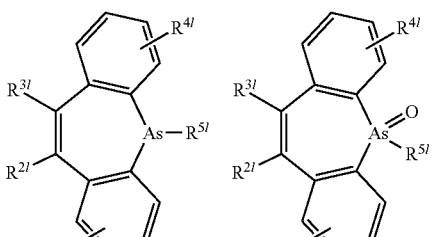
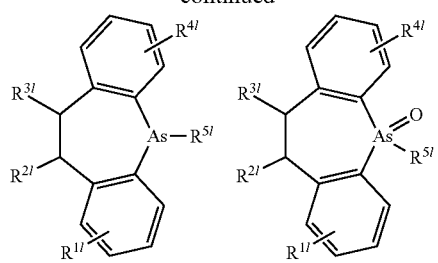
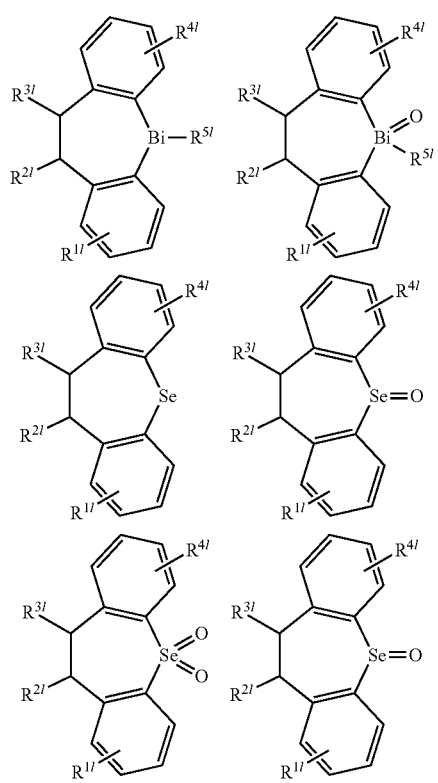
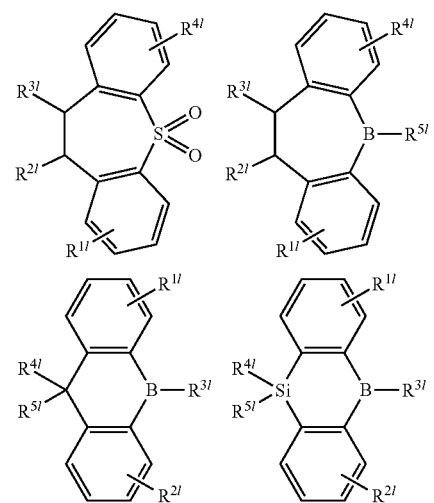

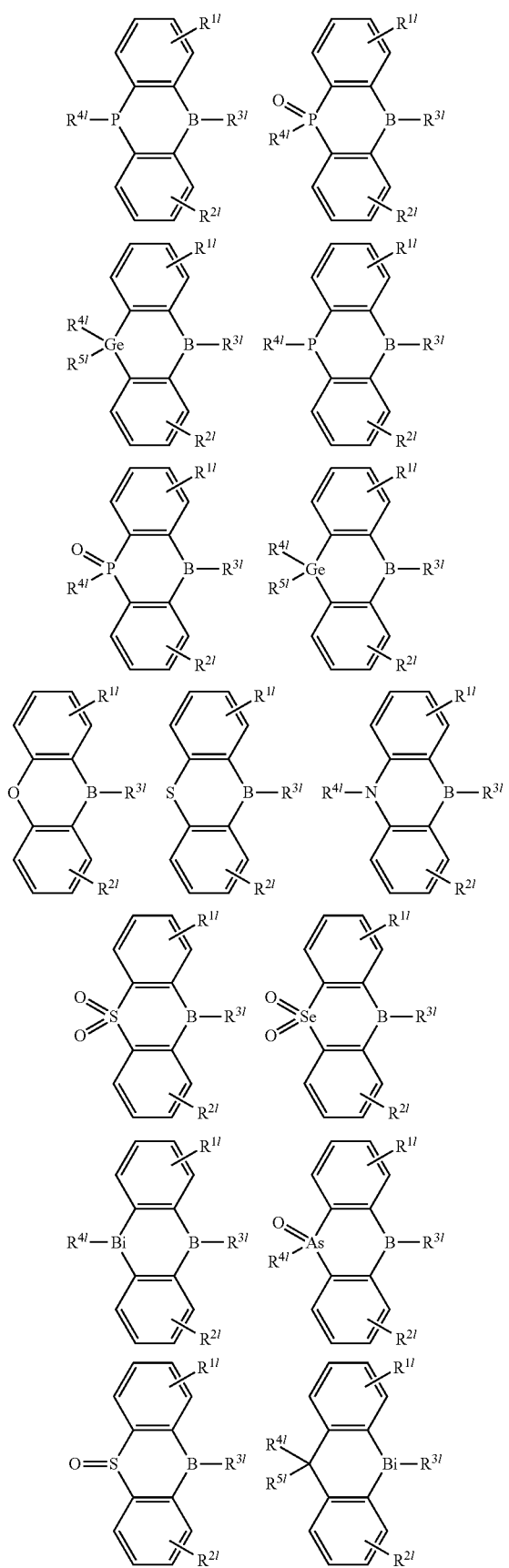
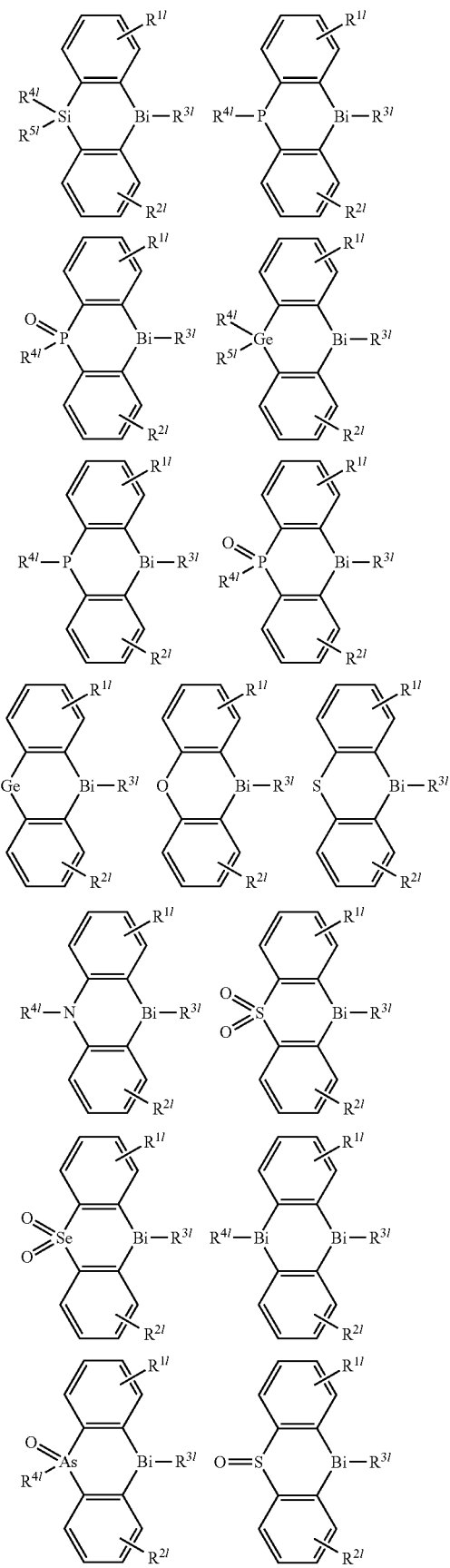

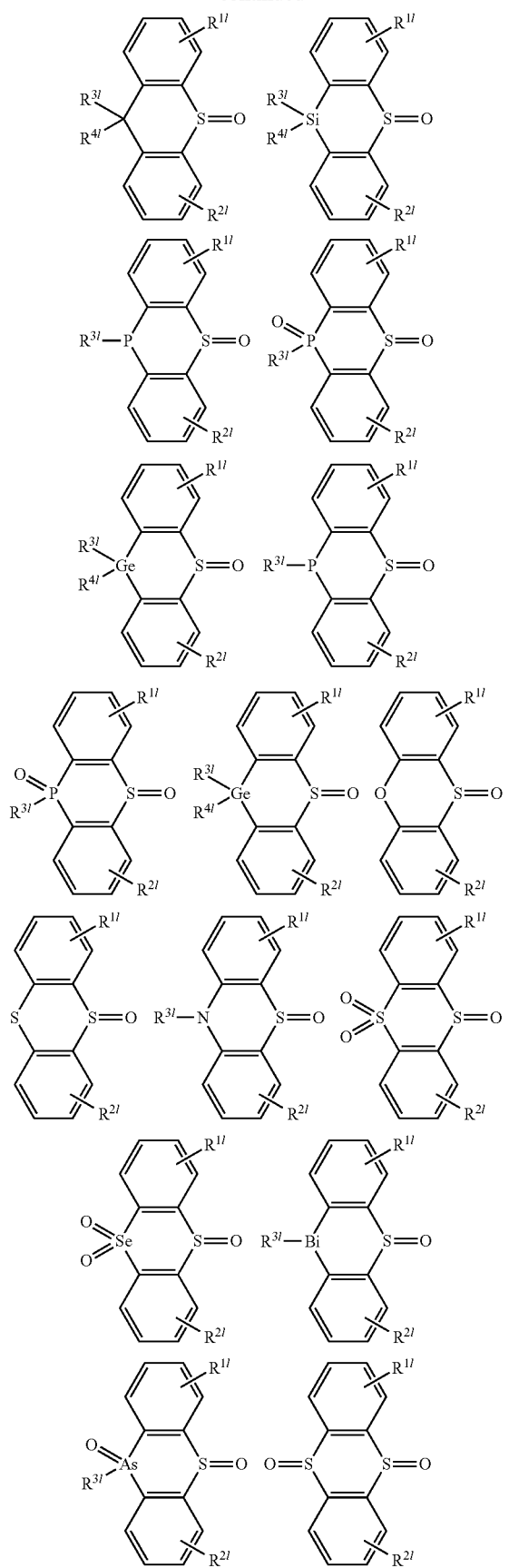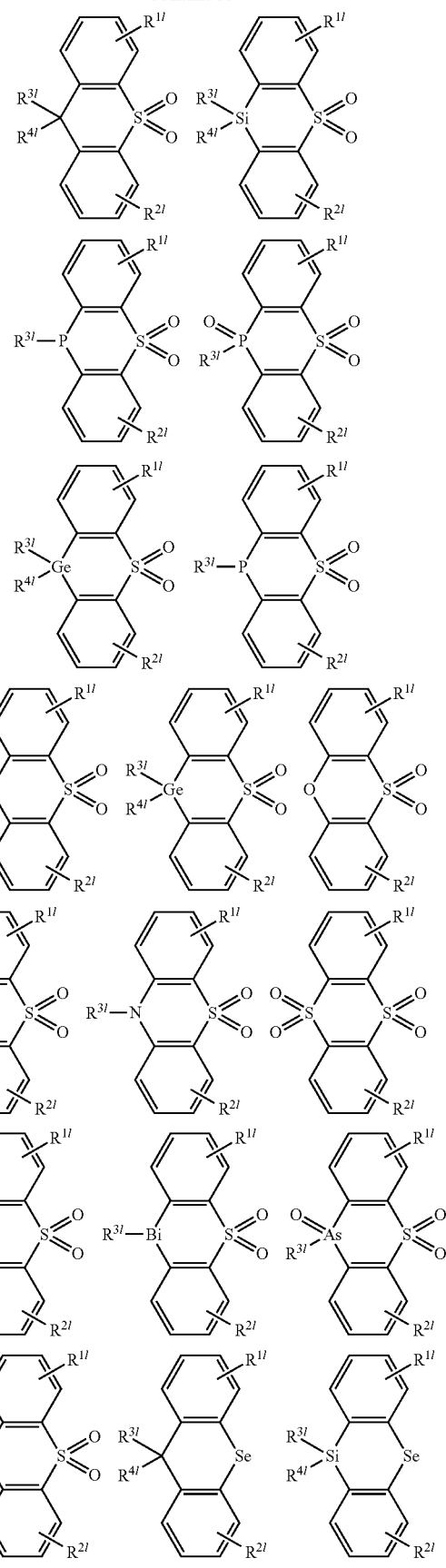

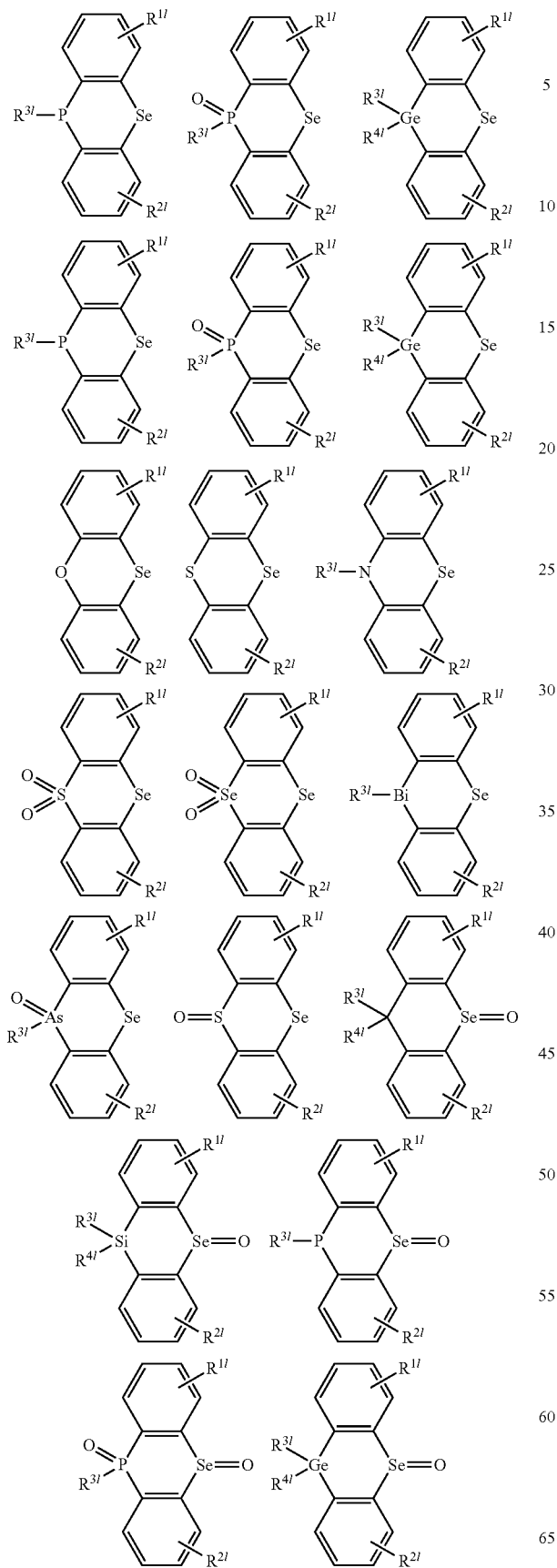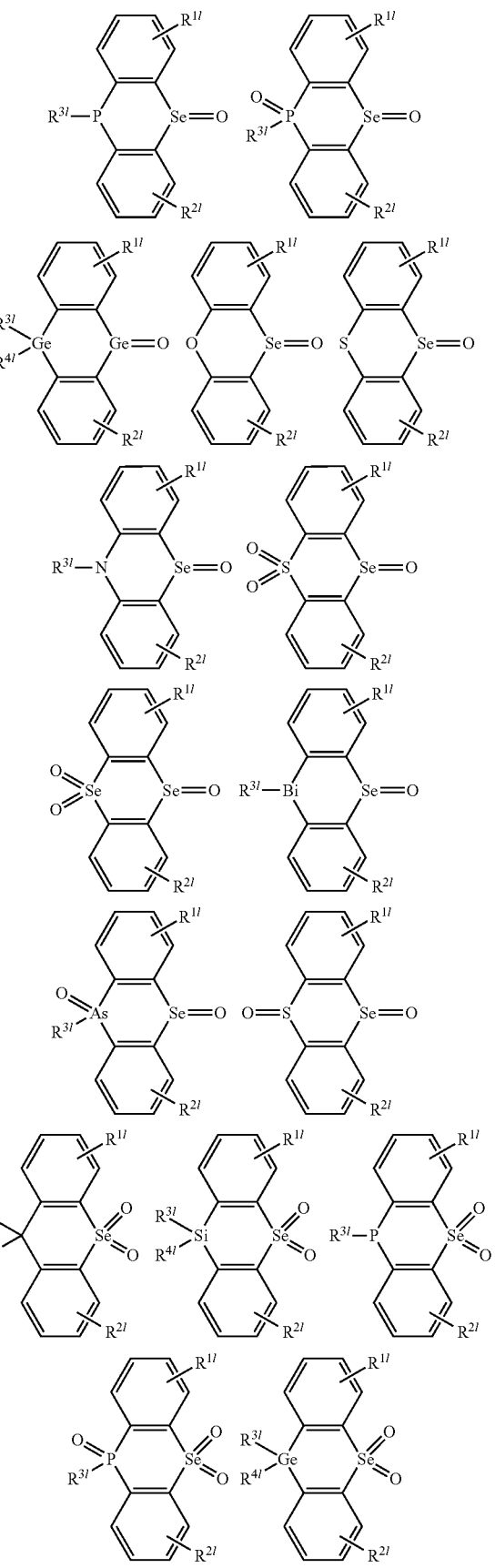

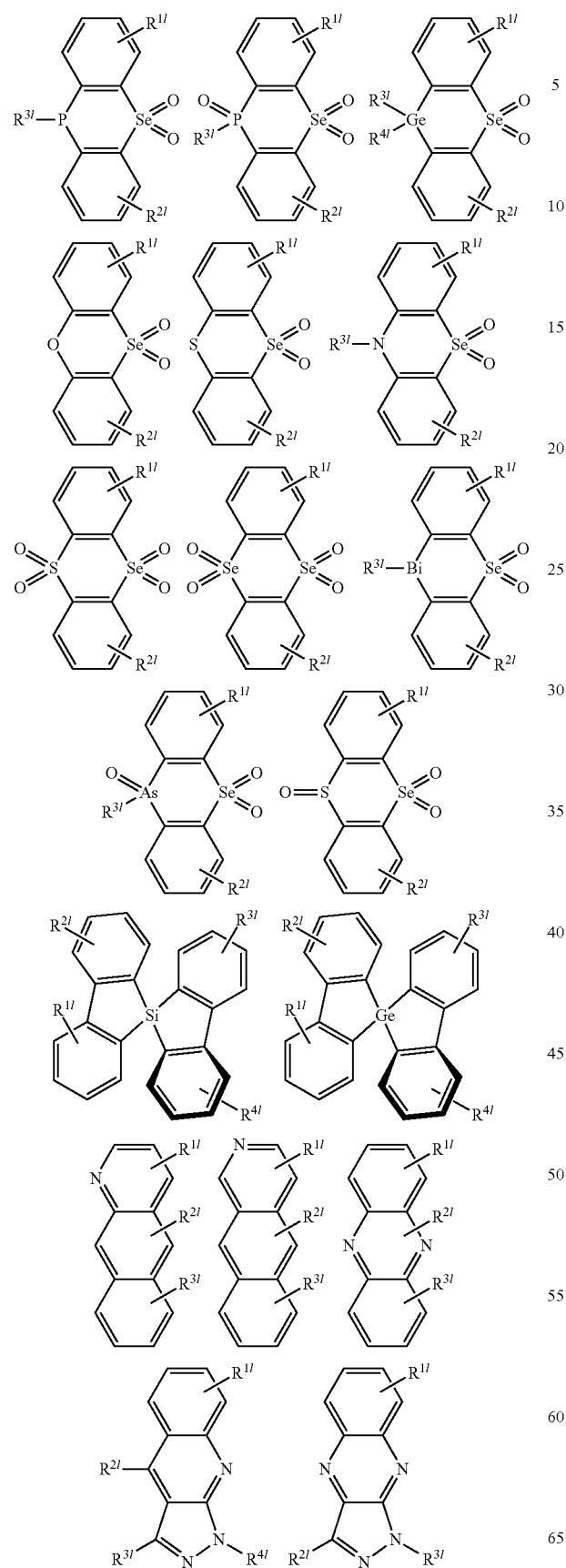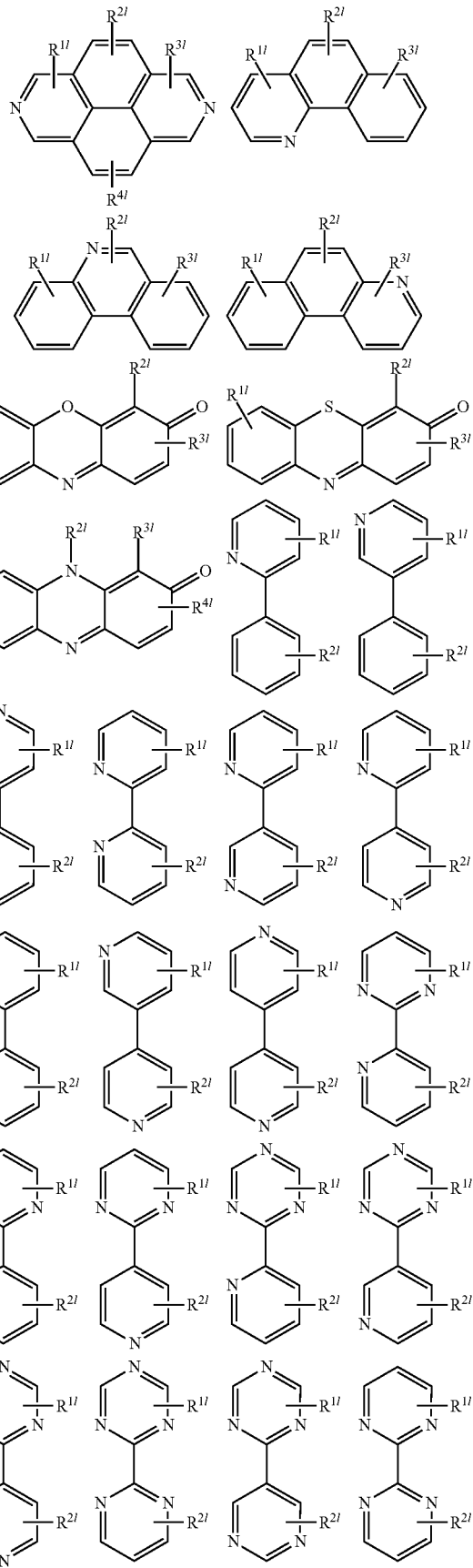

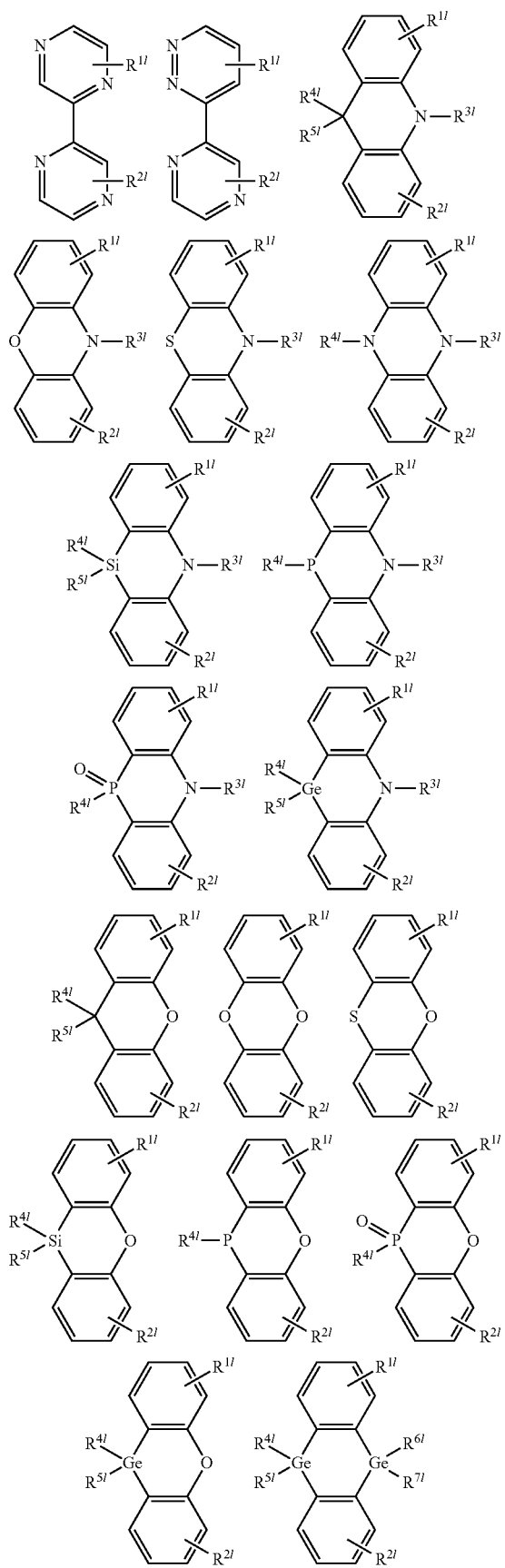
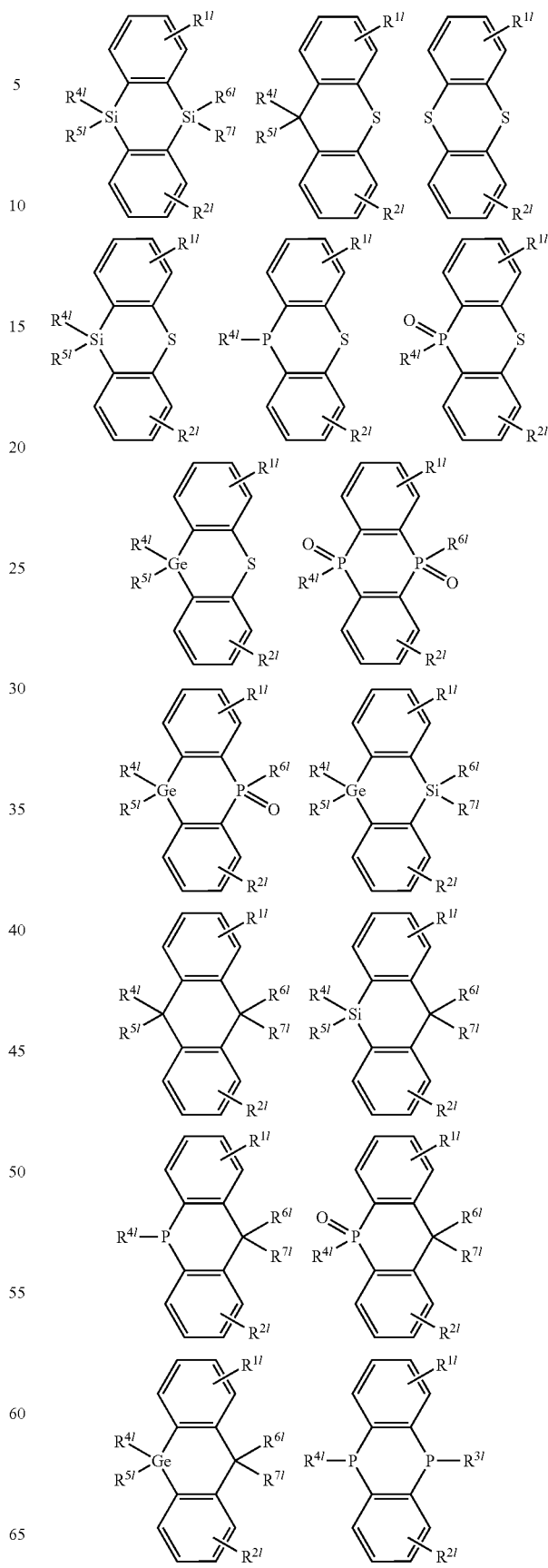

-continued
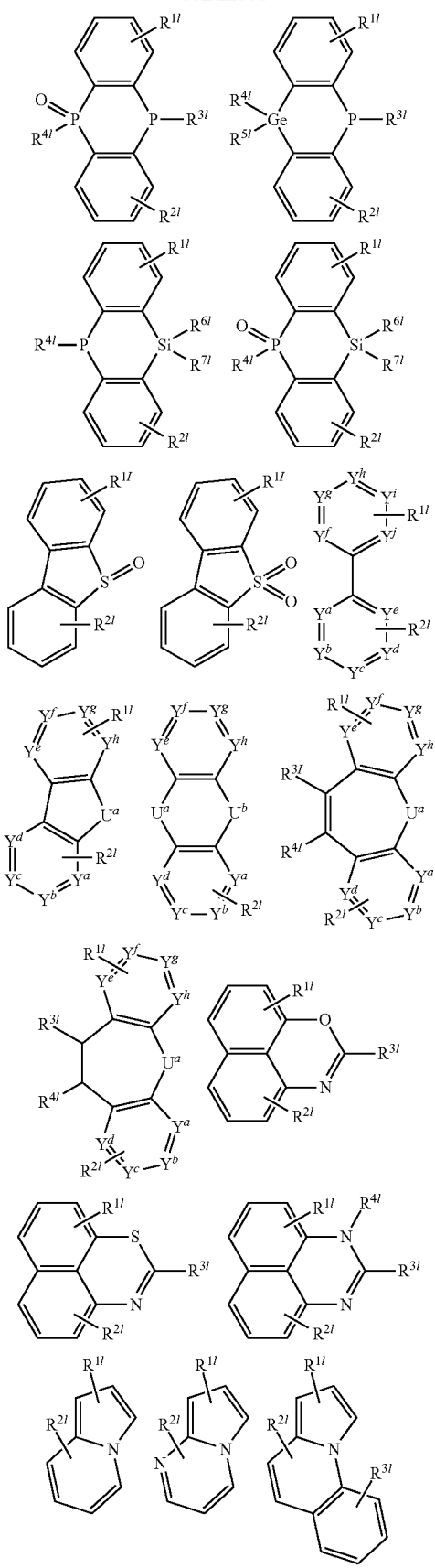
-continued
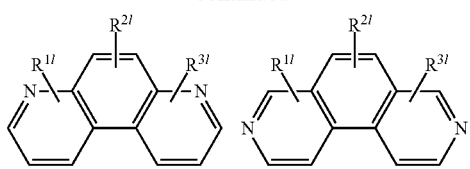
4. Other Fluorescent Luminophors
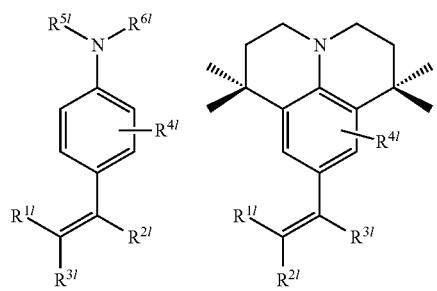
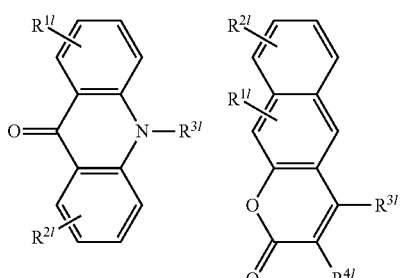
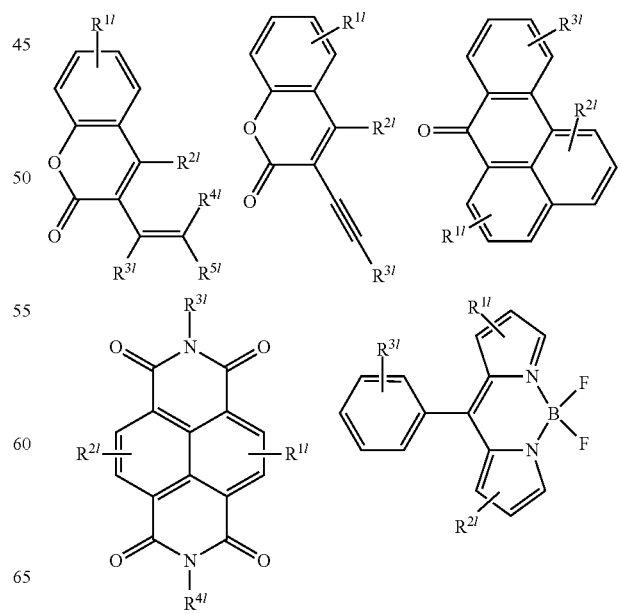

73
-continued
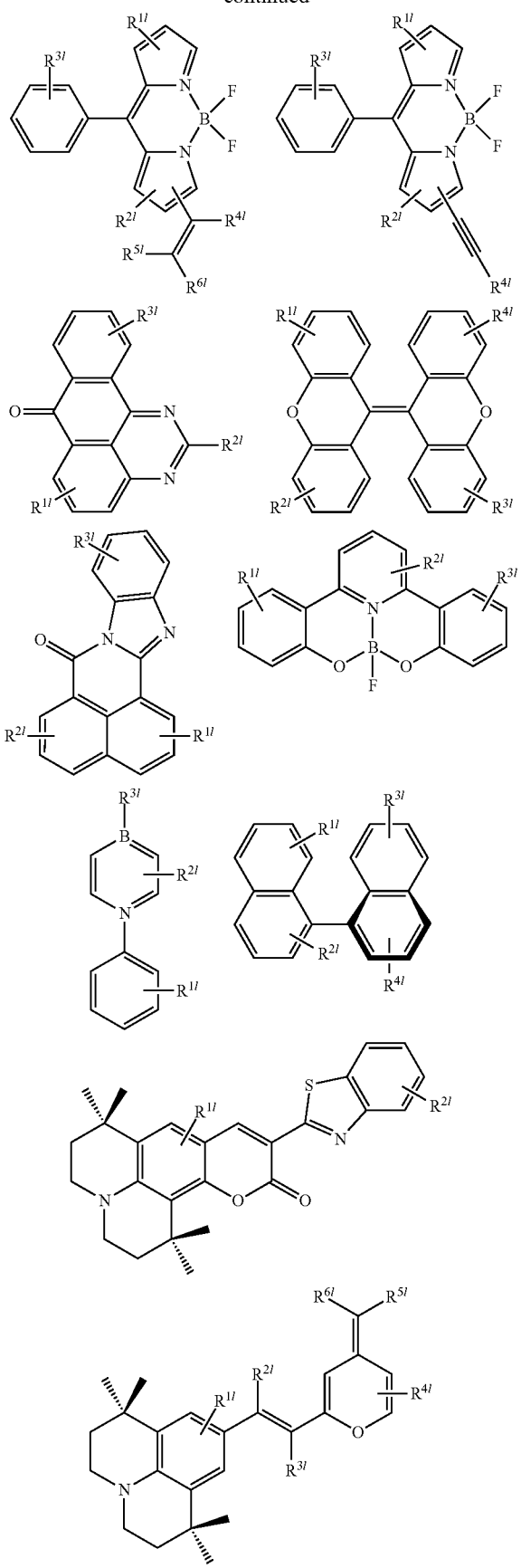
74
-continued
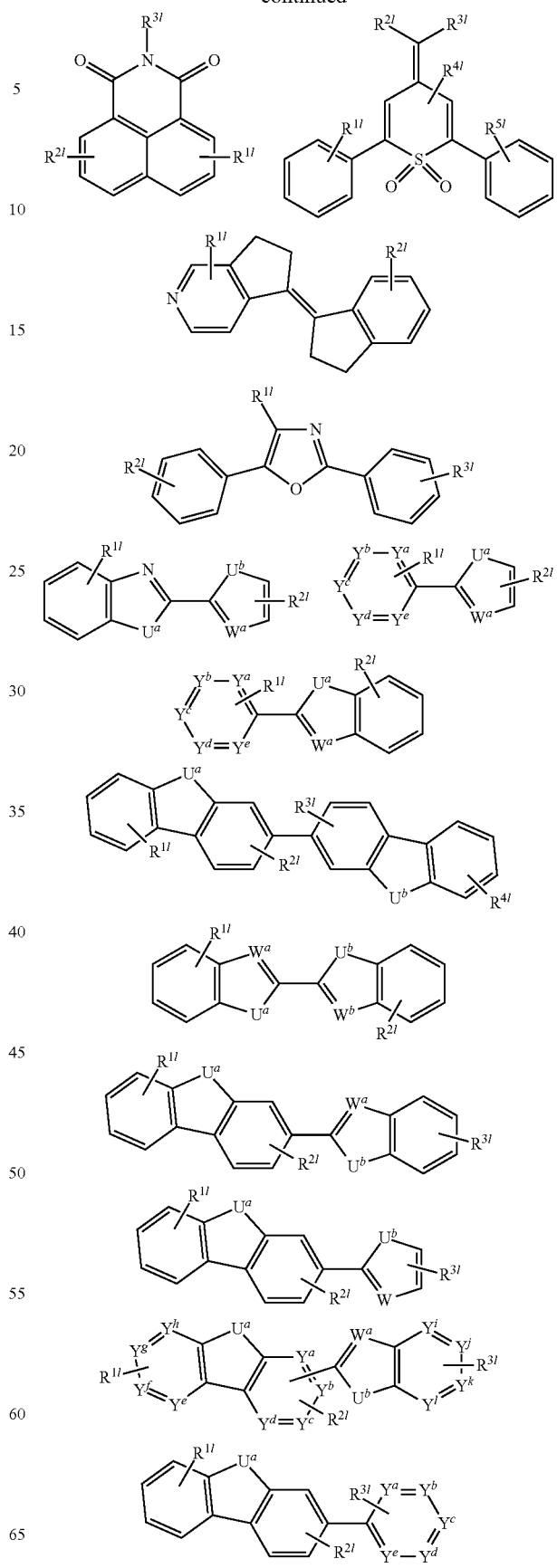

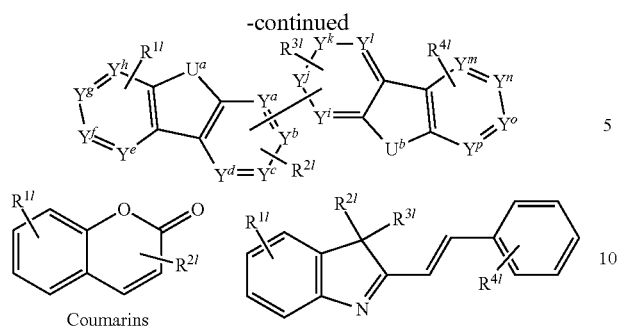

Coumarins wherein each of $R^{1l}$, $R^{2l}$, $R^{3l}$, $R^{4l}$, $R^{5l}$, $R^{6l}$, $R^{7l}$ and $R^{8l}$ is independently a mono-, di-, or tri-substitution, and if present each of $R^{1l}$, $R^{2l}$, $R^{3l}$, $R^{4l}$, $R^{5l}$, $R^{6l}$, $R^{7l}$ and $R^{8l}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, substituted or unsubstituted alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, wherein each of $Y^a$, $Y^b$, $Y^c$, $Y^d$, $Y^e$, $Y^f$, $Y^g$, $Y^h$, $Y^i$, $Y^j$, $Y^k$, $Y^l$, $Y^m$, $Y^n$, $Y^o$, and $Y^p$ is independently C, N, or B, wherein each of $U^a$, $U^b$, and $U^c$ is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, and wherein each of W, $W^a$, $W^b$, and $W^c$ is independently CH, $CR^1$, $SiR^1$, GeH, $GeR^1$, N, P, B, Bi, or Bi=O.

In one aspect, $F^1$ is covalently bonded to $L^1$ directly. In one aspect $F^2$ is covalently bonded to $L^2$ directly. In one aspect, $F^3$ is covalently bonded to $L^3$ directly. In one aspect, $F^4$ is covalently bonded to $L^4$ directly.

In another aspect, fluorescent luminophore $F^1$ is covalently bonded to $L^1$ by a linking atom or linking group. In another aspect, $F^2$ is covalently bonded to $L^2$ by a linking atom or linking group. In another aspect, $F^3$ is covalently bonded to $L^3$ by a linking atom or linking group. In another aspect, $F^4$ is covalently bonded to $L^4$ by a linking atom or linking group.

F. Linking Atoms or Linking Groups

In some cases, each linking atom or linking group in the structures disclosed herein is independently one of the atoms or groups depicted below:

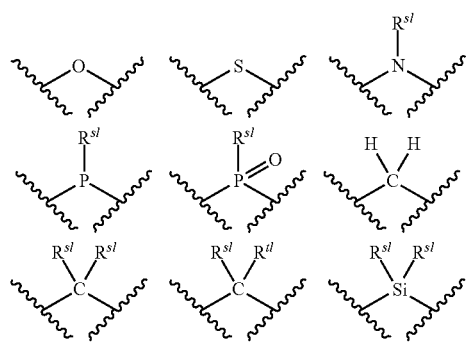

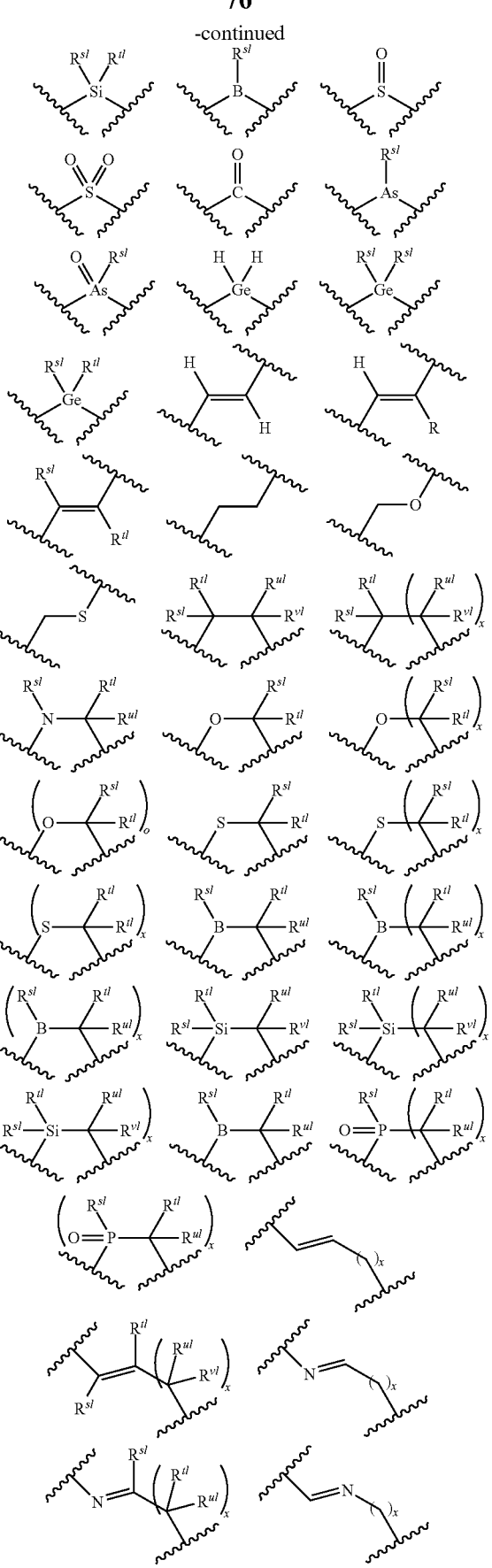

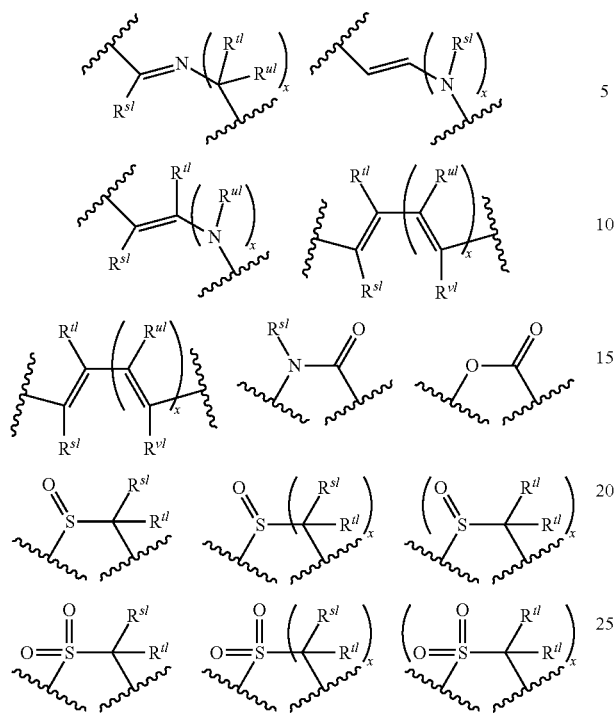

wherein x is an integer from 1 to 10, wherein each of $R^{sl}$, $R^{tl}$, $R^{ul}$, and $R^{vl}$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, or polymeric, or any conjugate or combination thereof. In other cases, a linking atom or linking group in the structures disclosed herein includes other structures or portions thereof not specifically recited herein, and the present disclosure is not intended to be limited to those structures or portions thereof specifically recited.

In one aspect, x is an integer from 1 to 3. In another aspect, x is 1. In yet another aspect, x is 2. In yet another aspect, x is 3. In yet another aspect, x is 4. In yet another aspect, x is 5. In yet another aspect, x is 6. In yet another aspect, x is 7. In yet another aspect, x is 8. In yet another aspect, x is 9. In yet another aspect, x is 10.

In one aspect, the linking atom and linking group recited above can be covalently bonded to any atom of the fluorescent luminophore $F^1$, $F^2$, $F^3$, and $F^4$ if valency permits. For example, if $F^1$ is

$F^1$–| can be

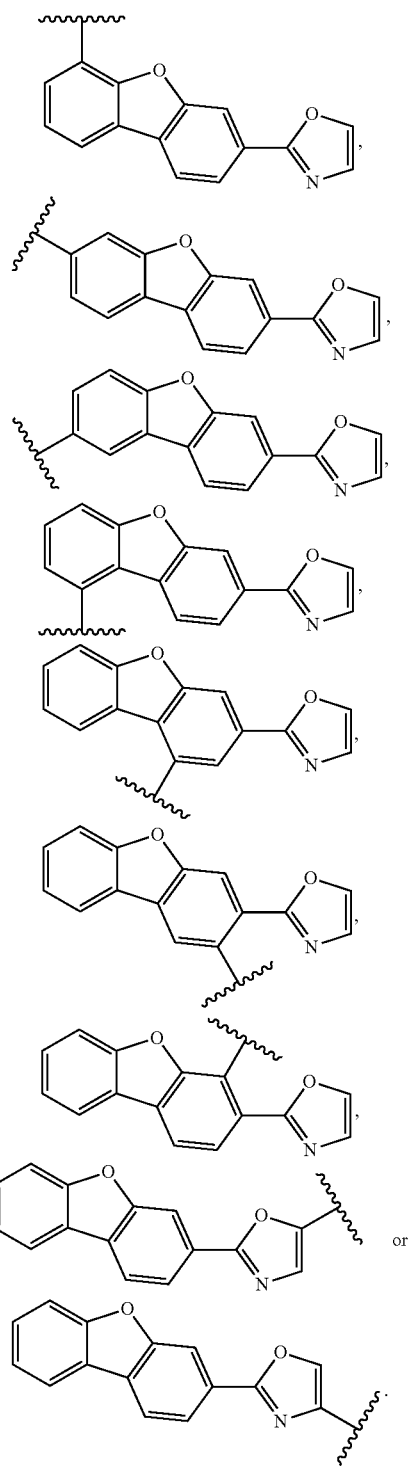

or

In one aspect, one or more of $F^1$, $F^2$, $F^3$, and $F^4$ is independently selected from Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DiA, DiD, DiI, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3.

In one aspect, a linking atom and linking group recited above is covalently bonded to any atom of a fluorescent luminophore $F^1$, $F^2$, $F^3$, and $F^4$ if present and if valency permits. In one example, if $F^1$ is

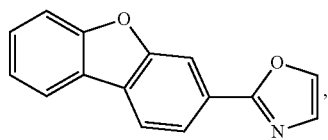 [SMILES: c1ccc2c(c1)oc1cc(-c3ncco3)ccc12]

$F^1-|$ can be

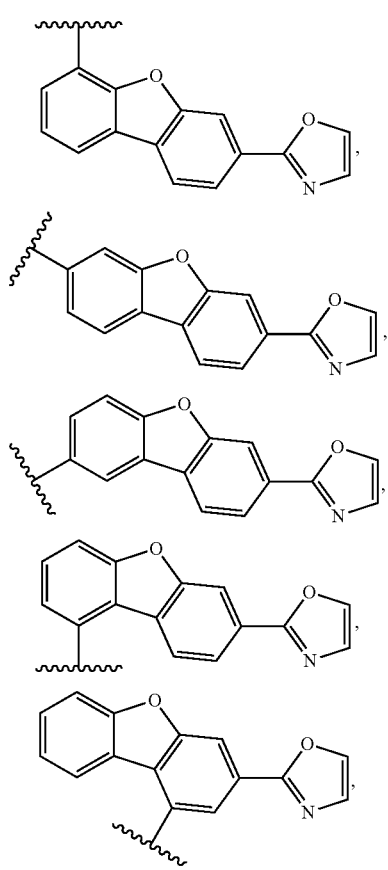

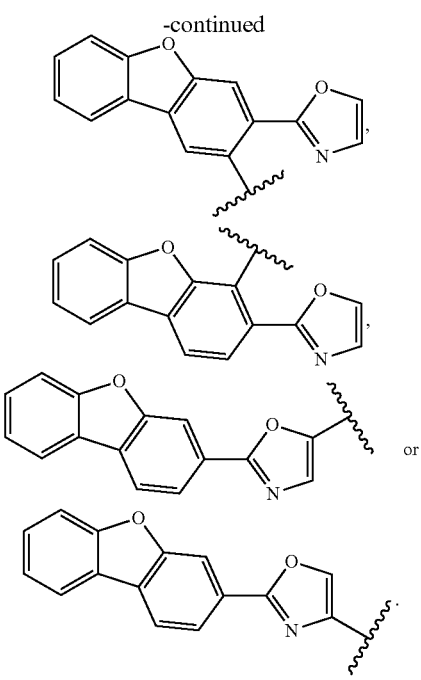

or

G. R Groups

In one aspect, at least one $R^a$ is present. In another aspect, $R^a$ is absent.

In one aspect, $R^a$ is a mono-substitution. In another aspect, $R^a$ is a di-substitution. In yet another aspect, $R^a$ is a tri-substitution.

In one aspect, $R^a$ is connected to at least $Y^1$. In another aspect, $R^a$ is connected to at least $Y^2$. In yet another aspect, $R^a$ is connected to at least $Y^3$. In one aspect, $R^a$s are independently connected to at least $Y^1$ and $Y^2$. In one aspect, $R^a$s are independently connected to at least $Y^1$ and $Y^3$. In one aspect, $R^a$s are independently connected to at least $Y^2$ and $Y^3$. In one aspect, $R^a$s are independently connected to $Y^1$, $Y^2$, and $Y^3$.

In one aspect, $R^a$ is a di-substitution and the $R^a$'s are linked together. When the $R^a$'s are linked together the resulting structure can be a cyclic structure that includes a portion of the five-membered cyclic structure as described herein. For example, a cyclic structure can be formed when the di-substitution is of $Y^1$ and $Y^2$ and the $R^a$'s are linked together. A cyclic structure can also be formed when the di-substitution is of $Y^2$ and $Y^3$ and the $R^a$'s are linked together. A cyclic structure can also be formed when the di-substitution is of $Y^3$ and $Y^4$ and the $R^a$'s are linked together.

In one aspect, each $R^a$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^a$ are optionally linked together. In one aspect, at least one $R^a$ is halogen, hydroxyl, substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^a$ are optionally linked together.

In one aspect, at least one $R^b$ is present. In another aspect, $R^b$ is absent.

In one aspect, $R^b$ is a mono-substitution. In another aspect, $R^b$ is a di-substitution. In yet another aspect, $R^b$ is a tri-substitution.

In one aspect, each $R^b$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^b$ are optionally linked together. In one aspect, at least one $R^b$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^b$ are optionally linked together.

In one aspect, at least one $R^c$ is present. In another aspect, $R^c$ is absent.

In one aspect, $R^c$ is a mono-substitution. In another aspect, $R^c$ is a di-substitution. In yet another aspect, $R^c$ is a tri-substitution.

In one aspect, each $R^c$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and wherein two or more of $R^c$ are optionally linked together. In one aspect, at least one $R^c$ is halogen, hydroxyl; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl; or any conjugate or combination thereof, and wherein two or more of $R^c$ are optionally linked together.

In one aspect, at least one $R^d$ is present. In another aspect, $R^d$ is absent.

In one aspect, $R^d$ is a mono-substitution. In another aspect, $R^d$ is a di-substitution. In yet another aspect, $R^d$ is a tri-substitution.

In one aspect, each $R^d$, if present, is independently deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, substituted silyl, polymeric, or any conjugate or combination thereof, and wherein two or more of $R^d$ are optionally linked together.

In one aspect, $R^1$ and $R^2$ are linked to form the cyclic structure:

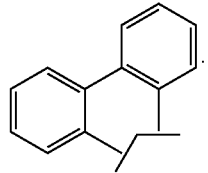

In one aspect, each of R, $R^1$, $R^2$, $R^3$, $R^4$, $R^5$, $R^6$, $R^7$, and $R^8$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

In another aspect, each of R, $R^1$, $R^2$, $R^3$, $R^4$, $R^5$, $R^6$, $R^7$, and $R^8$ is independently hydrogen, halogen, hydroxyl, thiol, nitro, cyano; substituted or unsubstituted: aryl, cycloalkyl, cycloalkenyl, heterocyclyl, heteroaryl, alkyl, alkenyl, alkynyl, or amino. In another aspect, each of R, $R^1$, $R^2$, $R^3$, $R^4$, $R^5$, $R^6$, $R^7$, and $R^8$ is independently hydrogen; or substituted or unsubstituted: aryl, cycloalkyl, cycloalkenyl, heterocyclyl, heteroaryl, alkyl, alkenyl, or alkynyl.

F. X Groups

In one aspect, X is N, P, P=O, As, As=O, $CR^1$, CH, $SiR^1$, SiH, $GeR^1$, GeH, B, Bi, or Bi=O. In one example, X is N or P. In another example, X is P=O, As, As=O, $CR^1$, CH, $SiR^1$, SiH, $GeR^1$, GeH, B, Bi, or Bi=O. In another aspect, X is Z, $Z^1$, or $Z^2$.

In one aspect, $X^1$ is N, P, P=O, As, As=O, $CR^1$, CH, $SiR^1$, SiH, $GeR^1$, GeH, B, Bi, or Bi=O. In one example, $X^1$ is N or P. In another example, $X^1$ is P=O, As, As=O, $CR^1$, CH, $SiR^1$, SiH, $GeR^1$, GeH, B, Bi, Bi=O. In another aspect, $X^1$ is Z, $Z^1$, or $Z^2$.

In one aspect, $X^2$ is N, P, P=O, As, As=O, $CR^1$, CH, $SiR^1$, SiH, $GeR^1$, GeH, B, Bi, or Bi=O. For example, $X^2$ is N or P. In another example, $X^2$ is P=O, As, As=O, $CR^1$, CH, $SiR^1$, SiH, $GeR^1$, GeH, B, Bi, Bi=O. In another aspect, $X^2$ is Z, $Z^1$, or $Z^2$.

G. Y Groups

In one aspect, each of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$ and $Y^{16}$ is independently C, N, O, S, S=O, $SO_2$, Se, Se=O, $SeO_2$, $PR^3$, $R^3P$=O, $AsR^3$, $R^3As$=O, or $BR^3$.

In another aspect, each of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Y^{15}$ and $Y^{16}$ is independently C or N.

H. Exemplary Compounds

Exemplary compounds include Structures 1-102 below. For any of Structures 1-102 below, as applicable:

M is palladium or platinum;

each of U, $U^1$ and $U^2$ is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH or $BiR^3$, each of R, $R^1$, $R^2$, $R^3$, and $R^4$ is independently hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroary, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof, and n is an integer from 1 to 100 (e.g., 1-10).

Structures 1

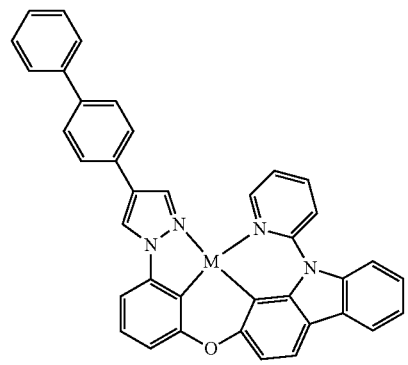

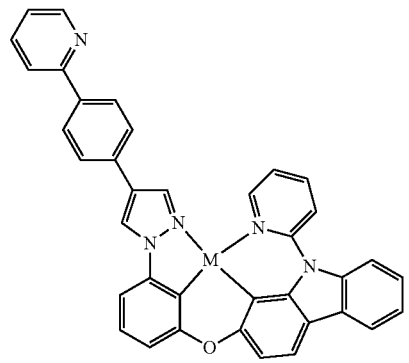

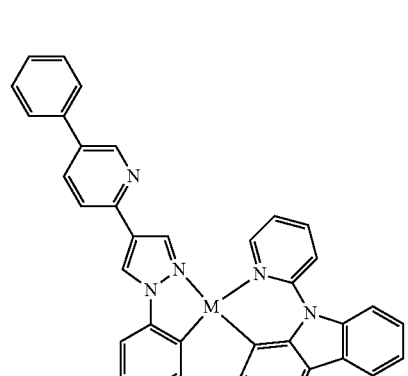

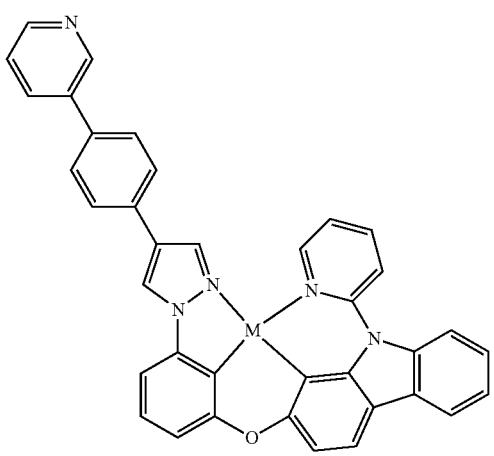

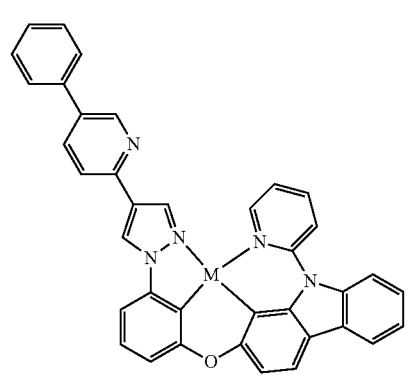

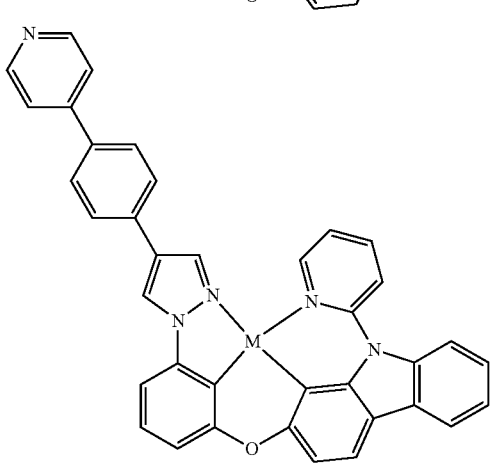

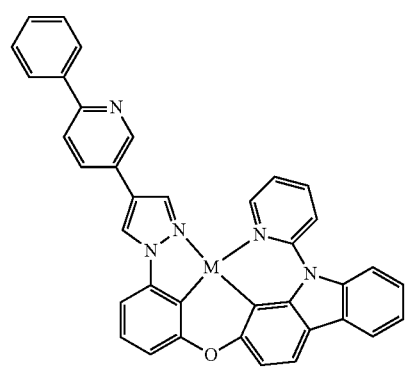

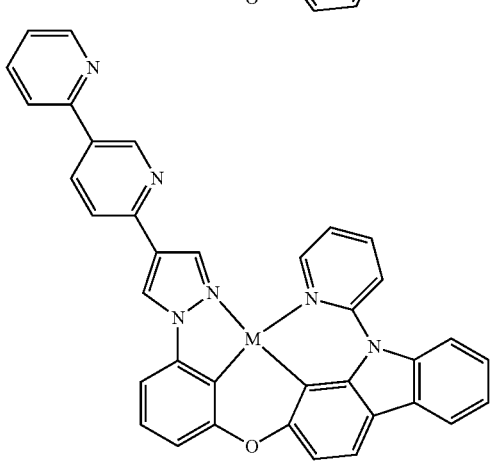

85
-continued
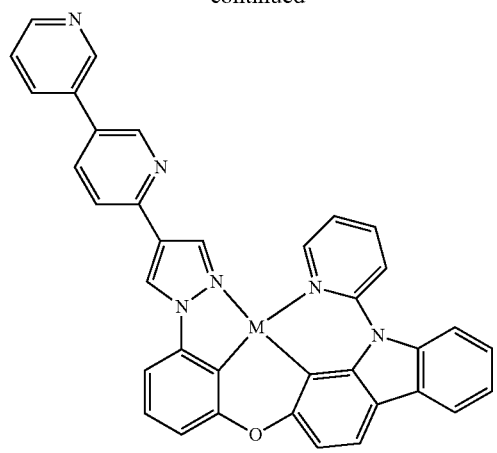
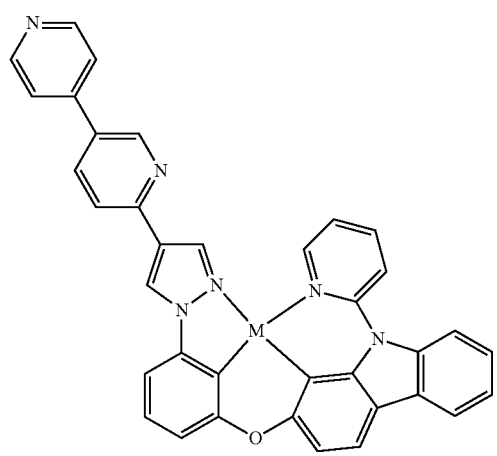
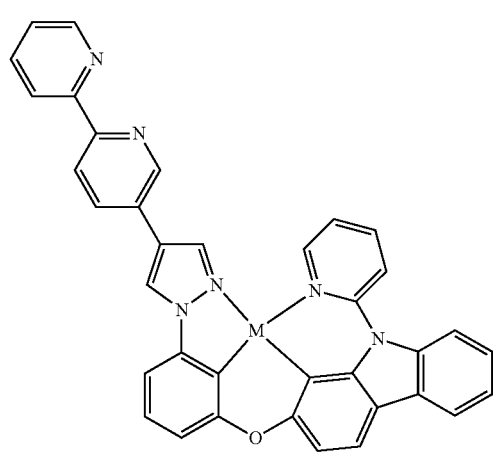
86
-continued
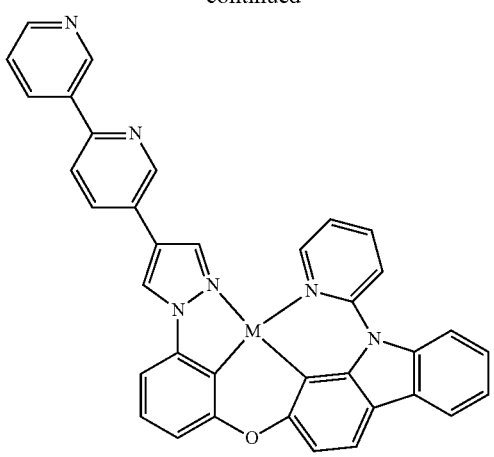
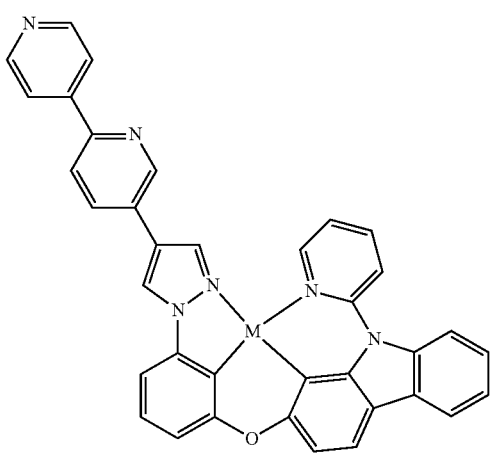
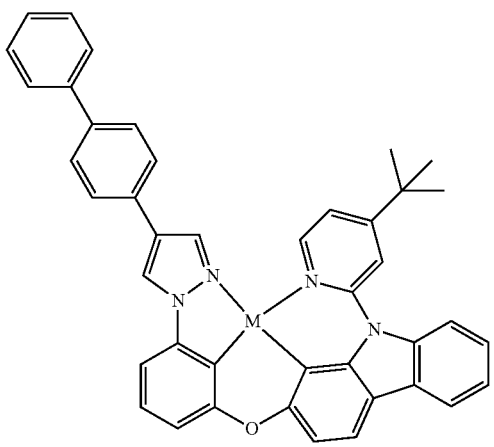

87
-continued
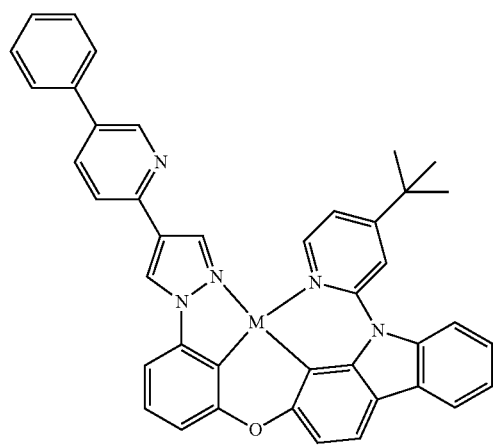
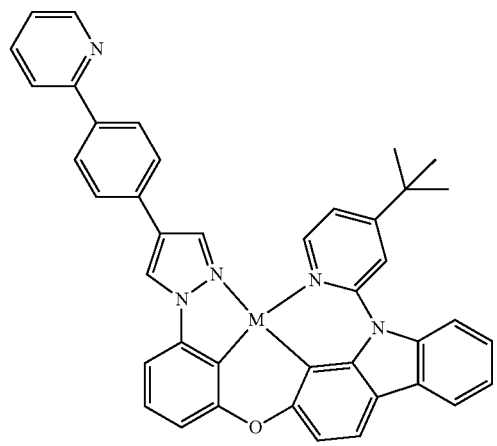
88
-continued
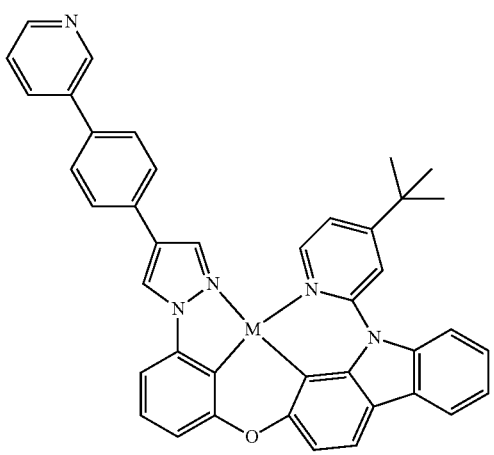
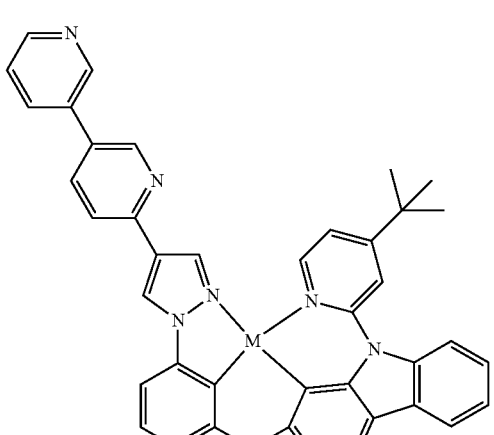

-continued
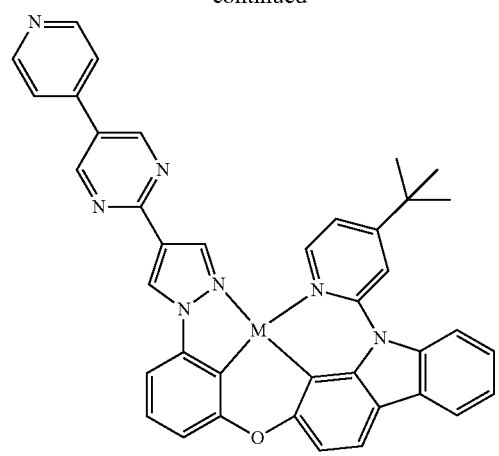
(M = Pt, Pd)
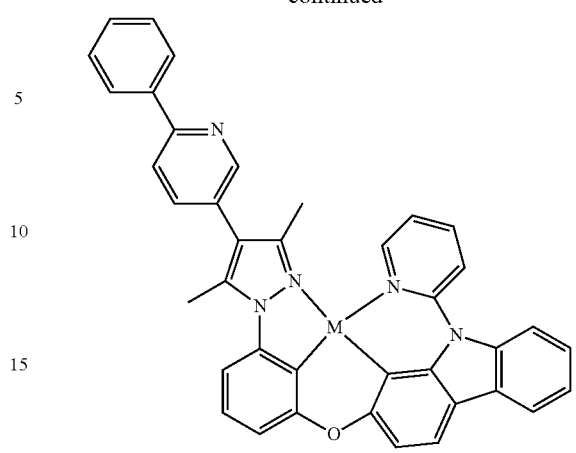
Structures 2
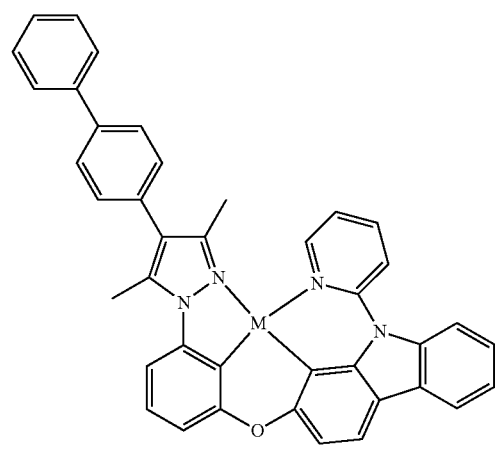
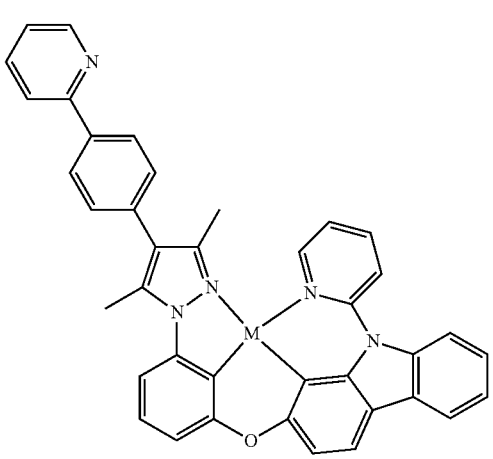
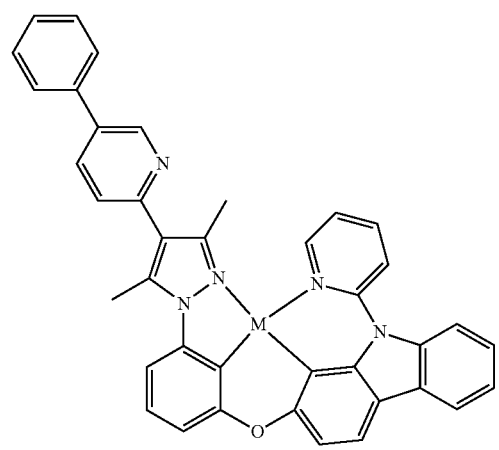
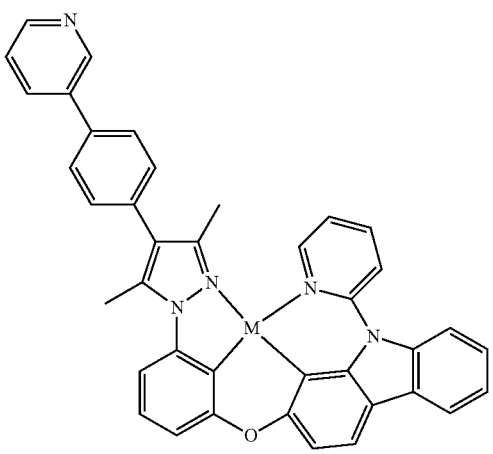

91
-continued
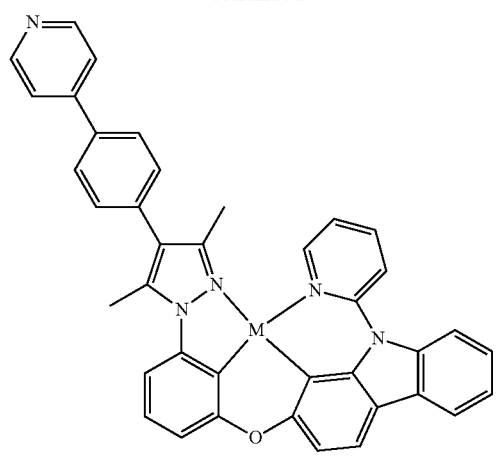
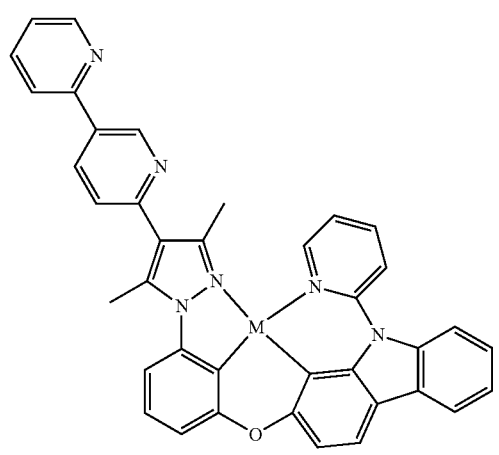
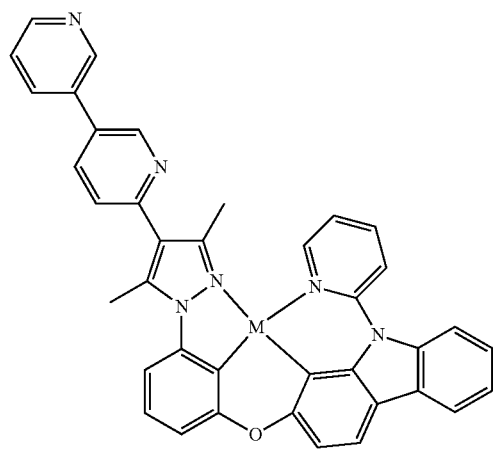
92
-continued
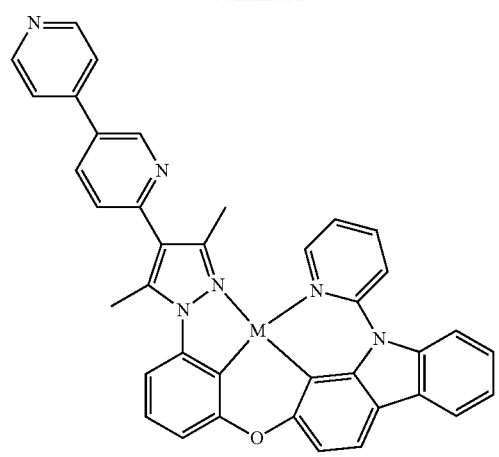
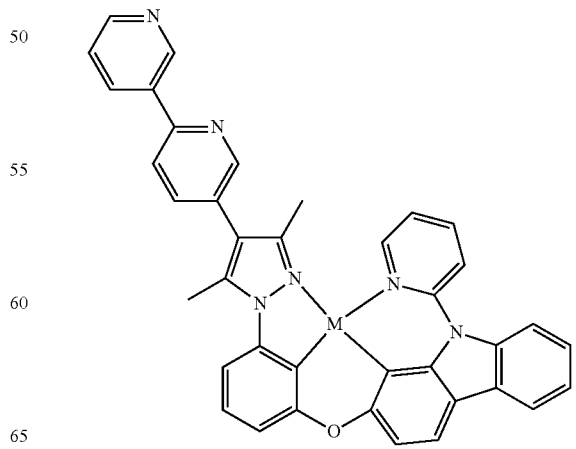

93
-continued
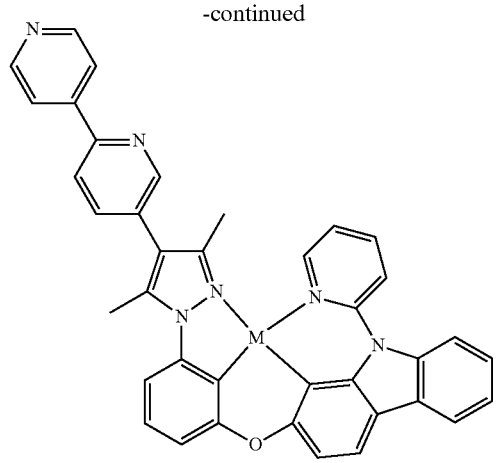
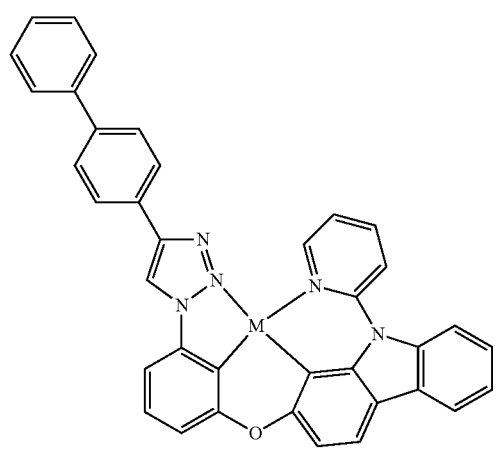
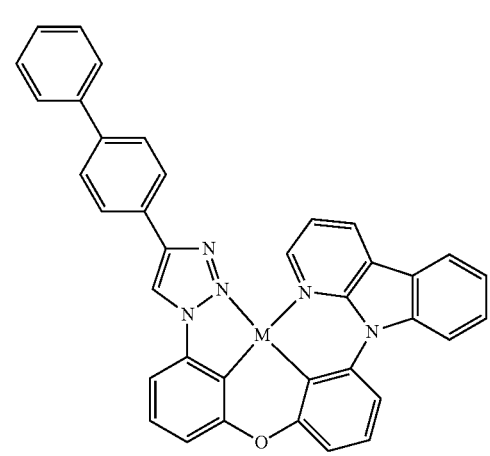
94
-continued
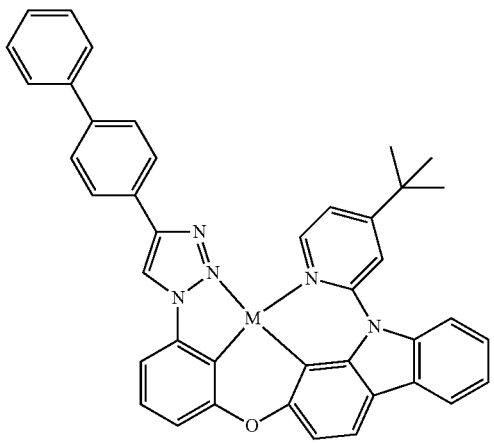
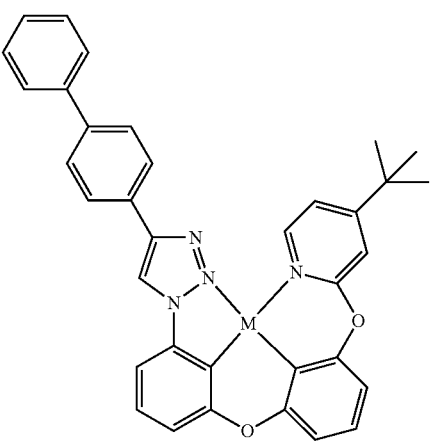
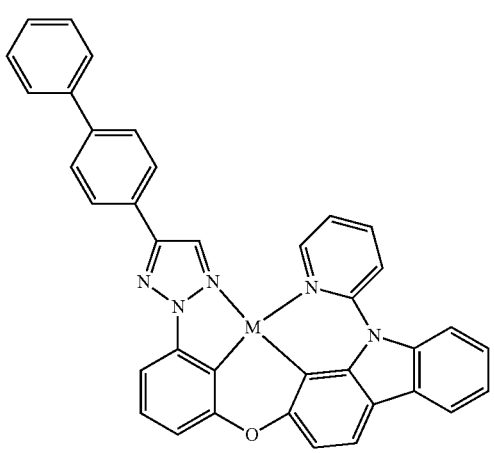

95
-continued
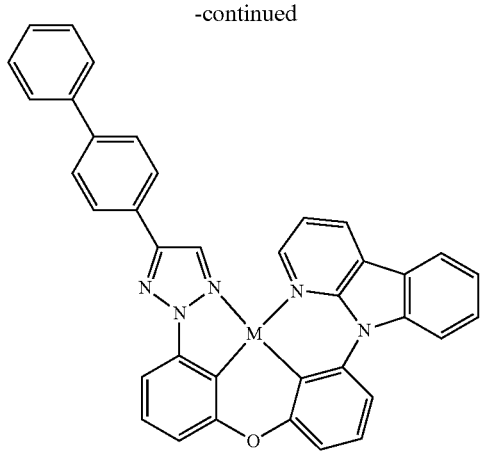
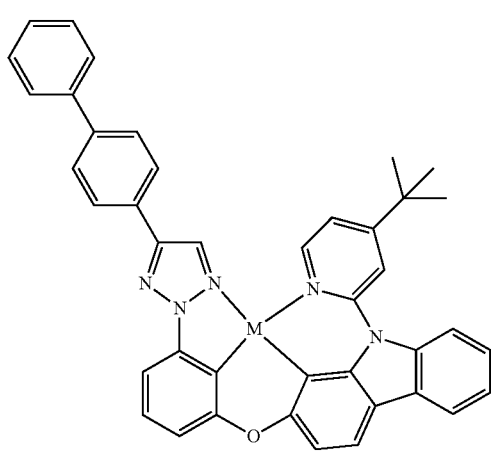
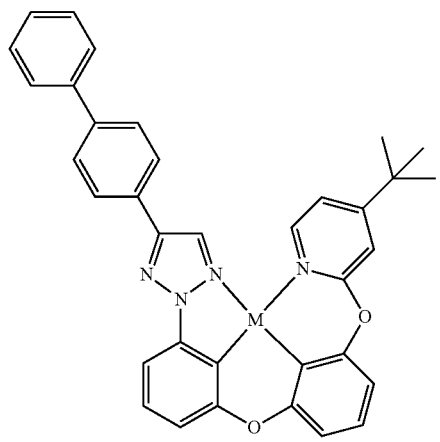
(M = Pt, Pd)
96
-continued
Structures 3
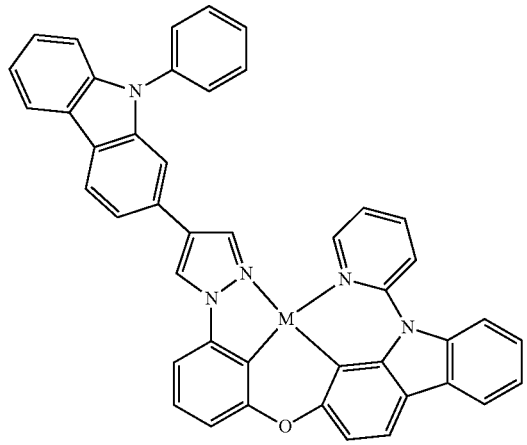
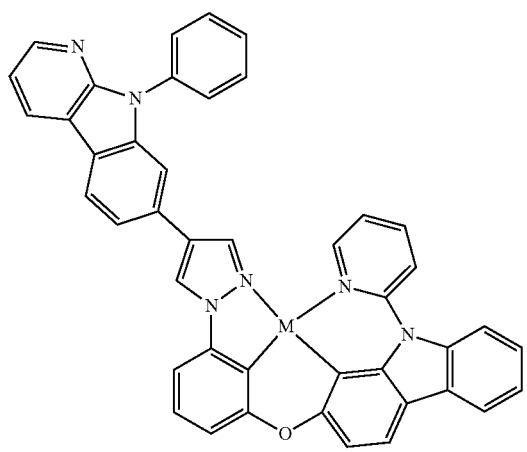
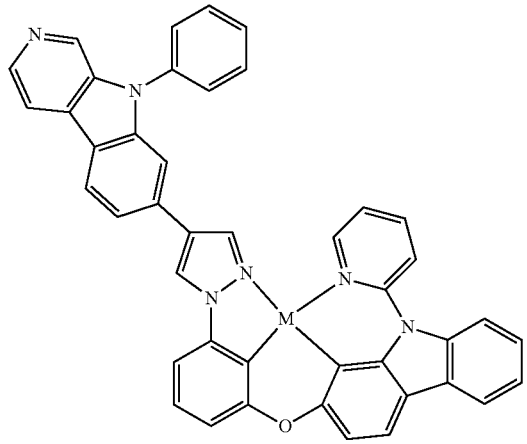

97
-continued
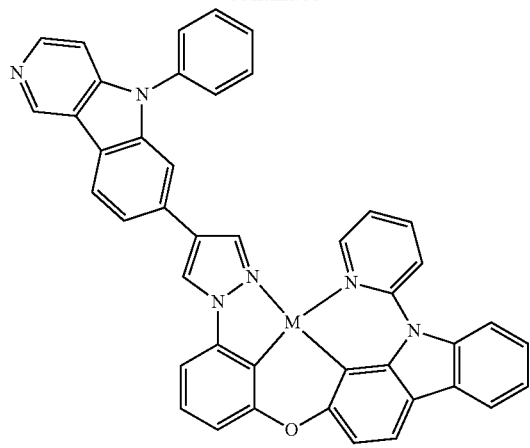
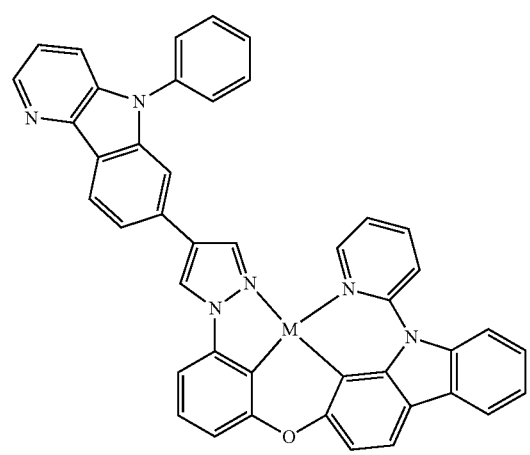
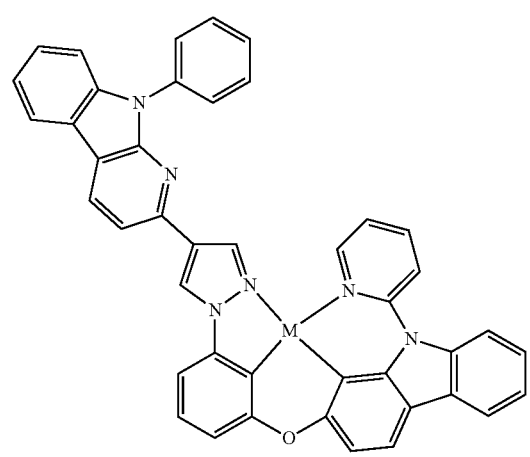
98
-continued
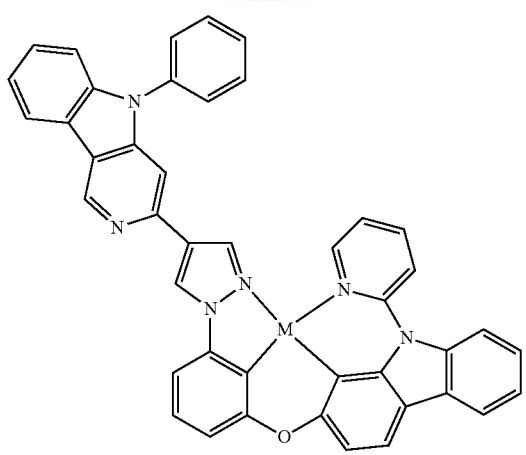
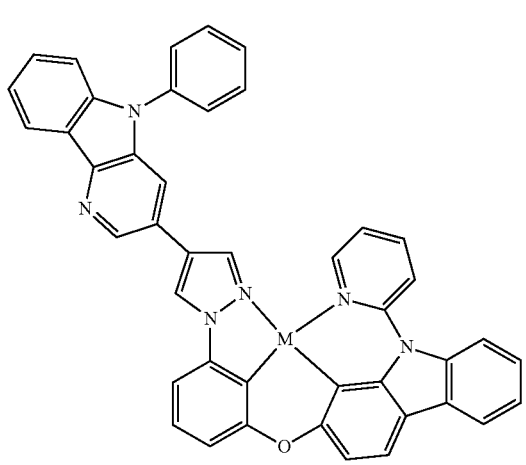
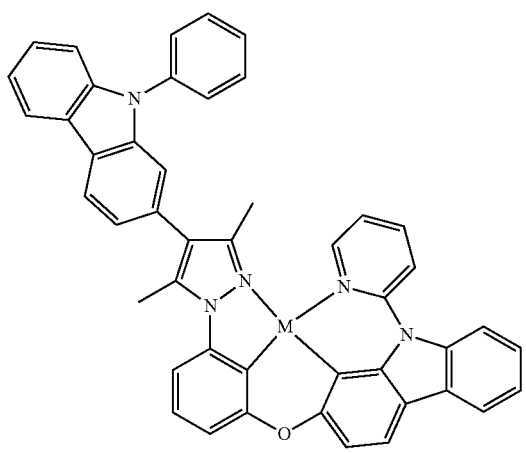

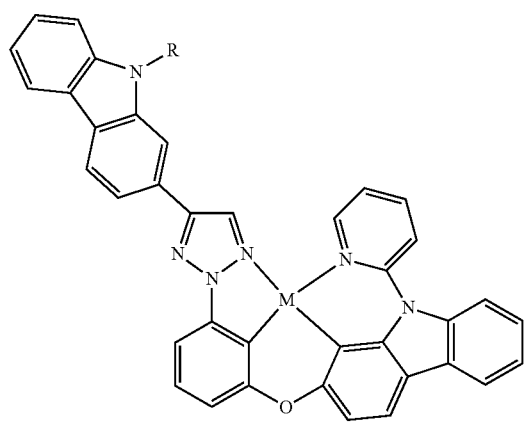
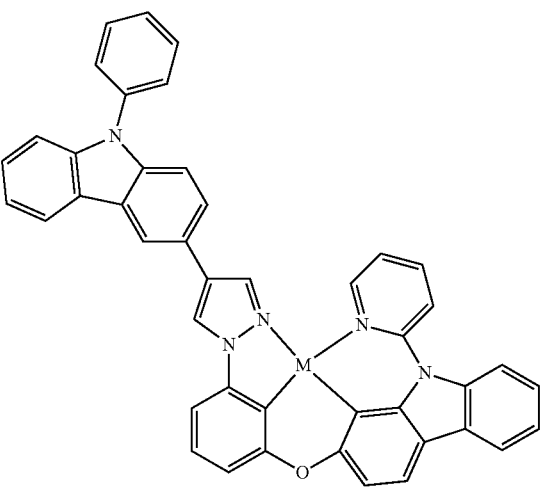
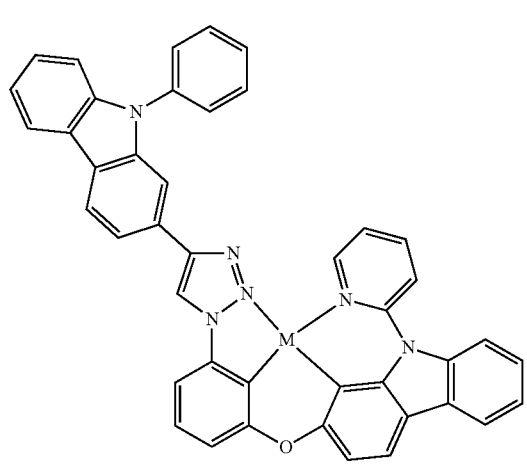
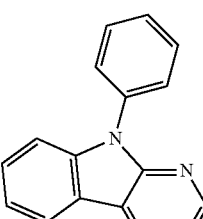
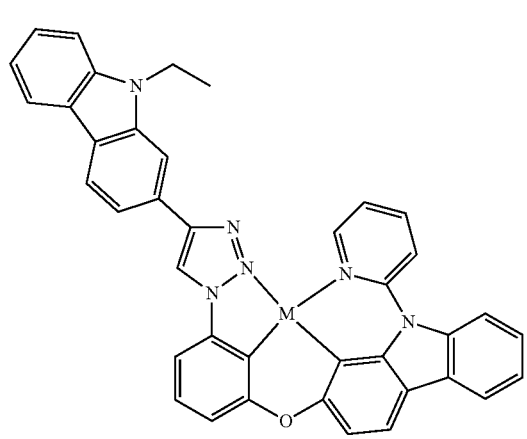
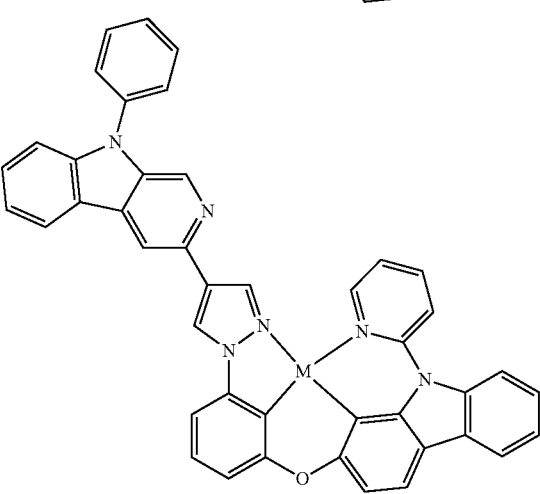

101
-continued
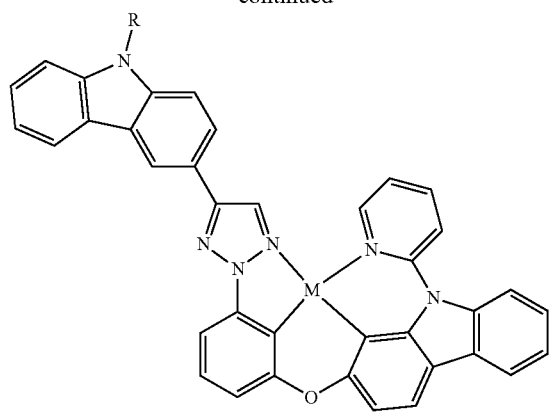
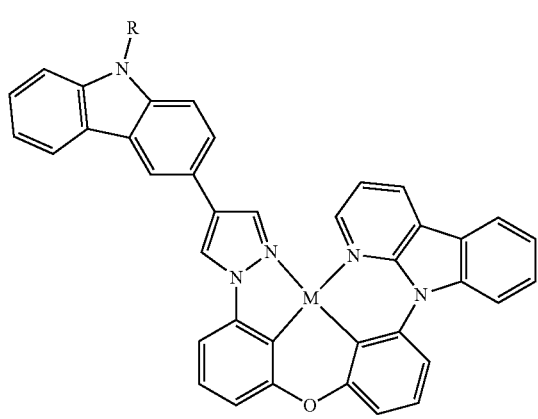
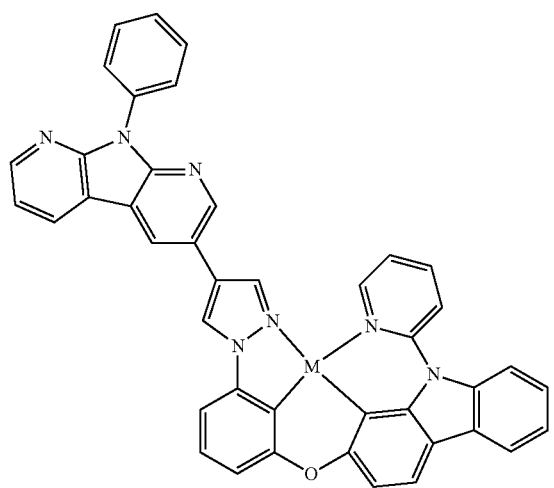
102
-continued
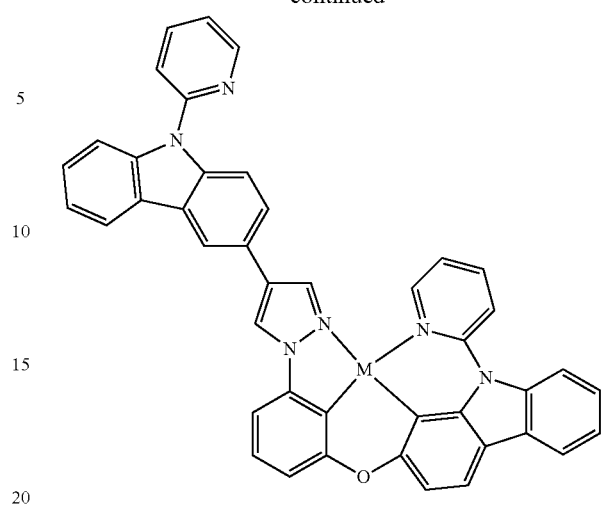
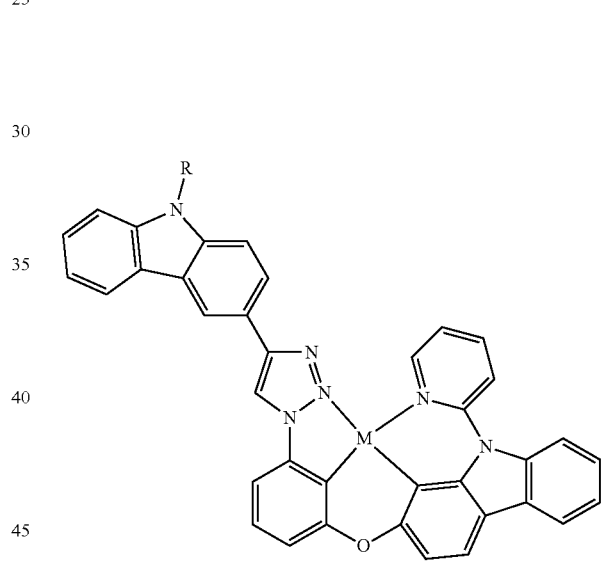
(M = Pt, Pd)
Structures 4
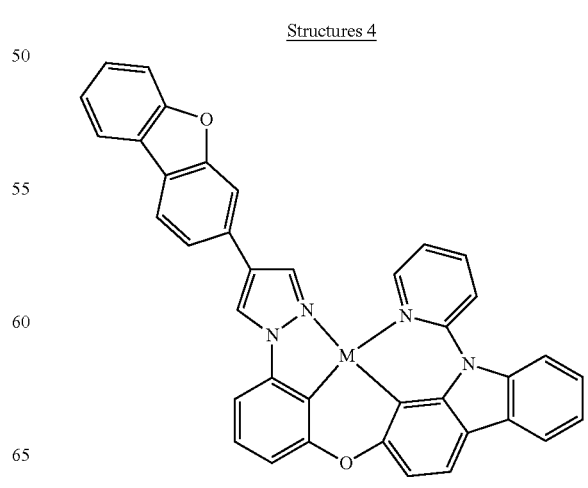

103
-continued
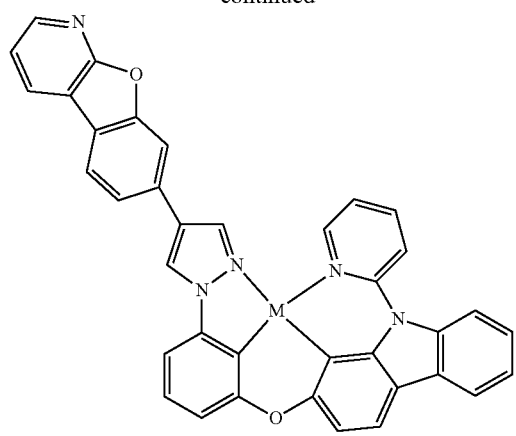
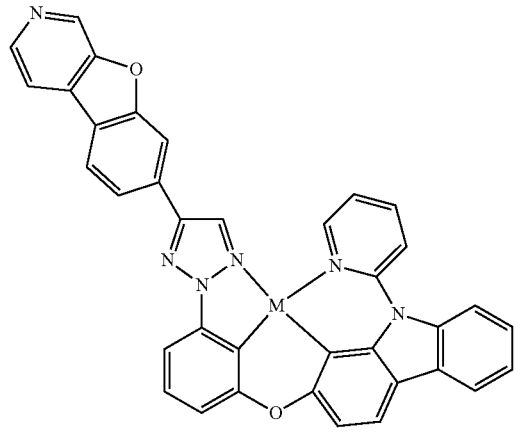
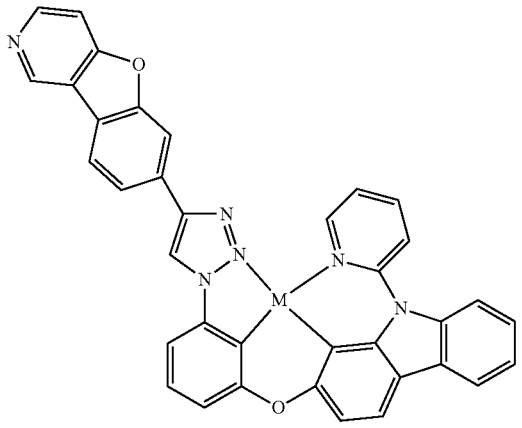
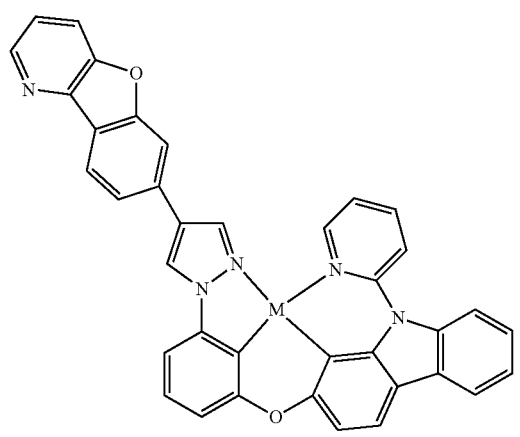
104
-continued
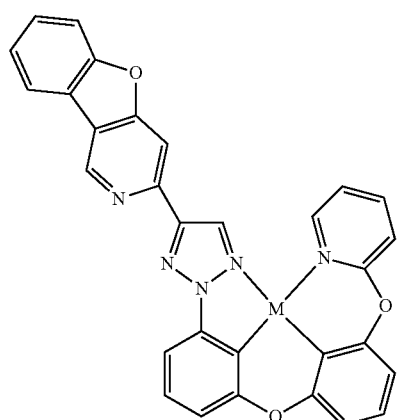
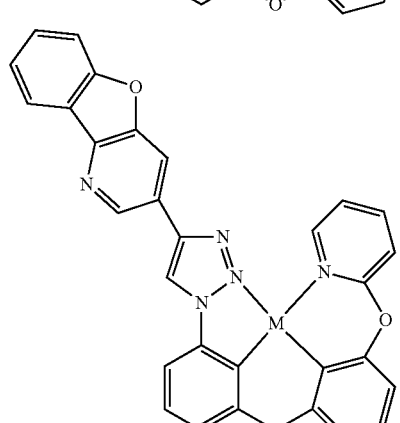
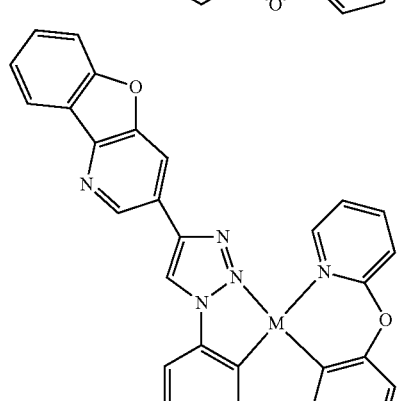
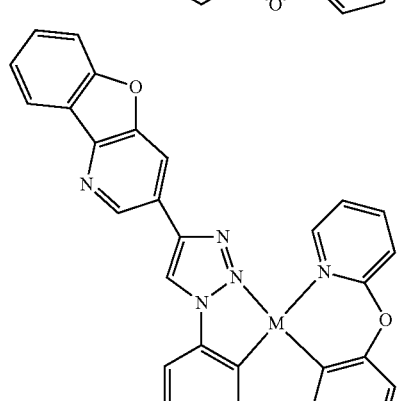

105
-continued
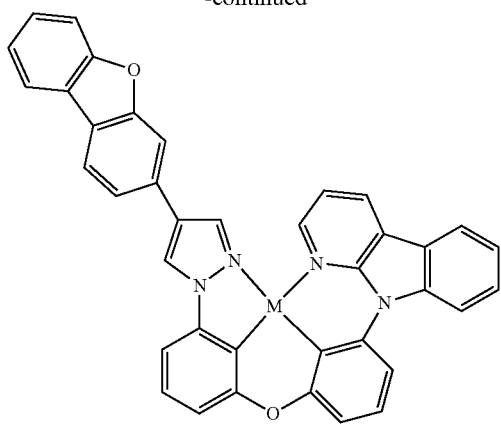
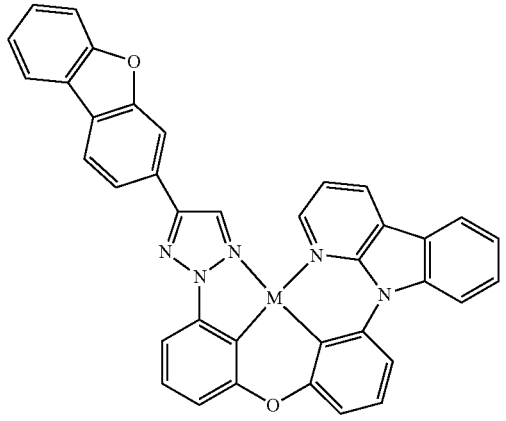
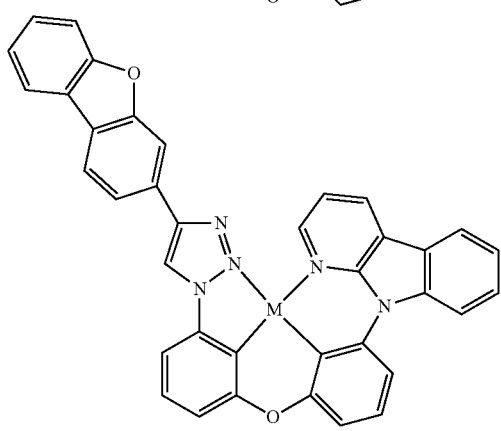
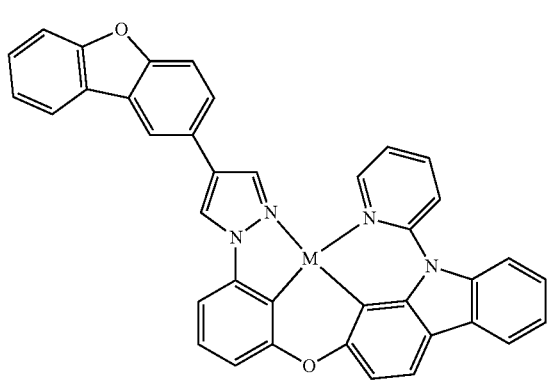
106
-continued
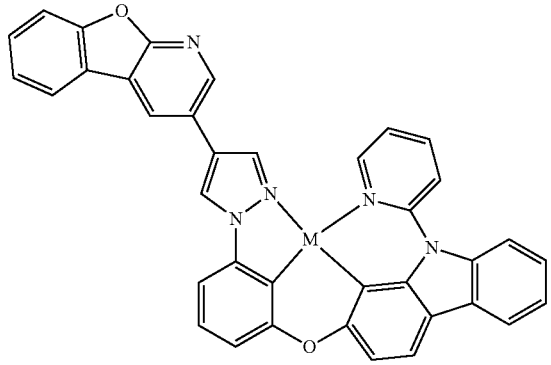
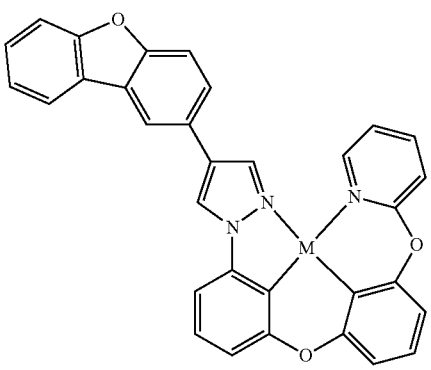
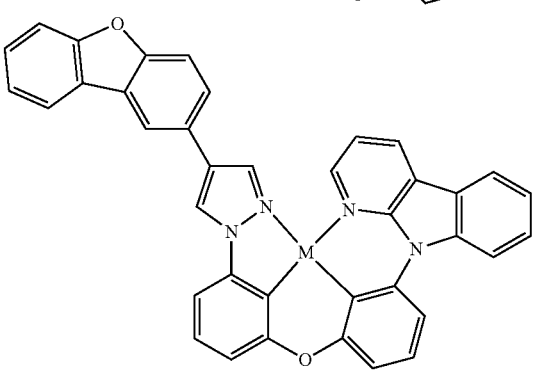
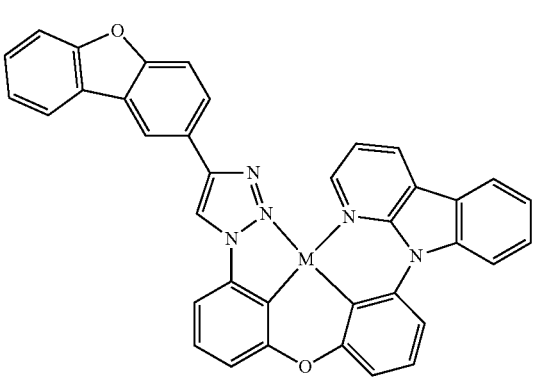

107
-continued
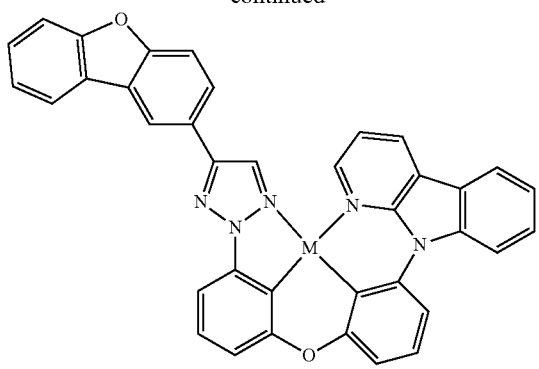
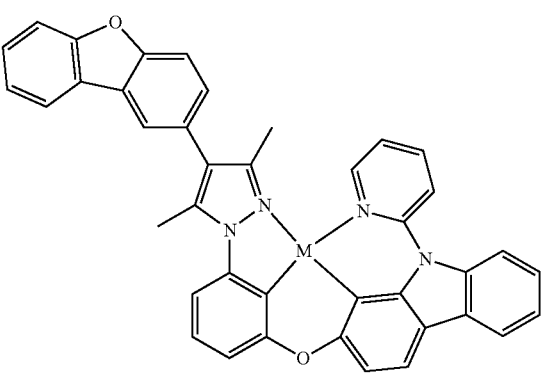
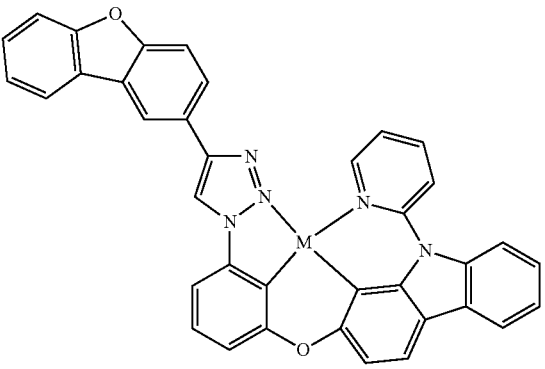
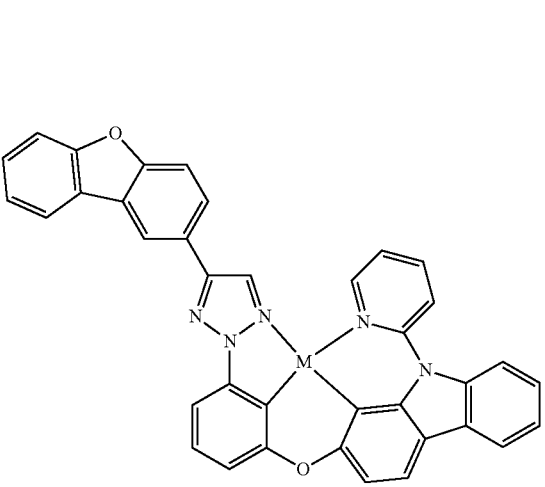
(M = Pt Pd)
108
-continued
Structure 5
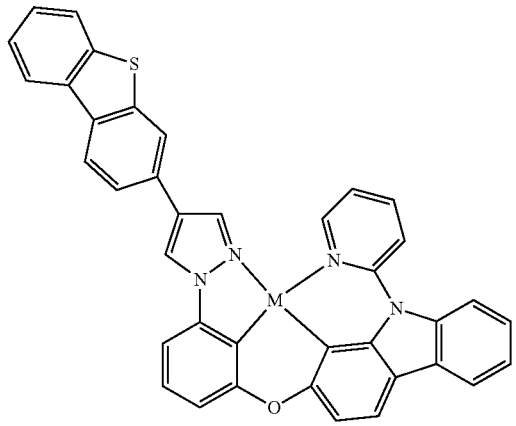
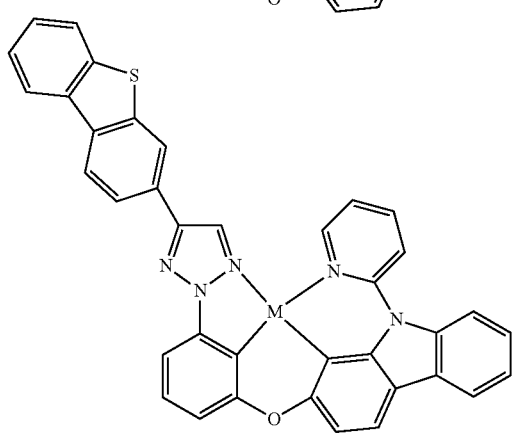
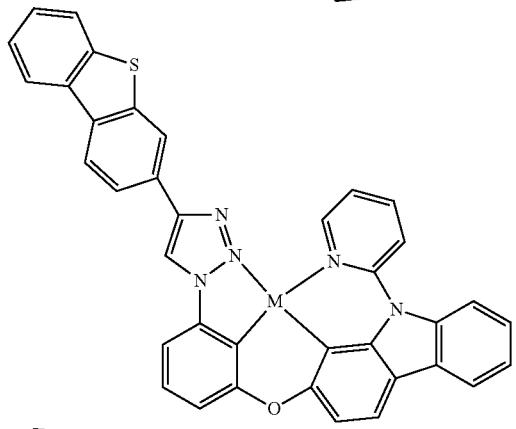
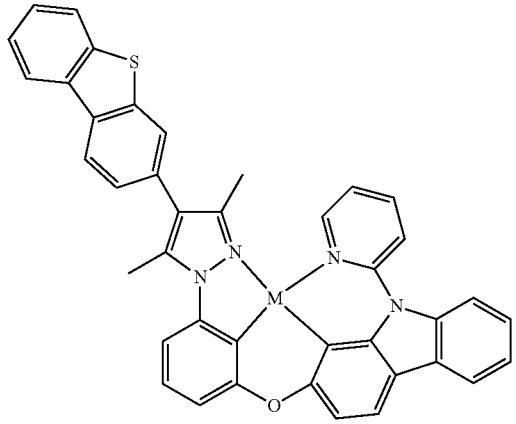

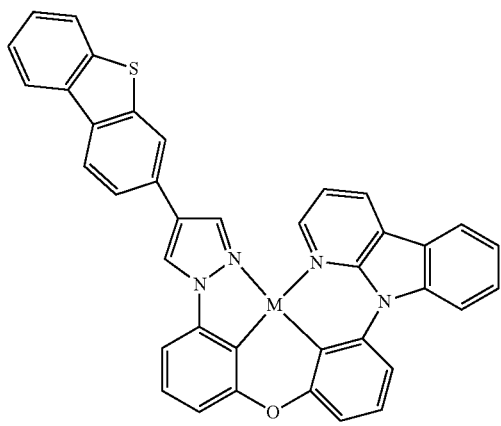
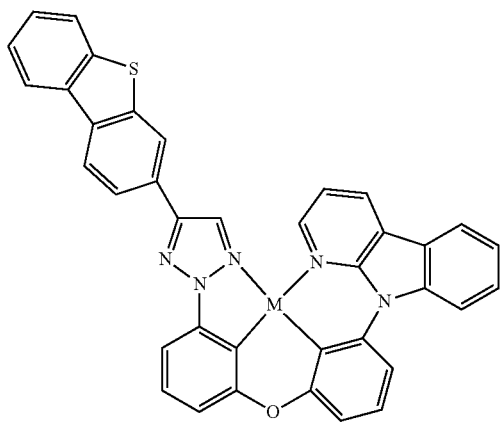
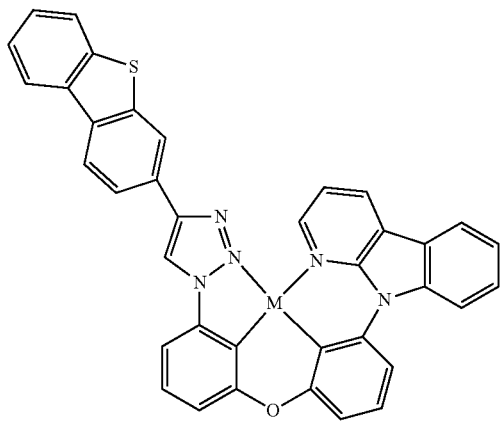
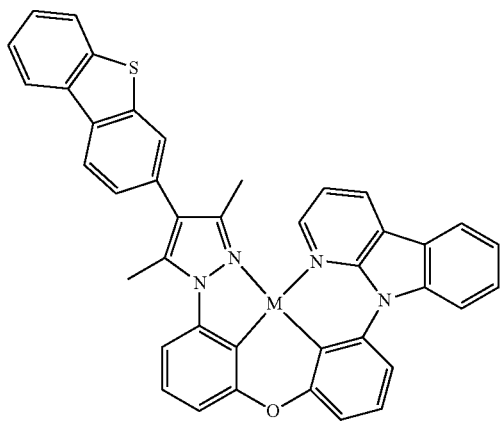
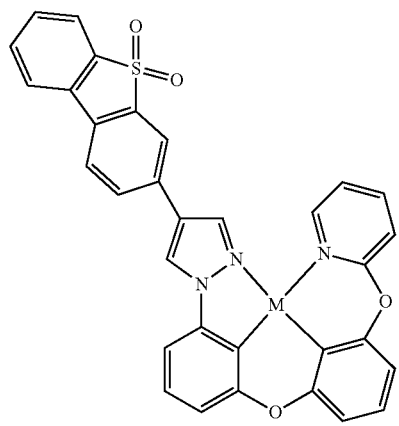
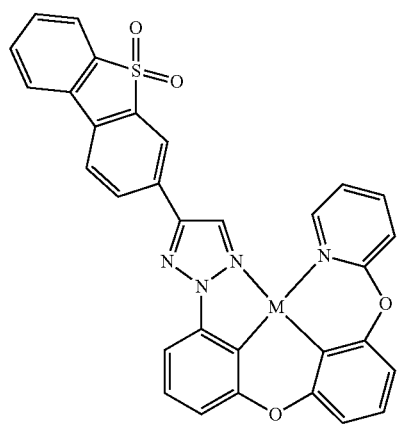
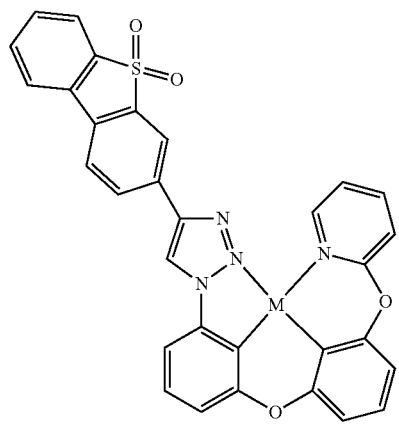
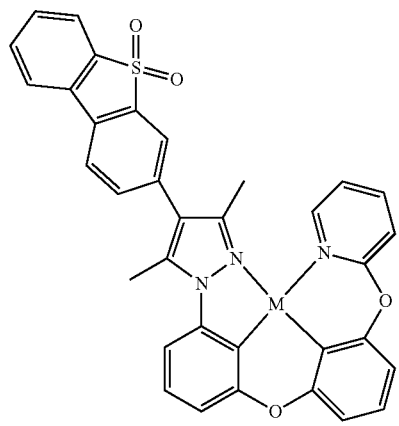

111
-continued
112
-continued
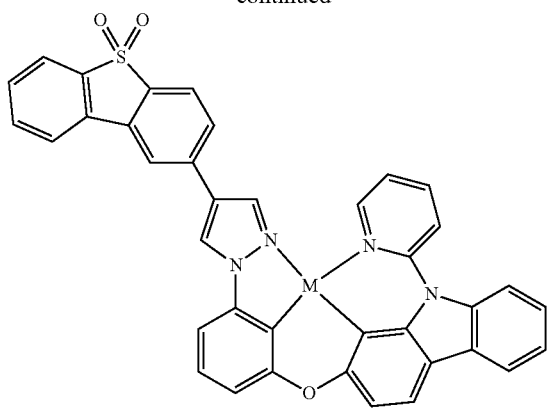
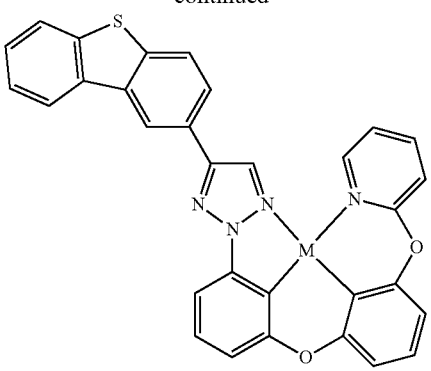
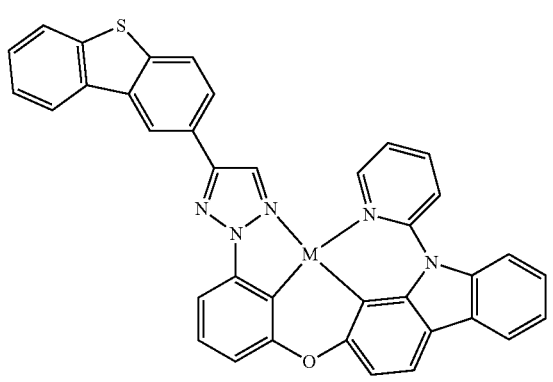
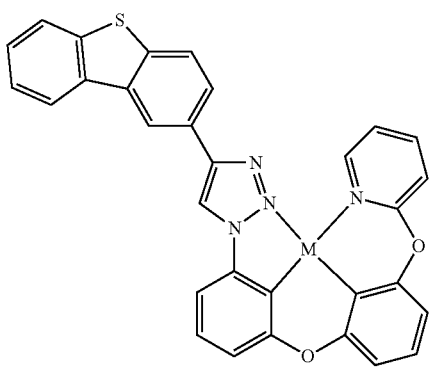
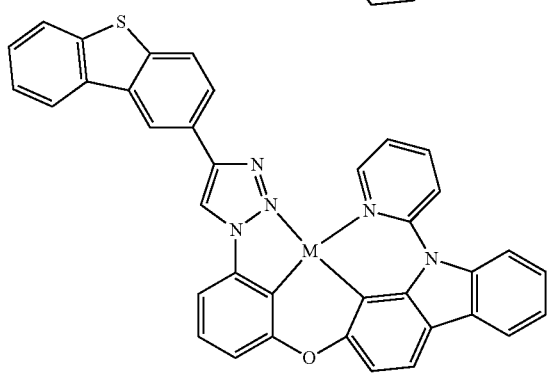
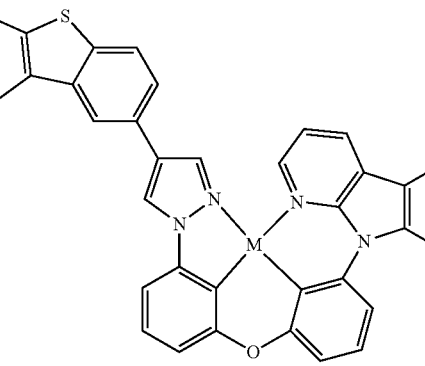
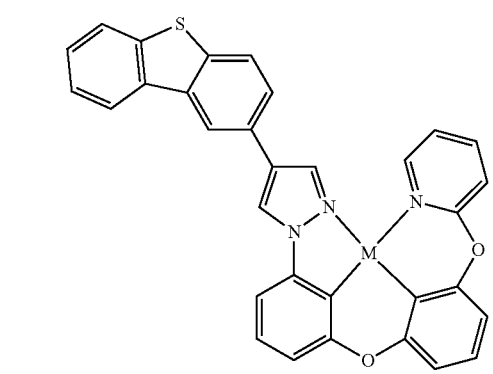
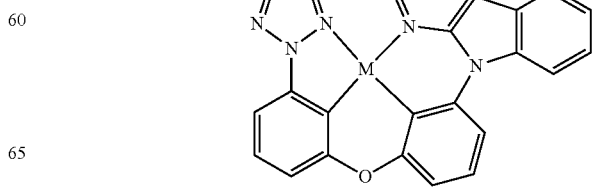

113
-continued
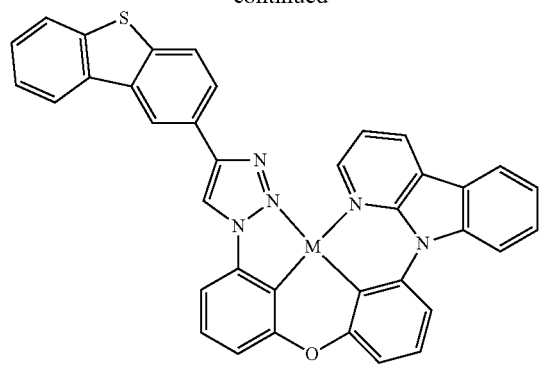
(M = Pt, Pd)
Structure 6
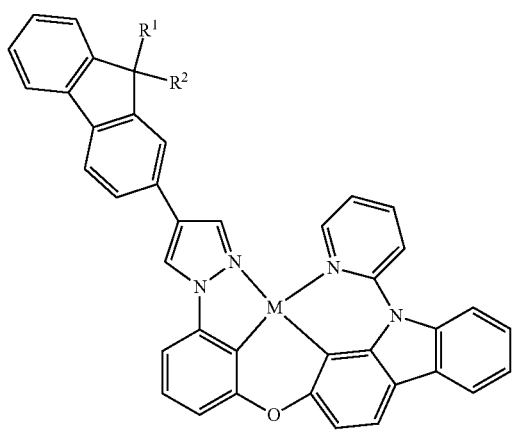
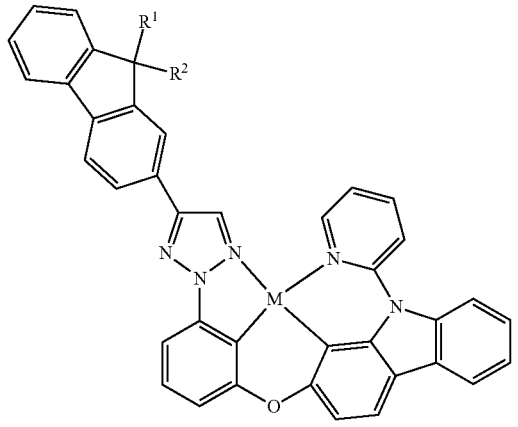
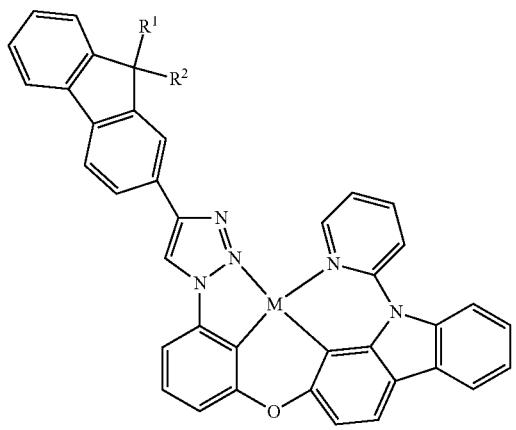
114
-continued
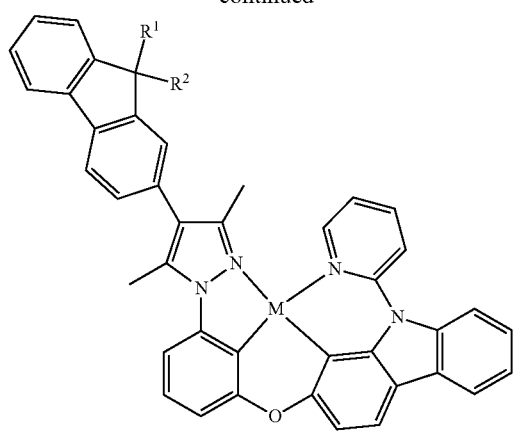
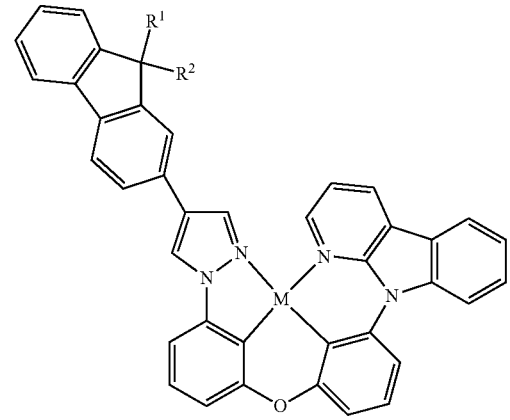
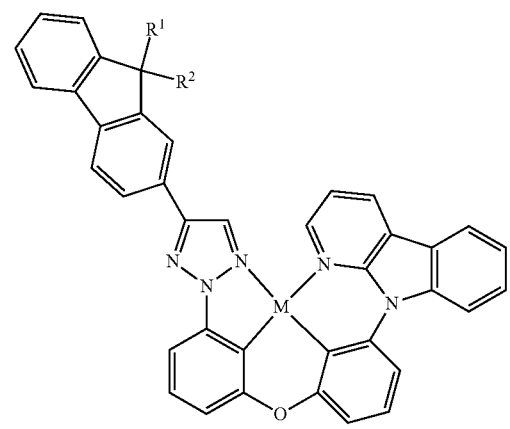
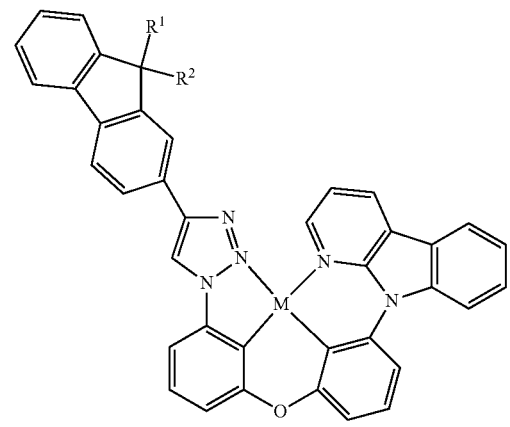

115
-continued
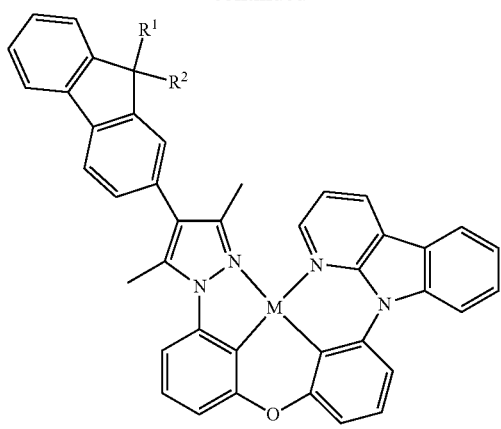
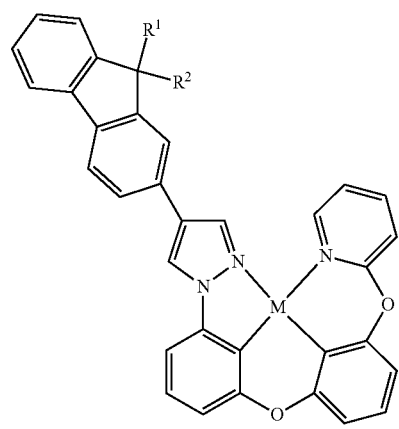
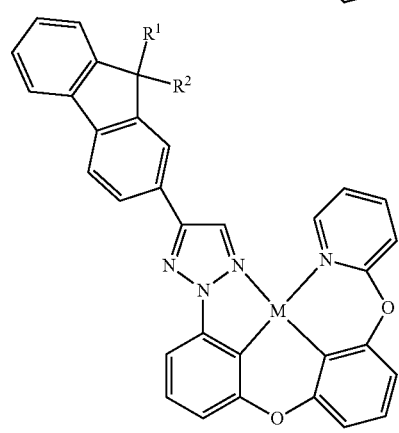
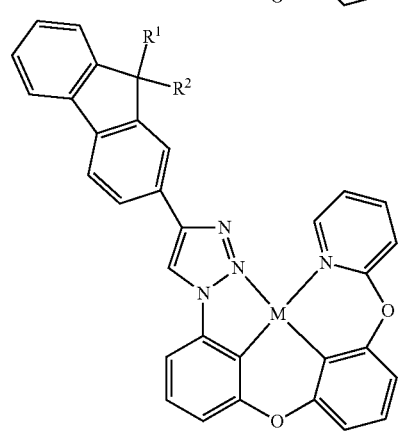
116
-continued
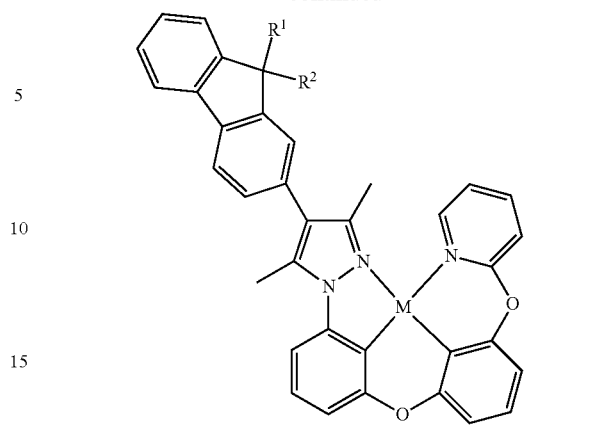
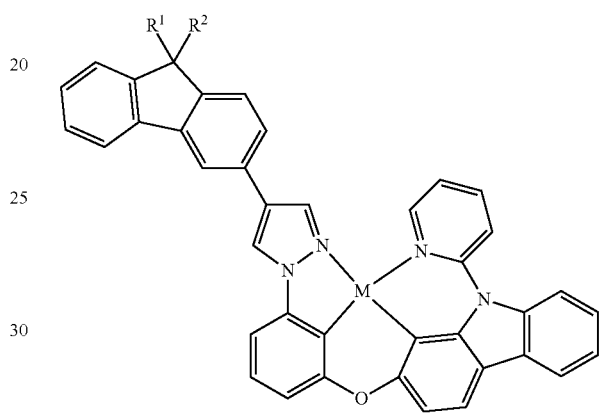
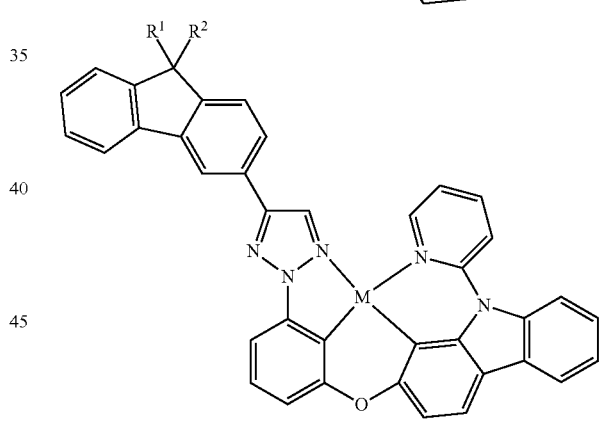
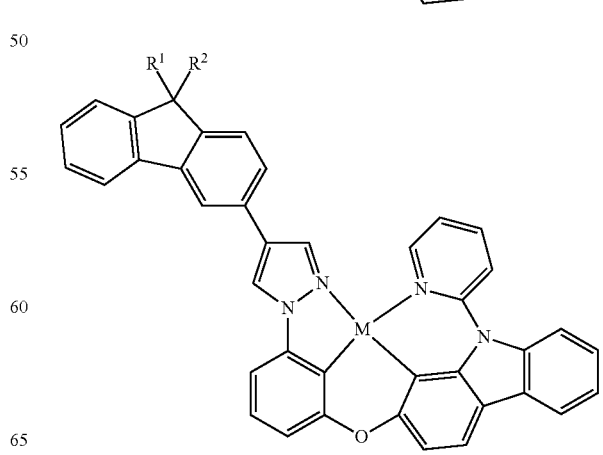

-continued
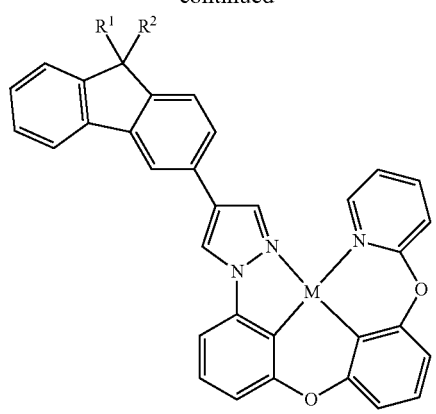
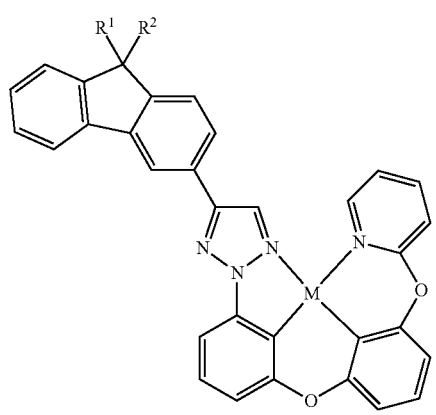
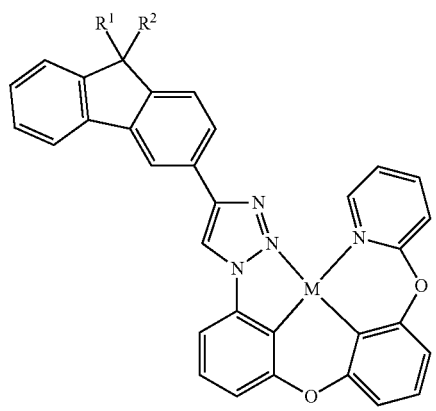
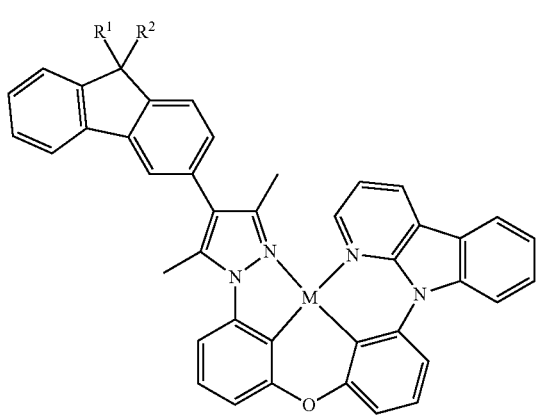
-continued
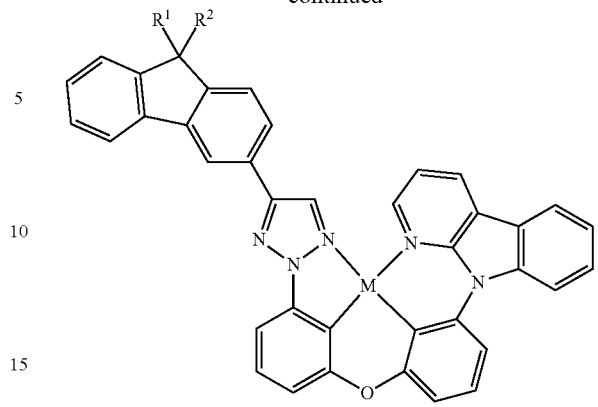
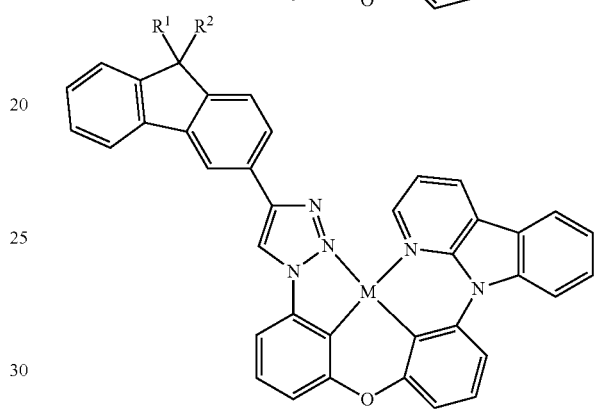
(M = Pt, Pd)
Structures 7
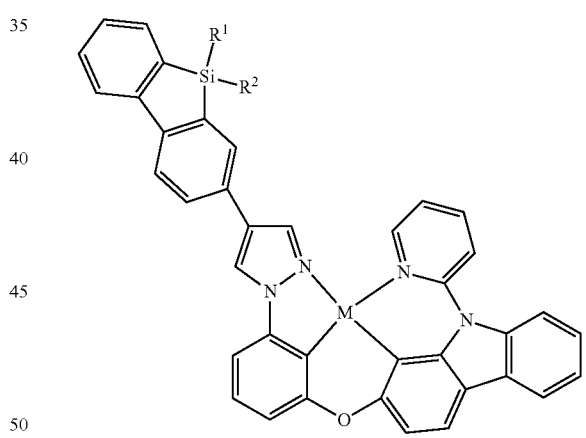
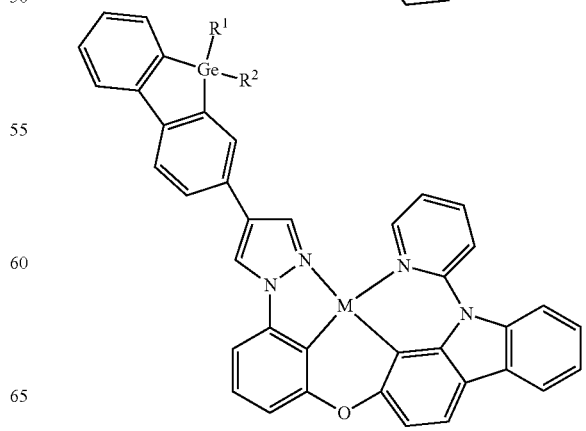

119
-continued
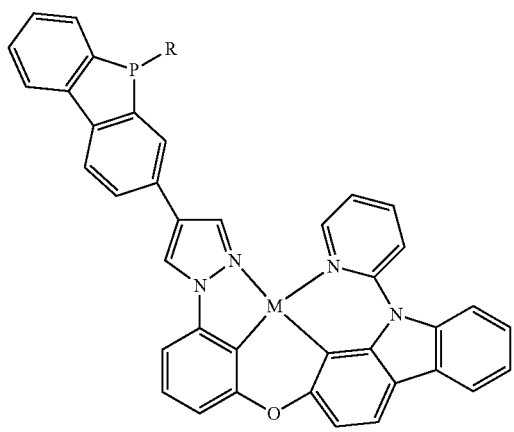
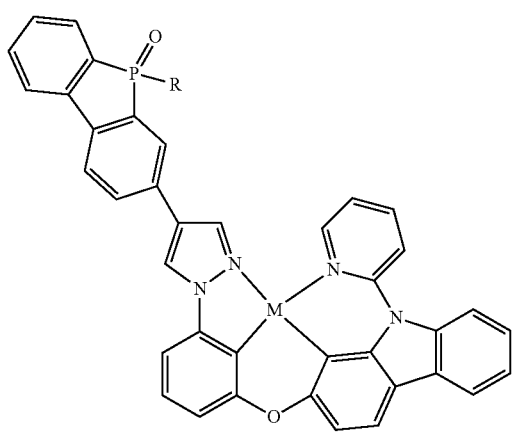
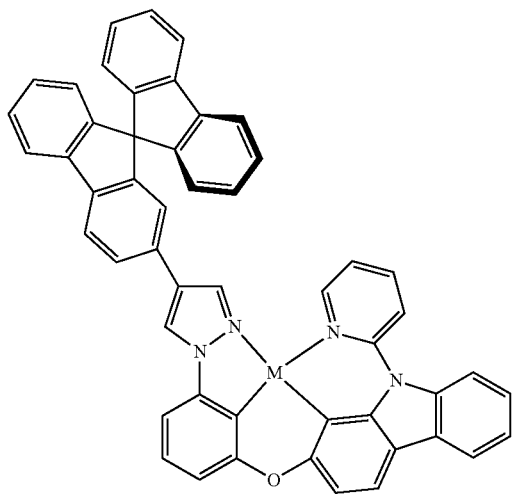
120
-continued
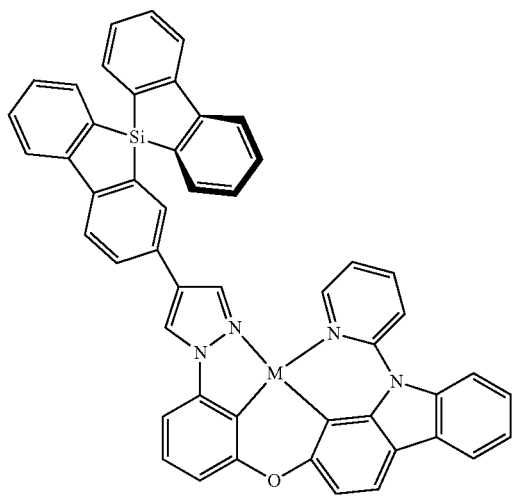
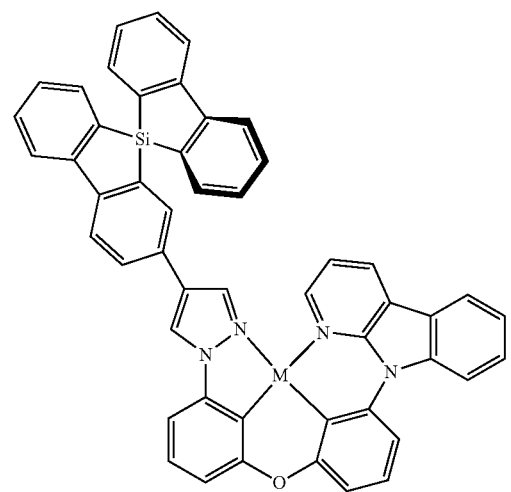

121
-continued
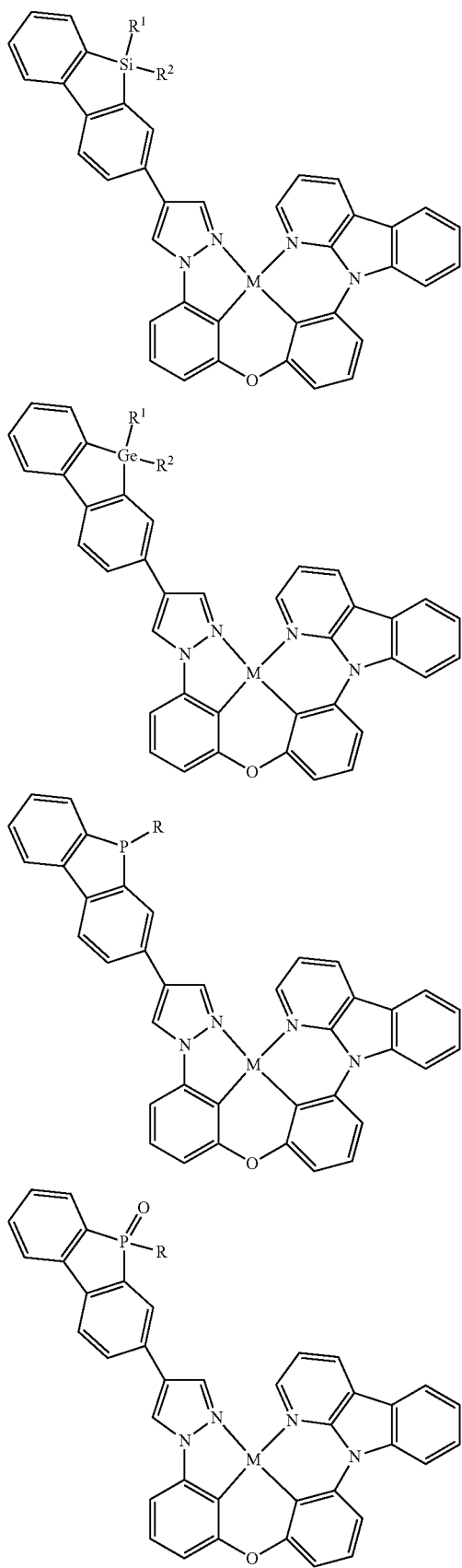
122
-continued
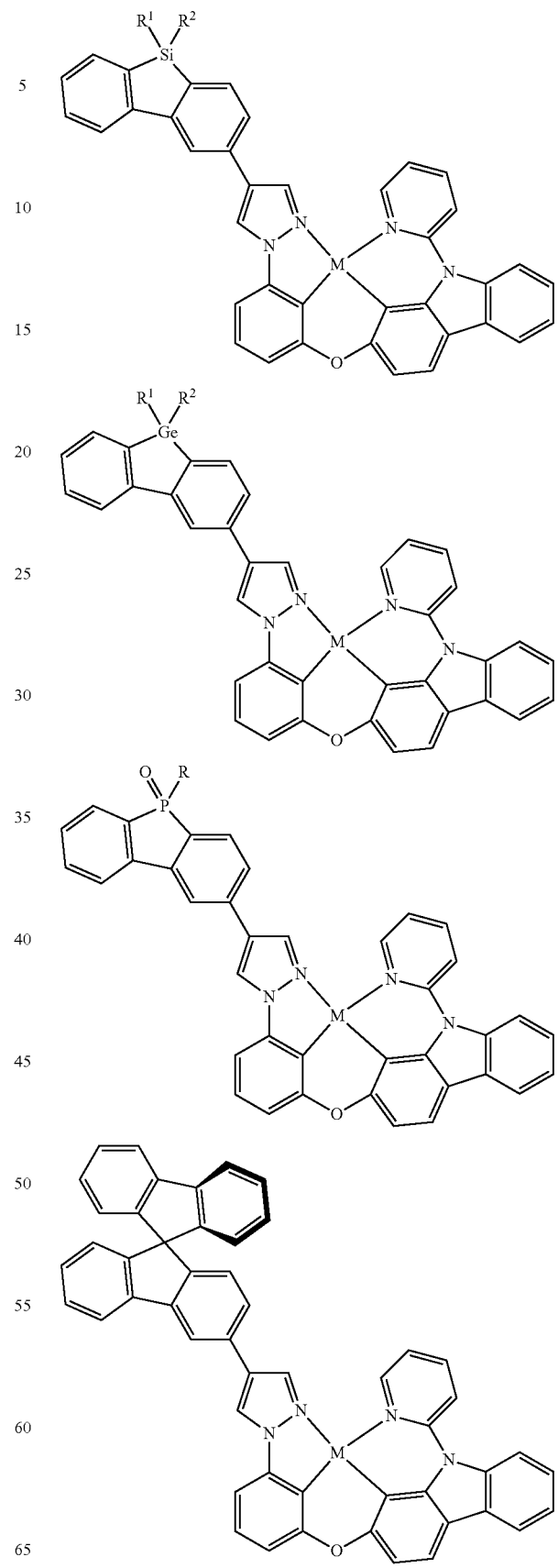

123
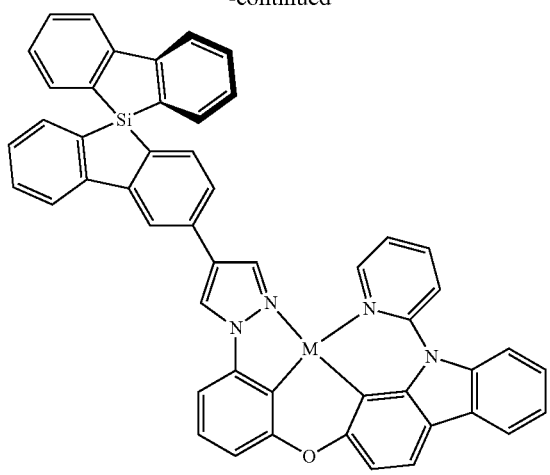
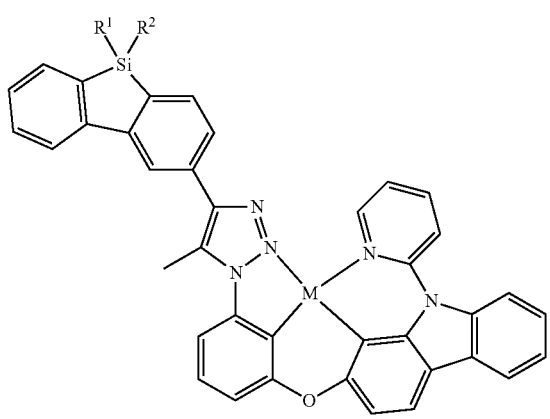
124
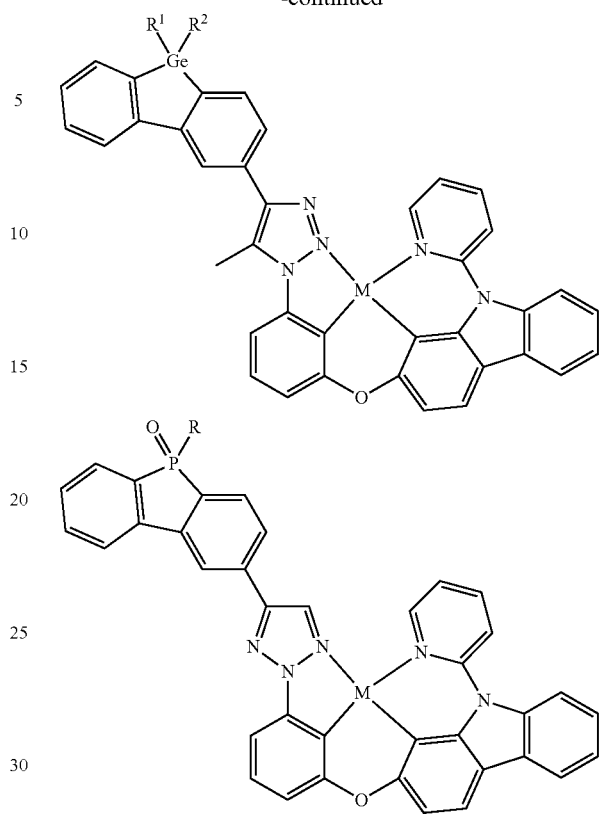
(M = Pt, Pd)
Structures 8
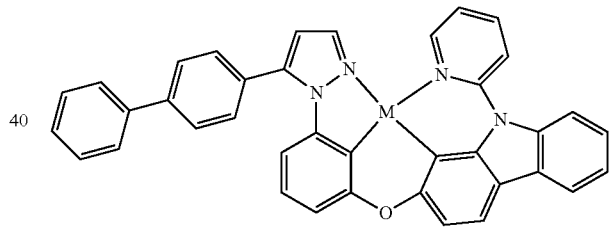
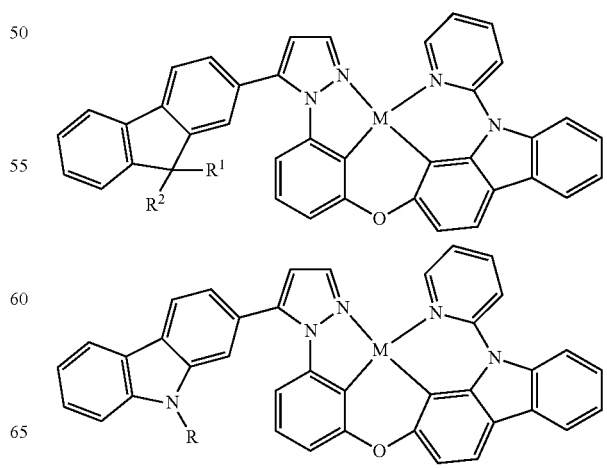

125
-continued
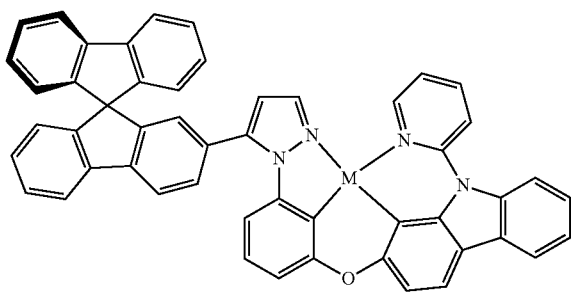
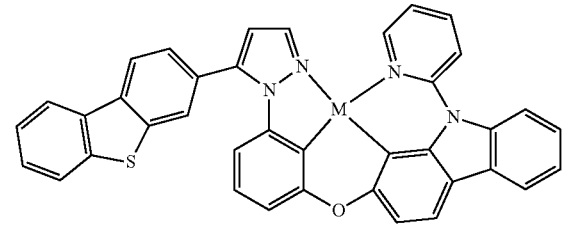
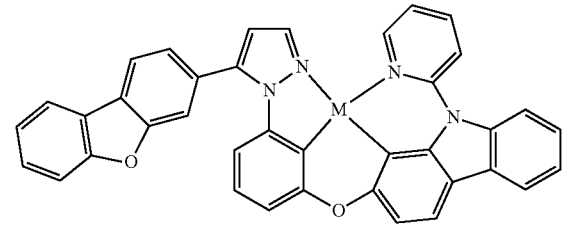
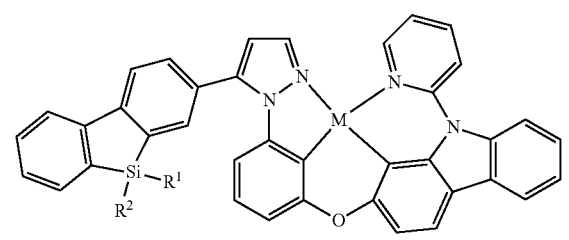
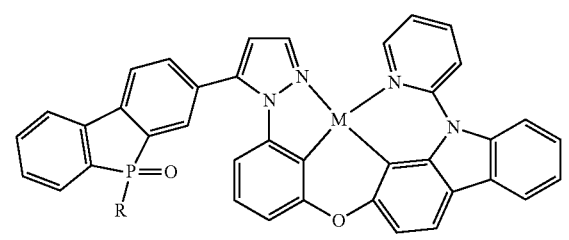
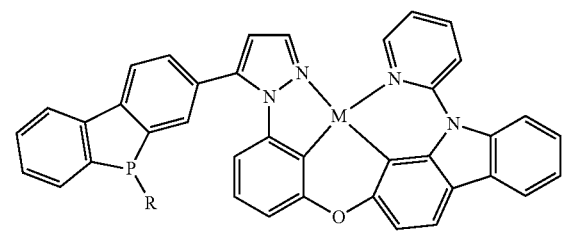
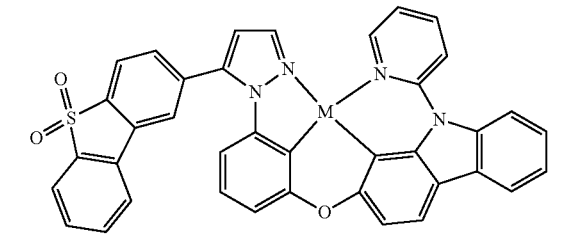
126
-continued
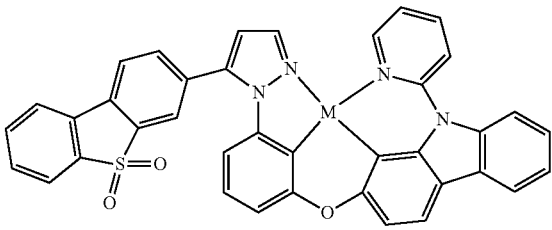
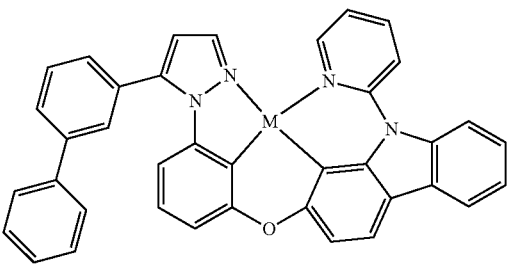
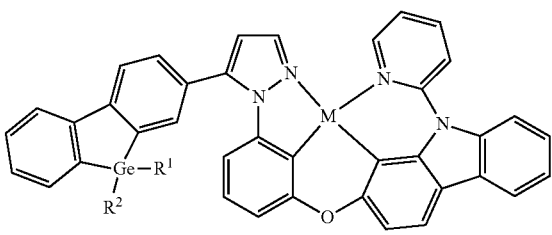
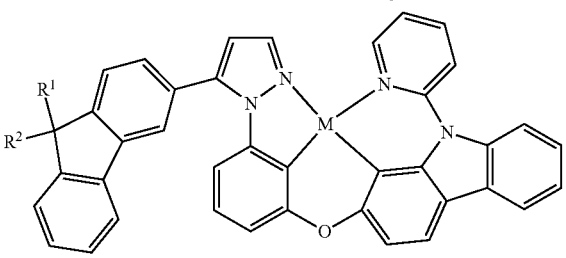
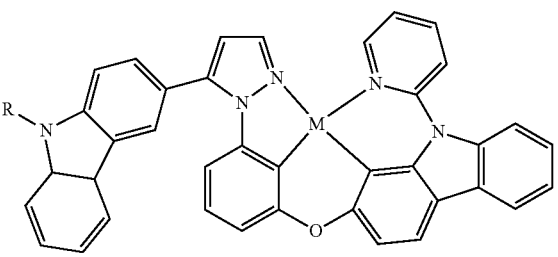
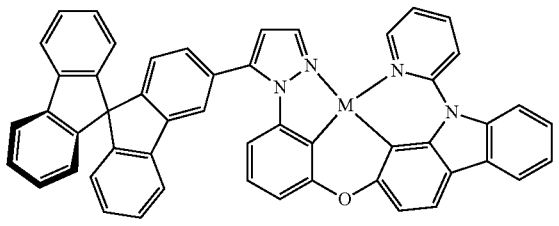
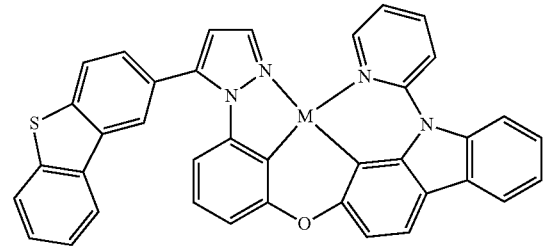

127
-continued
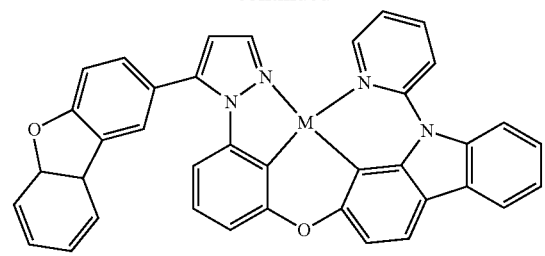
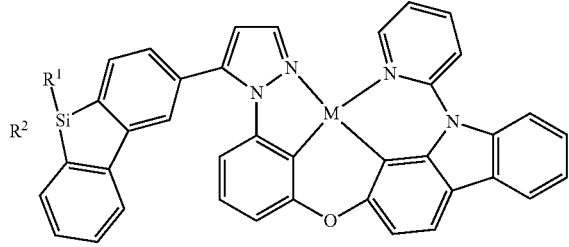
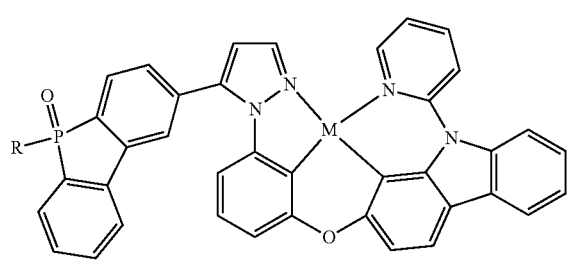
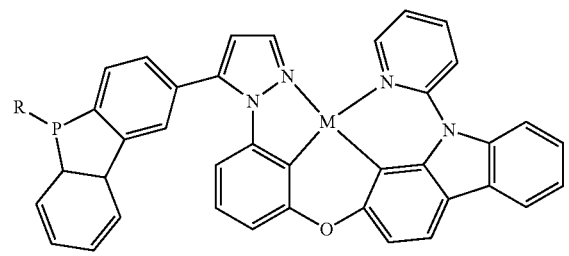
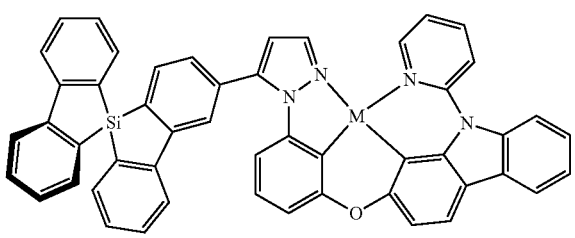
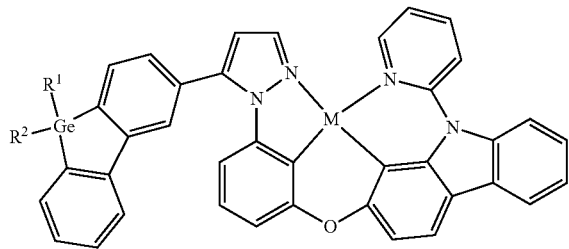
128
-continued
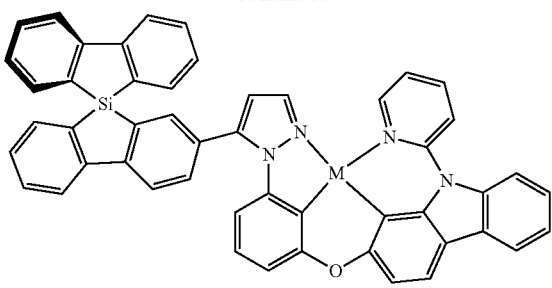
(M = Pt, Pd)
Structures 9
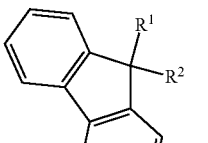
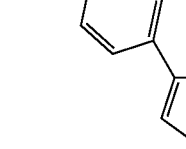

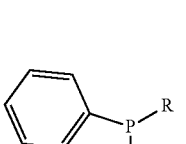
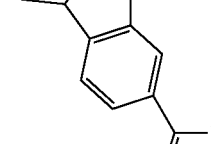

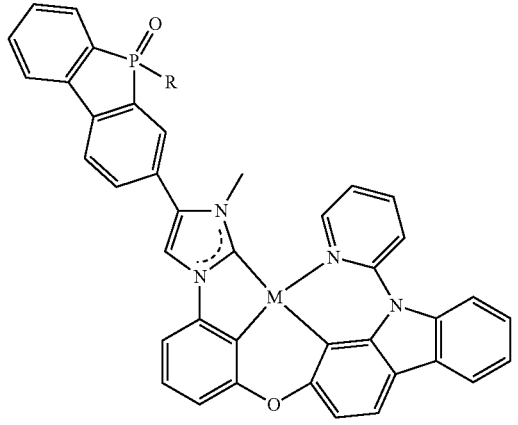

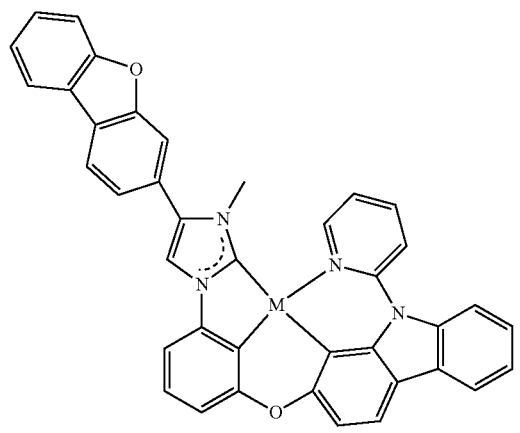

133
-continued

(M = Pt, Pd)
Structures 10
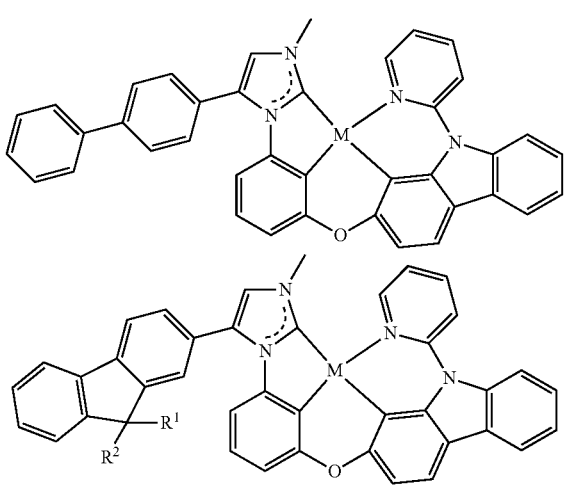
134
-continued

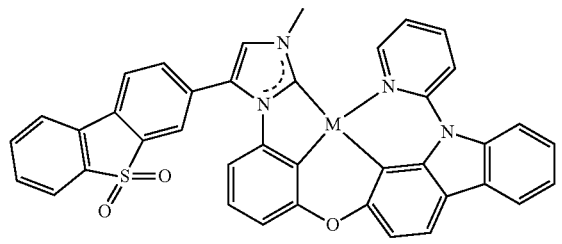
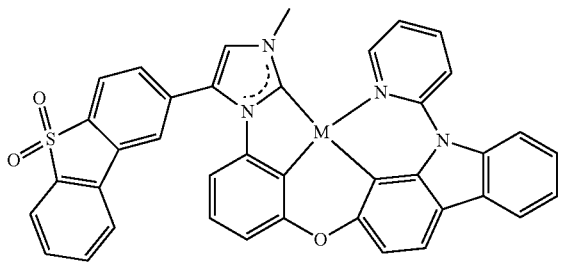
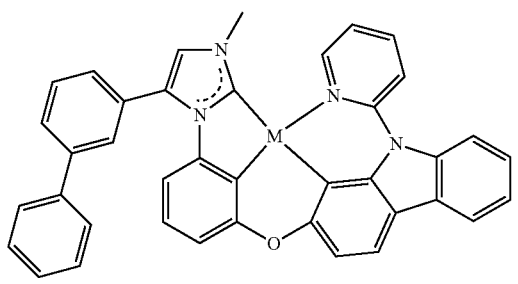
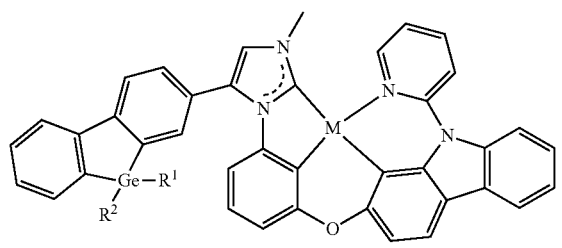
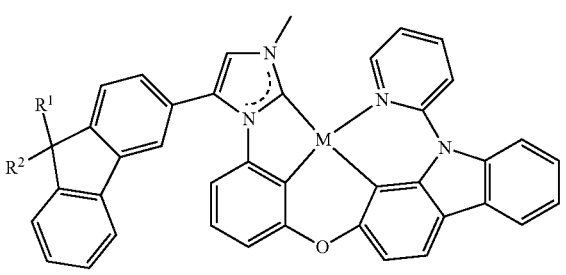
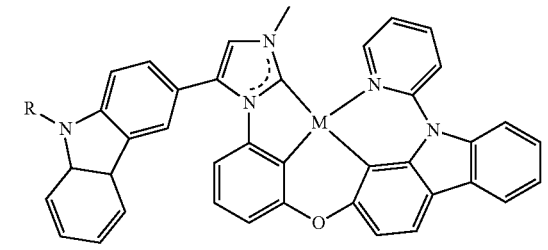
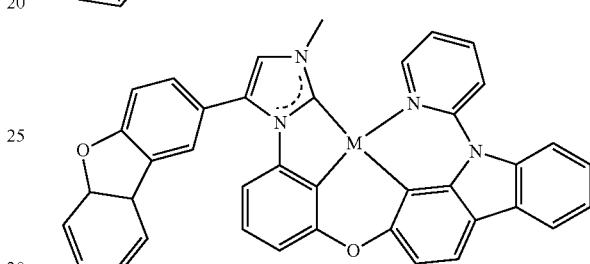
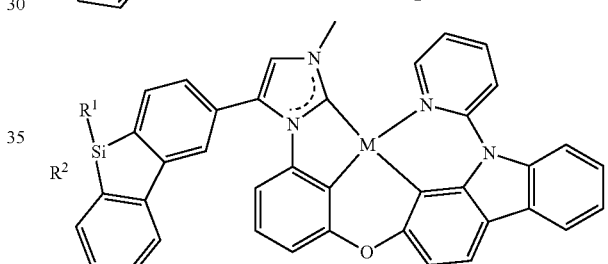
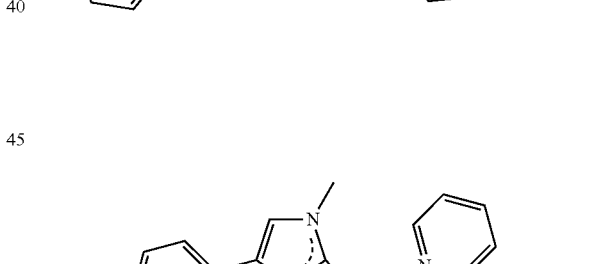
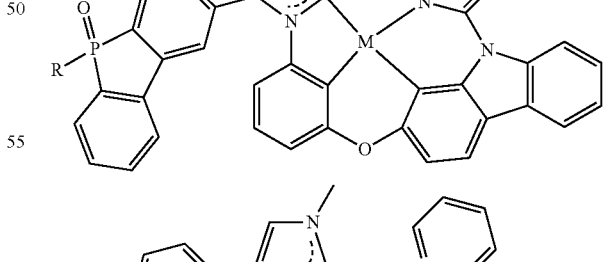
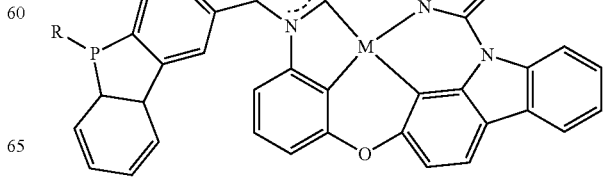

137
-continued
138
-continued
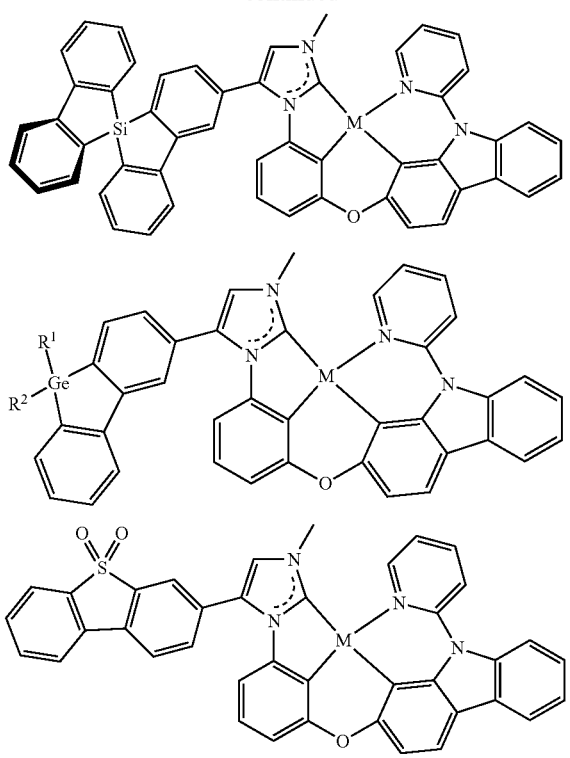
(M = Pt, Pd)
Structures 11
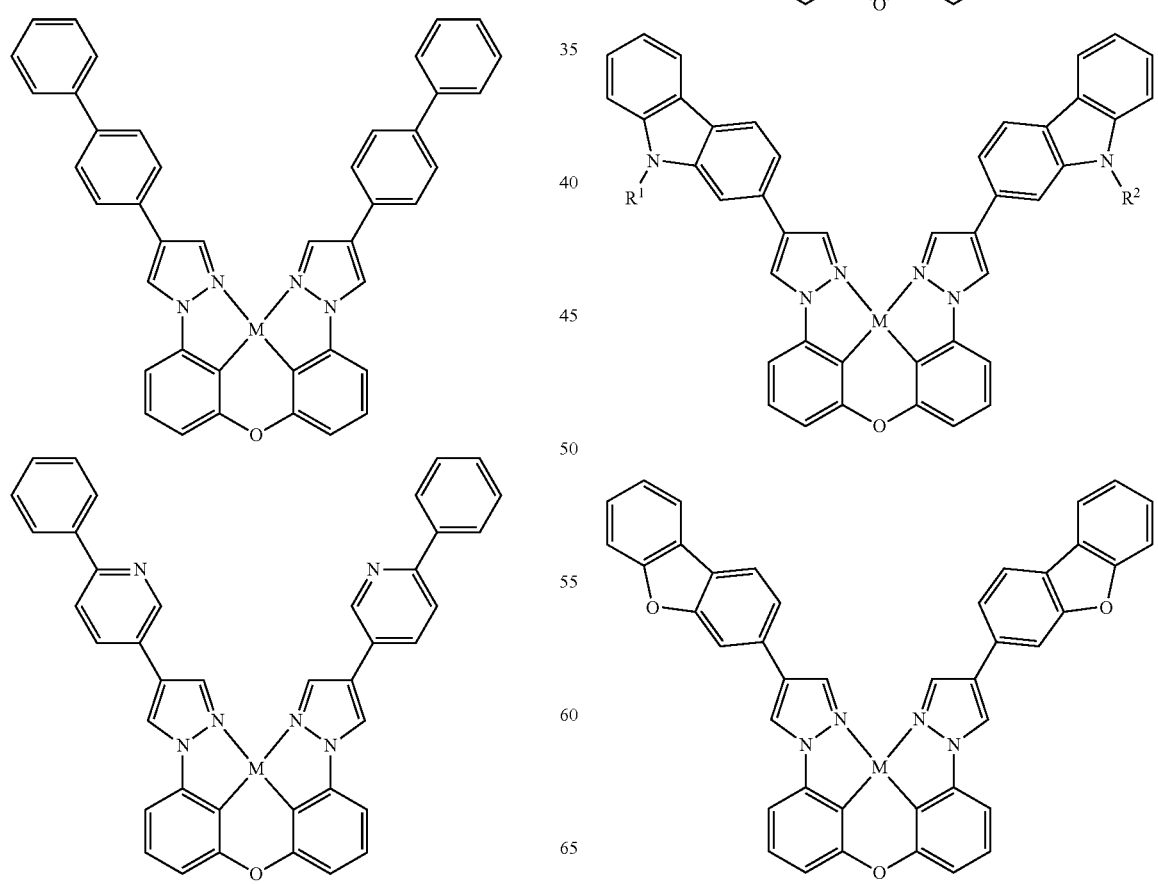
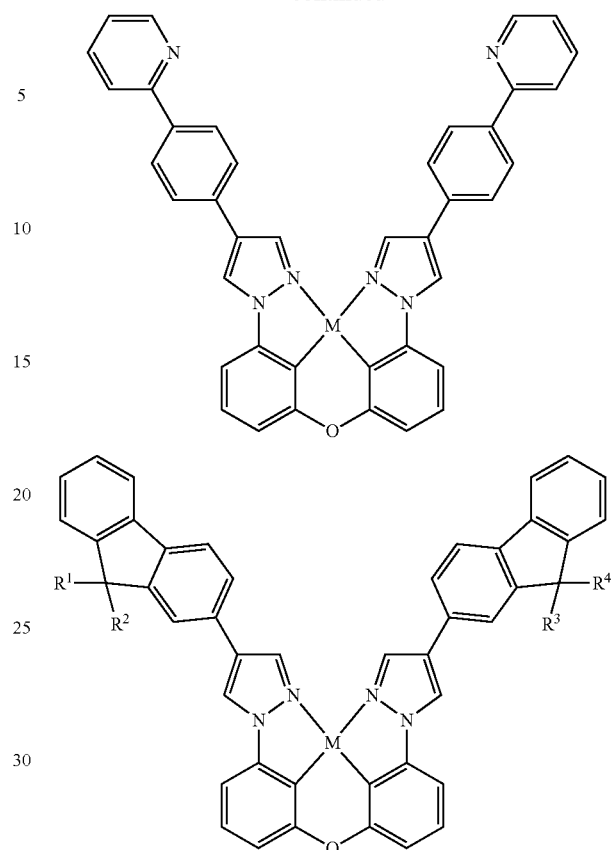

139
-continued
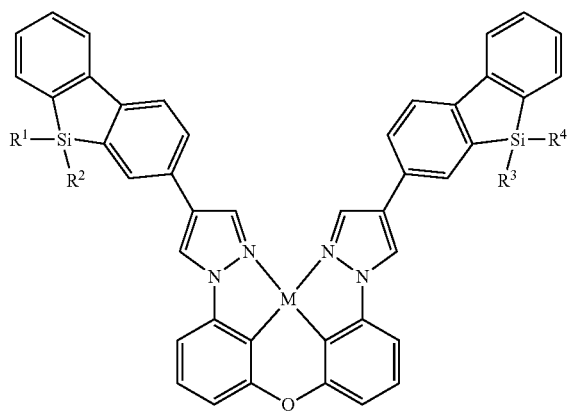
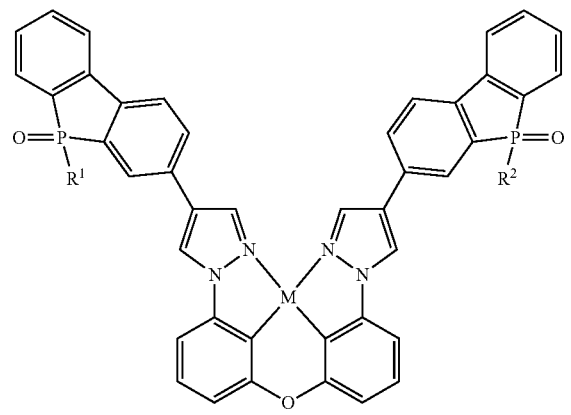
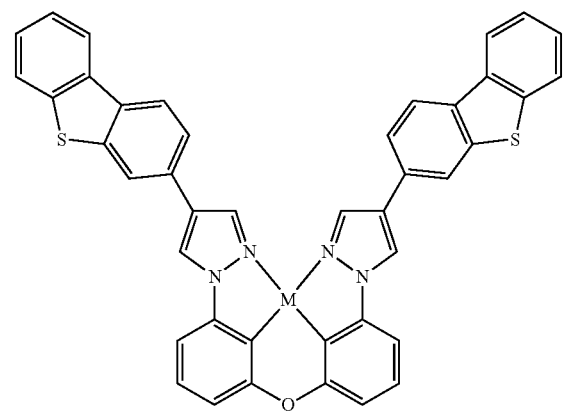
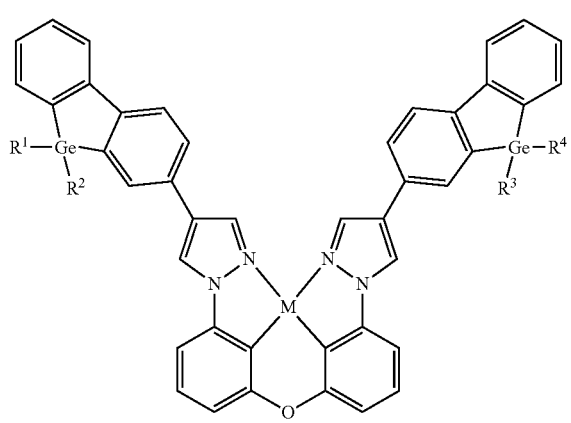
140
-continued
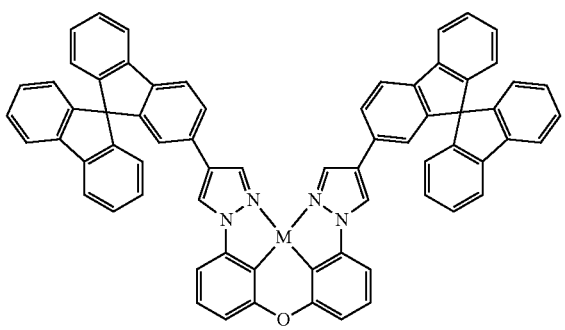
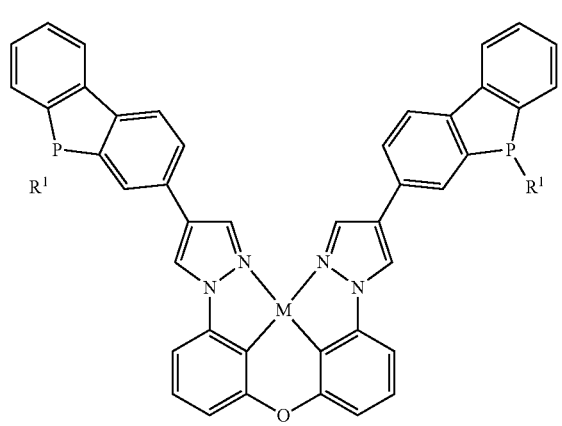
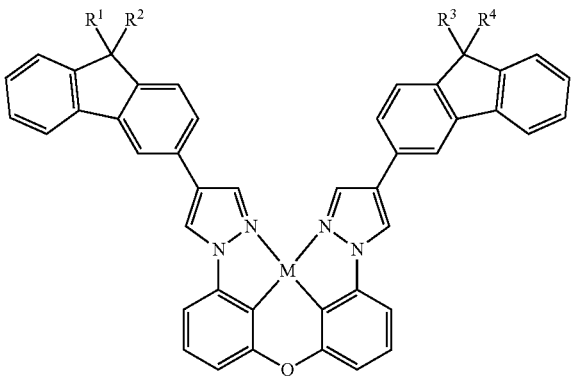
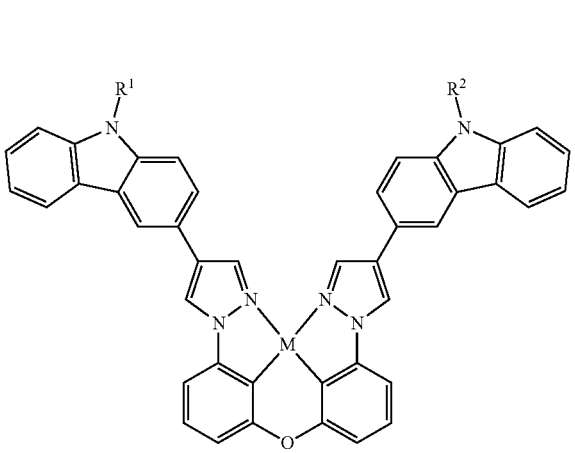

141
-continued
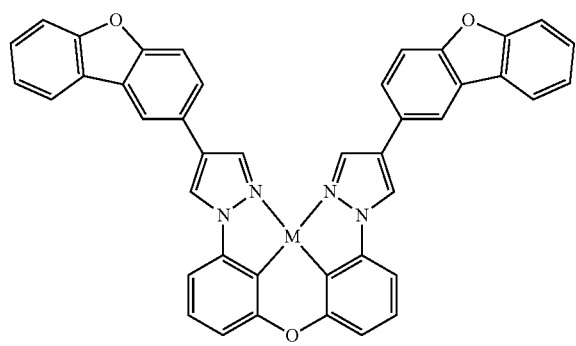
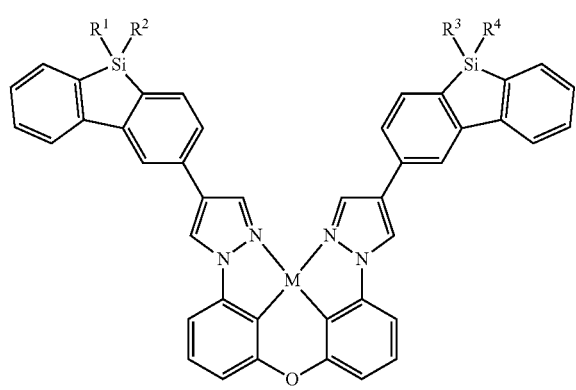
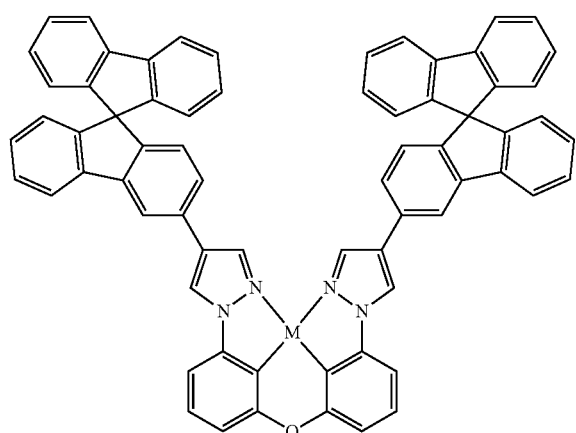
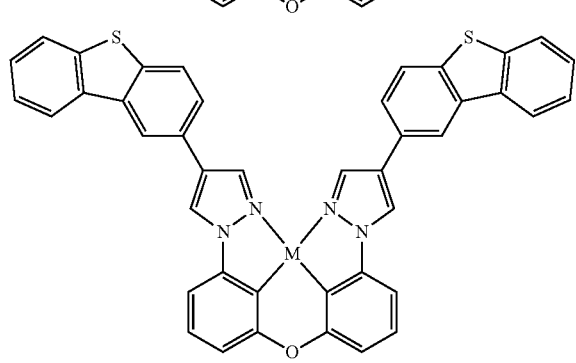
142
-continued
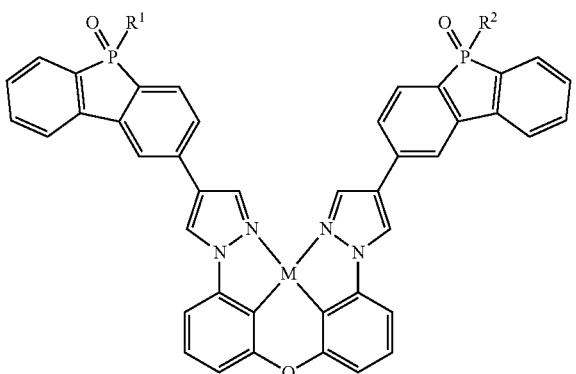
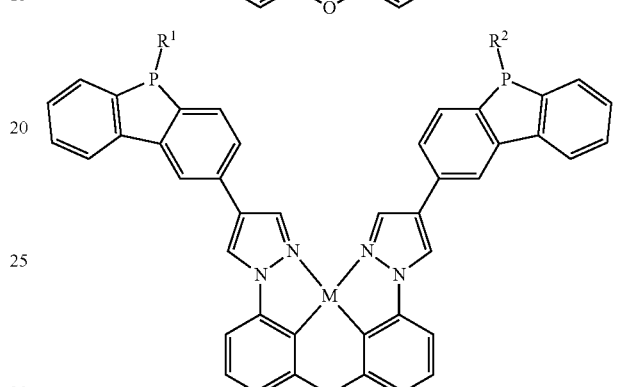
(M = Pt, Pd)
Structure 12
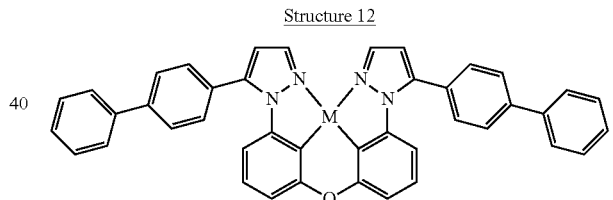
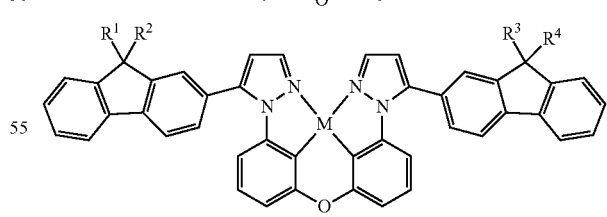
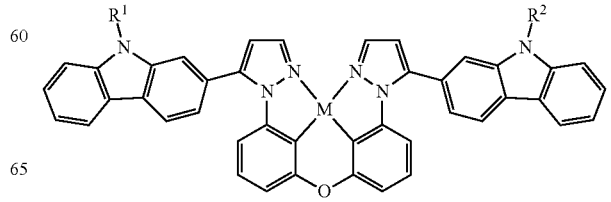

143
-continued
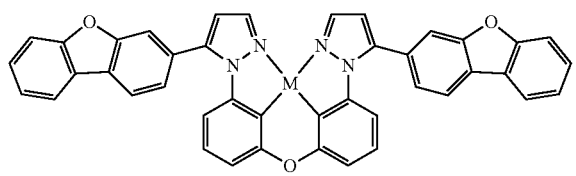
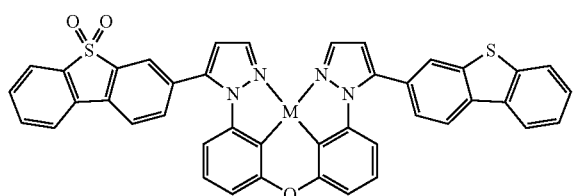
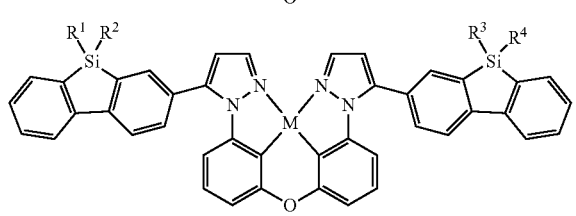
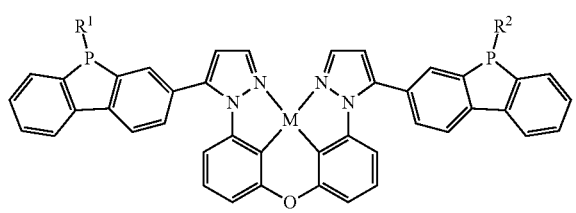
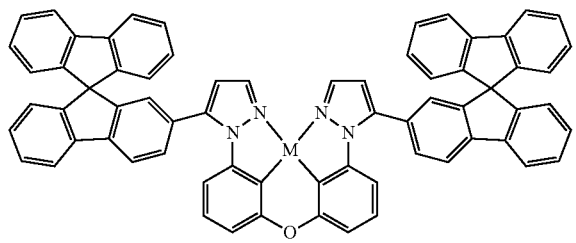
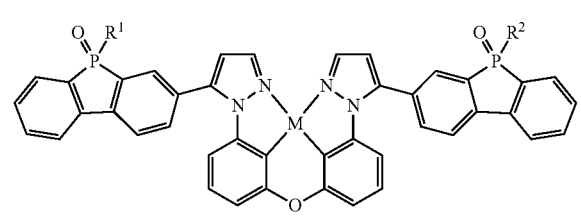
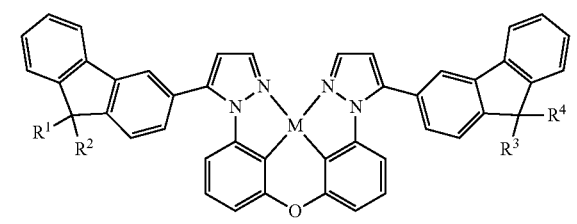
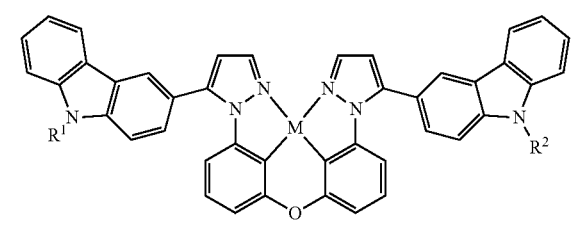
144
-continued
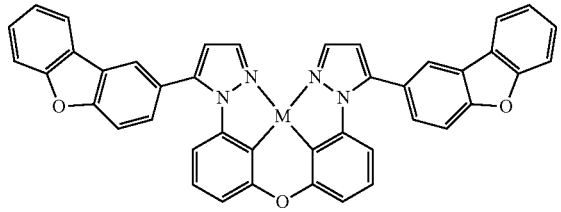
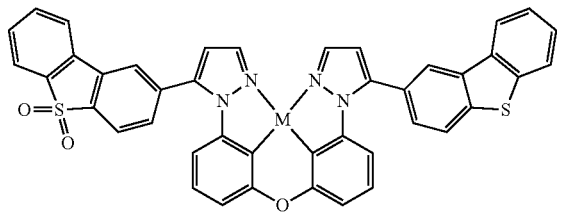
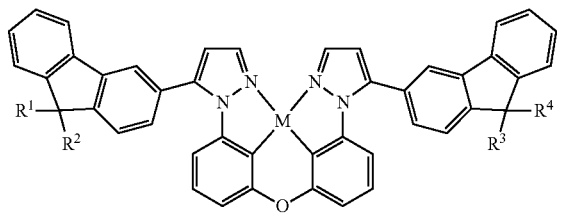
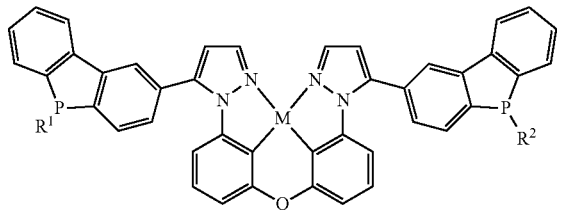
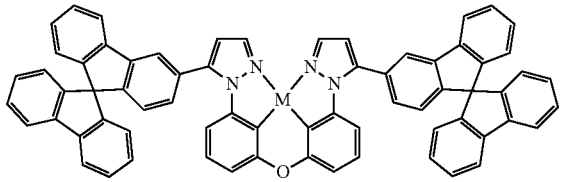
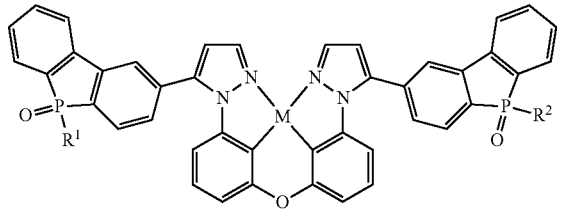
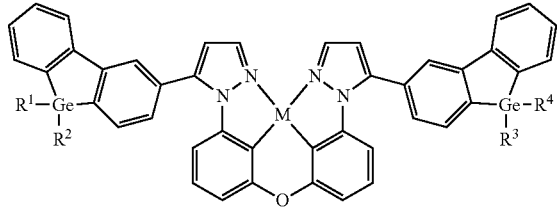
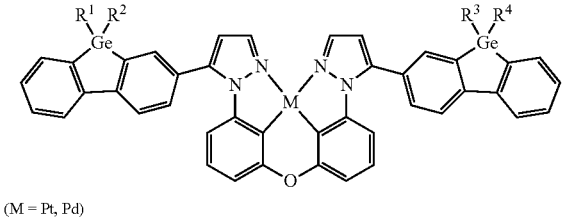
(M = Pt, Pd)

-continued
Structure 13
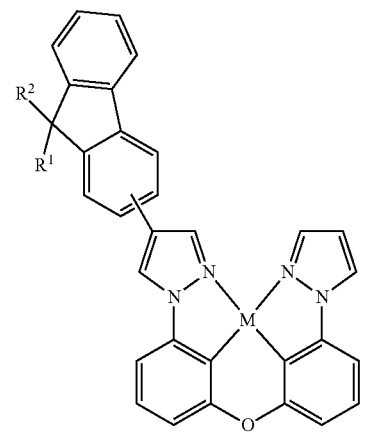
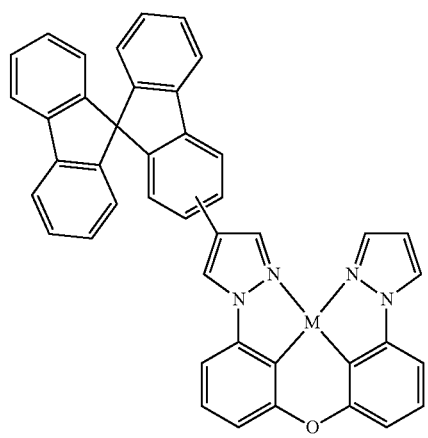
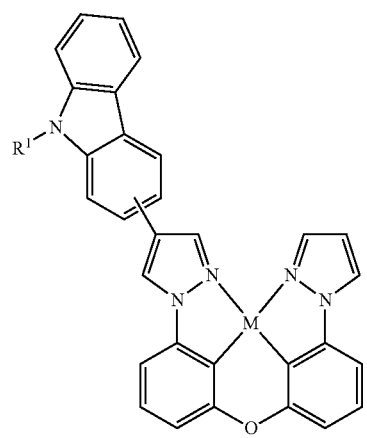
-continued
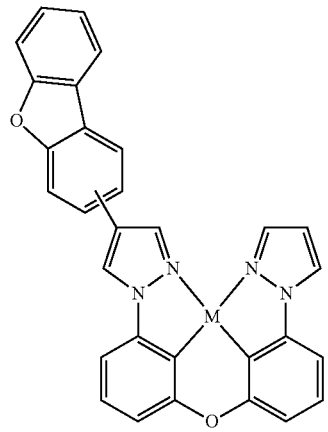
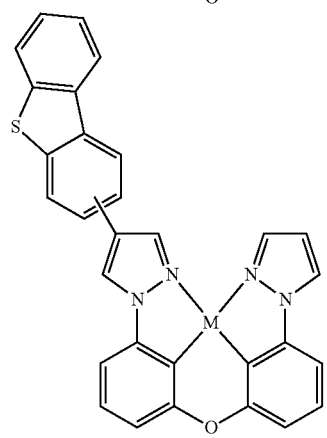
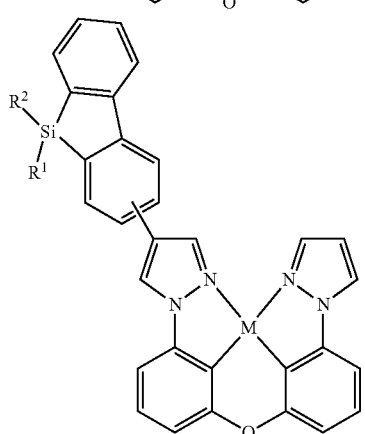
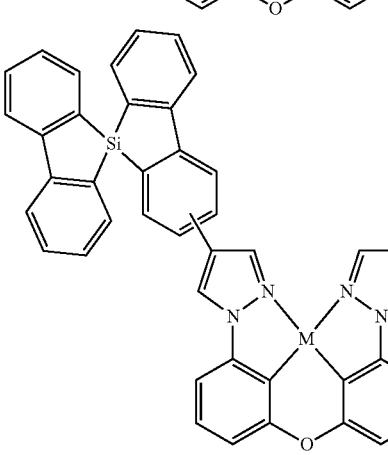

147
-continued
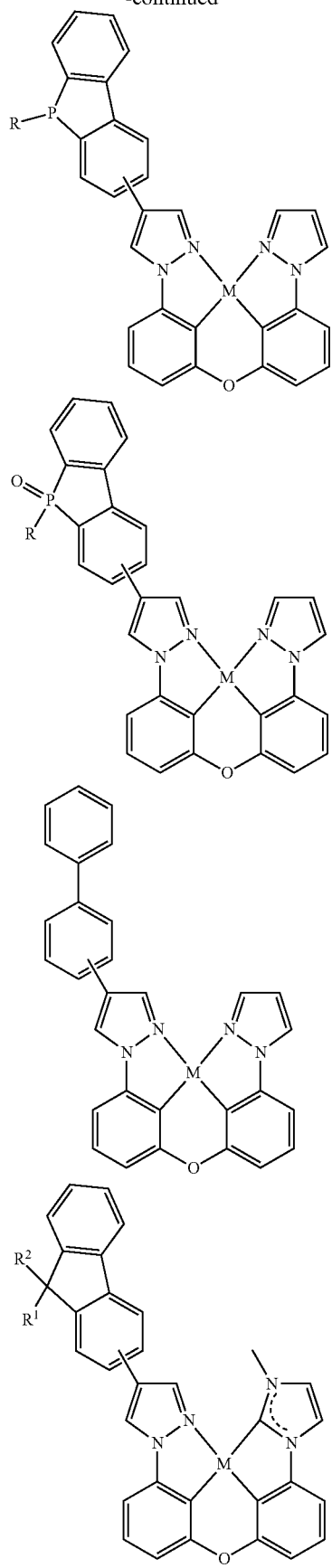
148
-continued
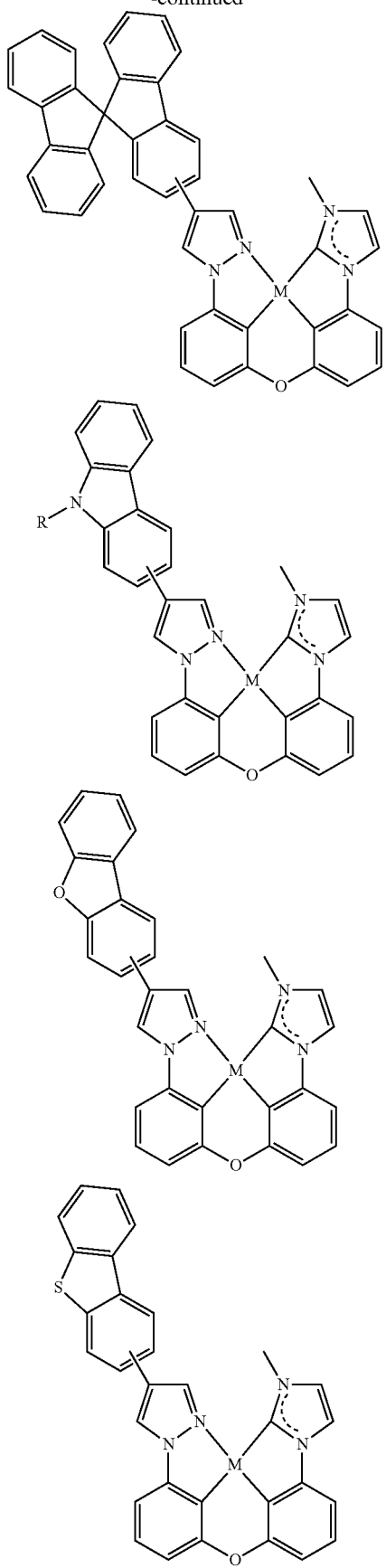

149
-continued
150
-continued
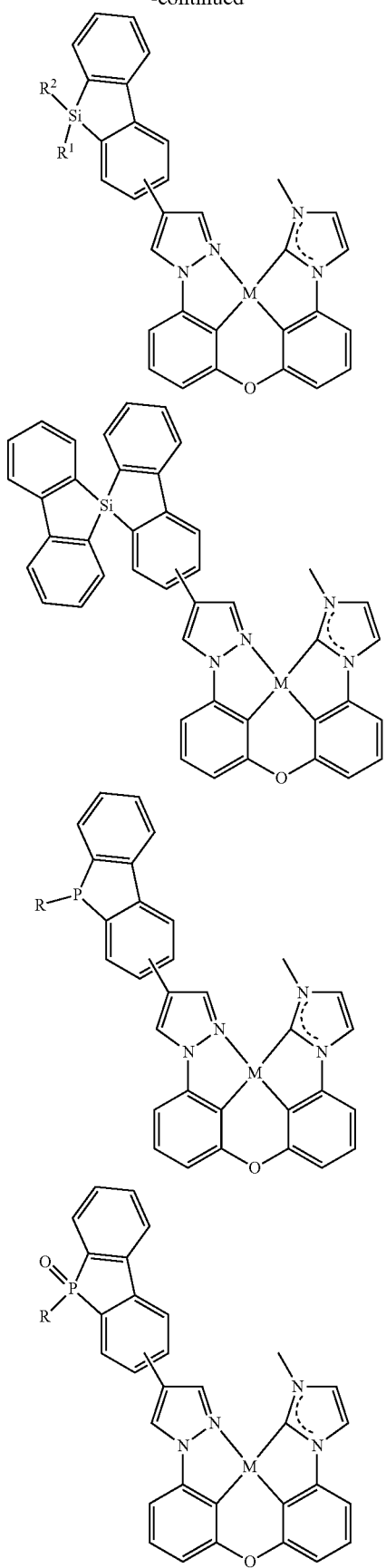
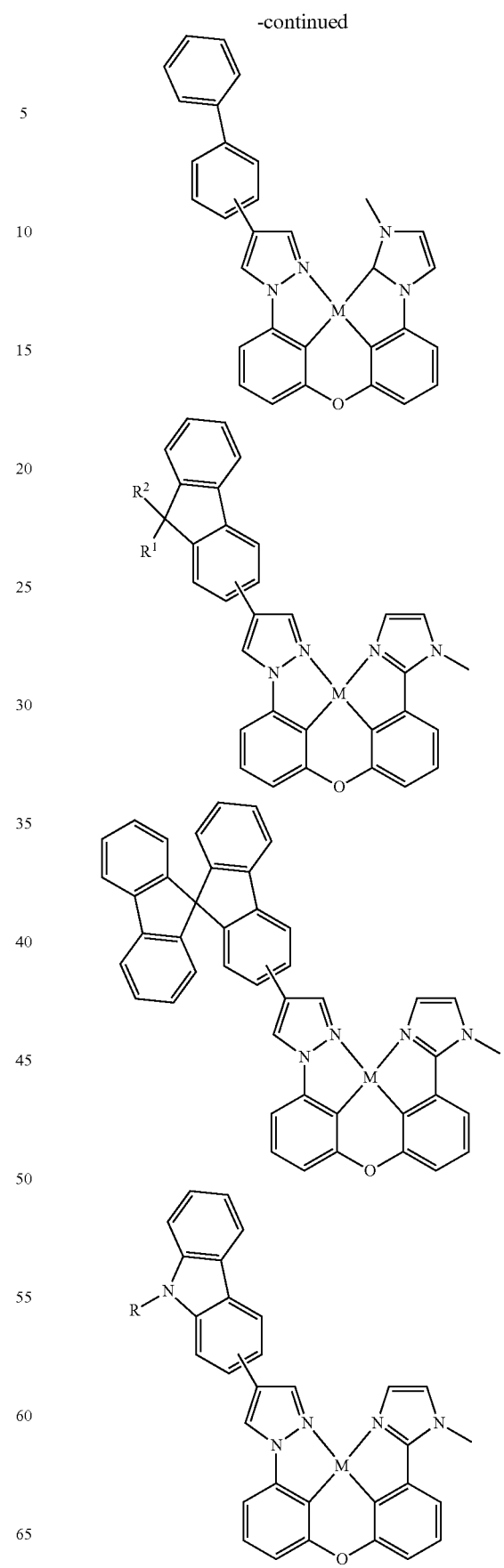

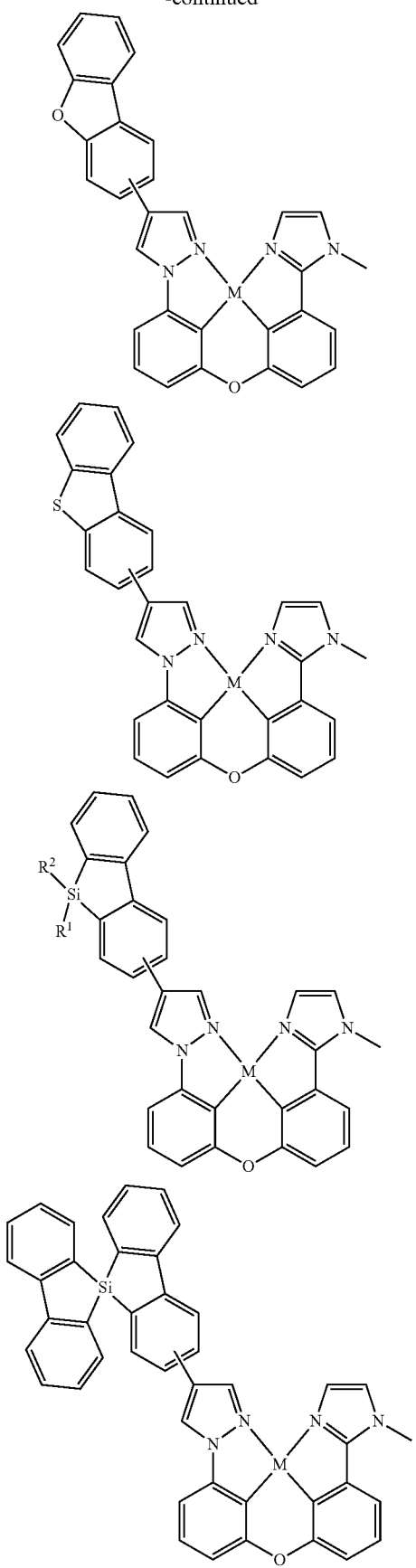
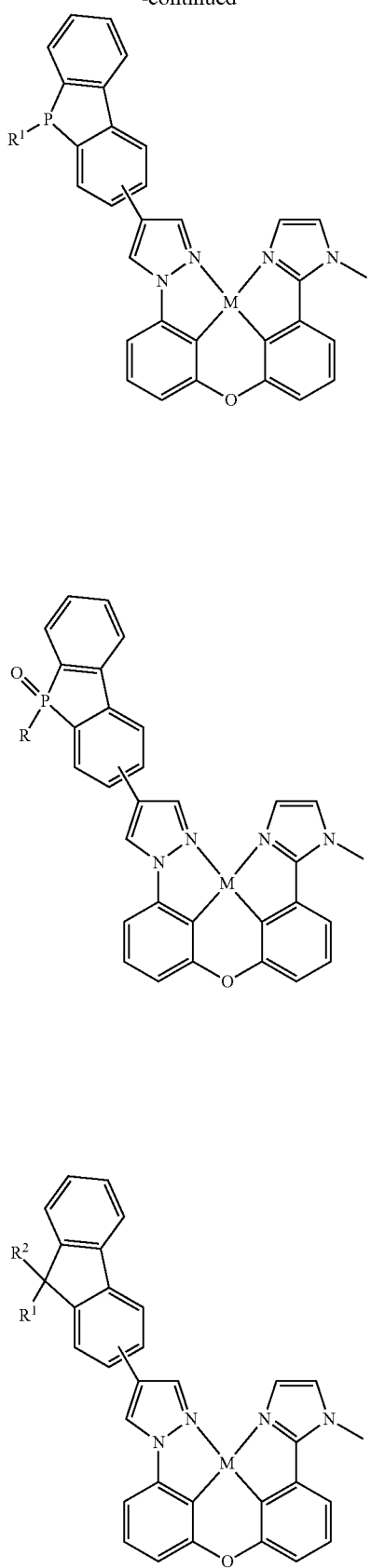
(M = Pt, Pd)

-continued
Structure 14
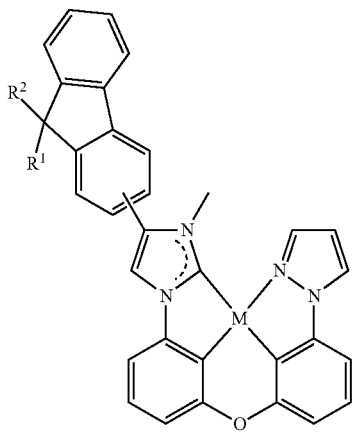
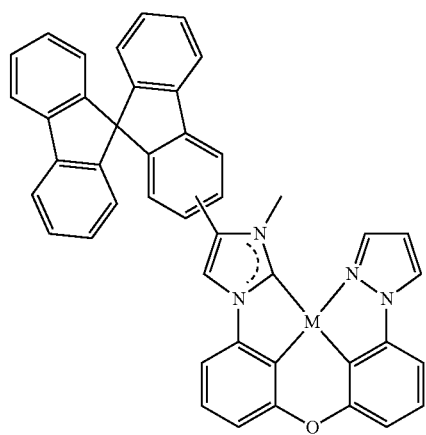
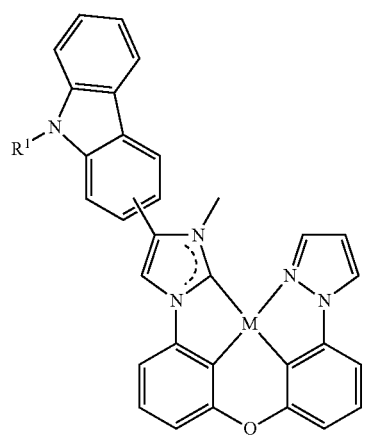
-continued
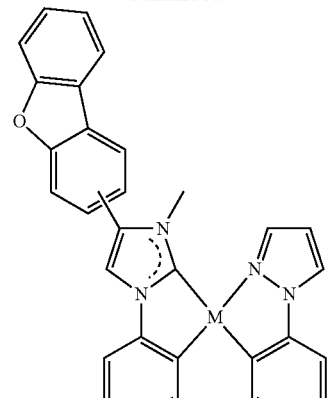
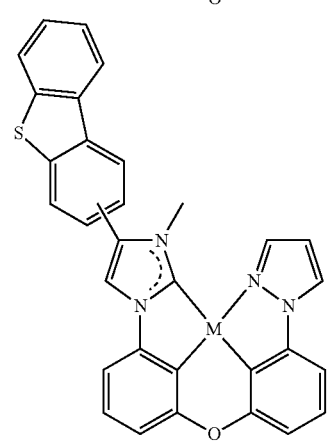
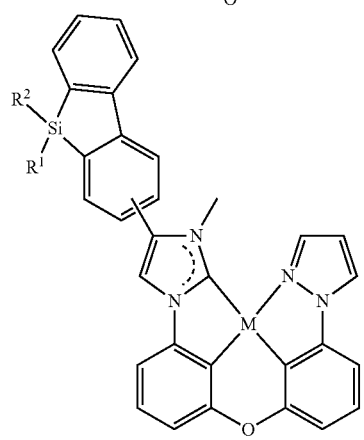
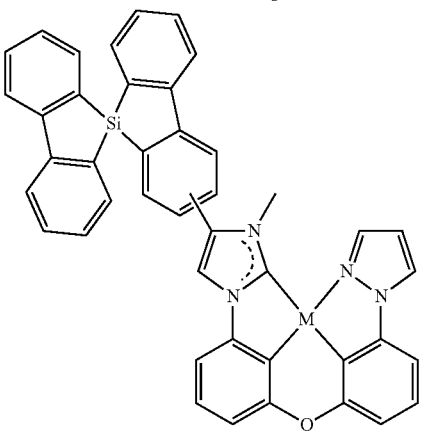

155
-continued
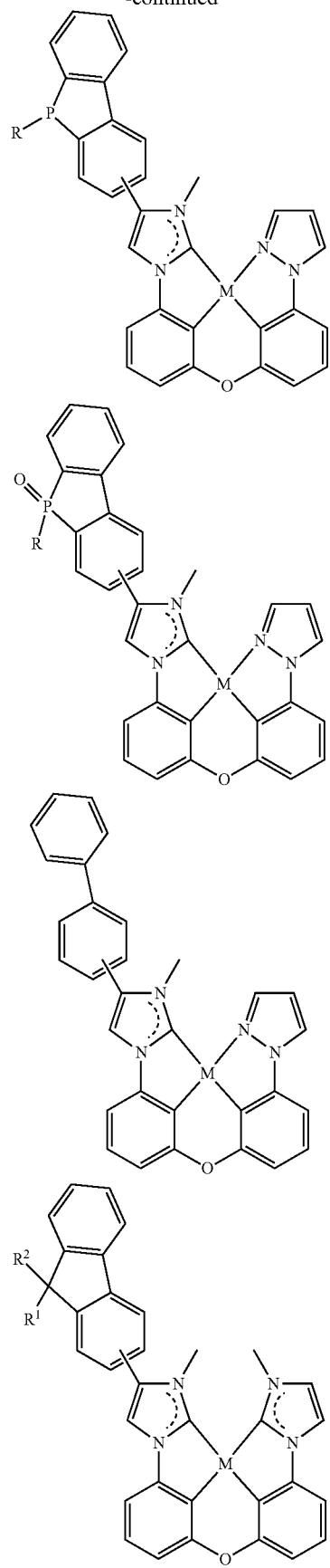
156
-continued
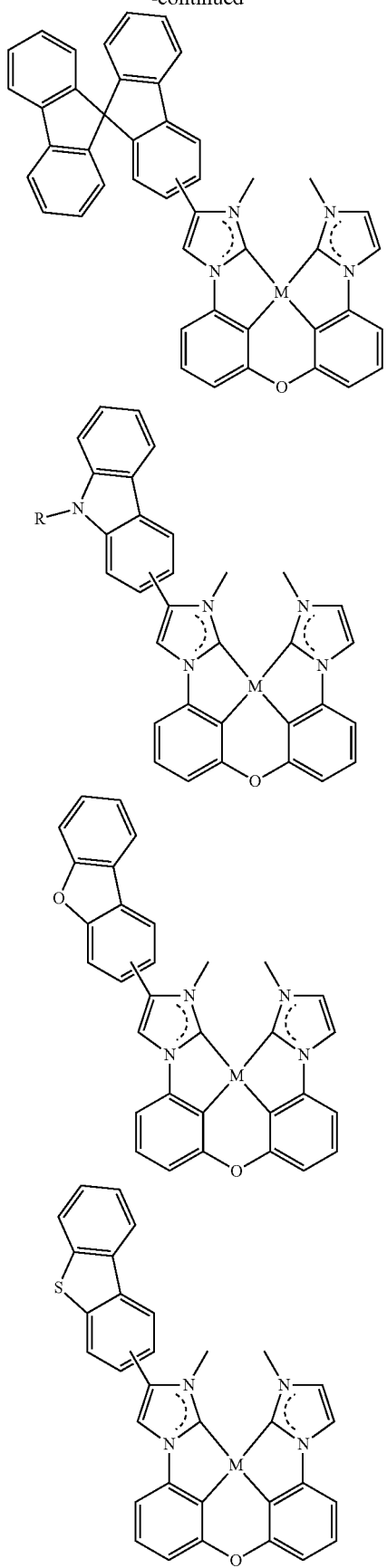

157
-continued
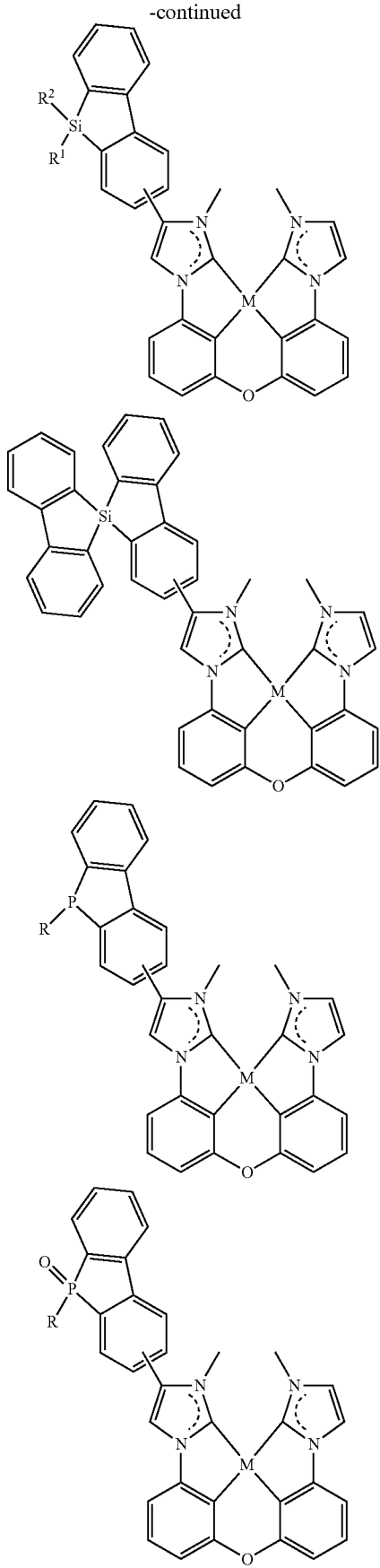
158
-continued
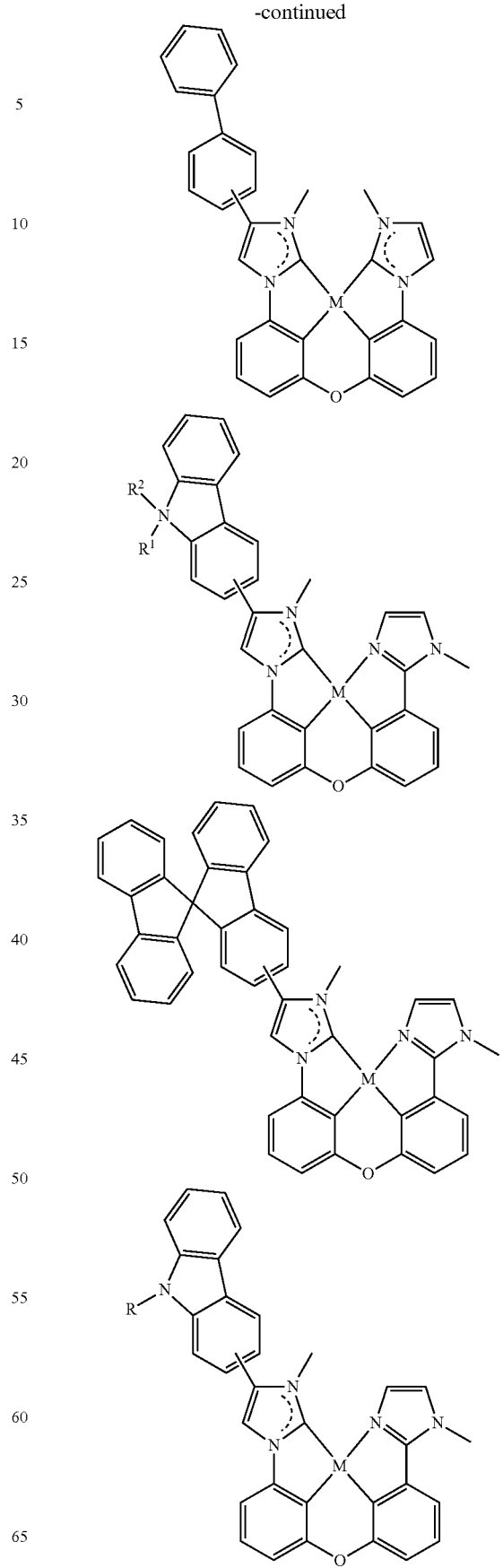

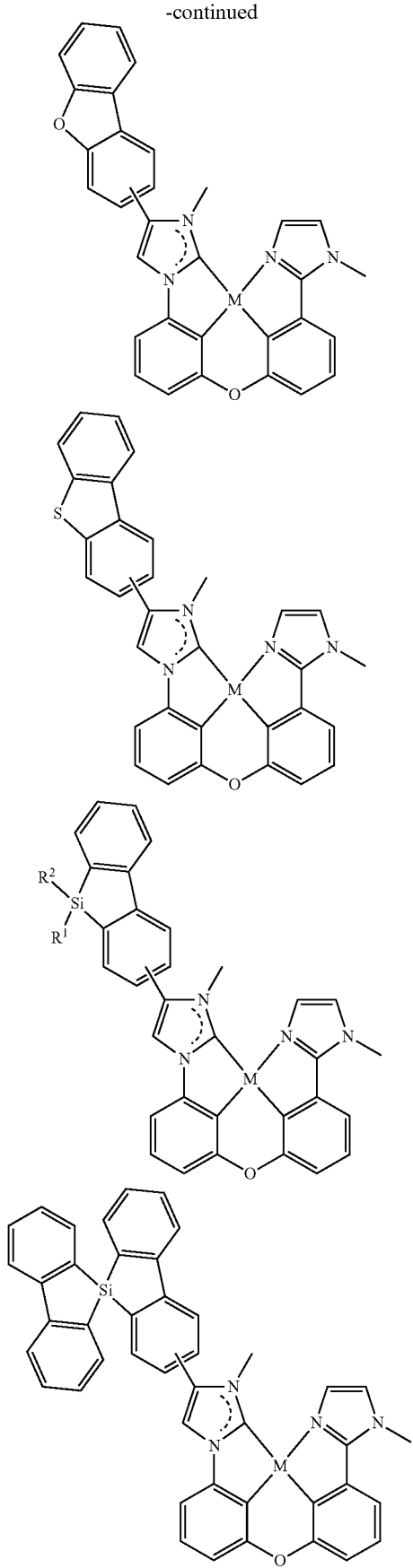

-continued
Structure 15
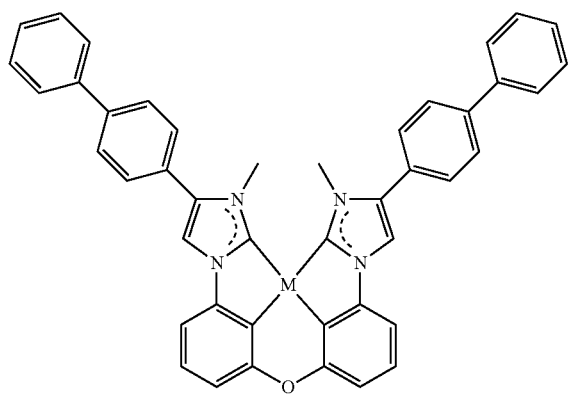
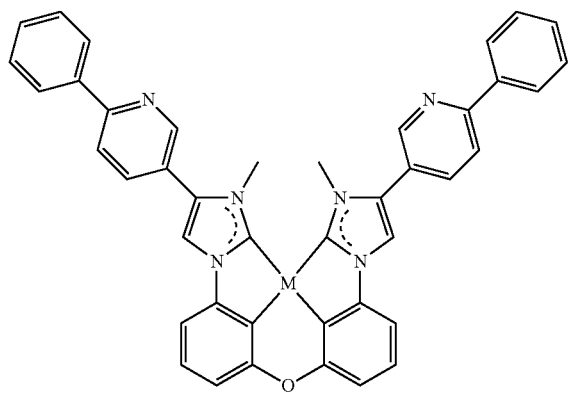
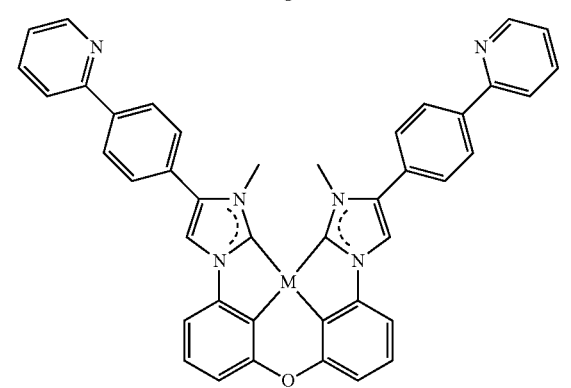
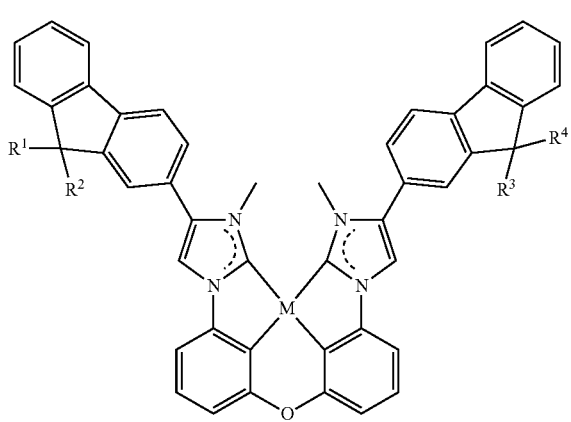
-continued
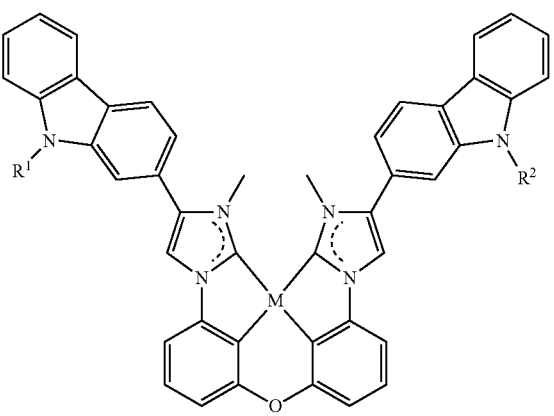
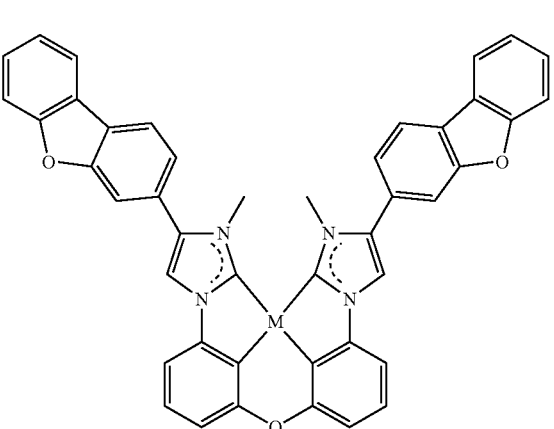
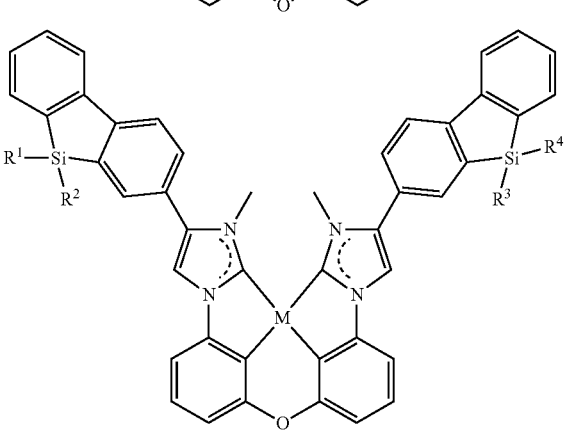
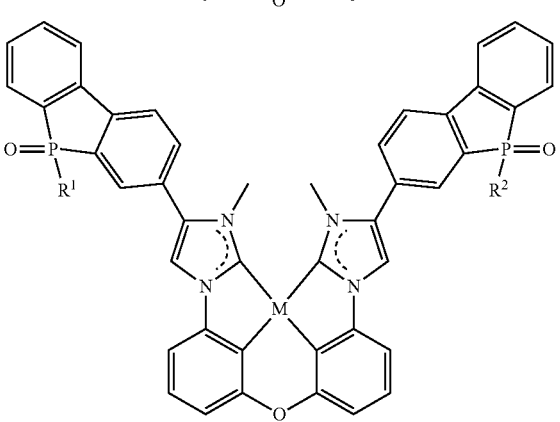

163
-continued
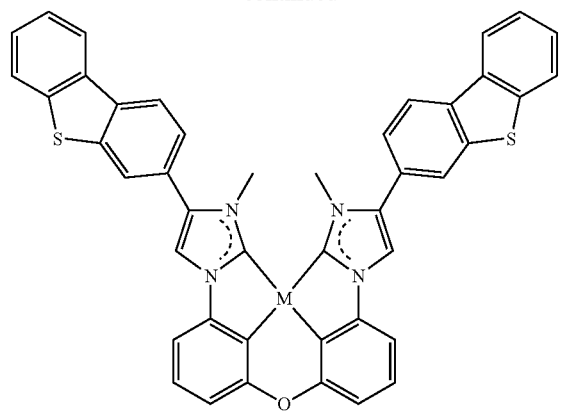
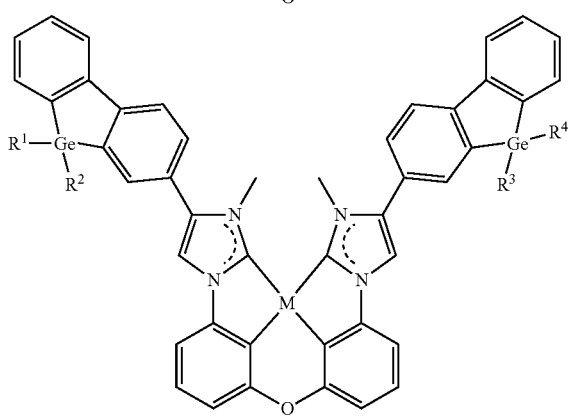
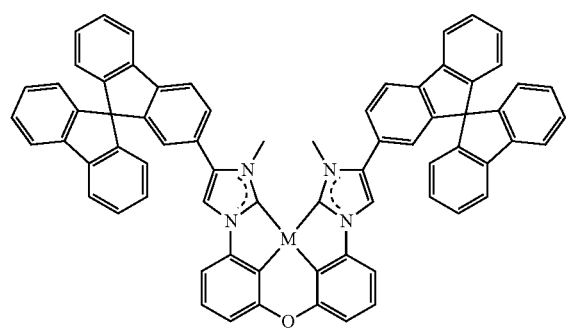
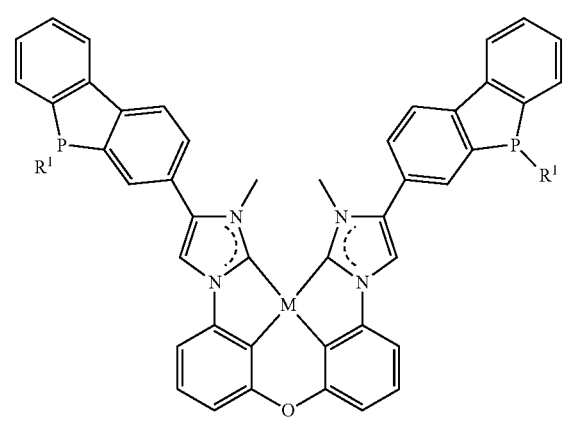
164
-continued
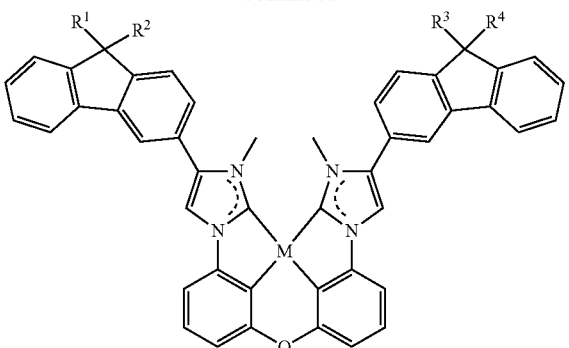
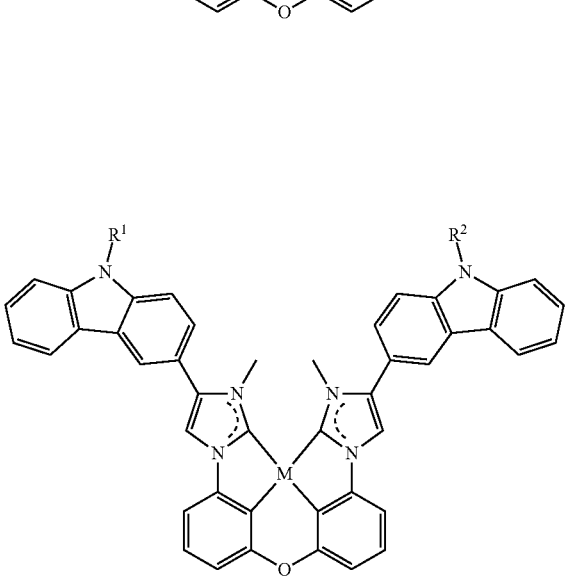
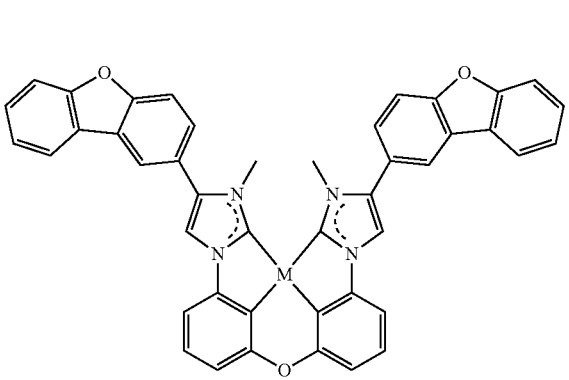
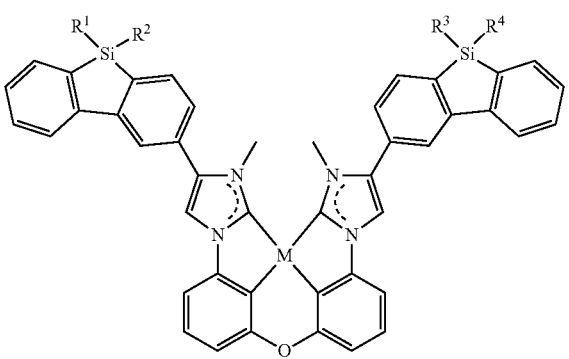

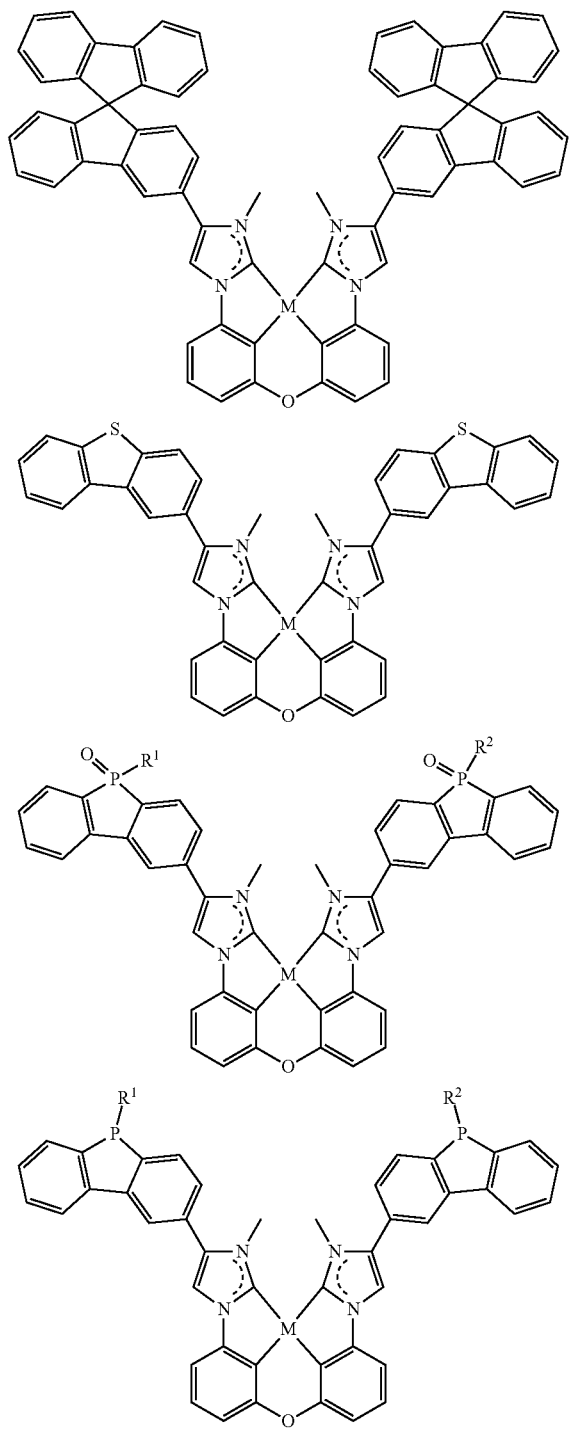
(M = Pt, Pd)
Structure 16
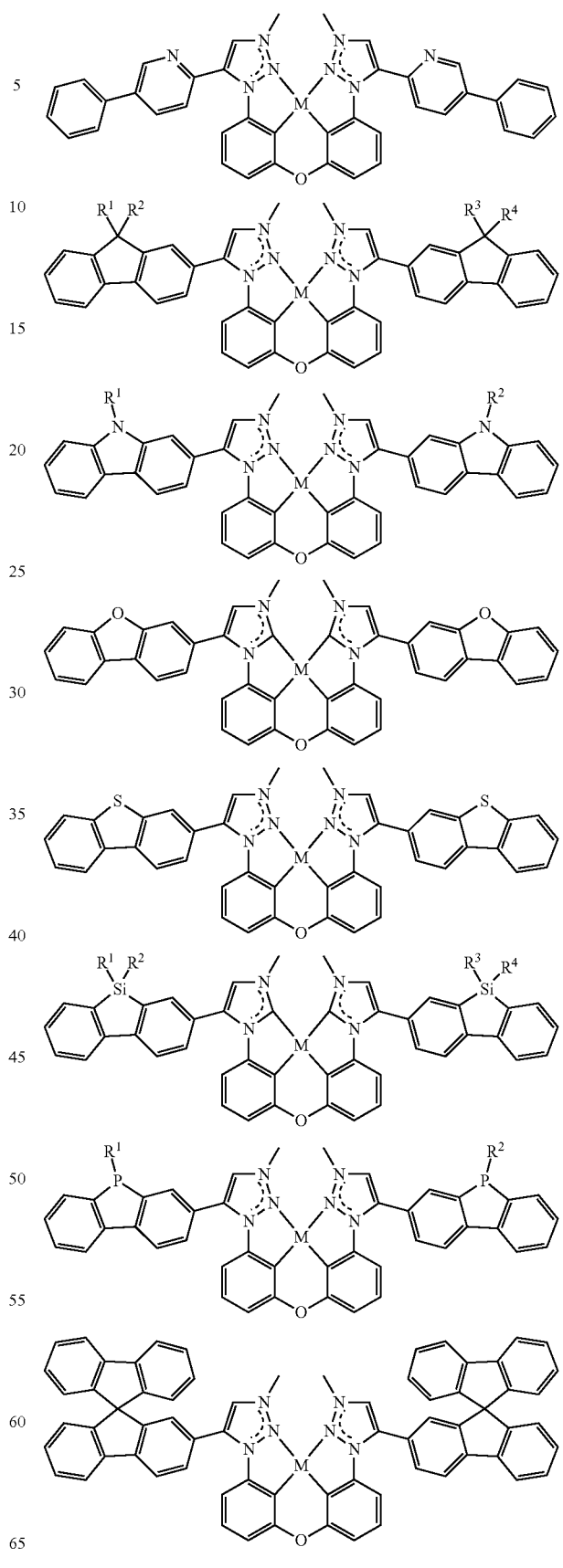

-continued
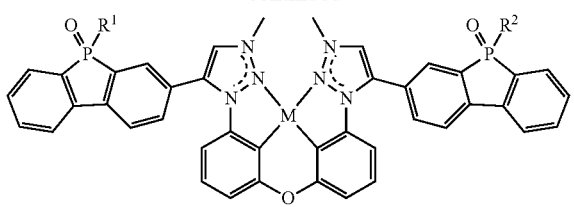
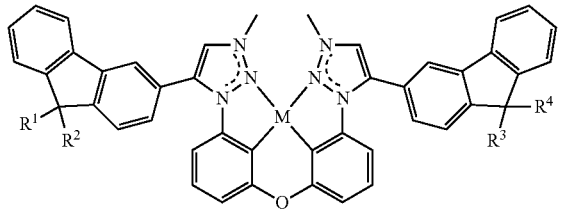
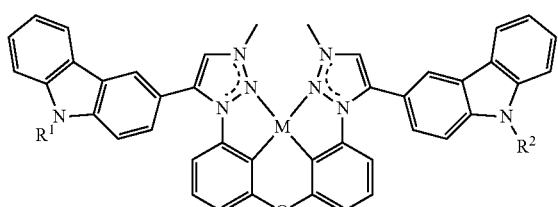
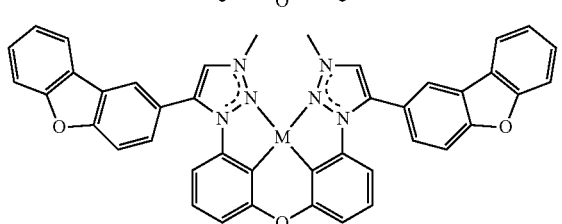
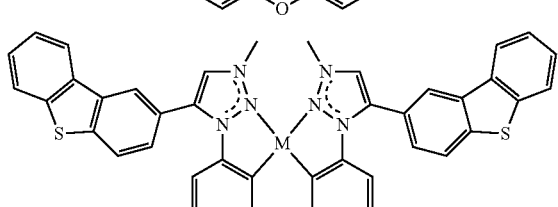
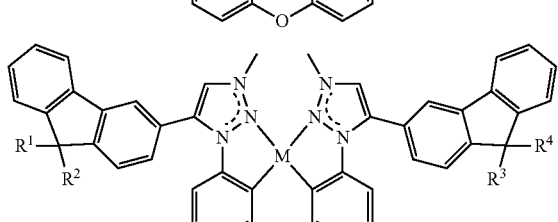
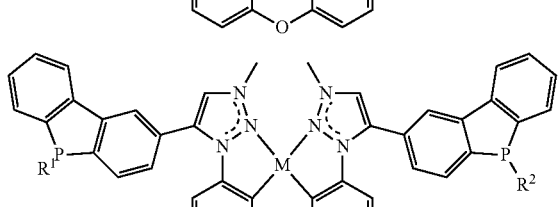
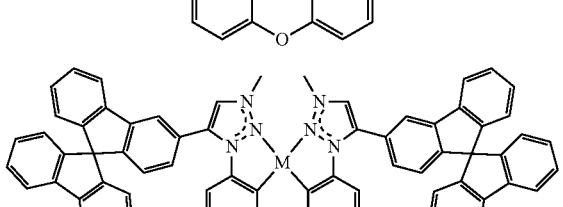
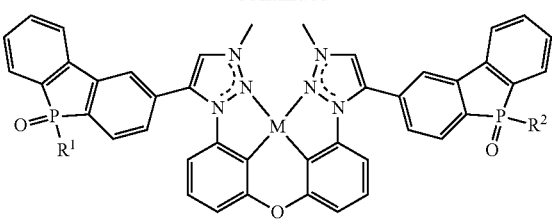
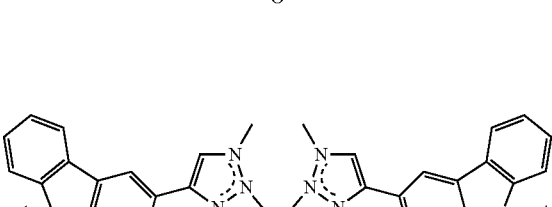
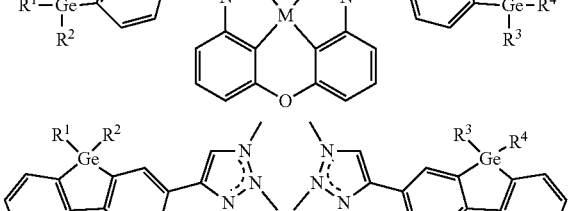
(M = Pt, Pd)
Structures 17
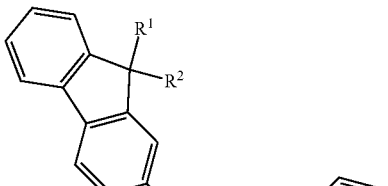
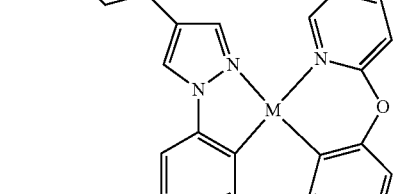

169
-continued
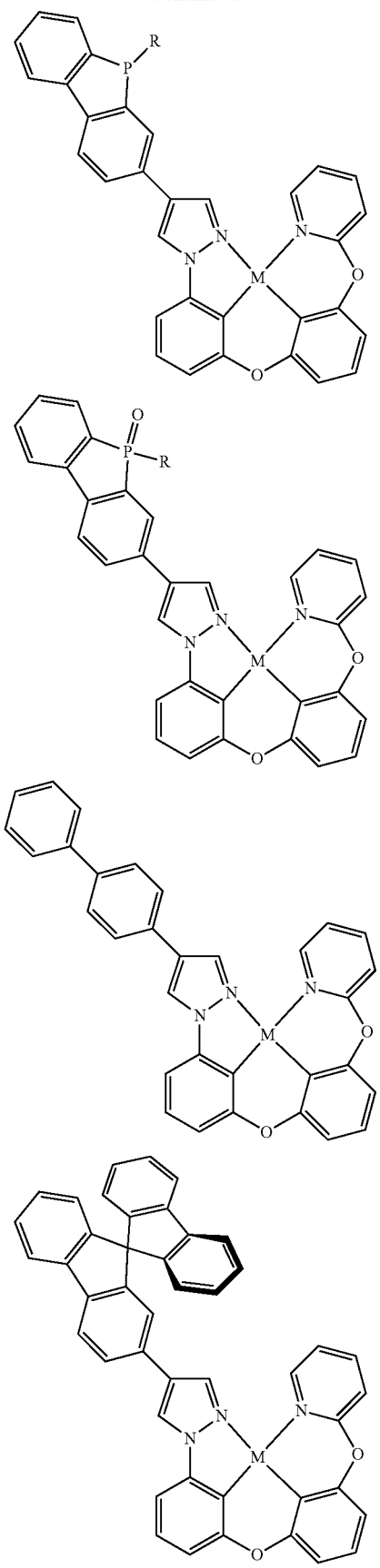
170
-continued
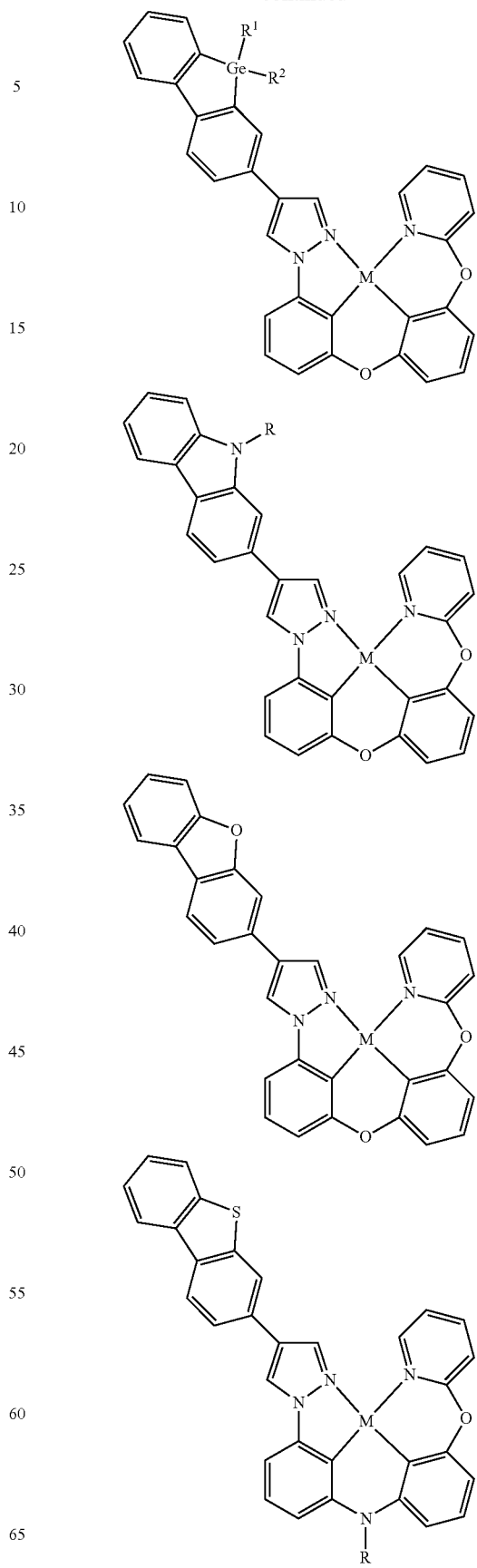

171
-continued
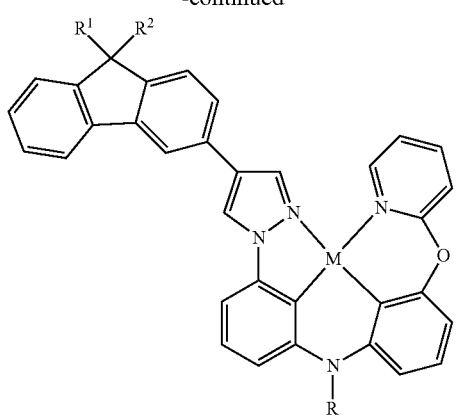
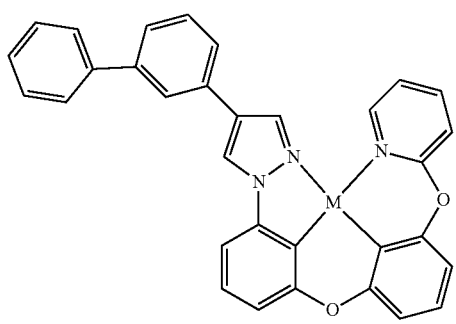
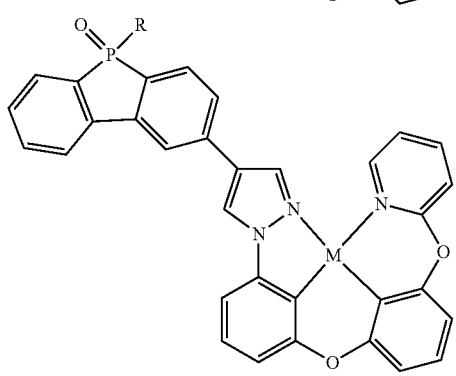
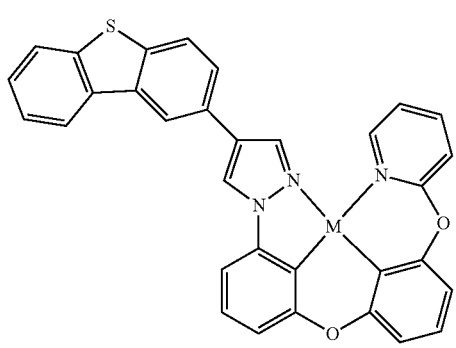
172
-continued
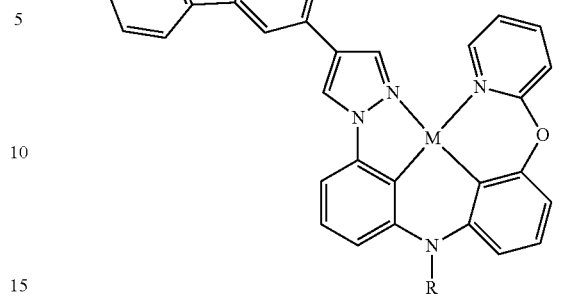
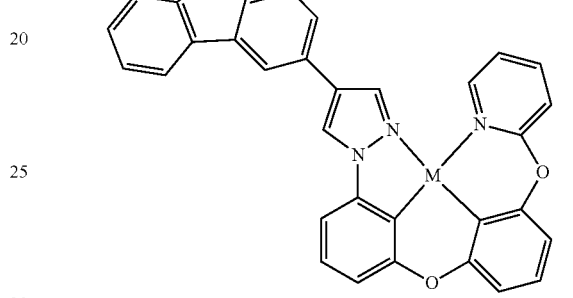
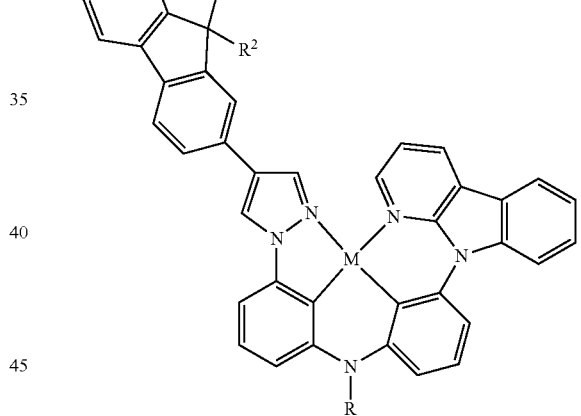
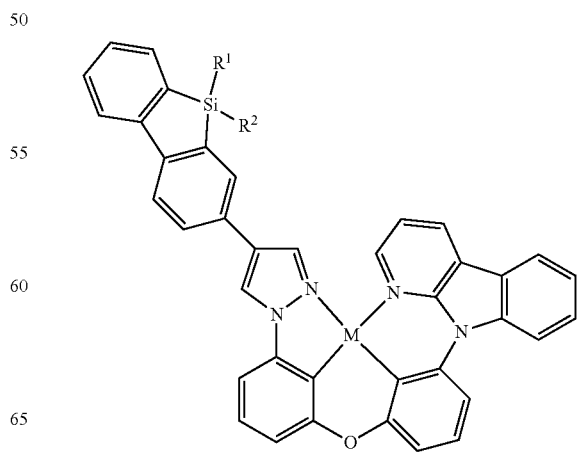

173
-continued
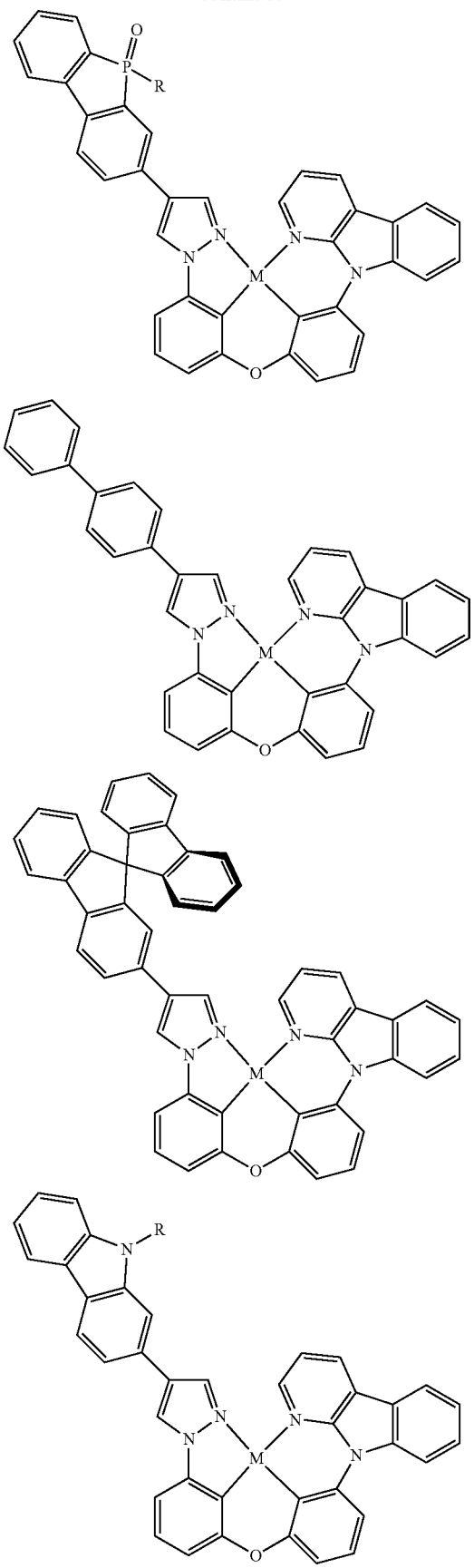
174
-continued
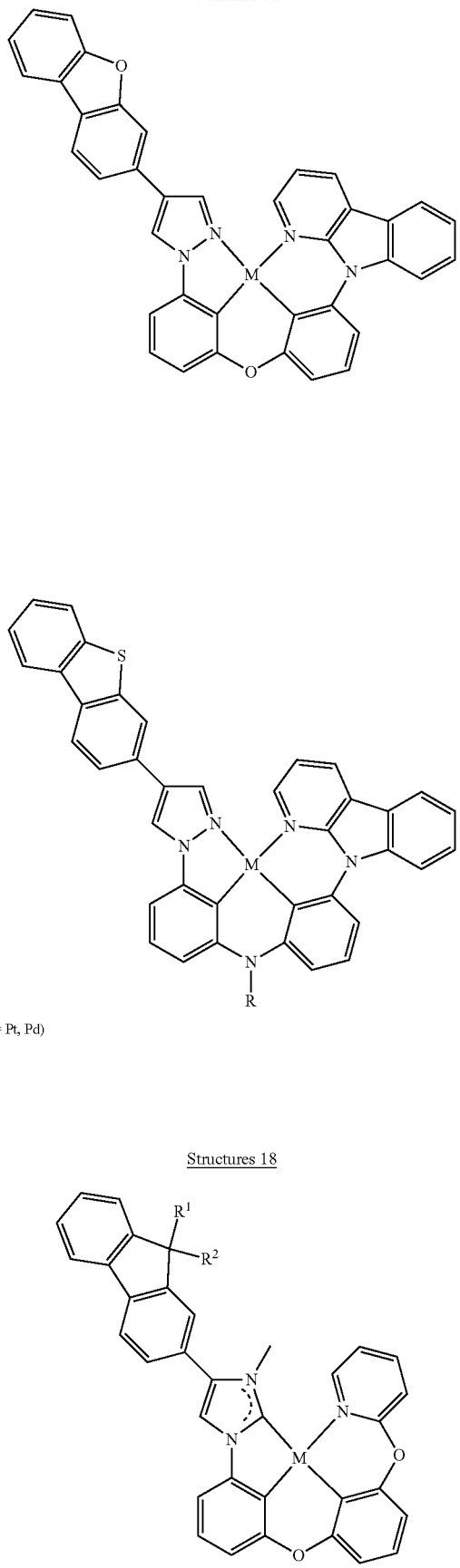
(M = Pt, Pd)
Structures 18

175
-continued
176
-continued
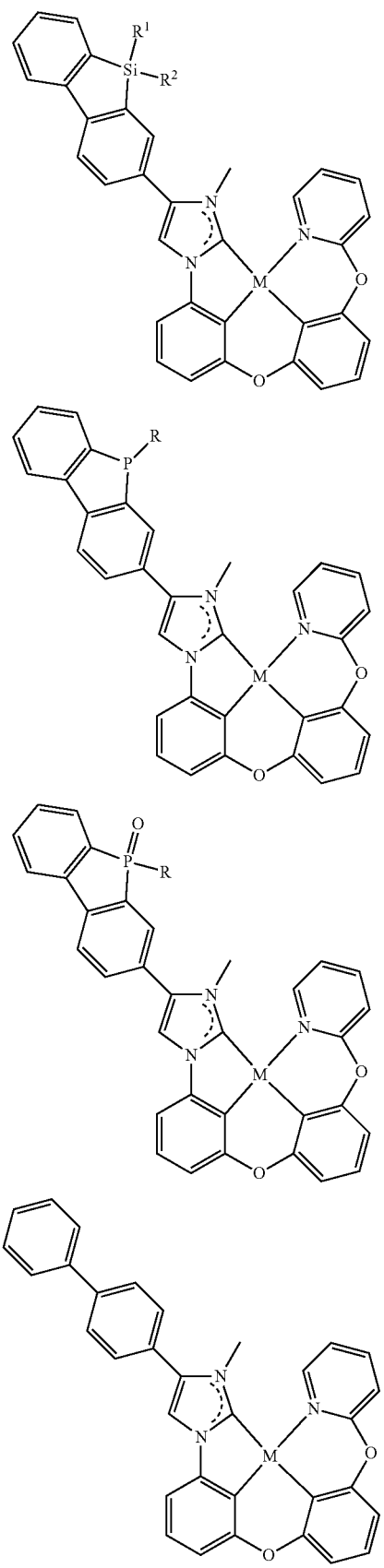
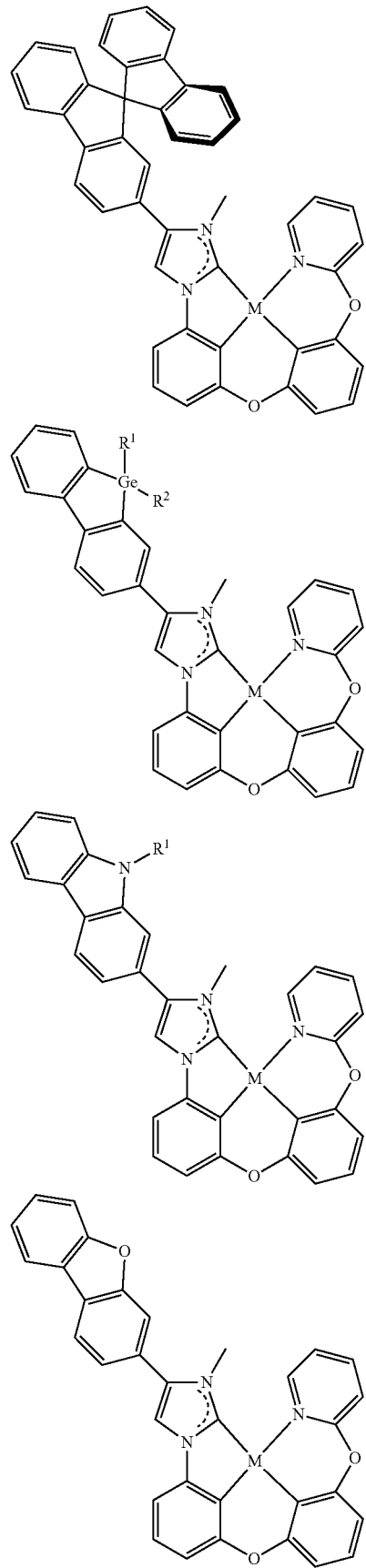

177
-continued
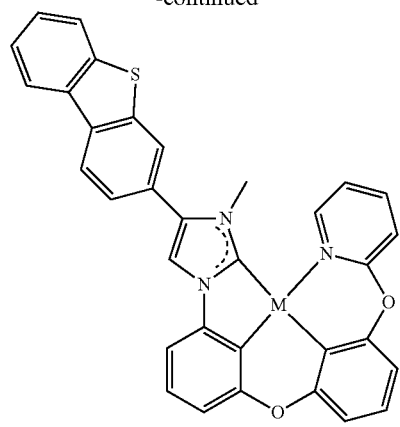
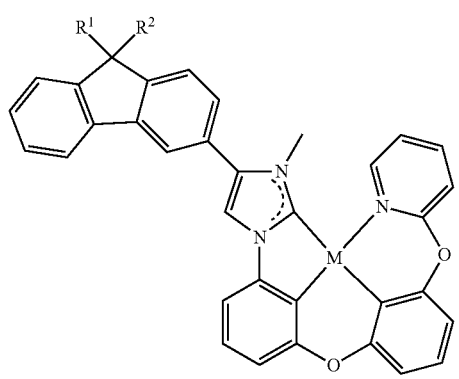
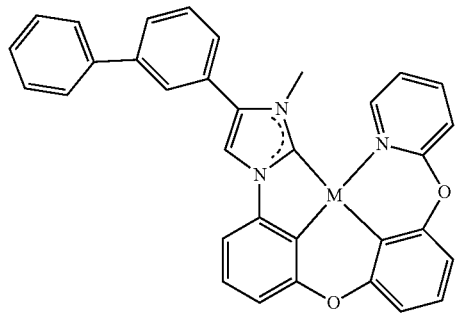
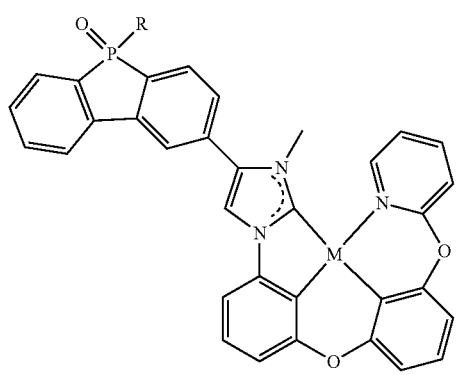
178
-continued
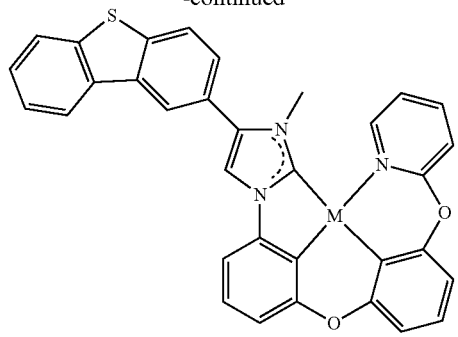
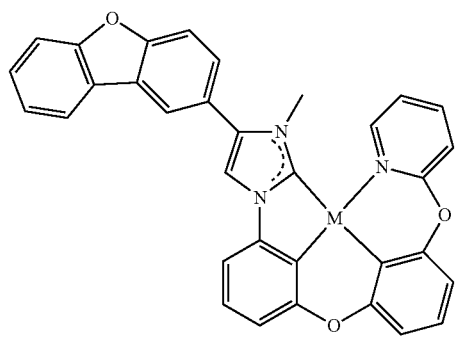
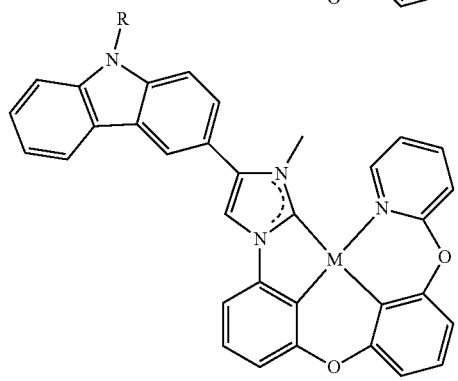
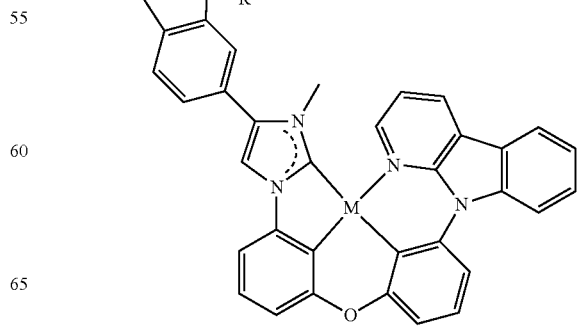

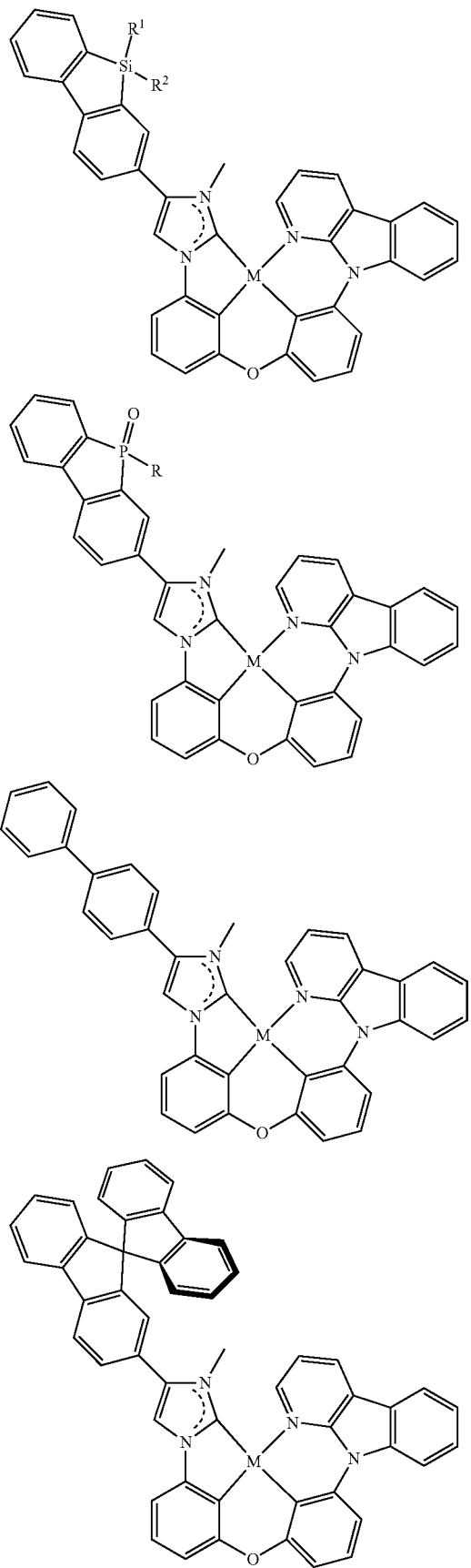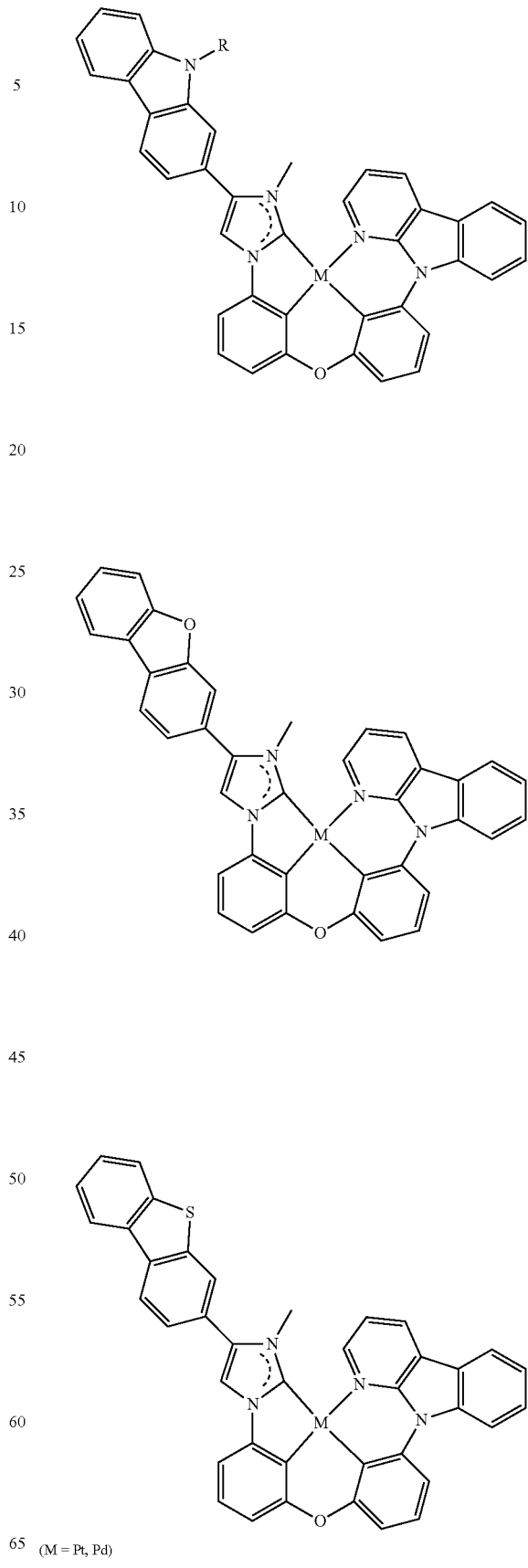
(M = Pt, Pd)

-continued
Structure 19
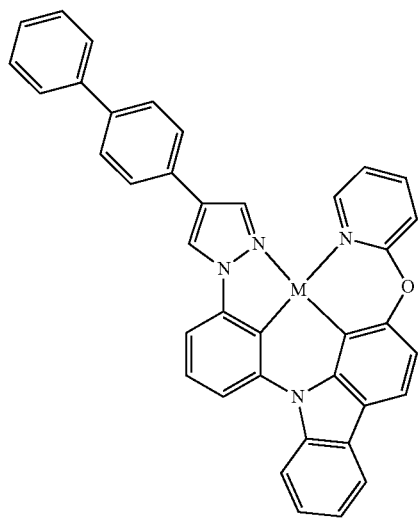
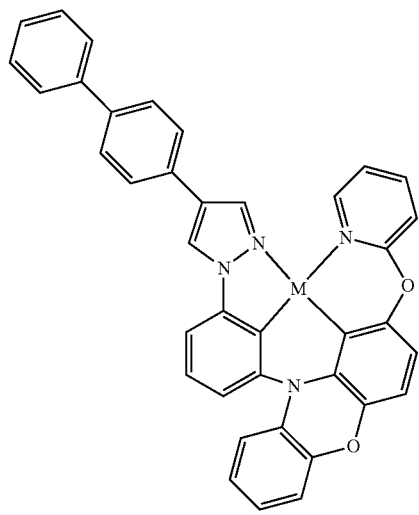
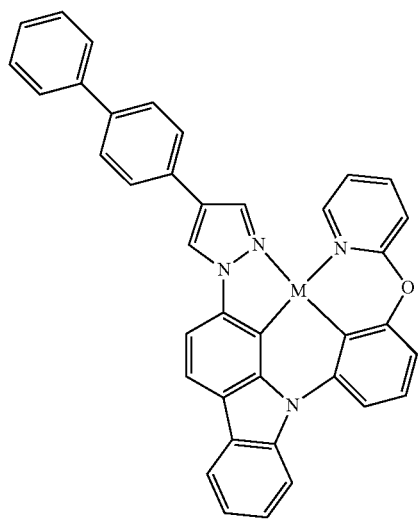
-continued
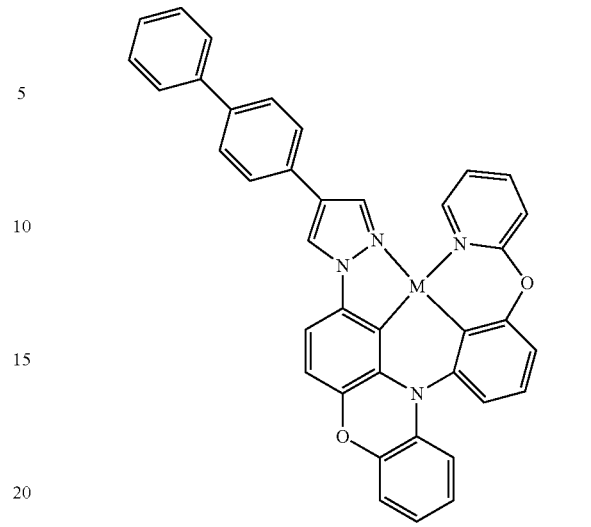
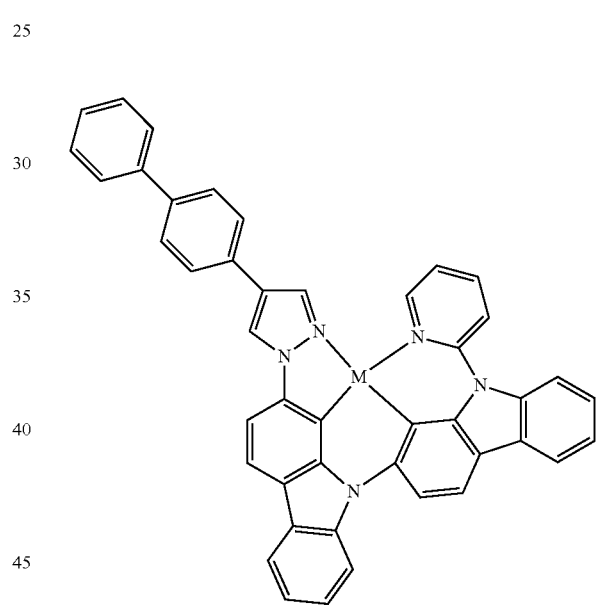
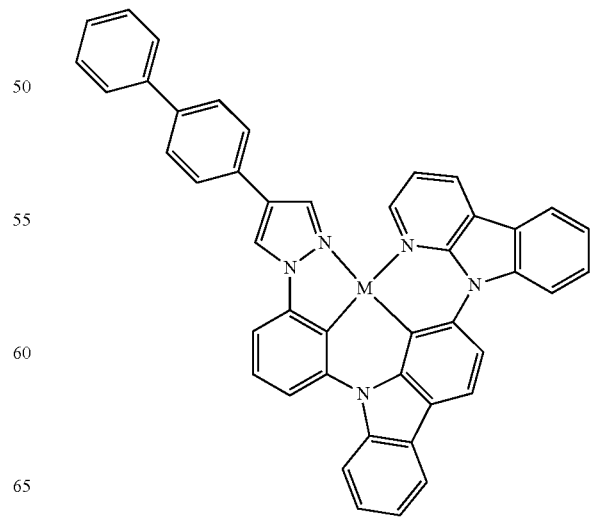

183
-continued
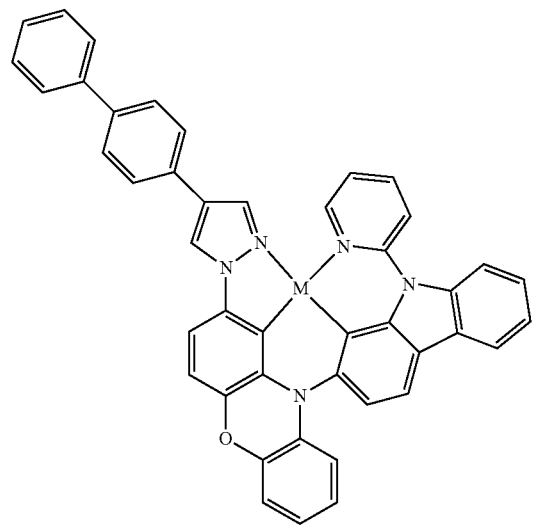
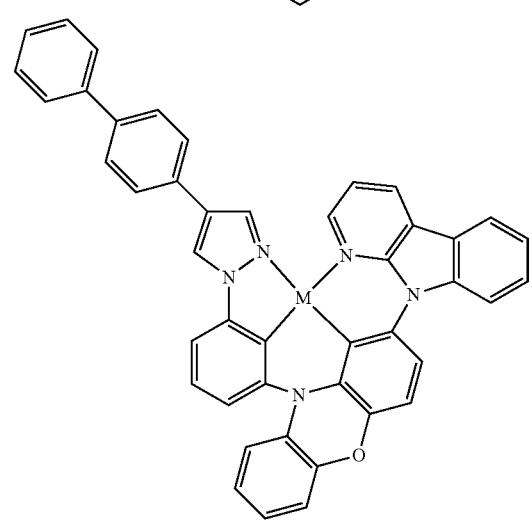
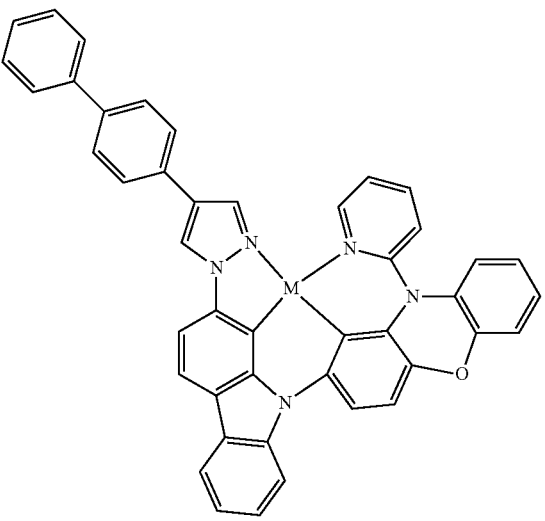
184
-continued
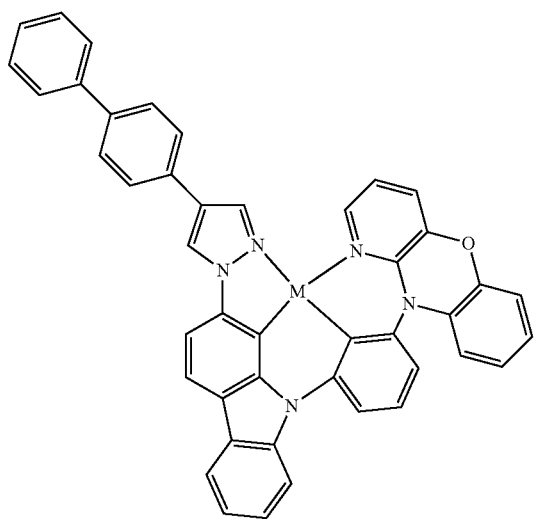
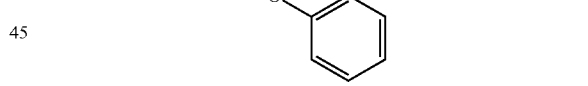
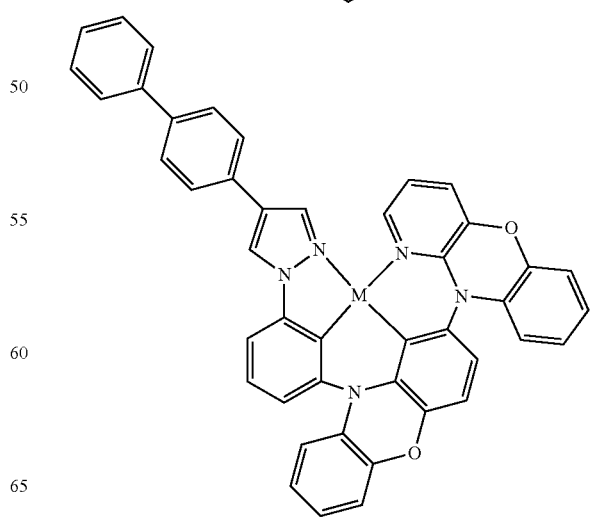

-continued
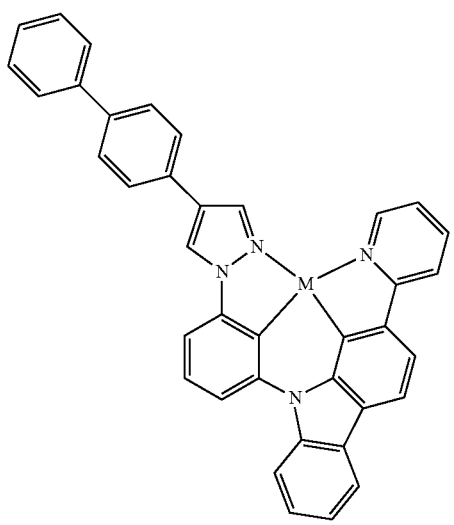
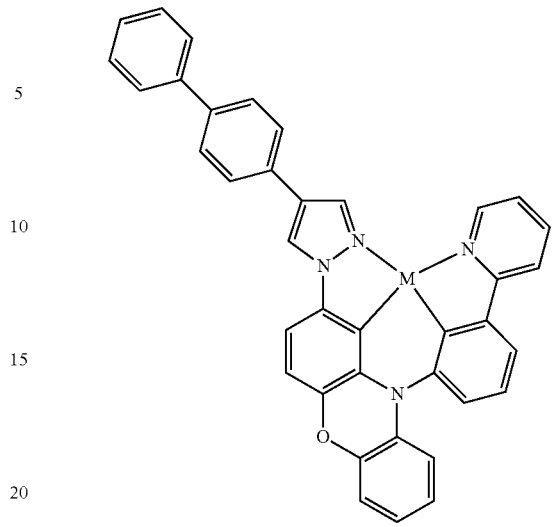
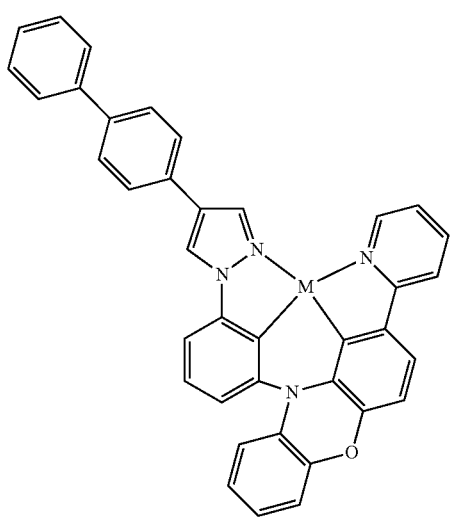
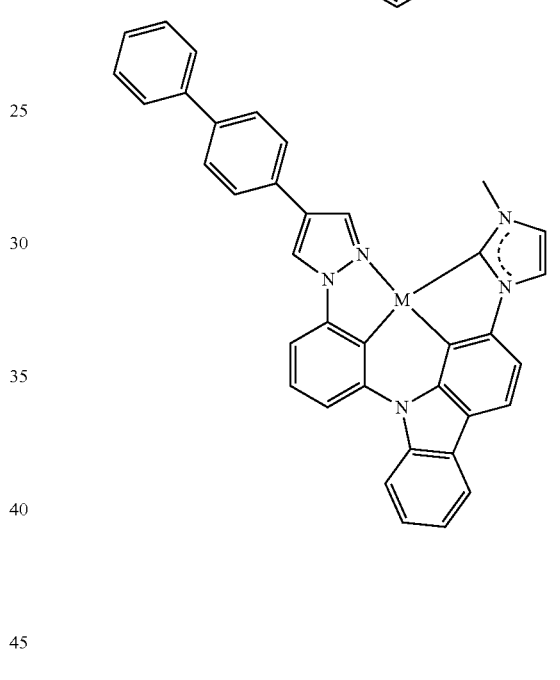
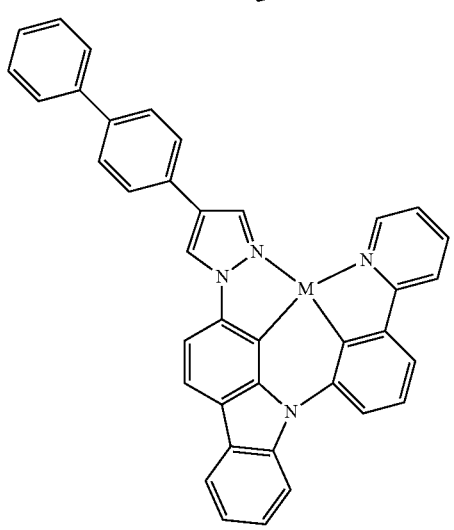
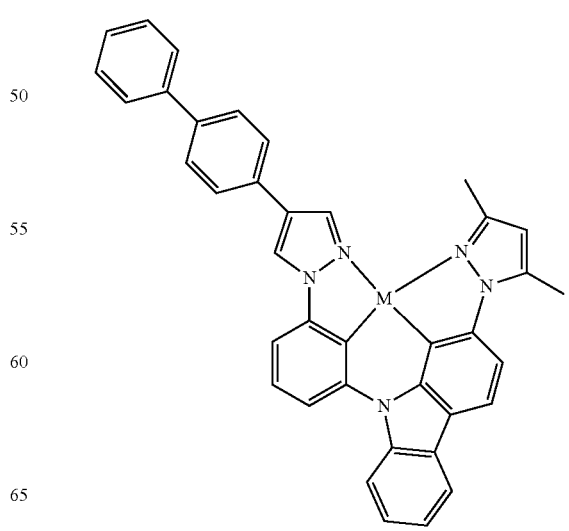

187
-continued
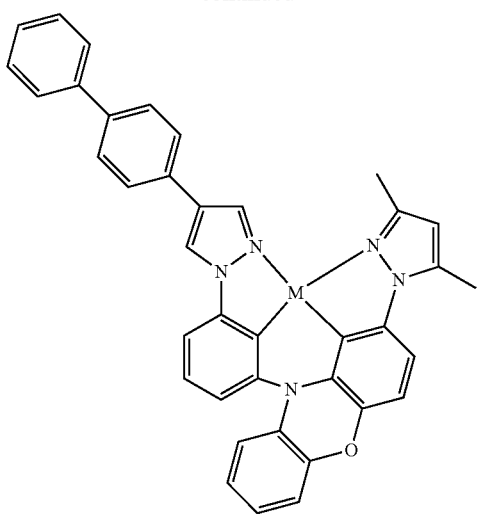
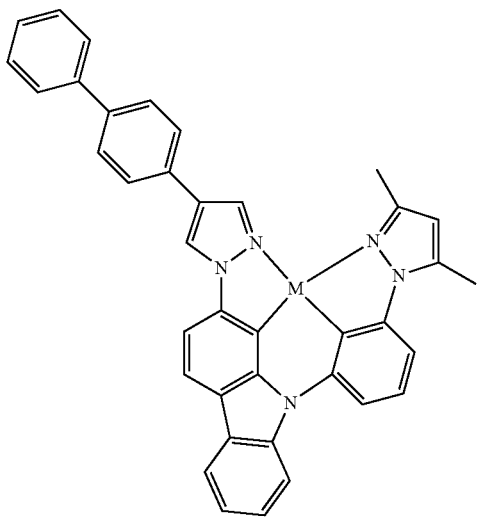
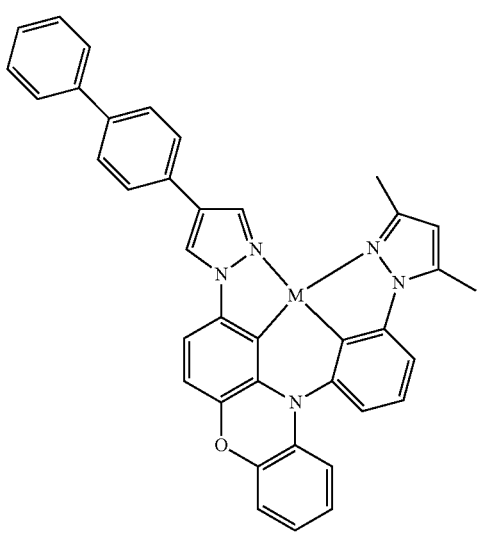
188
-continued
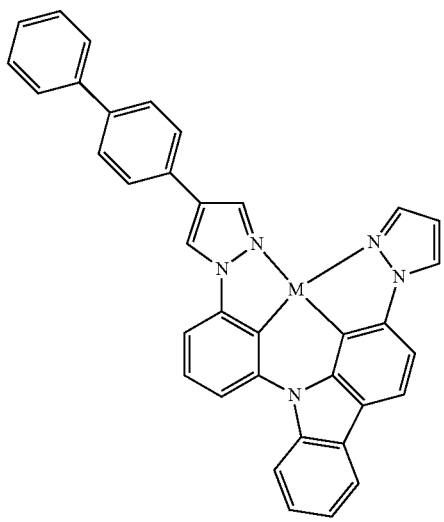
(M = Pt, Pd)
Structures 20
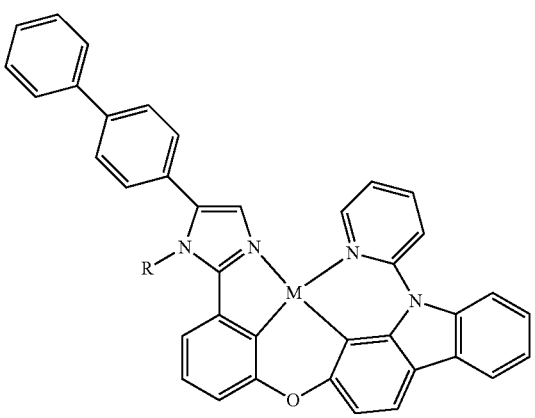
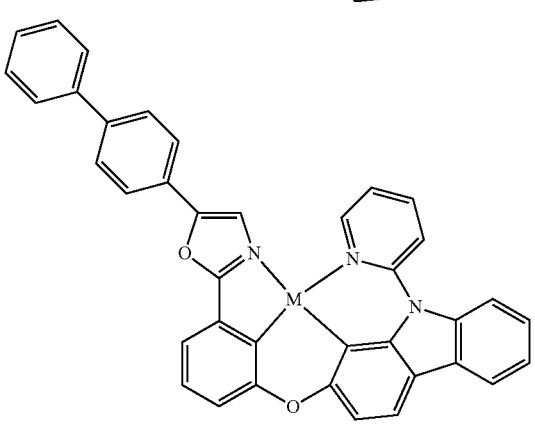

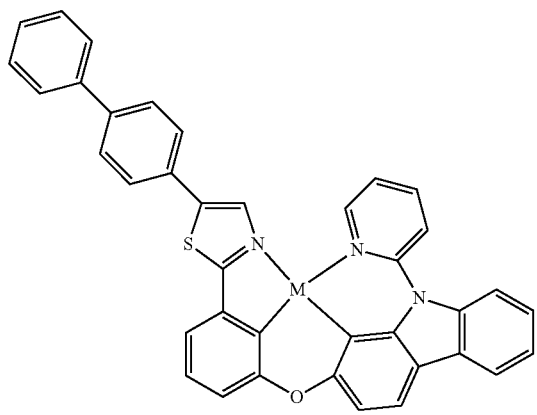
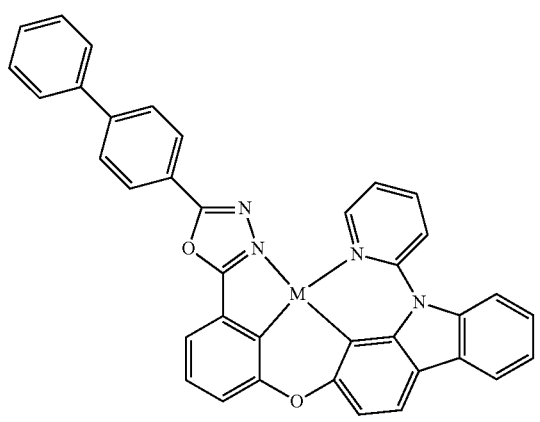
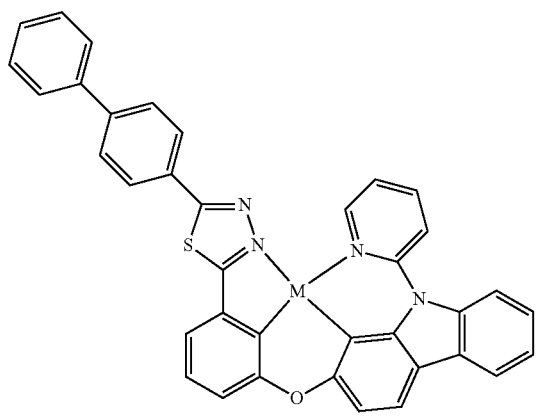
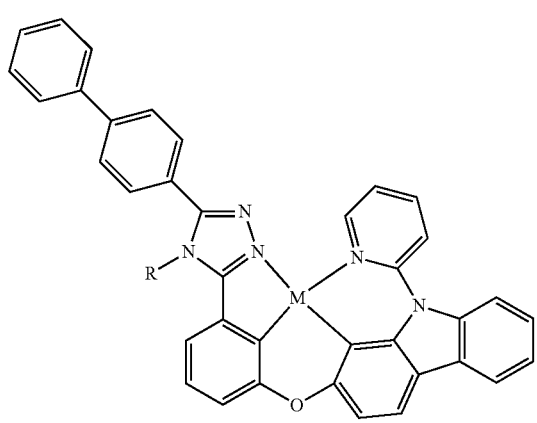
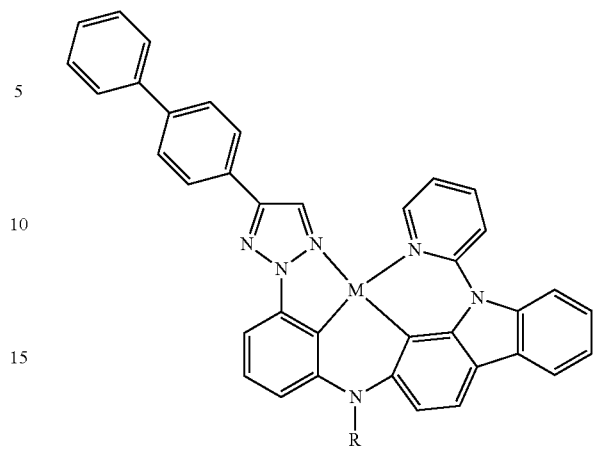
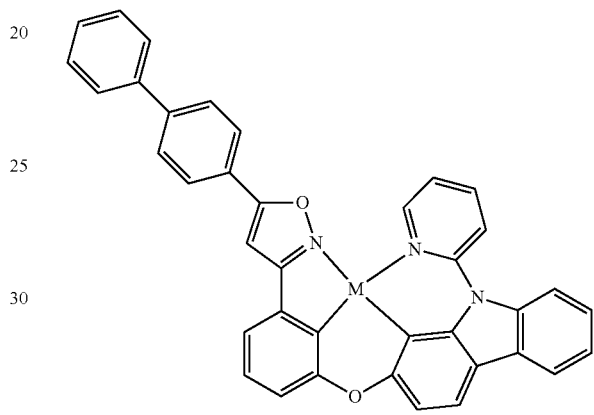
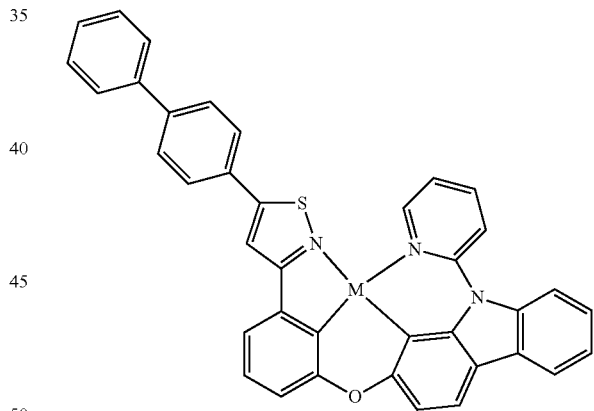
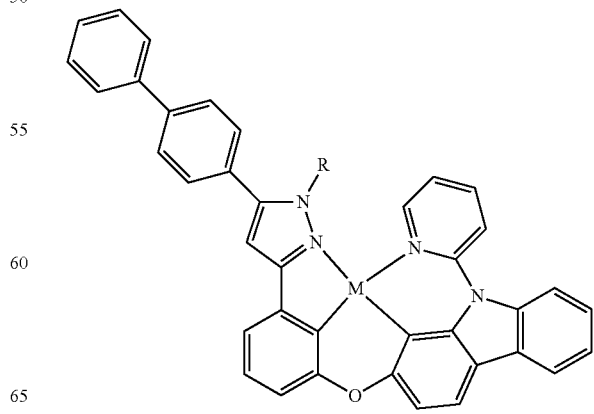

191
-continued
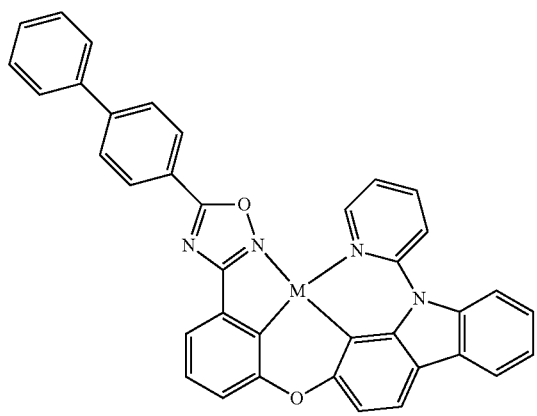
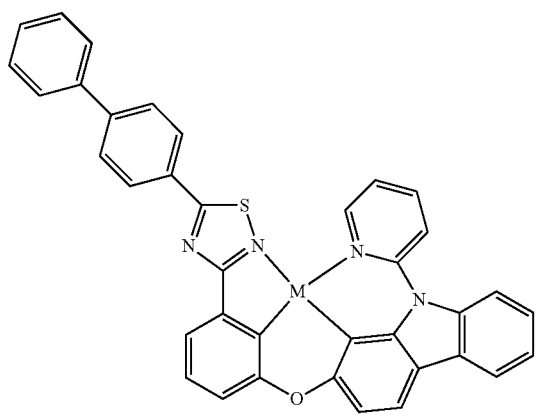
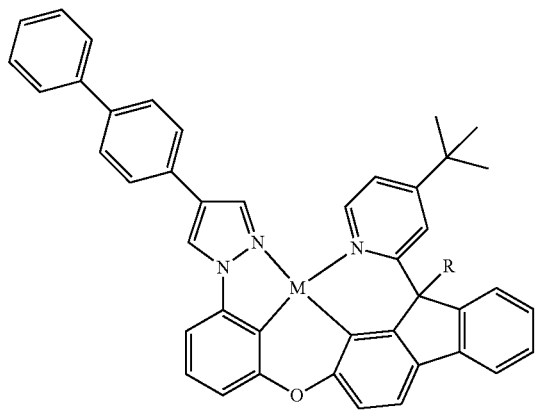
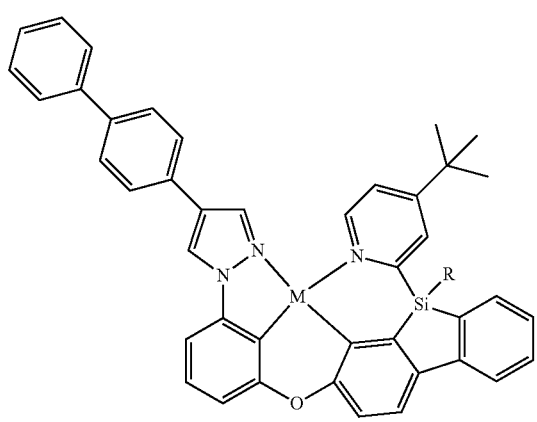
192
-continued
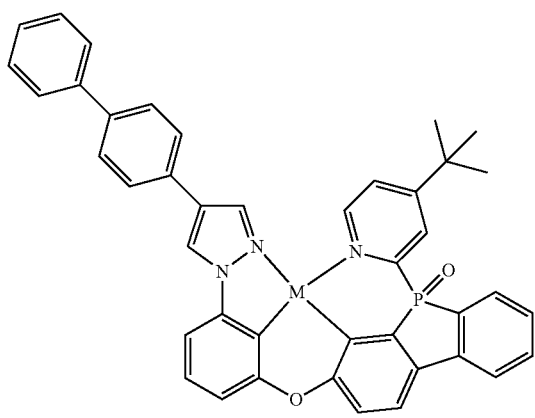
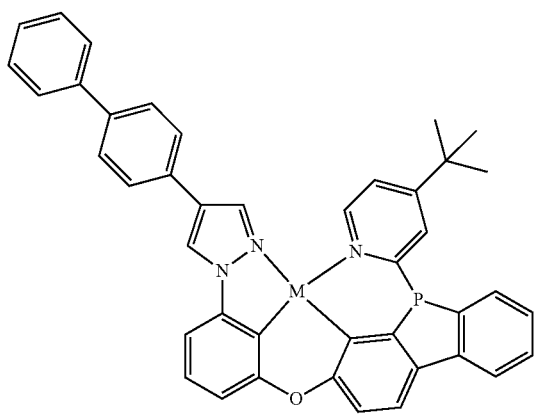
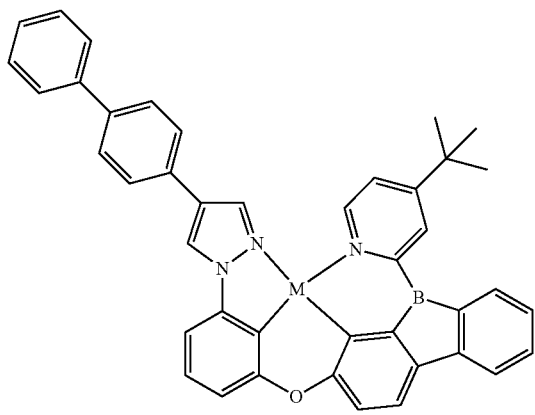
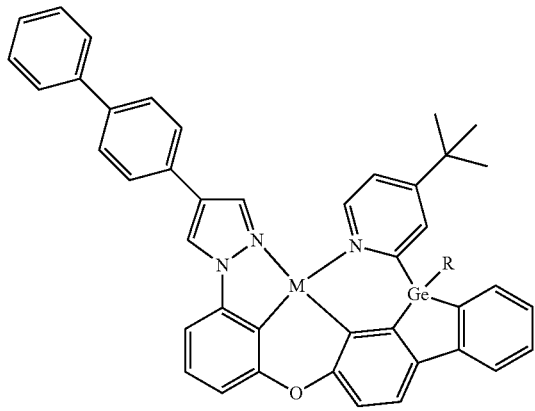

193
-continued
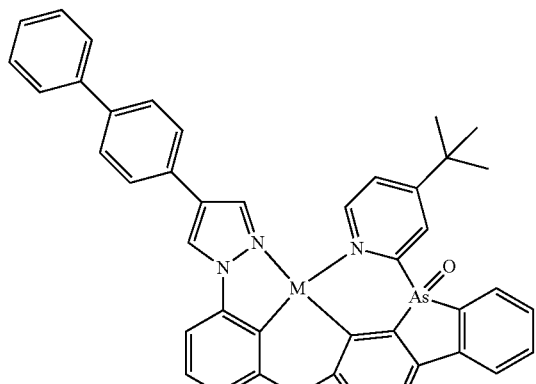
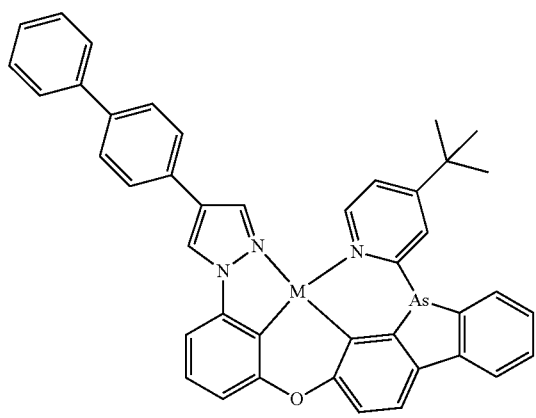
(M = Pt, Pd)
Structures 21
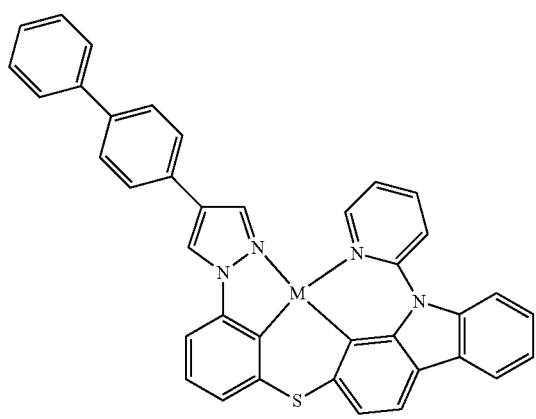
194
-continued
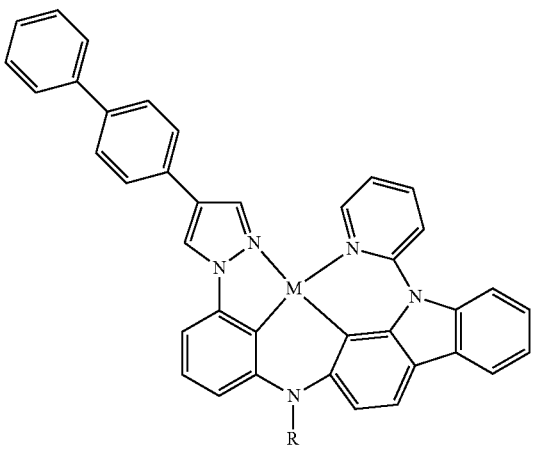
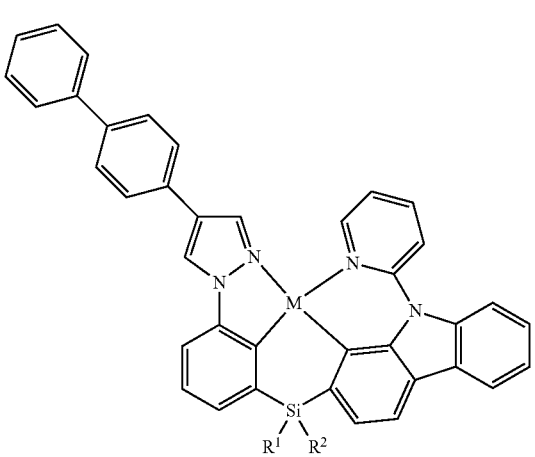

195
-continued
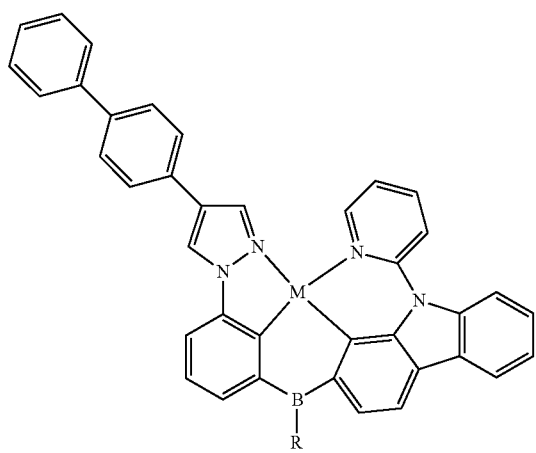
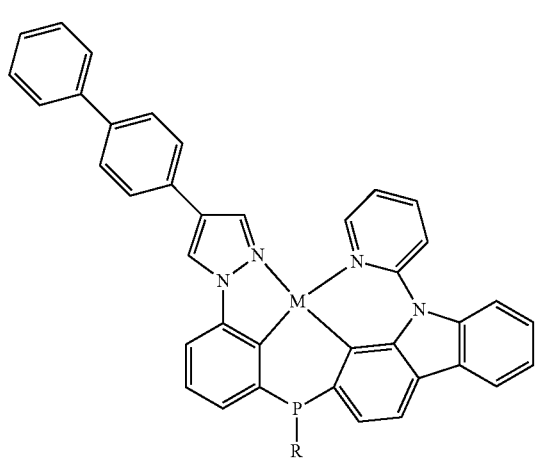
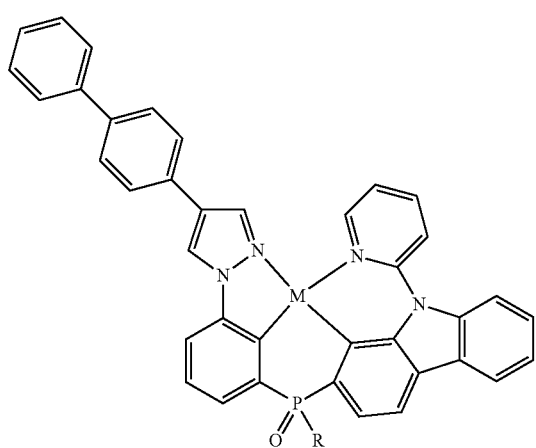
196
-continued
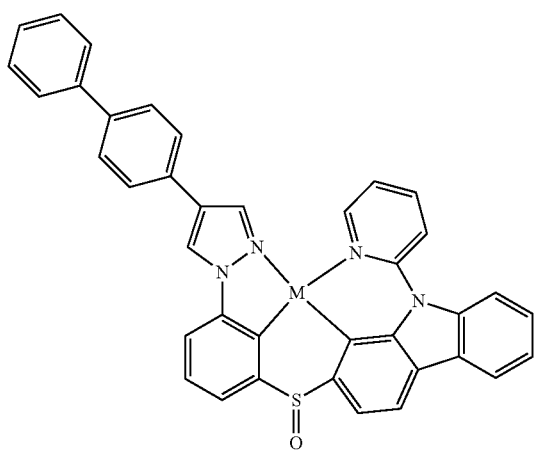
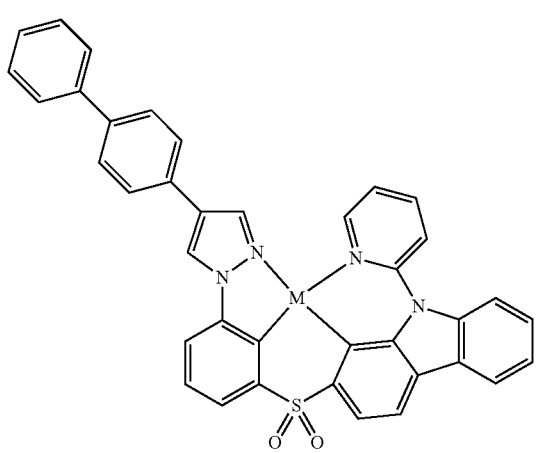
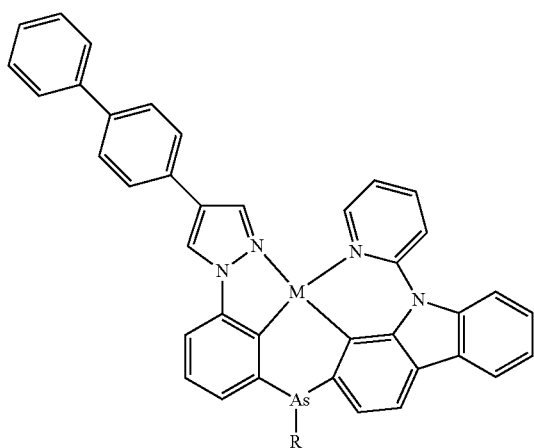

197
-continued
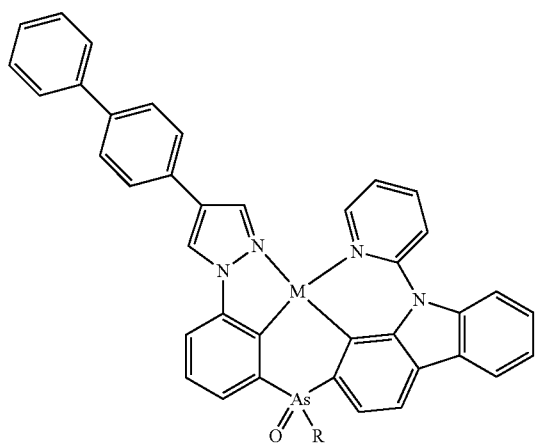
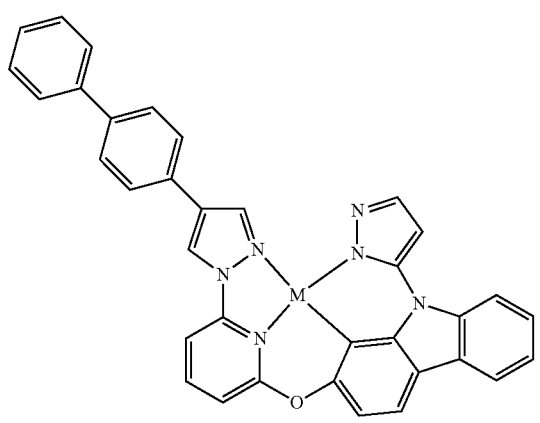
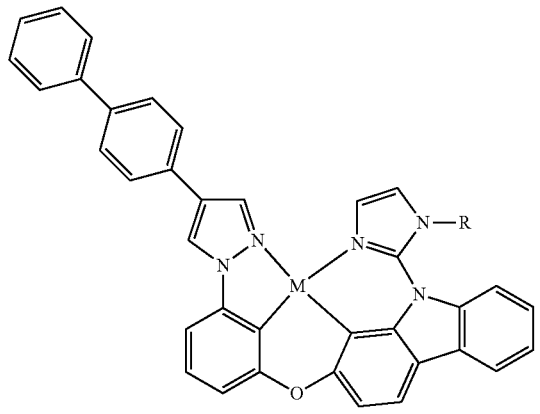
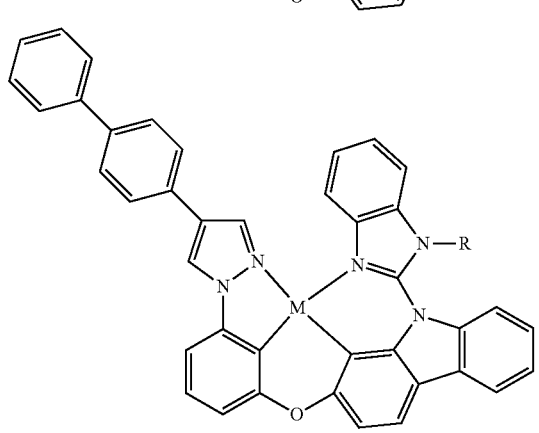
198
-continued
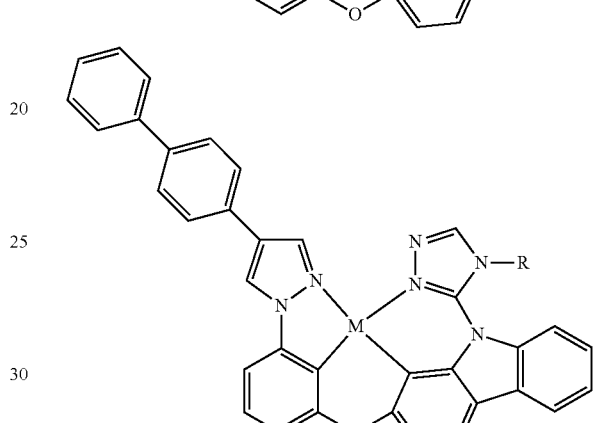
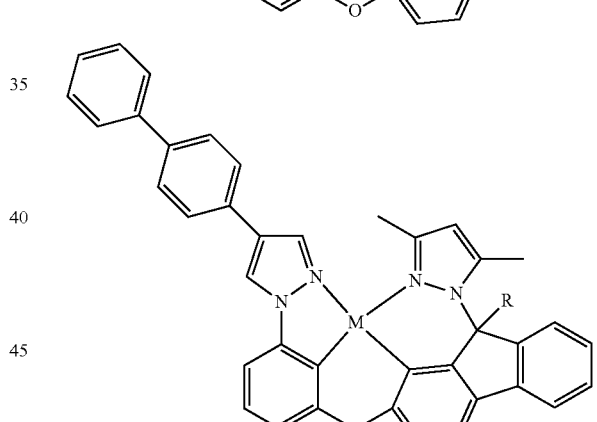
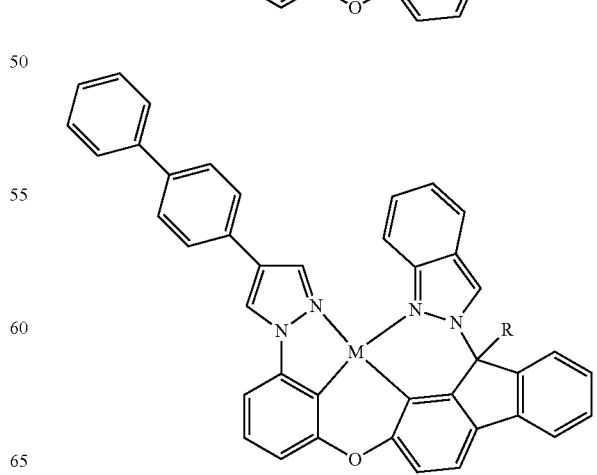

199
-continued
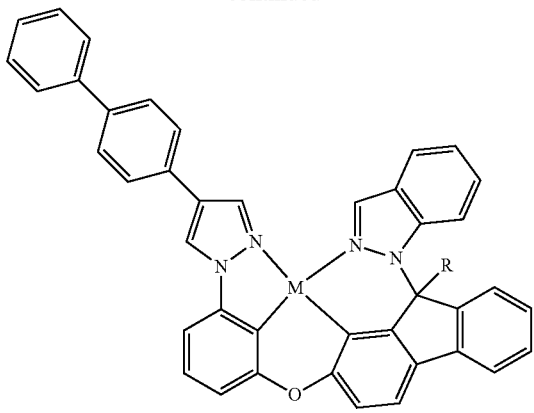
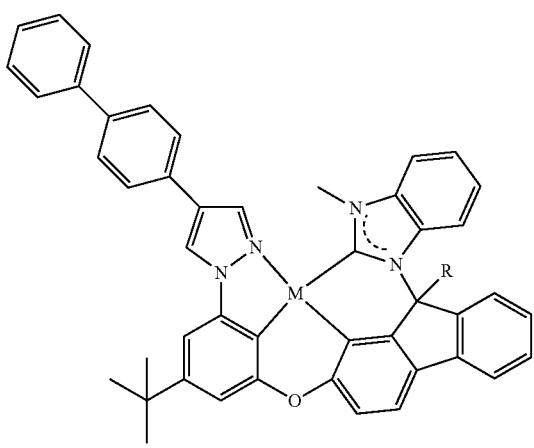
(M = Pt, Pd)
Structures 22
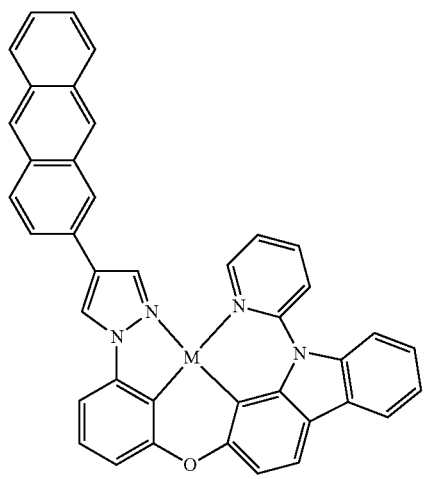
200
-continued
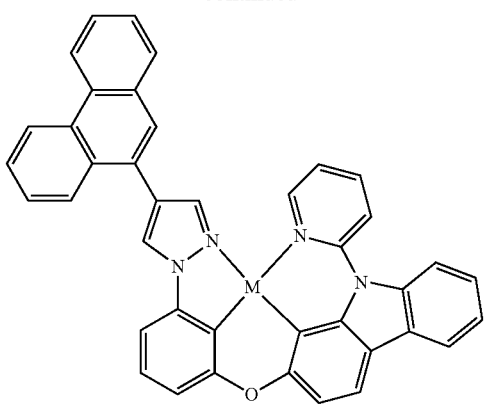
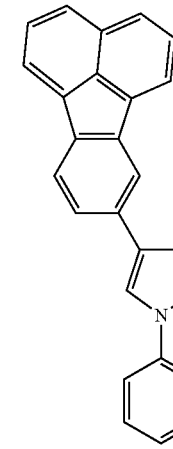
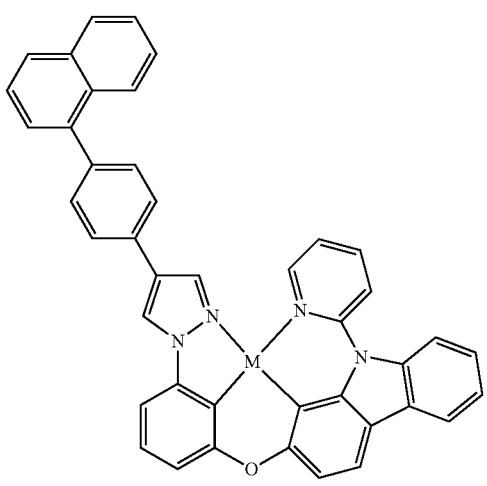

201
-continued
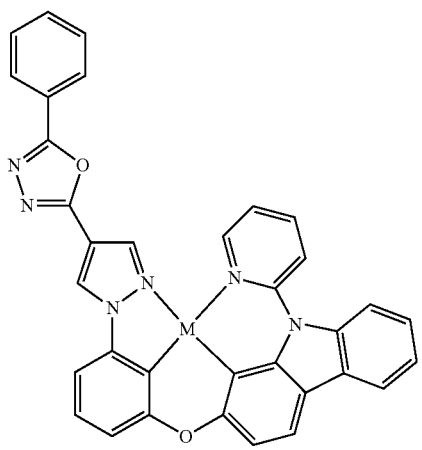
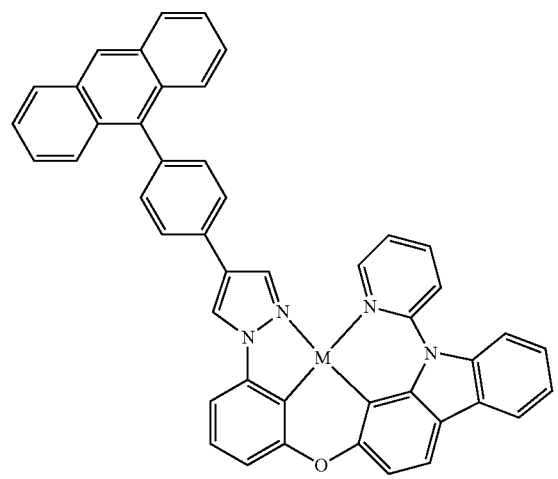
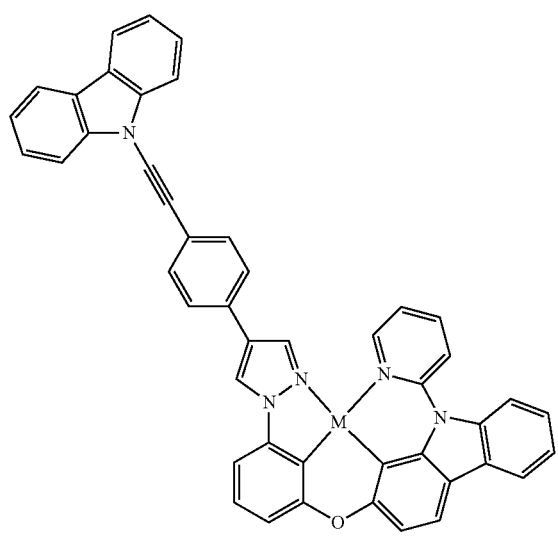
202
-continued
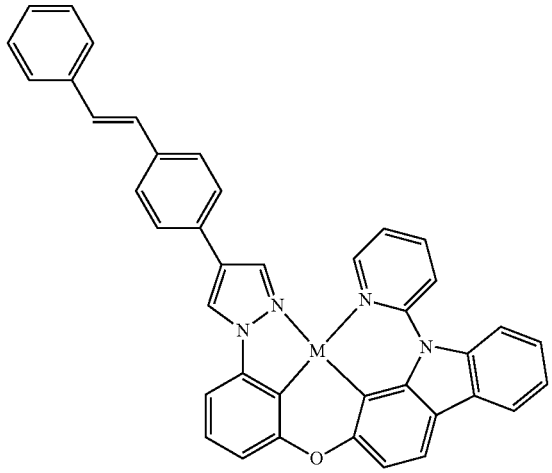
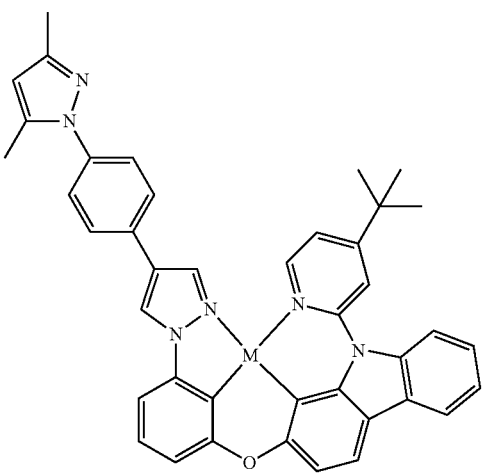

203
-continued
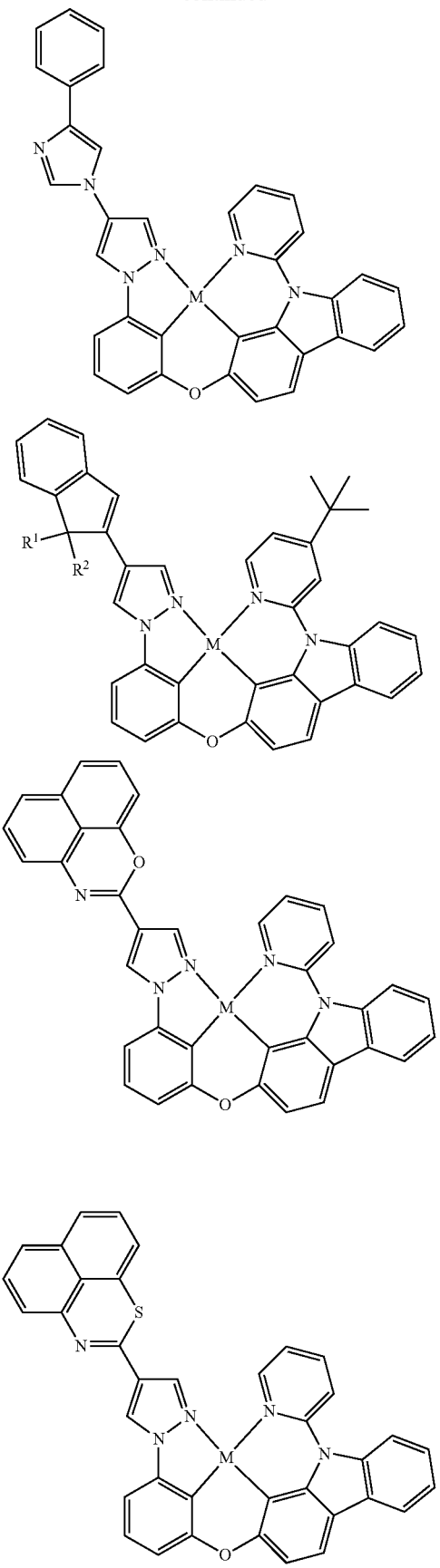
204
-continued
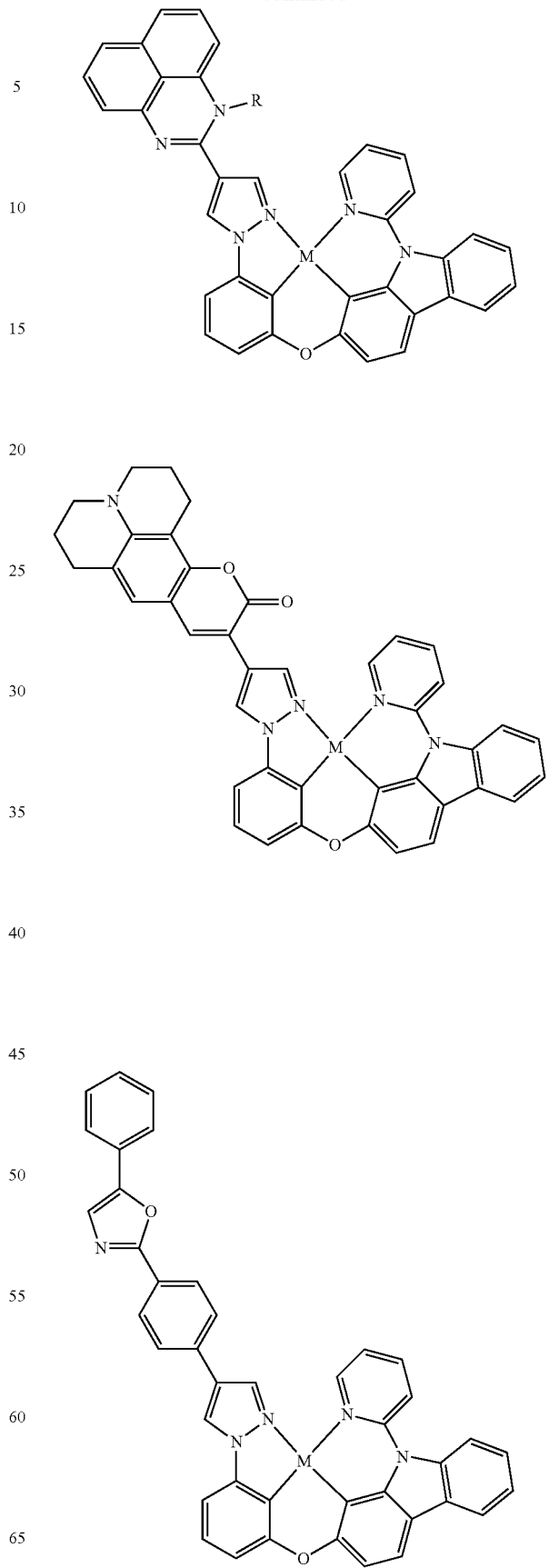

205
-continued
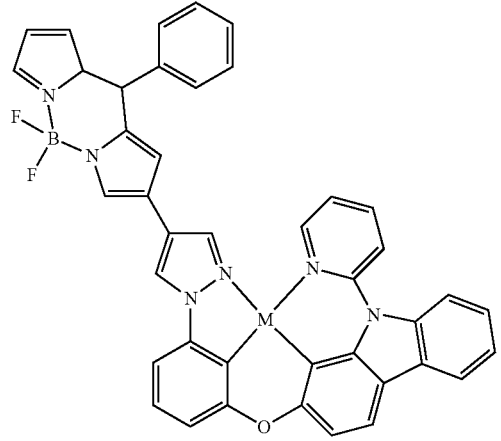
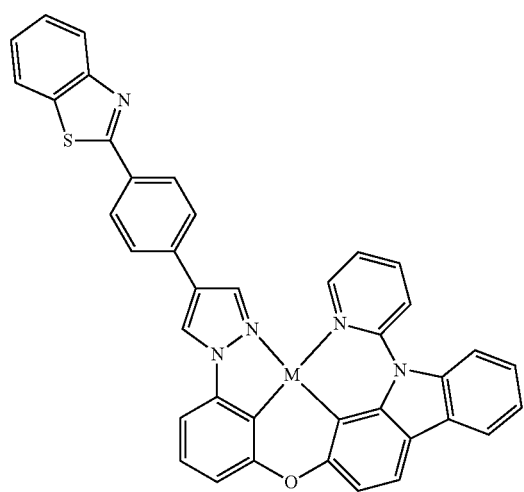
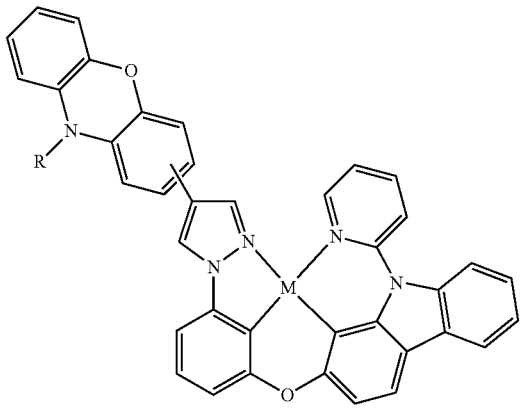
(M = Pt, Pd)
206
-continued
Structures 23
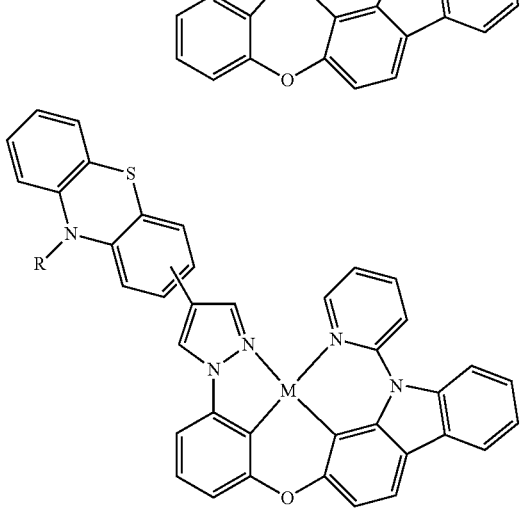
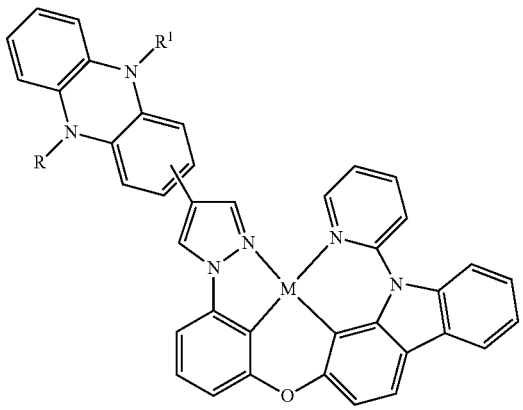
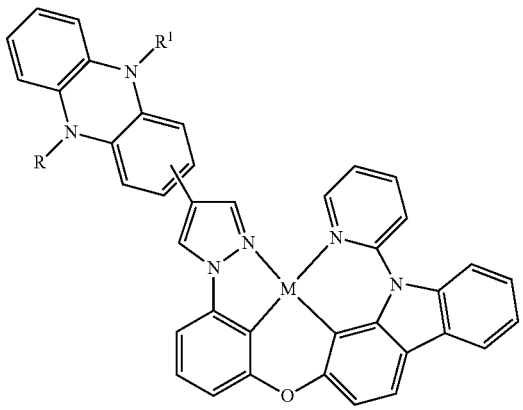
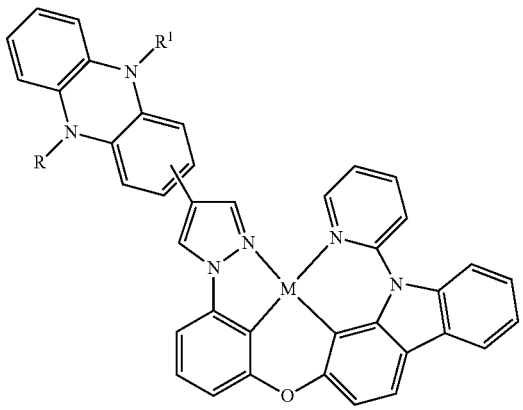
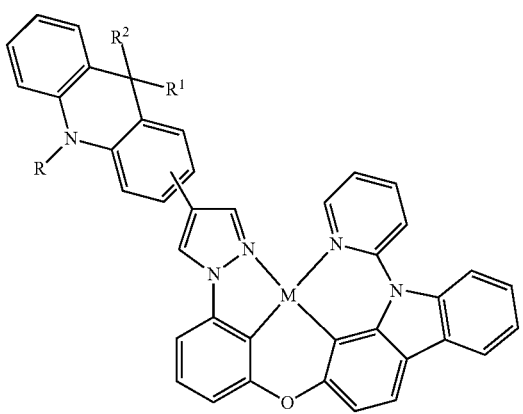

207
-continued
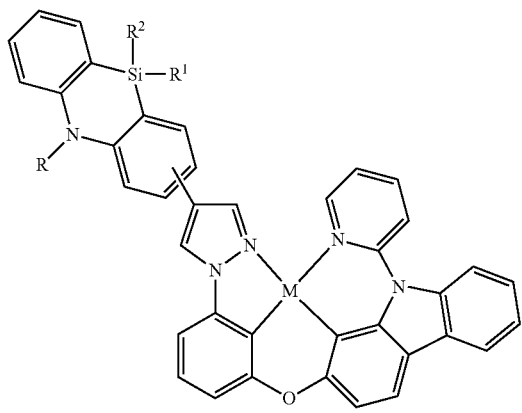
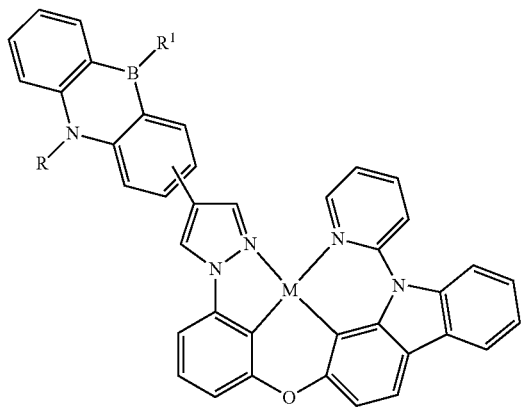
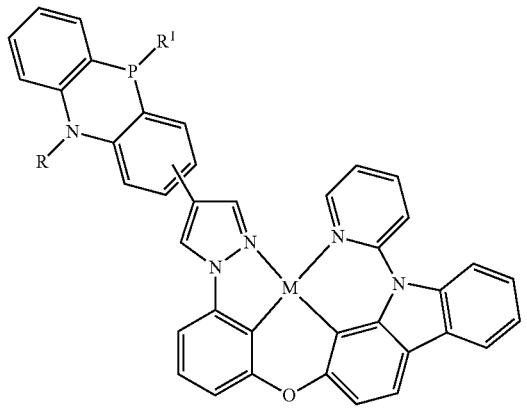
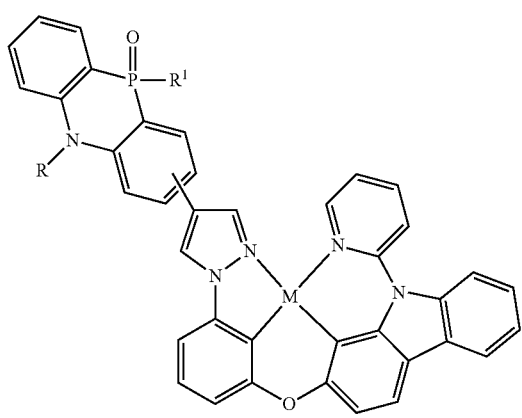
208
-continued
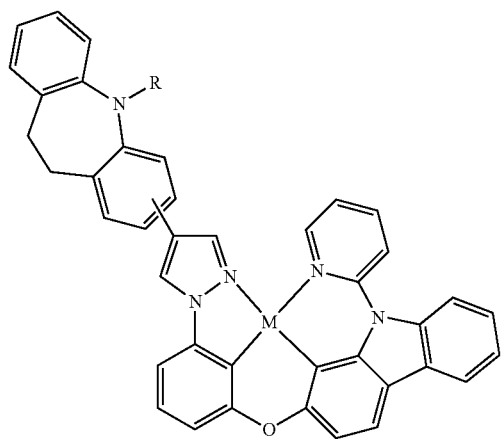
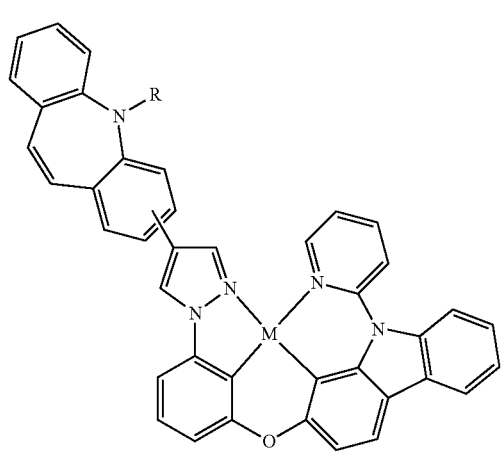
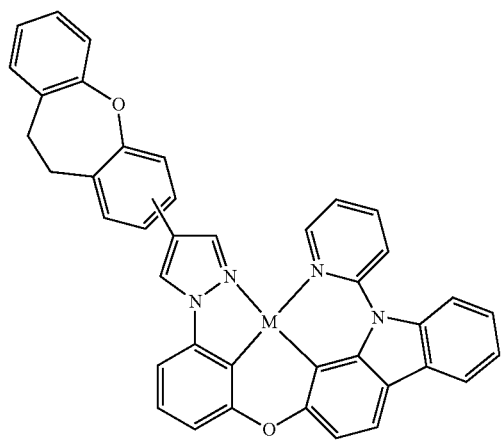

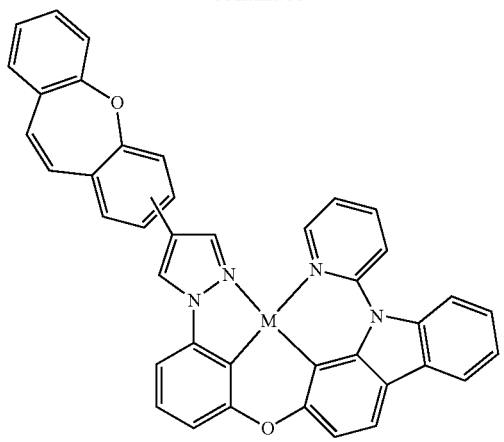
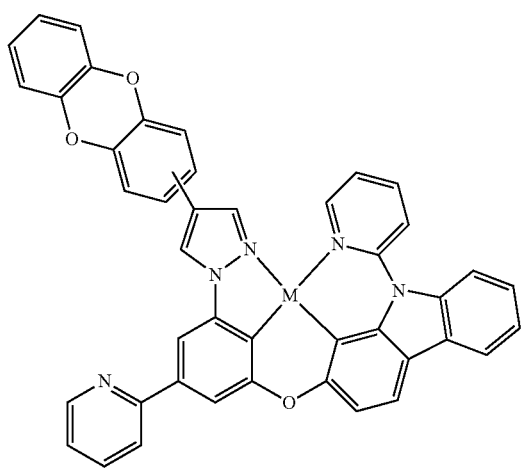
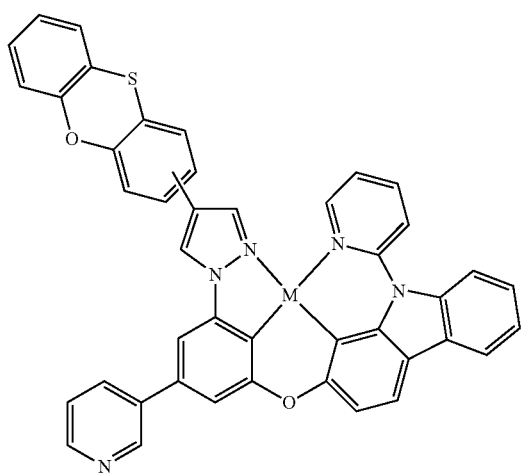
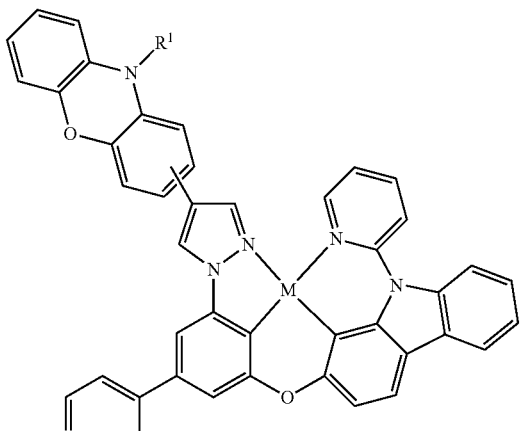
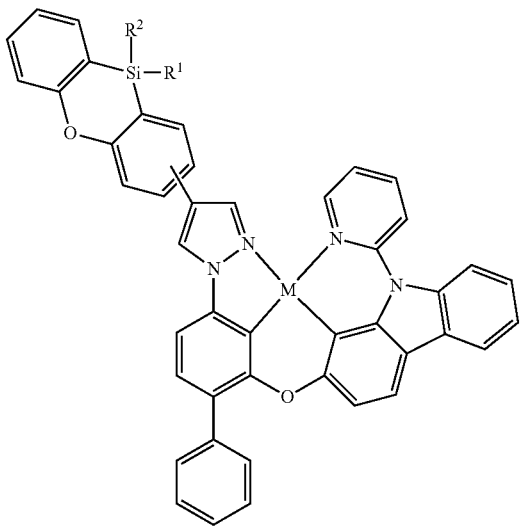

211
-continued
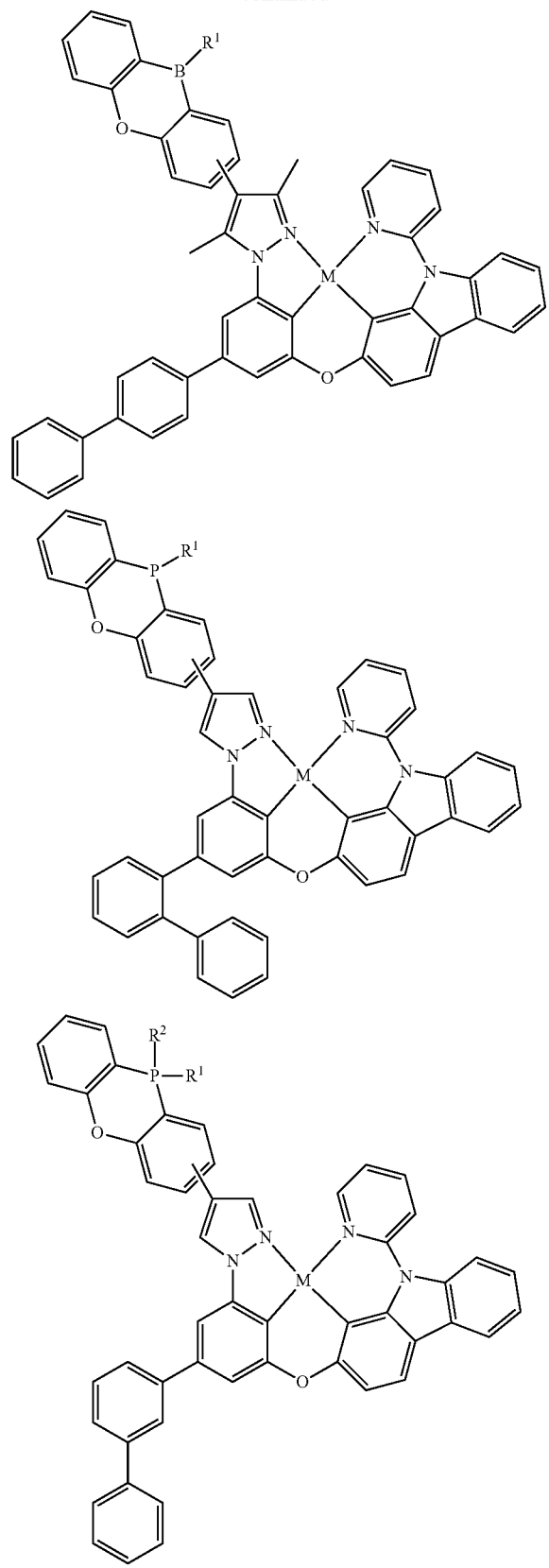
(M = Pt, Pd)
212
-continued
Structures 24
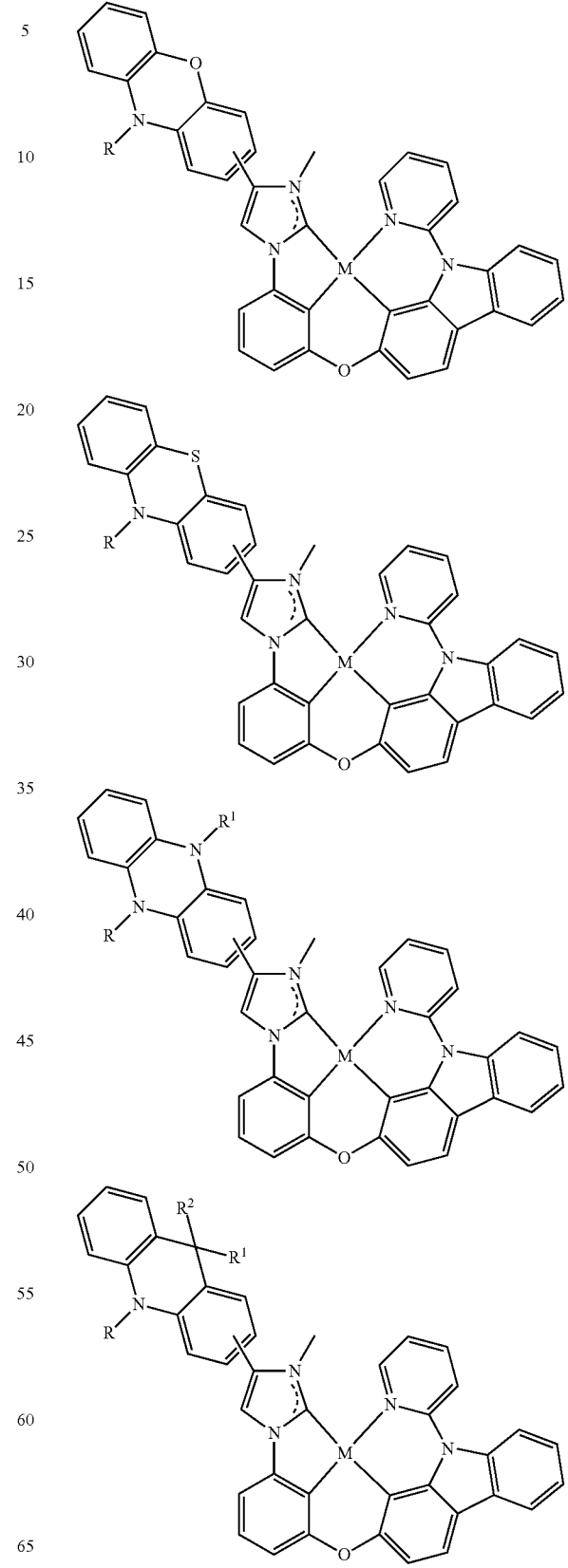

213
-continued
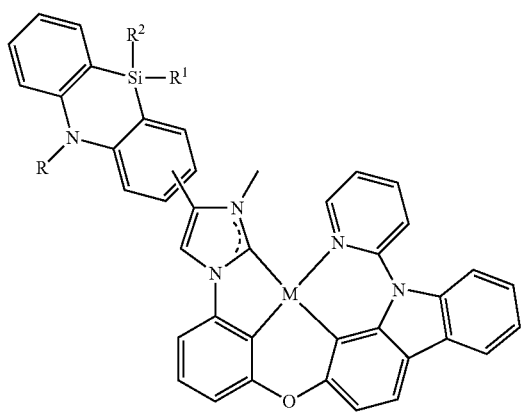
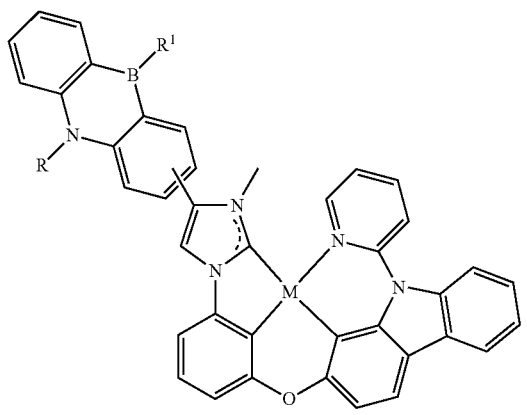
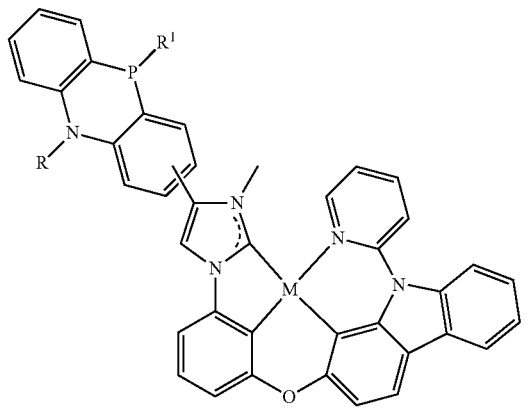
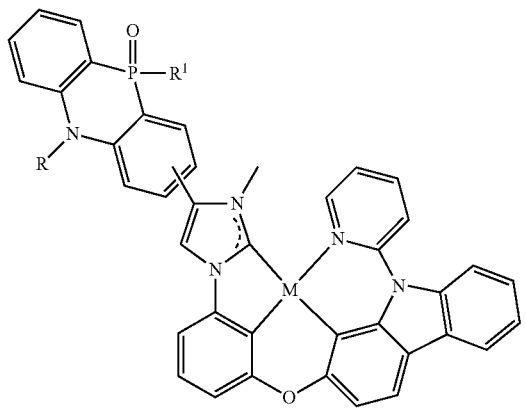
214
-continued
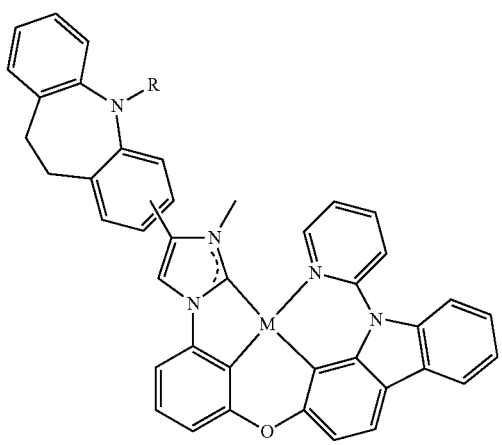
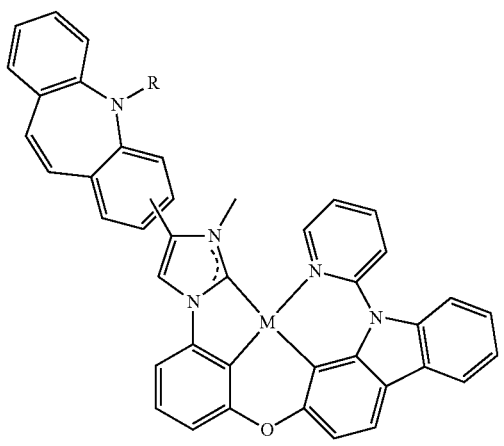
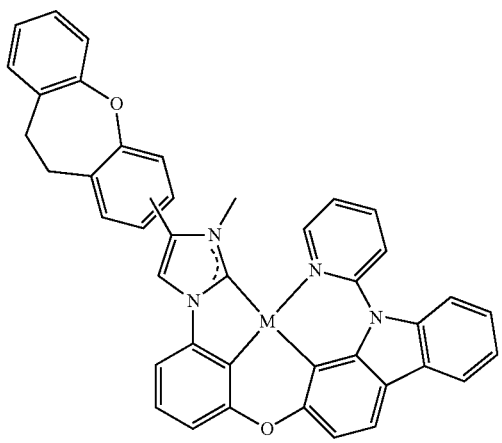

215
-continued
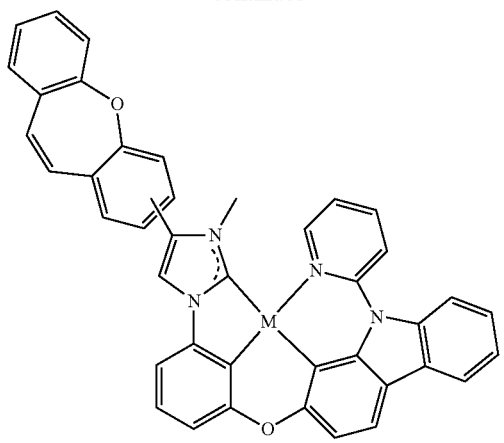
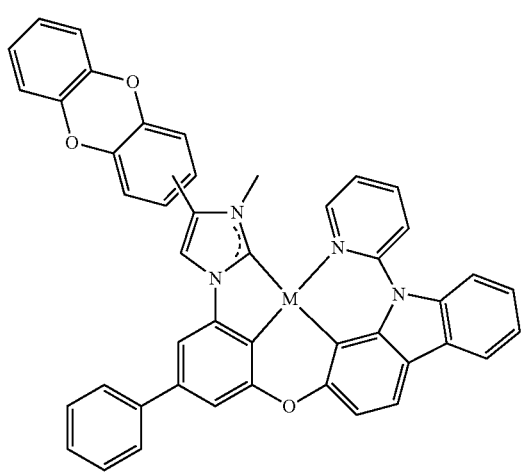
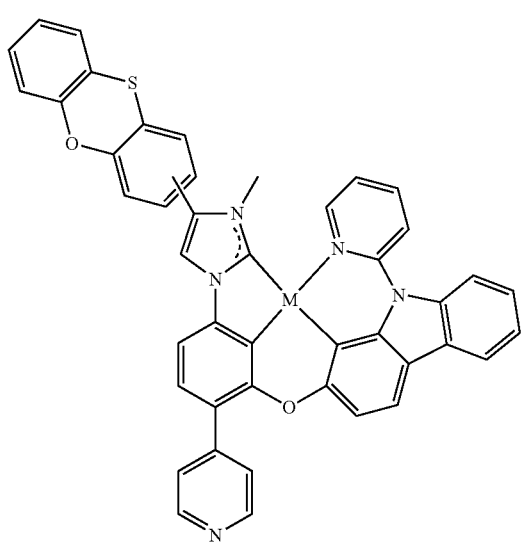
216
-continued
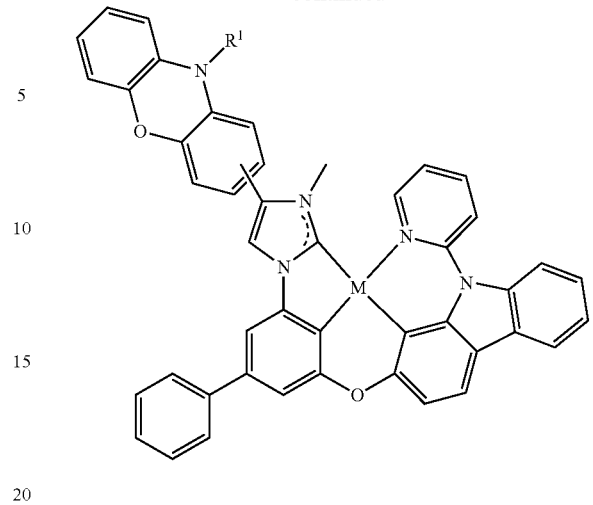
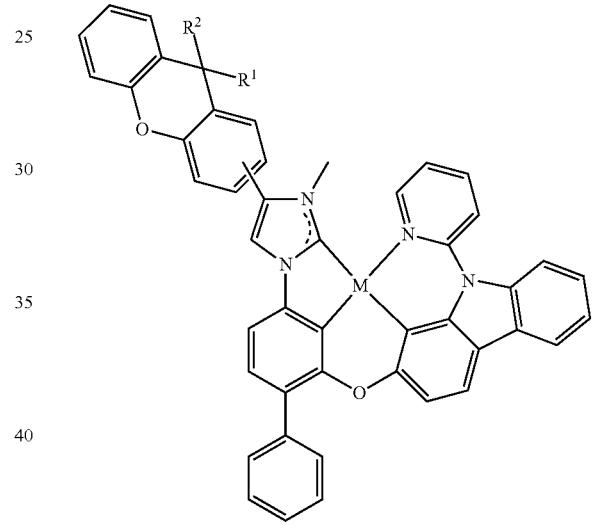
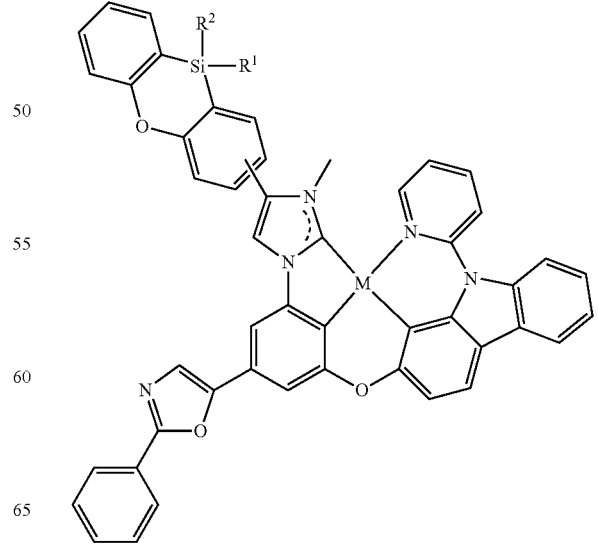

217
-continued
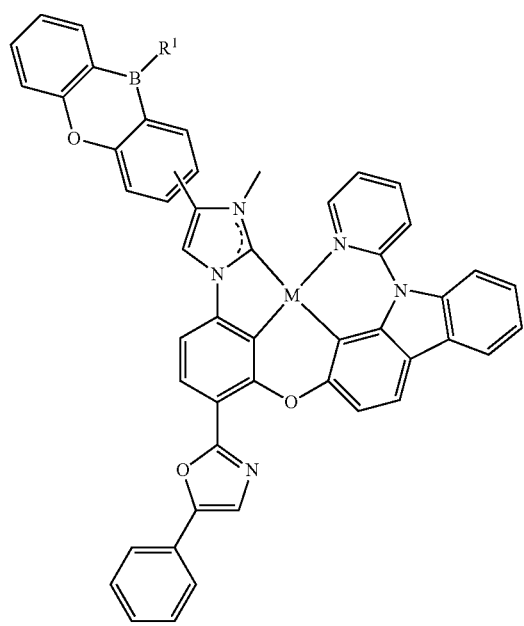
218
-continued
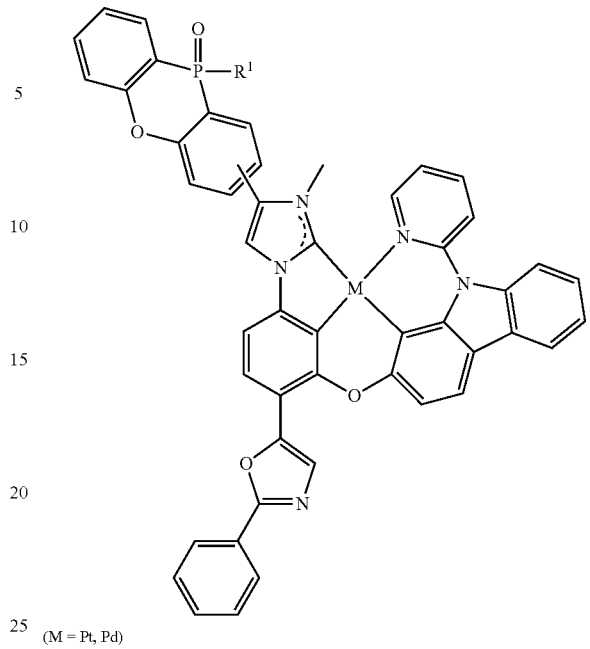
(M = Pt, Pd)
Structures 25
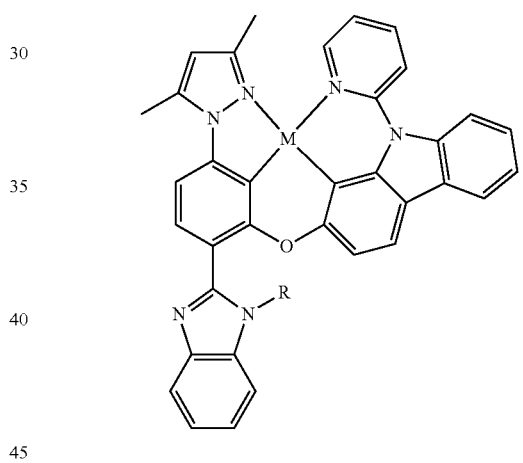
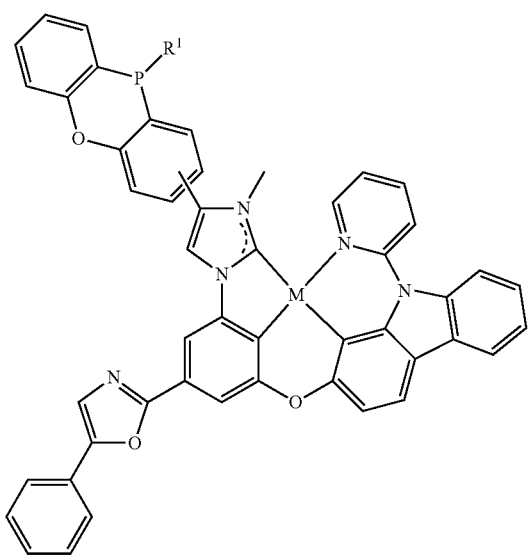
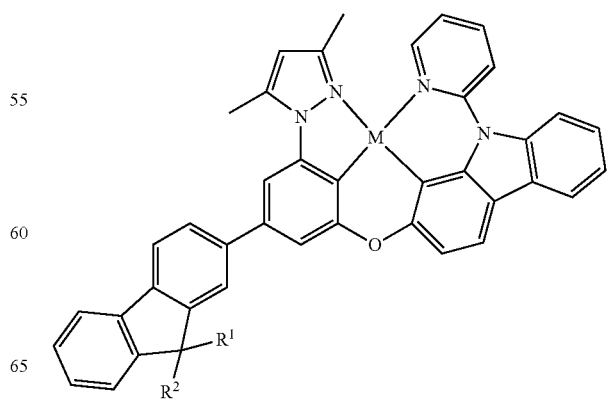

219
-continued
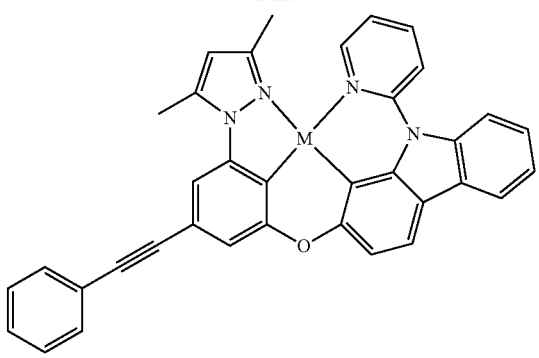
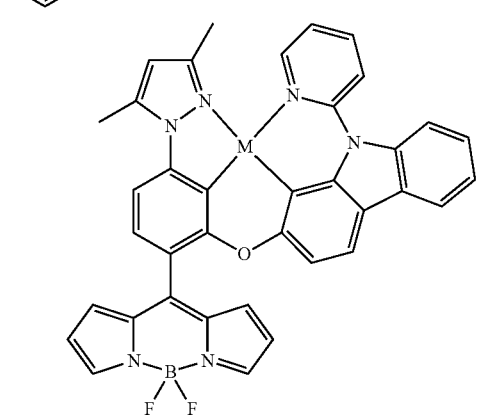
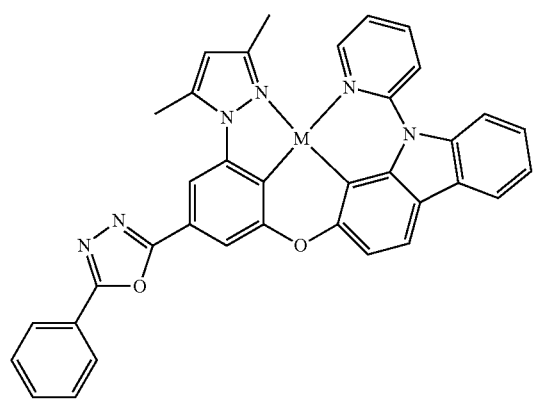
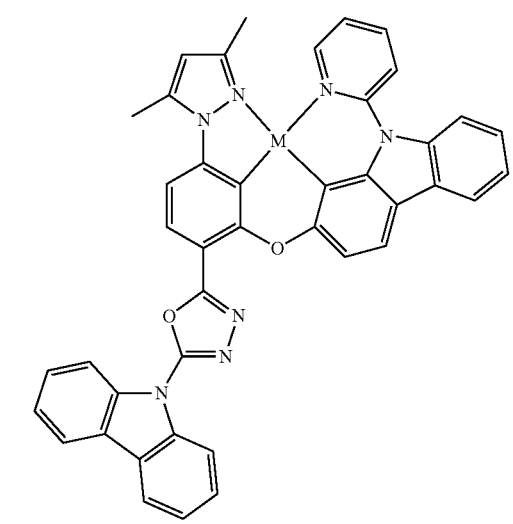
220
-continued
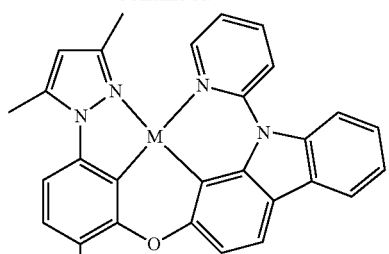
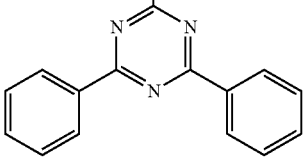
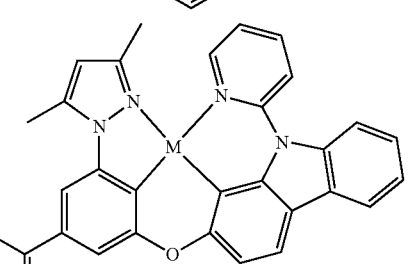
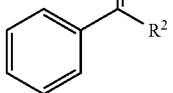
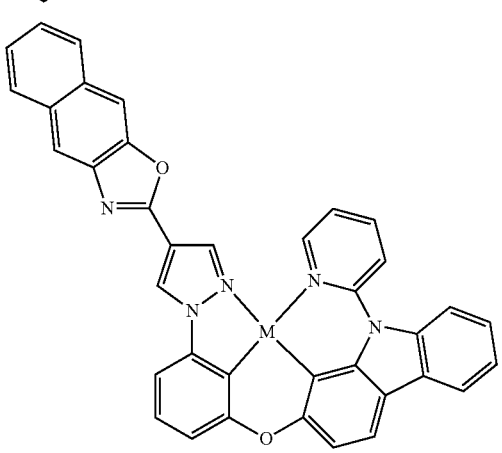
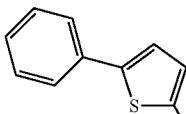
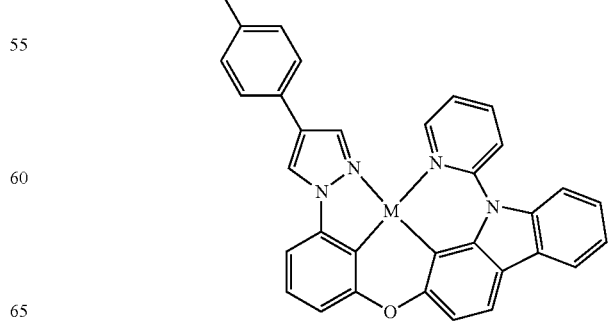

221
-continued
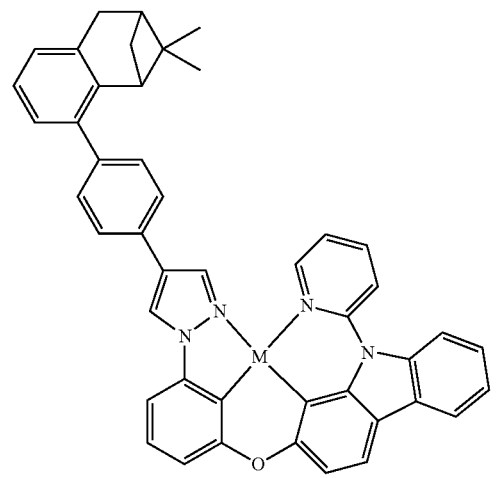
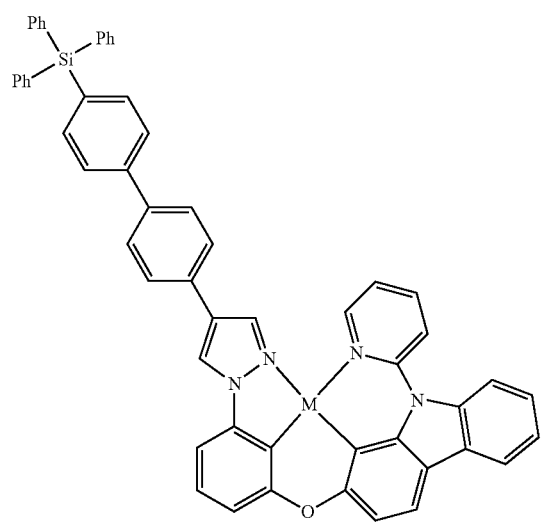
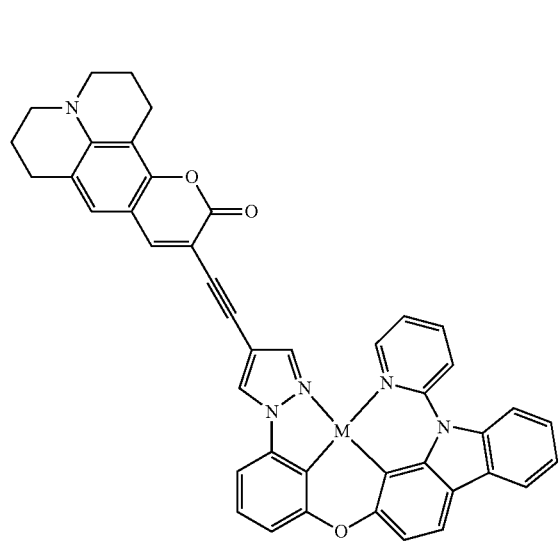
222
-continued
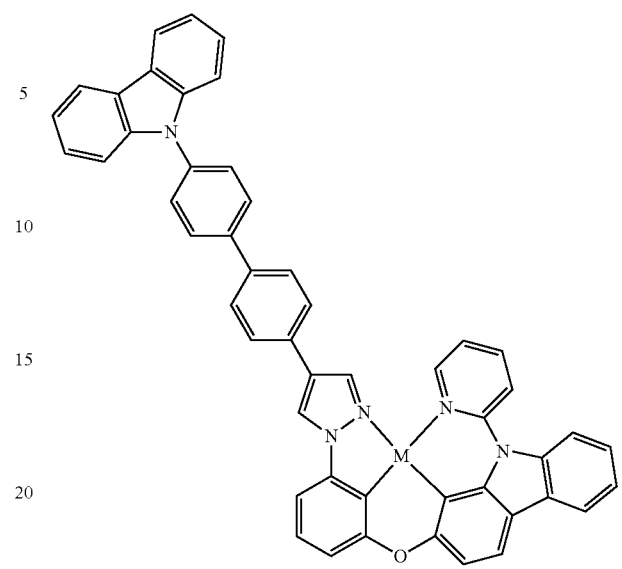
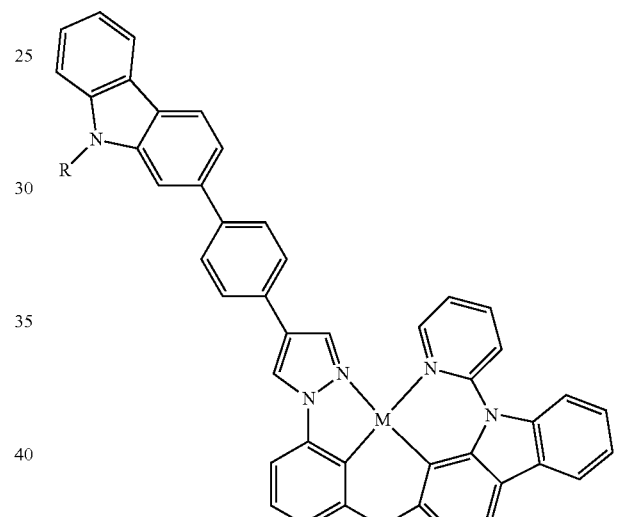
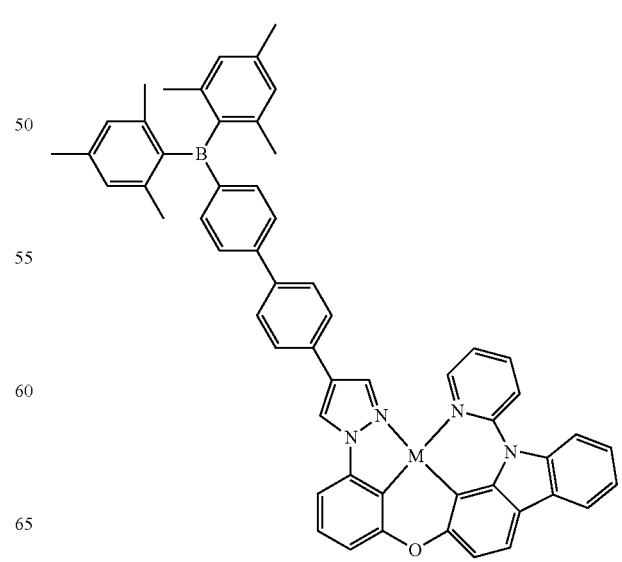

223
-continued
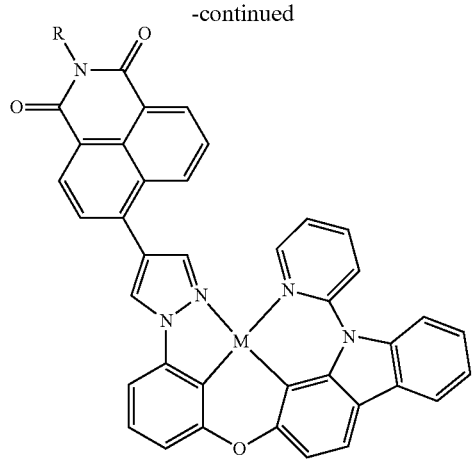
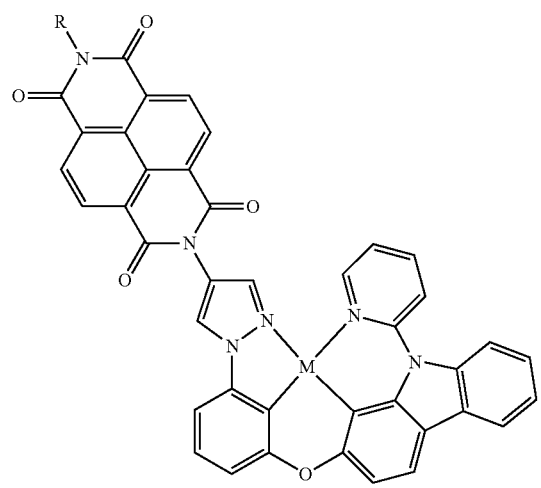
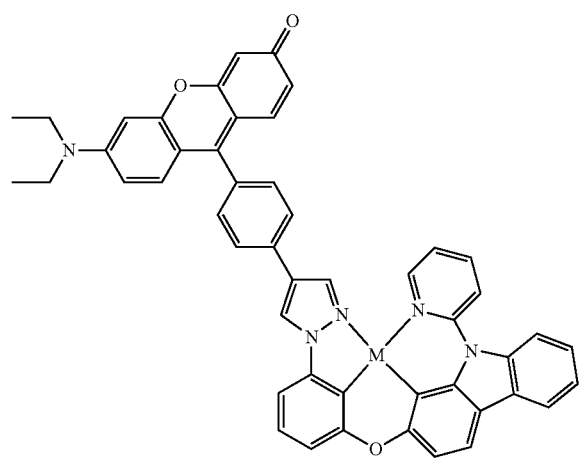
224
-continued
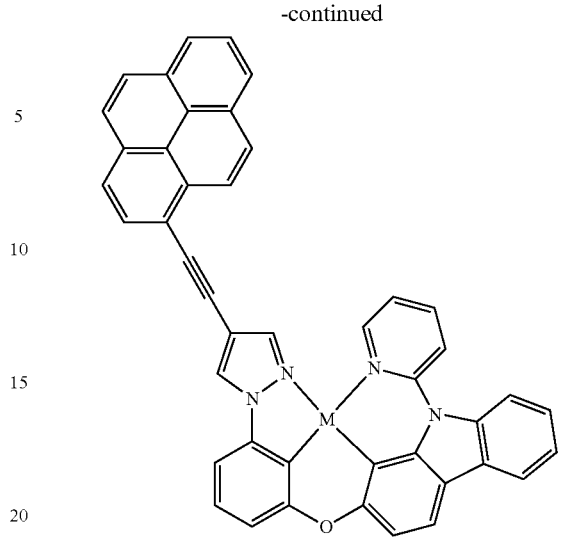
(M = Pt, Pd)
Structures 26
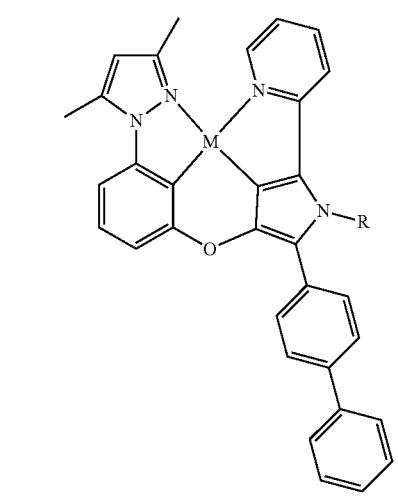

225
-continued
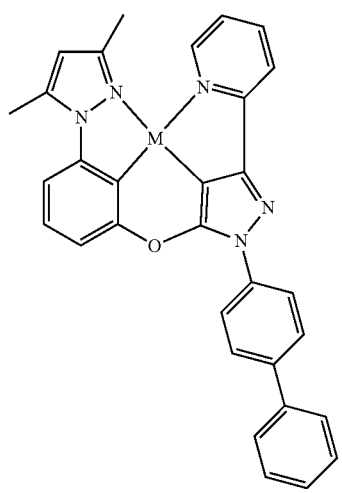
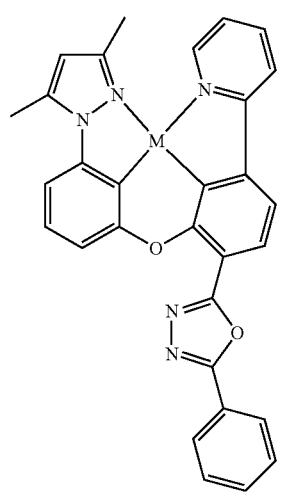
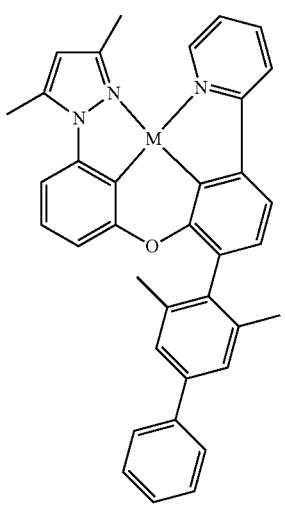
226
-continued
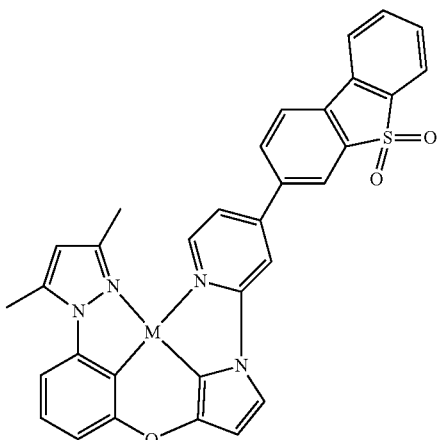
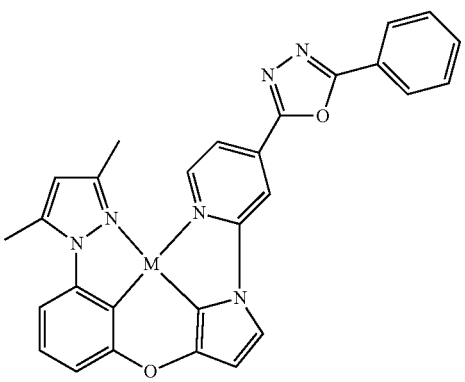
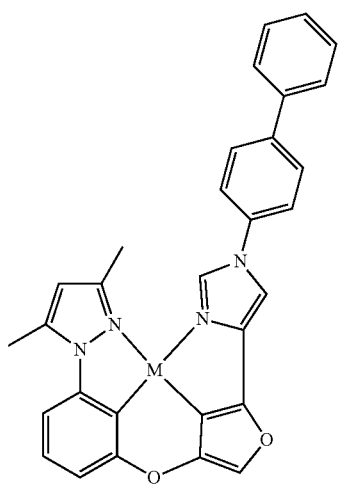

227
-continued
228
-continued
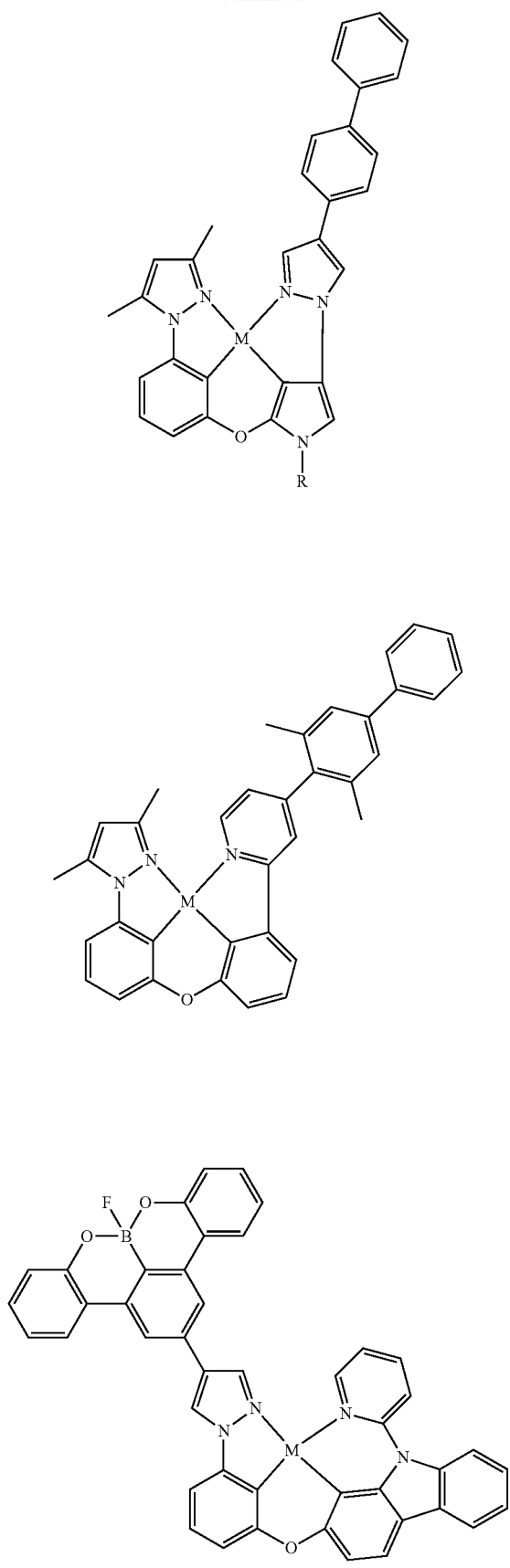
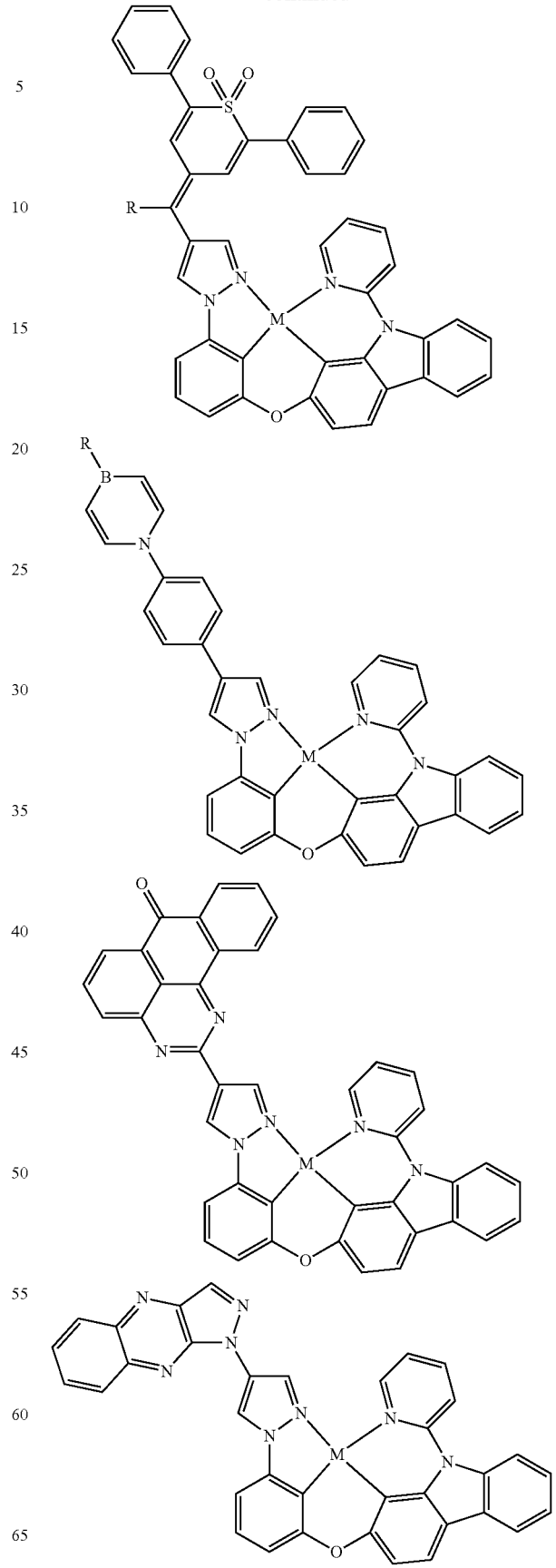

229
-continued
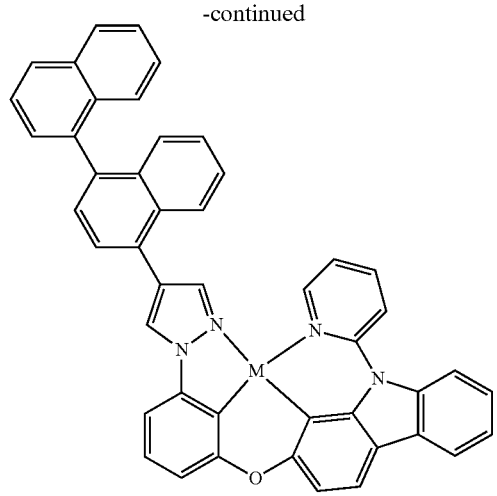
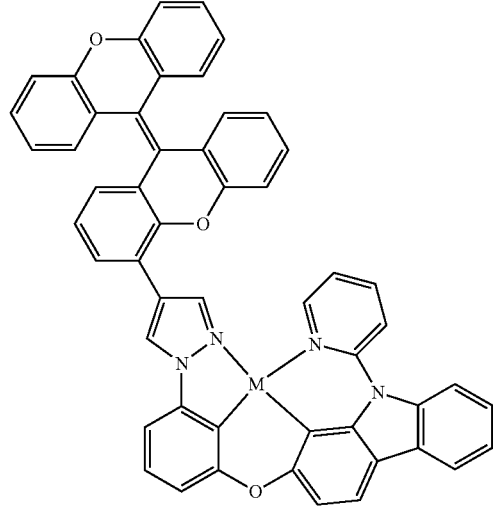
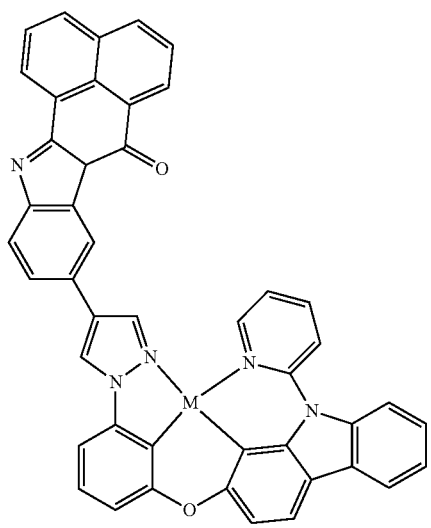
230
-continued
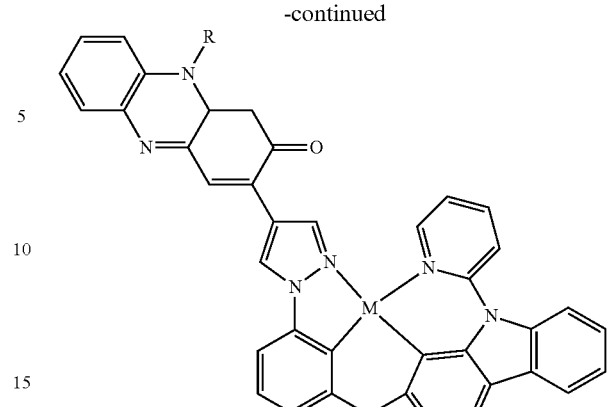
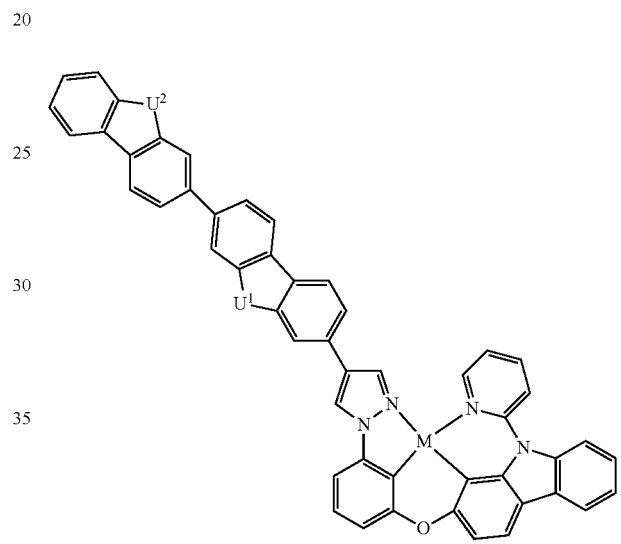
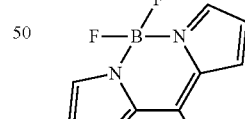
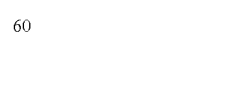

231
-continued
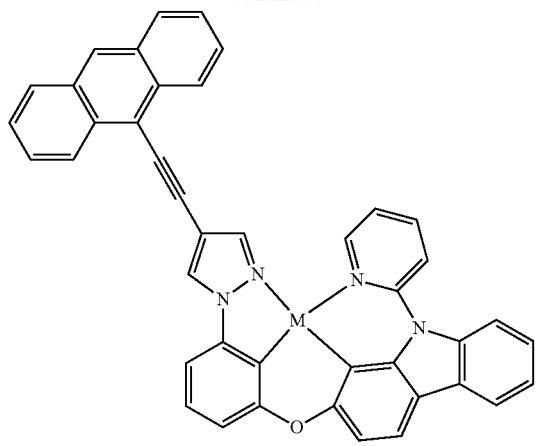
(M = Pt, Pd)
Structures 27
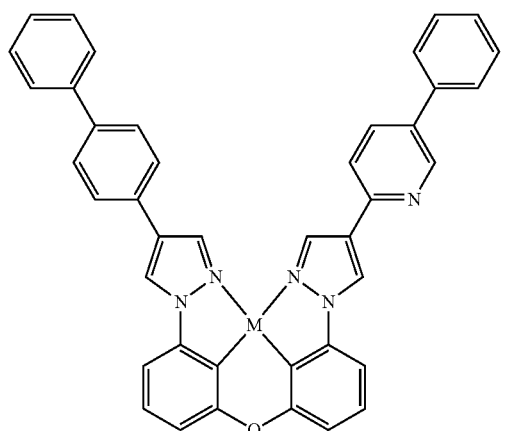
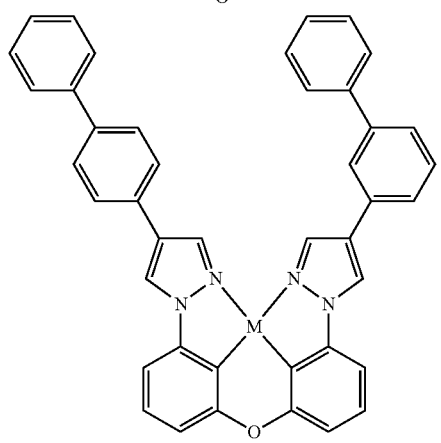
232
-continued
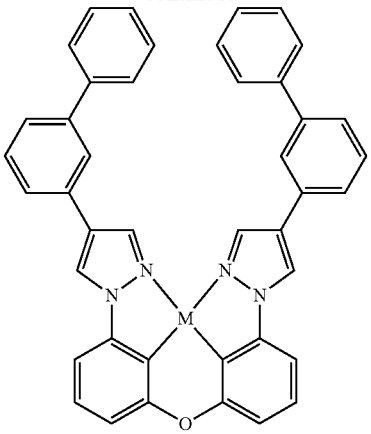
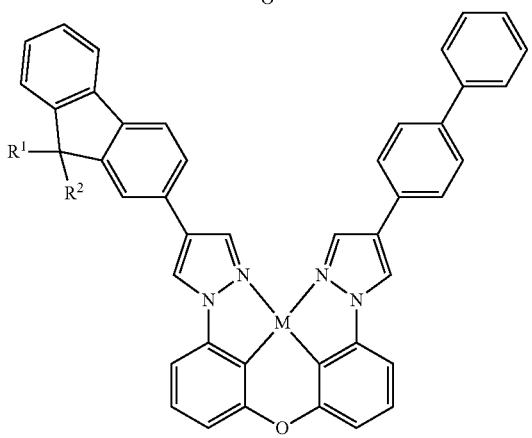
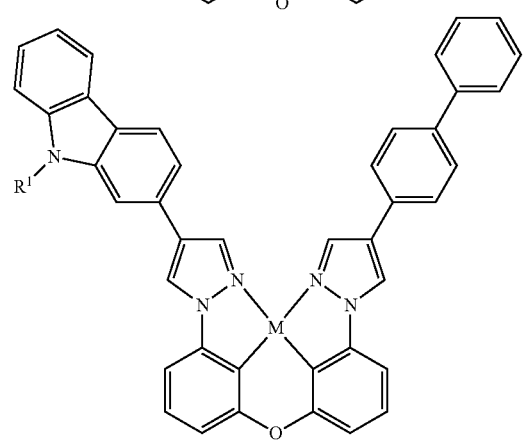
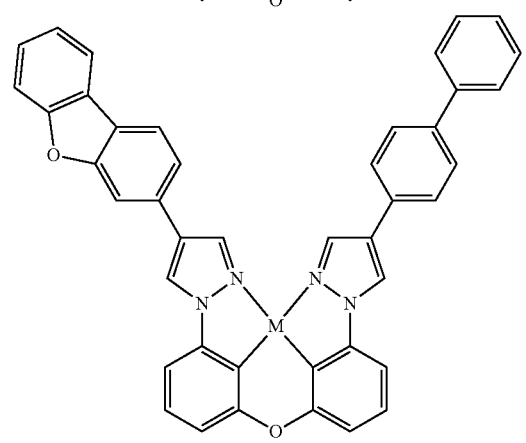

233
-continued
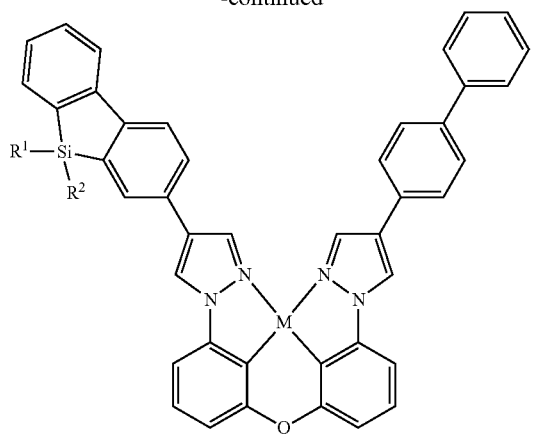
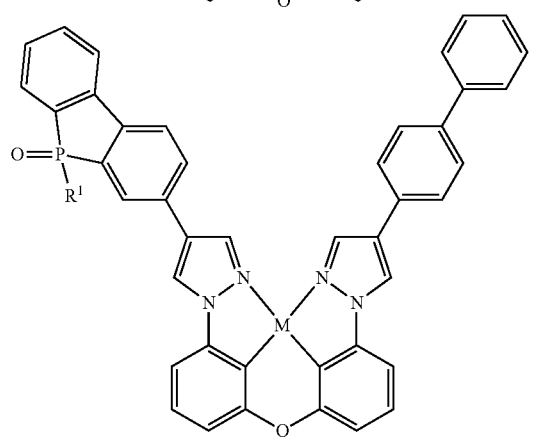
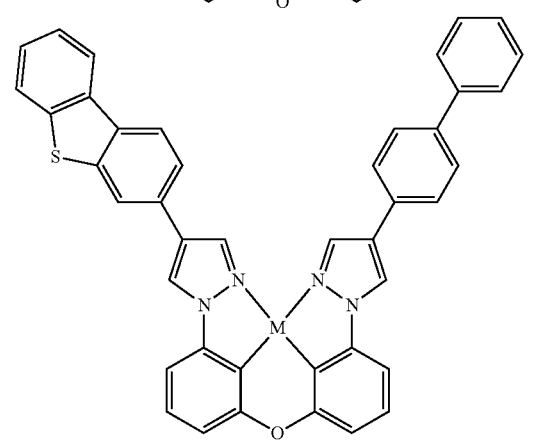
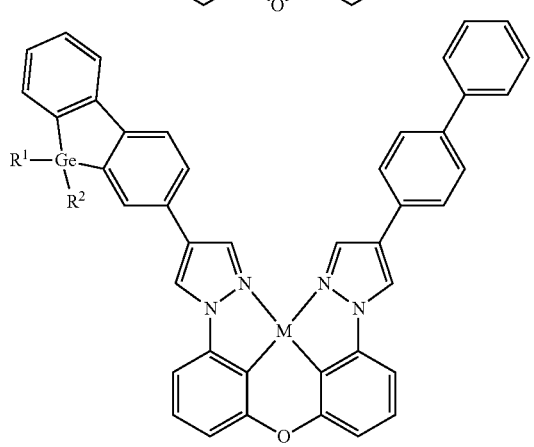
234
-continued
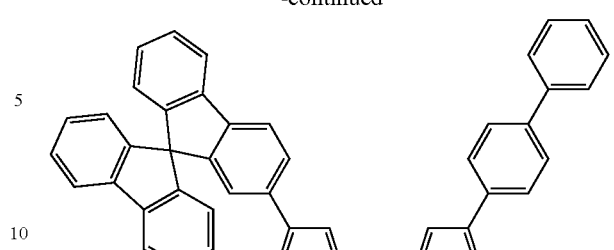
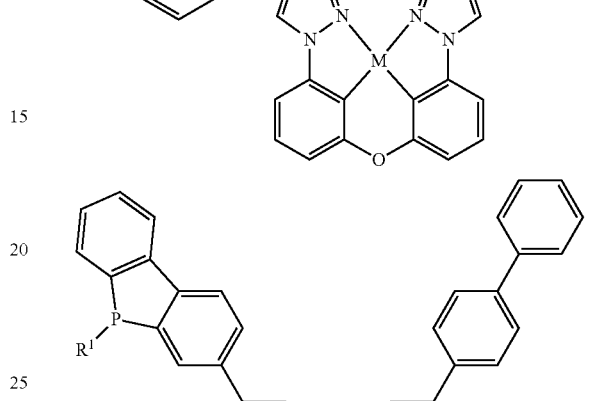
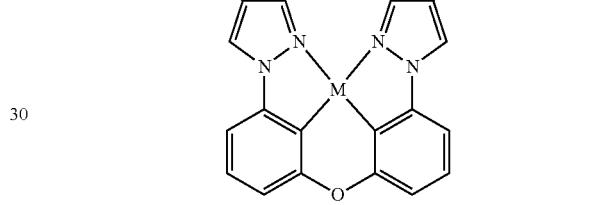
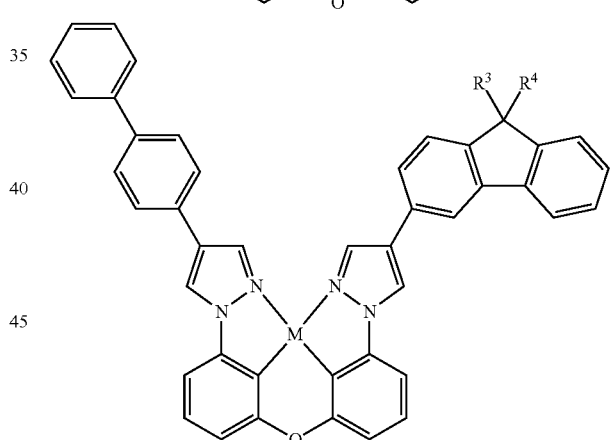
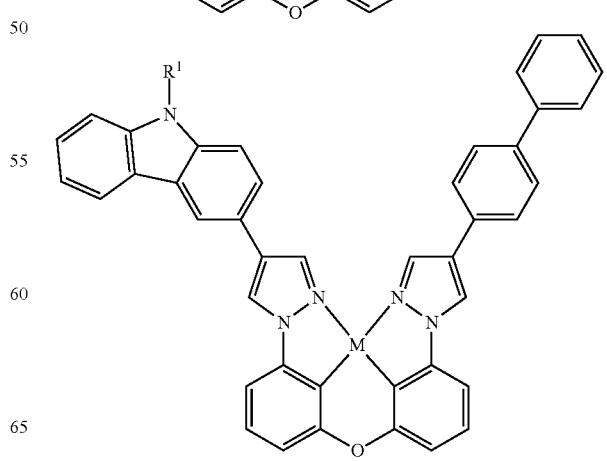

235
-continued
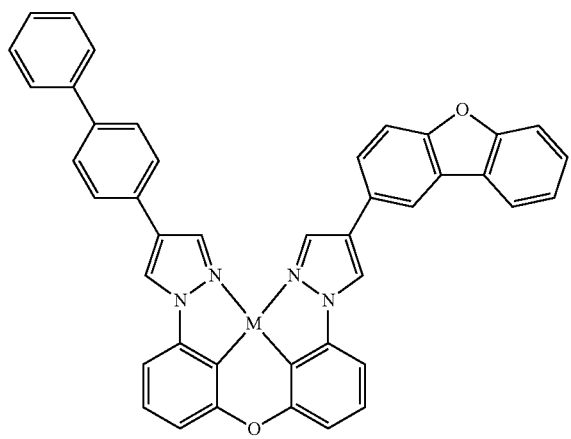
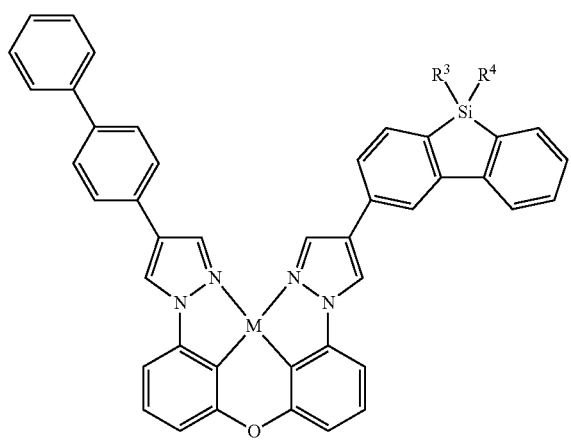
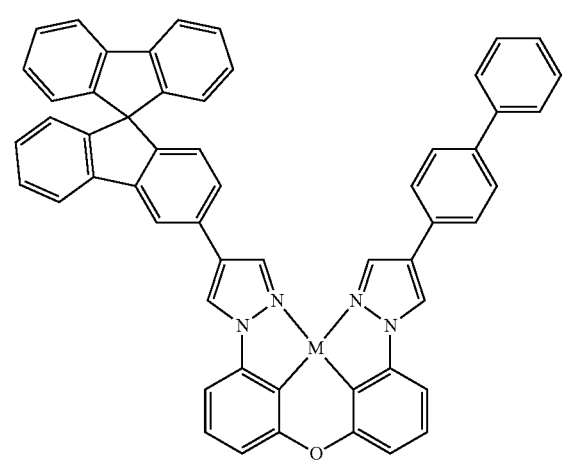
236
-continued
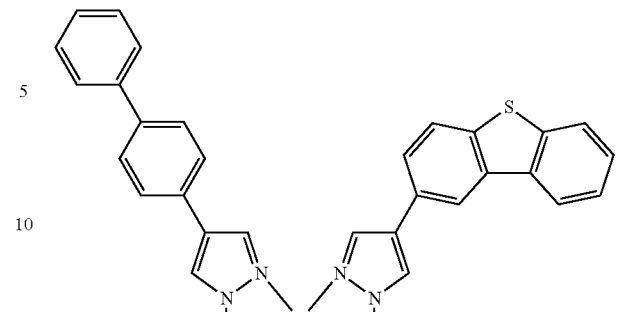
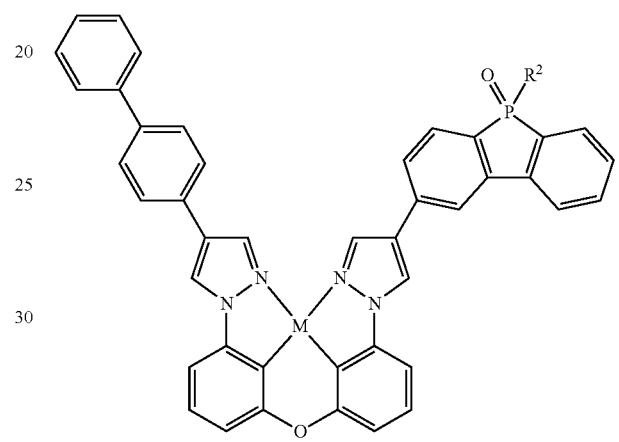
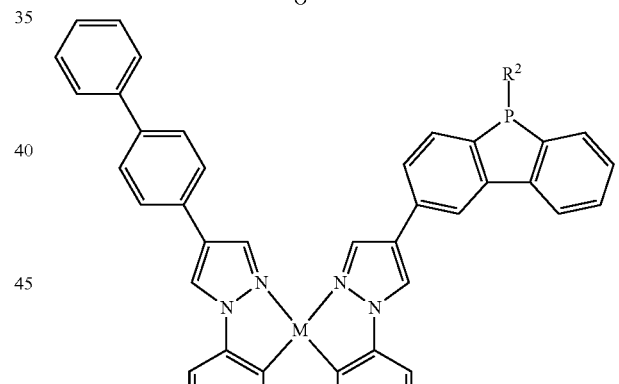
(M = Pt, Pd)
Structures 28
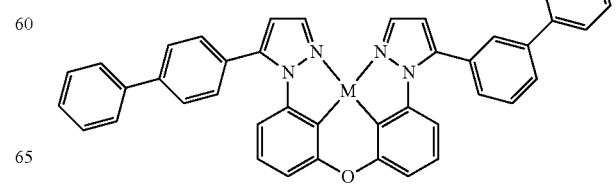

237
-continued
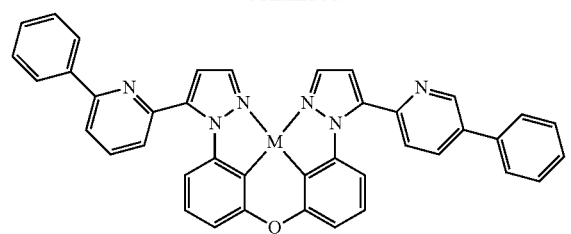
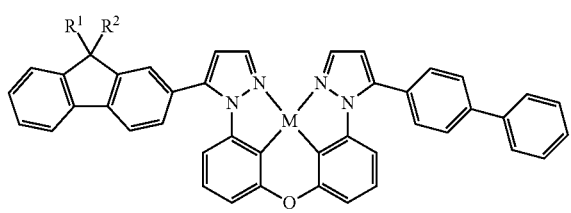
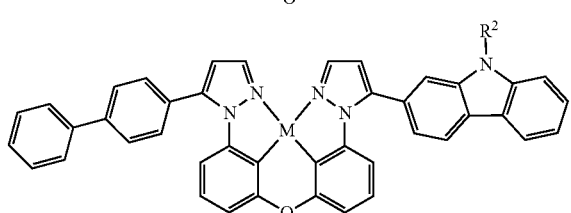
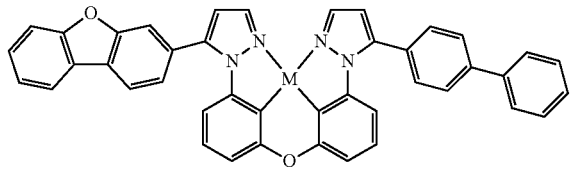
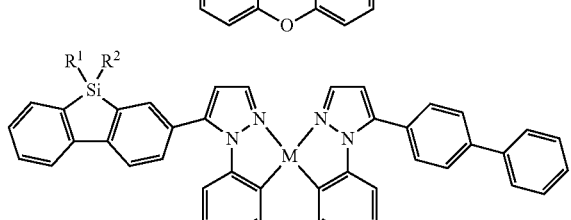
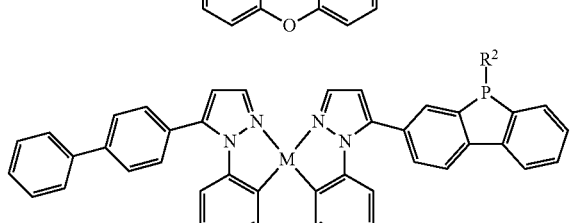
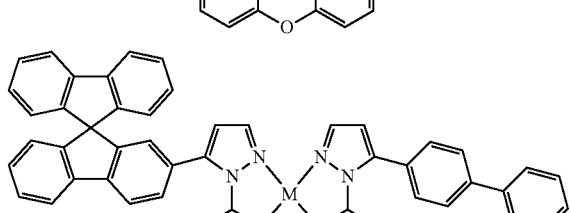
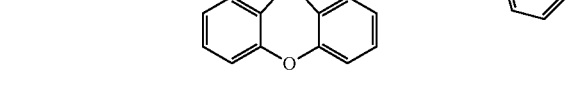
238
-continued
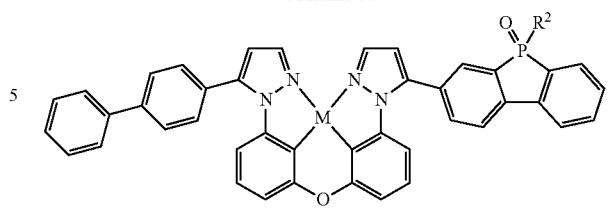
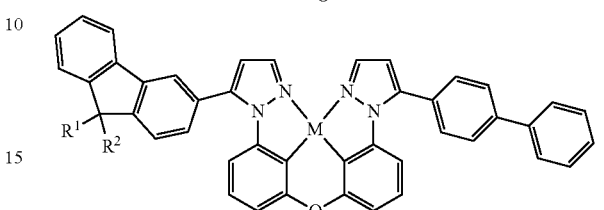
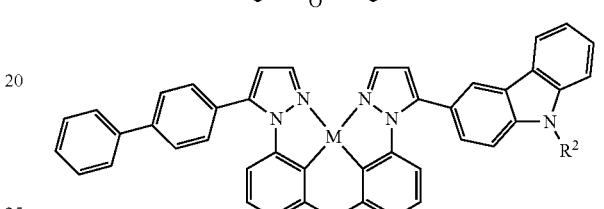
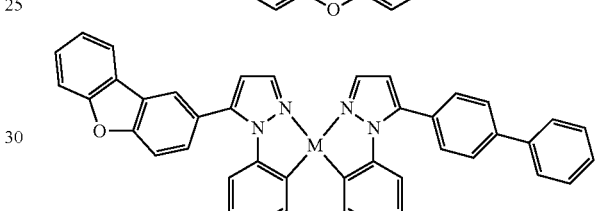
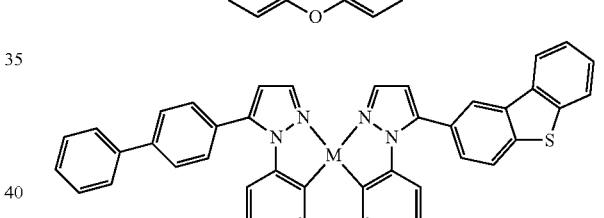
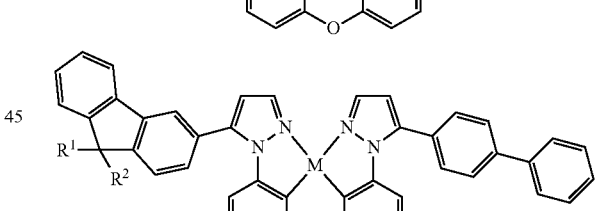
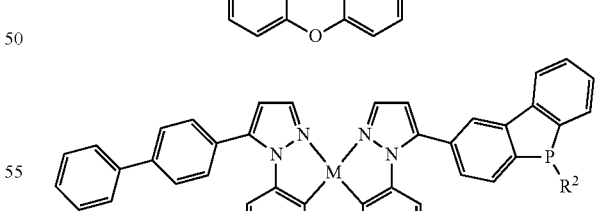
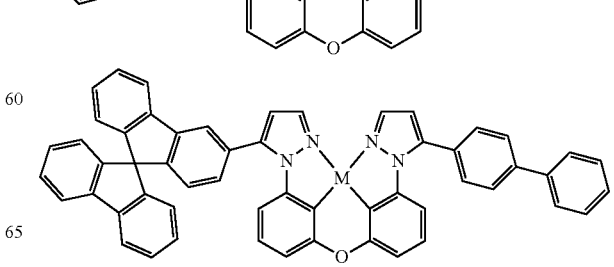

-continued
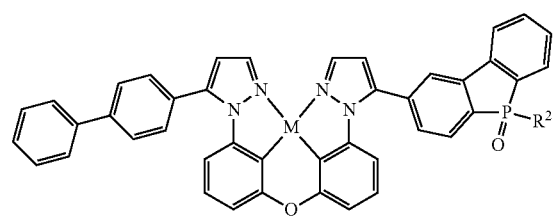
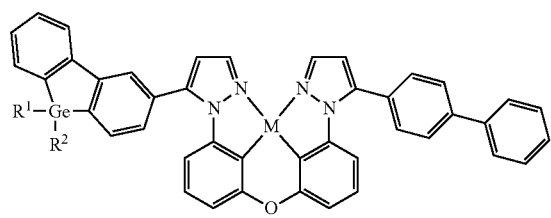
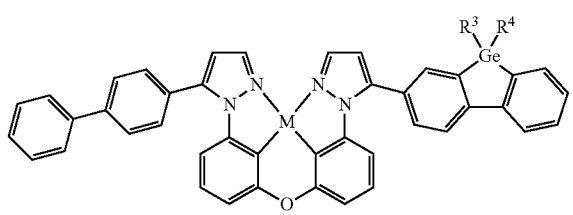
(M = Pt, Pd)
Structures 29
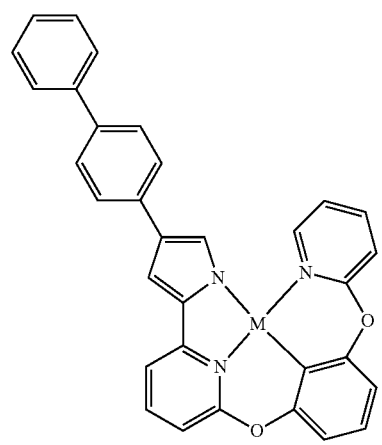
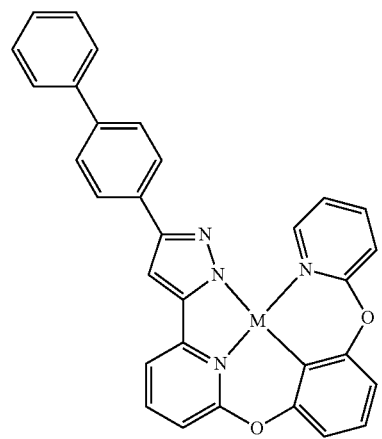
-continued
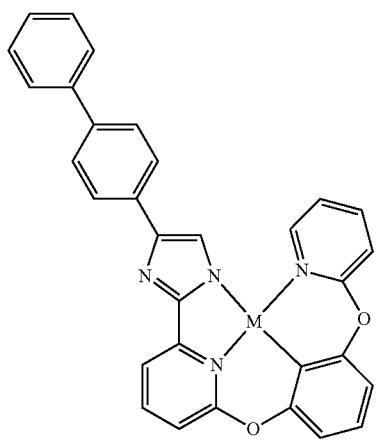
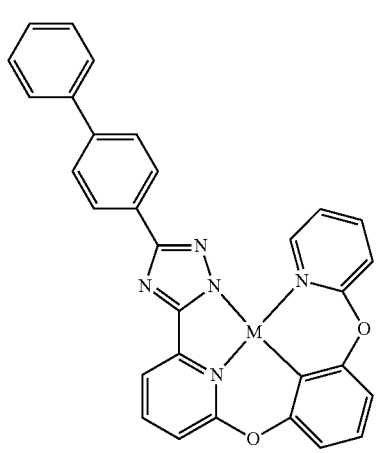
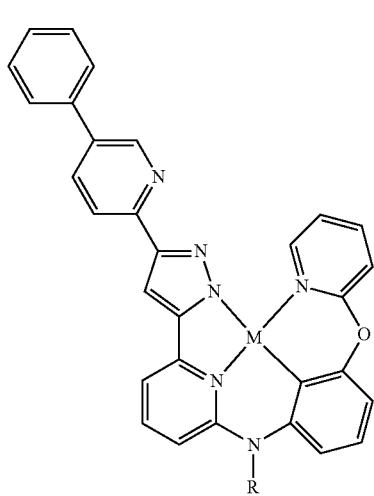

241
-continued
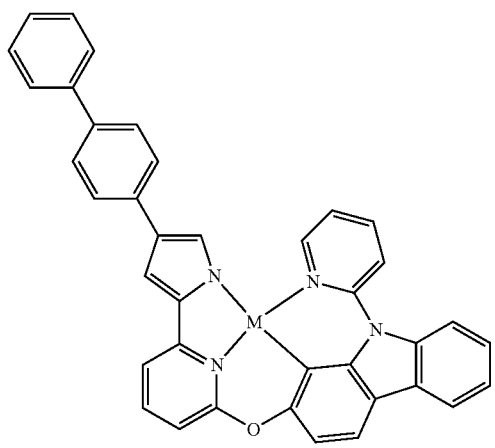
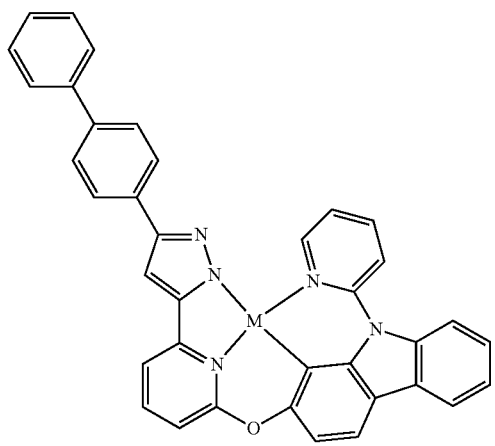
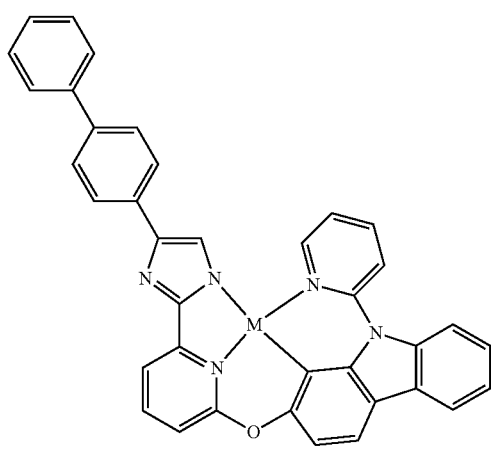
242
-continued
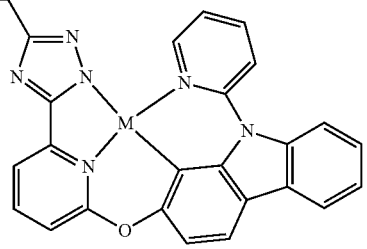
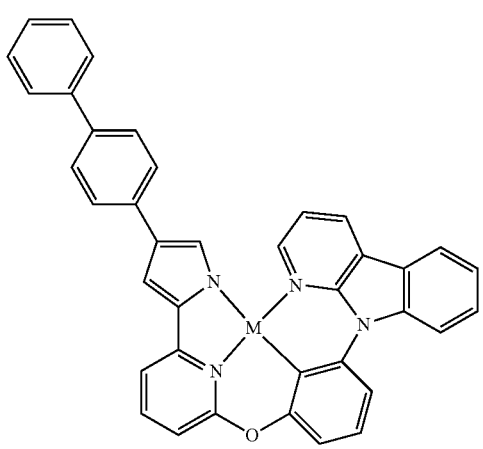
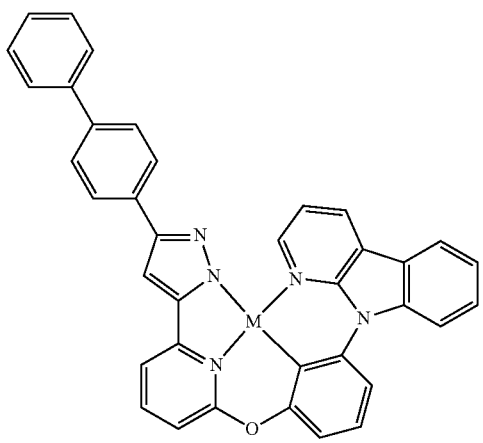

243
-continued
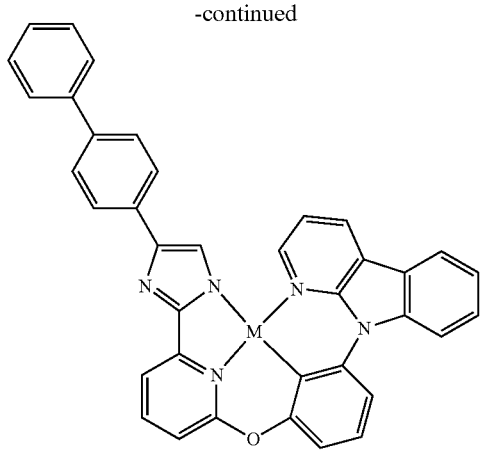
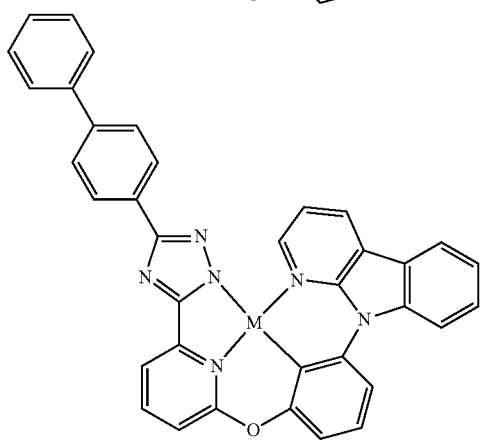
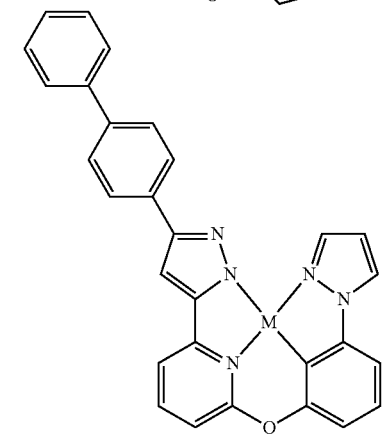
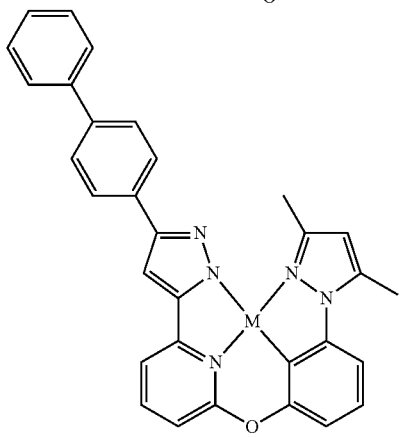
244
-continued
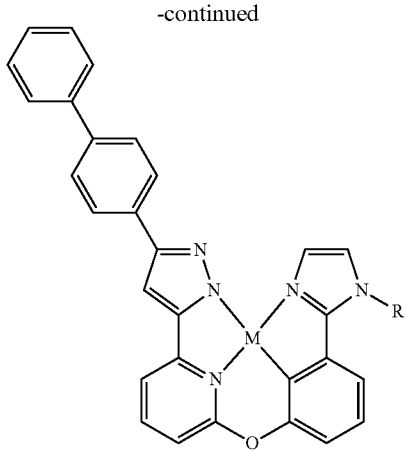
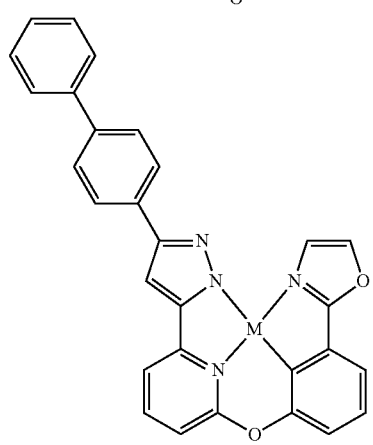
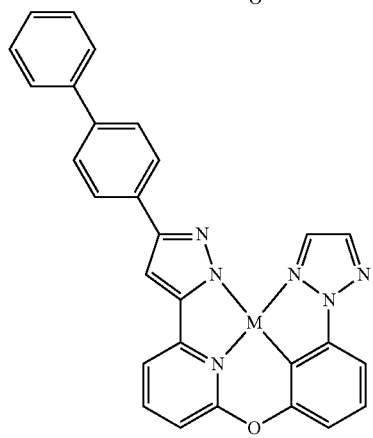

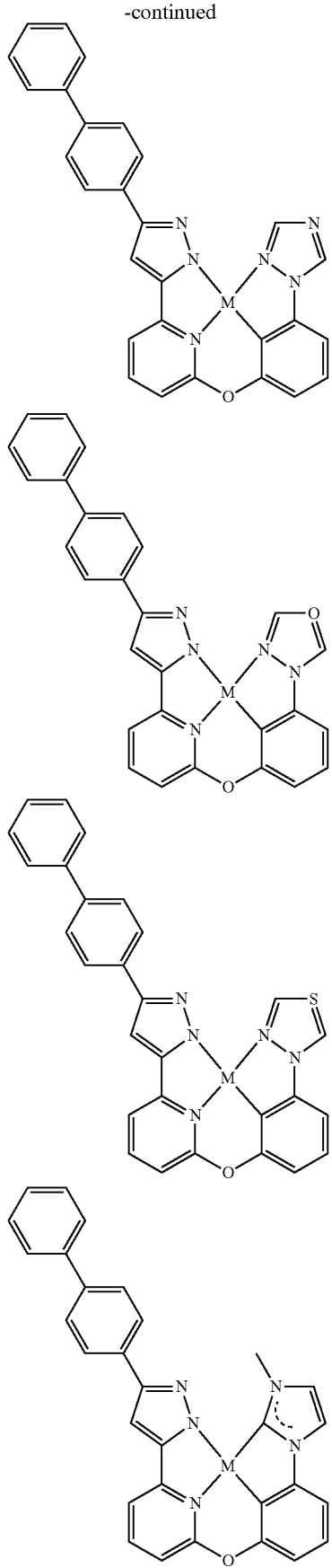
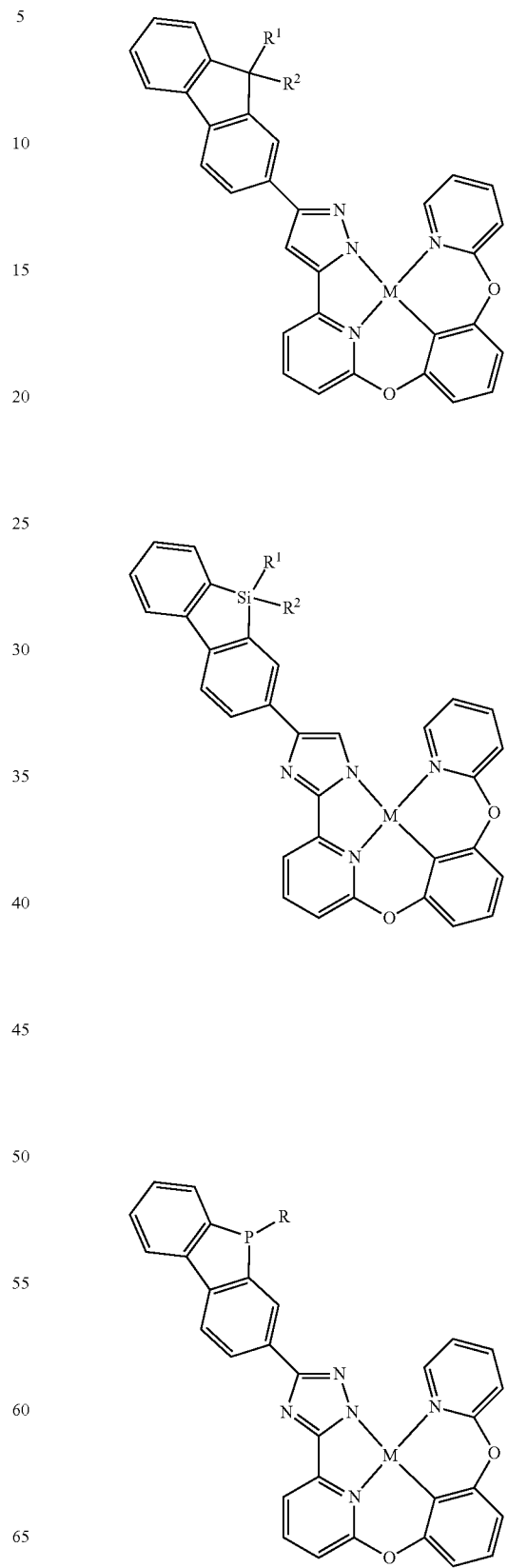
(M = Pt, Pd)
Structure 30

247
-continued
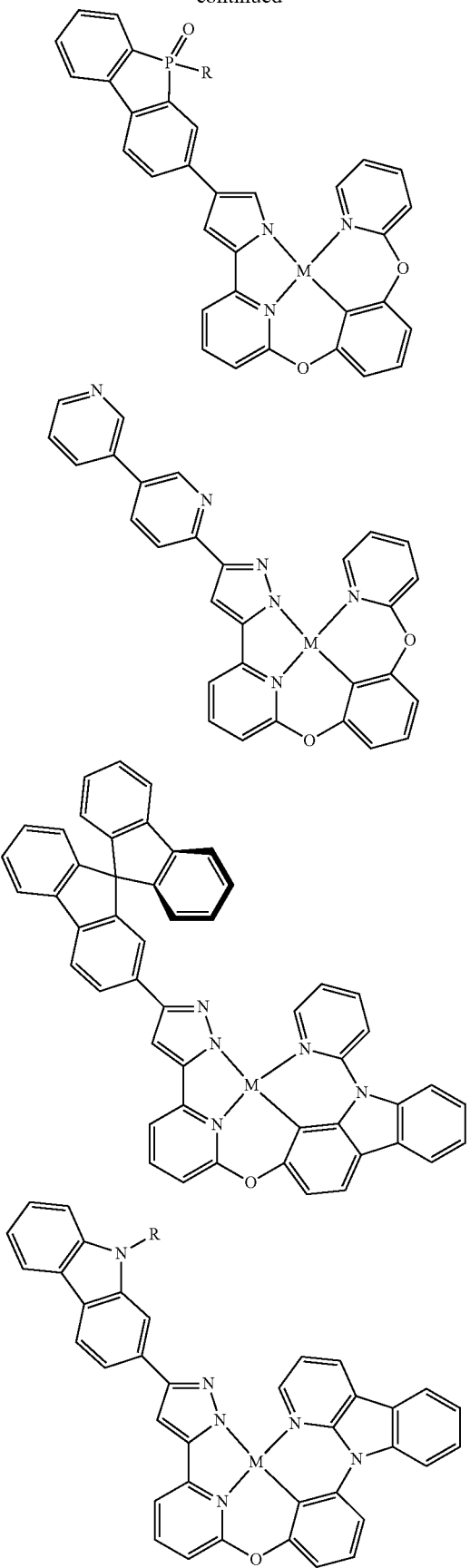
248
-continued
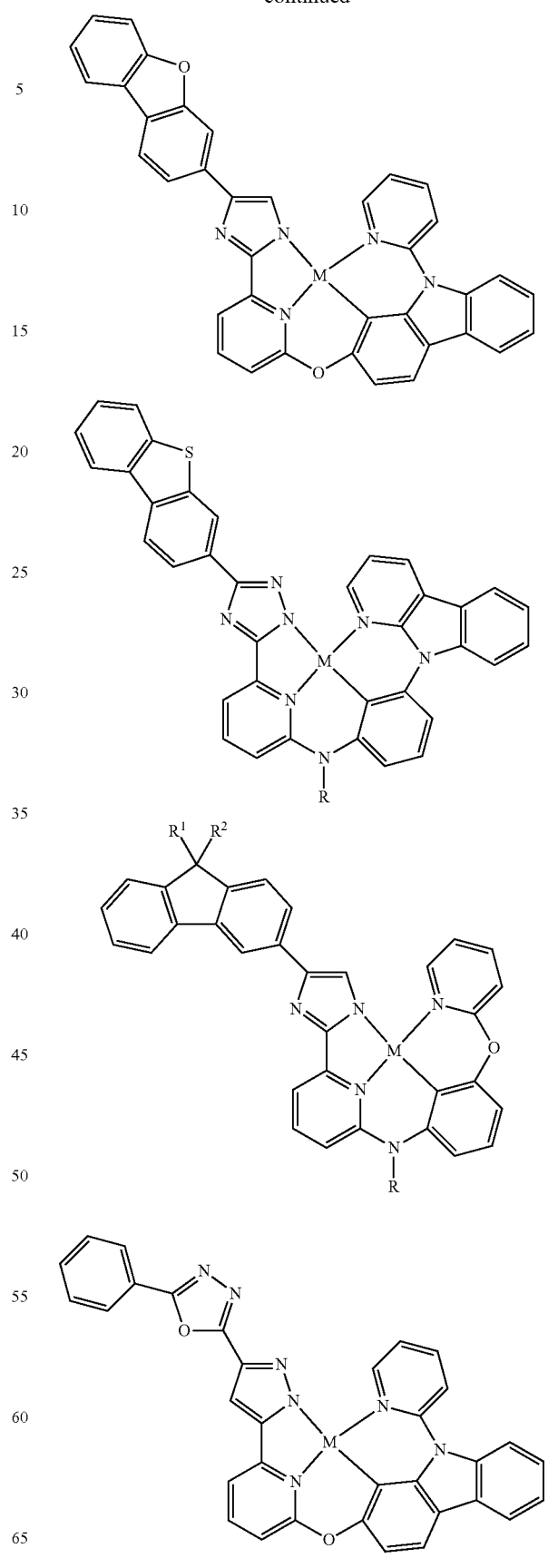

249
-continued
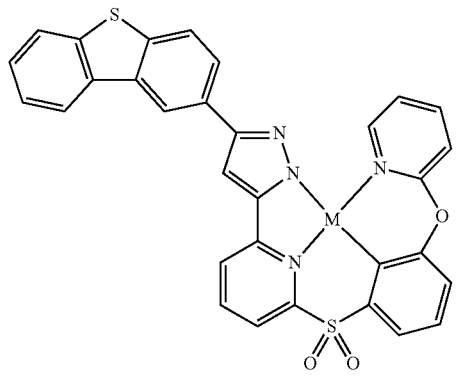
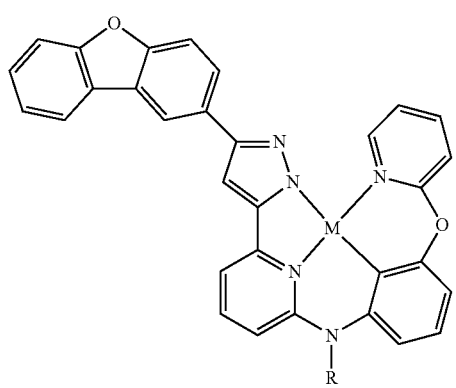
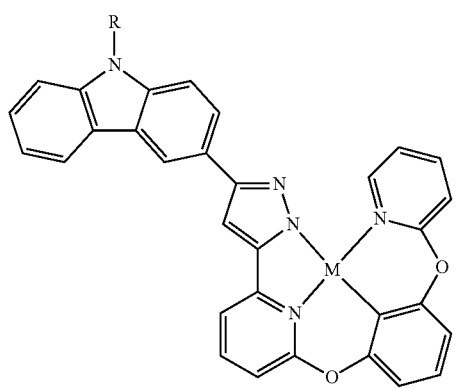
250
-continued
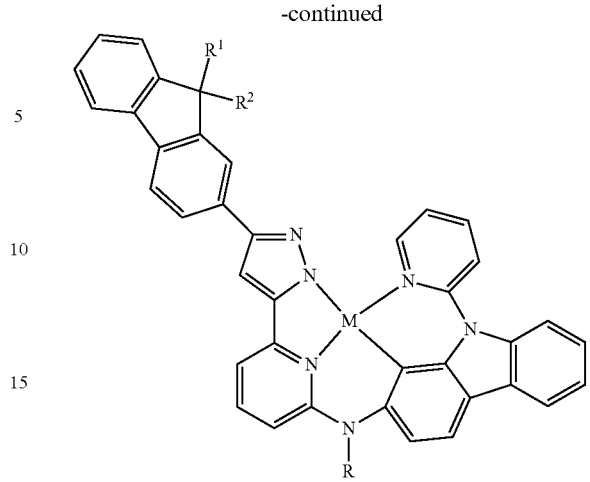
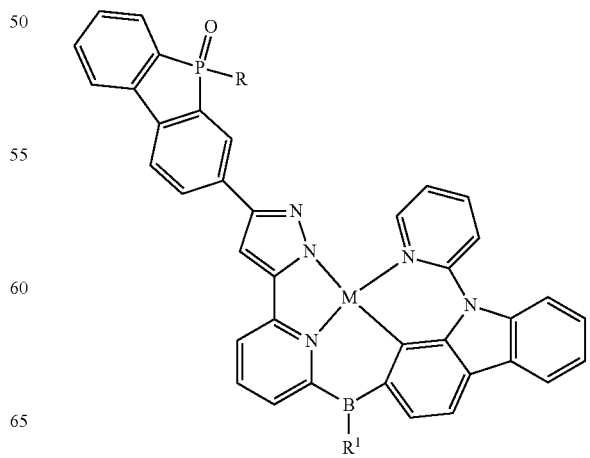

251
-continued
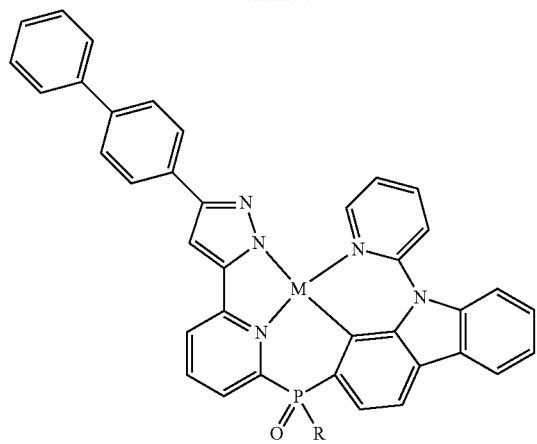
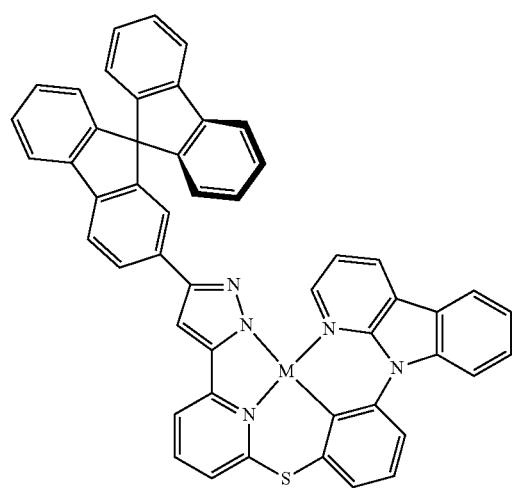
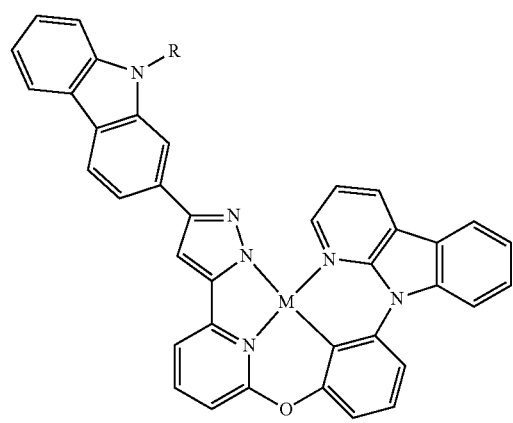
252
-continued
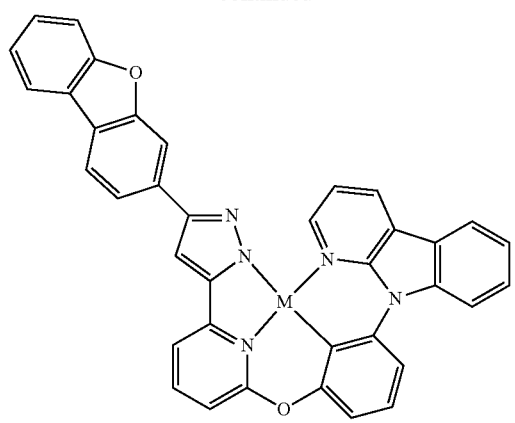
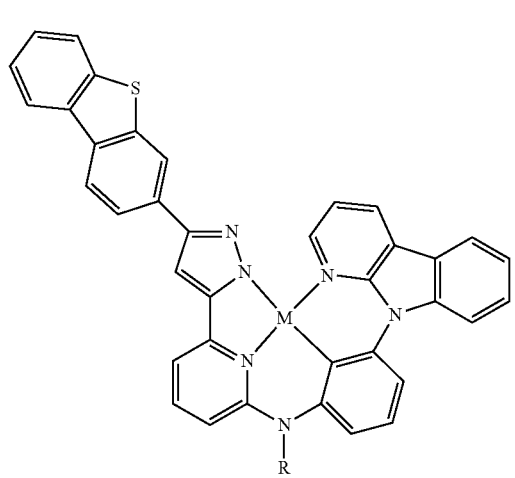
(M = Pt, Pd)
Structures 31
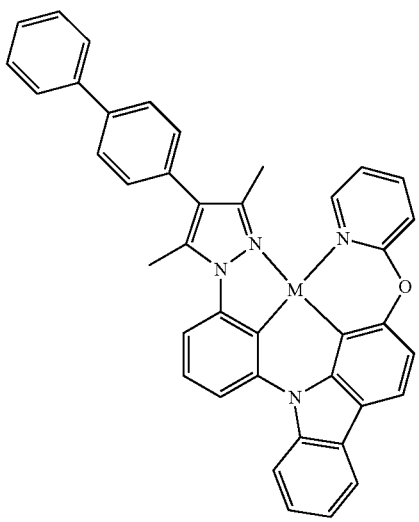

253
-continued
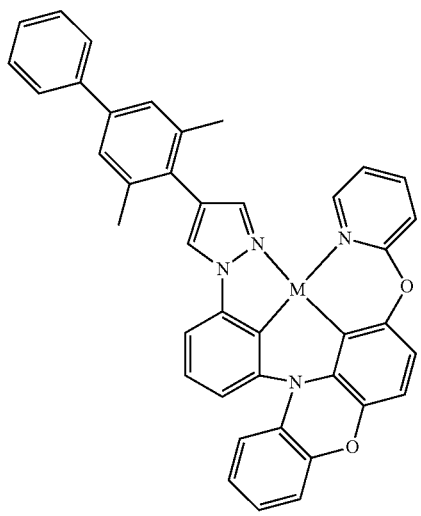
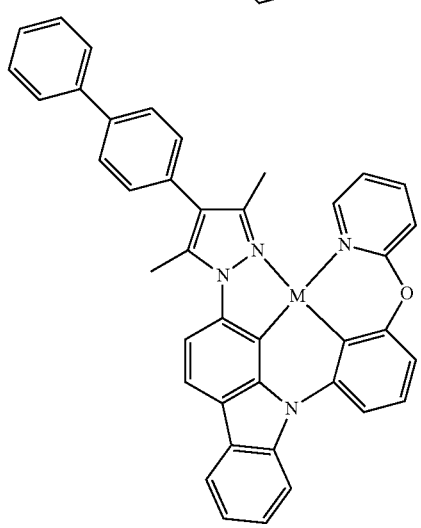
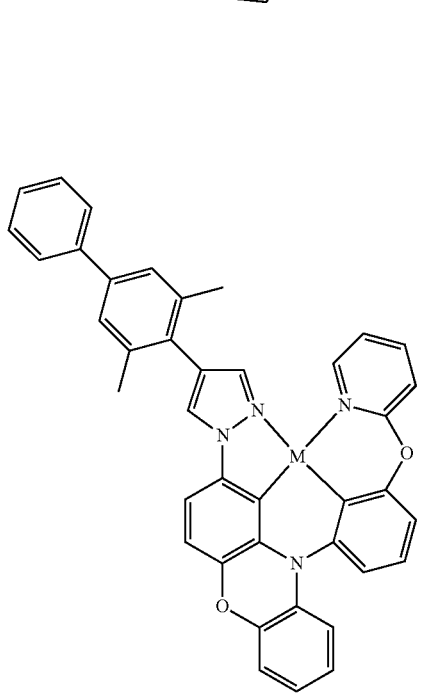
254
-continued
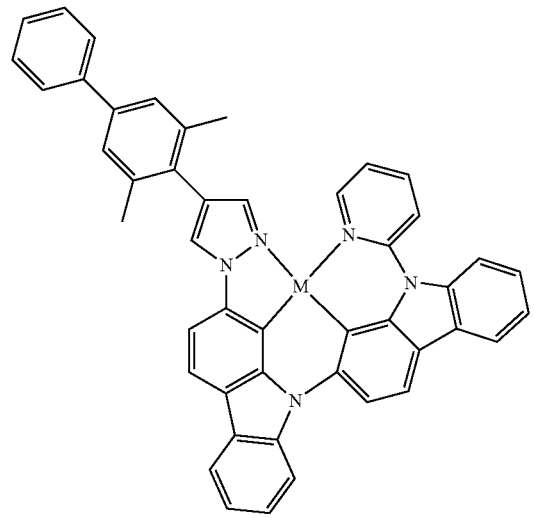
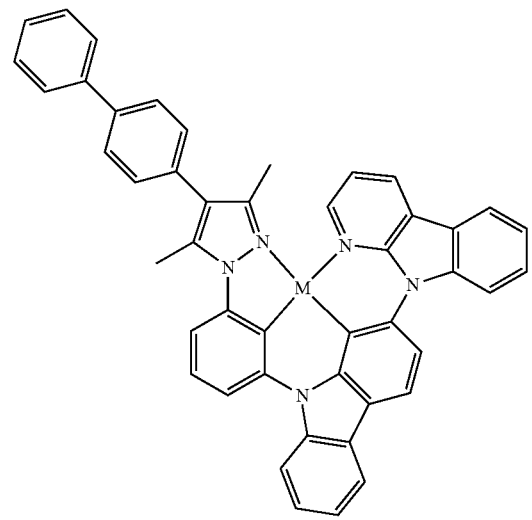
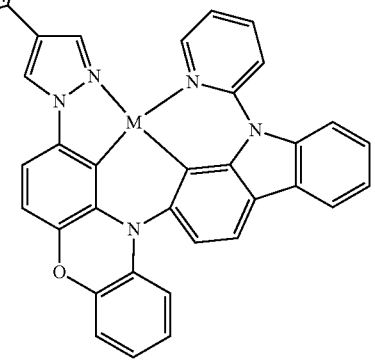

255
-continued
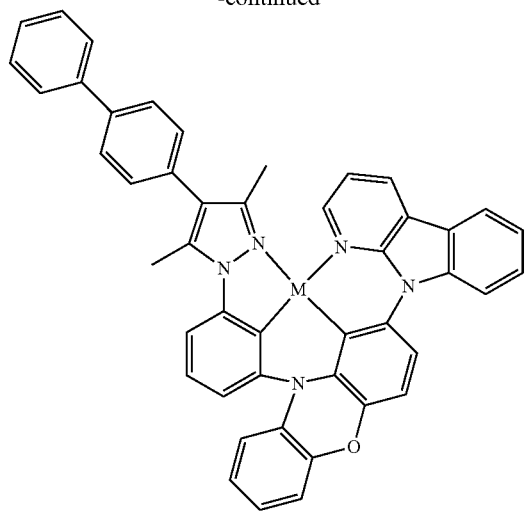
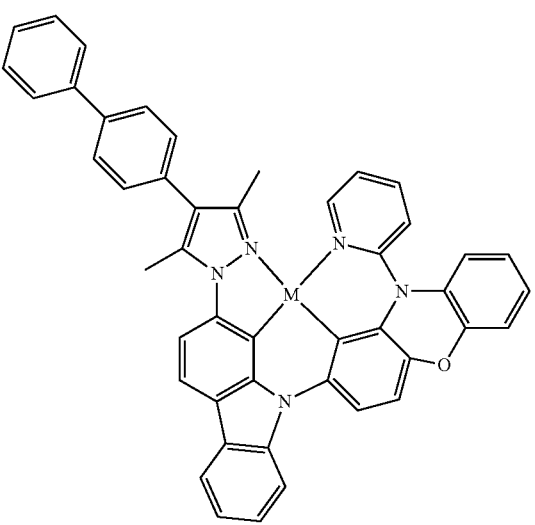
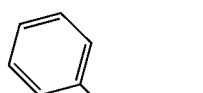
256
-continued
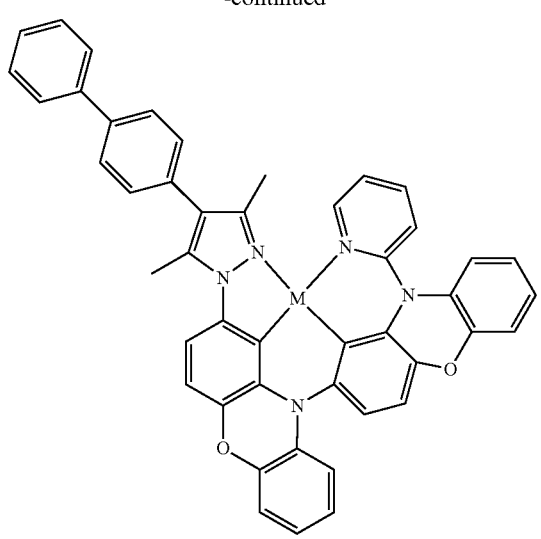
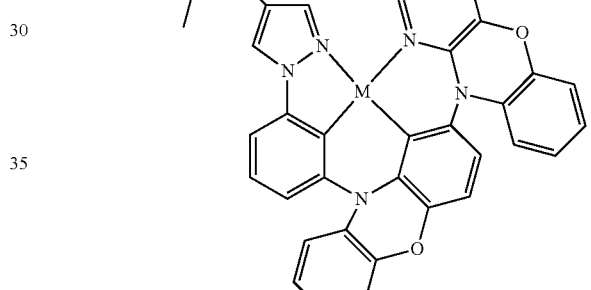
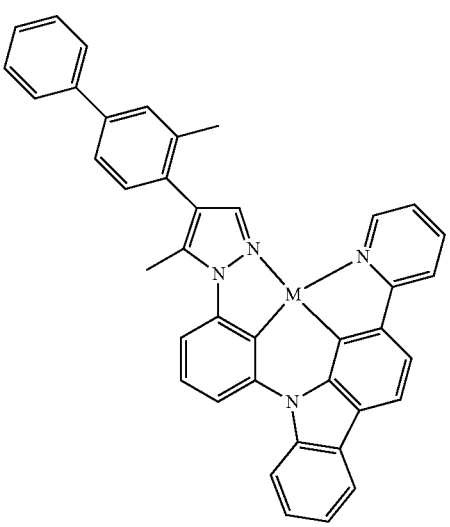

US 10,020,455 B2
257
-continued
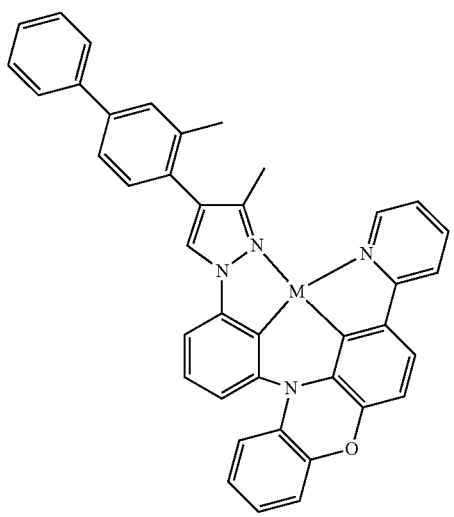
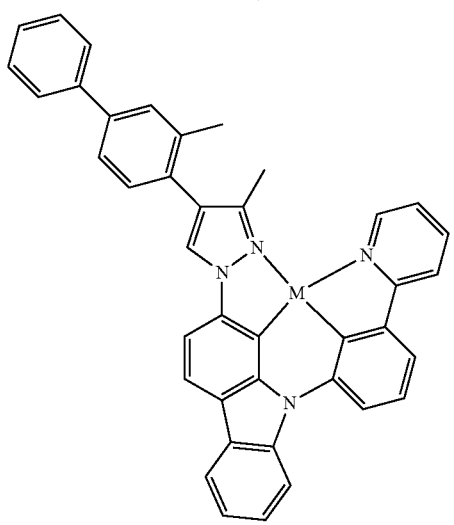

258
-continued
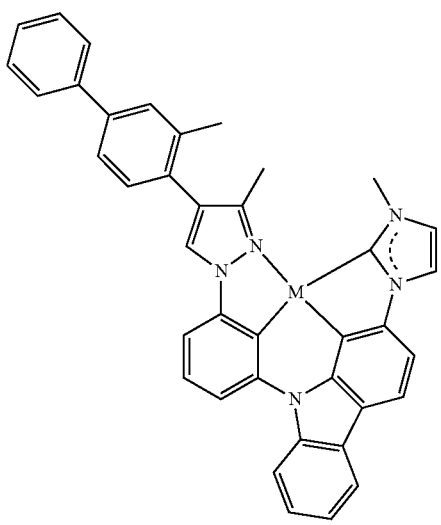
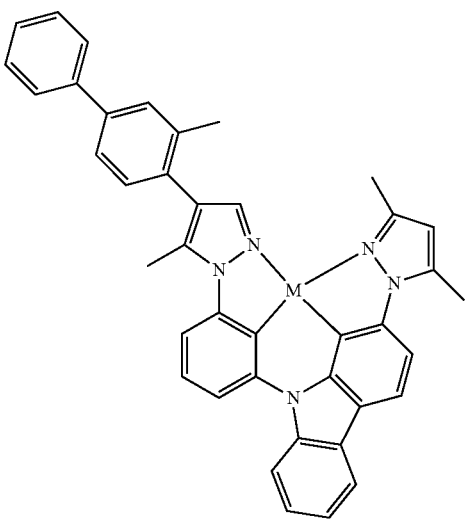
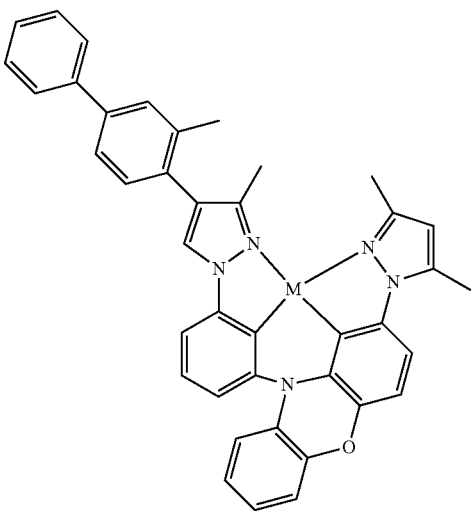

259
-continued
260
Structures 32
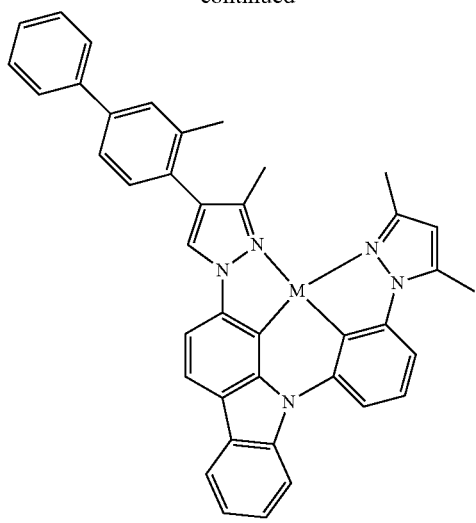
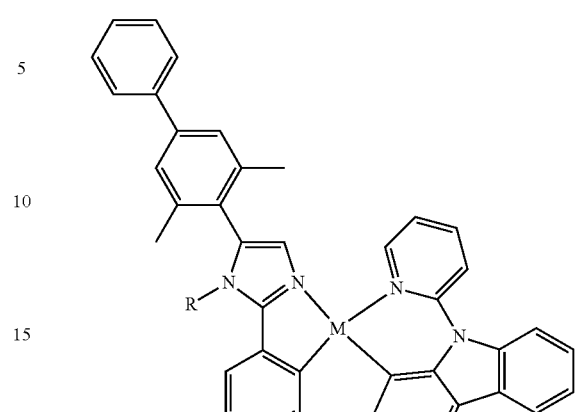
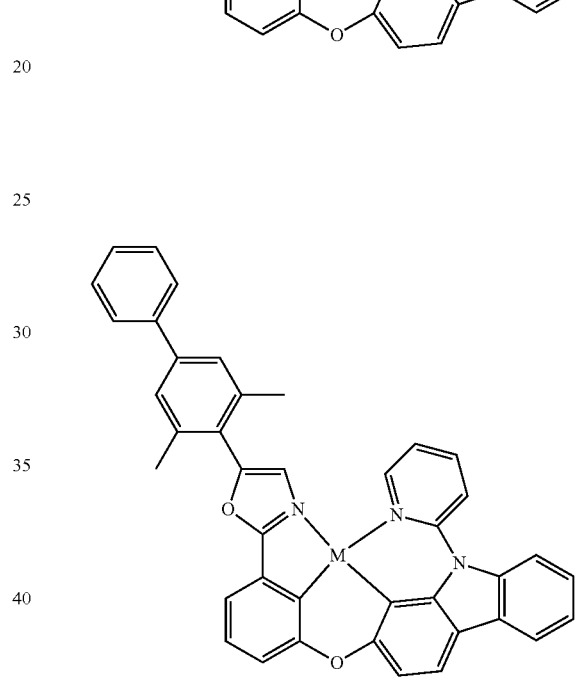
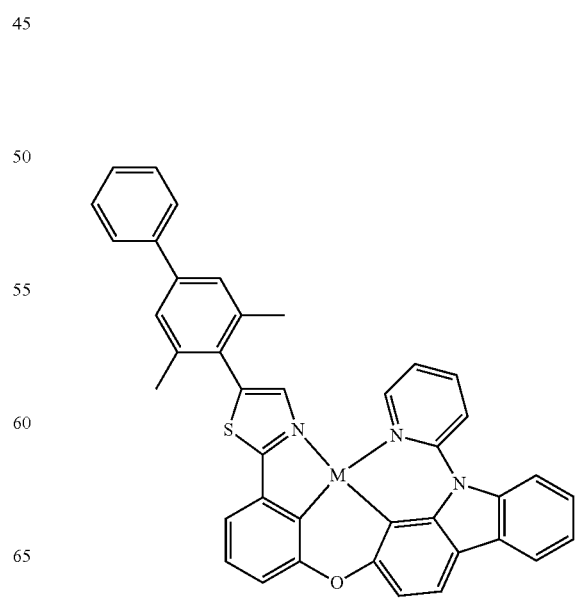
(M = Pt, Pd)

261
-continued
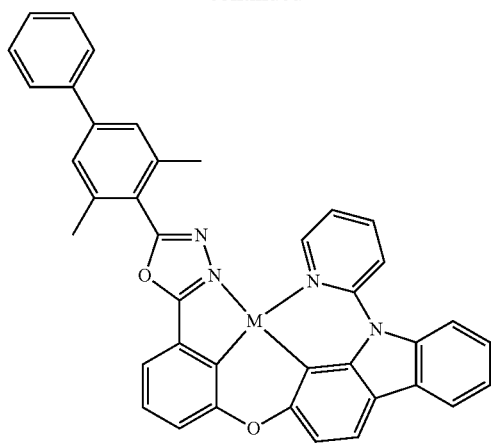
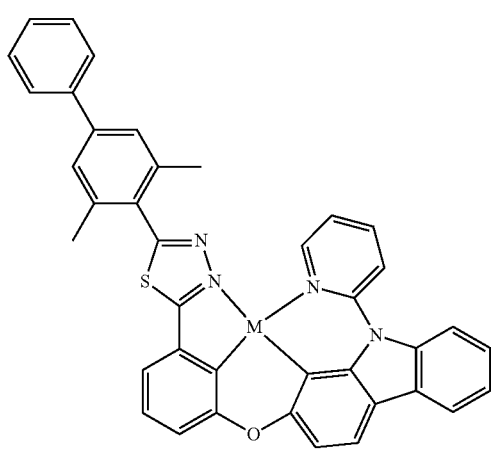
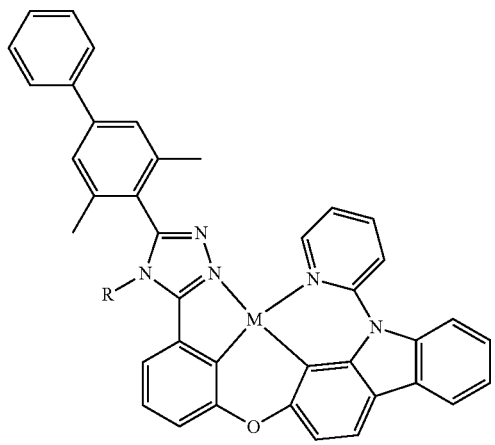
262
-continued
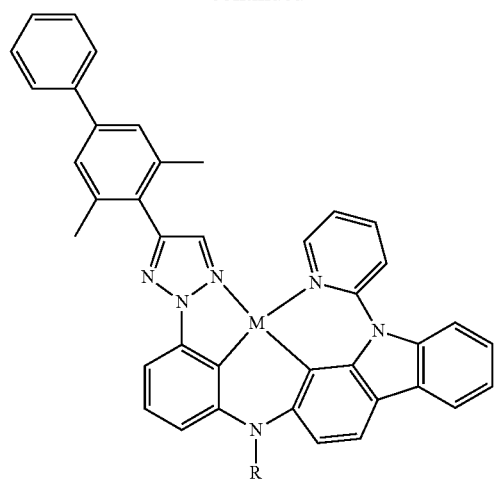
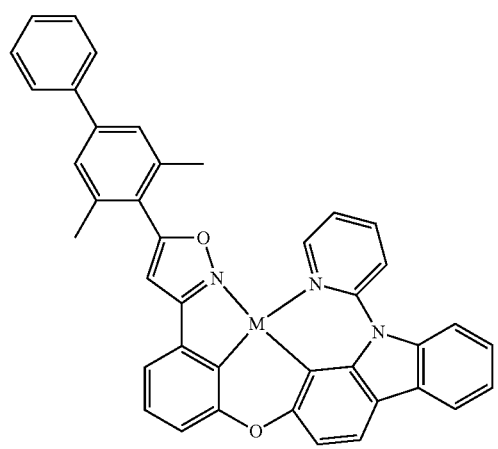
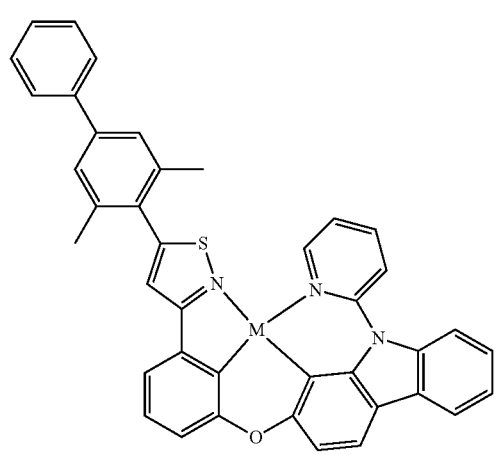

263
-continued
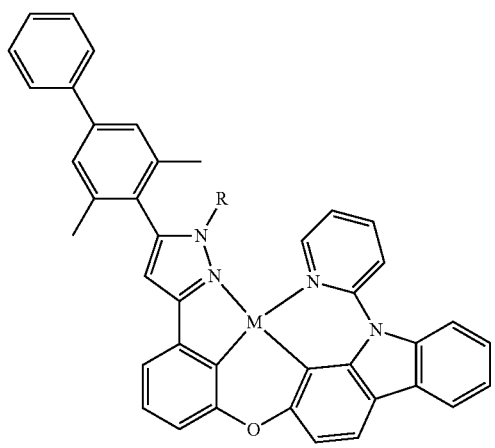
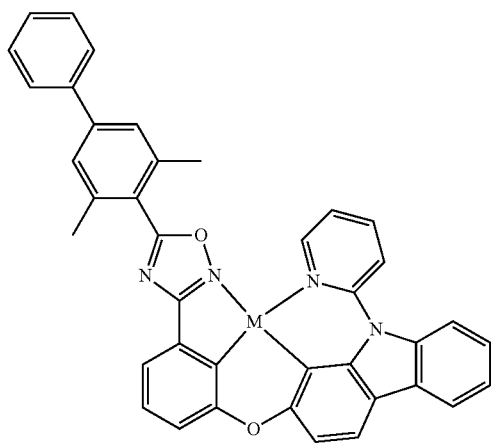
264
-continued
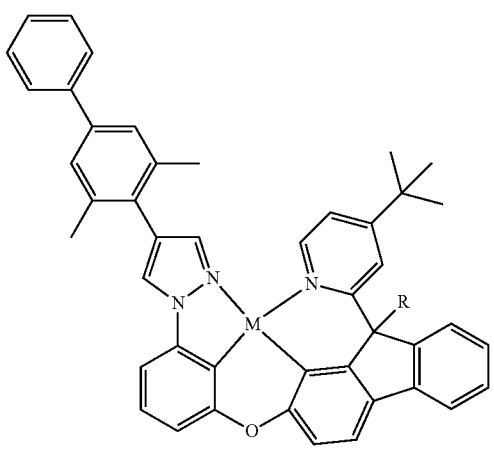
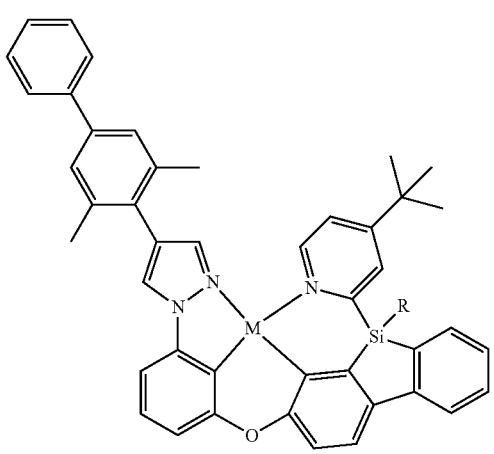
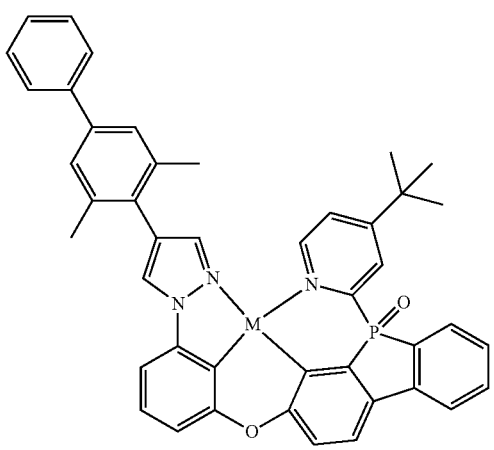

265
-continued
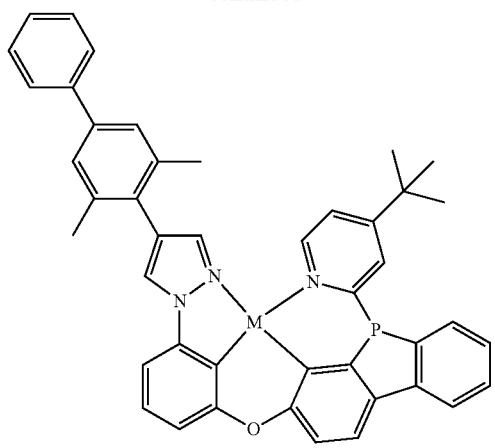
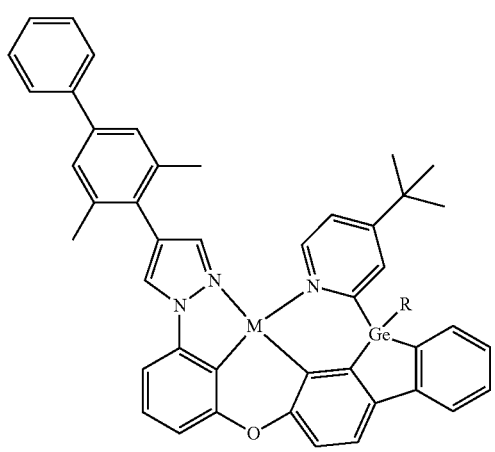
266
-continued
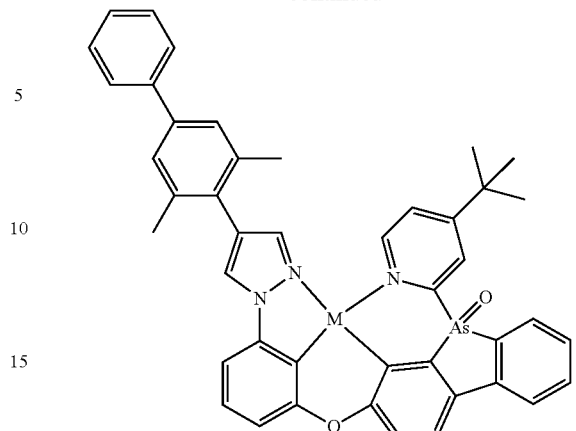
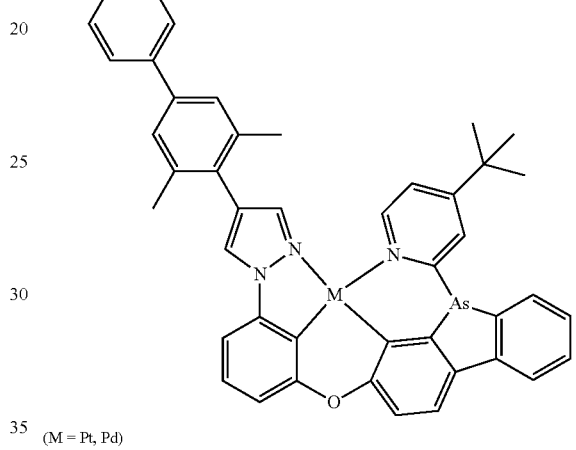
(M = Pt, Pd)
Structures 33
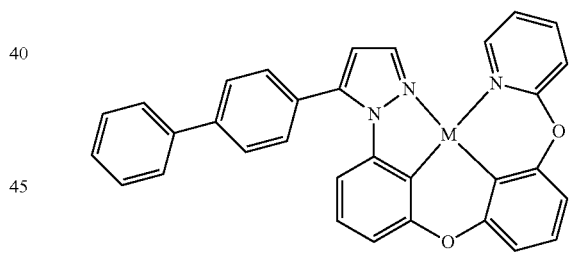
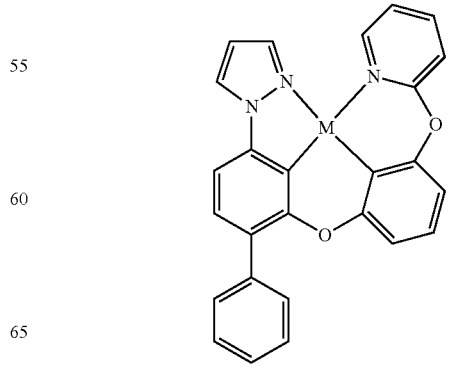

267
-continued
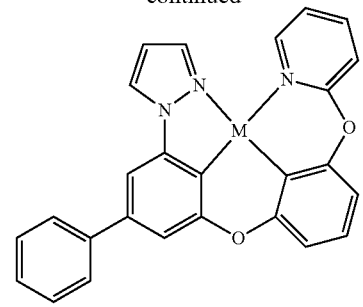
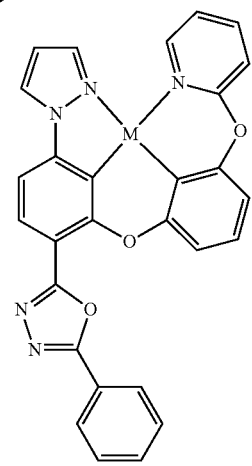
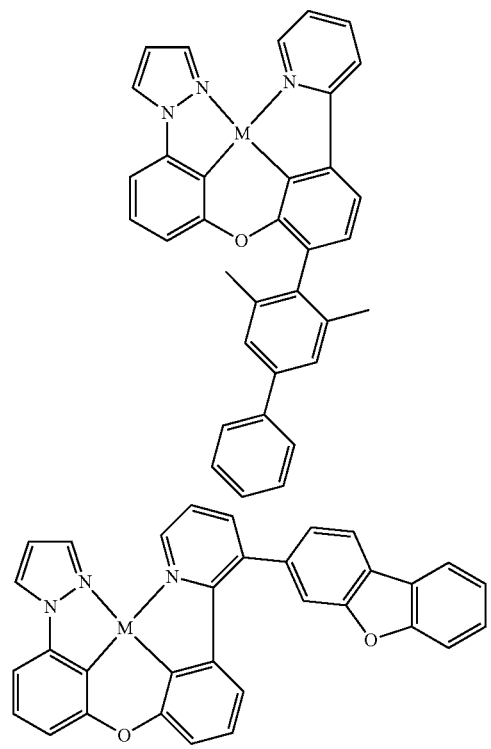
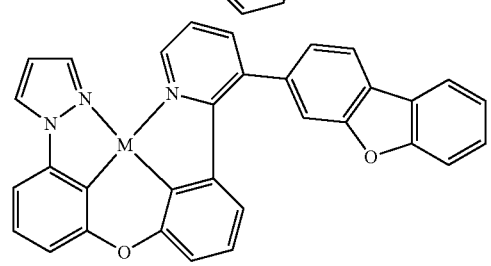
268
-continued
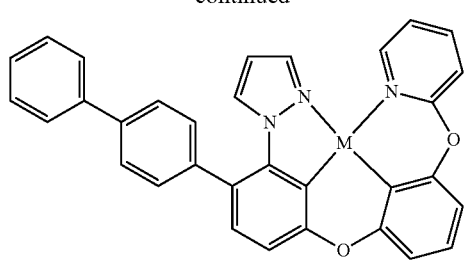
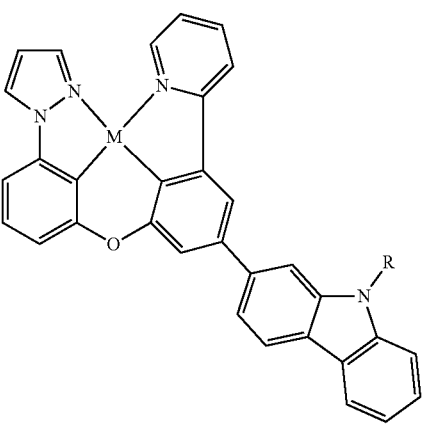
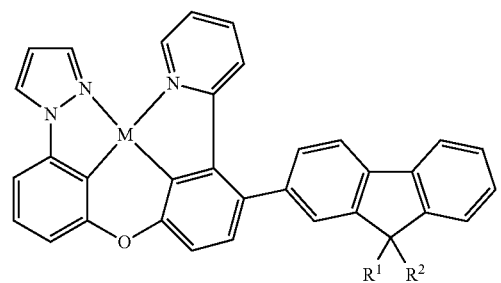
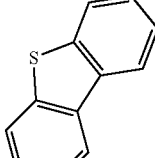
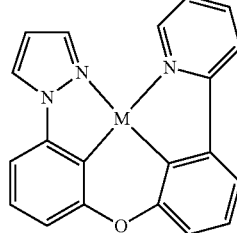
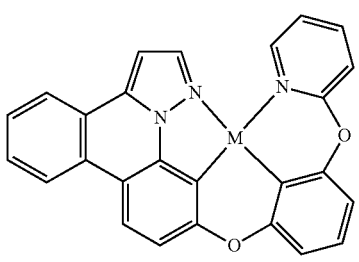

269
-continued
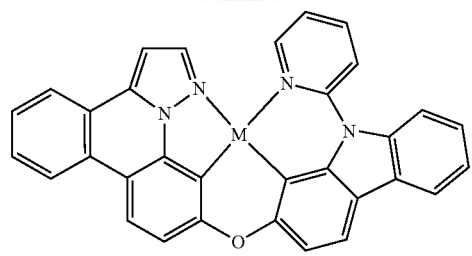
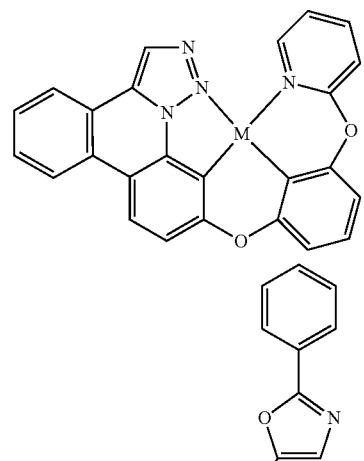
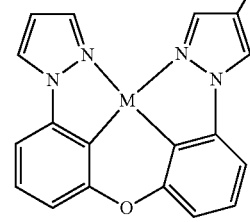
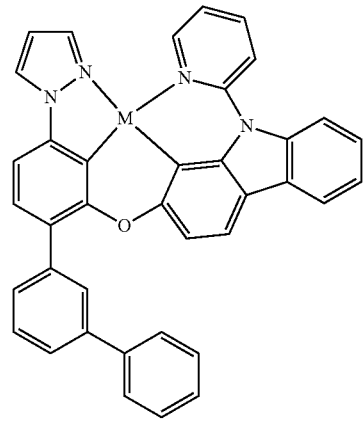
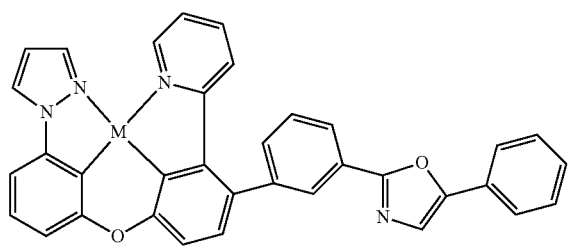
270
-continued
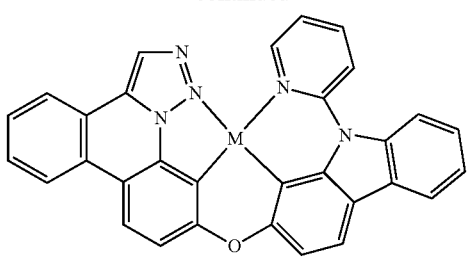
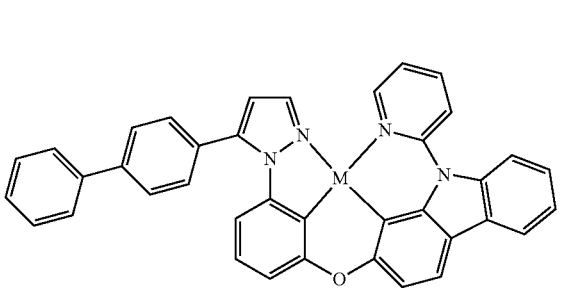
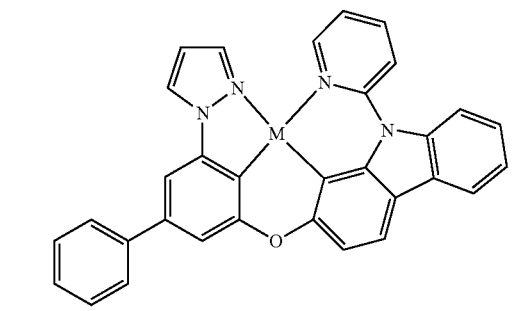
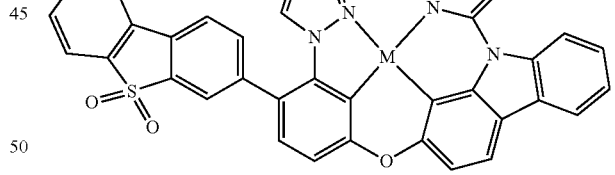
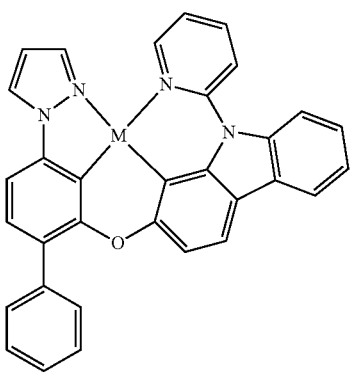

271
-continued
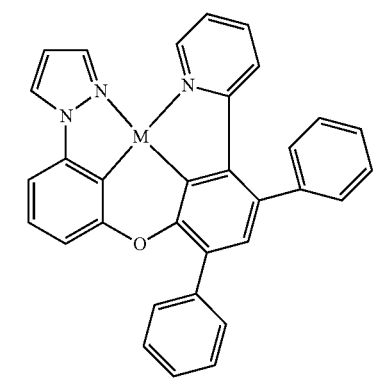
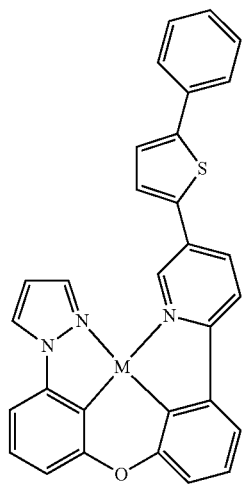
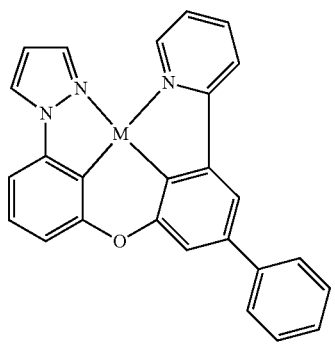
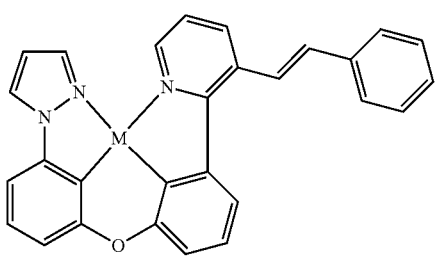
272
-continued
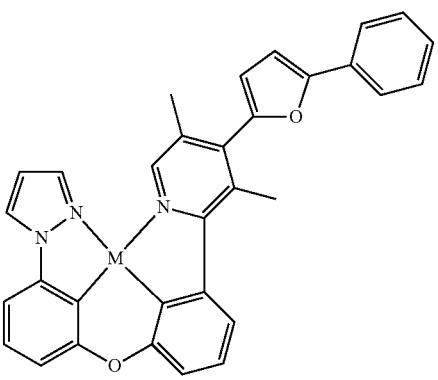
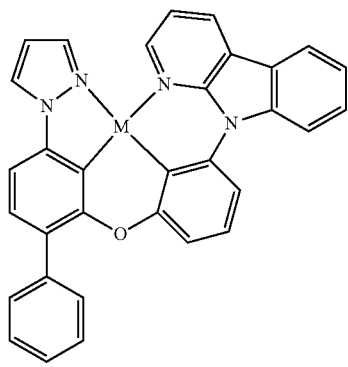
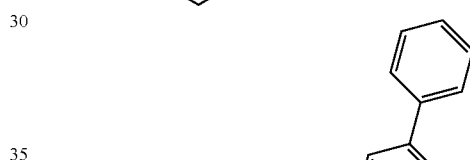
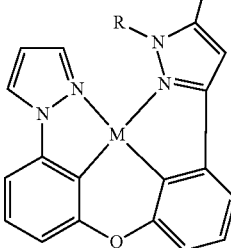
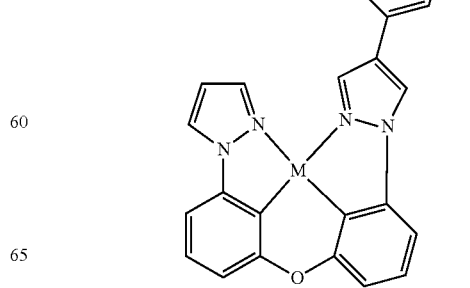

273
-continued
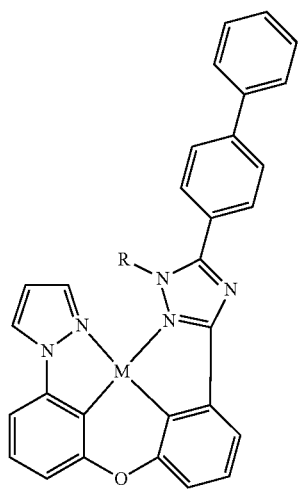
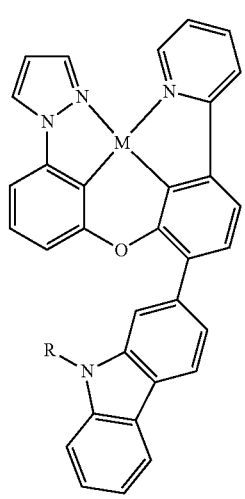
274
-continued
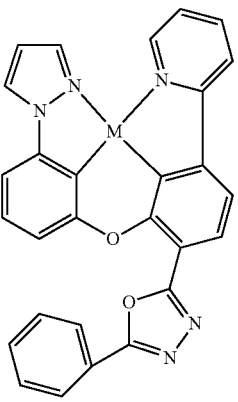
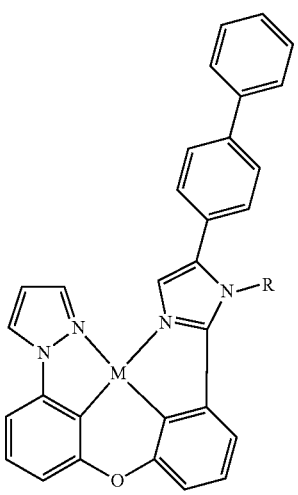
(M = Pt, Pd)
Structures 34
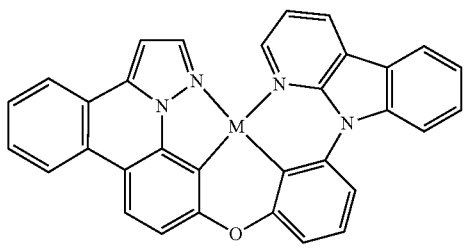
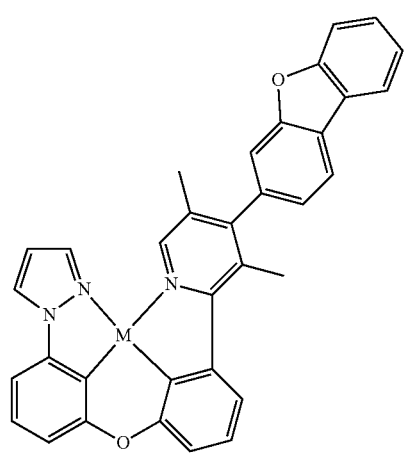
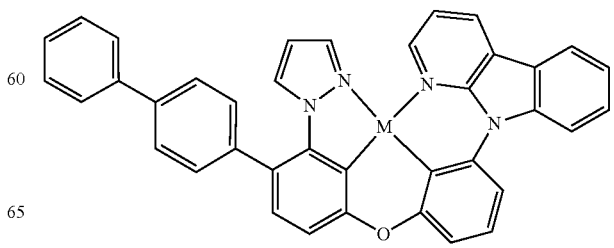

-continued
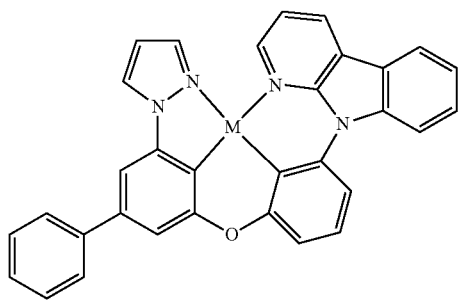
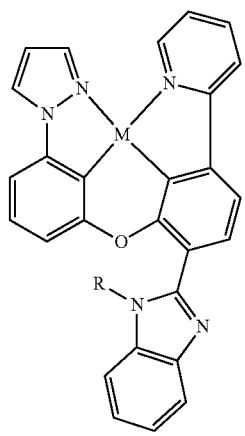
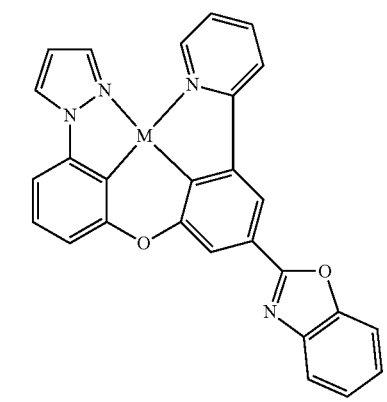
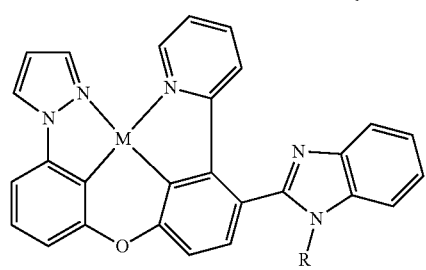
-continued
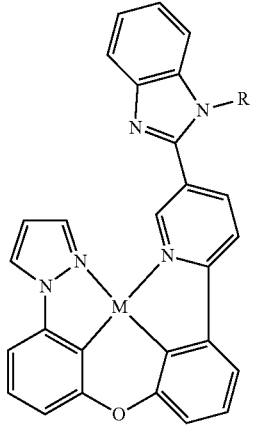
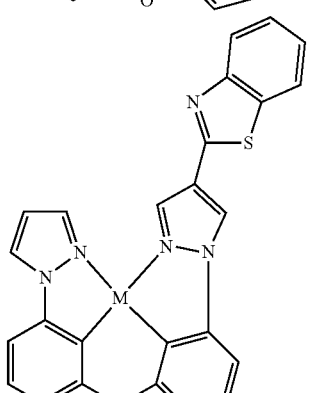
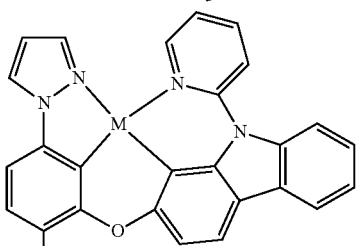
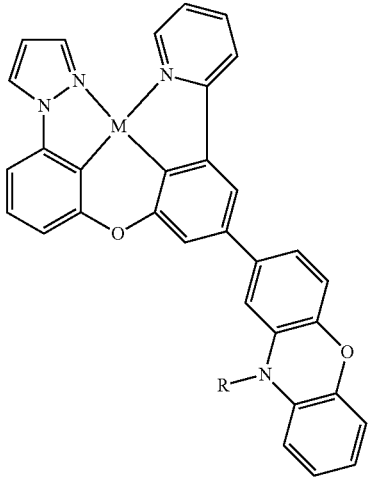

277
-continued
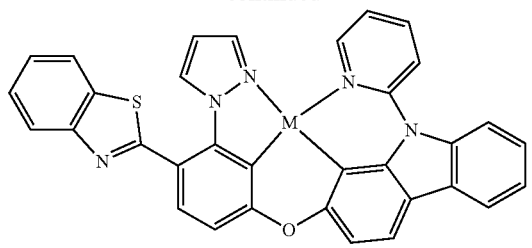
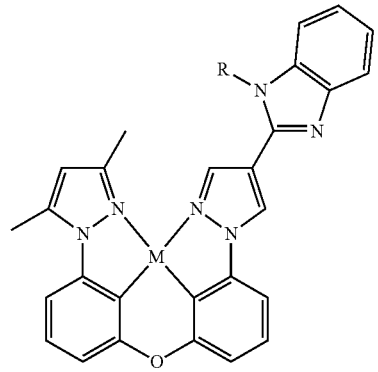
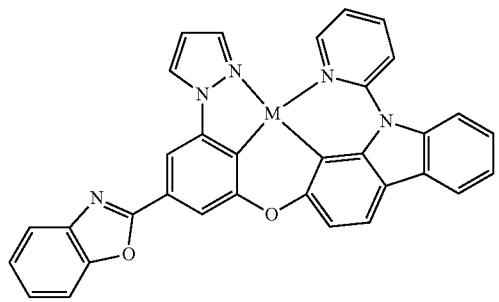
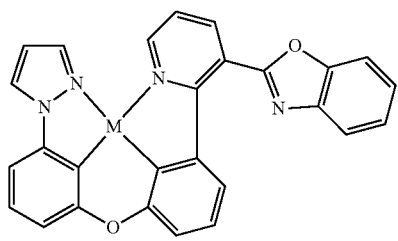
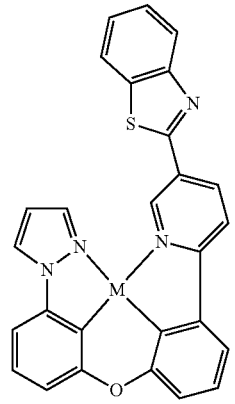
278
-continued
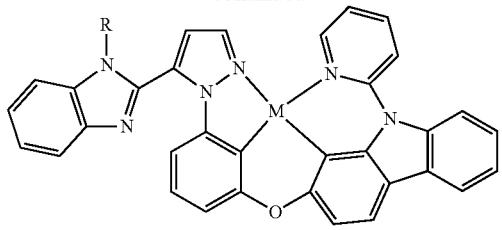
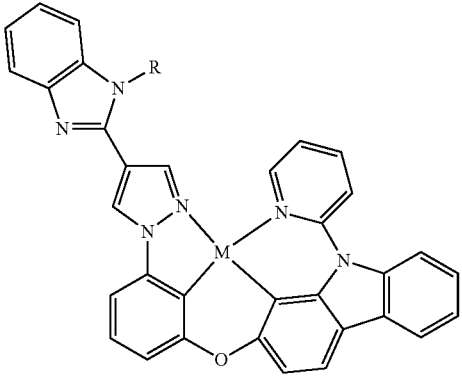
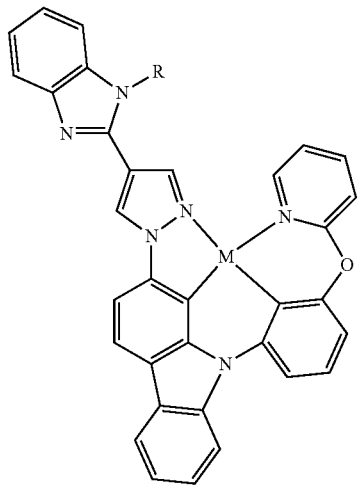
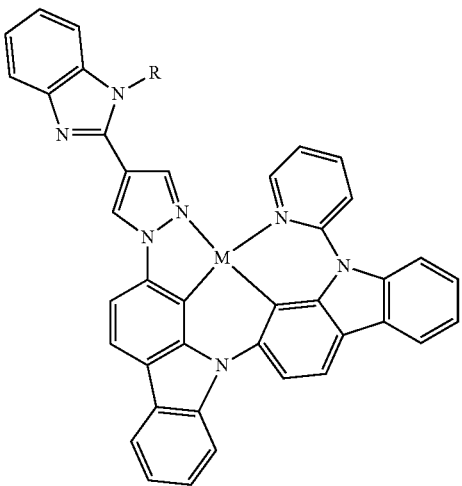

279
-continued
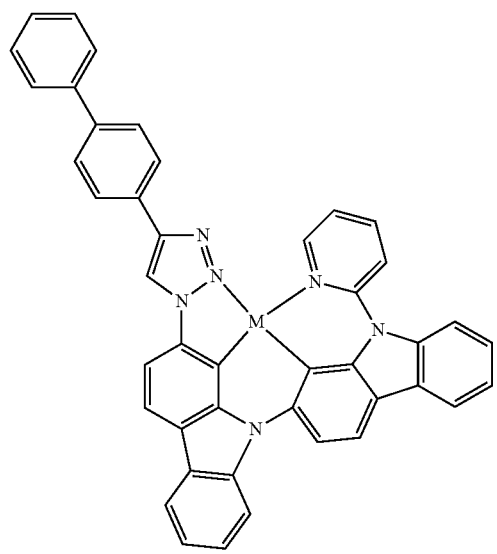
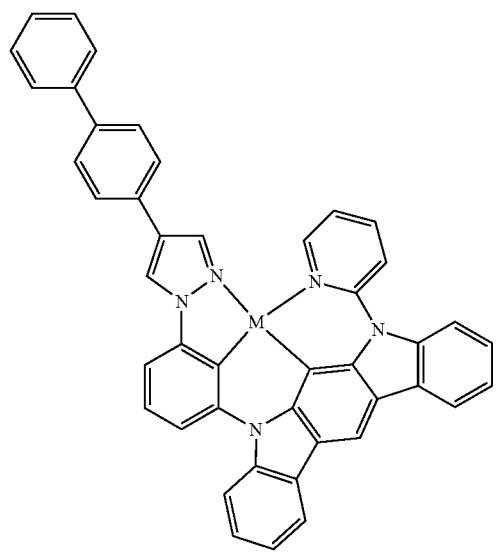
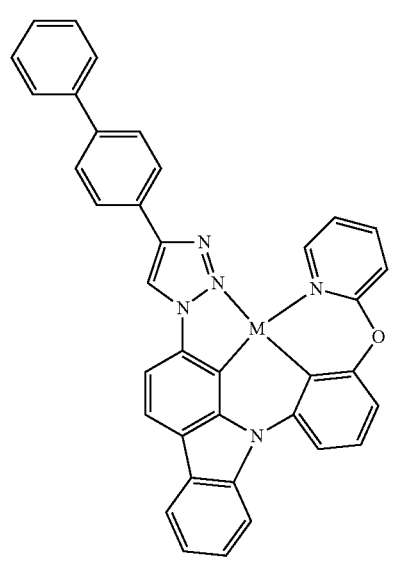
280
-continued
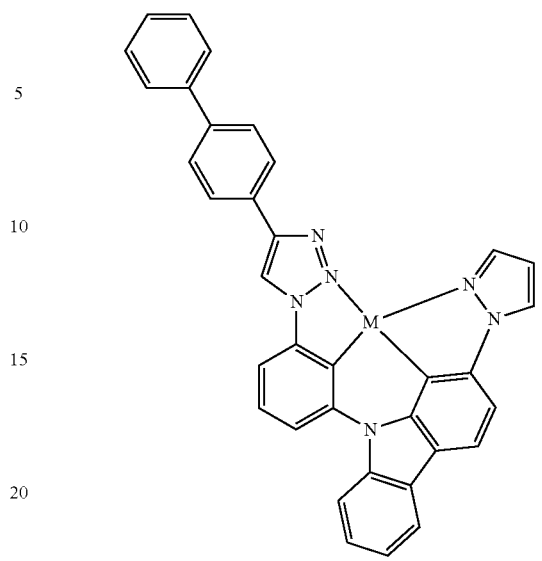
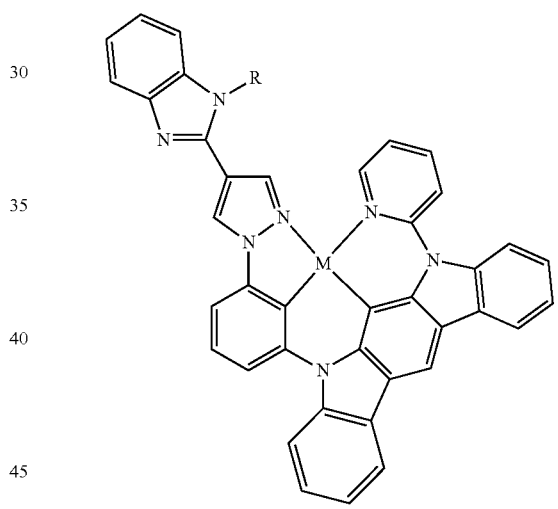
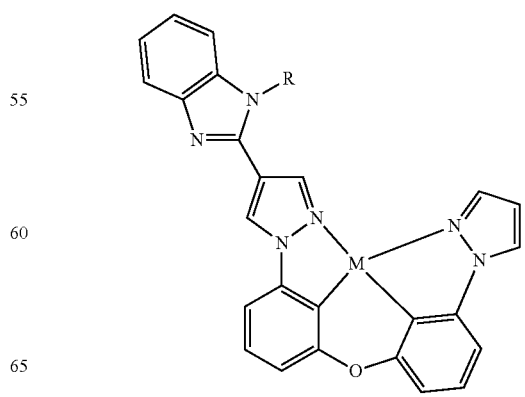

281
-continued
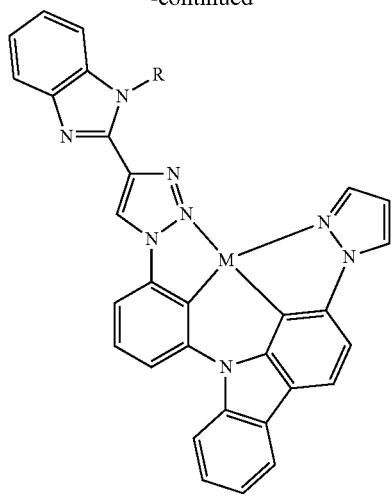
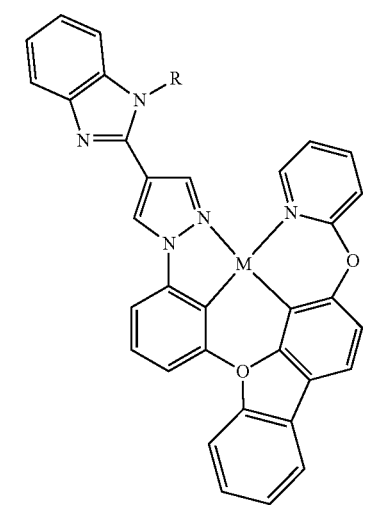
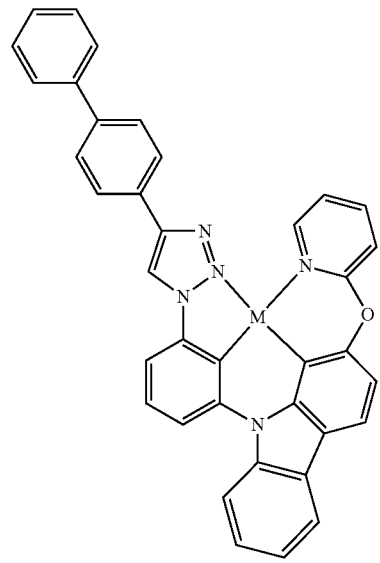
(M = Pt, Pd)
282
-continued
Structures 35
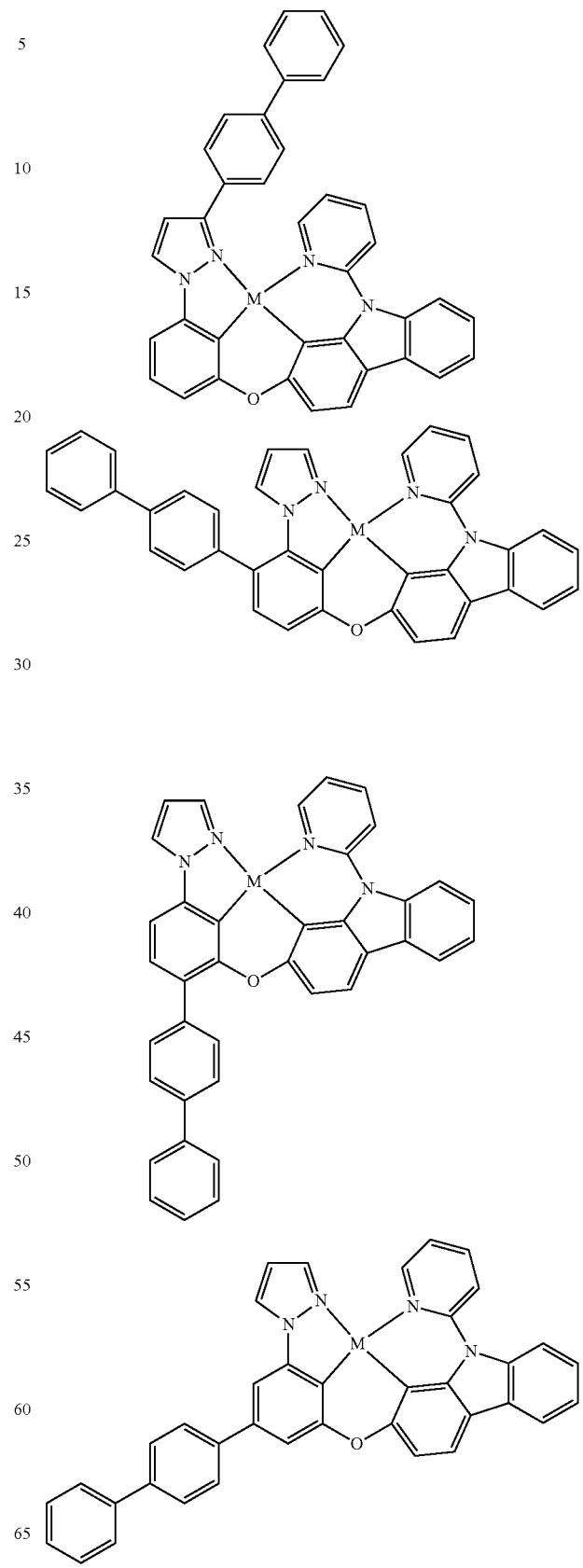

283
-continued
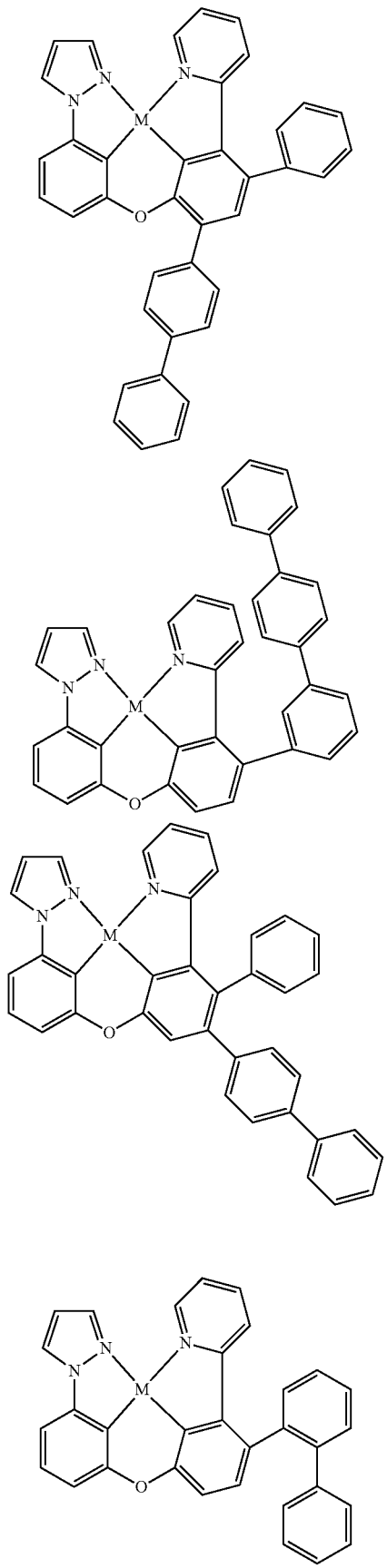
284
-continued
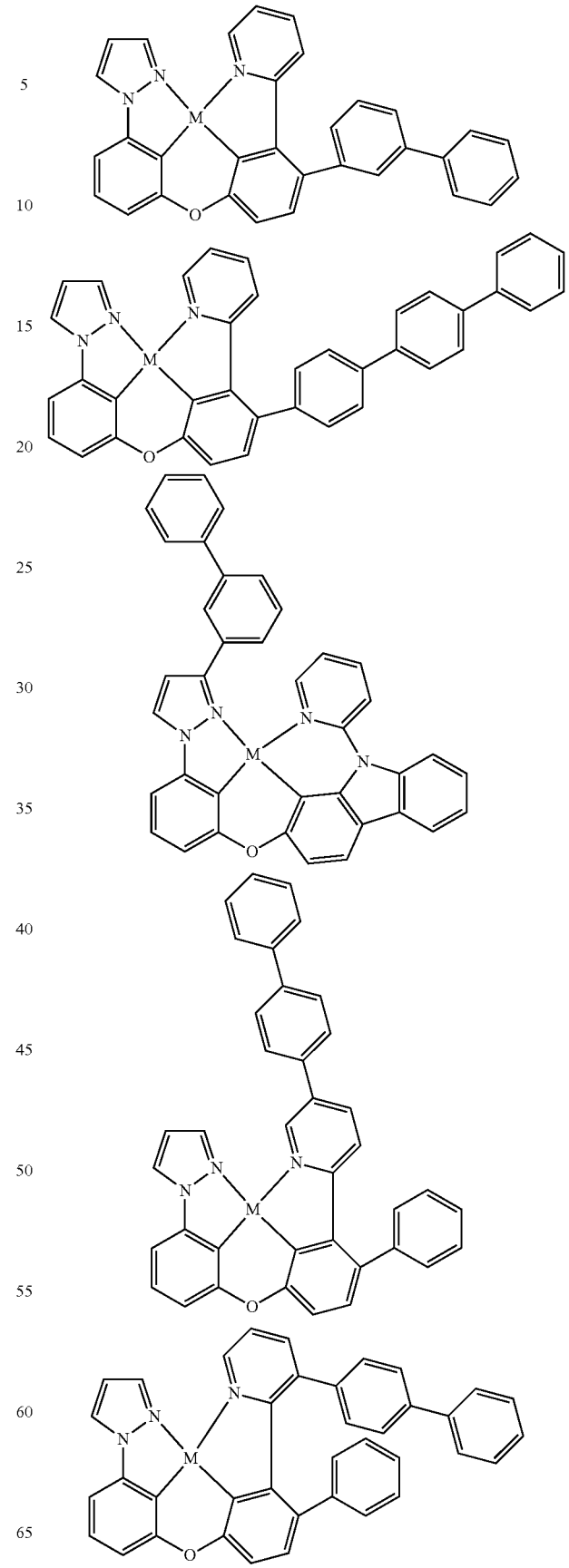

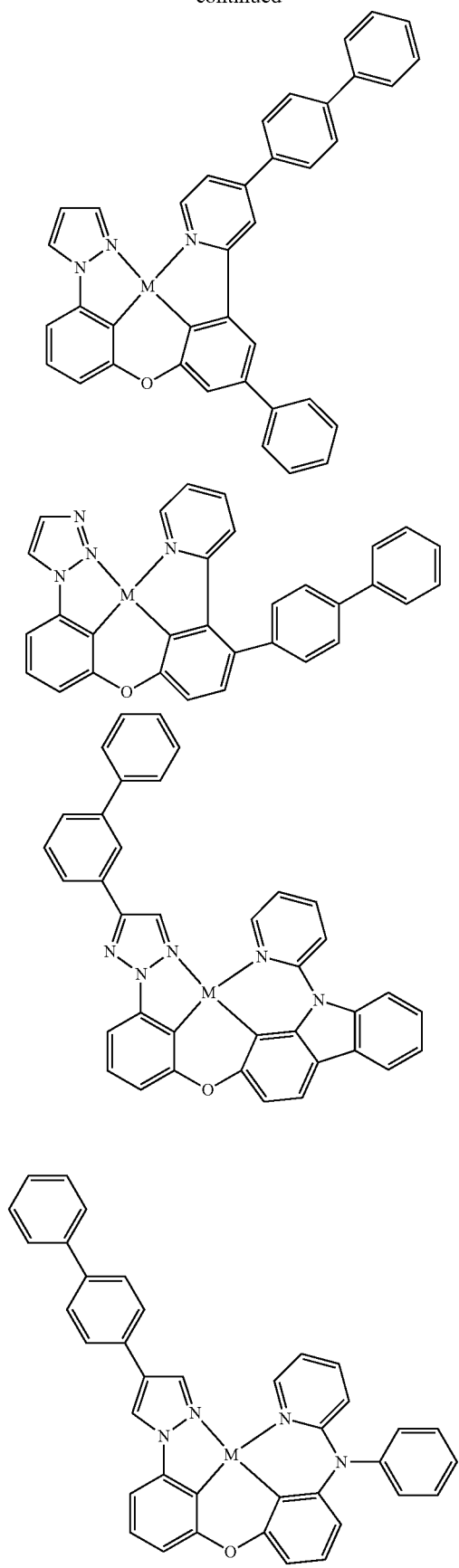
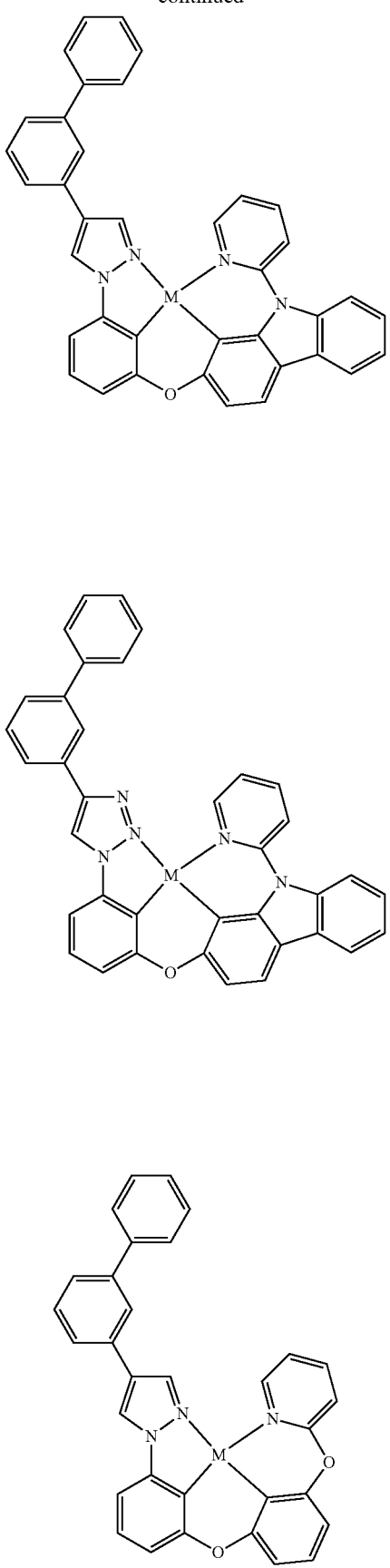

287
-continued
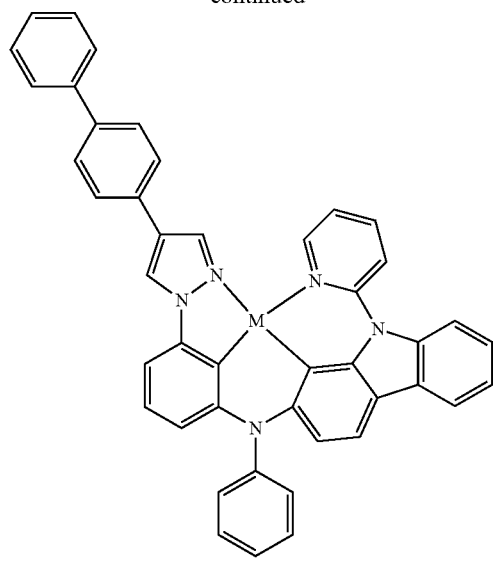
288
-continued
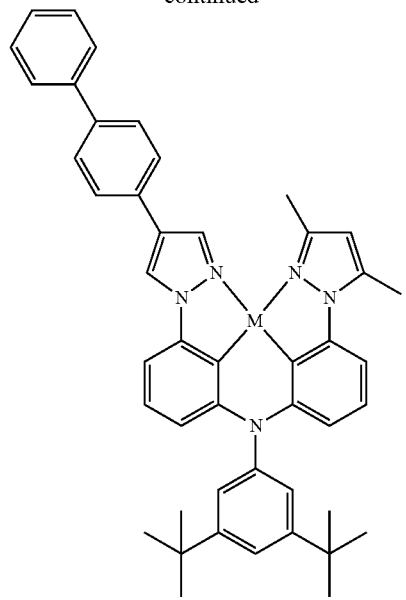
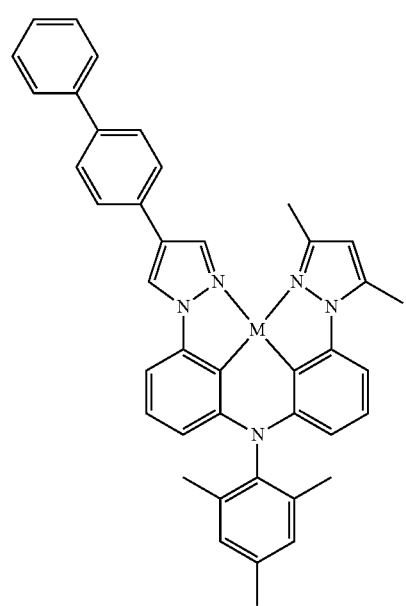
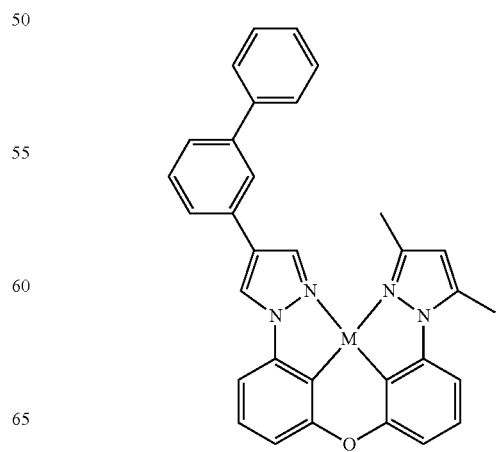

289
-continued
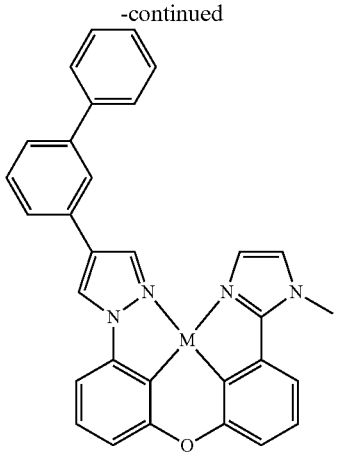
(M = Pt, Pd)
Structures 36
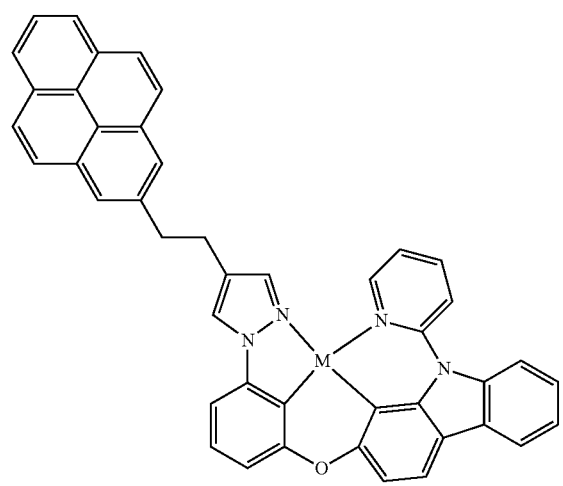
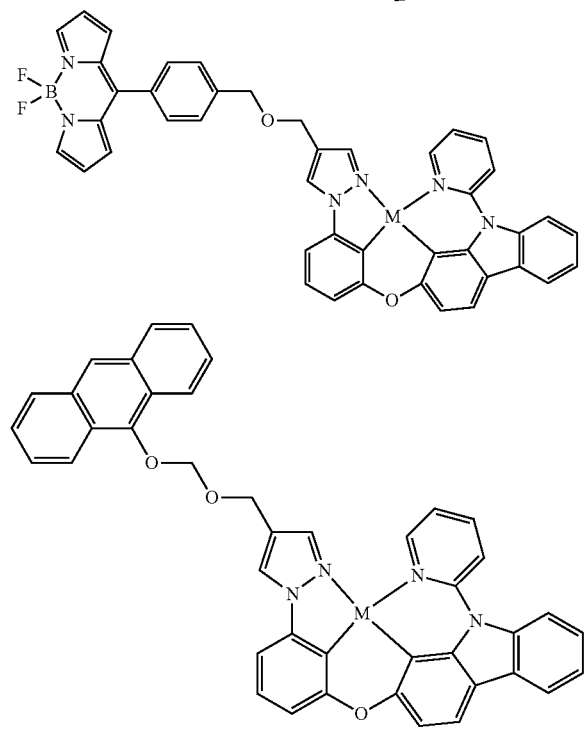
290
-continued
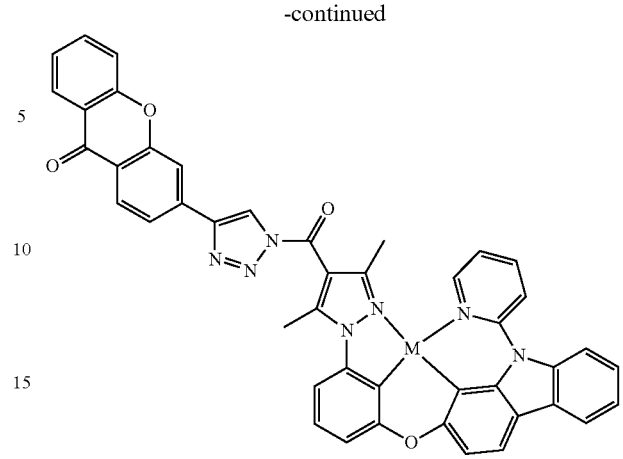
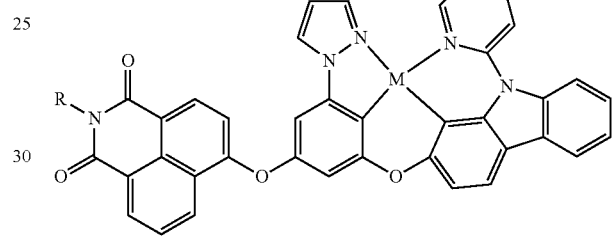
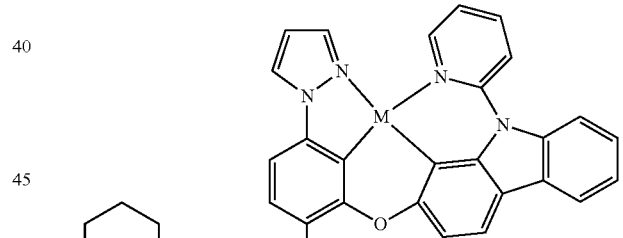
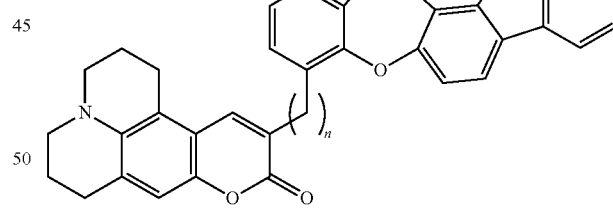
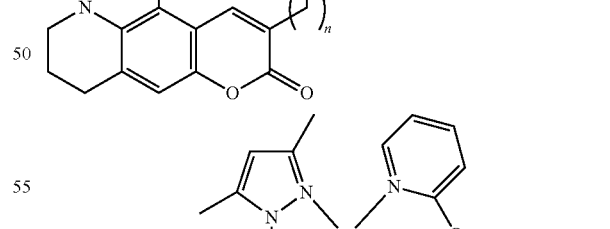
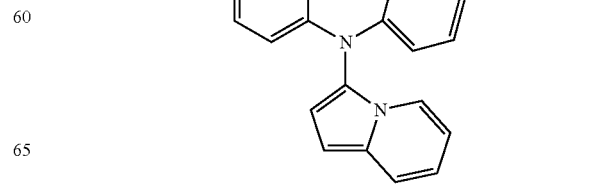

291
-continued
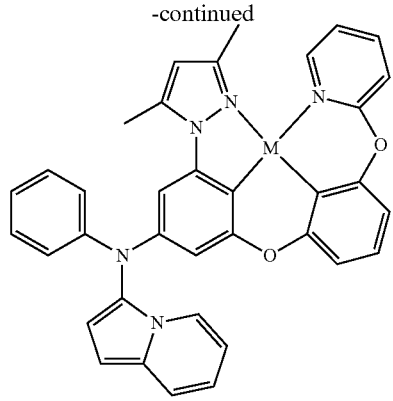
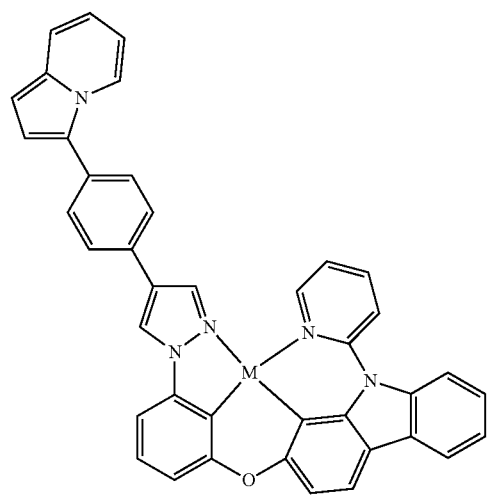
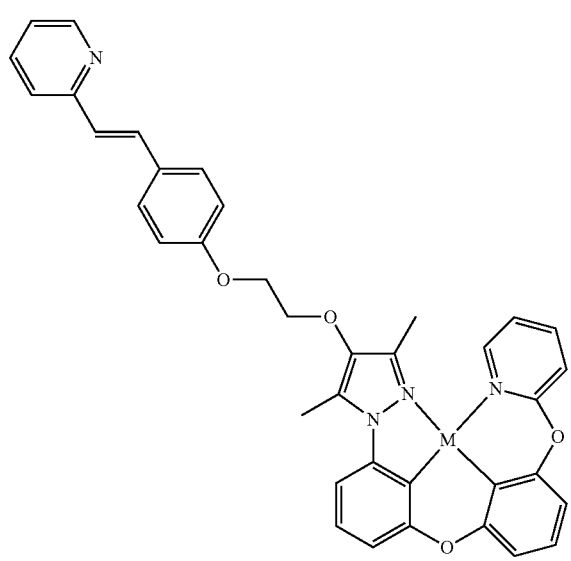
292
-continued
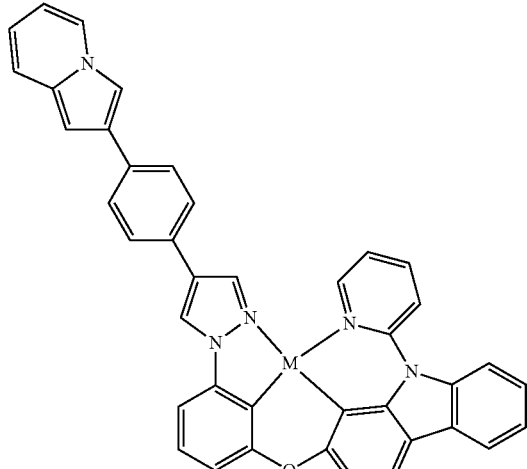
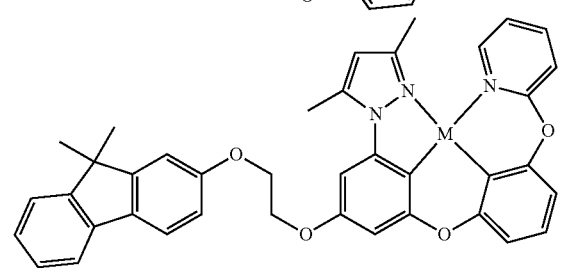
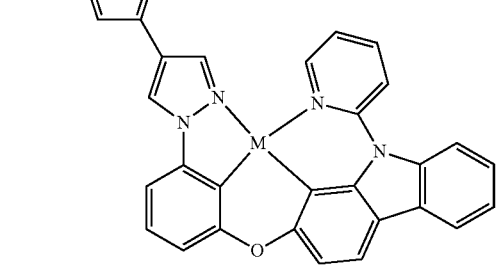
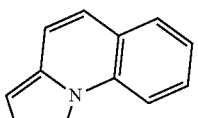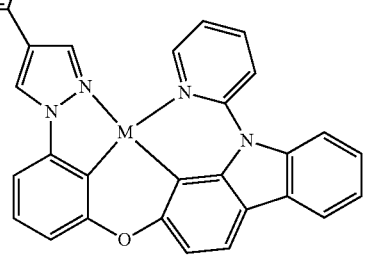

293
-continued
294
-continued
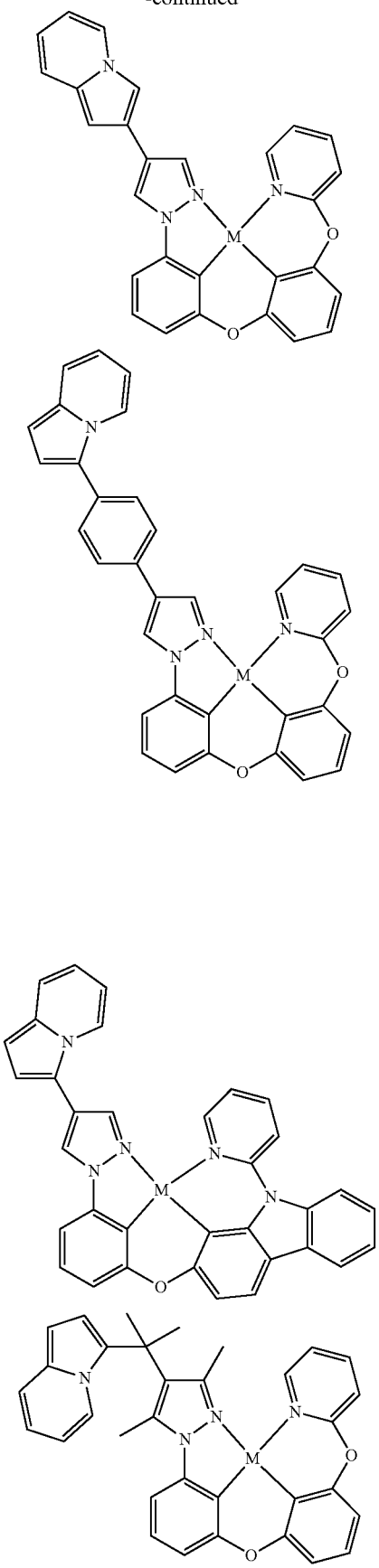
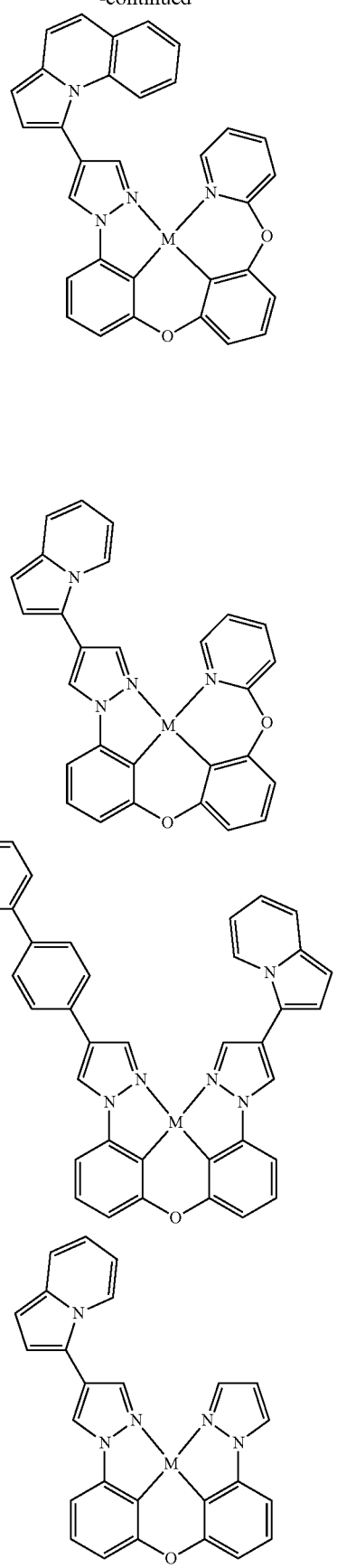

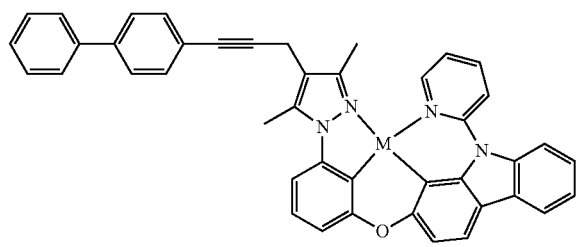
(M = Pd, Pt)
Structures 37
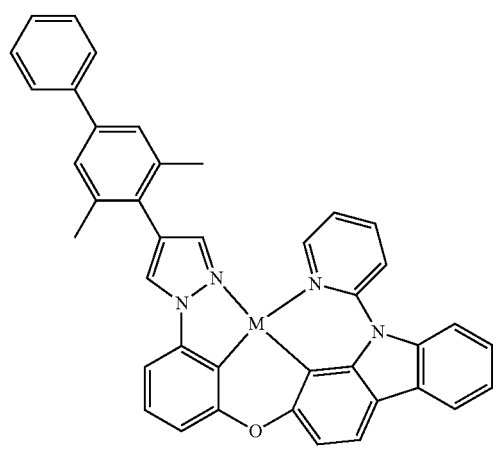
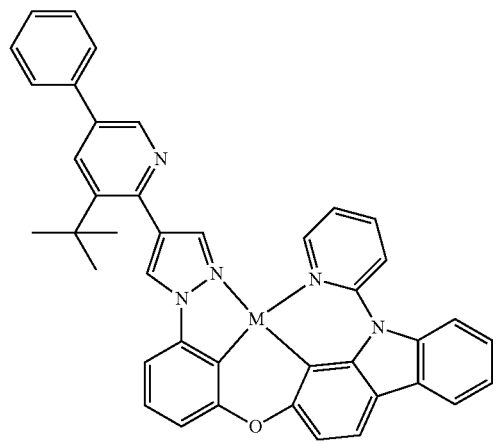
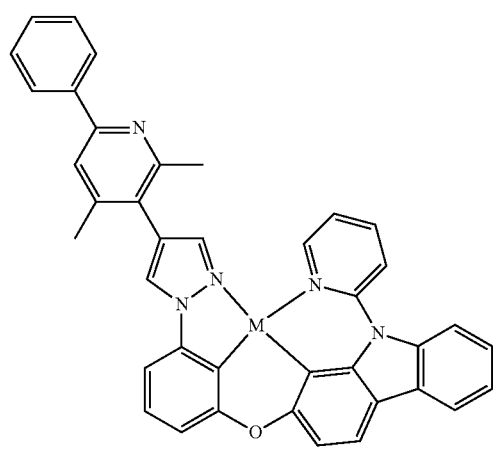
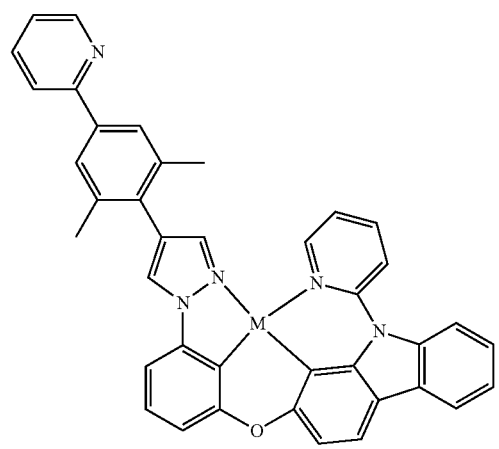
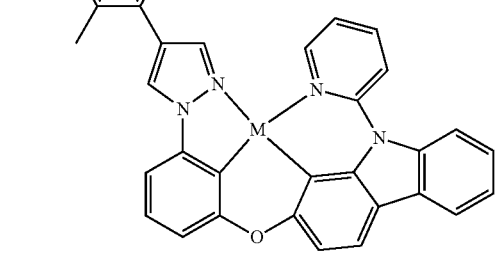
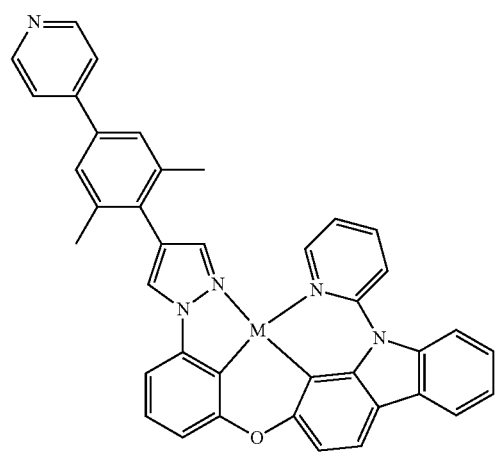

297
-continued
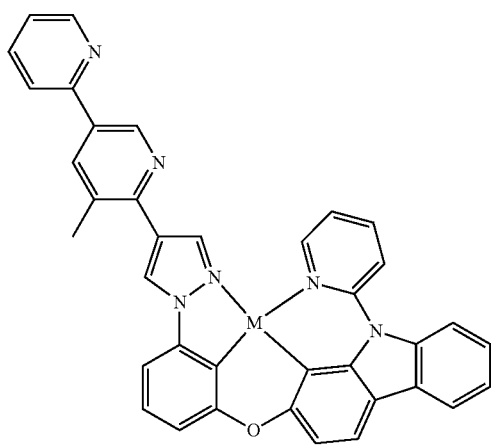
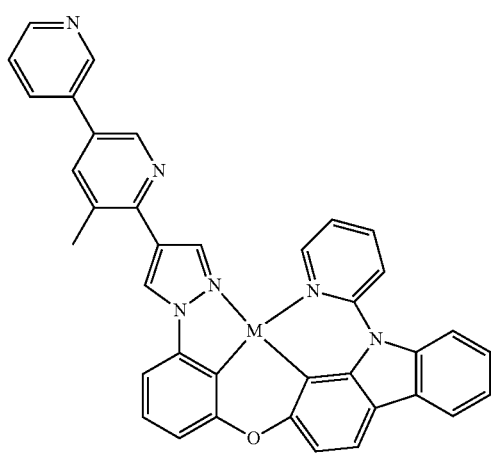
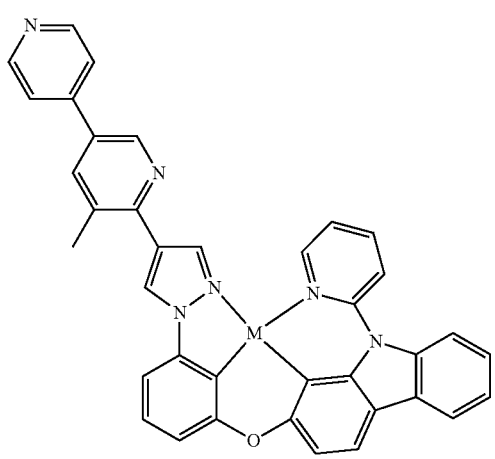
298
-continued
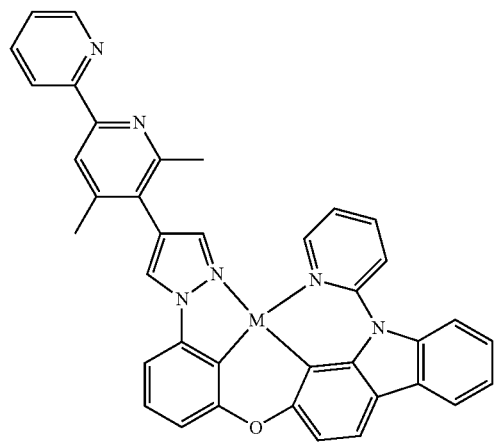
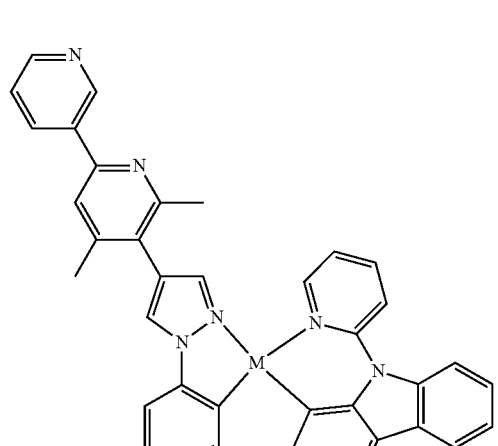
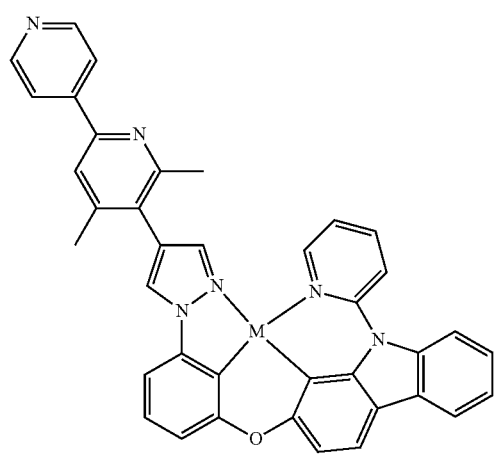

299
-continued
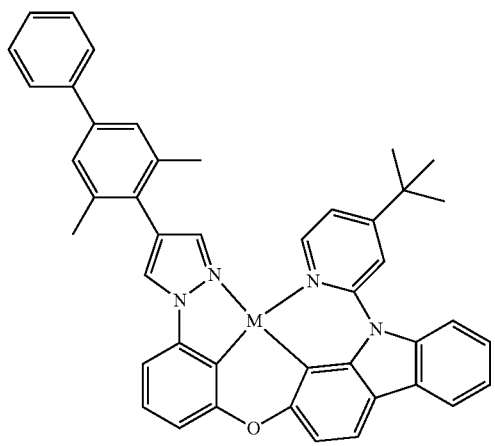
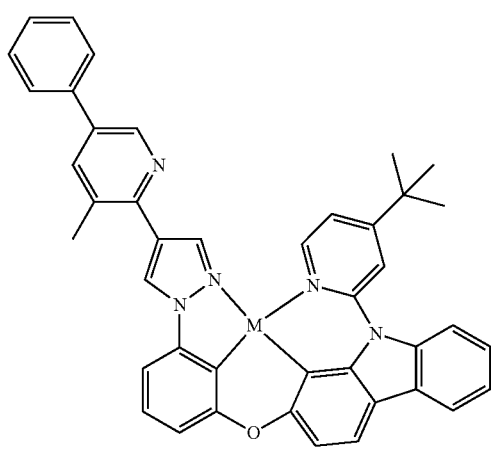
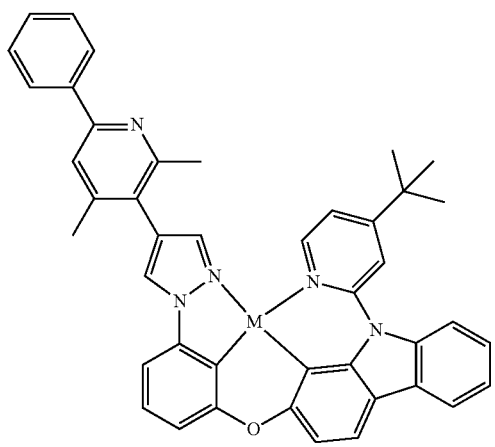
300
-continued
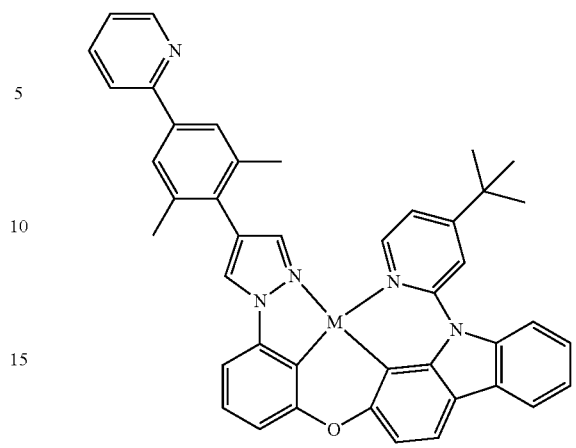
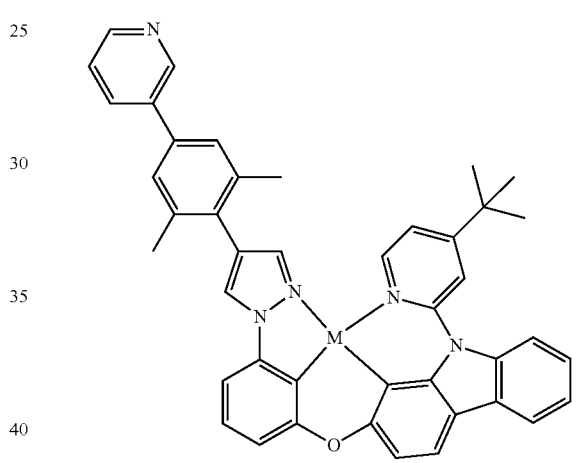
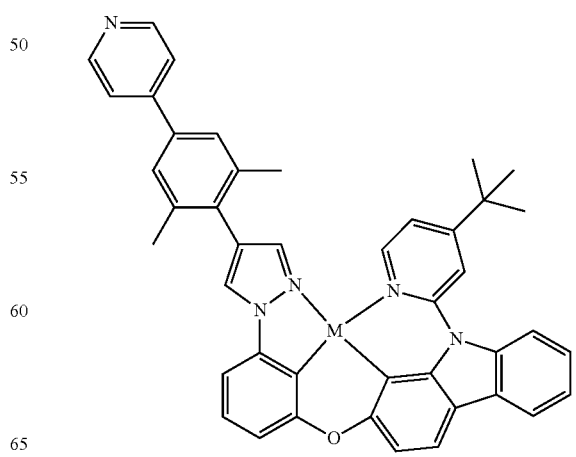

301
-continued
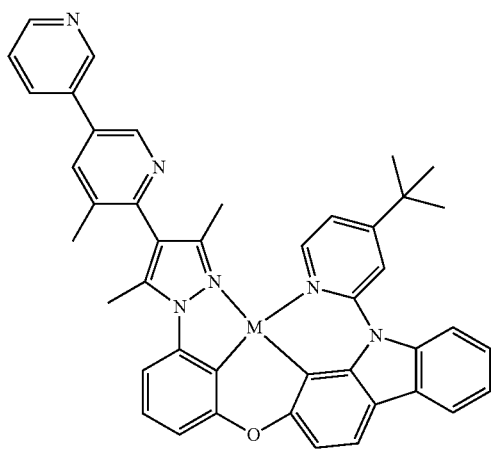
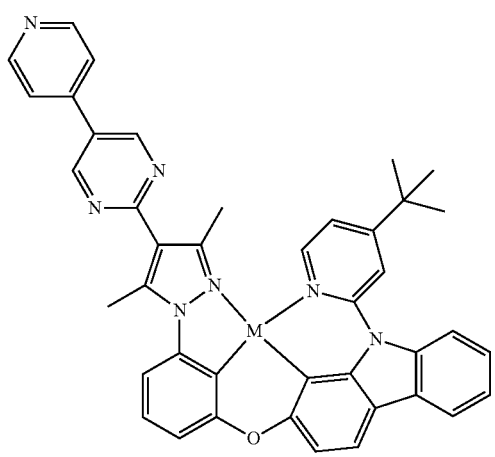
(M = Pt, Pd)
Structures 38
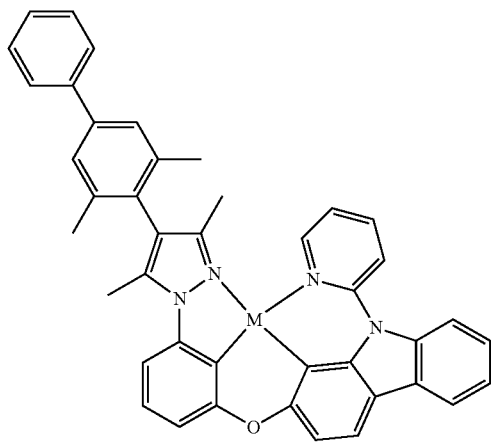
302
-continued
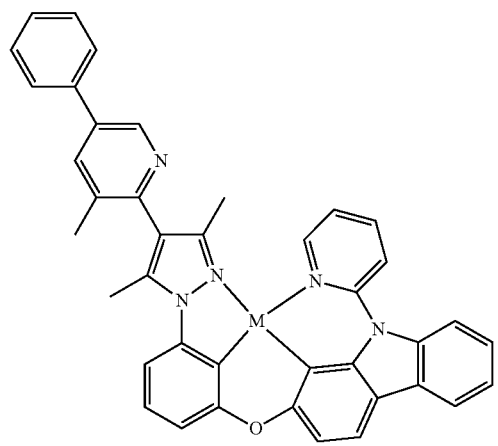
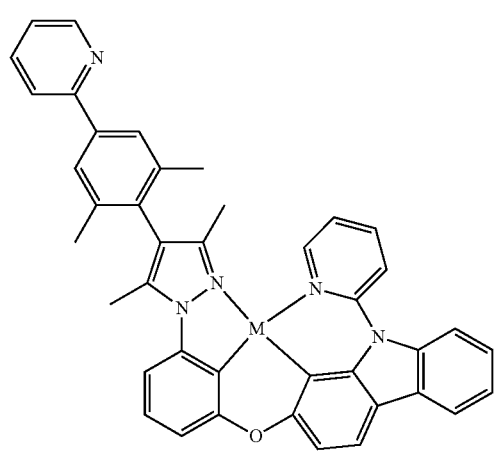

303
-continued
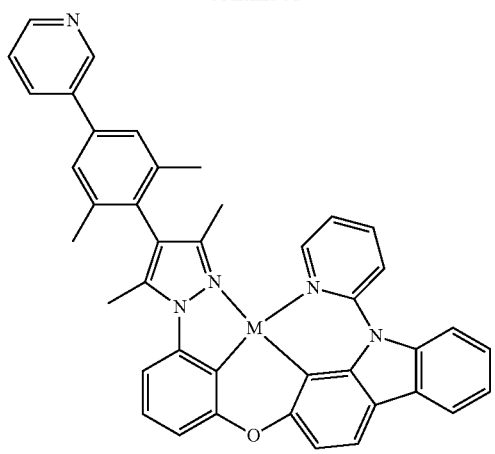
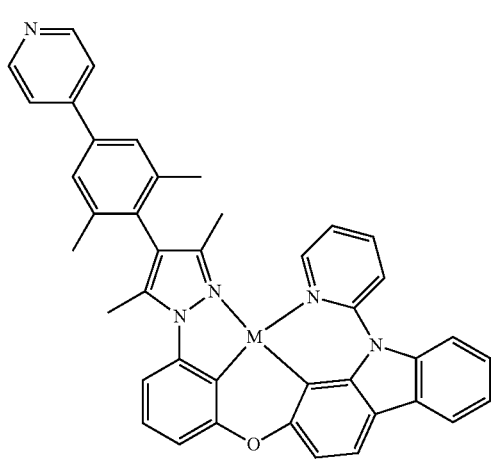
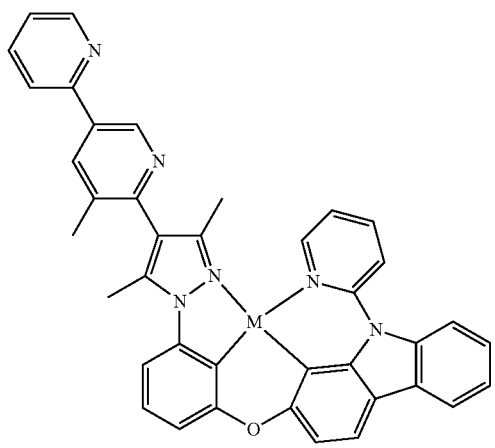
304
-continued
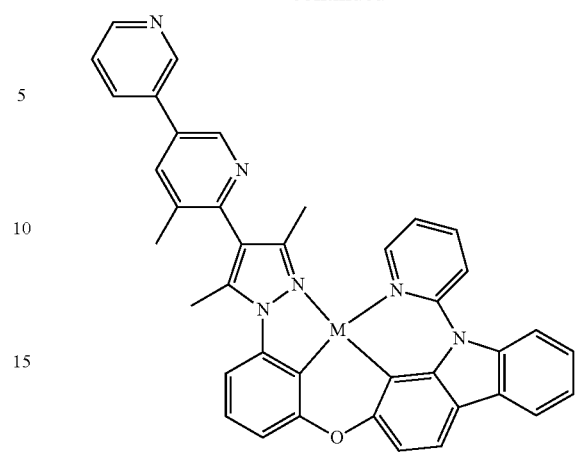
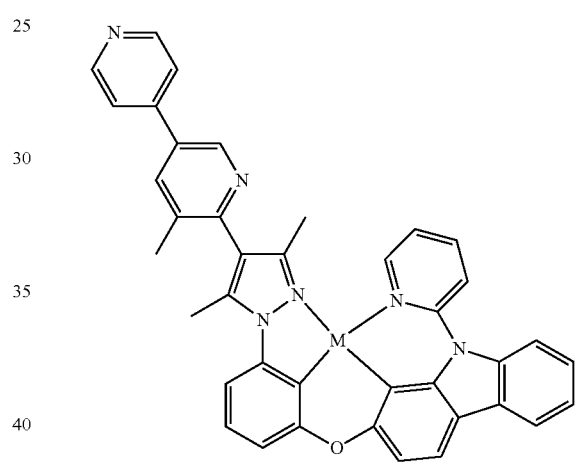
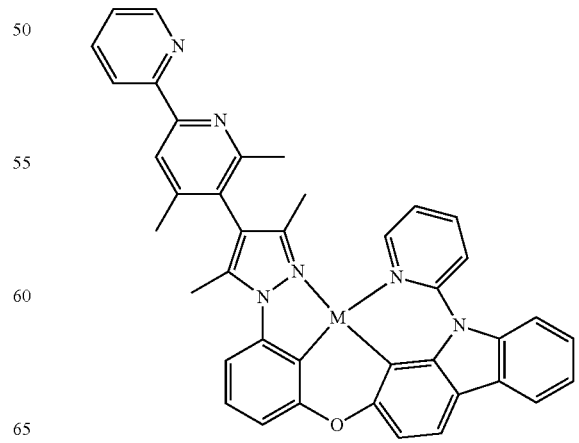

305
-continued
306
-continued
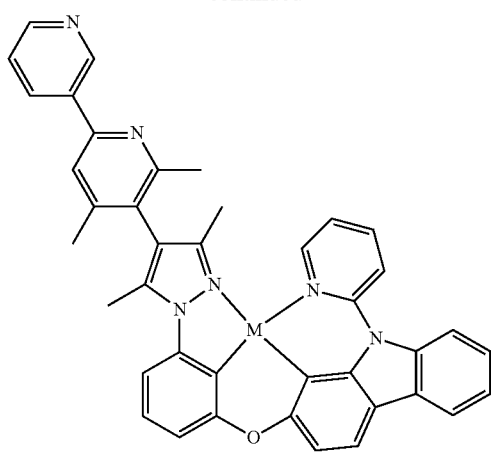
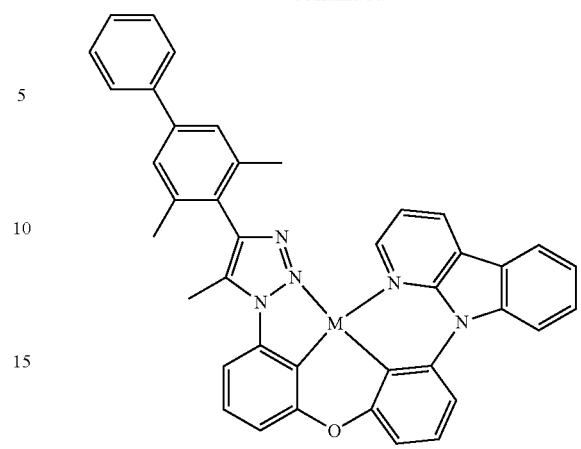
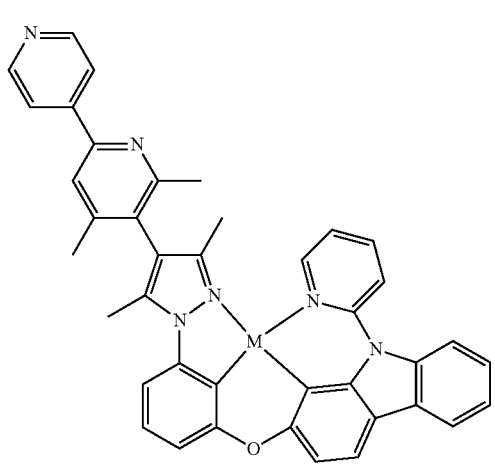
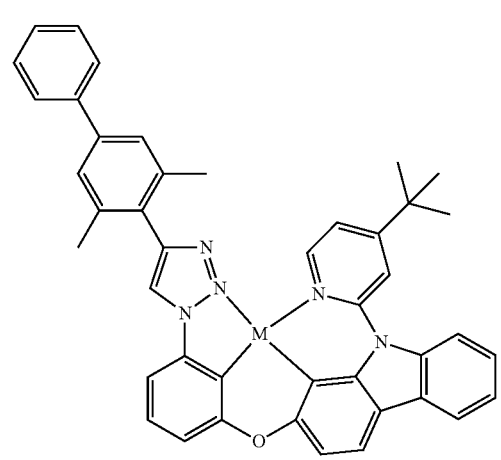
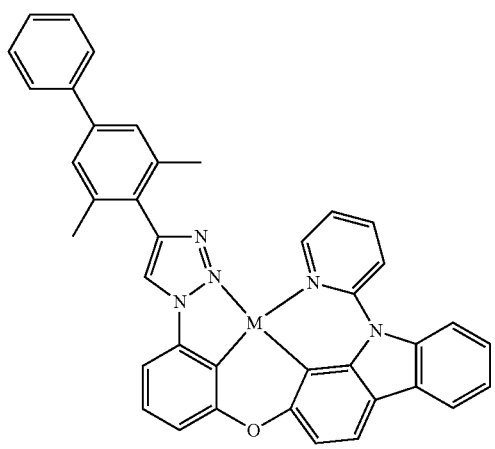
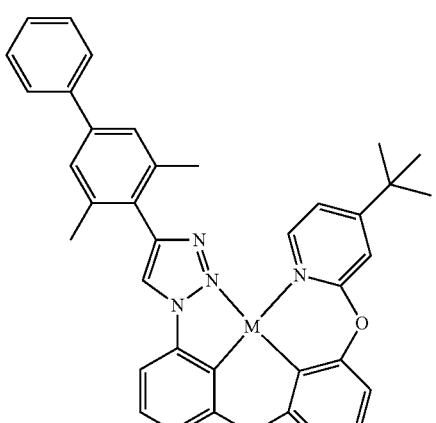

307
-continued
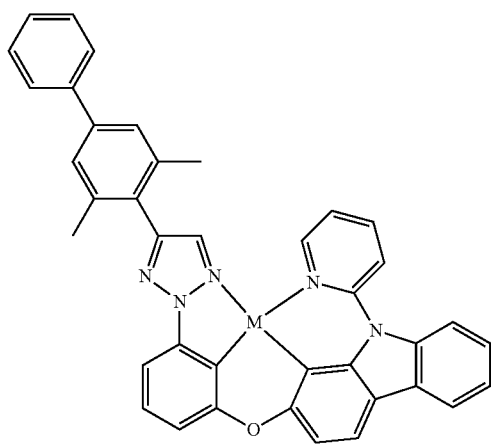
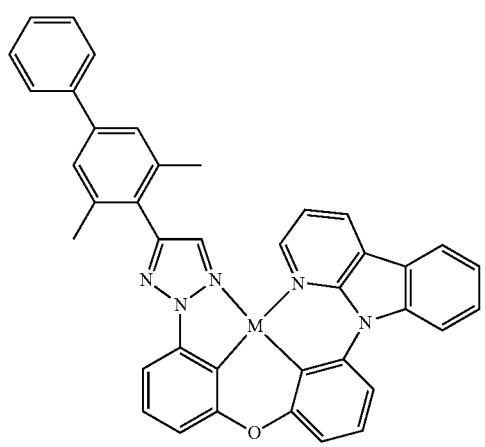
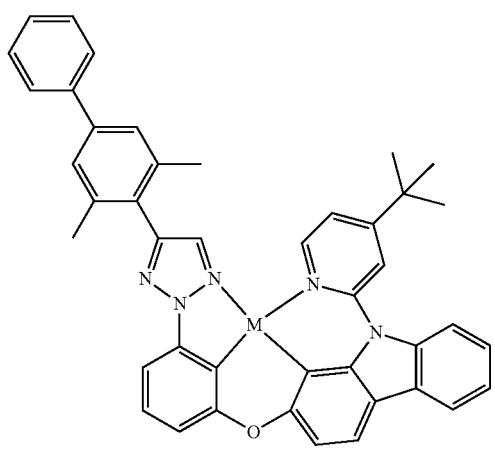
308
-continued
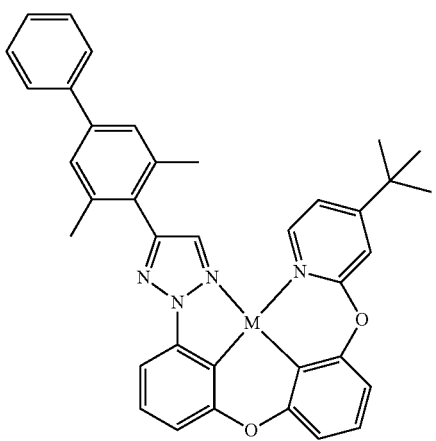
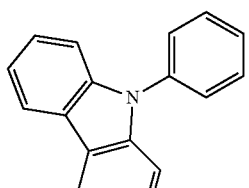
(M = Pt, Pd)
Structures 39
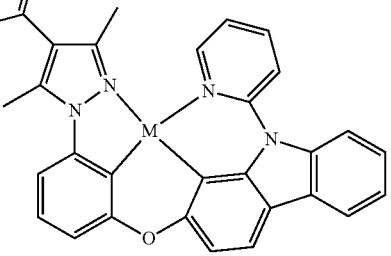
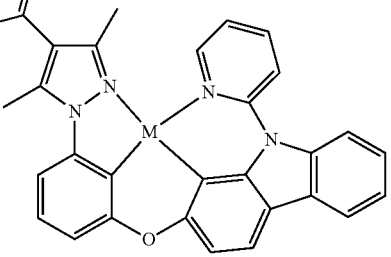

309
-continued
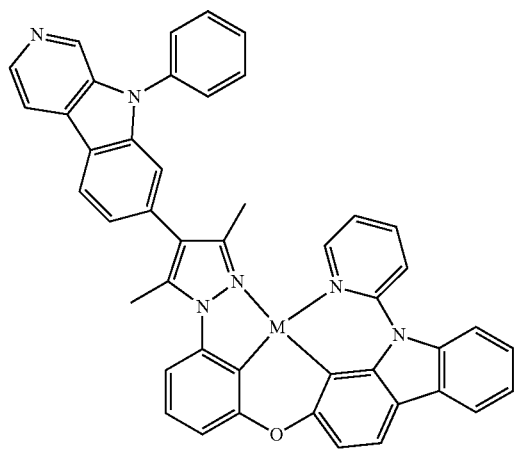
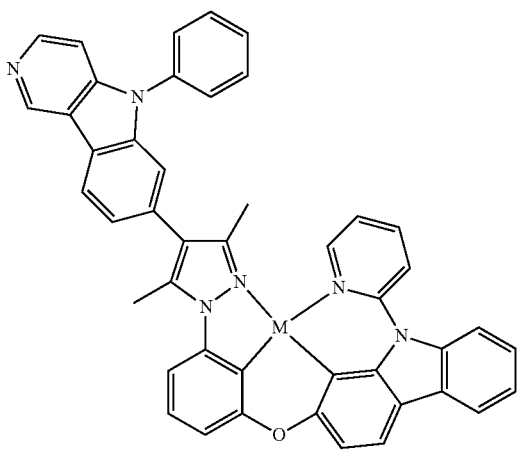
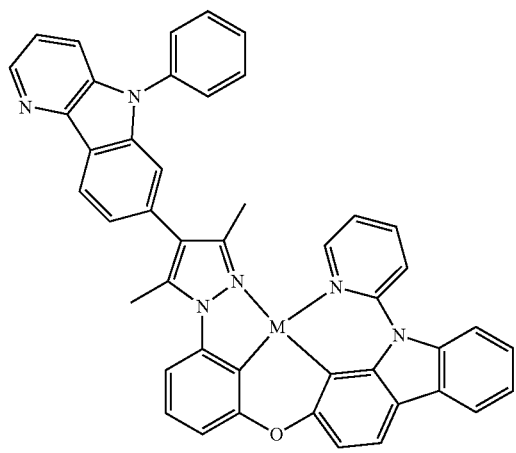
310
-continued
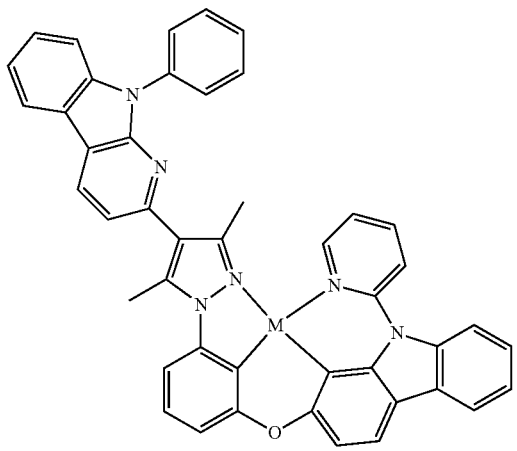
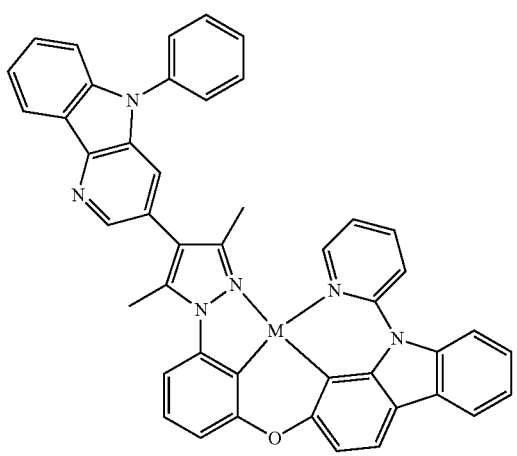

311
-continued
312
-continued
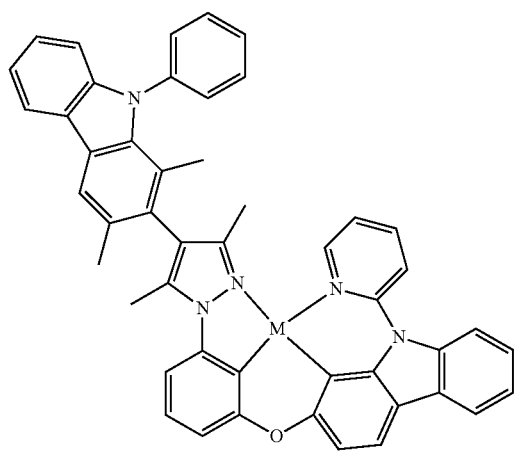
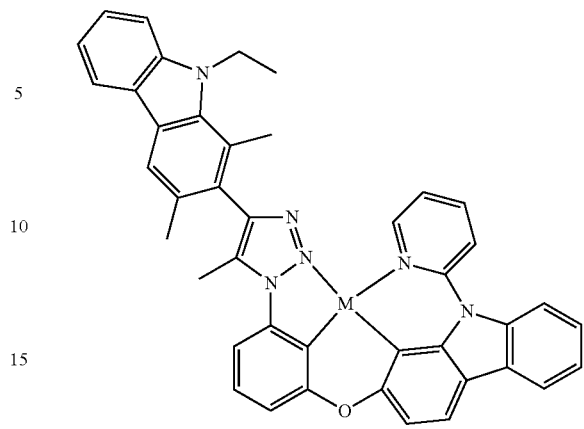
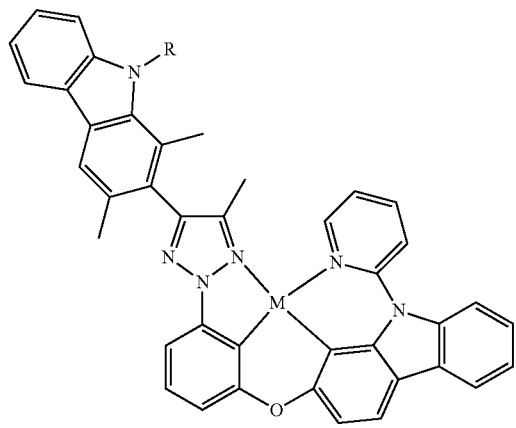
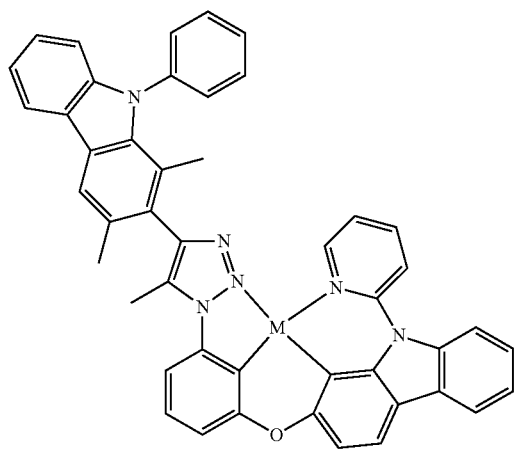

313
-continued
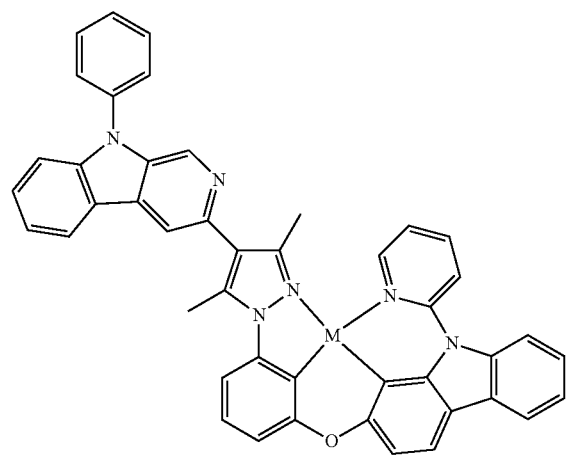
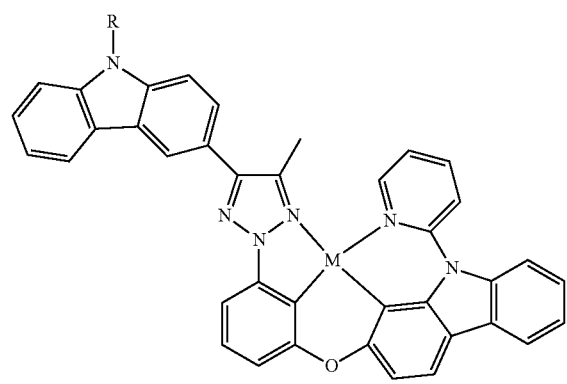
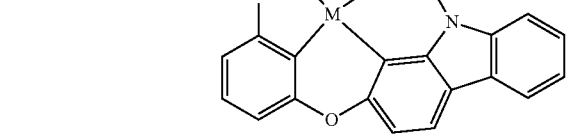
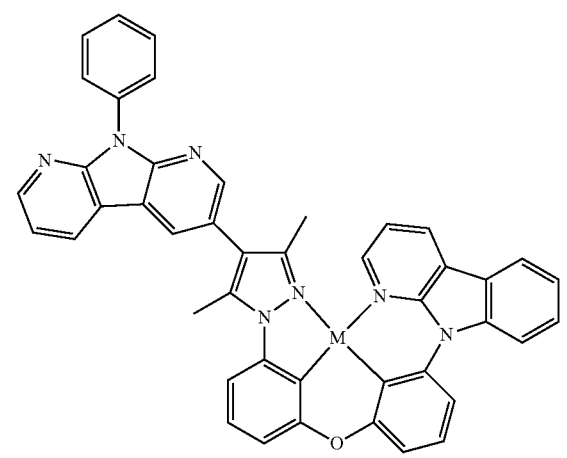
314
-continued
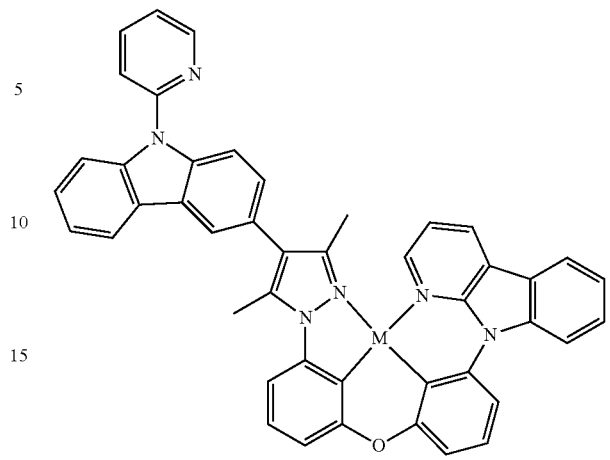
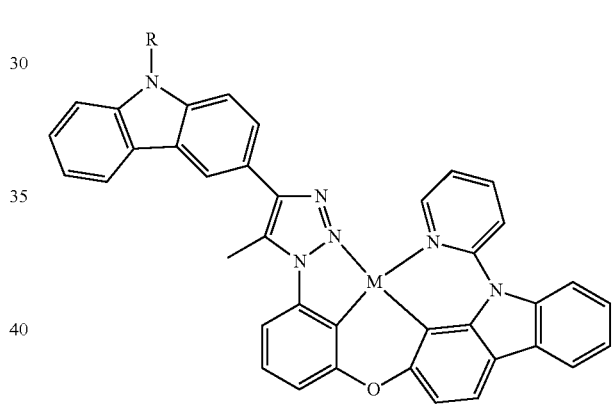
(M = Pt, Pd)
Structures 40
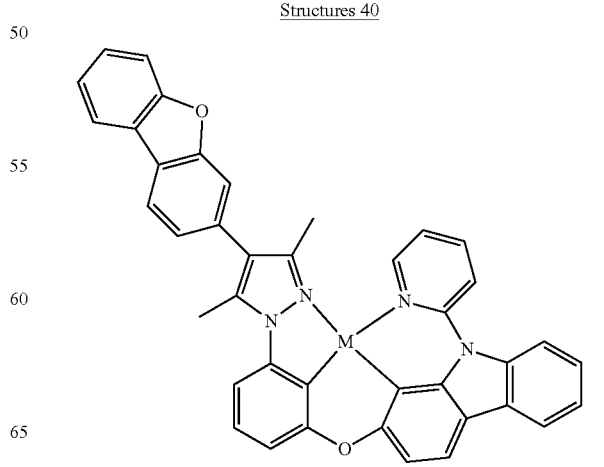

315
-continued
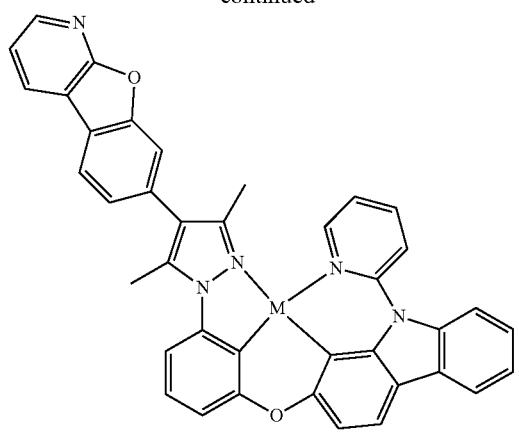
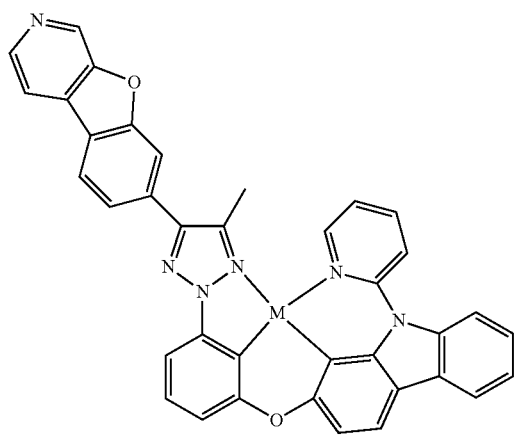
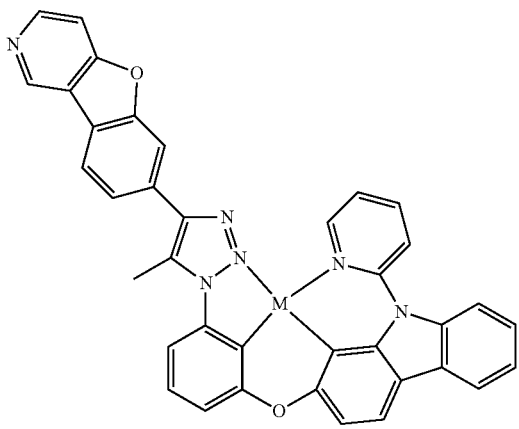
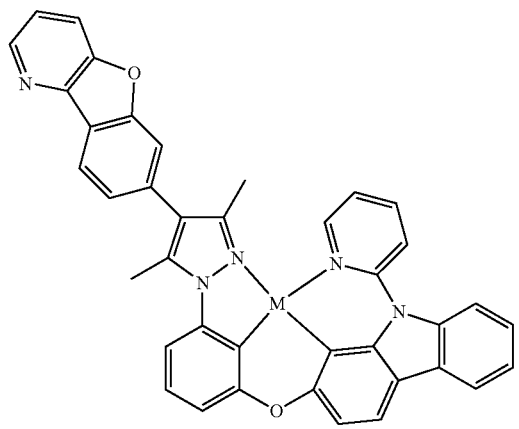
316
-continued
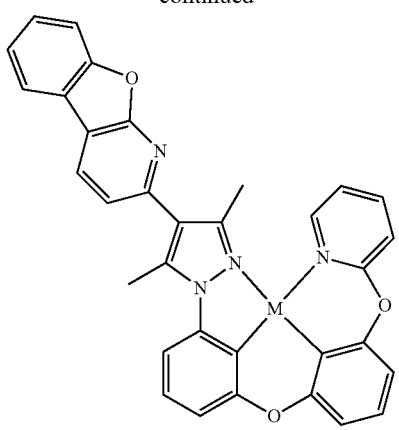
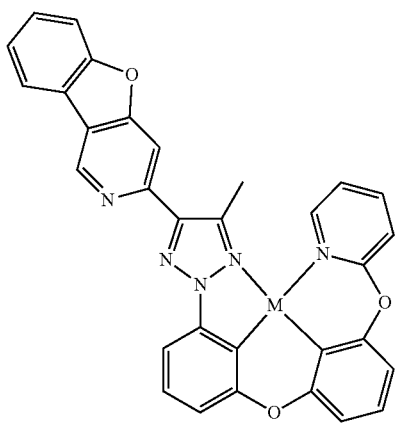
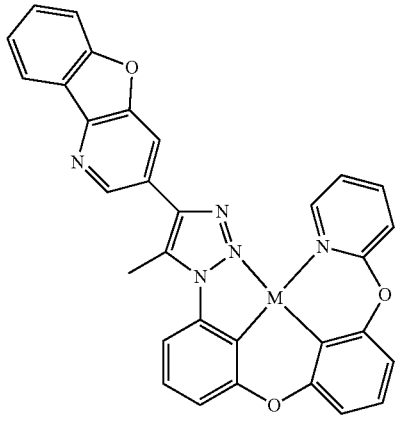
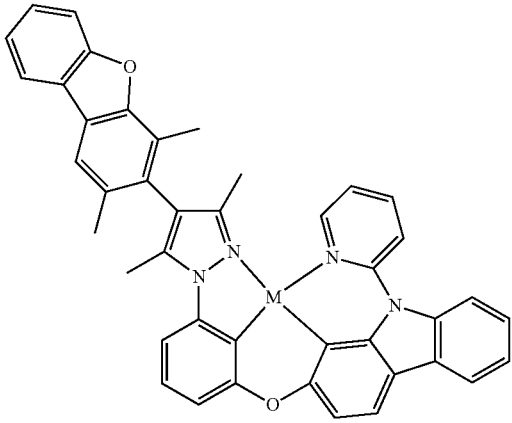

317
-continued
318
-continued
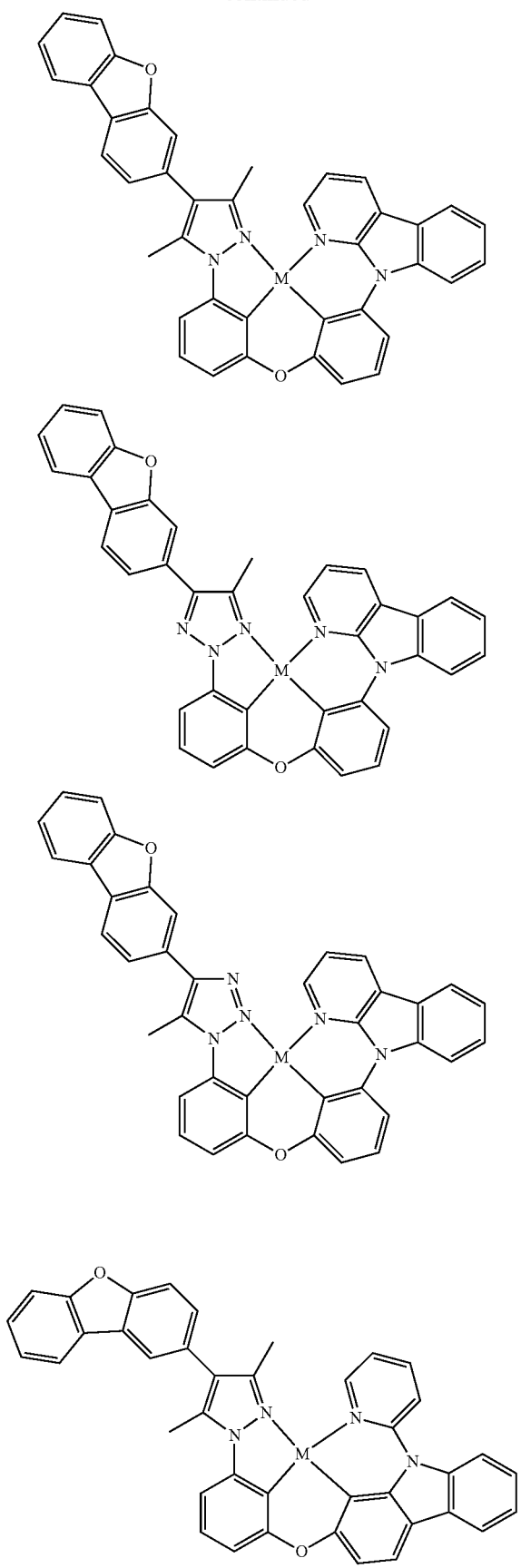
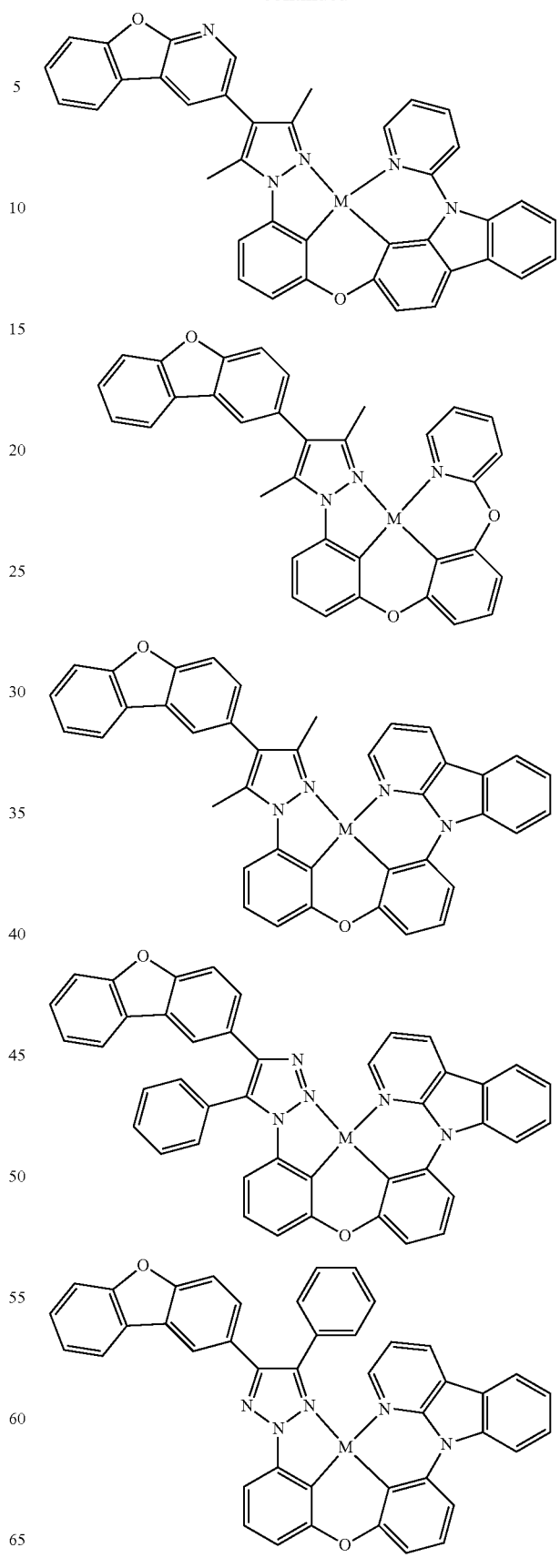

319
-continued
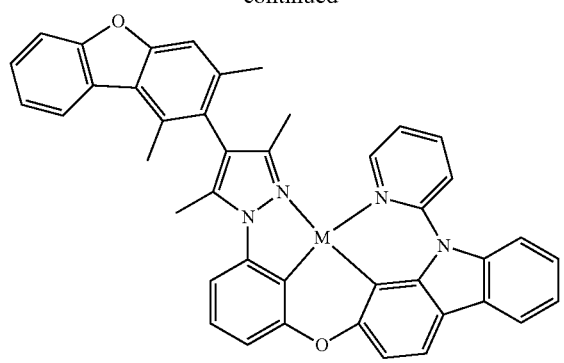
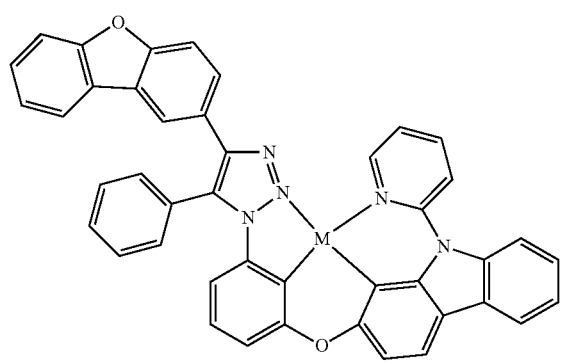
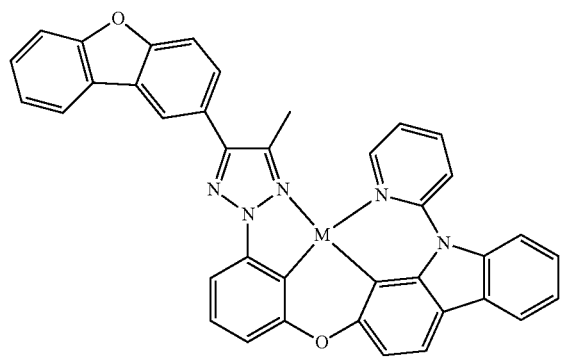
(M = Pt, Pd)
Structures 41
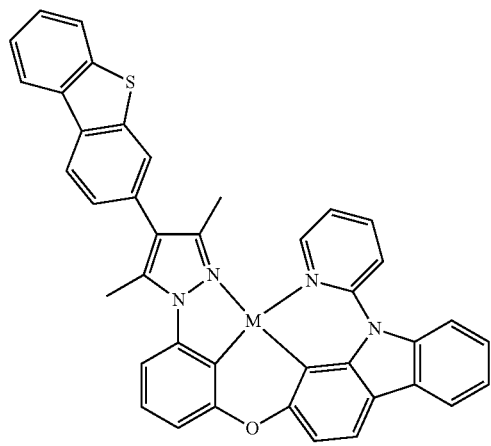
320
-continued

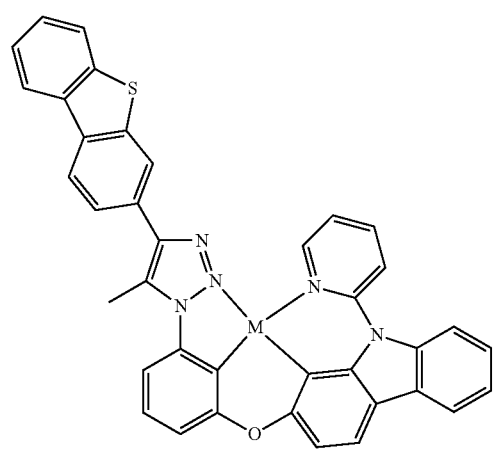
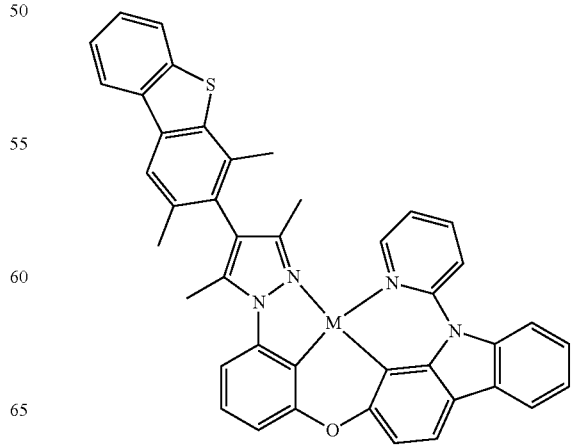
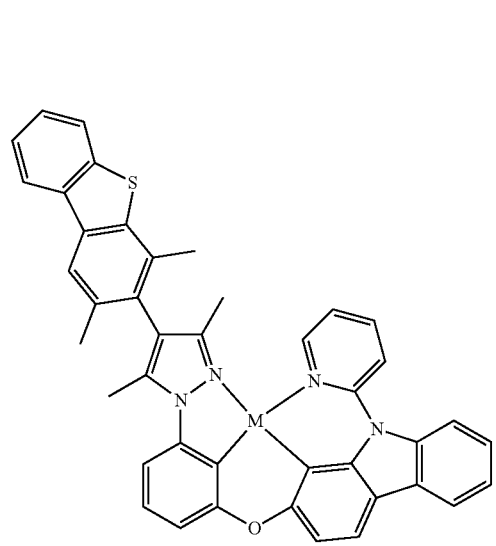

321
-continued
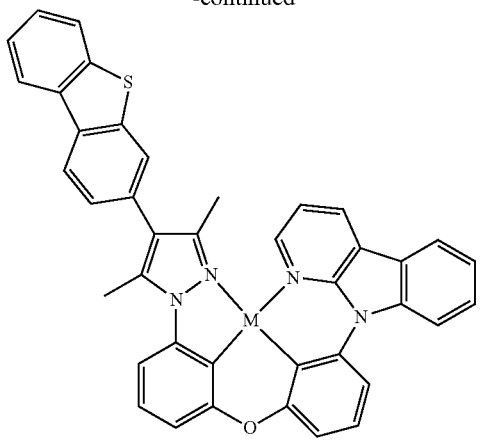
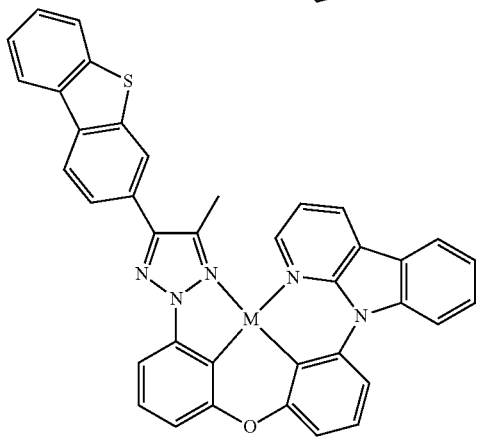
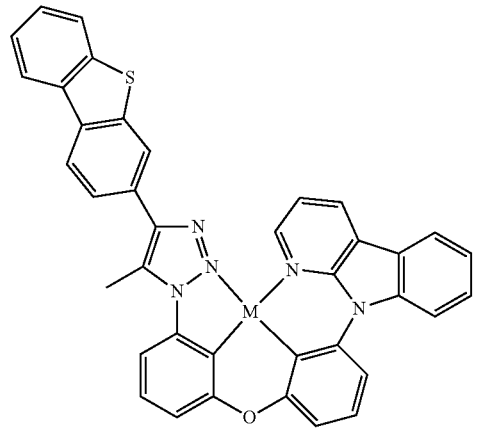
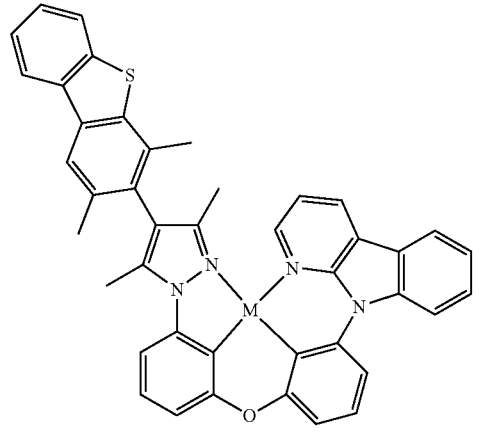
322
-continued
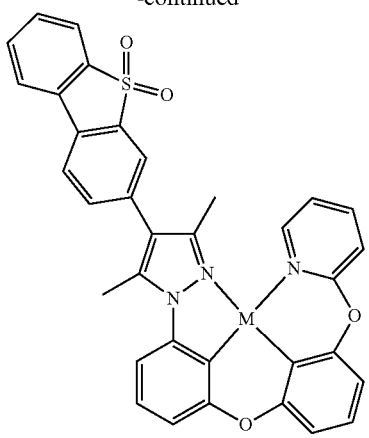
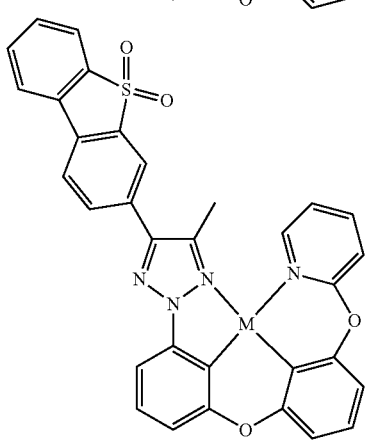
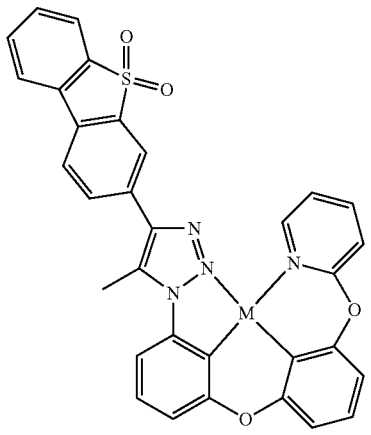
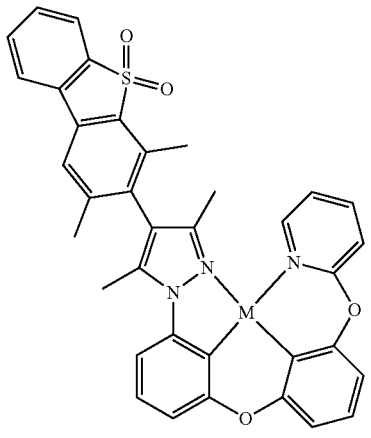

323
-continued
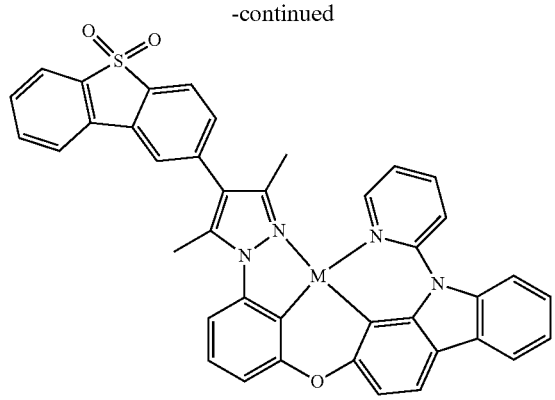
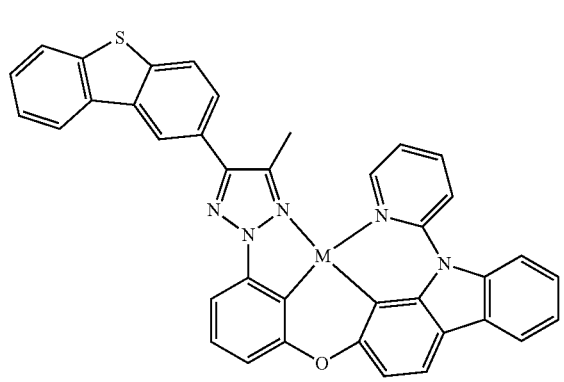
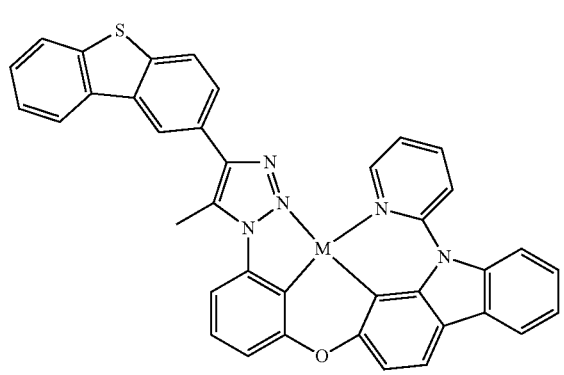
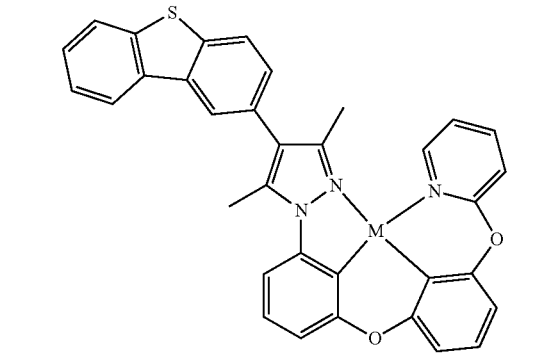
324
-continued
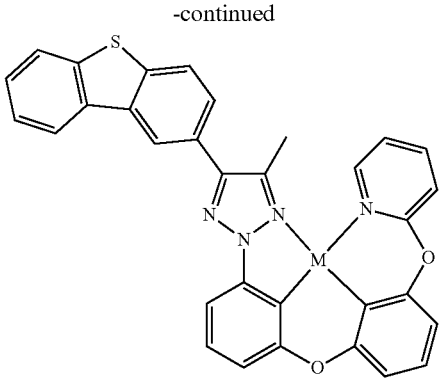
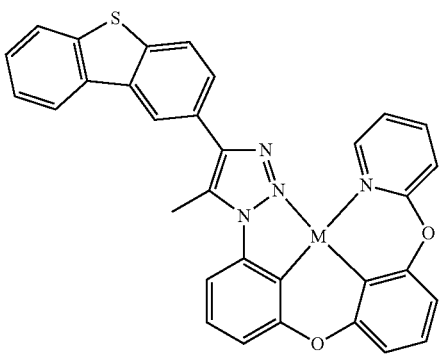
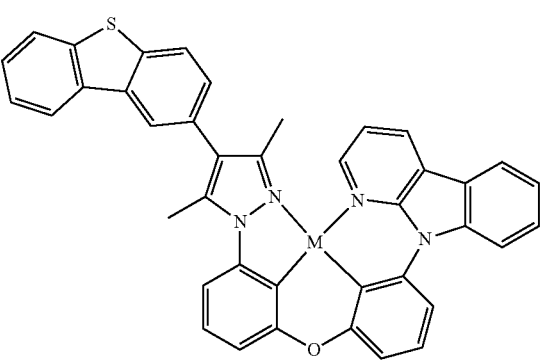
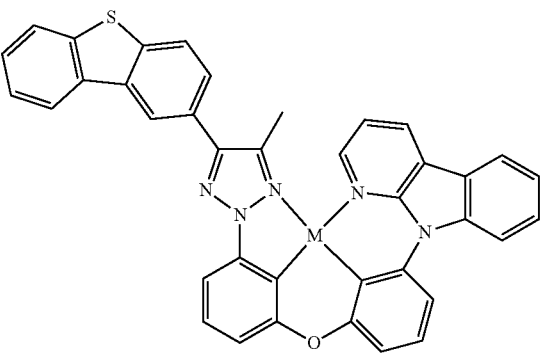

325
-continued
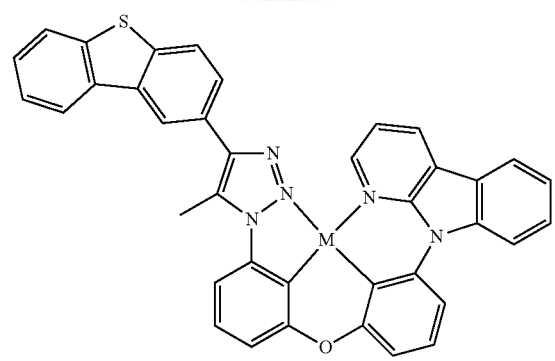
(M = Pt, Pd)
Structures 42
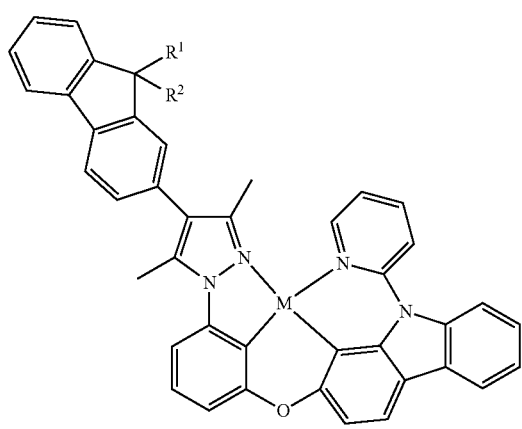
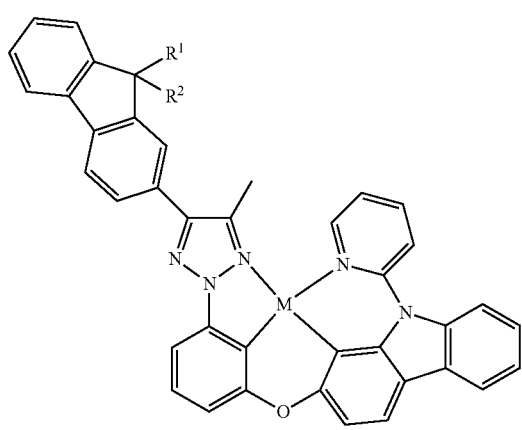
326
-continued
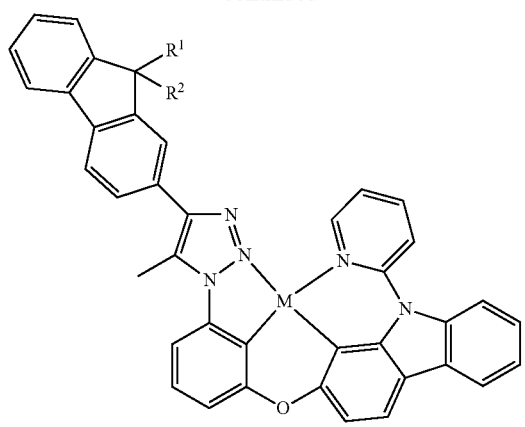
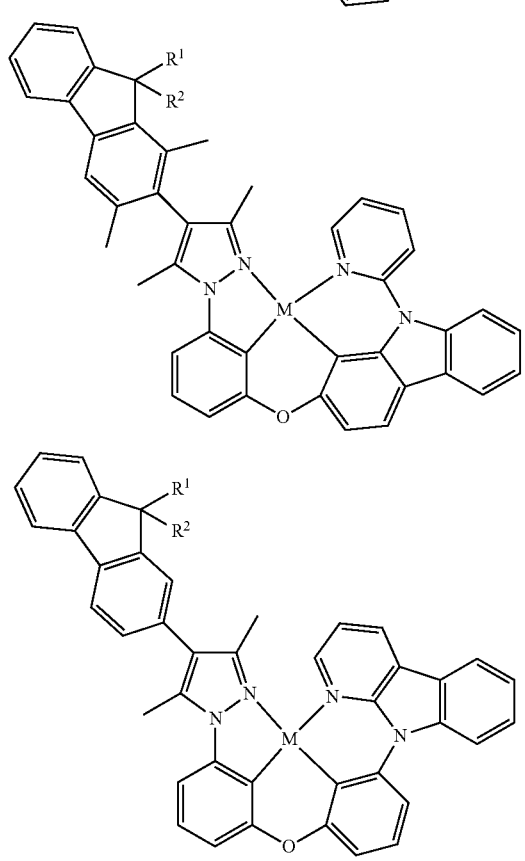
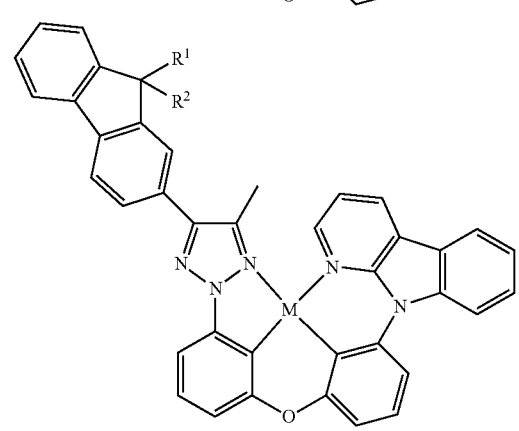

327
-continued
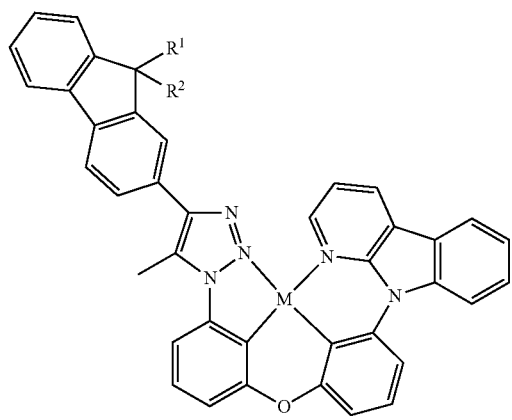

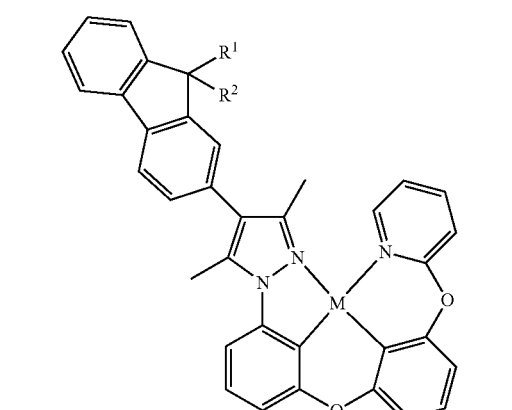
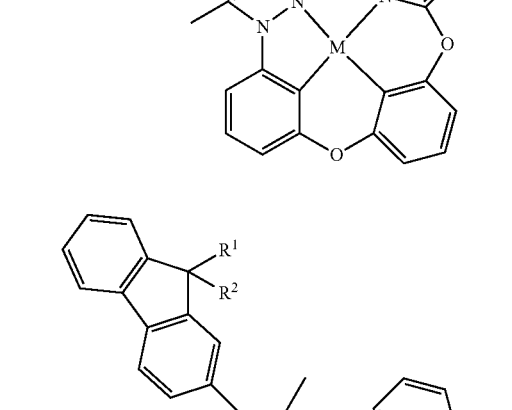
328
-continued
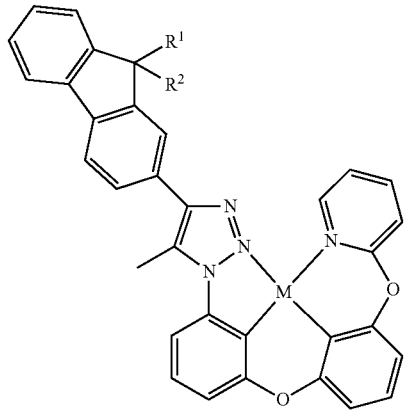
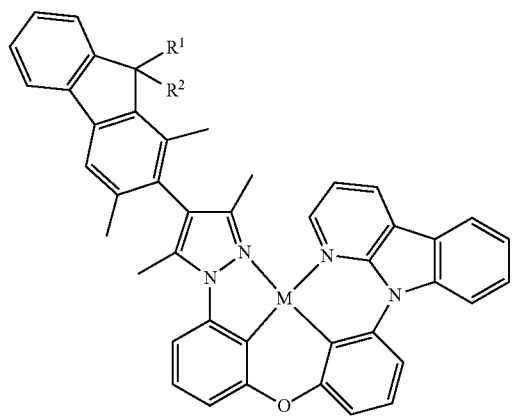
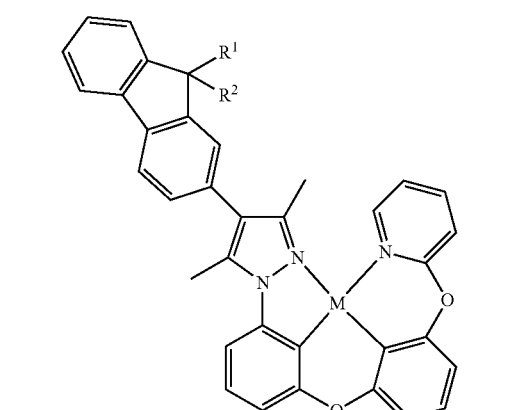
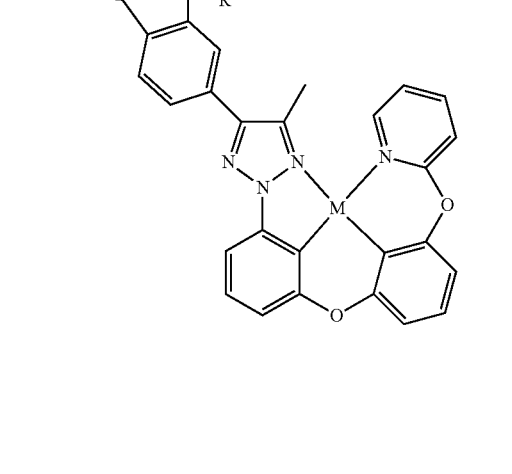
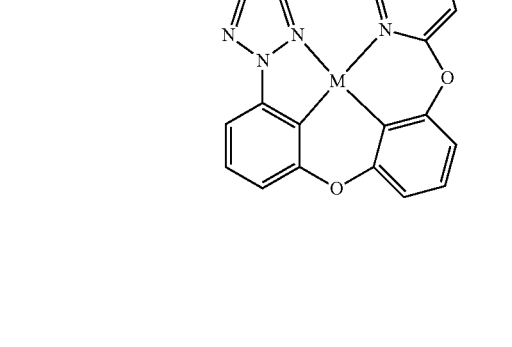

329 -continued
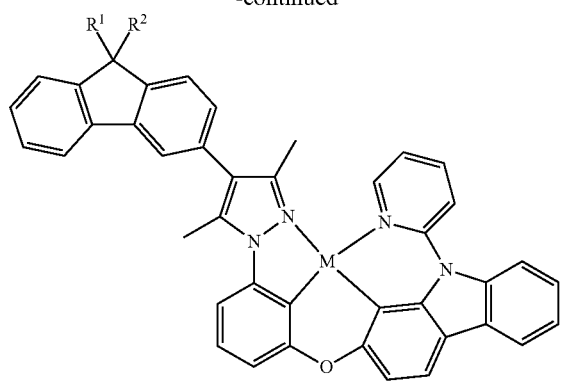
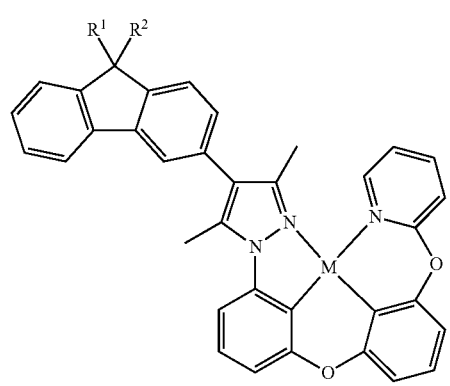
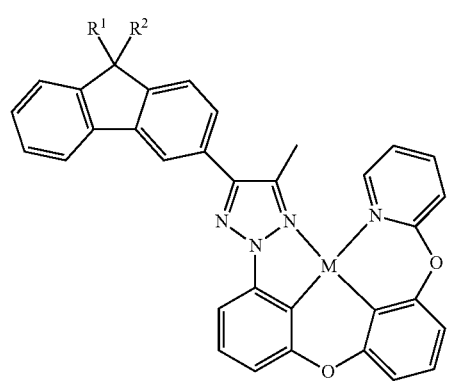
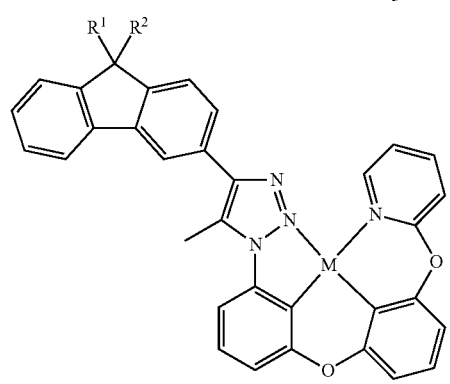
330 -continued
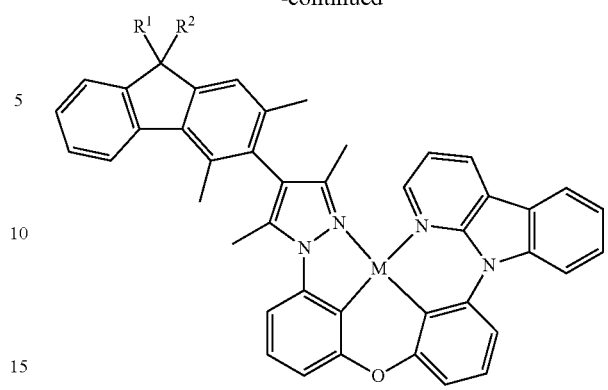
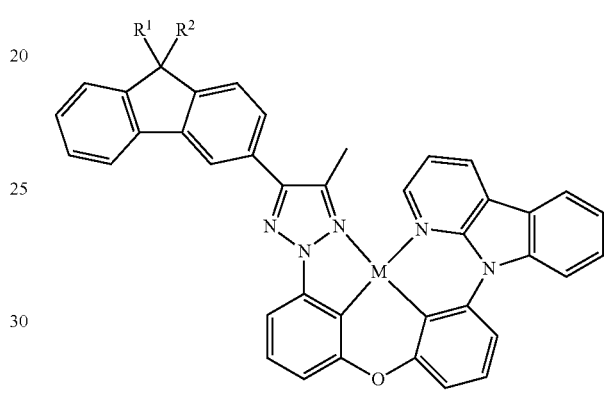
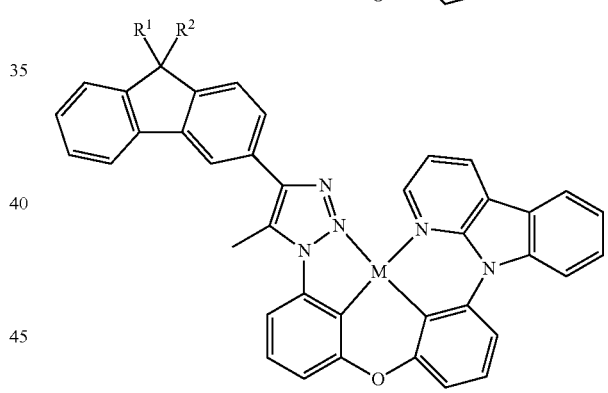
(M = Pt, Pd)
Structures 43
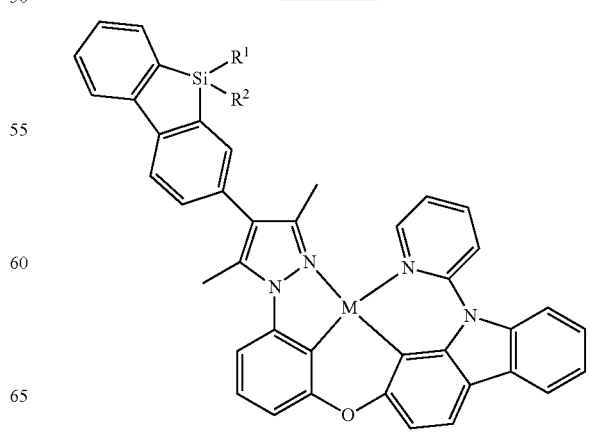

331
-continued
332
-continued
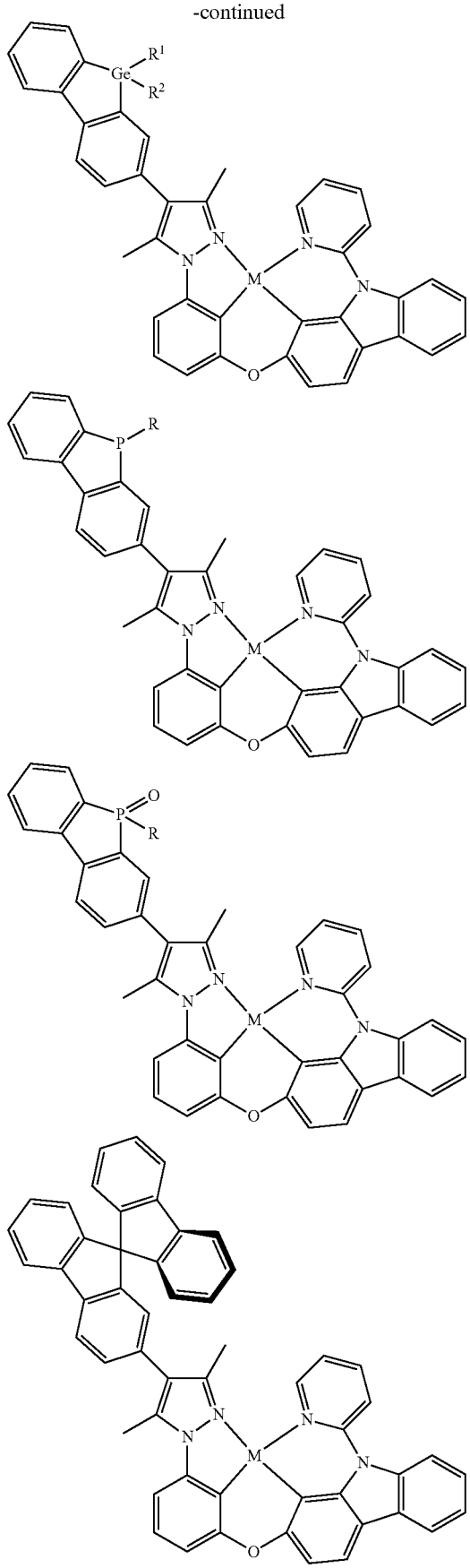
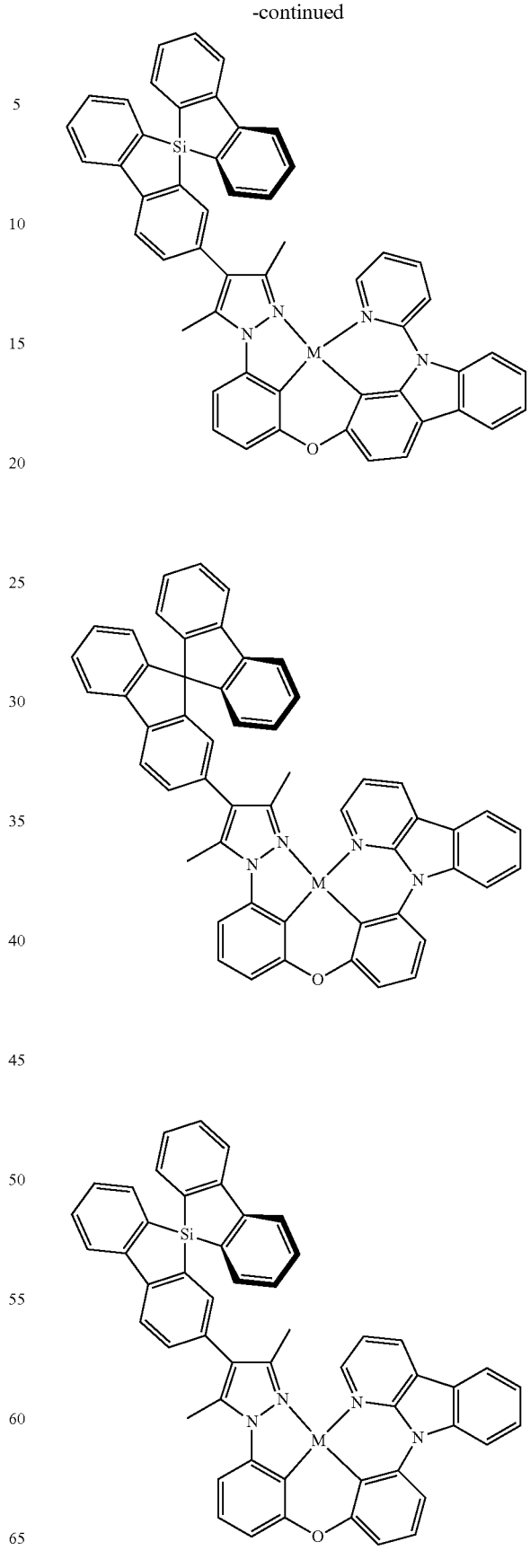

333
-continued
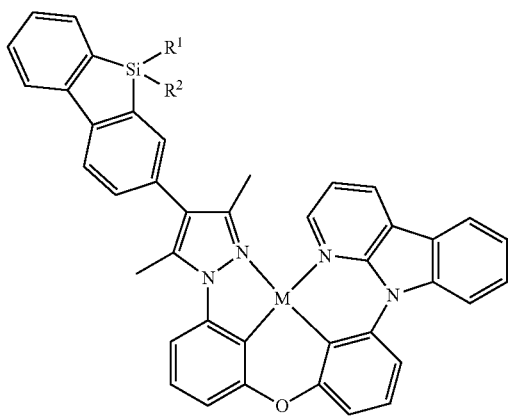
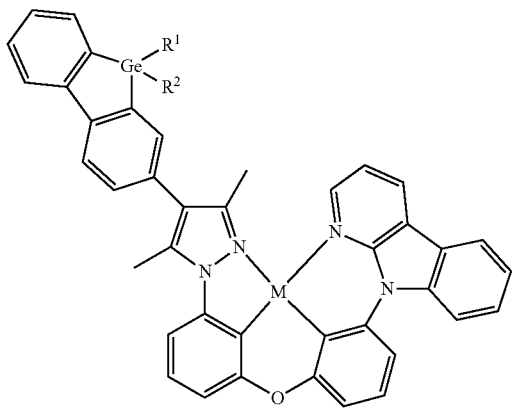
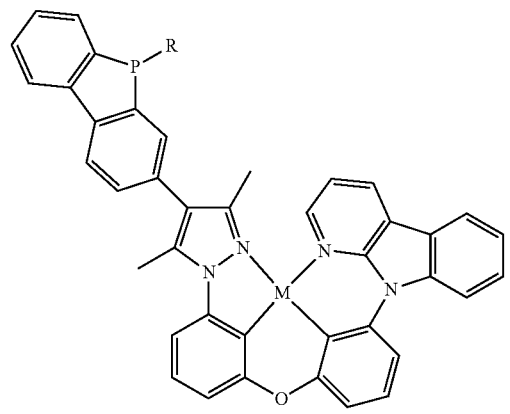
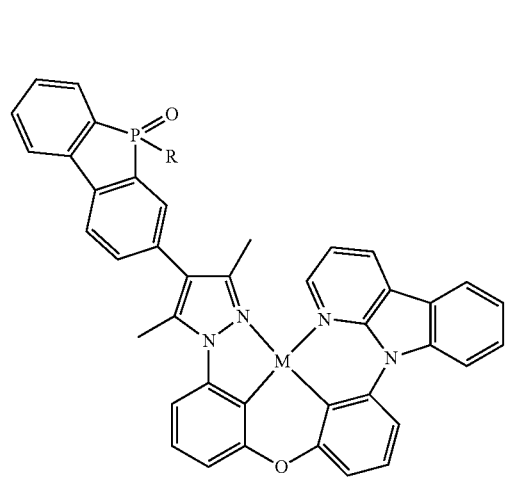
334
-continued
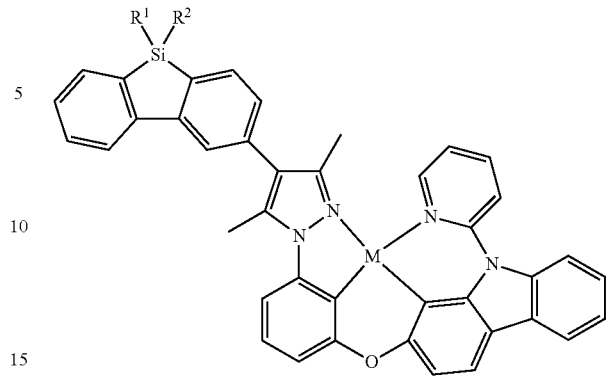
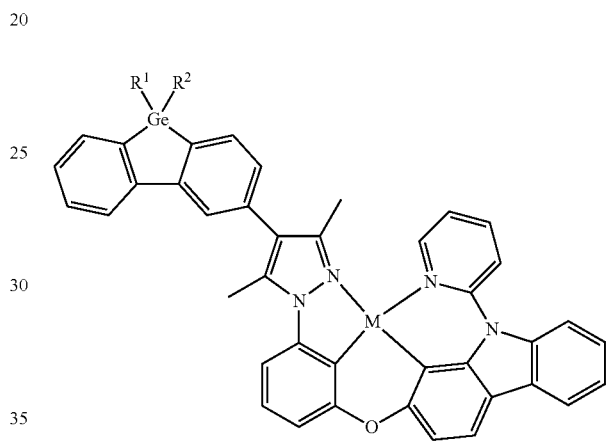
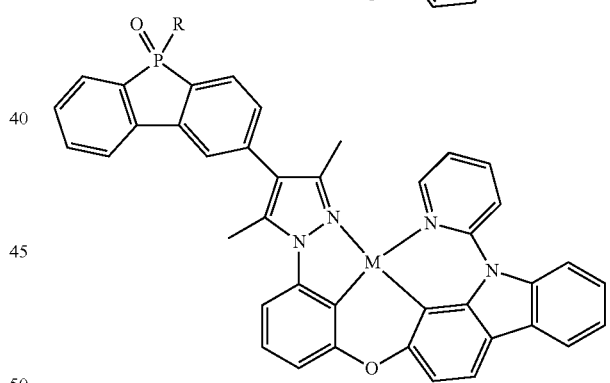
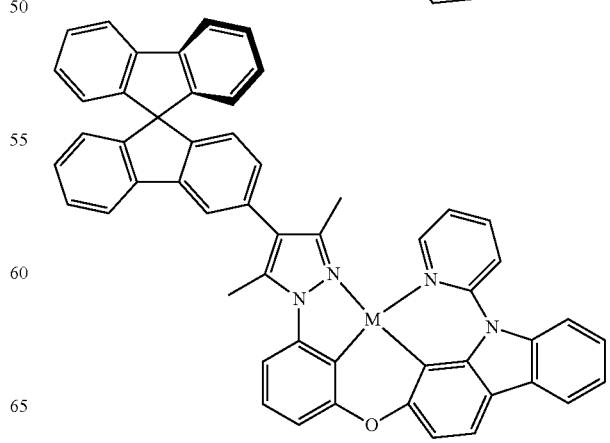

335
-continued
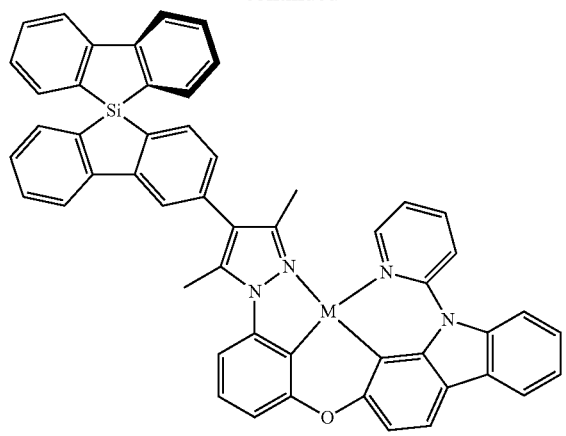
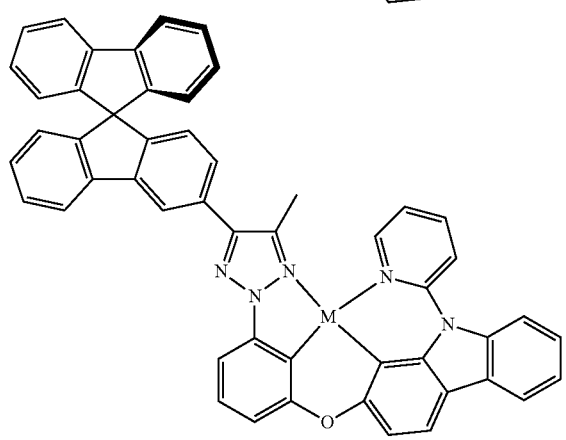
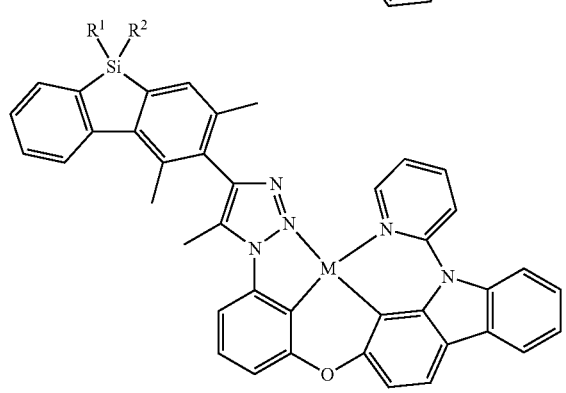
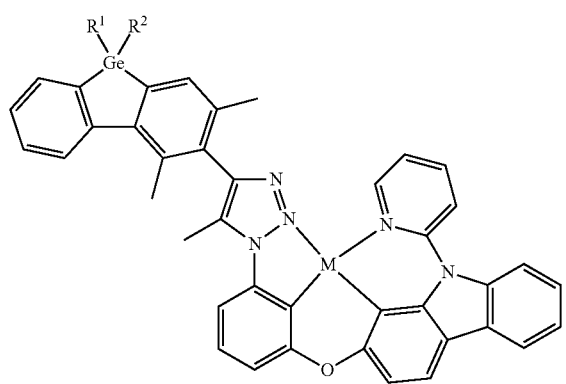
336
-continued
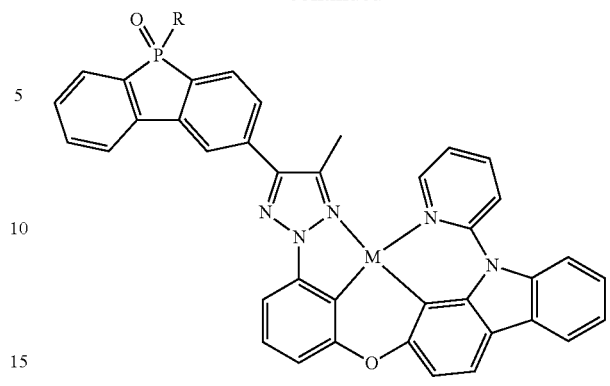
(M = Pt, Pd)
Structures 44
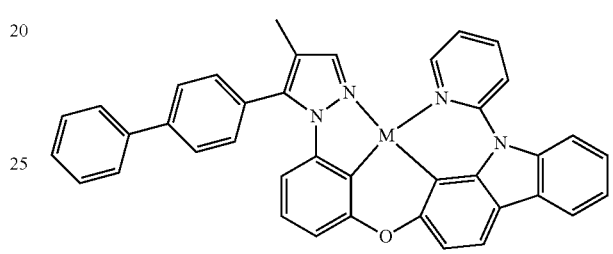
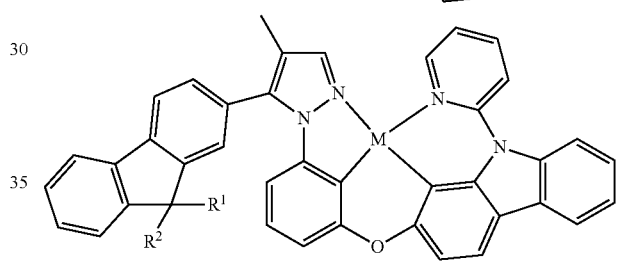
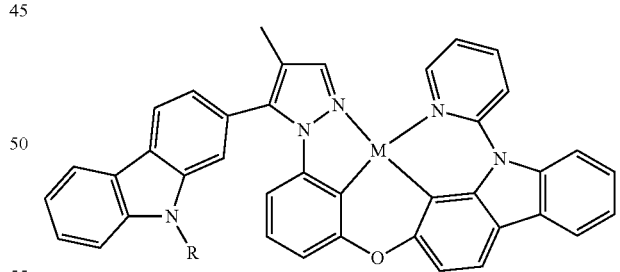
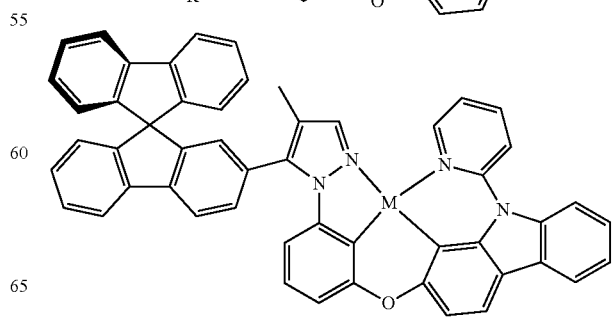

337
-continued
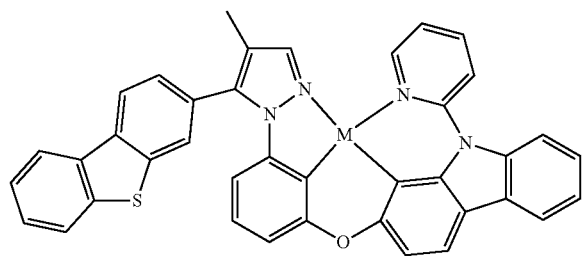
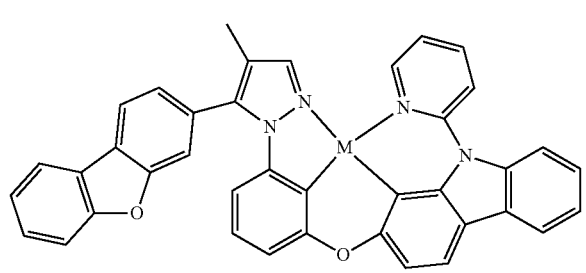
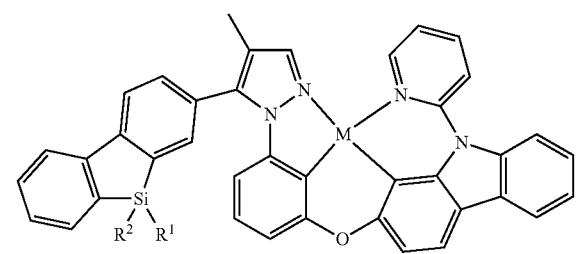
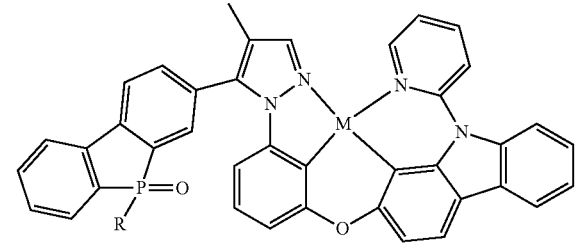
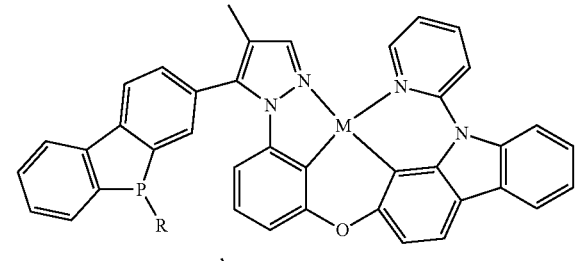
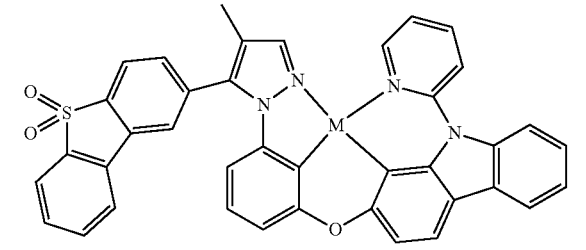
338
-continued
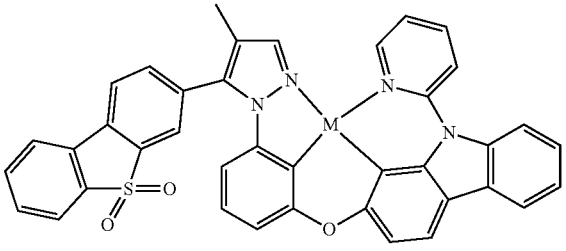
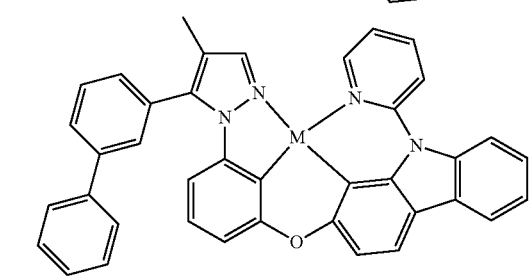
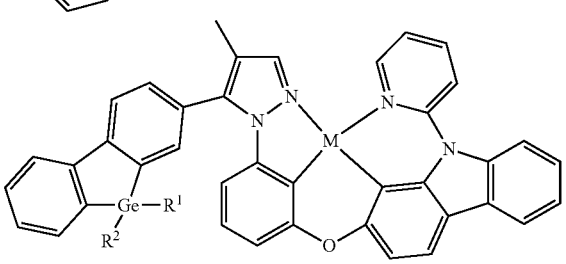
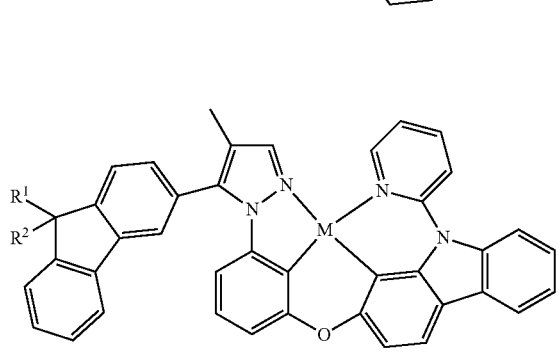
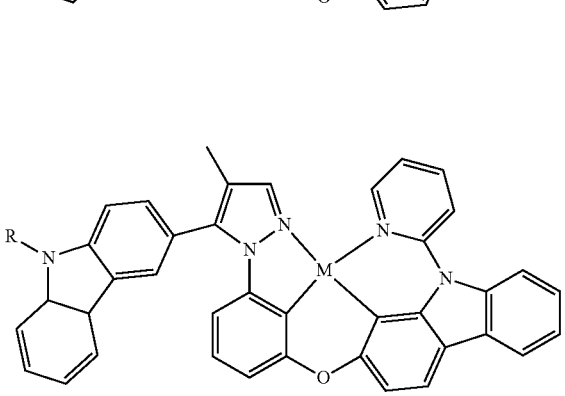
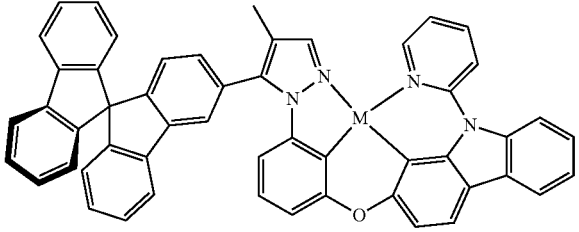

339
-continued
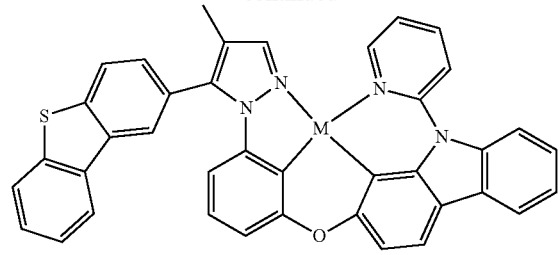
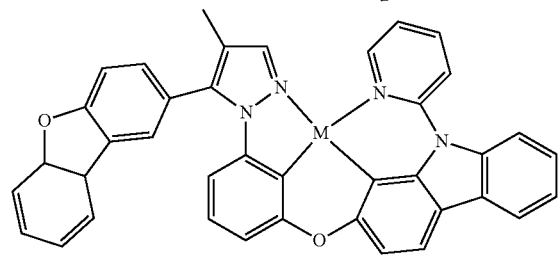
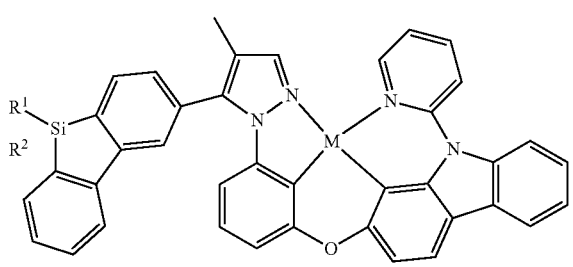
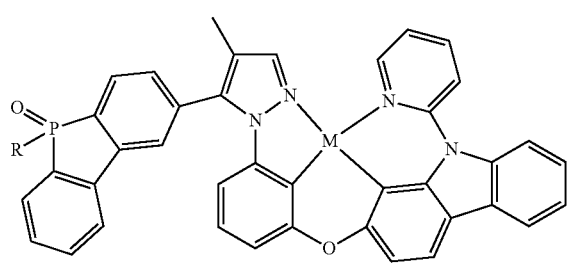
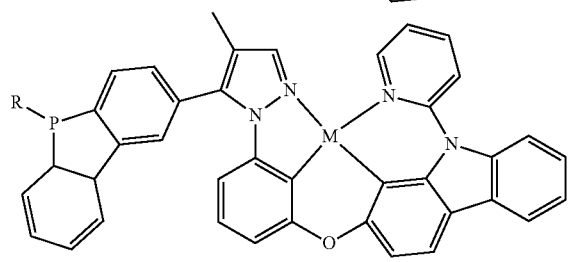
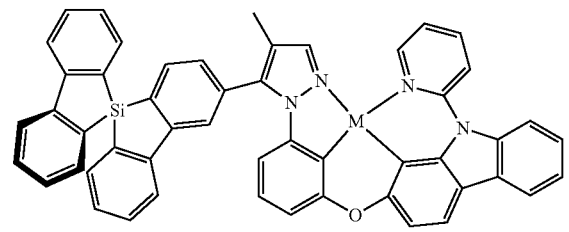
340
-continued
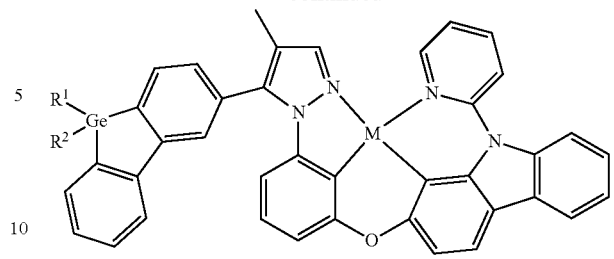
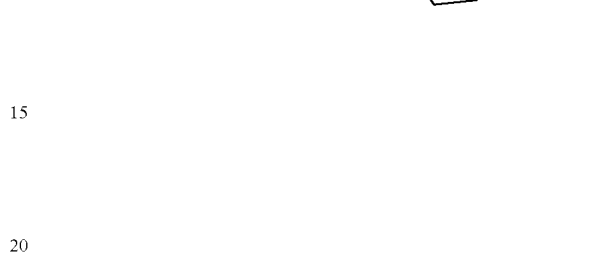
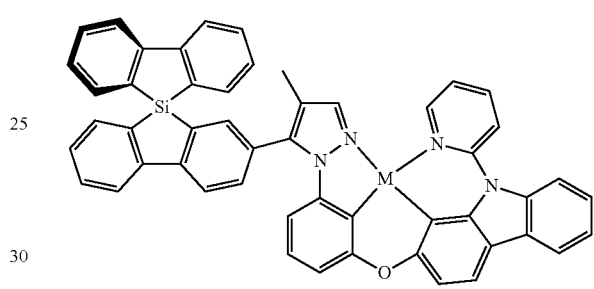
(M = Pt, Pd)
Structures 45
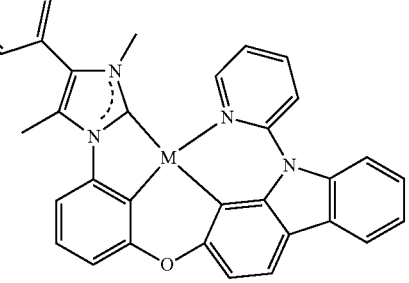
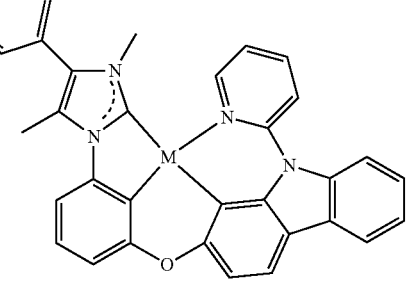

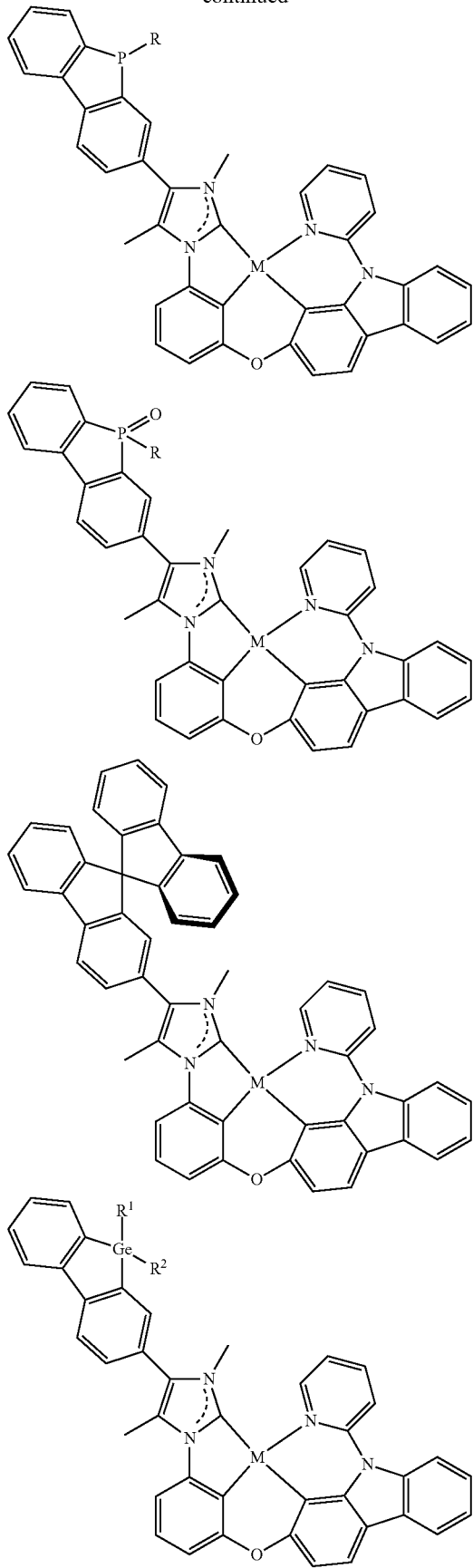
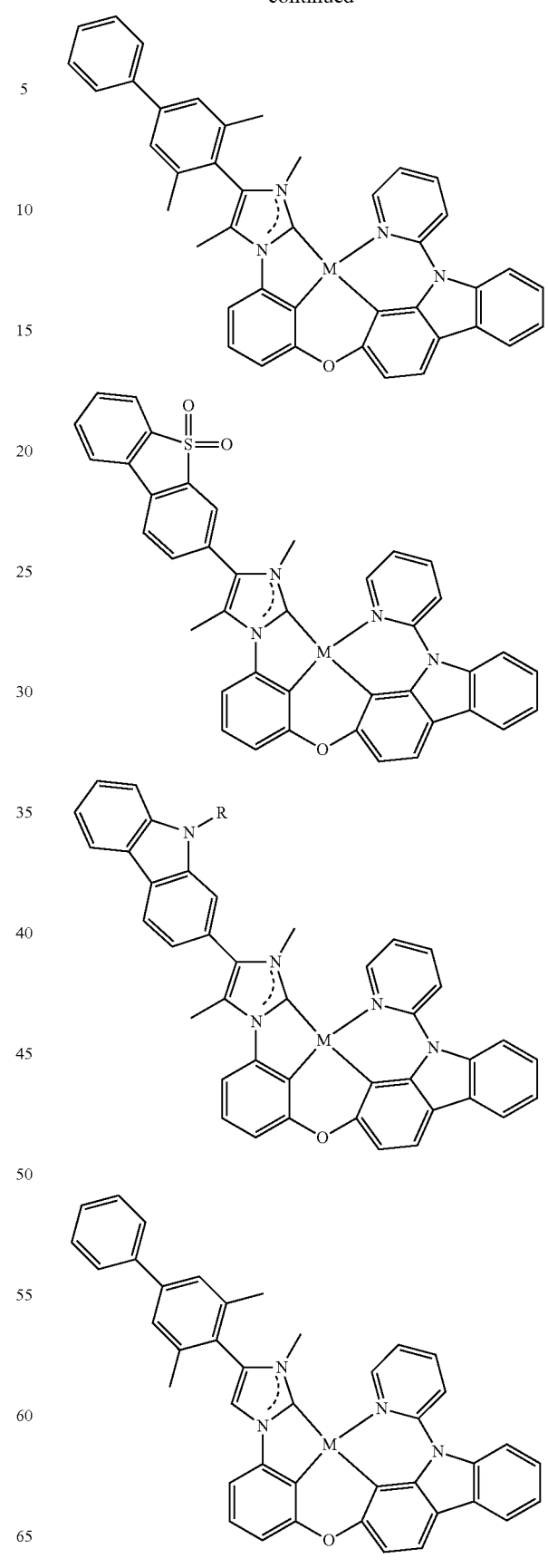

343
-continued
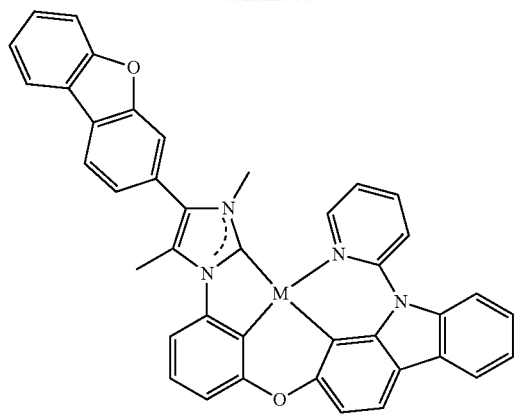
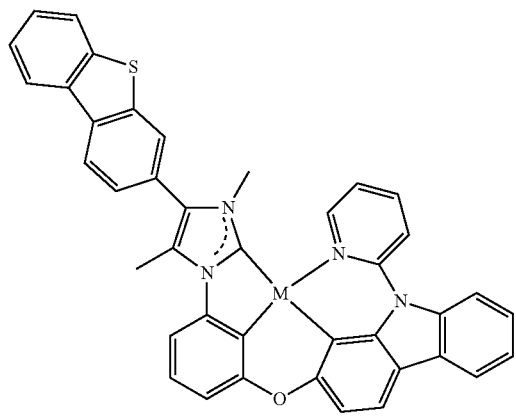
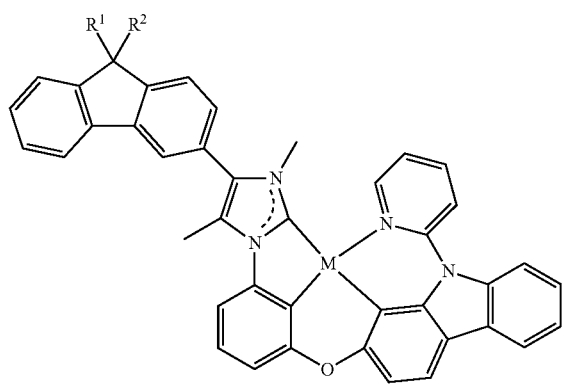
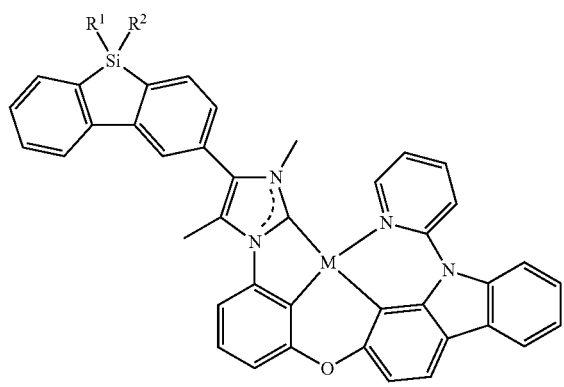
344
-continued
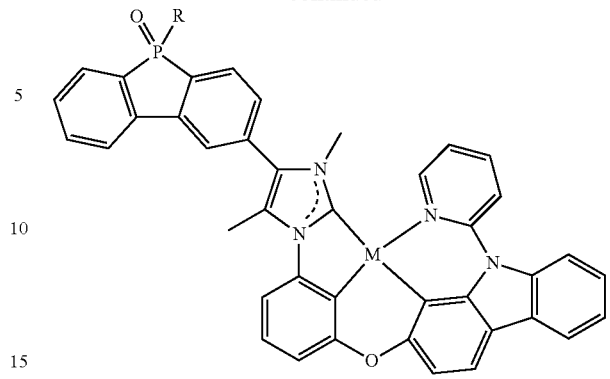
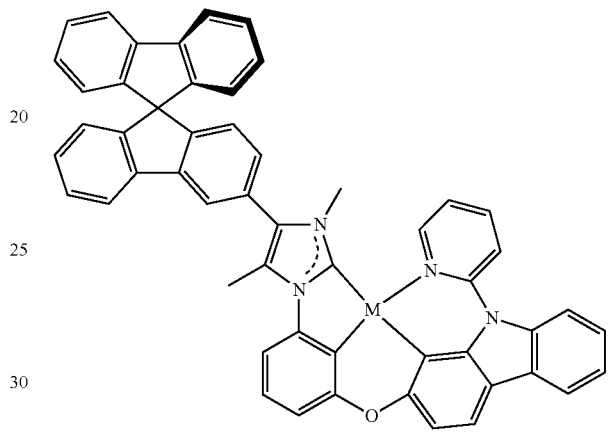
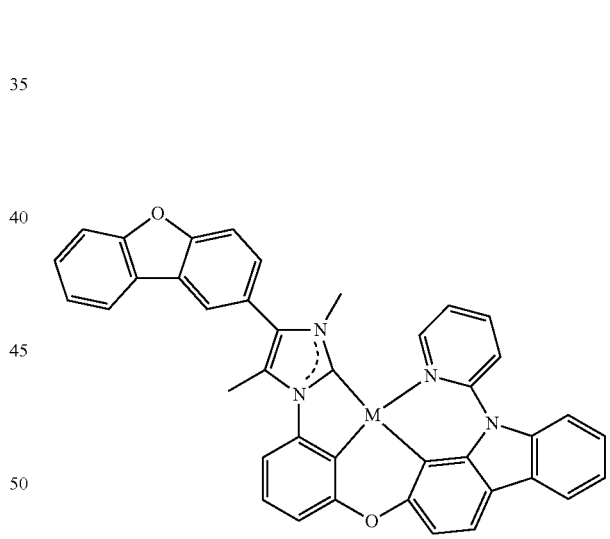
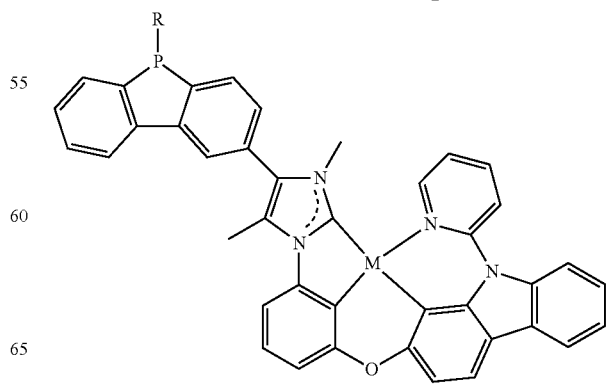

345
-continued
346
-continued
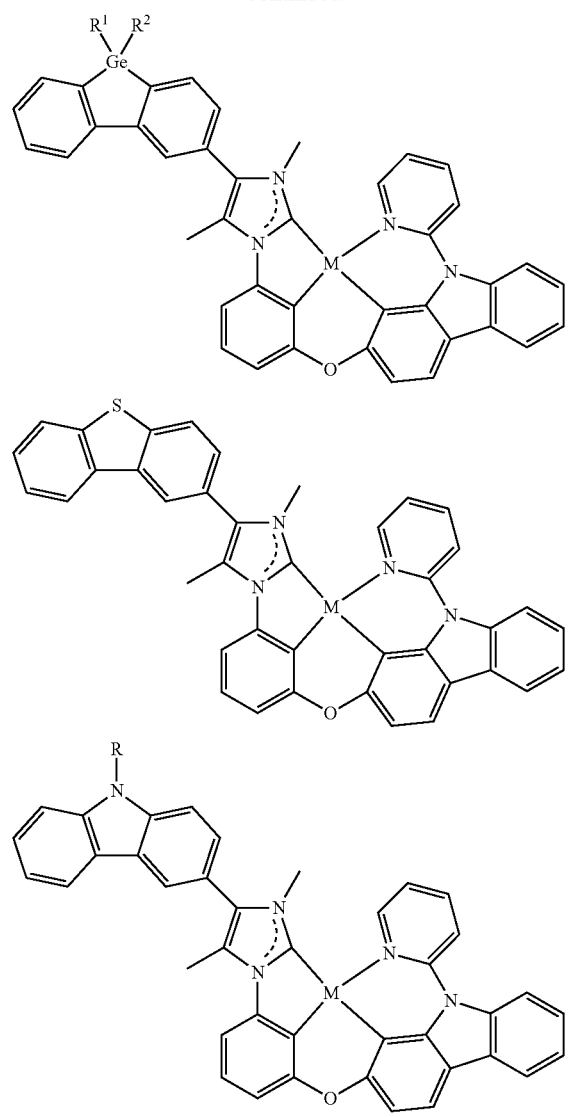
(M = Pt, Pd)
Structures 46
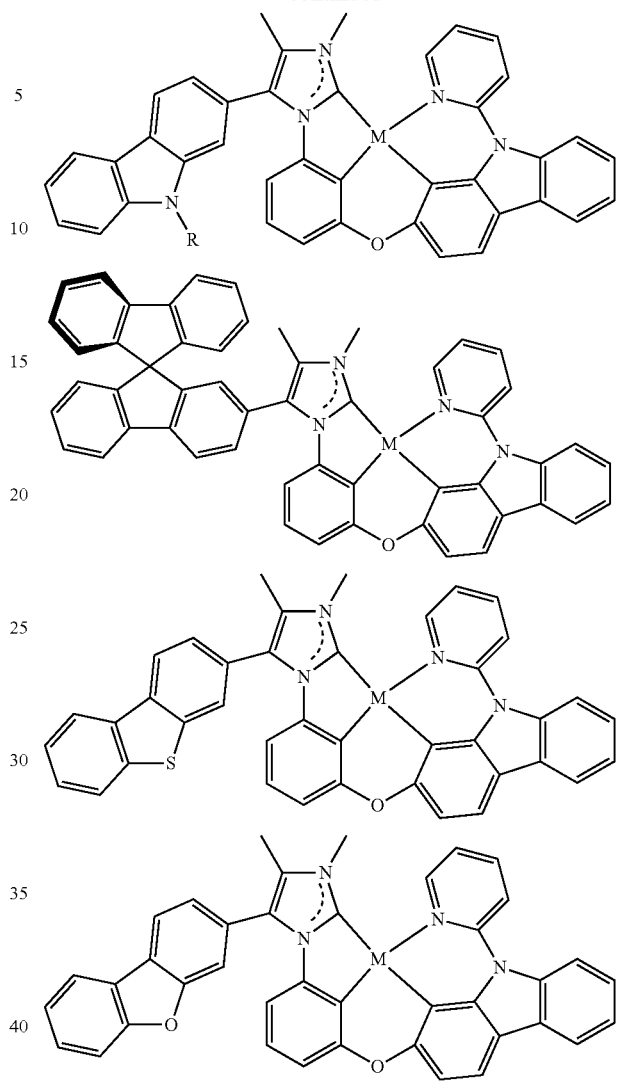
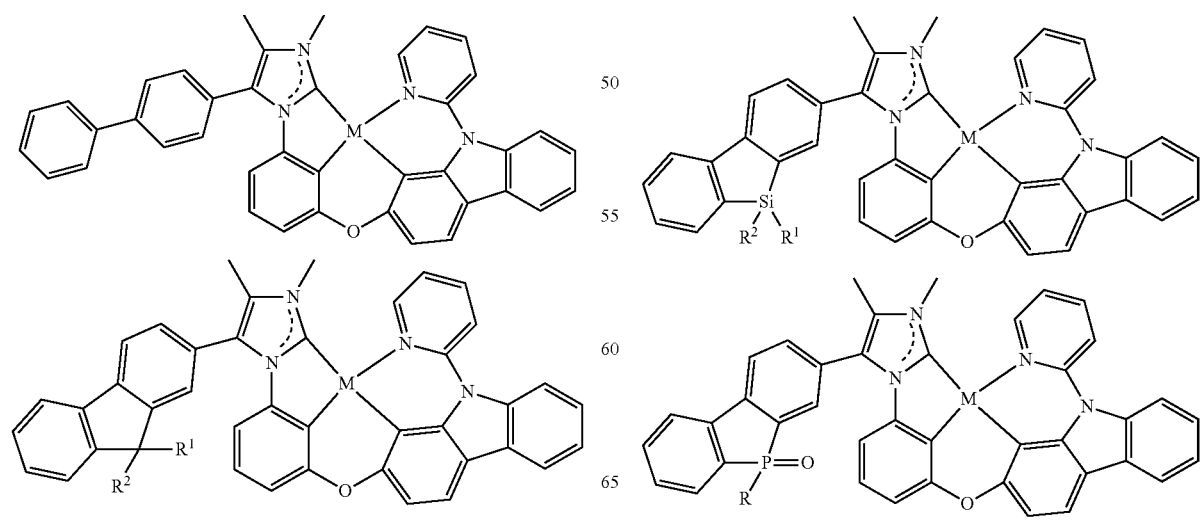

347
-continued
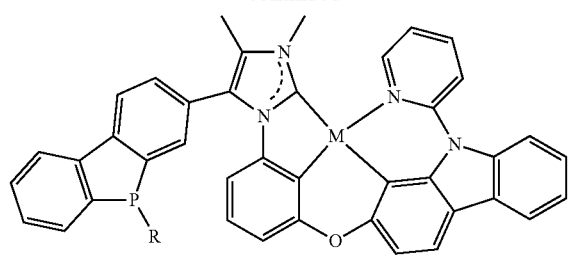
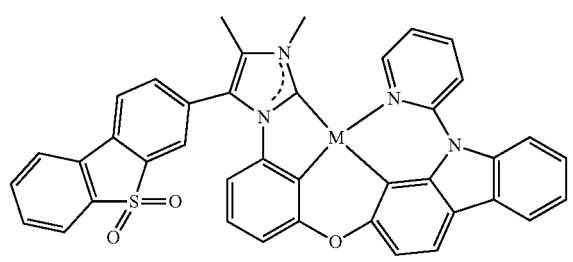
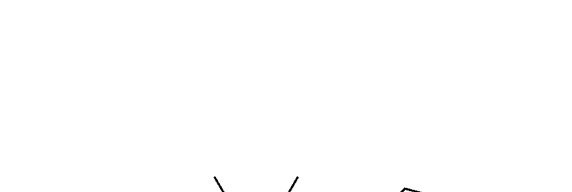
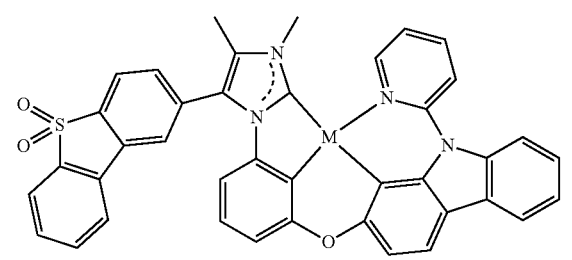
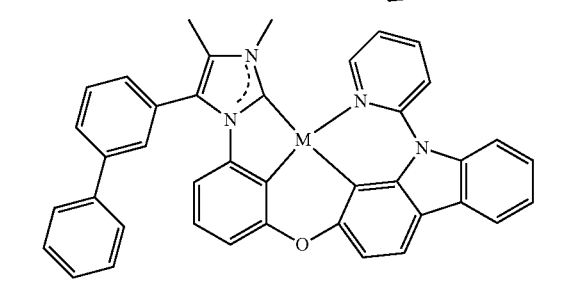
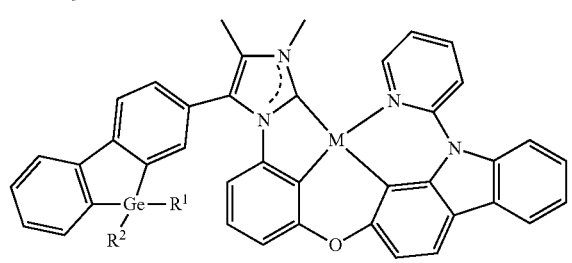
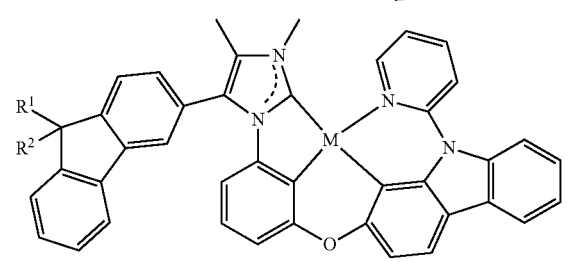
348
-continued

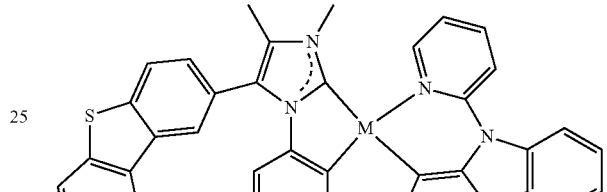
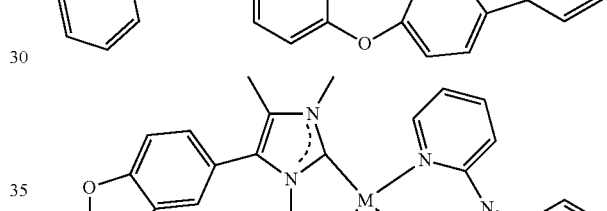
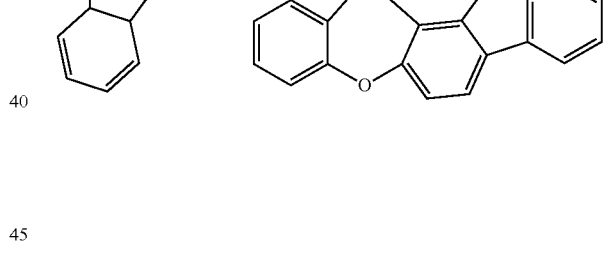
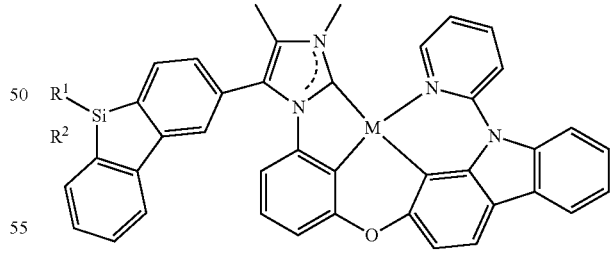

349
-continued
350
-continued
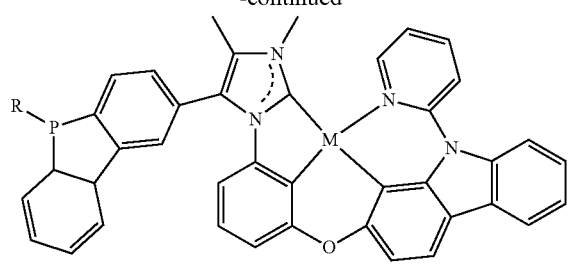
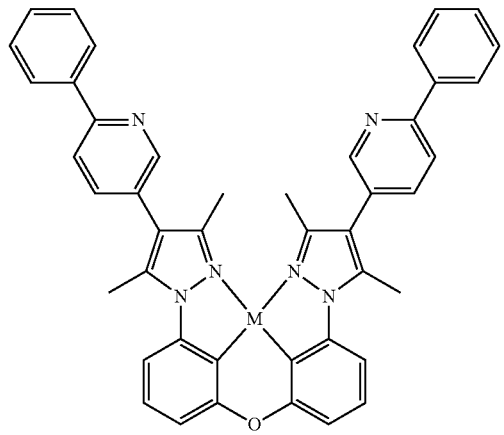
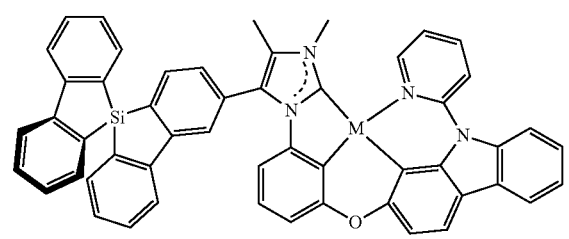
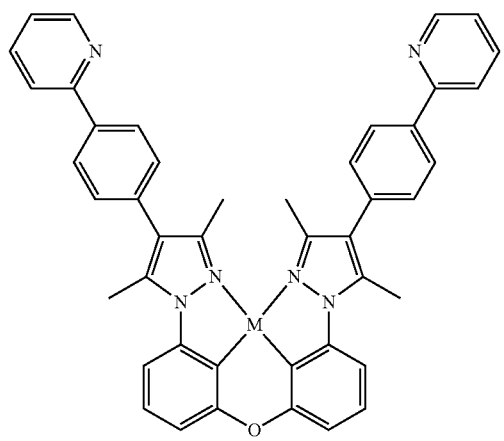
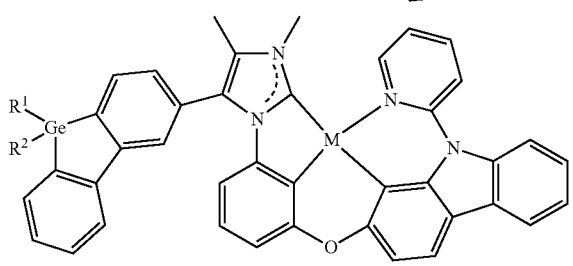
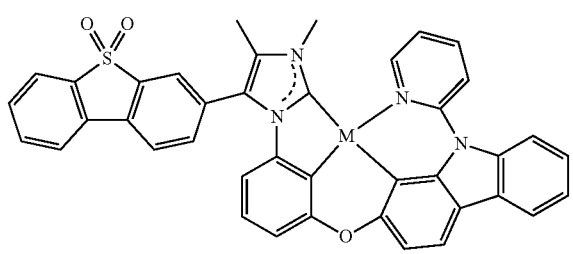
(M = Pt, Pd)
Structures 47
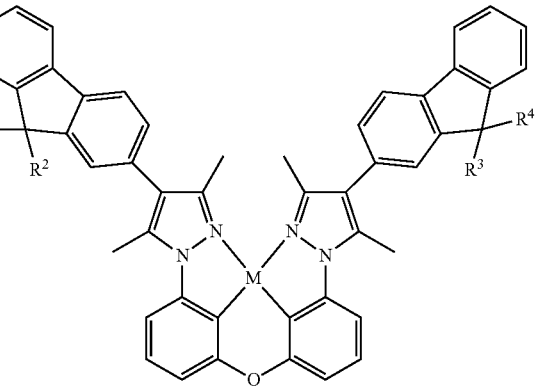
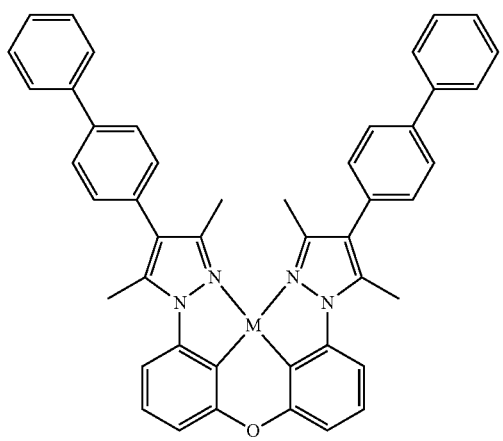
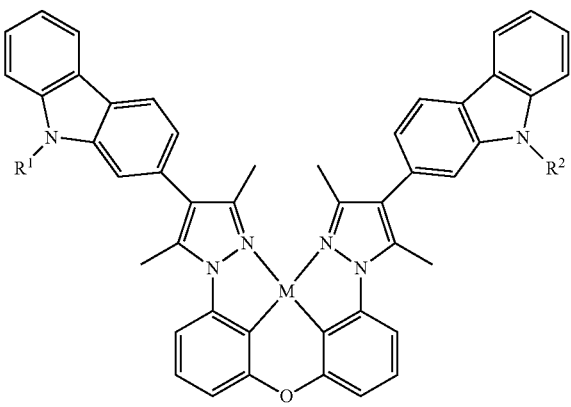

351
-continued
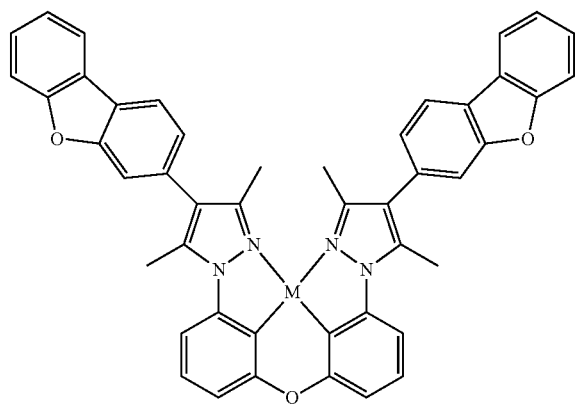
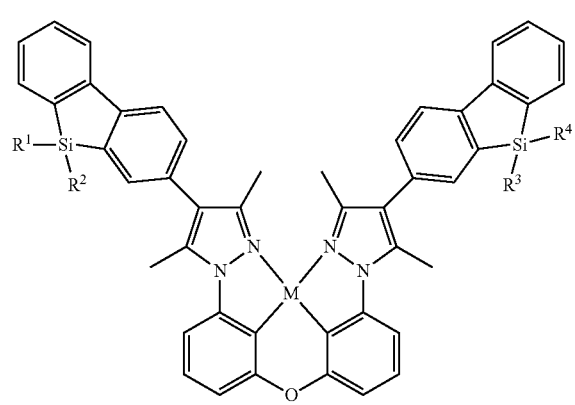
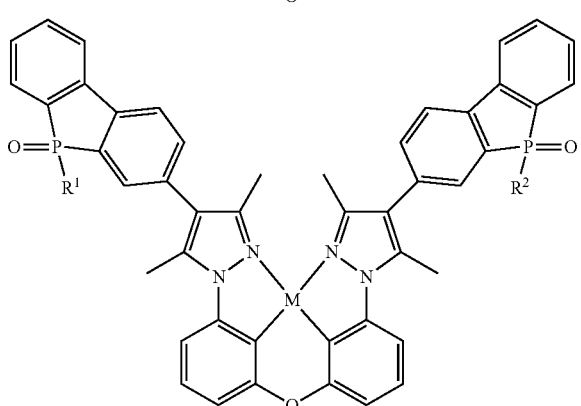
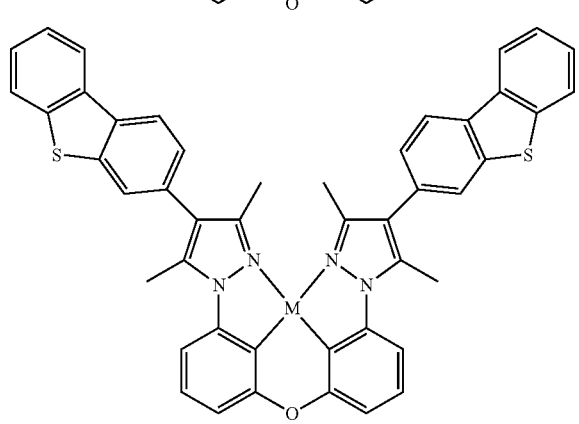
352
-continued
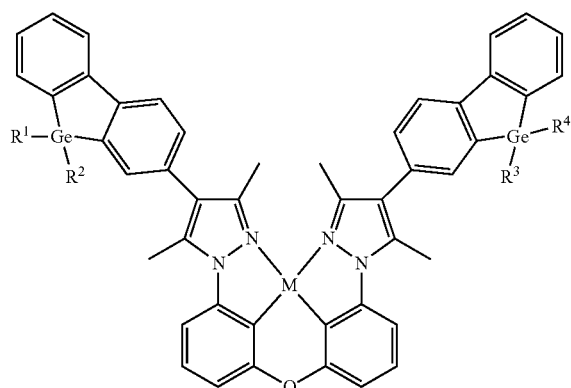
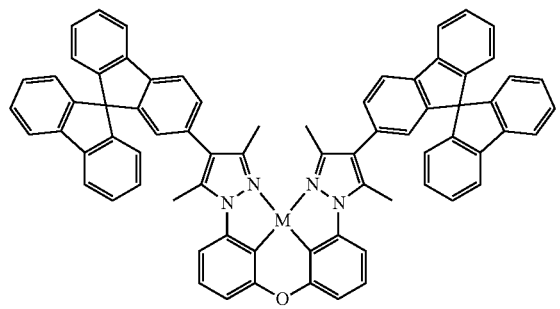
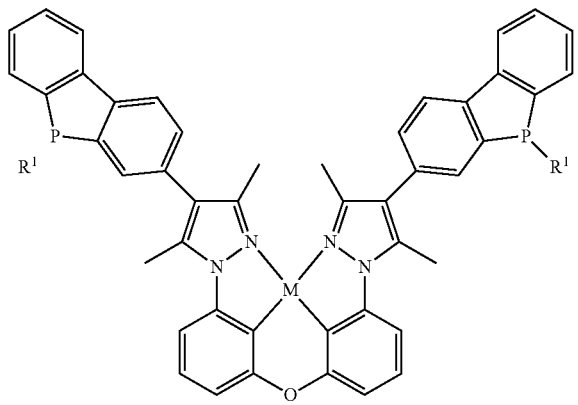
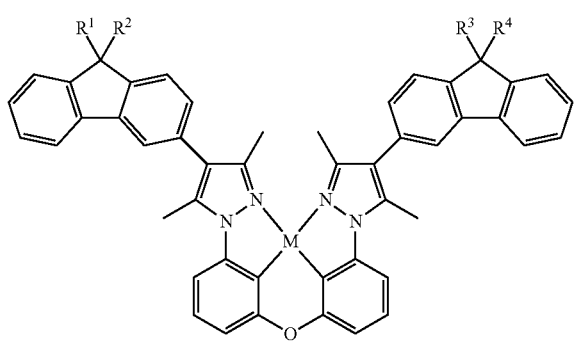

353
-continued
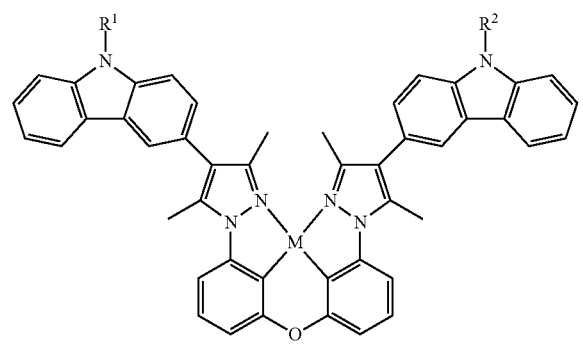
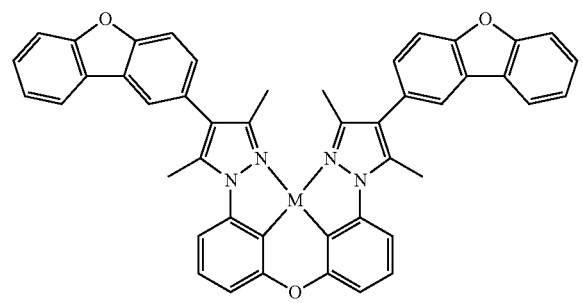
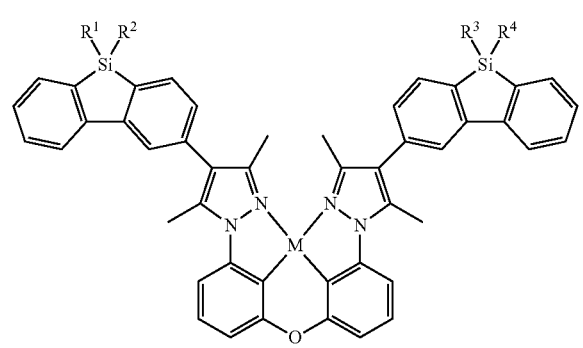
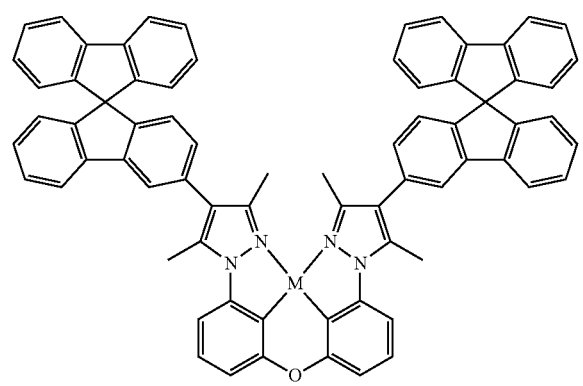
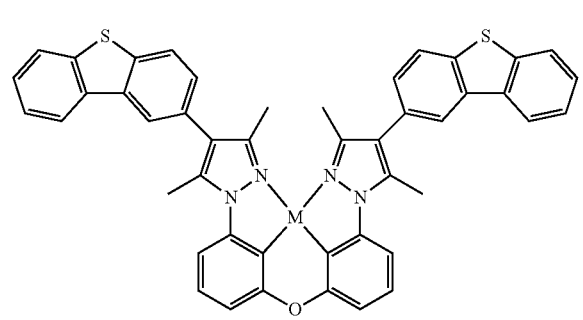
354
-continued
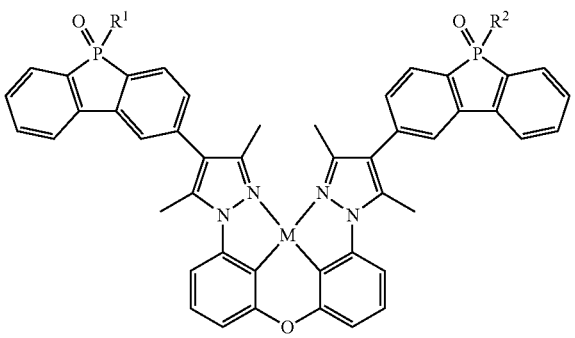
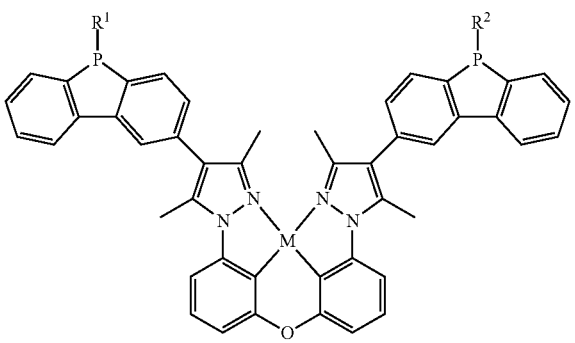
(M = Pt, Pd)
Structures 48
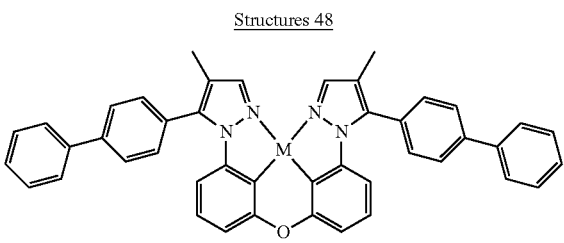
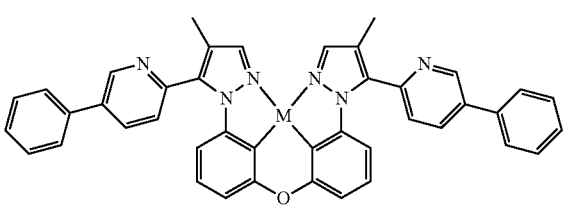
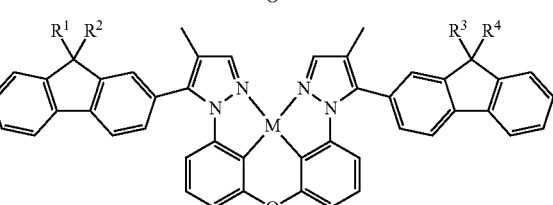
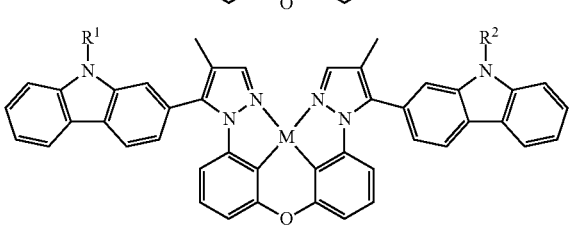

355
-continued
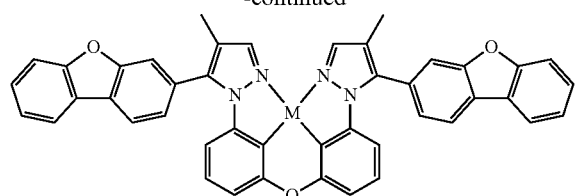
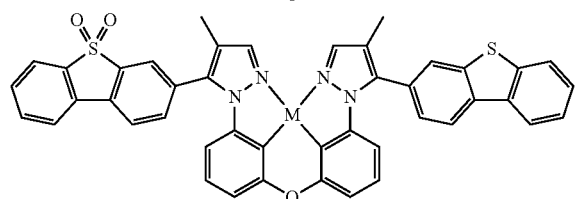
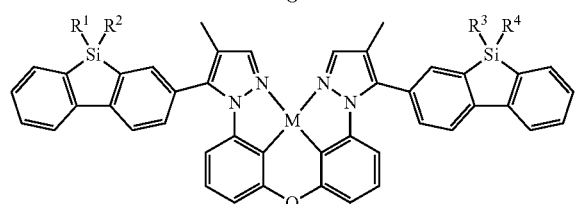
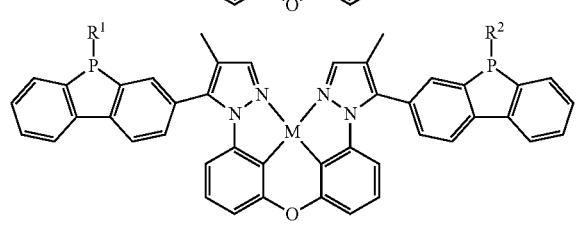
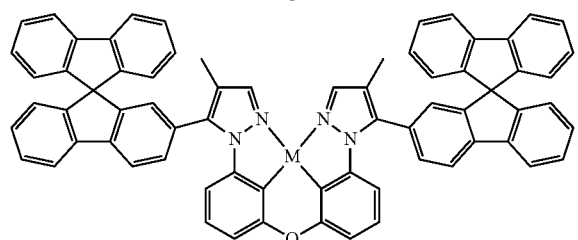
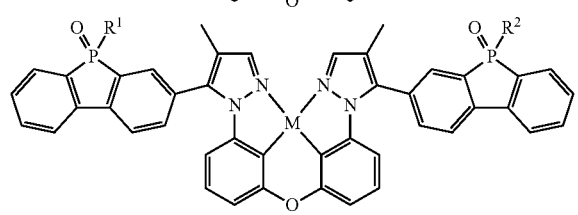
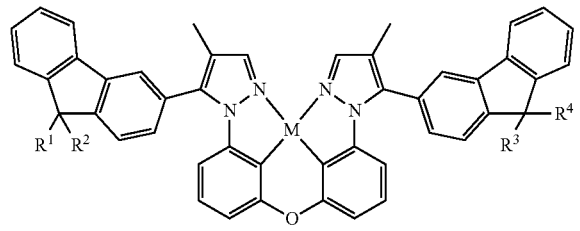
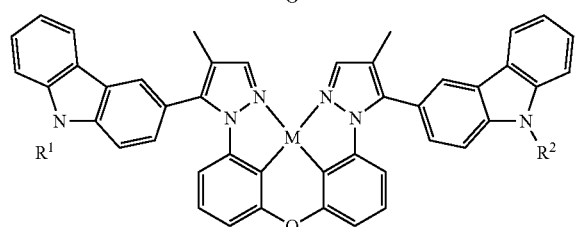
356
-continued
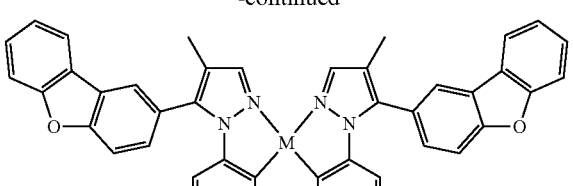
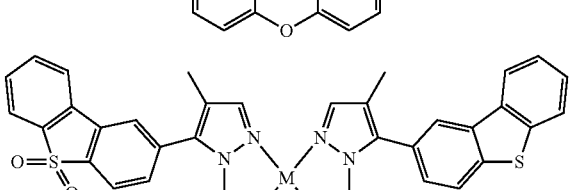
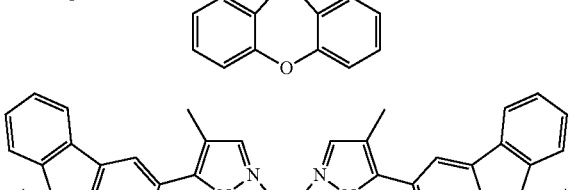
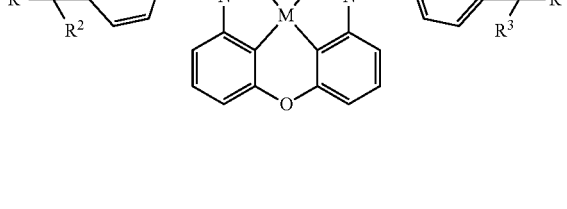
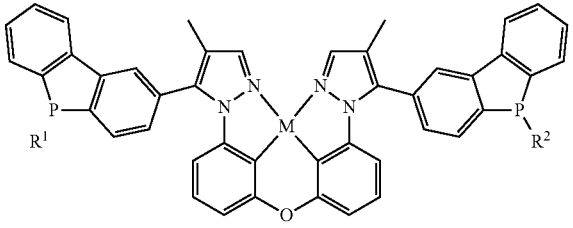
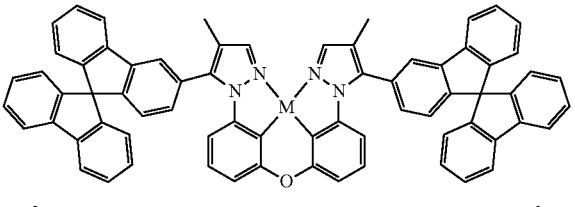
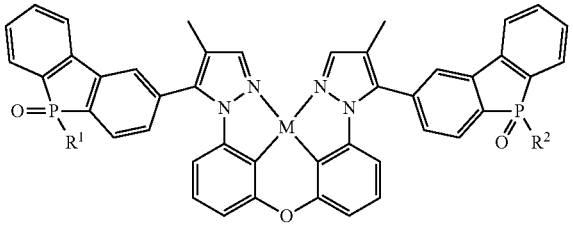
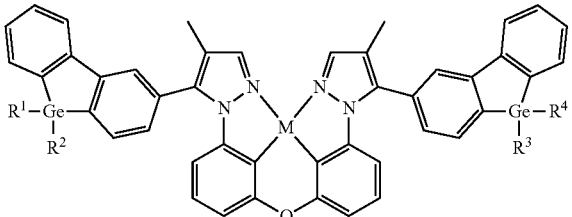

357
-continued
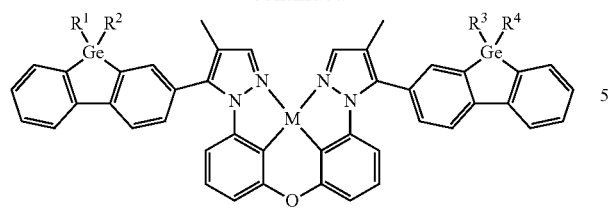
(M = Pt, Pd)
Structures 49
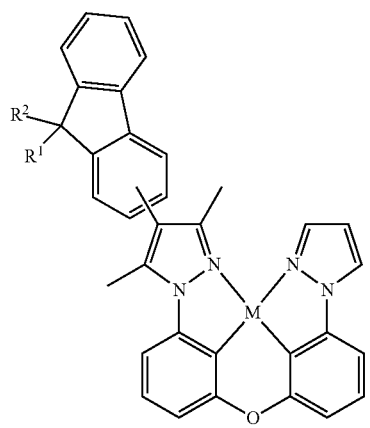
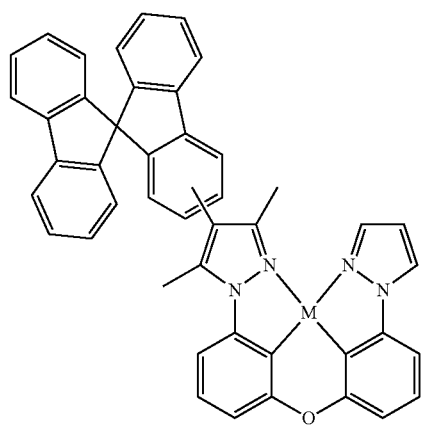
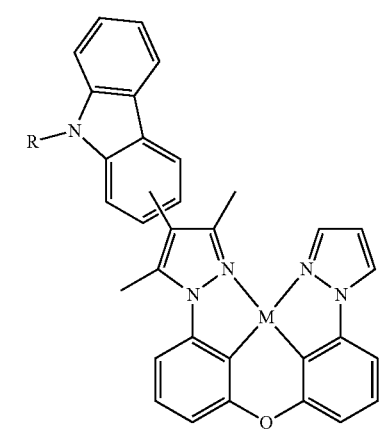
358
-continued
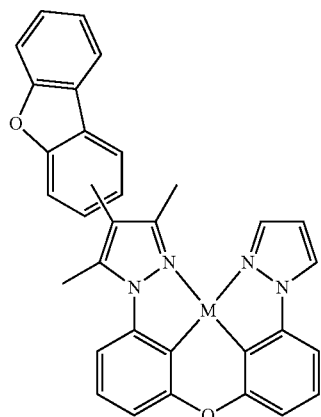
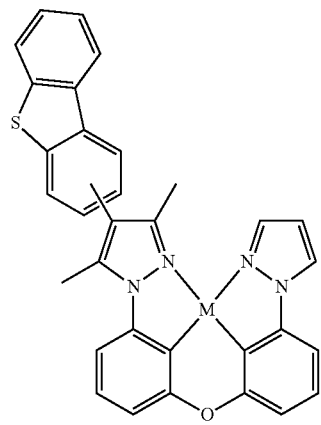
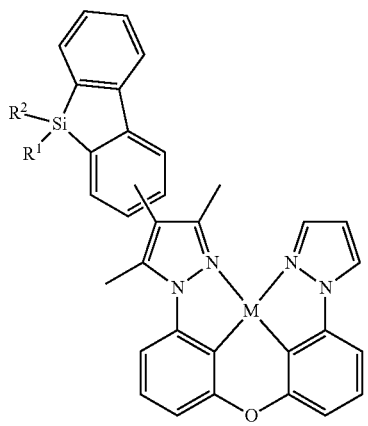
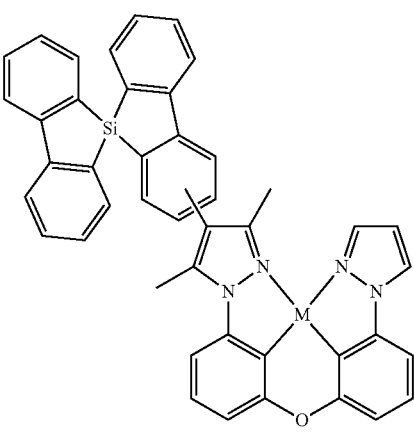

359
-continued
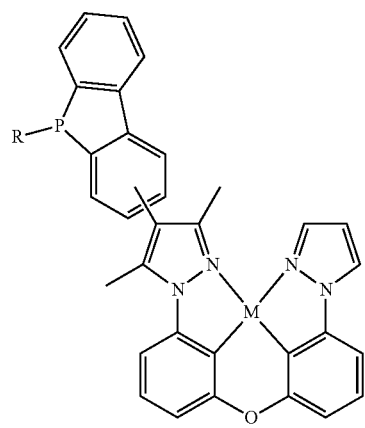
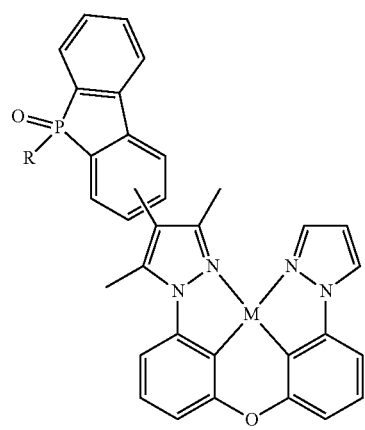
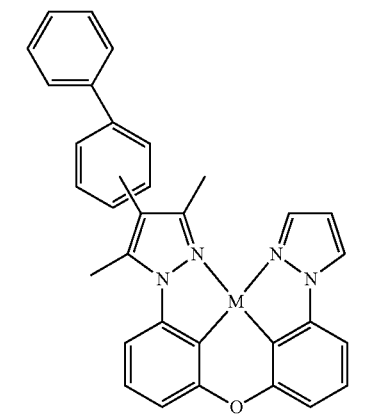
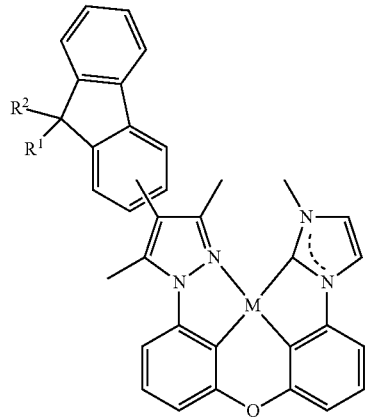
360
-continued
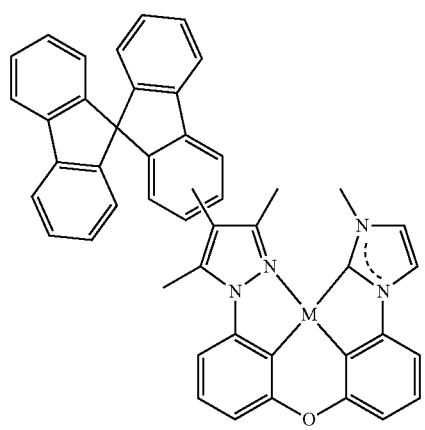
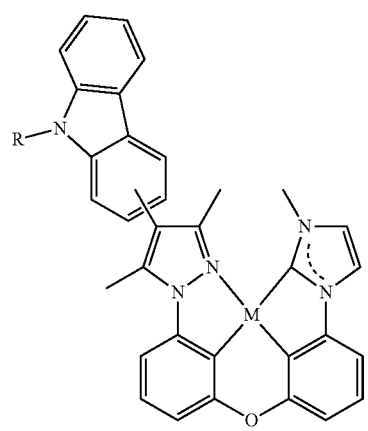
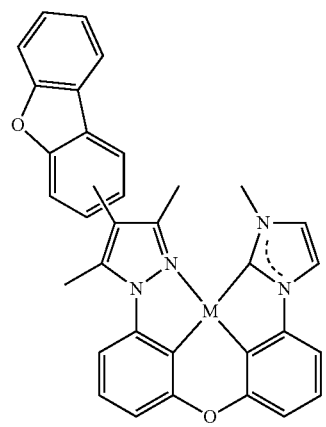
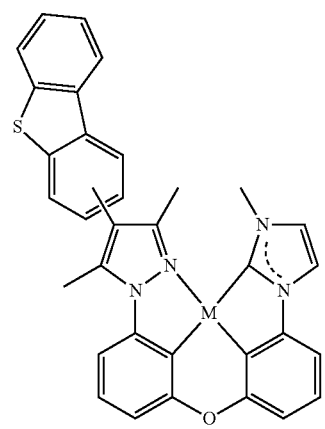

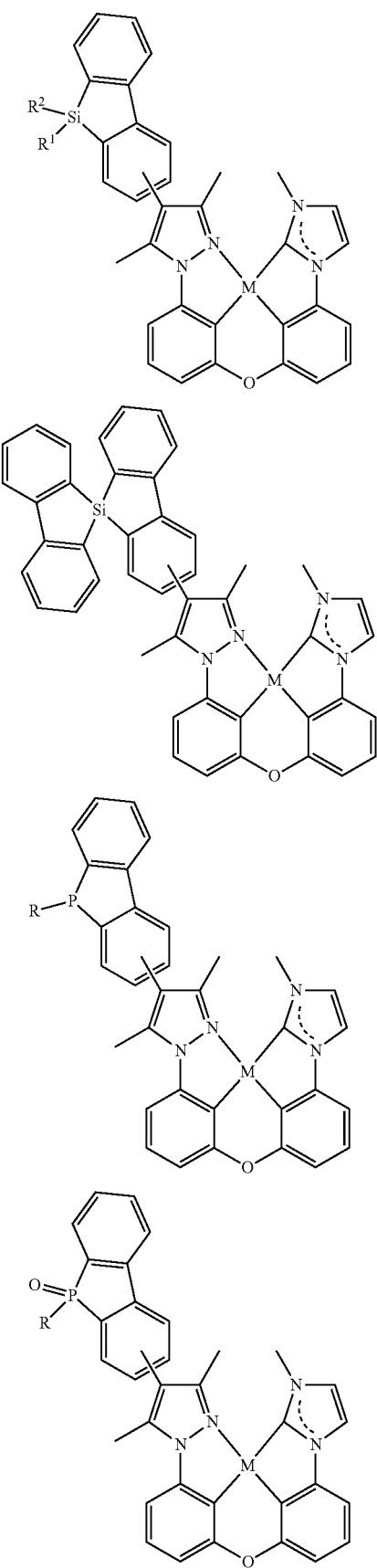
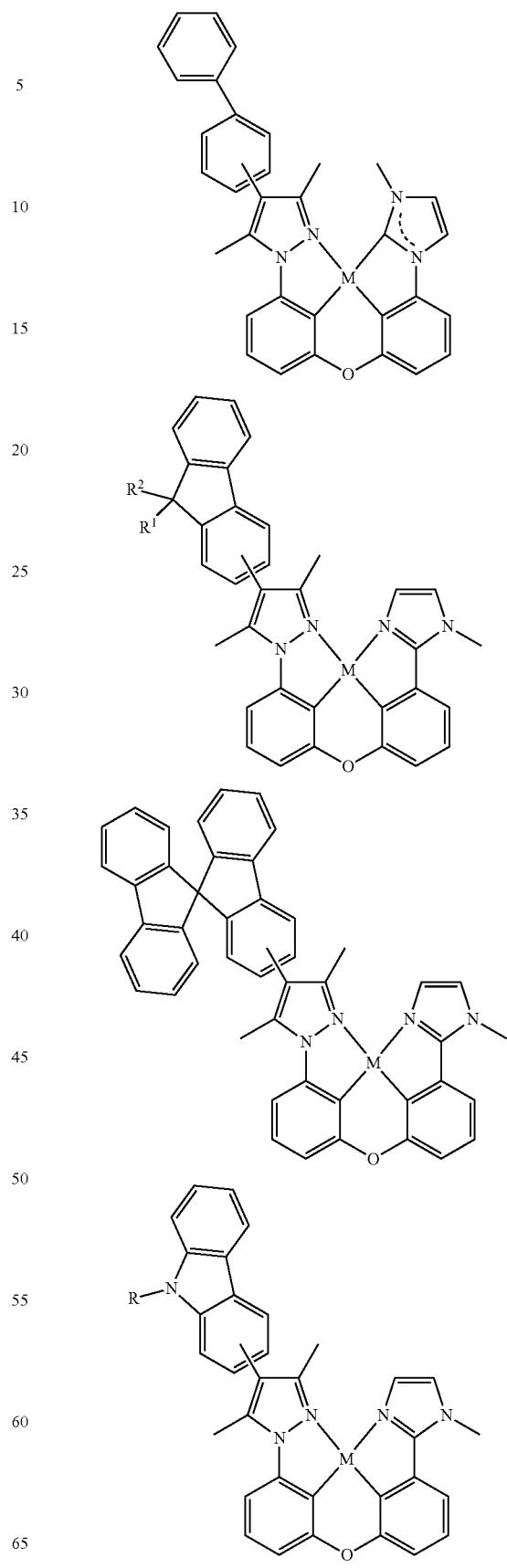

363
-continued
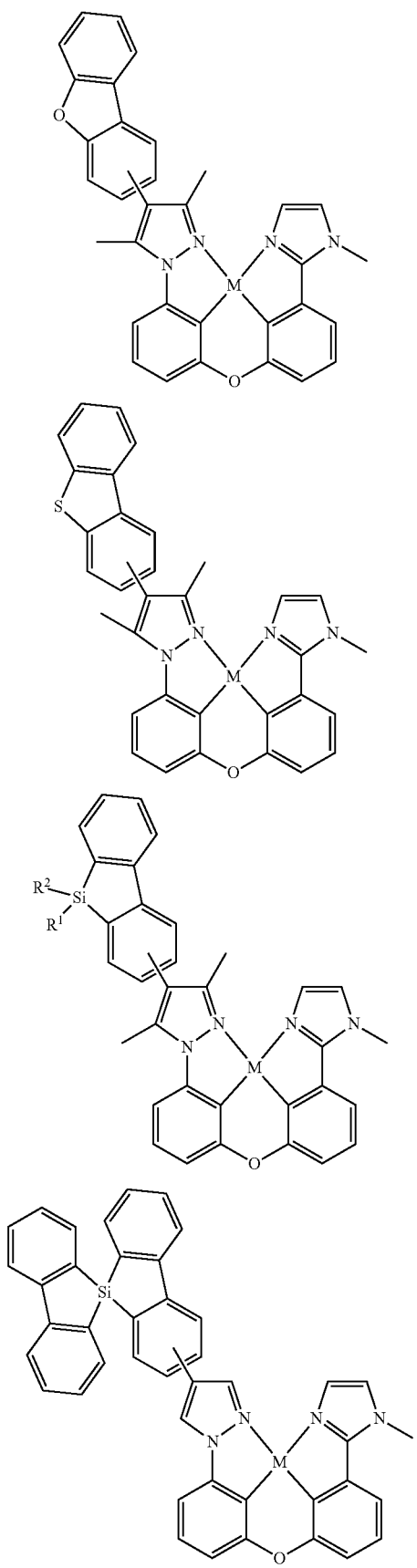
364
-continued
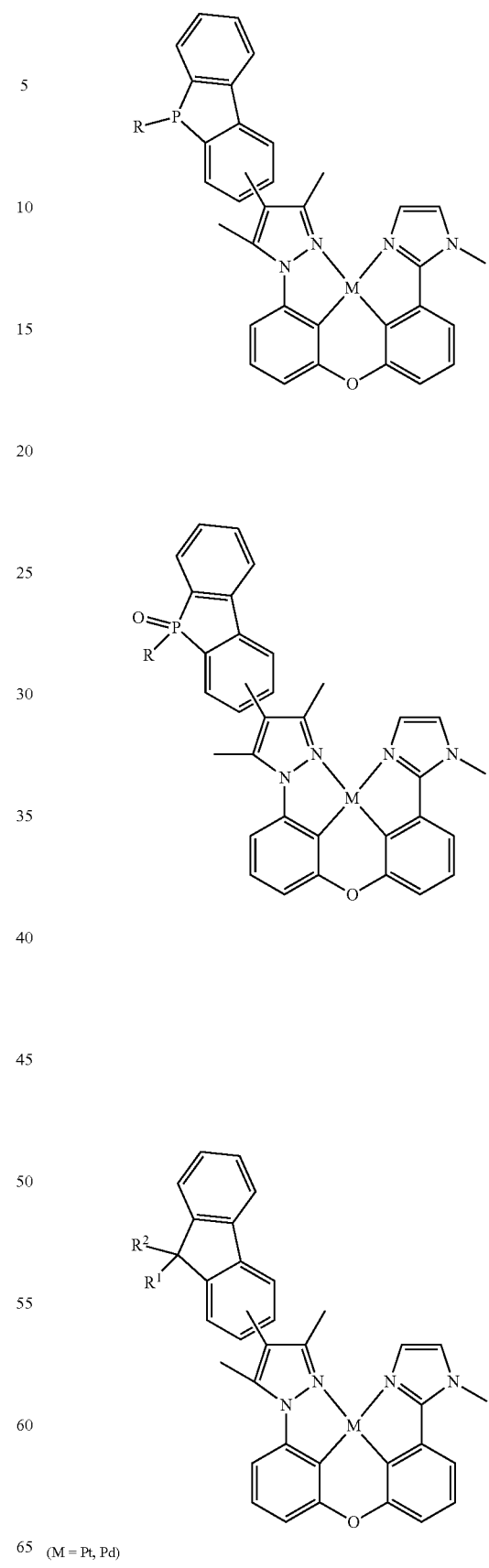
(M = Pt, Pd)

-continued
Structures 50
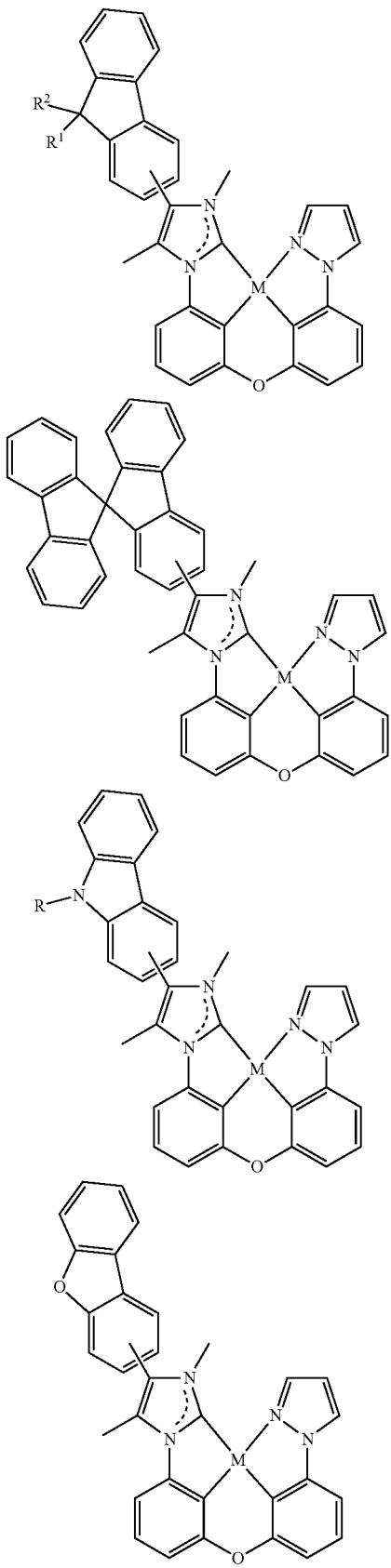
-continued
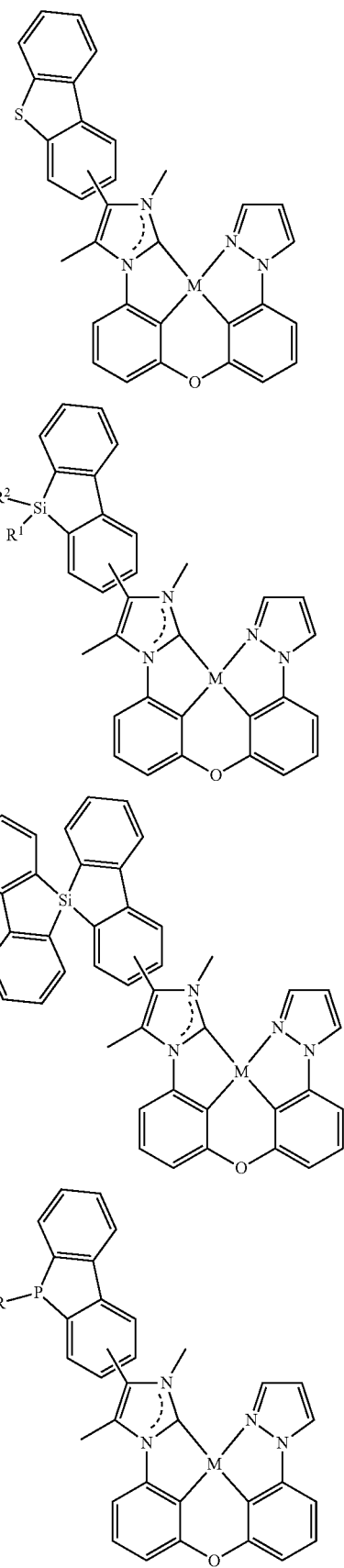

367
-continued
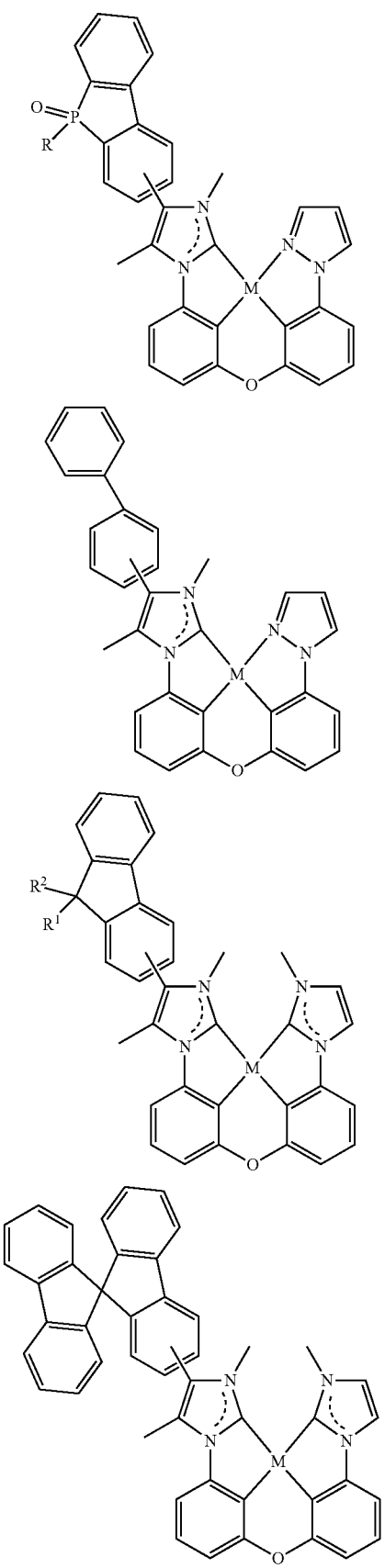
368
-continued
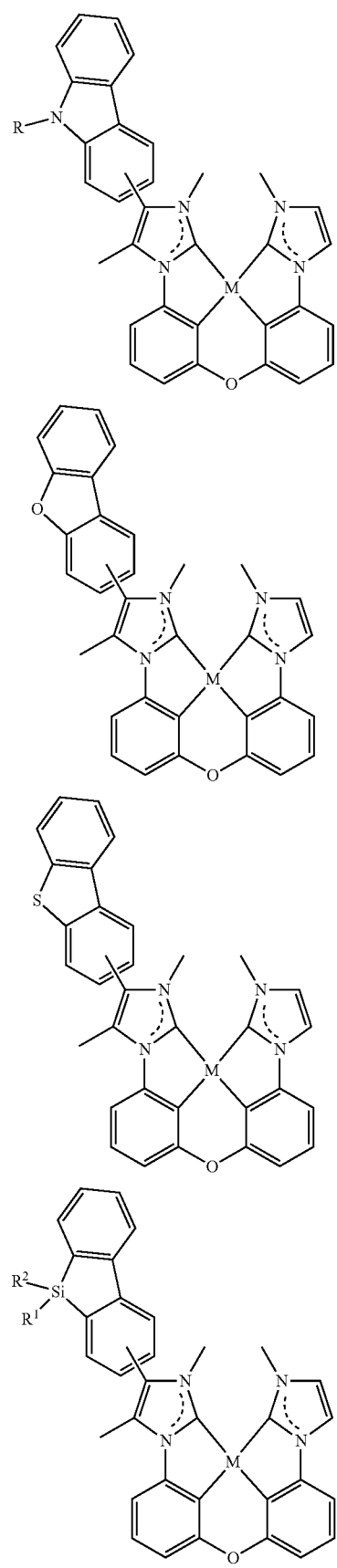

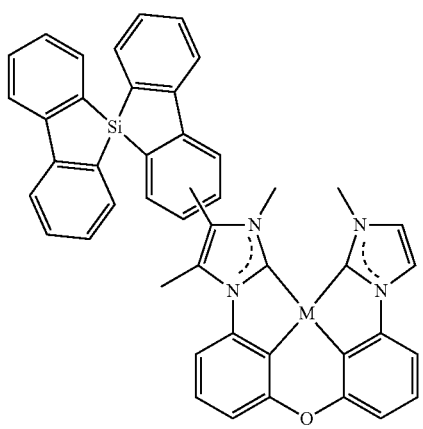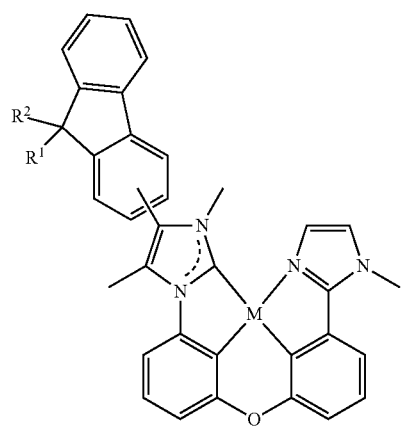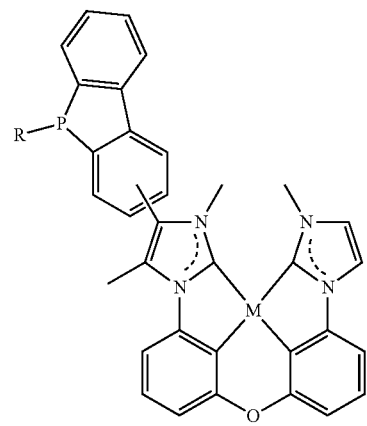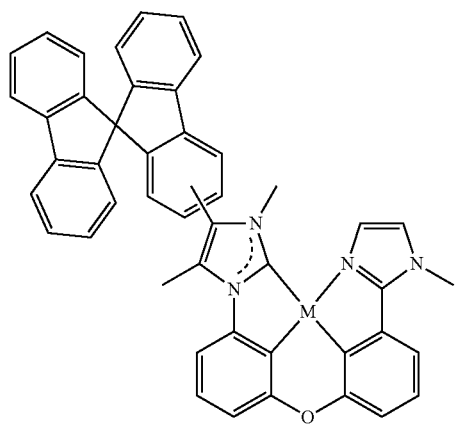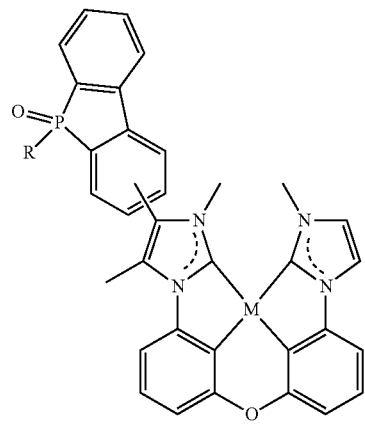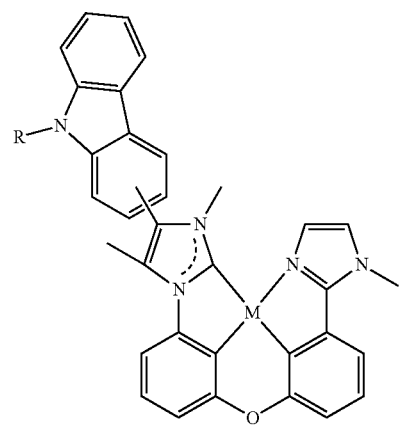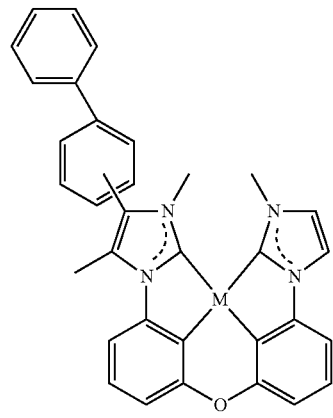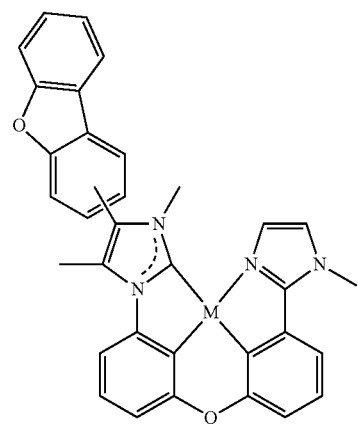

371
-continued
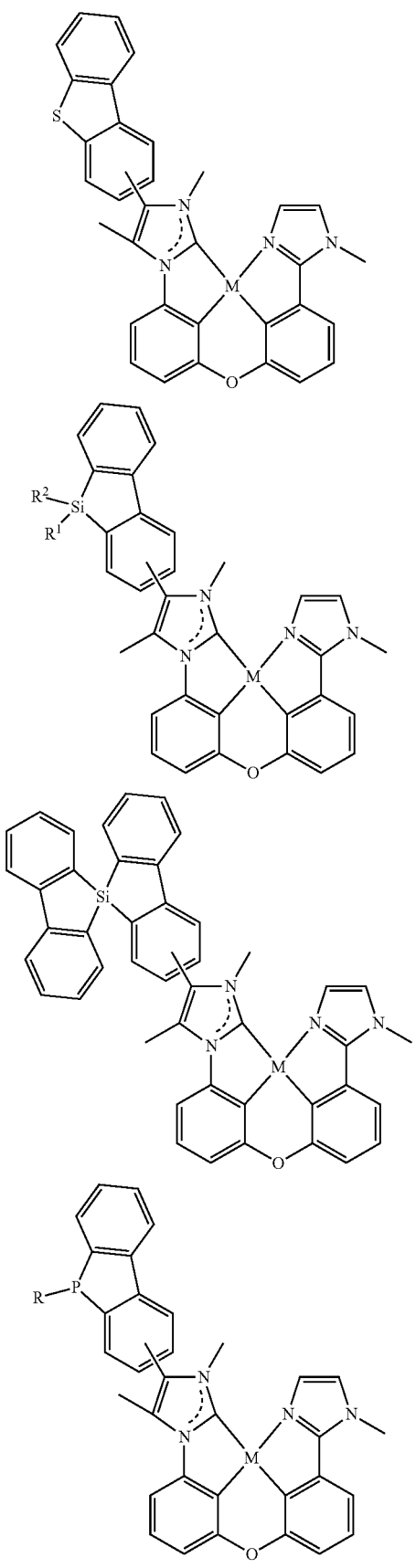
372
-continued
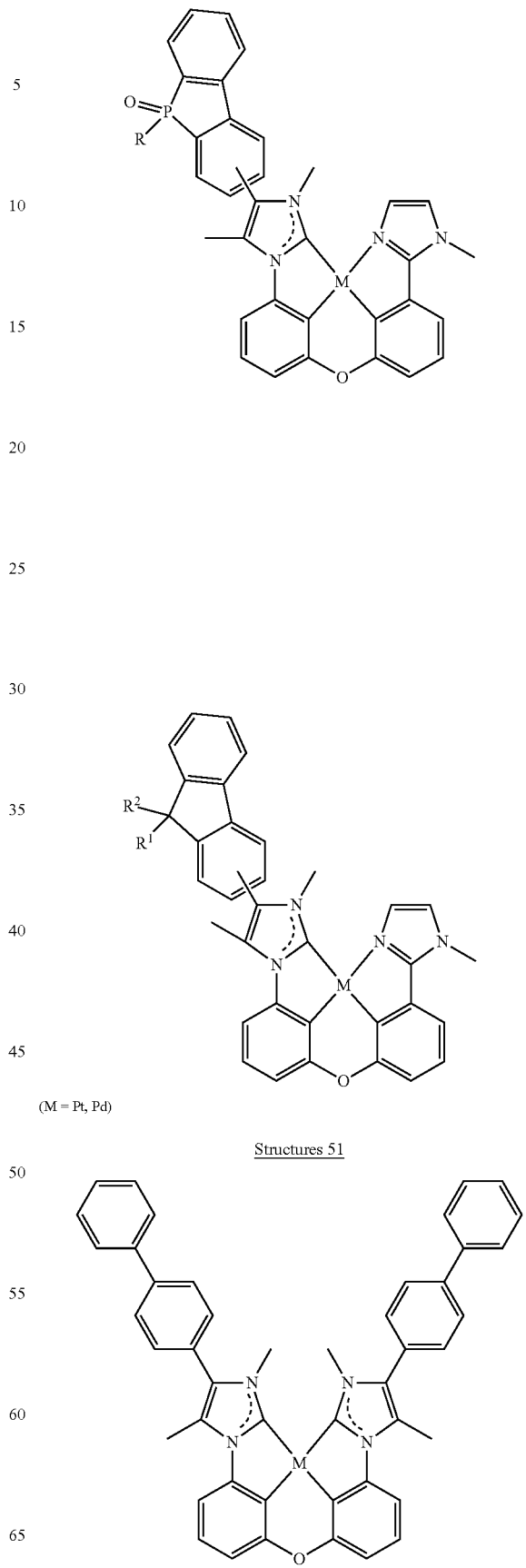
(M = Pt, Pd)
Structures 51

373
-continued
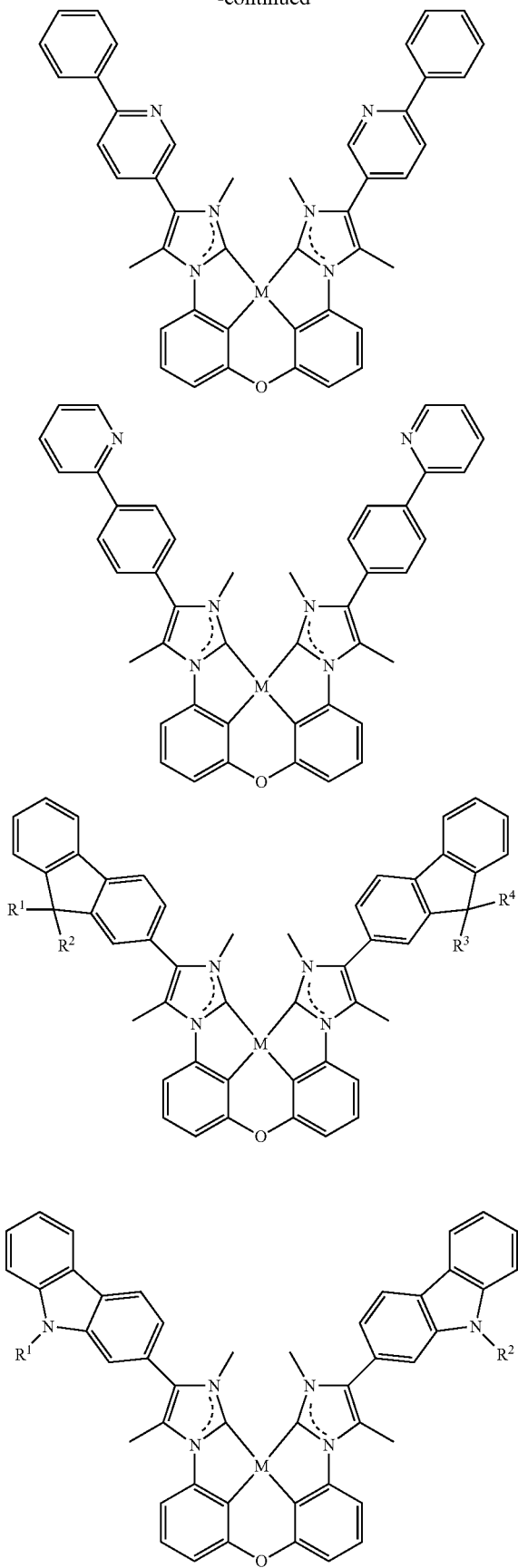
374
-continued
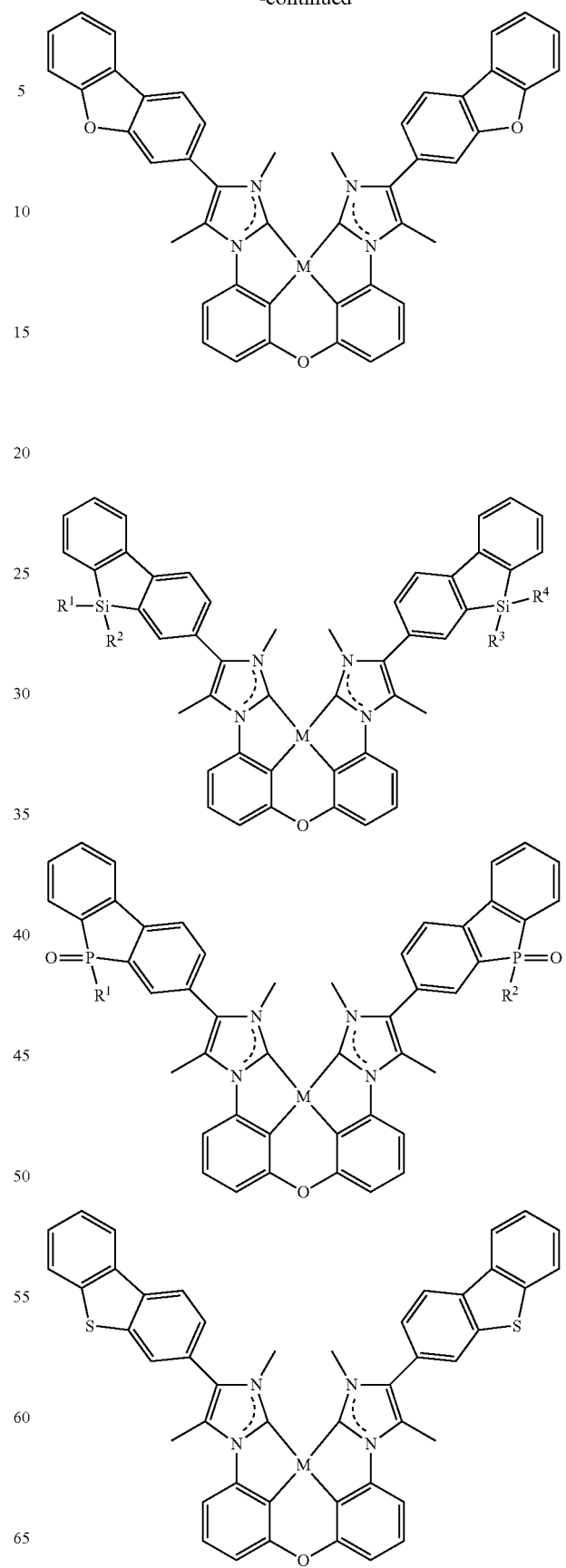

375
-continued
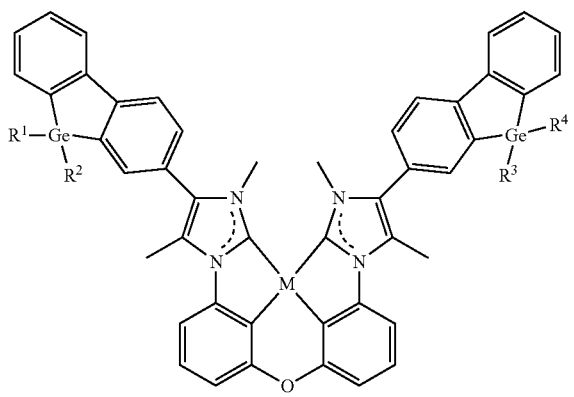
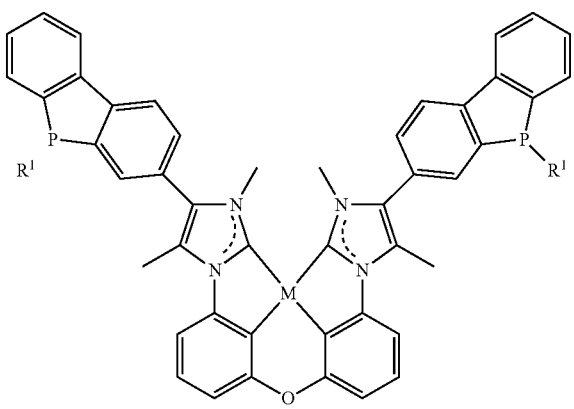
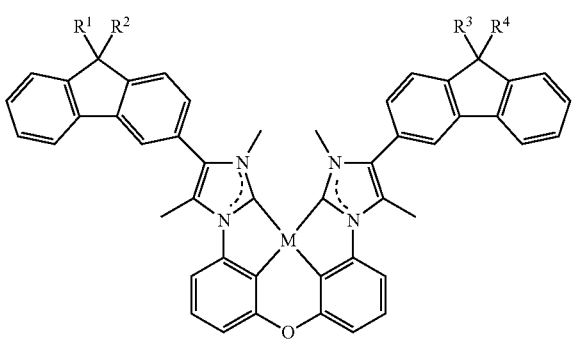
376
-continued
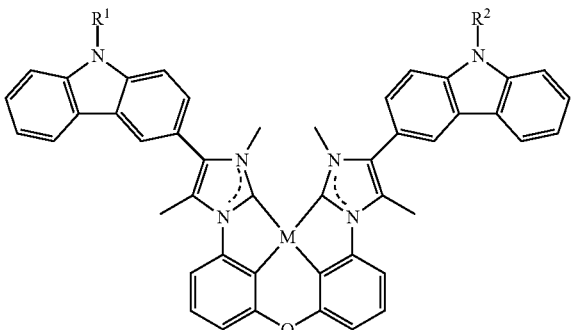
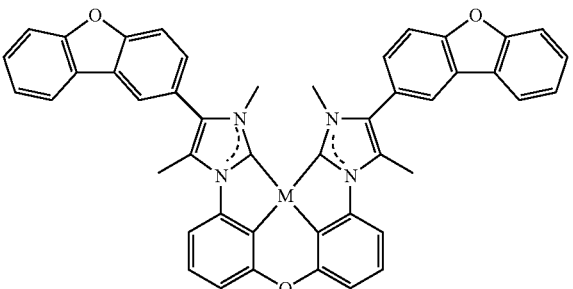
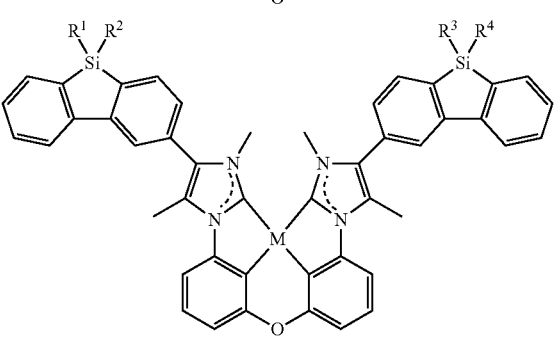
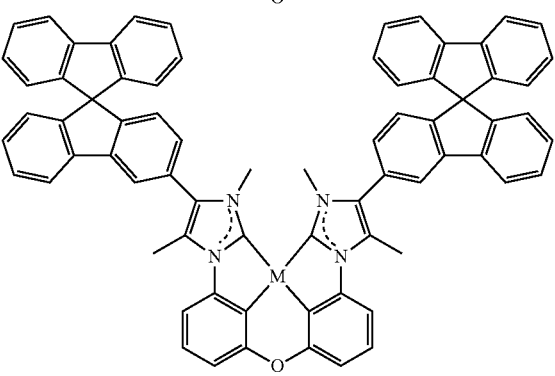
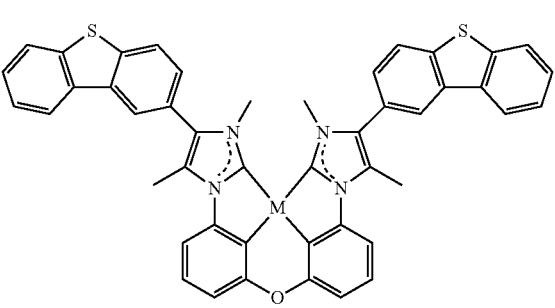

377
-continued
378
-continued
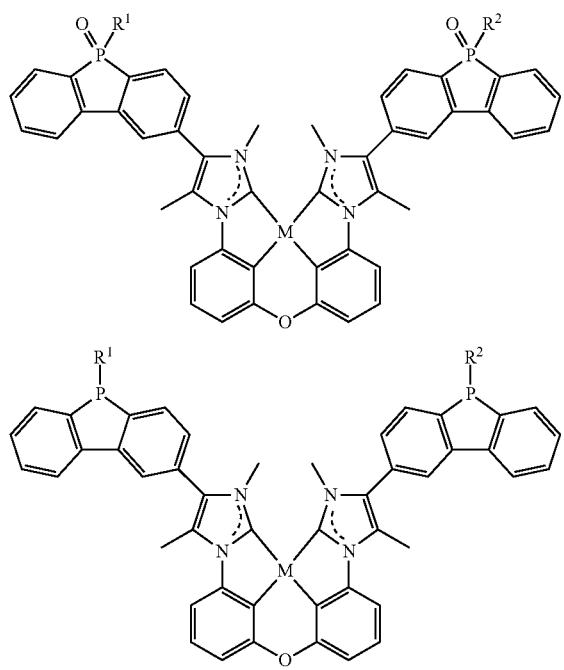
(M = Pt, Pd)
Structures 52
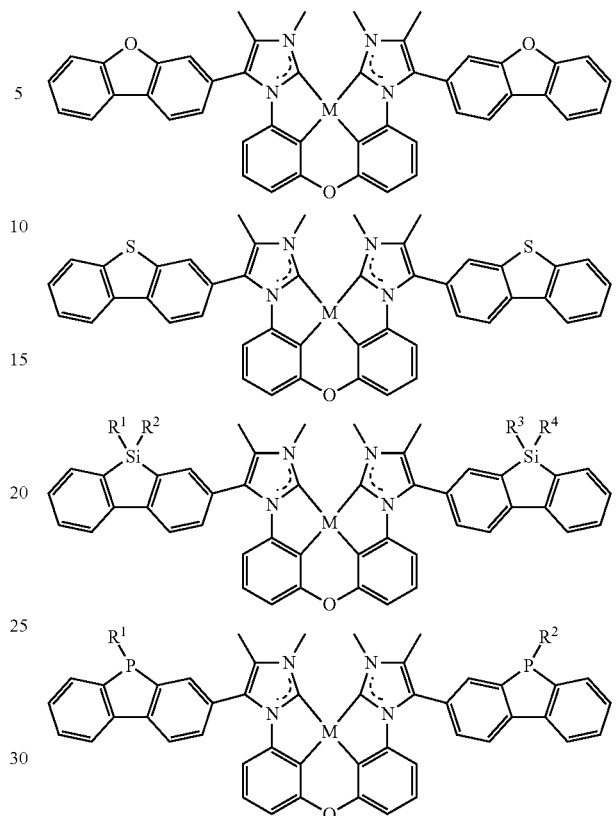

379
-continued
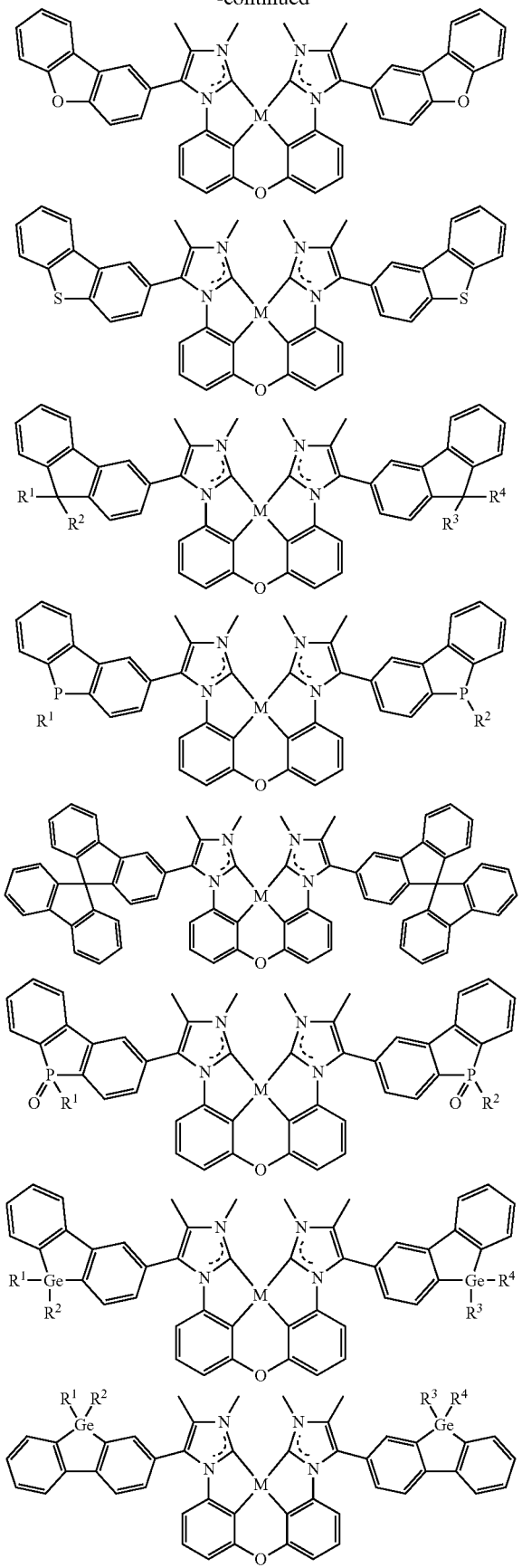
(M = Pt, Pd)
380
-continued
Structures 53
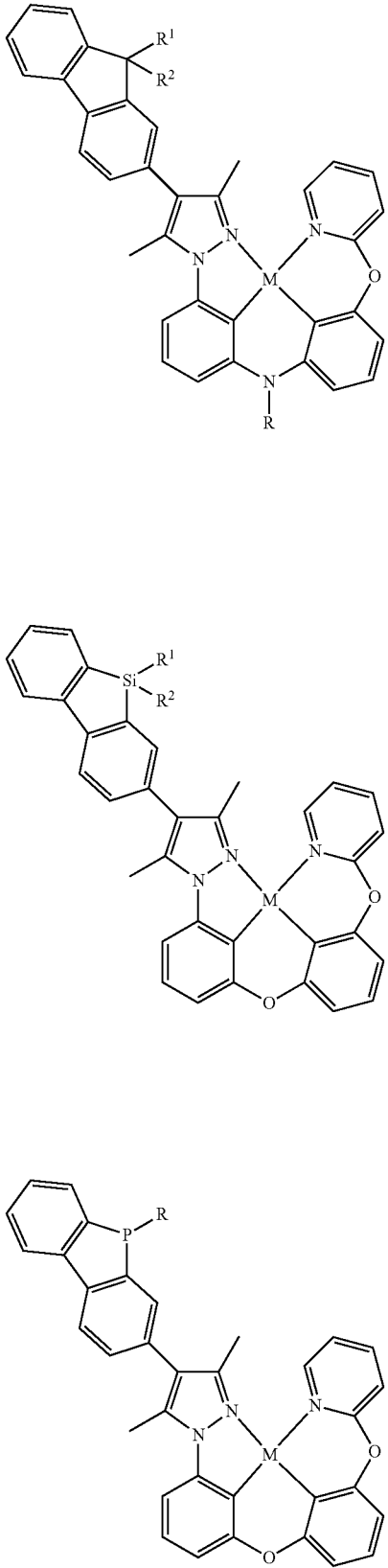

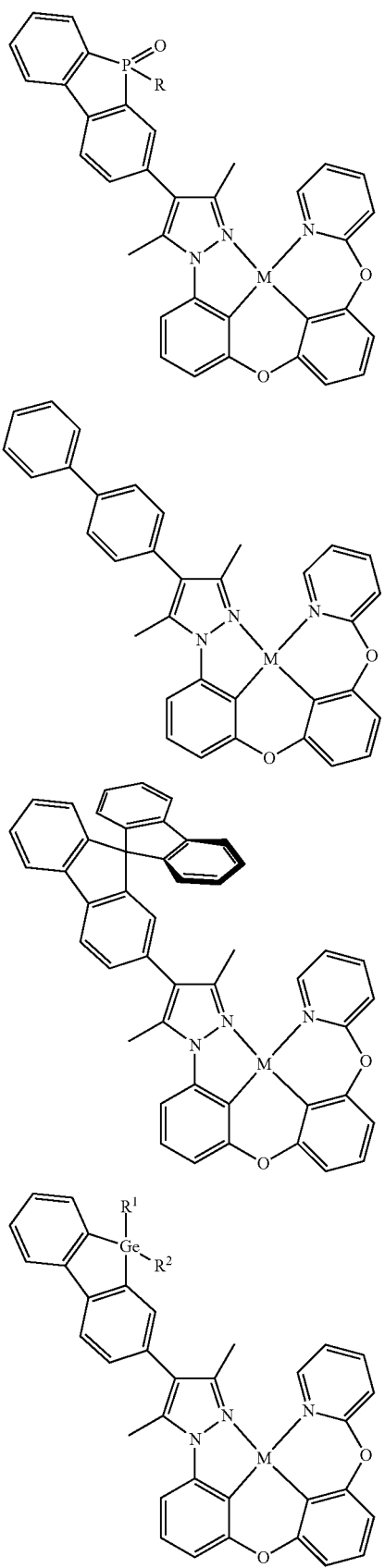
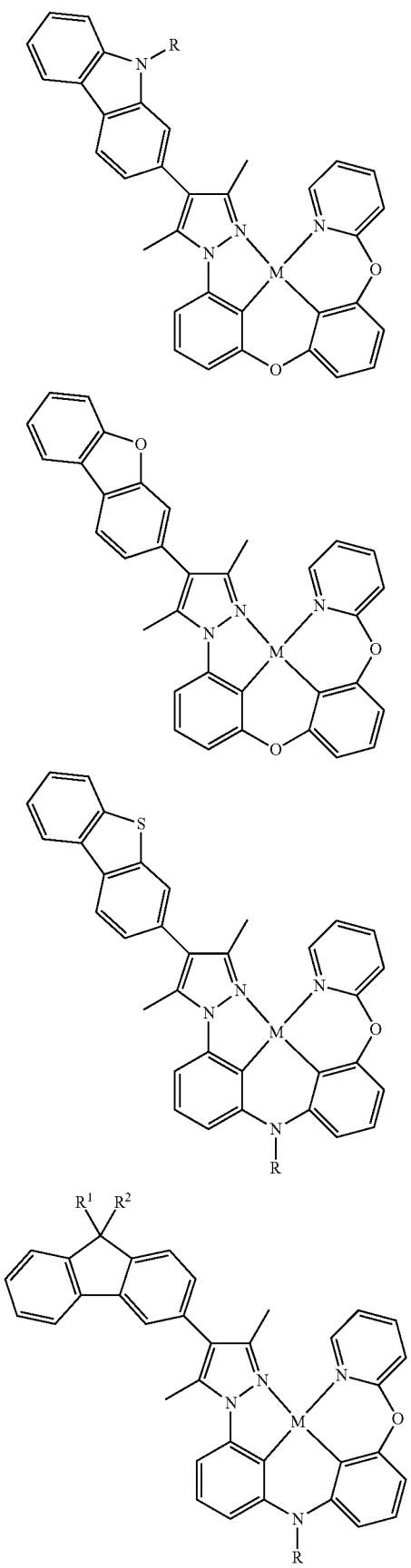

383
-continued
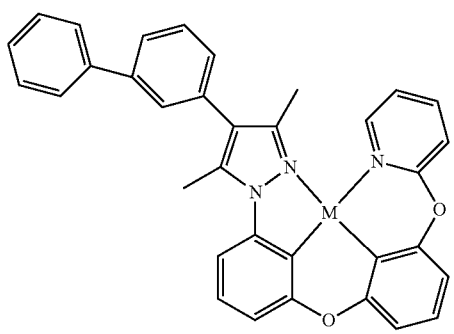
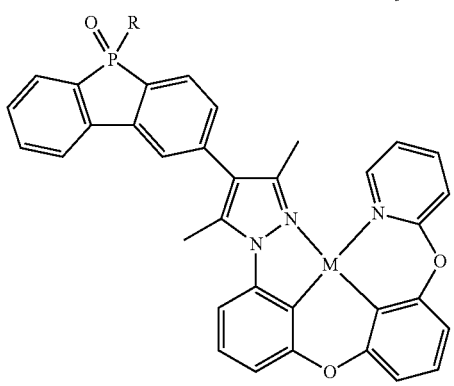
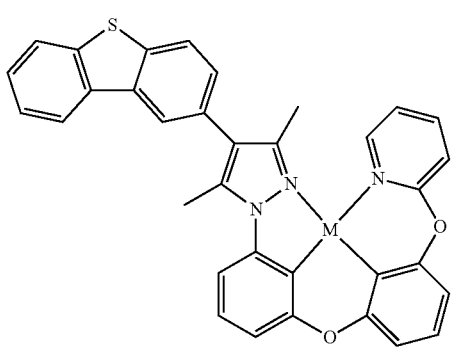
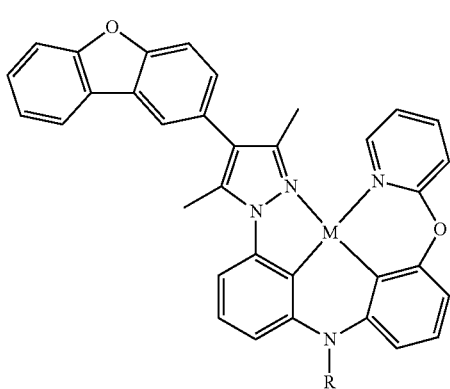
384
-continued
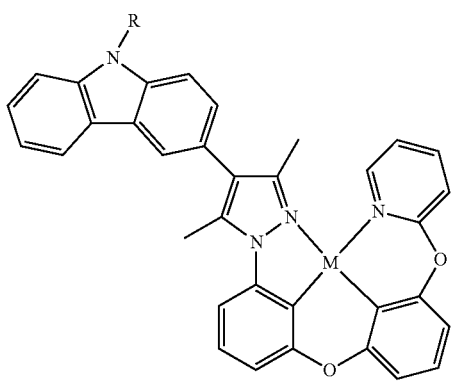
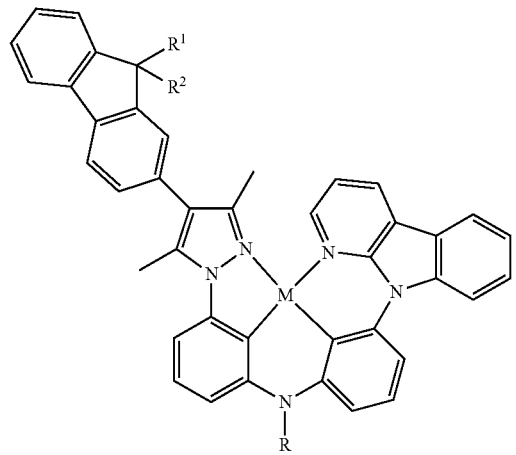
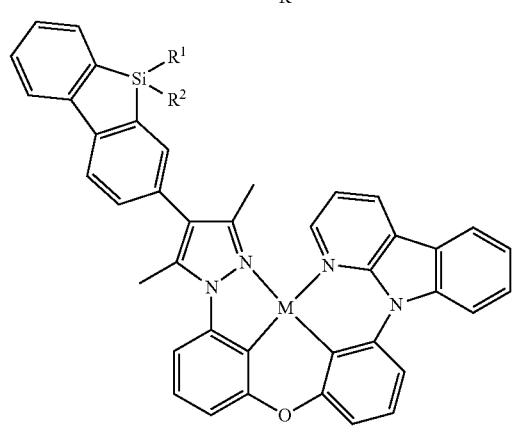
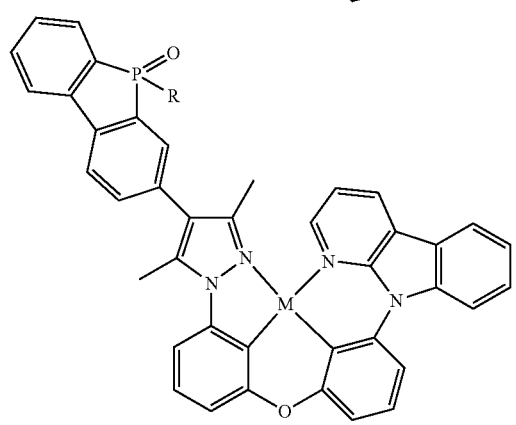

385
-continued
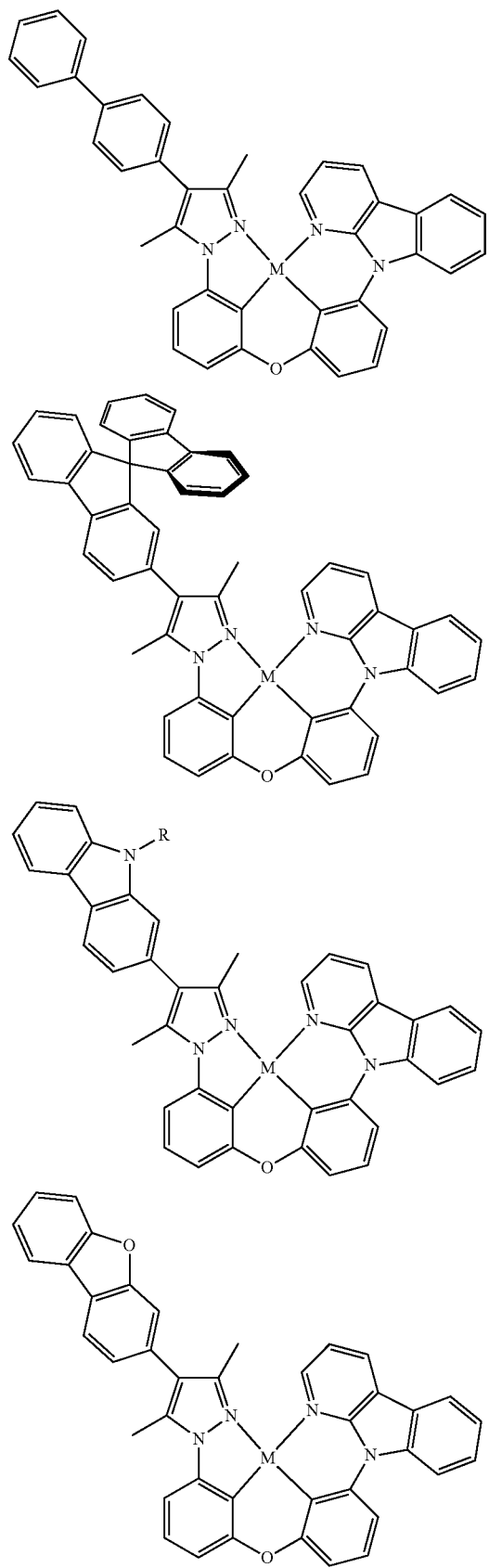
386
-continued
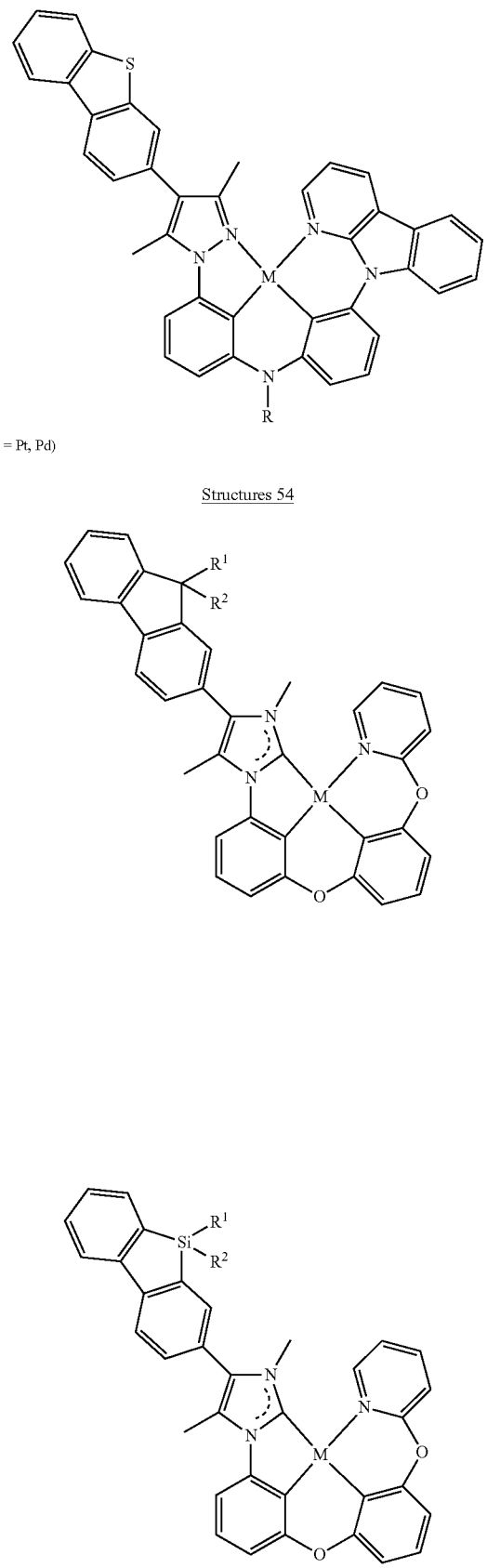
(M = Pt, Pd)
Structures 54

387
-continued
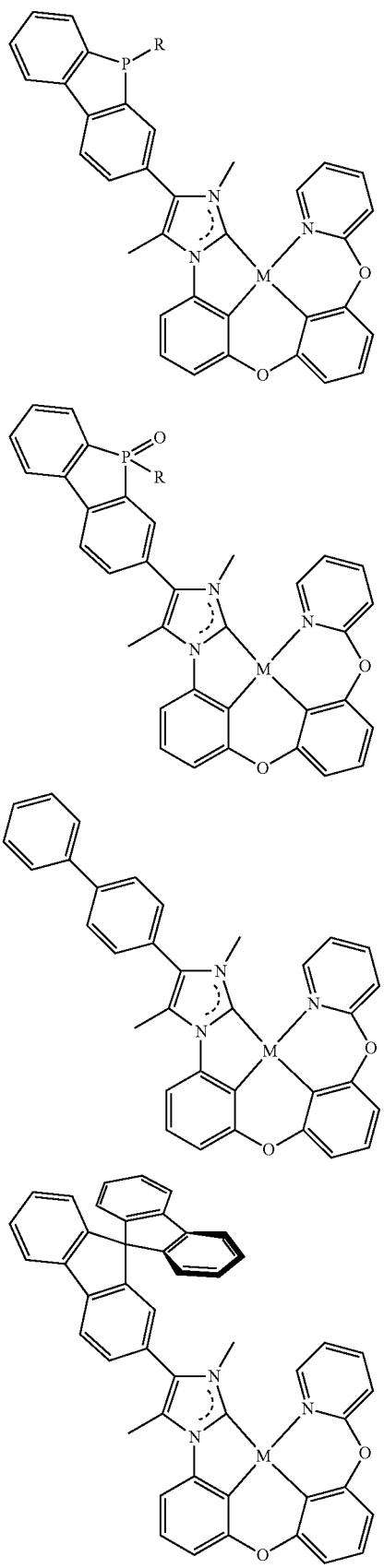
388
-continued
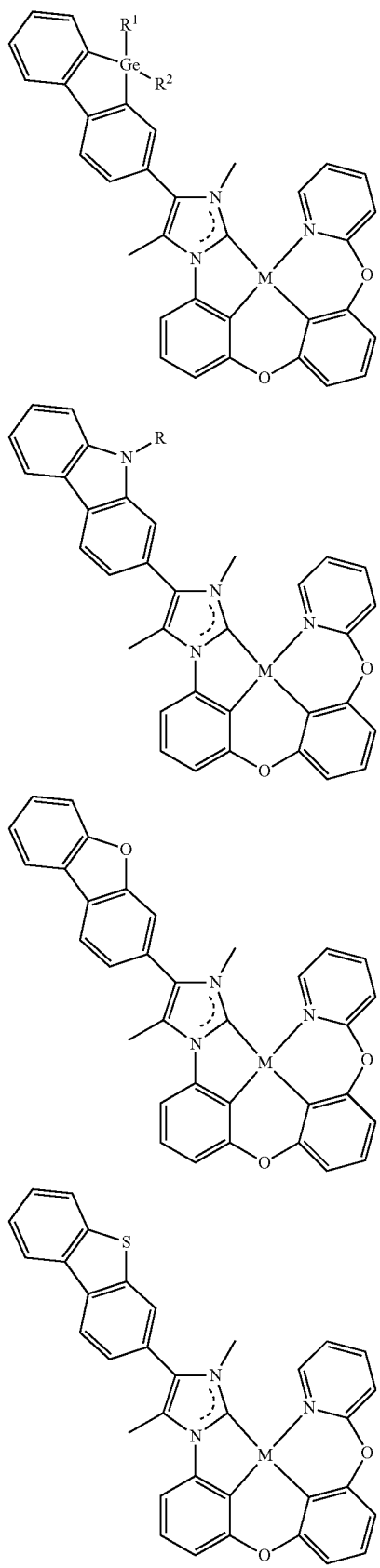

389
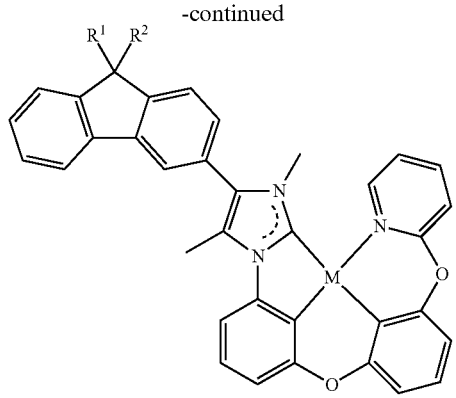
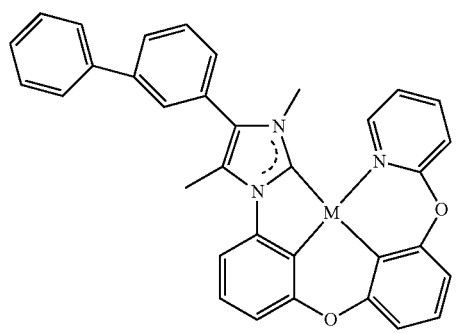
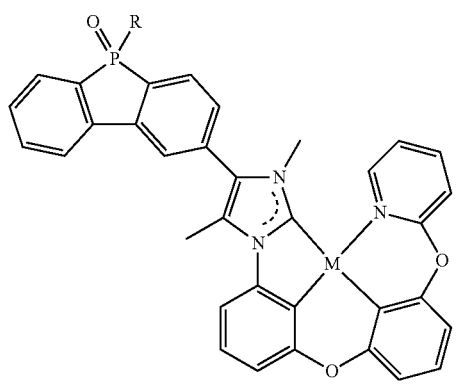
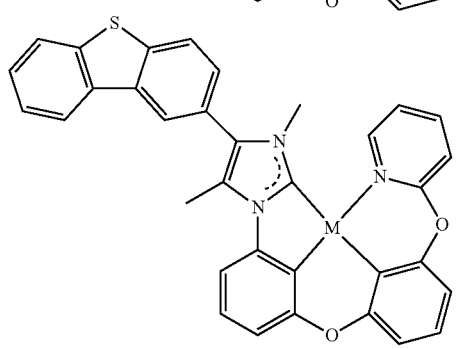
390
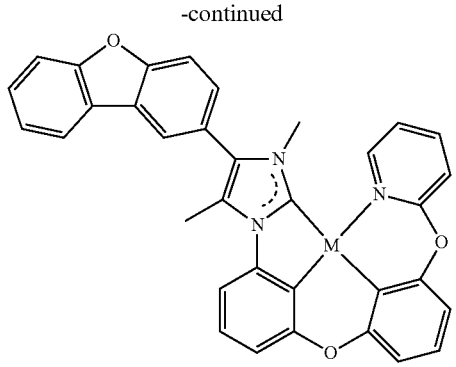
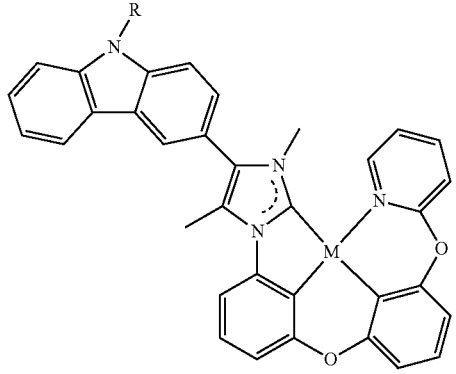
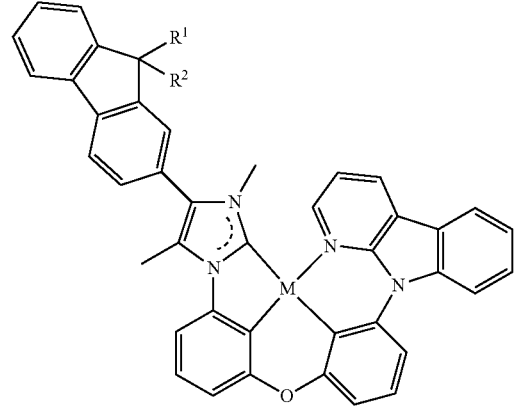
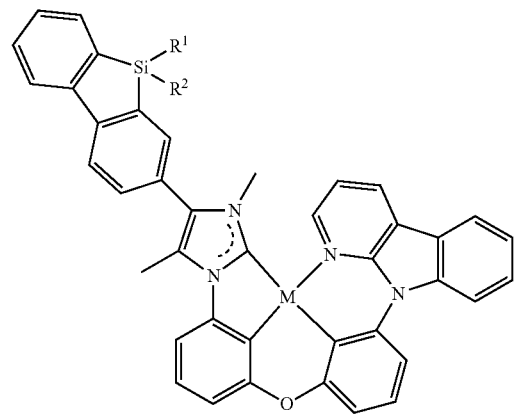

391
-continued
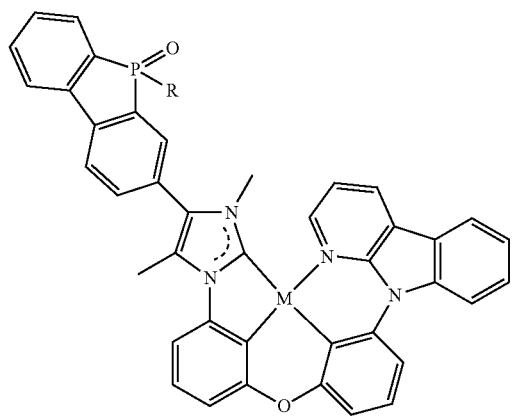
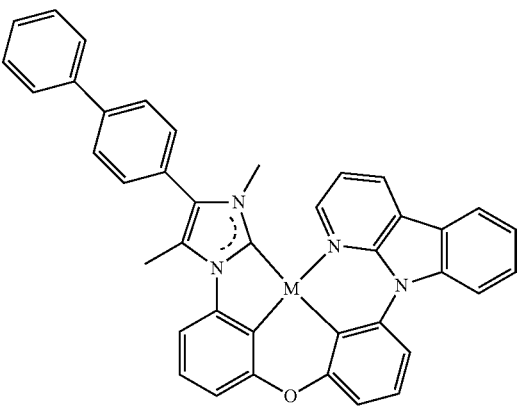
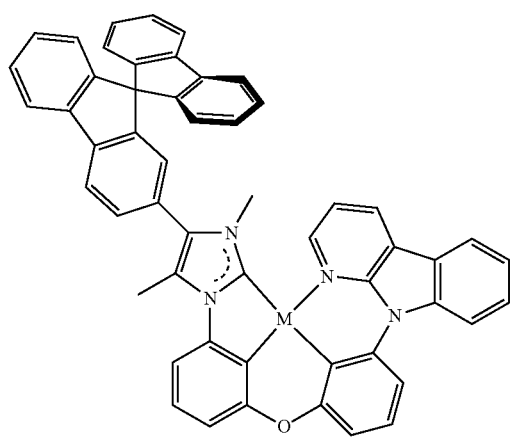
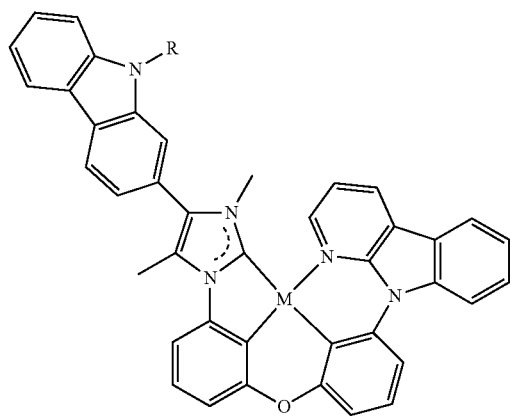
392
-continued
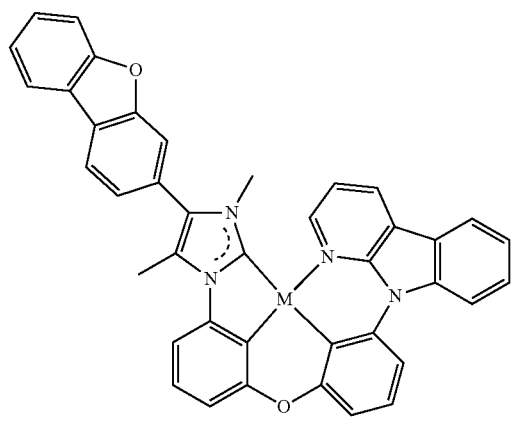
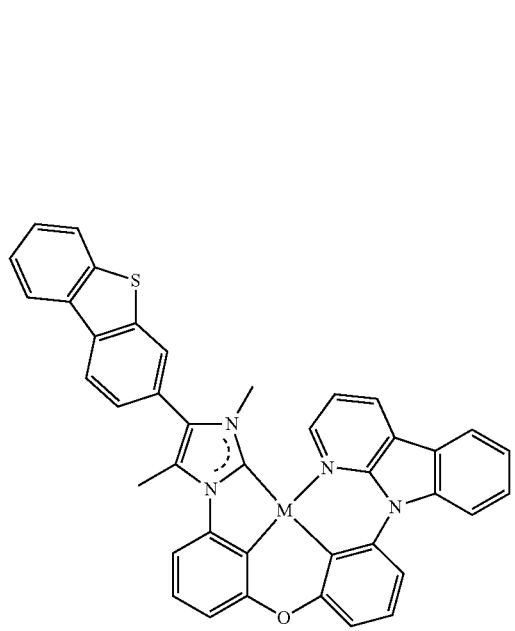
(M = Pt, Pd)
Structures 55
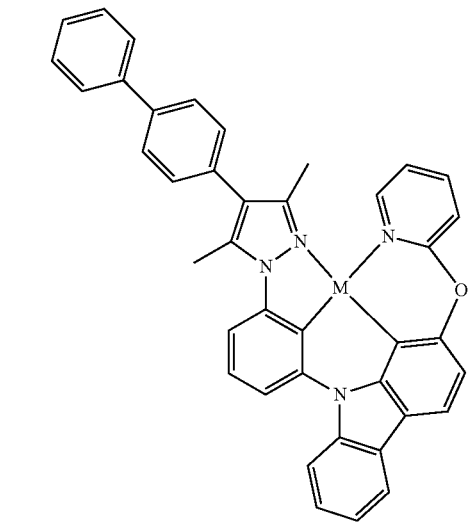

393
-continued
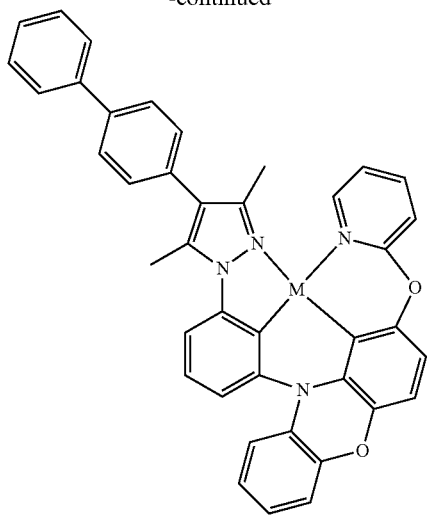
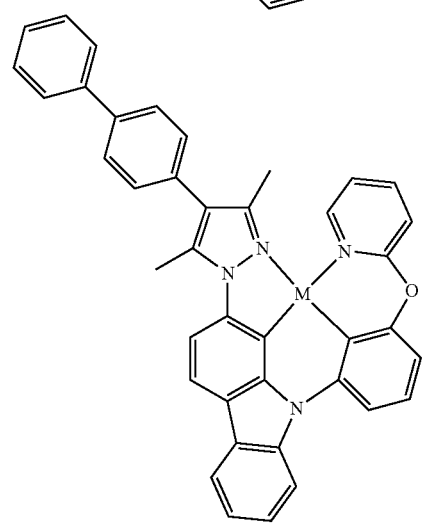
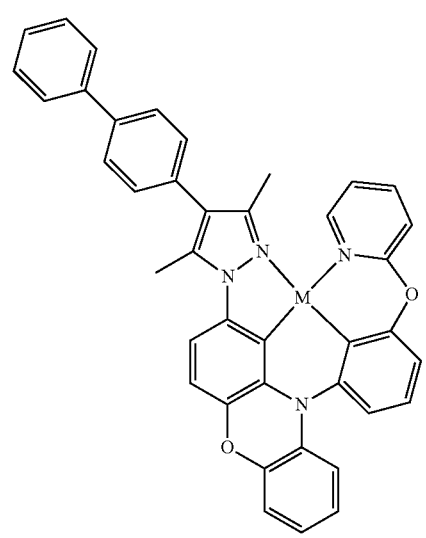
394
-continued
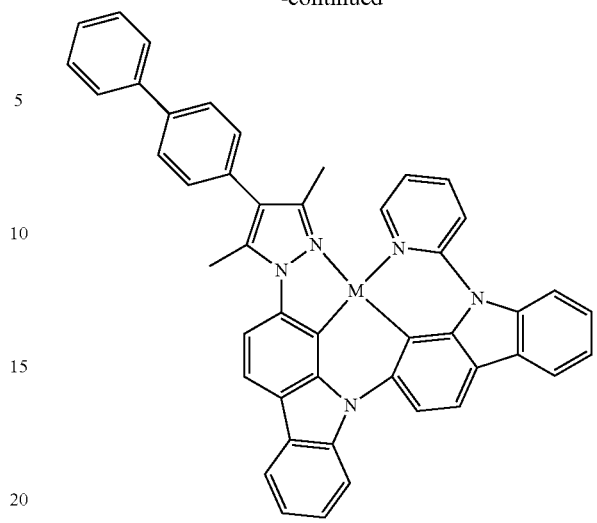
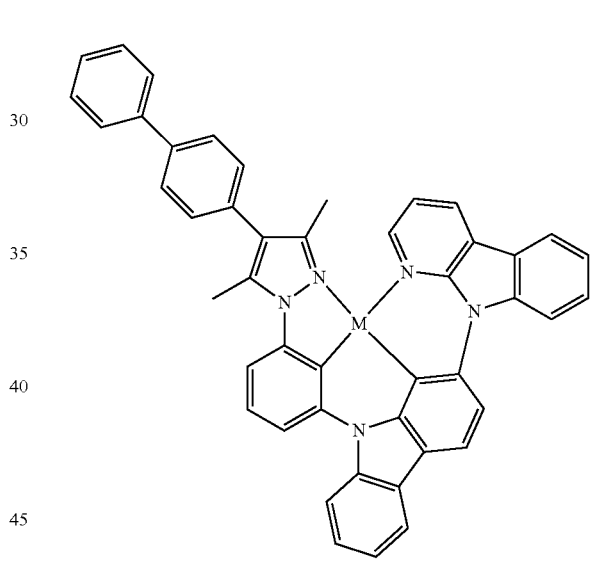
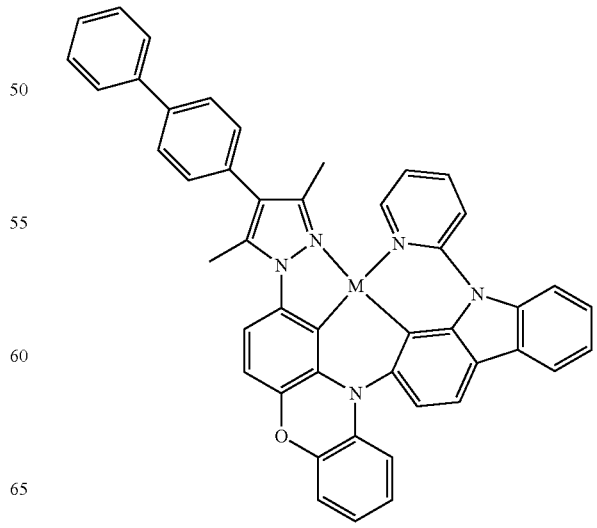

395
-continued
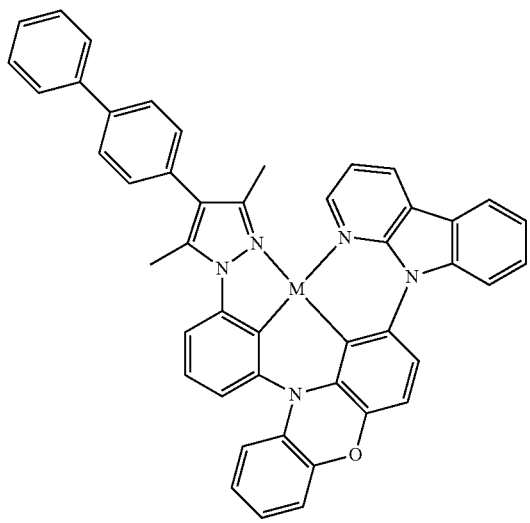
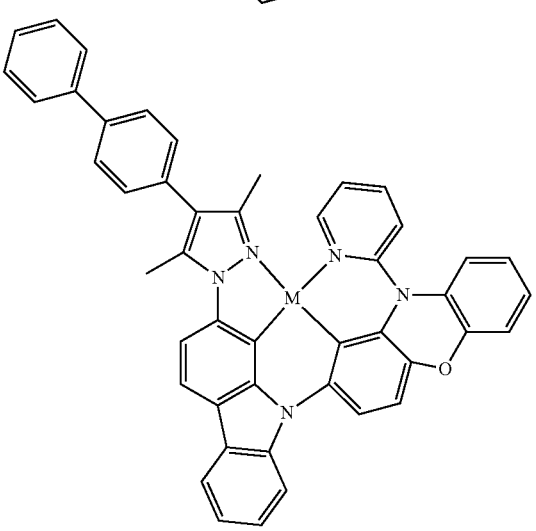
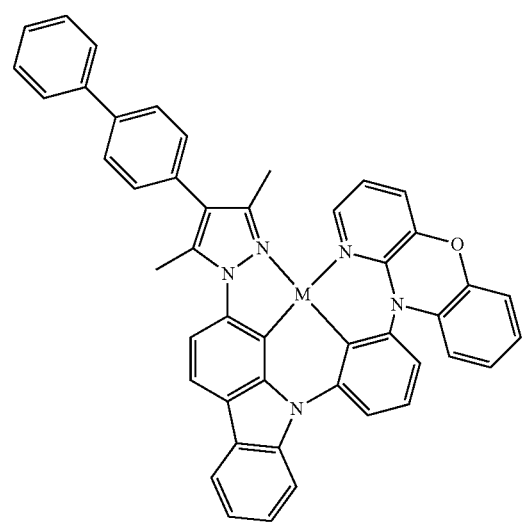
396
-continued
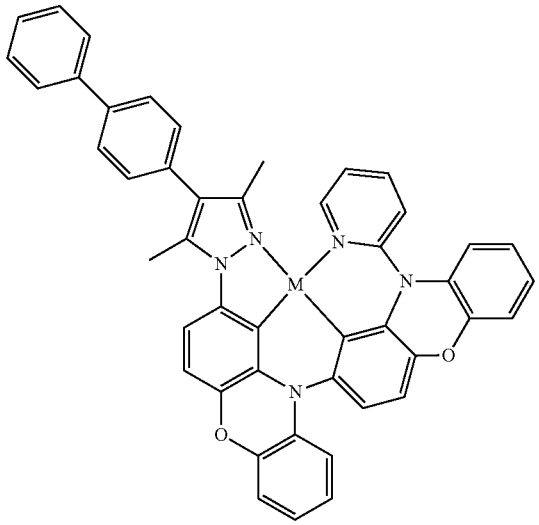
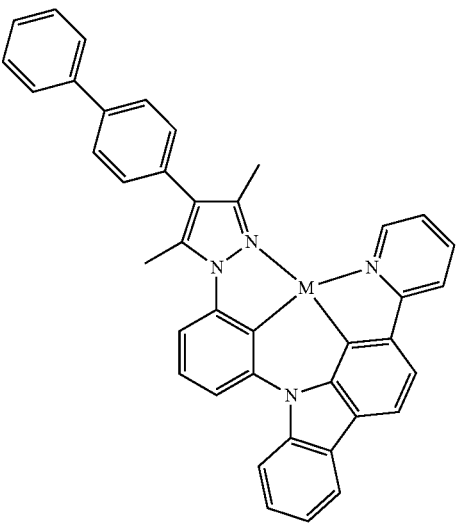

397
-continued
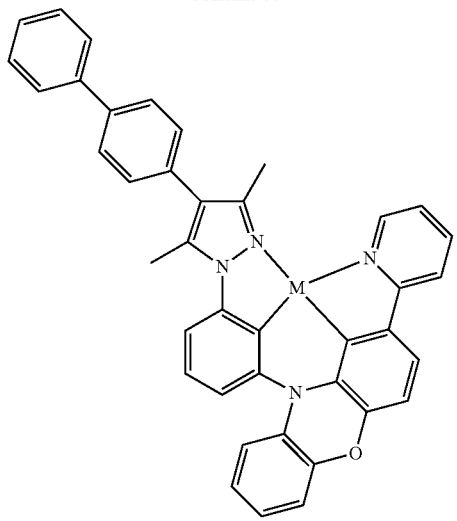
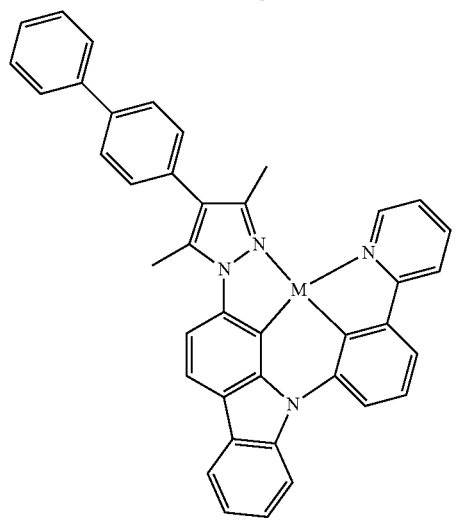
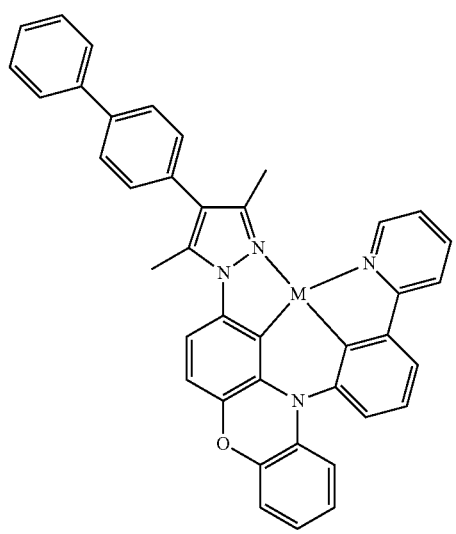
398
-continued
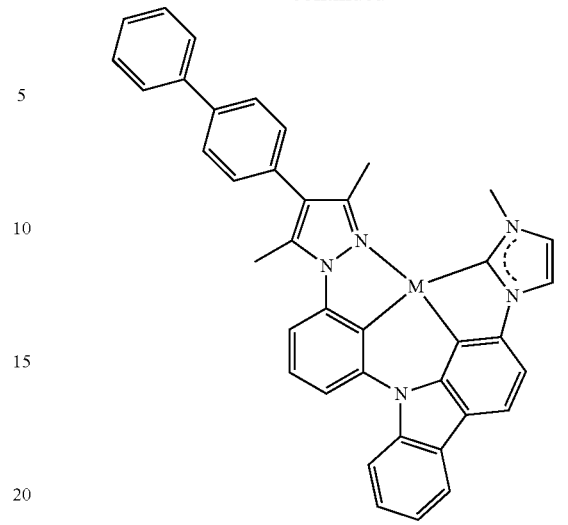
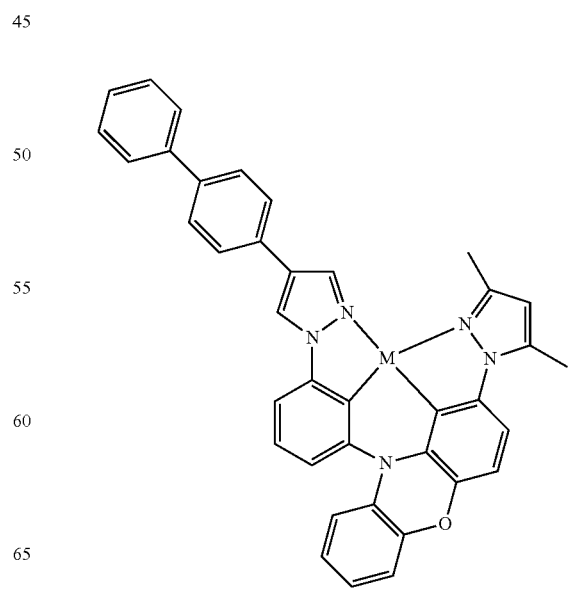

399
-continued
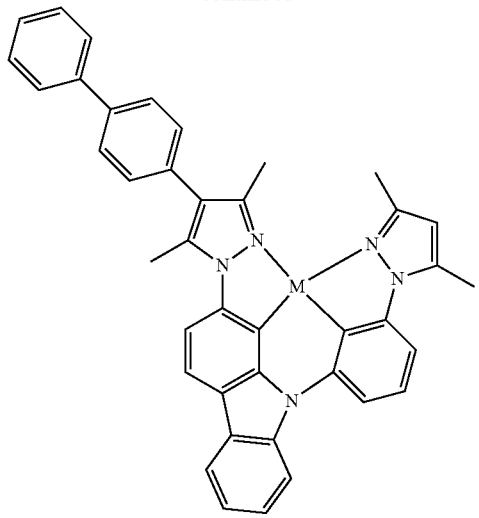
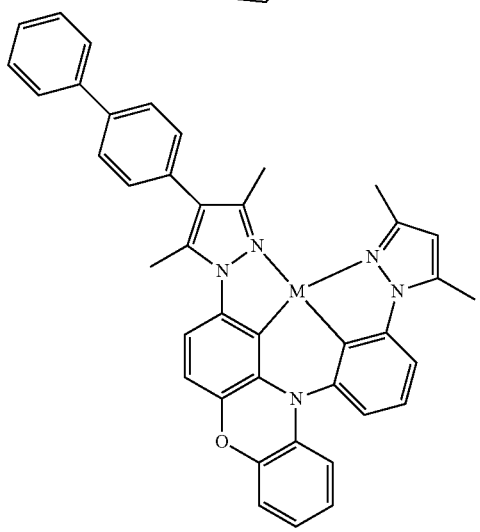
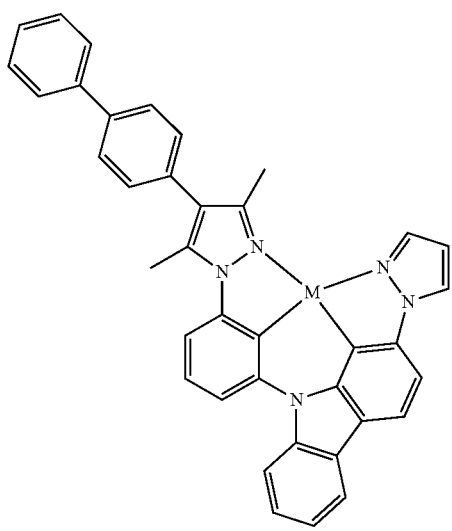
(M = Pt, Pd)
400
-continued
Structures 56
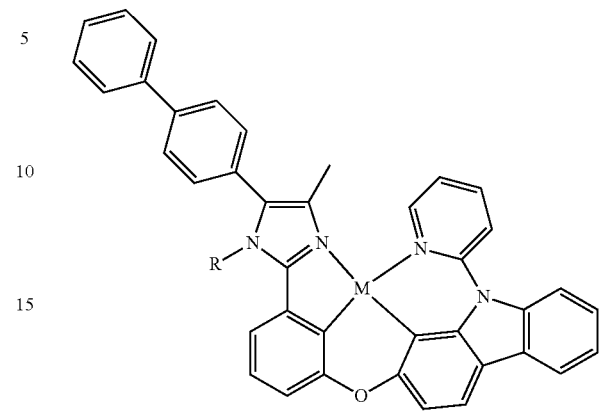
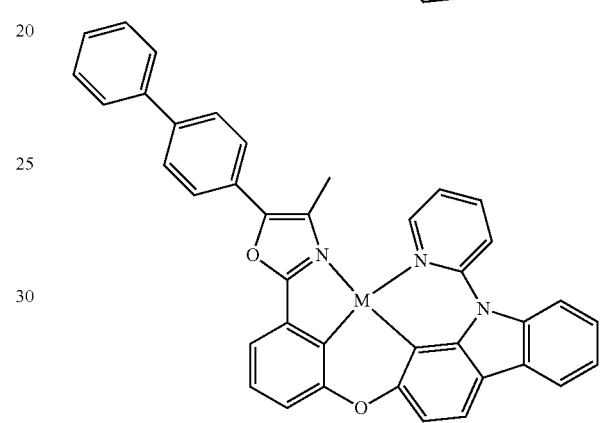
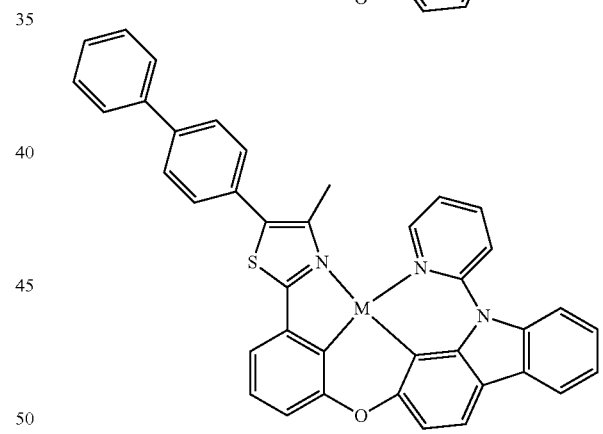
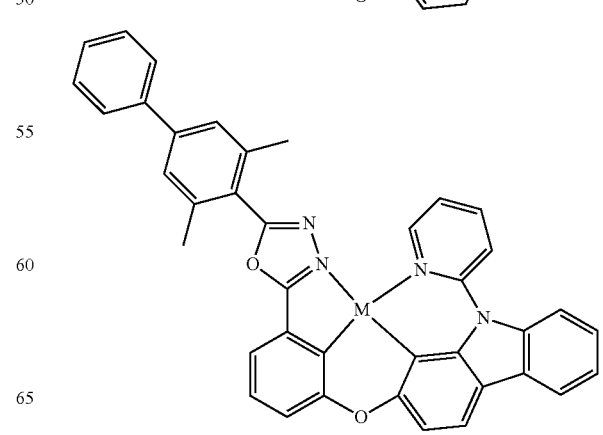

401
-continued
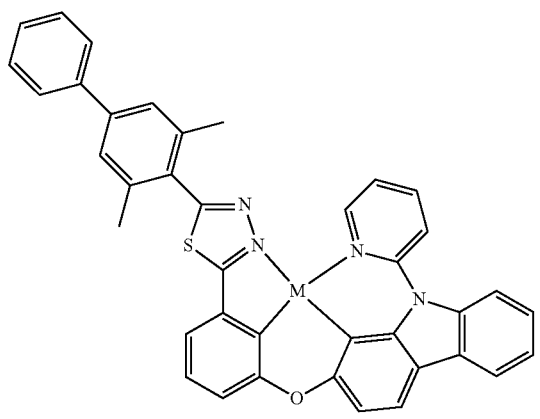
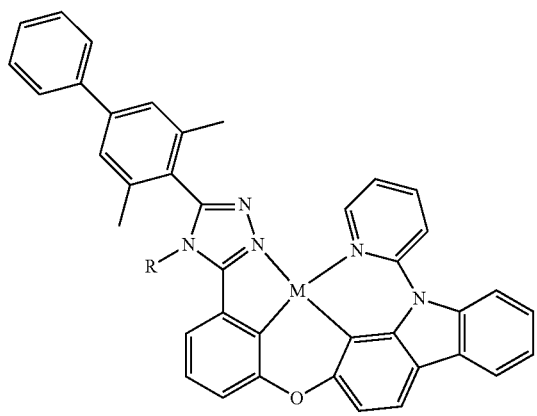
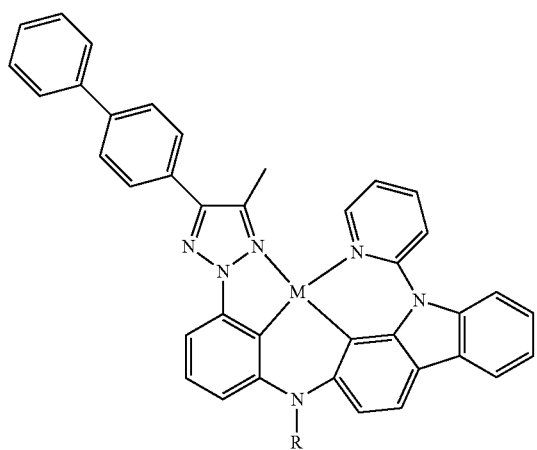
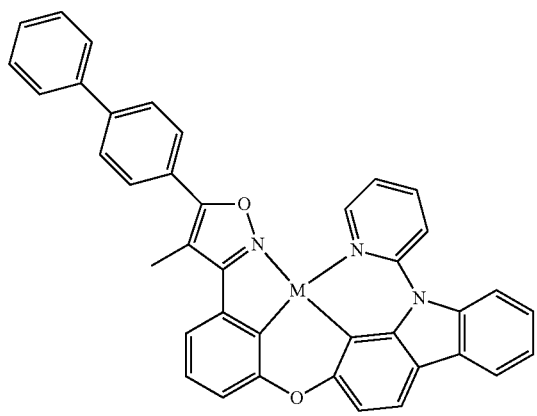
402
-continued
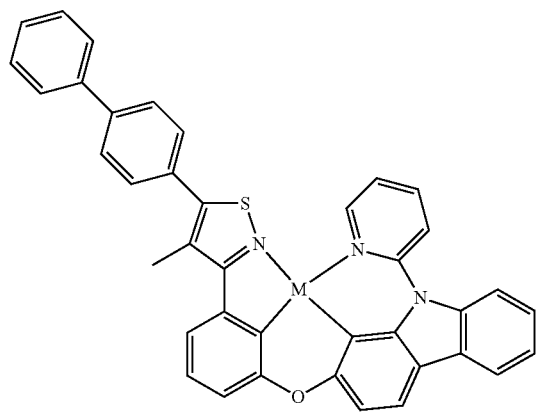
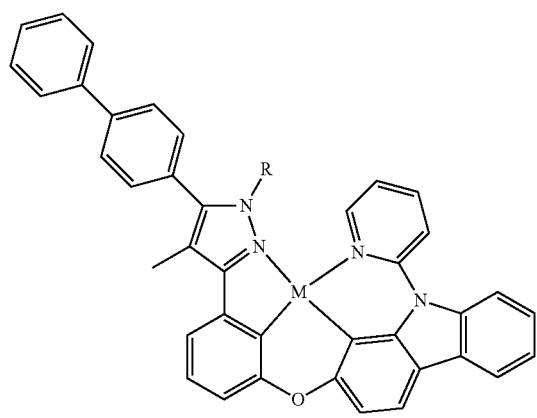
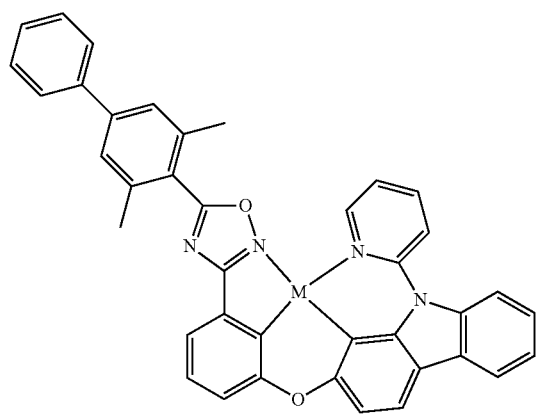
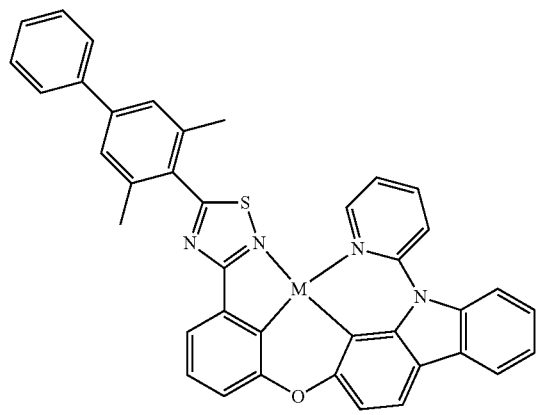

403
-continued
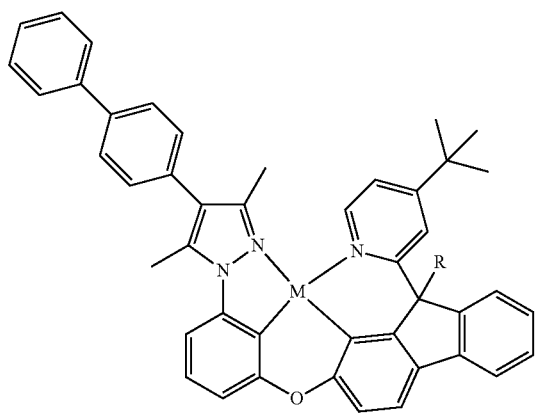
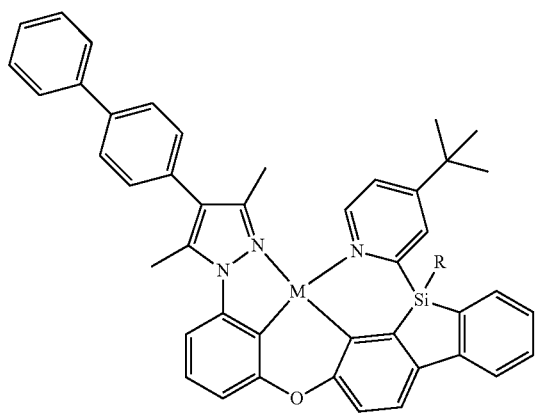
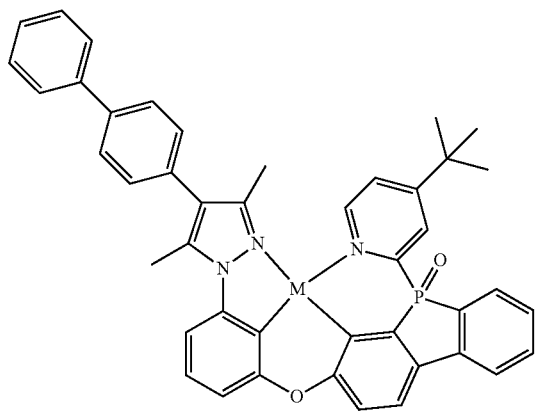
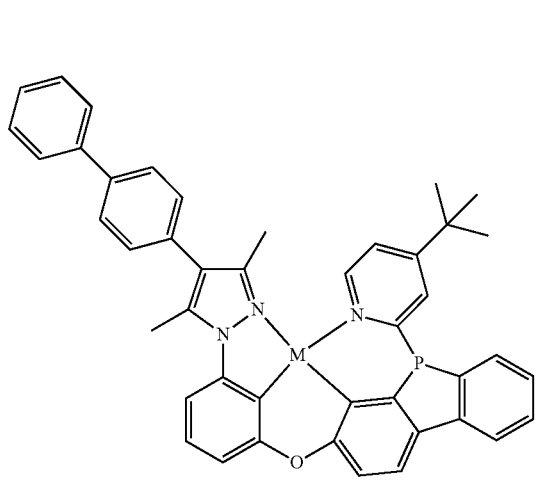
404
-continued
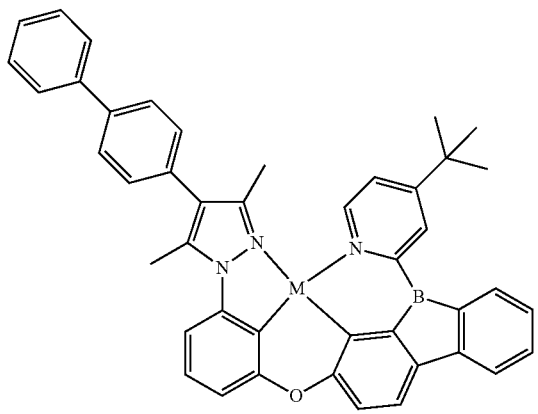
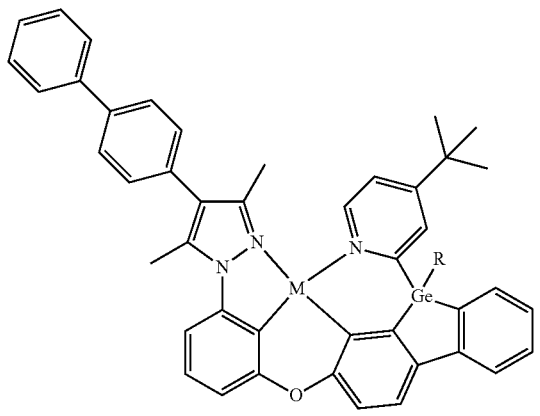
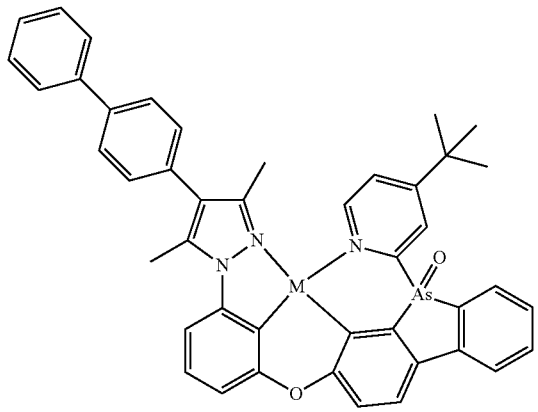
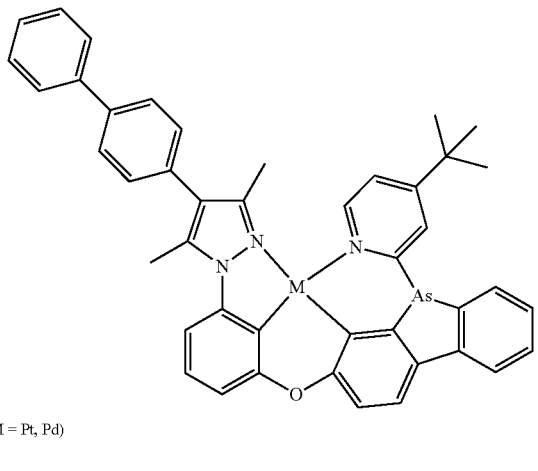
(M = Pt, Pd)

Structures 57
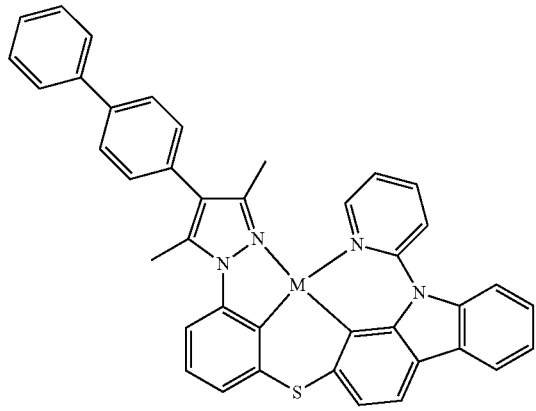
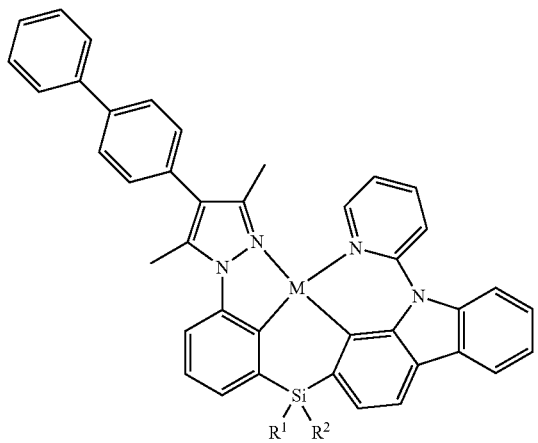
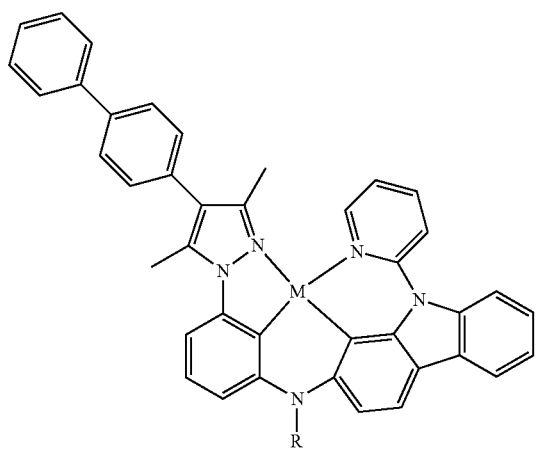
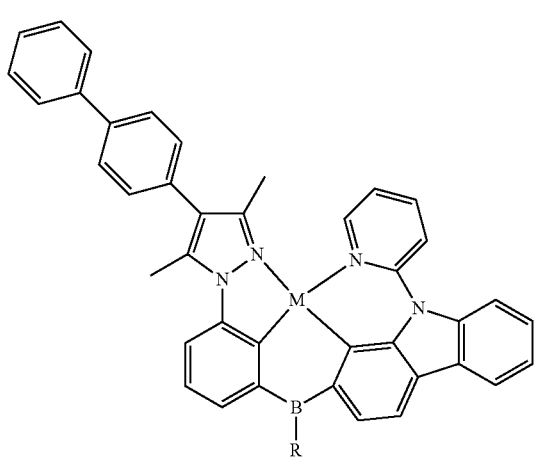
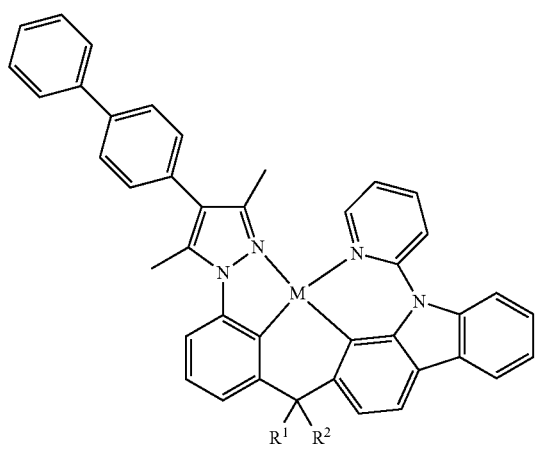
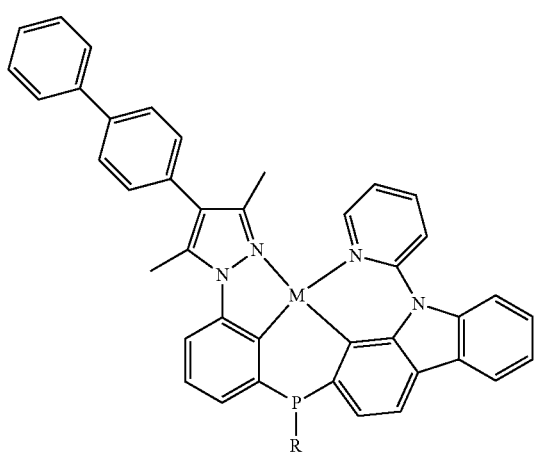

407
-continued
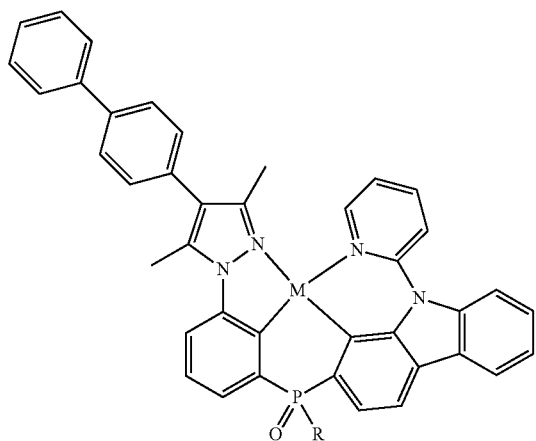
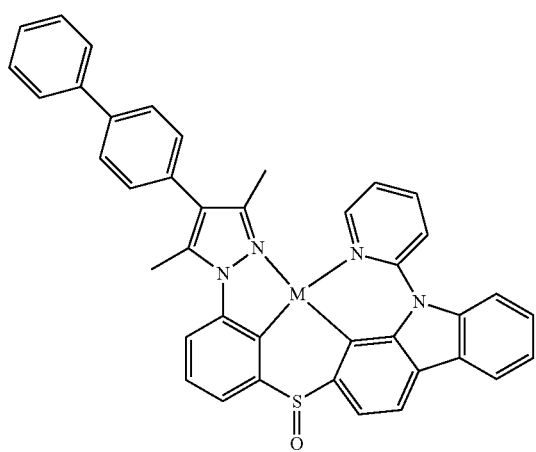
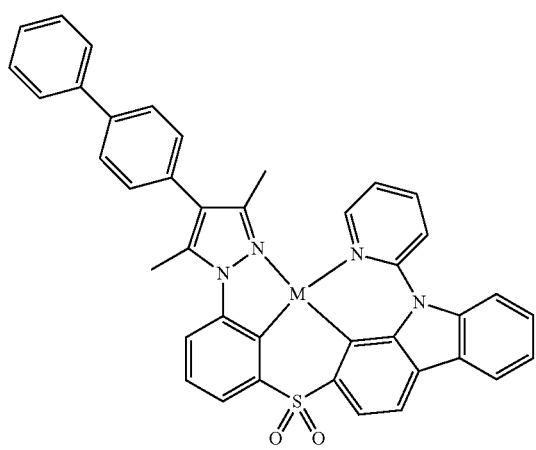
408
-continued
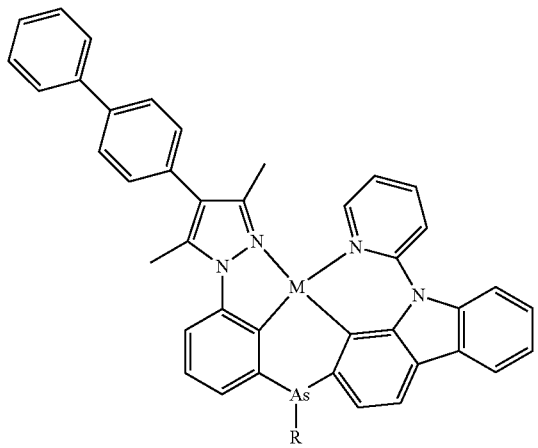
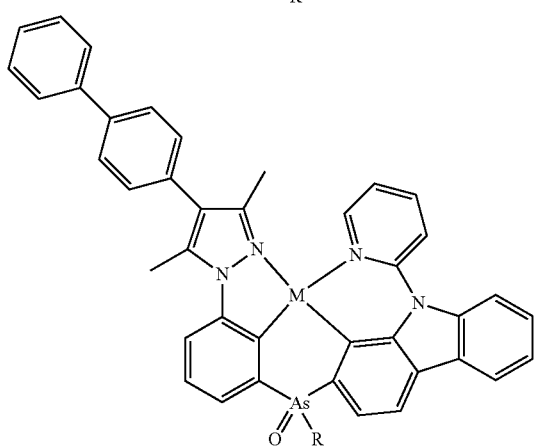
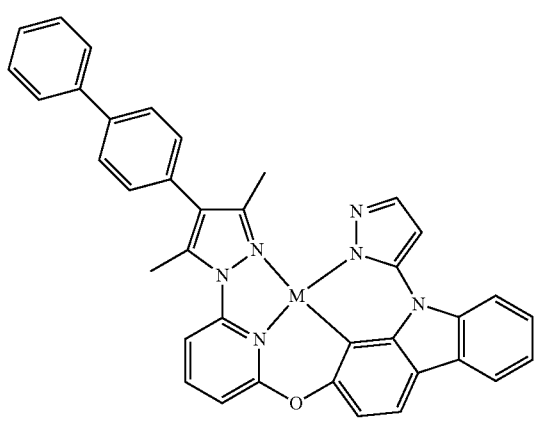
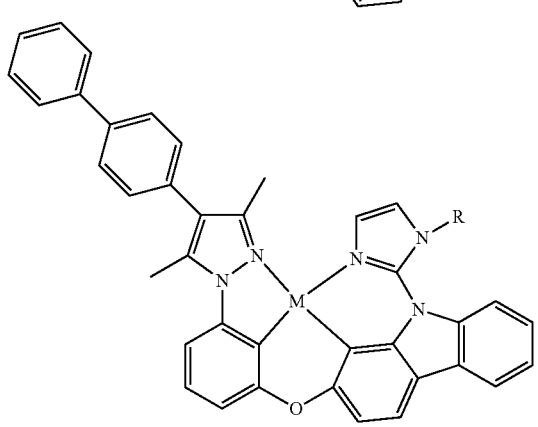

409
-continued
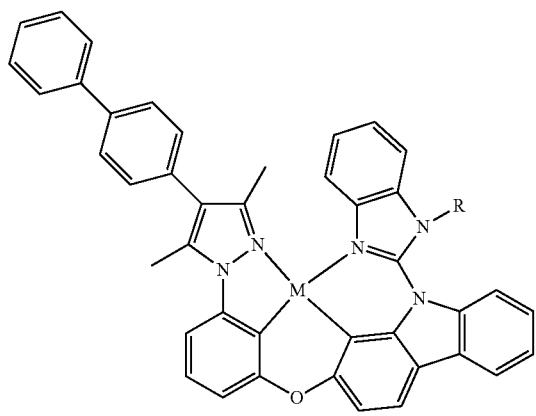
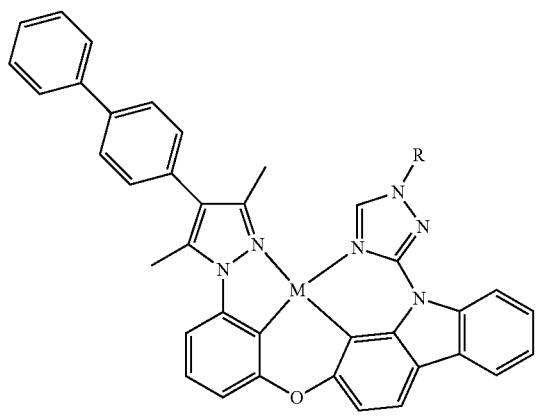
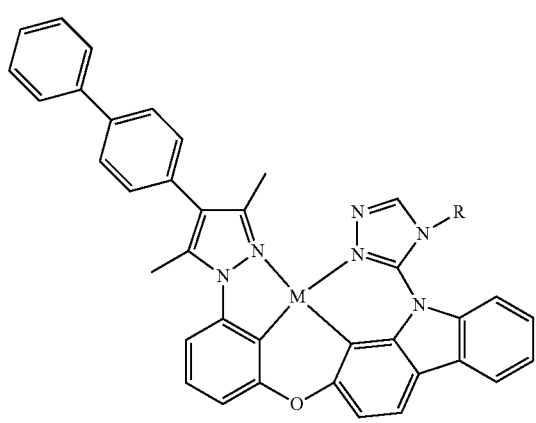
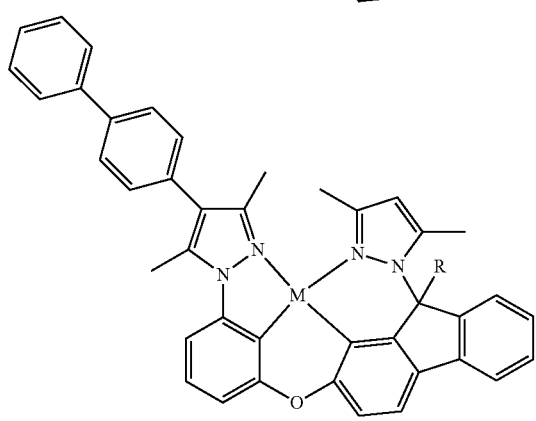
410
-continued
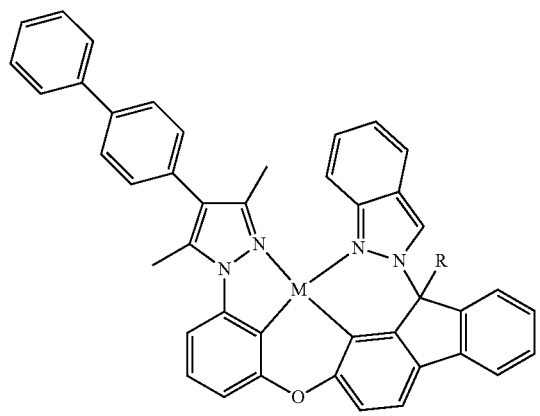
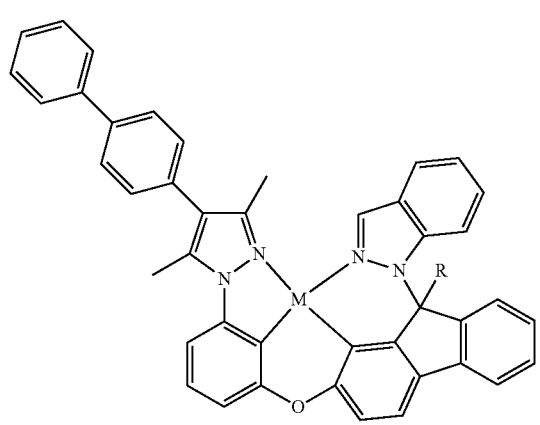
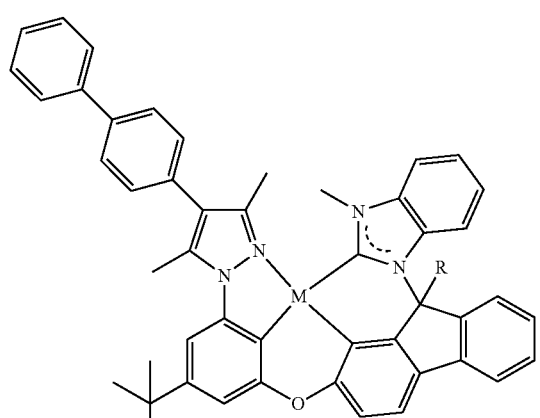
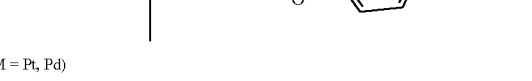
(M = Pt, Pd)

411
-continued
Structures 58
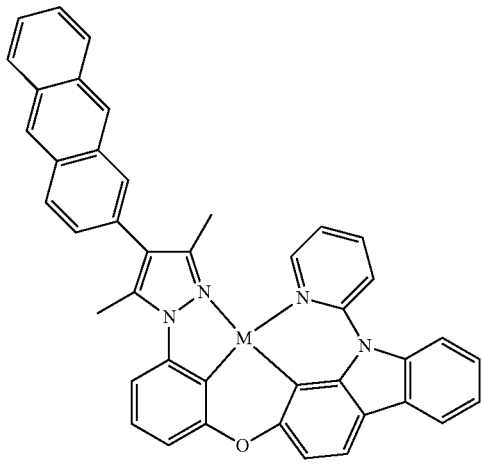
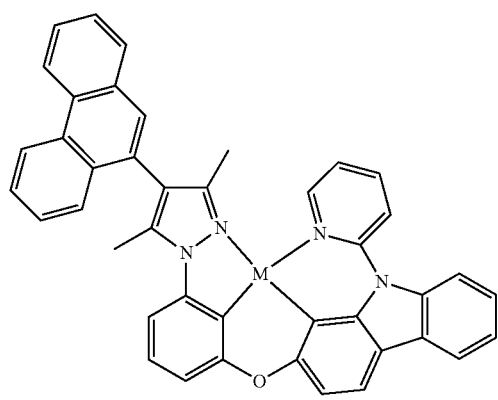
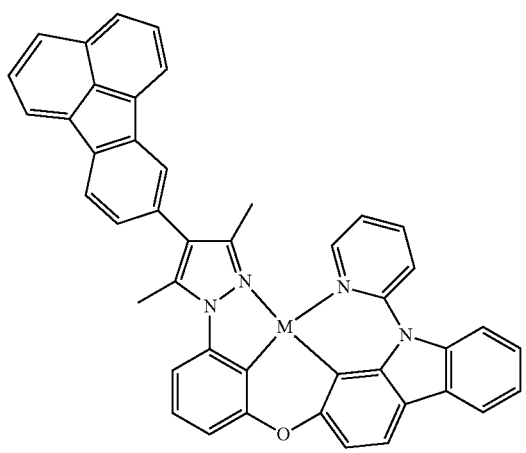
412
-continued
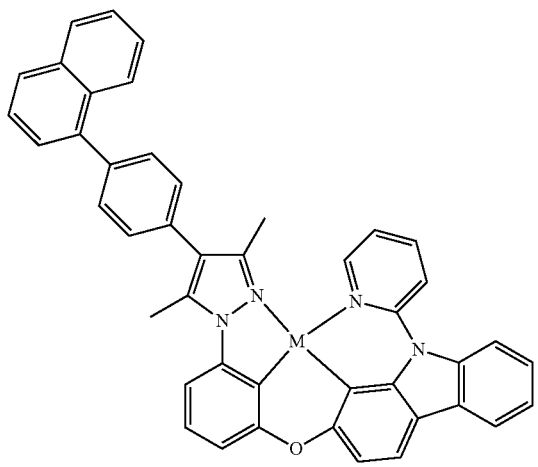
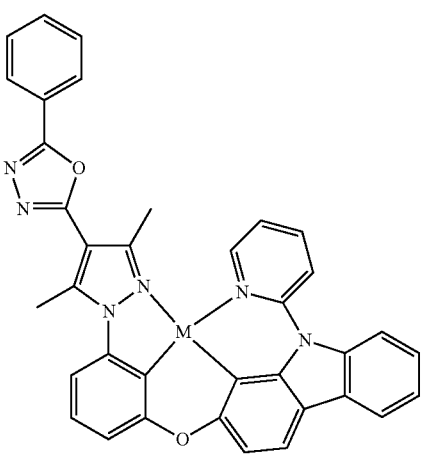
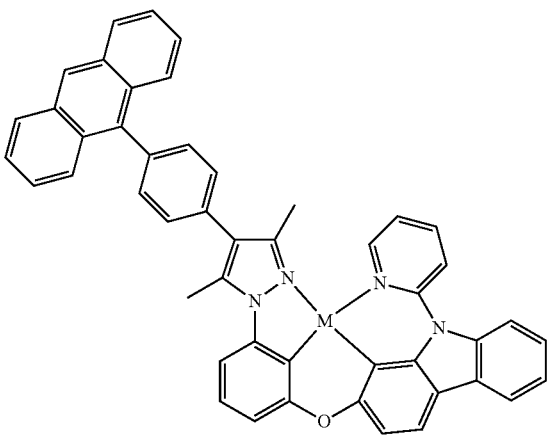

413
-continued
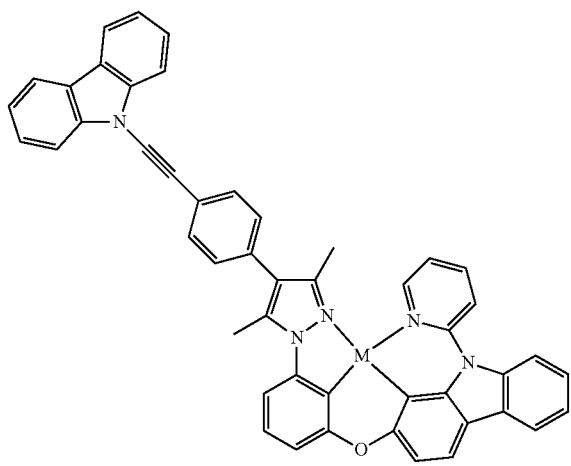
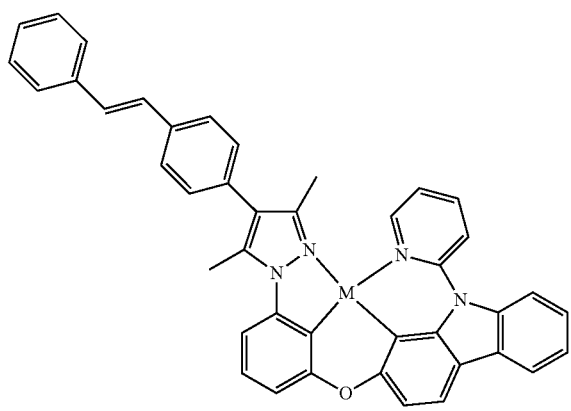
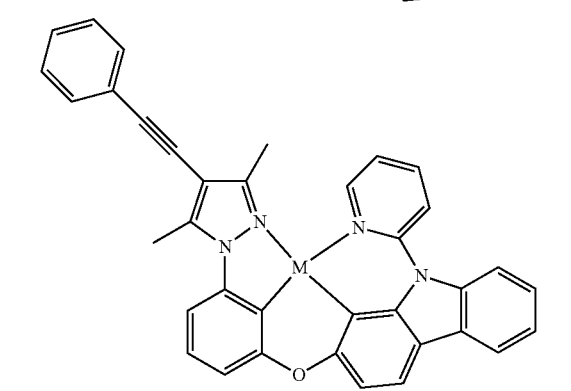
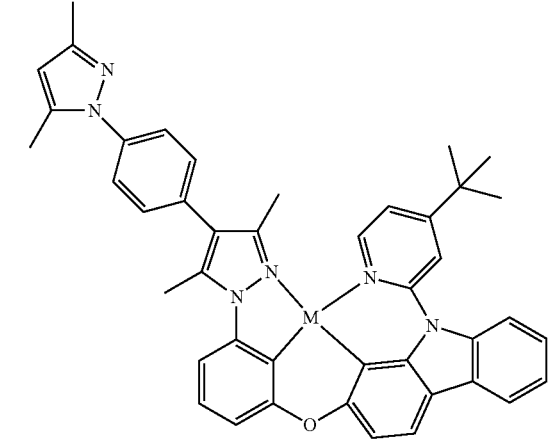
414
-continued
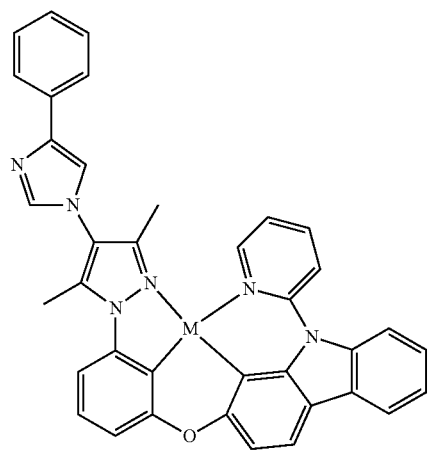
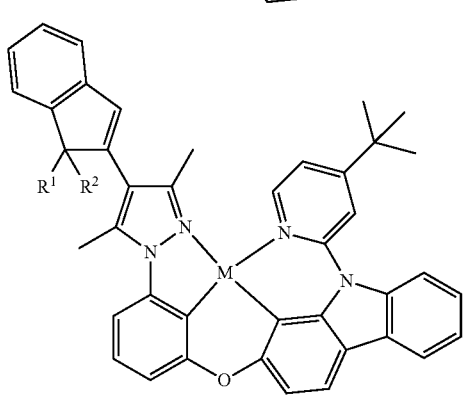
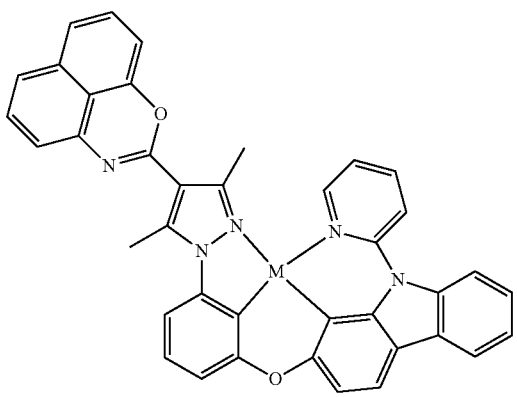
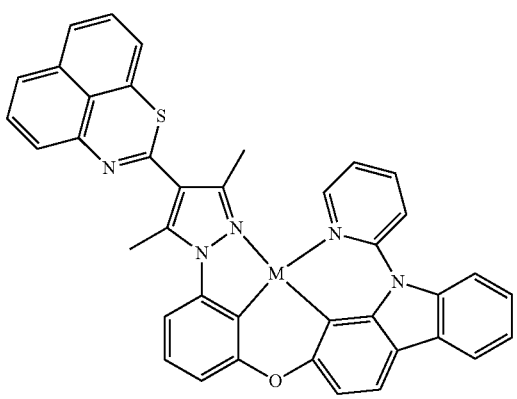

415
-continued
416
-continued
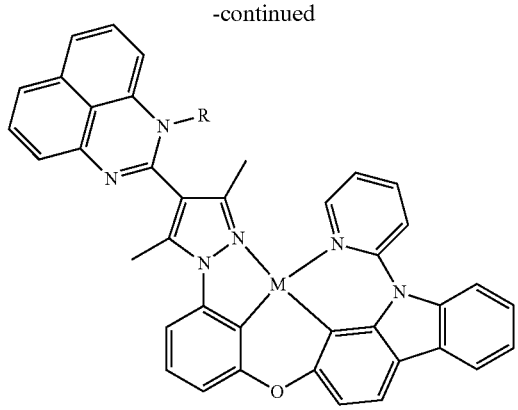
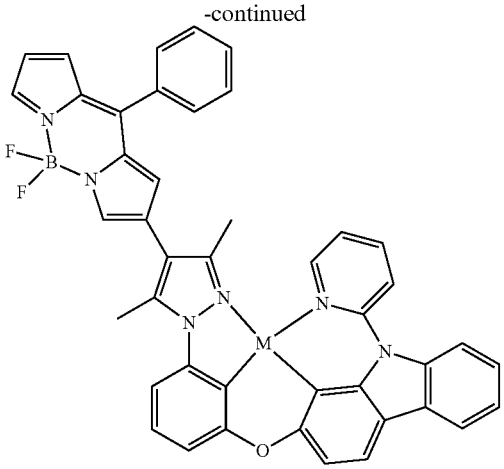
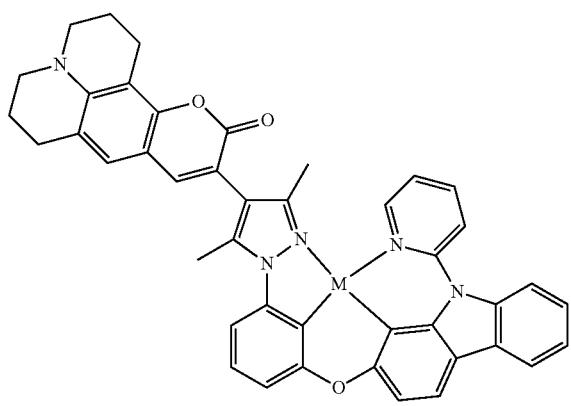
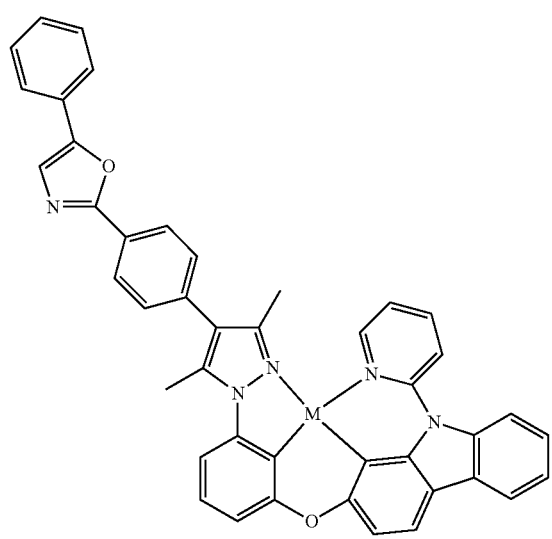
(M = Pt, Pd)

-continued
Structures 59
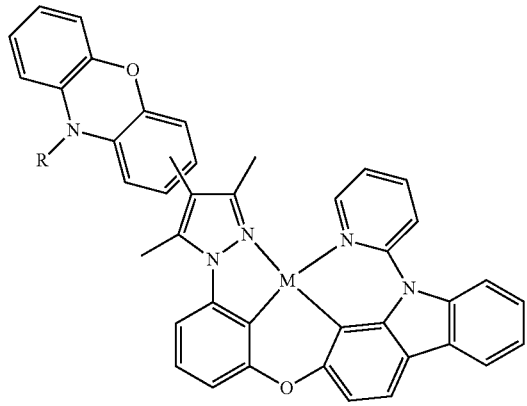
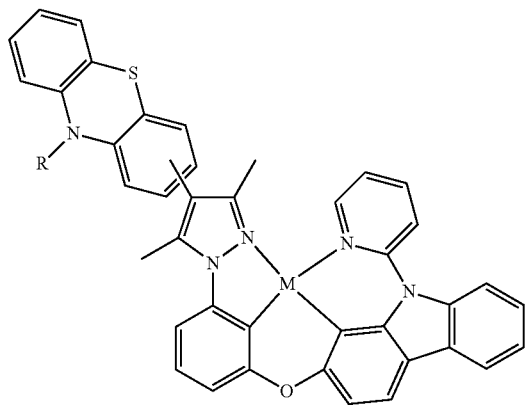
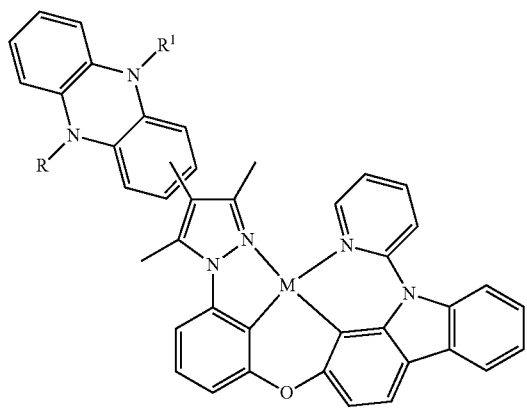
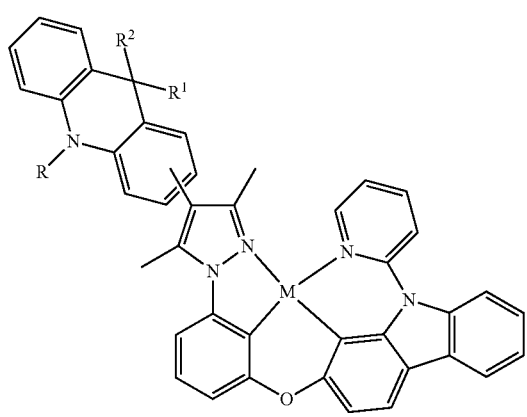
-continued
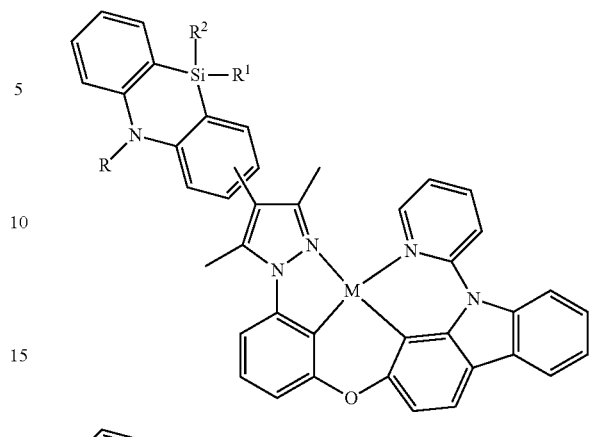
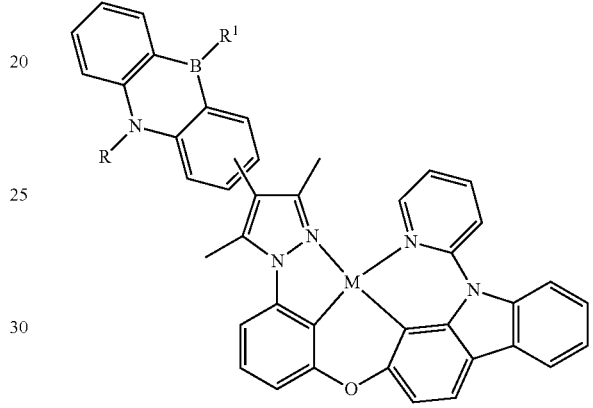
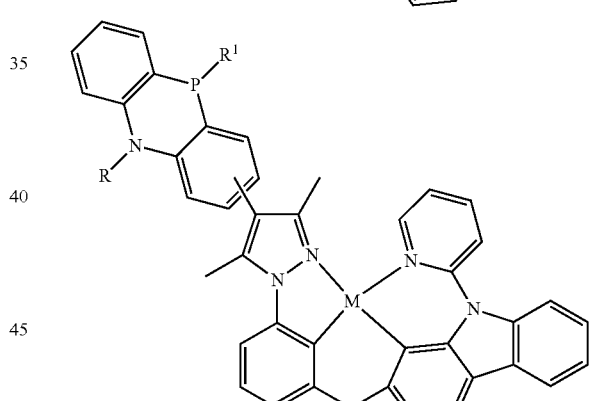
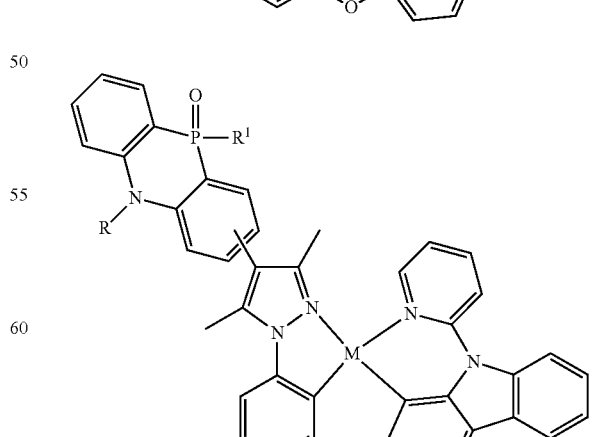

419
-continued
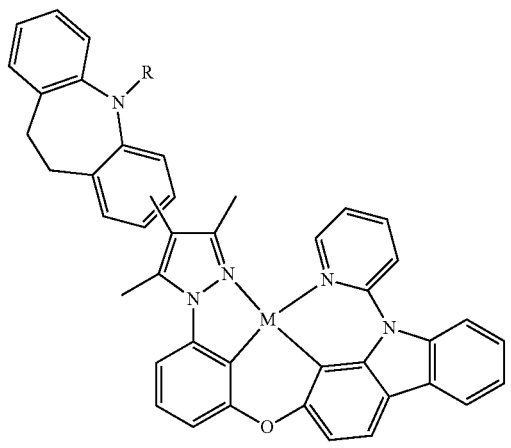
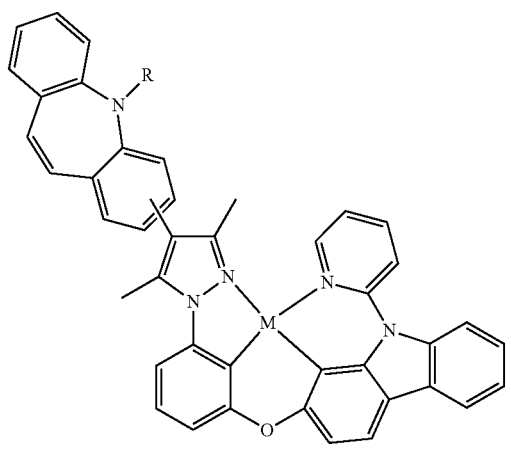
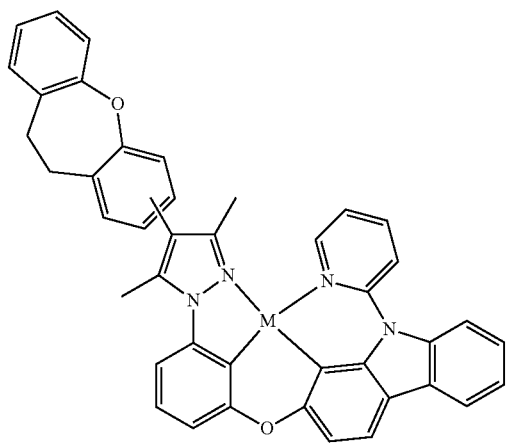
420
-continued
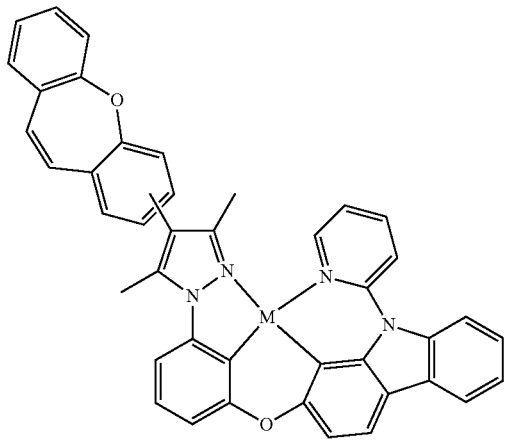
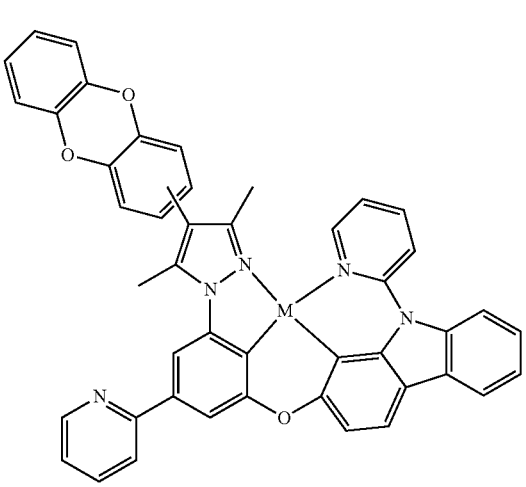

421
-continued
422
-continued
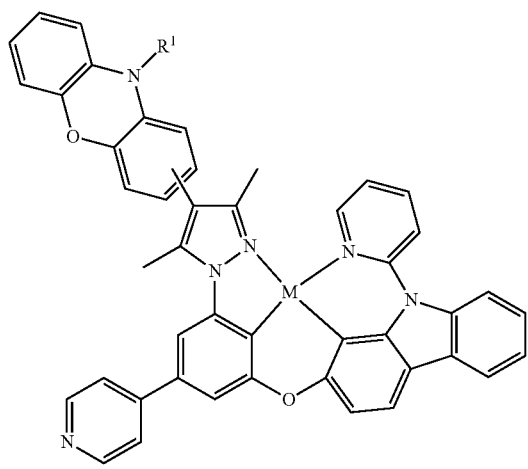
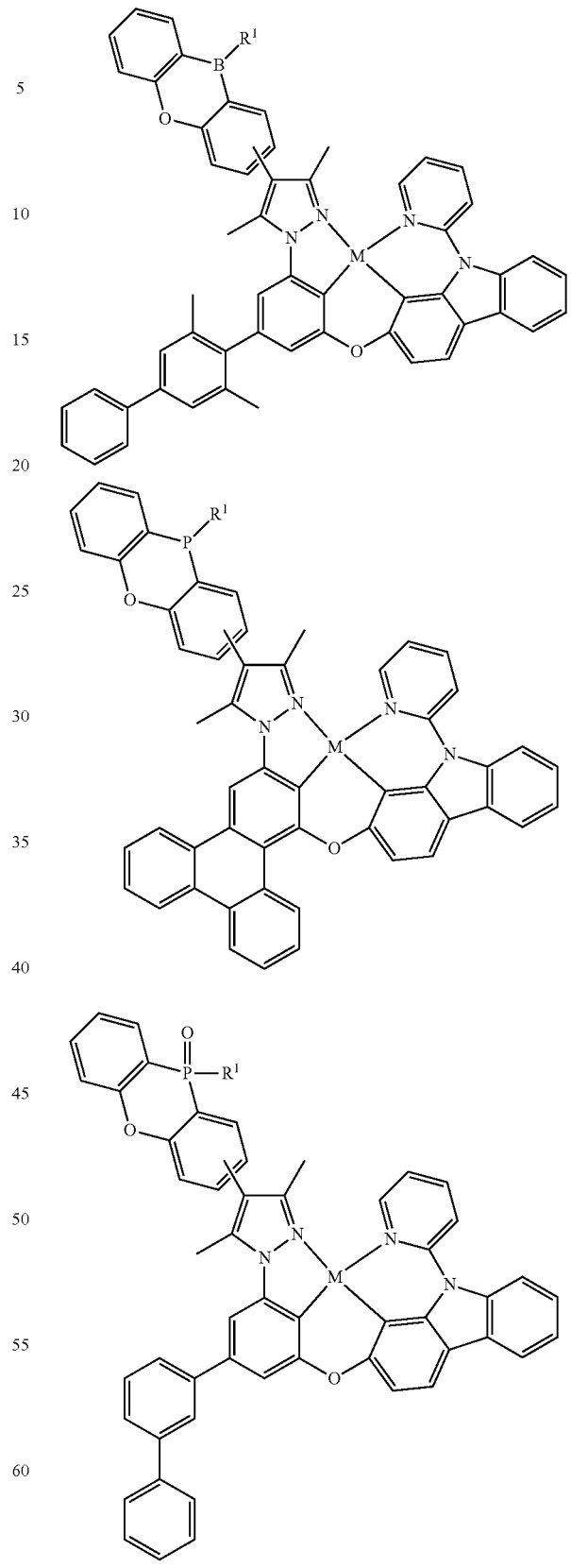
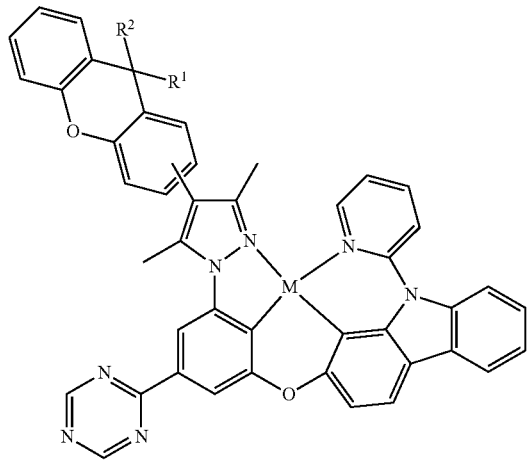
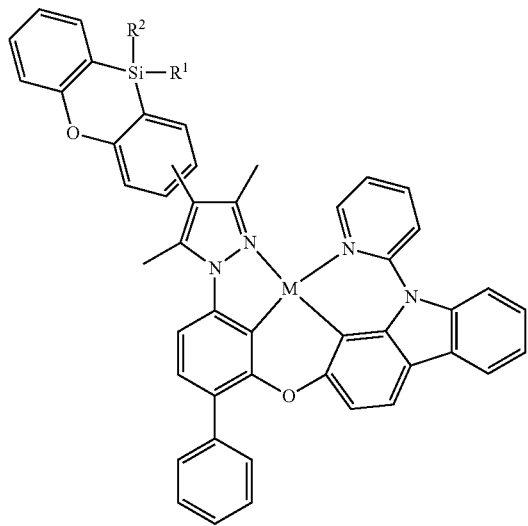
(M = Pt, Pd)

-continued
Structures 60
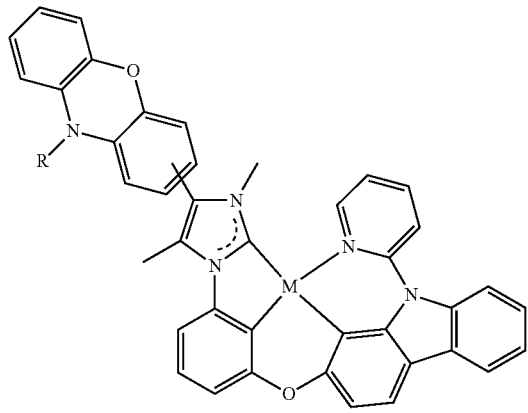
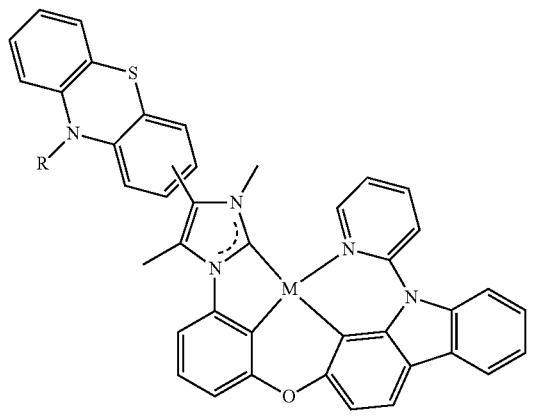
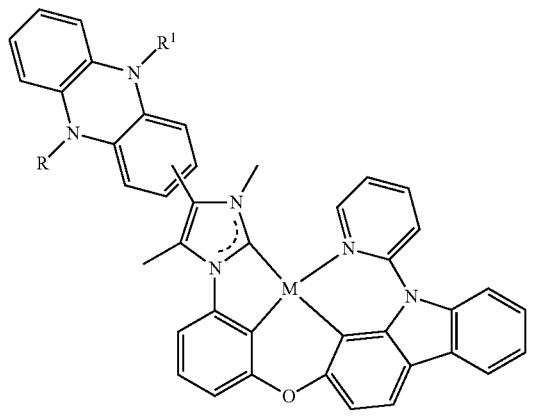
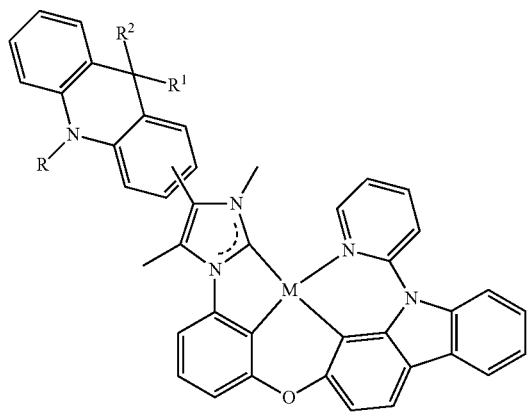
-continued
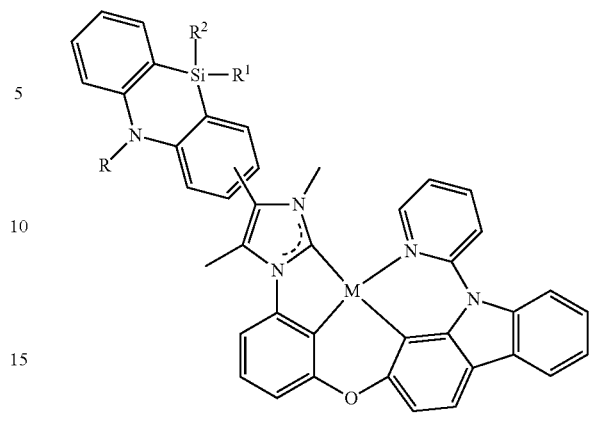
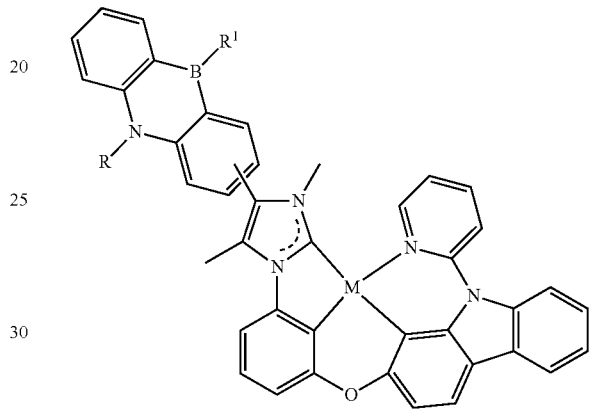
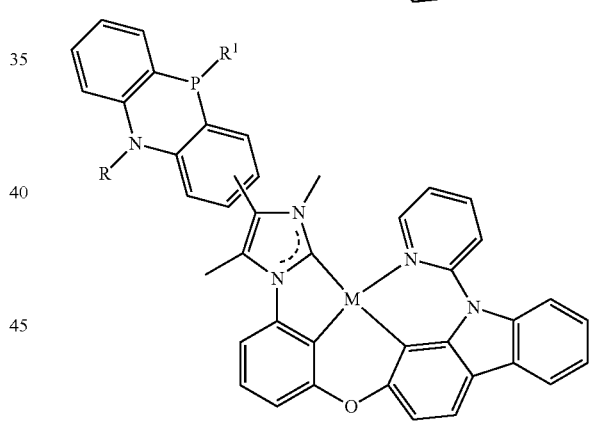
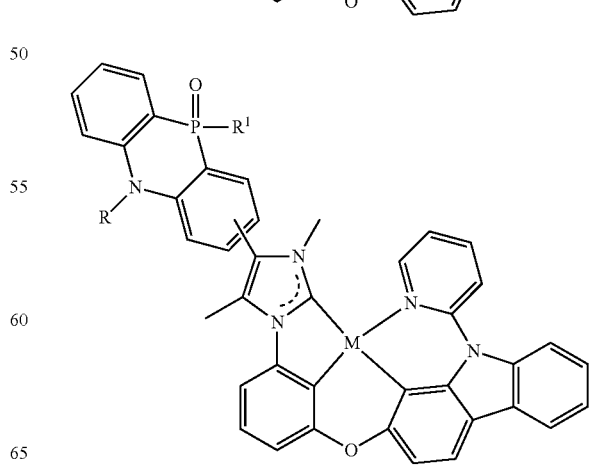

425
-continued
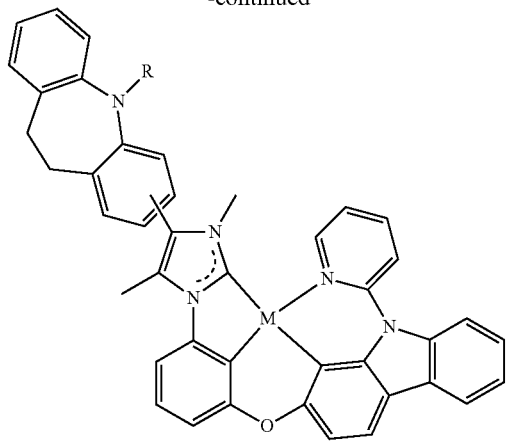
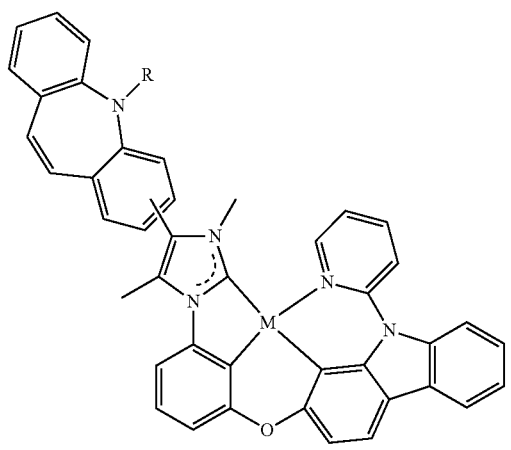
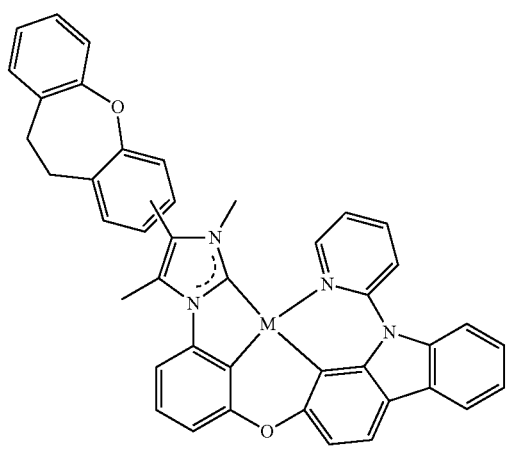
426
-continued
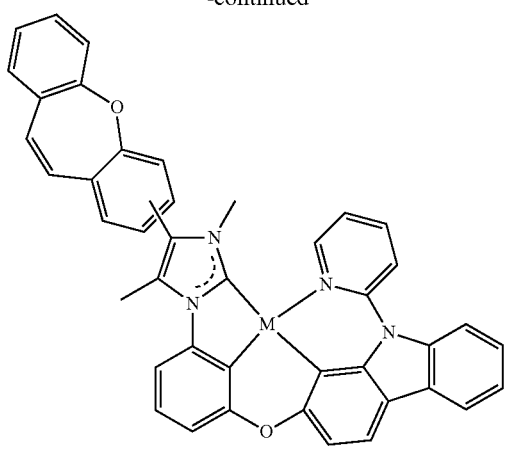
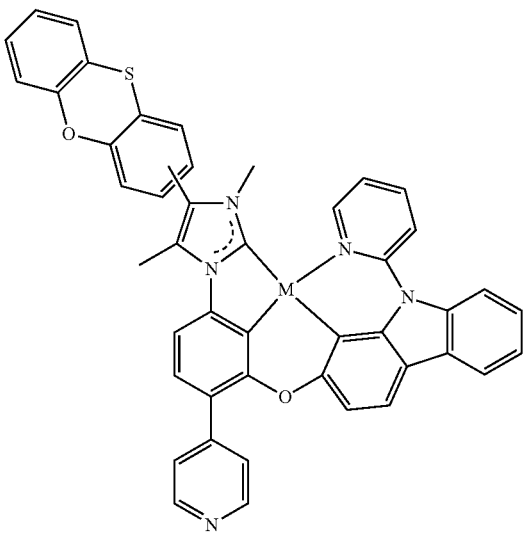

427
-continued
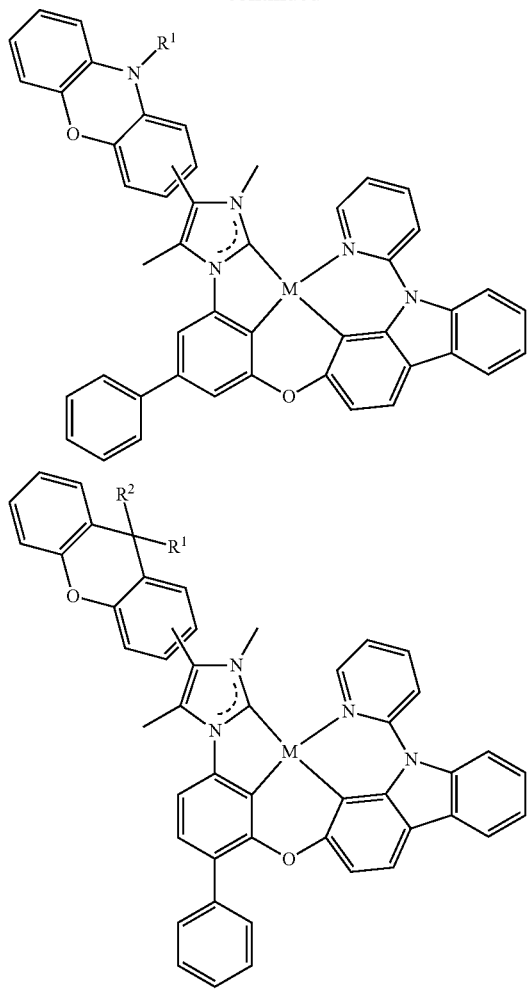
428
-continued
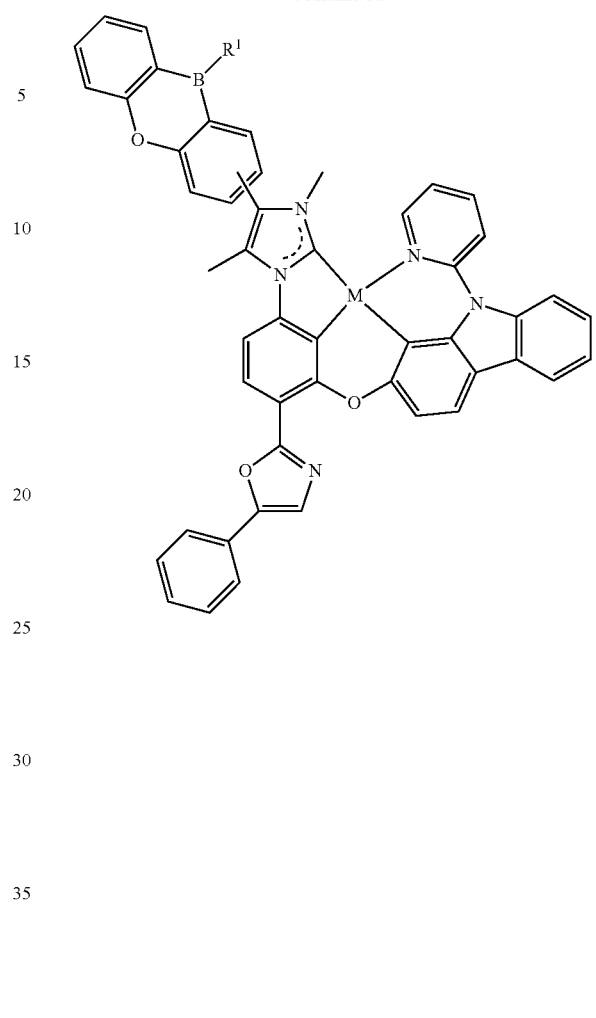
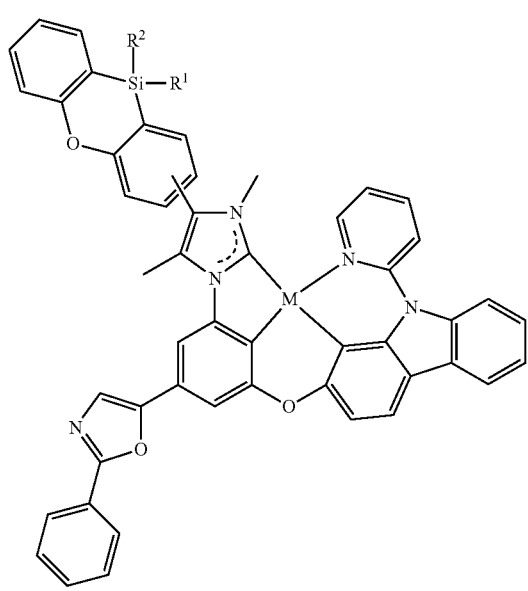
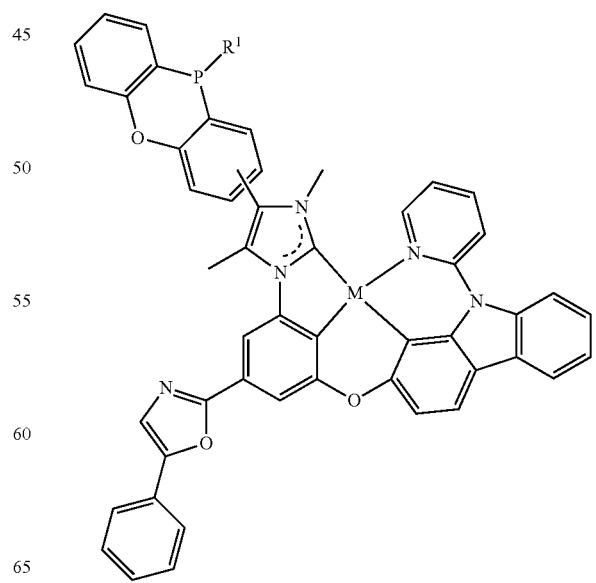

429
-continued
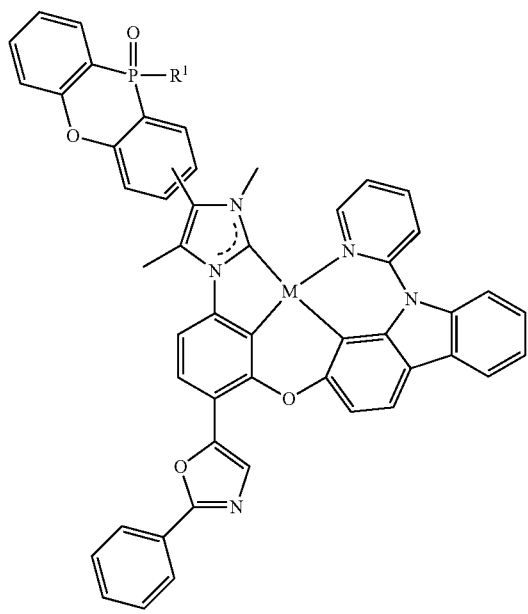
(M = Pt, Pd)
Structures 61
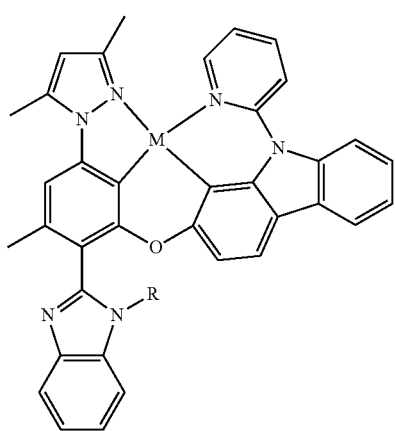
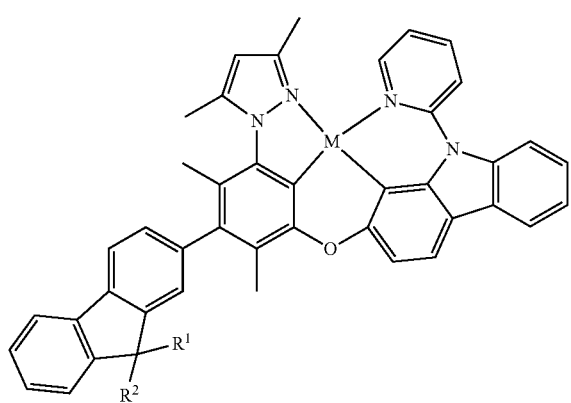
430
-continued
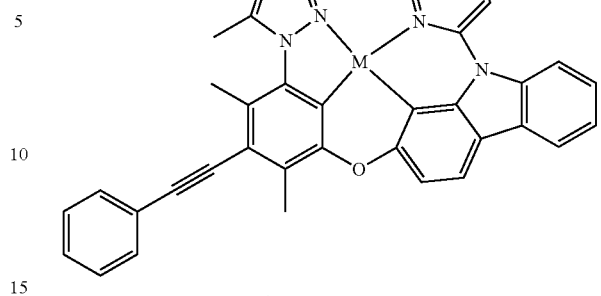
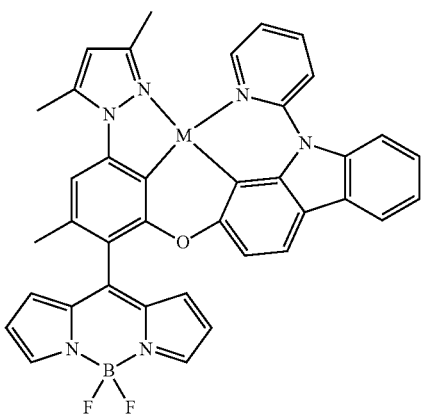
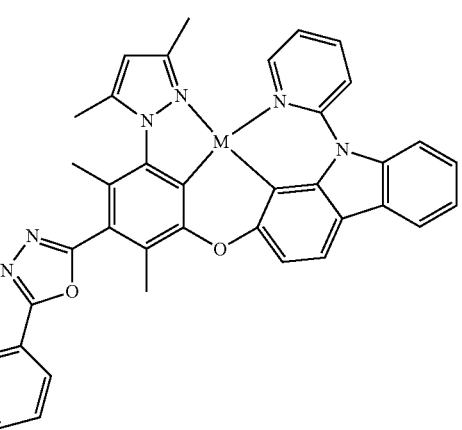
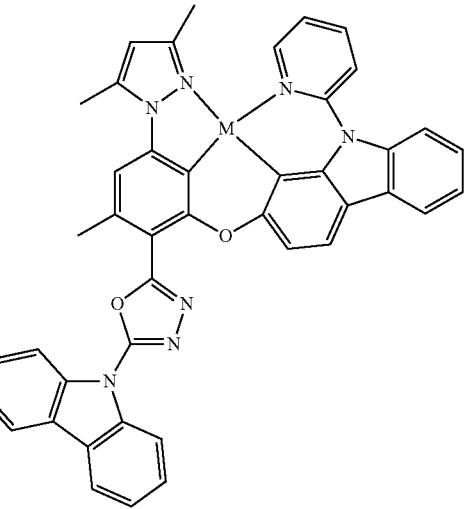

431
-continued
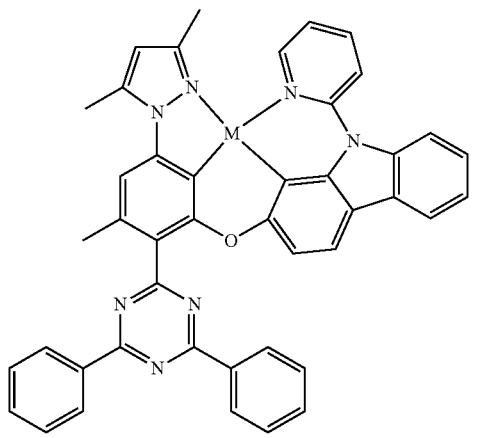
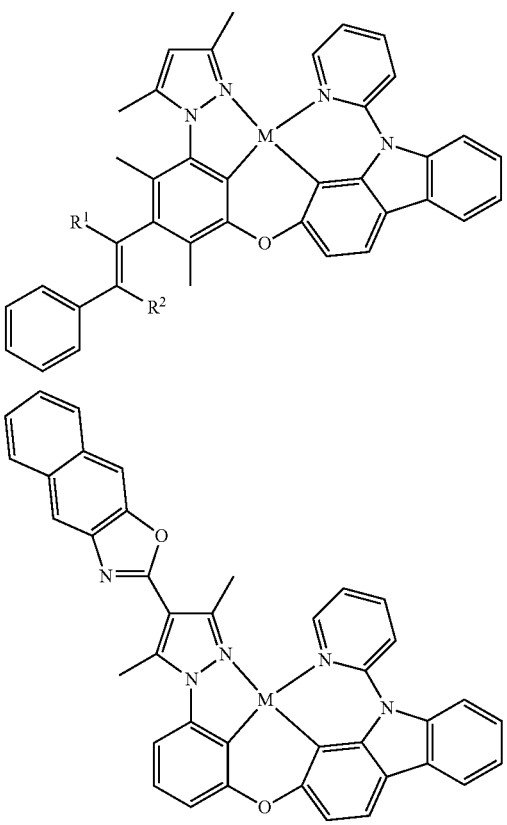
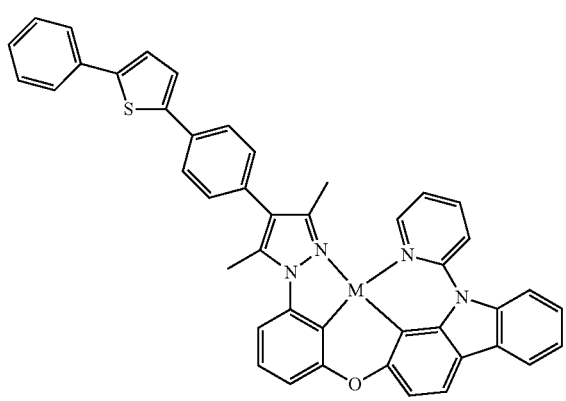
432
-continued
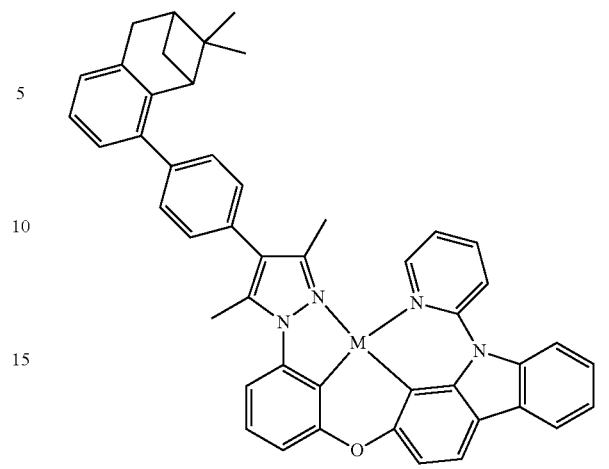
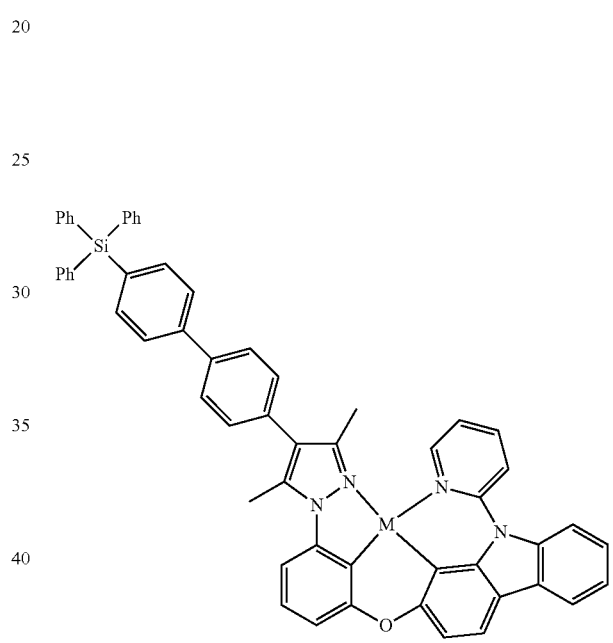
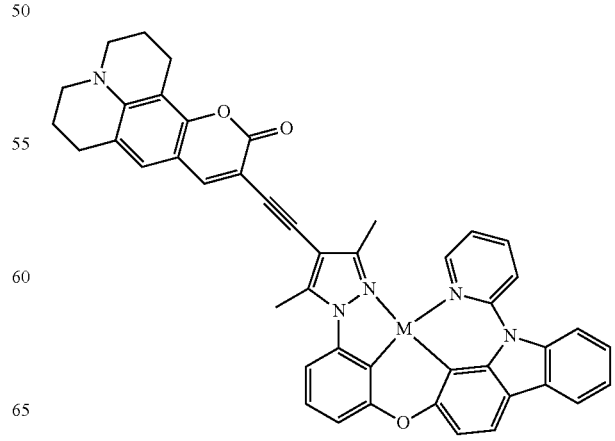

433
-continued
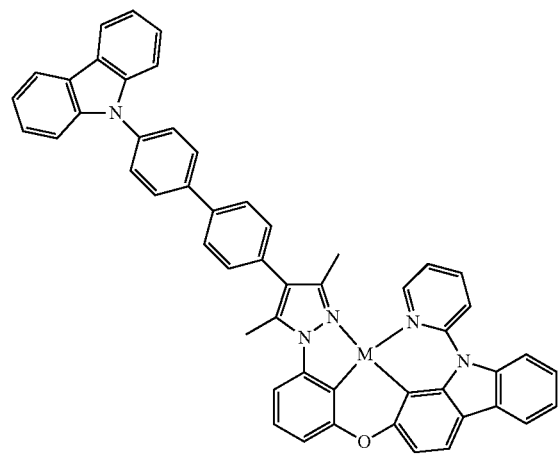
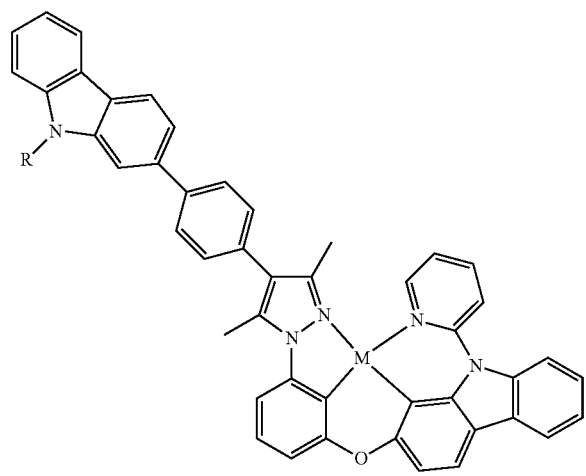
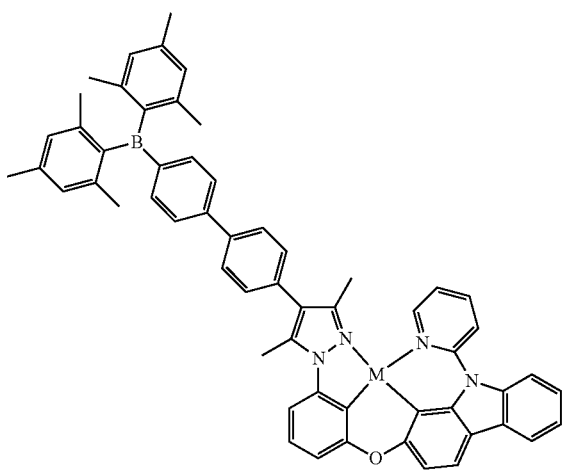
434
-continued
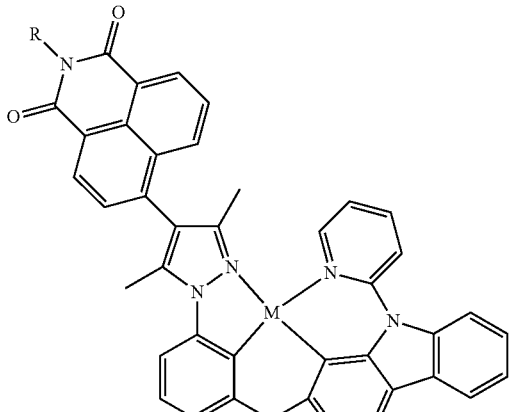
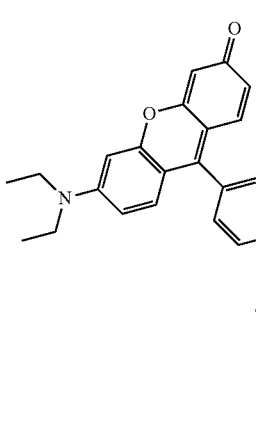

435
-continued
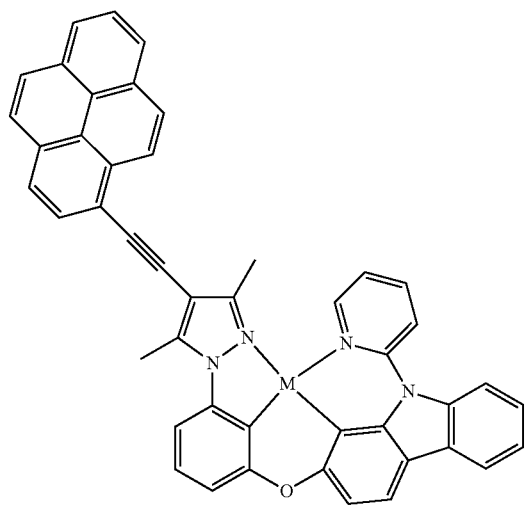
(M = Pt, Pd)
436
-continued
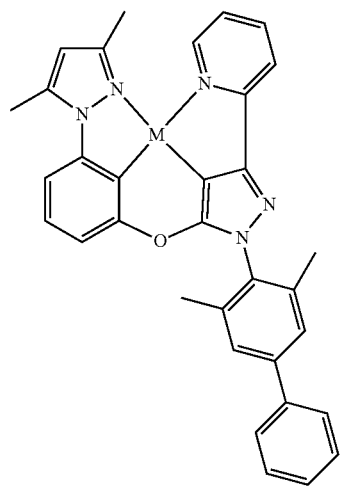
Structures 62
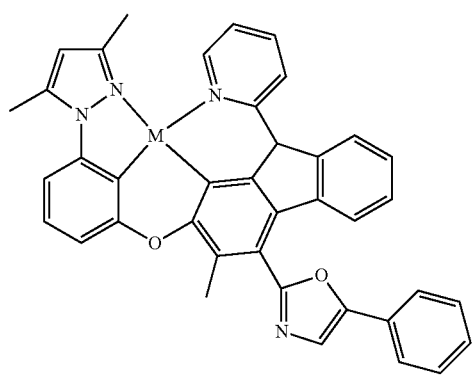
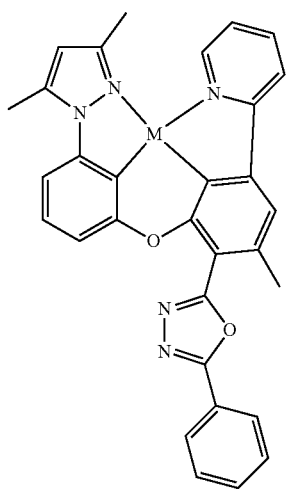
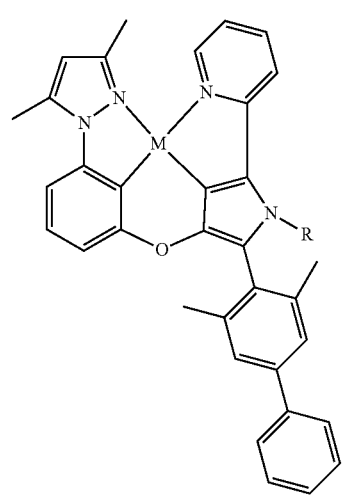
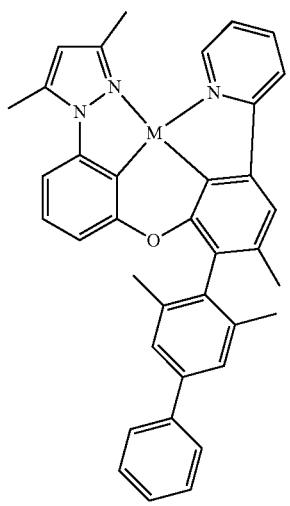

437
-continued
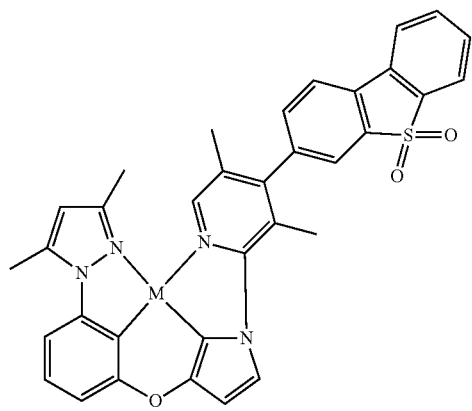
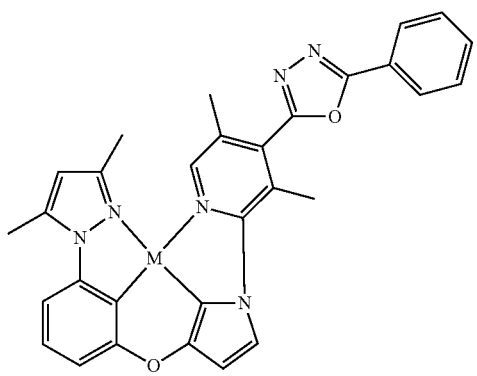
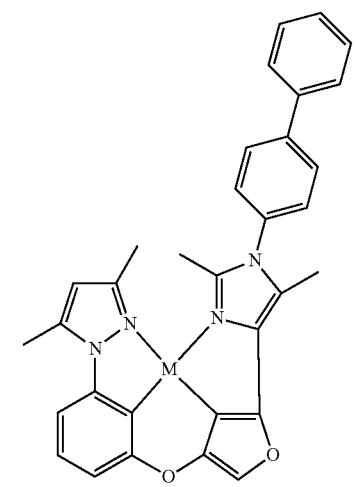
438
-continued
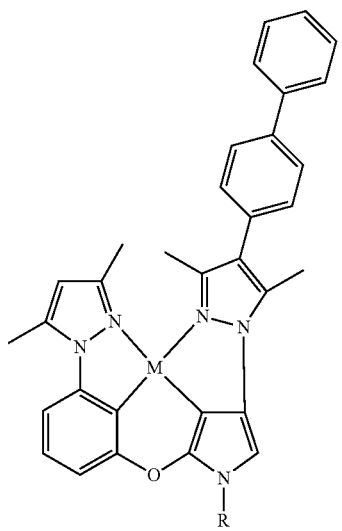
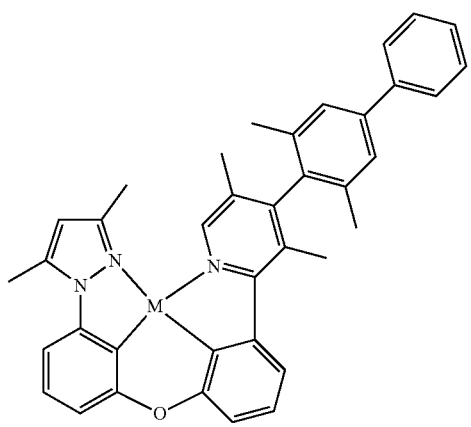
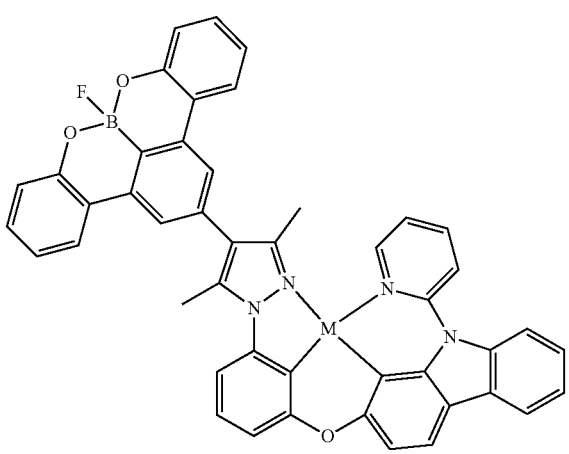

439
-continued
440
-continued
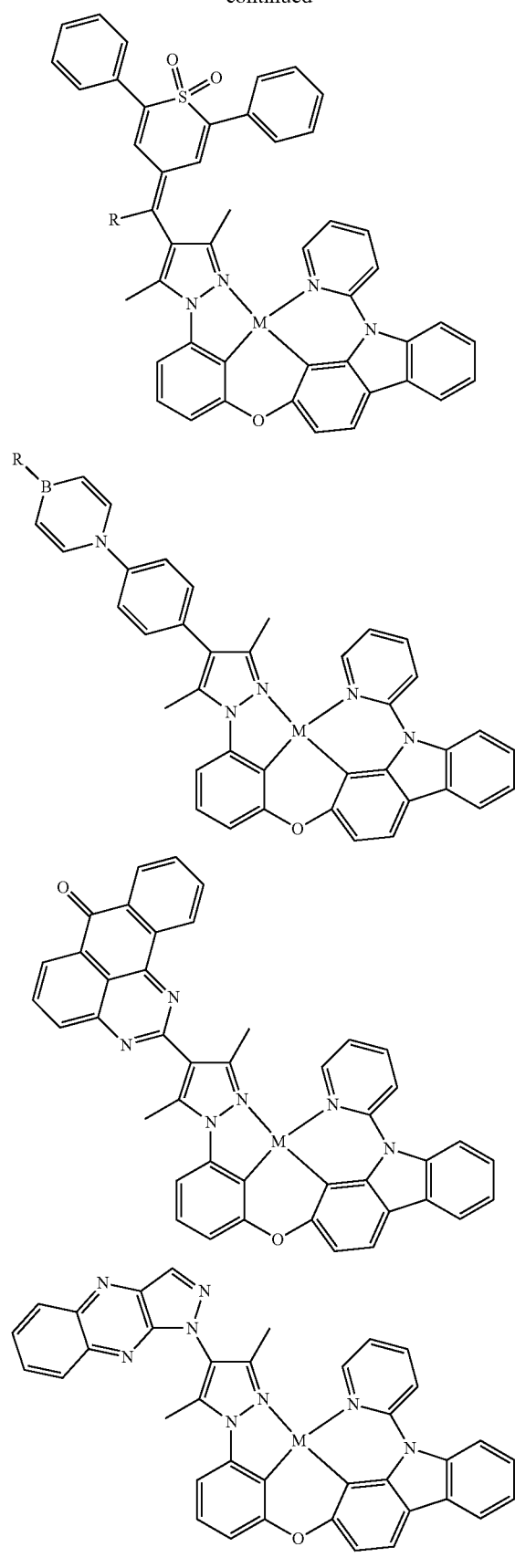

441
-continued
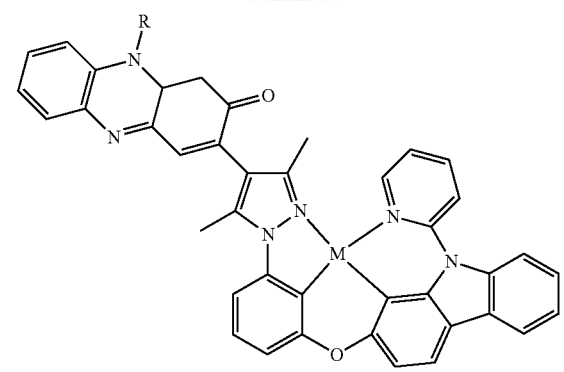
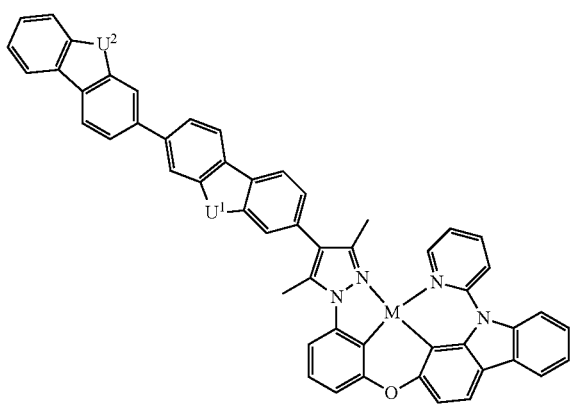
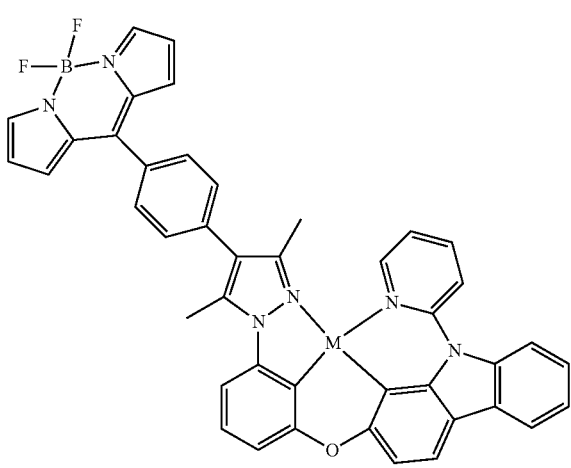
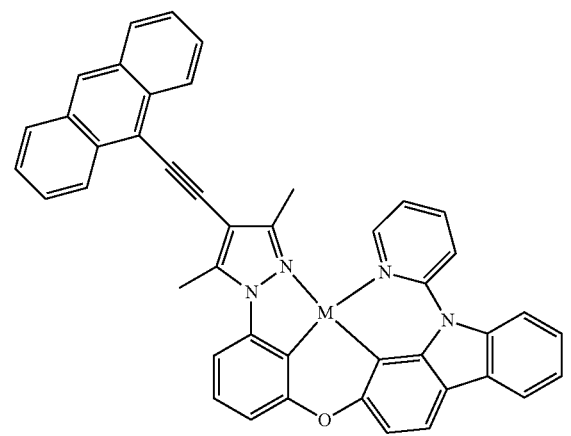
(M = Pt, Pd)
442
-continued
Structures 63
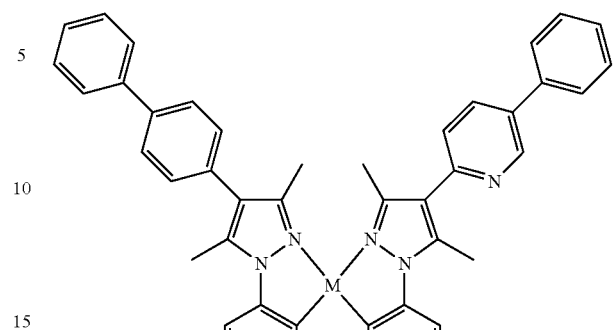
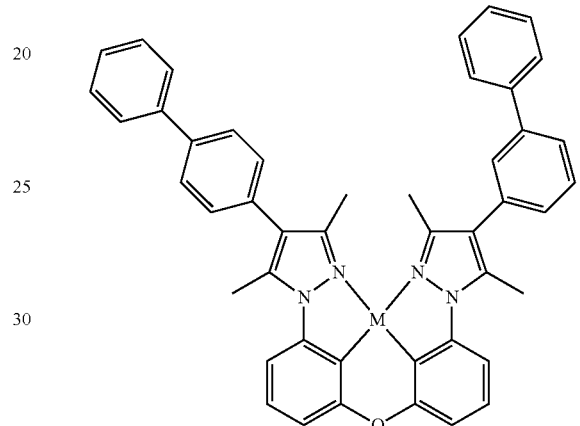
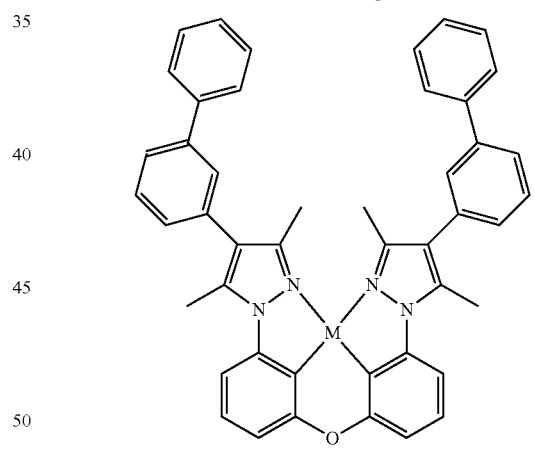
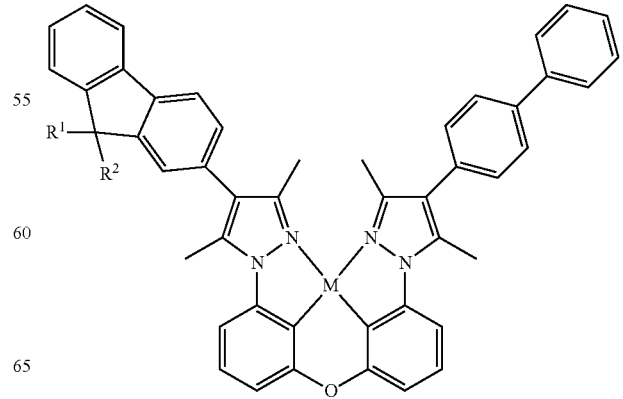

443
-continued
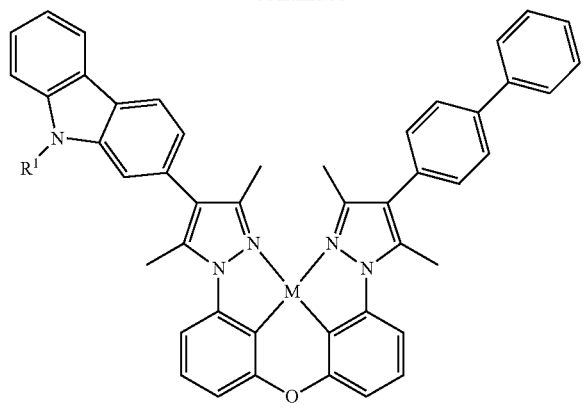
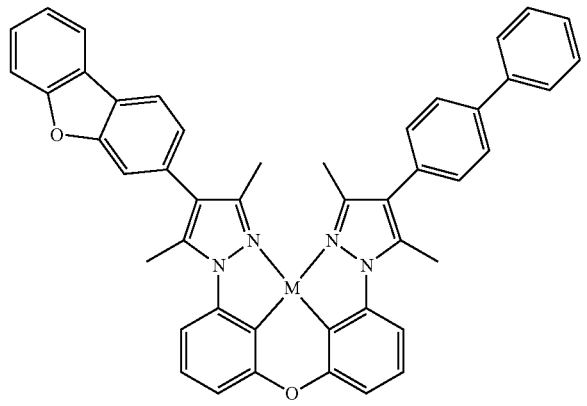
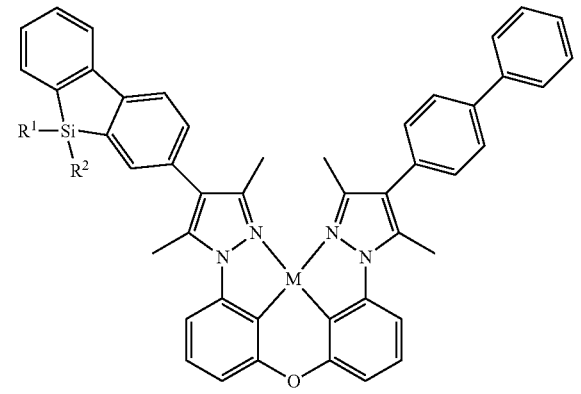
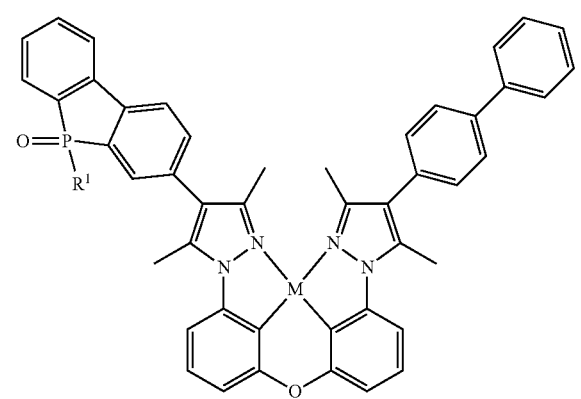
444
-continued
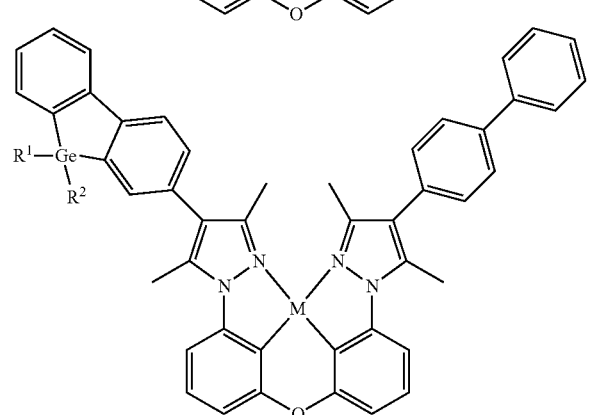
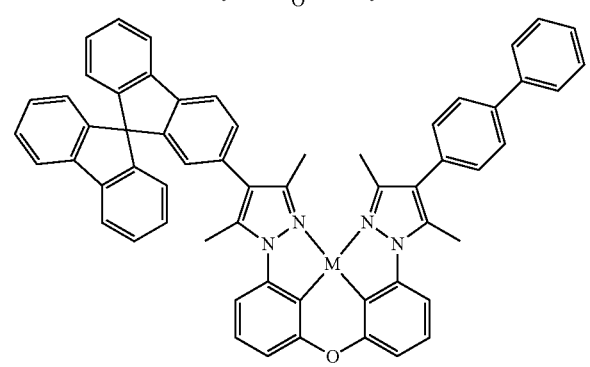
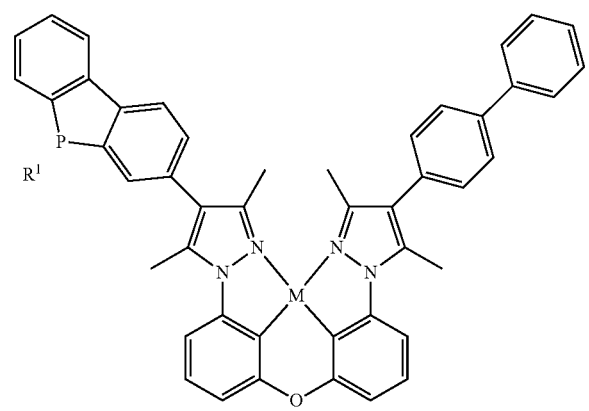

445
-continued
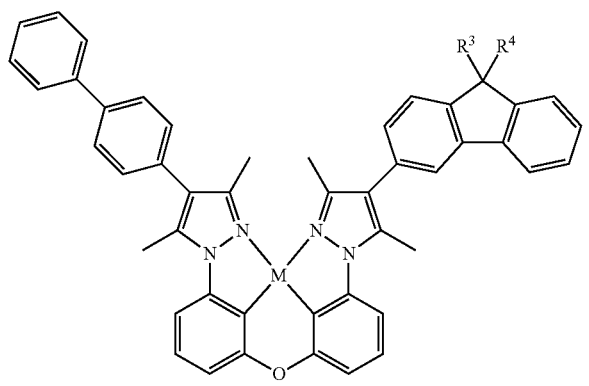
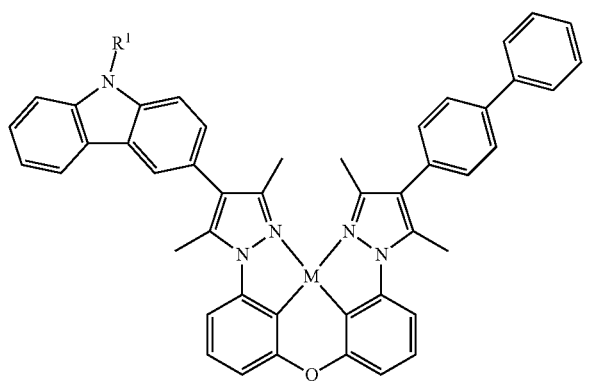
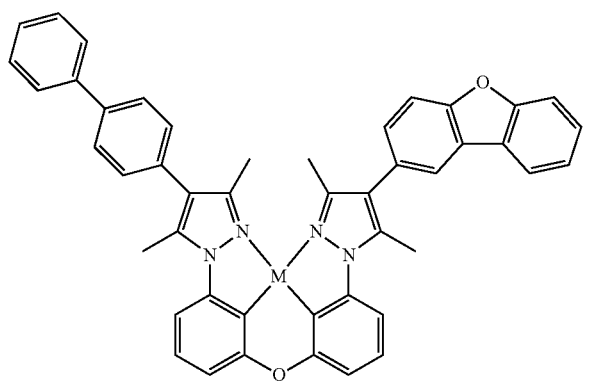
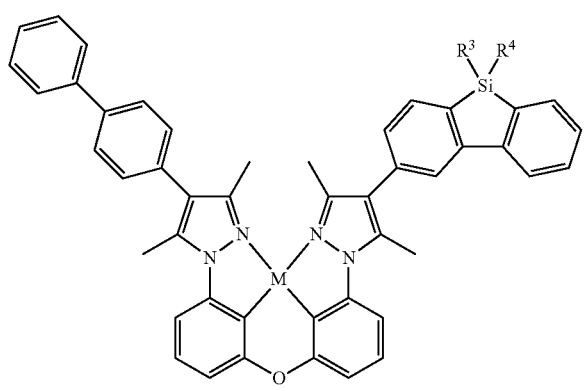
446
-continued
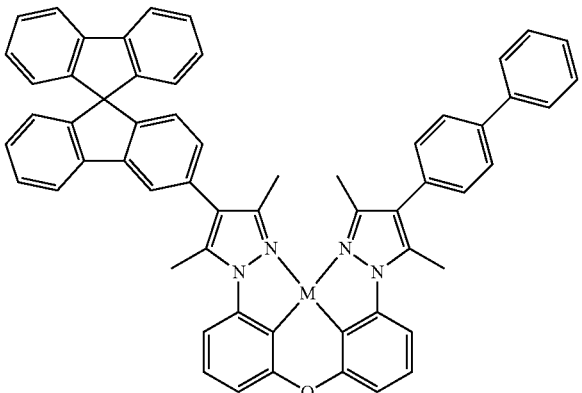
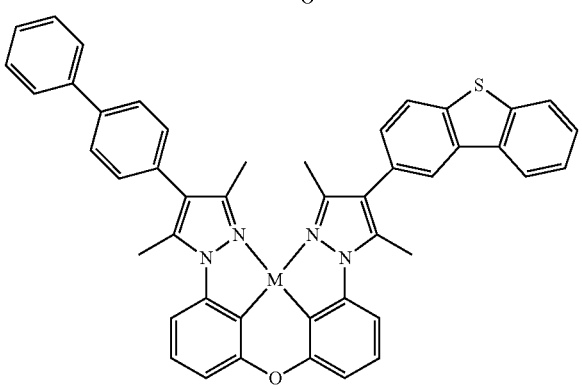
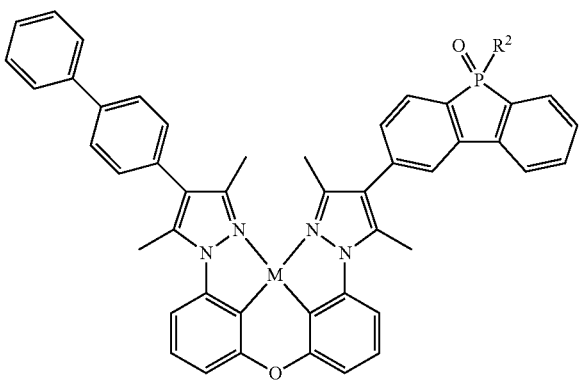
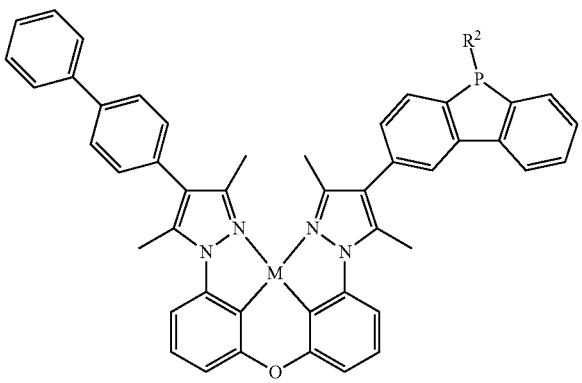
(M = Pt, Pd)

Structures 64
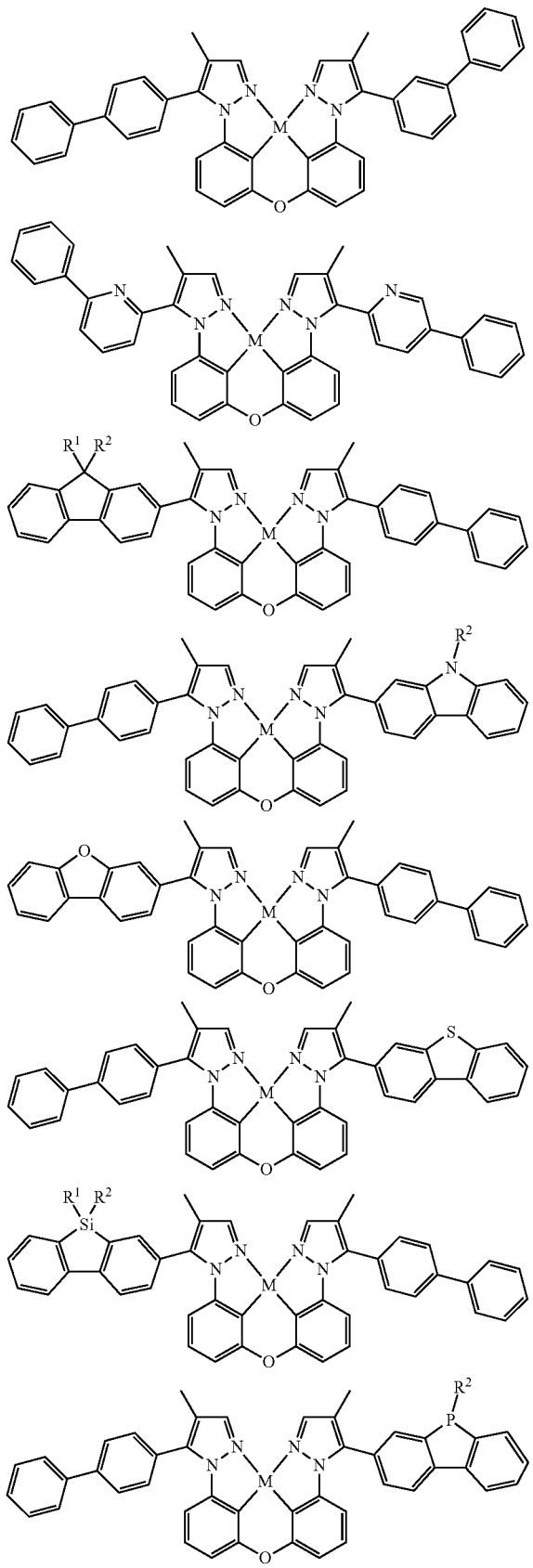
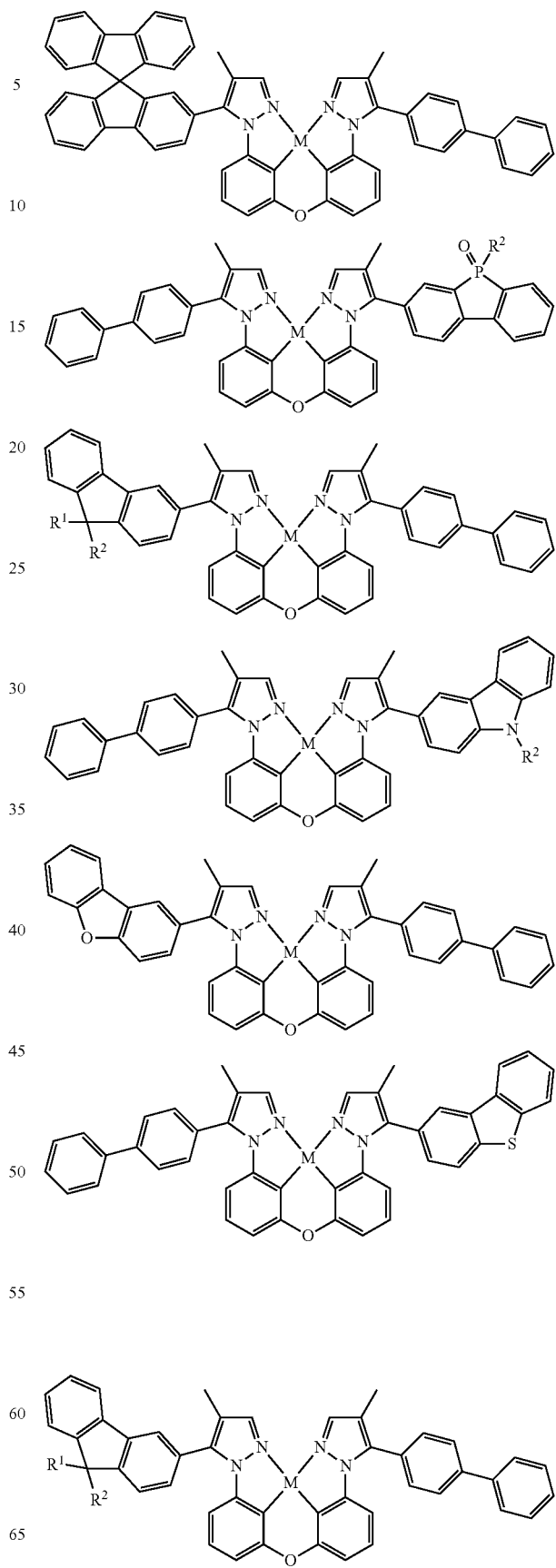

449
-continued
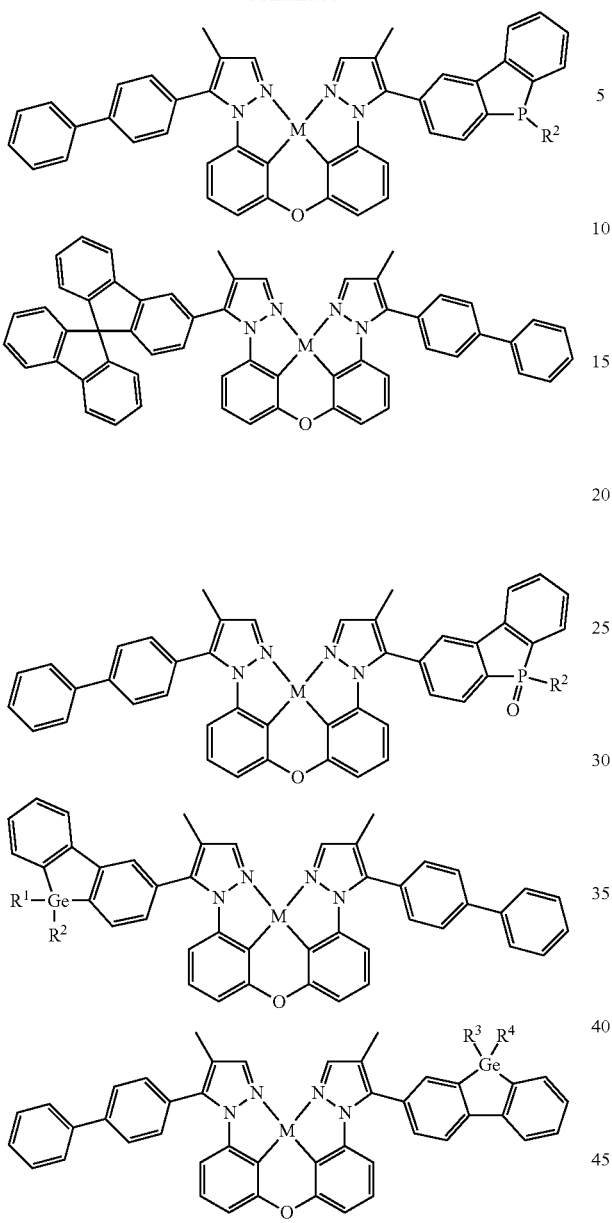
(M = Pt, Pd)
Structures 65
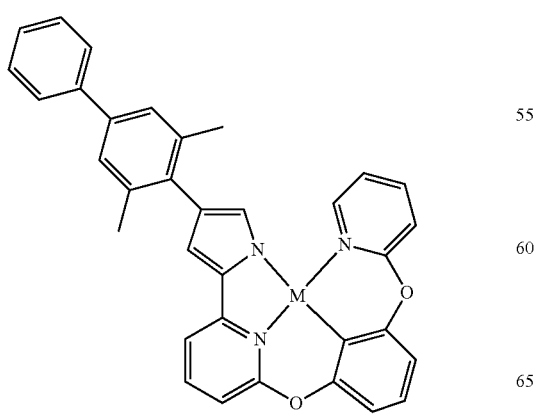
450
-continued
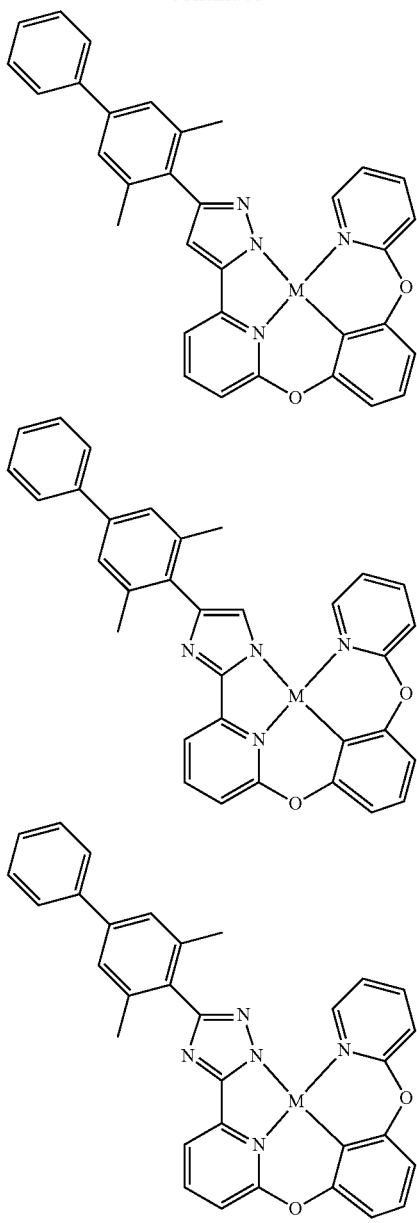

451
-continued
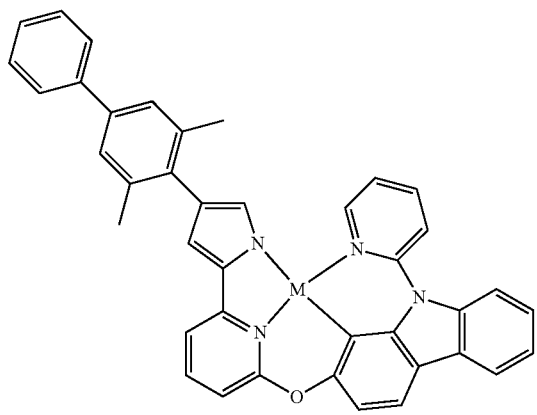
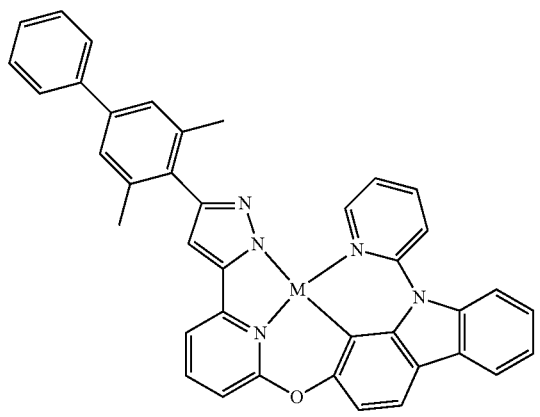
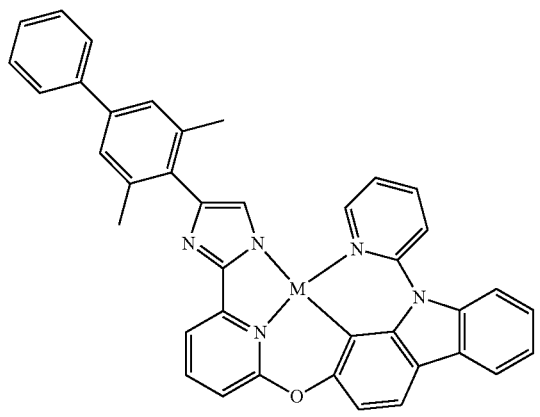
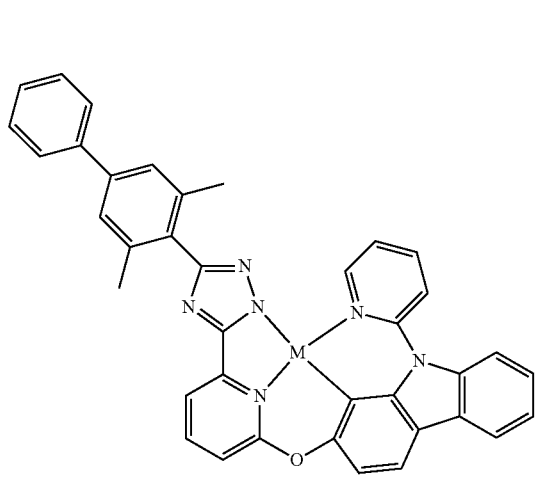
452
-continued
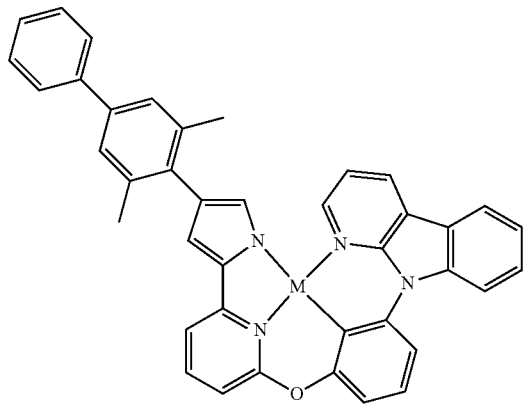
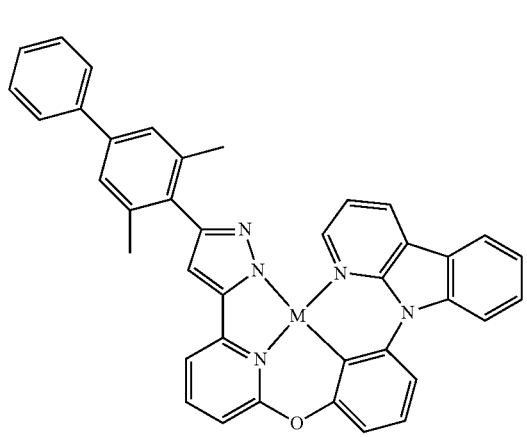
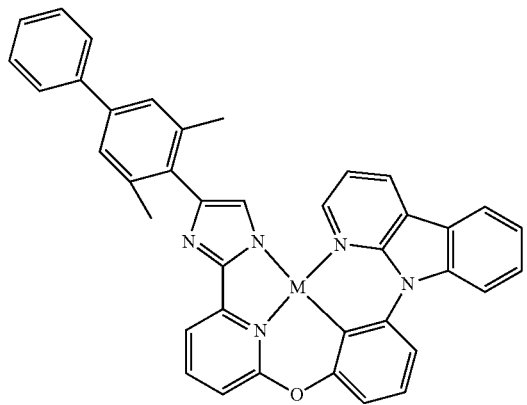
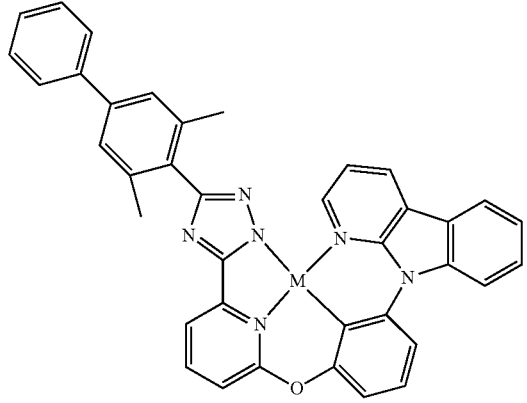

453
-continued
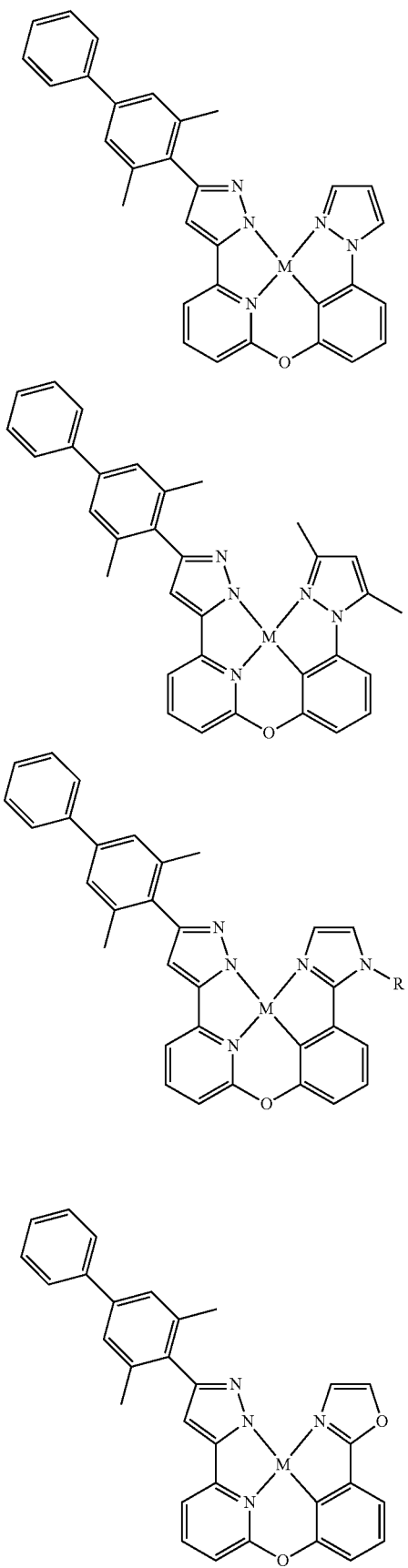
454
-continued
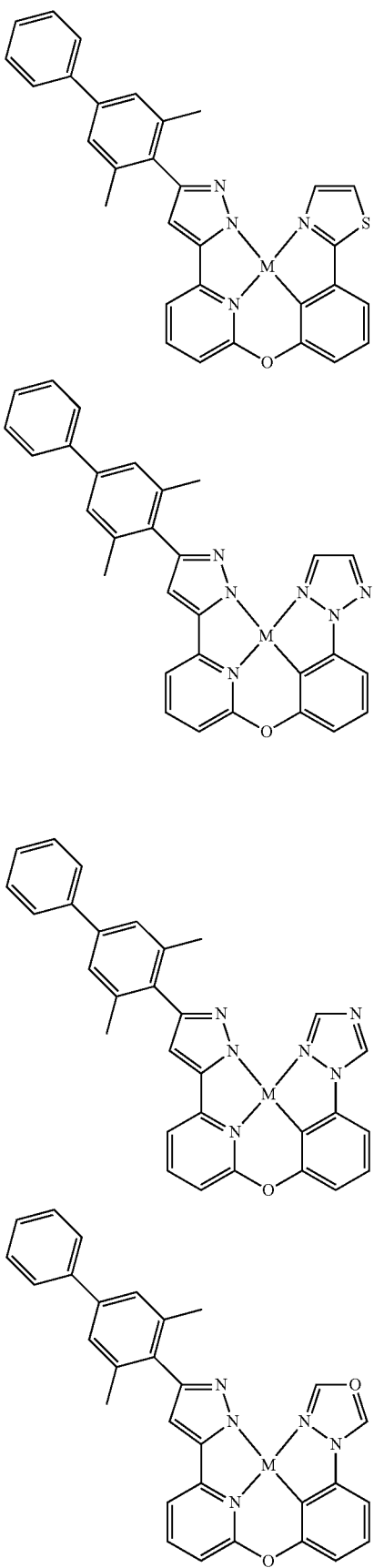

455
-continued
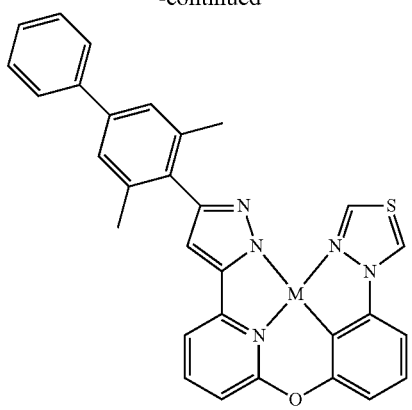
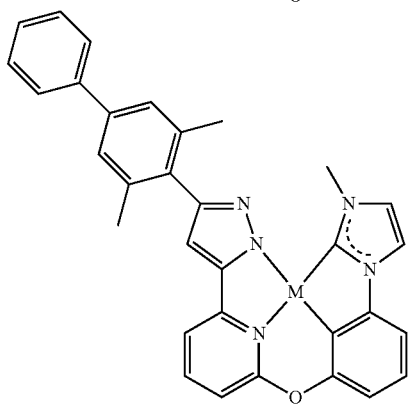
(M = Pt, Pd)
Structures 66
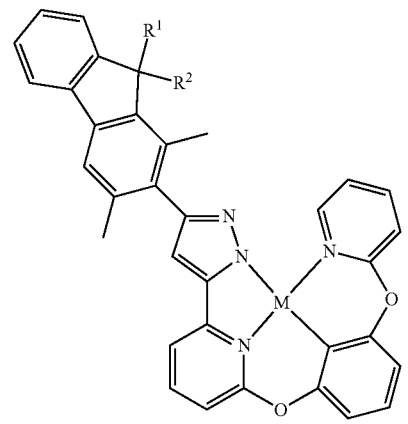
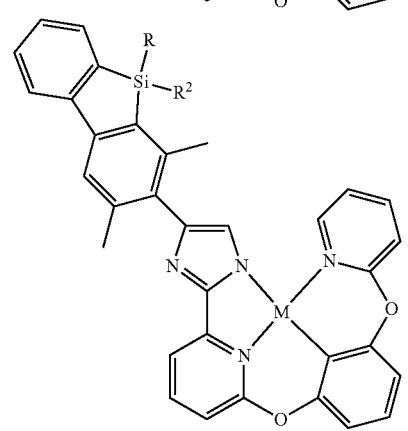
456
-continued
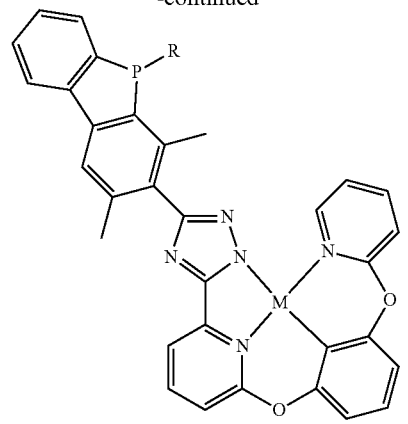
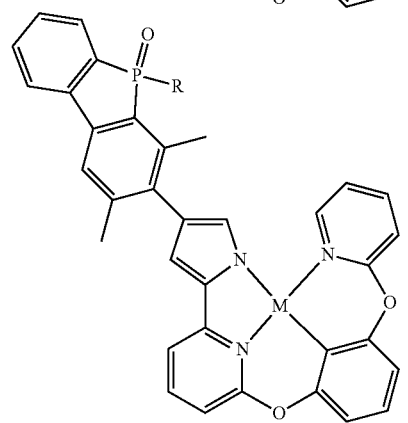
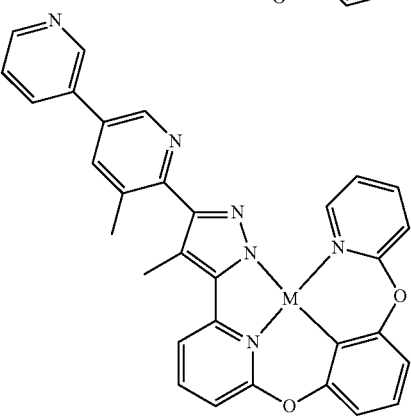
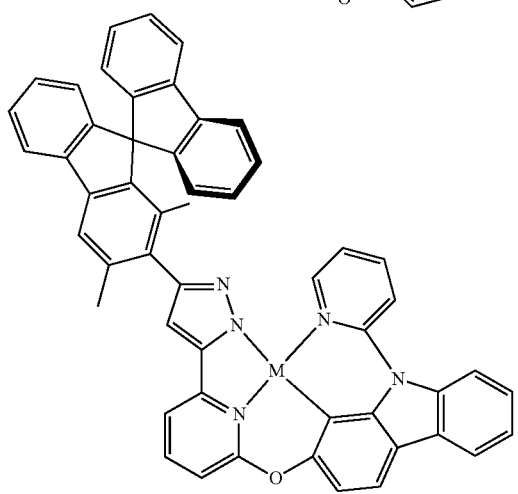

457
-continued
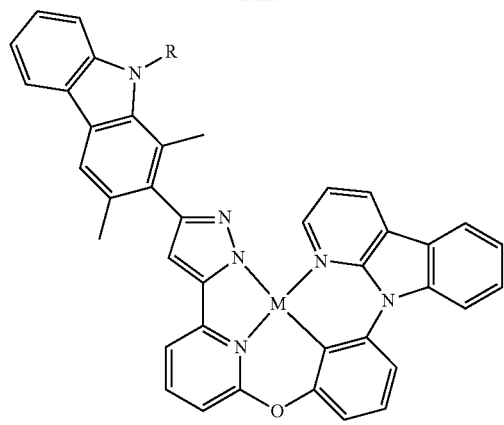
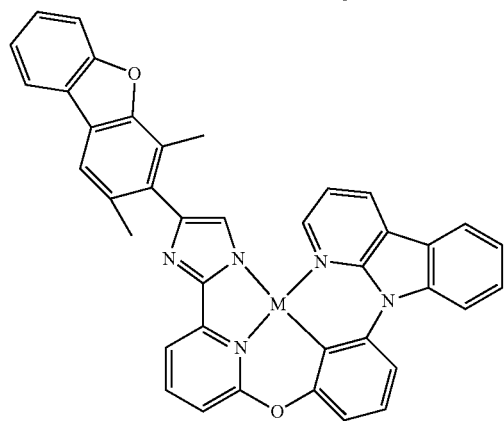
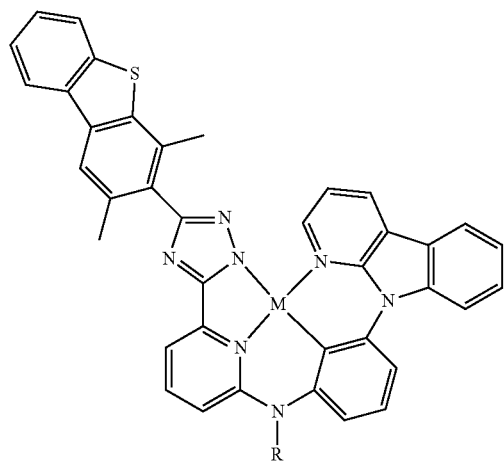
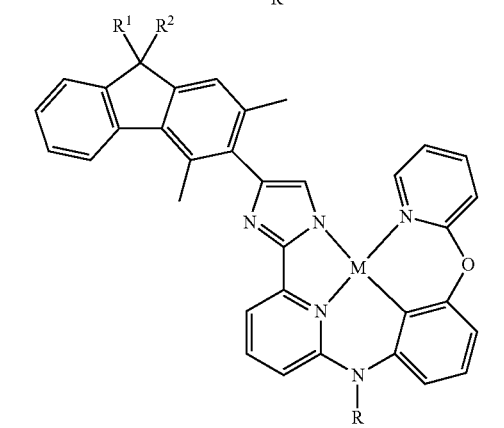
458
-continued
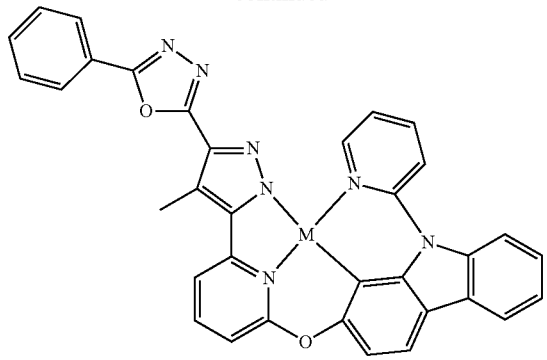
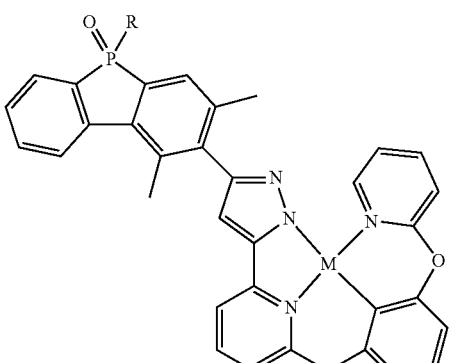
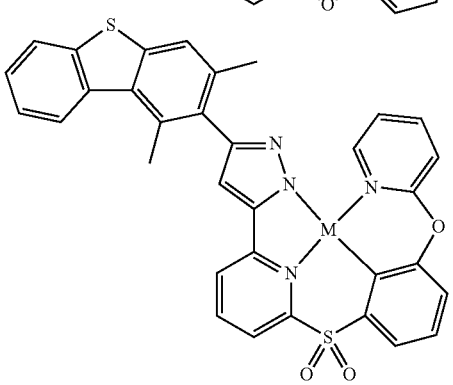
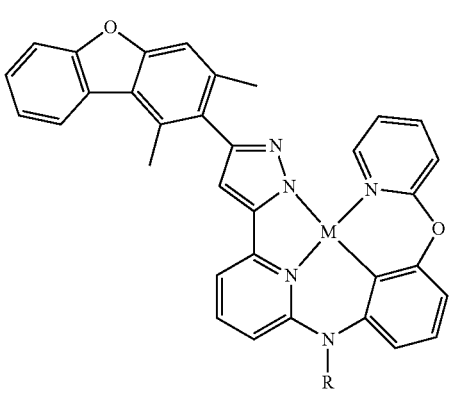

459
-continued
460
-continued
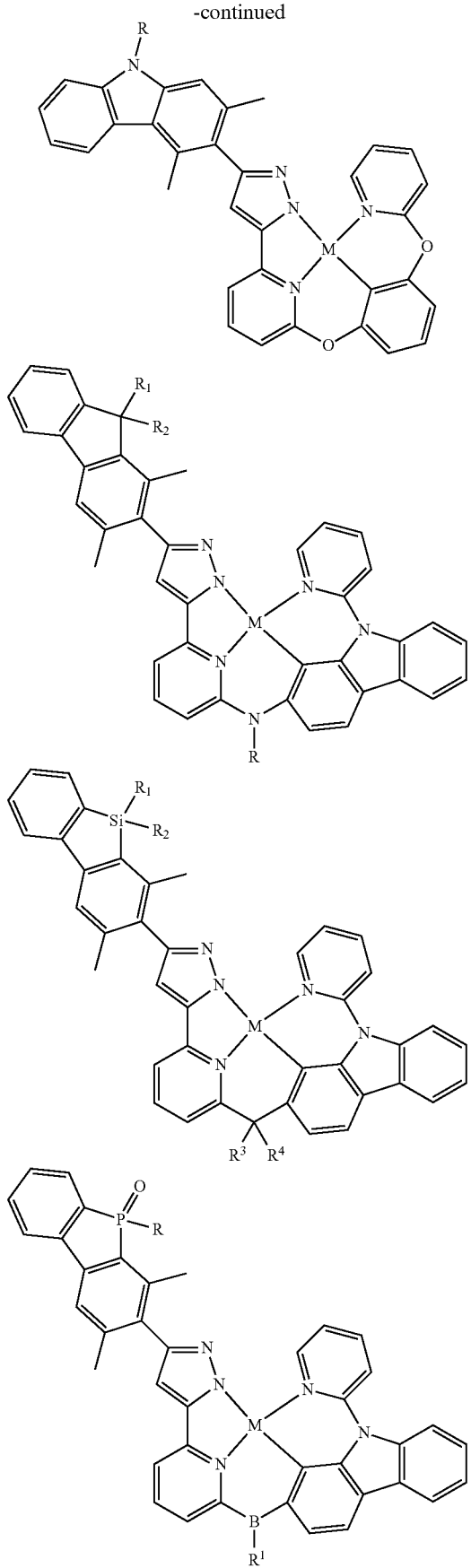
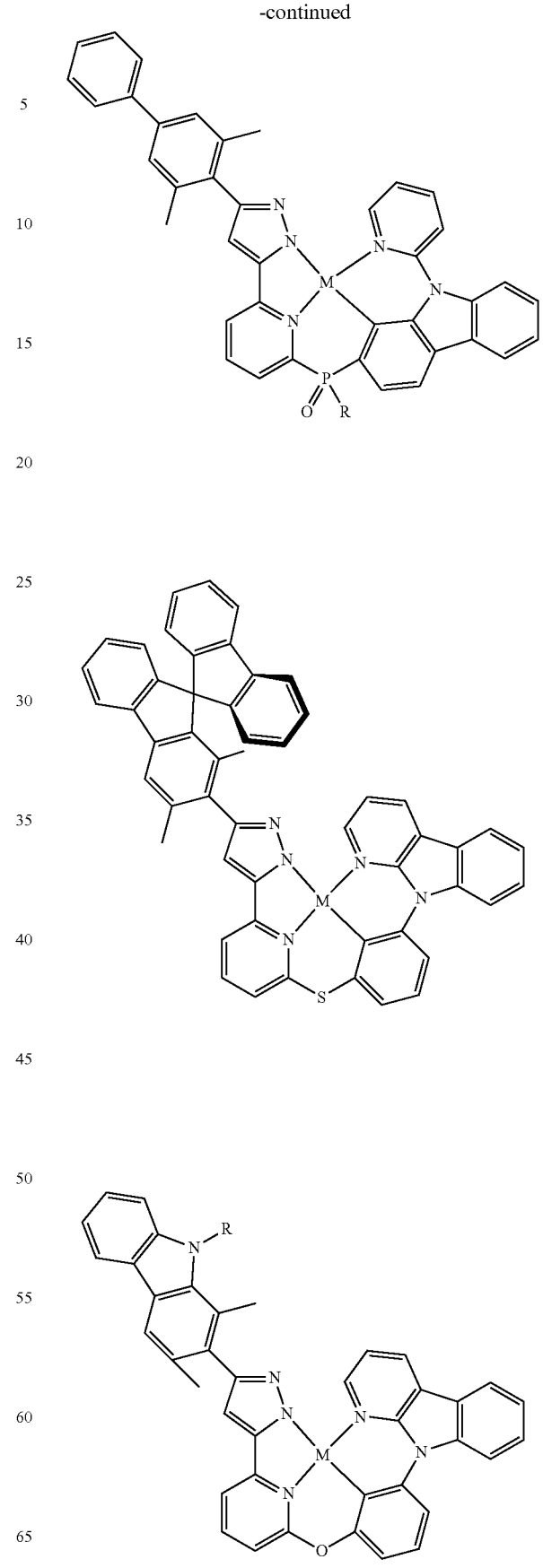

461
-continued
462
-continued
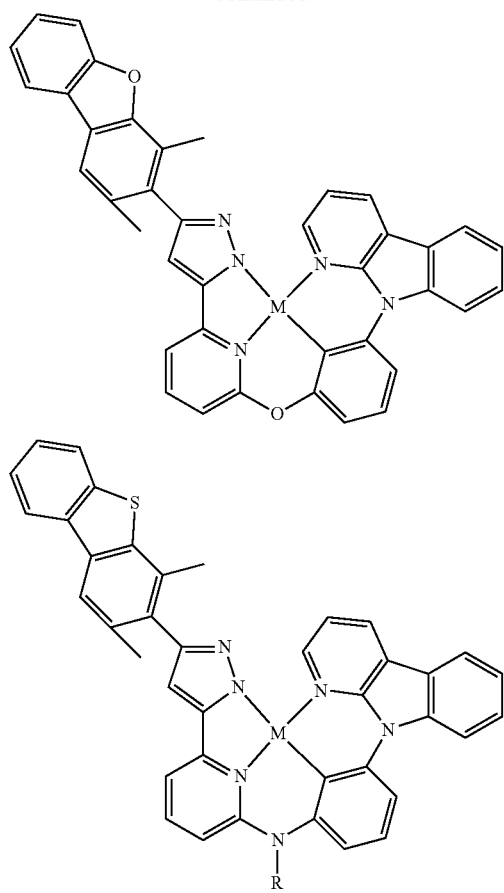
(M = Pt, Pd)
Structures 67
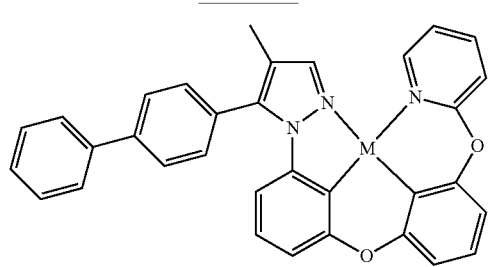
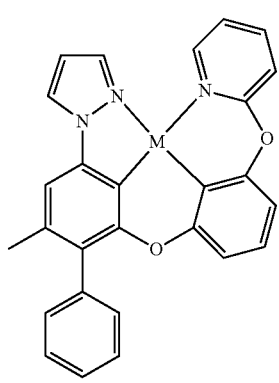
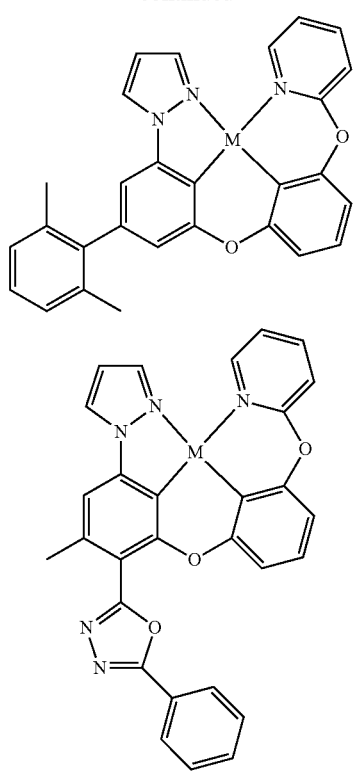
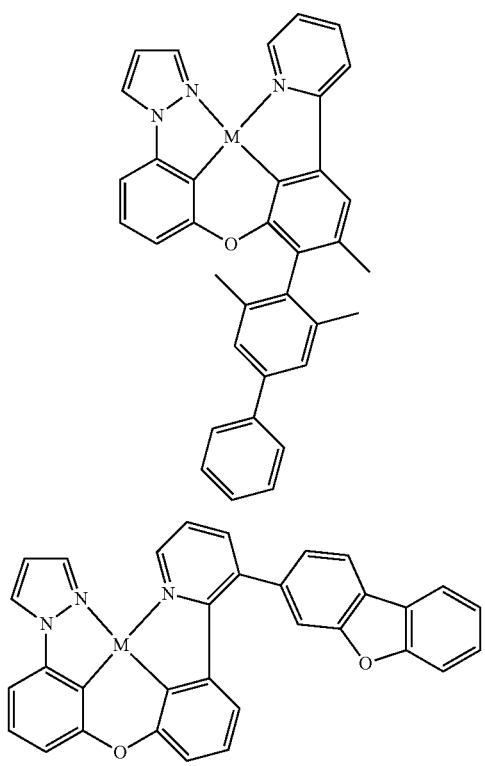

463
-continued
464
-continued
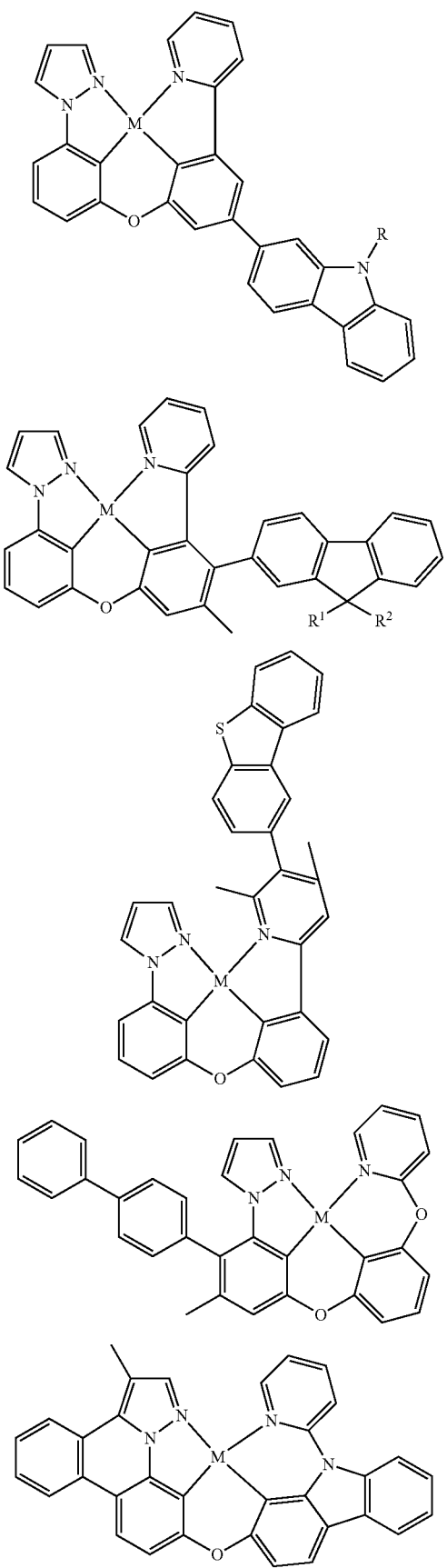
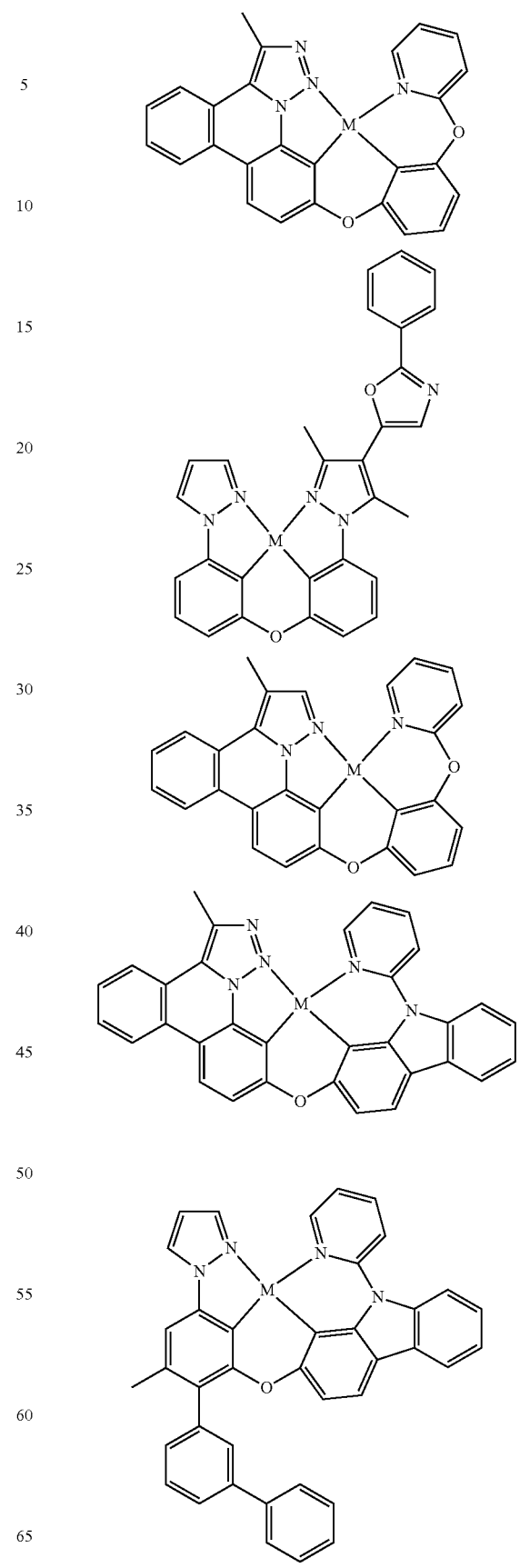

465
-continued
466
-continued
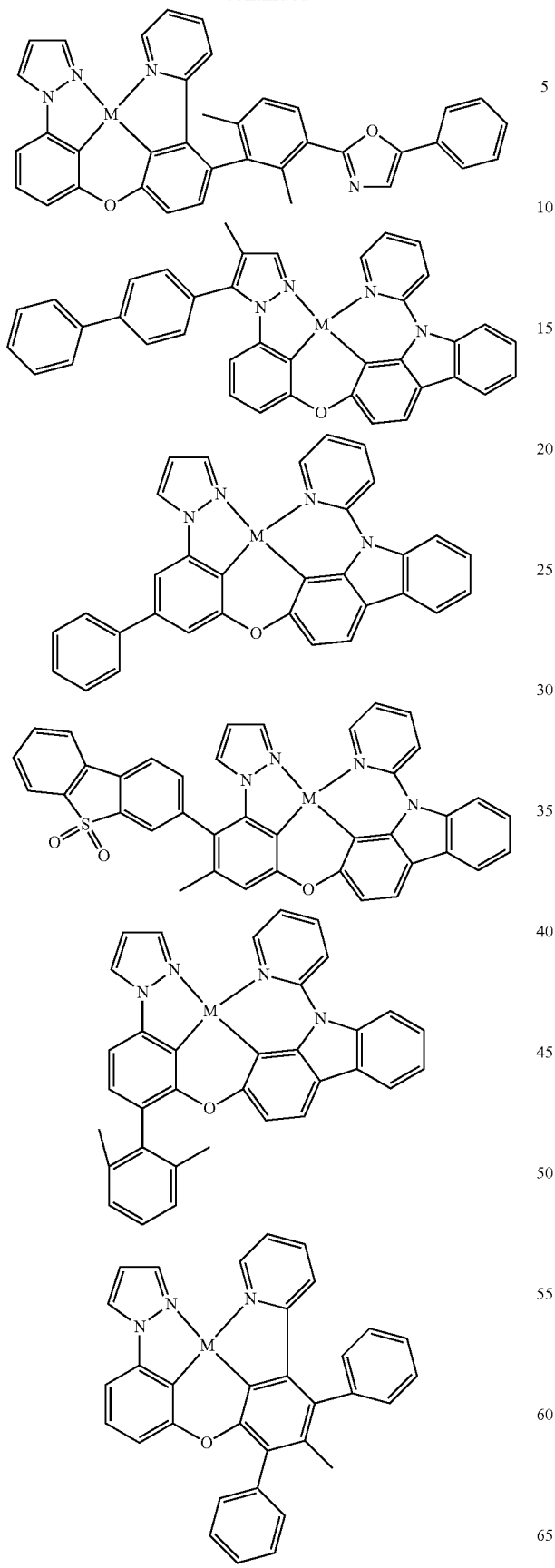
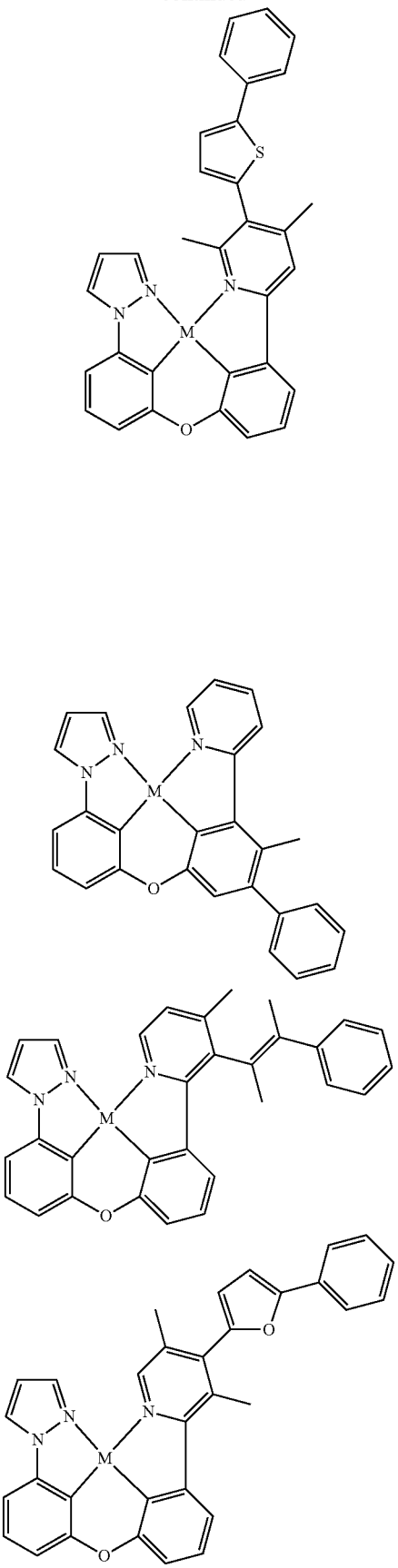

467
-continued
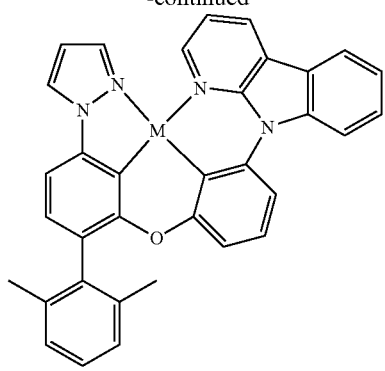
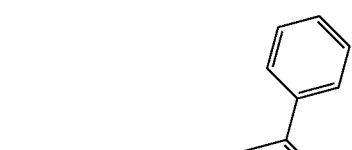
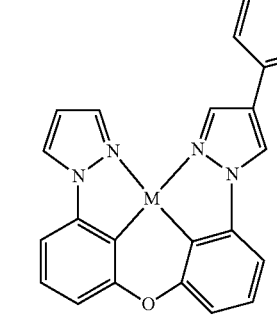
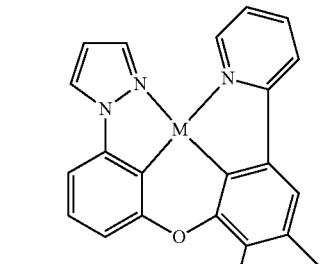
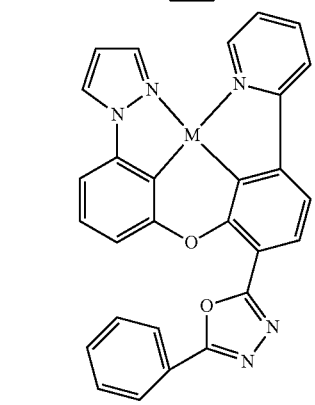
468
-continued
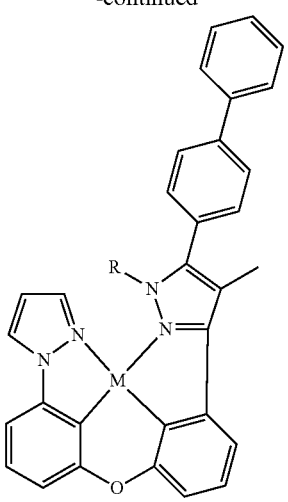
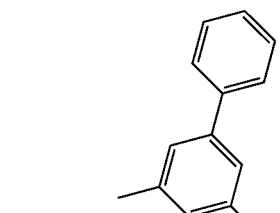
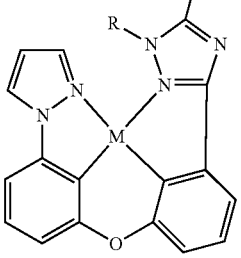
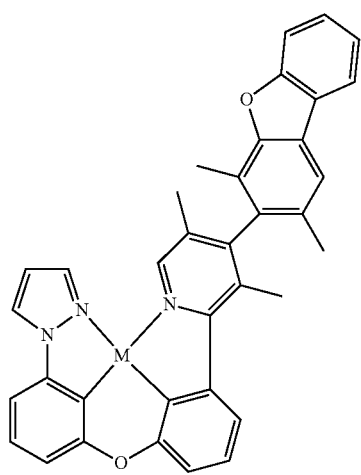

469
-continued
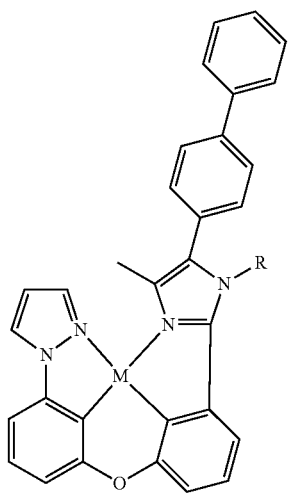
(M = Pt, Pd)
Structures 68
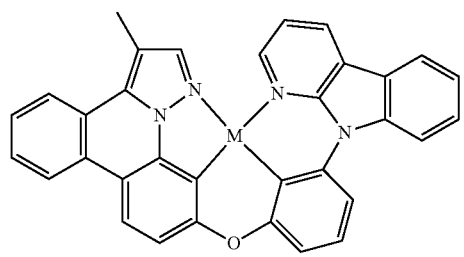
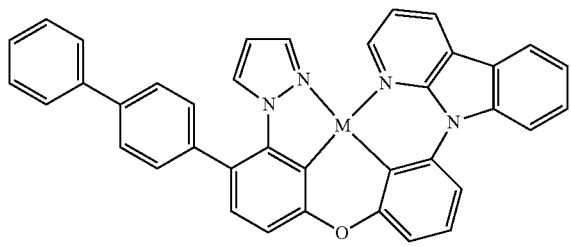
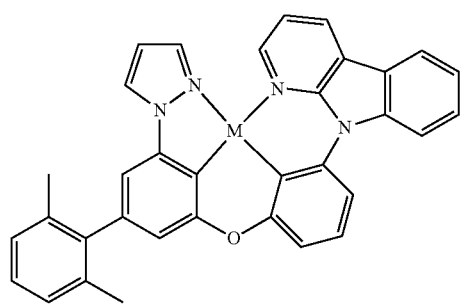
470
-continued
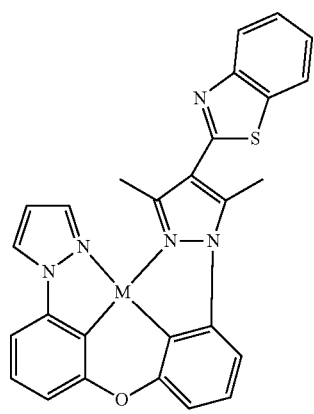
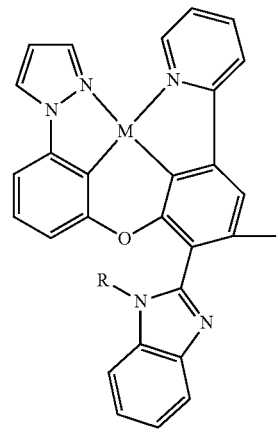
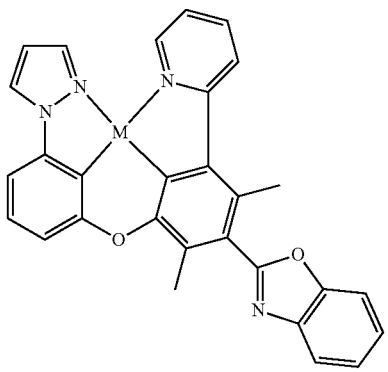
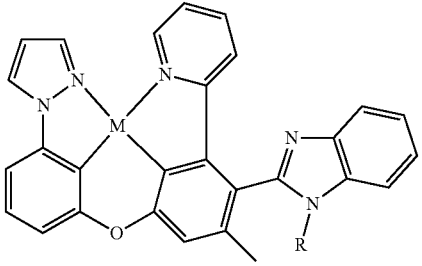

471
-continued
472
-continued
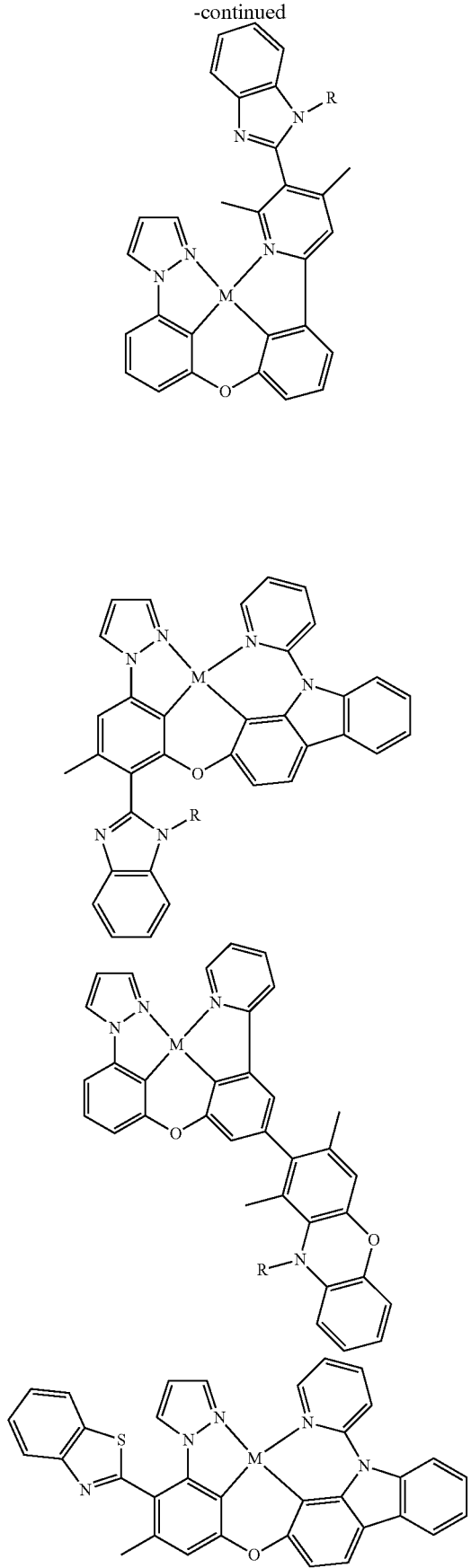
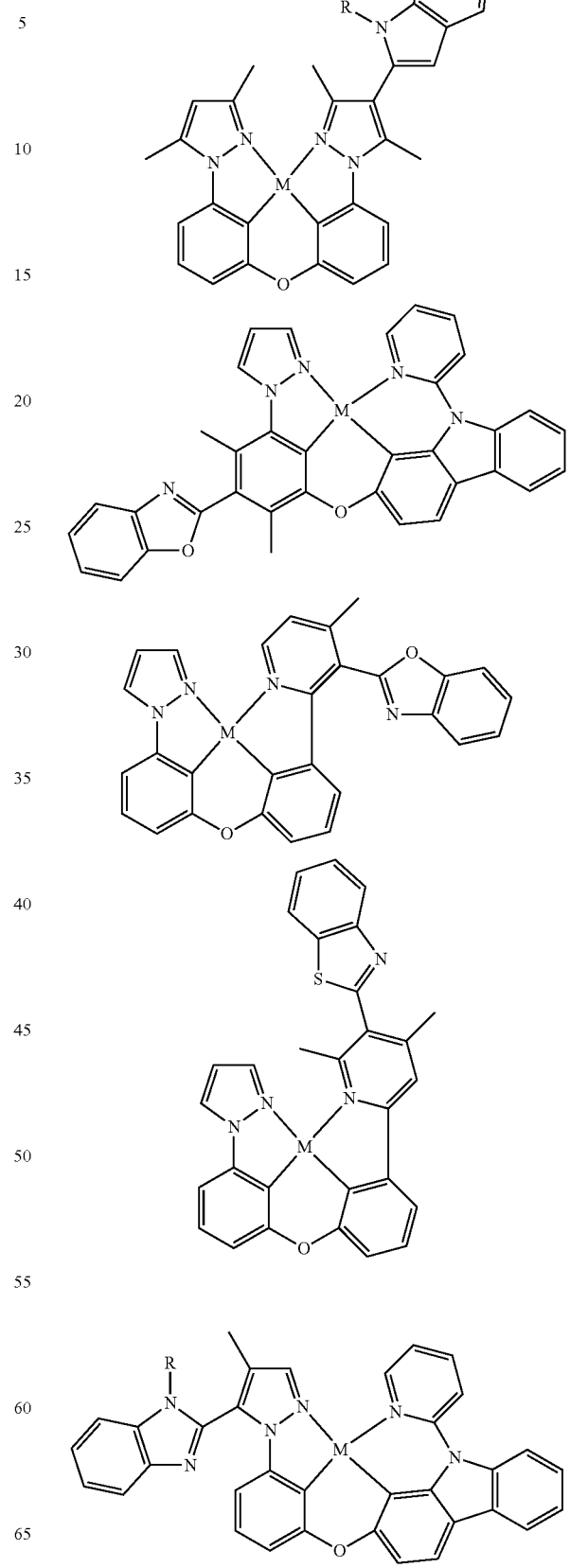

473
-continued
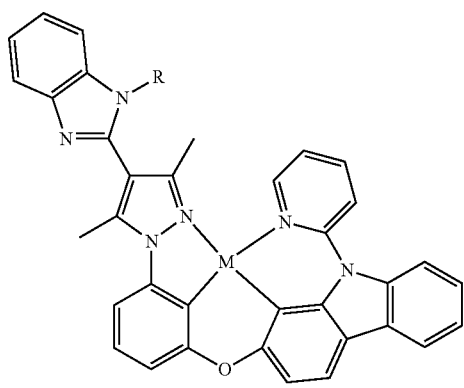
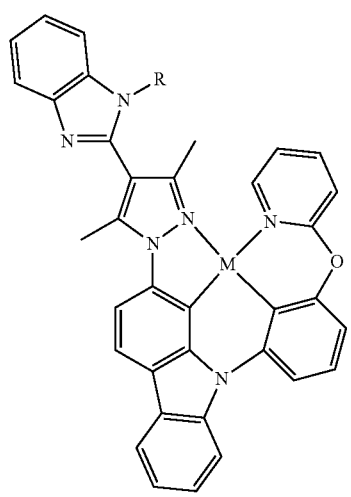
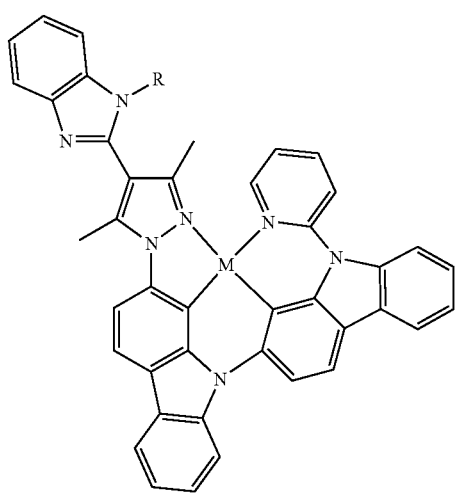
474
-continued
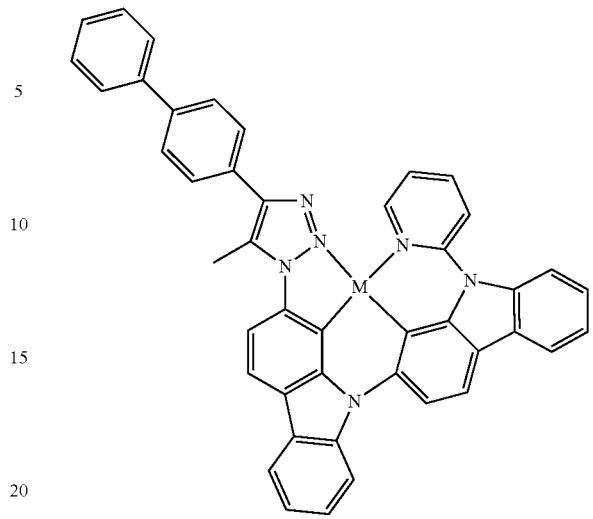
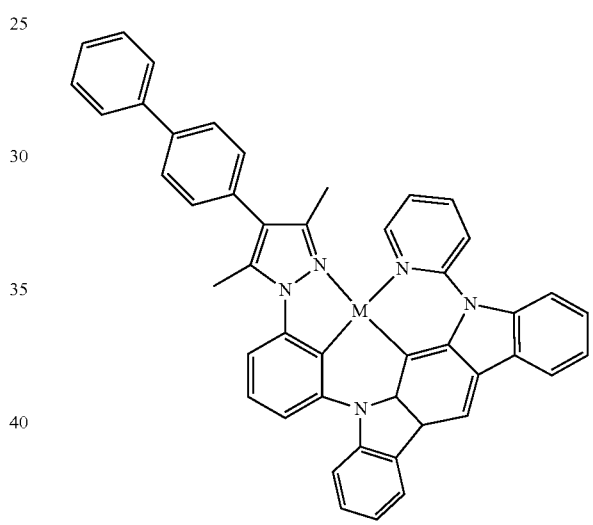
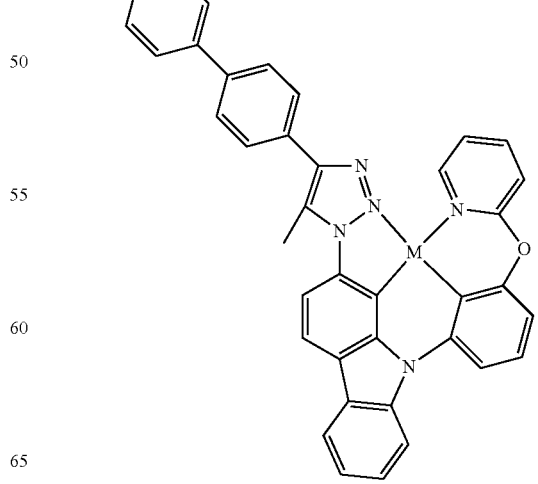

475
-continued
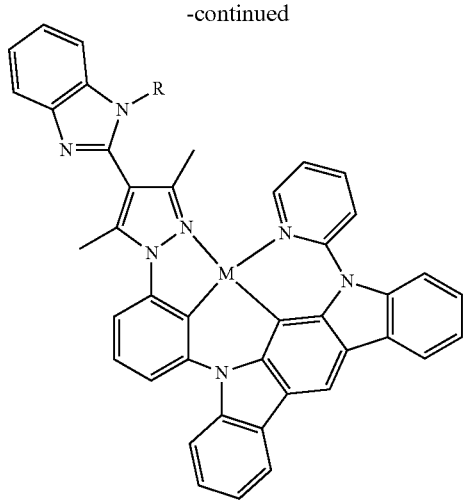
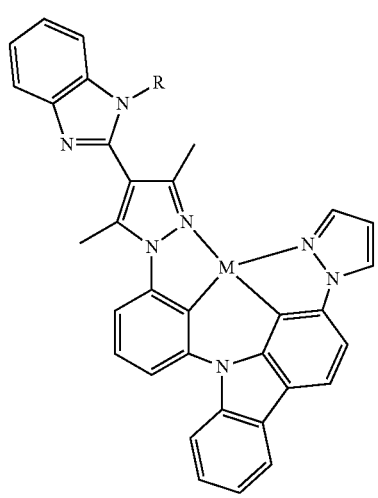
476
-continued
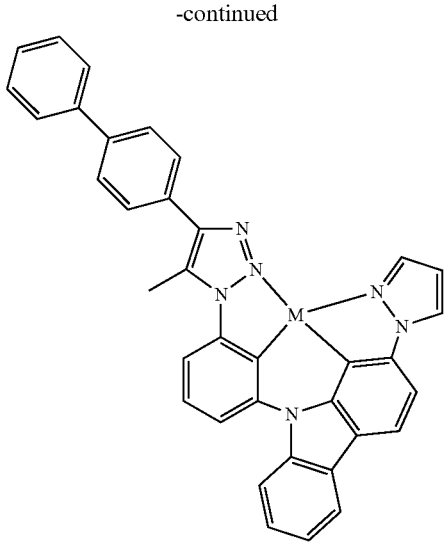
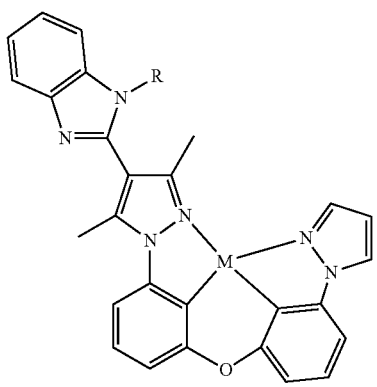
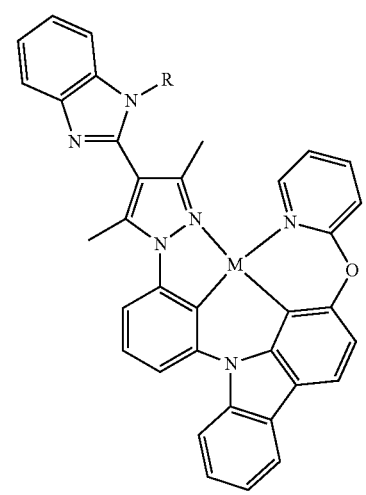

477
-continued
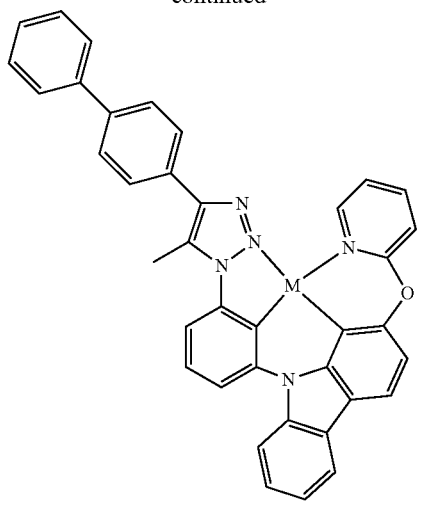
(M = Pt, Pd)
Structures 69
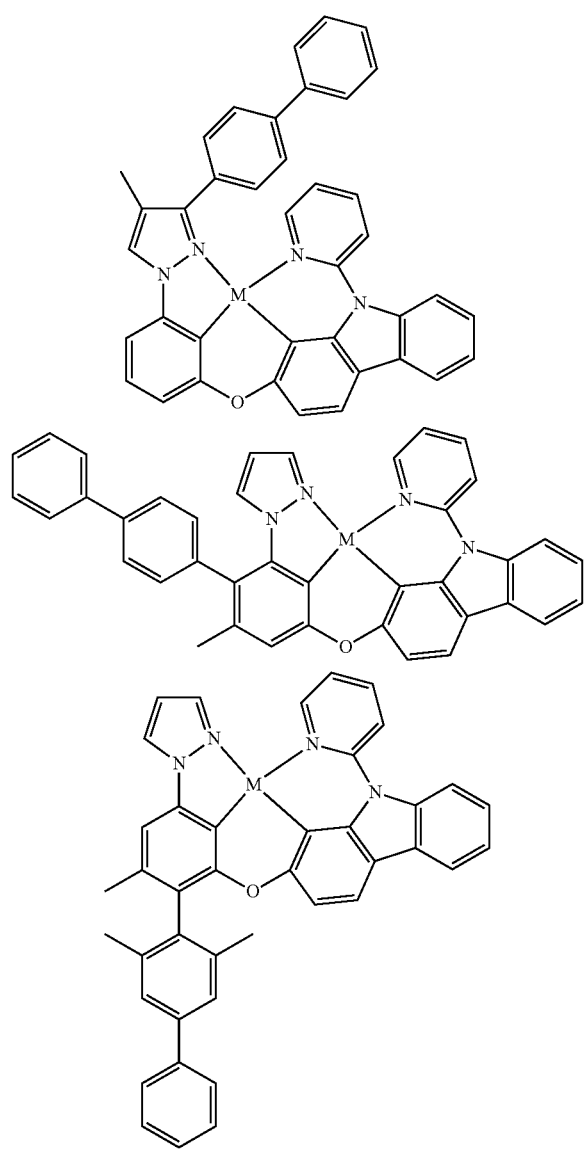
478
-continued
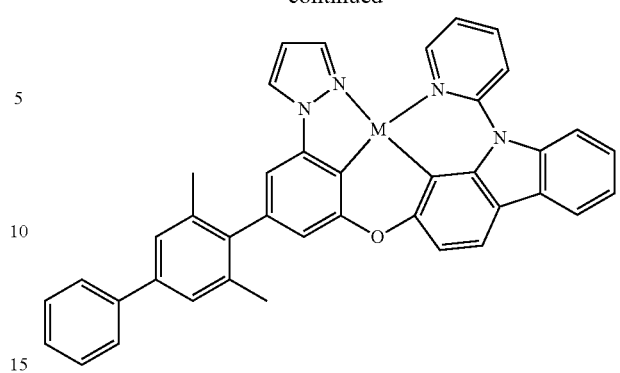
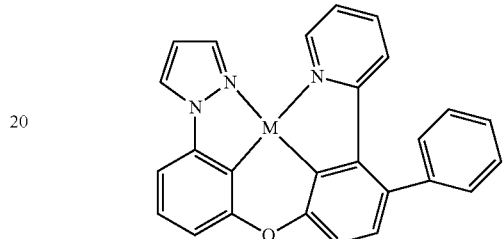
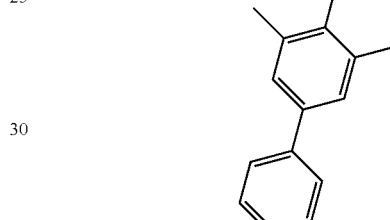
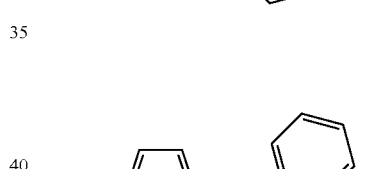
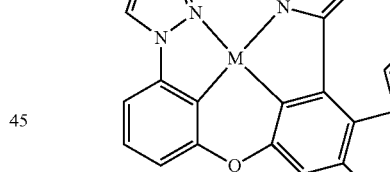
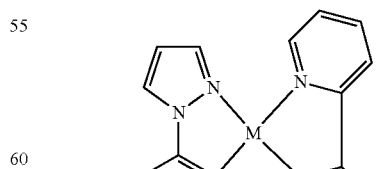
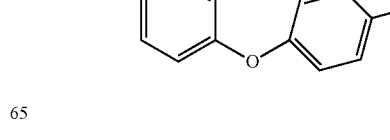

479
-continued
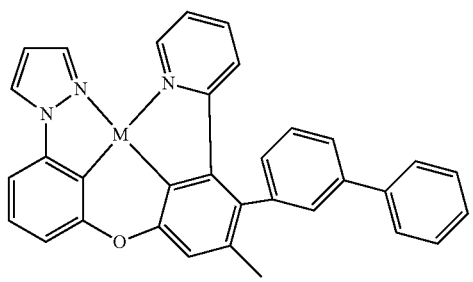
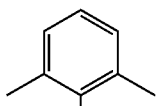
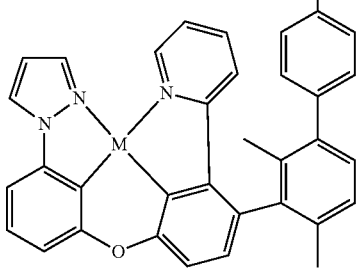
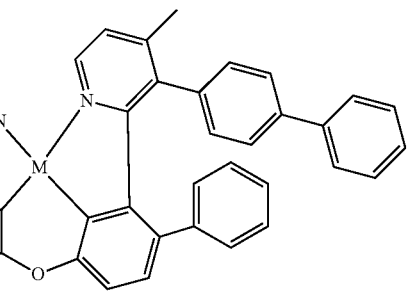
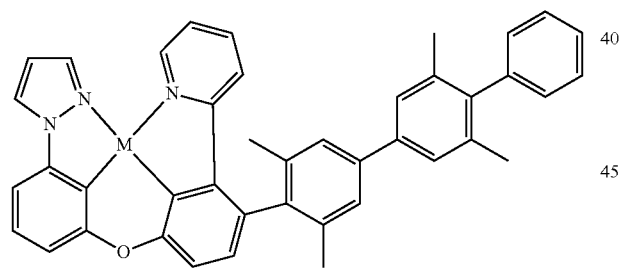
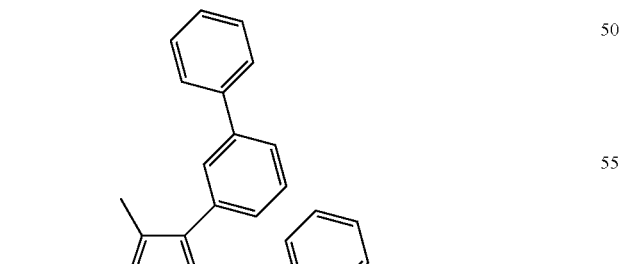
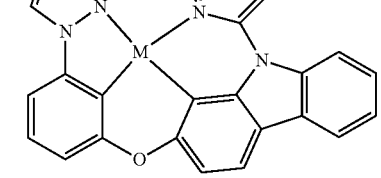
480
-continued
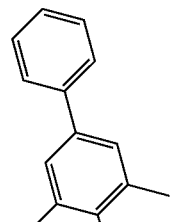
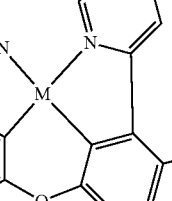
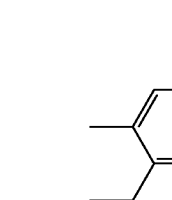
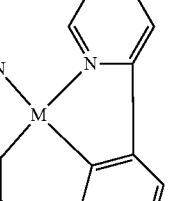
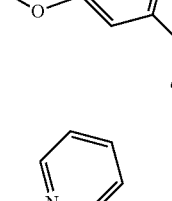
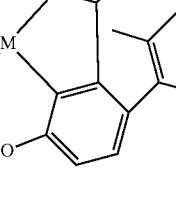

481
-continued
482
-continued
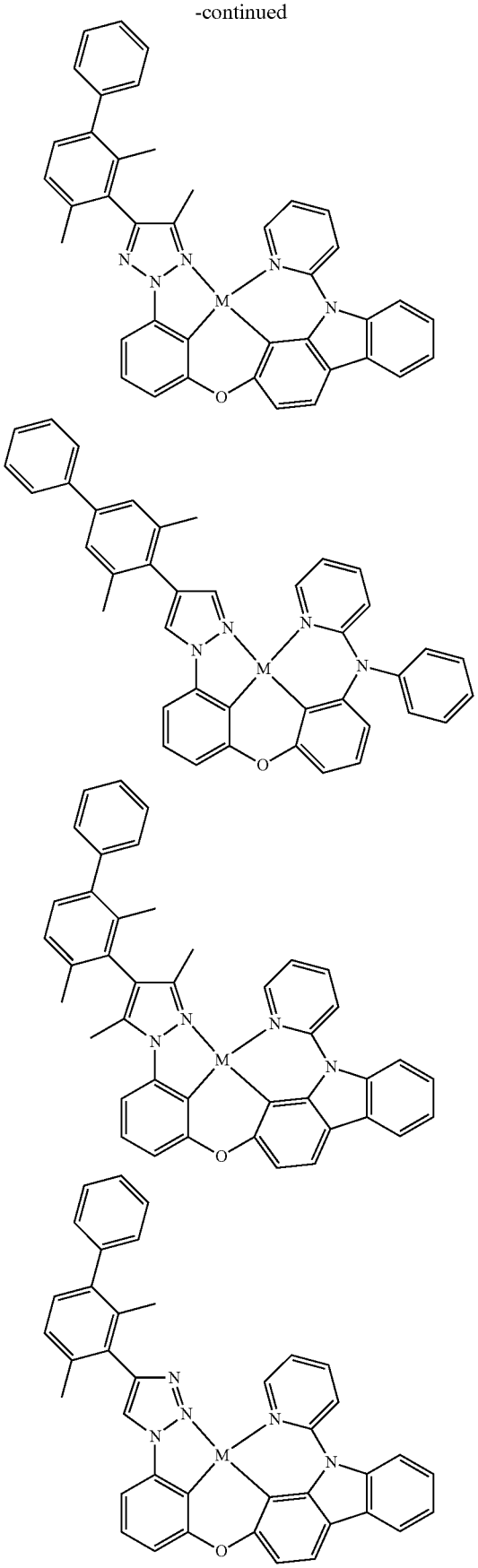
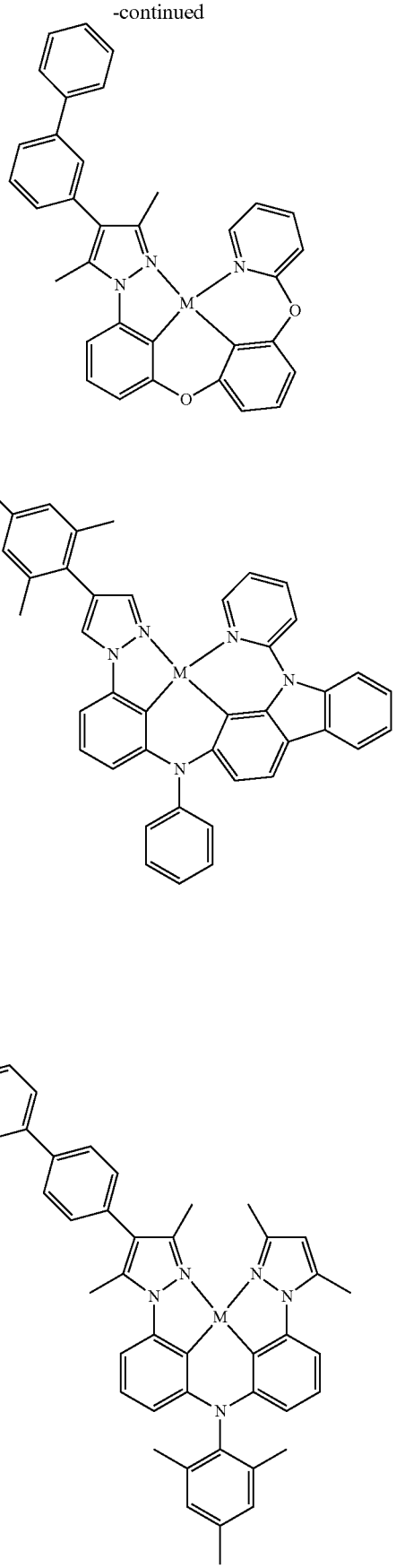

483
-continued
484
-continued
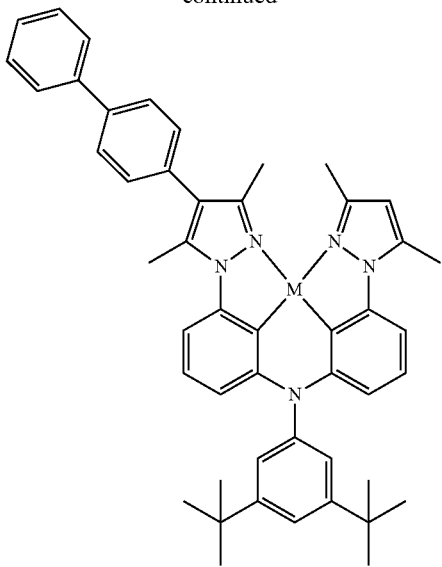
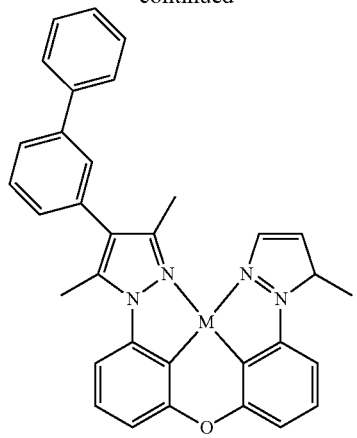
(M = Pt, Pd)
Structures 70
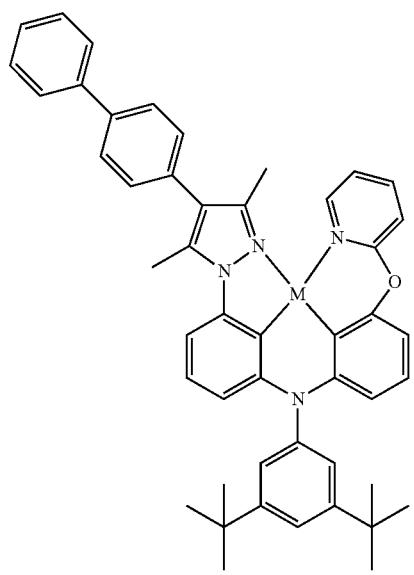
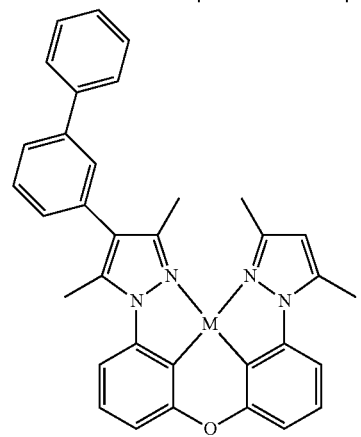
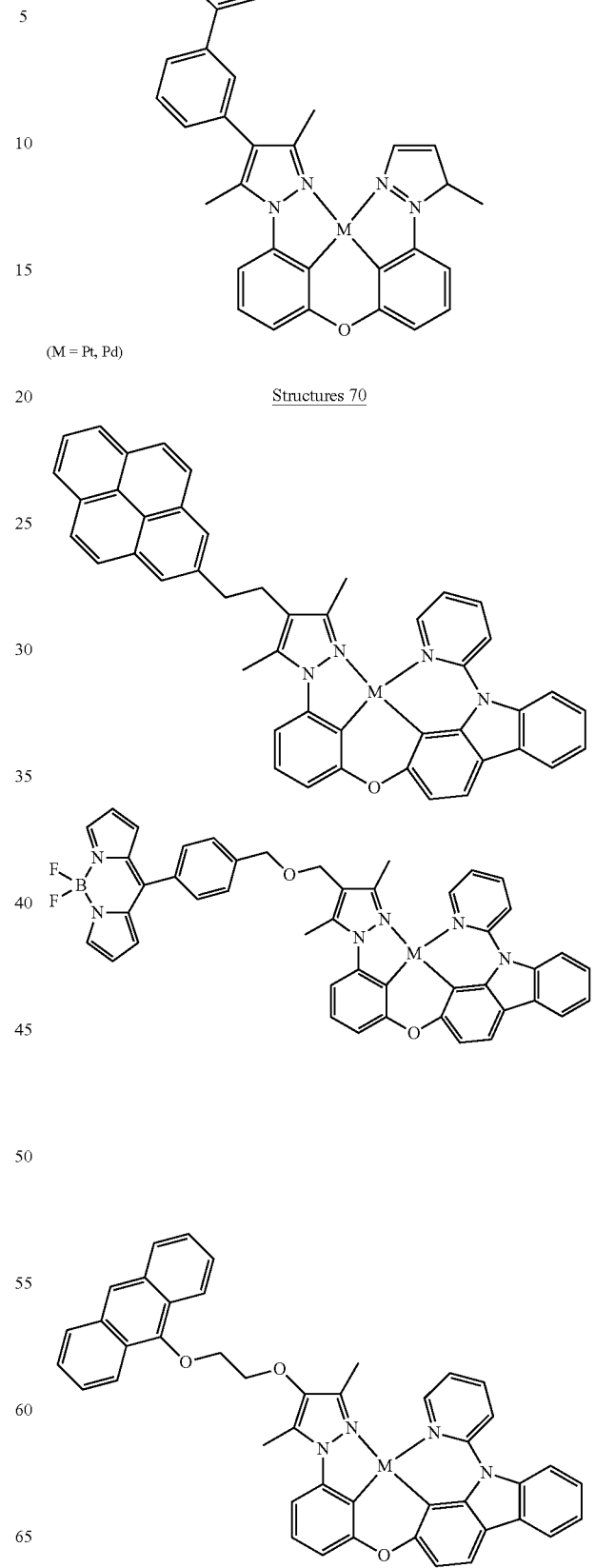

485
-continued
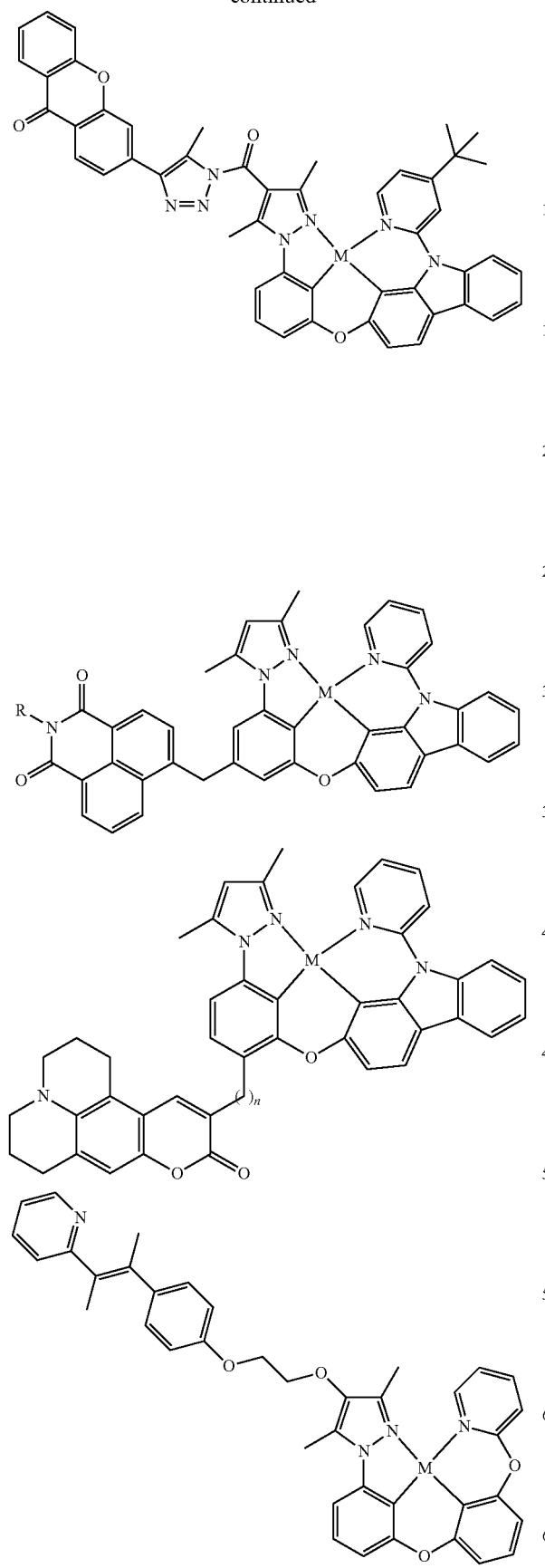
486
-continued
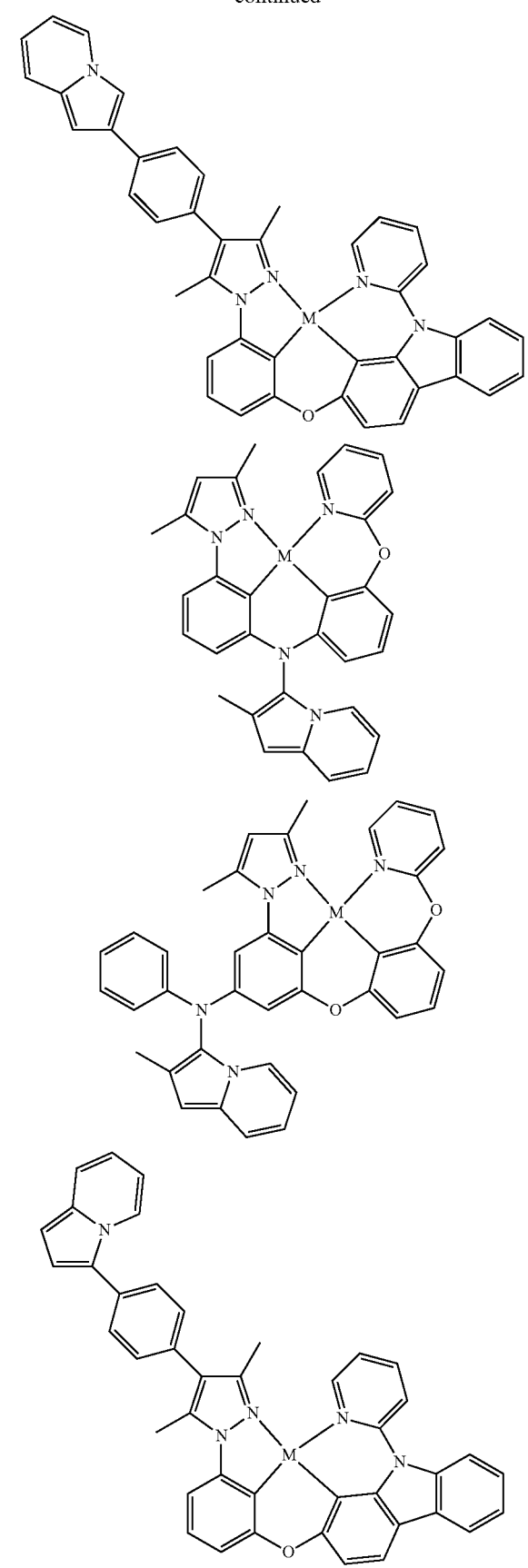

487
-continued
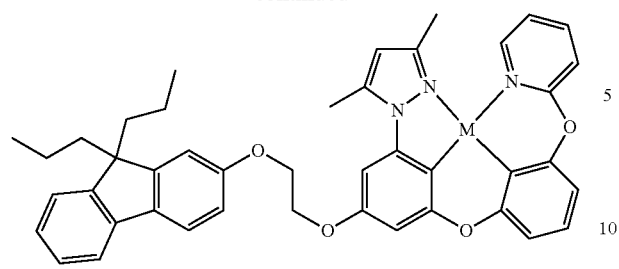
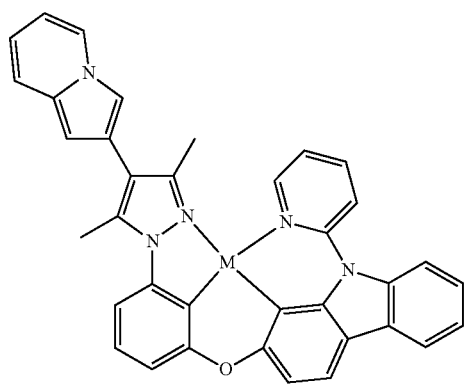
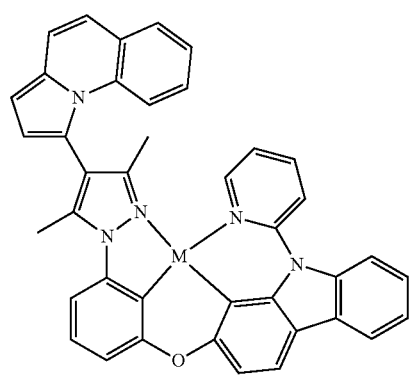
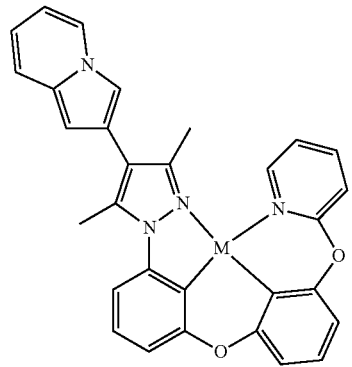
488
-continued
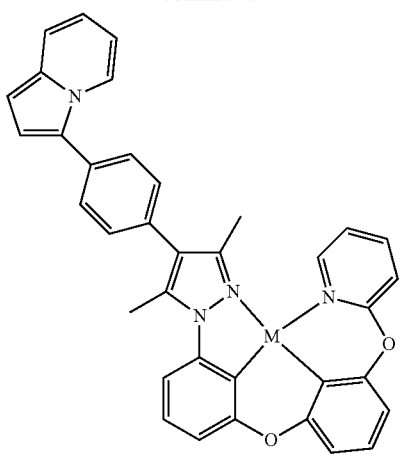
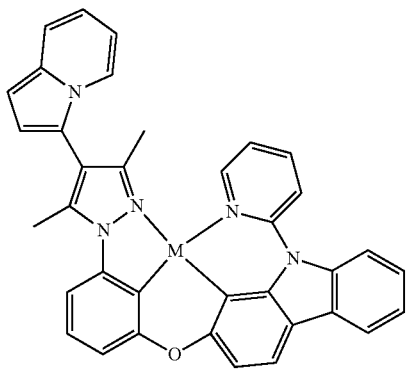
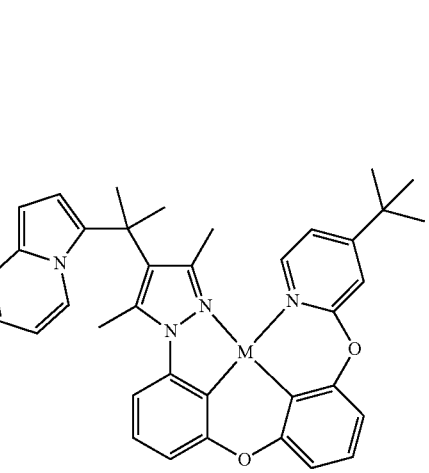
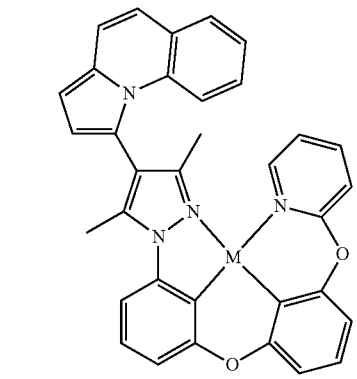

489
-continued
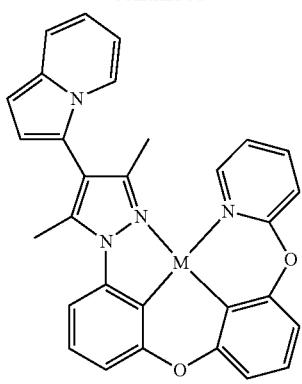
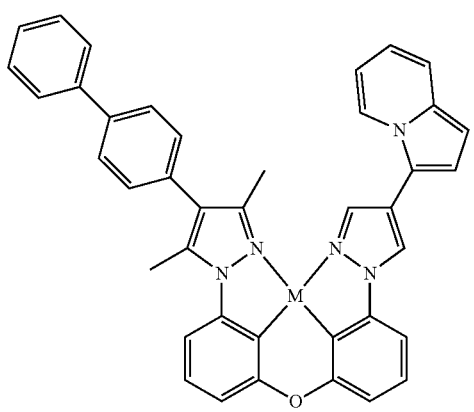
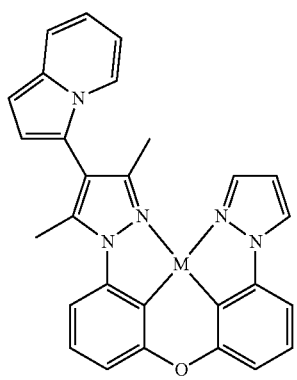
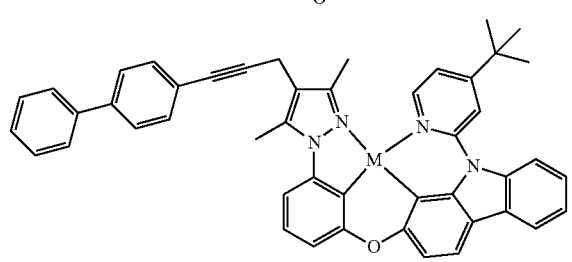
(M = Pt, Pd)
490
-continued
Structures 71
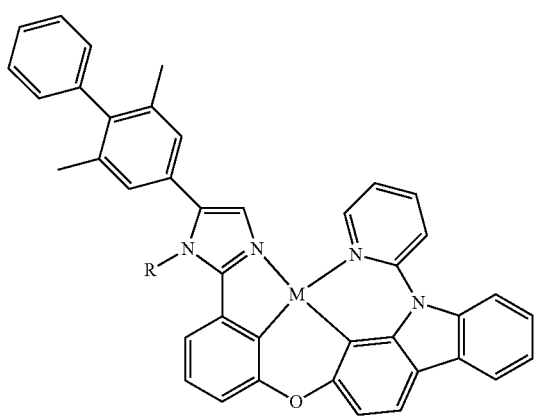
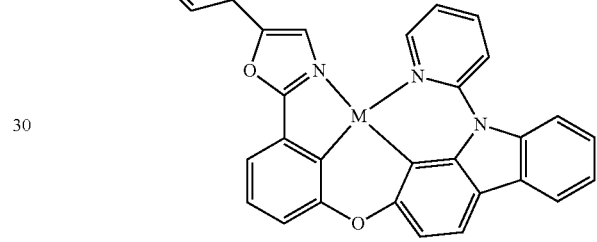
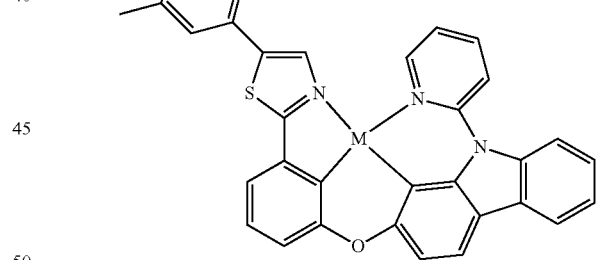
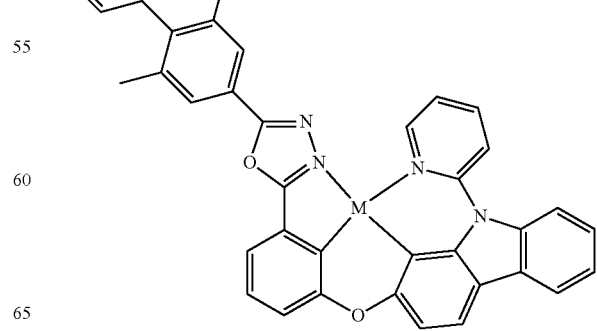

491
-continued
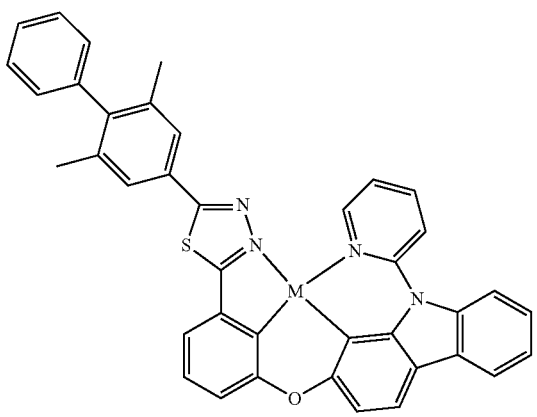
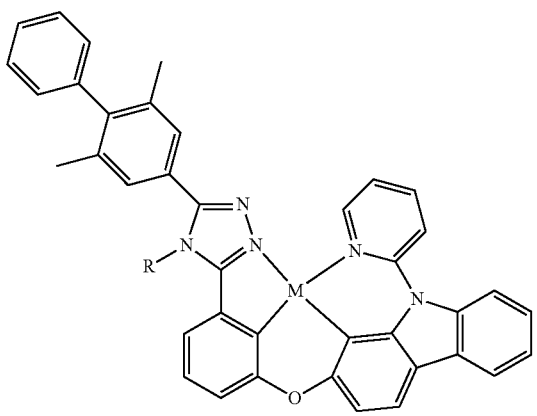
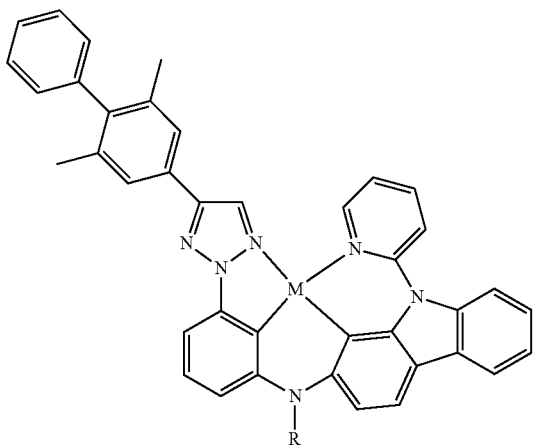
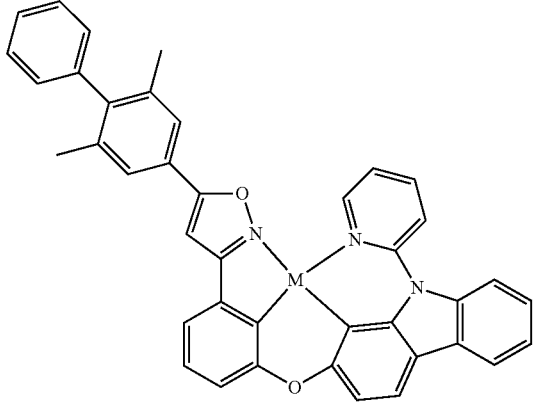
492
-continued
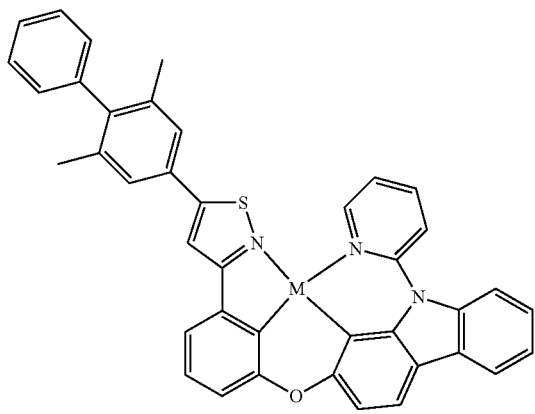
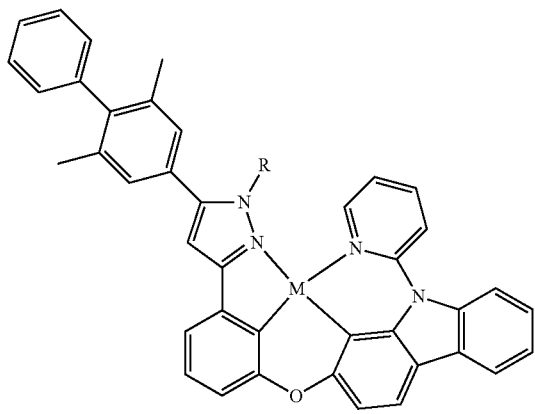
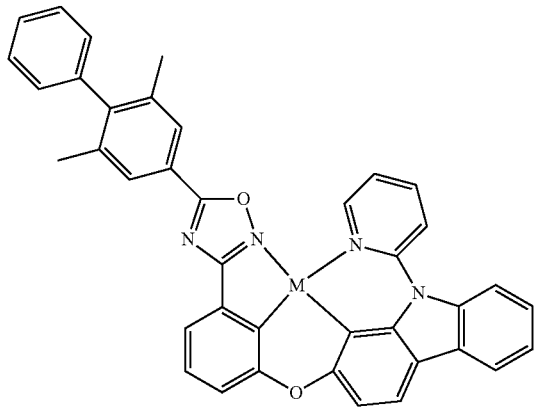
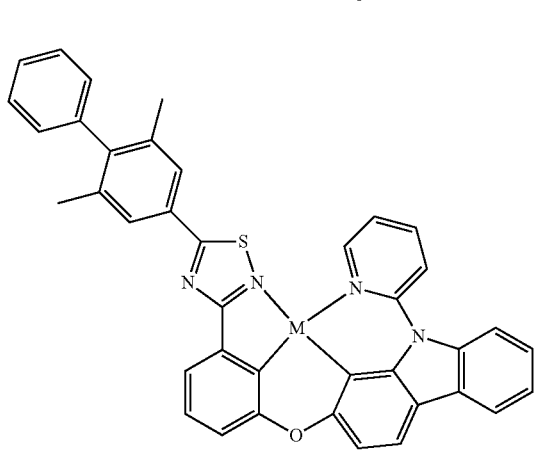

493
-continued
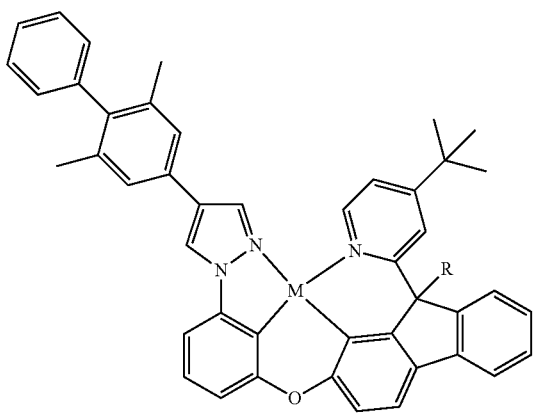
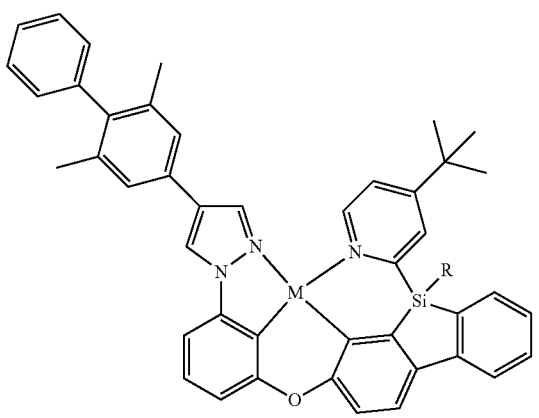
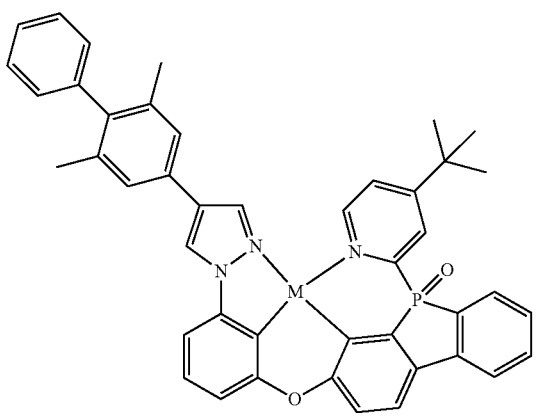
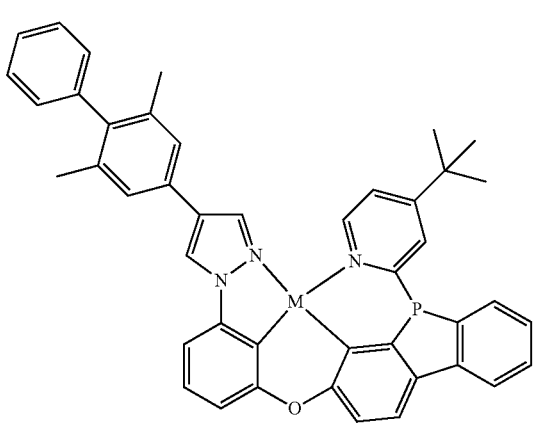
494
-continued
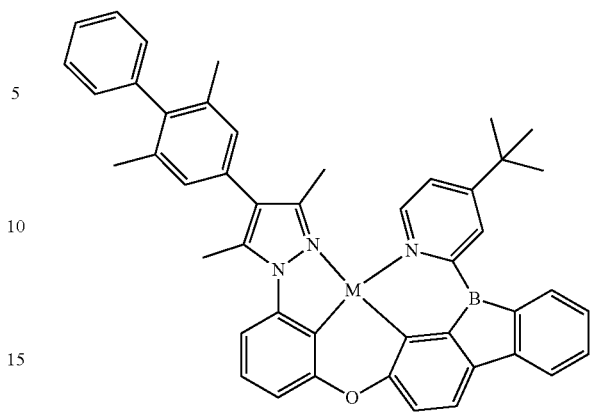
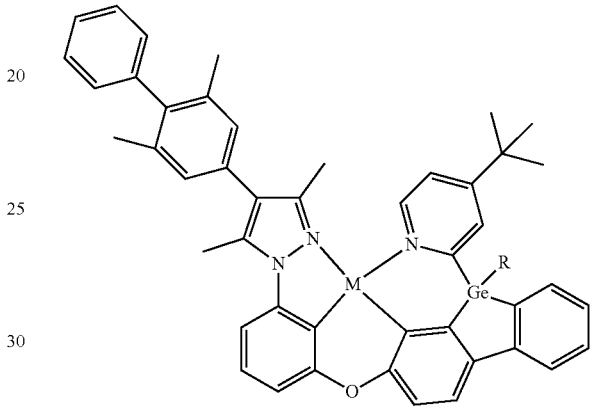
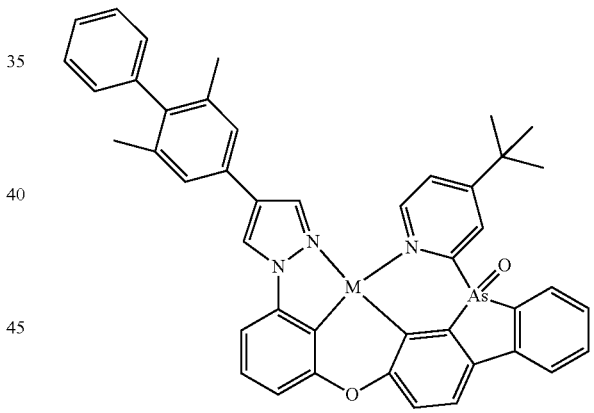
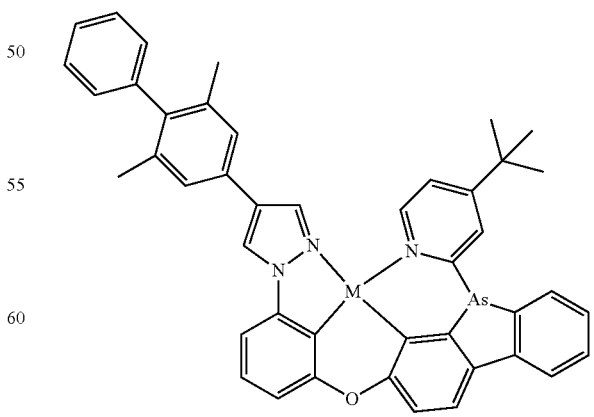
(M = Pt, Pd)

Structures 72
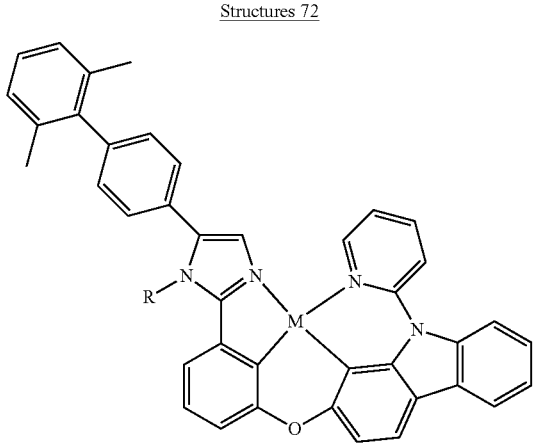
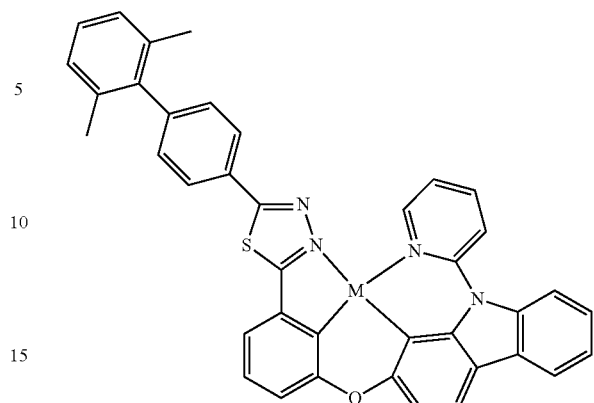
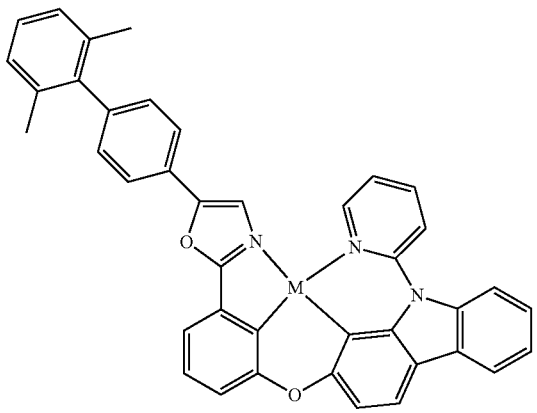
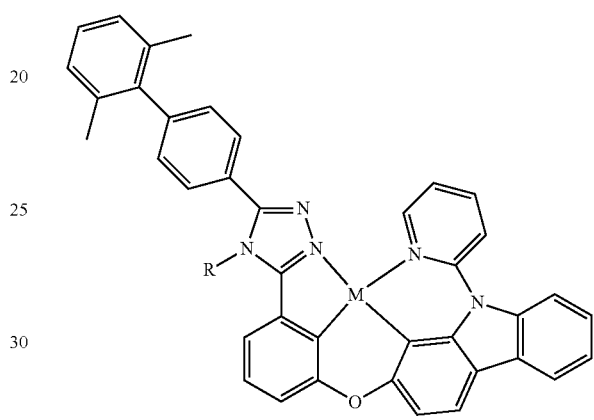
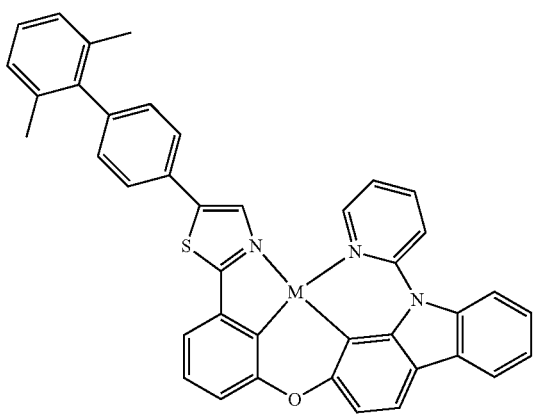
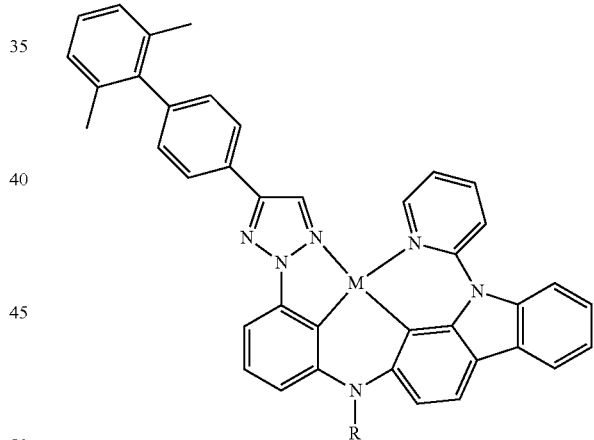
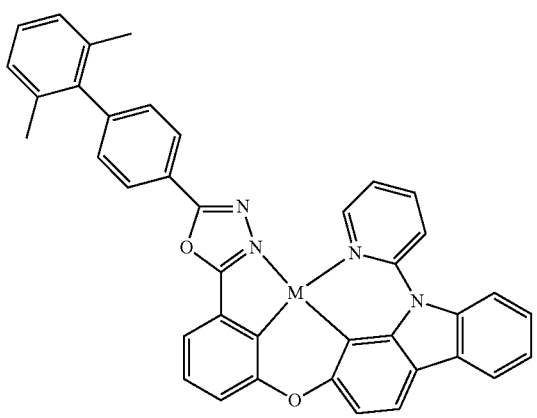
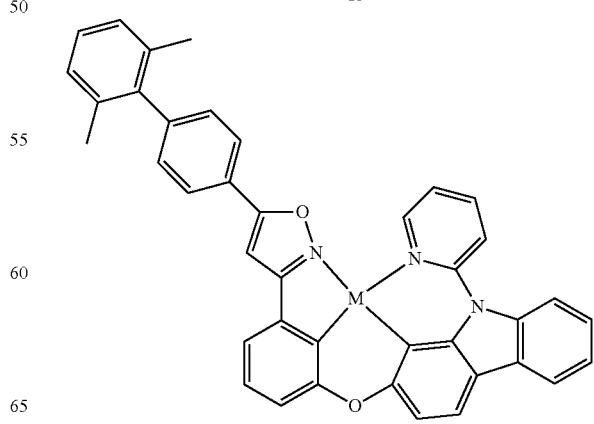

497
-continued
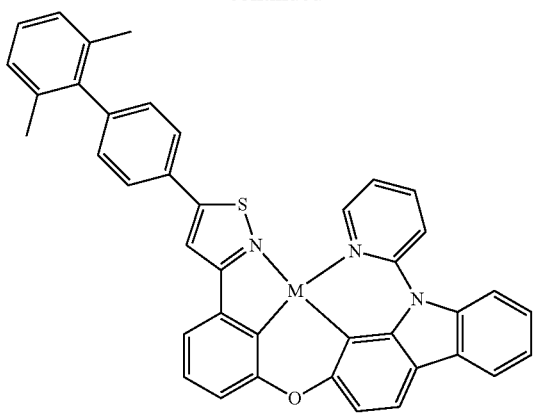
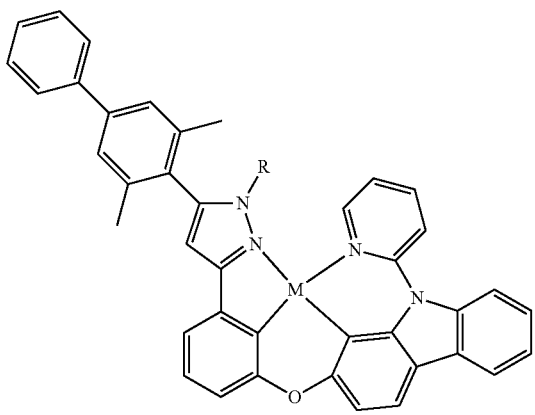
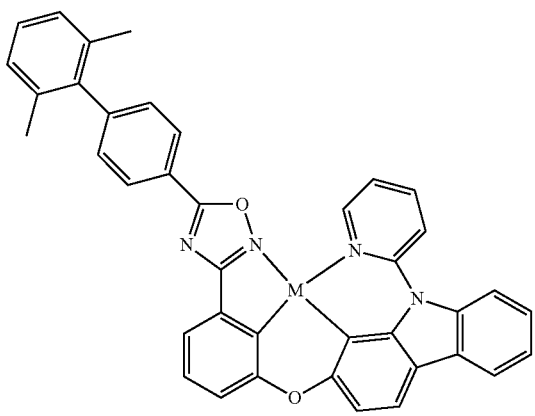
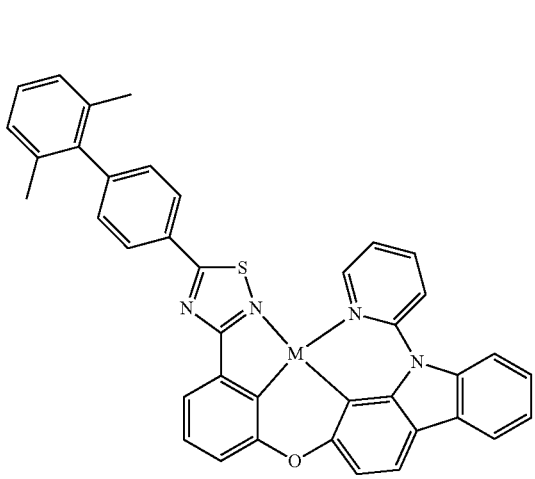
498
-continued
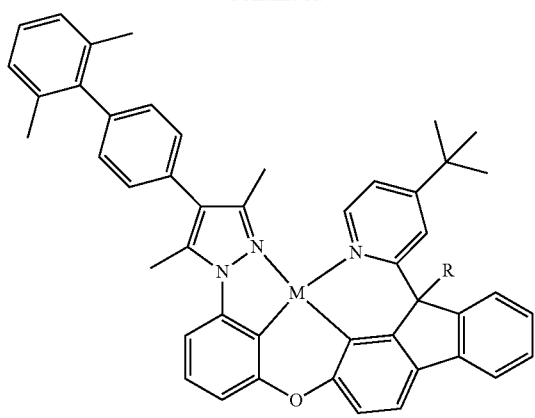
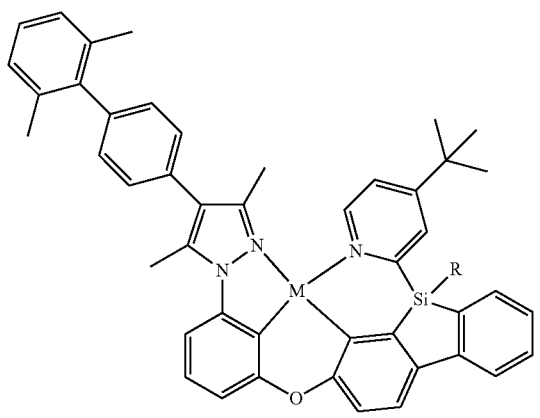
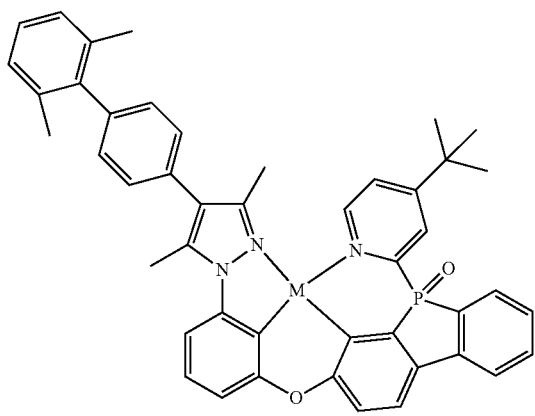
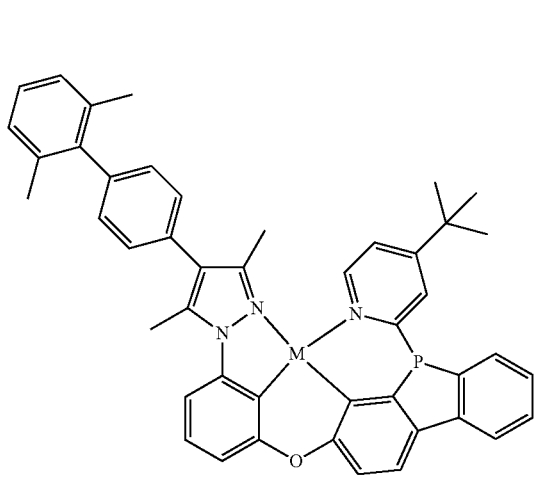

499
-continued
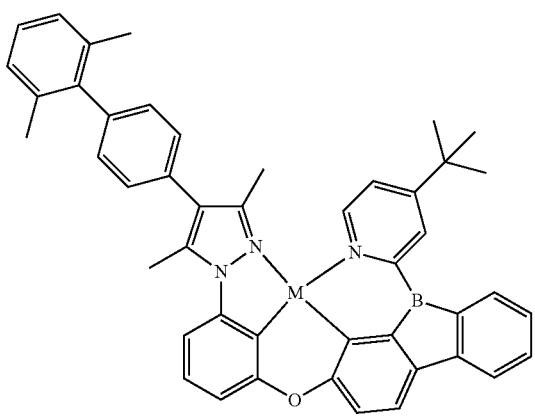
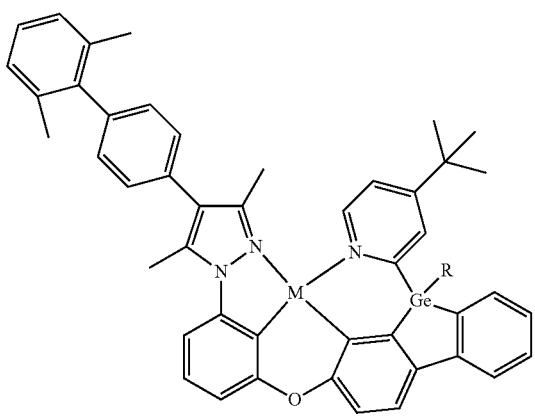
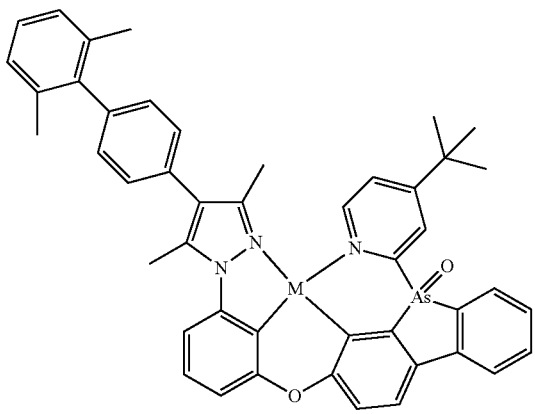
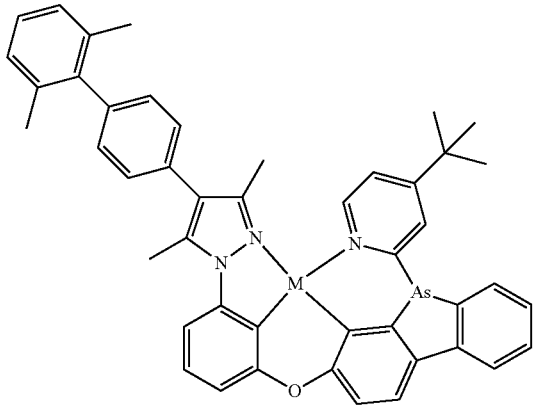
(M = Pt, Pd)
500
-continued
Structures 73
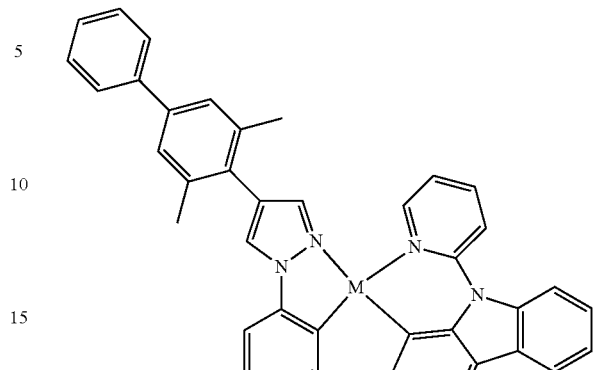
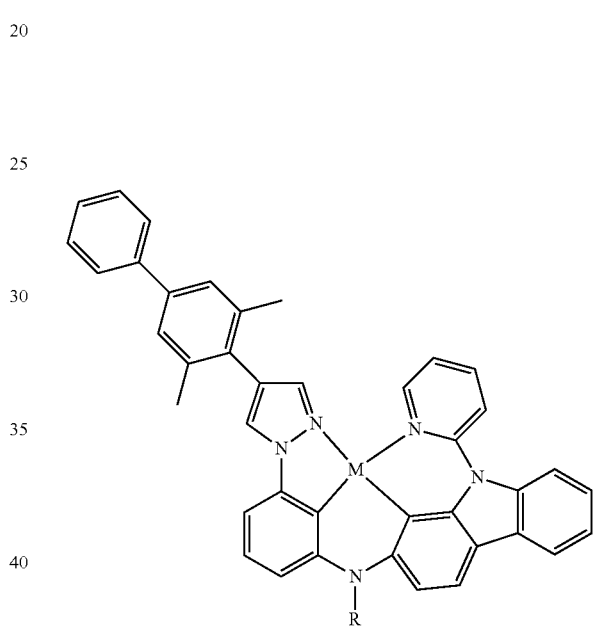
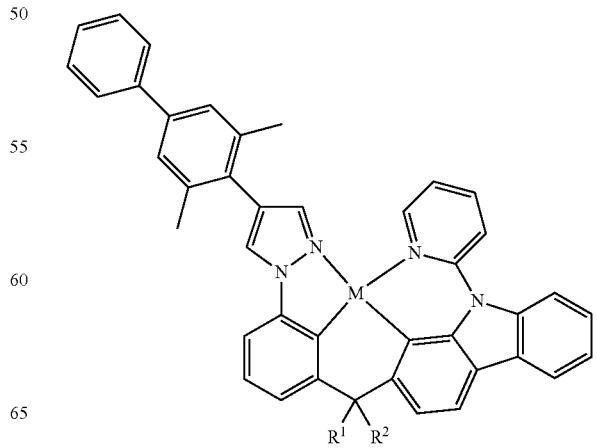

501
-continued
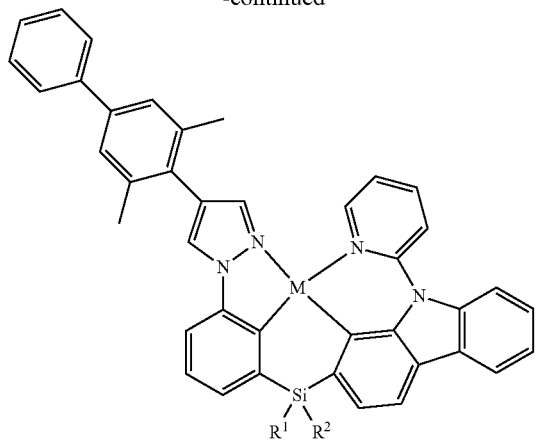
502
-continued
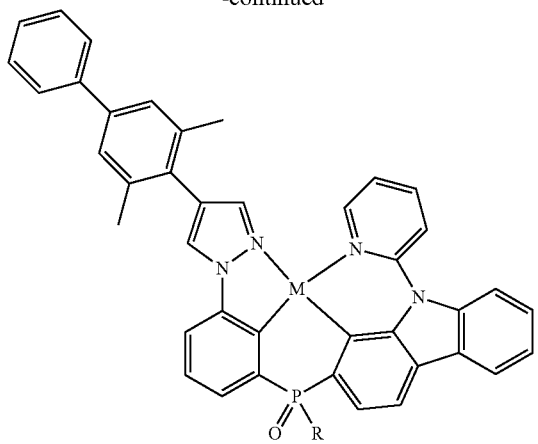
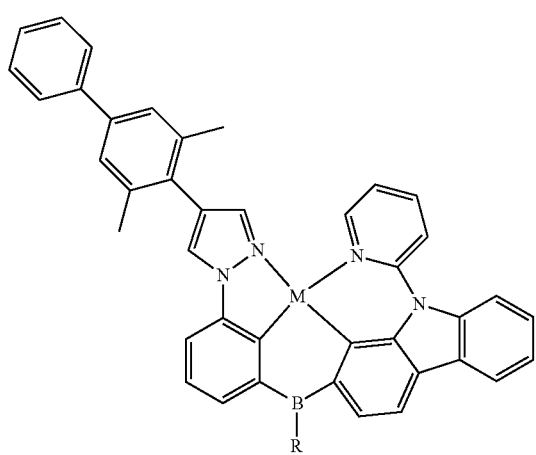
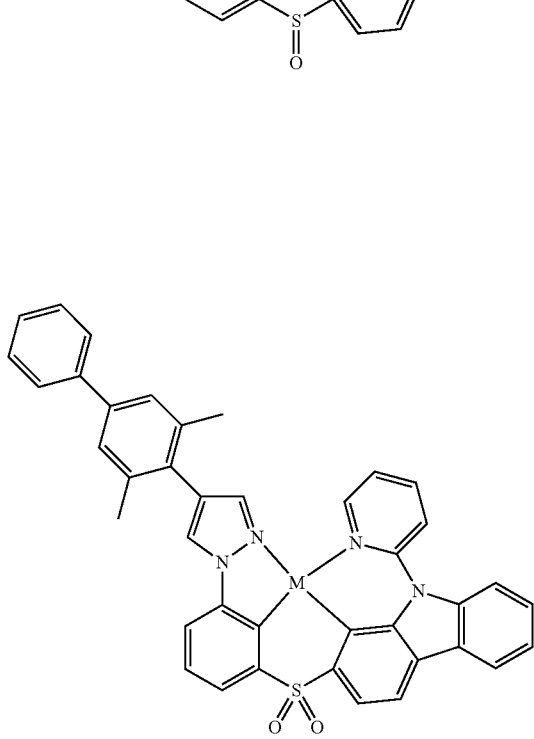
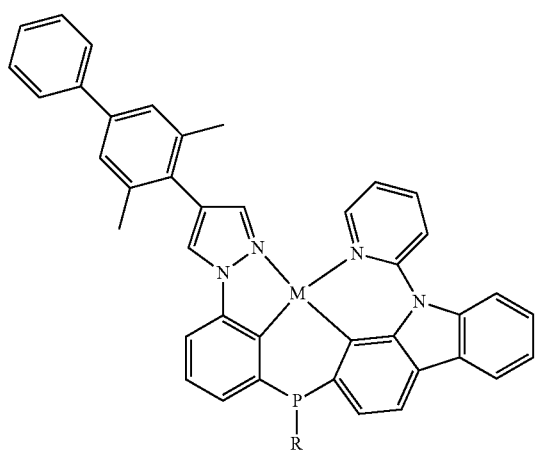

503
-continued
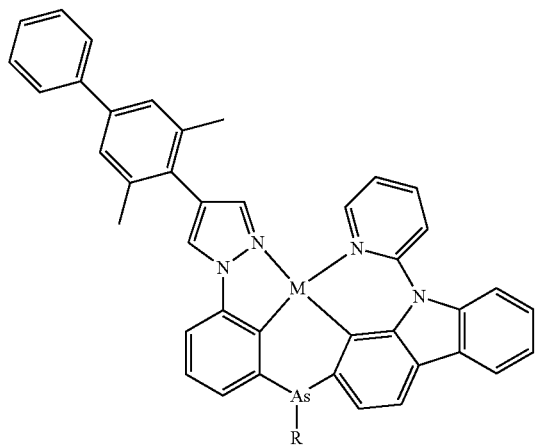
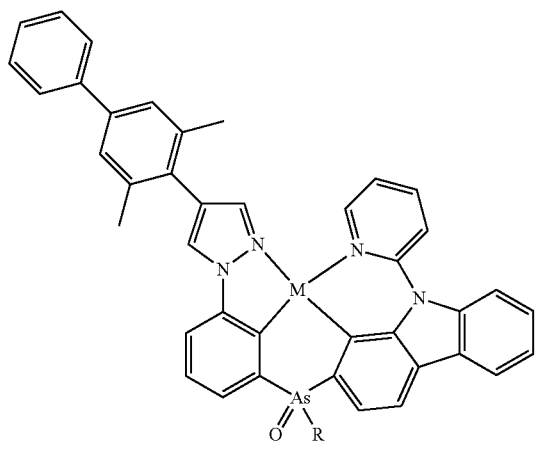
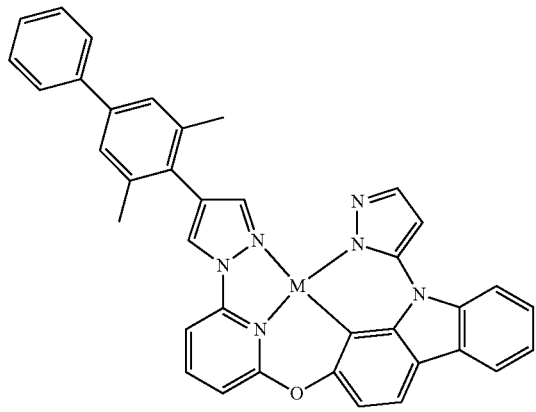
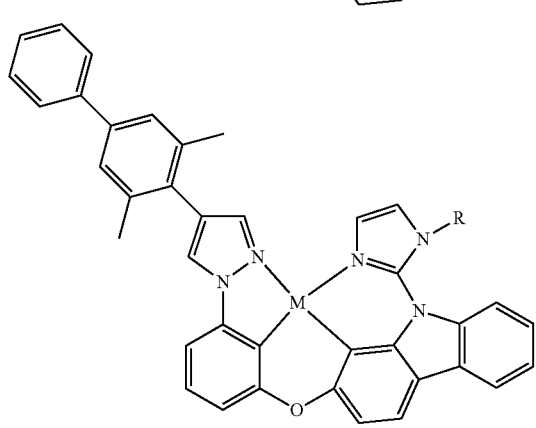
504
-continued
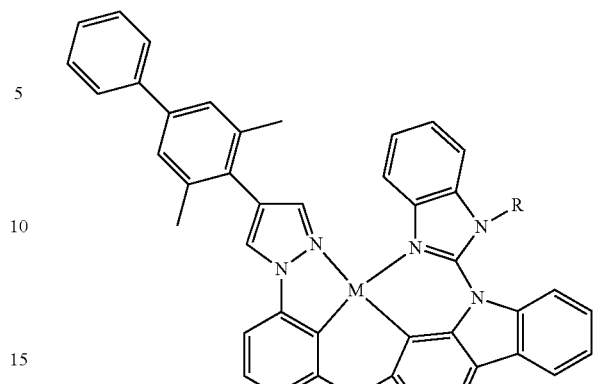
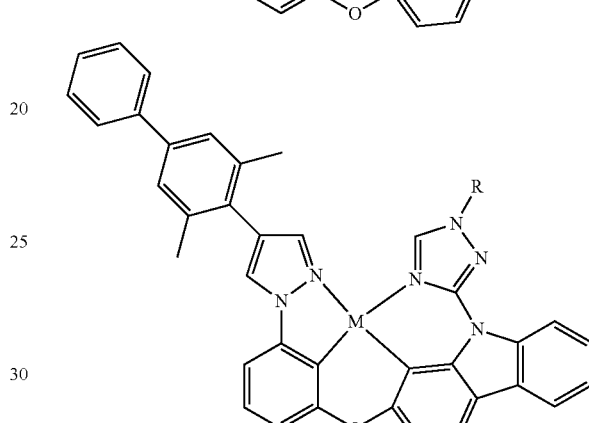
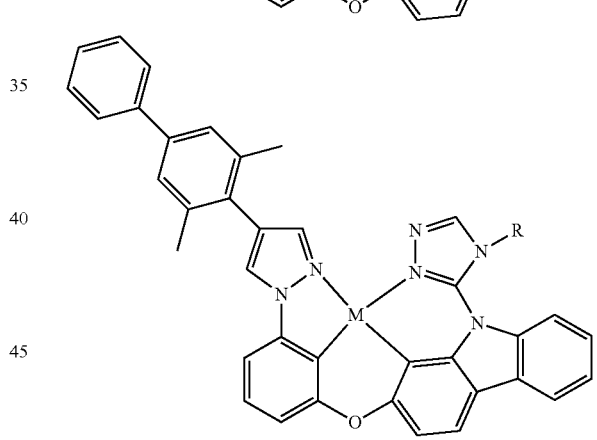
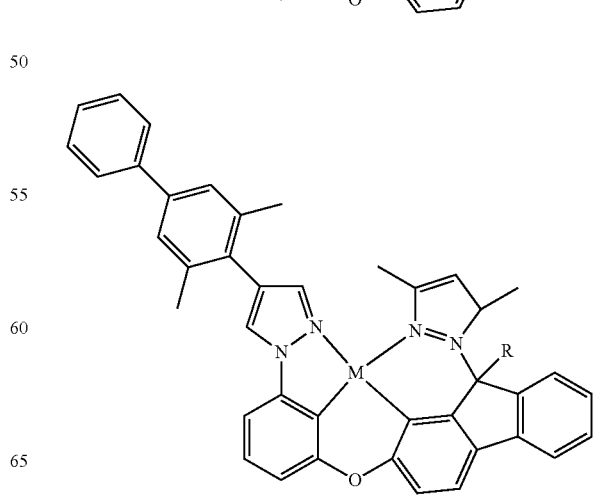

505
-continued
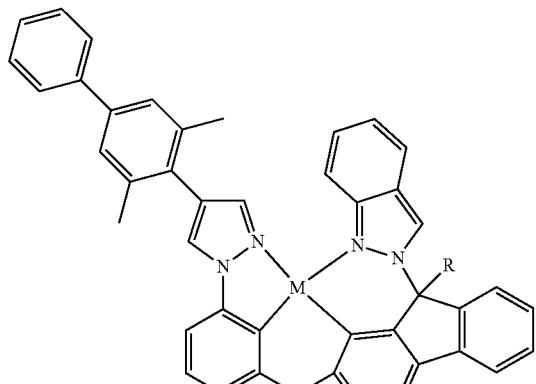
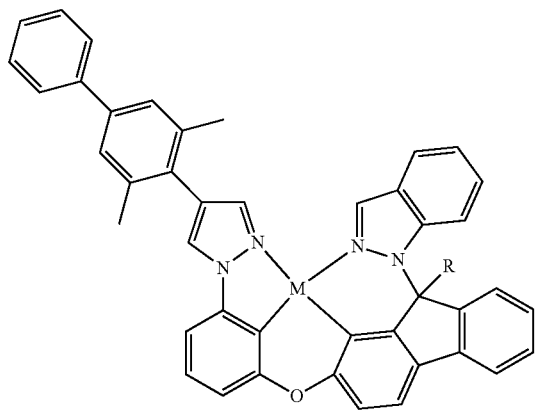
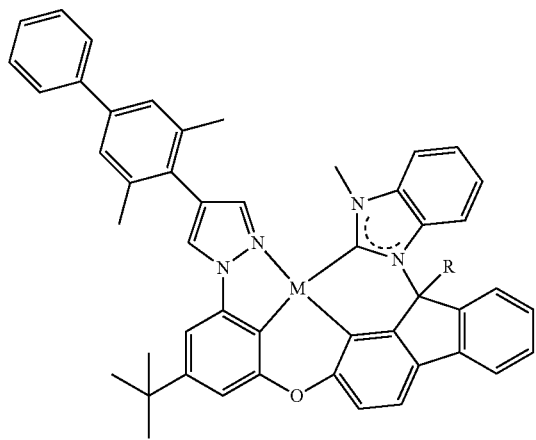
(M = Pt, Pd)
506
-continued
Structures 74
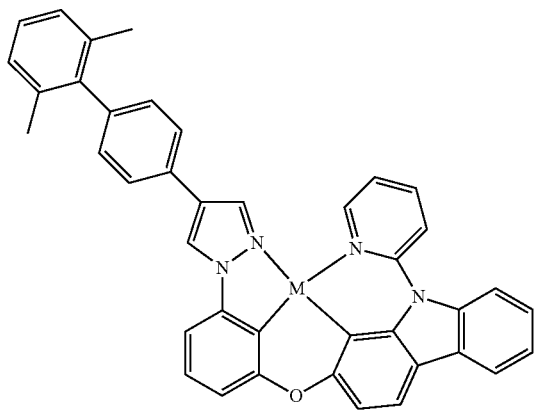
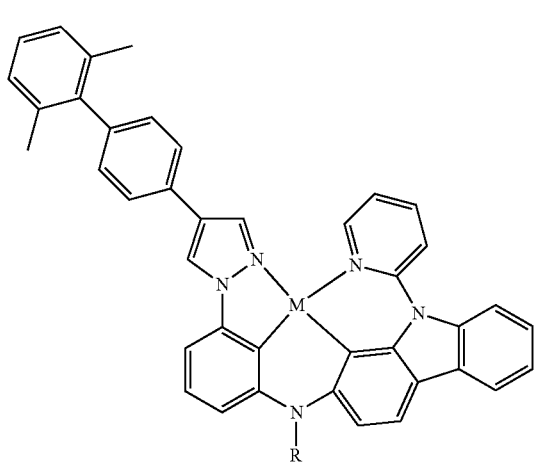
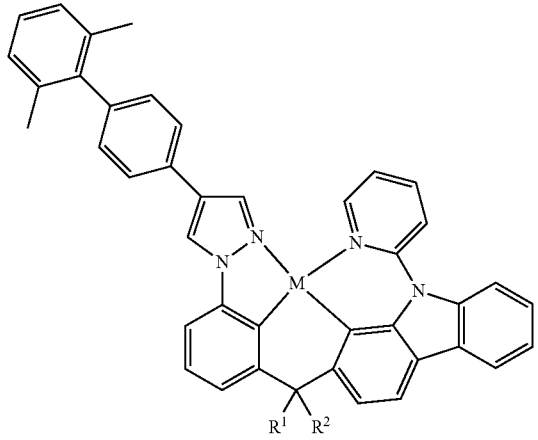

507
-continued
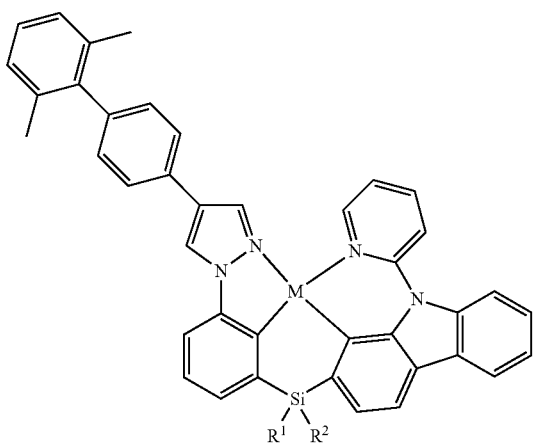
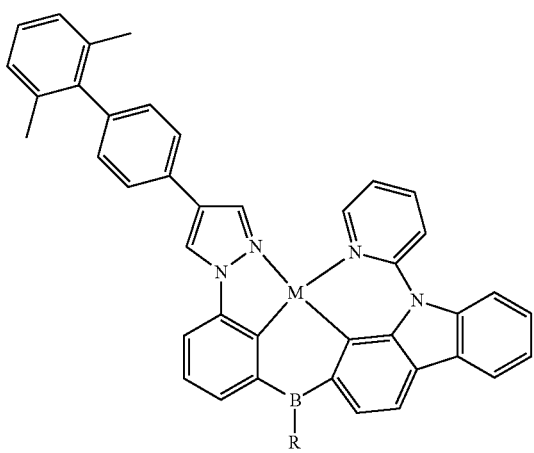
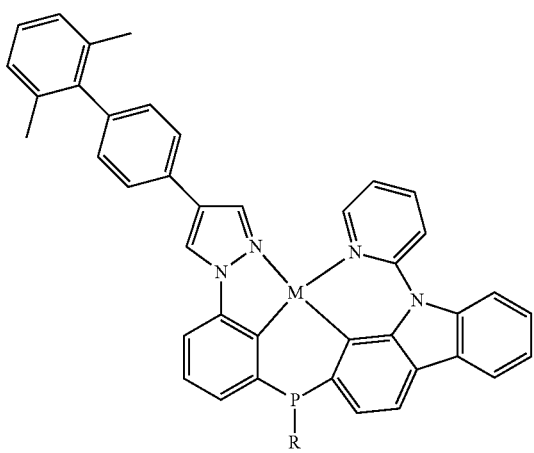
508
-continued
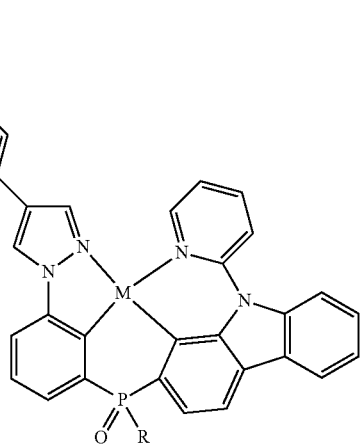
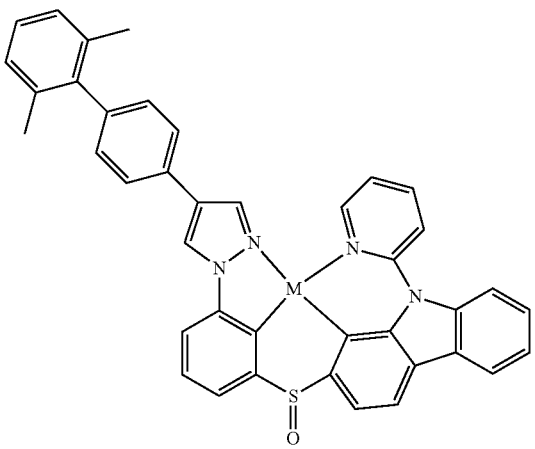
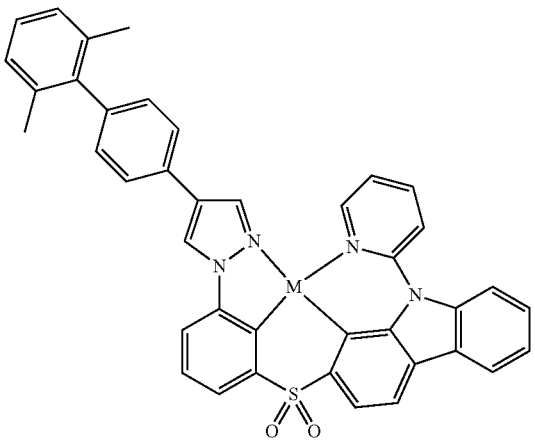

509
-continued
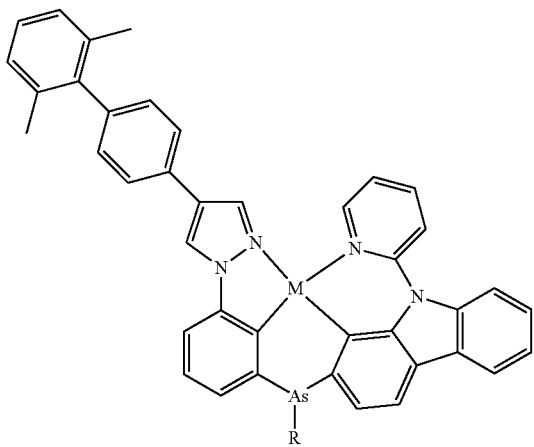
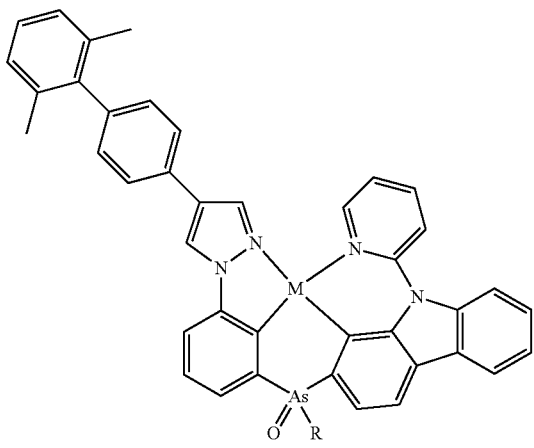
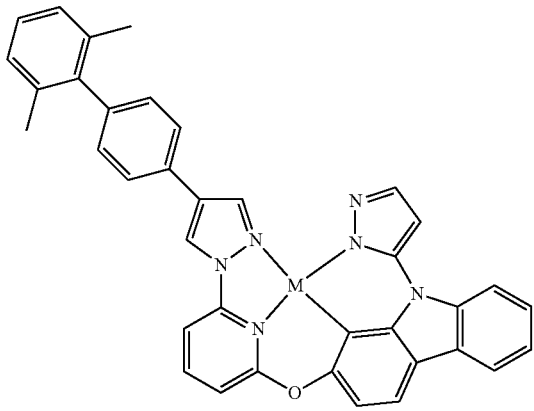
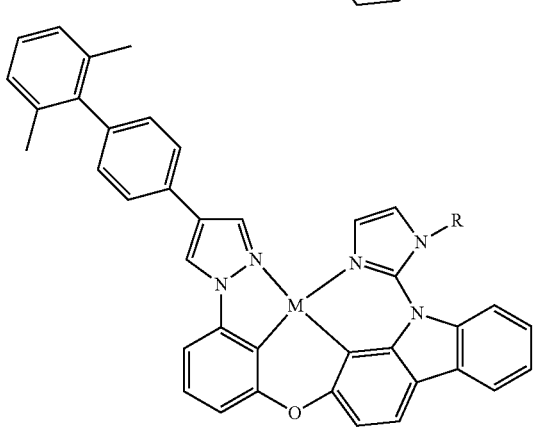
510
-continued
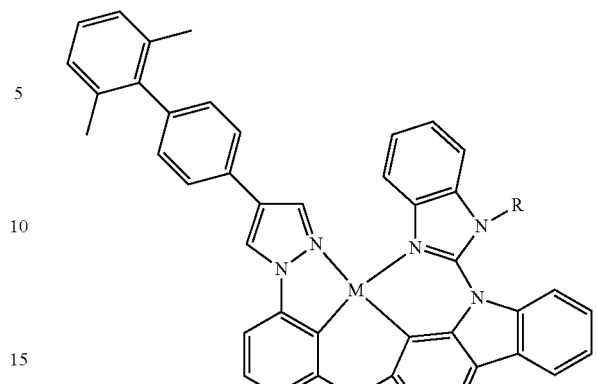
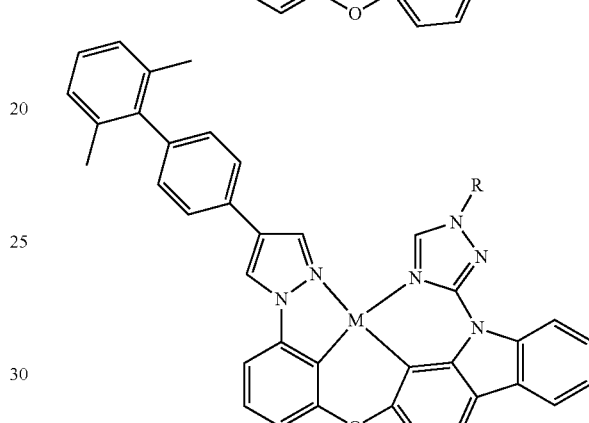
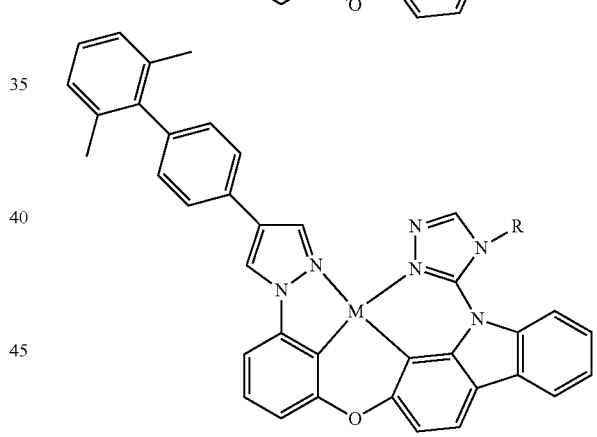
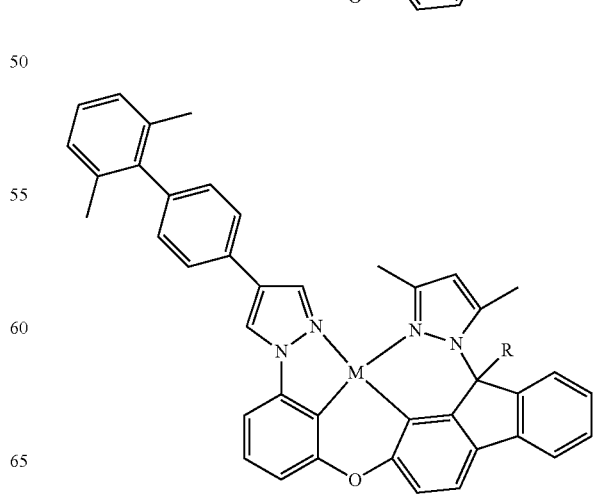

511
-continued
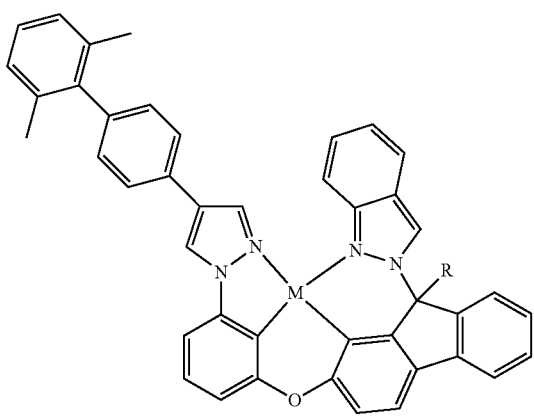
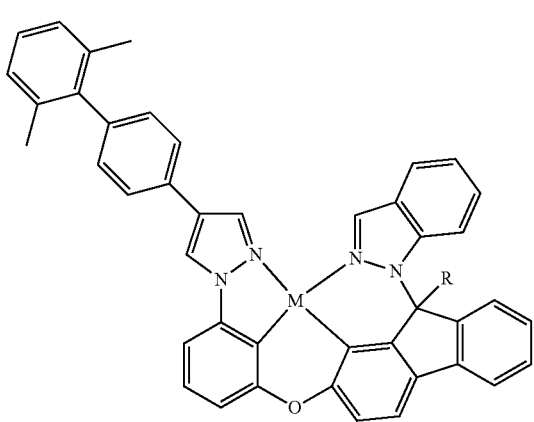
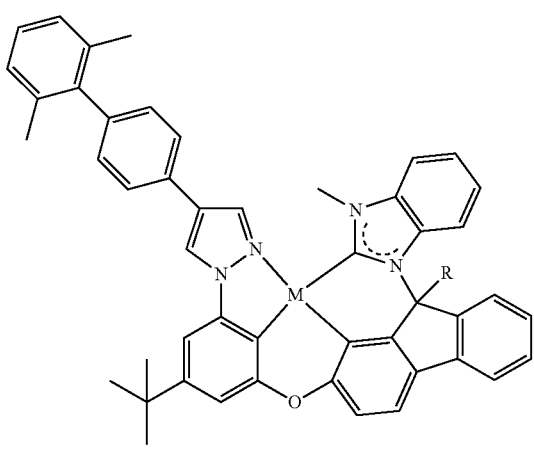
(M = Pt, Pd)
512
-continued
Structures 75
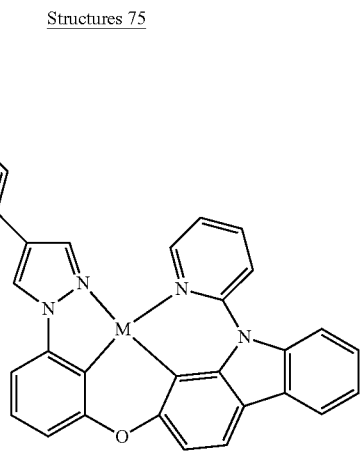
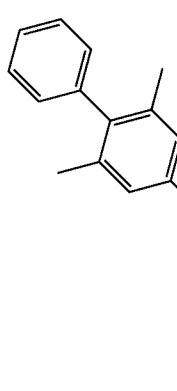
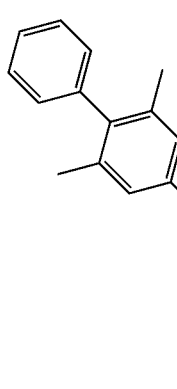

513
-continued

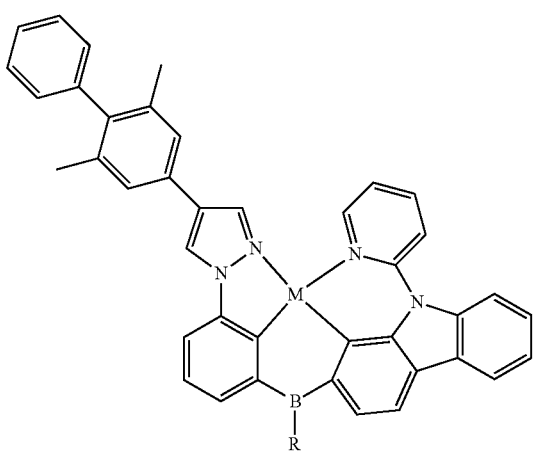
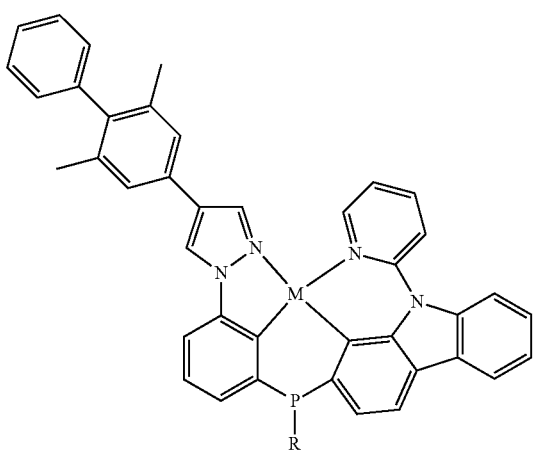
514
-continued

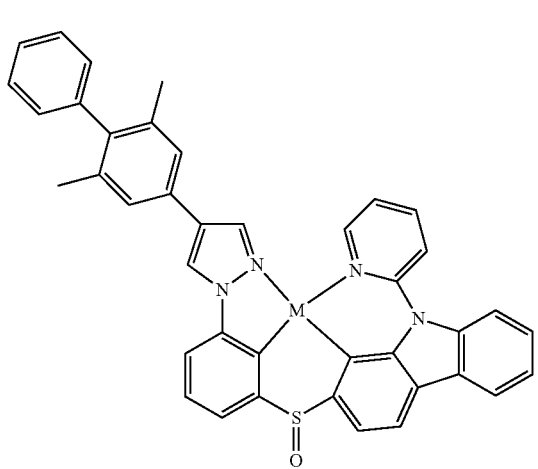
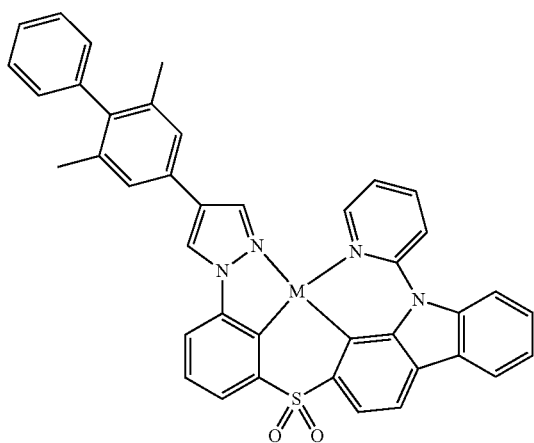

515
-continued
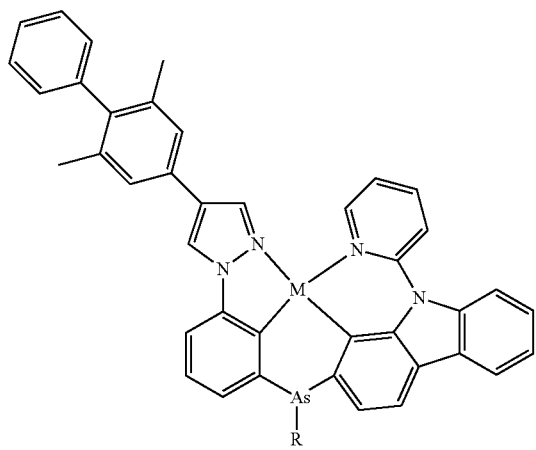
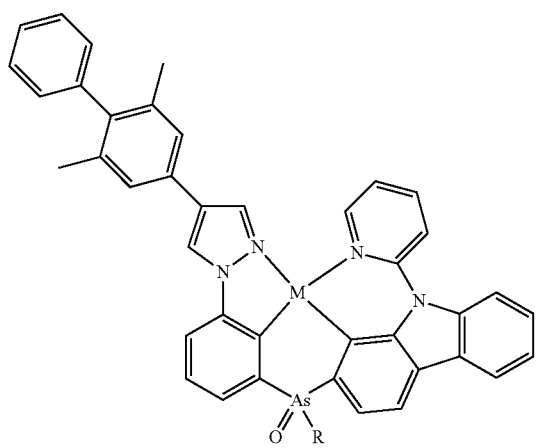
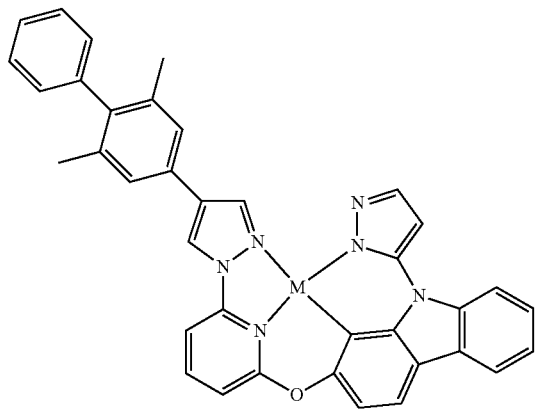
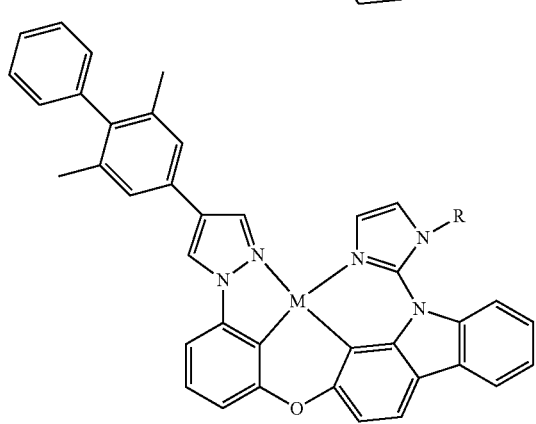
516
-continued
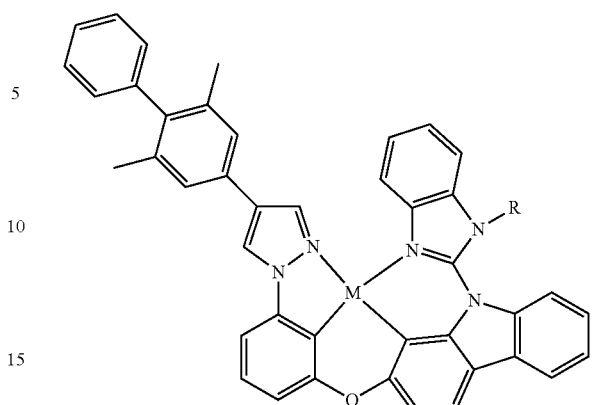
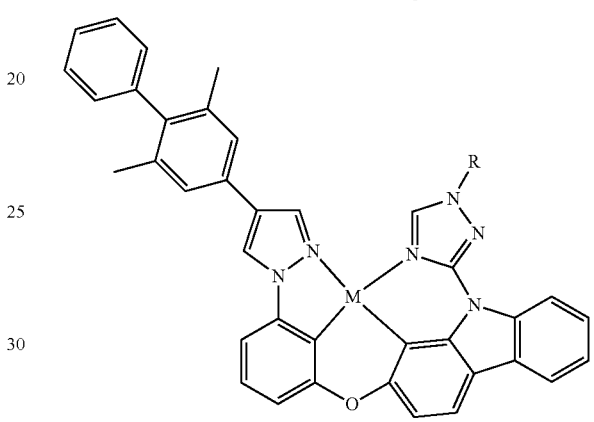
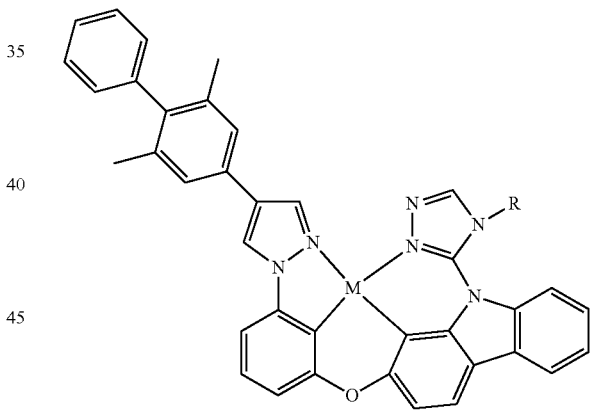
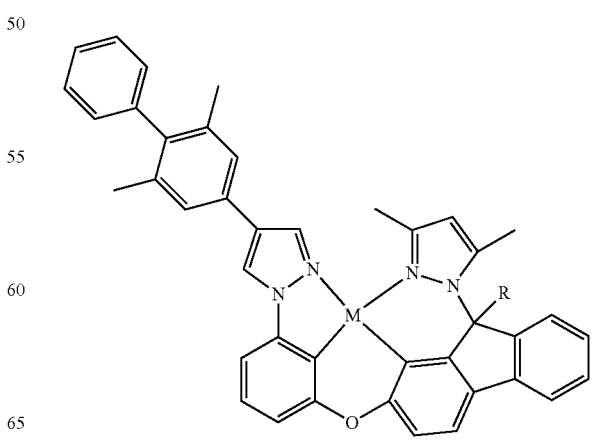

517
-continued
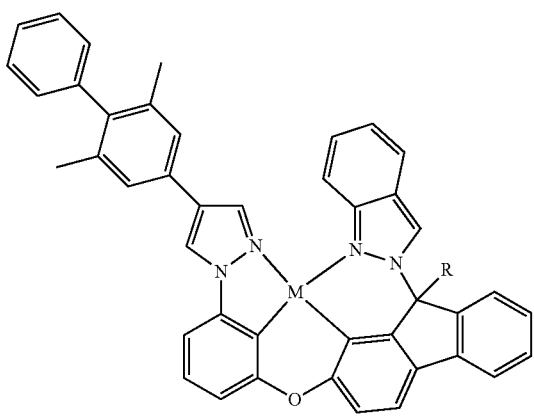
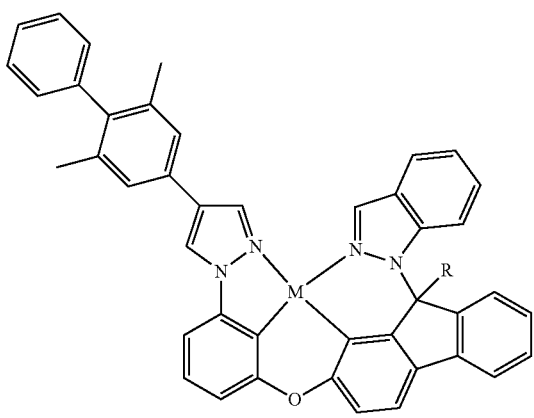
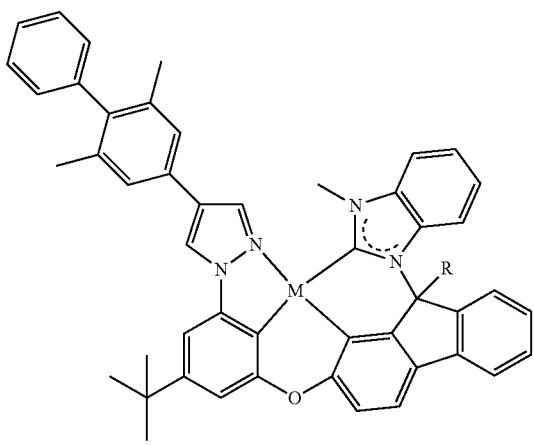
(M = Pt, Pd)
518
-continued
Structures 76
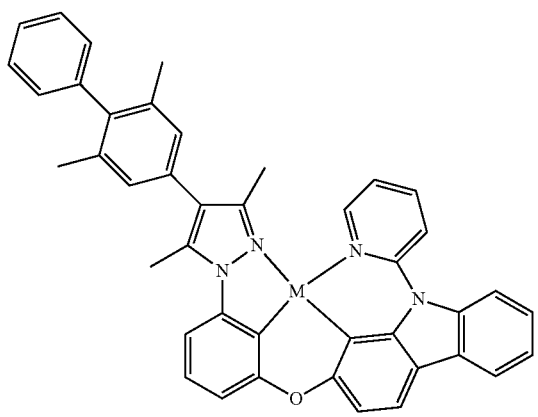
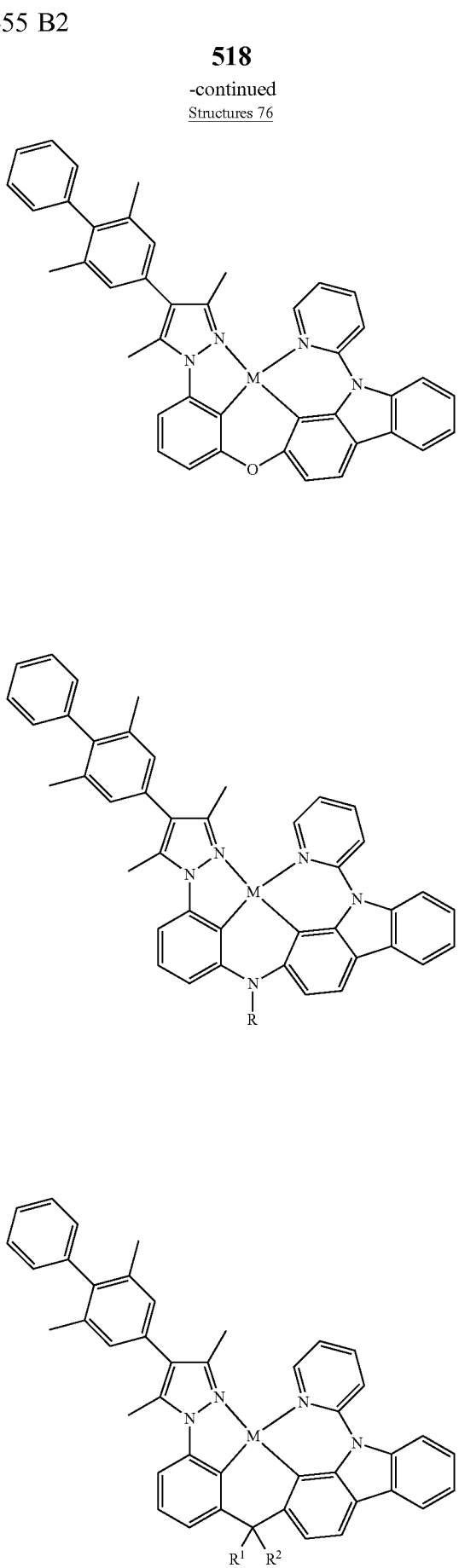

519
-continued
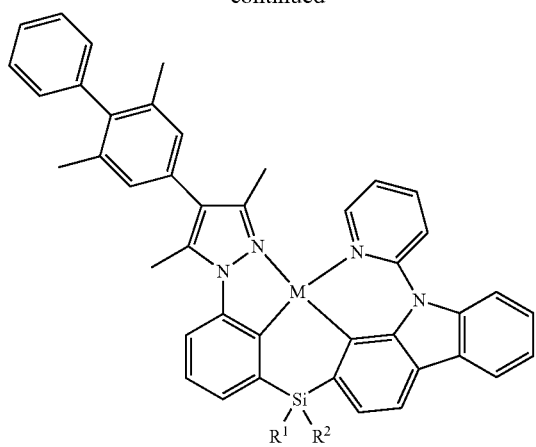
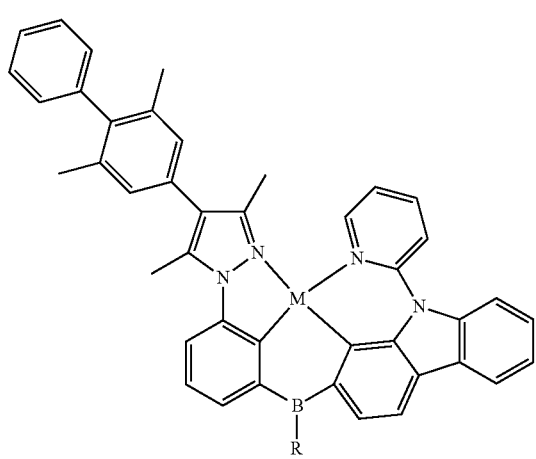
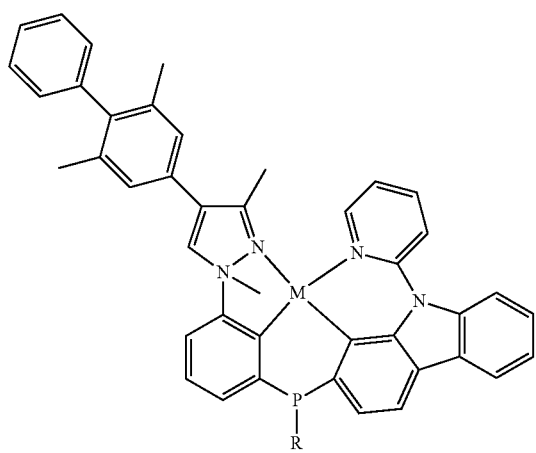
520
-continued
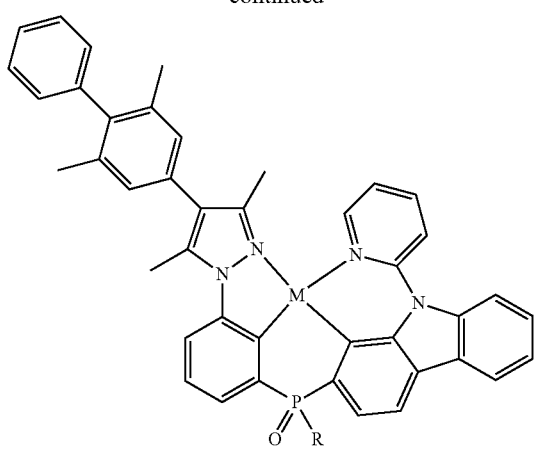
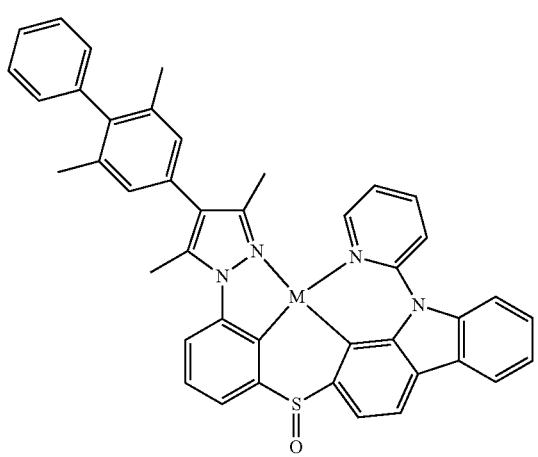
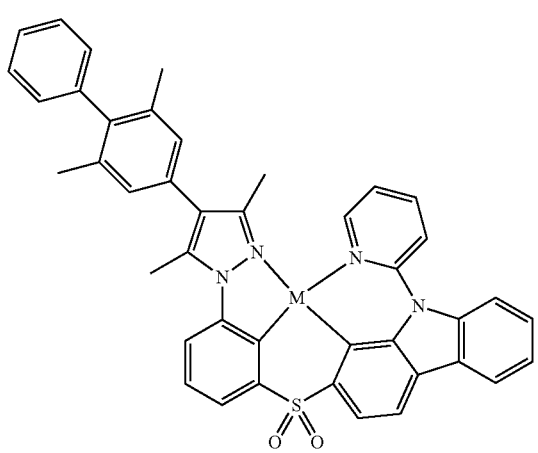

521
-continued
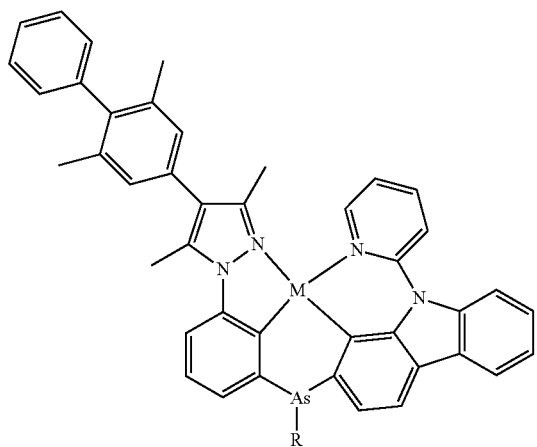
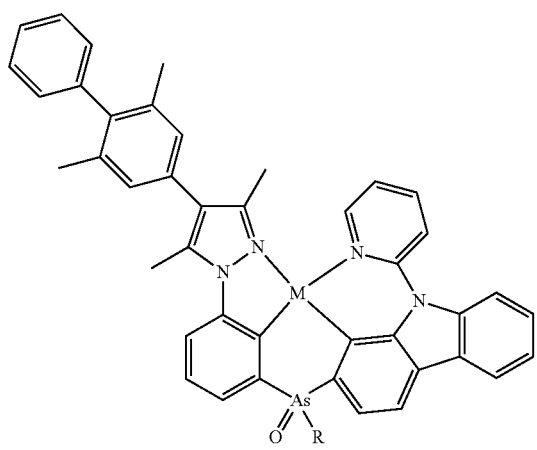
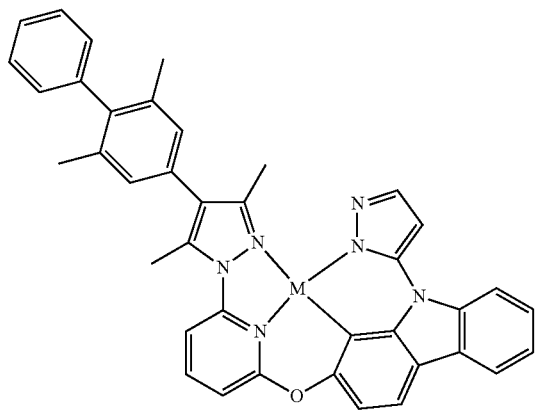
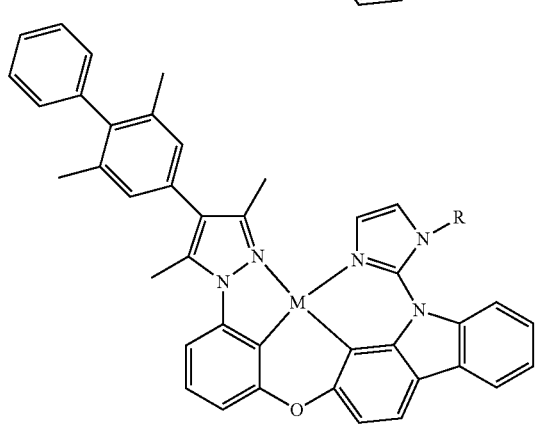
522
-continued
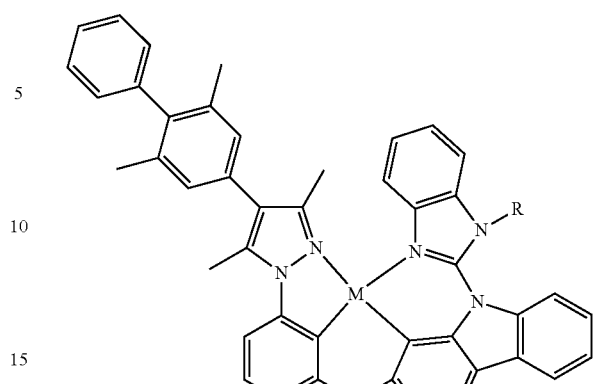
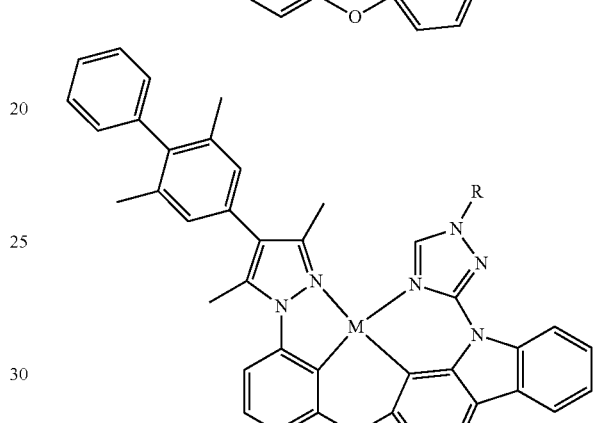
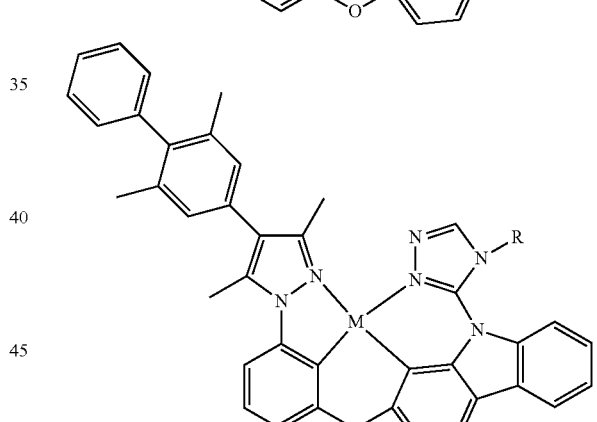
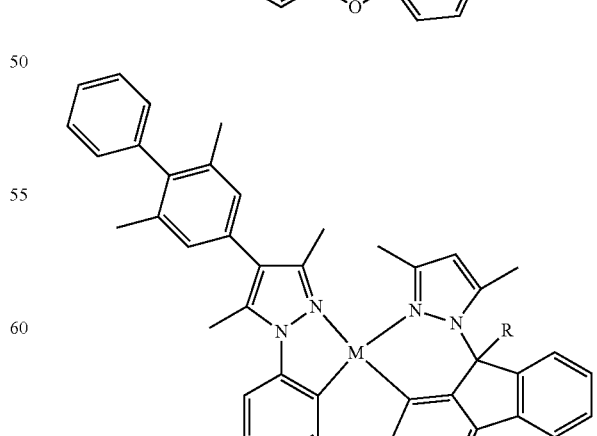

523
-continued
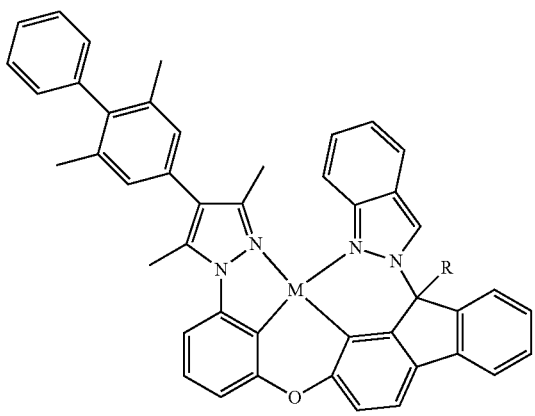
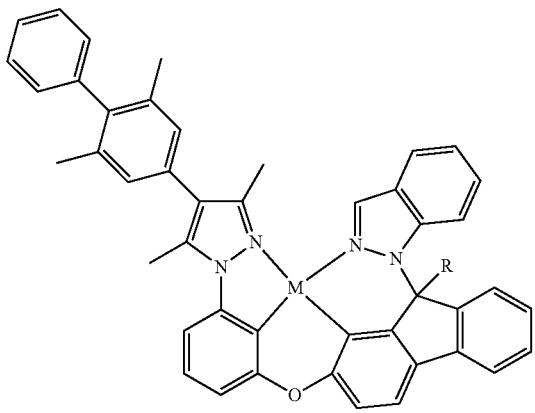
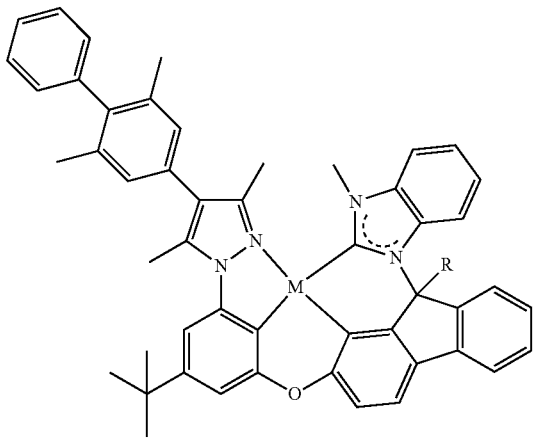
(M = Pt, Pd)
524
-continued
Structures 77
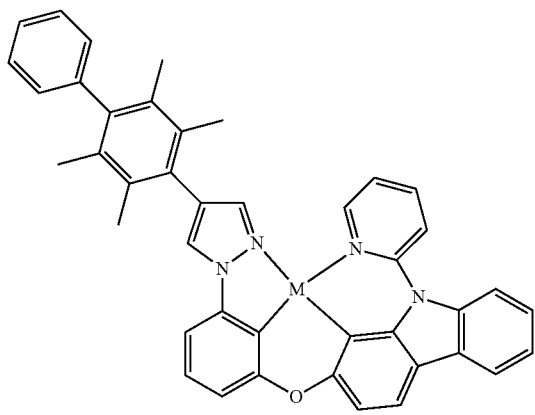
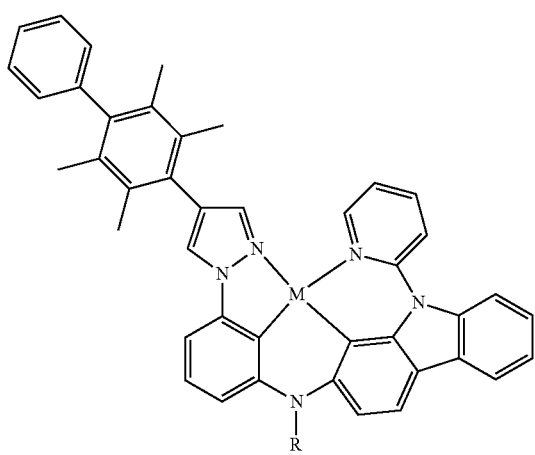
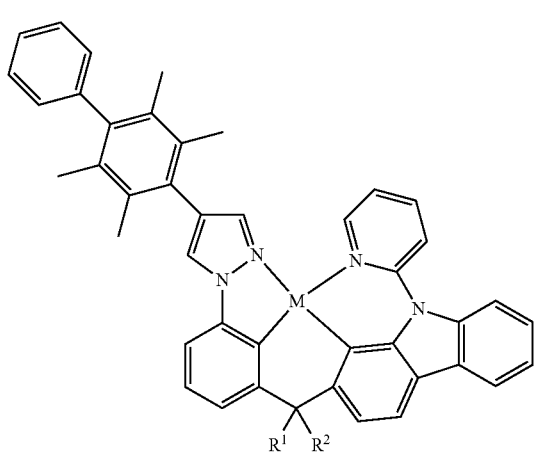

525
-continued
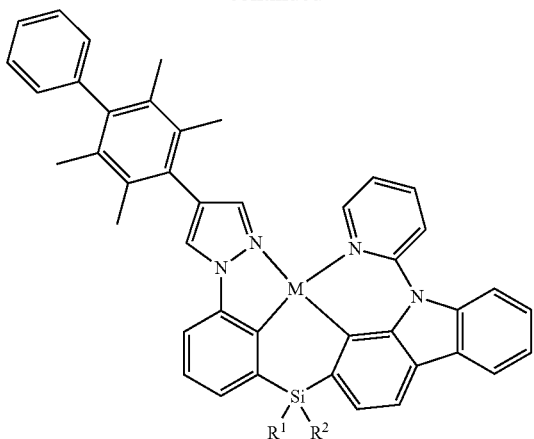
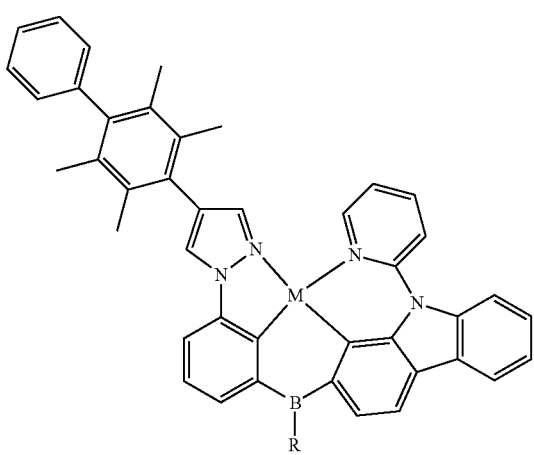
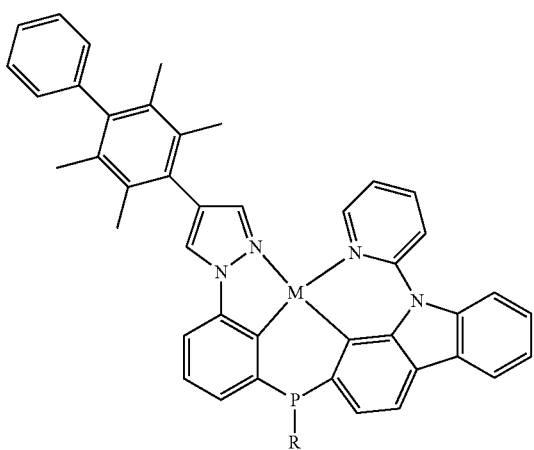
526
-continued
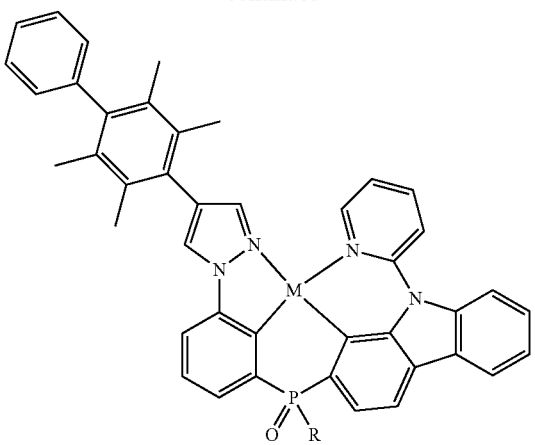
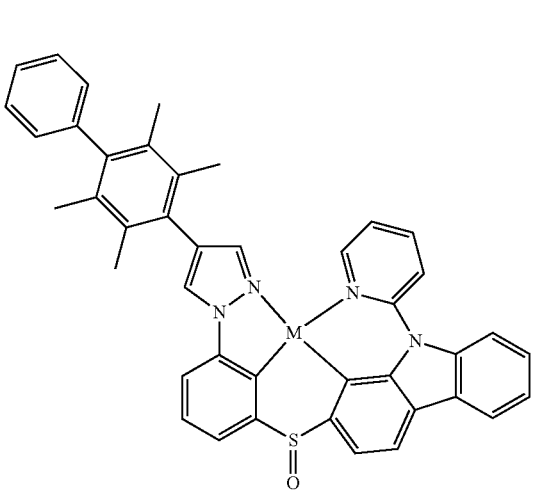
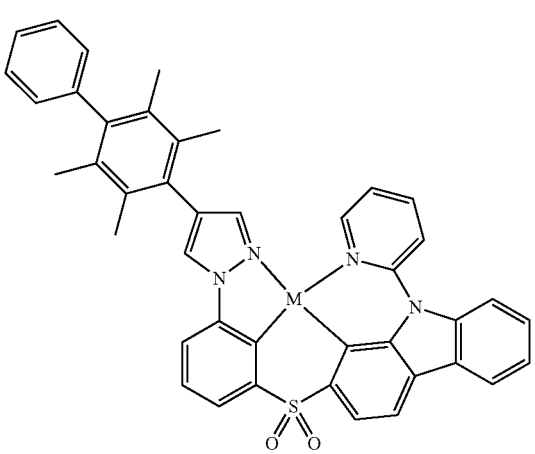

527
-continued
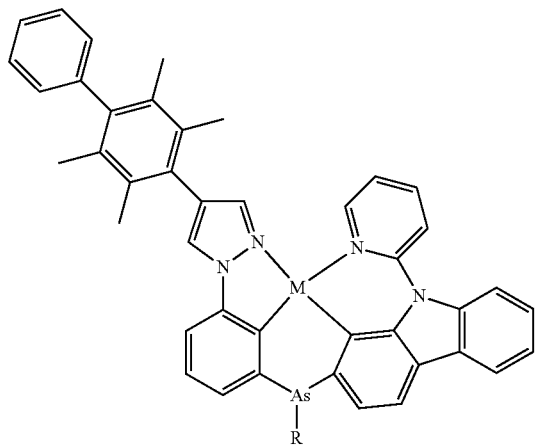
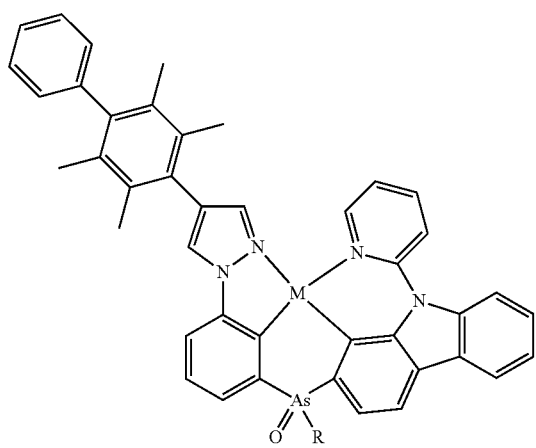
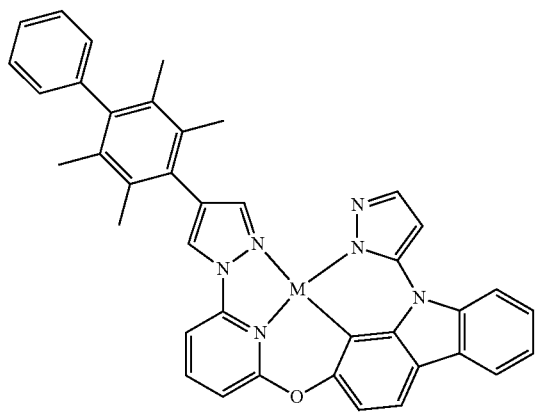
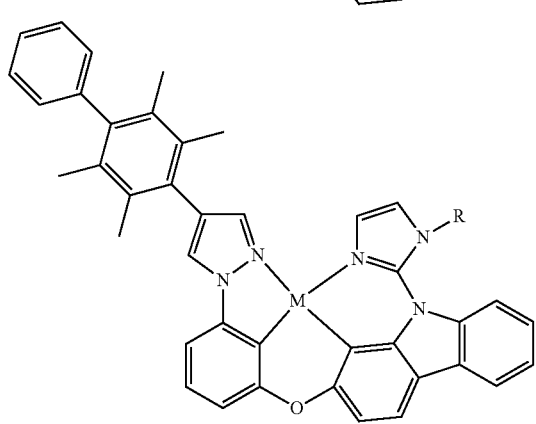
528
-continued
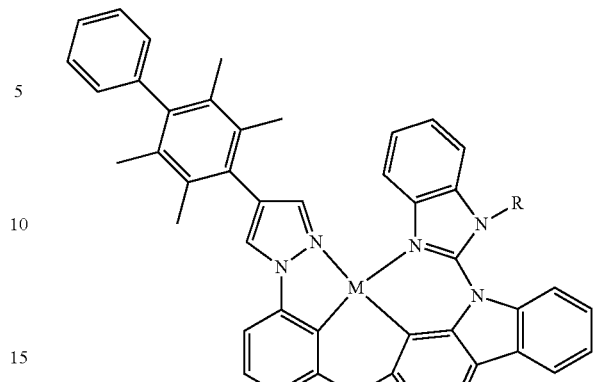
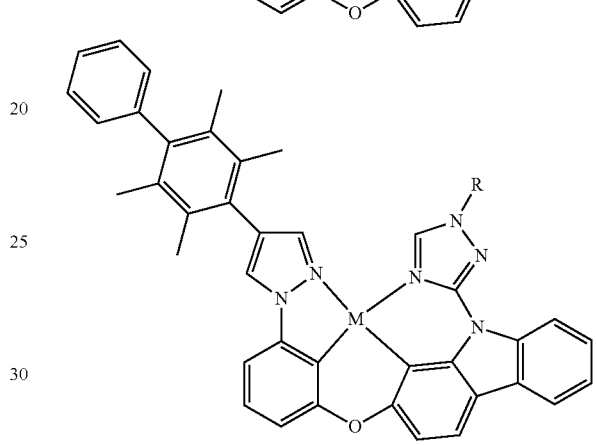
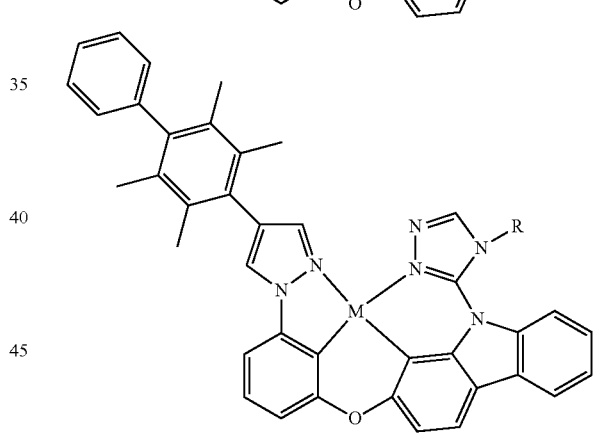
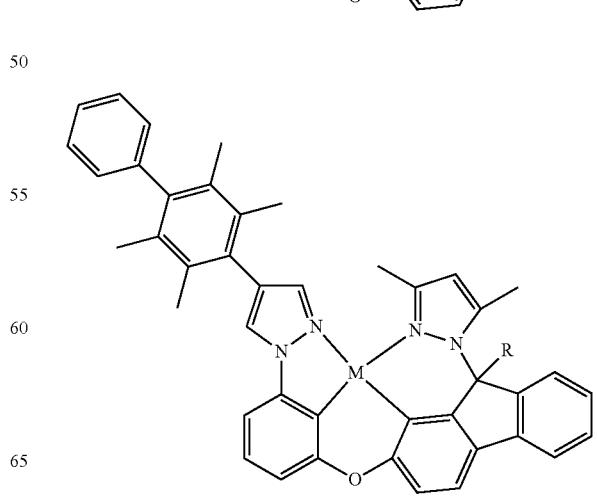

529
-continued
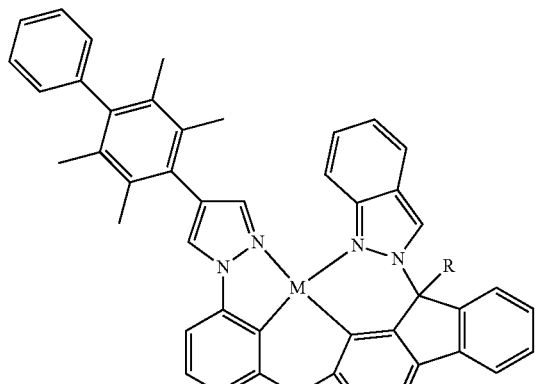
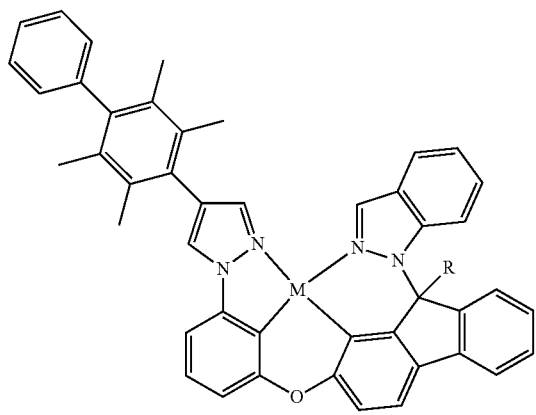
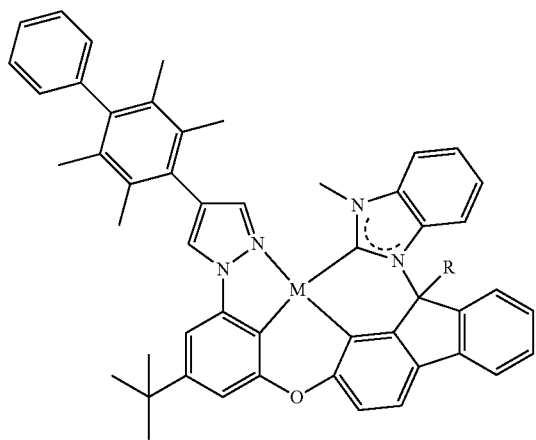
(M = Pt, Pd)
530
-continued
Structures 78
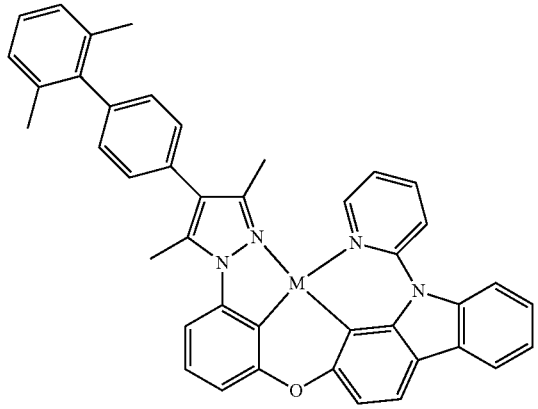

531
-continued
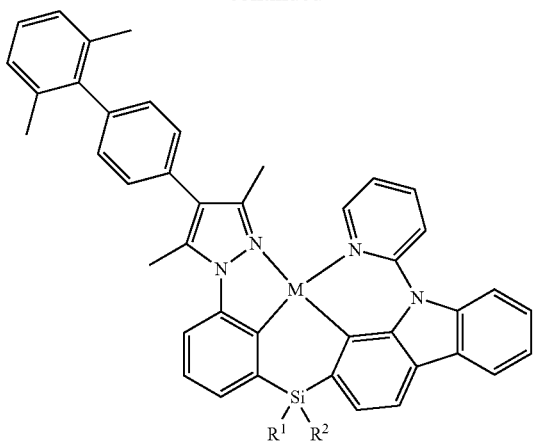
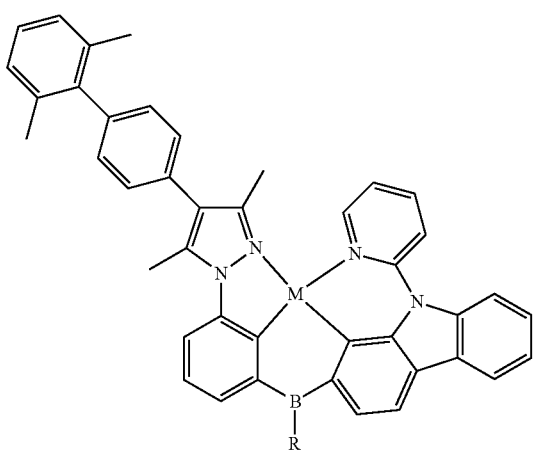
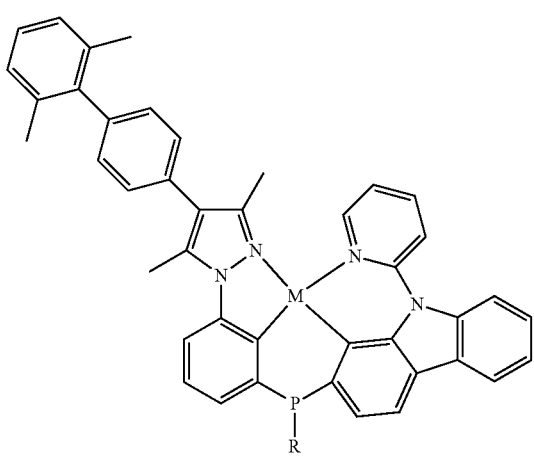
532
-continued
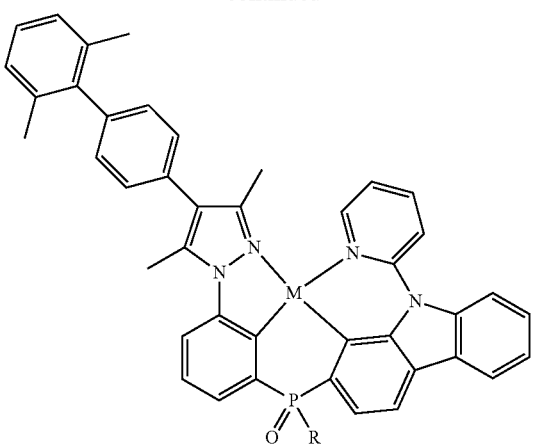
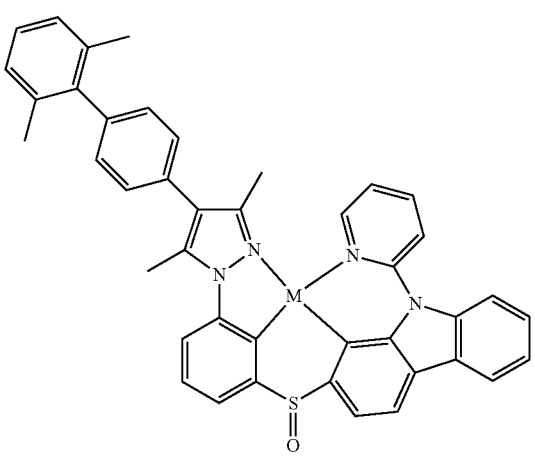
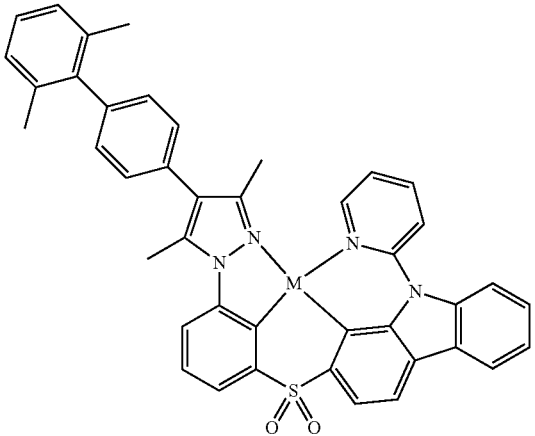

533
-continued
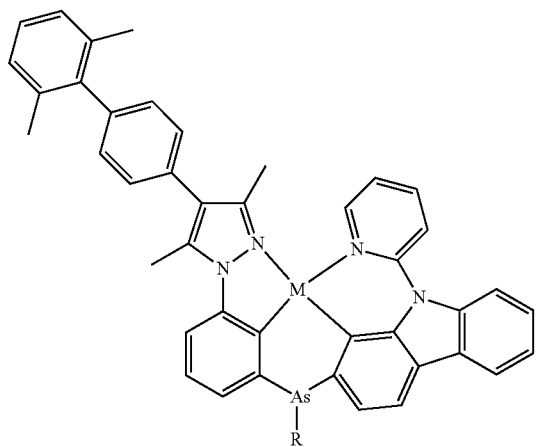
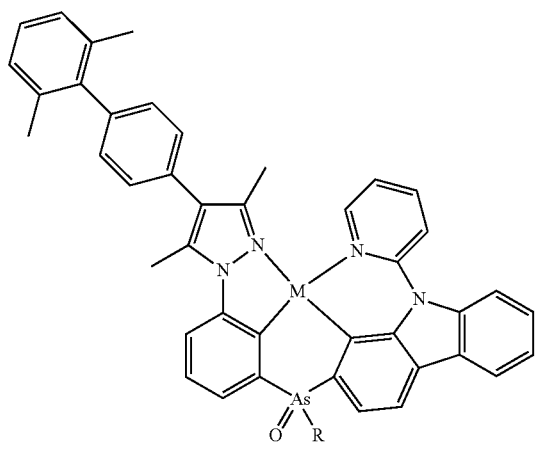
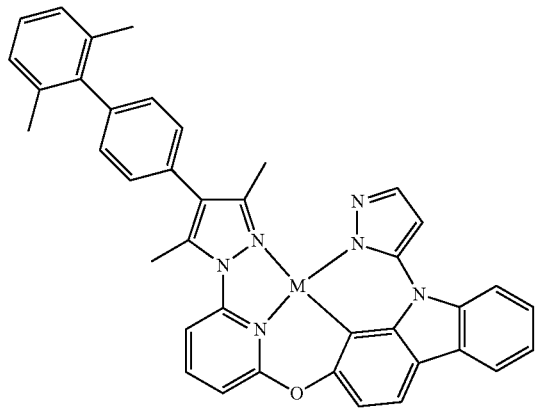
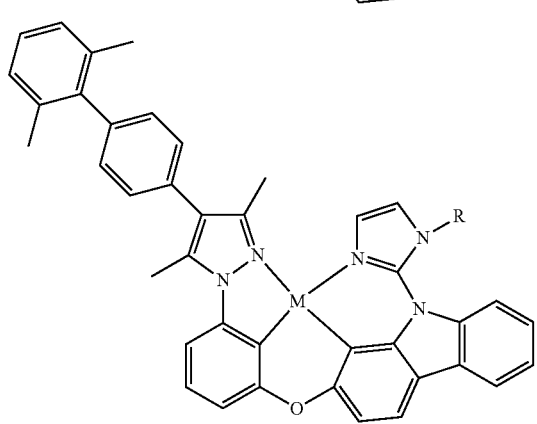
534
-continued
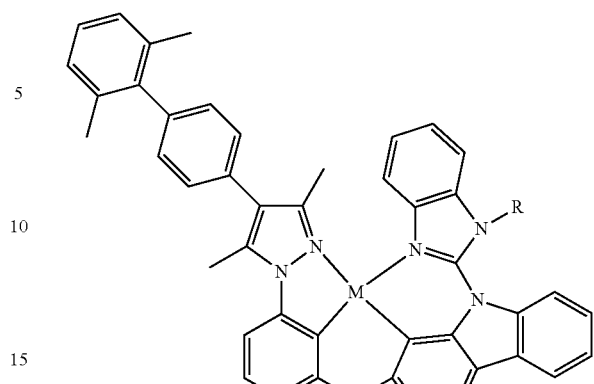
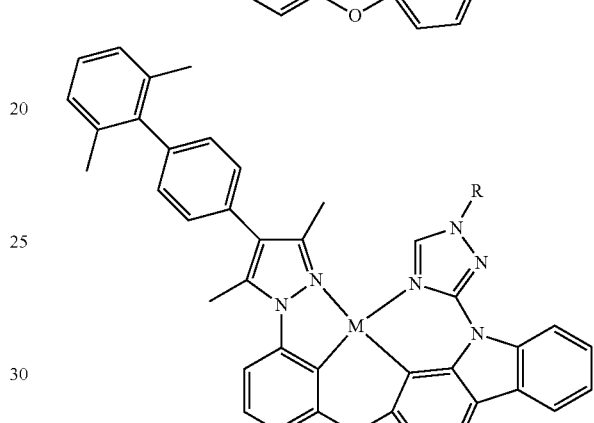
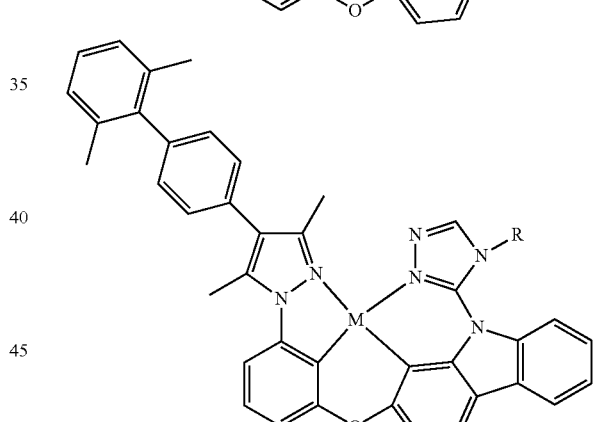
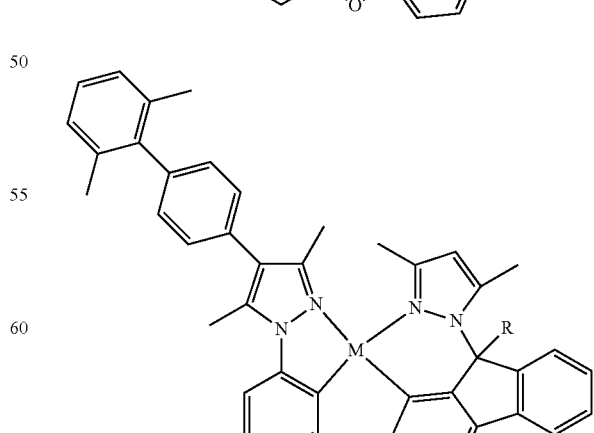

535
-continued
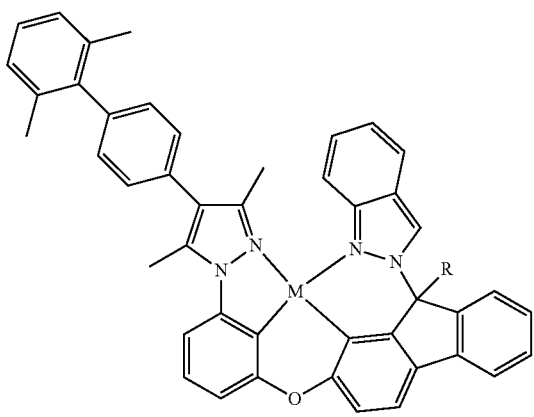
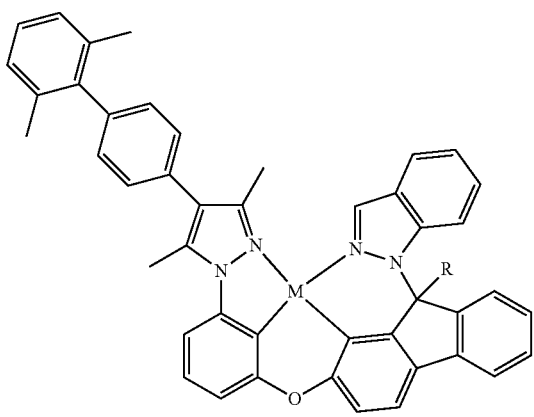
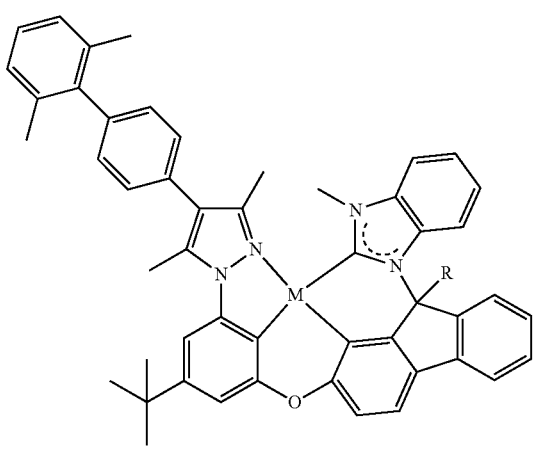
(M = Pt, Pd)
536
-continued
Structures 79
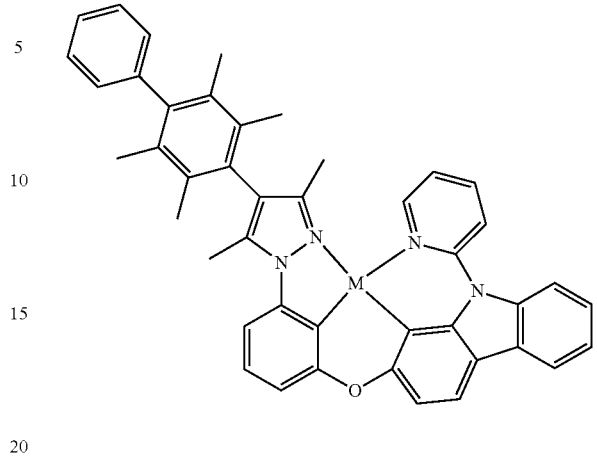
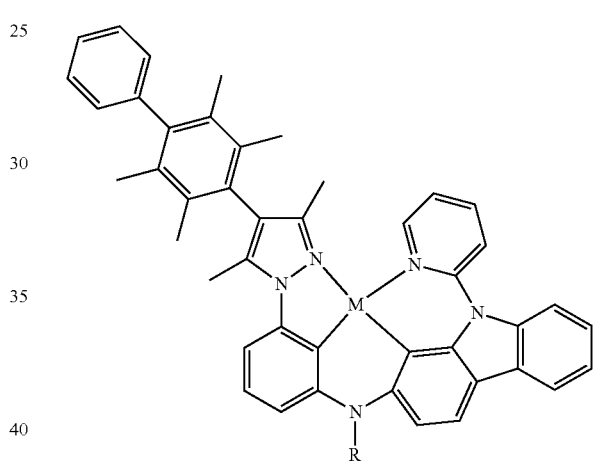
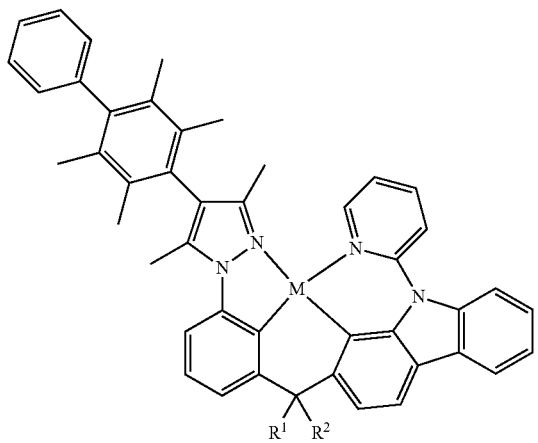

537
-continued
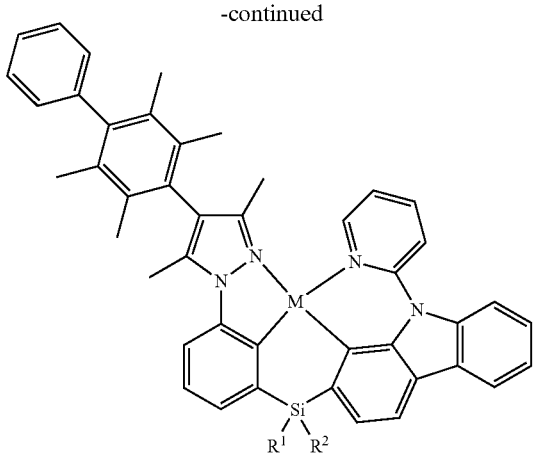
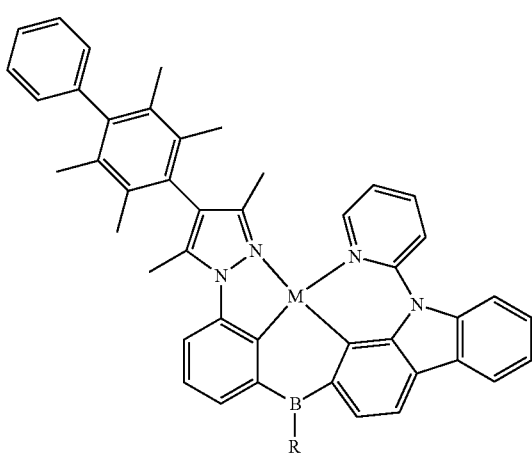
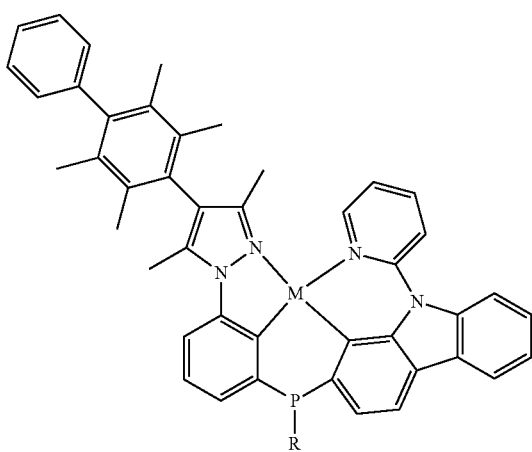
538
-continued
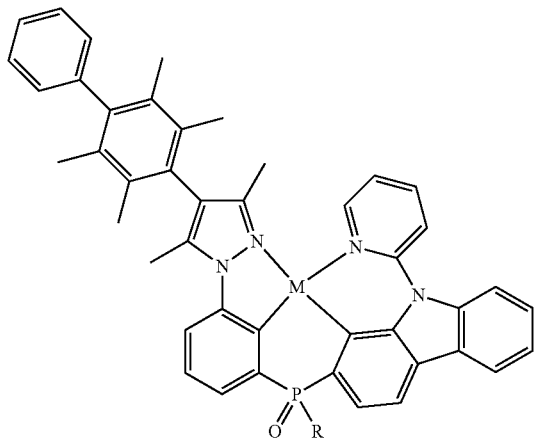
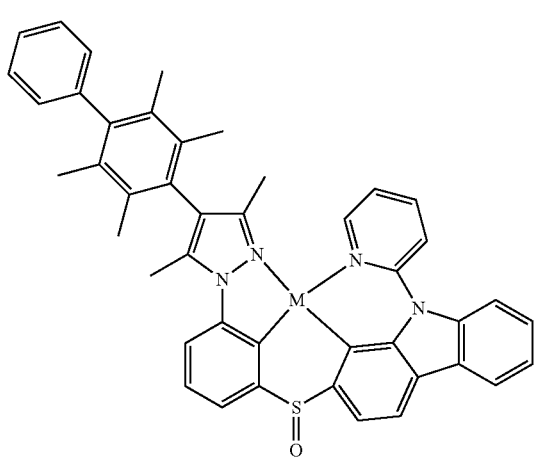
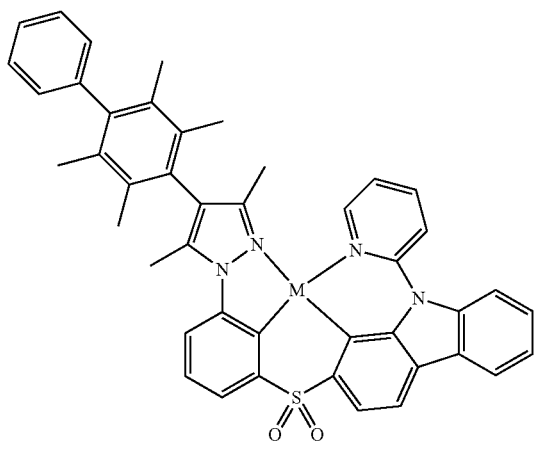

539
-continued
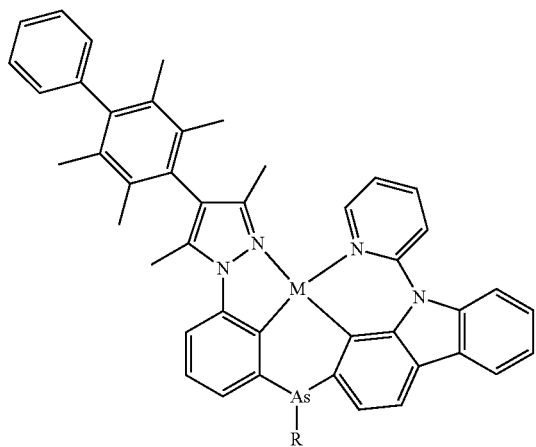
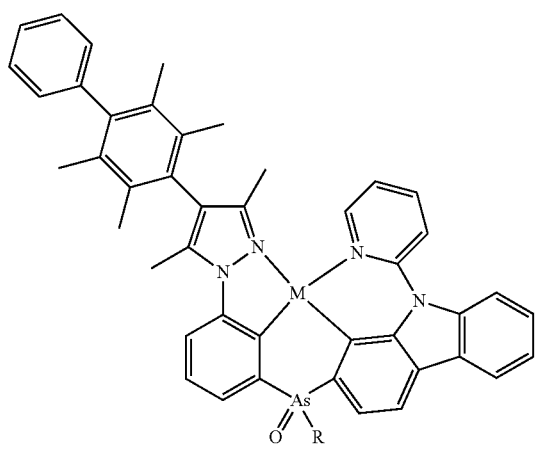
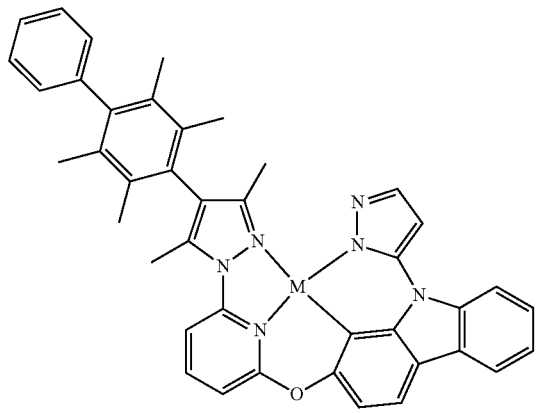
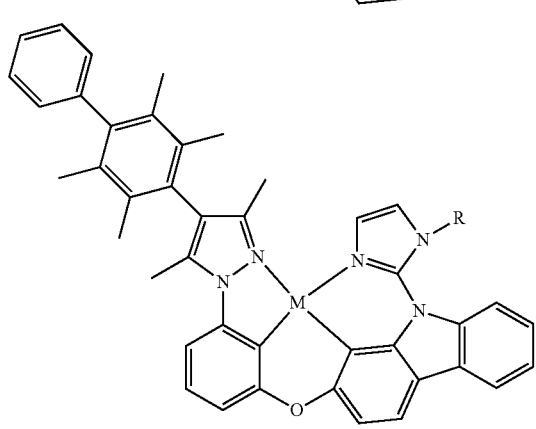
540
-continued
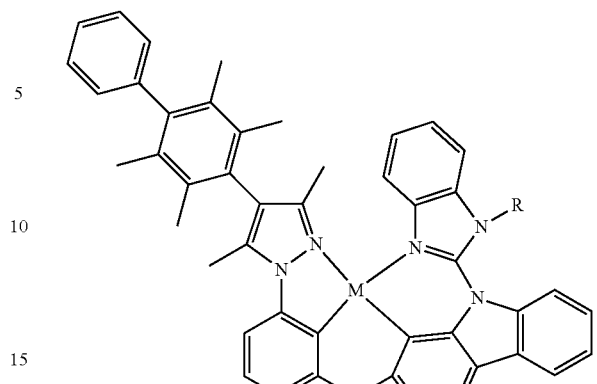
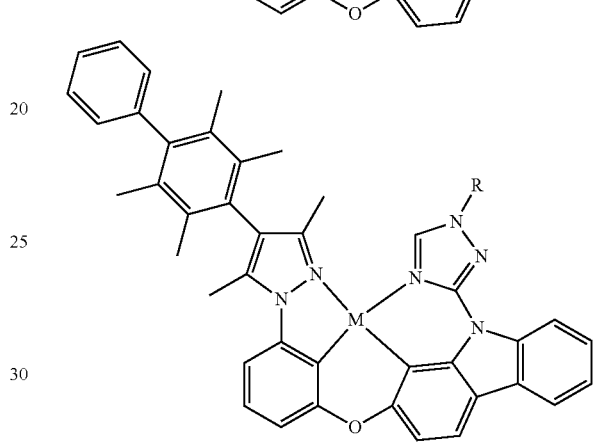
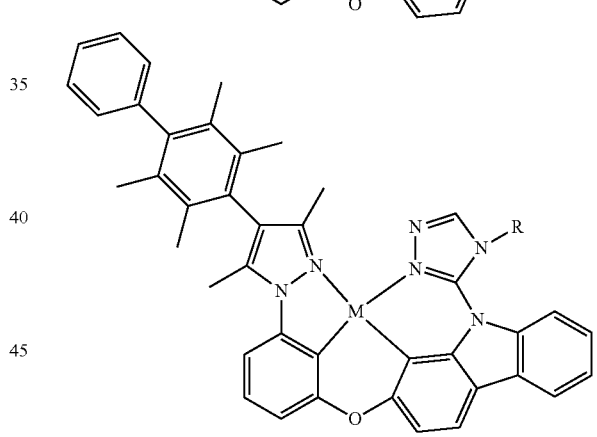
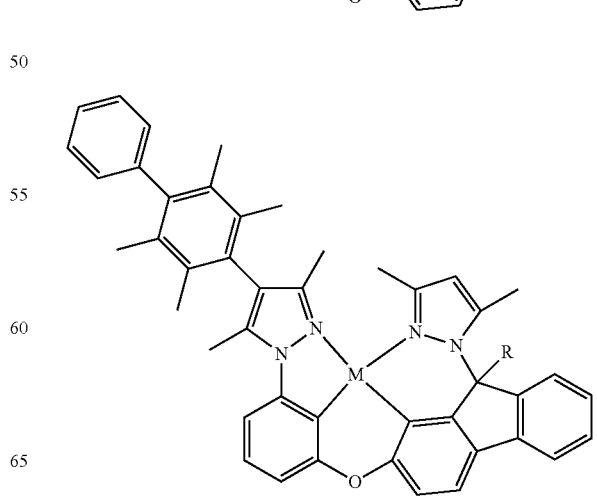

541
-continued
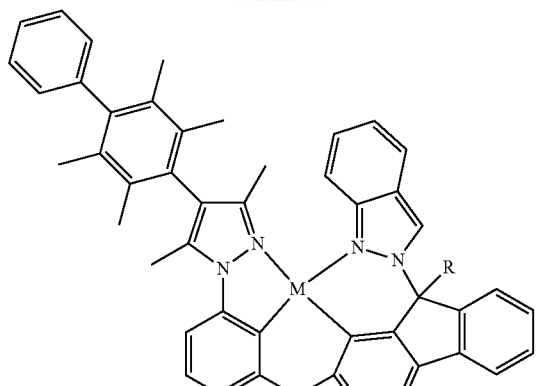
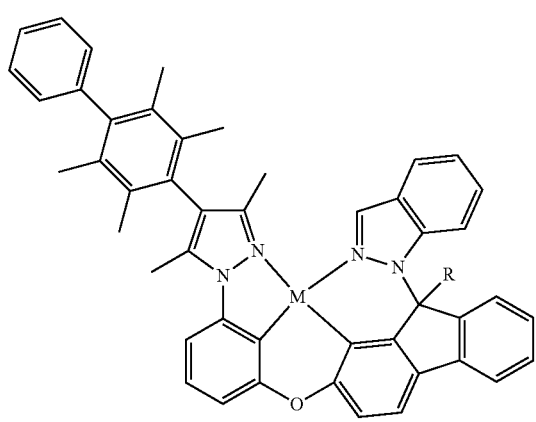
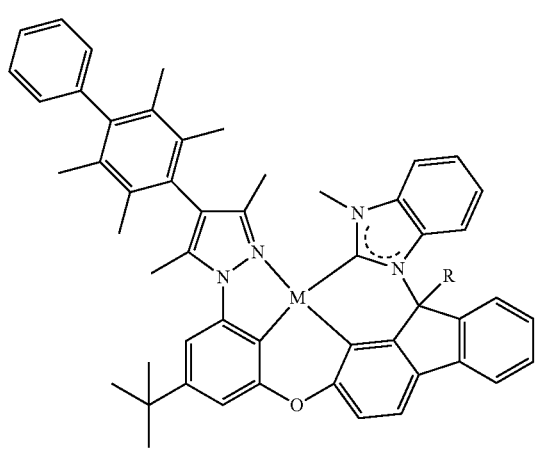
(M = Pt, Pd)
542
-continued
Structures 80
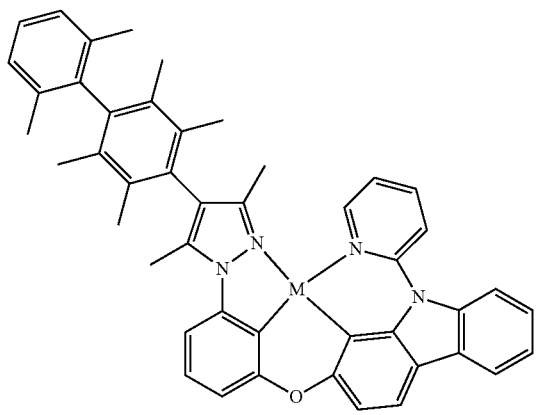
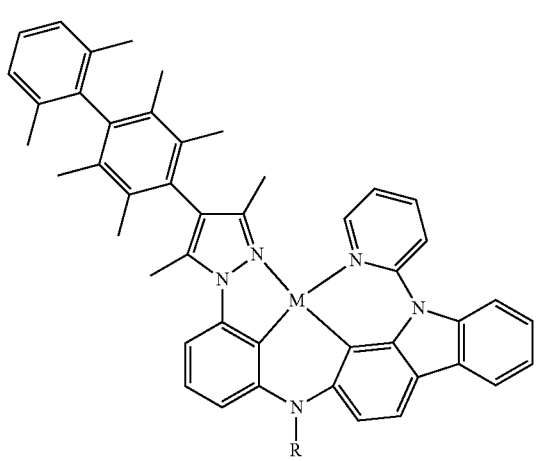
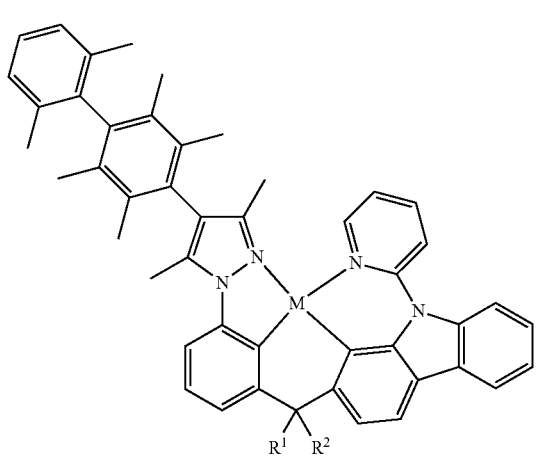

543
-continued
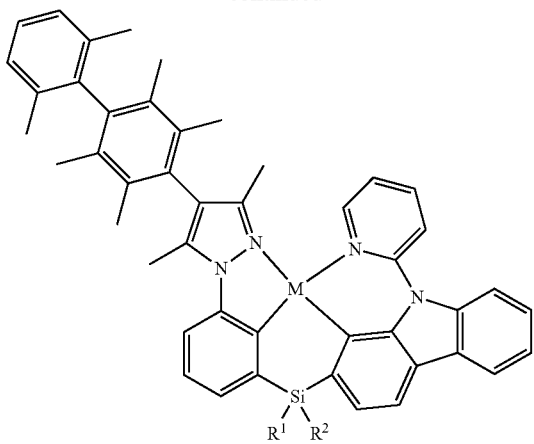
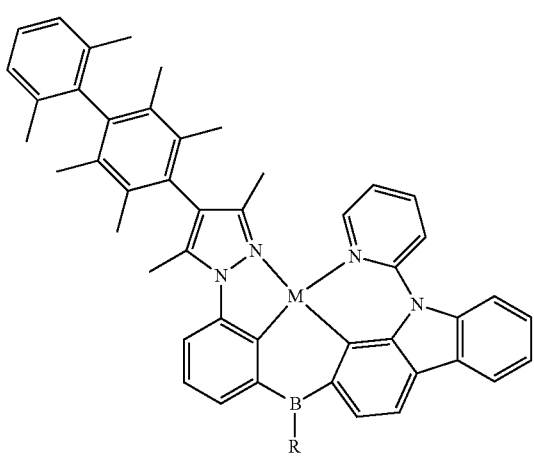
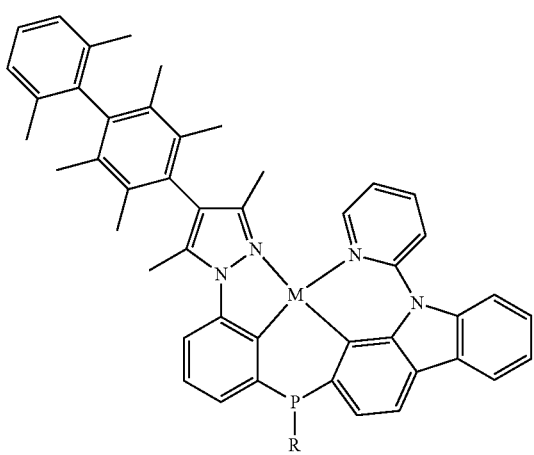
544
-continued
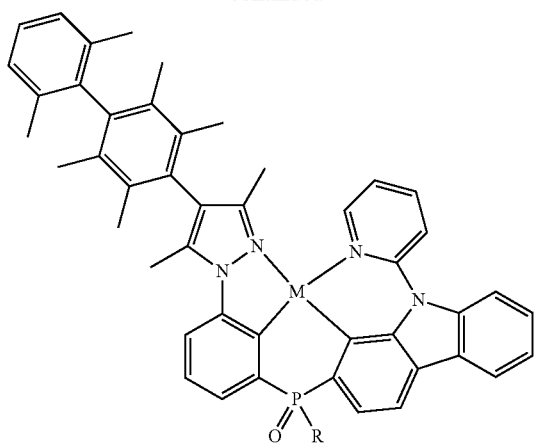
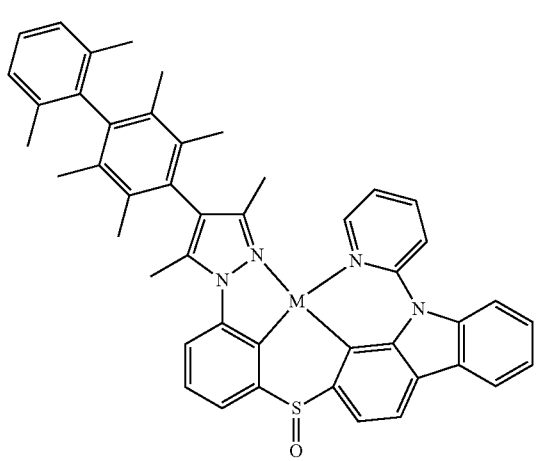
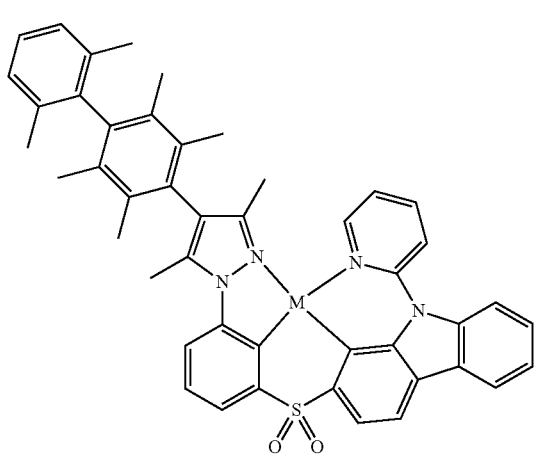

545
-continued
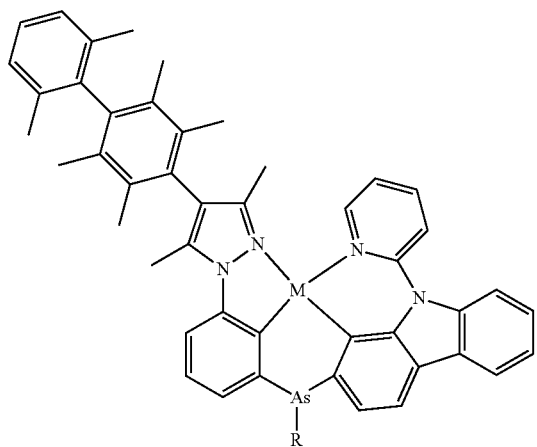
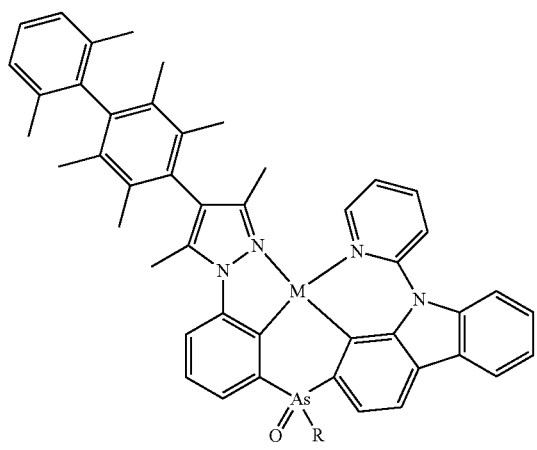
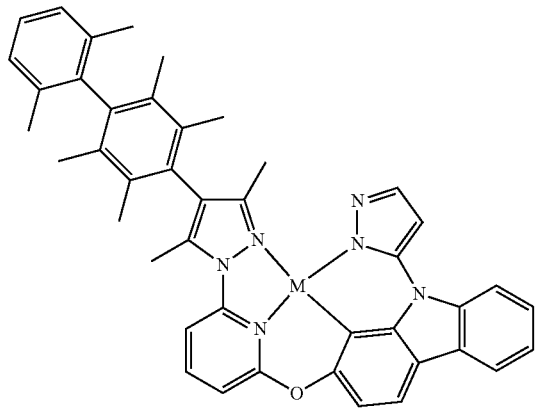
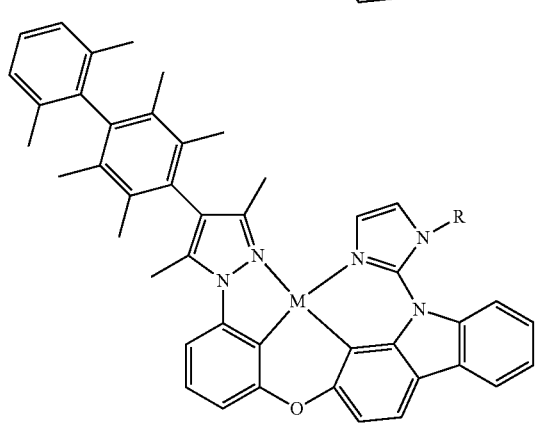
546
-continued
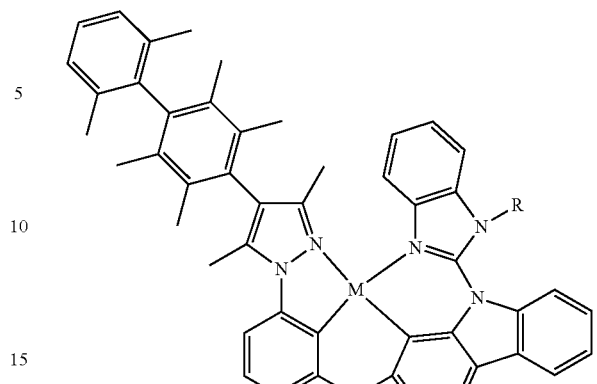
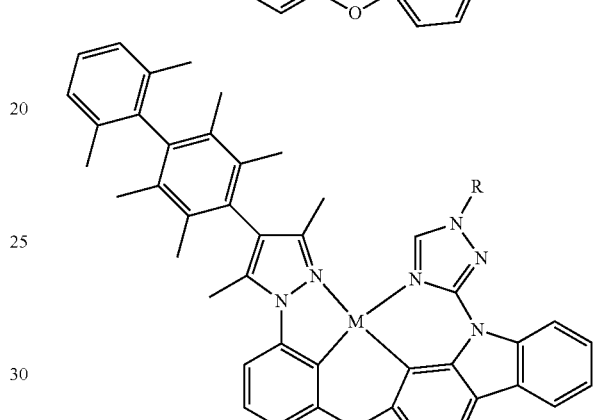
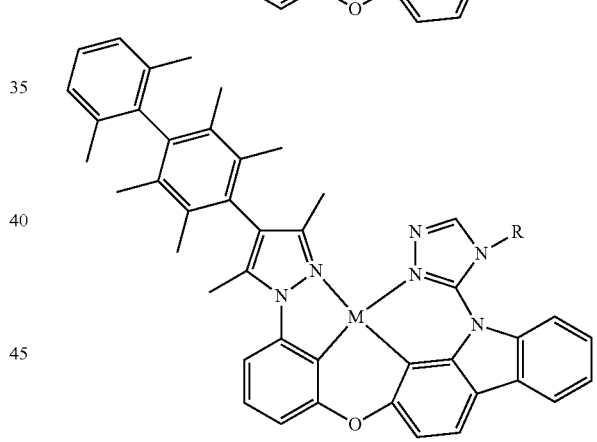
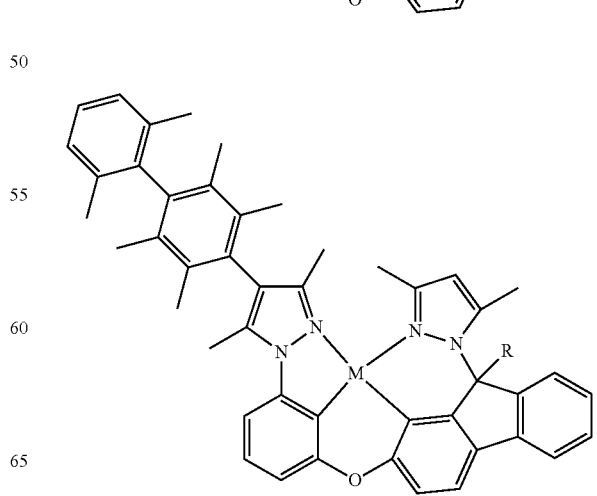

547
-continued
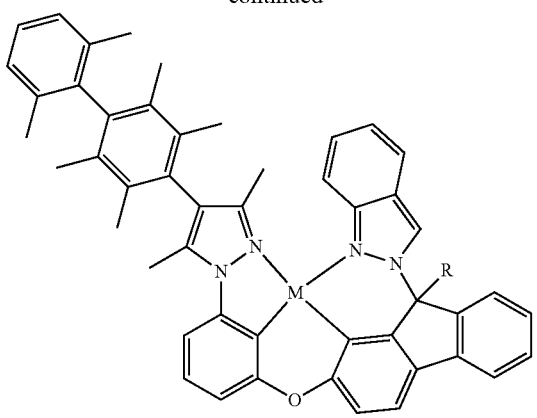
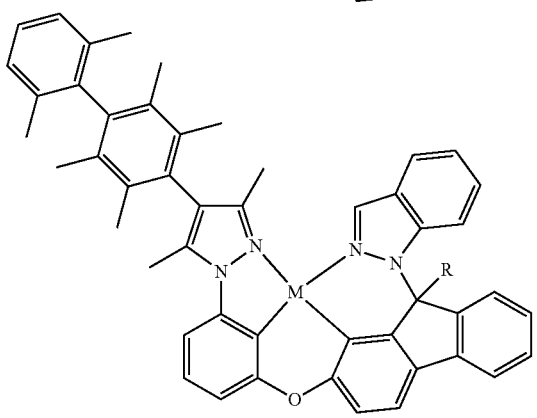
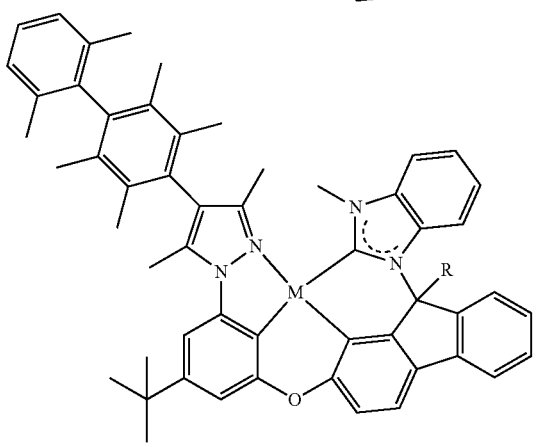
(M = Pt, Pd)
Structures 81
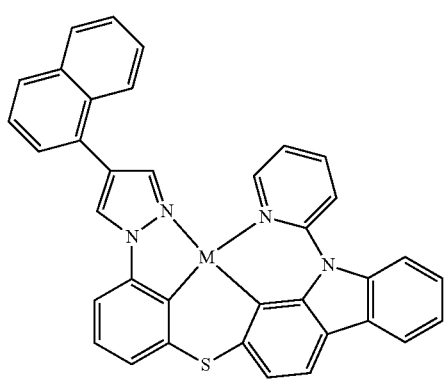
548
-continued
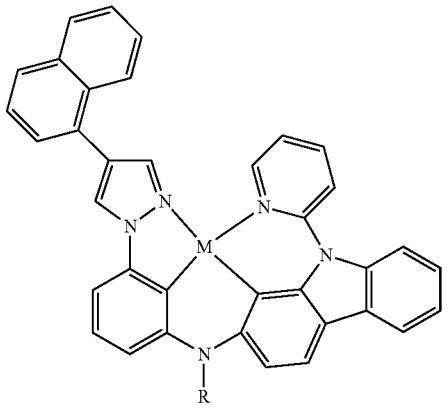
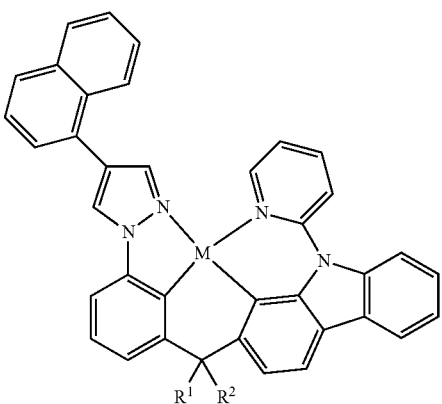
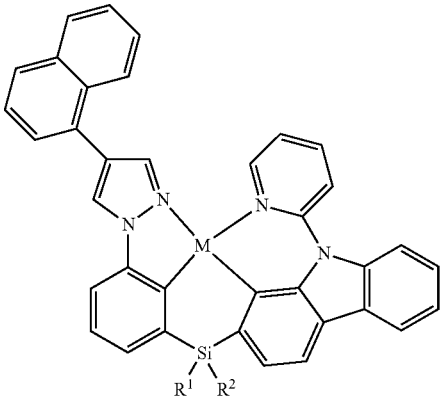
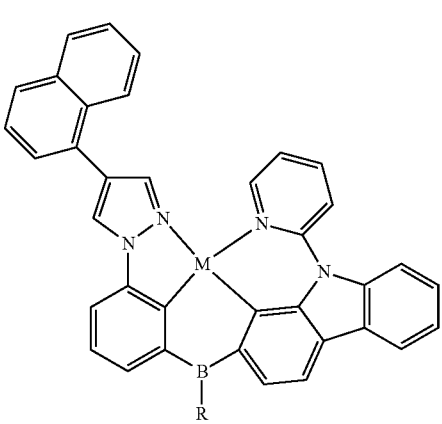

549
-continued
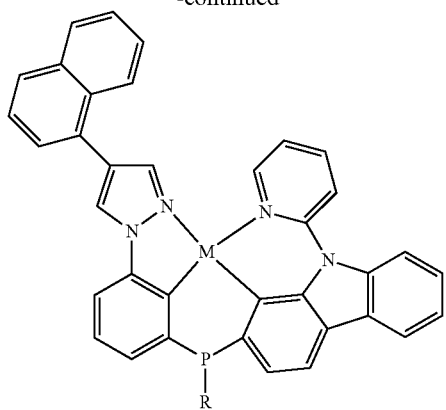
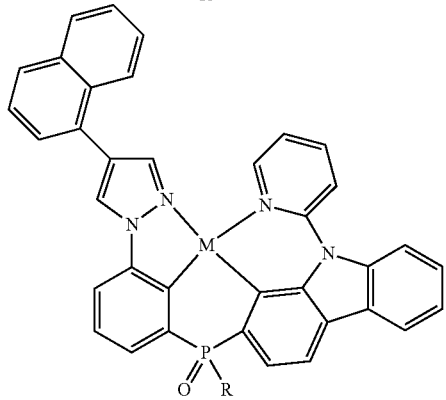
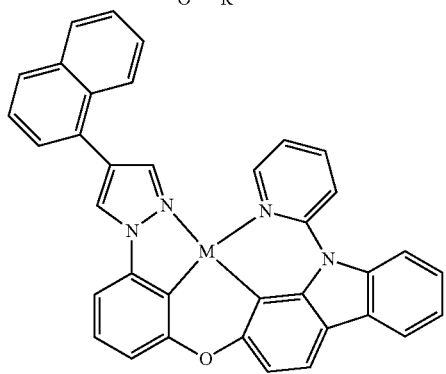
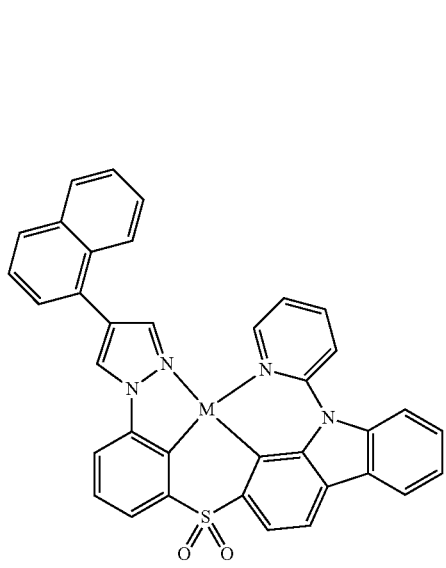
550
-continued
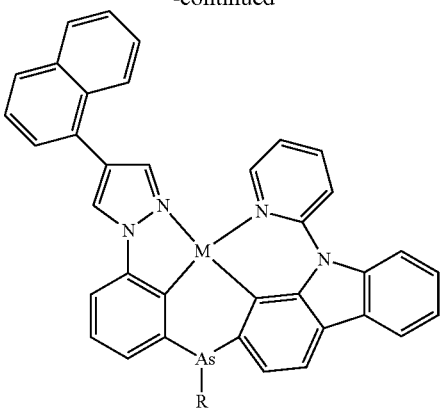
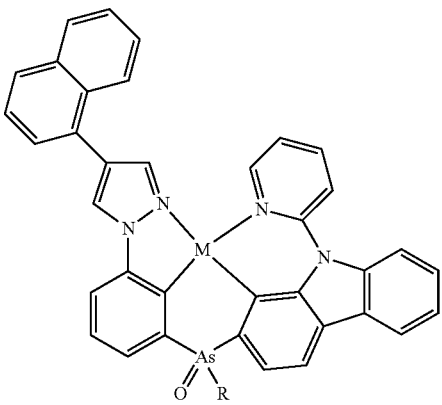
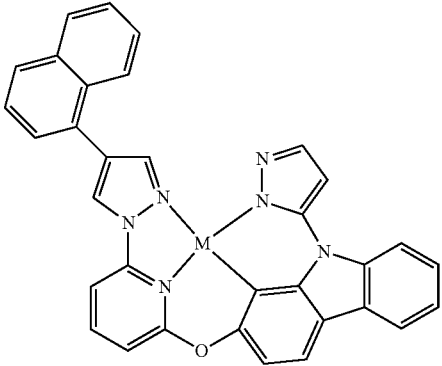
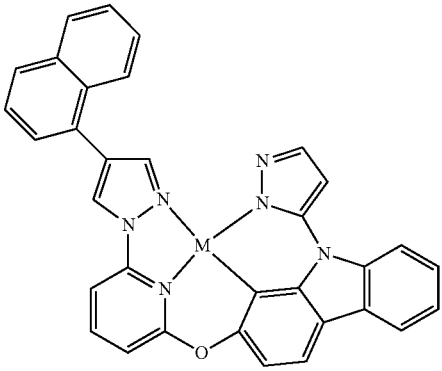
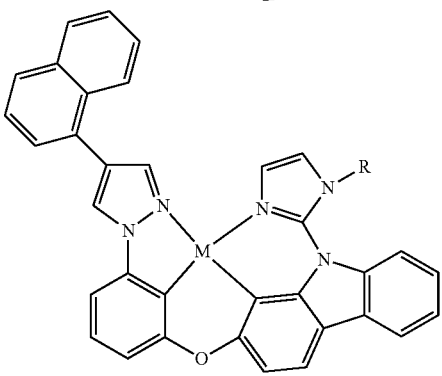

551
-continued
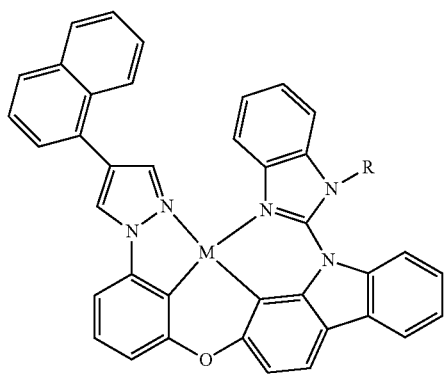
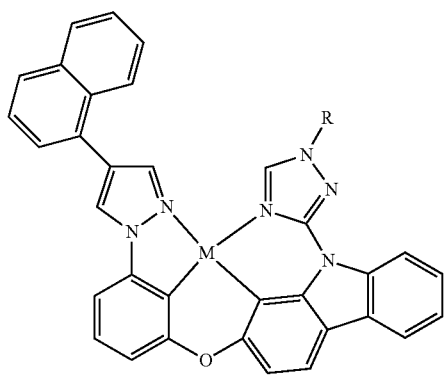
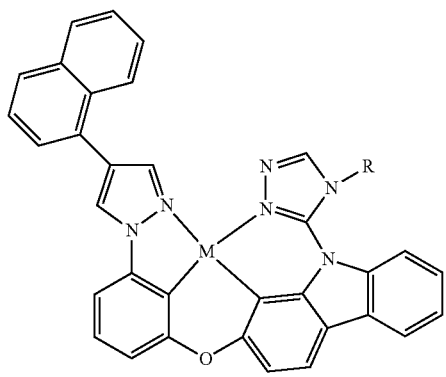
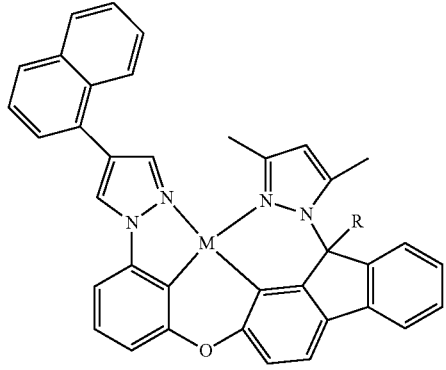
552
-continued
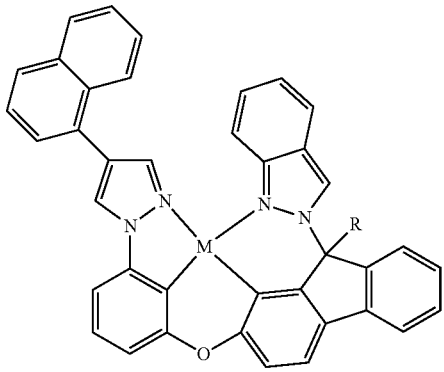
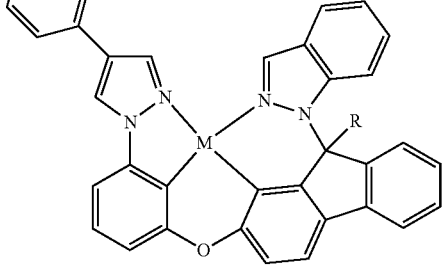
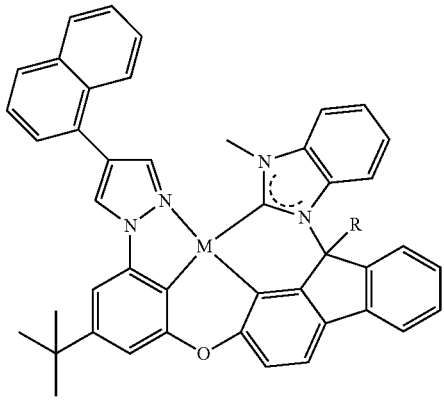
(M = Pt, Pd)
Structures 82
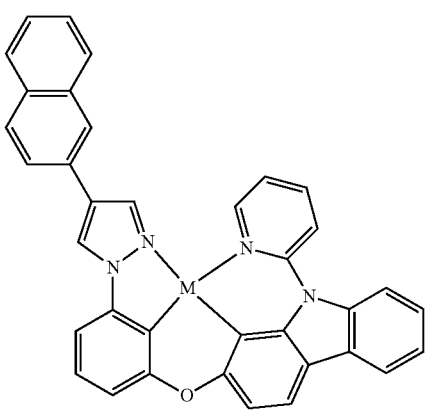

553
-continued
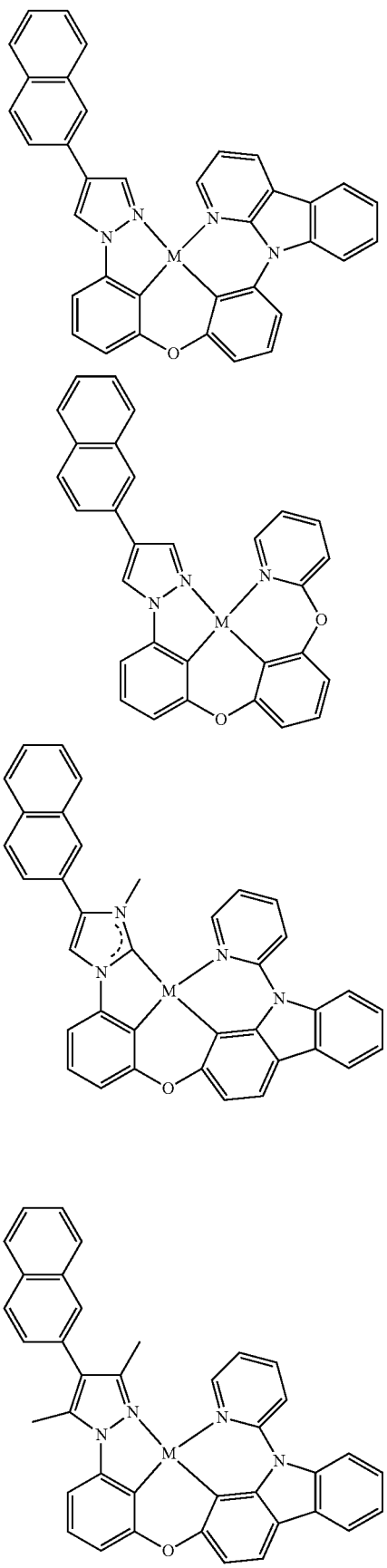
554
-continued
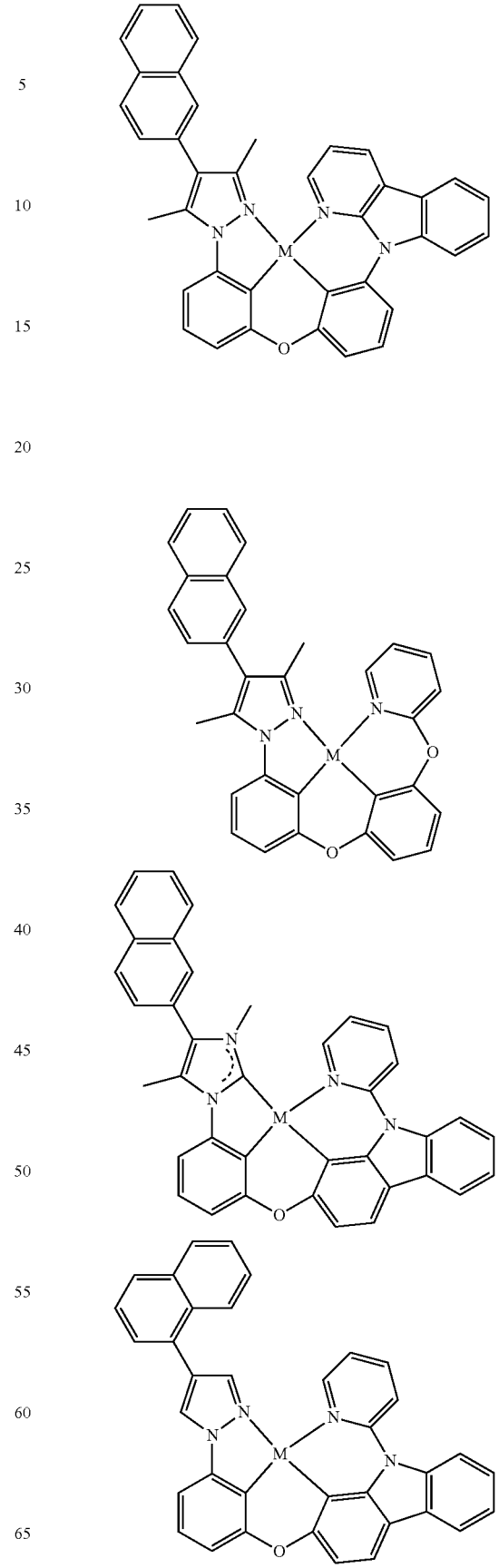

555
-continued
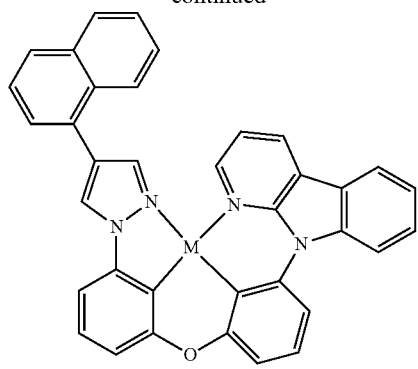
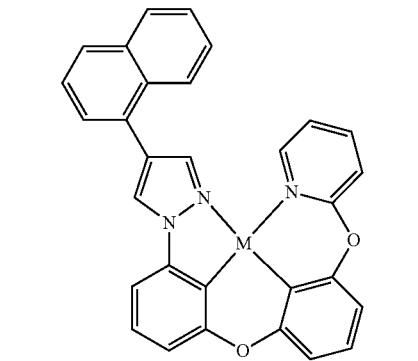
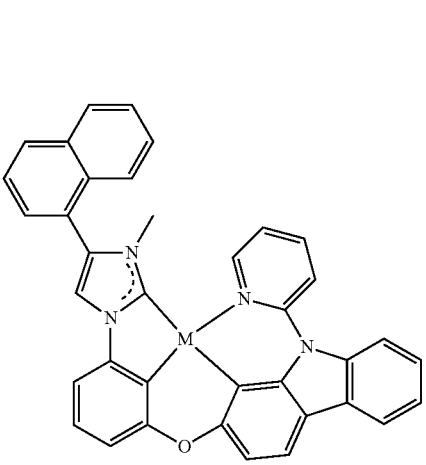
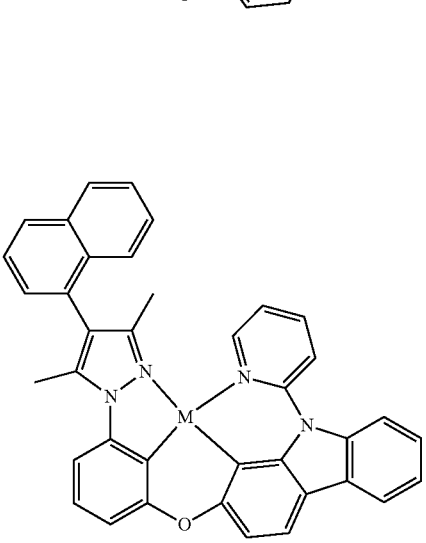
556
-continued
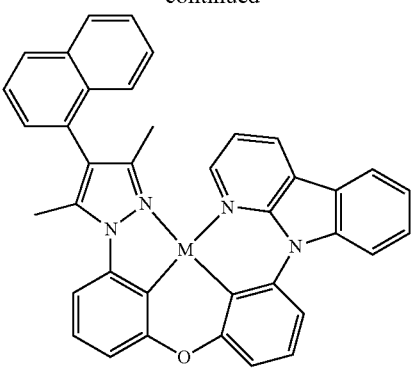
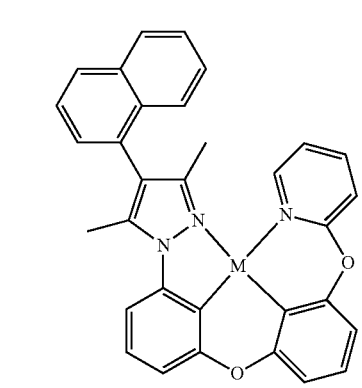
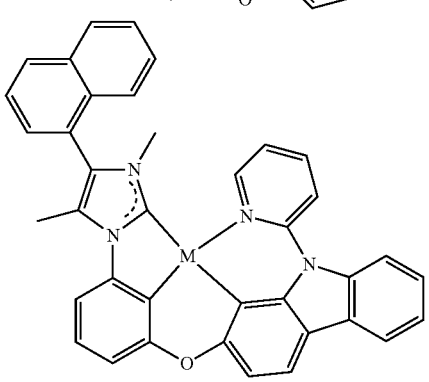
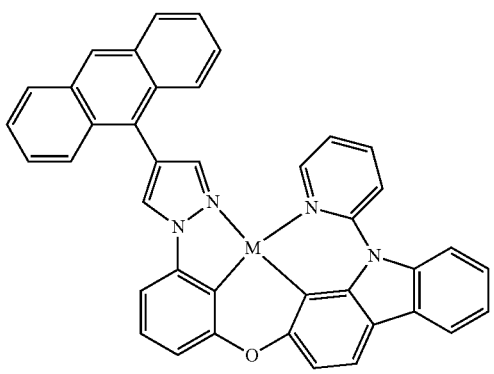

557
-continued
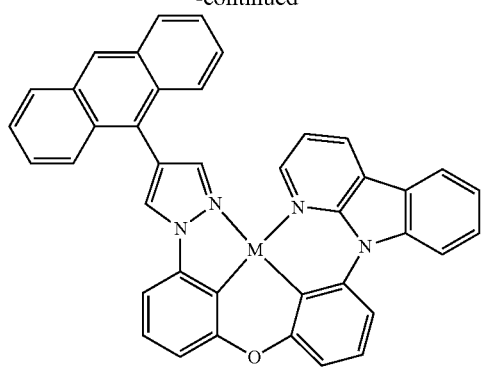
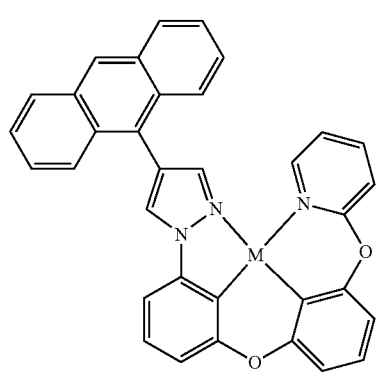
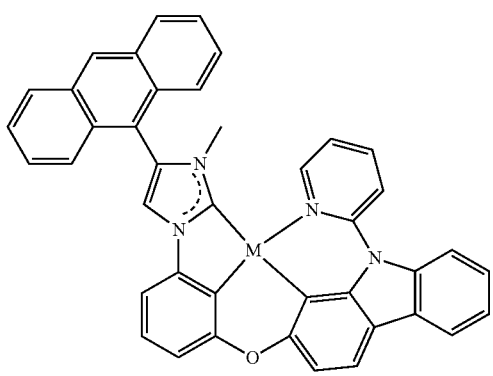
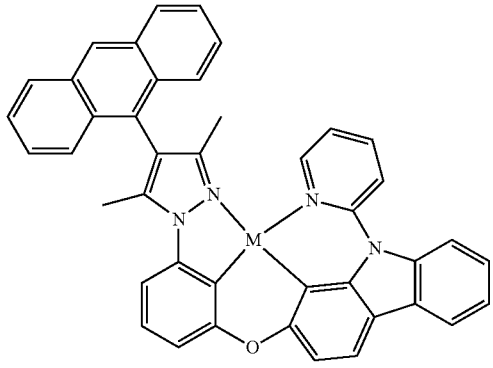
558
-continued
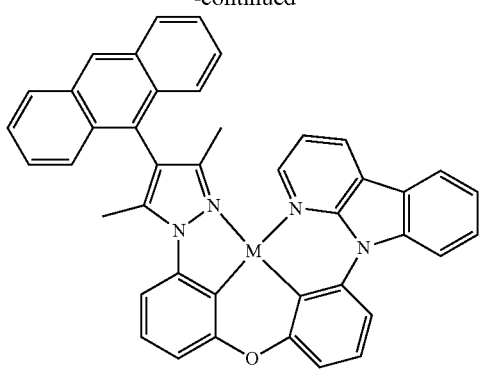
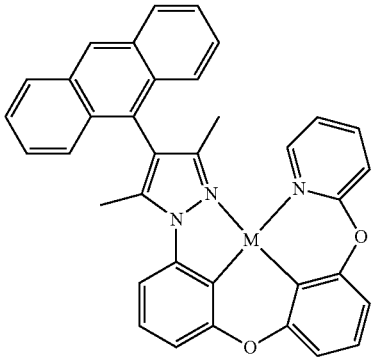
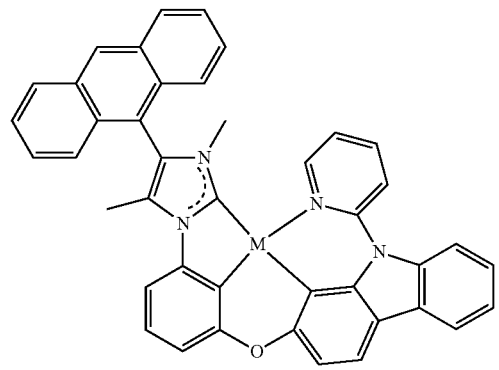
(M = Pt, Pd)
Structures 83
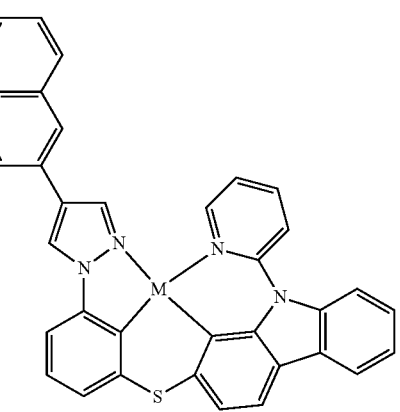

559
-continued
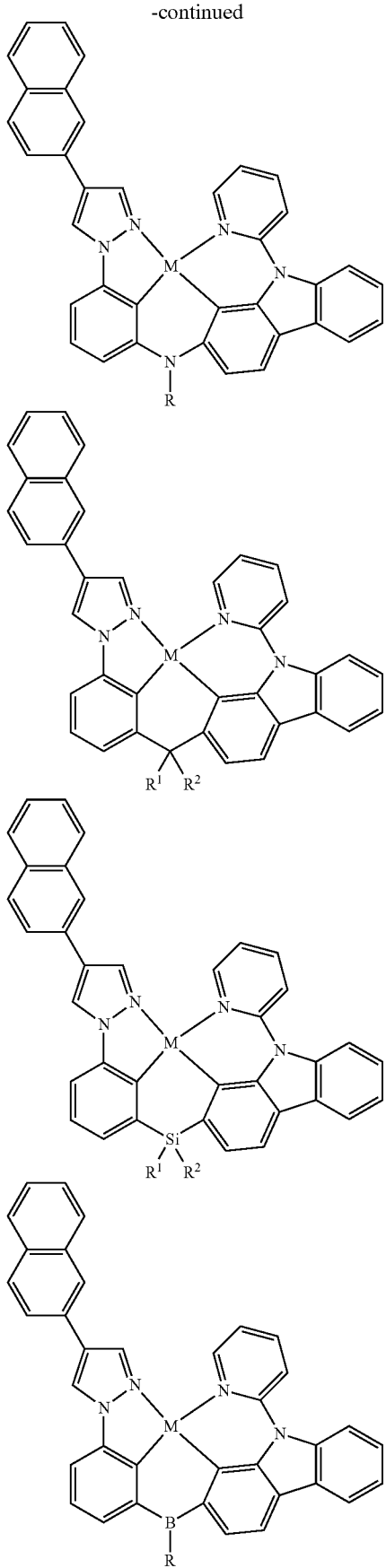
560
-continued
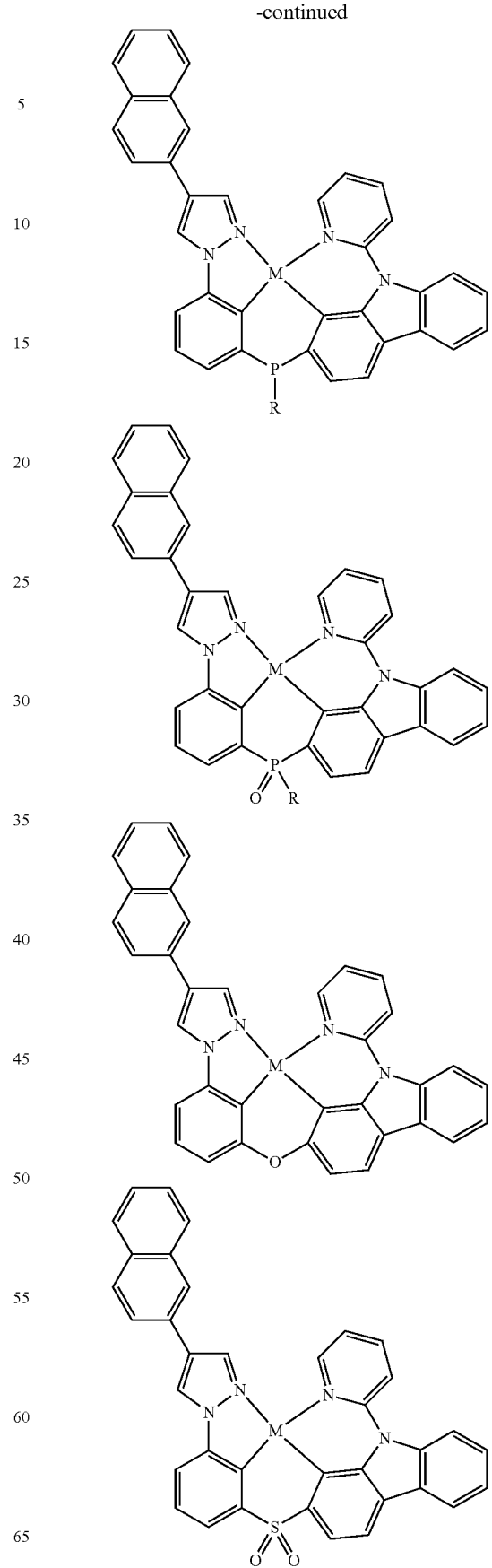

561
-continued
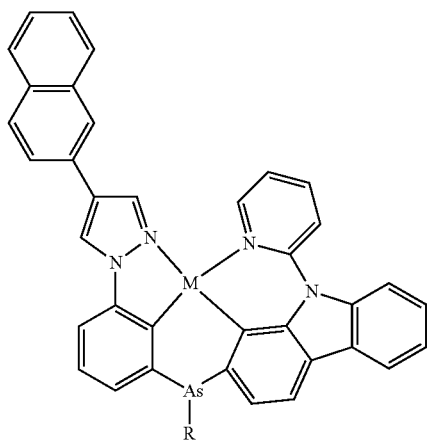
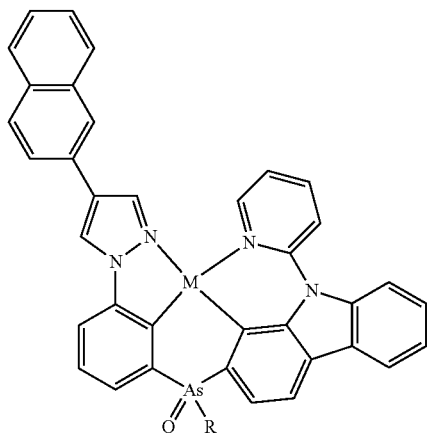
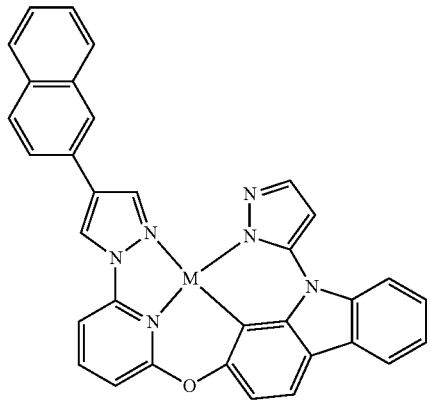
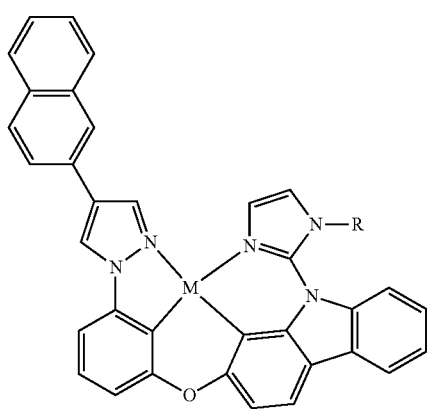
562
-continued
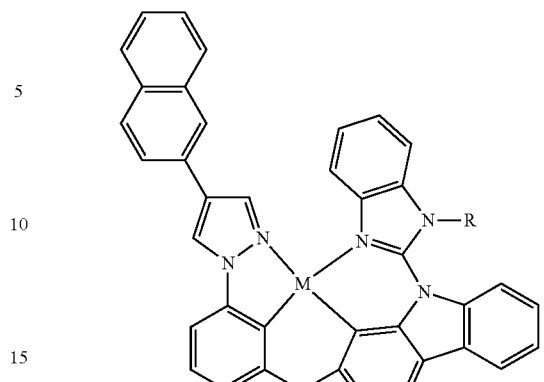
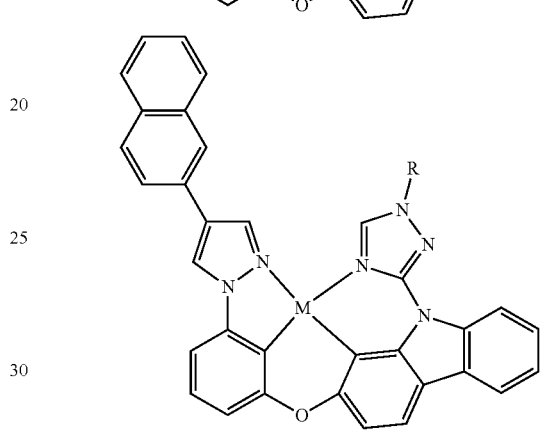
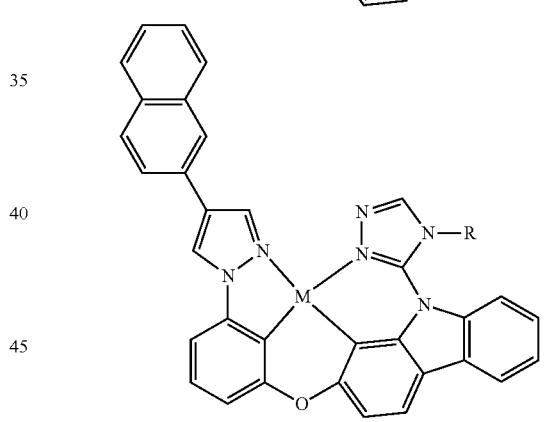
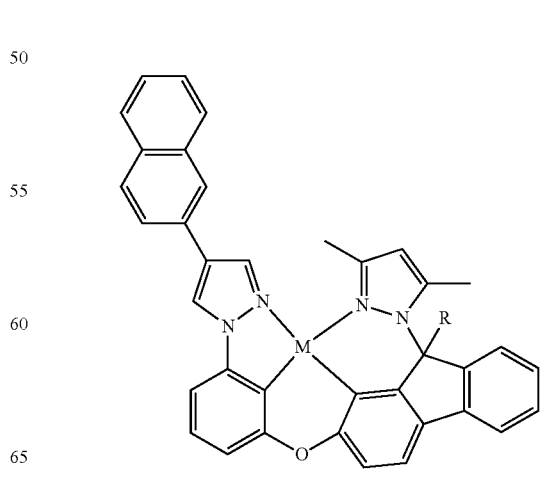

563
-continued
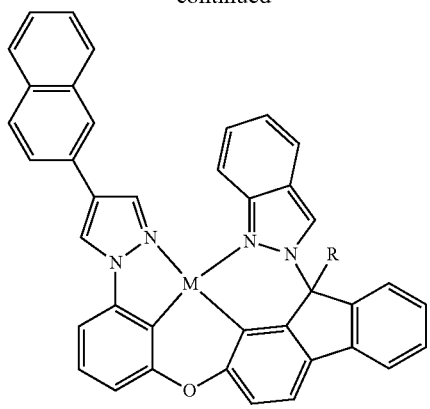
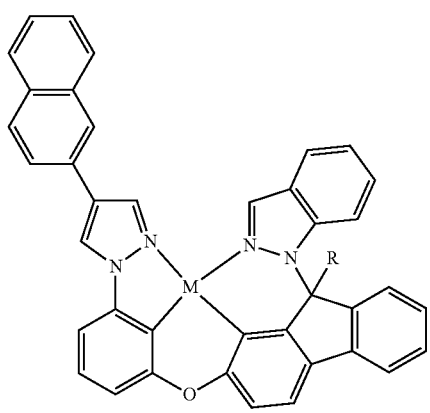
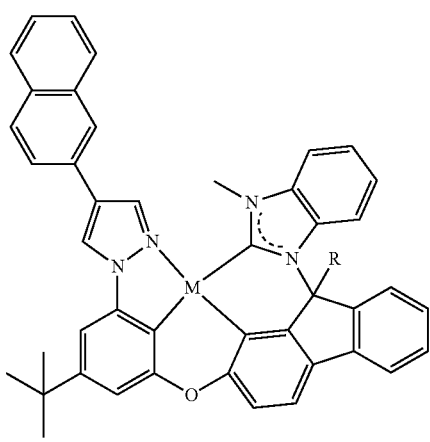
(M = Pt, Pd)
564
-continued
Structures 84
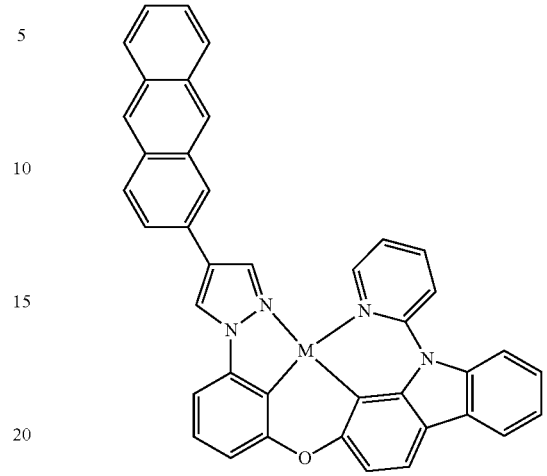
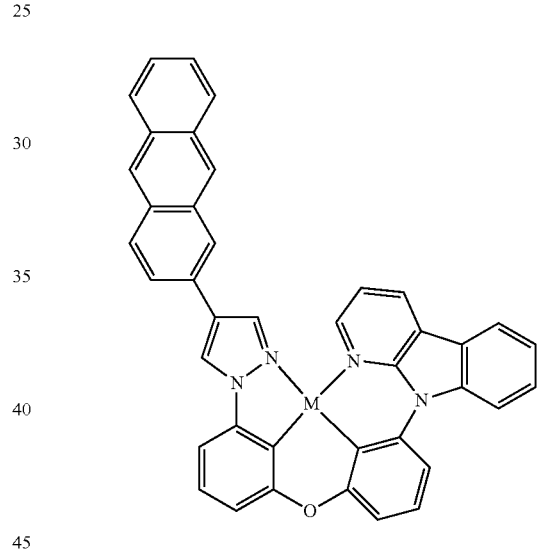
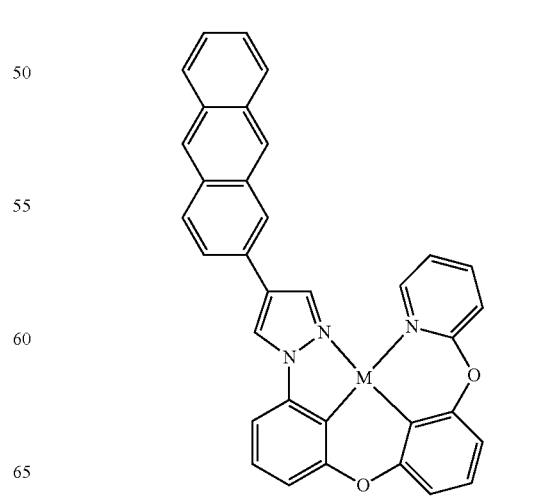

565
-continued
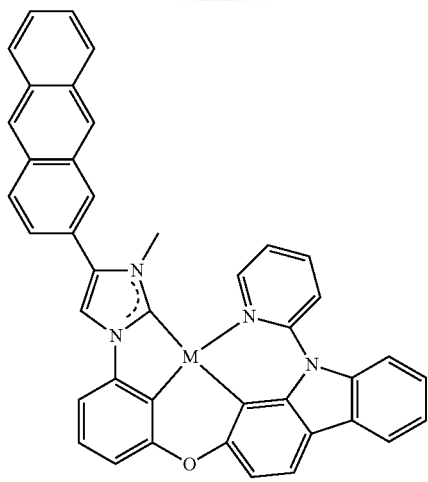
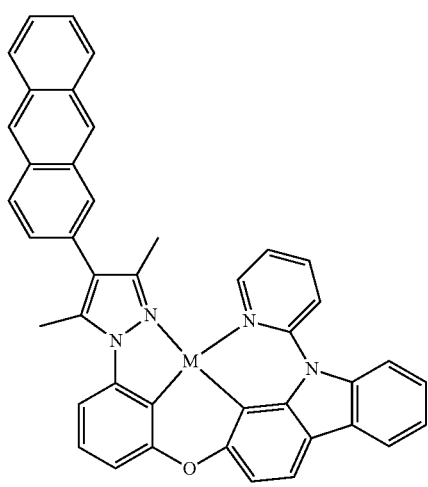
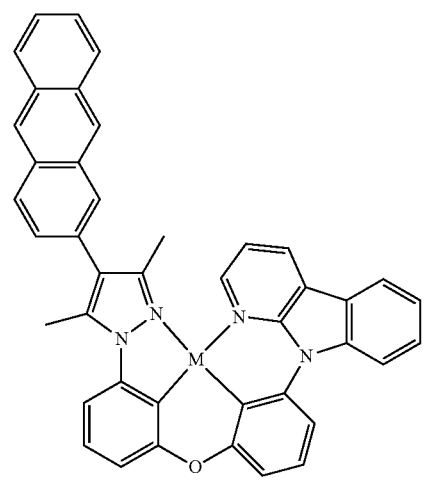
566
-continued
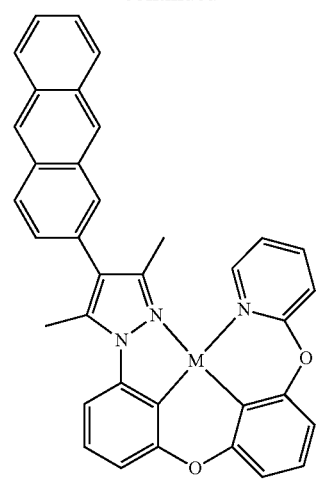
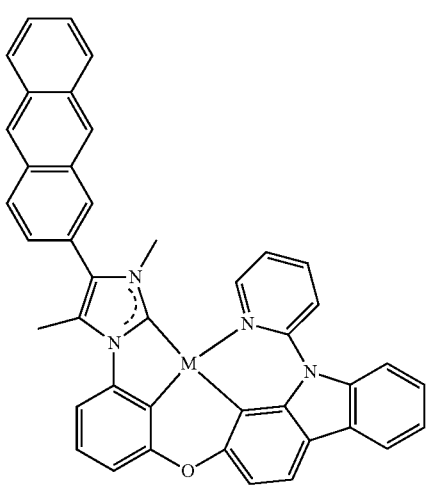
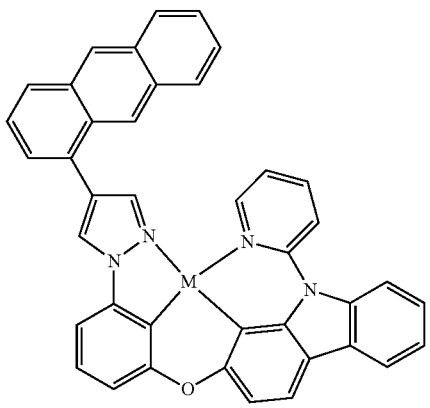

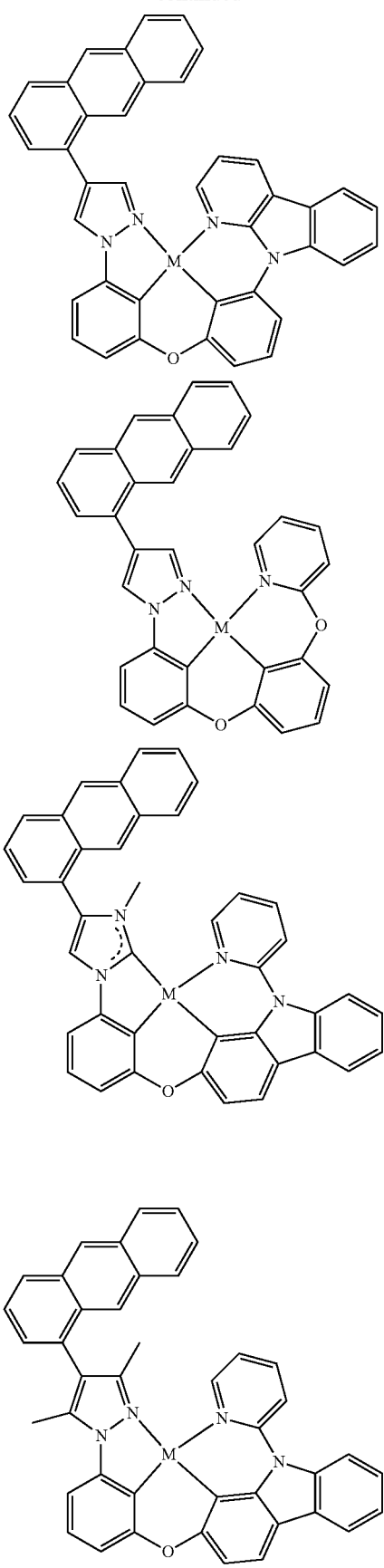

569
-continued
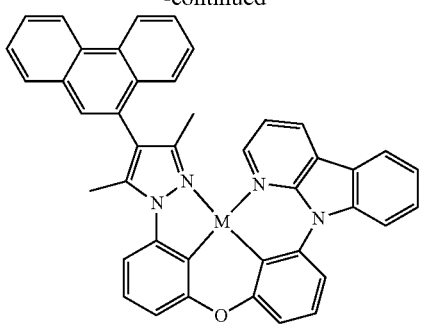
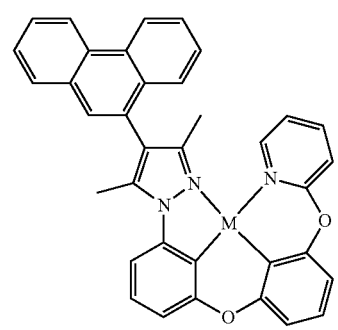
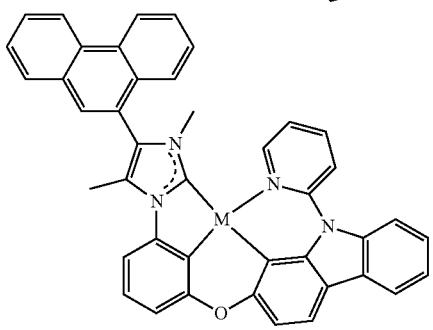
(M = Pt, Pd)
Structures 85
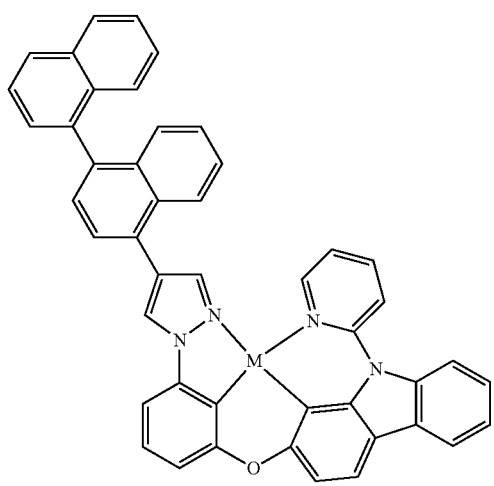
570
-continued
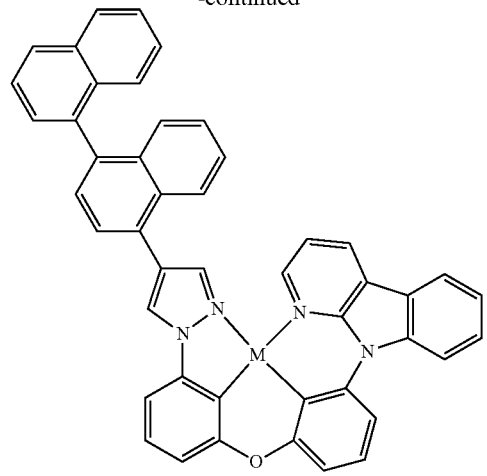
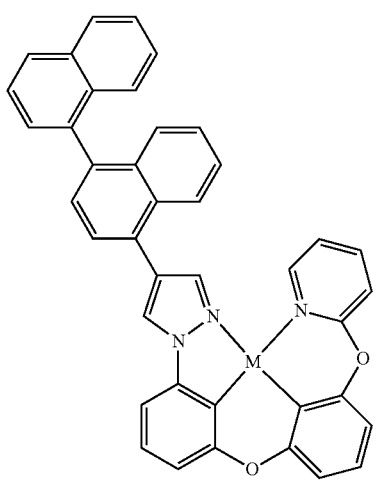
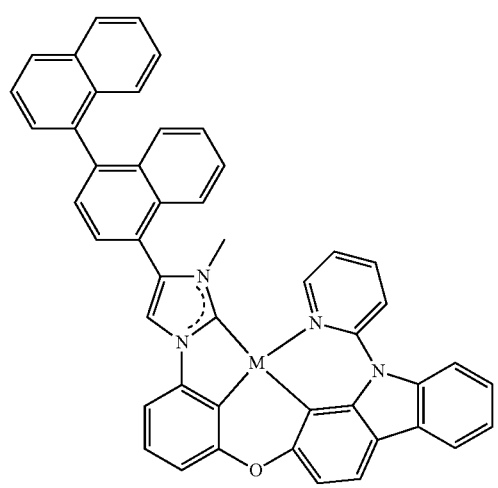

571
-continued
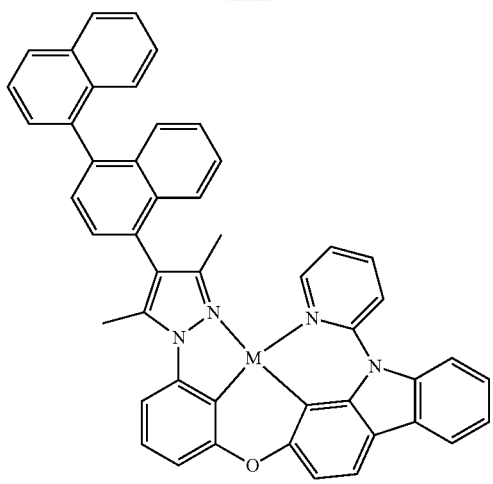
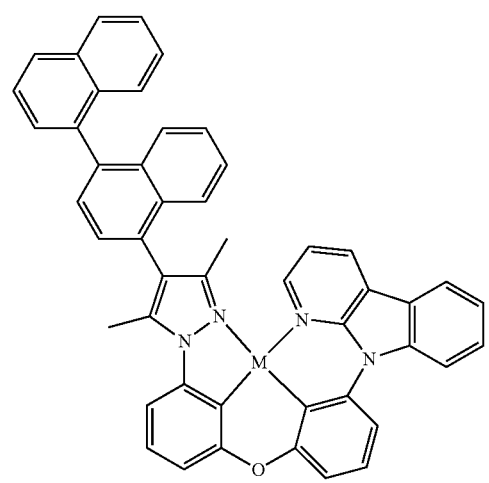
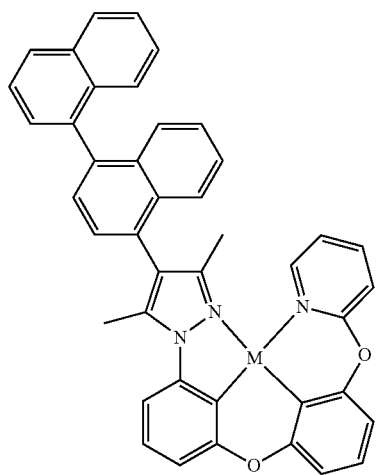
572
-continued
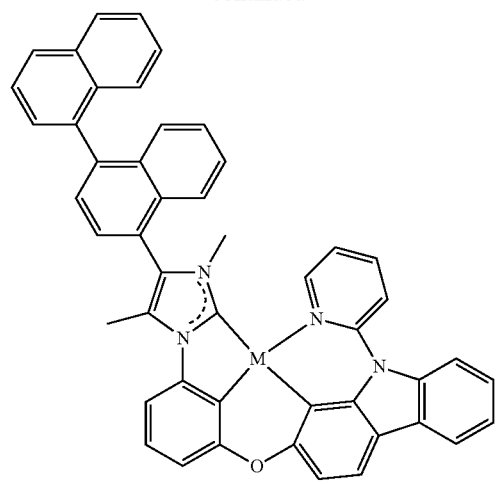
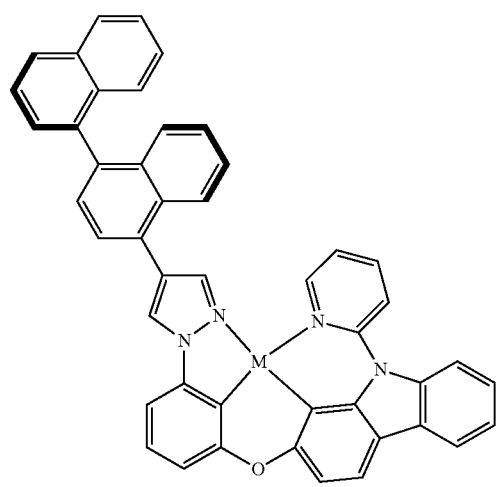
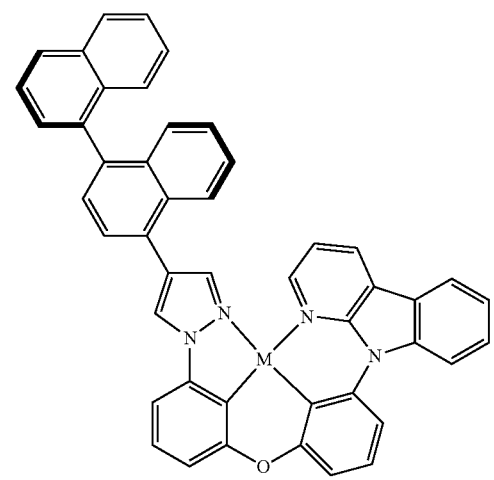

573
-continued
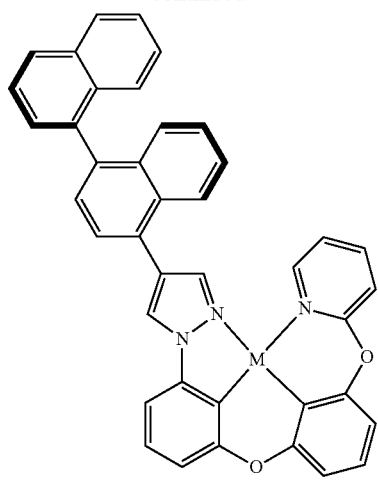
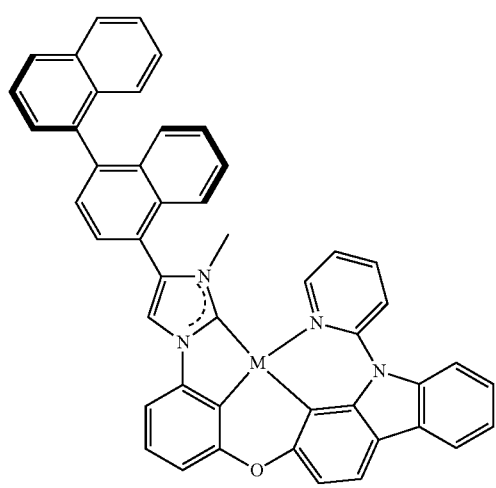
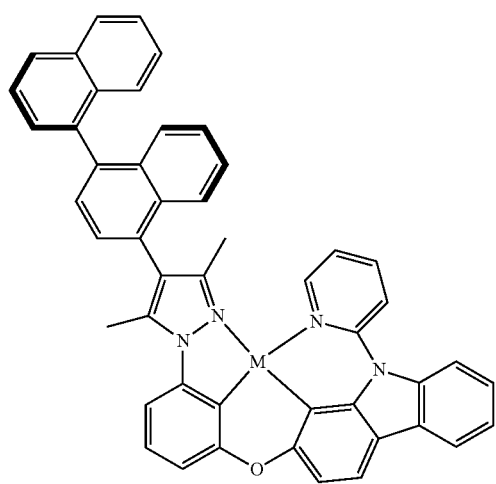
574
-continued
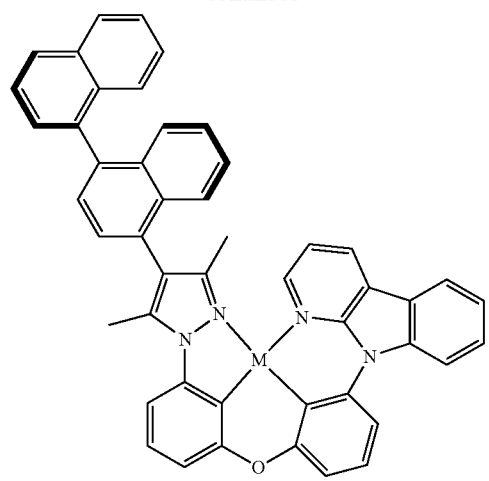
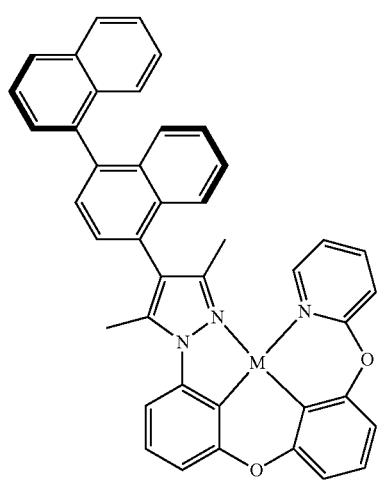
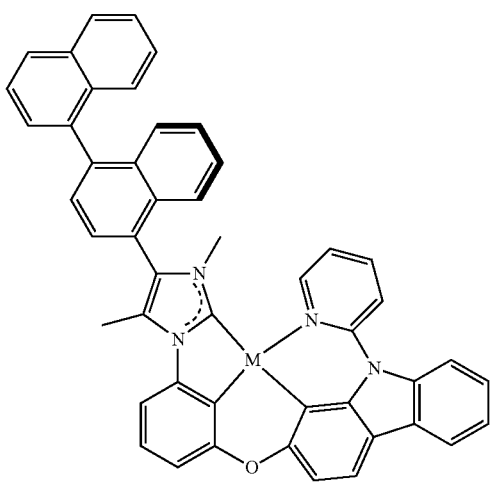

575
-continued
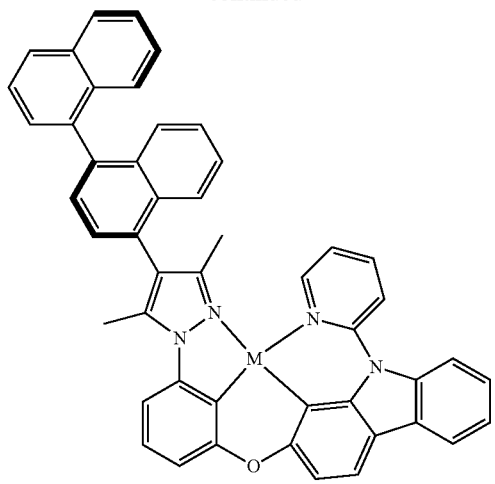
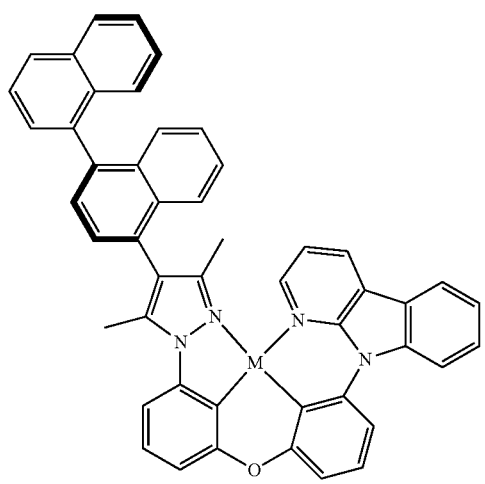
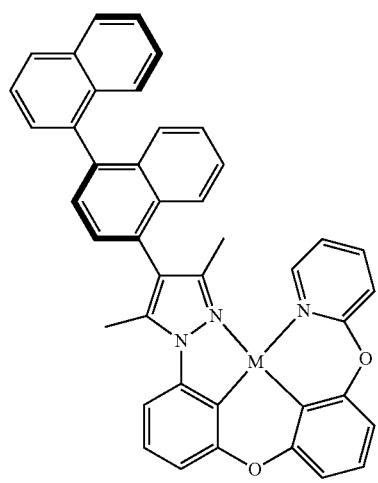
576
-continued
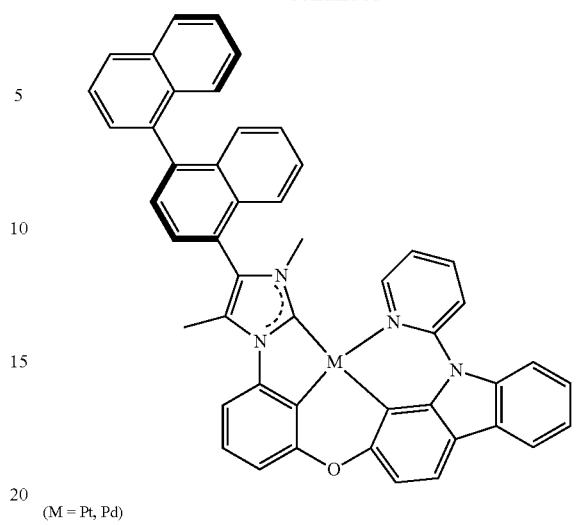
(M = Pt, Pd)
Structures 86
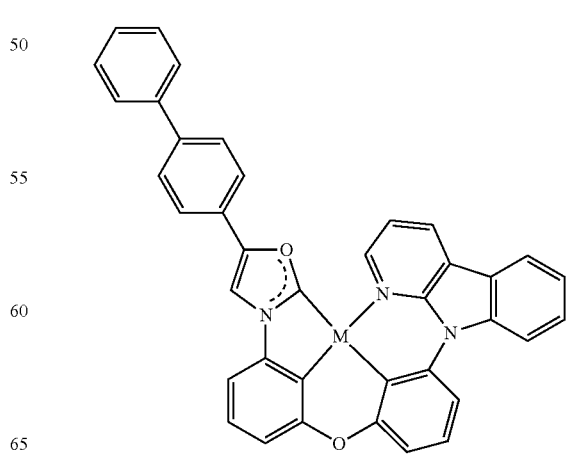

577
-continued
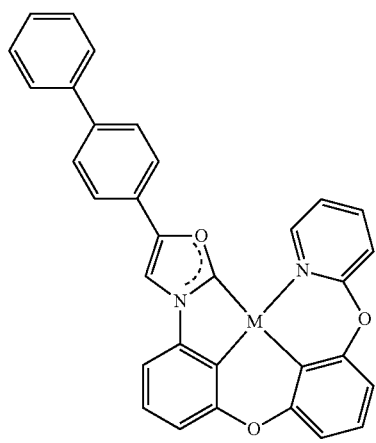
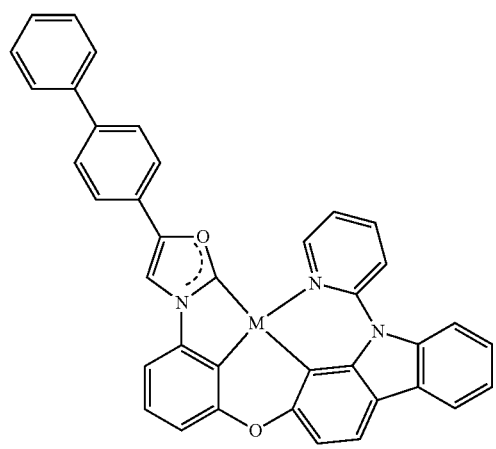
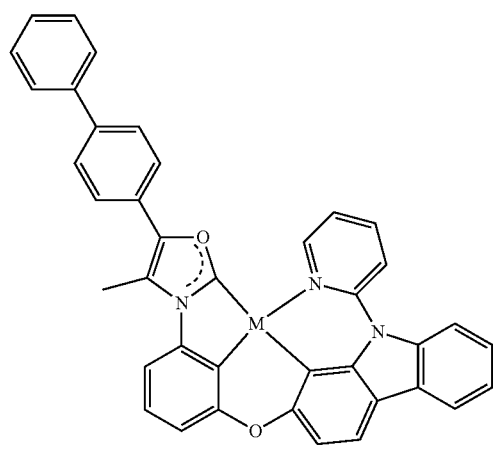
578
-continued
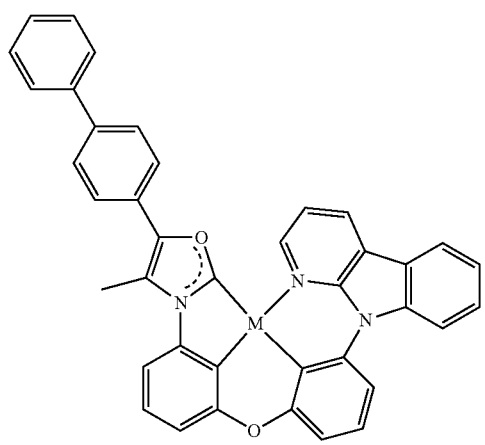
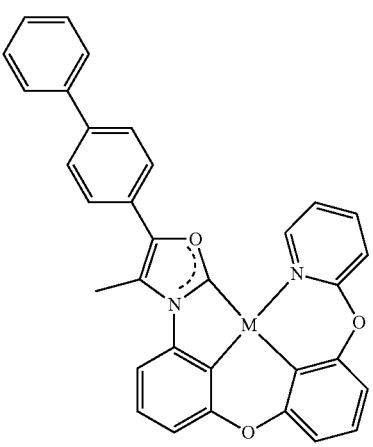
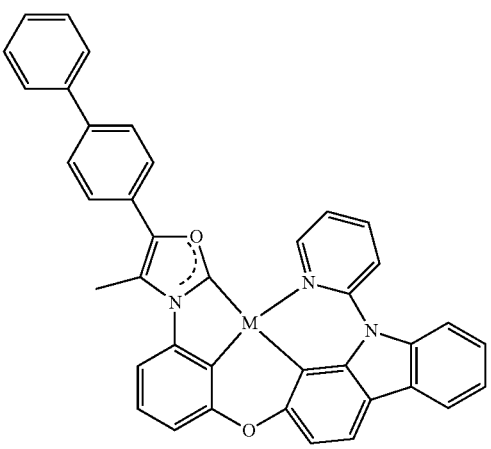

579
-continued
580
-continued
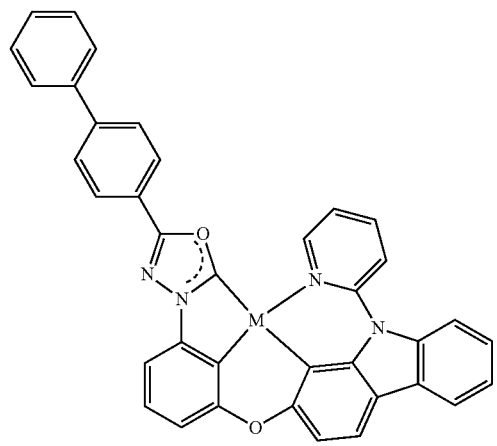
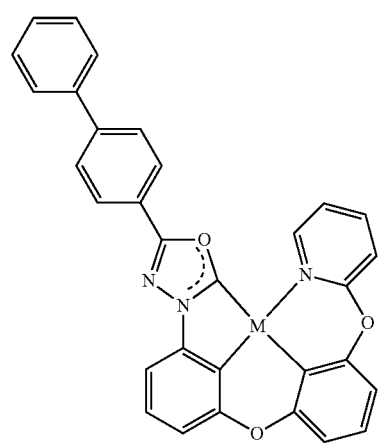
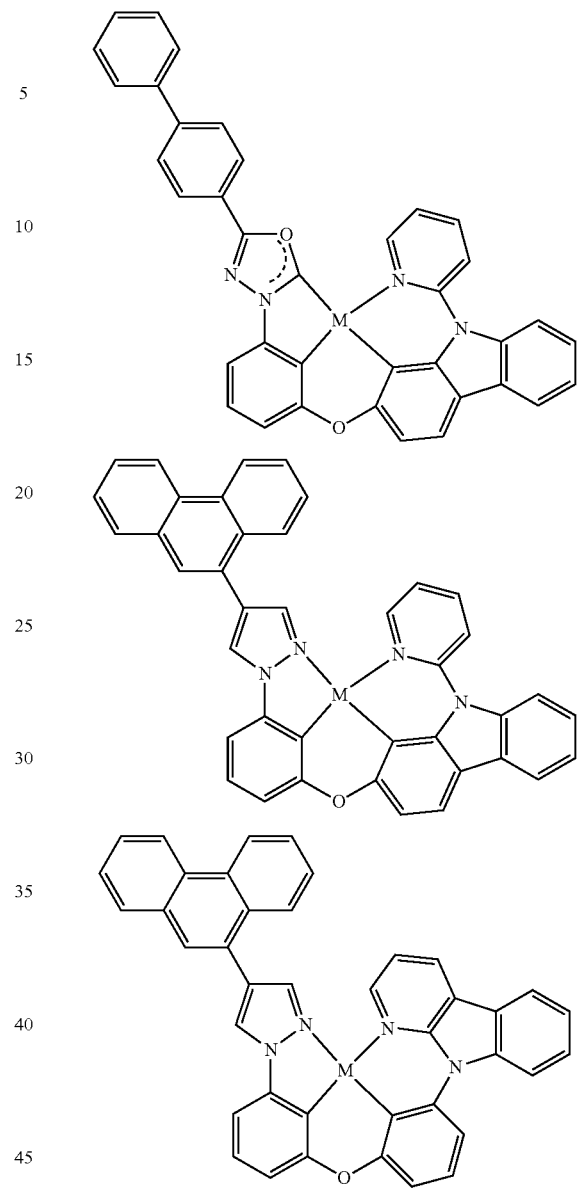
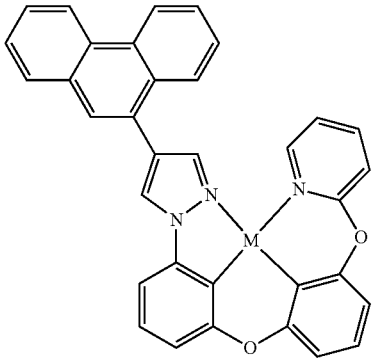

581
-continued
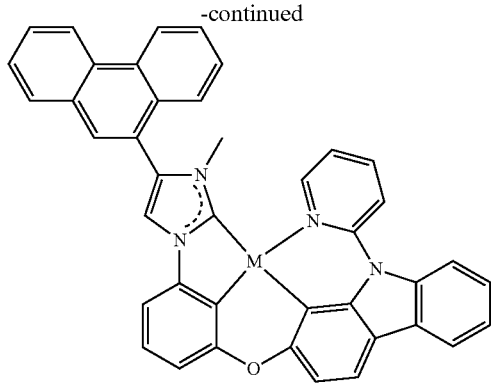
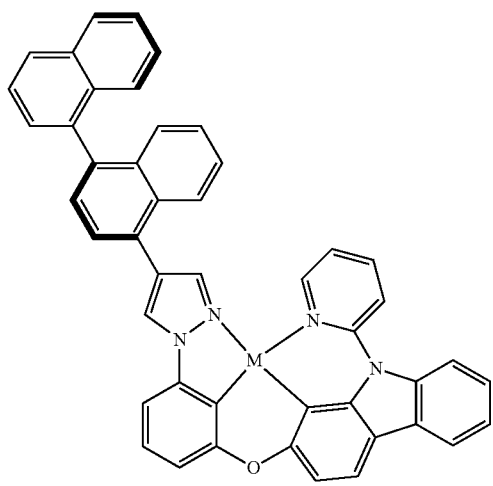
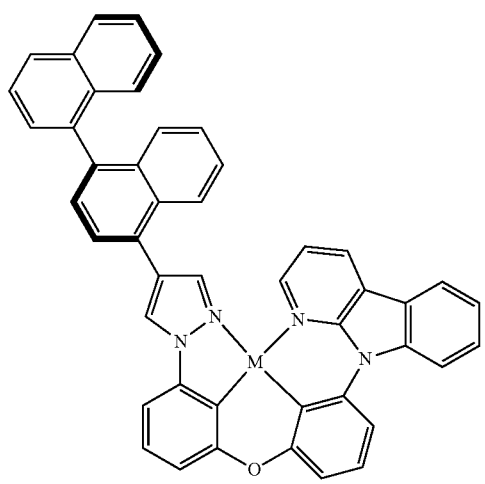
582
-continued
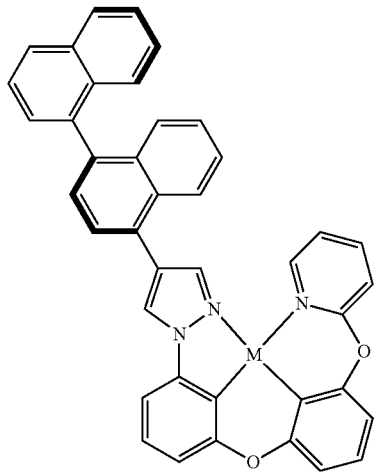
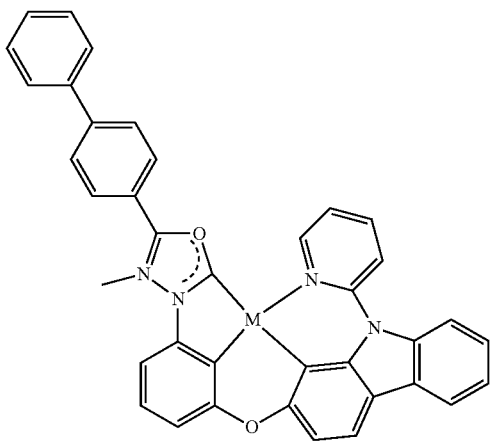
(M = Pt, Pd)
Structures 87

583
-continued
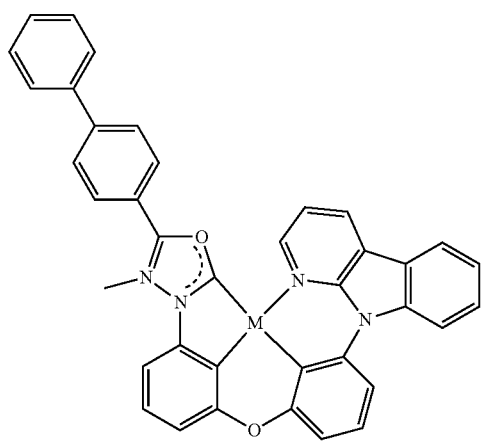
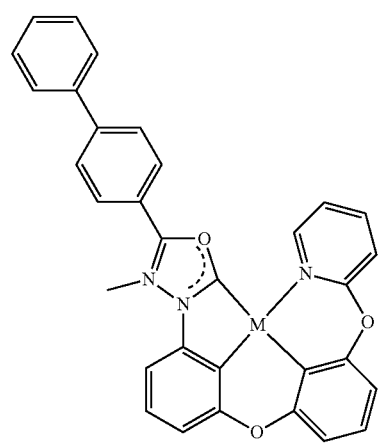
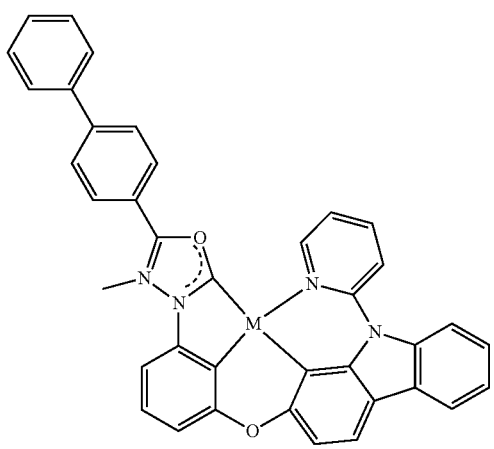
584
-continued
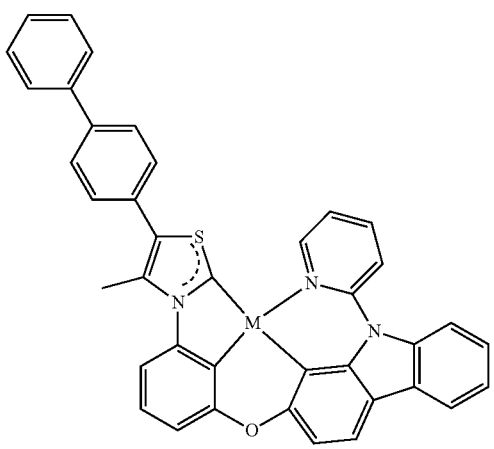
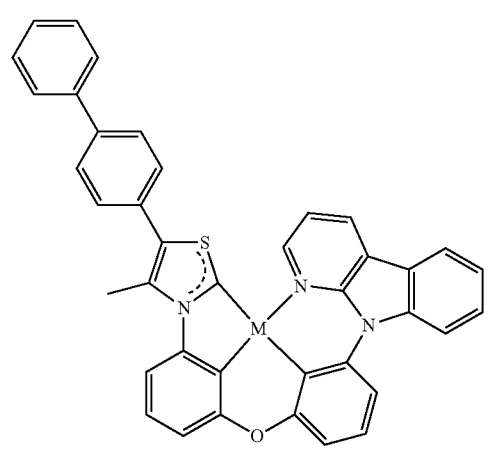
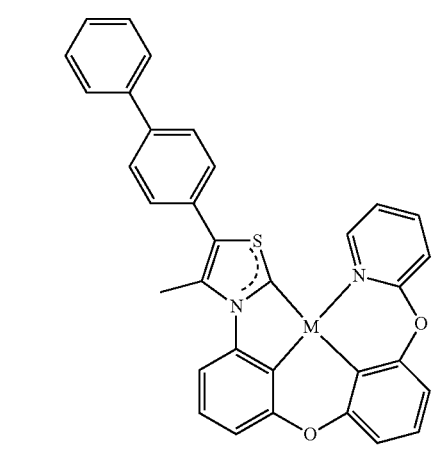

585
-continued
586
-continued
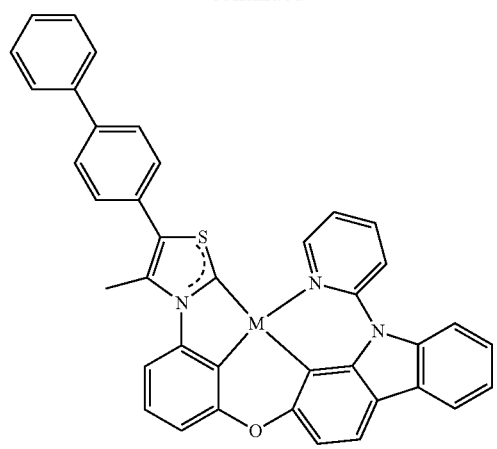
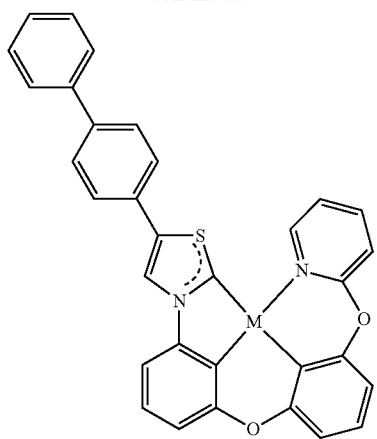
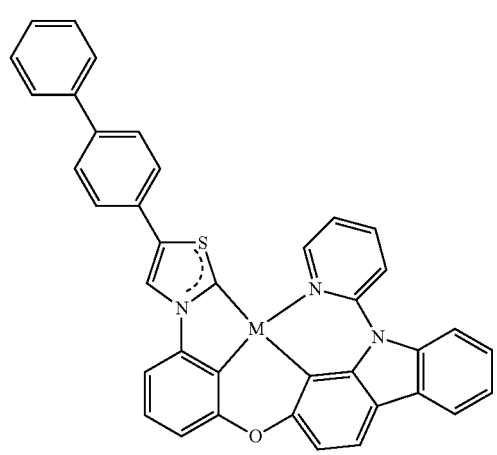
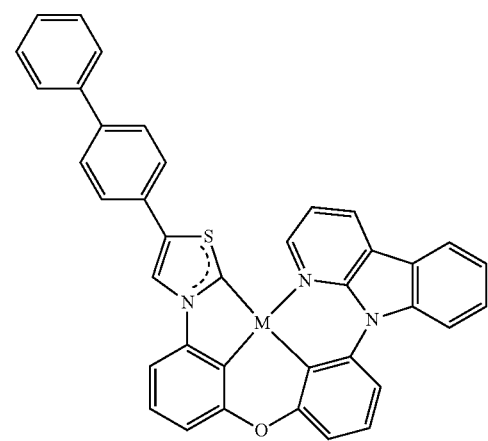
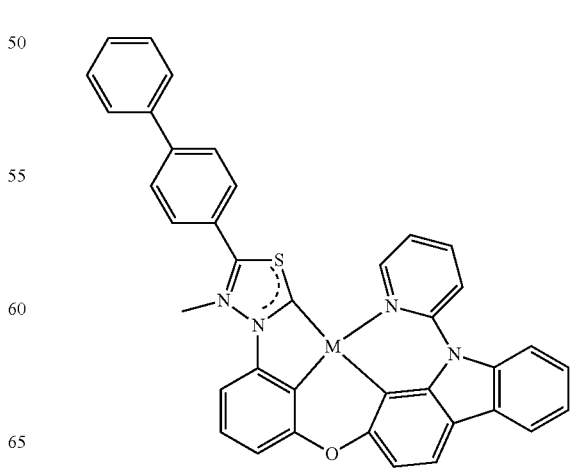

587
-continued
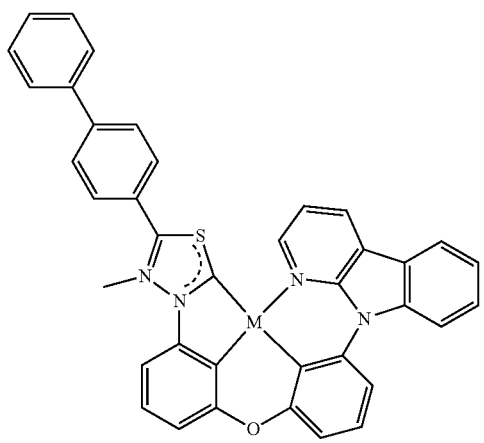
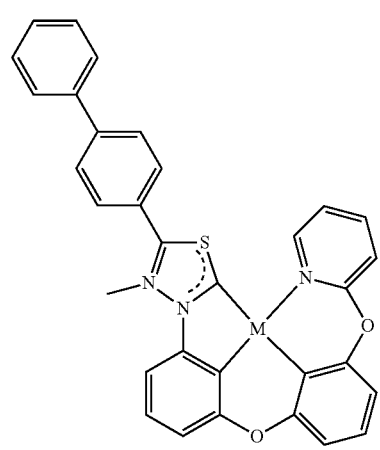
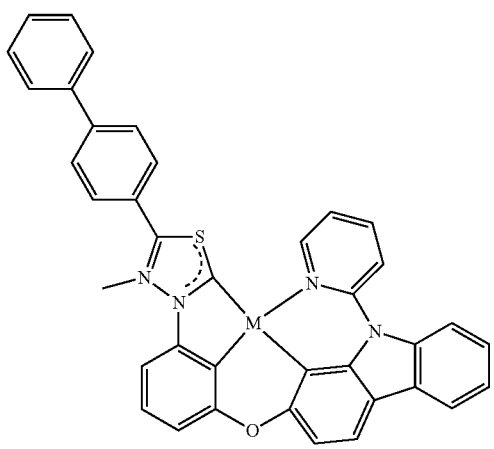
588
-continued
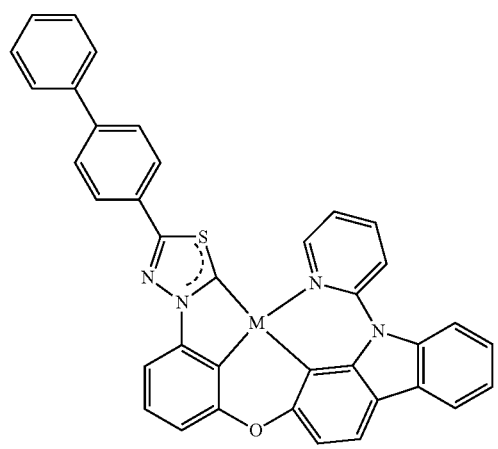
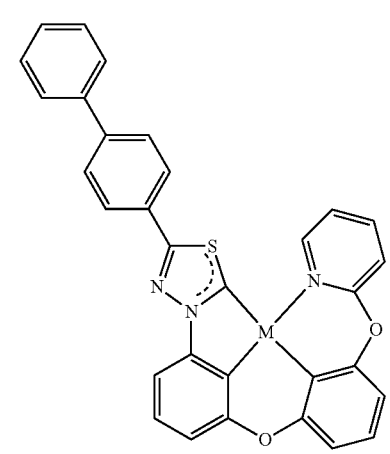

589
-continued
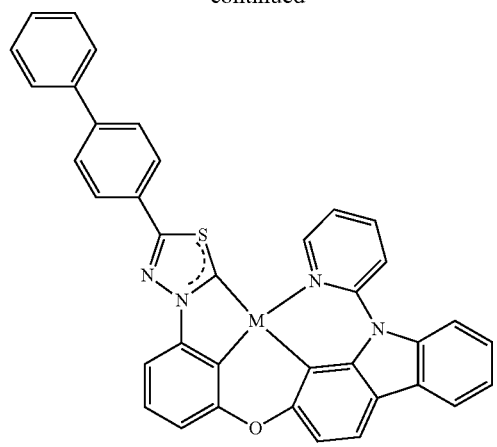
(M = Pt, Pd)
Structures 88
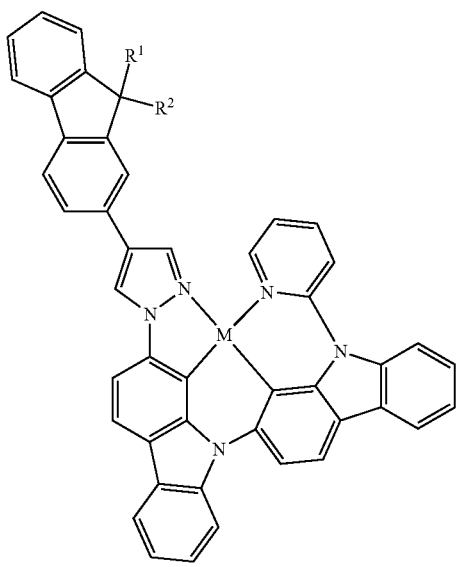
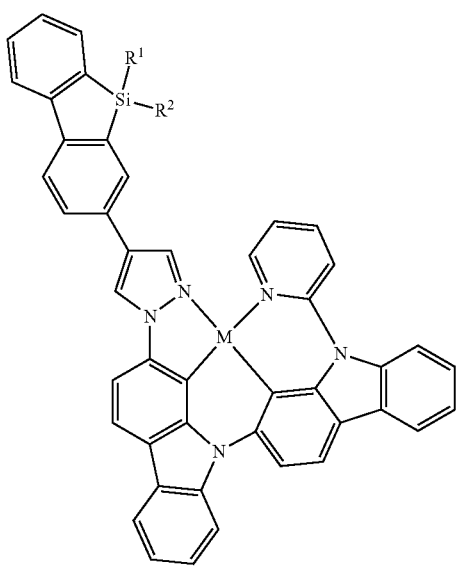
590
-continued
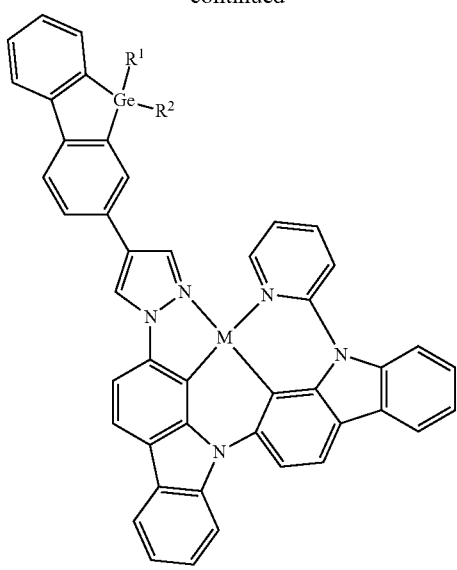
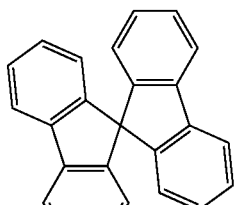
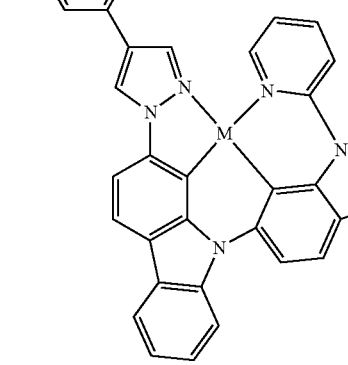
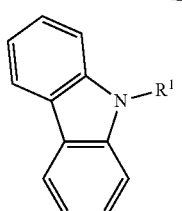
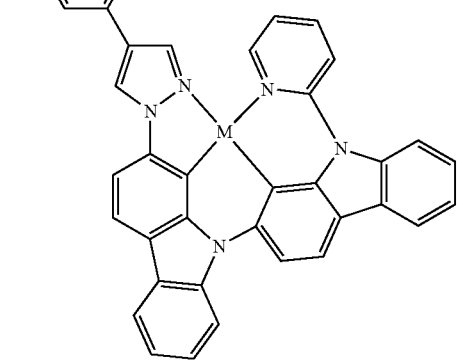

591
-continued
592
-continued
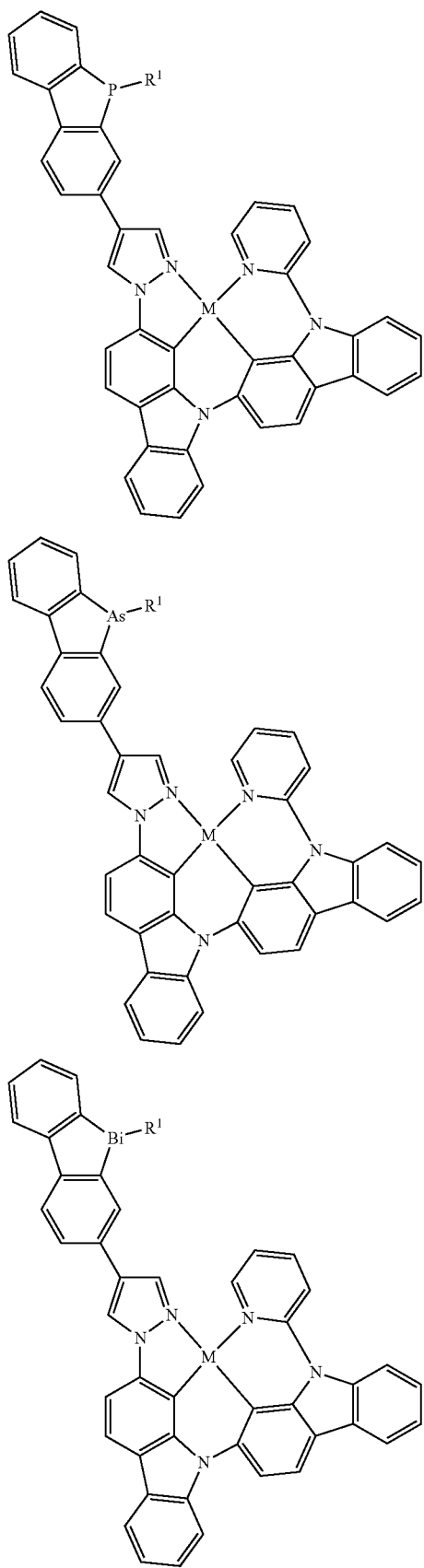
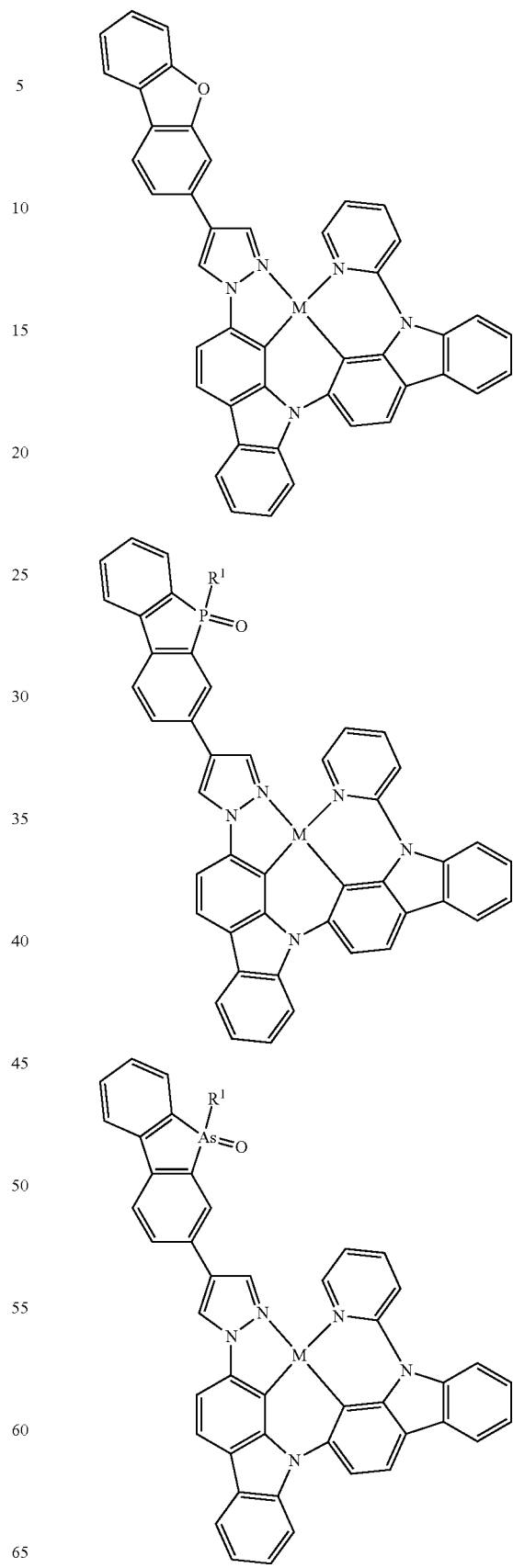

593
-continued
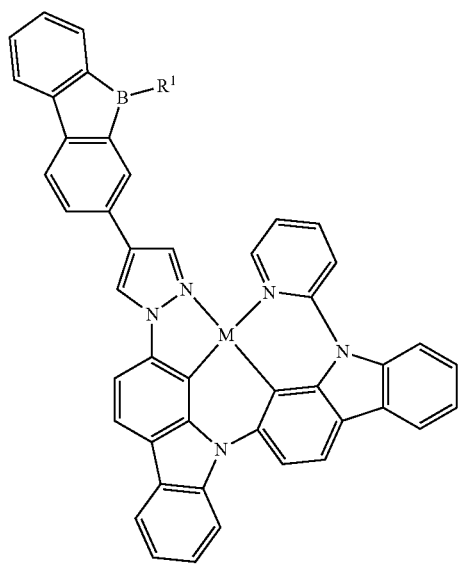
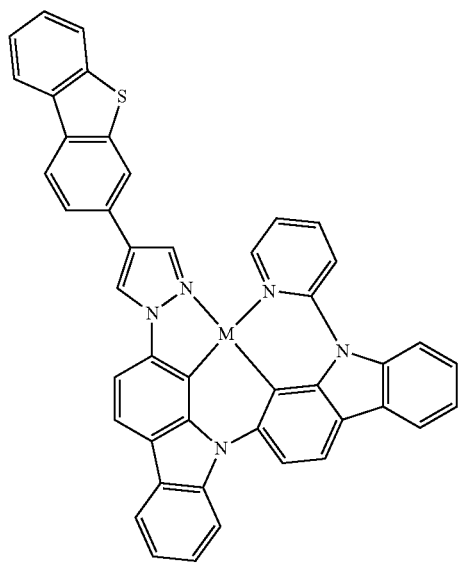
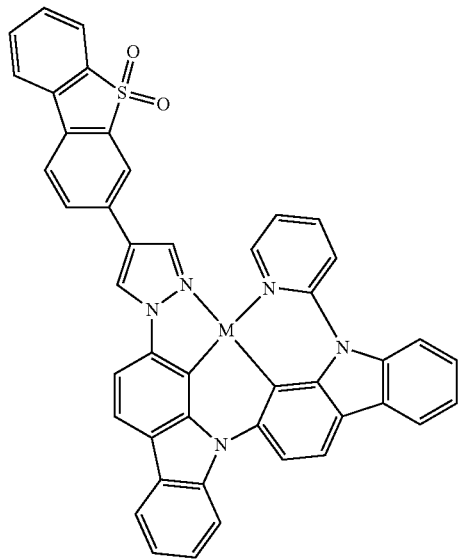
594
-continued
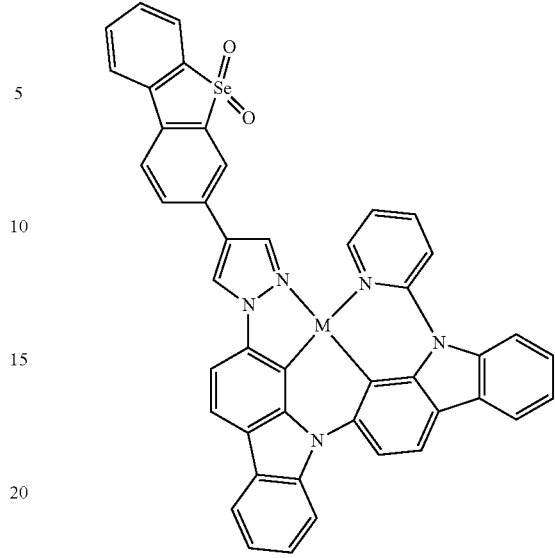
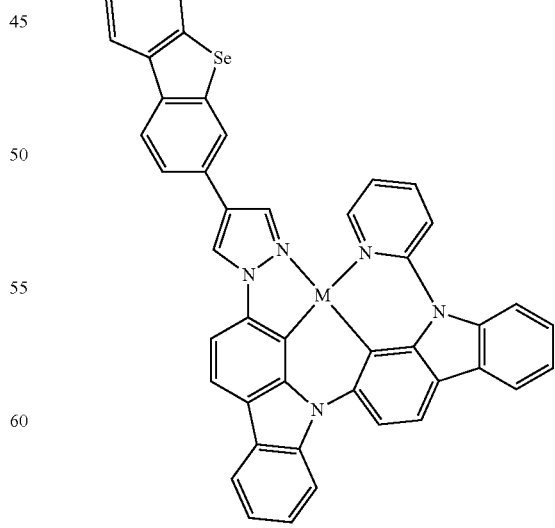
(M = Pt, Pd)

Structures 89
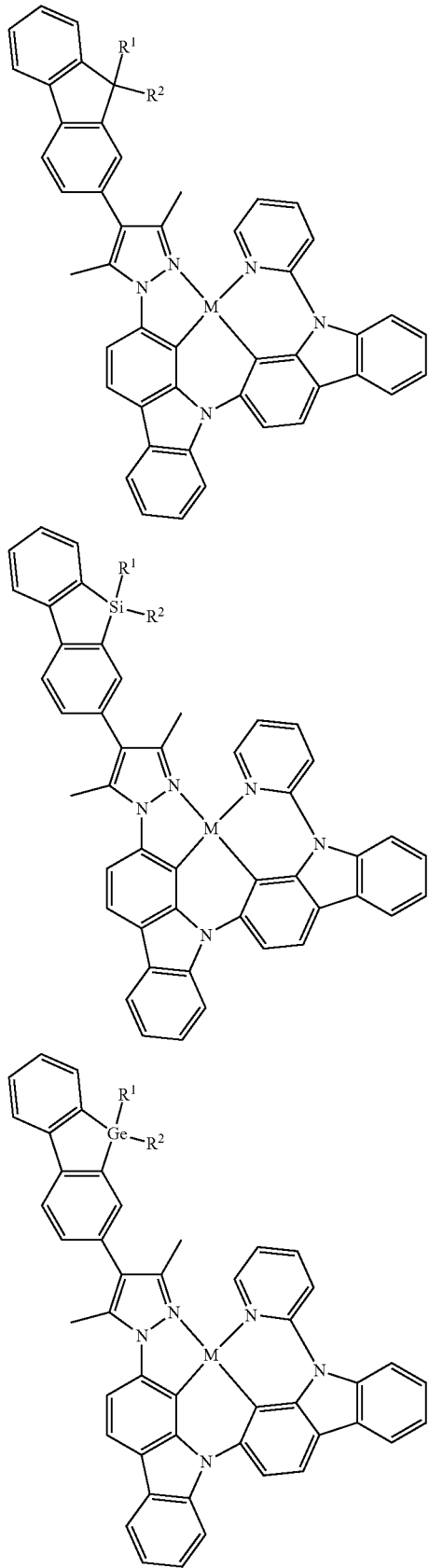
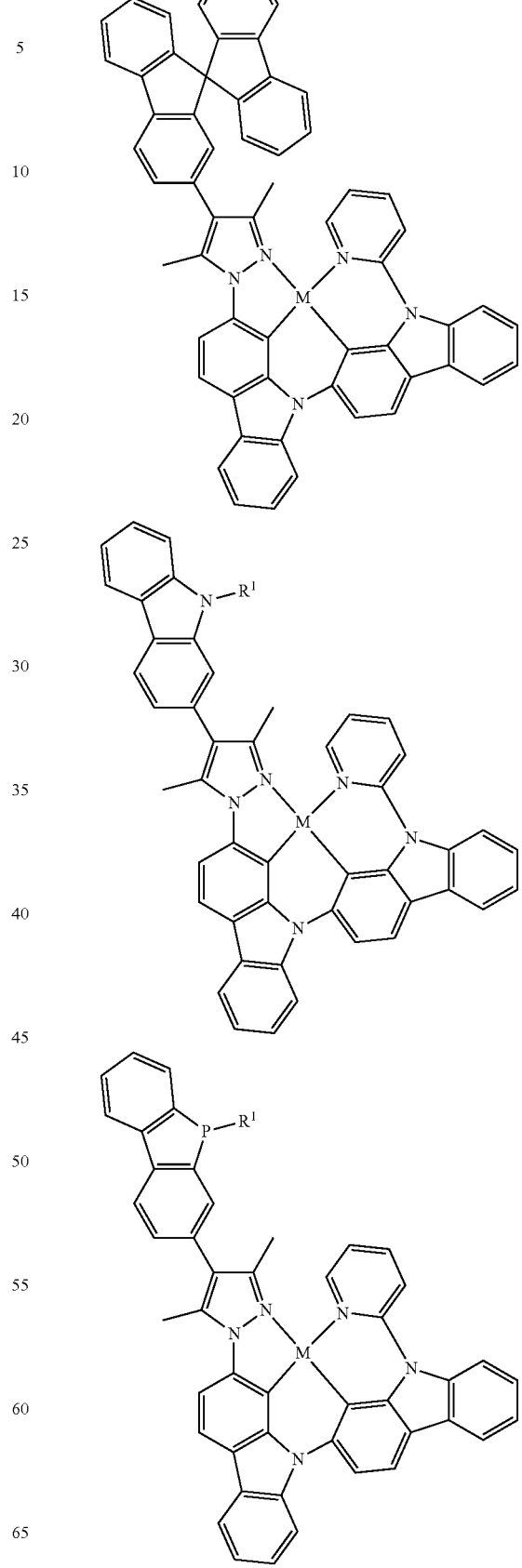

597
-continued
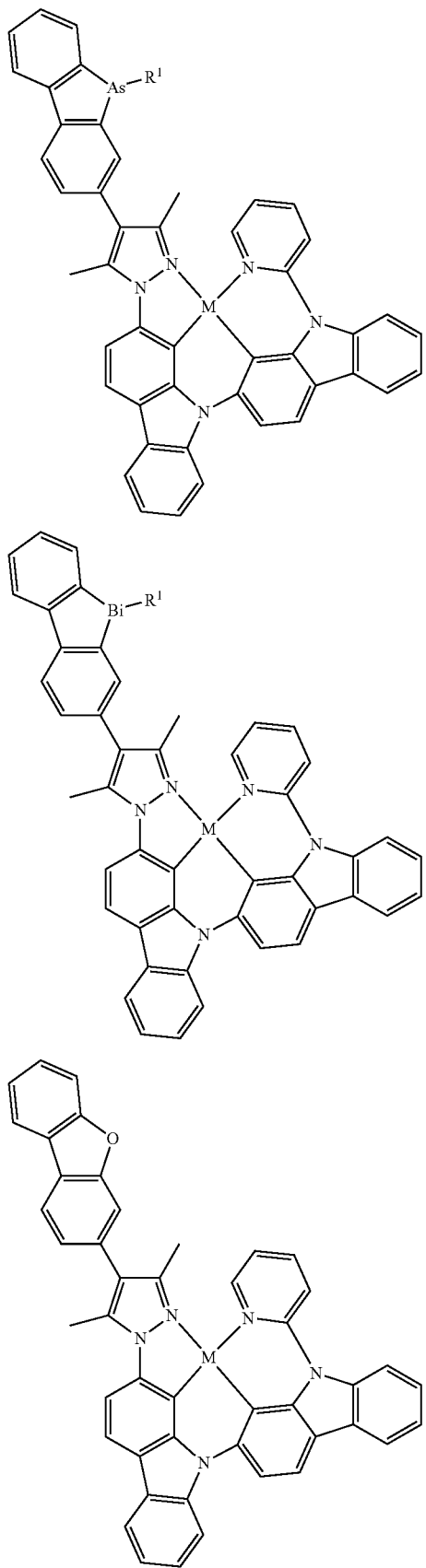
598
-continued
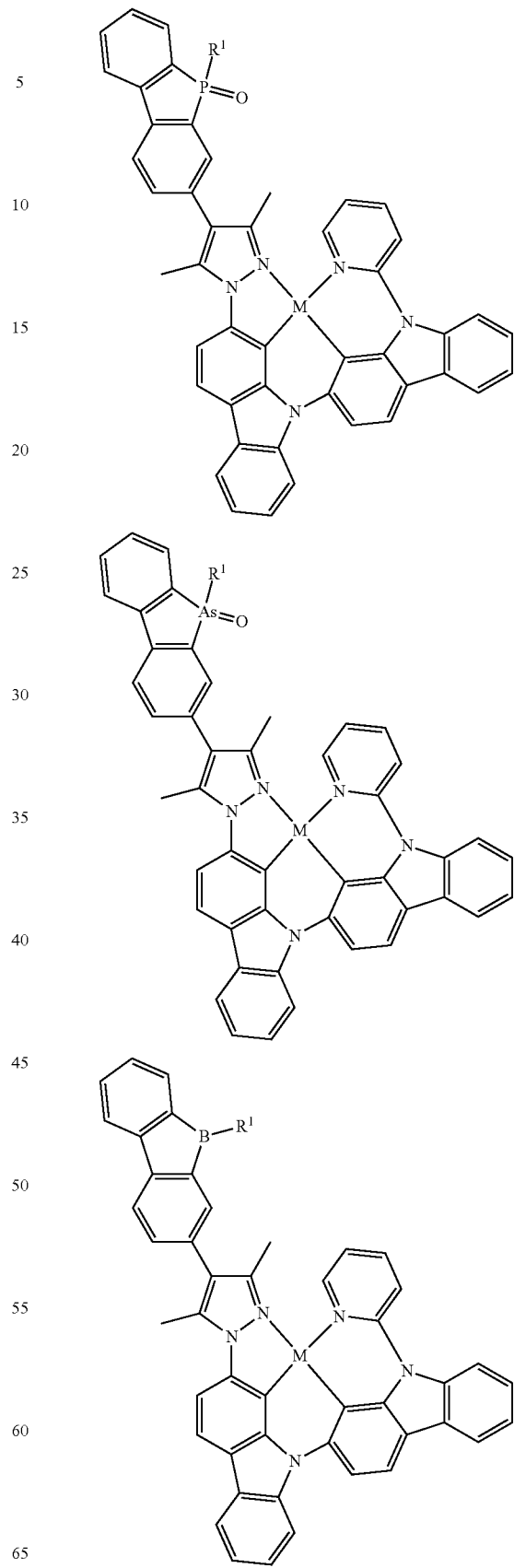

599
-continued
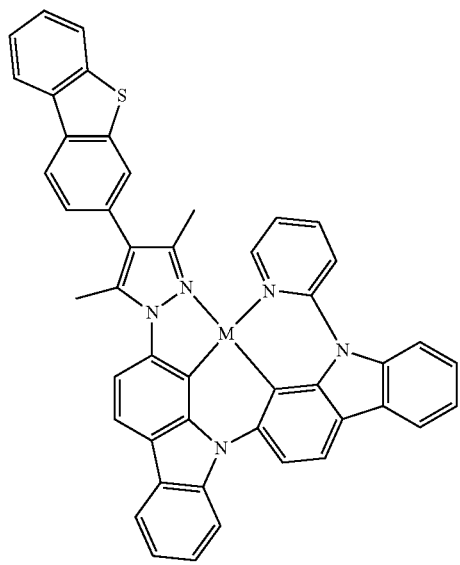
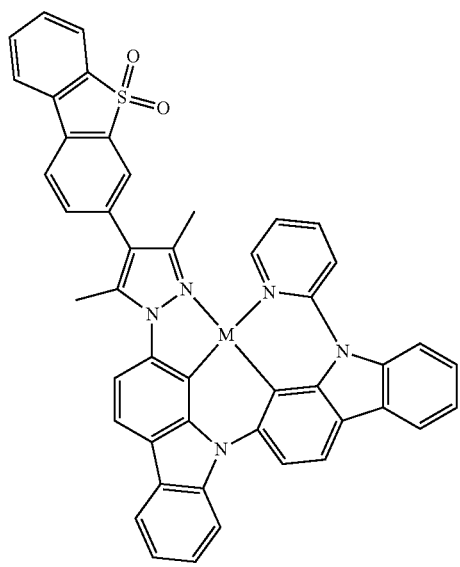
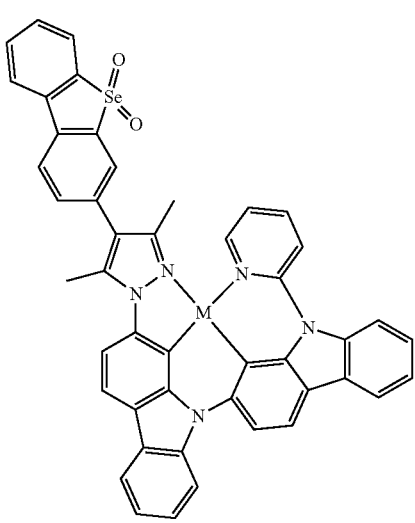
600
-continued
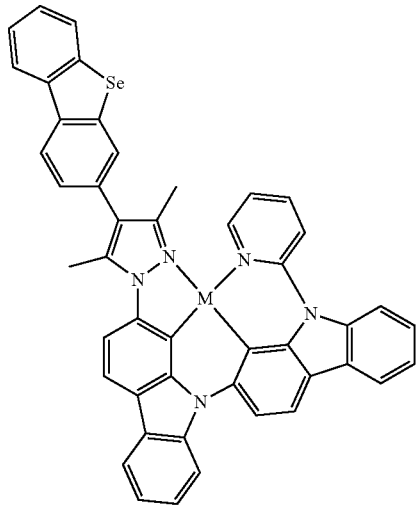
(M = Pt, Pd)
Structures 90
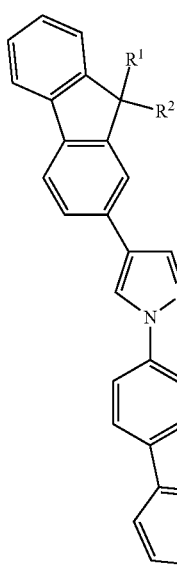
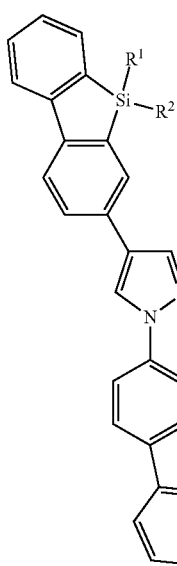

601
-continued
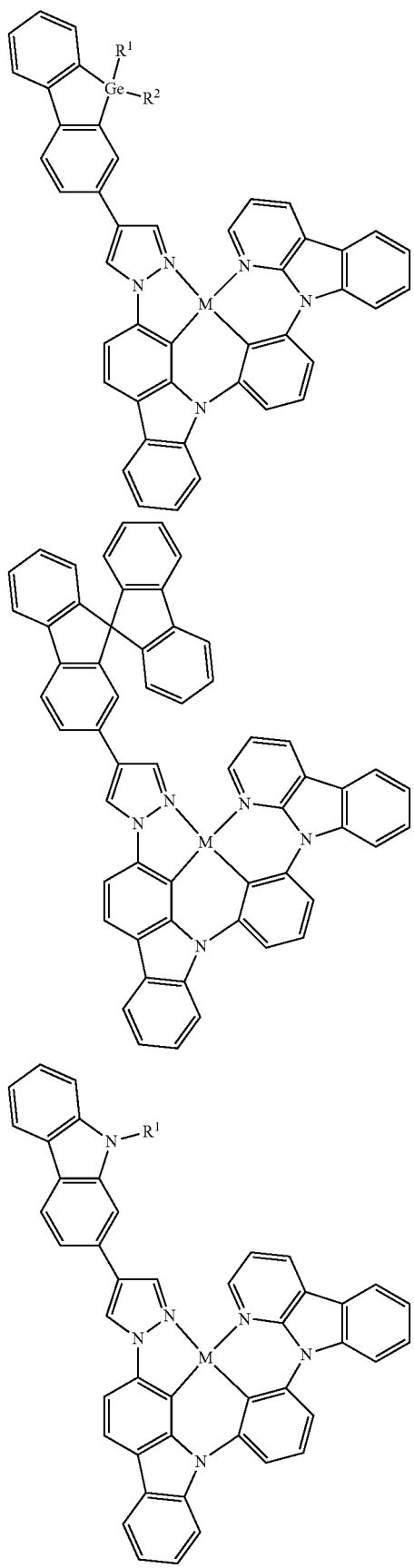
602
-continued
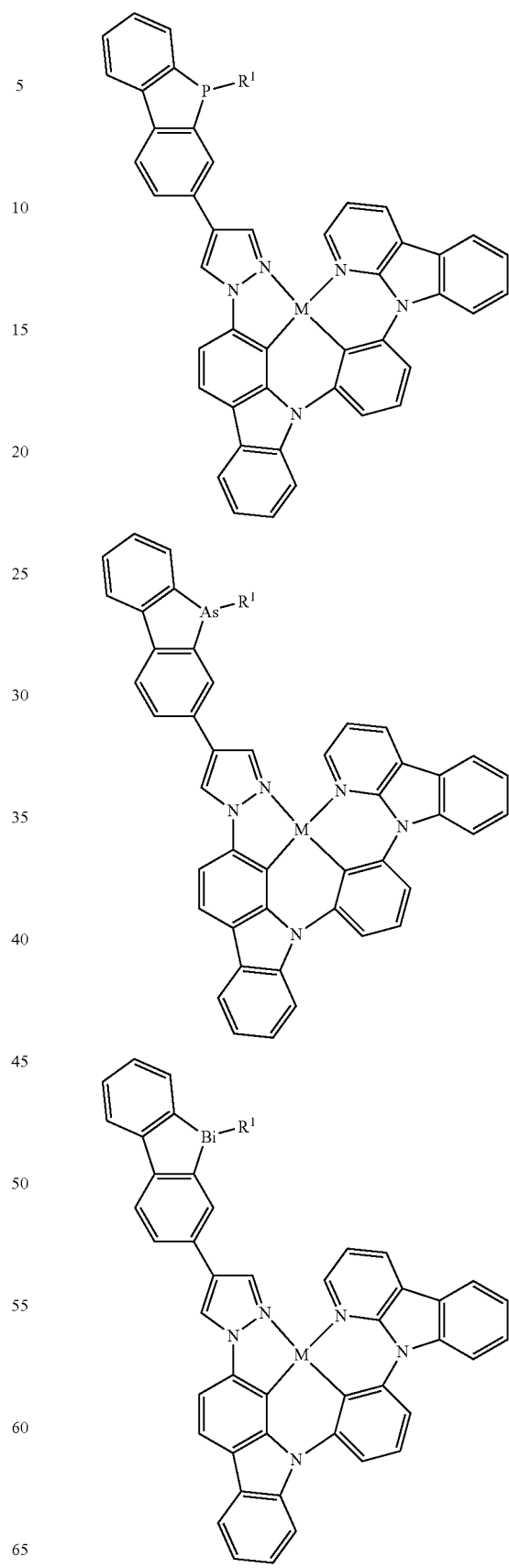

603
-continued
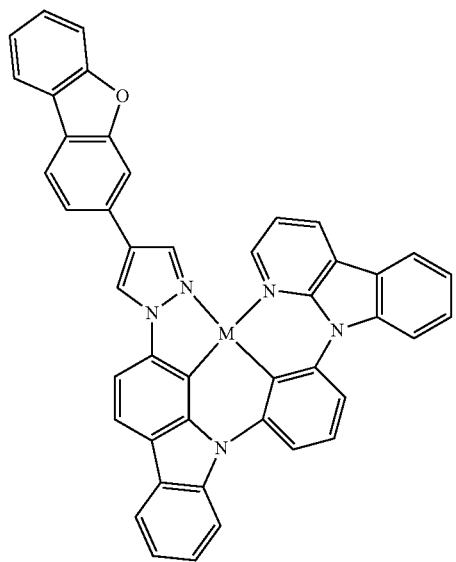
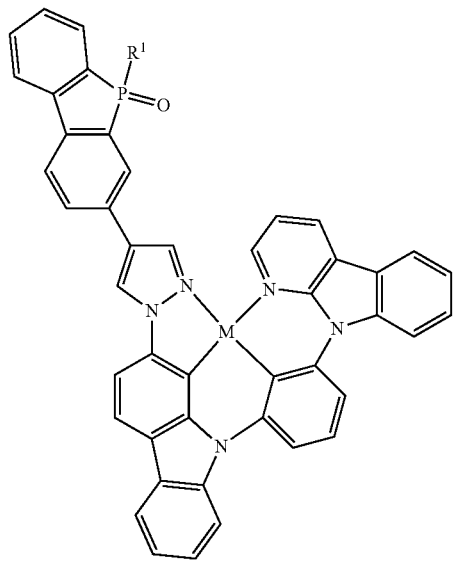
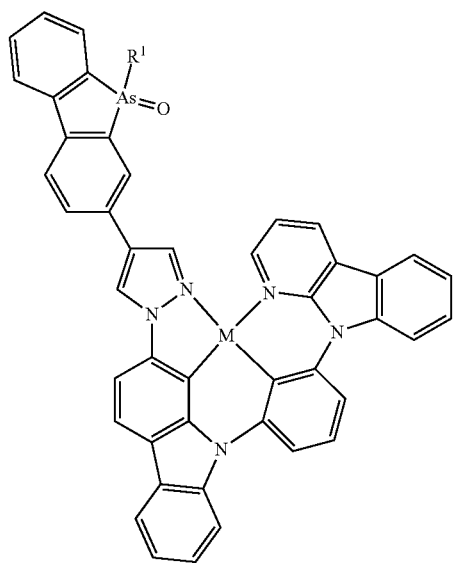
604
-continued
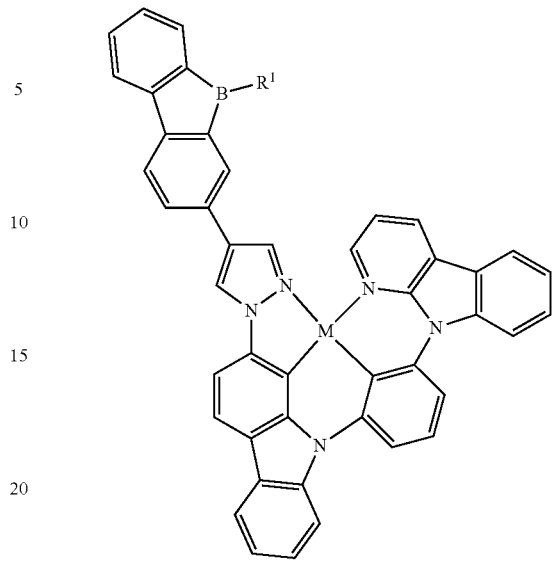
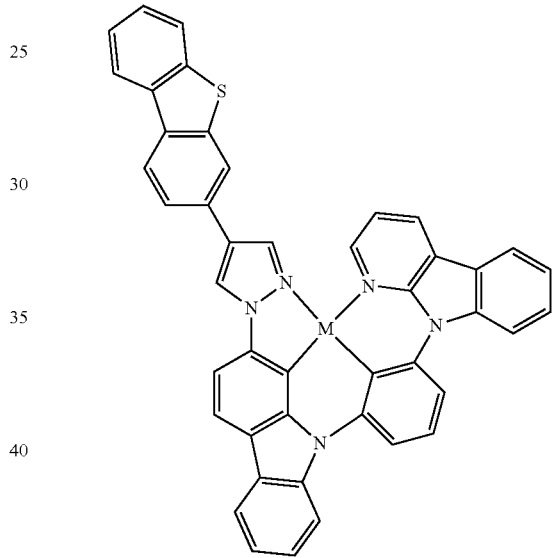

605
-continued
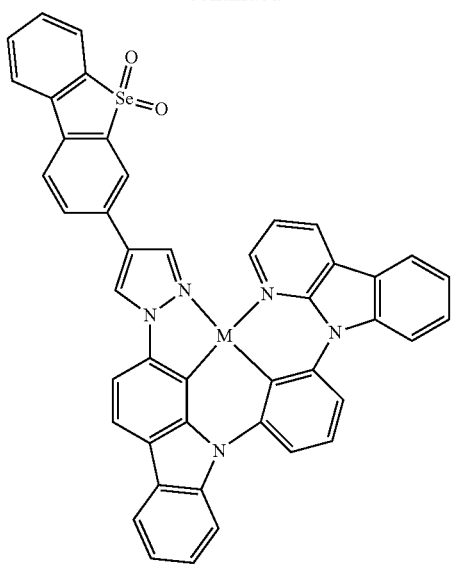
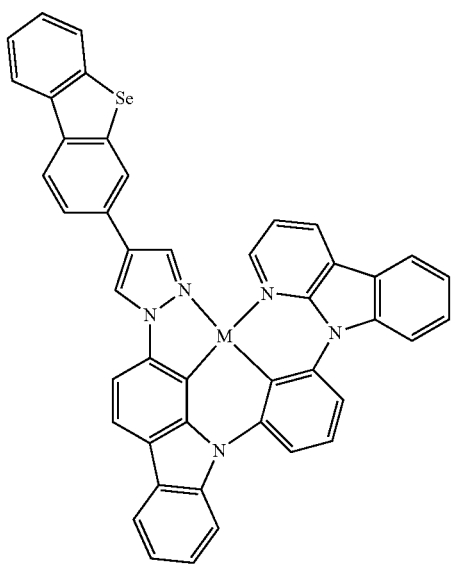
(M = Pt, Pd)
606
-continued
Structures 91
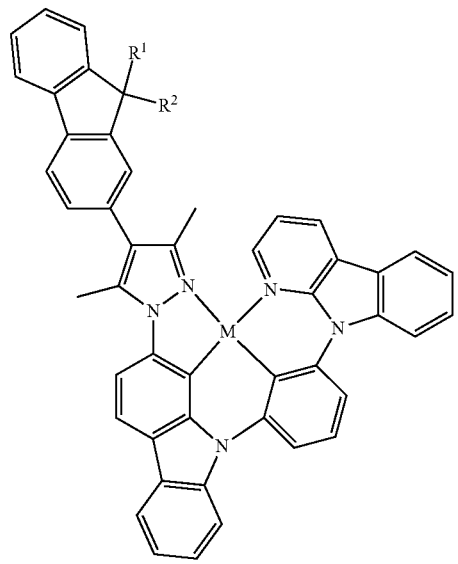
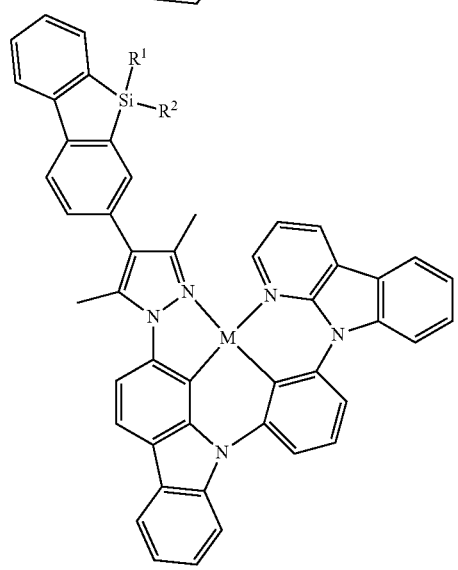
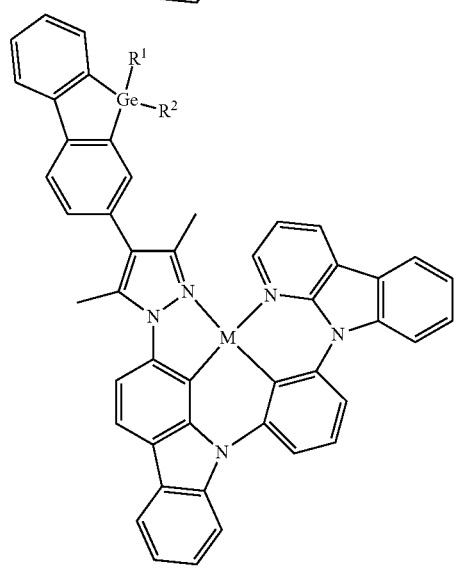

607
-continued
608
-continued
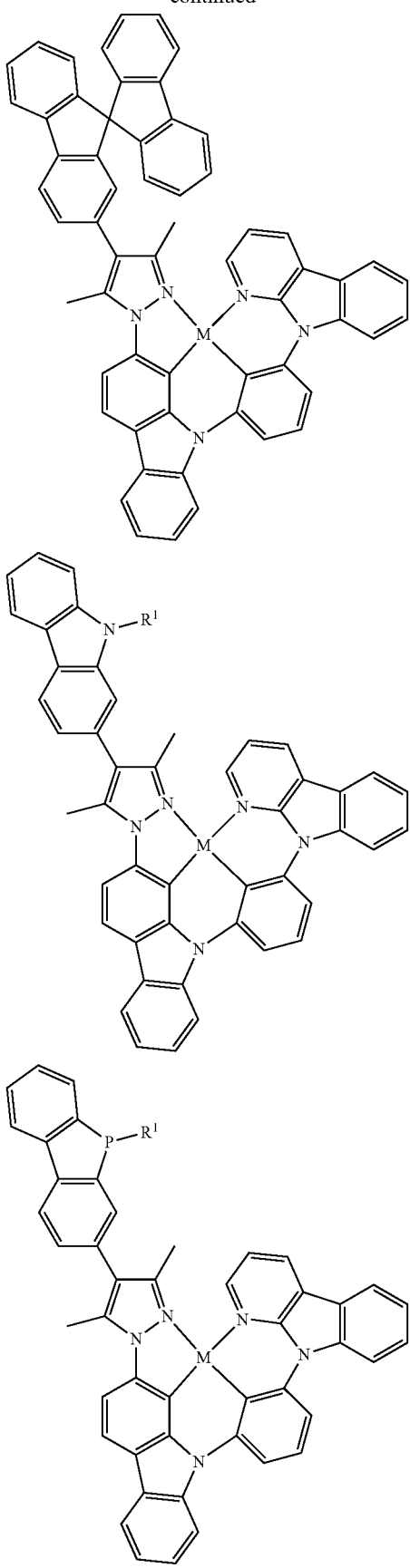
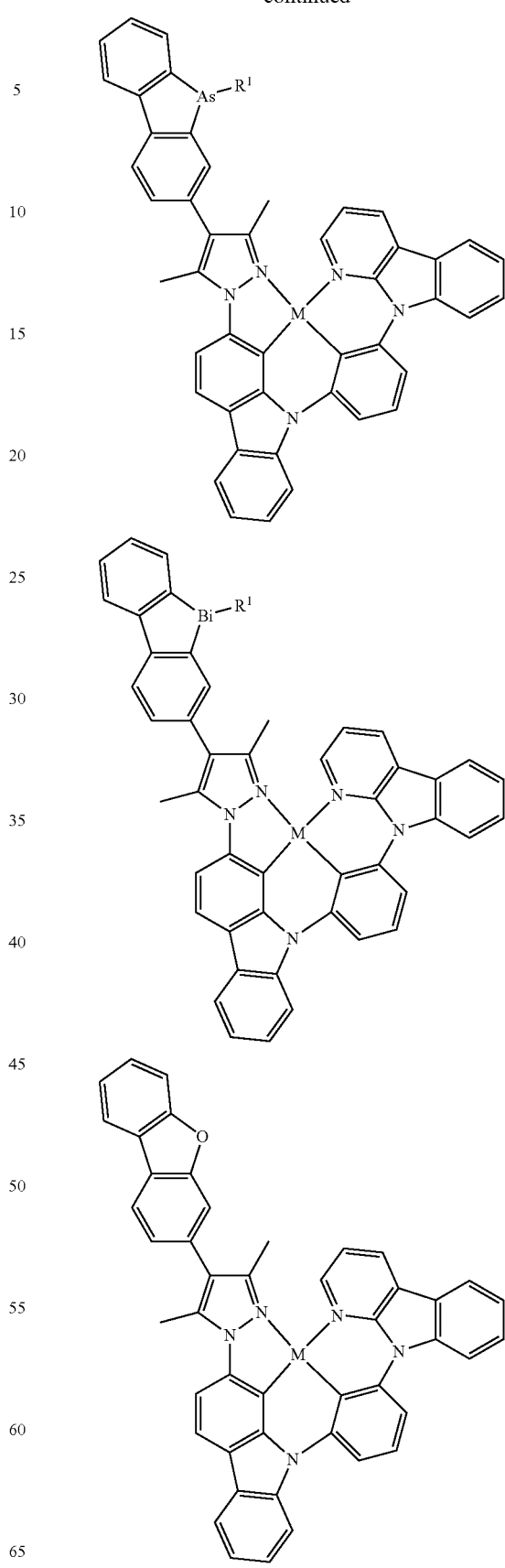

609
-continued
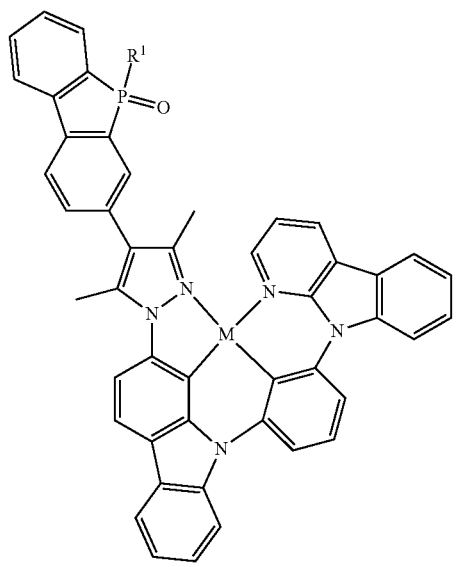
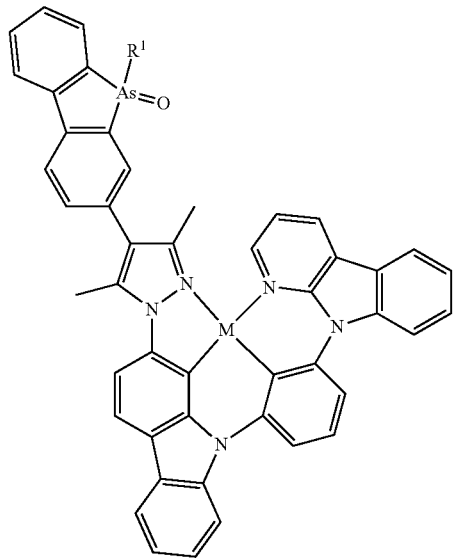
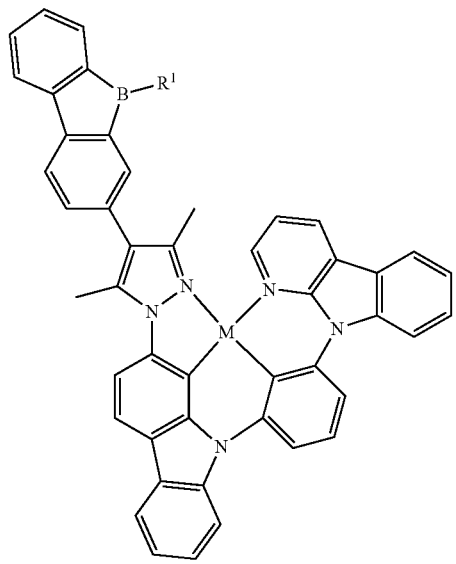
610
-continued
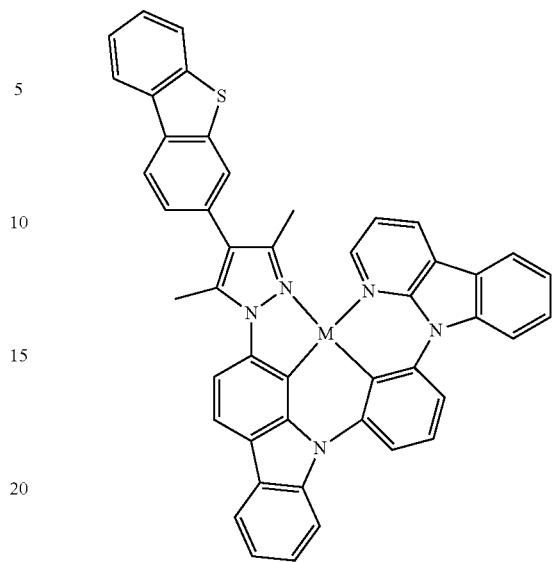
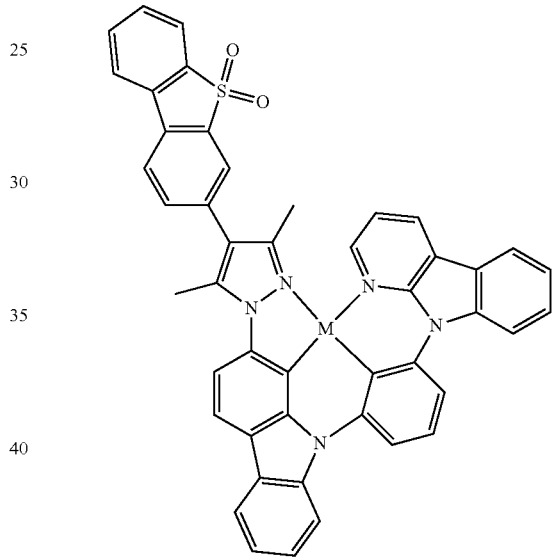

611
-continued
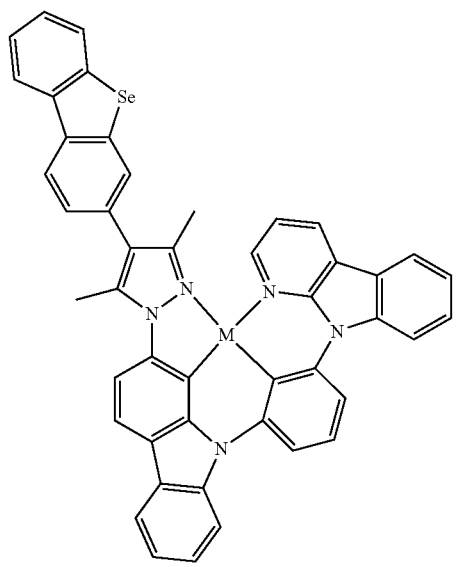
(M = Pt, Pd)
Structures 92
612
-continued
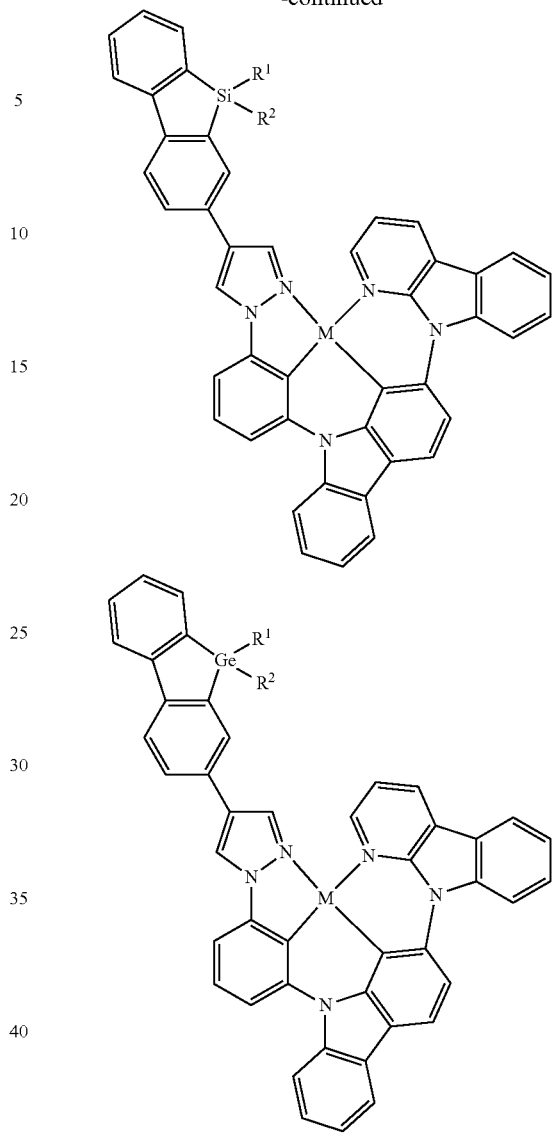

613
-continued
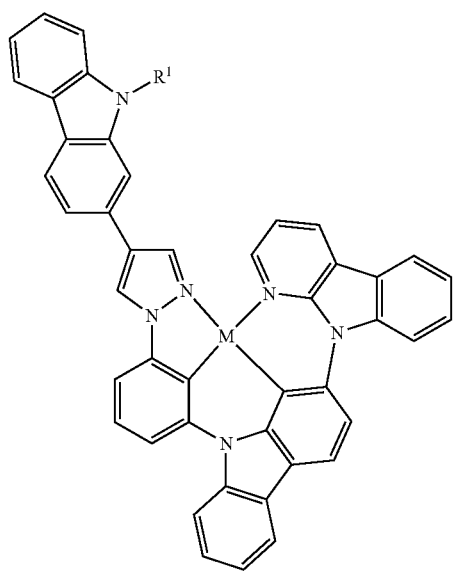
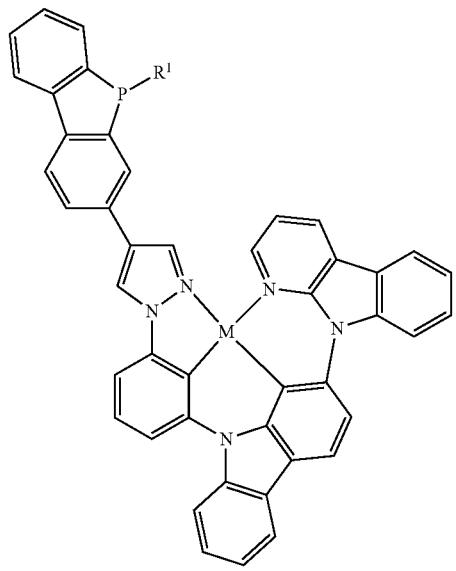
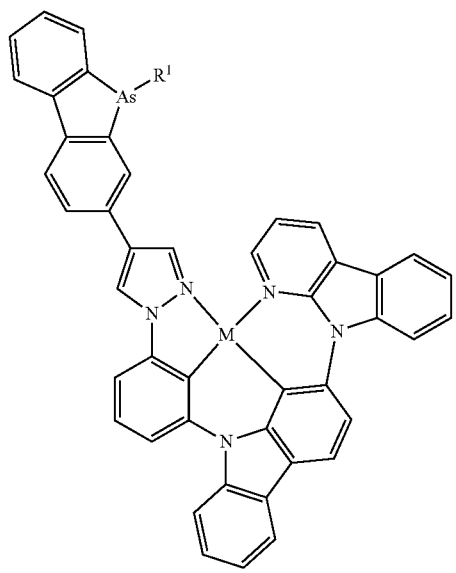
614
-continued
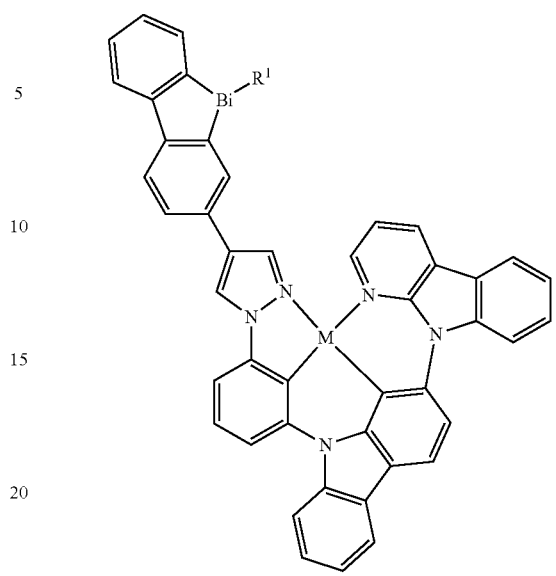
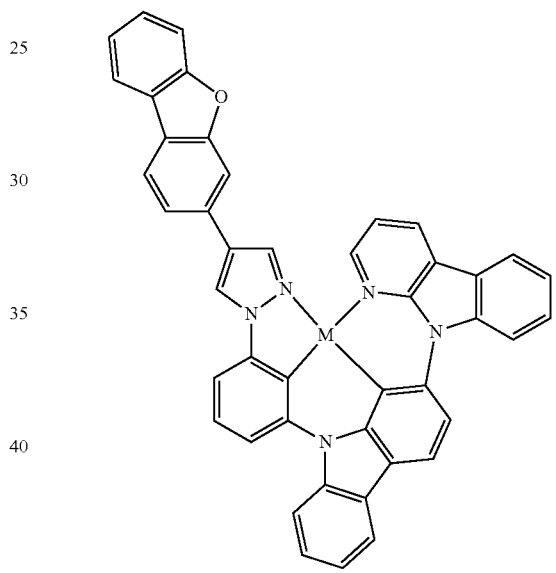
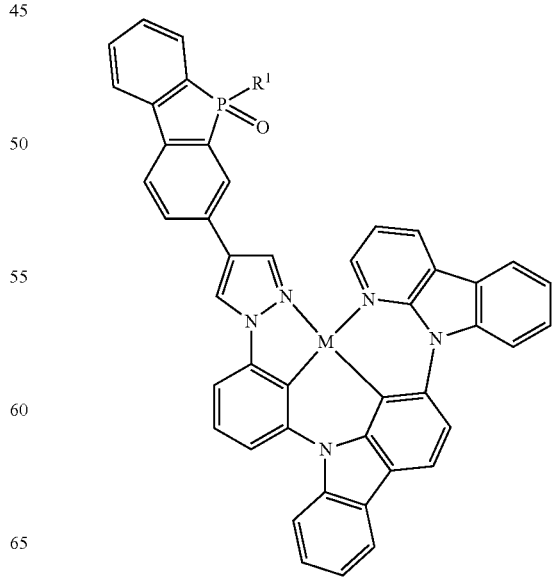

615
-continued
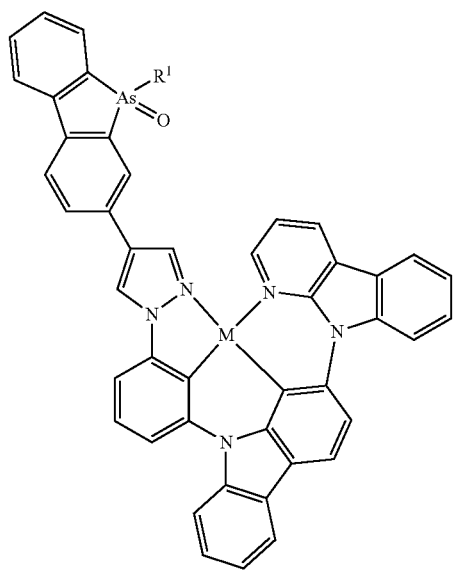
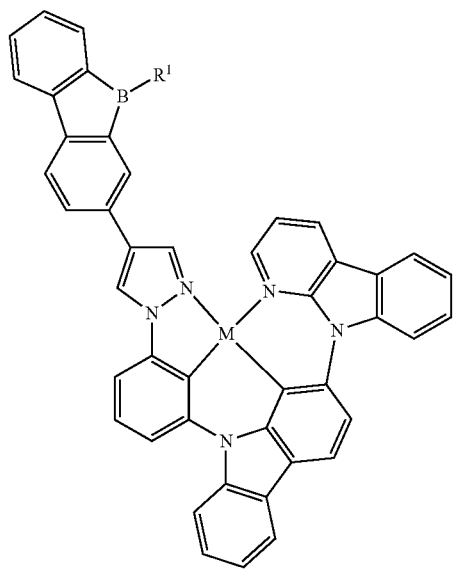
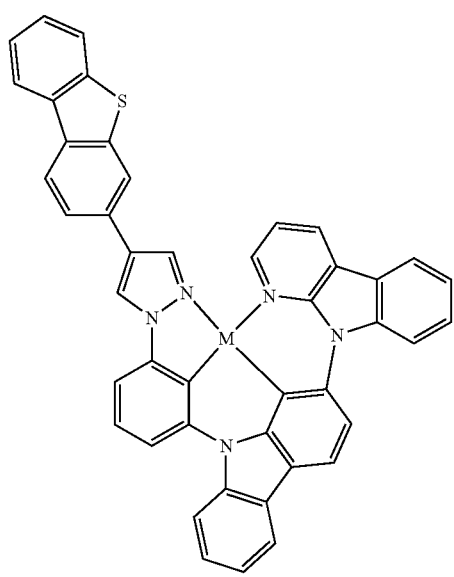
616
-continued
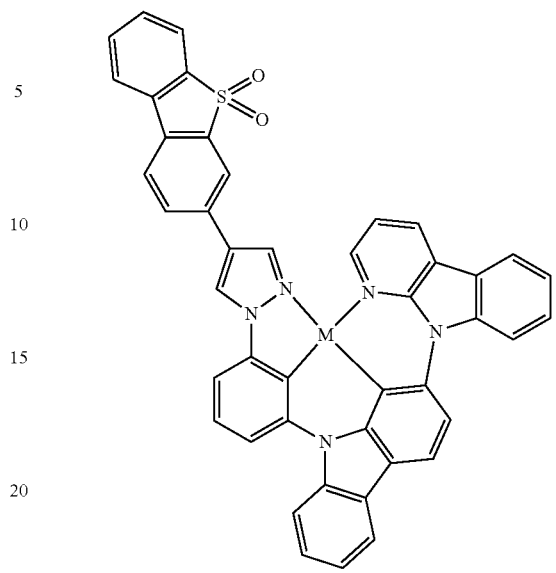
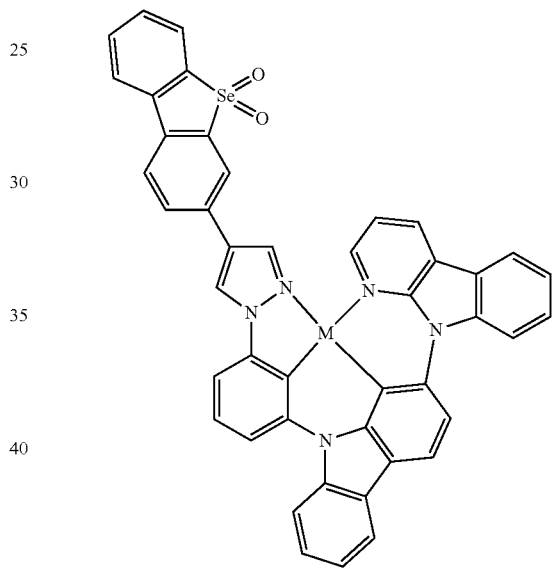
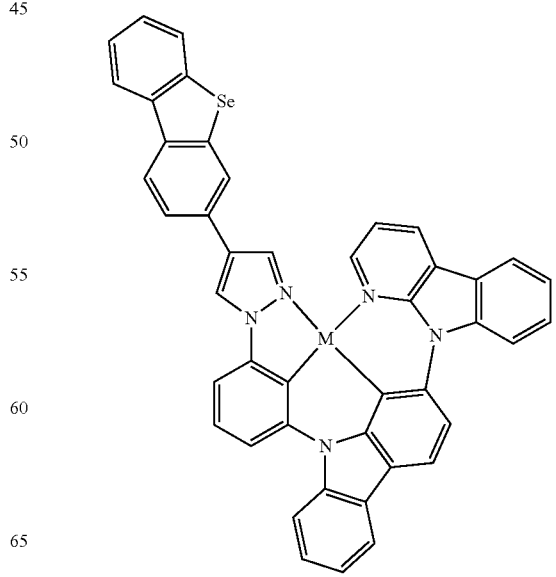

(M = Pt, Pd)
Structures 93
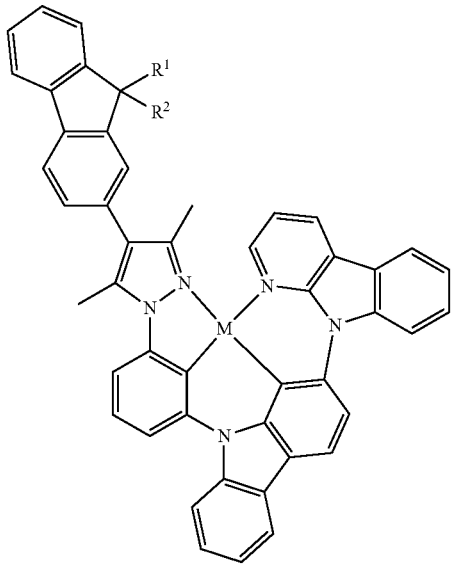
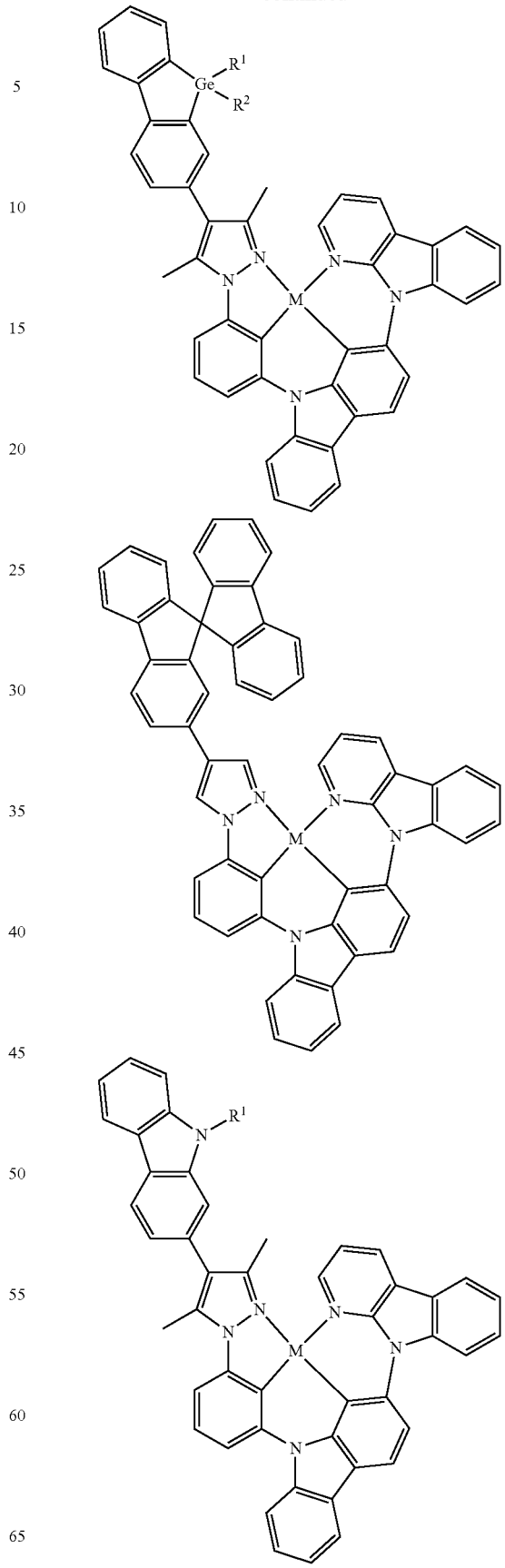
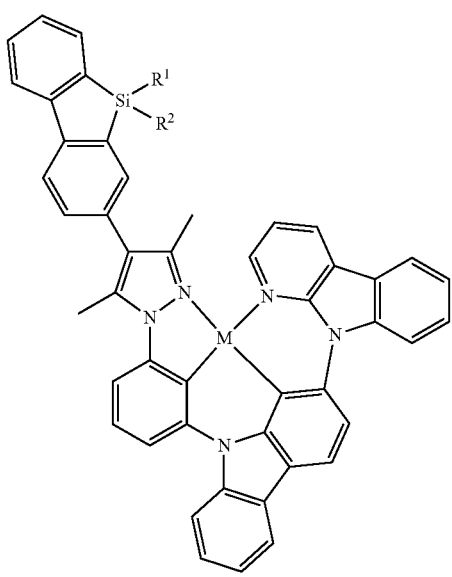

619
-continued
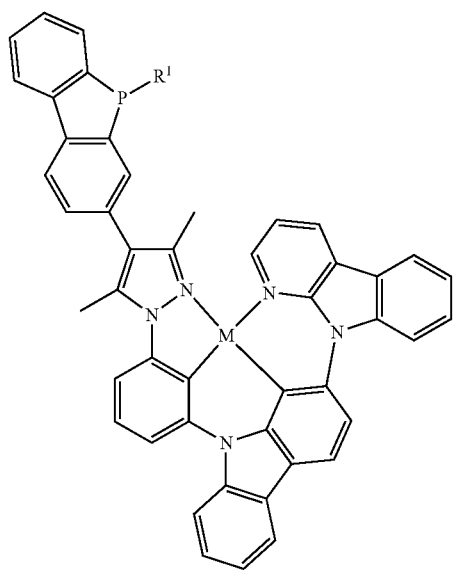
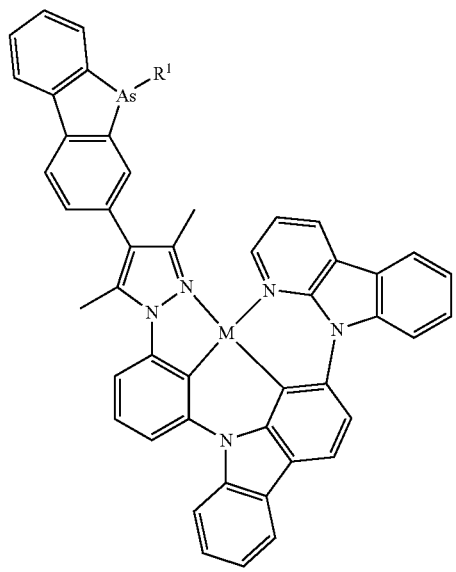
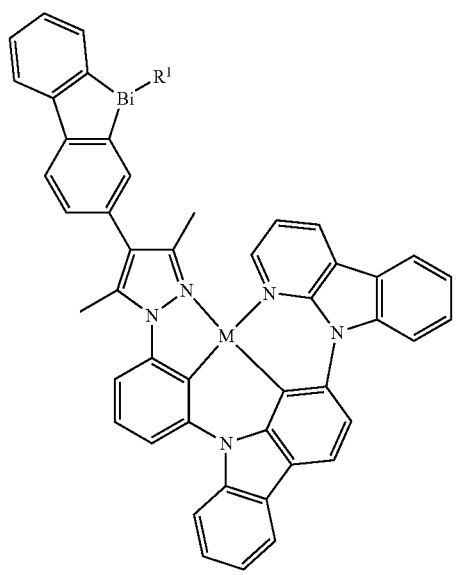
620
-continued
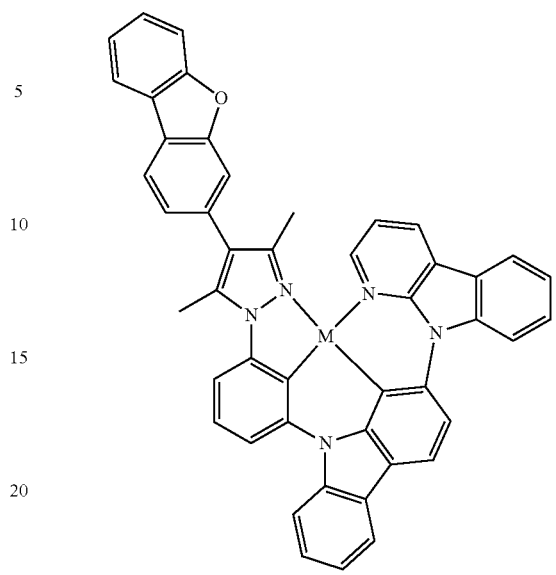
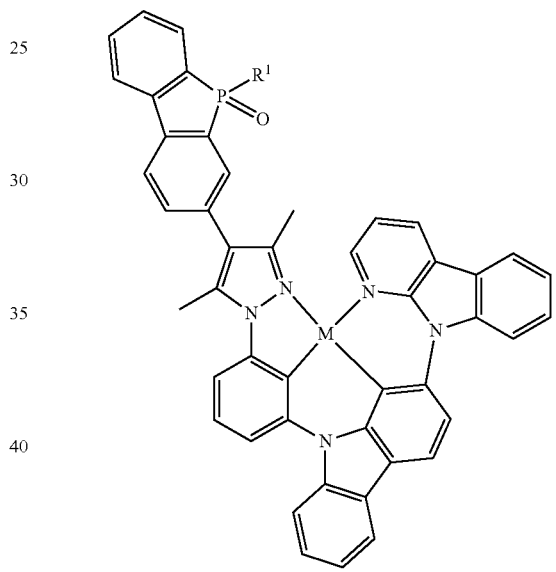
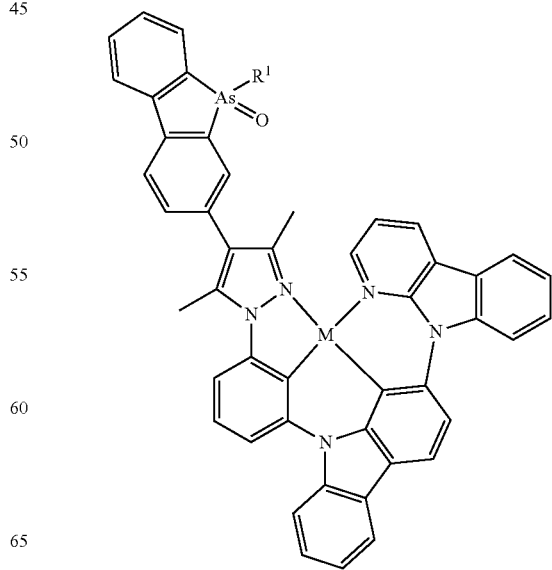

621
-continued
622
-continued
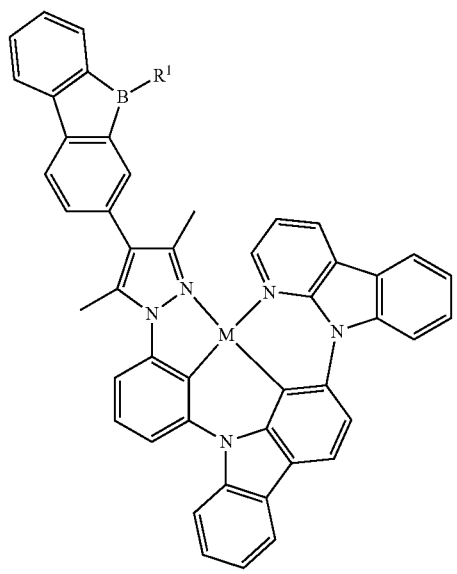
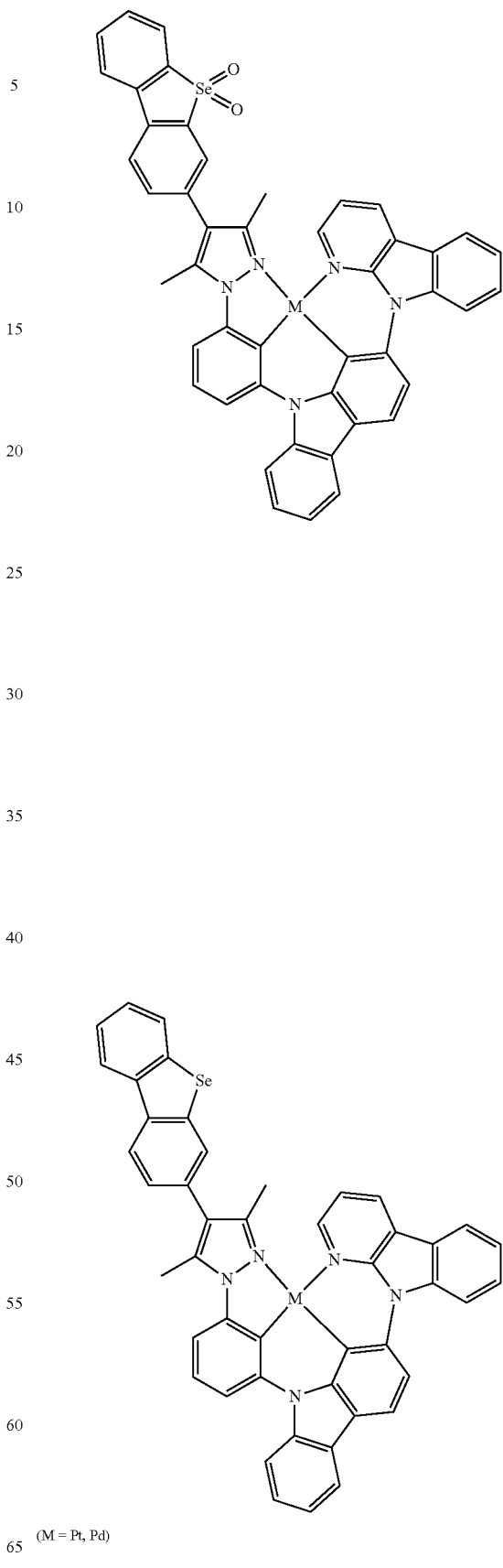
(M = Pt, Pd)

-continued
Structures 94
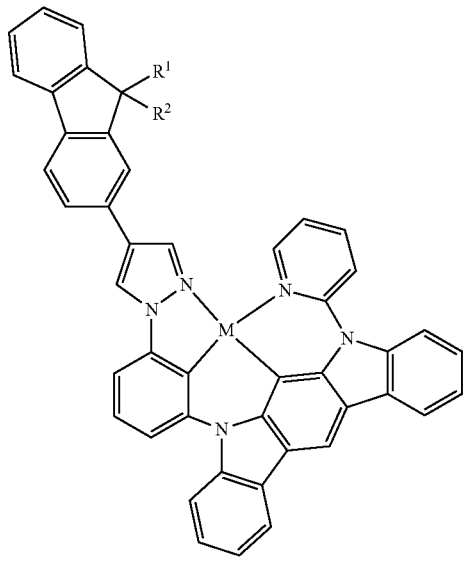
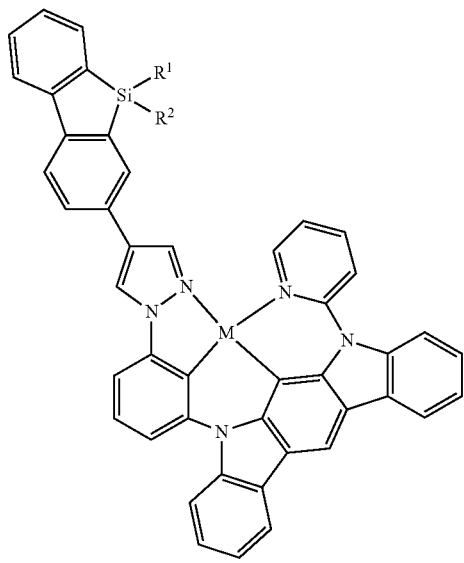
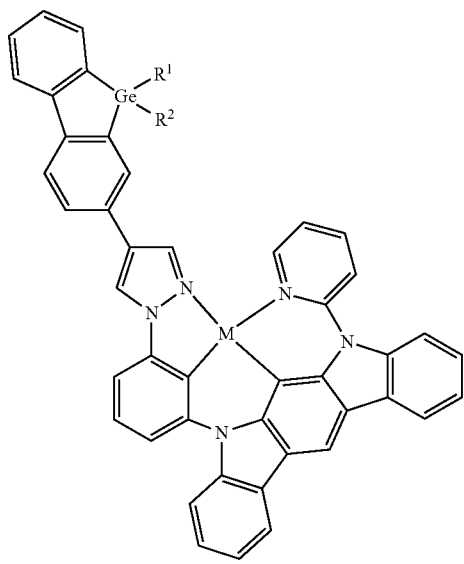
-continued
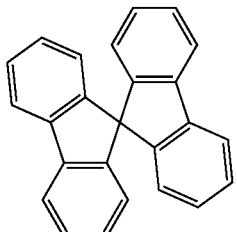
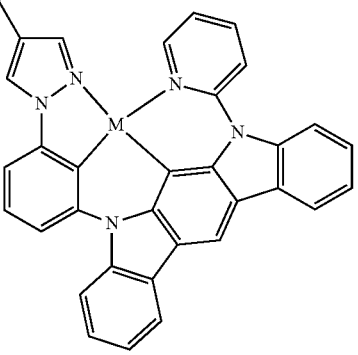
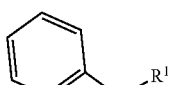
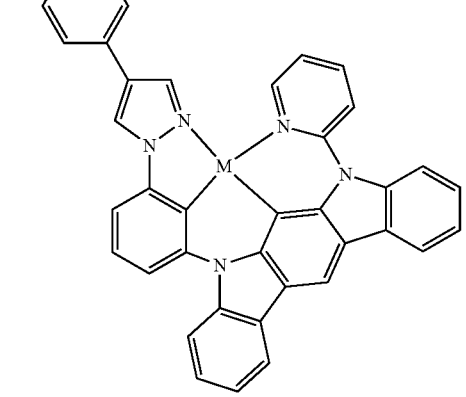
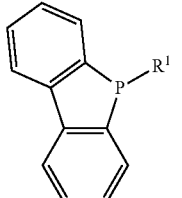
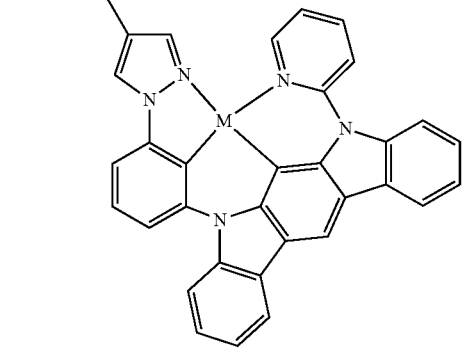

625
-continued
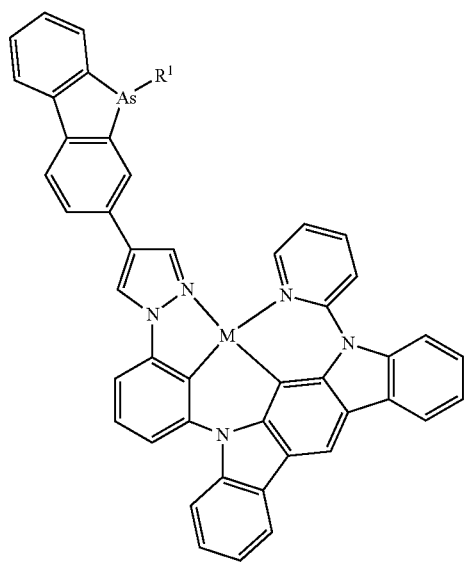
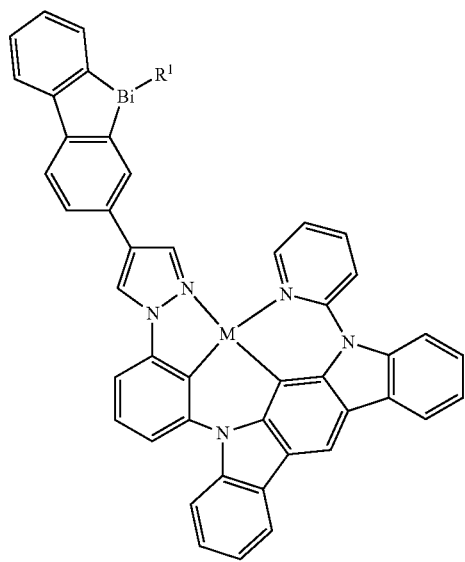
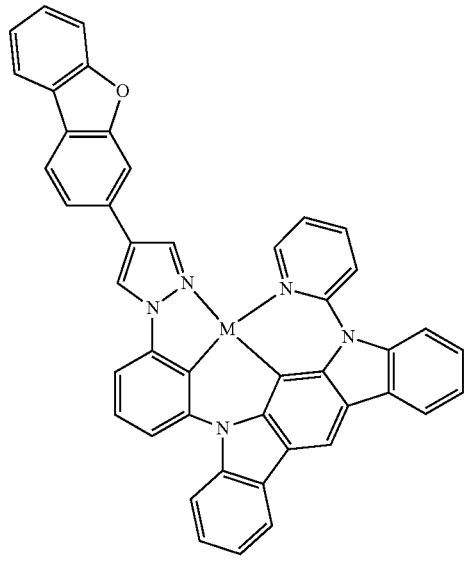
626
-continued
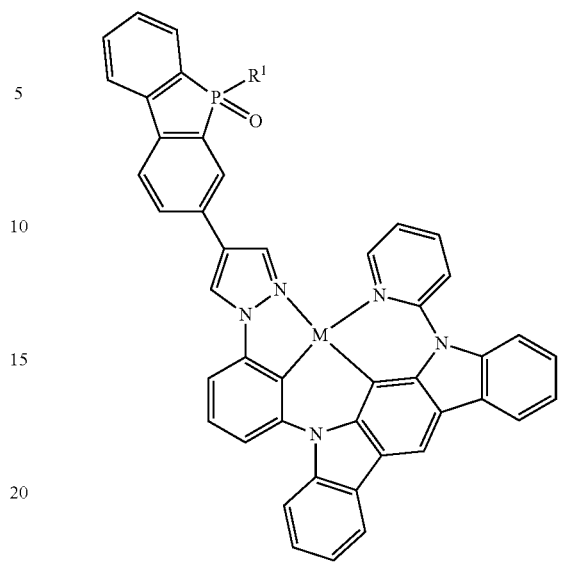
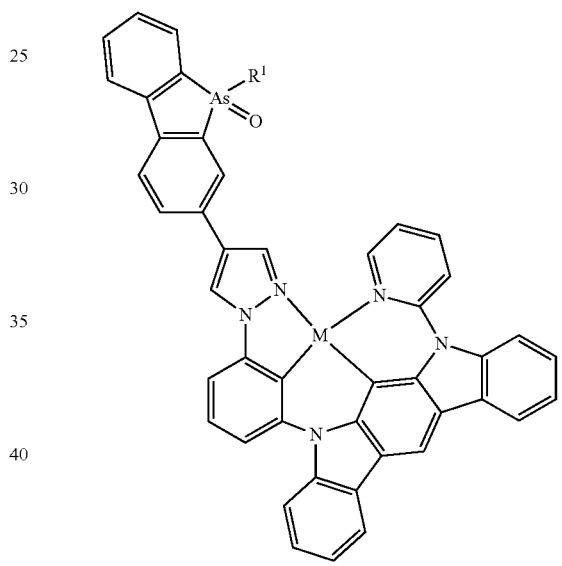
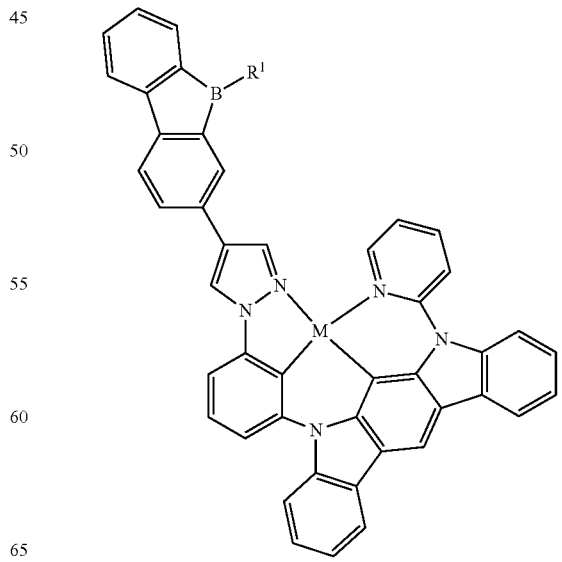

627
-continued
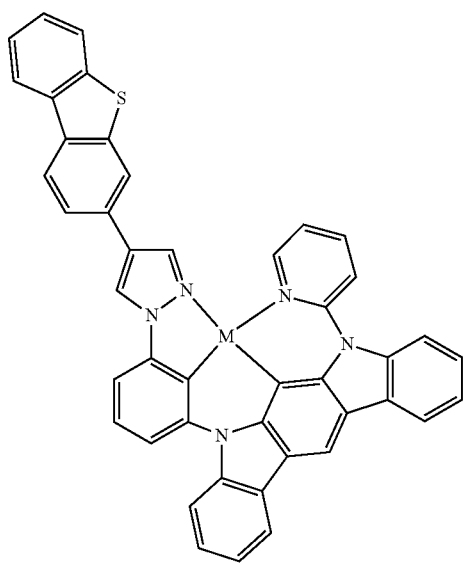
628
-continued
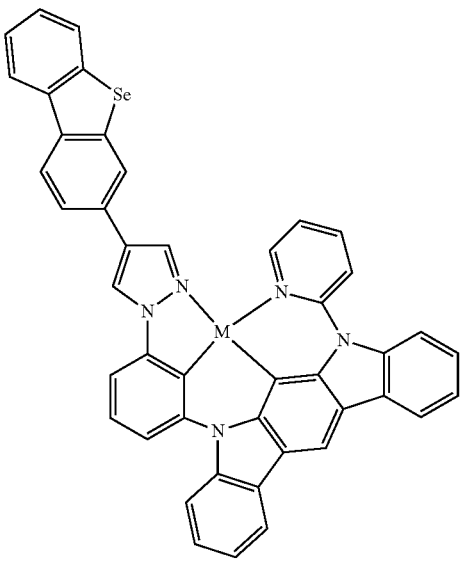
(M = Pt, Pd)
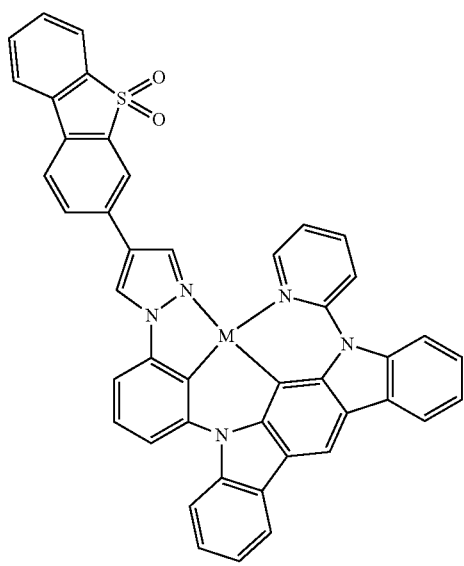
Structures 95
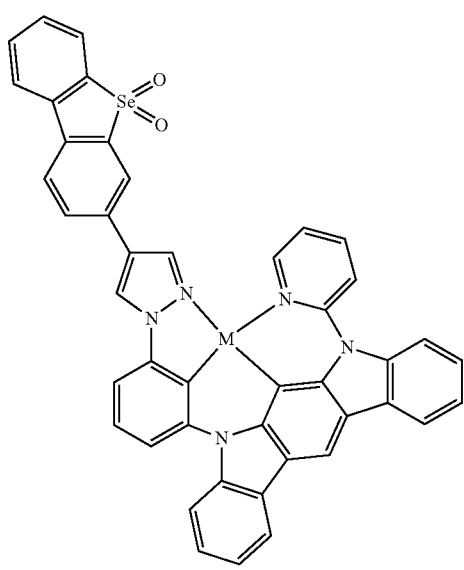
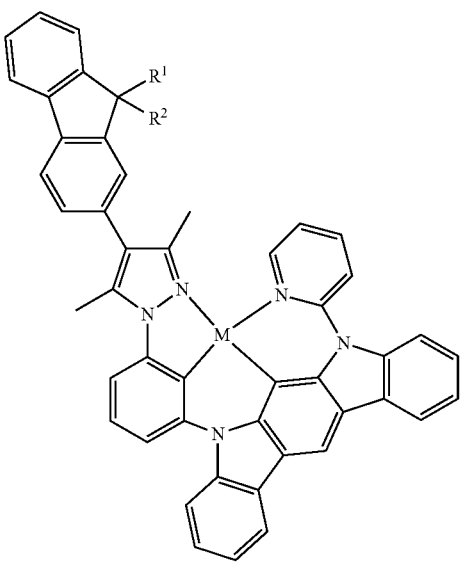

629
-continued
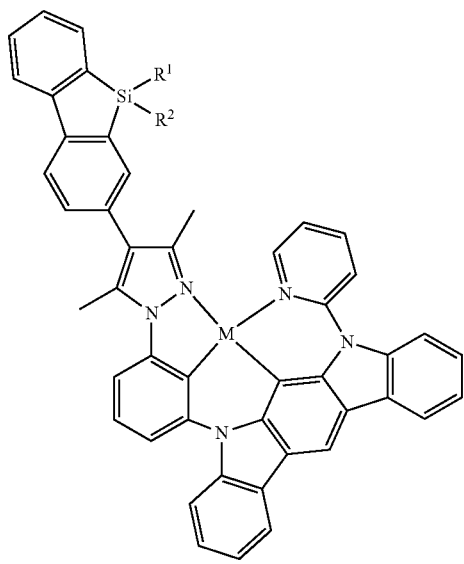
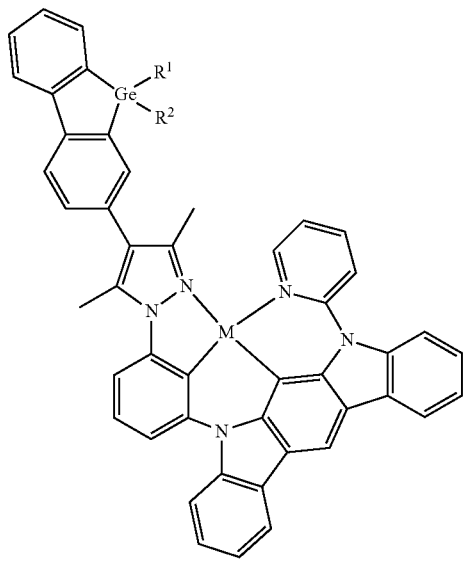
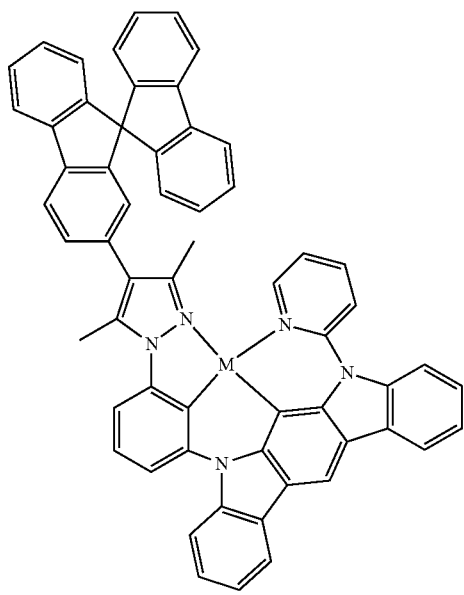
630
-continued
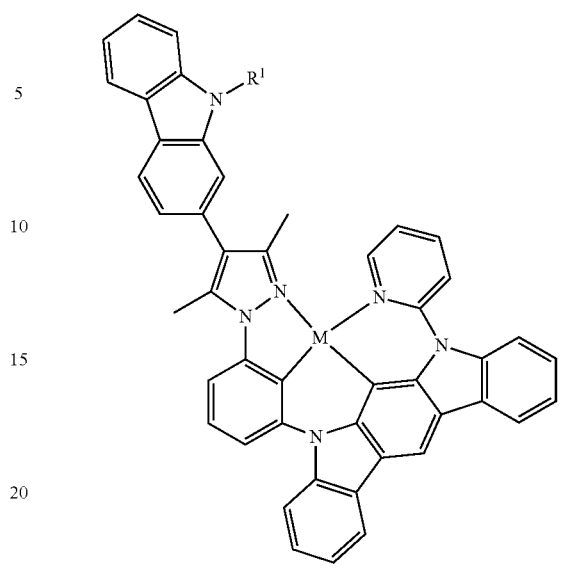
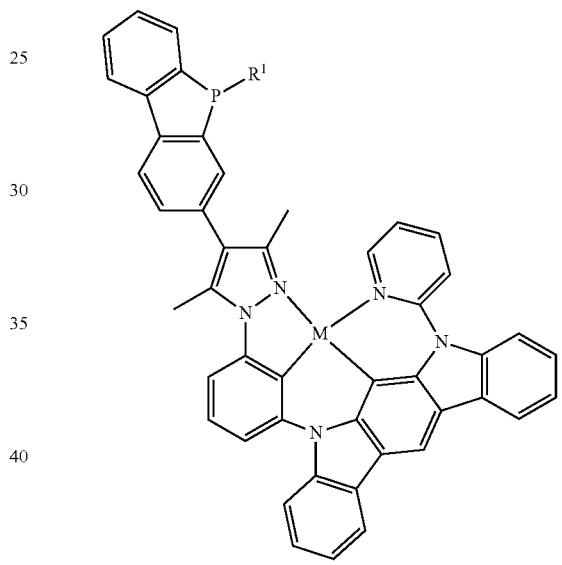
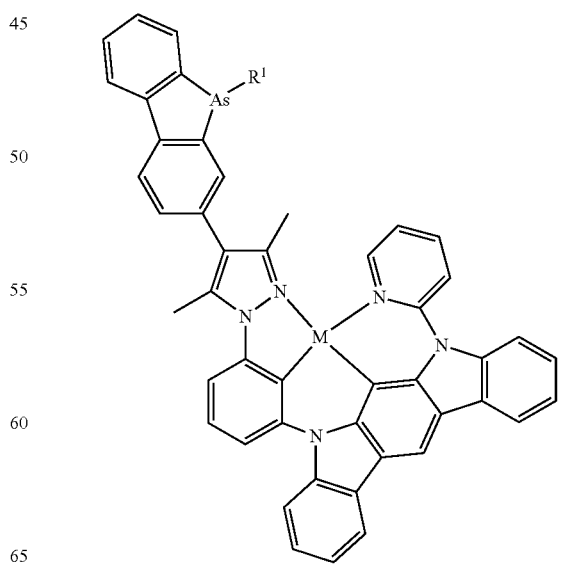

631
-continued
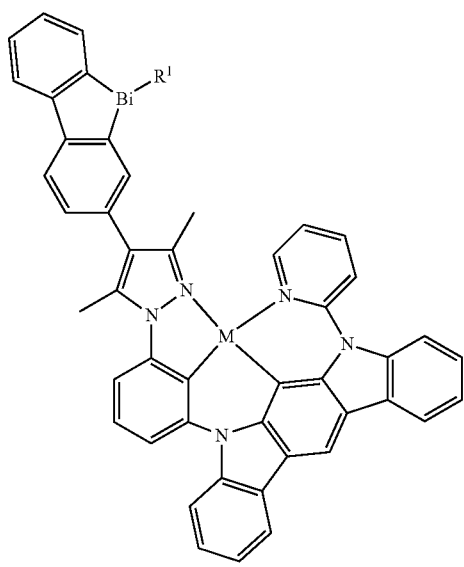
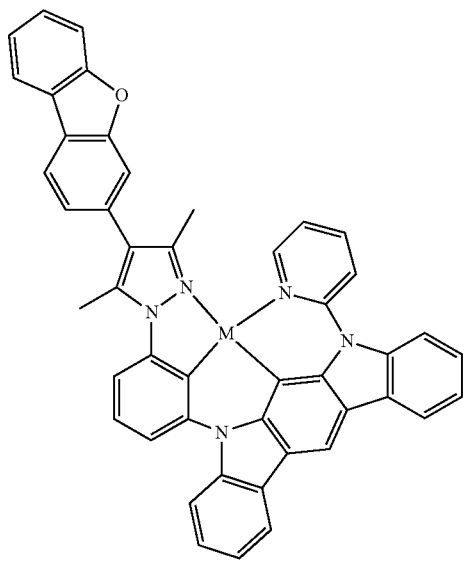
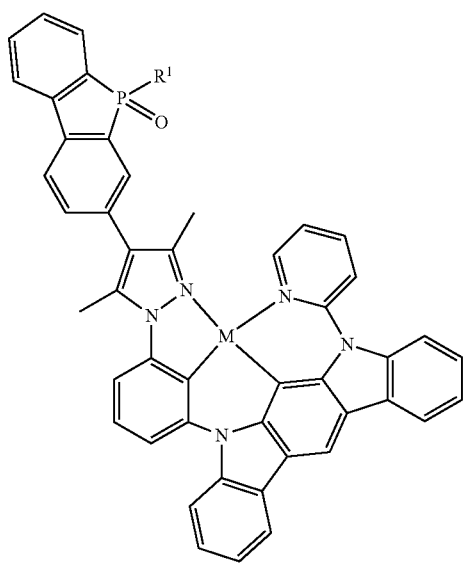
632
-continued
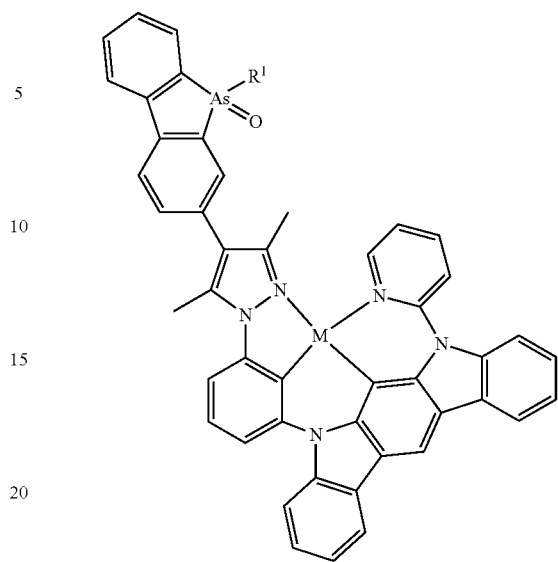
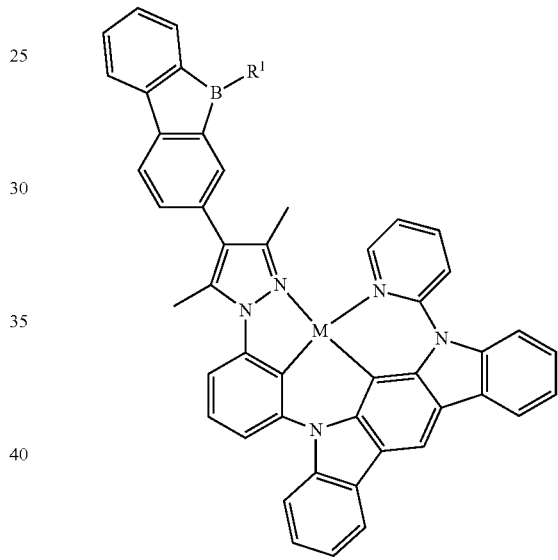
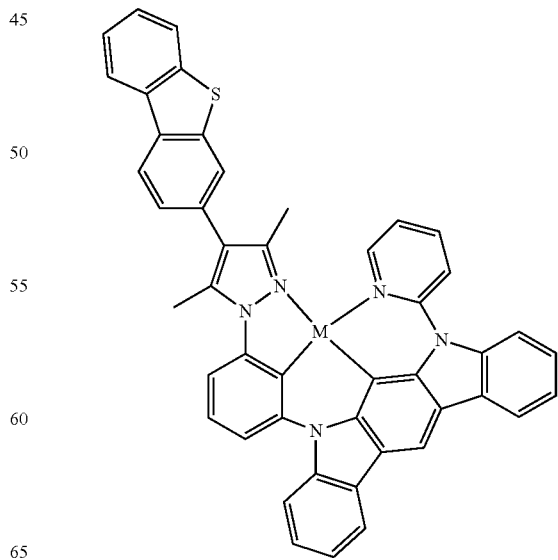

633
-continued
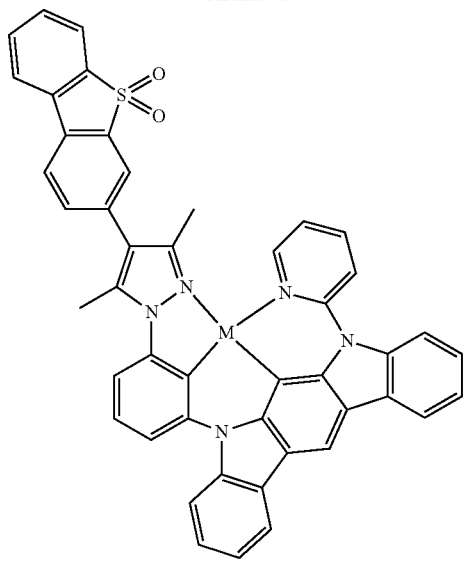
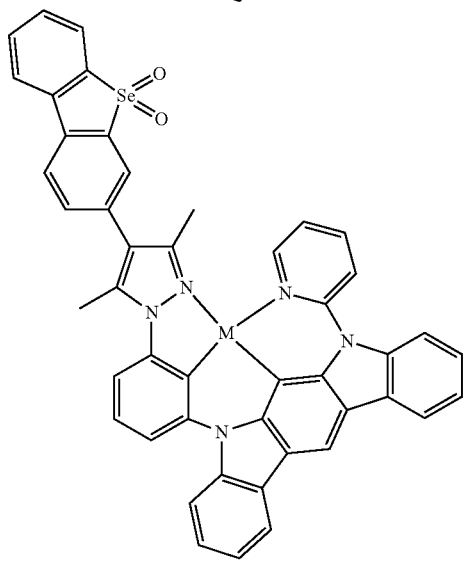
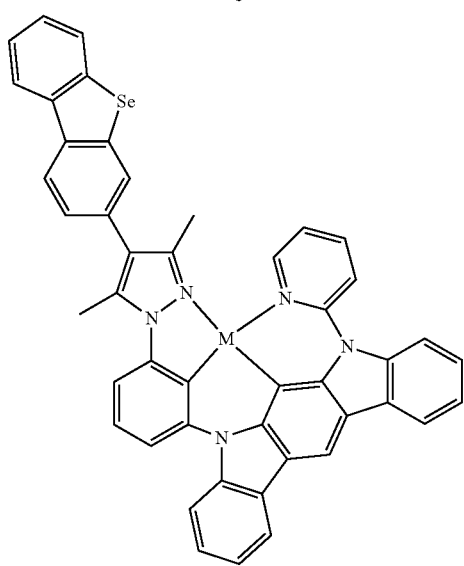
(M = Pt, Pd)
634
-continued
Structures 96
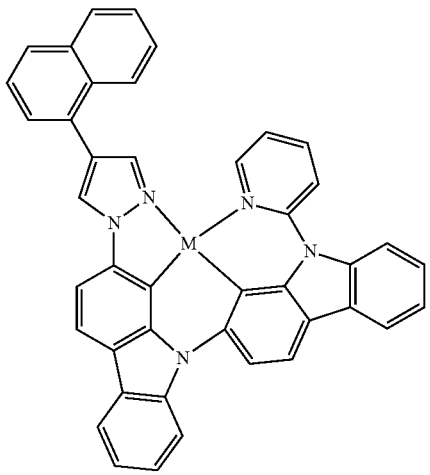
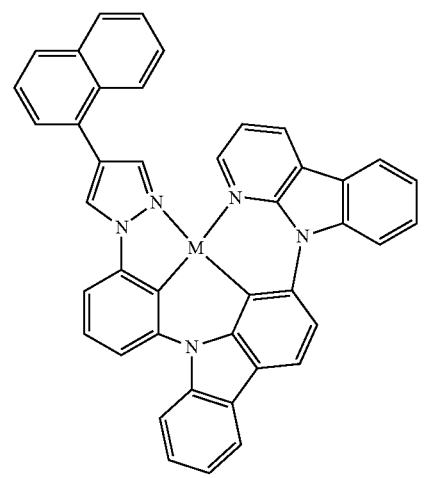
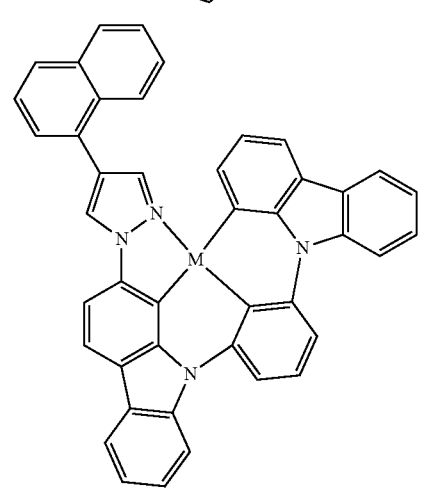

635
-continued
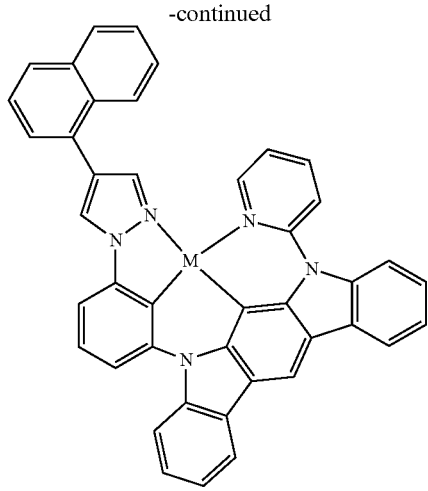
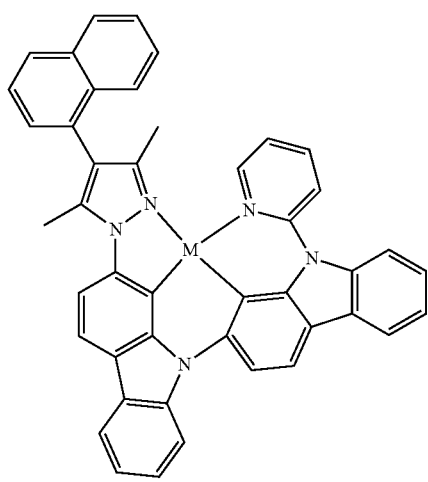
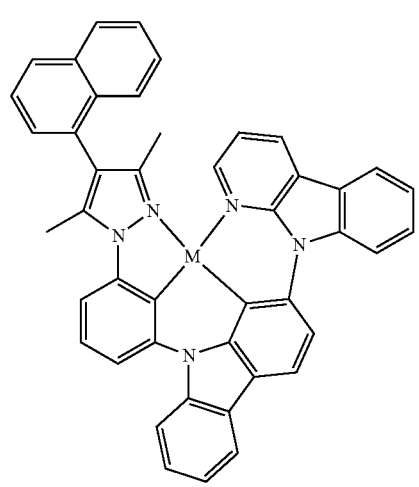
636
-continued
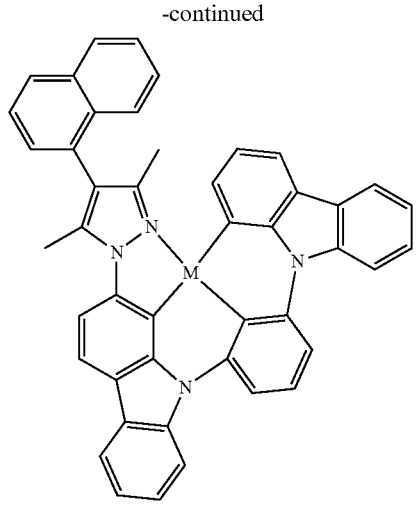
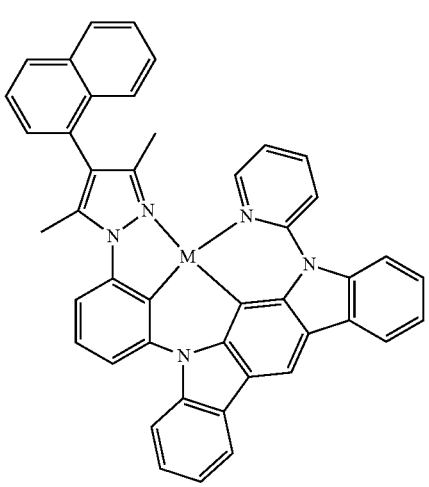
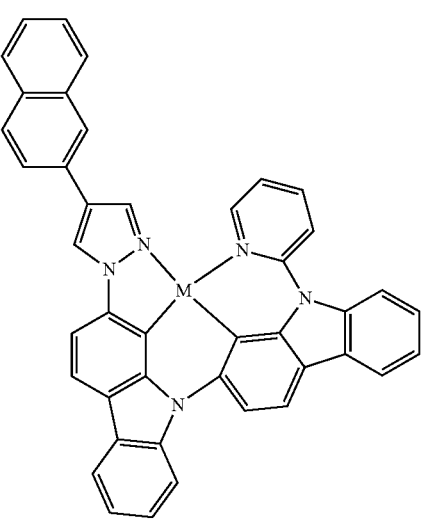

637
-continued
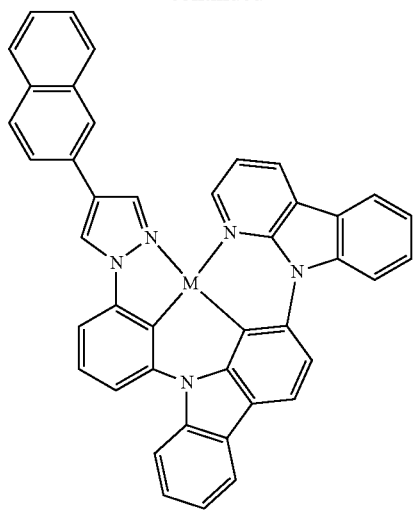
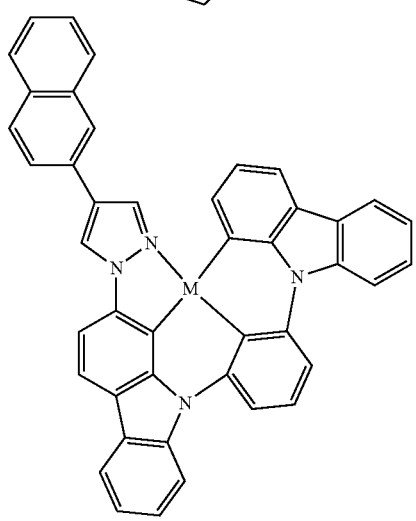
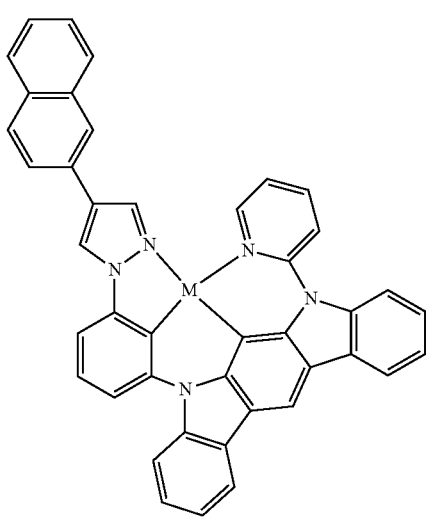
638
-continued
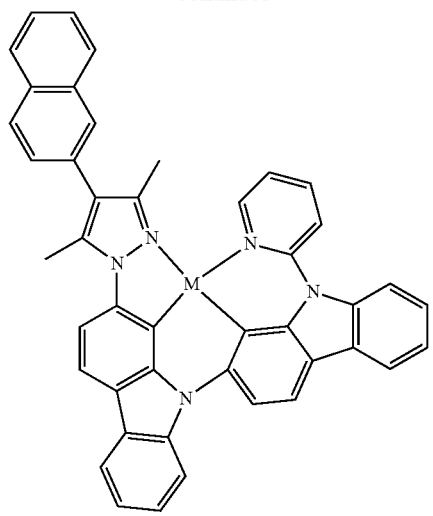
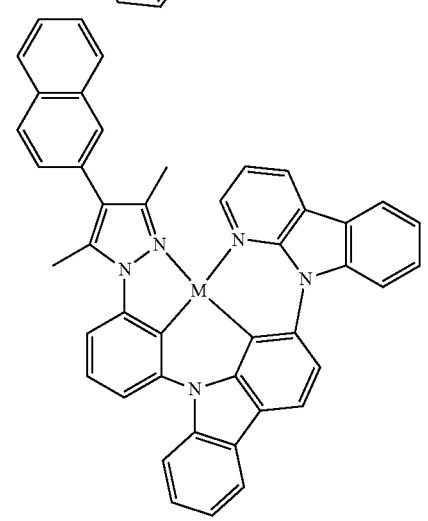
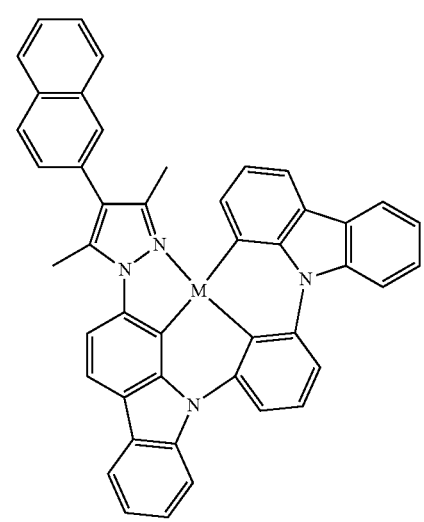

639
-continued
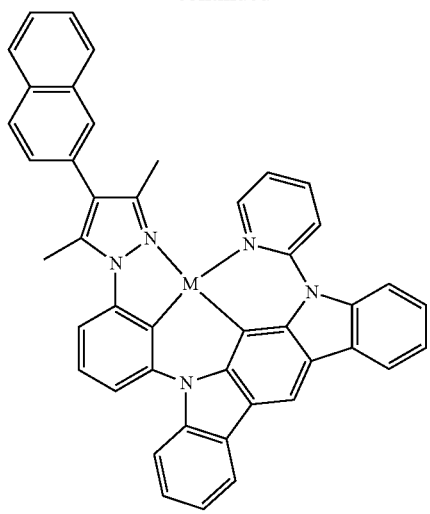
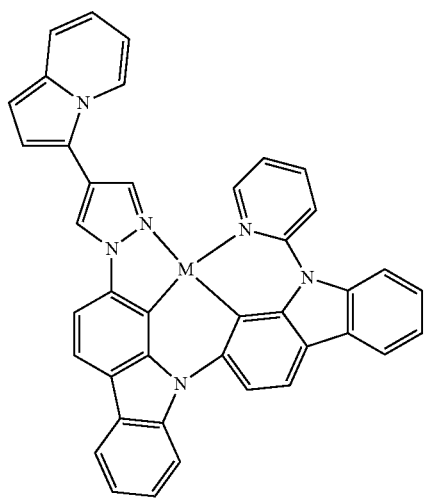
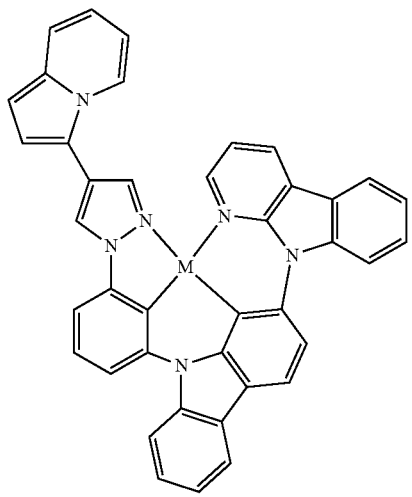
640
-continued
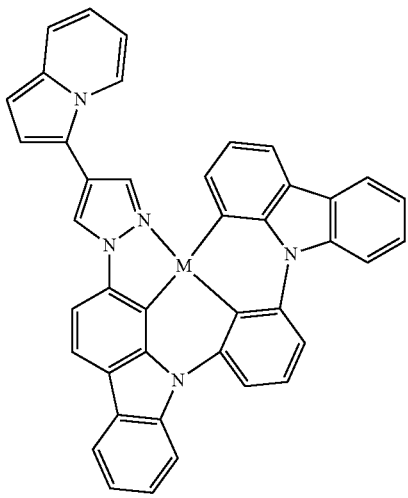
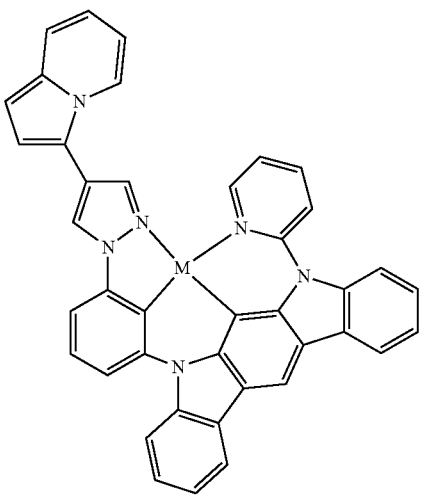
(M = Pt, Pd)
Structures 97
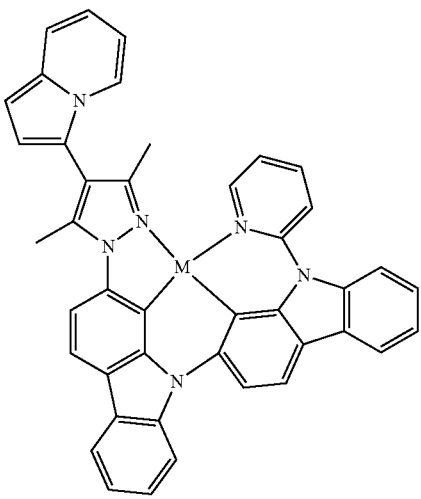

641
-continued
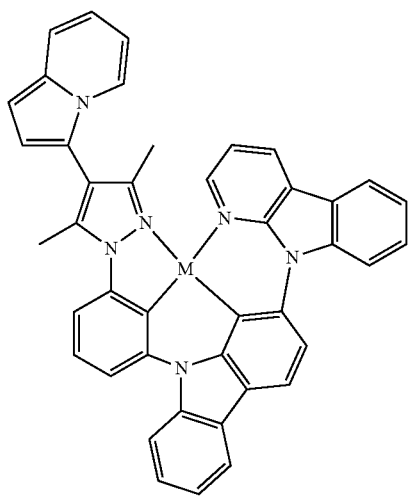
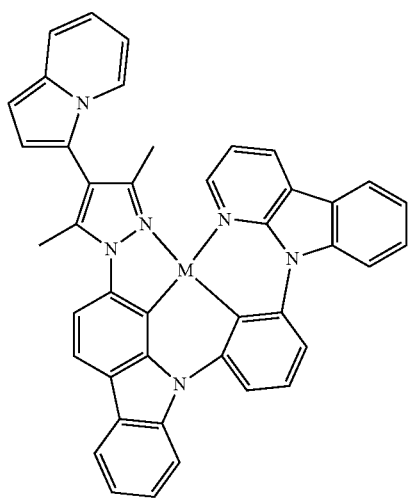

642
-continued
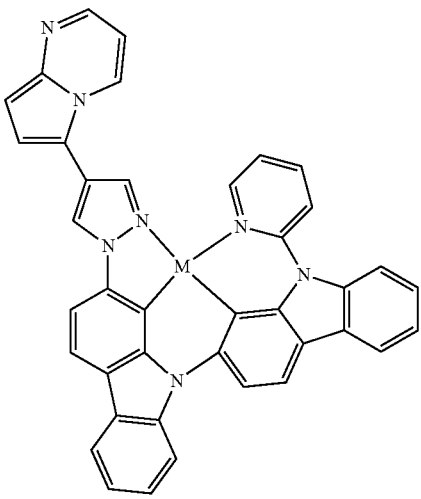
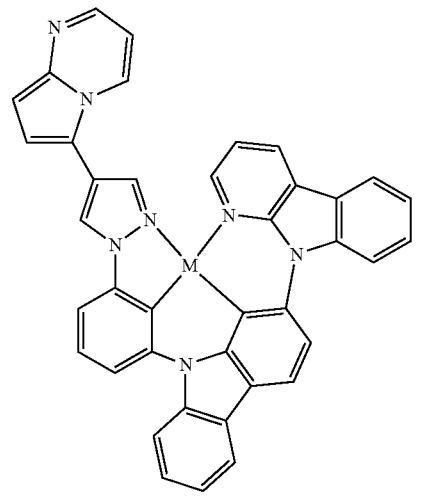
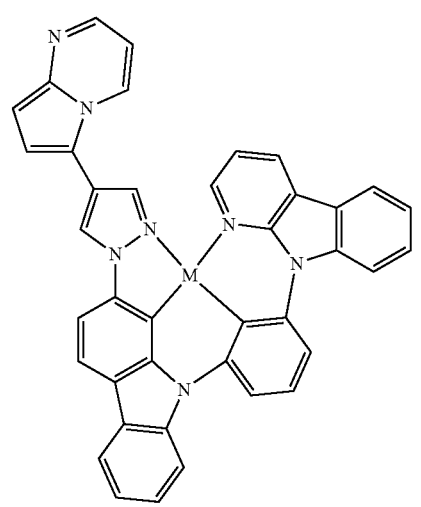

643
-continued
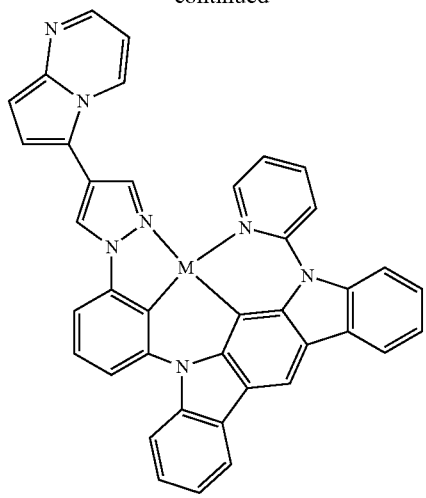
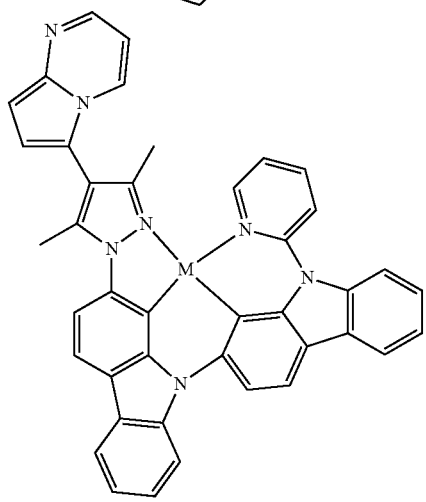
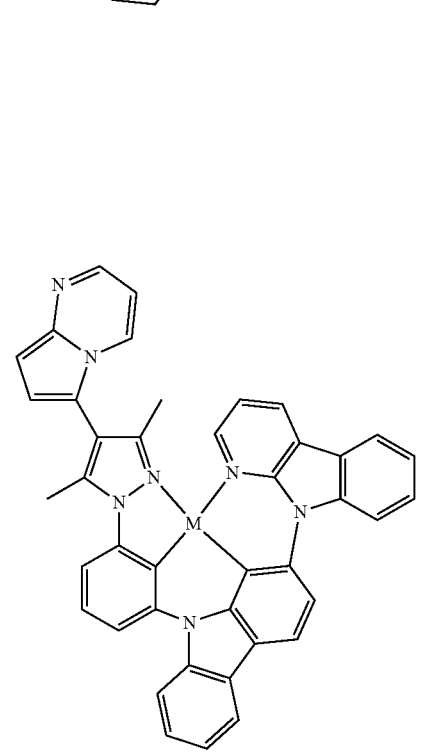
644
-continued
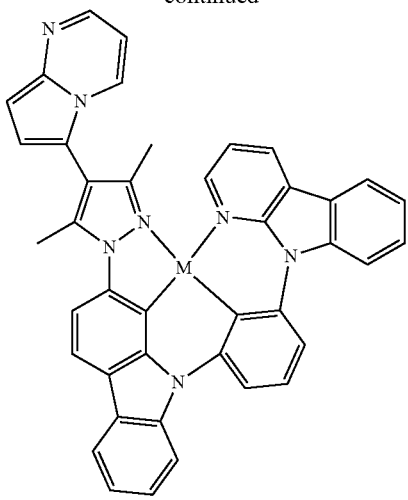
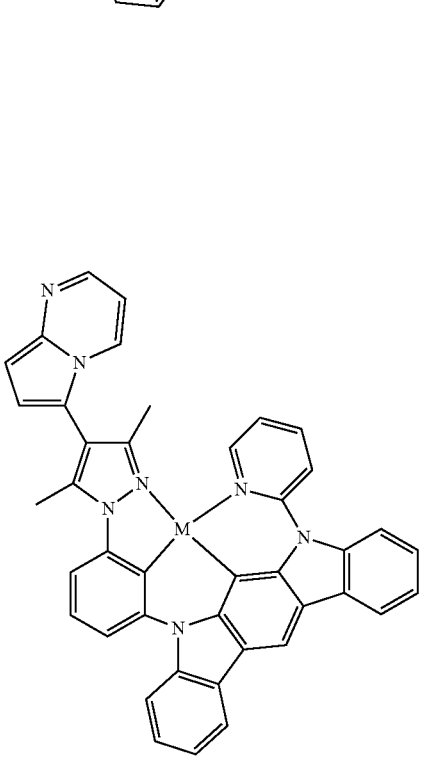

645
-continued
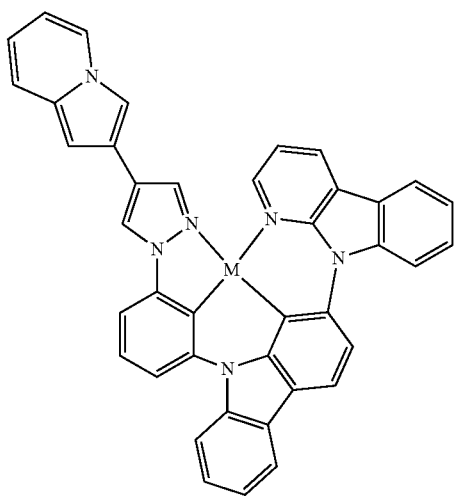
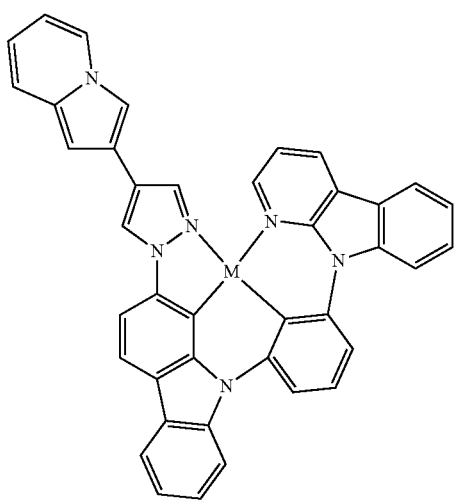
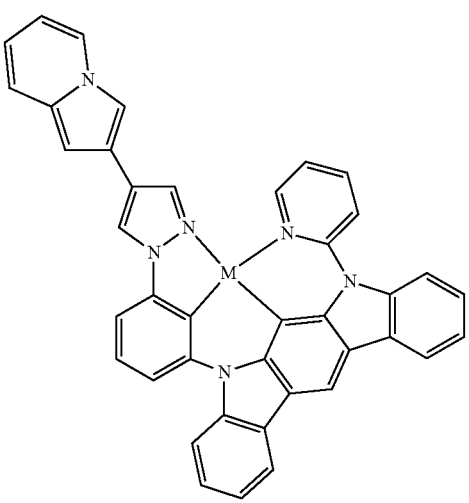
646
-continued
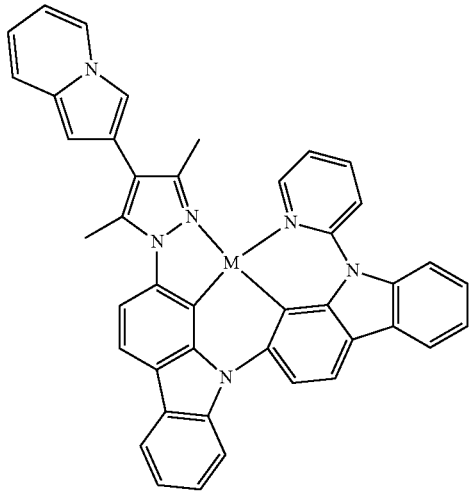
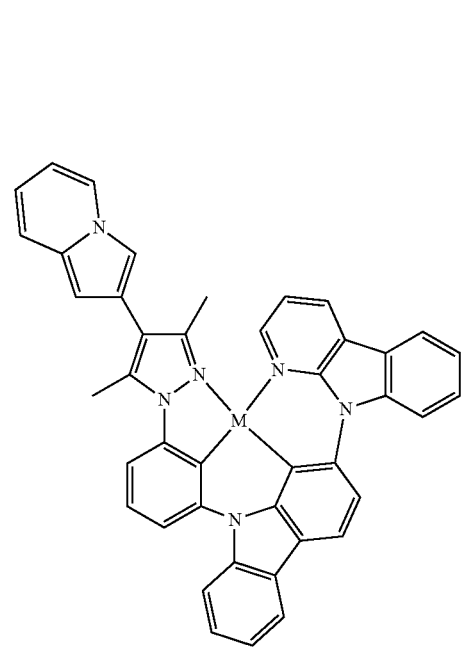
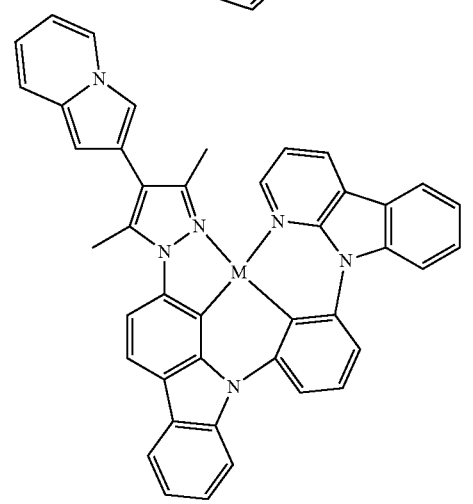

647
-continued
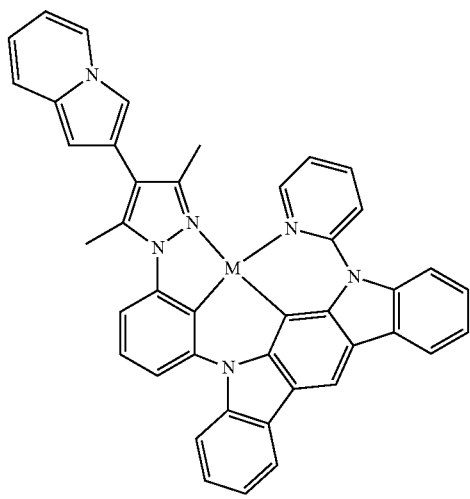
(M = Pt, Pd)
Structures 98
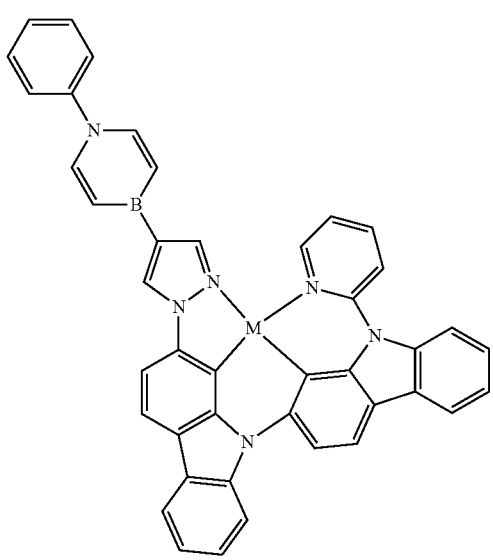
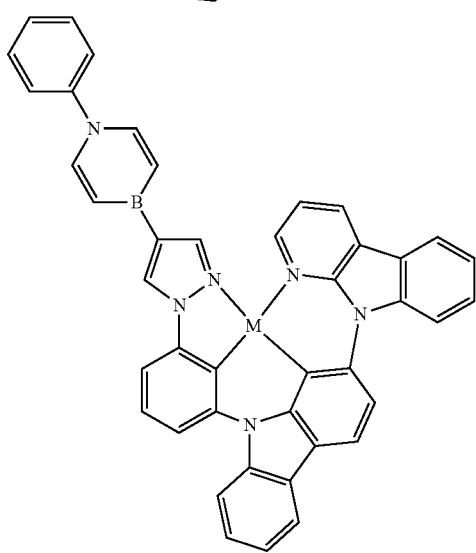
648
-continued
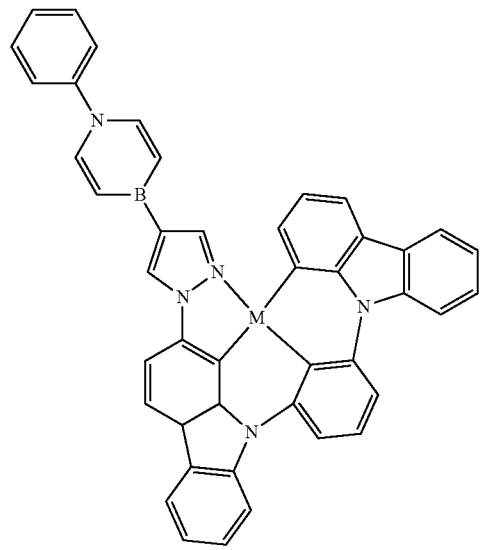
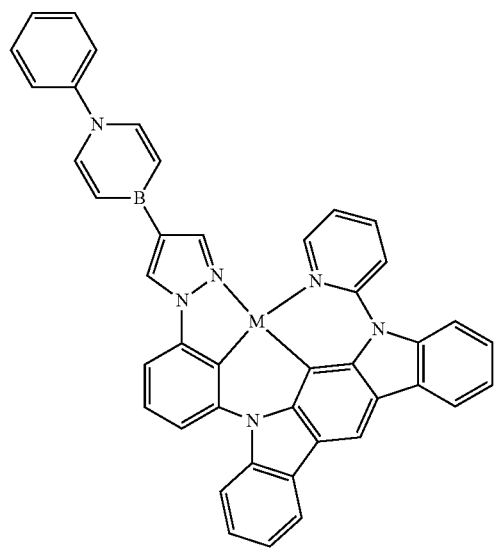
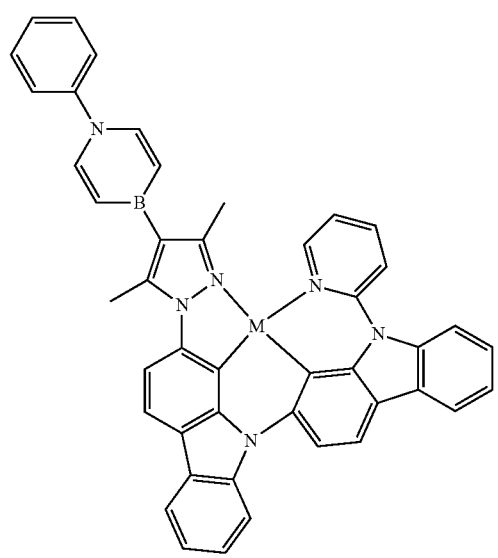

649
-continued
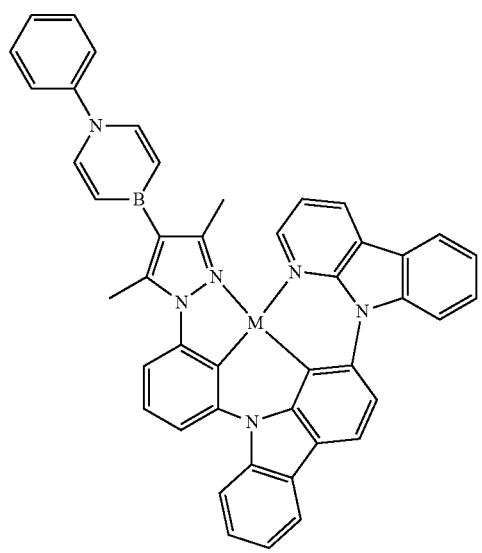
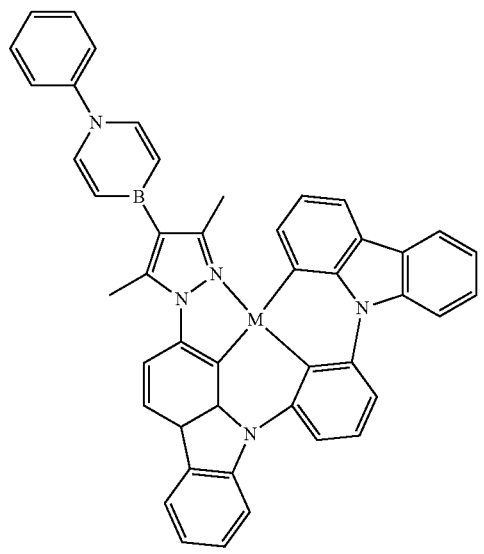
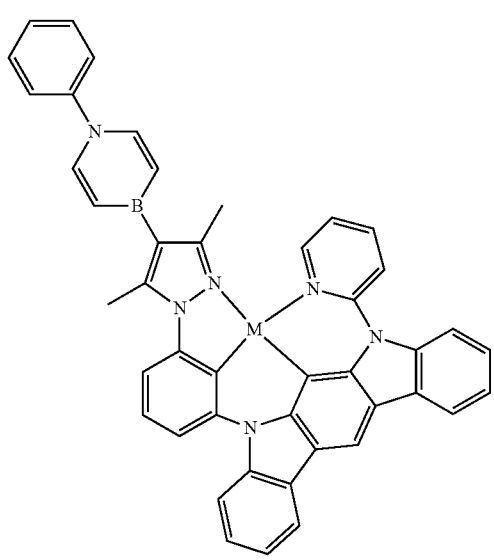
650
-continued
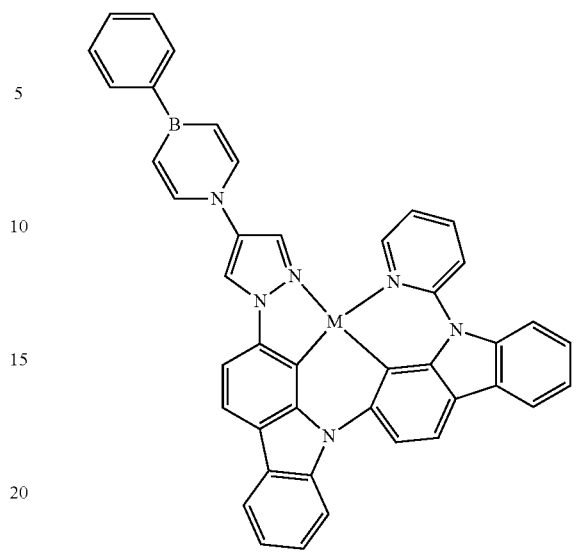
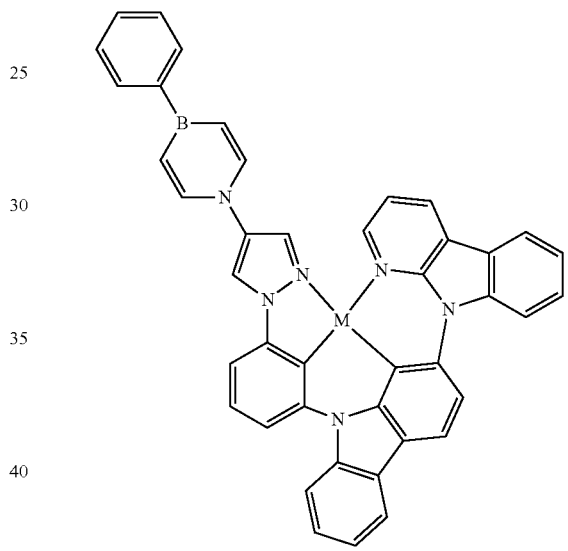

651
-continued
652
-continued
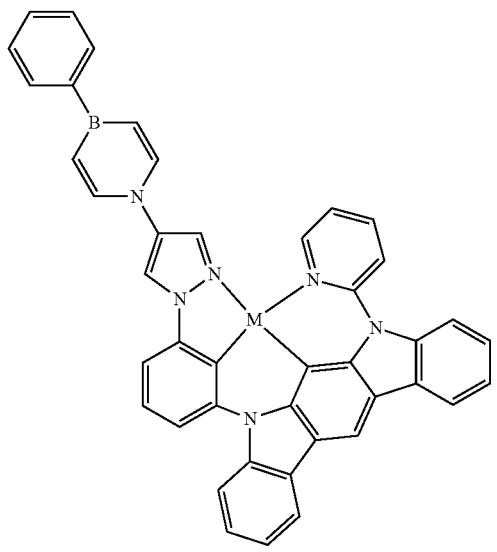
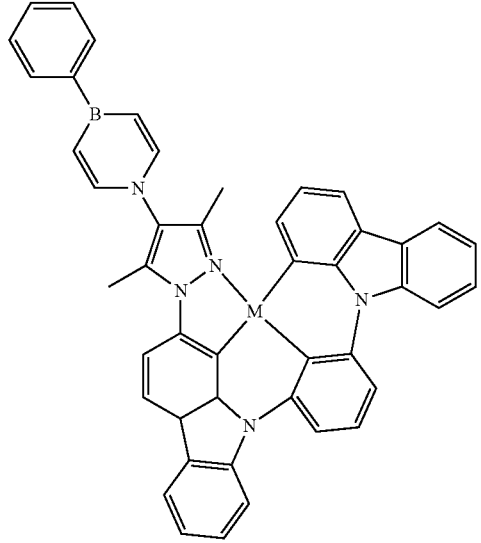
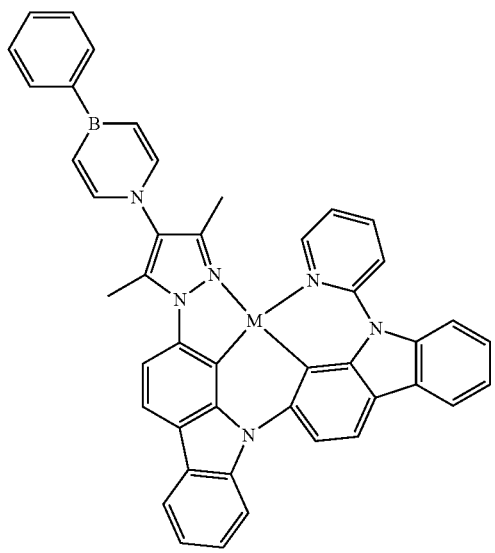
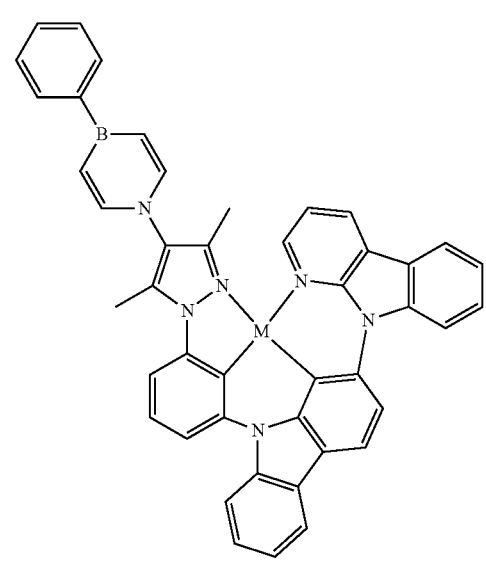
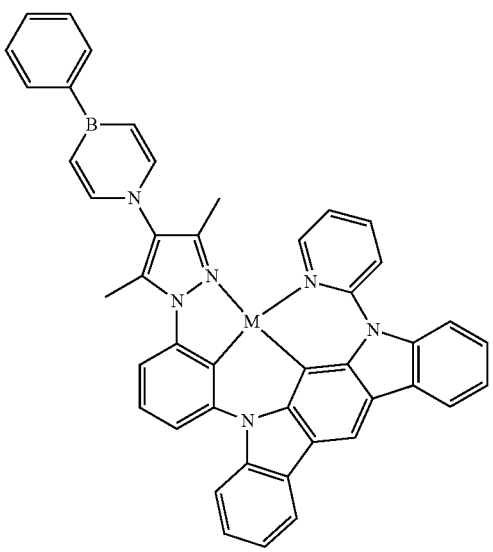
(M = Pt, Pd)

653
-continued
Structures 99
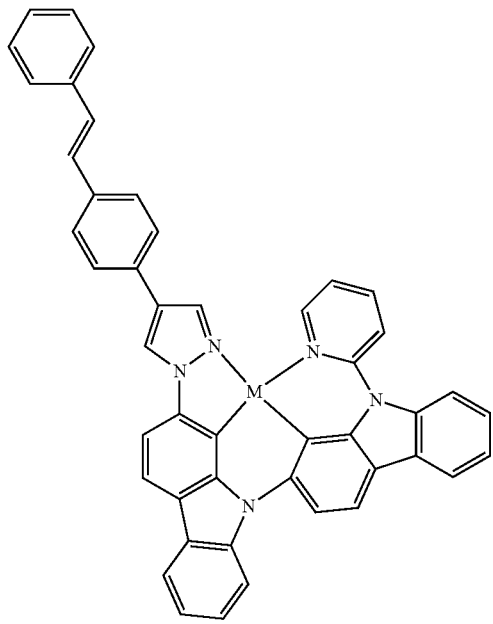
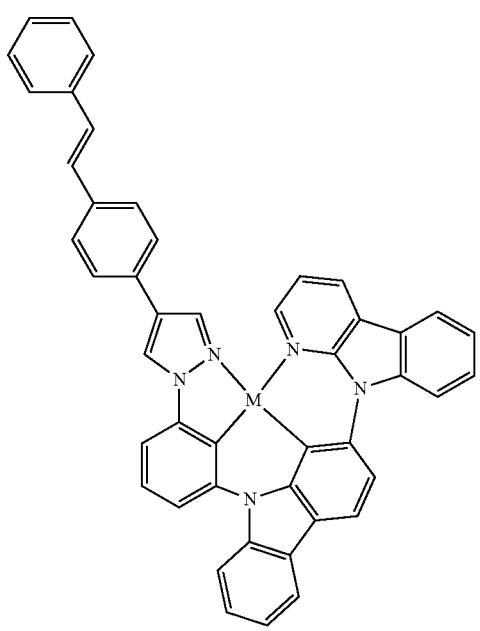
654
-continued
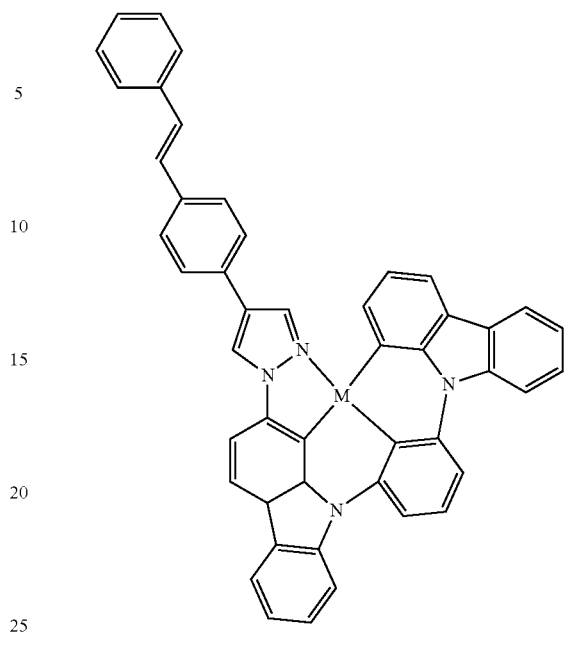
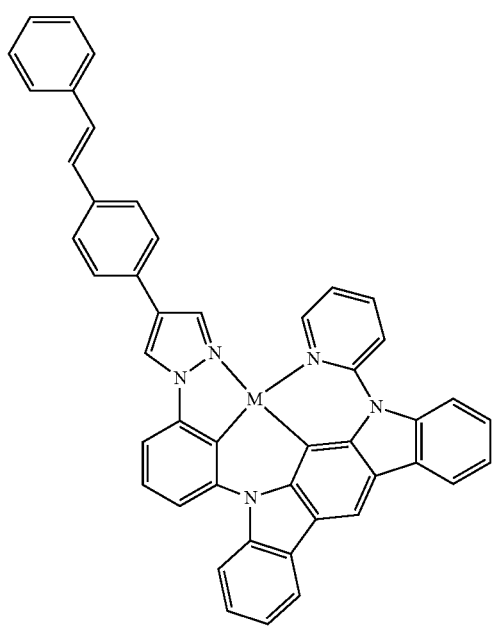

655
-continued
656
-continued
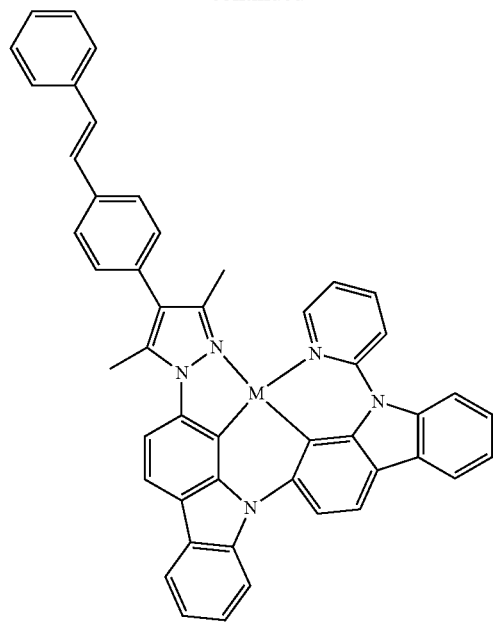
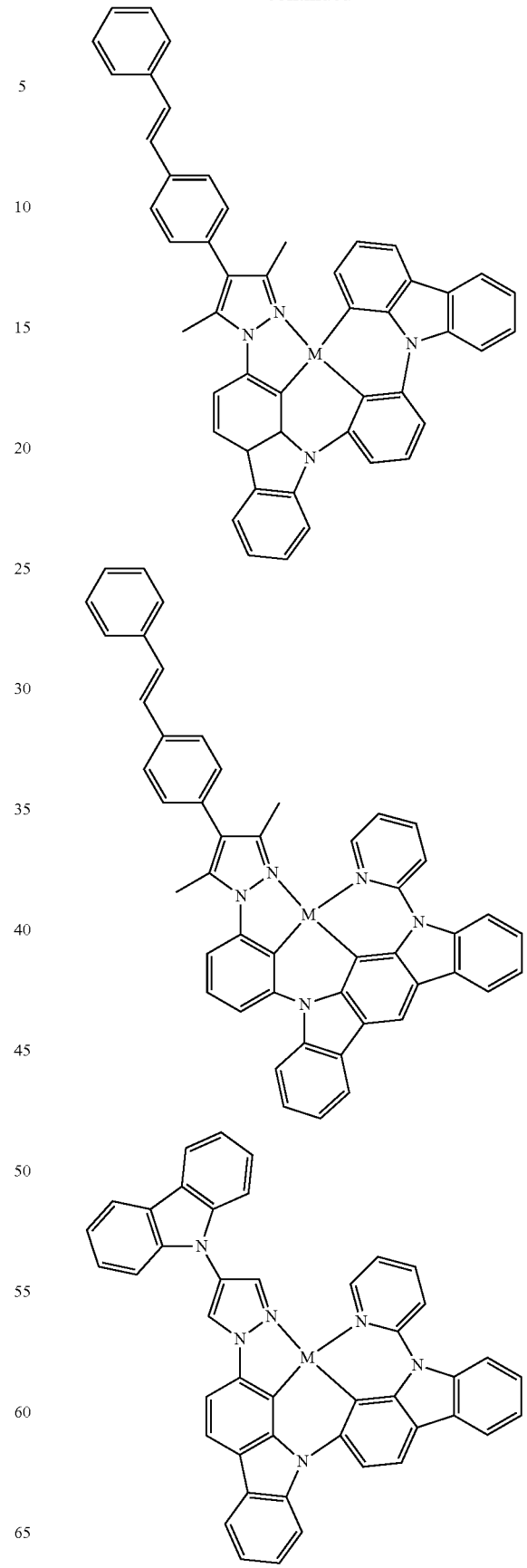

657
-continued
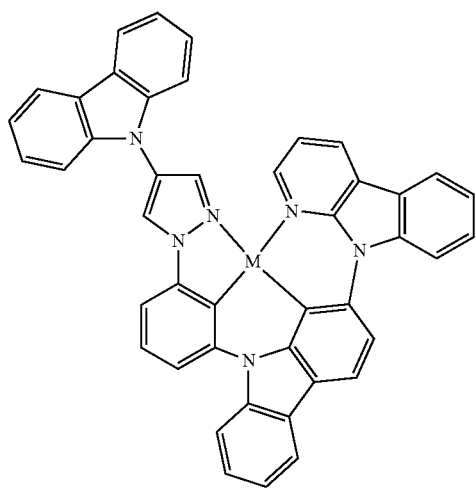
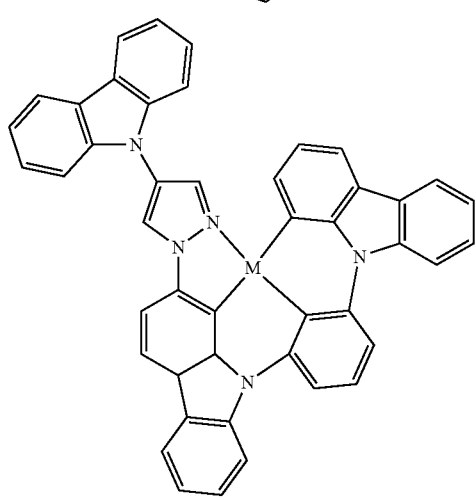
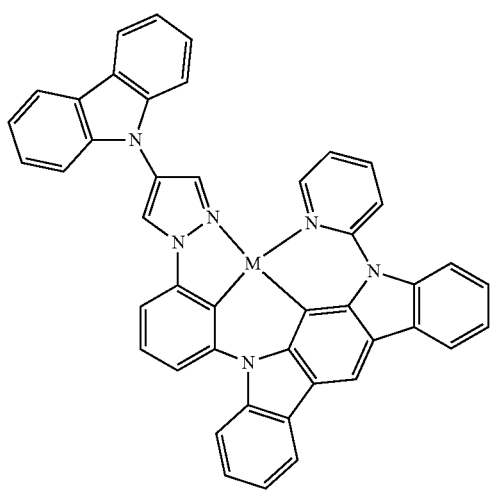
658
-continued
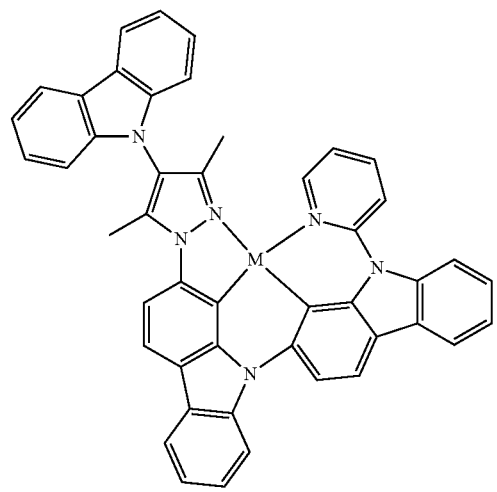
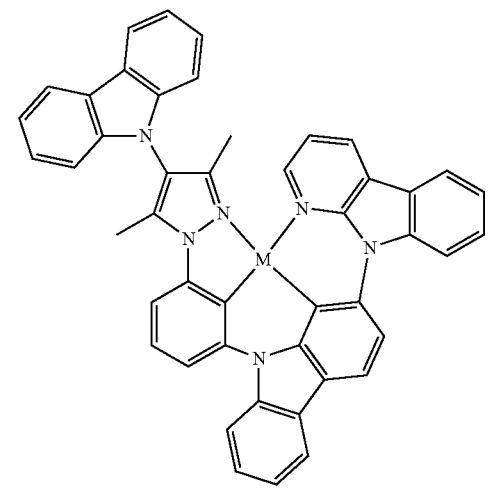
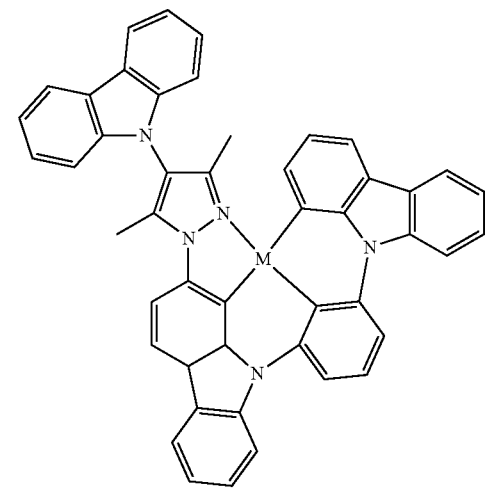

659
-continued
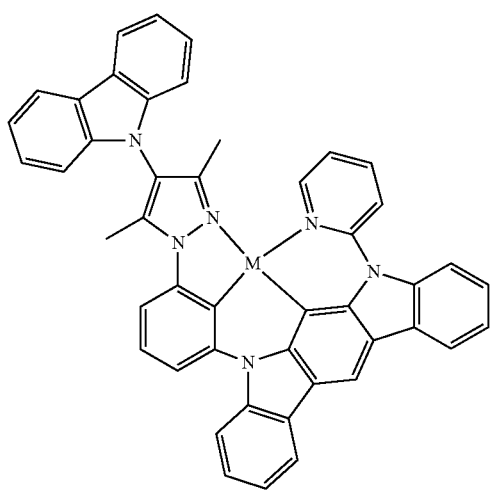
(M = Pt, Pd)
Structures 100
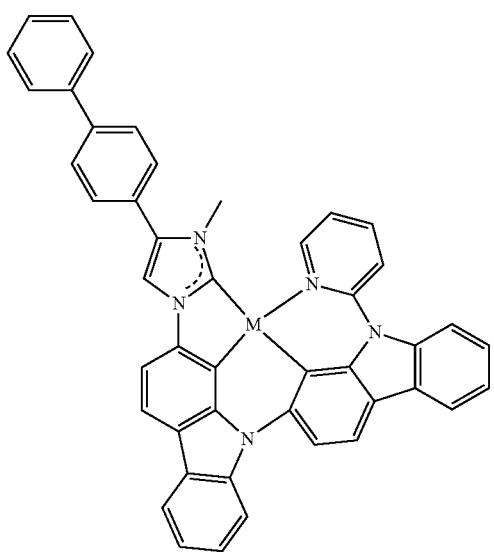
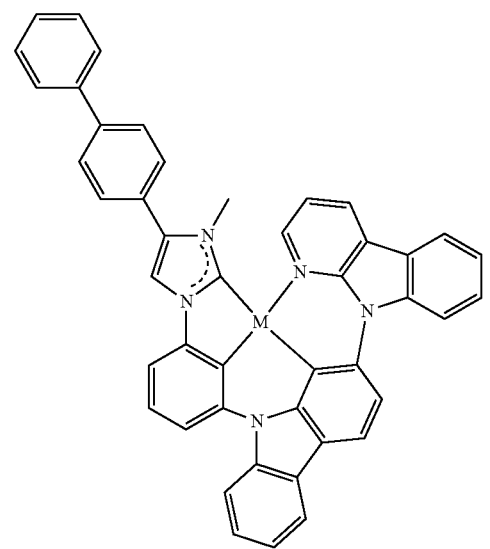
660
-continued
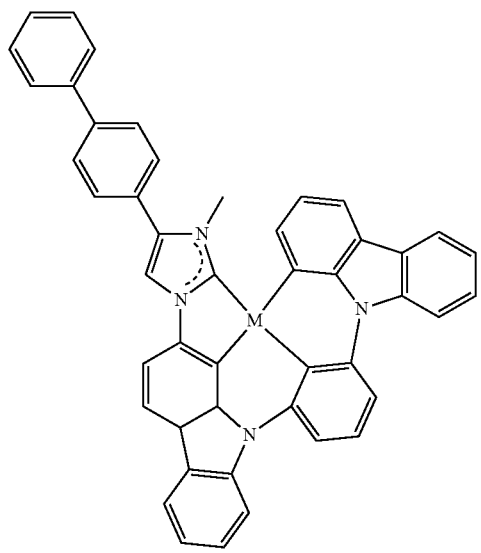
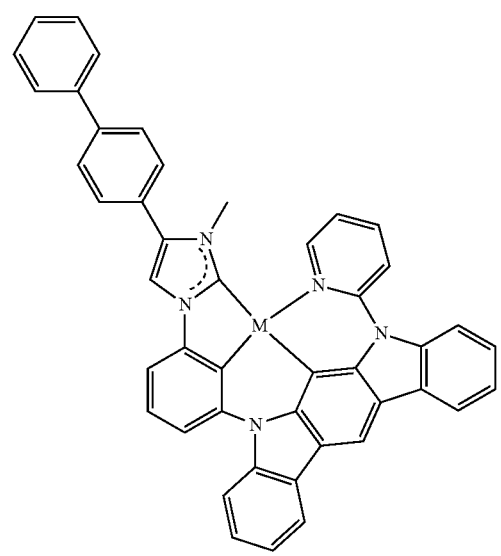
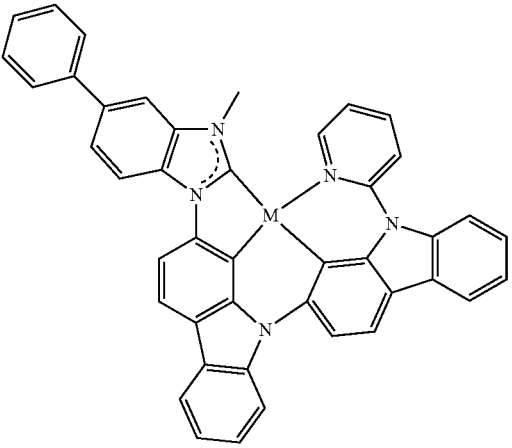

661
-continued
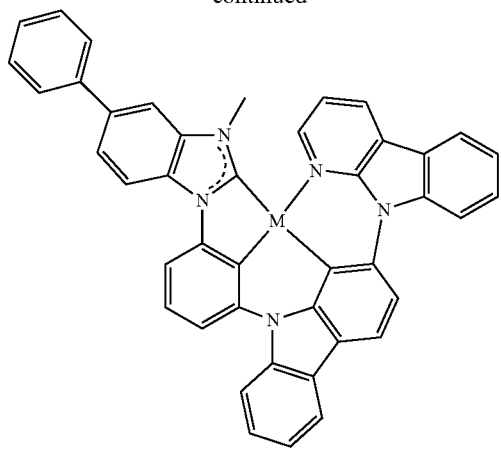
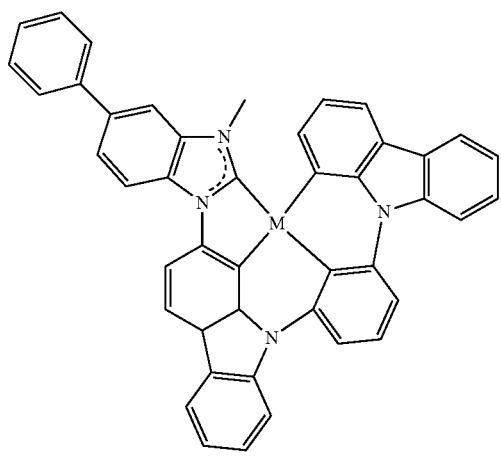
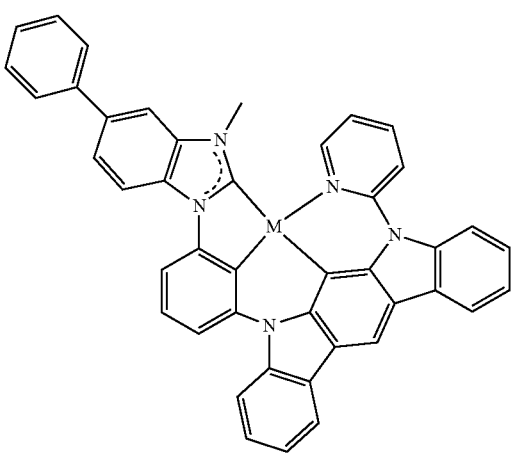
662
-continued
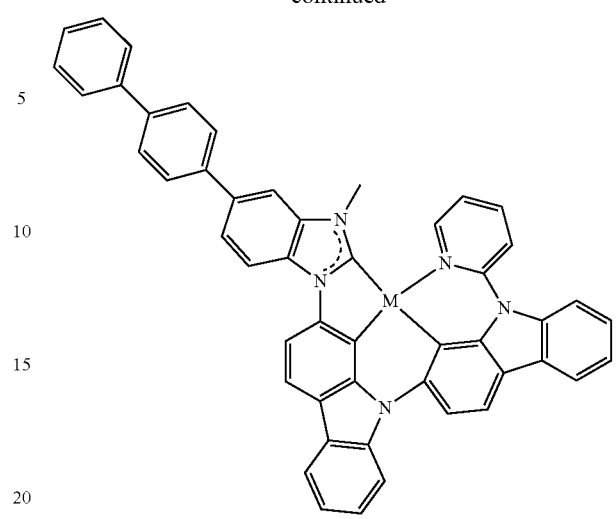
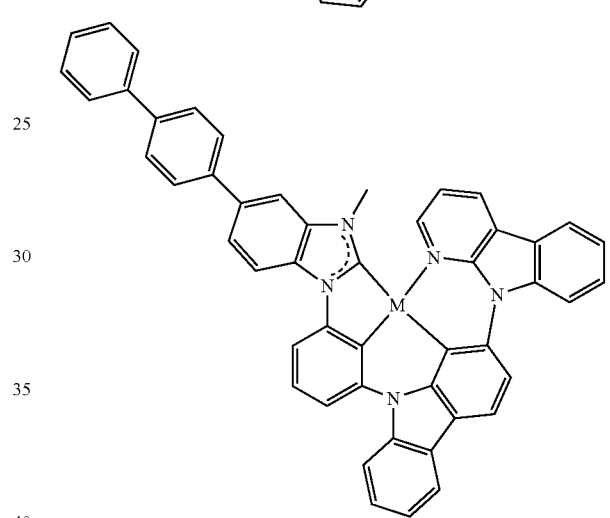
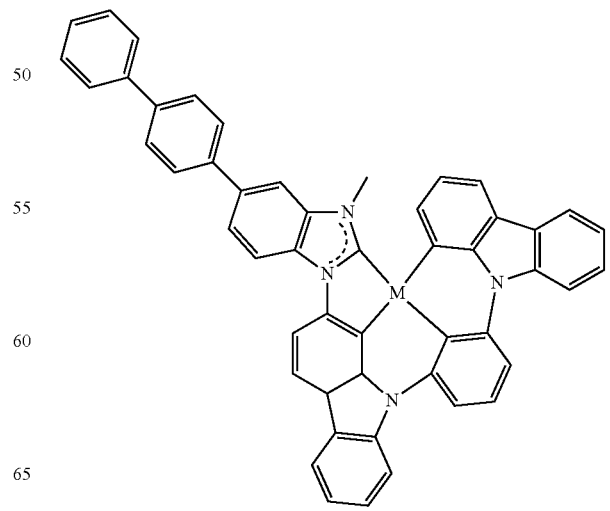

663
-continued
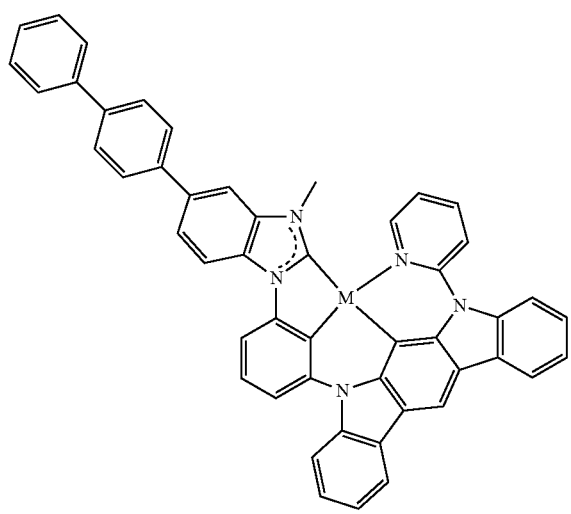
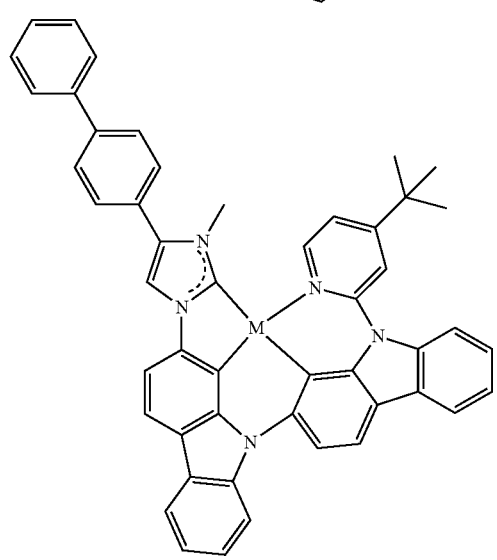
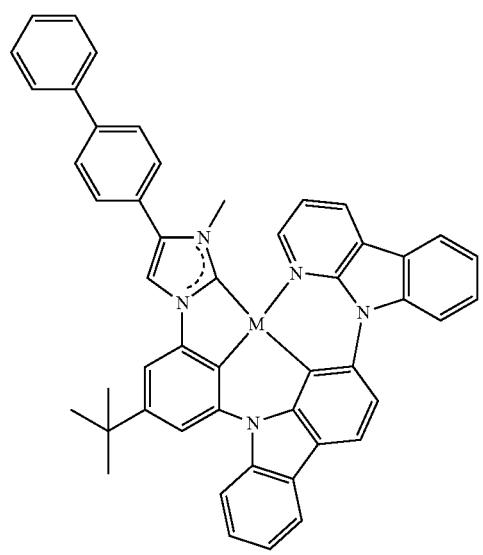
664
-continued
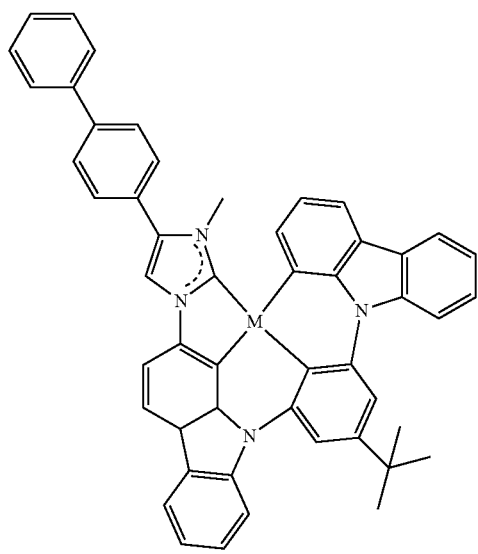
(M = Pt, Pd)
Structures 101
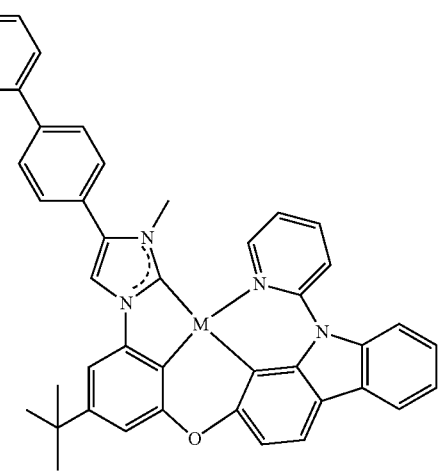

665
-continued
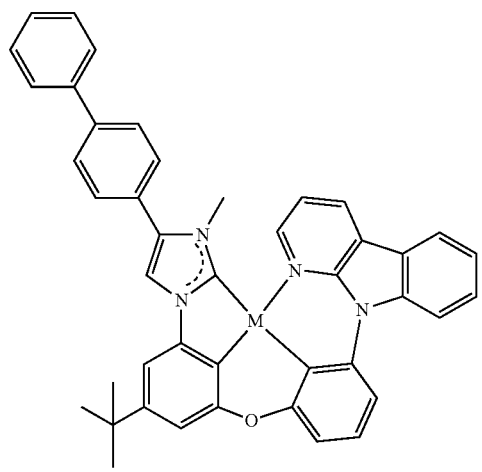
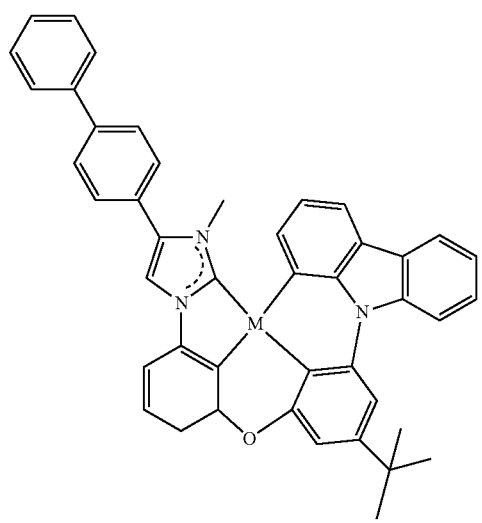
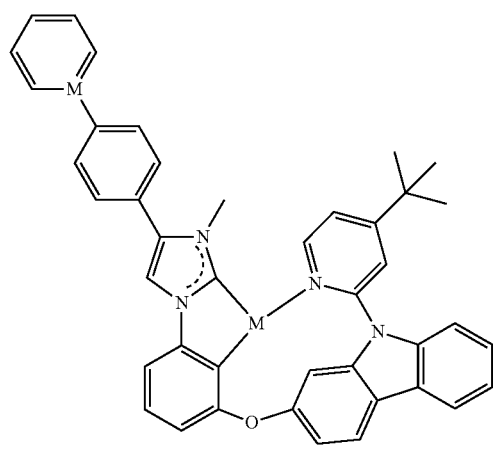
666
-continued
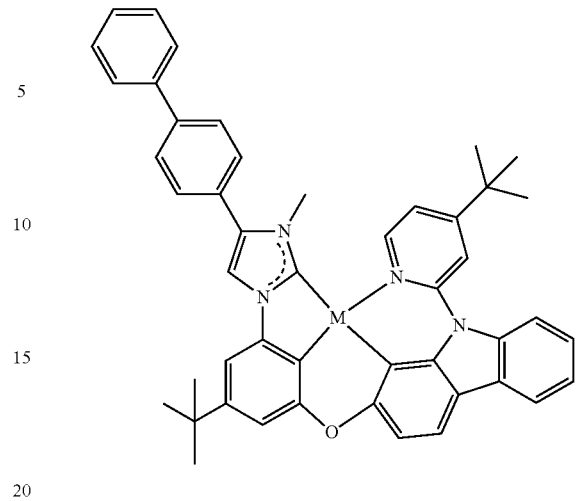
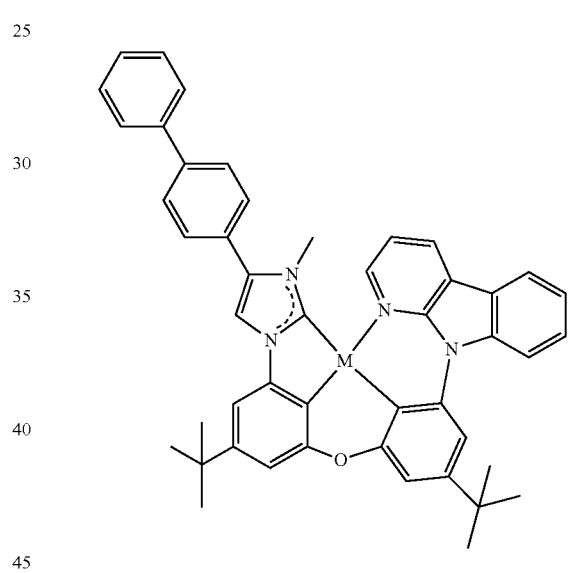
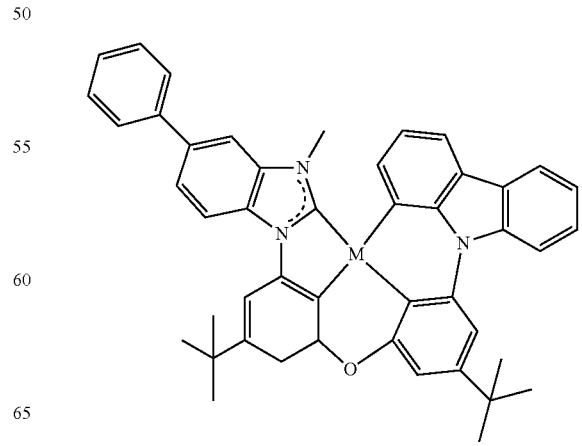

667
-continued
668
-continued
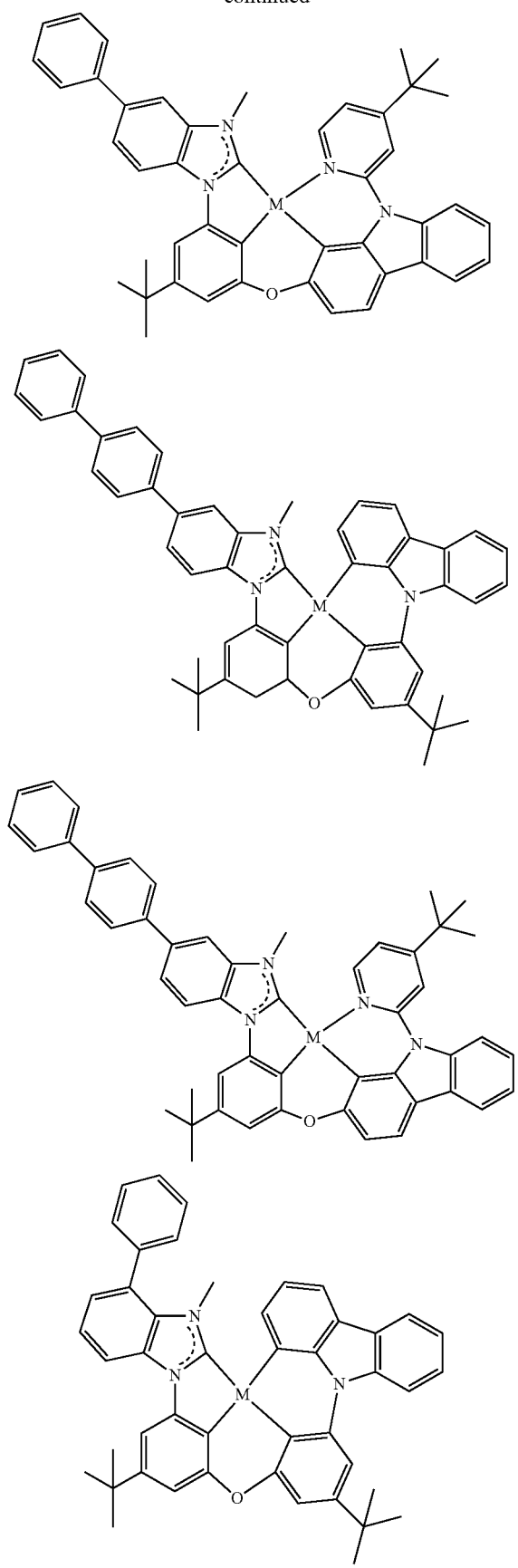
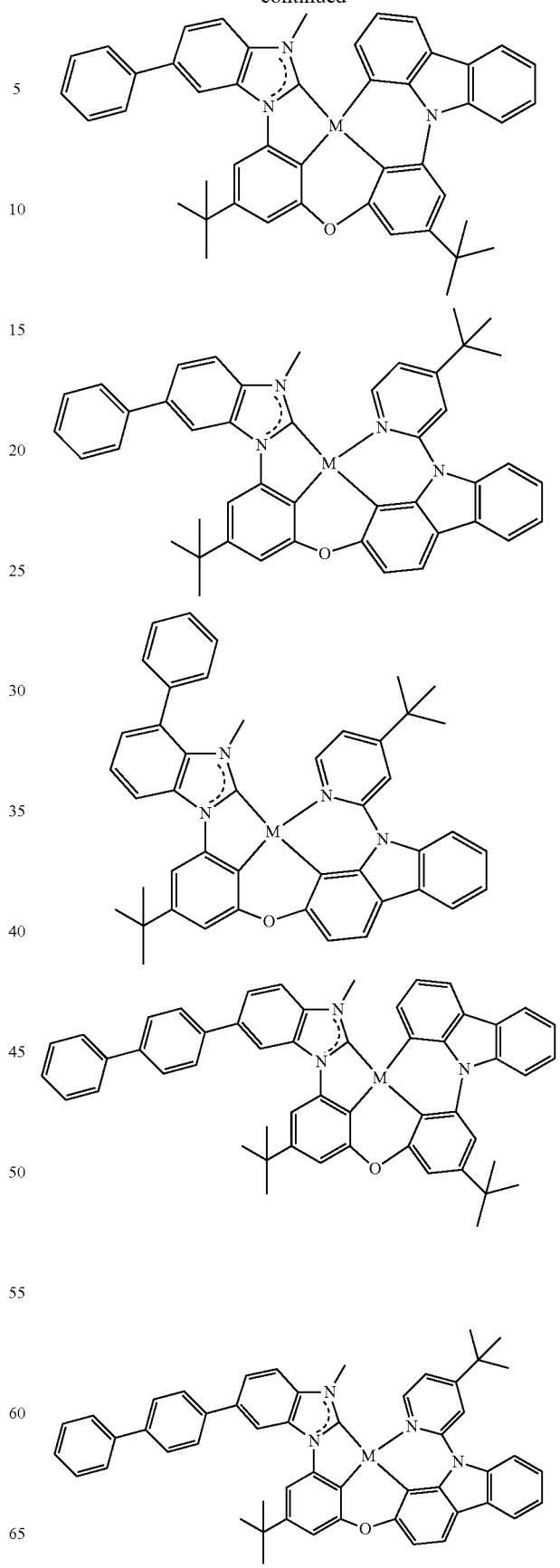

669
-continued
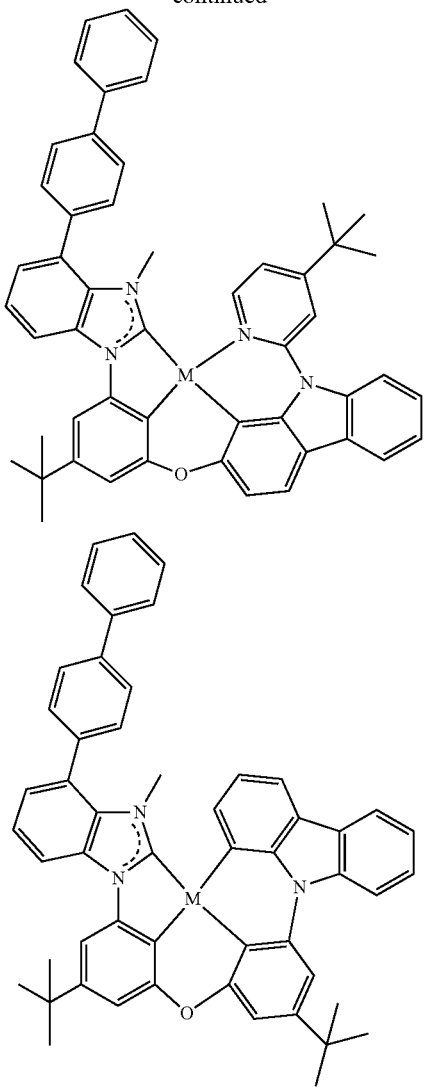
(M = Pt, Pd)
Structures 102
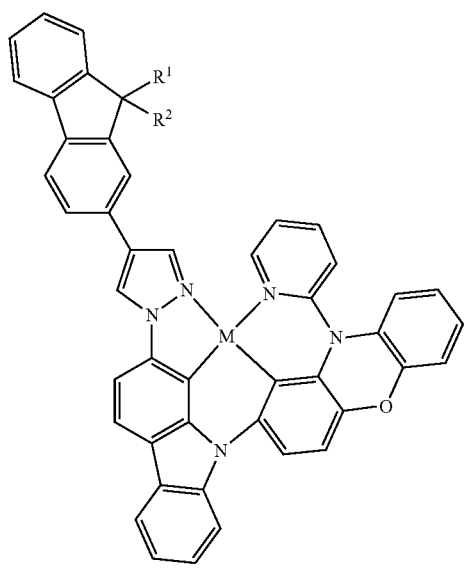
670
-continued
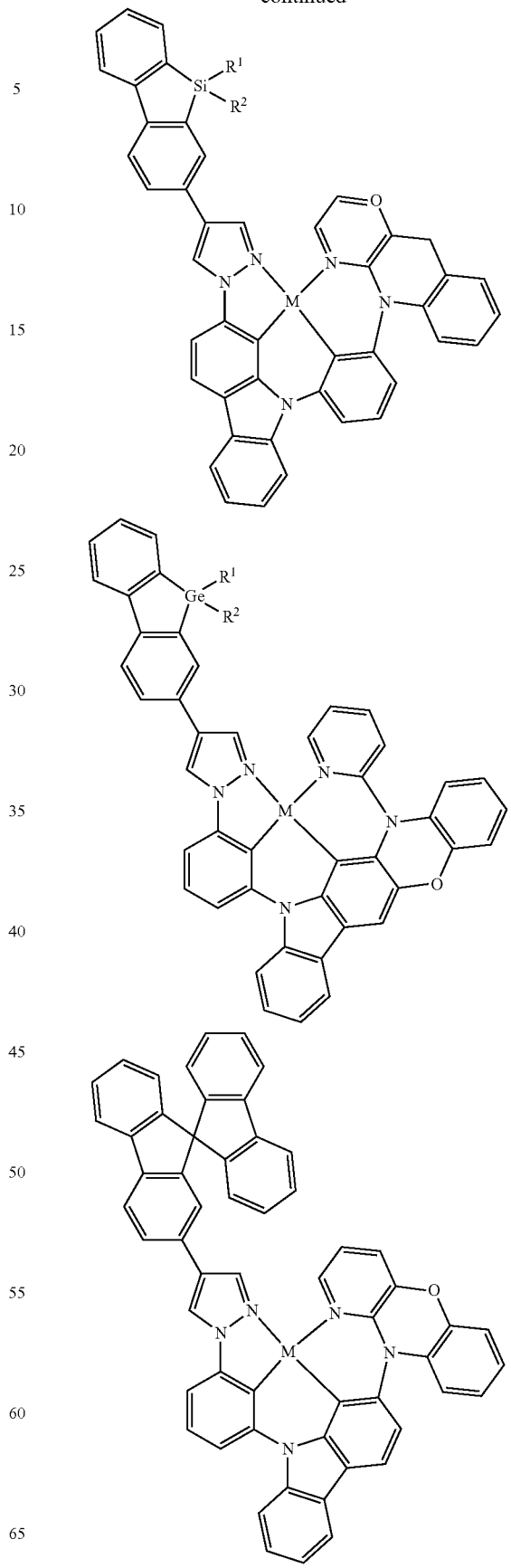

671
-continued
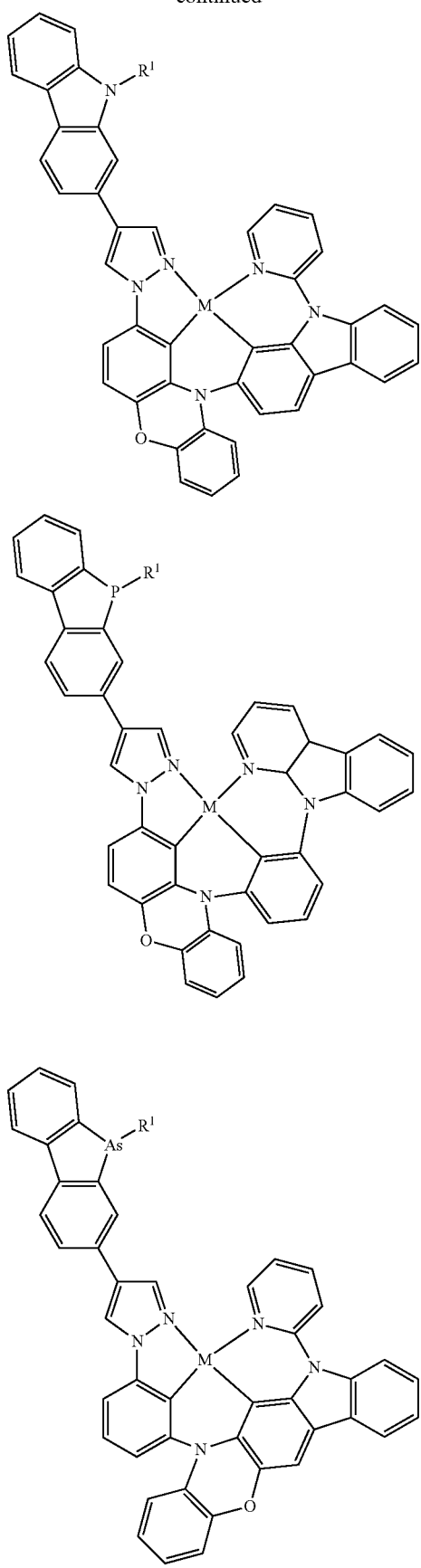
672
-continued
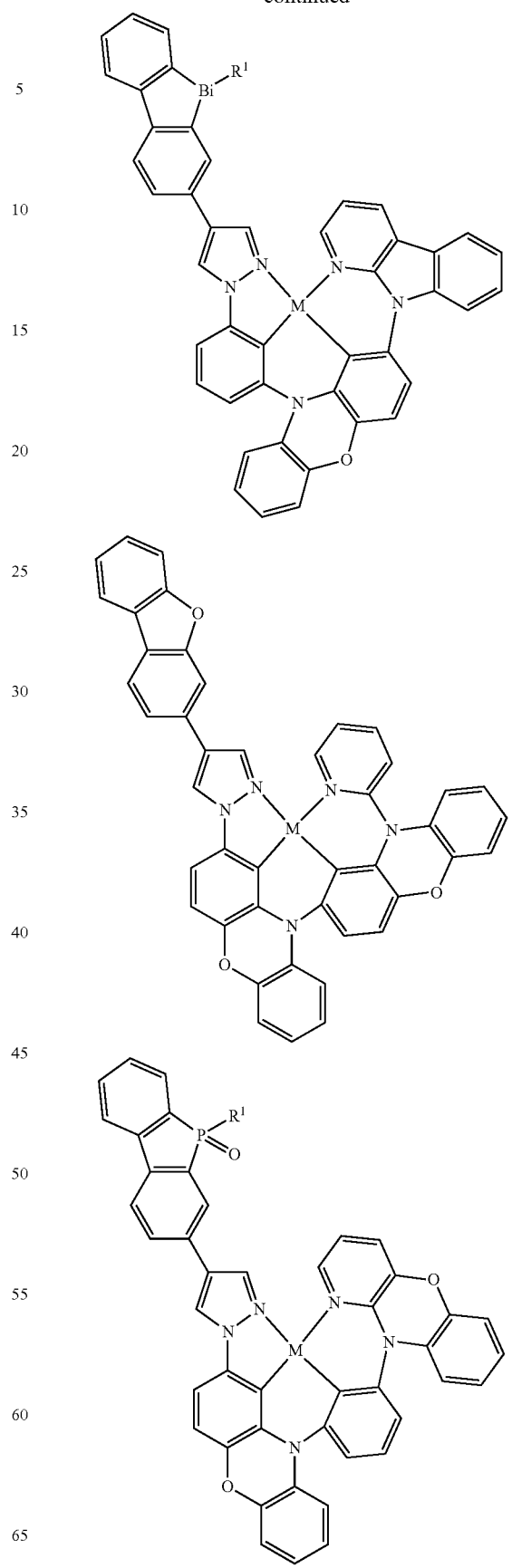

673
-continued
674
-continued
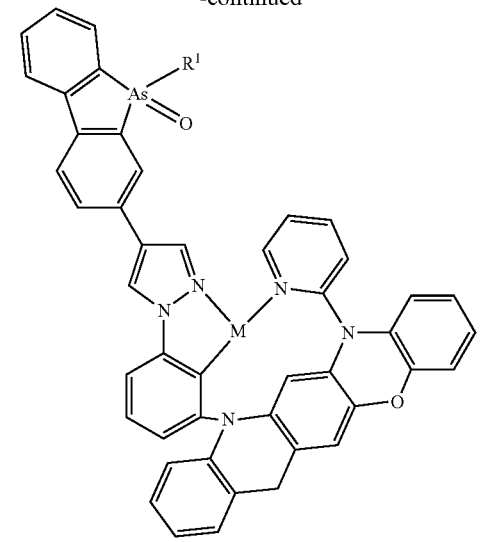
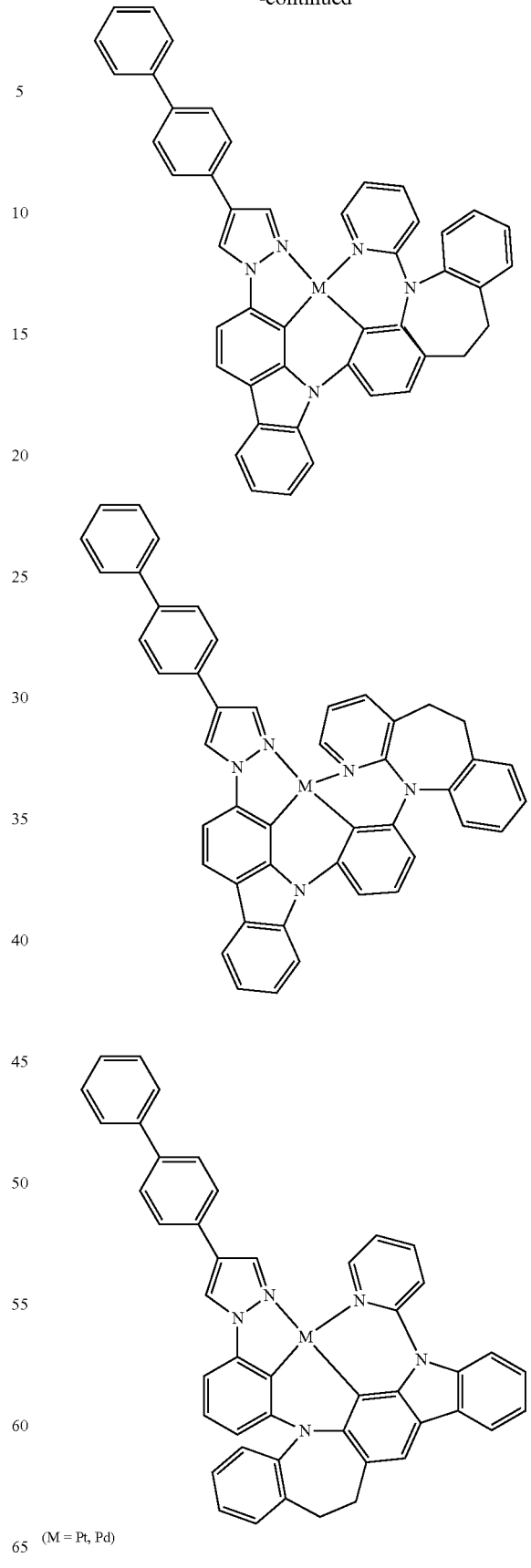
(M = Pt, Pd)

2. Devices

Also disclosed herein are devices including one or more of the compounds disclosed herein.

The compounds disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

Figure 2:
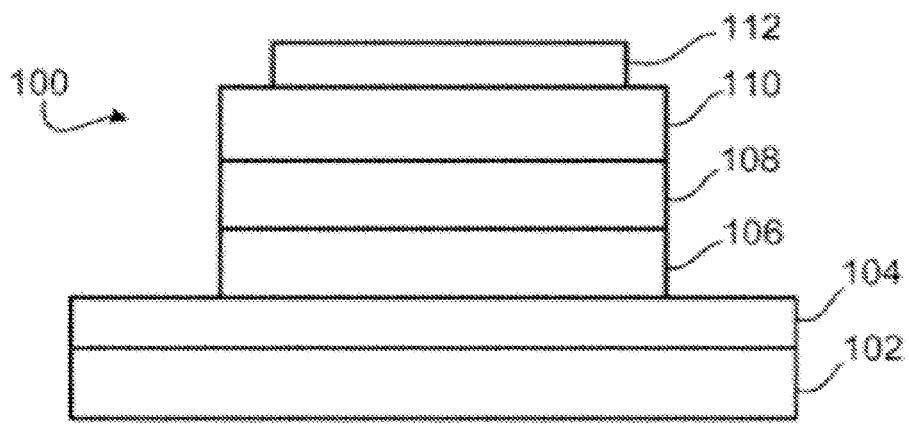
FIG. 2 depicts a device including a metal complex as disclosed herein.

Compounds described herein can be used in a light emitting device such as an OLED. FIG. 2 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4' diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and not intended to limit the scope of the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but this disclosure is not intended to be limited to any of the methods recited herein. Accordingly, one of skill in the art in possession of this disclosure could readily modify a recited method or utilize a different method to prepare one or more of the compounds. The following aspects are only exemplary and are not intended to limit the scope of the disclosure. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane ($\delta$=0.00 ppm) as internal reference; $^{13}$C NMR spectra were recorded with CDCl$_3$ ($\delta$=77.00 ppm) as internal reference. If DMSO-d$_6$ was used as solvent, $^1$H NMR spectra were recorded with residual H$_2$O ($\delta$=3.33 ppm) as internal reference; $^{13}$C NMR spectra were recorded with DMSO-d$_6$ ($\delta$=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

Synthetic Routes

A general synthetic route for the compounds disclosed herein includes:

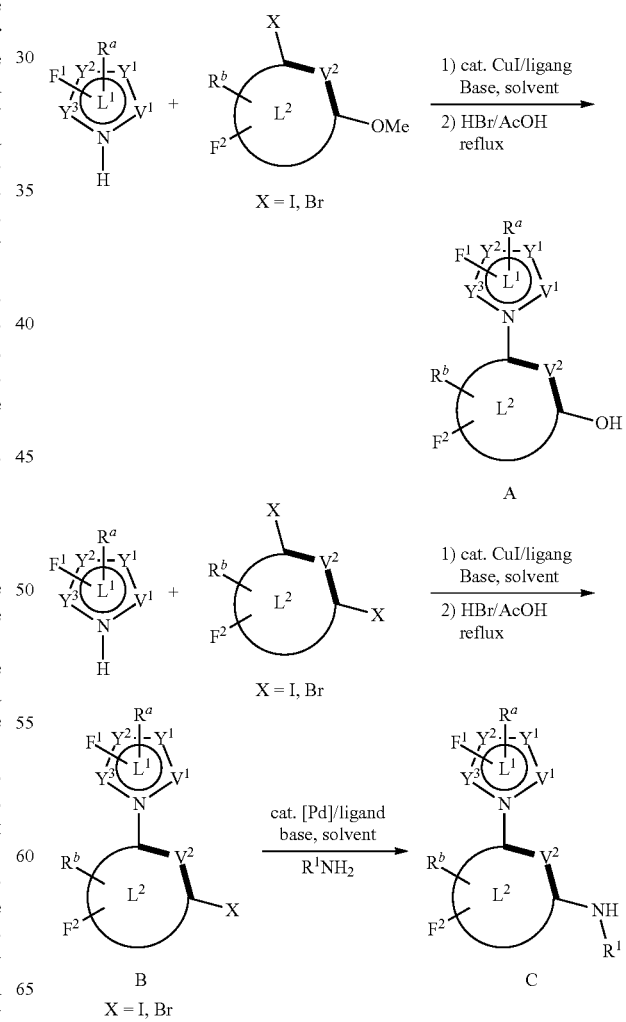

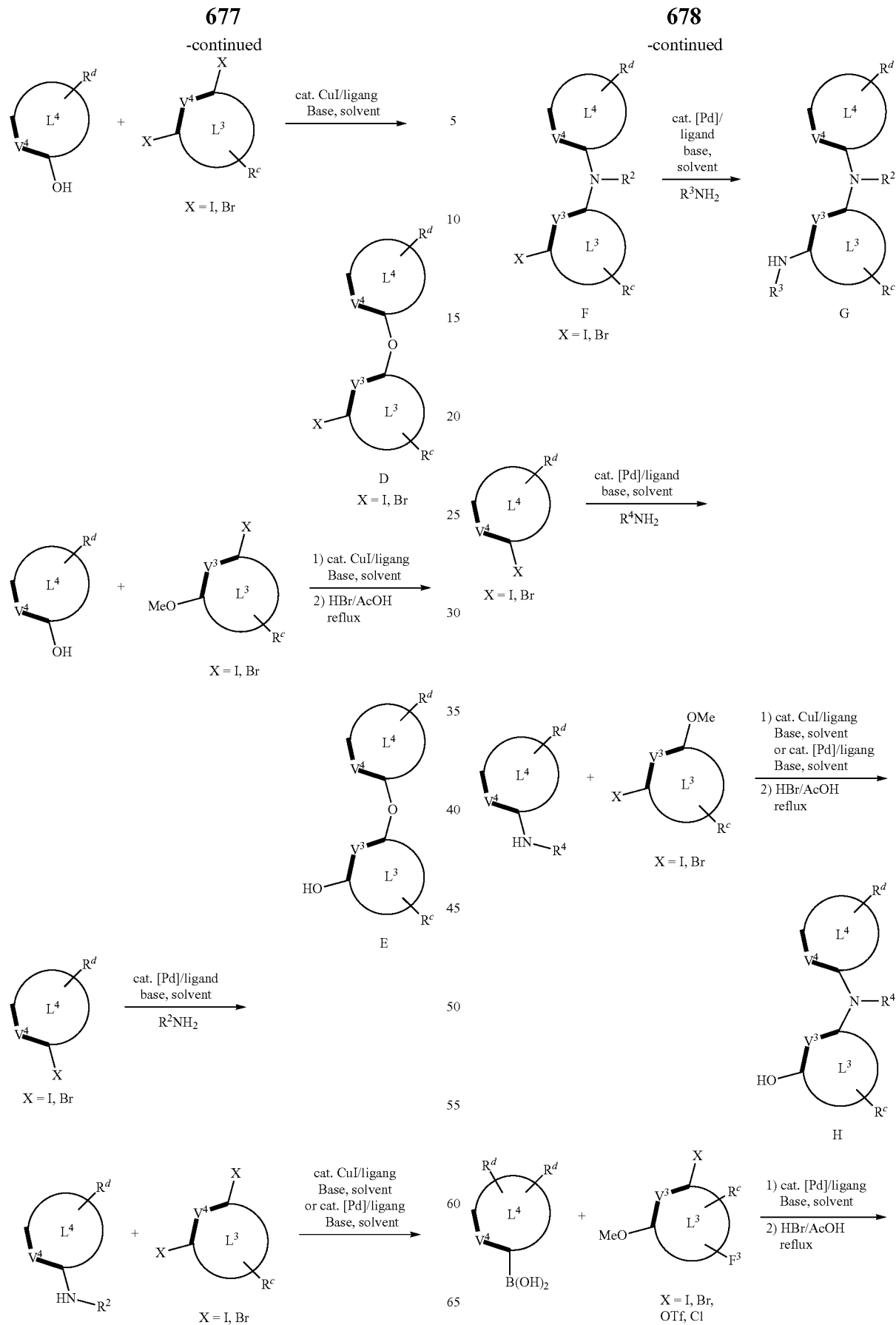

-continued
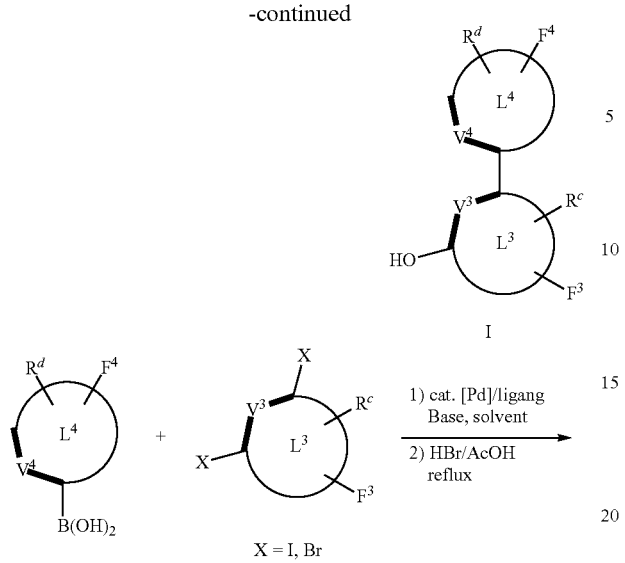
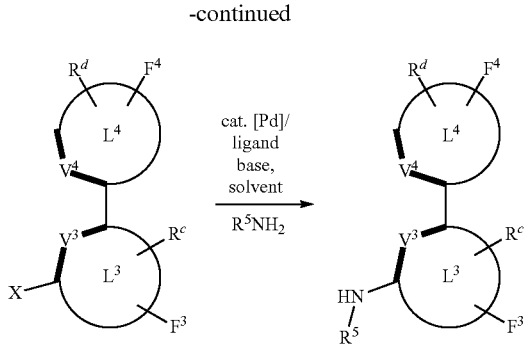
A synthetic route for the disclosed compounds herein also includes:
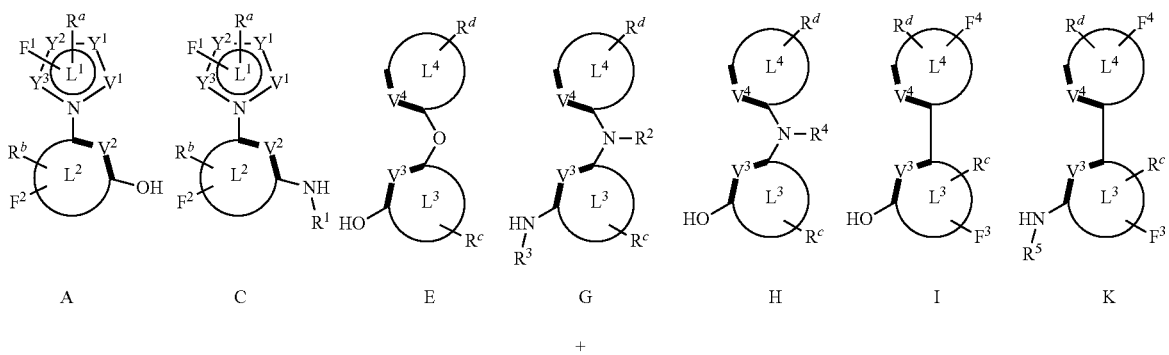
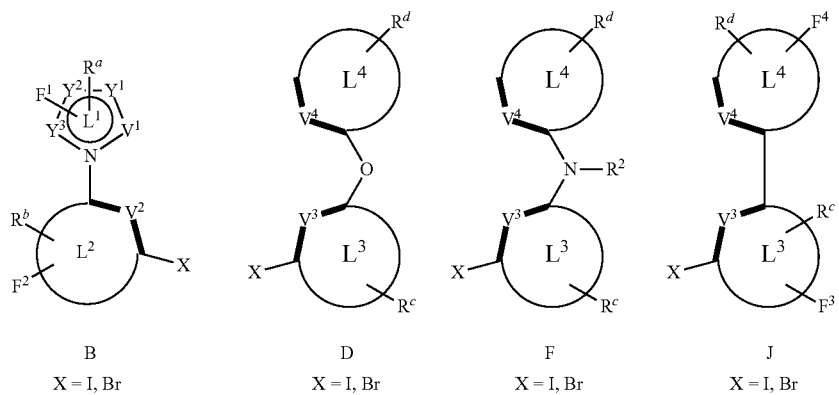

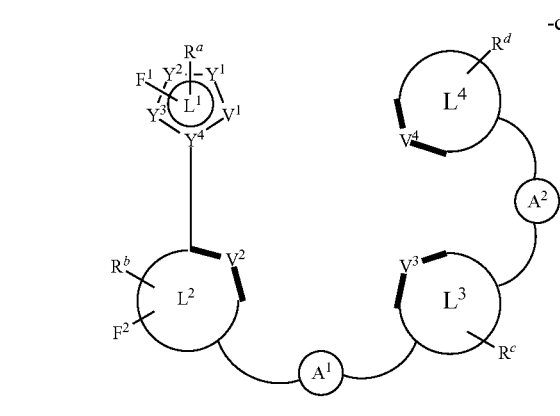

Ligand A-I

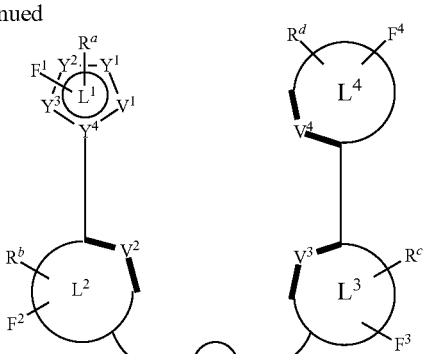

Ligand A-II

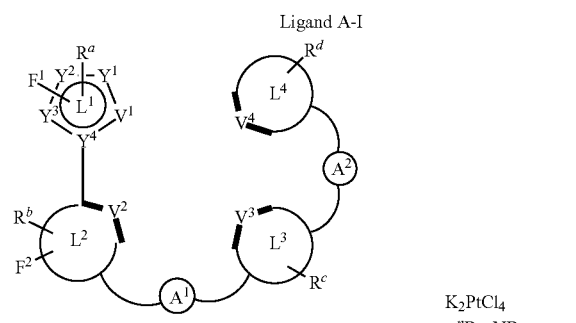

Ligand A-I

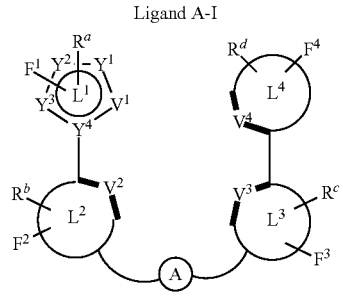

Ligand A-II $$\xrightarrow[\substack{\text{or Pd(OAc)}_2 \\ \text{cat. }^n\text{Bn}_4\text{NBr} \\ \text{AcOH, reflux} \\ A, A^1, A^2 = \text{O or NR} \\ M = \text{Pt or Pd}}]{\substack{K_2PtCl_4 \\ \text{cat. }^n\text{Bn}_4\text{NBr} \\ \text{AcOH, reflux}}}$$

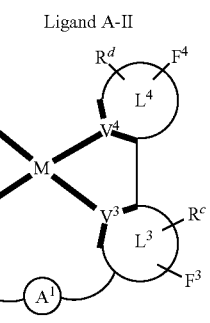

Formula A-I

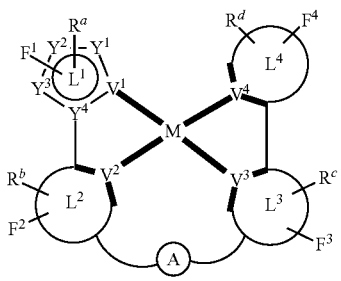

Formula A-II

1. Example 1

Platinum complex PtON1a can be prepared according to the following scheme:

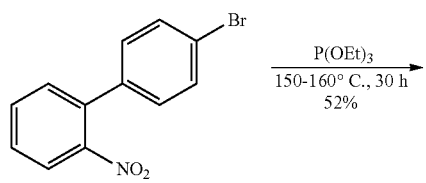

$$\xrightarrow[52\%]{\substack{\text{P(OEt)}_3 \\ 150\text{-}160°\text{ C., 30 h}}}$$

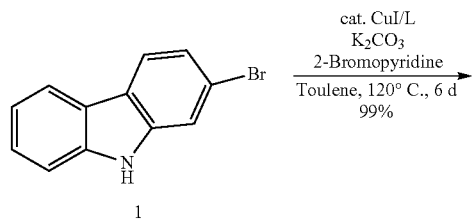

1

$$\xrightarrow[\substack{\text{Toulene, 120° C., 6 d} \\ 99\%}]{\substack{\text{cat. CuI/L} \\ K_2CO_3 \\ \text{2-Bromopyridine}}}$$

-continued

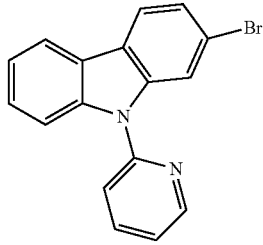

2

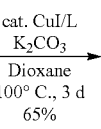 + 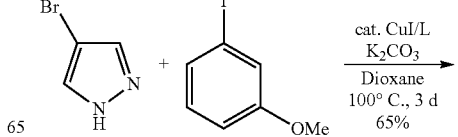

$$\xrightarrow[\substack{\text{Dioxane} \\ 100°\text{ C., 3 d} \\ 65\%}]{\substack{\text{cat. CuI/L} \\ K_2CO_3}}$$

-continued

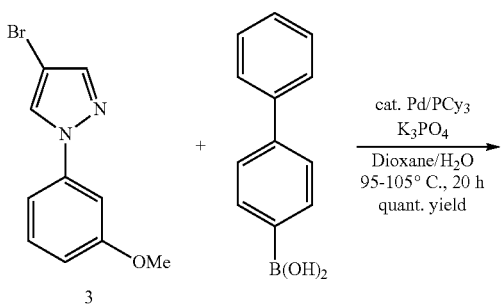

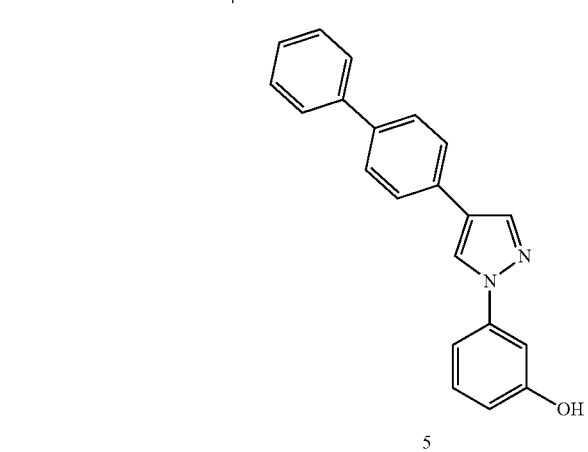

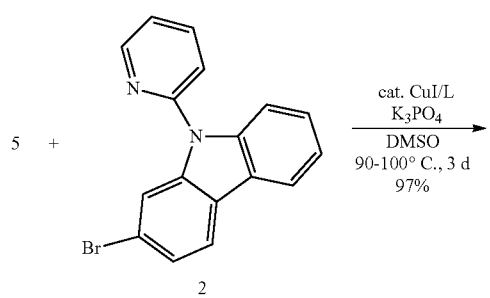

-continued

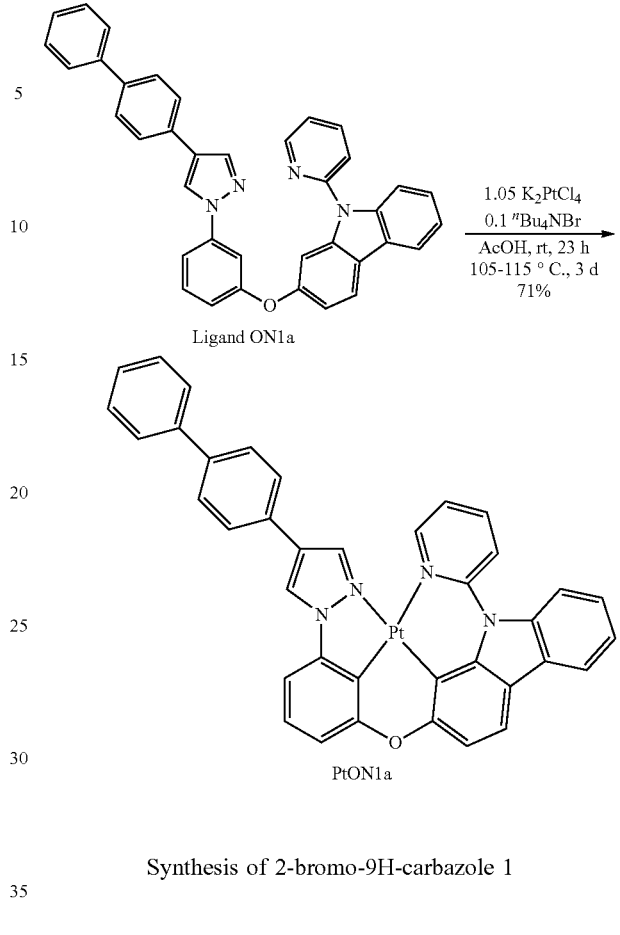

Synthesis of 2-bromo-9H-carbazole 1

4'-Bromo-2-nitrobiphenyl (22.40 g, 80.55 mmol) and P(OEt)$_3$ (150 mL) were added to a three-necked flask equipped with a magnetic stir bar and a condenser under the protection of nitrogen. The mixture was then stirred in an oil bath at a temperature of 150-160° C. for 30 hours, cooled to ambient temperature and the excess P(OEt)$_3$ was removed by distillation under high vacuum. The residue was recrystallized in toluene to get the desired product 2-bromo-9H-carbazole 8.30 g as a white crystal. The filtrate was concentrated and the residue was purified through column chromatography on silica gel using hexane and ethyl acetate (10:1-5:1) as eluent to obtain the desired product 2-bromo-9H-carbazole 2.00 g in 52% total yield. $^1$H NMR (DMSO-d$_6$, 400 MHz): δ 7.17 (t, J=7.6 Hz, 1H), 7.28 (dd, J=8.0, 1.6 Hz, 1H), 7.41 (t, J=7.6 Hz, 1H), 7.49 (d, J=8.4 Hz, 1H), 7.65 (d, J=1.6 Hz, 1H), 8.06 (d, J=8.4 Hz, 1H), 8.11 (d, J=7.6 Hz, 1H), 11.38 (s, 1H). $^{13}$C NMR (DMSO-d$_6$, 100 MHz): δ 111.22, 113.50, 118.11, 119.09, 120.36, 121.29, 121.58, 121.79, 121.90, 126.09, 139.89, 140.62.

Synthesis of 2-bromo-9-(pyridin-2-yl)-9H-carbazole 2

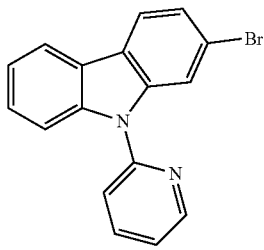 [SMILES: Brc1ccc2c3ccccc3n(-c3ccccn3)c2c1]

2-Bromo-9H-carbazole 1 (3.91 g, 15.89 mmol, 1.0 eq), CuI (0.30 g, 1.59 mmol, 0.1 eq) and $K_2CO_3$ (4.39 g, 31.78 mmol, 2.0 eq) were added to a dry pressure tube equipped with a magnetic stir bar. Then the tube was taken into a glove box. Solvent toluene (60 mL), 1-methyl-1H-imidazole (0.63 mL, 7.95 mmol, 0.5 eq) and 2-bromopyridine (4.55 mL, 47.68 mmol, 3.0 eq) were added. The mixture was bubbled with nitrogen for 10 minutes. The tube was sealed before being taken out of the glove box and the mixture was stirred in an oil bath at a temperature of 120° C. for 6 days, cooled to ambient temperature, filtered and washed with ethyl acetate. The filtrate was concentrated under reduced pressure to remove the solvent and the excess 2-bromopyridine (otherwise it is difficult to separate the desired product and 2-bromopyridine by silica gel column). The residue was purified through column chromatography on silica gel using dichloromethane as eluent to obtain the desired product 2-bromo-9-(pyridin-2-yl)-9H-carbazole 2 as an off-white solid 5.11 g in 99% yield. $^1$H NMR (DMSO-$d_6$, 400 MHz): δ 7.33 (t, J=7.6 Hz, 1H), 7.45-7.50 (m, 3H), 7.74 (d, J=8.4 Hz, 1H), 7.78 (d, J=8.0 Hz, 1H), 7.95 (d, J=2.0 Hz, 1H), 8.11 (td, J=8.0, 2.0 Hz, 1H), 8.19 (d, J=8.4 Hz, 1H), 8.24 (d, J=7.6 Hz, 1H), 8.72 (dd, J=4.8, 1.6 Hz, 1H). $^1$H NMR (CDCl$_3$, 400 MHz): δ 7.32 (t, J=7.6 Hz, 2H), 7.41-7.47 (m, 2H), 7.60 (d, J=8.0 Hz, 1H), 7.77 (d, J=8.4 Hz, 1H), 7.91-7.95 (m, 2H), 8.01 (d, J=2.0 Hz, 1H), 8.07 (d, J=8.0 Hz, 1H), 8.72-8.73 (m, 1H). $^{13}$C NMR (CDCl$_3$, 100 MHz): δ 111.10, 114.35, 119.01, 119.78, 120.21, 121.26, 121.30, 121.61, 123.16, 123.64, 124.06, 126.58, 138.65, 139.60, 140.29, 149.78, 151.26.

Synthesis of 4-bromo-1-(3-methoxyphenyl)-1H-pyrazole 3

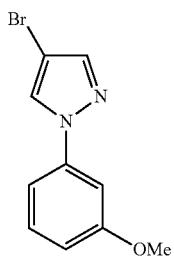 [SMILES: COc1cccc(-n2cc(Br)cn2)c1]

4-Bromo-1H-pyrazole (3674 mg, 25 mmol, 1.0 eq), CuI (95 mg, 0.5 mmol, 0.02 eq) and $K_2CO_3$ (7256 mg, 52.5 mmol, 2.1 eq) were added to a dry pressure tube equipped with a magnetic stir bar. Then trans-1,2-cyclohexanediamine (570 mg, 5 mmol, 0.2 eq), 1-iodo-3-methoxybenzene (3.57 mL, 30 mmol, 1.2 eq) and solvent dioxane (50 mL) were added in a nitrogen filled glove box. The mixture was bubbled with nitrogen for 5 minutes. The tube was sealed before being taken out of the glove box. The mixture was stirred in an oil bath at a temperature of 100° C. for two days. Then the mixture was cooled to ambient temperature, filtered and washed with ethyl acetate. The filtrate was concentrated and the residue was purified through column chromatography on silica gel using hexane and ethyl acetate (20:1-15:1) as eluent to obtain the desired product 4-bromo-1-(3-methoxyphenyl)-1H-pyrazole 3 as a colorless sticky liquid 4.09 g in 65% yield. $^1$H NMR (DMSO-$d_6$, 400 MHz): δ 3.82 (s, 3H), 6.89-6.92 (m, 1H), 7.39-7.41 (m, 3H), 7.86 (s, 1H), 8.81 (s, 1H). $^{13}$C NMR (DMSO-$d_6$, 100 MHz): 555.45, 94.92, 104.01, 110.35, 112.54, 128.30, 130.51, 140.26, 141.16, 160.15.

Synthesis of 4-(biphenyl-4-yl)-1-(3-methoxyphenyl)-1H-pyrazole 4

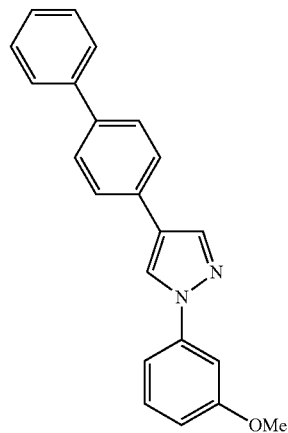 [SMILES: COc1cccc(-n2cc(-c3ccc(-c4ccccc4)cc3)cn2)c1]

To a three-necked flask equipped with a magnetic stir bar and a condenser was added biphenyl-4-ylboronic acid (1012 mg, 5.11 mmol, 1.2 eq), Pd$_2$(dba)$_3$ (156 mg, 0.17 mmol, 0.04 eq) and tricyclohexylphosphine PCy$_3$ (115 mg, 0.41 mmol, 0.096 eq). Then the flask was evacuated and backfilled with nitrogen, the evacuation and backfill procedure was repeated twice. Then a solution of 4-bromo-1-(3-methoxyphenyl)-1H-pyrazole 3 (1078 mg, 4.26 mmol, 1.0 eq) in dioxane (25 mL) and a solution of K$_3$PO$_4$ (1537 mg, 7.24 mmol, 1.7 eq) in H$_2$O (10 mL) were added by syringe independently under nitrogen. The mixture was stirred in an oil bath at a temperature of 95-105° C. for 20 hours, cooled to ambient temperature, filtered and washed with ethyl acetate. The organic layer of the filtrate was separated, dried over sodium sulfate, filtered, concentrated and the residue was purified through column chromatography on silica gel using hexane/ethyl acetate (10:1-5:1-3:1) as eluent to obtain the desired product 4-(biphenyl-4-yl)-1-(3-methoxyphenyl)-1H-pyrazole 4 as a brown solid in quantitative yield. $^1$H NMR (DMSO-$d_6$, 400 MHz): δ 3.85 (s, 3H), 6.90 (dd, J=8.0, 2.4 Hz, 1H), 7.36-7.50 (m, 6H), 7.70-7.73 (m, 4H), 7.82 (d, J=8.4 Hz, 2H), 8.26 (s, 1H), 9.07 (s, 1H).

Synthesis of 3-(4-(biphenyl-4-yl)-1H-pyrazol-1-yl)phenol 5

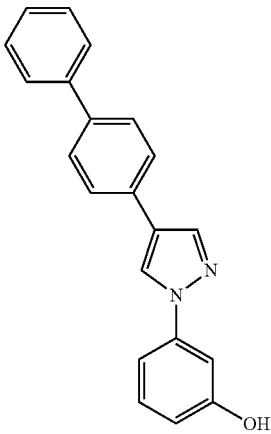 [SMILES: Oc1cccc(-n2cc(-c3ccc(-c4ccccc4)cc3)cn2)c1]

A solution of 4-(biphenyl-4-yl)-1-(3-methoxyphenyl)-1H-pyrazole 4 (4.26 mmol) in a mixture of acetic acid (20 mL) and hydrogen bromide acid (10 mL, 48%) refluxed (120-130° C.) for 18 hours at an atmosphere of nitrogen. Then the mixture was cooled. After most of the acetic acid was removed under reduced pressure, the residue was neutralized with a solution of $K_2CO_3$ in water until there was no gas to generate. Then the precipitate was filtered off and washed with water for several times. The collected solid was dried in air to afford the product 3-(4-(biphenyl-4-yl)-1H-pyrazol-1-yl)phenol 5 as a brown solid in quantitative yield. $^1$H NMR (DMSO-$d_6$, 400 MHz): δ 6.59 (dt, J=6.8, 2.0 Hz, 1H), 7.23-7.28 (m, 3H), 7.32 (t, J=7.6 Hz, 1H), 7.43 (t, J=8.0 Hz, 2H), 7.67 (d, J=8.8 Hz, 4H), 7.77 (d, J=8.4 Hz, 2H), 8.19 (s, 1H), 8.94 (s, 1H), 9.76 (bs, 1H).

Synthesis of 2-(3-(4-(biphenyl-4-yl)-1H-pyrazol-1-yl)phenoxy)-9-(pyridin-2-yl)-9H-carbazole Ligand ON1a

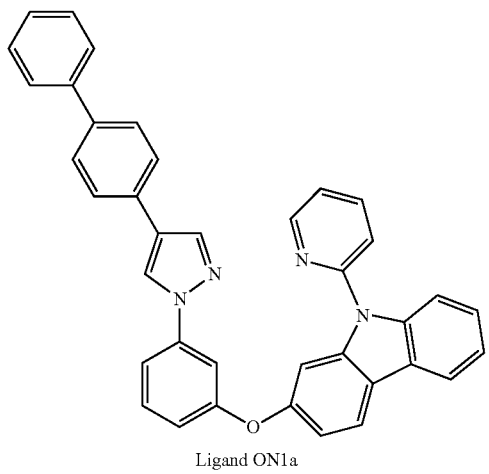 [SMILES: c1ccc(-c2ccc(-c3cnn(-c4cccc(Oc5ccc6c7ccccc7n(-c7ccccn7)c6c5)c4)c3)cc2)cc1]

Ligand ON1a

To a dry pressure vessel equipped with a magnetic stir bar was added 3-(4-(biphenyl-4-yl)-1H-pyrazol-1-yl)phenol 5 (2.13 mmol, 1.0 eq), 2-bromo-9-(pyridin-2-yl)-9H-carbazole 2 (827 mg, 2.56 mmol, 1.2 eq), CuI (40 mg, 0.21 mmol, 0.1 eq), picolinic acid (52 mg, 0.42 mmol, 0.2 eq) and $K_3PO_4$ (904 mg, 4.26 mmol, 2.0 eq). The tube was evacuated and backfilled with nitrogen. This evacuation and backfill procedure was repeated twice. Then solvent DMSO (12 mL) was added under nitrogen. The mixture was stirred at a temperature of 90-100° C. for 3 days and then cooled to ambient temperature. Water was added to dissolve solid. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1-5:1-3:1) as eluent to obtain the desired product Ligand ON1a as a brown solid 1143 mg in 97% yield. $^1$H NMR (DMSO-$d_6$, 400 MHz): δ 6.96 (dd, J=8.0, 2.0 Hz, 1H), 7.09 (dd, J=8.4, 2.0 Hz, 1H), 7.33 (t, J=8.0 Hz, 2H), 7.42-7.45 (m, 4H), 7.49 (t, J=8.0 Hz, 1H), 7.57 (d, J=1.6 Hz, 1H), 7.62 (s, 1H), 7.67-7.69 (m, 5H), 7.77 (d, J=8.4 Hz, 4H), 8.05 (td, J=7.6, 1.6 Hz, 1H), 8.21 (d, J=6.0 Hz, 1H), 8.22 (s, 1H), 8.27 (d, J=8.8 Hz, 1H), 8.67 (d, J=3.2 Hz, 1H), 9.07 (s, 1H). $^{13}$C NMR (DMSO-$d_6$, 100 MHz): δ 102.49, 107.87, 111.12, 112.56, 113.28, 115.55, 119.02, 120.07, 120.19, 121.25, 121.79, 122.11, 123.28, 123.86, 124.79, 125.83, 125.98, 126.40, 127.07, 127.34, 128.90, 130.80, 131.02, 138.27, 138.85, 139.35, 139.49, 139.67, 139.96, 140.89, 149.52, 150.48, 154.84, 158.53.

Synthesis of 2-(3-(4-(biphenyl-4-yl)-1H-pyrazol-1-yl)phenoxy)-9-(pyridin-2-yl)-9H-carbazole platinum Complex PtON1a

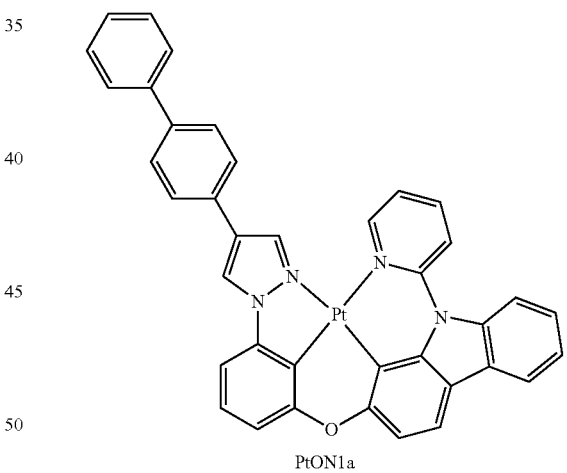

PtON1a

Figure 3:
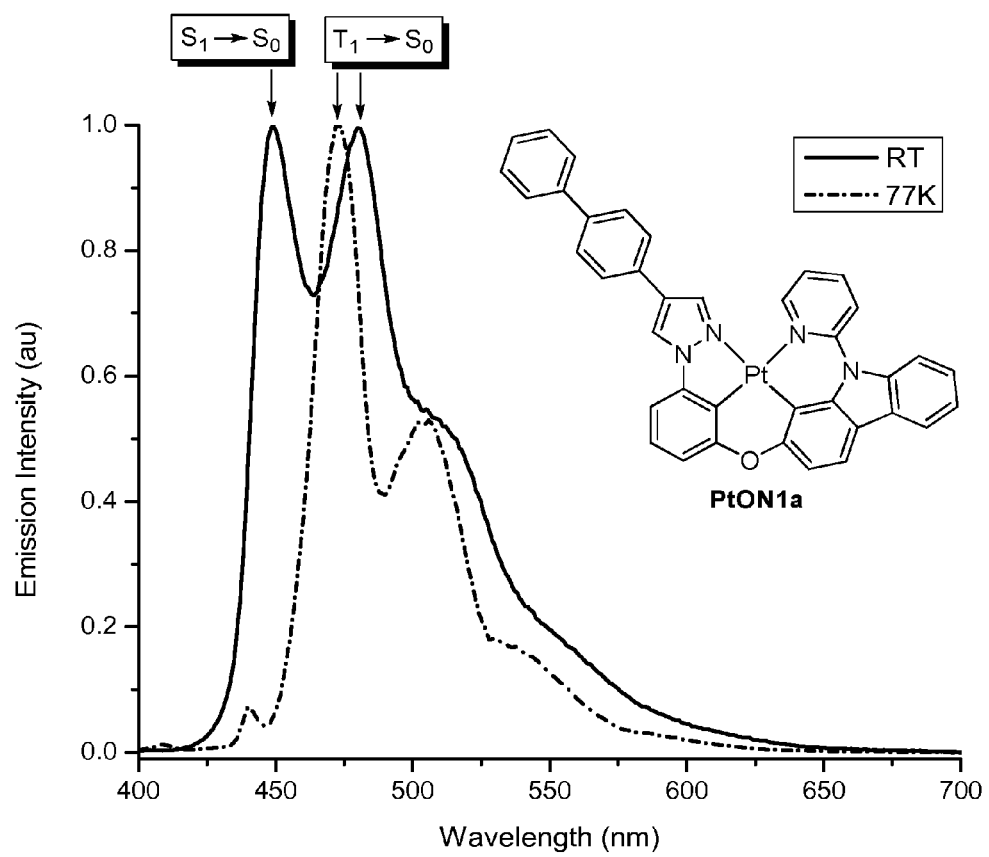
FIG. 3 shows emission spectra of PtON1a in $CH_2Cl_2$ at room temperature and in 2-methyltetrahydrofuran at 77K, in accordance with various aspects of the present disclosure.

To a dry pressure tube equipped with a magnetic stir bar was added Ligand ON1a (554 mg, 1.0 mmol, 1.0 eq), $K_2PtCl_4$ (440 mg, 1.05 mmol, 1.05 eq), $^nBu_4NBr$ (32 mg, 0.1 mmol, 0.1 eq) and solvent acetic acid (60 mL). The mixture was bubbled with nitrogen for 20 minutes in a nitrogen filled glove box. The tube was sealed before being taken out of the glove box. The mixture was stirred at room temperature for 23 hours and followed at 105-115° C. for 3 days, cooled to ambient temperature and water (120 mL) was added. The precipitate was filtered off and washed with water three times. Then the solid was dried in air under reduced pressure. The collected solid was purified through flash column chromatography on silica gel using dichloromethane as eluent to obtain the platinum complex PtON1a a yellow solid 530 mg in 71% total yield. $^1$H NMR (DMSO-d$_6$, 400 MHz): δ 7.01 (d, J=8.4 Hz, 1H), 7.24 (d, J=8.0, 1H), 7.29 (t, J=8.0 Hz, 1H), 7.39-7.45 (m, 2H), 7.49-7.54 (m, 4H), 7.58 (d, J=8.4 Hz, 1H), 7.78 (d, J=8.0 Hz, 2H), 7.82 (d, J=8.8 Hz, 2H), 7.90 (d, J=8.0 Hz, 1H), 8.02 (d, J=8.4 Hz, 2H), 8.11 (d, J=8.0 Hz, 1H), 8.18 (d, J=8.0 Hz, 1H), 8.27 (td, J=8.0, 1.6 Hz, 1H), 8.31 (d, J=8.0 Hz, 1H), 8.72 (s, 1H), 9.39 (d, J=4.8 Hz, 1H), 9.49 (s, 1H). $^{13}$C NMR (DMSO-d$_6$, 100 MHz): δ 98.84, 106.06, 110.98, 112.54, 113.29, 114.92, 115.64, 115.76, 116.14, 119.97, 120.60, 122.94, 123.39, 124.54, 124.83, 125.46, 126.21, 126.53, 127.18, 127.52, 127.87, 128.98, 129.93, 137.09, 137.98, 138.90, 139.61, 139.79, 141.83, 146.00, 147.50, 152.29, 152.49, 152.56. FIG. 3 shows emission spectra of PtON1a in CH$_2$Cl$_2$ at room temperature and in 2-methyltetrahydrofuran at 77K.

2. Example 2

Platinum complex PtON1a-tBu can be prepared according to the following scheme:

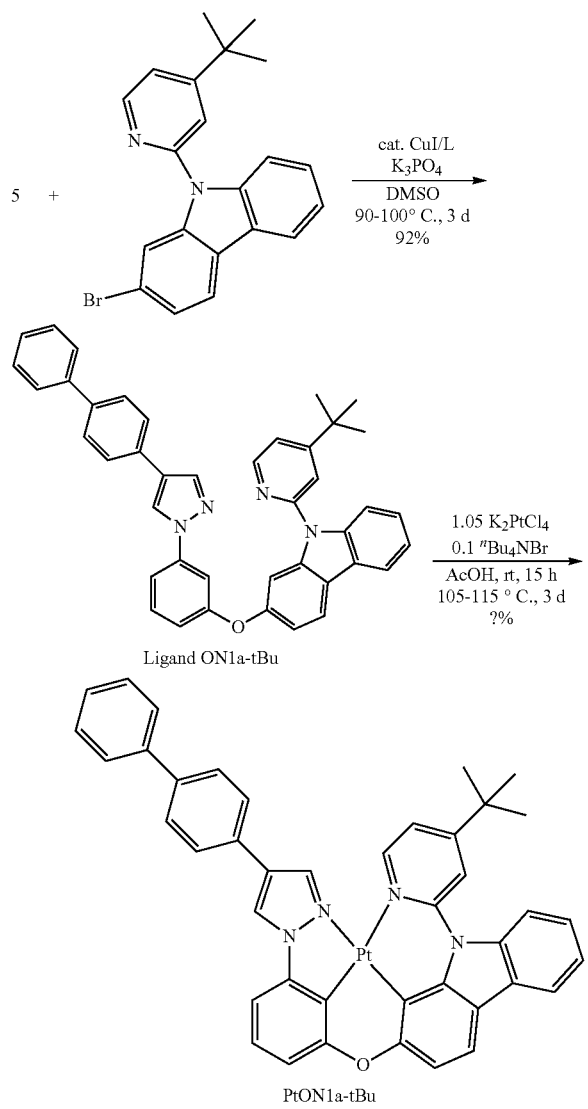

Synthesis of 2-(3-(4-(biphenyl-4-yl)-1H-pyrazol-1-yl)phenoxy)-9-(4-tert-butylpyridin-2-yl)-9H-carbazole Ligand ON1a-tBu

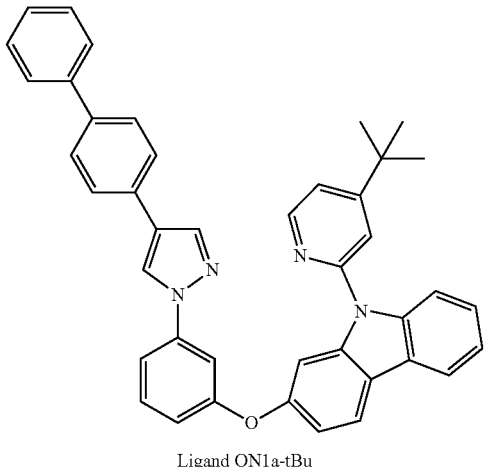 [SMILES: CC(C)(C)c1ccnc(-n2c3ccccc3c3ccc(Oc4cccc(-n5cc(-c6ccc(-c7ccccc7)cc6)cn5)c4)cc32)c1]

Ligand ON1a-tBu

To a dry pressure vessel equipped with a magnetic stir bar was added 3-(4-(biphenyl-4-yl)-1H-pyrazol-1-yl)phenol 5 (1.06 mmol, 1.0 eq), 2-bromo-9-(4-tert-butylpyridin-2-yl)-9H-carbazole (482 mg, 1.27 mmol, 1.2 eq), CuI (20 mg, 0.11 mmol, 0.1 eq), picolinic acid (26 mg, 0.21 mmol, 0.2 eq) and K$_3$PO$_4$ (452 mg, 2.13 mmol, 2.0 eq). The tube was evacuated and backfilled with nitrogen. This evacuation and backfill procedure was repeated twice. Then solvent DMSO (6 mL) was added under nitrogen. The mixture was stirred at a temperature of 90-100° C. for 3 days and then cooled to ambient temperature. Water was added to dissolve the salt. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1-3:1) as eluent to obtain the desired product as a brown solid 595 mg in 92% yield. $^1$H NMR (DMSO-d$_6$, 400 MHz): δ 1.20 (s, 9H), 7.01 (d, J=8.4 Hz, 1H), 7.13 (d, J=8.8 Hz, 1H), 7.29-7.34 (m, 3H), 7.38-7.45 (m, 4H), 7.50 (t, J=8.0 Hz, 1H), 7.59 (s, 1H), 7.66-7.71 (m, 6H), 7.75-7.78 (m, 3H), 8.20 (d, J=8.0 Hz, 1H), 8.22 (s, 1H), 8.27 (d, J=7.6 Hz, 1H), 8.54 (d, J=4.8 Hz, 1H), 9.09 (s, 1H). $^{13}$C NMR (DMSO-d$_6$, 100 MHz): δ 29.95, 34.75, 100.91, 108.60, 111.27, 112.86, 113.03, 115.69, 116.44, 119.24, 119.65, 120.08, 121.13, 121.89, 123.22, 123.87, 124.79, 125.80, 125.85, 126.40, 127.07, 127.34, 128.90, 130.82, 131.14, 138.27, 138.85, 139.45, 139.67, 139.89, 141.01, 149.38, 150.62, 155.66, 157.86, 162.99.

Synthesis of 2-(3-(4-(biphenyl-4-yl)-1H-pyrazol-1-yl)phenoxy)-9-(4-tert-butylpyridin-2-yl)-9H-carbazole platinum Complex PtON1a-tBu

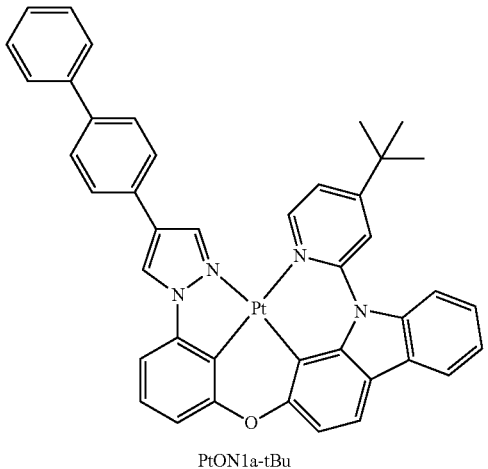

PtON1a-tBu

Figure 4:
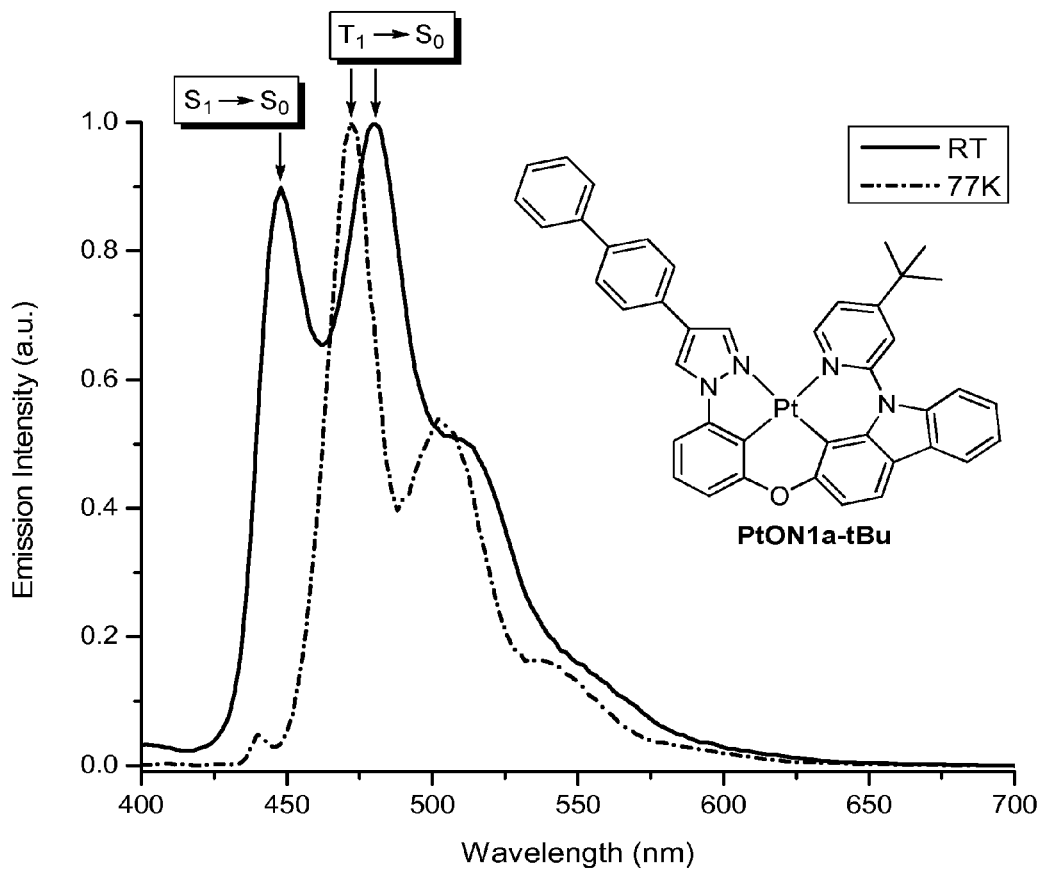
FIG. 4 shows emission spectra of PtON1a-tBu in $CH_2Cl_2$ at room temperature and in 2-methyltetrahydrofuran at 77K, in accordance with various aspects of the present disclosure.
Figure 5:
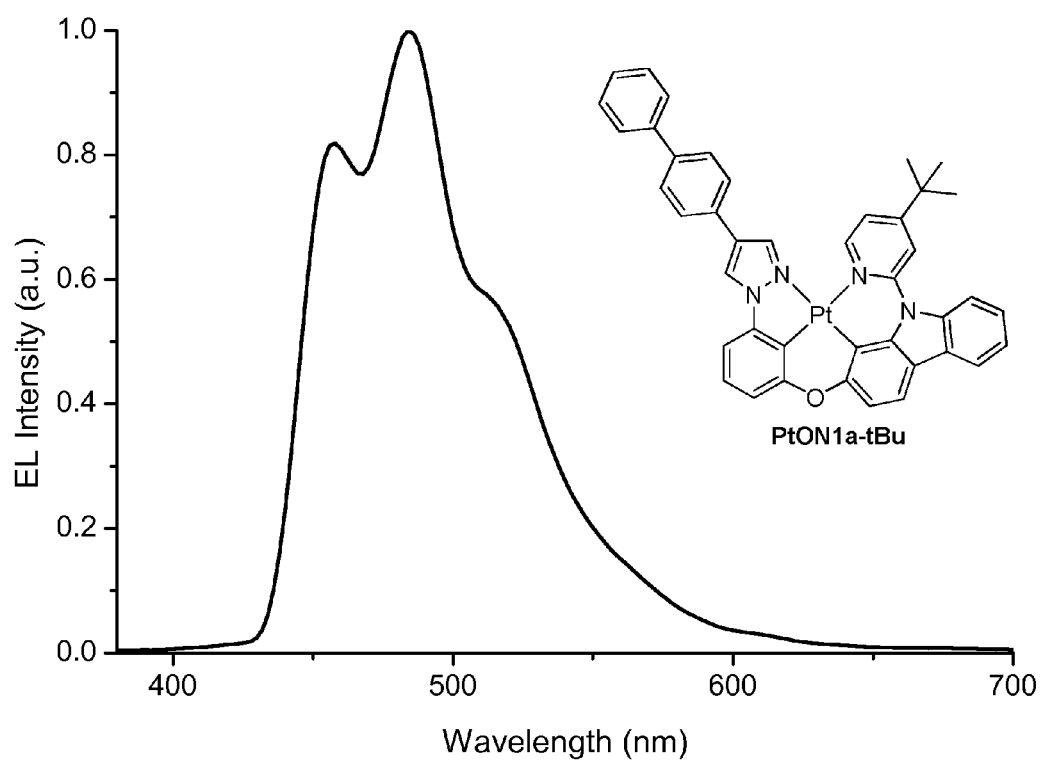
FIG. 5 shows EL spectra for the devices of ITO/HATCN (10 nm)/NPD (40 nm)/TAPC (10 nm)/26mCPy: 6% PtON1a-tBu/DPPS (10 nm)/BmPyPB (40 nm)/LiF/AL.
Figure 6:
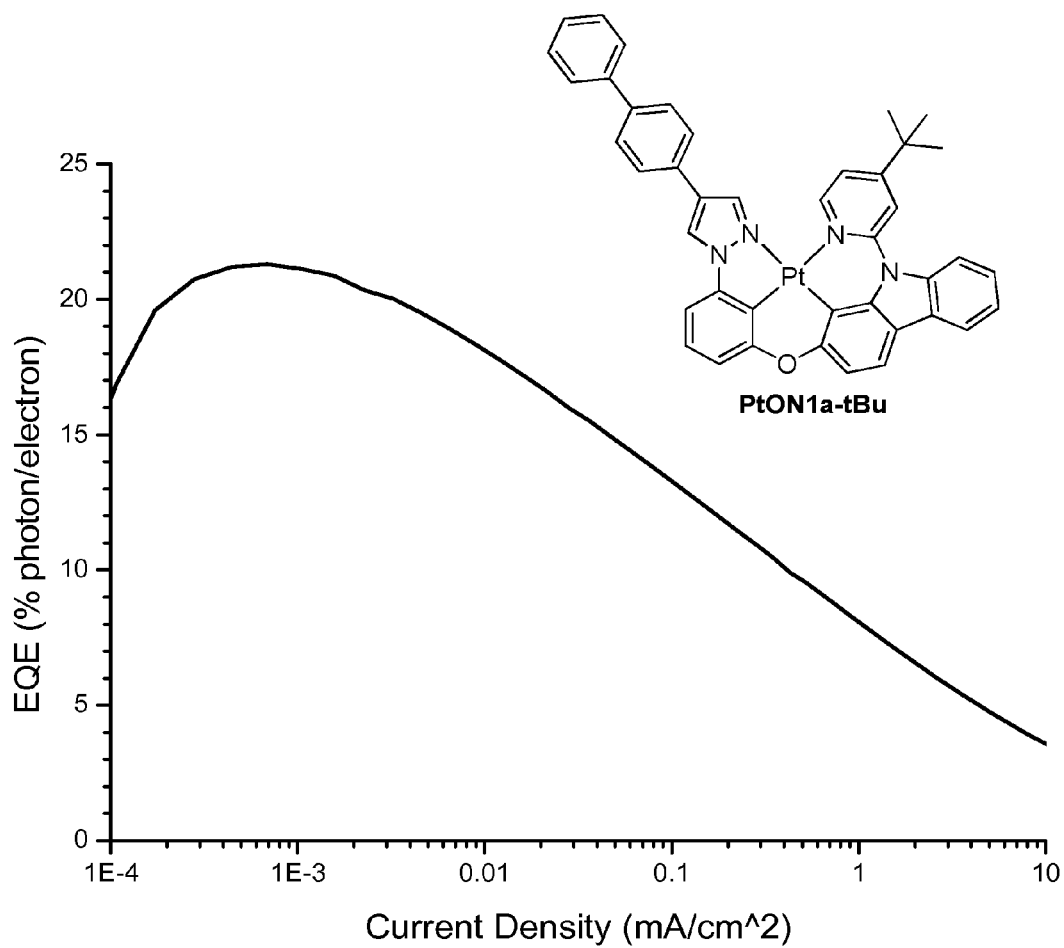
FIG. 6 shows external quantum efficiency (% photon/electron) vs. current density ($mA/cm^2$) for the devices of ITO/HATCN (10 nm)/NPD (40 nm)/TAPC (10 nm)/26mCPy: 6% PtON1a-tBu/DPPS (10 nm)/BmPyPB (40 nm)/LiF/AL.

To a dry pressure tube equipped with a magnetic stir bar was added Ligand ON1a-tBu (557 mg, 0.91 mmol, 1.0 eq), K$_2$PtCl$_4$ (400 mg, 0.95 mmol, 1.05 eq), $^n$Bu$_4$NBr (29 mg, 0.091 mmol, 0.1 eq) and solvent acetic acid (55 mL). The mixture was bubbled with nitrogen for 20 minutes in a nitrogen filled glove box. The tube was sealed before being taken out of the glove box. The mixture was stirred at room temperature for 15 hours and followed at 105-115° C. for 3 days, cooled to ambient temperature and water (110 mL) was added. The precipitate was filtered off and washed with water three times. Then the solid was dried in air under reduced pressure and purified through flash column chromatography on silica gel using hexane/dichloromethane (1:2) as eluent to obtain a yellow solid 367 mg. The product (320 mg) was further purified by sublimation to get PtON1a-tBu 85 mg as a yellow solid in 13% total yield. $^1$H NMR (DMSO-d$_6$, 400 MHz): δ 1.40 (s, 9H), 7.00 (d, J=8.8 Hz, 1H), 7.22 (d, J=8.4 Hz, 1H), 7.27 (t, J=8.0 Hz, 1H), 7.38-7.43 (m, 2H), 7.49-7.57 (m, 5H), 7.77 (d, J=6.8 Hz, 2H), 7.81 (d, J=8.0 Hz, 2H), 7.90 (d, J=8.0 Hz, 1H), 8.02 (d, J=8.0 Hz, 2H), 8.09 (d, J=8.0 Hz, 1H), 8.17 (s, 1H), 8.18 (d, J=8.4 Hz, 1H), 8.74 (s, 1H), 9.26 (d, J=6.4 Hz, 1H), 9.48 (s, 1H). $^{13}$C NMR (DMSO-d$_6$, 100 MHz): δ 29.71, 35.53, 98.81, 106.13, 111.26, 112.45, 112.58, 113.37, 114.63, 115.69, 115.79, 118.46, 120.20, 122.98, 123.49, 124.72, 124.85, 125.50, 126.32, 126.60, 127.25, 127.61, 127.95, 129.08, 129.99, 137.09, 138.15, 138.98, 139.69, 142.07, 146.04, 147.51, 152.02, 152.35, 152.61, 163.14. FIG. 4 shows emission spectra of PtON1a-tBu in CH$_2$Cl$_2$ at room temperature and in 2-methyltetrahydrofuran at 77K. FIG. 5 shows EL spectra for the devices of ITO/HATCN (10 nm)/NPD (40 nm)/TAPC (10 nm)/26mCPy: 6% PtON1a-tBu/DPPS (10 nm)/BmPyPB (40 nm)/LiF/AL. FIG. 6 shows external quantum efficiency (% photon/electron) vs. current density (mA/cm$^2$) for the devices of ITO/HATCN (10 nm)/NPD (40 nm)/TAPC (10 nm)/26mCPy: 6% PtON1a-tBu/DPPS (10 nm)/BmPyPB (40 nm)/LiF/AL 3. Example 3

Platinum complex PtOO1a can be prepared according to the following scheme:

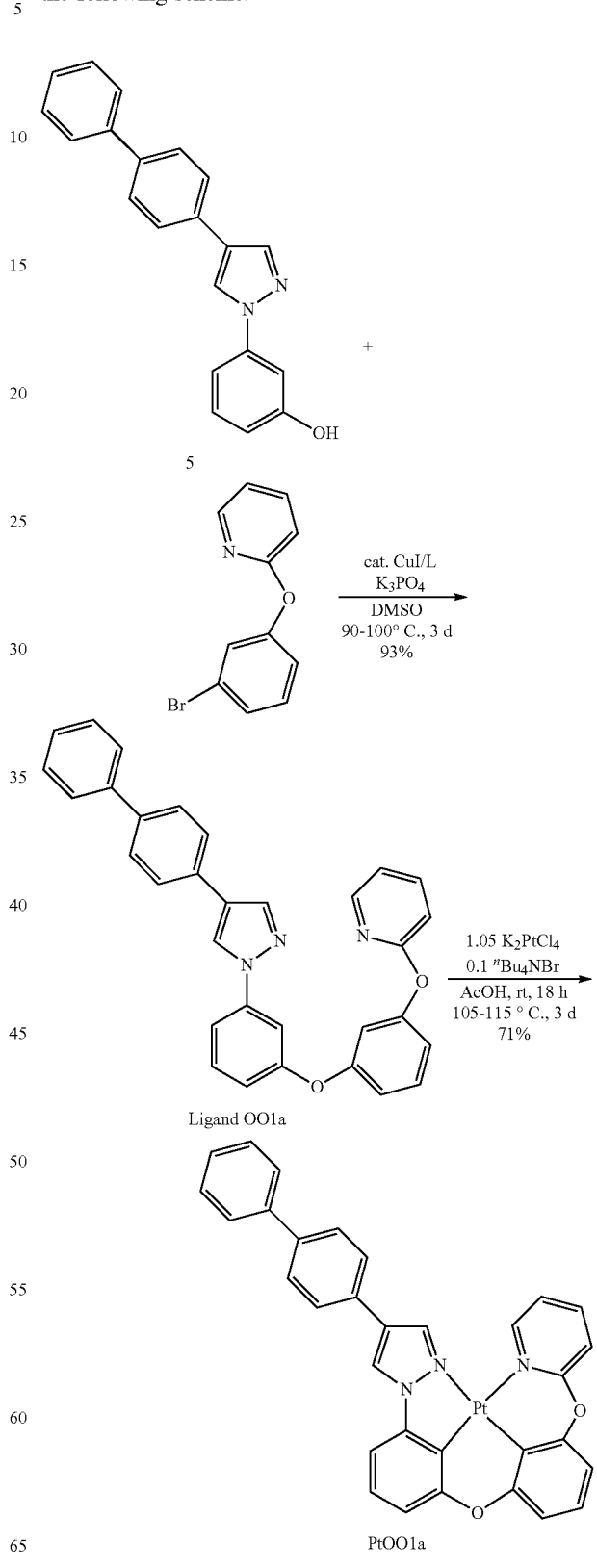

Ligand OO1a

PtOO1a

Synthesis of 2-(3-(3-(4-(biphenyl-4-yl)-1H-pyrazol-1-yl)phenoxy)phenoxy)pyridine Ligand OO1a

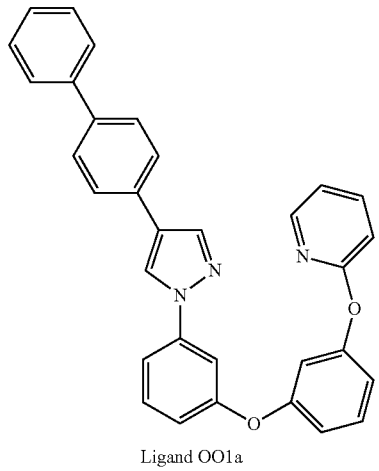 [SMILES: c1ccc(-c2ccc(-c3cnn(-c4cccc(Oc5cccc(Oc6ccccn6)c5)c4)c3)cc2)cc1]

Ligand OO1a

To a dry pressure vessel equipped with a magnetic stir bar was added 3-(4-(biphenyl-4-yl)-1H-pyrazol-1-yl)phenol (1.06 mmol, 1.0 eq), 2-(3-bromophenoxy)pyridine (318 mg, 1.27 mmol, 1.2 eq), CuI (20 mg, 0.11 mmol, 0.1 eq), picolinic acid (26 mg, 0.21 mmol, 0.2 eq) and $K_3PO_4$ (452 mg, 2.13 mmol, 2.0 eq). The tube was evacuated and backfilled with nitrogen. This evacuation and backfill procedure was repeated twice. Then solvent DMSO (6 mL) was added under nitrogen. The mixture was stirred at a temperature of 90-100° C. for 3 days and then cooled to ambient temperature. Water was added to dissolve the salt. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1-3:1) as eluent to obtain the desired product as a brown solid 425 mg in 93% yield. $^1$H NMR (DMSO-$d_6$, 400 MHz): δ 6.87 (t, J=2.0 Hz, 1H), 6.91-6.94 (m, 2H), 7.00 (dd, J=8.4, 2.0 Hz, 1H), 7.05 (d, J=8.0 Hz, 1H), 7.11-7.14 (m, 1H), 7.35 (t, J=7.6 Hz, 1H), 7.42-7.47 (m, 3H), 7.54 (t, J=7.6 Hz, 1H), 7.65-7.66 (m, 1H), 7.69-7.72 (m, 5H), 7.80-7.86 (m, 3H), 8.16-8.18 (m, 1H), 8.27 (s, 1H), 9.10 (s, 1H). $^{13}$C NMR (DMSO-$d_6$, 100 MHz): δ 108.74, 111.70, 111.75, 113.27, 114.48, 116.34, 116.38, 119.36, 123.92, 124.83, 125.84, 126.42, 127.09, 127.36, 128.92, 130.82, 131.16, 138.30, 138.94, 139.69, 140.27, 140.96, 147.46, 155.22, 157.17, 157.34, 162.62.

Synthesis of 2-(3-(3-(4-(biphenyl-4-yl)-1H-pyrazol-1-yl)phenoxy)phenoxy)pyridine platinum Complex PtOO1a

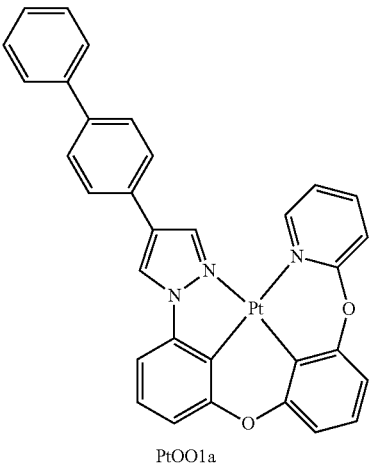

PtOO1a

Figure 7:
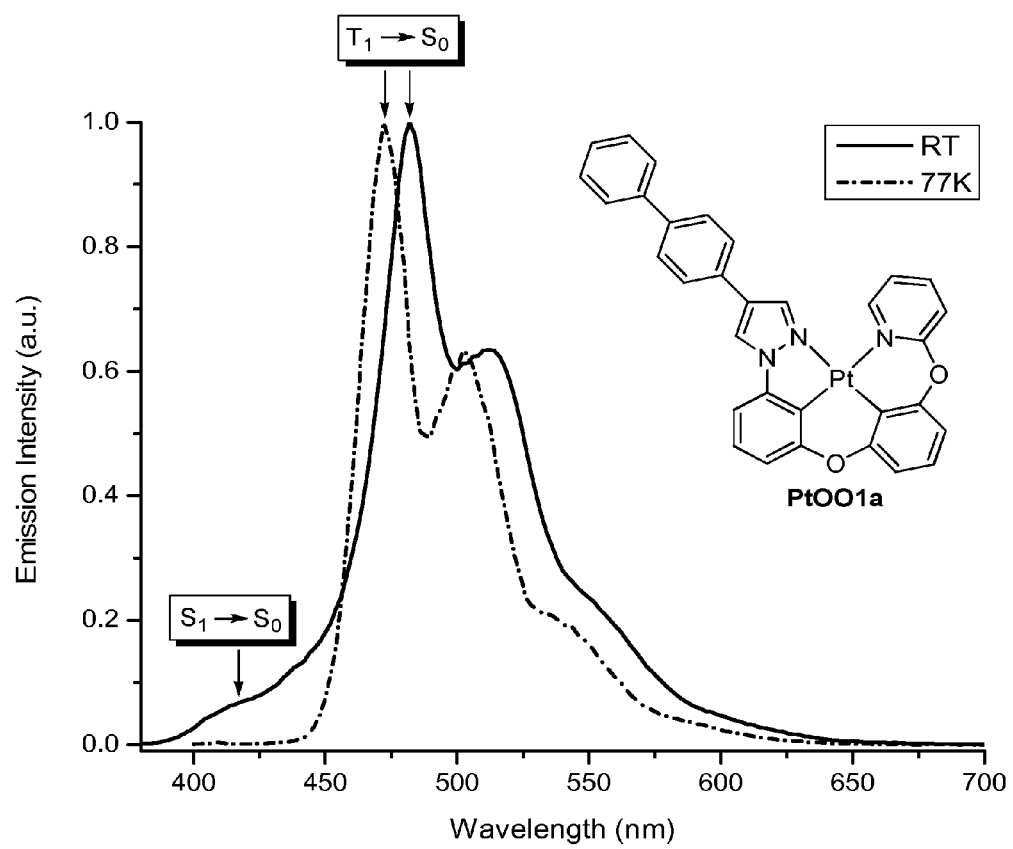
FIG. 7 shows emission spectra of PtOO1a at room temperature in $CH_2Cl_2$ and at 77K in 2-methyltetrahydrofuran, in accordance with various aspects of the present disclosure.

To a dry pressure tube equipped with a magnetic stir bar was added 2-(3-(3-(4-(biphenyl-4-yl)-1H-pyrazol-1-yl)phenoxy)phenoxy)pyridine Ligand OO1a (452 mg, 0.94 mmol, 1.0 eq), $K_2PtCl_4$ (415 mg, 0.99 mmol, 1.05 eq), $^nBu_4NBr$ (30 mg, 0.094 mmol, 0.1 eq) and solvent acetic acid (56 mL). The mixture was bubbled with nitrogen for 20 minutes in a nitrogen filled glove box. The tube was sealed before being taken out of the glove box. The mixture was stirred at room temperature for 18 hours and followed at 105-115° C. for 3 days, cooled to ambient temperature and water (112 mL) was added. The precipitate was filtered off and washed with water three times. Then the solid was dried in air under reduced pressure and purified through flash column chromatography on silica gel using hexane/dichloromethane (1:2) as eluent to obtain PtOO1a as a yellow solid 449 mg in 71% yield. $^1$H NMR (DMSO-$d_6$, 400 MHz): δ 6.88 (d, J=7.6 Hz, 1H), 6.91 (d, J=8.4 Hz, 1H), 6.96 (dd, J=8.4, 0.8 Hz 1H), 7.08 (t, J=8.0 Hz, 1H), 7.20 (d, J=8.0 Hz, 1H), 7.33 (t, J=7.6 Hz, 1H), 7.40-7.45 (m, 3H), 7.47 (d, J=7.6 Hz, 1H), 7.49 (d, J=8.4 Hz, 1H), 7.68 (d, J=7.6 Hz, 2H), 7.71 (d, J=8.0 Hz, 2H), 7.88 (d, J=8.0 Hz, 2H), 8.15-8.19 (m, 1H), 8.37 (s, 1H), 8.91 (d, J=4.0 Hz, 1H), 9.34 (s, 1H). $^{13}$C NMR (DMSO-$d_6$, 100 MHz): δ 102.98, 106.19, 109.99, 111.80, 112.34, 112.99, 115.59, 121.24, 123.21, 124.44, 124.88, 125.19, 126.18, 126.49, 127.11, 127.46, 128.93, 129.80, 136.91, 138.84, 139.58, 141.39, 145.83, 149.78, 152.20, 153.55, 154.54, 158.11. FIG. 7 shows emission spectra of PtOO1a at room temperature in $CH_2Cl_2$ and at 77K in 2-methyltetrahydrofuran.

4. Example 4
Platinum complex PtON1b can be prepared according to the following scheme:
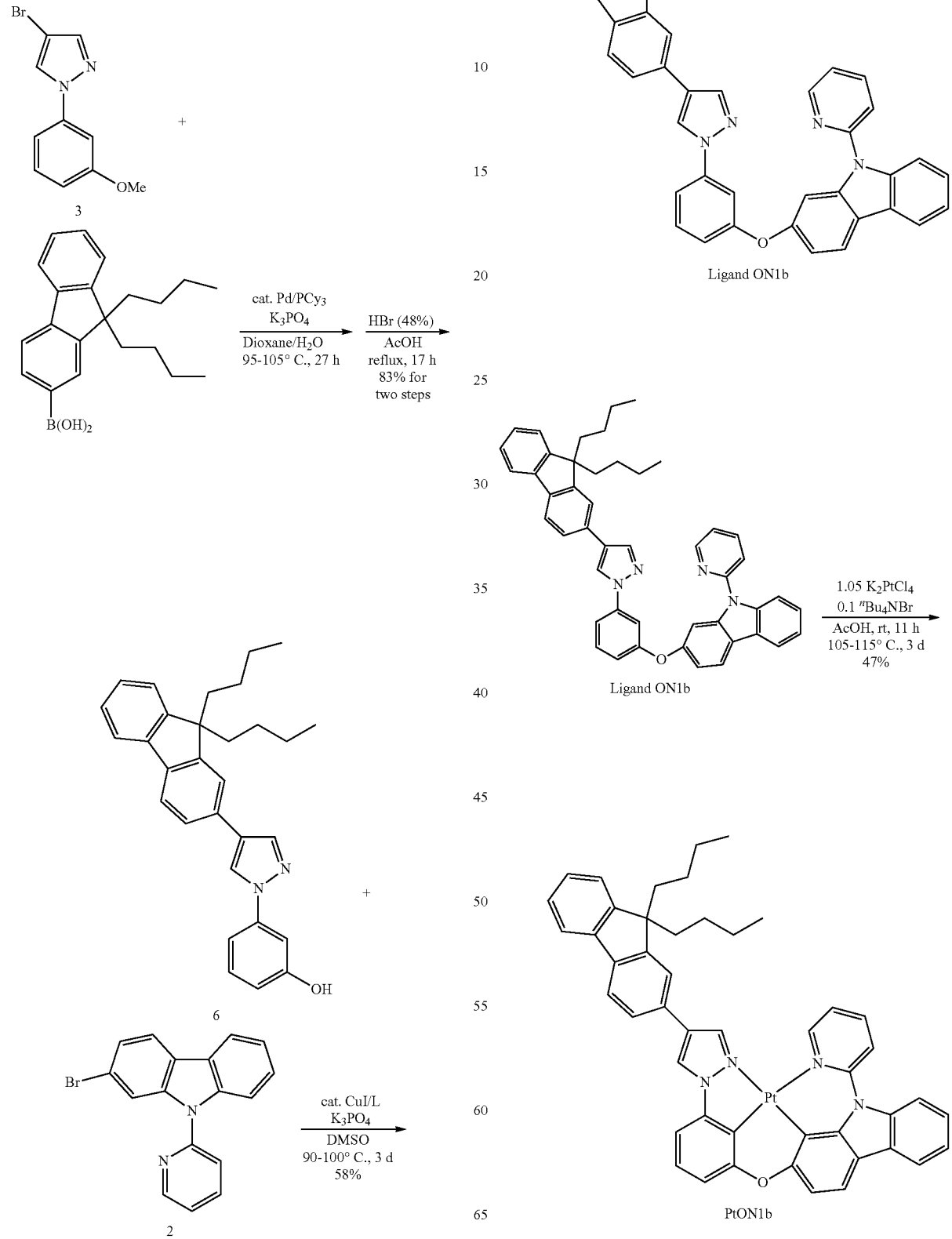

697
Synthesis of 3-(4-(9,9-dibutyl-9H-fluoren-2-yl)-1H-pyrazol-1-yl)phenol 6

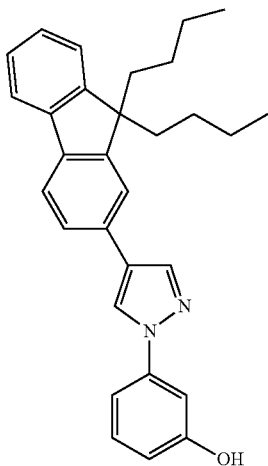 [SMILES: CCCCC1(CCCC)c2ccccc2-c2ccc(-c3cnn(-c4cccc(O)c4)c3)cc21]

To a three-necked flask equipped with a magnetic stir bar and a condenser was added 9,9-dibutyl-9H-fluoren-2-ylboronic acid (1805 mg, 5.60 mmol, 1.4 eq), $Pd_2(dba)_3$ (14 mg, 70.16 mmol, 0.04 eq) and tricyclohexylphosphine $PCy_3$ (108 mg, 0.38 mmol, 0.096 eq). Then the flask was evacuated and backfilled with nitrogen, the evacuation and backfill procedure was repeated twice. Then a solution of 4-bromo-1-(3-methoxyphenyl)-1H-pyrazole 3 (1012 mg, 4.00 mmol, 1.0 eq) in dioxane (25 mL) and a solution of $K_3PO_4$ (1443 mg, 6.80 mmol, 1.7 eq) in $H_2O$ (10 mL) were added by syringe independently under nitrogen. The mixture was stirred at a temperature of 95-105° C. for 27 hours, cooled to ambient temperature, filtered and washed with ethyl acetate. The organic layer of the filtrate was separated, dried over sodium sulfate, filtered, concentrated and the residue was purified through column chromatography on silica gel using hexane/ethyl acetate (20:1-15) as eluent to obtain a colorless sticky liquid which was used directly for the next step. A solution of the sticky liquid in a mixture of acetic acid (30 mL) and hydrogen bromide acid (15 mL, 48%) stirred at a temperature of 125-130° C. for 17 hours under nitrogen. Then the mixture was cooled. After most of the acetic acid was removed under reduced pressure, the residue was neutralized with a solution of $K_2CO_3$ in water until there was no gas to generate. Then the precipitate was filtered off and washed with water for several times. The collected solid was dried in air to afford the product 3-(4-(9,9-dibutyl-9H-fluoren-2-yl)-1H-pyrazol-1-yl)phenol 6 as a brown solid in 83% total yield for the two steps. $^1$H NMR (DMSO-$d_6$, 400 MHz): δ 0.19-0.32 (m, 4H), 0.37 (t, J=7.2 Hz, 6H), 0.74-0.84 (m, 4H), 1.78 (t, J=7.2 Hz, 4H), 6.48 (dt, J=6.8, 2.0 Hz, 1H), 7.03-7.10 (m, 5H), 7.18 (dd, J=6.4, 2.0 Hz, 1H), 7.44 (dd, J=8.0, 1.6 Hz, 1H), 7.53-7.58 (m, 3H), 8.01 (s, 1H), 8.75 (s, 1H), 9.55 (bs, 1H).

698
Synthesis of 2-(3-(4-(9,9-dibutyl-9H-fluoren-2-yl)-1H-pyrazol-1-yl)phenoxy)-9-(pyridin-2-yl)-9H-carbazole Ligand ON1b

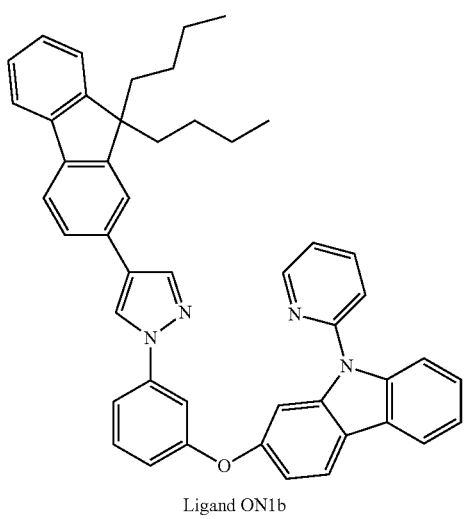 [SMILES: CCCCC1(CCCC)c2ccccc2-c2ccc(-c3cnn(-c4cccc(Oc5ccc6c7ccccc7n(-c7ccccn7)c6c5)c4)c3)cc21]

Ligand ON1b

To a dry pressure vessel equipped with a magnetic stir bar was added 3-(4-(9,9-dibutyl-9H-fluoren-2-yl)-1H-pyrazol-1-yl)phenol 6 (262 mg, 0.60 mmol, 1.0 eq), 2-bromo-9-(pyridin-2-yl)-9H-carbazole 2 (233 mg, 0.72 mmol, 1.2 eq), CuI (11 mg, 0.06 mmol, 0.1 eq), picolinic acid (15 mg, 0.12 mmol, 0.2 eq) and $K_3PO_4$ (255 mg, 1.20 mmol, 2.0 eq). The tube was evacuated and backfilled with nitrogen. This evacuation and backfill procedure was repeated twice. Then solvent DMSO (4 mL) was added under nitrogen. The mixture was stirred at a temperature of 90-100° C. for 3 days and then cooled to ambient temperature. Water was added to dissolve the salt. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1-3:1) as eluent to obtain the desired product as a brown solid 240 mg in 58% yield.

Synthesis of 2-(3-(4-(9,9-dibutyl-9H-fluoren-2-yl)-1H-pyrazol-1-yl)phenoxy)-9-(pyridin-2-yl)-9H-carbazole platinum Complex PtON1b

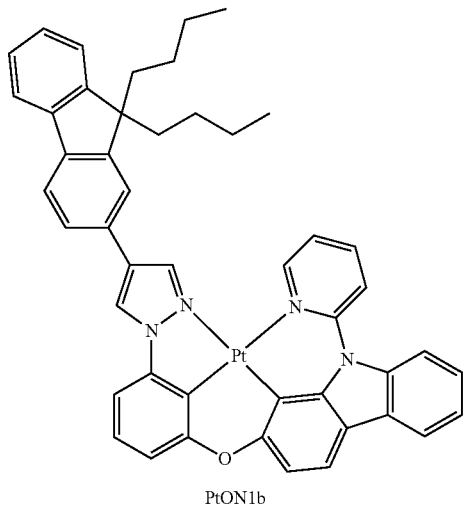

PtON1b

Figure 8:
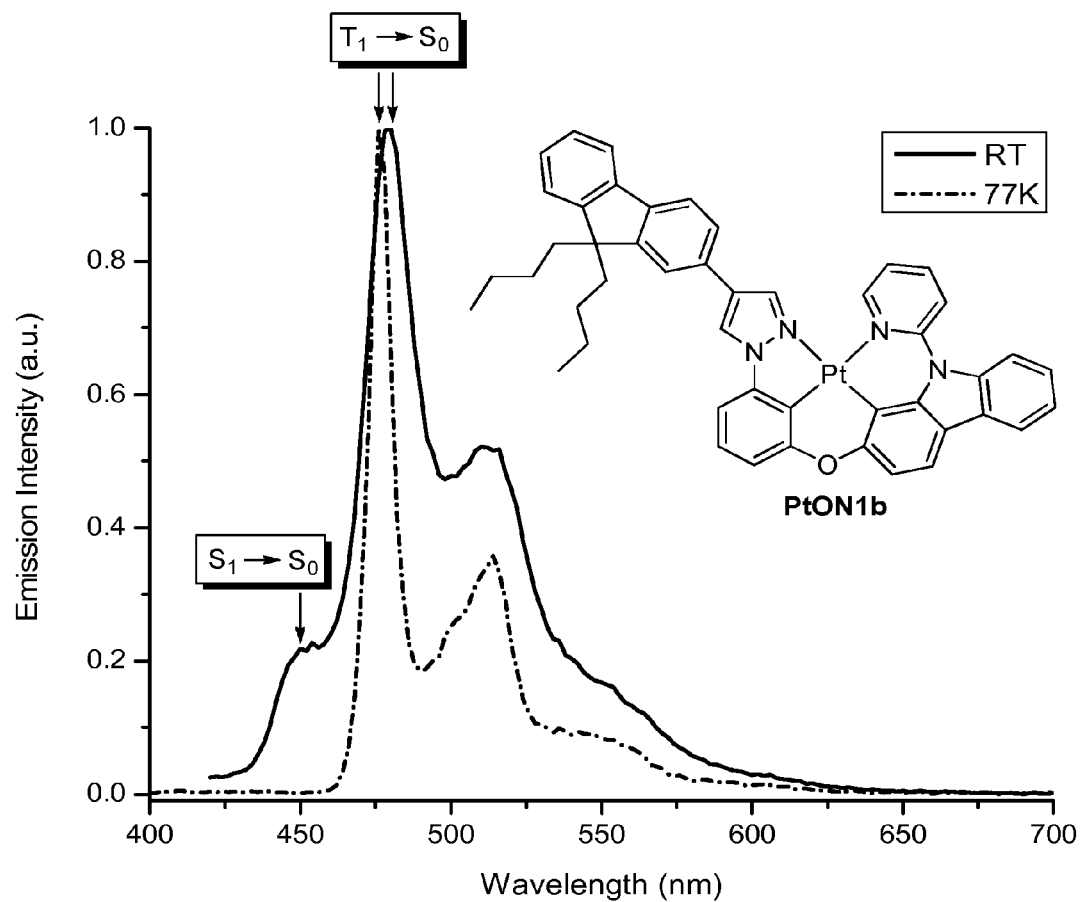
FIG. 8 shows emission spectra of PtON1b in $CH_2Cl_2$ at room temperature and in 2-methyltetrahydrofuran at 77K, in accordance with various aspects of the present disclosure.

To a dry pressure tube equipped with a magnetic stir bar was added 2-(3-(4-(9,9-dibutyl-9H-fluoren-2-yl)-1H-pyrazol-1-yl)phenoxy)-9-(pyridin-2-yl)-9H-carbazole Ligand ON1b (115 mg, 0.165 mmol, 1.0 eq), $K_2PtCl_4$ (73 mg, 0.173 mmol, 1.05 eq), $^nBu_4NBr$ (5 mg, 0.017 mmol, 0.1 eq) and solvent acetic acid (10 mL). The mixture was bubbled with nitrogen for 20 minutes in a nitrogen filled glove box. The tube was sealed before being taken out of the glove box. The mixture was stirred at room temperature for 11 hours and followed at 105-115° C. for 3 days, cooled to ambient temperature. The solvent was removed under reduced pressure and the residue was purified through flash column chromatography on silica gel using hexane/dichloromethane (1:1) as eluent to afford the desired product PtON1b as a yellow solid 69 mg in 47% yield. $^1$H NMR (DMSO-$d_6$, 400 MHz): δ 0.48-0.58 (m, 4H), 0.62 (t, J=7.6 Hz, 6H), 1.00-1.09 (m, 4H), 2.06 (t, J=8.0 Hz 4H), 7.00 (d, J=8.0 Hz, 1H), 7.22 (d, J=8.4 Hz, 1H), 7.28 (t, J=7.6 Hz, 1H), 7.31-7.36 (m, 2H), 7.40 (t, J=8.0 Hz, 1H), 7.43-7.50 (m, 3H), 7.57 (d, J=7.6 Hz, 1H), 7.83 (dd, J=6.0, 2.4 Hz, 1H), 7.86-7.90 (m, 3H), 7.97 (s, 1H), 8.08 (d, J=8.4 Hz, 1H), 8.16 (d, J=7.6 Hz, 1H), 8.24 (td, J=8.4, 1.6 Hz, 1H), 8.29 (d, J=8.4 Hz, 1H), 8.70 (s, 1H), 9.39 (d, J=6.4 Hz, 1H), 9.46 (s, 1H). $^{13}$C NMR (DMSO-$d_6$, 100 MHz): δ 13.79, 22.47, 25.82, 54.70, 98.96, 106.05, 111.05, 112.54, 113.22, 114.88, 115.53, 115.75, 116.16, 119.92, 120.00, 120.35, 120.63, 122.91, 122.95, 124.33, 124.55, 124.79, 125.44, 126.93, 127.20, 127.88, 129.70, 137.16, 137.99, 139.79, 139.83, 140.35, 141.89, 146.10, 147.54, 150.13, 151.18, 152.32, 152.57. FIG. 8 shows emission spectra of PtON1b in $CH_2Cl_2$ at room temperature and in 2-methyltetrahydrofuran at 77K.

5. Example 5

Platinum complex PtON1aMe can be prepared according to the following scheme:

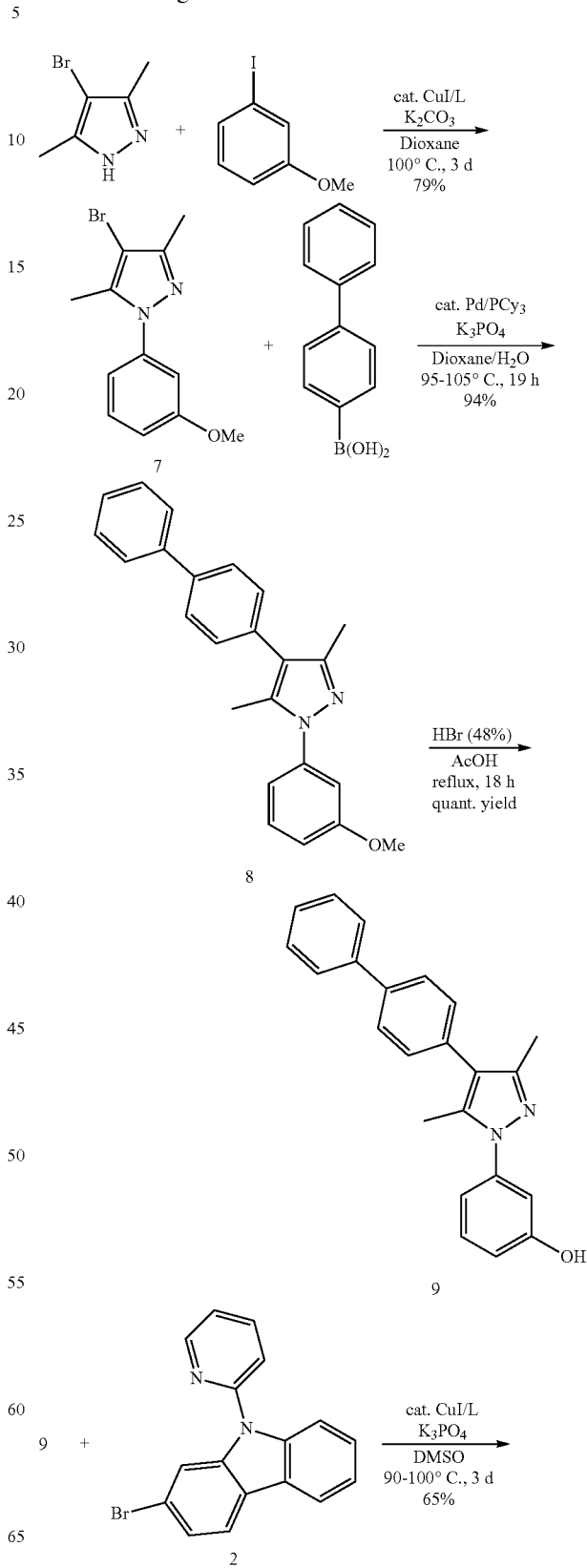

-continued

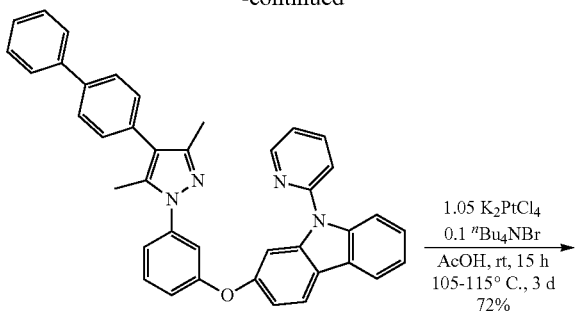

Ligand ON1aMe 1.05 K₂PtCl₄
0.1 ⁿBu₄NBr
———————→
AcOH, rt, 15 h
105-115° C., 3 d
72%

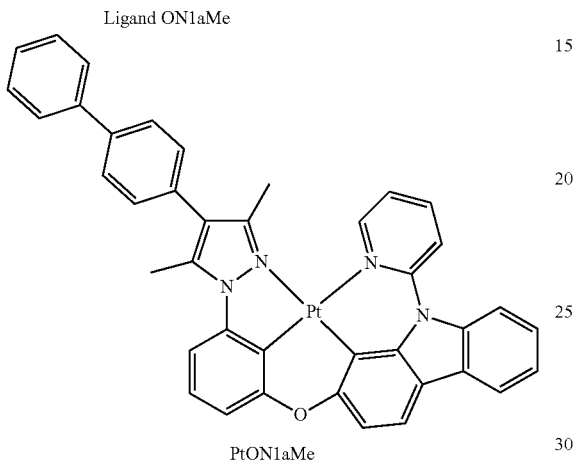

PtON1aMe

Synthesis of 4-bromo-1-(3-methoxyphenyl)-3,5-dimethyl-1H-pyrazole 7

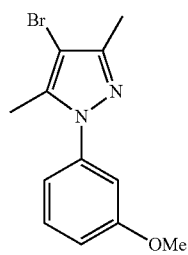

4-bromo-3,5-dimethyl-1H-pyrazole (8752 mg, 50 mmol, 1.0 eq), CuI (476 mg, 2.5 mmol, 0.02 eq) and K₂CO₃ (14.51 g, 105 mmol, 2.1 eq) were added to a dry pressure tube equipped with a magnetic stir bar. Then trans-1,2-cyclohexanediamine (1142 mg, 10 mmol, 0.2 eq), 1-iodo-3-methoxybenzene (11.91 mL, 100 mmol, 2.0 eq) and solvent dioxane (50 mL) were added in a nitrogen filled glove box. The mixture was bubbled with nitrogen for 5 minutes. The tube was sealed before being taken out of the glove box. The mixture was stirred in an oil bath at a temperature of 100° C. for three days, cooled to ambient temperature, filtered and washed with ethyl acetate. The filtrate was concentrated and the residue was purified through column chromatography on silica gel using hexane and ethyl acetate (10:1-5:1) as eluent to obtain the desired product 4-bromo-1-(3-methoxyphenyl)-3,5-dimethyl-1H-pyrazole 7 as a brown sticky liquid 11.065 g in 79% yield. ¹H NMR (DMSO-d₆, 400 MHz): δ 2.20 (s, 3H), 2.30 (s, 3H), 3.81 (s, 3H), 6.99-7.02 (m, 1H), 7.05-7.08 (m, 2H), 7.40-7.44 (m, 1H). ¹³C NMR (DMSO-d₆, 100 MHz): δ 11.53, 12.07, 55.45, 95.61, 109.94, 113.60, 116.36, 129.98, 137.51, 140.46, 146.34, 159.71.

Synthesis of 4-(biphenyl-4-yl)-1-(3-methoxyphenyl)-3,5-dimethyl-1H-pyrazole 8

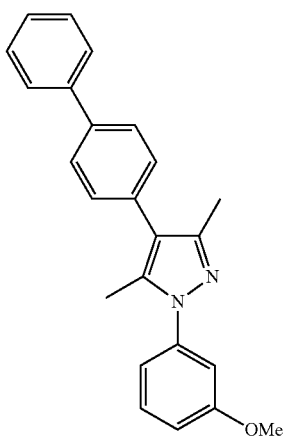 [SMILES: COc1cccc(-n2nc(C)c(-c3ccc(-c4ccccc4)cc3)c2C)c1]

To a three-necked flask equipped with a magnetic stir bar and a condenser was added biphenyl-4-ylboronic acid (2376 mg, 12.00 mmol, 1.2 eq), Pd₂(dba)₃ (366 mg, 0.40 mmol, 0.04 eq) and tricyclohexylphosphine PCy₃ (269 mg, 0.96 mmol, 0.096 eq). Then the flask was evacuated and backfilled with nitrogen, the evacuation and backfill procedure was repeated twice. Then a solution of 4-bromo-1-(3-methoxyphenyl)-3,5-dimethyl-1H-pyrazole 7 (2812 mg, 10.00 mmol, 1.0 eq) in dioxane (63 mL) and a solution of K₃PO₄ (3608 mg, 17.00 mmol, 1.7 eq) in H₂O (25 mL) were added by syringe independently under nitrogen. The mixture was stirred in an oil bath at a temperature of 95-105° C. for 19 hours, cooled to ambient temperature, filtered and washed with ethyl acetate. The organic layer of the filtrate was separated, dried over sodium sulfate, filtered, concentrated and the residue was purified through column chromatography on silica gel using hexane/ethyl acetate (10:1-5:1-3:1) as eluent to obtain the desired product 4-(biphenyl-4-yl)-1-(3-methoxyphenyl)-3,5-dimethyl-1H-pyrazole 8 as a yellow solid in 94%. ¹H NMR (DMSO-d₆, 400 MHz): δ 2.28 (s, 3H), 2.34 (s, 3H), 3.83 (s, 3H), 7.00 (dd, J=8.4, 2.0 Hz, 1H), 7.11-7.14 (m, 2H), 7.38 (t, J=7.6 Hz, 1H), 7.42-7.51 (m, 5H), 7.72-7.74 (m, 2H), 7.76 (d, J=7.6 Hz, 2H).

Synthesis of 3-(4-(biphenyl-4-yl)-3,5-dimethyl-1H-pyrazol-1-yl)phenol 9

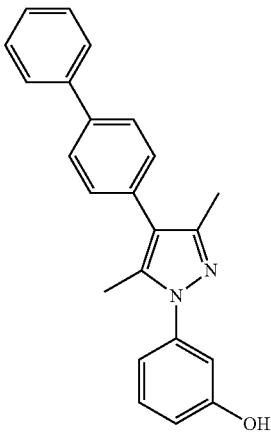 [SMILES: Cc1nn(-c2cccc(O)c2)c(C)c1-c1ccc(-c2ccccc2)cc1]

A solution of 4-(biphenyl-4-yl)-1-(3-methoxyphenyl)-3,5-dimethyl-1H-pyrazole 8 (3.30 g, 9.31 mmol) in a mixture of acetic acid (40 mL) and hydrogen bromide acid (20 mL, 48%) refluxed (120-130° C.) for 18 hours at an atmosphere of nitrogen, then cooled. After most of the acetic acid was removed under reduced pressure, the residue was neutralized with a solution of $K_2CO_3$ in water until there was no gas to generate. Then the precipitate was filtered off and washed with water for several times. The collected solid was dried in air to afford the product 3-(4-(biphenyl-4-yl)-3,5-dimethyl-1H-pyrazol-1-yl)phenol 9 as a brown solid in quantitative yield. $^1$H NMR (DMSO-$d_6$, 400 MHz): δ 2.27 (s, 3H), 2.32 (s, 3H), 6.80-6.82 (m, 1H), 6.94-6.97 (m, 2H), 7.31 (t, J=7.6 Hz, 1H), 7.38 (t, J=7.6 Hz, 1H), 7.45-7.51 (m, 4H), 7.71-7.77 (m, 4H), 9.77 (bs, 1H).

Synthesis of 2-(3-(4-(biphenyl-4-yl)-3,5-dimethyl-1H-pyrazol-1-yl)phenoxy)-9-(pyridin-2-yl)-9H-carbazole Ligand ON1aMe

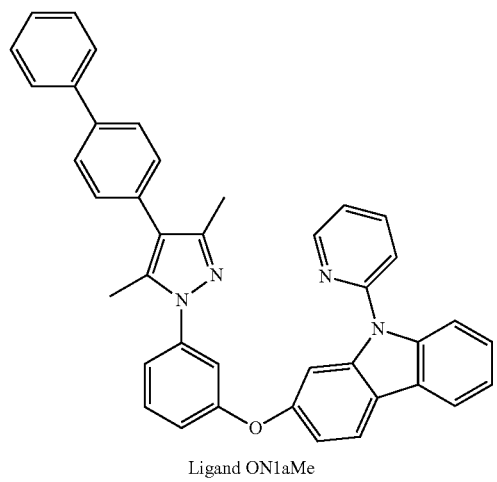 [SMILES: Cc1nn(-c2cccc(Oc3ccc4c5ccccc5n(-c5ccccn5)c4c3)c2)c(C)c1-c1ccc(-c2ccccc2)cc1]

Ligand ON1aMe

To a dry pressure vessel equipped with a magnetic stir bar was added 3-(4-(biphenyl-4-yl)-3,5-dimethyl-1H-pyrazol-1-yl)phenol 9 (163 mg, 0.48 mmol, 1.0 eq), 2-bromo-9-(pyridin-2-yl)-9H-carbazole 2 (188 mg, 0.58 mmol, 1.2 eq), CuI (9 mg, 0.048 mmol, 0.1 eq), picolinic acid (12 mg, 0.096 mmol, 0.2 eq) and $K_3PO_4$ (204 mg, 0.96 mmol, 2.0 eq). The tube was evacuated and backfilled with nitrogen. This evacuation and backfill procedure was repeated twice. Then solvent DMSO (4 mL) was added under nitrogen. The mixture was stirred at a temperature of 90-100° C. for 3 days and then cooled to ambient temperature. Water was added to dissolve salt. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1-5:1-3:1) as eluent to obtain the desired product 2-(3-(4-(biphenyl-4-yl)-3,5-dimethyl-1H-pyrazol-1-yl)phenoxy)-9-(pyridin-2-yl)-9H-carbazole Ligand ON1aMe as a colorless solid 182 mg in 65% yield. $^1$H NMR (DMSO-$d_6$, 400 MHz): δ 2.22 (s, 3H), 2.28 (s, 3H), 7.09-7.14 (m, 2H), 7.18 (s, 1H), 7.31-7.49 (m, 9H), 7.52 (t, J=8.0 Hz, 1H), 7.56 (s, 1H), 7.71 (t, J=8.4 Hz, 4H), 7.79 (dd, J=8.0, 3.2 Hz, 2H), 8.08 (t, J=8.0 Hz, 1H), 8.24 (d, J=7.6 Hz, 1H), 8.30 (d, J=8.8 Hz, 1H), 8.68 (d, J=3.6 Hz, 1H). $^{13}$C NMR (DMSO-$d_6$, 100 MHz): δ 11.80, 12.61, 102.53, 111.14, 113.42, 113.62, 116.66, 118.74, 119.08, 120.02, 120.11, 120.25, 121.29, 121.87, 122.18, 123.27, 126.04, 126.58, 126.80, 127.40, 128.98, 129.67, 130.54, 132.25, 136.30, 138.15, 139.37, 139.55, 139.81, 139.96, 140.77, 146.43, 149.55, 150.47, 154.74, 158.05.

Synthesis of 2-(3-(4-(biphenyl-4-yl)-3,5-dimethyl-1H-pyrazol-1-yl)phenoxy)-9-(pyridin-2-yl)-9H-carbazole platinum Complex PtON1aMe

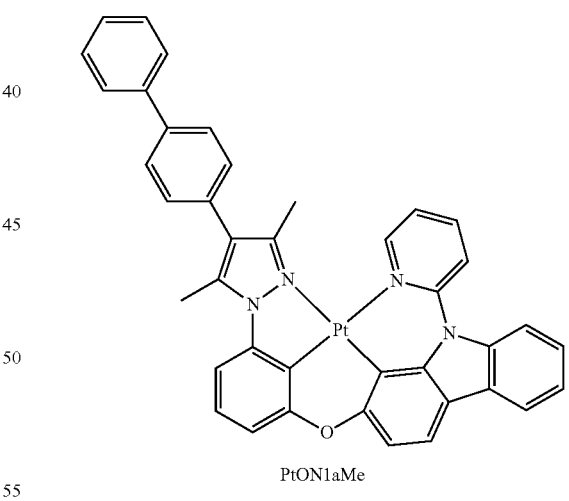

PtON1aMe

Figure 9:
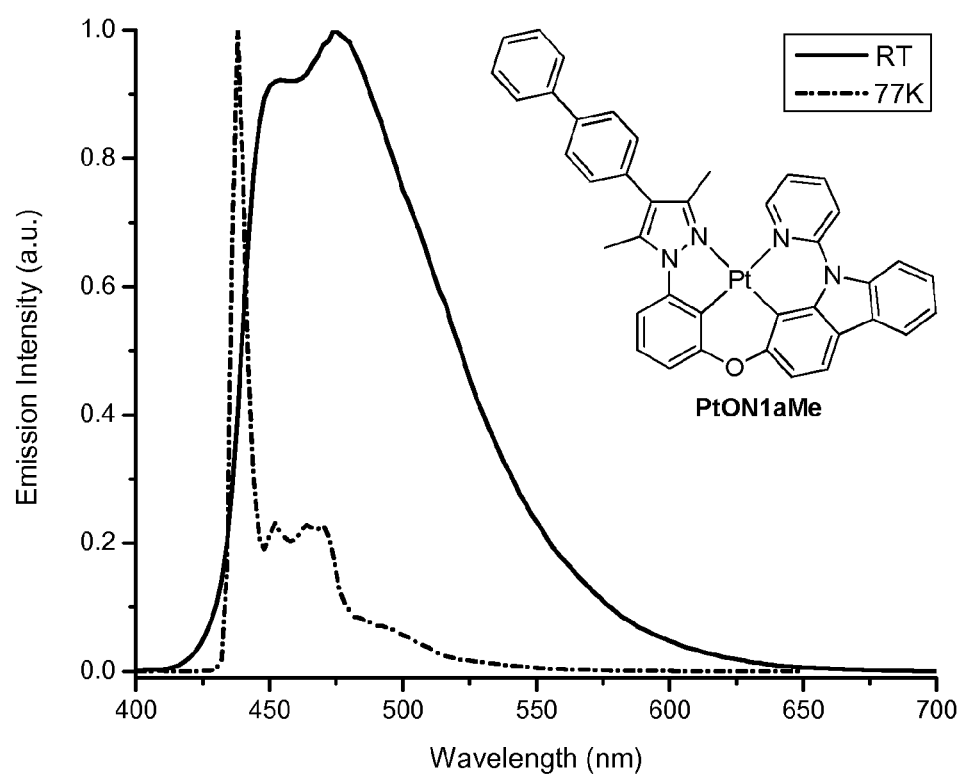
FIG. 9 shows emission spectra of PtON1aMe in $CH_2Cl_2$ at room temperature and in 2-methyltetrahydrofuran at 77K, in accordance with various aspects of the present disclosure.

To a dry pressure tube equipped with a magnetic stir bar was added 2-(3-(4-(biphenyl-4-yl)-3,5-dimethyl-1H-pyrazol-1-yl)phenoxy)-9-(pyridin-2-yl)-9H-carbazole Ligand ON1aMe (170 mg, 0.29 mmol, 1.0 eq), $K_2PtCl_4$ (128 mg, 0.30 mmol, 1.05 eq), $^nBu_4NBr$ (9 mg, 0.029 mmol, 0.1 eq) and solvent acetic acid (17.4 mL). The mixture was bubbled with nitrogen for 20 minutes in a nitrogen filled glove box. The tube was sealed before being taken out of the glove box. The mixture was stirred at room temperature for 15 hours and followed at 105-115° C. for 3 days, cooled to ambient temperature. The solvent was removed under reduced pressure and the residue was purified through flash column chromatography on silica gel using dichloromethane as eluent to obtain the platinum complex PtON1aMe a yellow solid 163 mg in 72% yield. $^1$H NMR (DMSO-d$_6$, 400 MHz): δ 2.44 (s, 3H), 2.76 (s, 3H), 7.00 (d, J=8.0 Hz, 1H), 7.20 (d, J=8.8, 1H), 7.26 (t, J=8.0 Hz, 1H), 7.30-7.34 (m, 1H), 7.38-7.42 (m, 3H), 7.45-7.52 (m, 3H), 7.56 (d, J=8.0 Hz, 2H), 7.75 (d, J=8.0 Hz, 2H), 7.82 (d, J=8.4 Hz, 2H), 7.88 (d, J=8.0 Hz, 1H), 8.10 (d, J=8.0 Hz, 1H), 8.13-8.21 (m, 3H), 9.34 (d, J=4.8 Hz, 1H). $^{13}$C NMR (DMSO-d$_6$, 100 MHz): δ 13.23, 13.88, 100.10, 107.42, 111.07, 112.22, 112.64, 115.10, 115.40, 115.62, 115.80, 119.13, 119.94, 122.27, 122.90, 124.50, 124.83, 126.71, 127.01, 127.63, 127.95, 129.01, 130.52, 130.69, 137.86, 138.94, 139.25, 139.64, 140.24, 141.84, 147.65, 147.88, 148.04, 151.55, 151.95, 153.92. FIG. 9 shows emission spectra of PtON1aMe in CH$_2$Cl$_2$ at room temperature and in 2-methyltetrahydrofuran at 77K.

6. Example 6

Platinum complex PtOO1aMe can be prepared according to the following scheme:

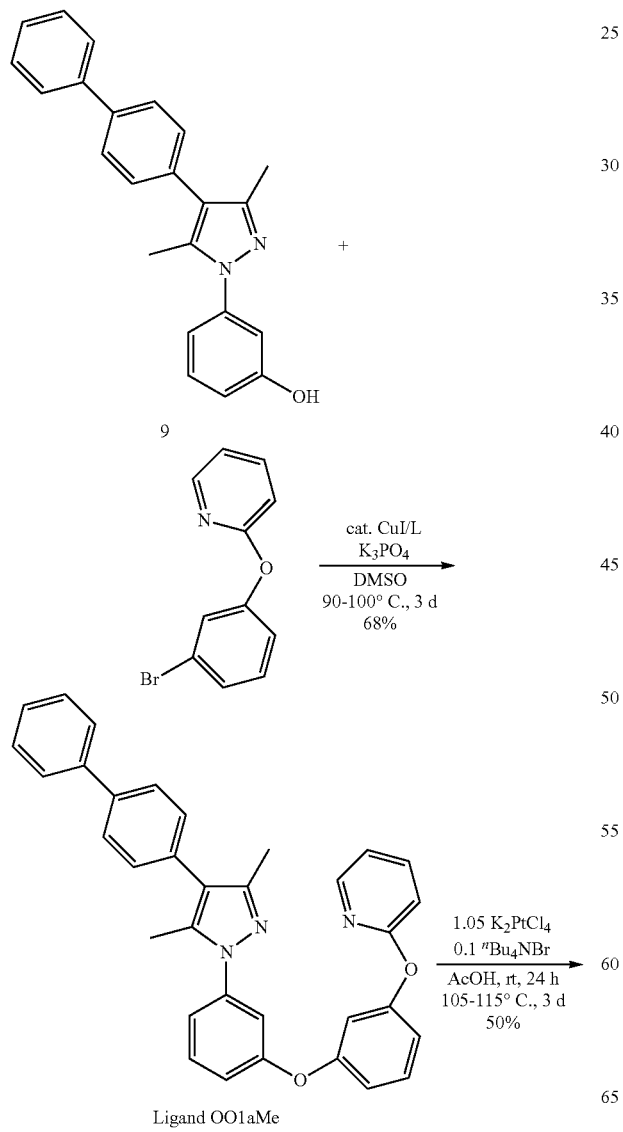

Ligand OO1aMe

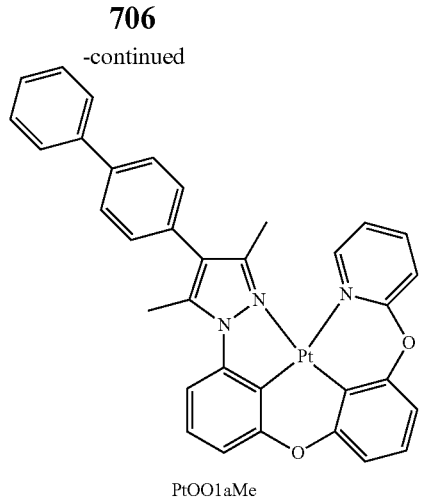

PtOO1aMe

Synthesis of 2-(3-(3-(4-(biphenyl-4-yl)-3,5-dimethyl-1H-pyrazol-1-yl)phenoxy)phenoxy)pyridine Ligand OO1aMe To a dry pressure vessel equipped with a magnetic stir bar was added 3-(4-(biphenyl-4-yl)-3,5-dimethyl-1H-pyrazol-1-yl)phenol 9 (511 mg, 1.50 mmol, 1.0 eq), 2-(3-bromophenoxy)pyridine (450 mg, 1.80 mmol, 1.2 eq), CuI (29 mg, 0.15 mmol, 0.1 eq), picolinic acid (37 mg, 0.30 mmol, 0.2 eq) and K$_3$PO$_4$ (637 mg, 3.00 mmol, 2.0 eq). The tube was evacuated and backfilled with nitrogen. This evacuation and backfill procedure was repeated twice. Then solvent DMSO (9 mL) was added under nitrogen. The mixture was stirred at a temperature of 90-100° C. for 3 days and then cooled to ambient temperature. Water was added to dissolve the salt. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1-5:1-3:1) as eluent to obtain the desired product as a brown solid 521 mg in 68% yield. $^1$H NMR (DMSO-d$_6$, 400 MHz): δ 2.25 (s, 3H), 2.31 (s, 3H), 6.88 (t, J=2.0 Hz, 1H), 6.94 (dd, J=8.4, 2.0 Hz, 2H), 7.05 (d, J=8.0 Hz, 1H), 7.09-7.14 (m, 2H), 7.22 (t, J=2.0 Hz, 1H), 7.34-7.38 (m, 2H), 7.43-7.49 (m, 5H), 7.54 (t, J=8.0 Hz, 1H), 7.70 (d, J=7.2 Hz, 2H), 7.74 (d, J=8.0 Hz, 2H), 7.82-7.87 (m, 1H), 8.14-8.16 (m, 1H). $^{13}$C NMR (DMSO-$d_6$, 100 MHz): δ 11.81, 12.62, 111.78, 111.96, 114.35, 114.78, 116.52, 117.30, 119.30, 119.37, 120.07, 126.58, 126.82, 127.40, 128.97, 129.68, 130.60, 130.86, 132.25, 136.33, 138.17, 139.81, 140.29, 140.85, 146.48, 147.45, 155.22, 156.83, 157.11, 162.61.

Synthesis of 2-(3-(3-(4-(biphenyl-4-yl)-3,5-dimethyl-1H-pyrazol-1-yl)phenoxy)phenoxy)pyridine platinum Complex PtOO1aMe

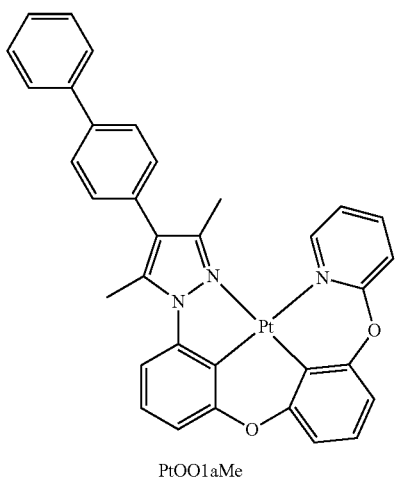

PtOO1aMe

Figure 10:
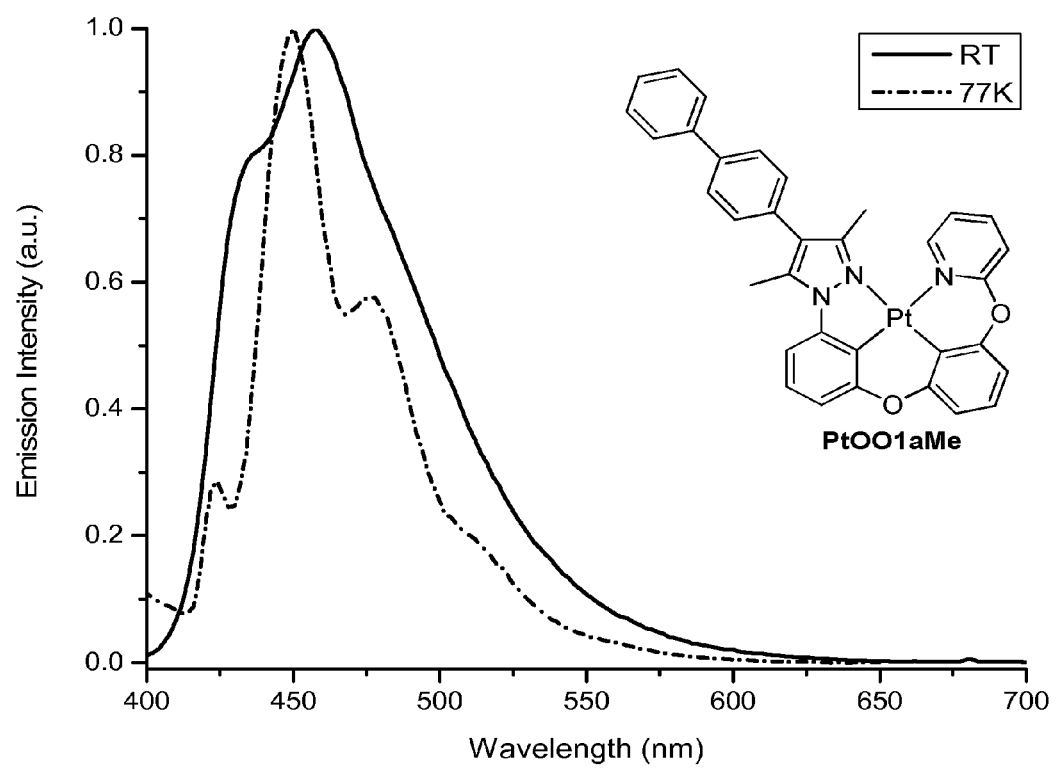
FIG. 10 shows emission spectra of PtOO1aMe in $CH_2Cl_2$ at room temperature and in 2-methyltetrahydrofuran at 77K, in accordance with various aspects of the present disclosure.

To a dry pressure tube equipped with a magnetic stir bar was added 2-(3-(3-(4-(biphenyl-4-yl)-3,5-dimethyl-1H-pyrazol-1-yl)phenoxy)phenoxy)pyridine Ligand OO1aMe (245 mg, 0.48 mmol, 1.0 eq), K$_2$PtCl$_4$ (211 mg, 0.504 mmol, 1.05 eq), $^n$Bu$_4$NBr (15 mg, 0.048 mmol, 0.1 eq) and solvent acetic acid (29 mL). The mixture was bubbled with nitrogen for 20 minutes in a nitrogen filled glove box. The tube was sealed before being taken out of the glove box. The mixture was stirred at room temperature for 24 hours and followed at 105-115° C. for 3 days, cooled to ambient temperature and water (58 mL) was added. The precipitate was filtered off and washed with water three times. Then the solid was dried in air under reduced pressure and purified through flash column chromatography on silica gel using hexane/dichloromethane (1:2) as eluent to obtain PtOO1aMe as a yellow solid 167 mg in 50% yield. $^1$H NMR (DMSO-$d_6$, 400 MHz): δ 2.24 (s, 3H), 2.74 (s, 3H), 6.90-6.96 (m, 3H), 7.08 (t, J=8.0 Hz, 1H), 7.22 (t, J=8.0 Hz, 1H), 7.32-7.42 (m, 3H), 7.49-7.53 (m, 4H), 7.57 (d, J=8.4 Hz, 1H), 7.75 (d, J=7.6 Hz, 2H), 7.81 (d, J=8.0 Hz, 2H), 8.15-8.20 (m, 1H), 8.96 (dd, J=6.0, 1.6 Hz, 1H). $^{13}$C NMR (DMSO-$d_6$, 100 MHz): δ 13.09, 13.40, 105.33, 107.76, 110.10, 111.91, 112.19, 112.51, 115.74, 120.26, 122.21, 124.25, 124.93, 126.70, 127.01, 127.63, 129.02, 130.46, 130.66, 138.65, 139.24, 139.62, 142.21, 147.37, 148.09, 151.91, 151.97, 152.98, 155.41, 159.42. FIG. 10 shows emission spectra of PtOO1aMe in CH$_2$Cl$_2$ at room temperature and in 2-methyltetrahydrofuran at 77K.

7. Example 7

Platinum complex Pt1aO1Me can be prepared according to the following scheme:

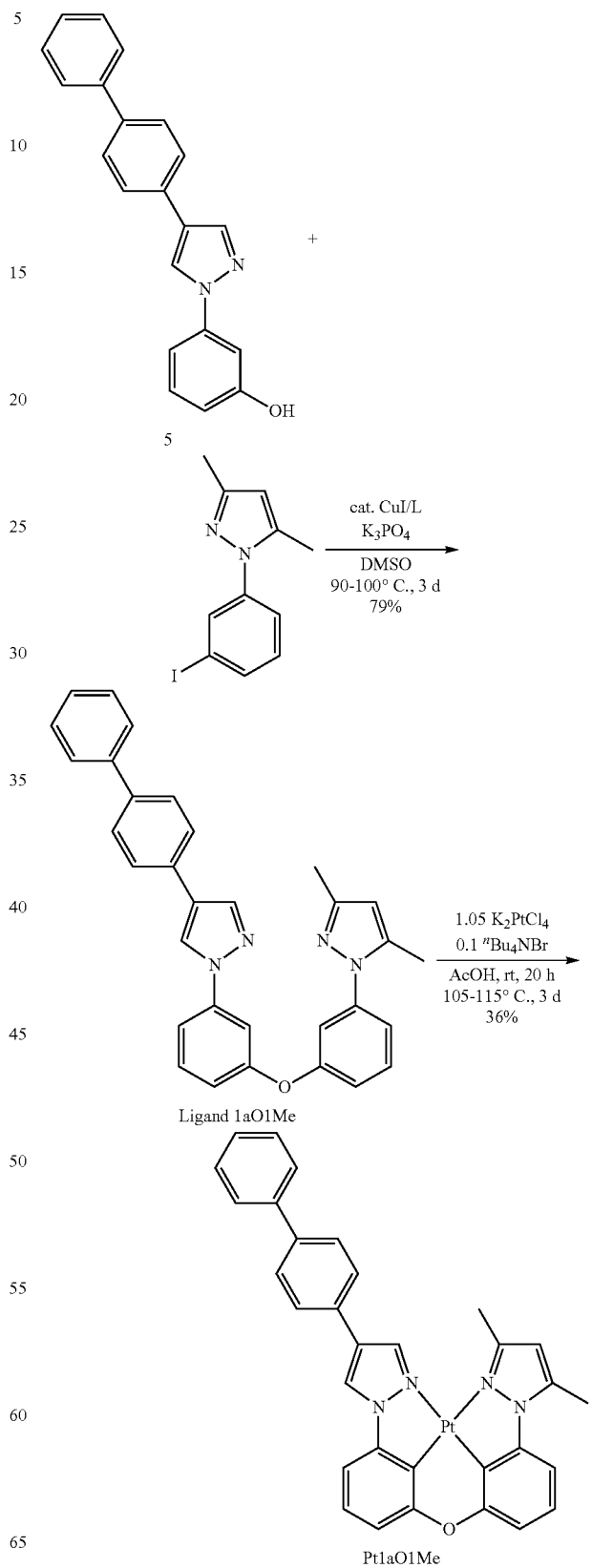

Synthesis of 1-(3-(3-(4-(biphenyl-4-yl)-1H-pyrazol-1-yl)phenoxy)phenyl)-3,5-dimethyl-1H-pyrazole Ligand 1aO1Me

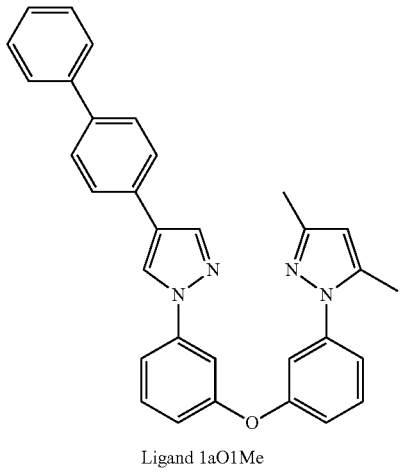 [SMILES: Cc1cc(C)n(-c2cccc(Oc3cccc(-n4cc(-c5ccc(-c6ccccc6)cc5)cn4)c3)c2)n1]

Ligand 1aO1Me

To a dry pressure vessel equipped with a magnetic stir bar was added 3-(4-(biphenyl-4-yl)-1H-pyrazol-1-yl)phenol 5 (1.50 mmol, 469 mg, 1.0 eq), 1-(3-iodophenyl)-3,5-dimethyl-1H-pyrazole (581 mg, 1.95 mmol, 1.3 eq), CuI (29 mg, 0.15 mmol, 0.1 eq), picolinic acid (37 mg, 0.30 mmol, 0.2 eq) and $K_3PO_4$ (637 mg, 3.00 mmol, 2.0 eq). The tube was evacuated and backfilled with nitrogen. This evacuation and backfill procedure was repeated twice. Then solvent DMSO (9 mL) was added under nitrogen. The mixture was stirred at a temperature of 90-100° C. for 3 days and then cooled to ambient temperature. Water was added to dissolve the salt. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1-5:1-3:1) as eluent to obtain the desired product as a brown solid 569 mg in 79% yield. $^1$H NMR (DMSO-$d_6$, 400 MHz): δ 2.13 (s, 3H), 2.29 (s, 3H), 6.04 (s, 1H), 7.01 (dd, J=8.4, 2.0 Hz, 1H), 7.01-7.70 (m, 1H), 7.19 (t, J=1.6 Hz, 1H), 7.29-7.32 (m, 1H), 7.35 (d, J=7.2 Hz, 1H), 7.44 (t, J=7.6 Hz, 2H), 7.51 (t, J=8.0 Hz, 1H), 7.54 (t, J=7.6 Hz, 1H), 7.67-7.70 (m, 5H), 7.72-7.75 (m, 1H), 7.79 (d, J=8.4 Hz, 2H), 8.26 (s, 1H), 9.10 (s, 1H). $^{13}$C NMR (DMSO-$d_6$, 100 MHz): δ 12.30, 13.26, 107.61, 108.85, 113.39, 113.99, 116.49, 116.87, 118.90, 123.94, 124.84, 125.84, 126.43, 127.09, 127.36, 128.92, 130.60, 130.81, 131.24, 138.31, 138.96, 139.34, 139.69, 141.02, 141.11, 148.19, 156.86, 157.20.

Synthesis of 1-(3-(3-(4-(biphenyl-4-yl)-1H-pyrazol-1-yl)phenoxy)phenyl)-3,5-dimethyl-1H-pyrazole platinum Complex Pt1aO1Me

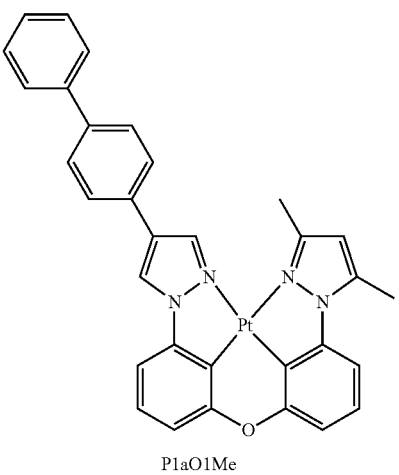

Pt1aO1Me

Figure 11:
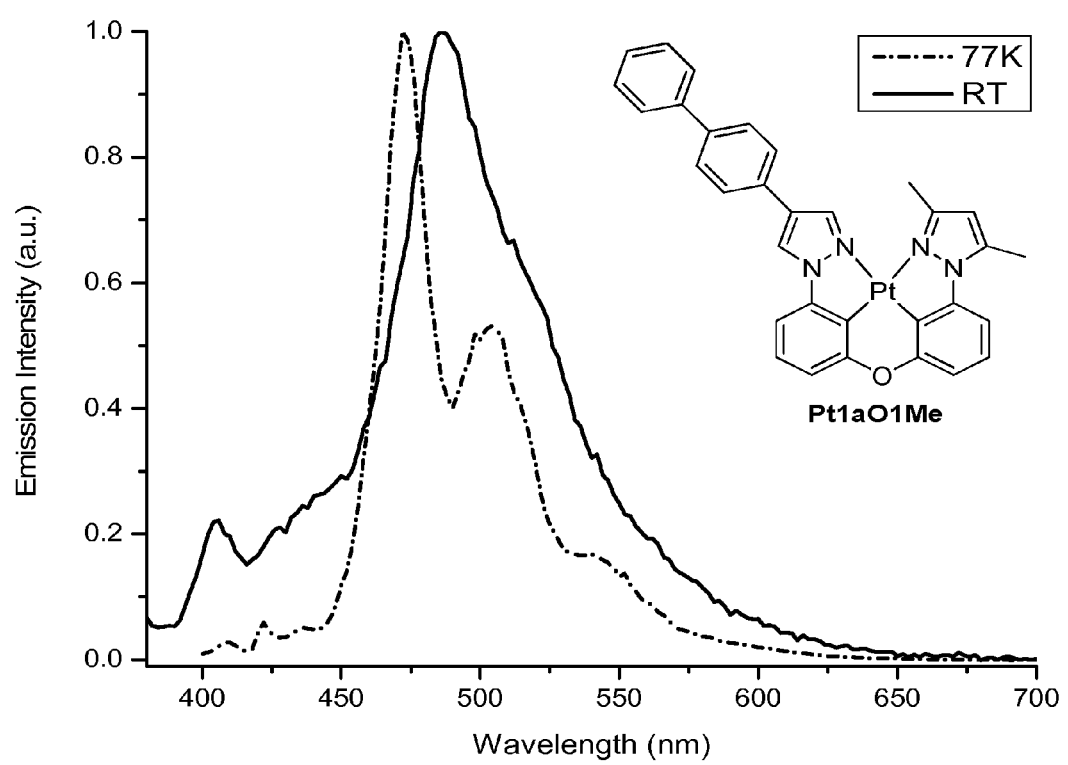
FIG. 11 shows emission spectra of Pt1aO1Me in $CH_2Cl_2$ at room temperature and in 2-methyltetrahydrofuran at 77K, in accordance with various aspects of the present disclosure.

To a dry pressure tube equipped with a magnetic stir bar was added 1-(3-(3-(4-(biphenyl-4-yl)-1H-pyrazol-1-yl)phenoxy)phenyl)-3,5-dimethyl-1H-pyrazole Ligand 1aO1Me (260 mg, 0.572 mmol, 1.0 eq), $K_2PtCl_4$ (252 mg, 0.601 mmol, 1.05 eq), $^nBu_4NBr$ (18 mg, 0.057 mmol, 0.1 eq) and solvent acetic acid (34 mL). The mixture was bubbled with nitrogen for 20 minutes in a nitrogen filled glove box. The tube was sealed before being taken out of the glove box. The mixture was stirred at room temperature for 20 hours and followed at 105-115° C. for 3 days, cooled to ambient temperature. The solvent was removed under reduced pressure and the residue was purified through flash column chromatography on silica gel using hexane/dichloromethane (1:2) as eluent to obtain a yellow solid 138 mg in 36% yield. $^1$H NMR (DMSO-$d_6$, 400 MHz): δ 2.78 (s, 3H), 2.80 (s, 3H), 6.50 (s, 1H), 6.98 (t, J=7.6 Hz, 2H), 7.22 (t, J=7.6 Hz, 1H), 7.27 (t, J=8.0 Hz, 1H), 7.32 (d, J=7.6 Hz, 1H), 7.39 (t, J=7.2 Hz, 1H), 7.50 (t, J=7.6 Hz, 2H), 7.54 (d, J=7.6 Hz, 1H), 7.74-7.76 (m, 2H), 7.80 (d, J=8.4 Hz, 2H), 7.94 (d, J=8.4 Hz, 2H), 8.61 (s, 1H), 9.43 (s, 1H). FIG. 11 shows emission spectra of Pt1aO1Me in $CH_2Cl_2$ at room temperature and in 2-methyltetrahydrofuran at 77K.

8. Example 8

Platinum complex PdON1a can be prepared according to the following scheme

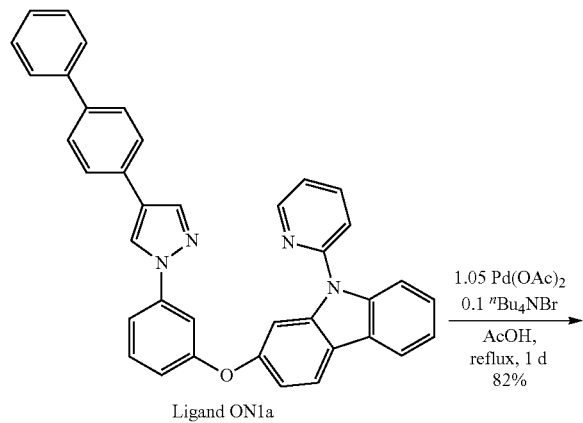

Ligand ON1a

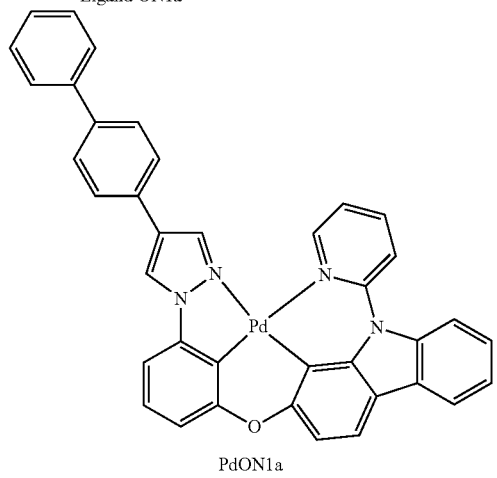

PdON1a

Synthesis of 2-(3-(4-(biphenyl-4-yl)-1H-pyrazol-1-yl)phenoxy)-9-(pyridin-2-yl)-9H-carbazole palladium Complex PdON1a

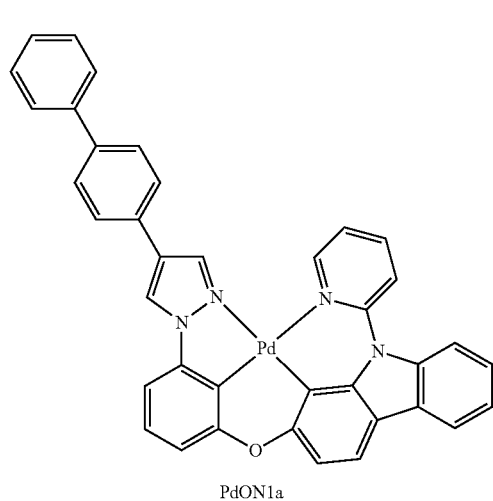

PdON1a

Figure 12:
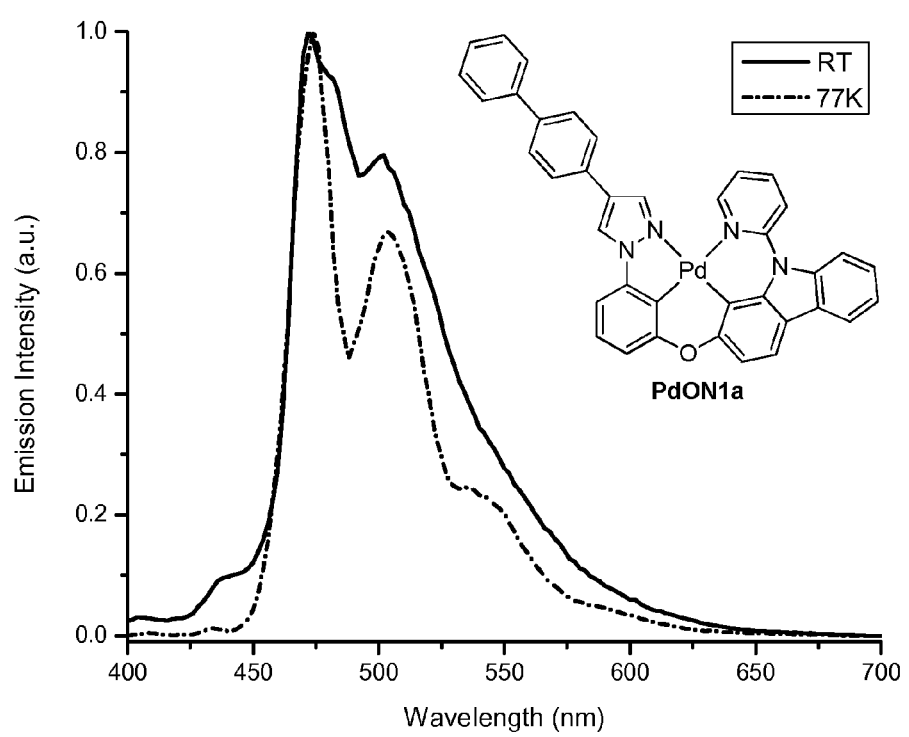
FIG. 12 shows emission spectra of PdON1a in $CH_2Cl_2$ at room temperature and in 2-methyltetrahydrofuran at 77K, in accordance with various aspects of the present disclosure.

Ligand ON1a (222 mg, 0.4 mmol, 1.0 eq), Pd(OAc)$_2$ (94 mg, 1.05 mmol, 1.05 eq), $^n$Bu$_4$NBr (13 mg, 0.1 mmol, 0.1 eq) were added to a flask equipped with a magnetic stir bar and a condenser. The flask was evacuated and backfilled with nitrogen. This evacuation and backfill procedure was repeated twice. Then solvent acetic acid (24 mL) was added under nitrogen. The mixture refluxed for 1 day, cooled to ambient temperature. The solvent was removed under reduced pressure and the residue was purified through flash column chromatography on silica gel using dichloromethane/hexane (2:1) as eluent to obtain the product PdON1a as a white solid 215 mg in 82% yield. $^1$H NMR (DMSO-d$_6$, 400 MHz): δ 7.07 (d, J=8.4 Hz, 1H), 7.25 (d, J=8.4, 1H), 7.34 (t, J=8.0 Hz, 1H), 7.39-7.44 (m, 2H), 7.48-7.56 (m, 4H), 7.58 (d, J=8.0 Hz, 1H), 7.78 (d, J=8.0 Hz, 2H), 7.82 (d, J=8.0 Hz, 2H), 7.97 (d, J=8.4 Hz, 1H), 8.01 (d, J=8.4 Hz, 2H), 8.10 (d, J=8.0 Hz, 1H), 8.19 (d, J=8.4 Hz, 1H), 8.22-8.26 (m, 2H), 8.73 (s, 1H), 9.21 (d, J=5.2 Hz, 1H), 9.49 (s, 1H). FIG. 12 shows emission spectra of PdON1a in CH$_2$Cl$_2$ at room temperature and in 2-methyltetrahydrofuran at 77K.

9. Example 9

Platinum complex PdON1b can be prepared according to the following scheme:

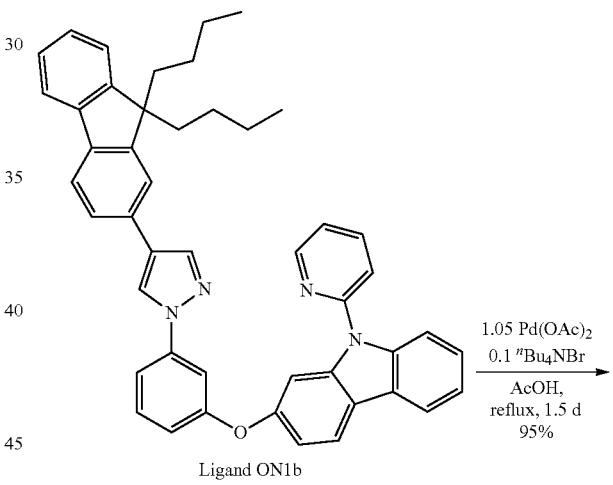

Ligand ON1b

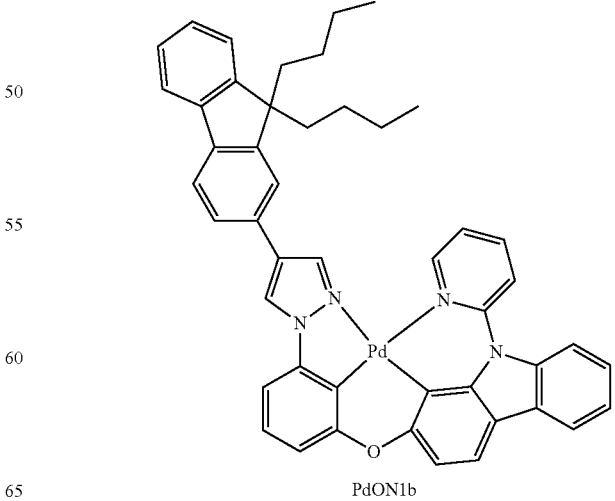

PdON1b

Synthesis of 2-(3-(4-(9,9-dibutyl-9H-fluoren-2-yl)-1H-pyrazol-1-yl)phenoxy)-9-(pyridin-2-yl)-9H-carbazole palladium Complex PdON1b 10. Example 10

Palladium complex PdOO1aMe can be prepared according to the following scheme:

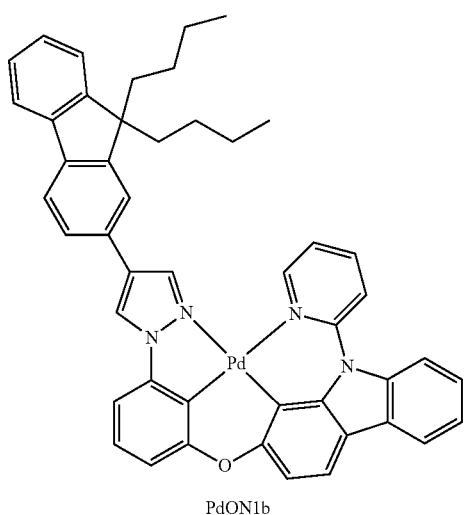

PdON1b

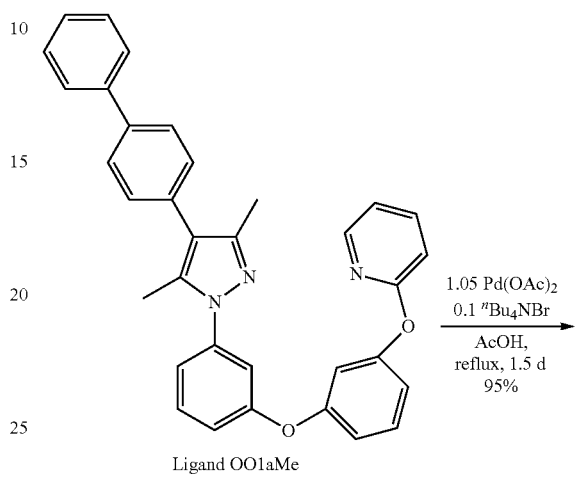

Figure 13:
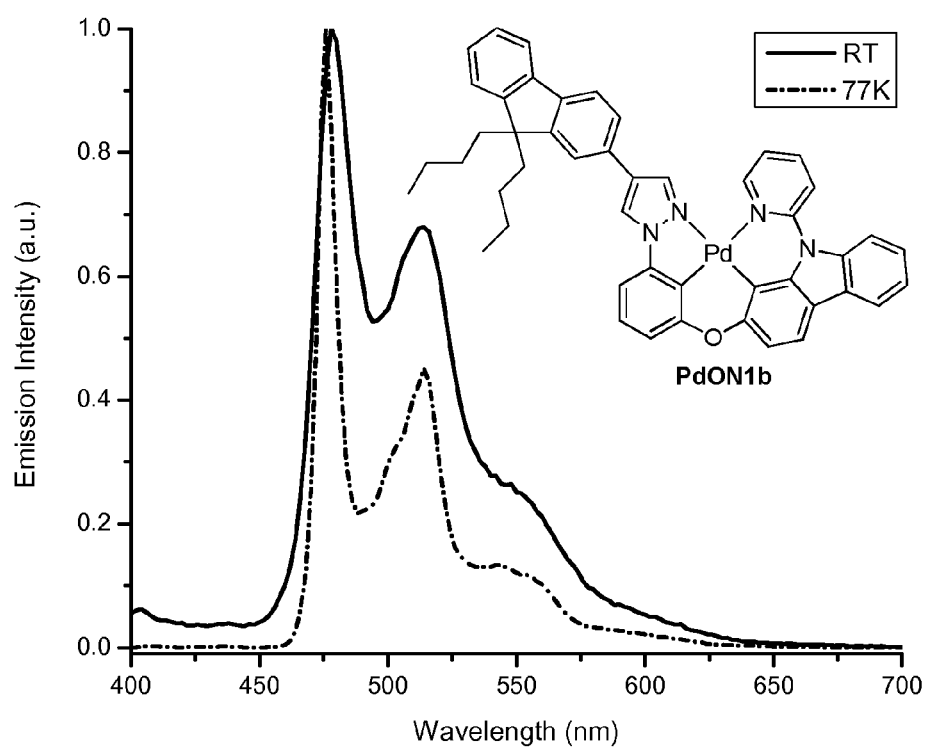
FIG. 13 shows emission spectra of PdON1b in $CH_2Cl_2$ at room temperature and in 2-methyltetrahydrofuran at 77K, in accordance with various aspects of the present disclosure.

Ligand OO1aMe 2-(3-(4-(9,9-dibutyl-9H-fluoren-2-yl)-1H-pyrazol-1-yl)phenoxy)-9-(pyridin-2-yl)-9H-carbazole Ligand ON1b (115 mg, 0.165 mmol, 1.0 eq), Pd(OAc)$_2$ (39 mg, 0.173 mmol, 1.05 eq) and $^n$Bu$_4$NBr (5 mg, 0.017 mmol, 0.1 eq) were added to a three-necked flask equipped with a magnetic stir bar and a condenser. The flask was evacuated and backfilled with nitrogen. This evacuation and backfill procedure was repeated twice. Then solvent acetic acid (10 mL) was added under nitrogen and the mixture refluxed for 1.5 days, cooled to ambient temperature. The solvent was removed under reduced pressure and the residue was purified through flash column chromatography on silica gel using hexane/dichloromethane (1:2) as eluent to afford the desired product PdON1b as a white solid 123 mg in 95% yield. $^1$H NMR (DMSO-d$_6$, 400 MHz): δ 0.52-0.60 (m, 4H), 0.64 (t, J=7.2 Hz, 6H), 1.04-1.10 (m, 4H), 2.08 (t, J=8.0 Hz, 4H), 7.06 (d, J=8.0 Hz, 1H), 7.24 (dd, J=8.0, 1.2 Hz, 1H), 7.32-7.38 (m, 3H), 7.41 (t, J=7.6 Hz, 1H), 7.46-7.56 (m, 3H), 7.58 (d, J=8.0 Hz, 1H), 7.84-7.92 (m, 3H), 7.96 (d, J=8.0 Hz, 1H), 7.98 (s, 1H), 8.08 (d, J=8.4 Hz, 1H), 8.18 (d, J=7.2 Hz, 1H), 8.21-8.25 (m, 2H), 8.72 (s, 1H), 9.21 (d, J=5.2 Hz, 1H), 9.47 (s, 1H). FIG. 13 shows emission spectra of PdON1b in CH$_2$Cl$_2$ at room temperature and in 2-methyltetrahydrofuran at 77K.

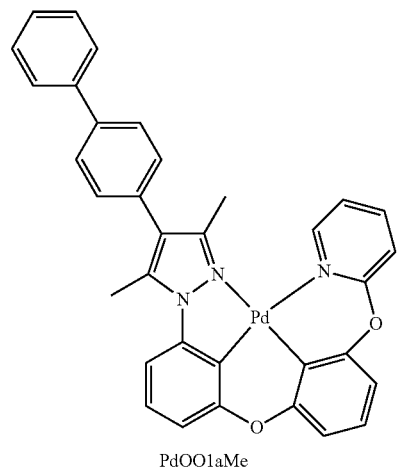

PdOO1aMe

Synthesis of 2-(3-(3-(4-(biphenyl-4-yl)-3,5-dimethyl-1H-pyrazol-1-yl)phenoxy)phenoxy)pyridine palladium Complex PdOO1aMe

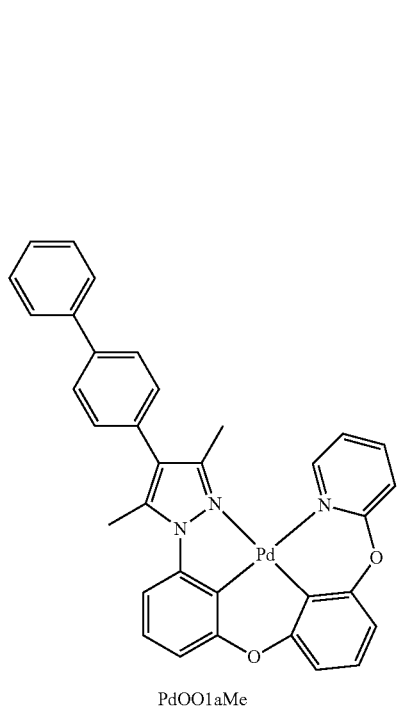

Figure 14:
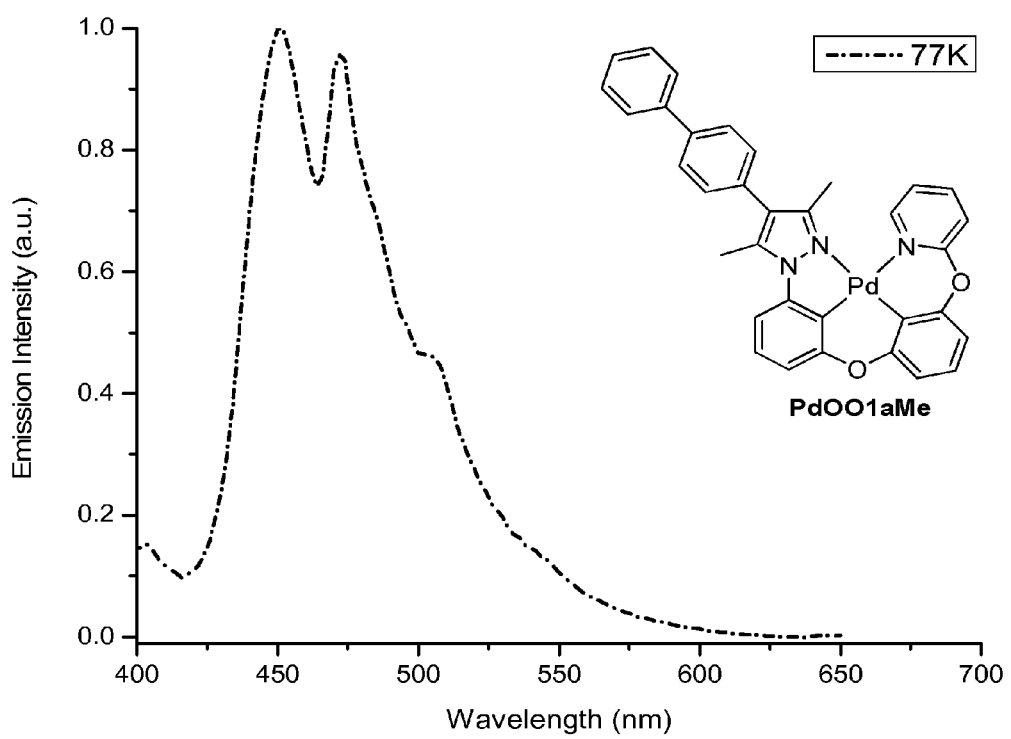
FIG. 14 shows emission spectrum of PdOO1aMe at 77K, in accordance with various aspects of the present disclosure.

PdOO1aMe 2-(3-(3-(4-(biphenyl-4-yl)-3,5-dimethyl-1H-pyrazol-1-yl)phenoxy)phenoxy)pyridine Ligand OO1aMe (245 mg, 0.48 mmol, 1.0 eq), Pd(OAc)$_2$ (113 mg, 0.504 mmol, 1.05 eq) and $^n$Bu$_4$NBr (15 mg, 0.048 mmol, 0.1 eq) were added to a three-necked flask equipped with a magnetic stir bar and a condenser. The flask was evacuated and backfilled with nitrogen. This evacuation and backfill procedure was repeated twice. Then solvent acetic acid (29 mL) was added under nitrogen and the mixture refluxed for 2 days, cooled to ambient temperature. The solvent was removed under reduced pressure and the residue was purified through flash column chromatography on silica gel using hexane/dichloromethane (1:2) as eluent to afford the desired product PdOO1aMe as a white solid 278 mg in 94% yield. $^1$H NMR (DMSO-d$_6$, 400 MHz): δ 2.16 (s, 3H), 2.70 (s, 3H), 6.93 (dd, J=8.4, 1.6 Hz, 1H), 6.98-7.00 (m, 2H), 7.15 (t, J=8.0 Hz, 1H), 7.28 (t, J=8.0 Hz, 1H), 7.36-7.42 (m, 3H), 7.49-7.55 (m, 5H), 7.75 (d, J=8.4 Hz, 2H), 7.81 (d, J=8.4 Hz, 2H), 8.13-8.18 (m, 1H), 8.80 (dd, J=5.6, 1.6 Hz, 1H). FIG. 14 shows emission spectrum of PdOO1aMe at 77K.

11. Example 11

Palladium complex Pd1aO1Me can be prepared according to the following scheme:

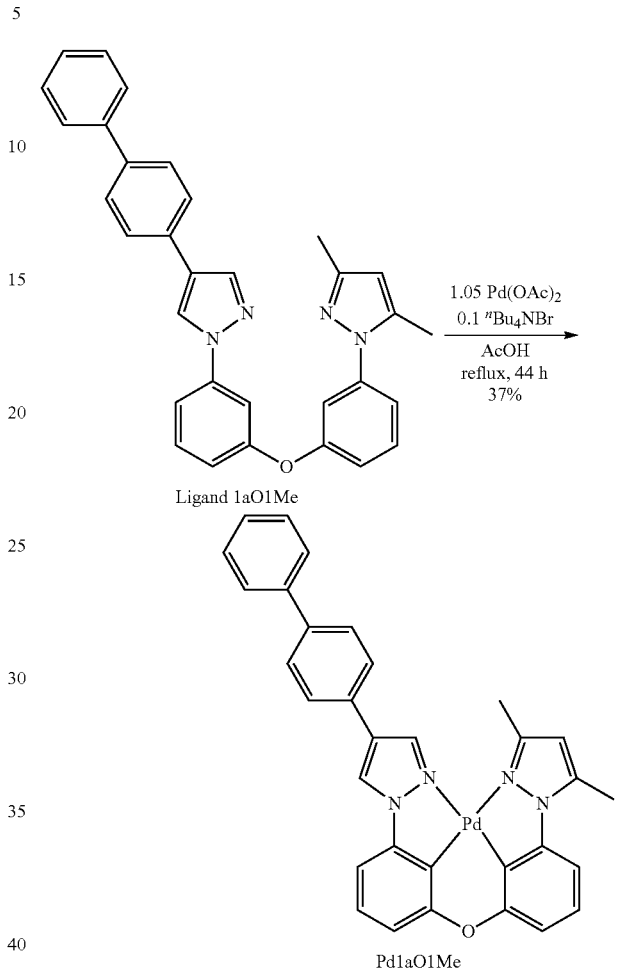

Synthesis of 1-(3-(3-(4-(biphenyl-4-yl)-1H-pyrazol-1-yl)phenoxy)phenyl)-3,5-dimethyl-1H-pyrazole palladium Complex Pd1aO1Me

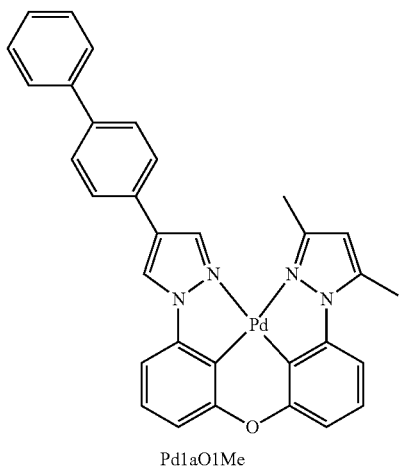

Figure 15:
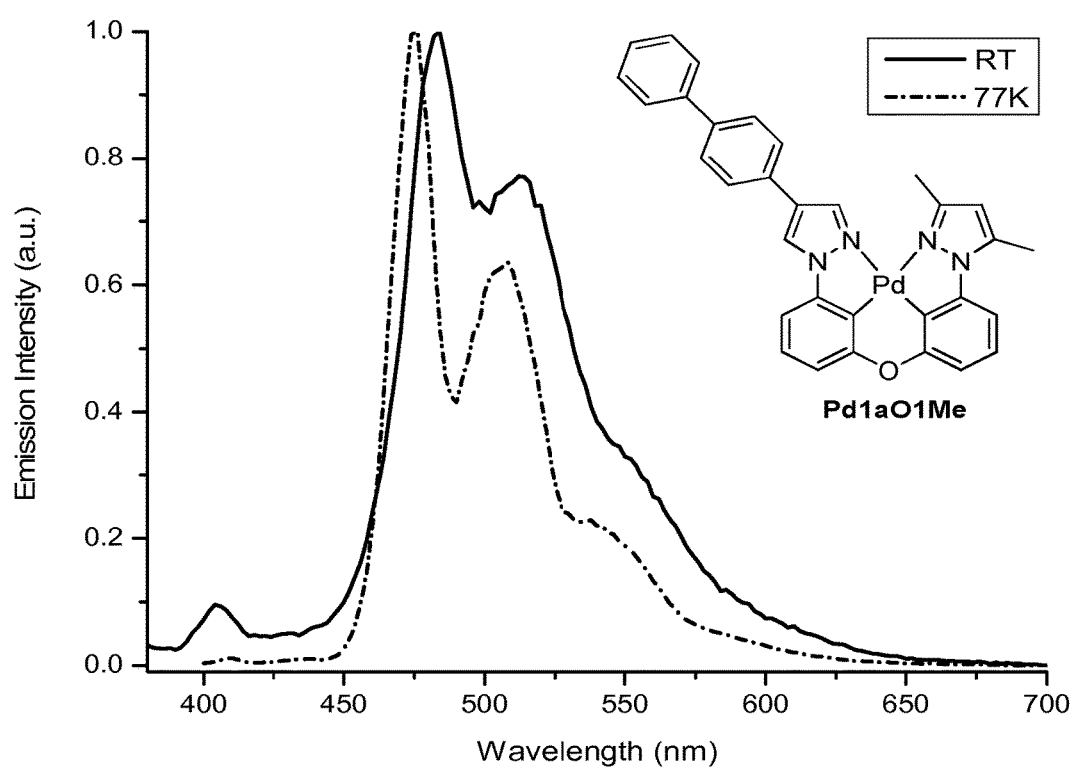
FIG. 15 shows emission spectra of Pd1aO1Me in $CH_2Cl_2$ at room temperature and in 2-methyltetrahydrofuran at 77K, in accordance with various aspects of the present disclosure.

Pd1aO1Me 1-(3-(3-(4-(biphenyl-4-yl)-1H-pyrazol-1-yl)phenoxy)phenyl)-3,5-dimethyl-1H-pyrazole Ligand ON1b (260 mg, 0.572 mmol, 1.0 eq), Pd(OAc)$_2$ (135 mg, 0.601 mmol, 1.05 eq) and $^n$Bu$_4$NBr (18 mg, 0.057 mmol, 0.1 eq) were added to a three-necked flask equipped with a magnetic stir bar and a condenser. The flask was evacuated and backfilled with nitrogen. This evacuation and backfill procedure was repeated twice. Then solvent acetic acid (34 mL) was added under nitrogen and the mixture refluxed for 44 hours, cooled to ambient temperature. The solvent was removed under reduced pressure and the residue was purified through flash column chromatography on silica gel using hexane/dichloromethane (1:2) as eluent to afford the desired product Pd1aO1Me as a white solid 123 mg in 37% yield. $^1$H NMR (DMSO-d$_6$, 400 MHz): δ 2.71 (s, 3H), 2.74 (s, 3H), 6.41 (s, 1H), 7.03 (t, J=7.6 Hz, 2H), 7.27 (t, J=8.0 Hz, 1H), 7.31 (t, J=8.0 Hz, 2H), 7.40 (t, J=7.6 Hz, 1H), 7.51 (t, J=7.6 Hz, 2H), 7.56 (d, J=7.2 Hz, 1H), 7.76 (d, J=7.6 Hz, 2H), 7.80 (d, J=8.0 Hz, 2H), 7.94 (d, J=8.4 Hz, 2H), 8.52 (s, 1H), 9.45 (s, 1H). FIG. 15 shows emission spectra of Pd1aO1Me in CH$_2$Cl$_2$ at room temperature and in 2-methyltetrahydrofuran at 77K.

12. Example 12

Palladium complex Pd1aO1a can be prepared according to the following scheme:

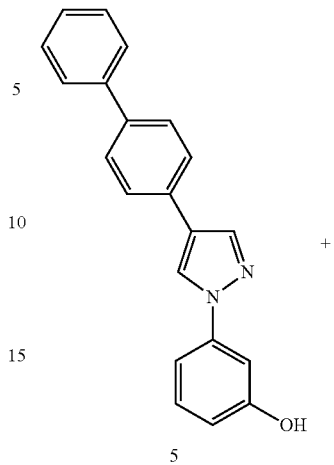

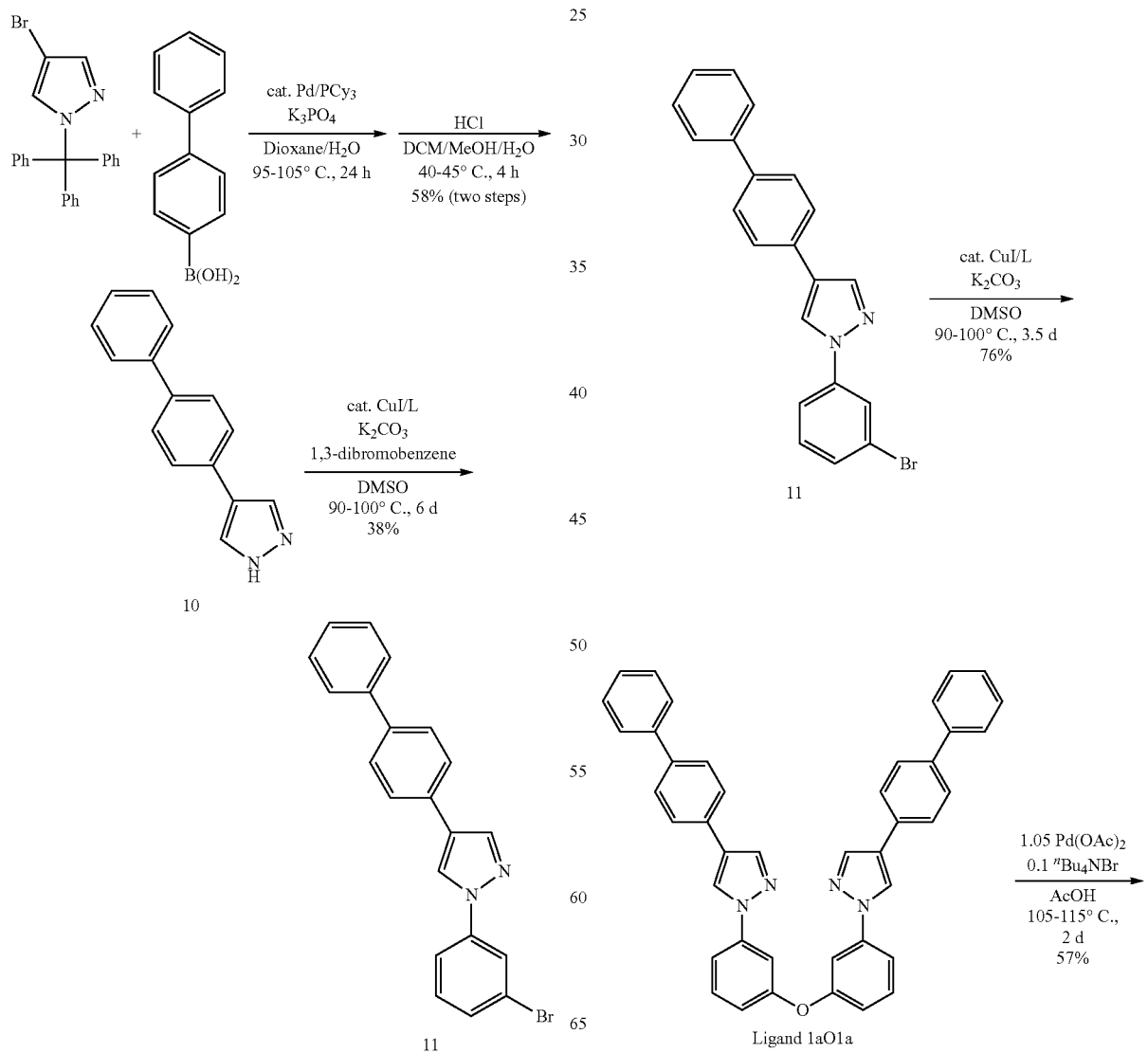

-continued

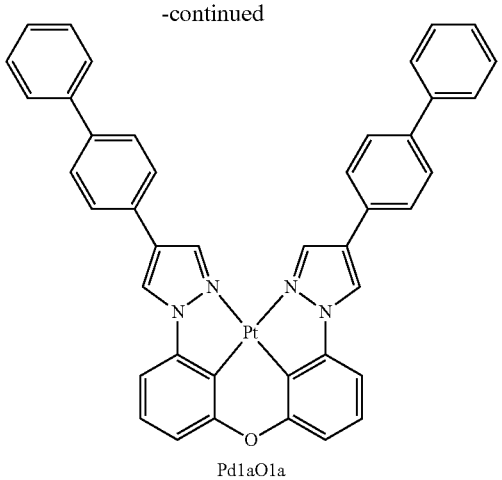

Pd1aO1a

Synthesis of 4-(biphenyl-4-yl)-1H-pyrazole 10

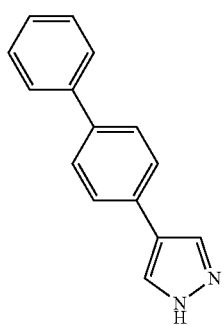

10

4-Bromo-1-trityl-1H-pyrazole (970 mg, 3.35 mmol, 1.0 eq), biphenyl-4-ylboronic acid (796 mg, 4.02 mmol, 1.2 eq), Pd$_2$(dba)$_3$ (123 mg, 0.134 mmol, 0.04 eq), PCy$_3$ (90 mg, 0.322 mmol, 0.096 eq) and K$_3$PO$_4$ (1210 mg, 5.70 mmol, 1.7 eq) were added to a dry pressure tube equipped with a magnetic stir bar. Then the tube was evacuated and backfilled with nitrogen, this evacuation and backfill procedure was repeated twice. Solvent dioxane (21 mL) and H$_2$O (9 mL) were added under nitrogen. The mixture was stirred in an oil bath at a temperature of 95-105° C. for 24 hours. Then the mixture was cooled to ambient temperature, the precipitate was filtered off and washed with ethyl acetate, dried in air to obtain a brown solid 1053 mg which was used directly for the next step. A mixture of the brown solid (1053 mg) in MeOH (32 mL)/H$_2$O (27 mL)/HCl (5 mL) was stirred at 40-45° C. for 4 hours, cooled. The organic solvent was removed under reduced pressure. The precipitate was filtered off and washed with water for twice, dried in air. The collected solid was purified through flash column chromatography on silica gel using hexane/ethyl acetate (3:1) first, then dichloromethane/methanol (10:1) as eluent to afford the desired product 4-(biphenyl-4-yl)-1H-pyrazole 10 as a brown solid 430 mg in 58% total yield for the two steps. $^1$H NMR (DMSO-d$_6$, 400 MHz): δ 7.36 (t, J=7.6 Hz, 1H), 7.47 (t, J=8.0 Hz, 2H), 7.65-7.72 (m, 6H), 7.98 (bs, 1H), 8.25 (bs, 1H), 12.97 (bs, 1H).

Synthesis of 4-(biphenyl-4-yl)-1-(3-bromophenyl)-1H-pyrazole 11

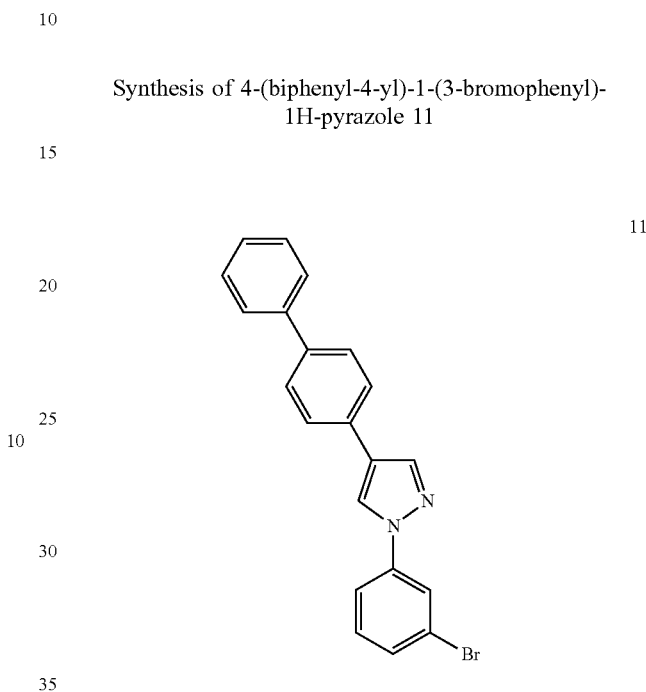

11

To a dry pressure vessel equipped with a magnetic stir bar was added 4-(biphenyl-4-yl)-1H-pyrazole 10 (430 mg, 1.95 mmol, 1.0 eq), L-prolin (90 mg, 0.78 mmol, 0.4 eq), CuI (76 mg, 0.40 mmol, 0.2 eq) and K$_2$CO$_3$ (539 mg, 3.90 mmol, 2.0 eq). The tube was evacuated and backfilled with nitrogen. This evacuation and backfill procedure was repeated twice. Then solvent DMSO (20 mL) and 1,3-dibromobenzene (1.42 mL, 11.70 mmol, 6.0 eq) were added under nitrogen. The mixture was stirred at a temperature of 90-100° C. for 6 days and then cooled to ambient temperature. Water was added to dissolve solid. The mixture was extracted with ethyl acetate three times. The combined organic layer was washed with water three times and then dried over sodium sulfate and filtered. The filtrate was concentrated under reduced pressure and the residue was purified through column chromatography on silica gel using hexane/ethyl acetate (10:1-5:1) as eluent to obtain the desired product 4-(biphenyl-4-yl)-1-(3-bromophenyl)-1H-pyrazole 11 as a brown solid 278 mg in 38% yield. $^1$H NMR (DMSO-d$_6$, 500 MHz): δ 7.37 (t, J=7.0 Hz, 1H), 7.46-7.54 (m, 4H), 7.73 (t, J=7.5 Hz, 4H), 7.83 (d, J=9.0 Hz, 2H), 7.95 (d, J=8.0 Hz, 1H), 8.15 (s, 1H), 8.32 (s, 1H), 9.16 (s, 1H).

721
Synthesis of 1,1'-(3,3'-oxybis(3,1-phenylene))bis(4-(biphenyl-4-yl)-1H-pyrazole) Ligand 1aO1a

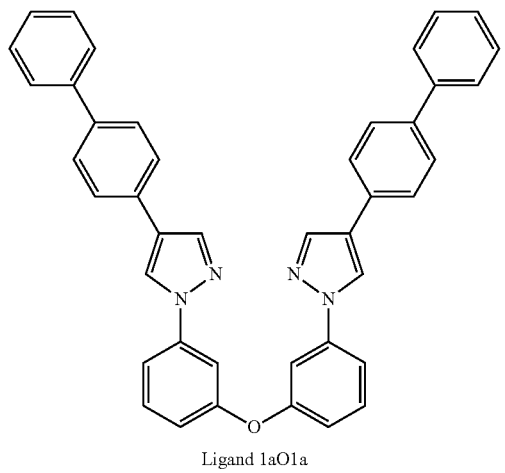 [SMILES: c1ccc(-c2ccc(-c3cnn(-c4cccc(Oc5cccc(-n6cc(-c7ccc(-c8ccccc8)cc7)cn6)c5)c4)c3)cc2)cc1]

Ligand 1aO1a

To a dry pressure vessel equipped with a magnetic stir bar was added 3-(4-(biphenyl-4-yl)-1H-pyrazol-1-yl)phenol 5 (210 mg, 0.67 mmol, 1.0 eq), 4-(biphenyl-4-yl)-1-(3-bromophenyl)-1H-pyrazole 11 (278 mg, 0.74 mmol, 1.1 eq), CuI (13 mg, 0.067 mmol, 0.1 eq), picolinic acid (16 mg, 0.134 mmol, 0.2 eq) and $K_3PO_4$ (185 mg, 1.34 mmol, 2.0 eq). The tube was evacuated and backfilled with nitrogen. This evacuation and backfill procedure was repeated twice. Then solvent DMSO (10 mL) was added under nitrogen. The mixture was stirred at a temperature of 90-100° C. for 3.5 days and then cooled to ambient temperature. Water was added. The precipitate was filtered off. The filtrate was extracted with ethyl acetate three times. The combined organic layer was washed with water three times and then dried over sodium sulfate and filtered. The filtrate was concentrated under reduced pressure. The residue and the collected solid were purified through column chromatography on silica gel using hexane/ethyl acetate (4:1) and then dichloromethane/methane (10:1) as eluent to obtain the desired product 1,1'-(3,3'-oxybis(3,1-phenylene))bis(4-(biphenyl-4-yl)-1H-pyrazole) Ligand 1aO1a as a brown solid 309 mg in 76% yield. $^1$H NMR (DMSO-$d_6$, 400 MHz): δ 7.06 (dd, J=8.0, 2.0 Hz, 2H), 7.36 (t, J=7.6 Hz, 2H), 7.47 (t, J=8.0 Hz, 4H), 7.59 (t, J=8.0 Hz, 2H), 7.69-7.73 (m, 10H), 7.76 (dd, J=8.0, 2.0 Hz, 2H), 7.82 (d, J=8.4 Hz, 4H), 8.28 (s, 2H), 9.13 (s, 2H).

722
Synthesis of 1,1'-(3,3'-oxybis(3,1-phenylene))bis(4-(biphenyl-4-yl)-1H-pyrazole) palladium Complex Pd$_1$aO1a

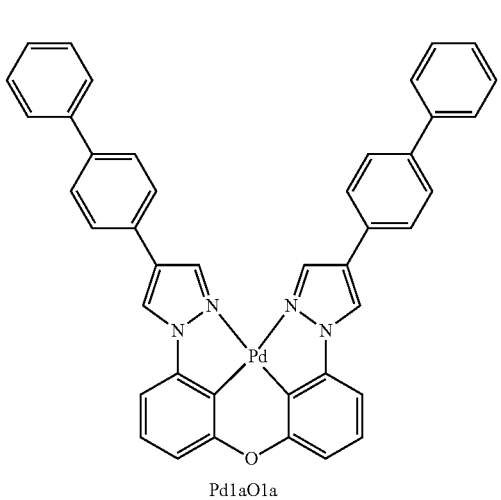

Pd1aO1a 1,1'-(3,3'-oxybis(3,1-phenylene))bis(4-(biphenyl-4-yl)-1H-pyrazole) Ligand 1aO1a (96 mg, 0.158 mmol, 1.0 eq), Pd(OAc)$_2$ (37 mg, 0.166 mmol, 1.05 eq) and $^n$Bu$_4$NBr (5 mg, 0.016 mmol, 0.1 eq) were added to a three-necked flask equipped with a magnetic stir bar and a condenser. The flask was evacuated and backfilled with nitrogen. This evacuation and backfill procedure was repeated twice. Then solvent acetic acid (10 mL) was added under nitrogen and the mixture refluxed for 2 days, cooled to ambient temperature. The solvent was removed under reduced pressure and the residue was purified through flash column chromatography on silica gel using hexane/dichloromethane (1:3) as eluent to afford the desired product palladium complex Pd$_1$aO1a as a white solid 63.7 mg in 57% yield. δ 7.06 (d, J=7.6 Hz, 2H), 7.32 (t, J=8.0 Hz, 2H), 7.39-7.43 (m, 2H), 7.50-7.56 (m, 6H), 7.79 (d, J=7.6 Hz, 4H), 7.85 (d, J=8.4 Hz, 4H), 8.01 (d, J=8.4 Hz, 4H), 9.05 (s, 2H), 9.45 (s, 2H).

16. Example 16
Platinum complex PtON7a-dtb can be prepared according to the following scheme:
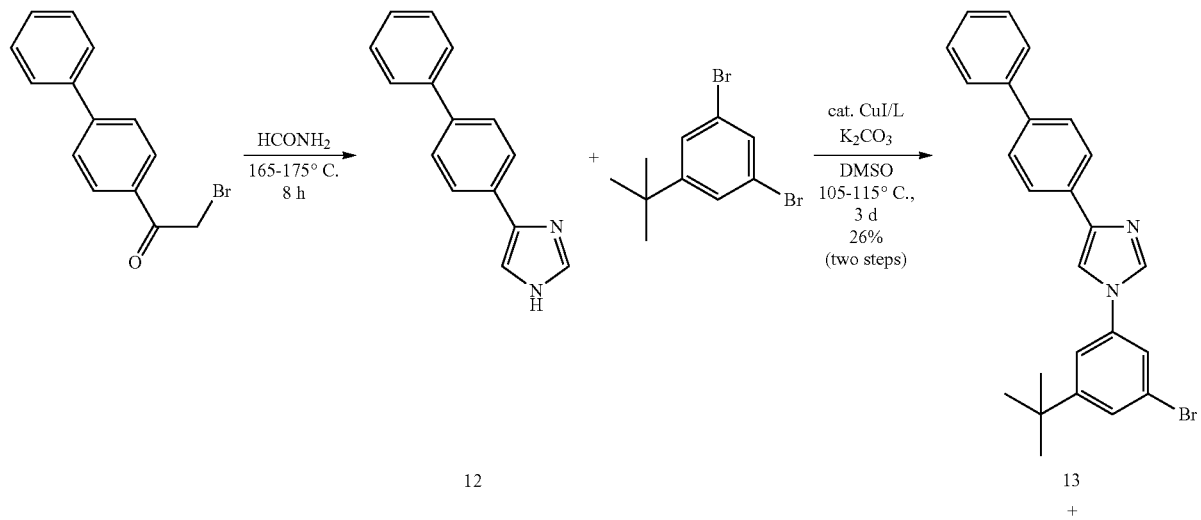
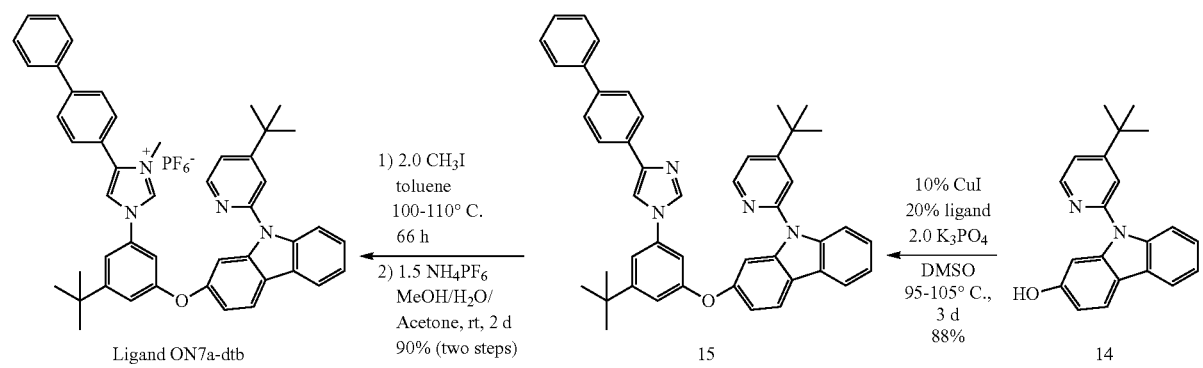
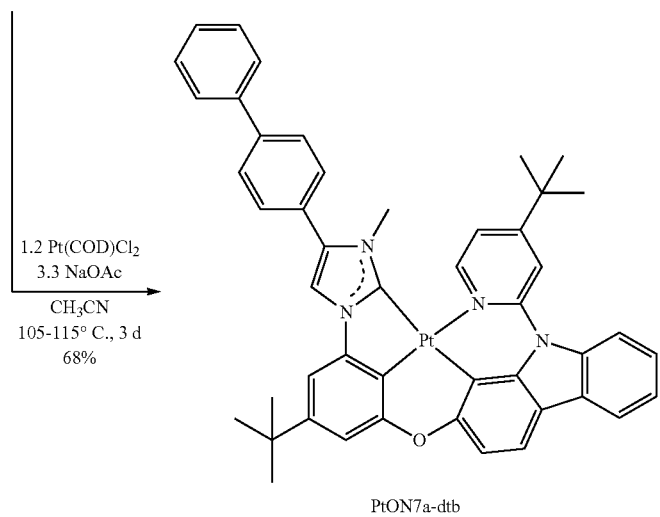
PtON7a-dtb

Synthesis of 4-(biphenyl-4-yl)-1H-imidazole 12

A mixture of (8254 mg, 30 mmol, 1.0 eq) and (9458 mg, 7.3 mL, 210 mmol, 7.0 eq) was stirred in an oil bath at 165-175° C. for 8 hours under nitrogen, cooled and then recrystallized in ethyl acetate. Filtered, washed with a little ethyl acetate. The collected solid was dried in air to obtain the desired product 6.23 g as a grey solid.

Synthesis of intermediate 4-(biphenyl-4-yl)-1-(3-bromo-5-tert-butylphenyl)-1H-imidazole 13

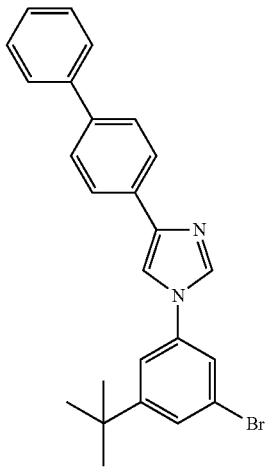

4-(Biphenyl-4-yl)-1H-imidazole 12 (3773 mg, 17.13 mmol, 1.0 eq), CuI (326 mg, 1.71 mmol, 0.1 eq), L-proline (394 mg, 3.42 mmol, 0.2 eq), 1,3-dibromo-5-(1,1-dimethylethyl)-benzene (8.00 g, 27.40 mmol, 1.6 eq) and $K_2CO_3$ (4735 mg, 34.26 mmol, 2.0 eq) were added to a dry pressure tube equipped with a magnetic stir bar. The vessel was then evacuated and backfilled with nitrogen, this evacuation and backfill procedure was repeated for a total of three times. Then DMSO (35 mL) were added in a nitrogen filled glove box. The mixture was bubbled with nitrogen for 5 minutes. The tube was sealed before being taken out of the glove box. The mixture was stirred in an oil bath at a temperature of 105-115° C. for 3 days. Then the mixture was cooled to ambient temperature, filtered and washed with a plenty of ethyl acetate. The filtrate was washed with water three times, dried over sodium sulfate, filtered, concentrated under reduced pressure and the residue was purified through column chromatography on silica gel using hexane and ethyl acetate (10:1-5:1-3:1) as eluent to obtain the desired product 13 as a brown-red solid 2.023 g in 26% total yield for the two steps. $^1$H NMR (DMSO-$d_6$, 400 MHz): δ 1.37 (s, 9H), 7.38 (t, J=7.2 Hz, 1H), 7.49 (t, J=8.0 Hz, 2H), 7.55 (d, J=1.6 Hz, 1H), 7.32-7.75 (m, 5H), 7.88 (d, J=1.2 Hz, 1H), 7.98 (d, J=8.4 Hz, 2H), 8.49 (s, 2H).

Synthesis of 2-(3-(4-(biphenyl-4-yl)-1H-imidazol-1-yl)-5-tert-butylphenoxy)-9-(4-tert-butylpyridin-2-yl)-9H-carbazole 15

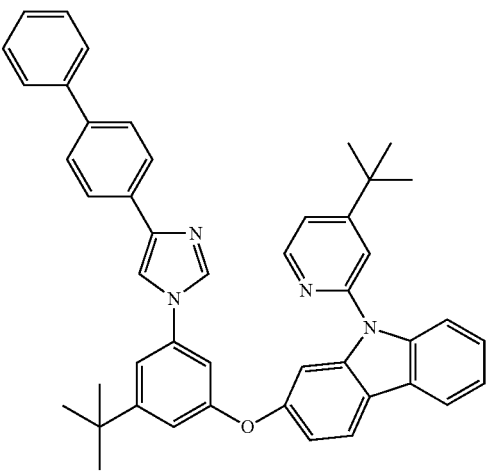

A mixture of 4-(biphenyl-4-yl)-1H-imidazole 12 (2.00 g, 4.64 mmol, 1.19 eq), 9-(4-tert-butylpyridin-2-yl)-9H-carbazol-2-ol 14 (1.23 g, 3.90 mmol, 1.0 eq), CuI (74 mg, 0.39 mmol, 0.1 eq), picolinic acid (96 mg, 0.78 mmol, 0.20 eq) and $K_3PO_4$ (1.66 g, 7.80 mmol, 2.0 eq) in DMSO (25 mL) was stirred at a temperature of 95-105° C. for three days under a nitrogen atmosphere, then cooled to ambient temperature. The solid was filtered off and washed with plenty of ethyl acetate. The filtrate was washed with water for three time and then dried over sodium sulfate and filtered. The filtrate was concentrated under reduced pressure and the residue was purified through column chromatography on silica gel using hexane/ethyl acetate (110:1-5:1-3:1) as eluent to obtain the desired product as a brown solid 2.28 g in 88% yield. $^1$H NMR (DMSO-$d_6$, 400 MHz): δ 1.25 (s, 9H), 1.33 (s, 9H), 7.12 (s, 1H), 7.16 (dd, J=8.8, 2.0 Hz, 1H), 7.32-7.50 (m, 8H), 7.55 (s, 1H), 7.62 (s, 1H), 7.71-7.75 (m, 4H), 7.78 (d, J=8.4 Hz, 1H), 7.96 (d, J=8.4 Hz, 2H), 8.23 (d, J=7.6 Hz, 1H), 8.30 (d, J=8.4 Hz, 1H), 8.44 (d, J=4.0 Hz, 2H), 8.57 (d, J=5.2 Hz, 1H).

Synthesis of 1-(3-tert-butyl-5-(9-(4-tert-butylpyridin-2-yl)-9H-carbazol-2-yloxy)phenyl)-3-methyl-4-(biphenyl-4-yl)-1H-imidazol-3-ium hexafluorophosphate(V) Ligand ON7a-dtb

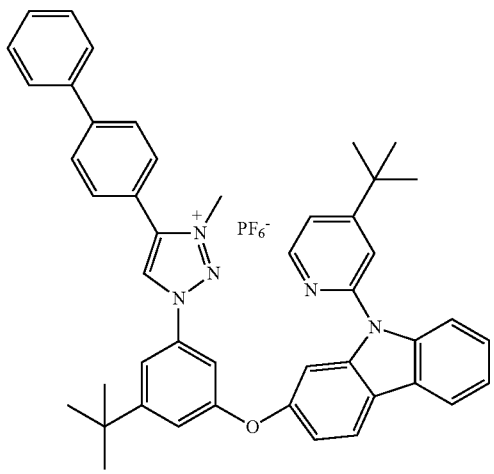

Ligand ON7a-dtb

A solution of $CH_3I$ (0.42 mL, 6.75 mmol, 2.0 eq) and 2-(3-(4-(biphenyl-4-yl)-1H-imidazol-1-yl)-5-tert-butylphenoxy)-9-(4-tert-butylpyridin-2-yl)-9H-carbazole 15 (2.25 g, 3.37 mmol, 1.0 eq) in toluene (50 mL) was stirred in a sealed vessel at 100-110° C. for 66 hours, cooled, the precipitate was filtered off and washed with $Et_2O$. Then the collected solid dried in air to obtain brown solid 2.52 g which was used directly for the next step. The brown solid (2.50 g, 3.09 mmol, 1.0 eq) was added to a mixture of $MeOH/H_2O$/Acetone (80 mL/15 mL/15 mL). The mixture was stirred for 30 min until the solid was entirely dissolved. Then $NH_4PF_6$ (0.76 g, 4.64 mmol, 1.5 eq) was added to the solution. The mixture was stirred at room temperature for 2 days, then removed most of the organic solvent. More deionized water was added. The precipitate was collected through filtration, washed with water three times. Then the solid was dried in air to give the desired product Ligand ON7a-dtb as a grey powder 2.468 g in 90% total yield for the two steps. $^1H$ NMR (DMSO-$d_6$, 400 MHz): δ 1.30 (s, 9H), 1.35 (s, 9H), 3.96 (s, 3H), 7.16 (dd, J=8.4, 2.0 Hz, 1H), 7.36-7.55 (m, 9H), 7.65 (s, 1H), 7.68 (s, 1H), 7.77-7.81 (m, 5H), 7.92 (d, J=8.0 Hz, 2H), 8.26 (d, J=8.0 Hz, 1H), 8.33 (d, J=8.0 Hz, 1H), 8.59 (d, J=5.6 Hz, 1H), 8.64 (s, 1H), 9.90 (s, 1H).

Synthesis of Platinum (II) [6-(1,3-dihydro-3-methyl-4-(biphenyl-4-yl)-2H-imidazol-2-ylidene-κC²)-4-tert-butyl-1,2-phenylen e-κC¹]oxy[9-(4-tert-butyltpyridin-2-yl-κN)-9H-carbazole-1,2-diyl-κC¹] (PtON7a-dtb)

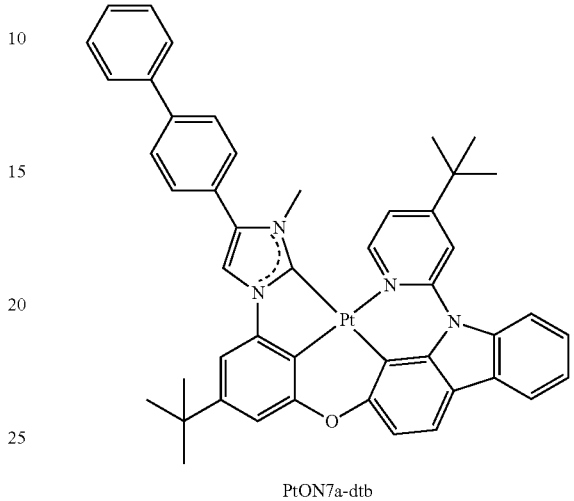

PtON7a-dtb

A mixture of 1-(3-tert-butyl-5-(9-(4-tert-butylpyridin-2-yl)-9H-carbazol-2-yloxy)phenyl)-3-methyl-4-(biphenyl-4-yl)-1H-imidazol-3-ium hexafluorophosphate(V) Ligand ON7a-dtb (2.04 g, 2.07 mmol, 1.0 eq), Pt(COD)$Cl_2$ (1.12 g, 2.99 mmol, 1.2 eq; COD=cyclooctadiene) and NaOAc (0.67 g, 8.16 mmol, 3.3 eq) in $CH_3CN$ (109 mL) was stirred in a pressure vessel at a temperature of 105-115° C. for 3 days under a nitrogen atmosphere, cooled to ambient temperature. The reaction was quenched with water, then extracted with dichloromethane three times. Dried over sodium sulfate. Filtered, the filtrate was concentrated under reduced pressure and the residue was purified through column chromatography on silica gel using hexane/dichloromethane (1:1) as eluent to obtain the desired product platinum complex PtON7a-dtb as a yellow solid 1.46 g in 68% yield. $^1H$ NMR (DMSO-$d_6$, 400 MHz): δ 1.36 (s, 9H), 1.39 (s, 9H), 3.94 (s, 3H), 6.90 (d, J=1.2 Hz, 1H), 7.23 (d, J=8.4 Hz, 1H), 7.33 (dd, J=6.0, 2.0 Hz, 1H), 7.36-7.54 (m, 6H), 7.79 (d, J=7.6 Hz, 2H), 7.84-7.90 (m, 5H), 8.08 (d, J=8.4 Hz, 1H), 8.09 (d, J=2.0 Hz, 1H), 8.14 (d, J=7.6 Hz, 1H), 8.48 (s, 1H), 9.56 (d, J=6.0 Hz, 1H).

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A compound of Formula I:

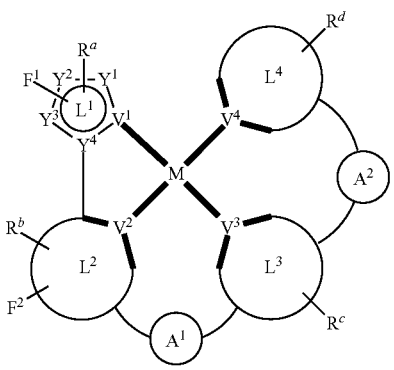

Formula I wherein M is platinum or palladium,
L¹ is diazolyl,
each L² and L³ is phenyl,
L⁴ is pyridyl,
each of F¹ and F² is independently present or absent, wherein at least one of F¹ and F² is present, and each of F¹ and F² present is independently selected from the following structures:

1. Aromatic Hydrocarbons and their Derivatives

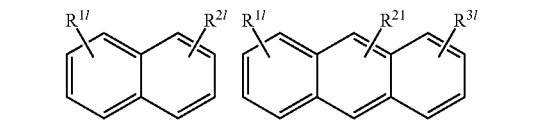

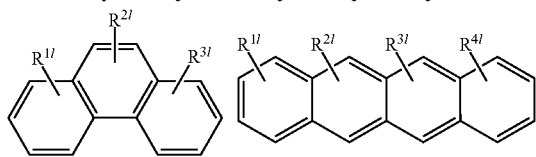

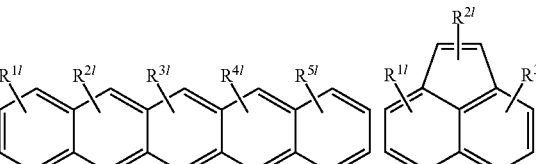

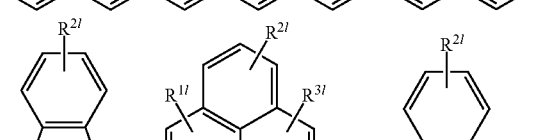

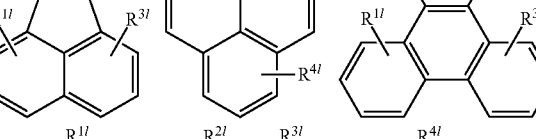

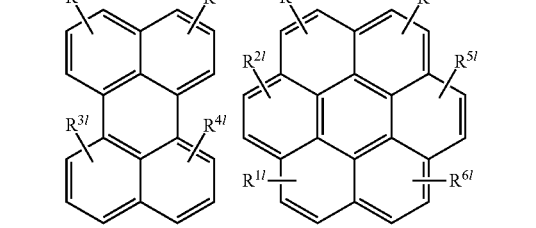

-continued

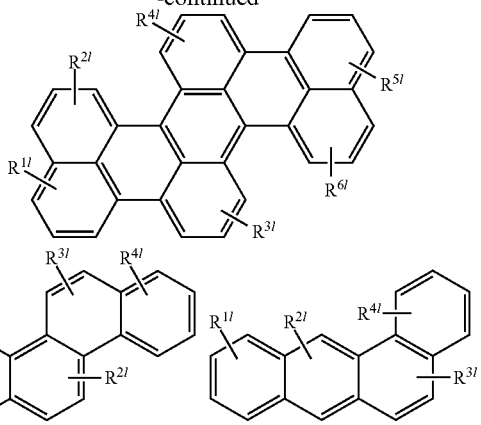

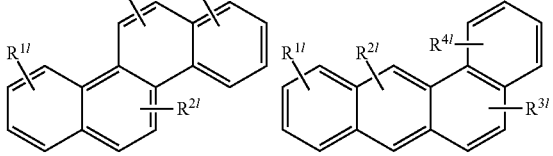

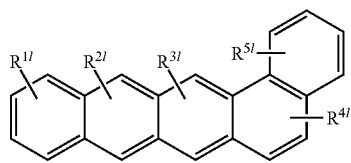

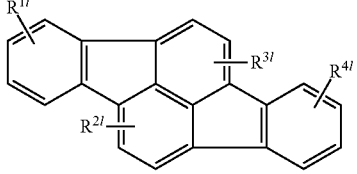

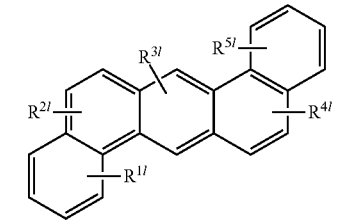

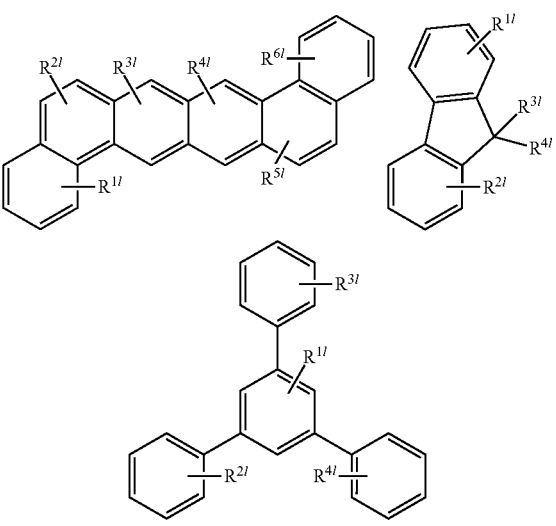

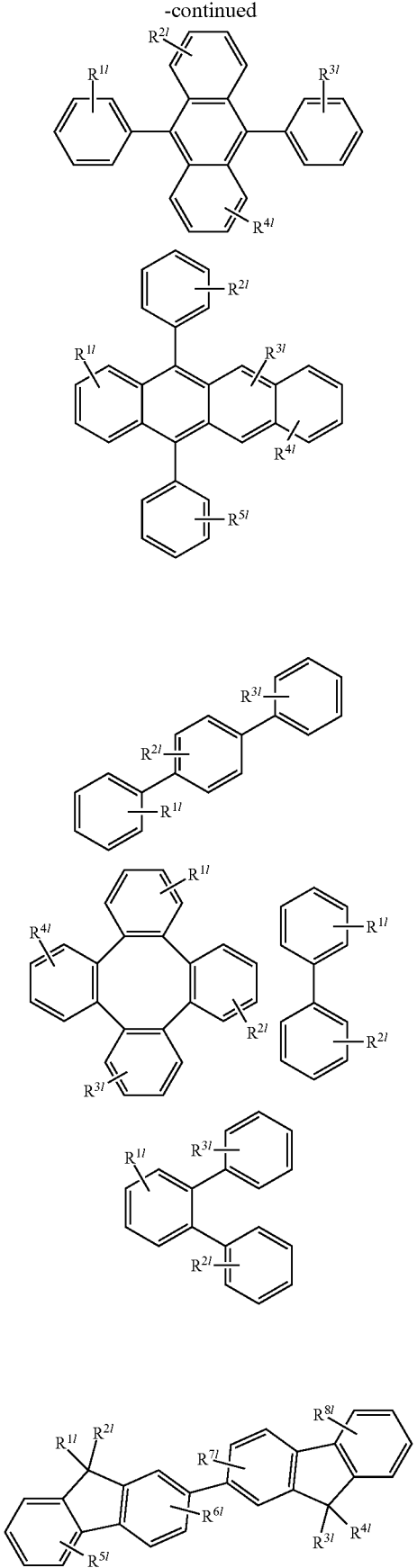
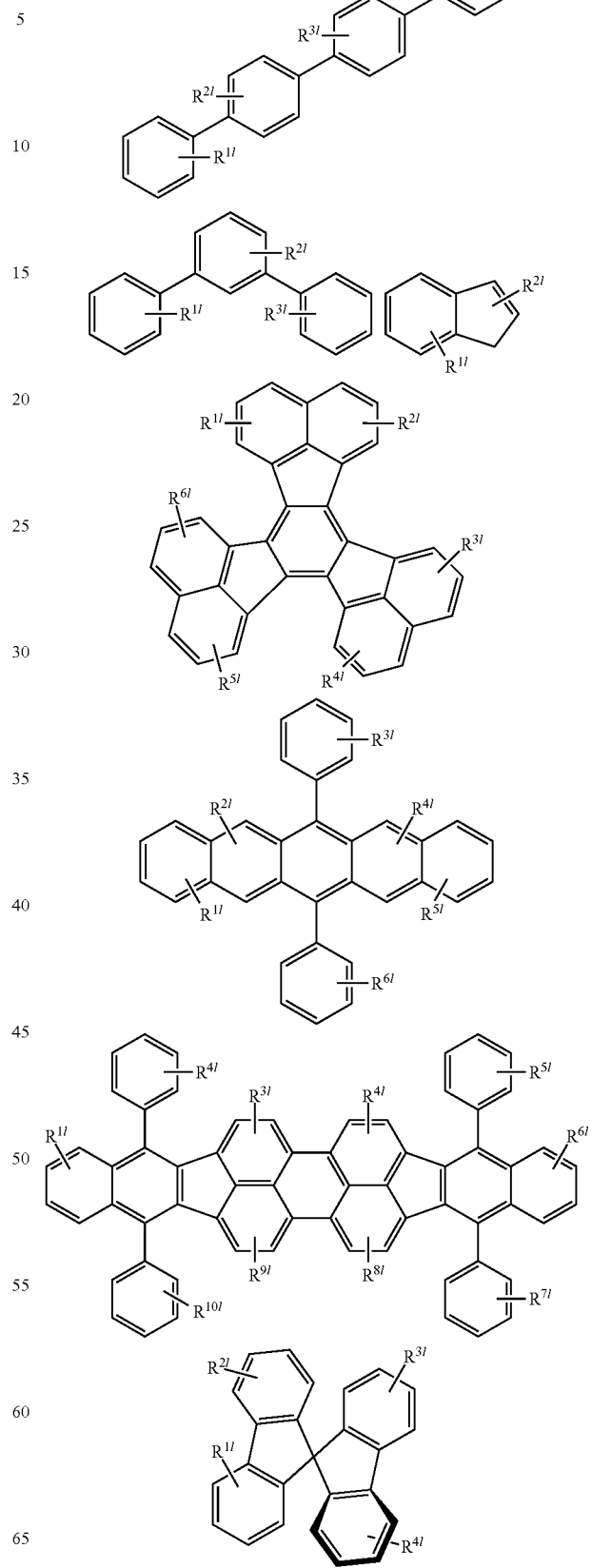

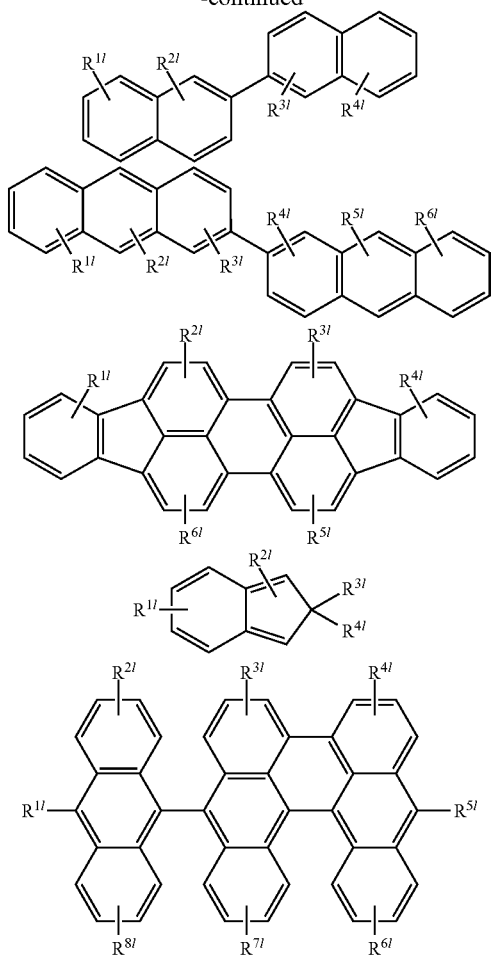
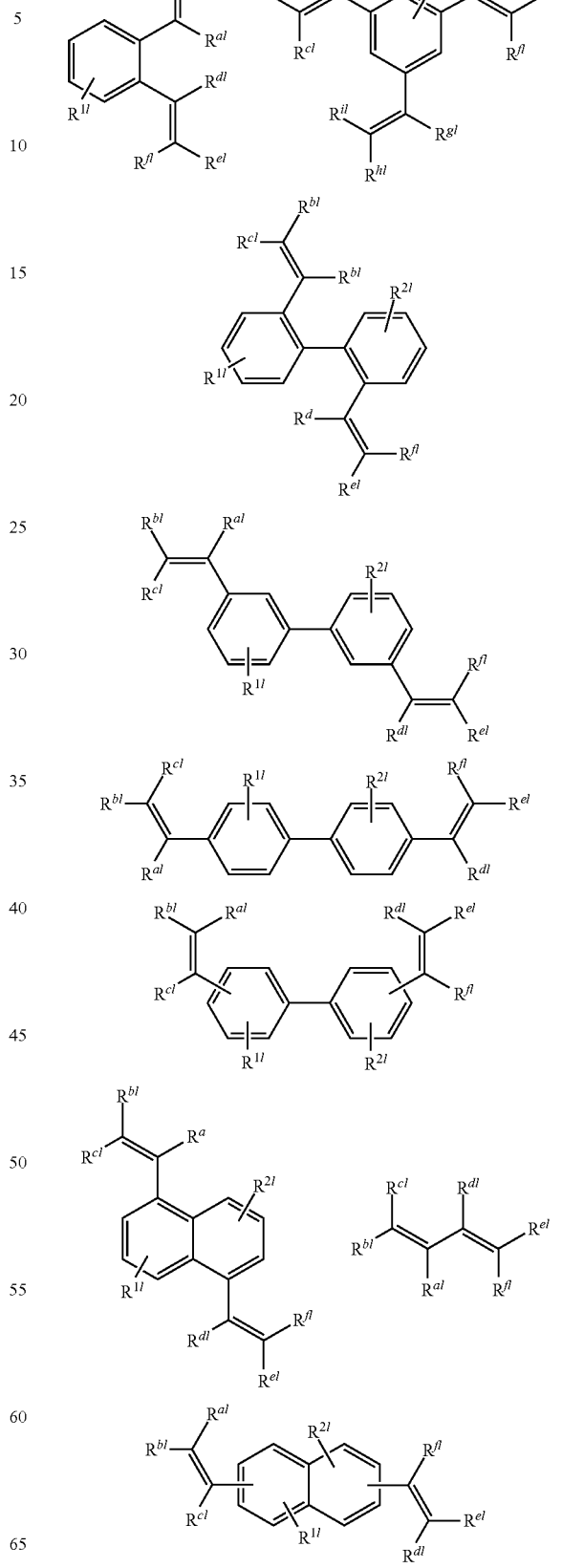
2. Arylethylene, Arylacetylene and their Derivatives
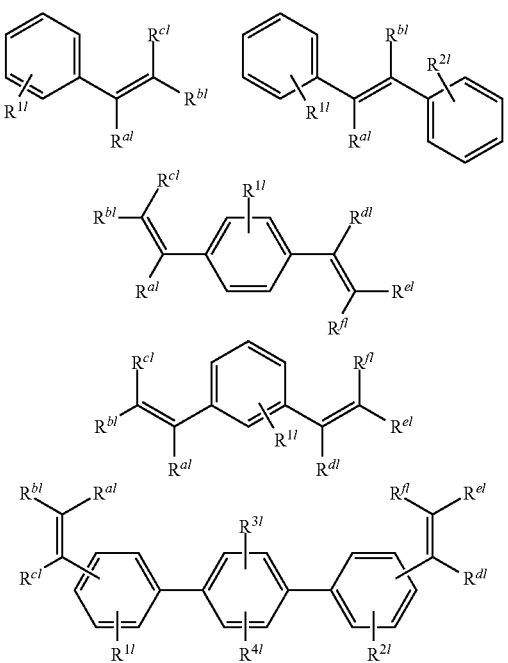

735
-continued
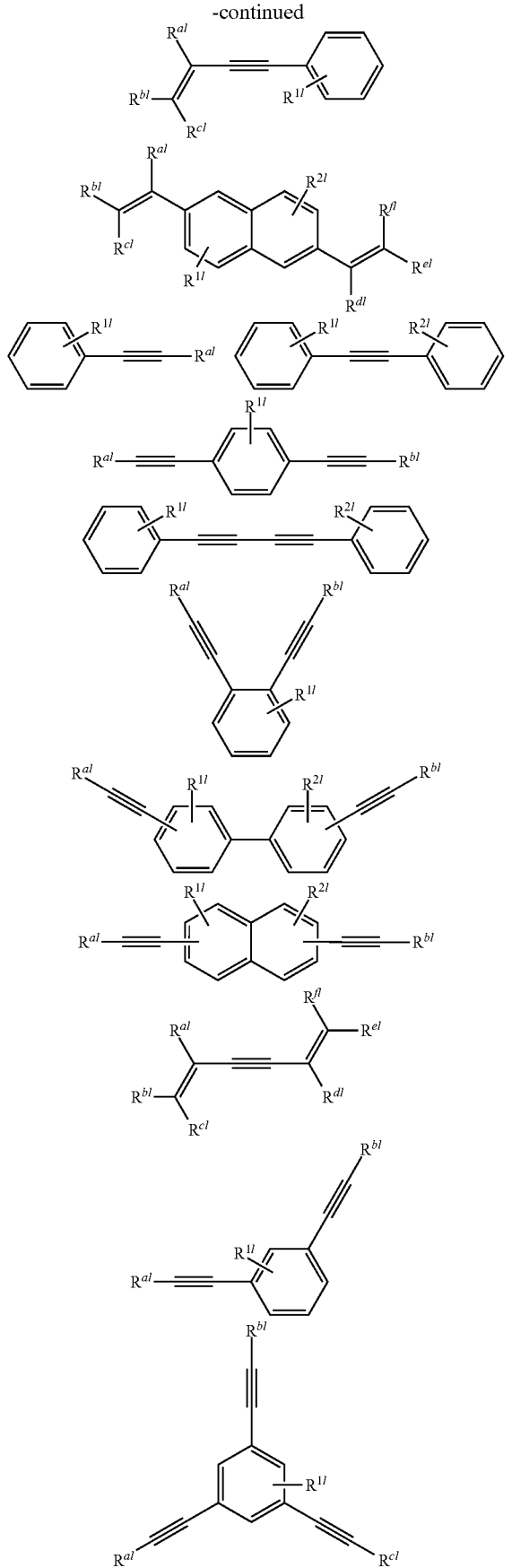
736
-continued
where each of $R^{al}$, $R^{bl}$, $R^{cl}$, $R^{dl}$, $R^{el}$, $R^{fl}$, $R^{gl}$, $R^{hl}$ and $R^{il}$ can be one of the following structure:
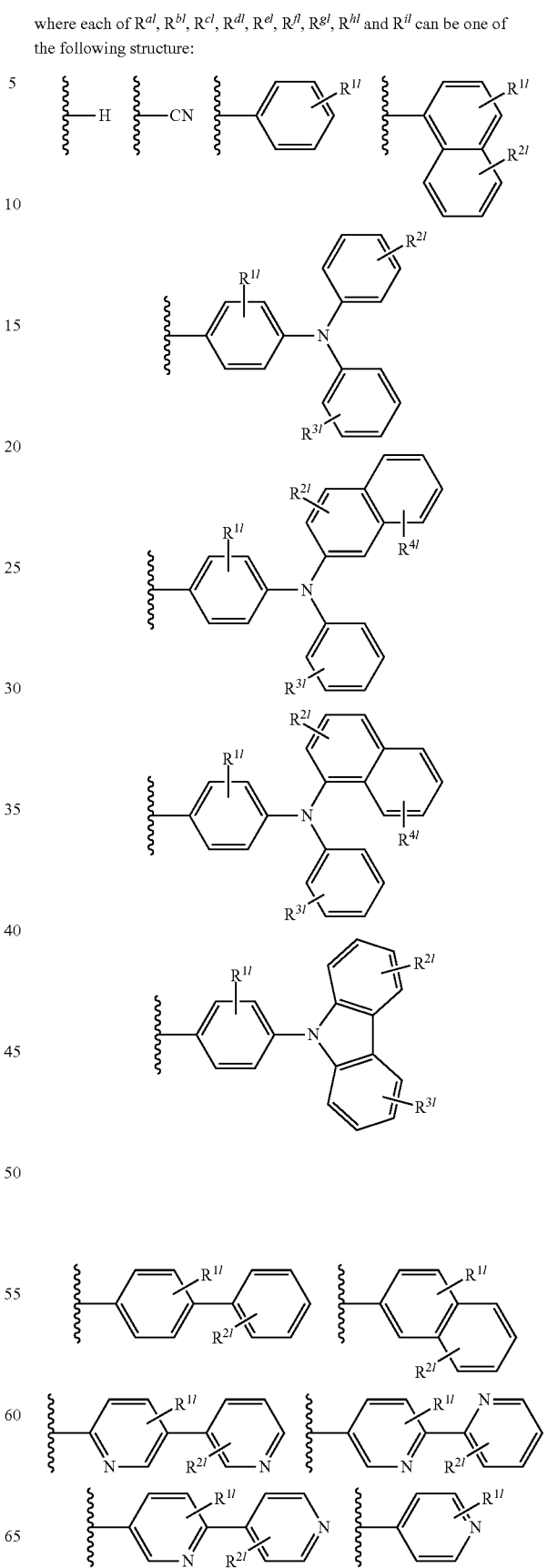

-continued
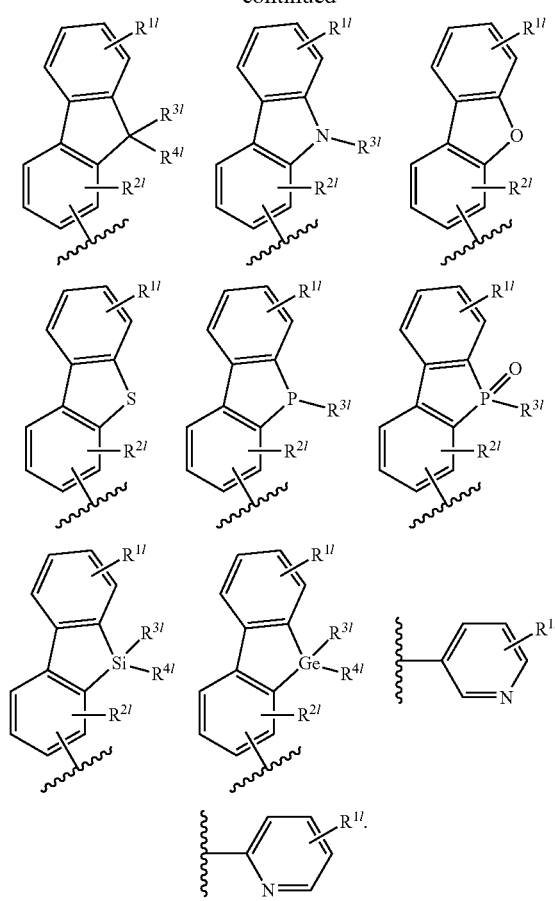
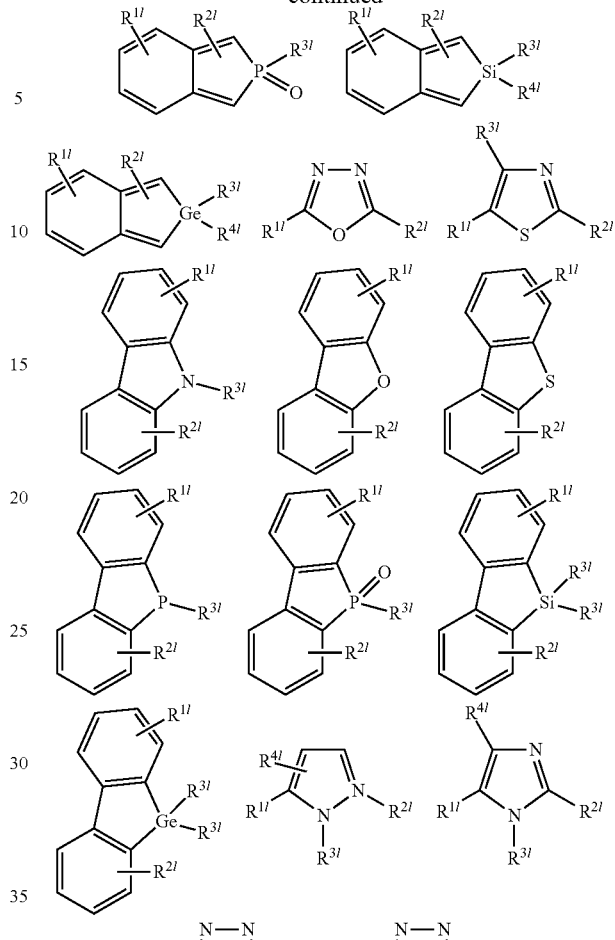
3. Heterocyclic Compounds and their Derivatives
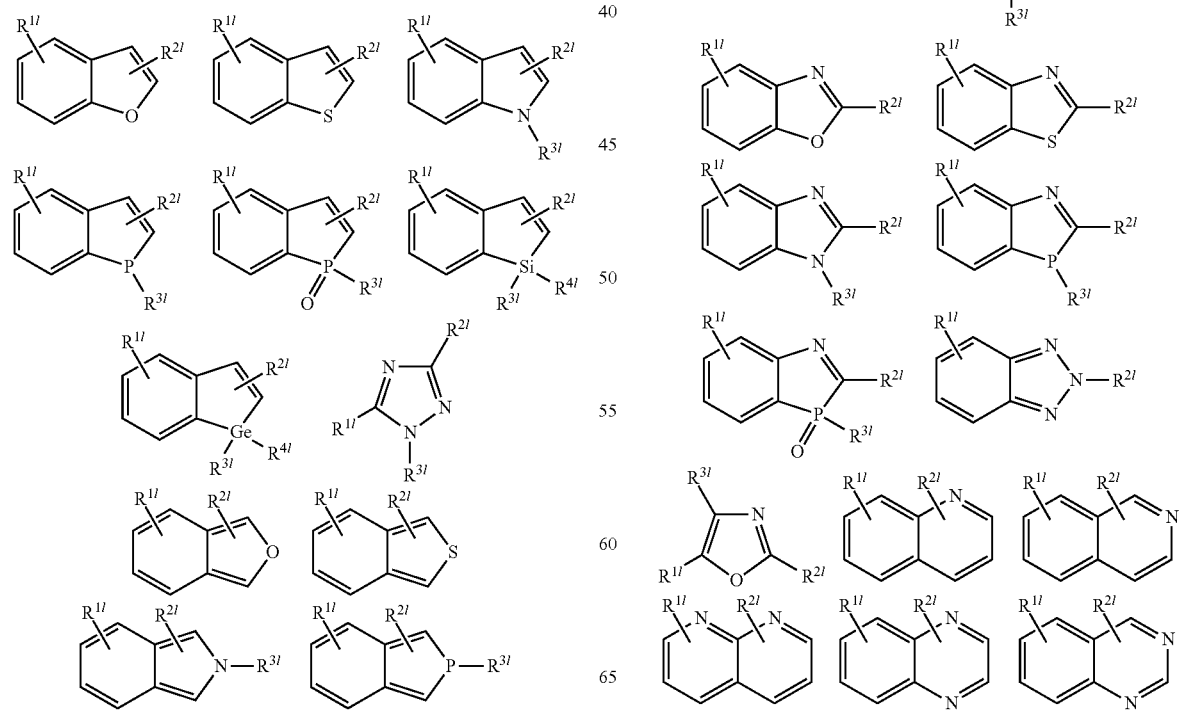

-continued
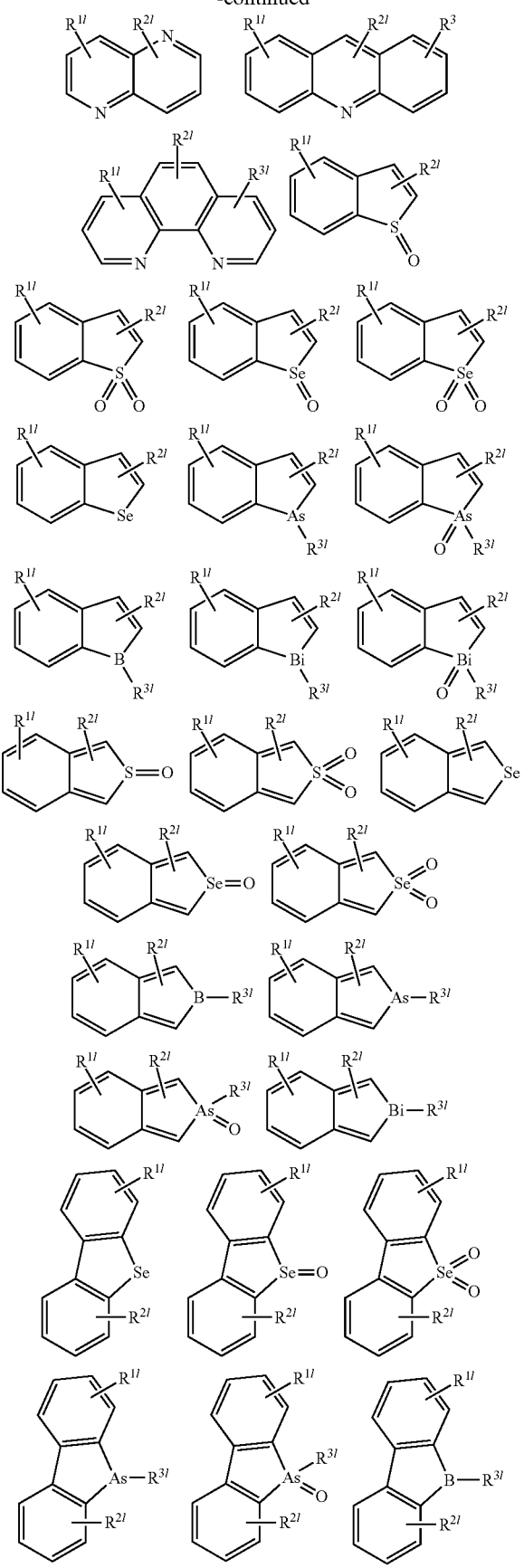
-continued
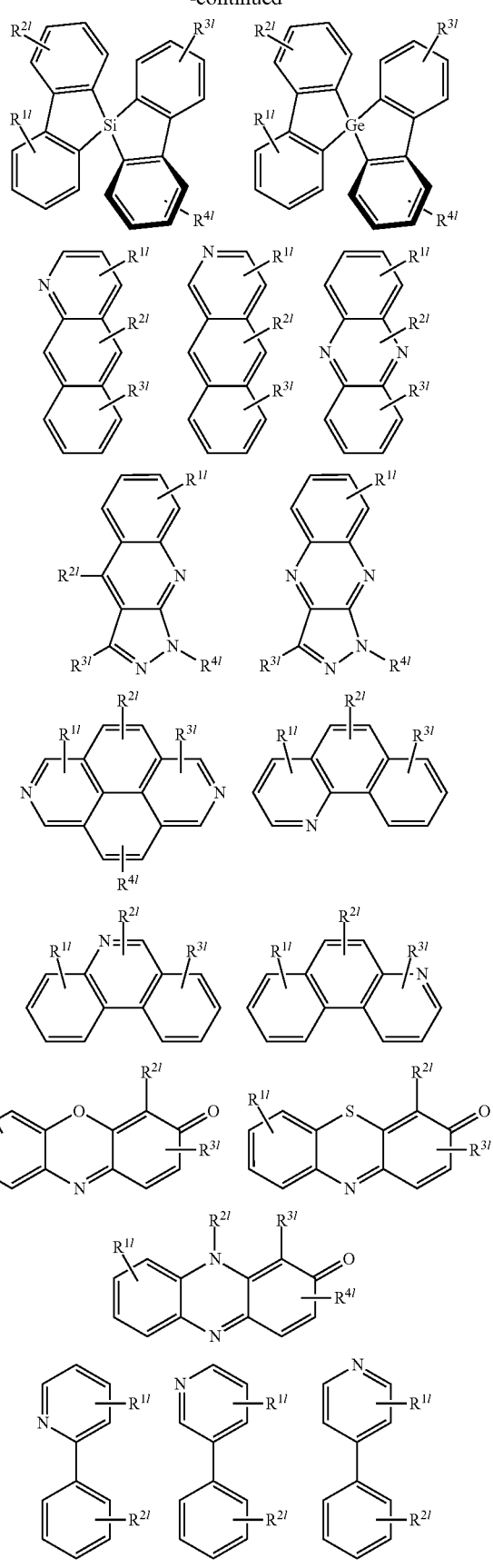

741
-continued
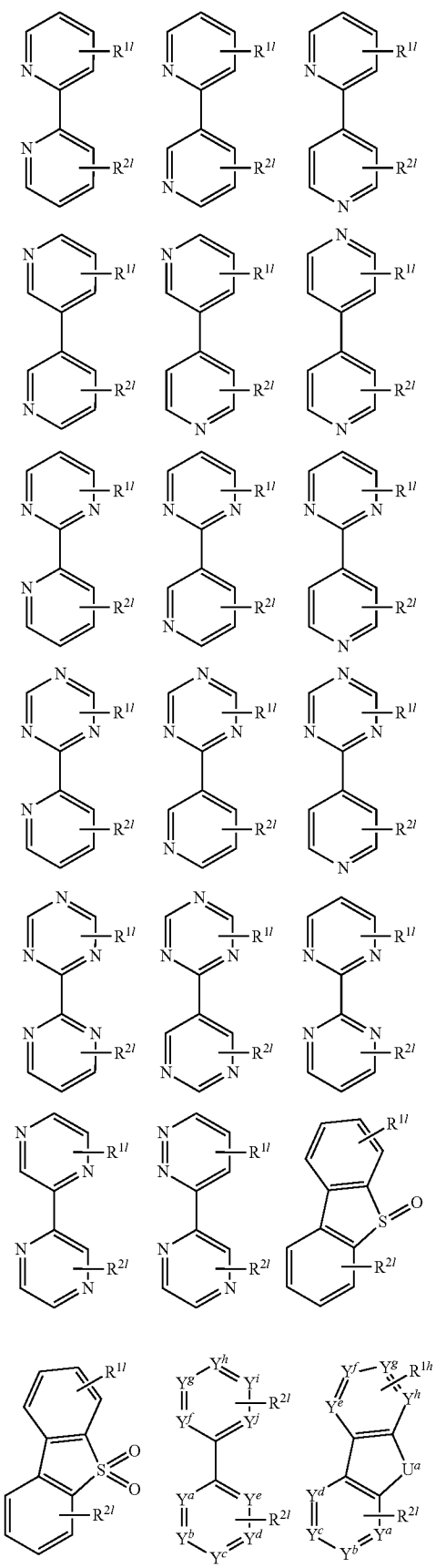
742
-continued
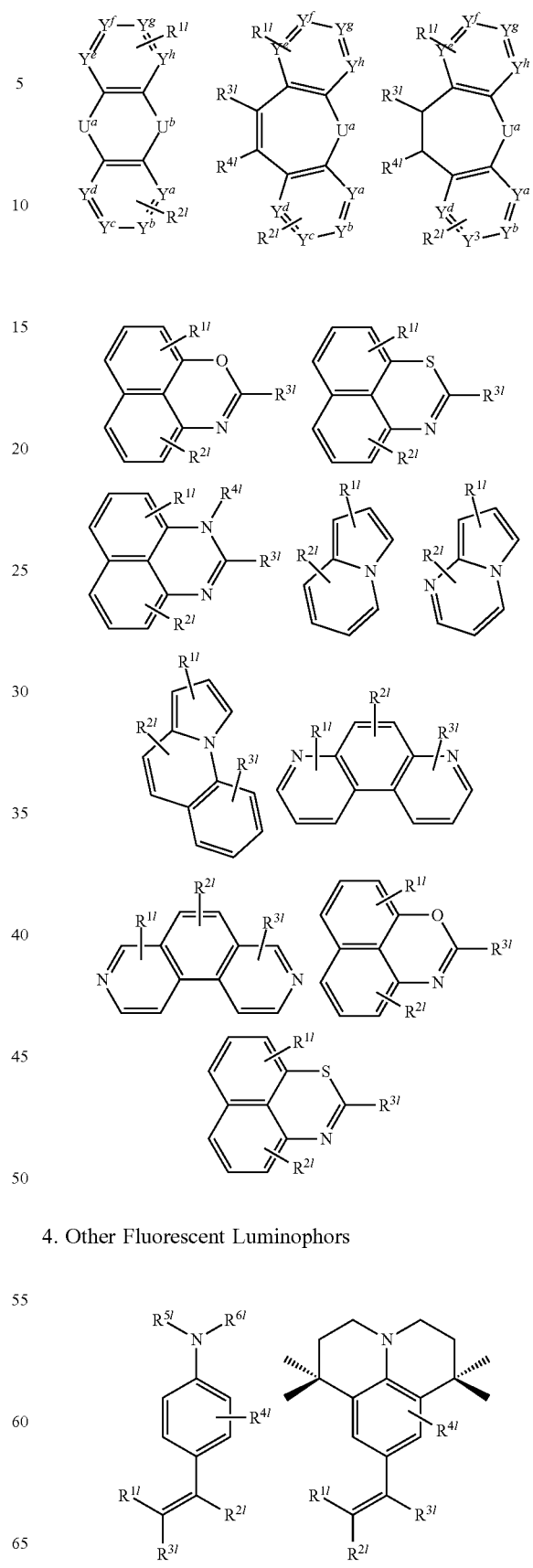
4. Other Fluorescent Luminophors
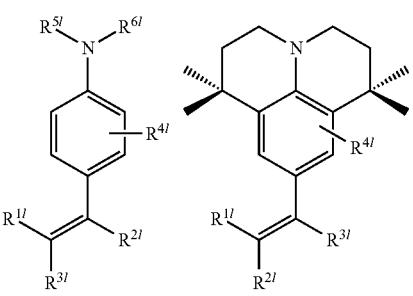

743
-continued
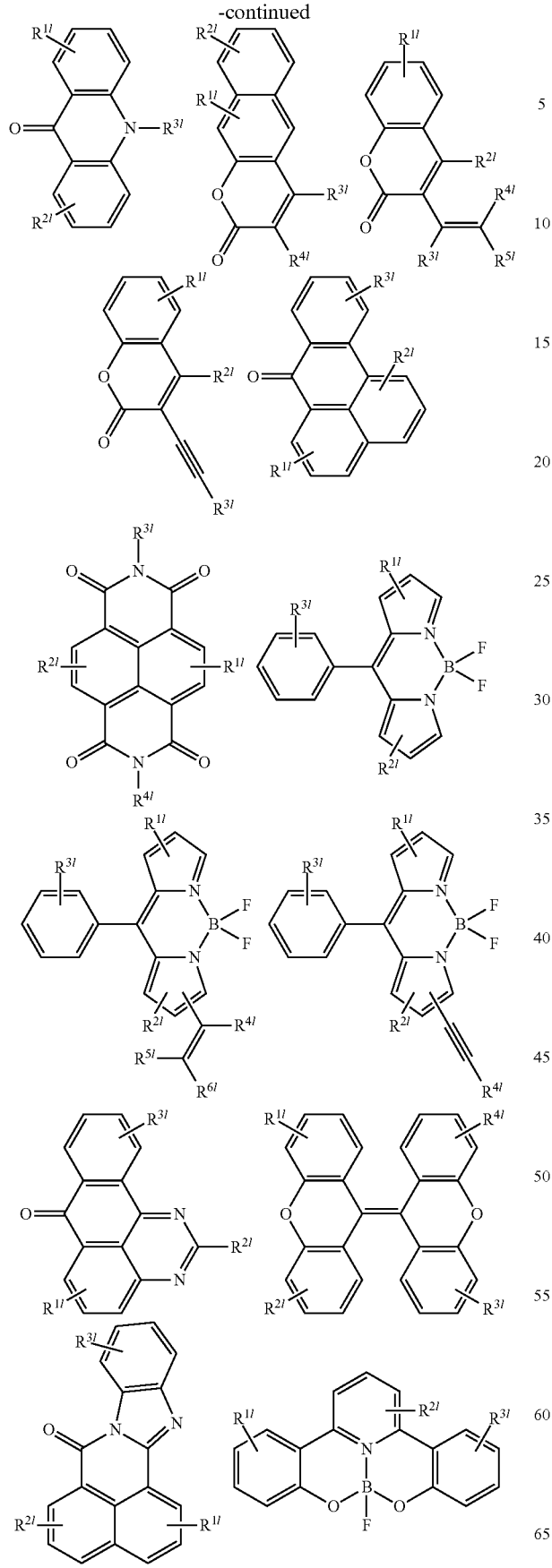
744
-continued
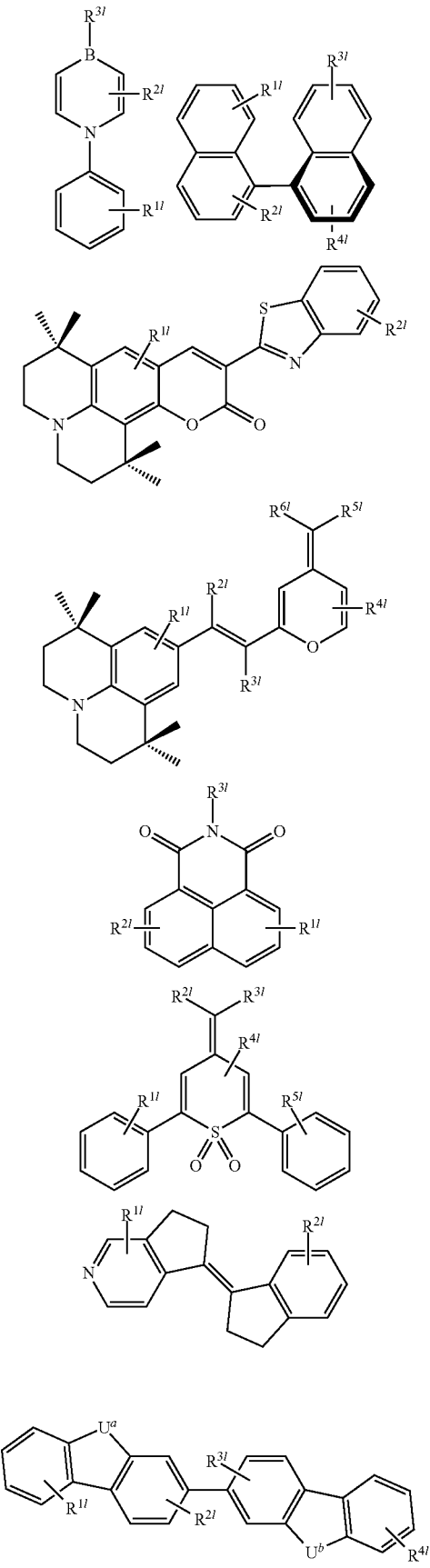

-continued

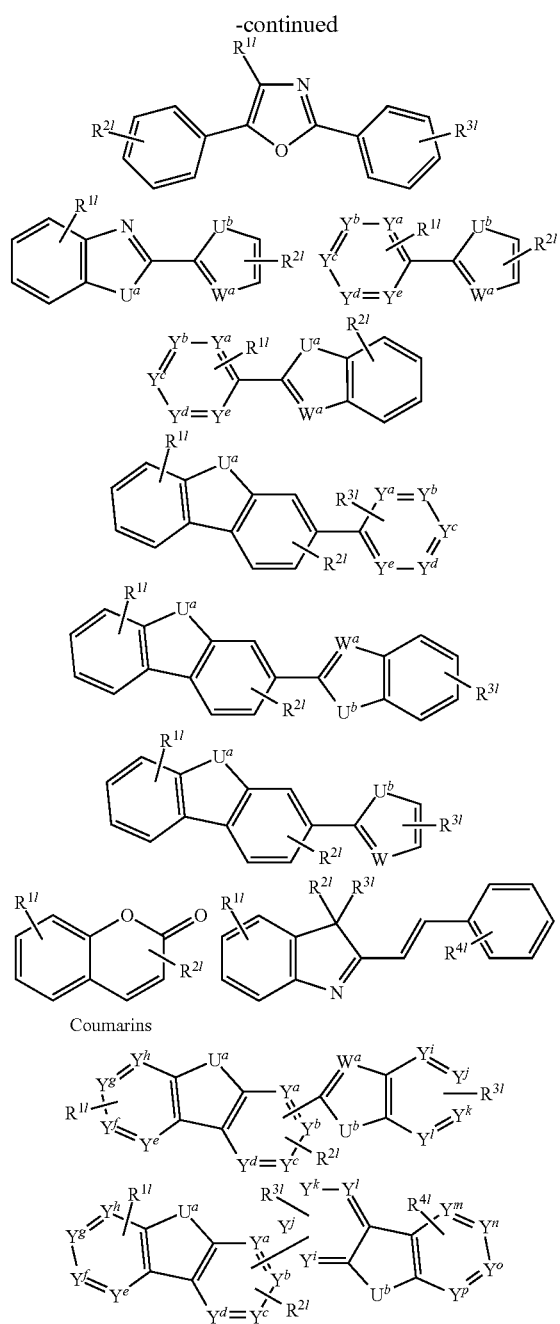

each of $R^{1l}$, $R^{2l}$, $R^{3l}$, $R^{4l}$, $R^{5l}$, $R^{6l}$, $R^{7l}$, $R^{8l}$, $R^{9l}$ and $R^{10l}$ is independently a mono-, di-, or tri-substitution, and each of $R^{1l}$, $R^{2l}$, $R^{3l}$, $R^{4l}$, $R^{5l}$, $R^{6l}$, $R^{7l}$, $R^{8l}$, $R^{9l}$ and $R^{10l}$, if present, is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, each of $Y^a$, $Y^b$, $Y^c$, $Y^d$, $Y^e$, $Y^f$, $Y^g$, $Y^h$, $Y^i$, $Y^j$, $Y^k$, $Y^l$, $Y^m$, $Y^n$, $Y^o$, and $Y^p$, if present, is independently C, N or B, each of $U^a$ and $U^b$, if present, is independently $CH_2$, $CR^1R^2$, C=O, $CH_2$, $SiR^1R^2$, $GeH_2$, $GeR^1R^2$, NH, $NR^3$, PH, $PR^3$, $R^3P$=O, $AsR^3$, $R^3As$=O, O, S, S=O, $SO_2$, Se, Se=O, $SeO_2$, BH, $BR^3$, $R^3Bi$=O, BiH, or $BiR^3$, each of W, $W^a$, and $W^b$, if present, is independently CH, $CR^1$, $SiR^1$, GeH, $GeR^1$, N, P, B, Bi, or Bi=O, $A^1$ is O, $A^2$ is O, N, or $NR^3$, each $V^1$ and $V^4$ is N;

each $V^2$ and $V^3$ is C, each $Y^1$, $Y^2$, and $Y^3$ is C, $Y^4$ is N, $R^a$ is present or absent, wherein $R^b$ is present or absent, wherein $R^c$ is present or absent, wherein $R^d$ is present or absent, and if present each of $R^a$, $R^b$, $R^c$, and $R^d$ independently represents mono-, di-, or tri-substitutions, and wherein each of $R^a$, $R^b$, $R^c$, and $R^d$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, or two $R^a$, two $R^b$, two $R^c$, or two $R^d$ optionally combine together form a ring; and each of $R^1$, $R^2$, and $R^3$ is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof; wherein each pair of $R^3$ and $R^c$, $R^3$ and $R^d$, $R^3$ and $L^3$, and $R^3$ and $L^4$ optionally combine together form a ring.

2. The compound of claim 1, wherein the compound has the structure of Formula III or Formula V:

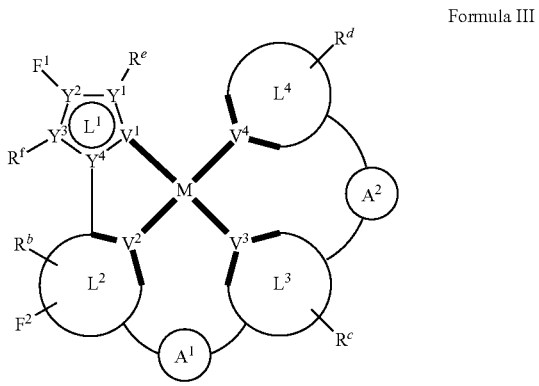

Formula III

-continued

Formula V

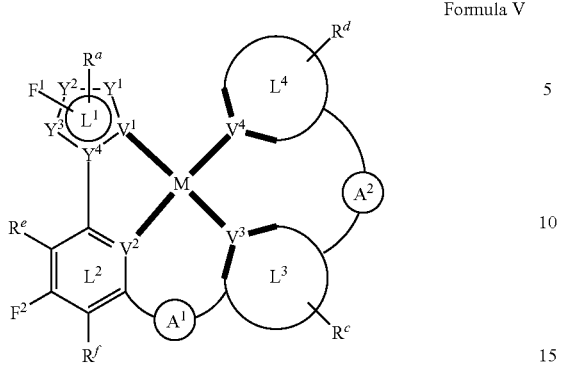

wherein each of $R^e$ and $R^f$ is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

3. The compound of claim 1, wherein the compound has the structure of Formula VII:

Formula VII

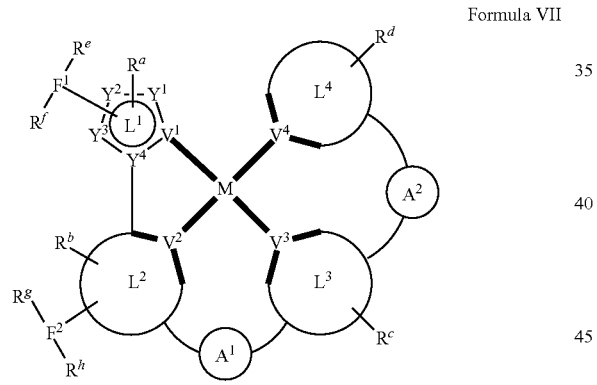

wherein, if $F^1$ is present, $R^e$ and $R^f$ are on the ortho-positions of the bond between $F^1$ and $L^1$, wherein, if $F^2$ is present, $R^g$ and $R^h$ are on the ortho-positions of the bond between $F^2$ and $L^2$, wherein each of $R^e$, $R^f$, $R^g$, and $R^h$, if present, is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

4. The compound of claim 1, wherein the compound has the structure of anyone of Formulas A1-A23:

A-1

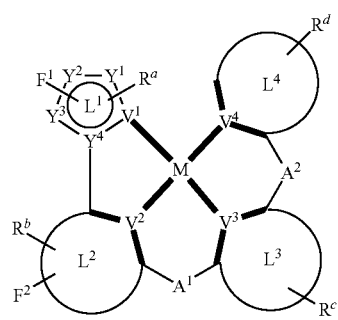

A-2

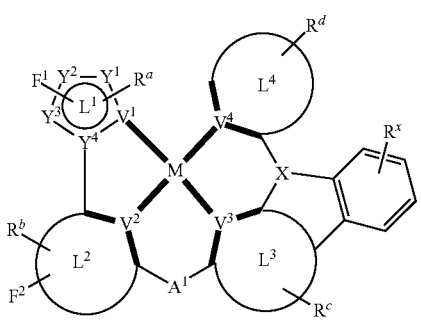

A-3

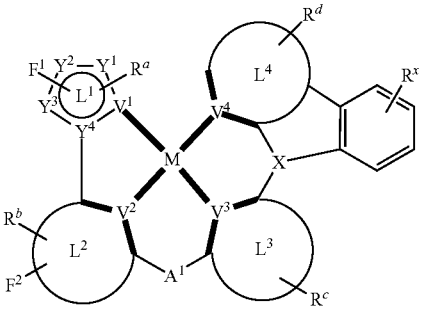

A-4

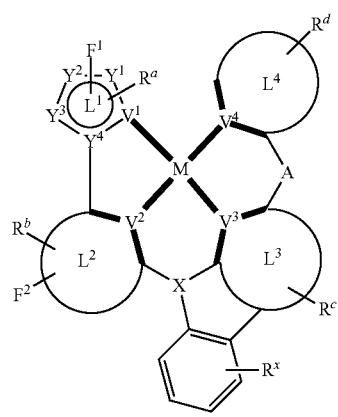

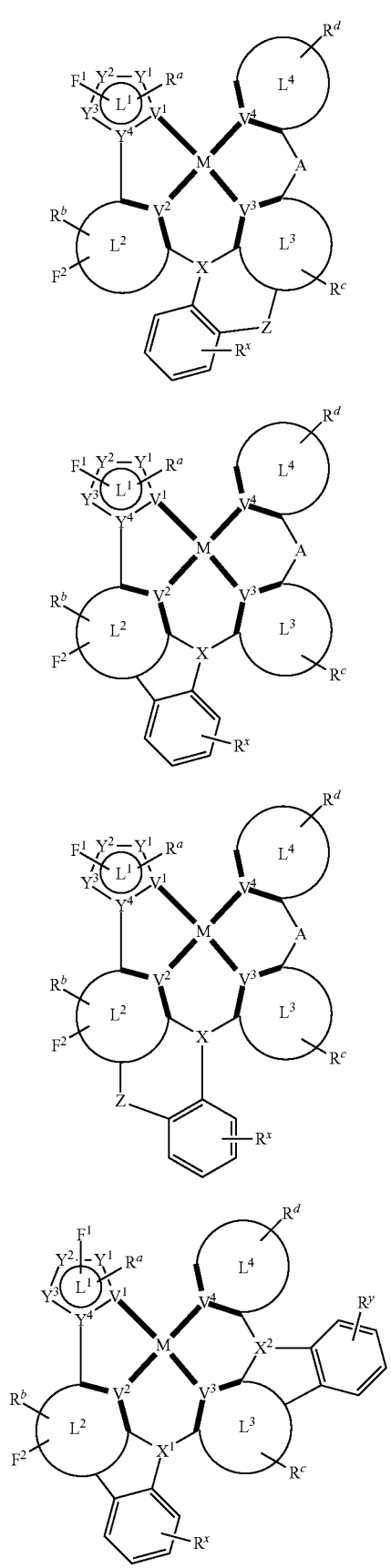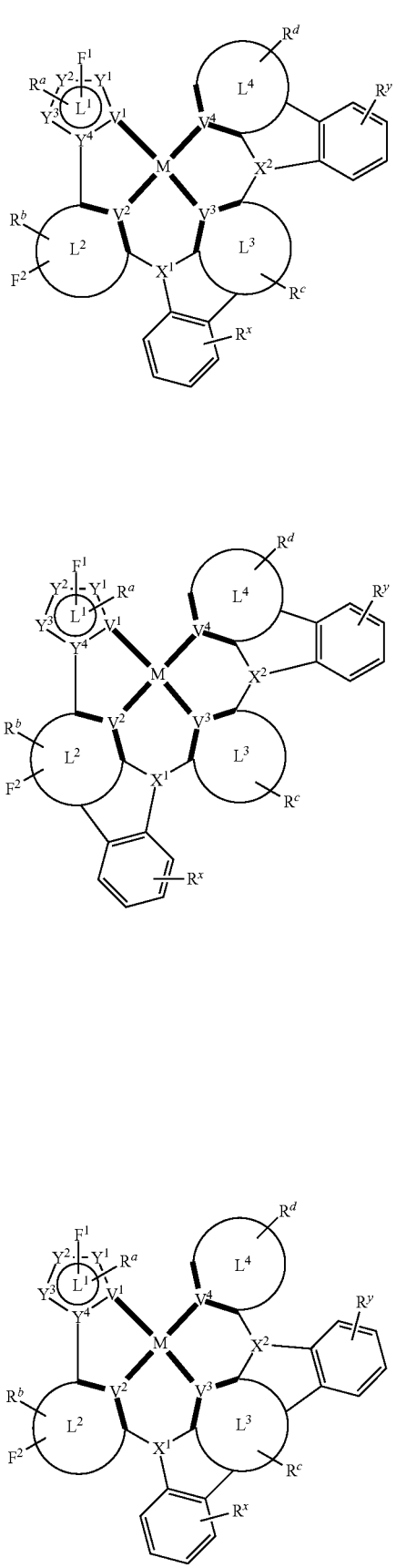

A-12
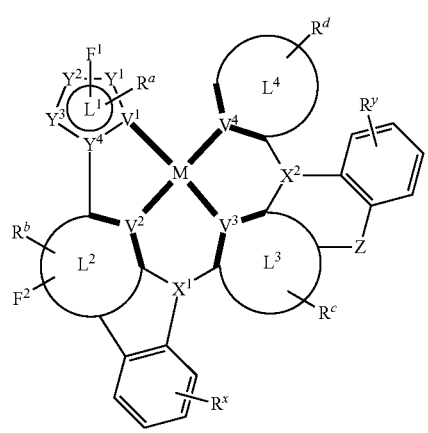
A-13
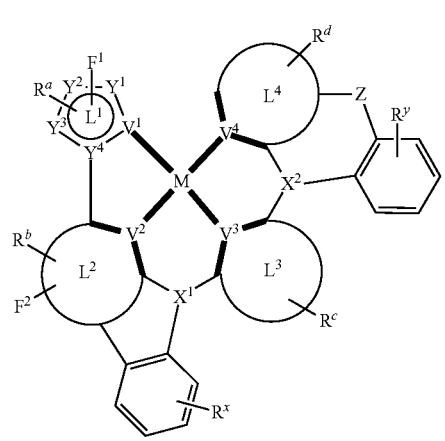
A-14
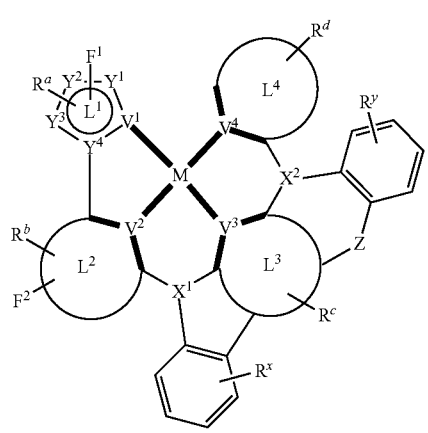
A-15
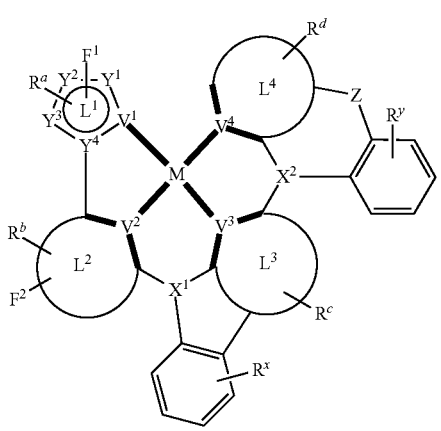
A-16
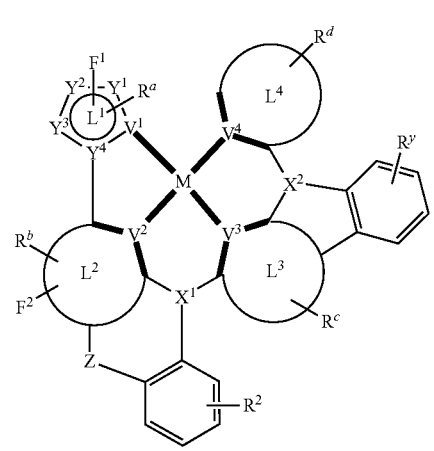
A-17
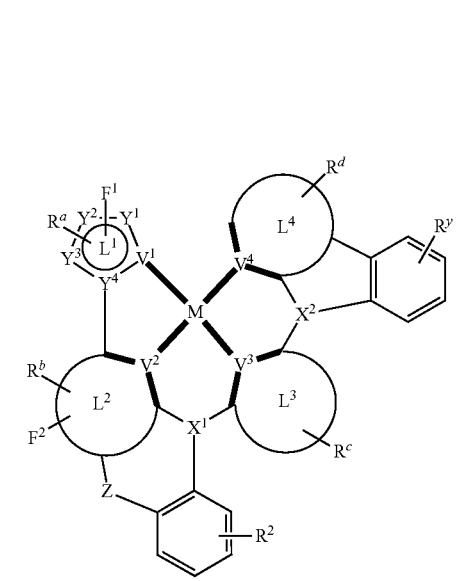

A-18
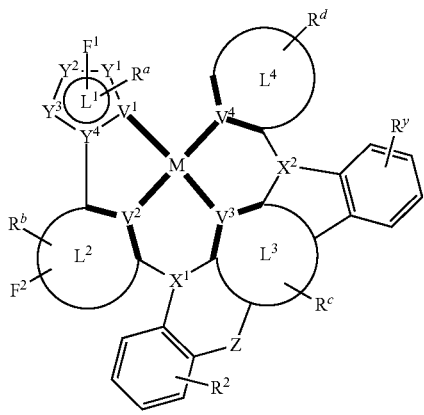

A-19
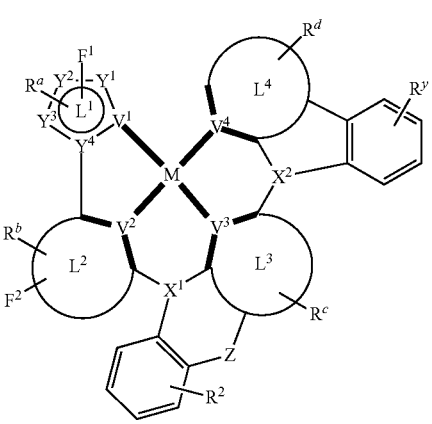

A-20
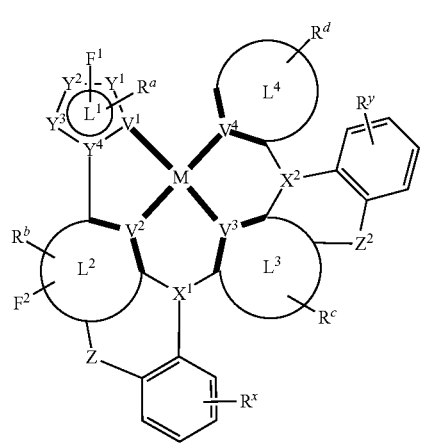

A-21
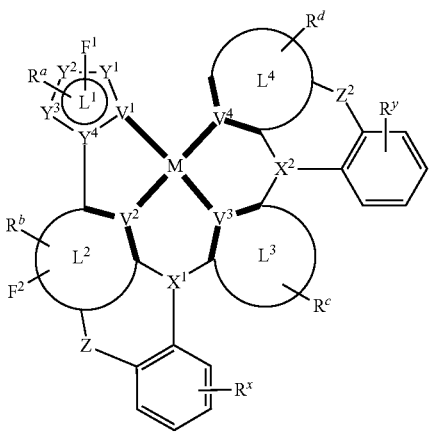

A-22
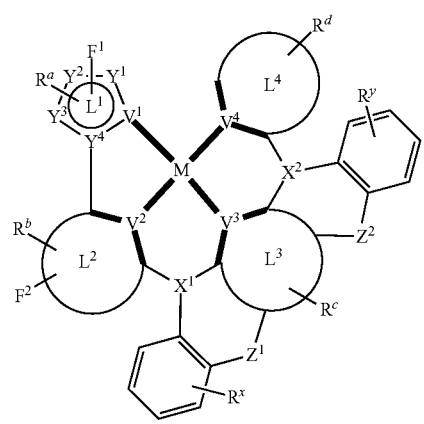

A-23
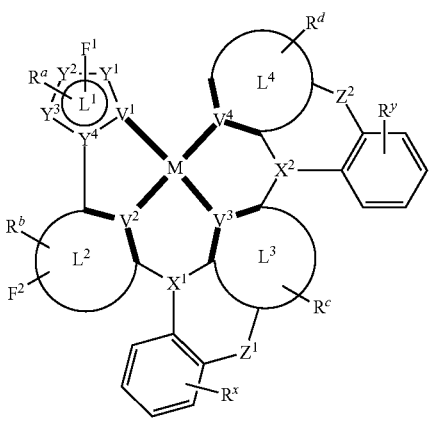

wherein each A, $A^1$, X and $X^1$ between ring $L^2$ and $L^3$ is O, each A, $A^2$, X, and $X^2$ between rings $L^3$ and $L^4$ is N or O, wherein each Z, $Z^1$, and $Z^2$ is independently a linking atom or group, wherein $R^x$ is present or absent, wherein $R^y$ is present or absent, and if present each of $R^x$ and $R^y$ independently represents mono-, di- or tri-substitutions, and wherein each of $R^x$ and $R^y$ present is independently deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

5. The compound of claim 1, wherein the compound has a neutral charge.

6. The compound of claim 4, wherein each of Z, $Z^1$, and $Z^2$ is independently selected from the following:

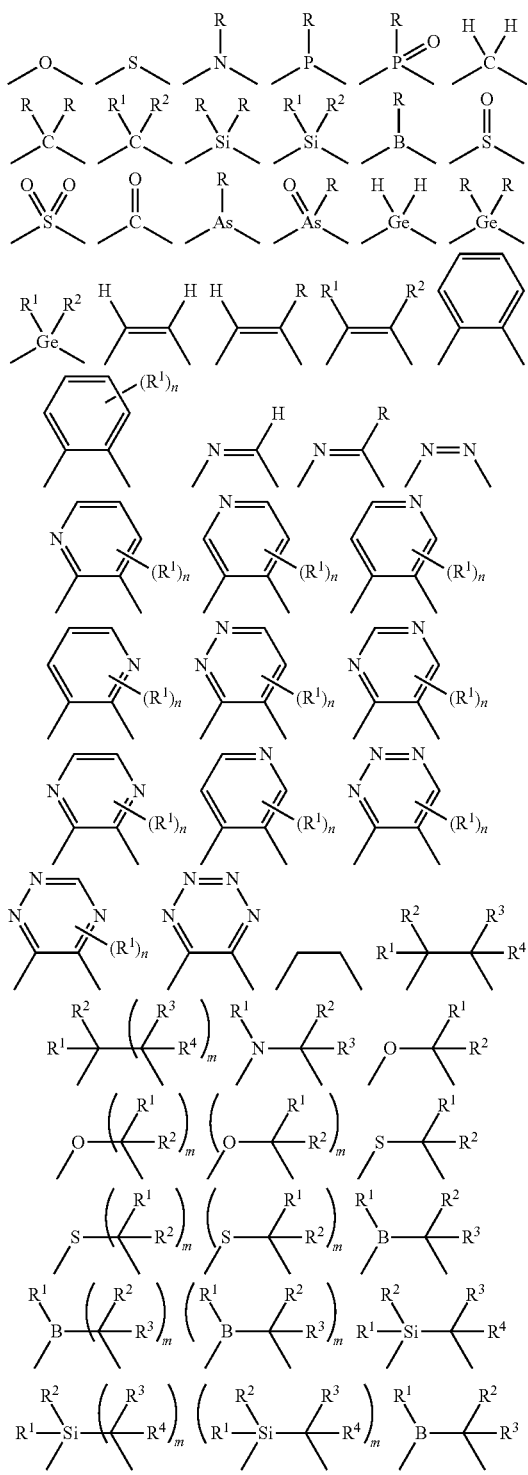

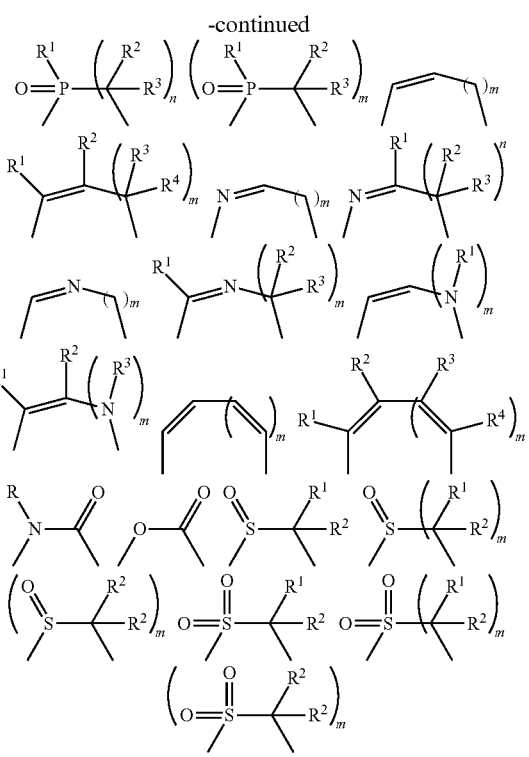

wherein n is an integer from 0 to 4,
wherein m is an integer from 1 to 3,
wherein each of R, $R^1$, $R^2$, $R^3$, and $R^4$ is independently hydrogen, deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

7. The compound of claim 1, wherein $F^1$, if present, is covalently bonded to $L^1$ directly, $F^2$, if present, is covalently bonded to $L^2$ directly, or a combination thereof.

8. The compound of claim 7, wherein $F^1$, if present, is covalently bonded to $L^1$ by a linking atom or linking group, $F^2$, if present, is covalently bonded to $L^2$ by a linking atom or linking group.

9. The compound of claim 8, wherein each linking atom or linking group is independently selected from the following:

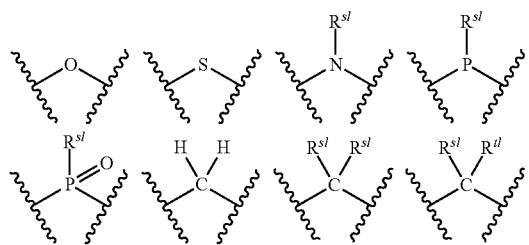

-continued

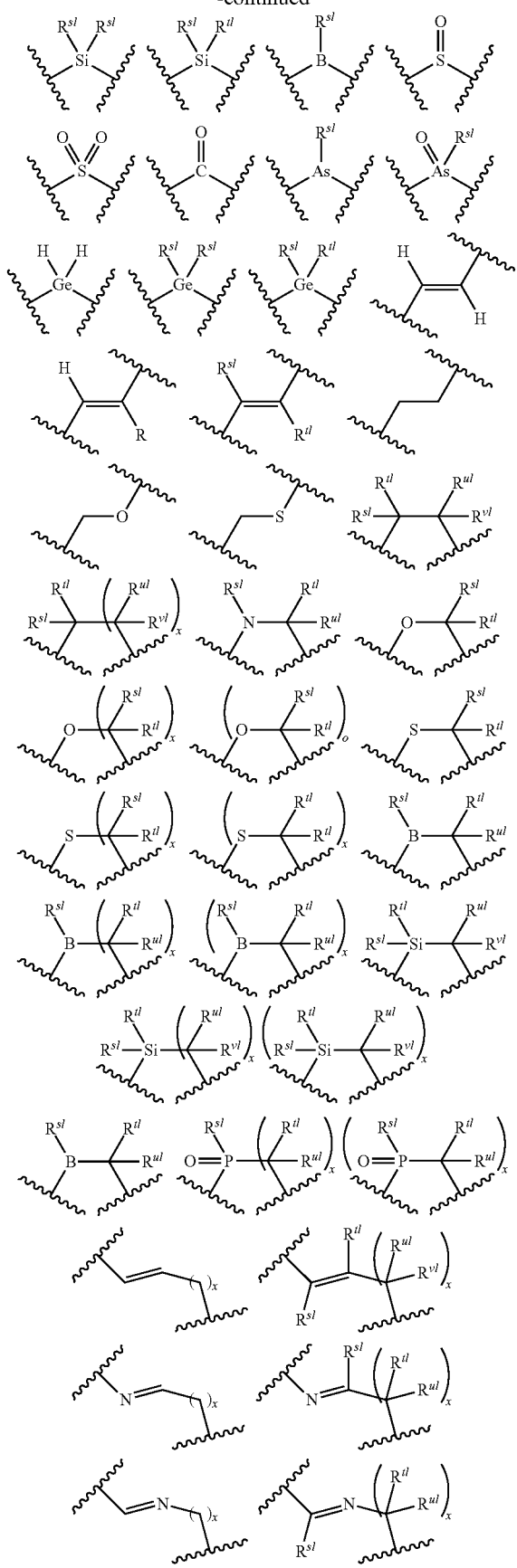

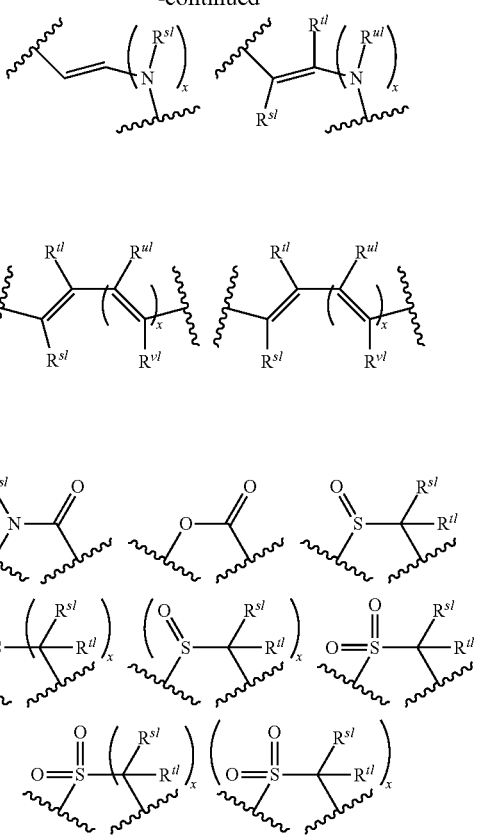

wherein x is an integer from 1 to 10, wherein each of $R^{sl}$, $R^{tl}$, $R^{ul}$, and $R^{vl}$, if present, is independently hydrogen, deuterium, halogen, hydroxyl, thiol, nitro, cyano, nitrile, isonitrile, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

10. An emitter comprising the compound of claim 1, wherein the emitter is a delayed fluorescent and phosphorescent emitter.

11. An emitter comprising the compound claim 1, wherein the emitter is a phosphorescent emitter.

12. An emitter comprising the compound of claim 1, wherein the emitter is a delayed fluorescent emitter.

13. A light-emitting device comprising a compound of claim 1.

14. The light-emitting device of claim 13, wherein the compound demonstrates 100% internal quantum efficiency in the device settings.

15. The light emitting device of claim 13, wherein the device is an organic light emitting diode.

16. A compound represented by one of the following structures:

759
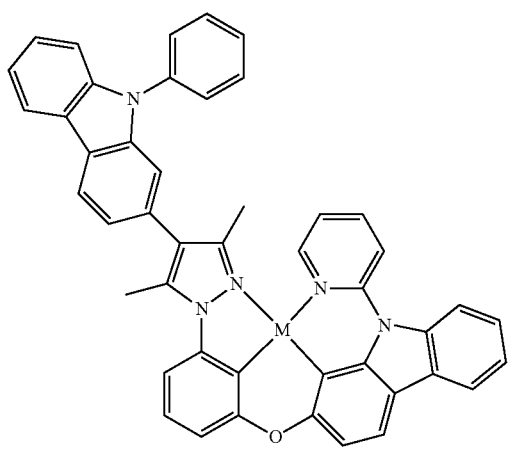
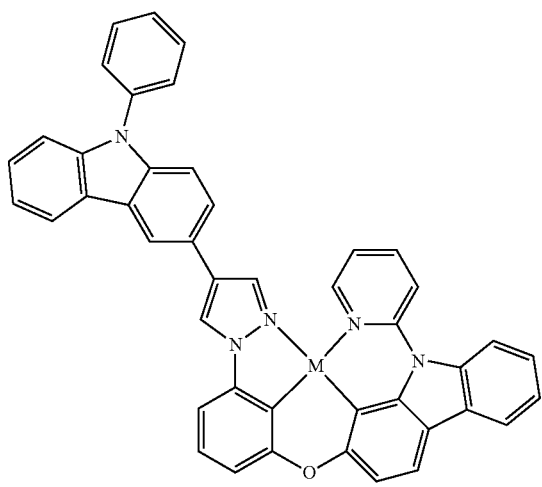
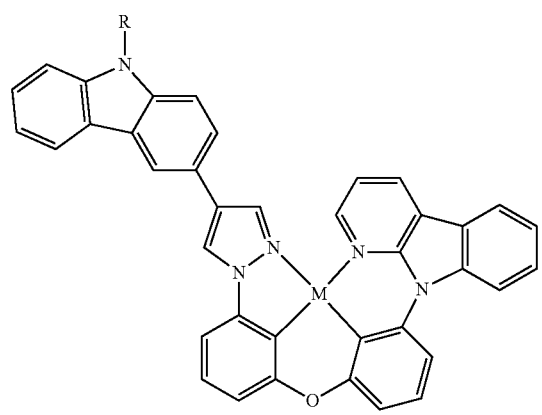
760
-continued
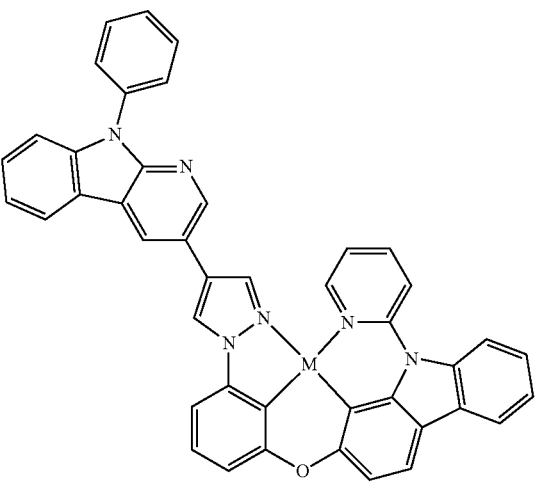
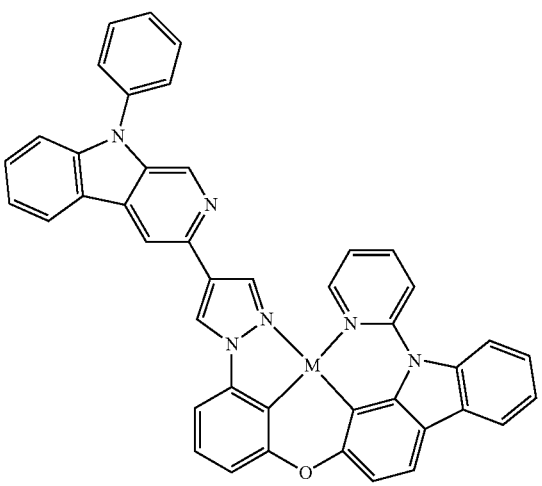
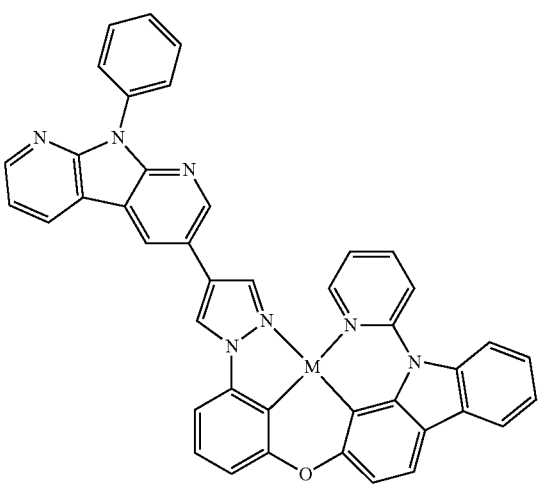

761
-continued
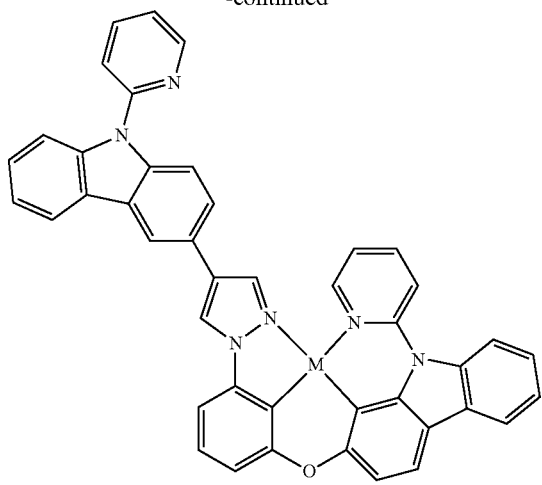
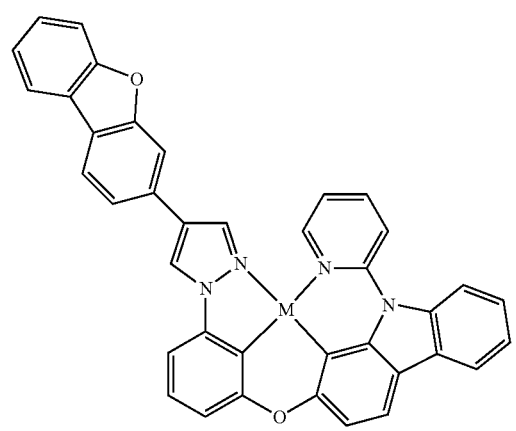
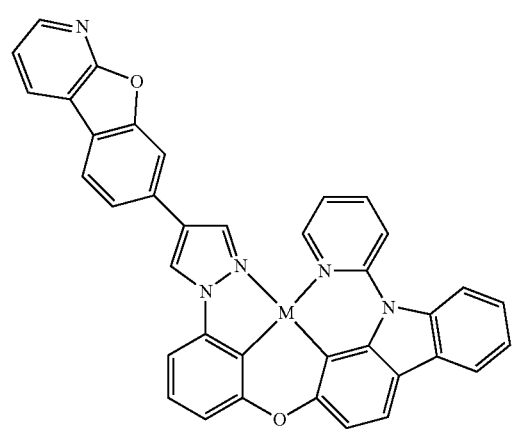
762
-continued
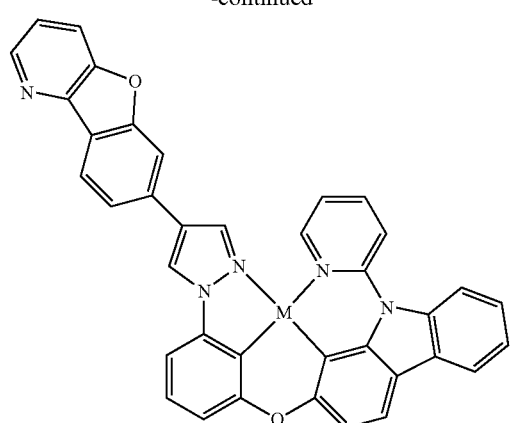
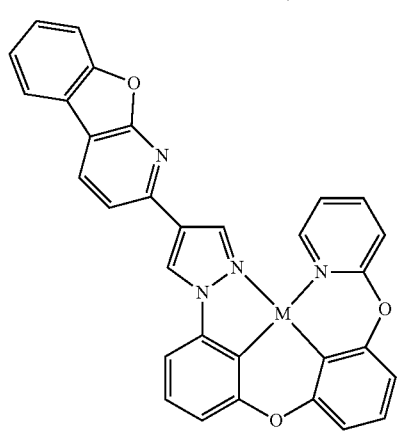
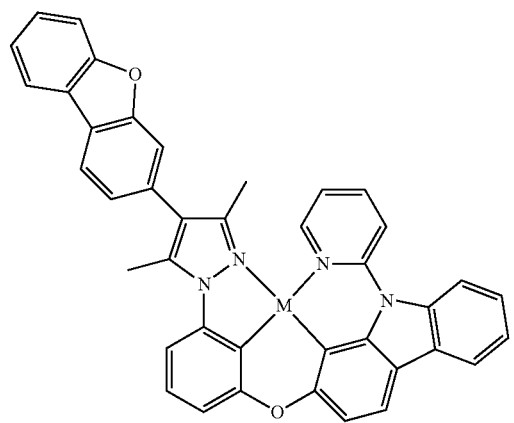
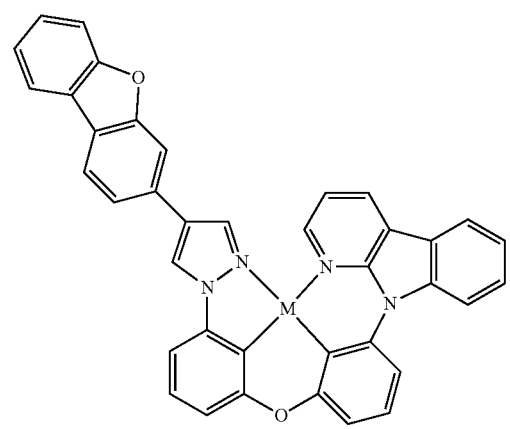

763
-continued
764
-continued
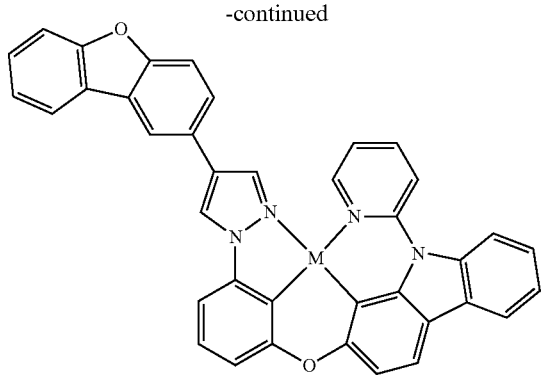
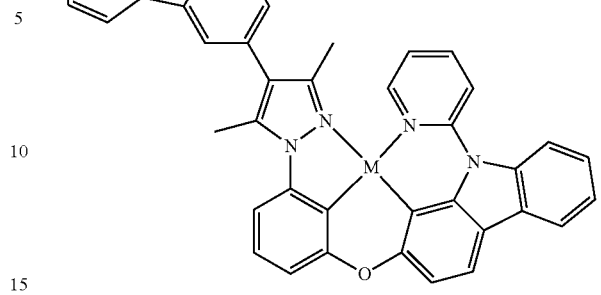
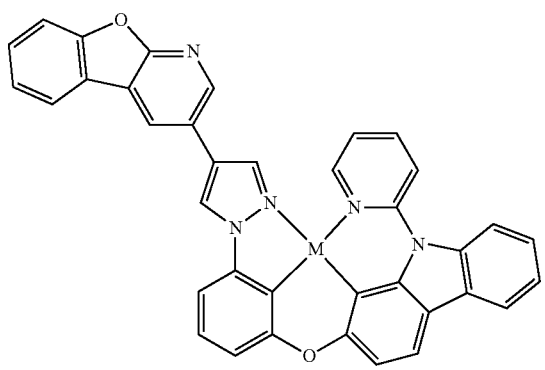
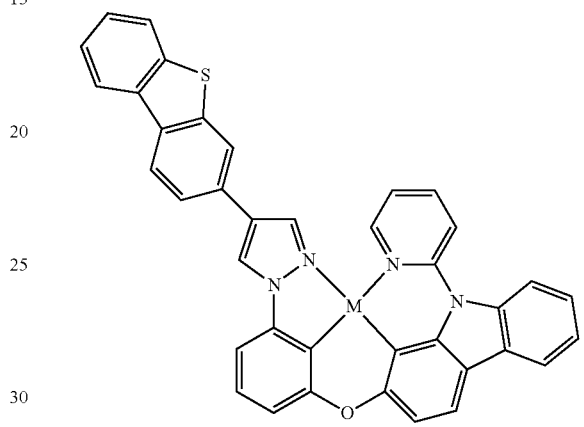
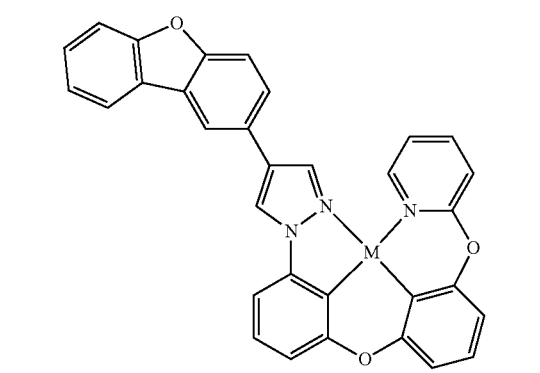
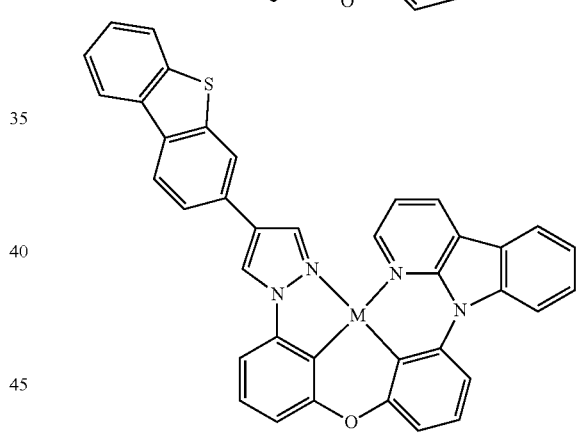
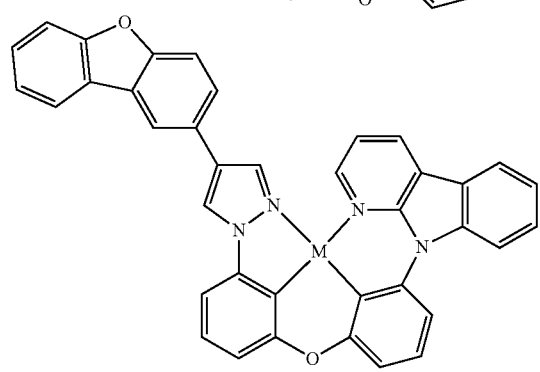
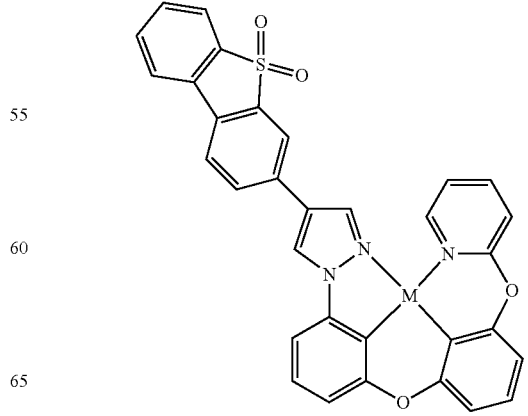

765
-continued
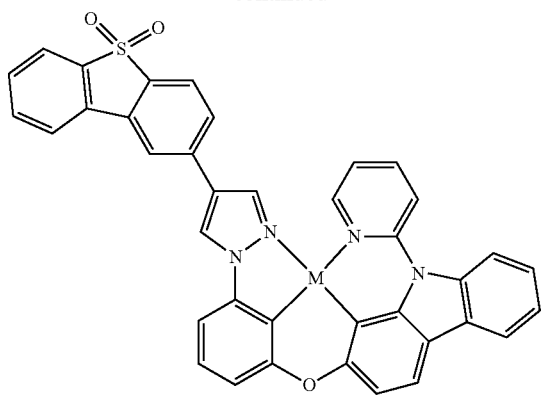
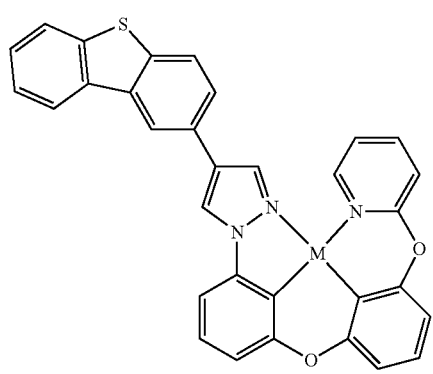
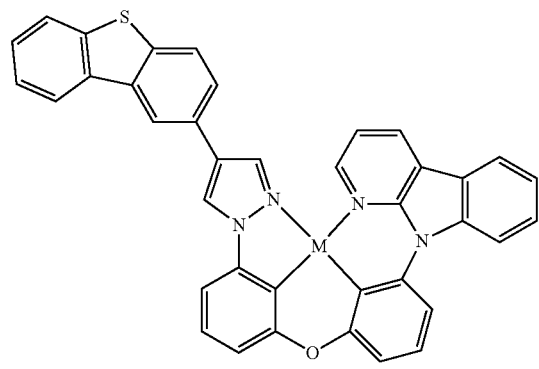
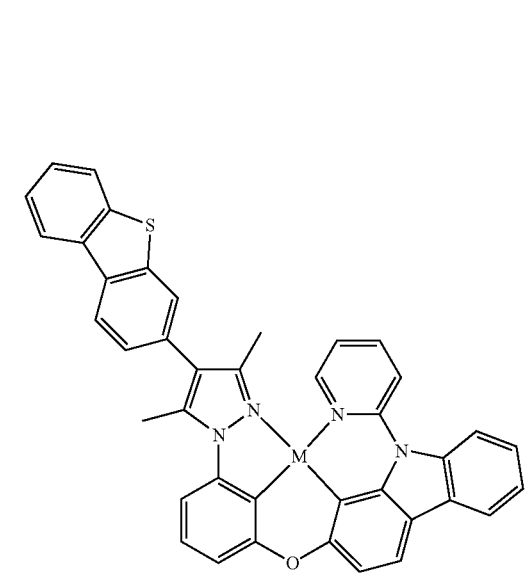
766
-continued
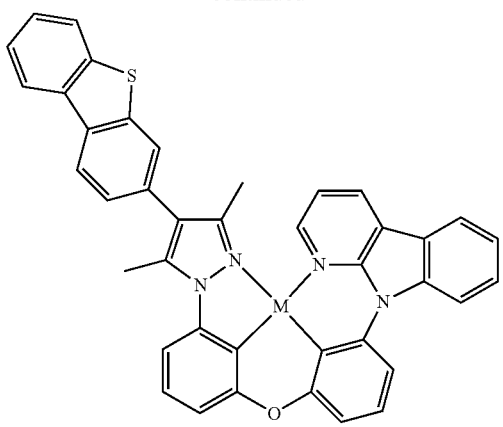
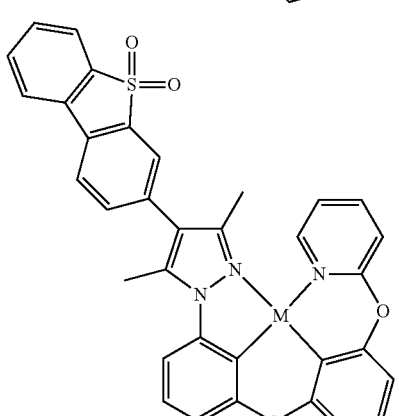
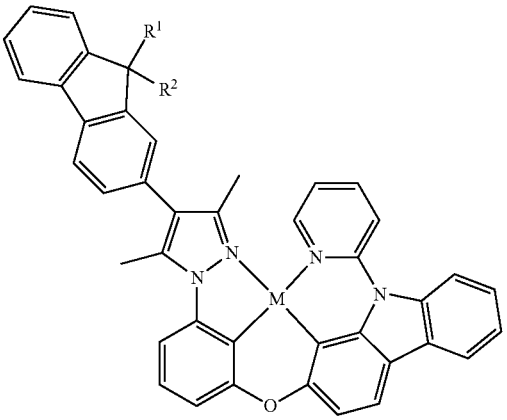
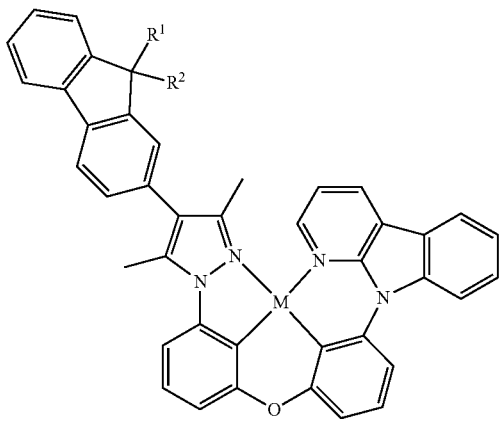

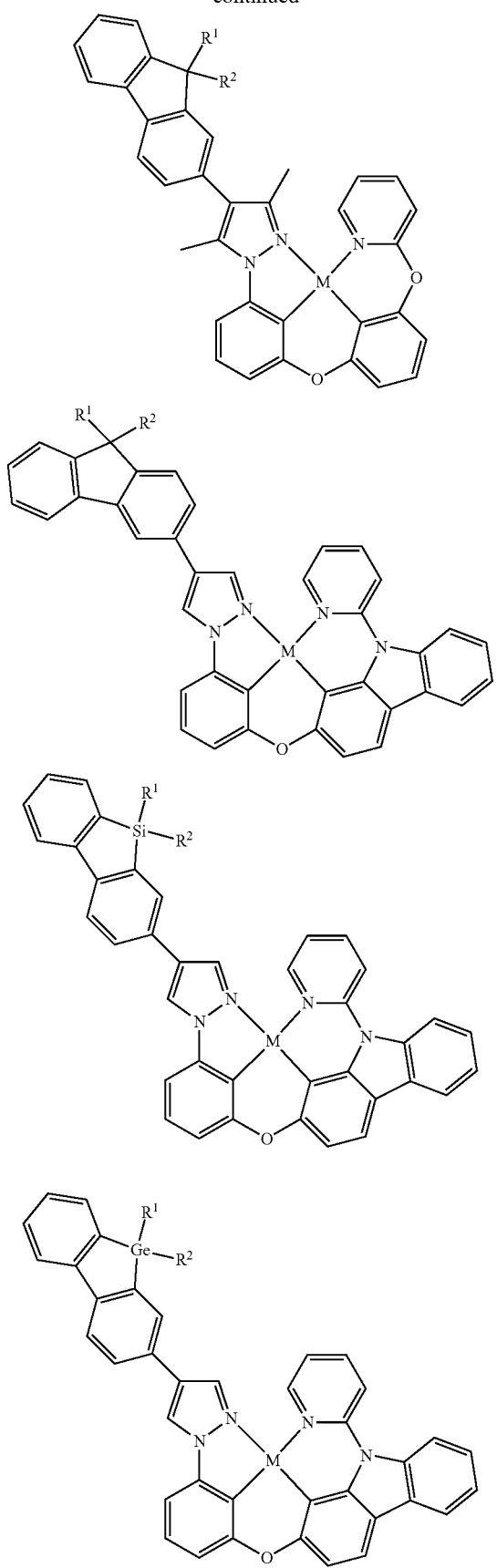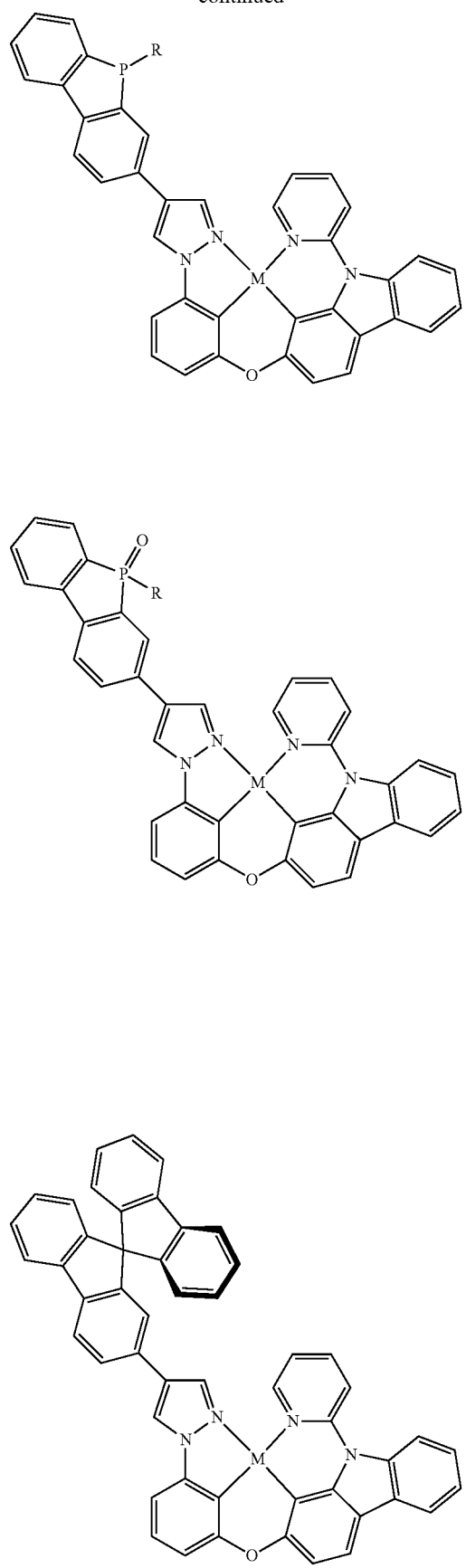

769
-continued
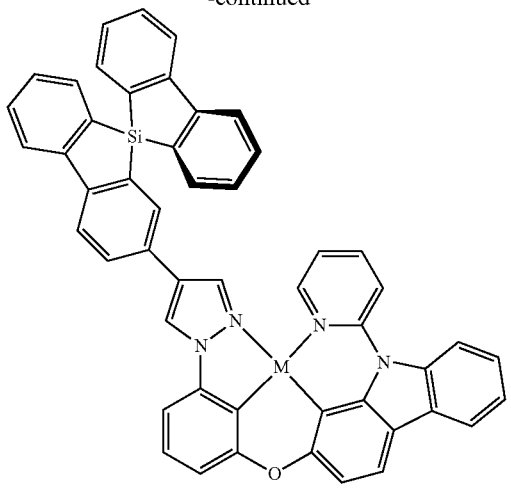
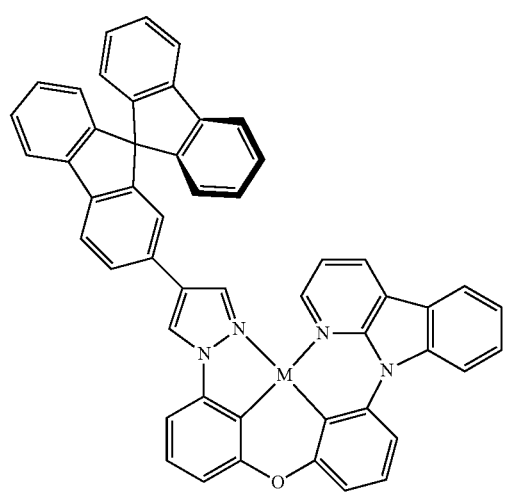
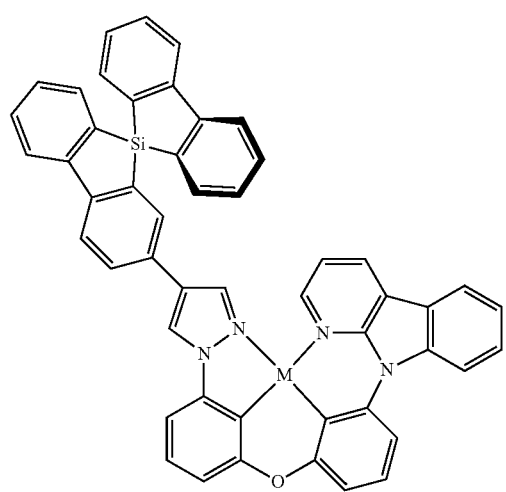
770
-continued
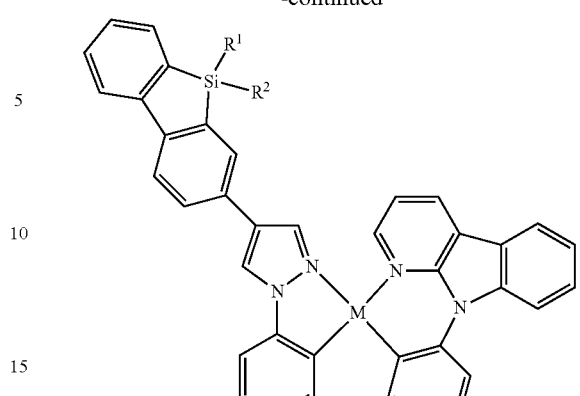
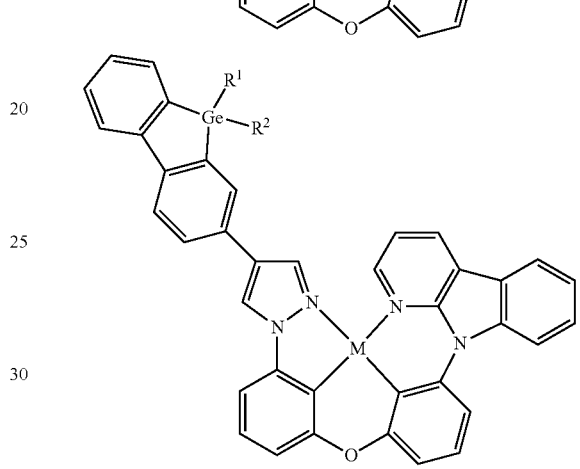
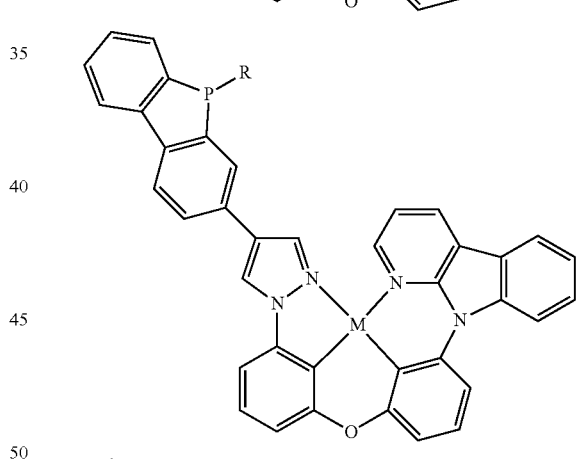
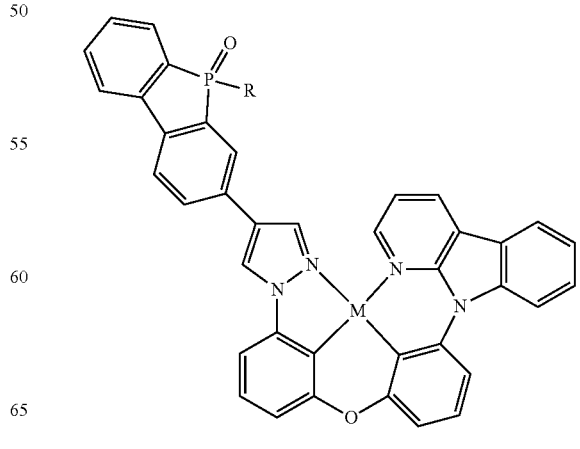

771
-continued
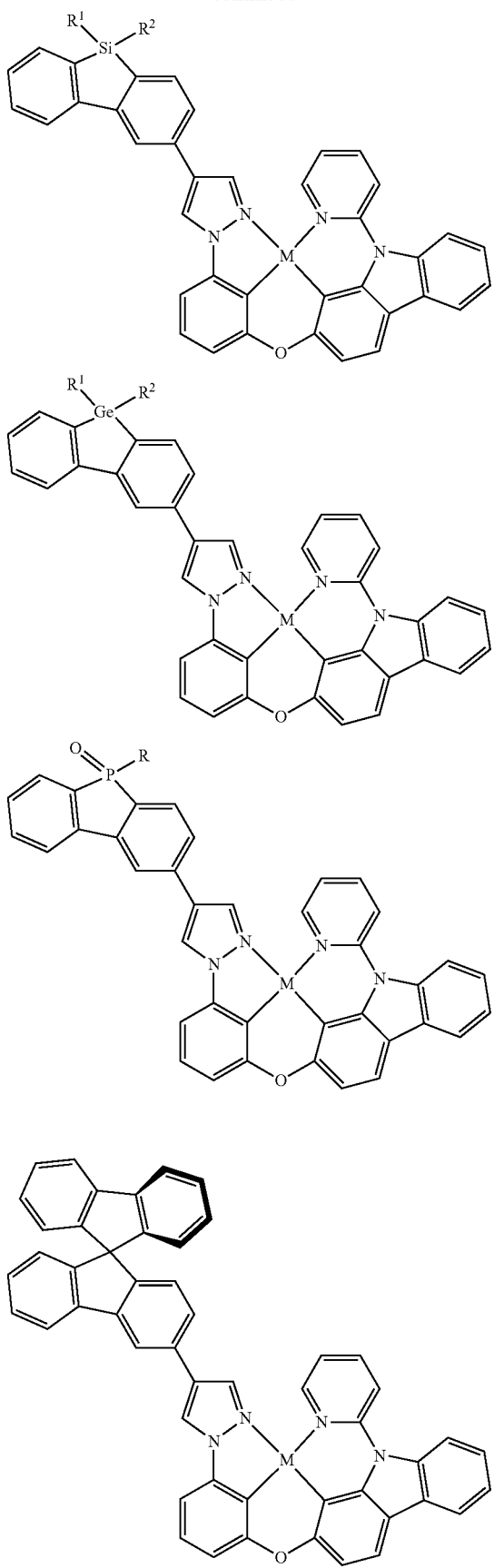
772
-continued
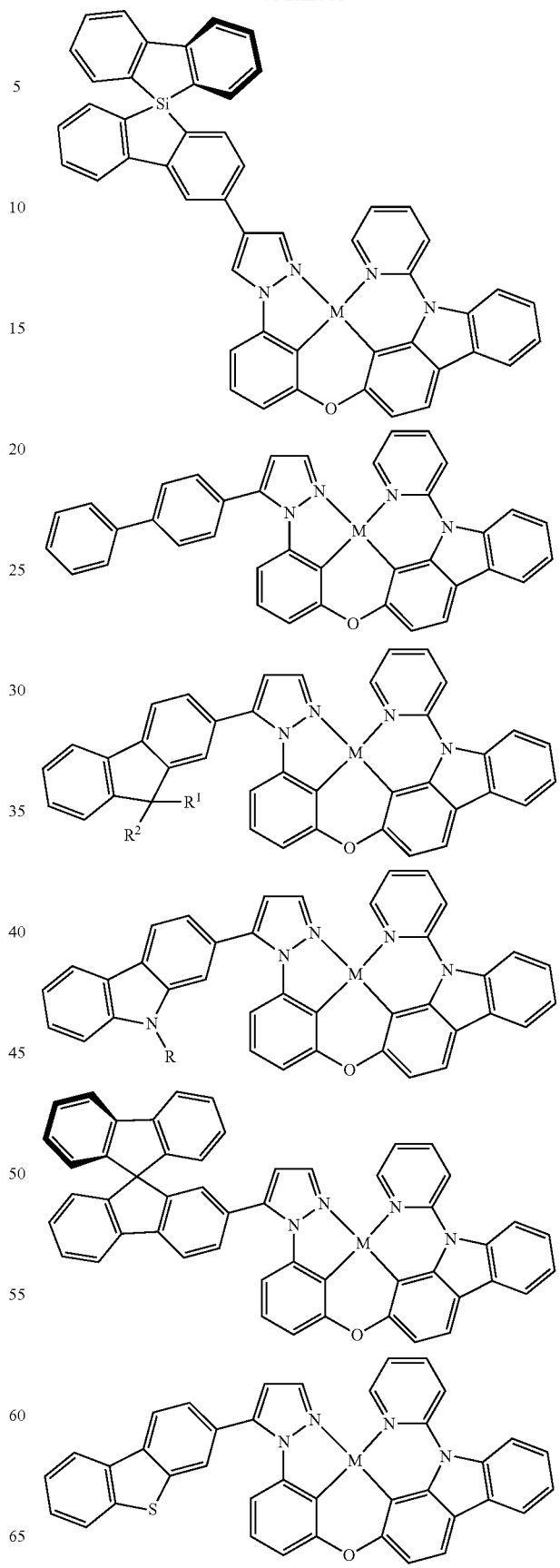

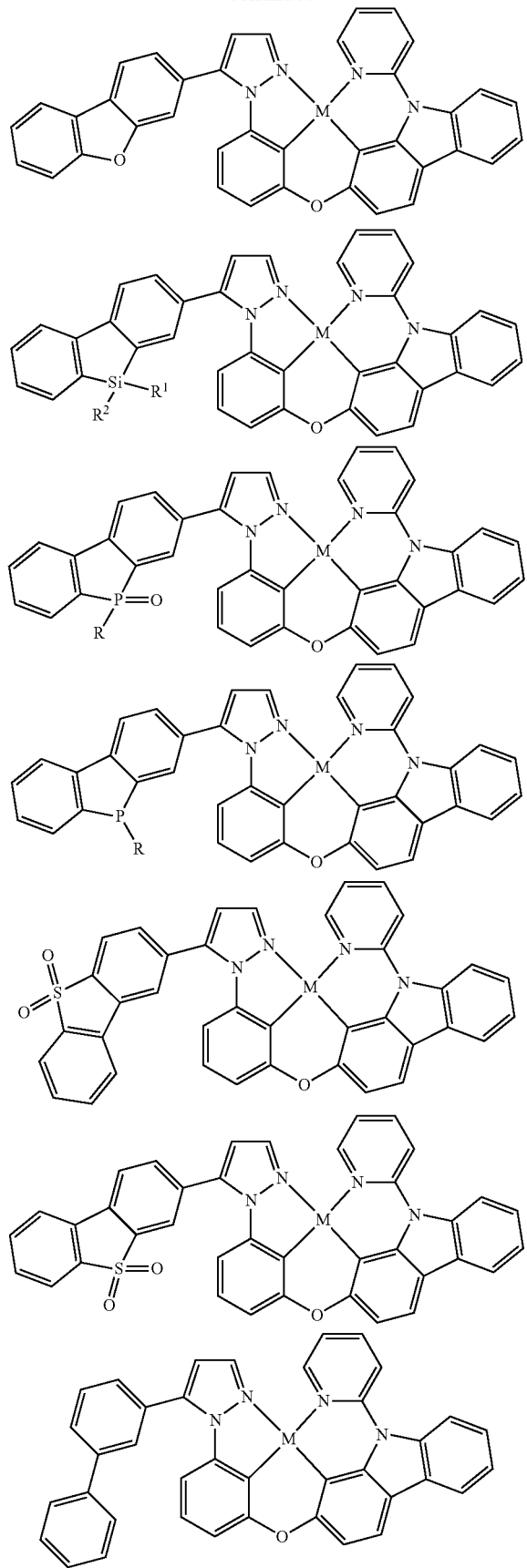
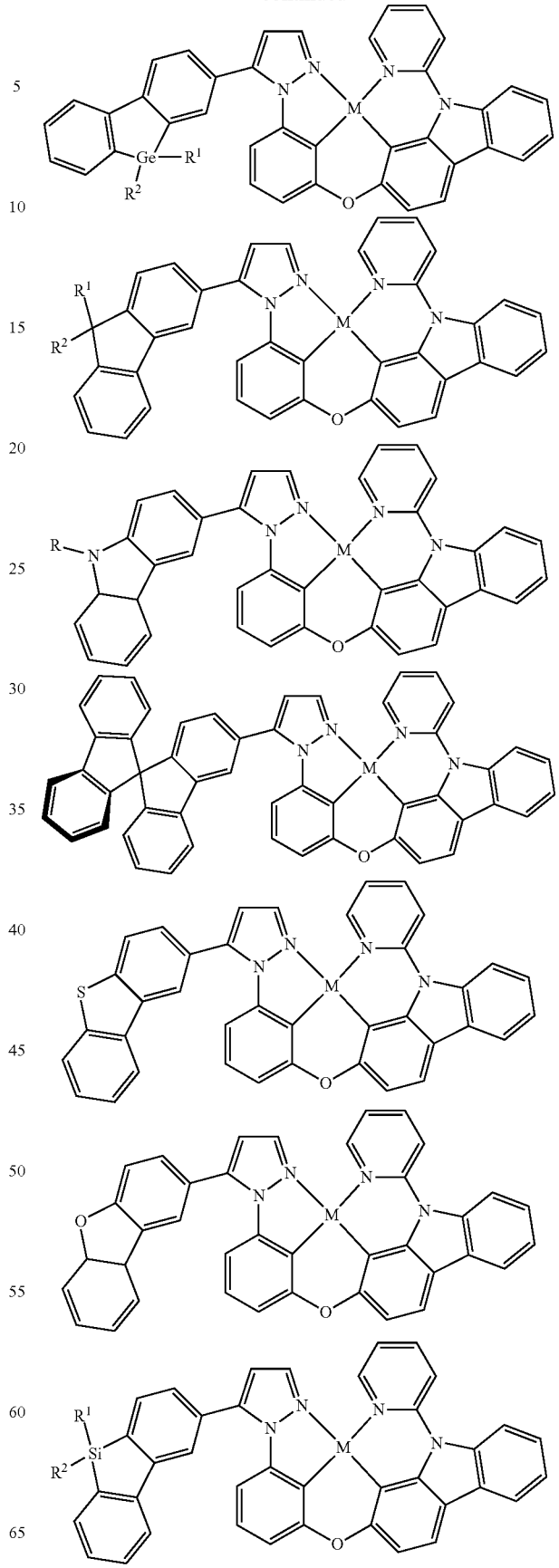

775
-continued
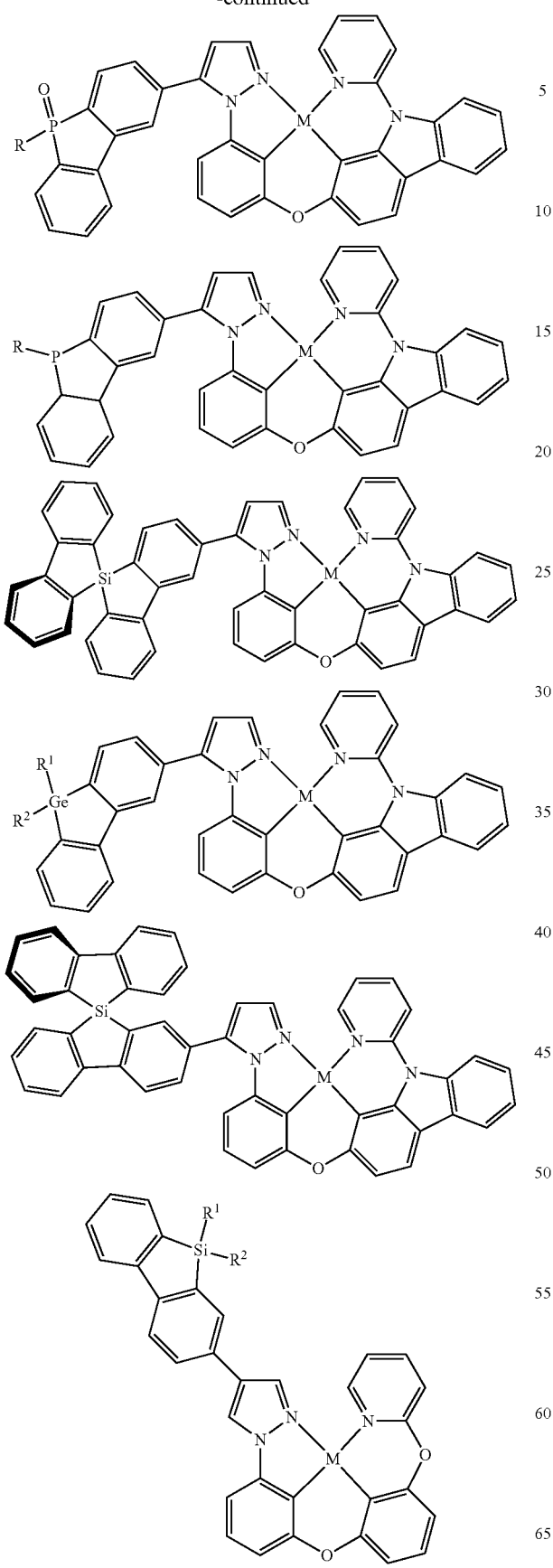
776
-continued
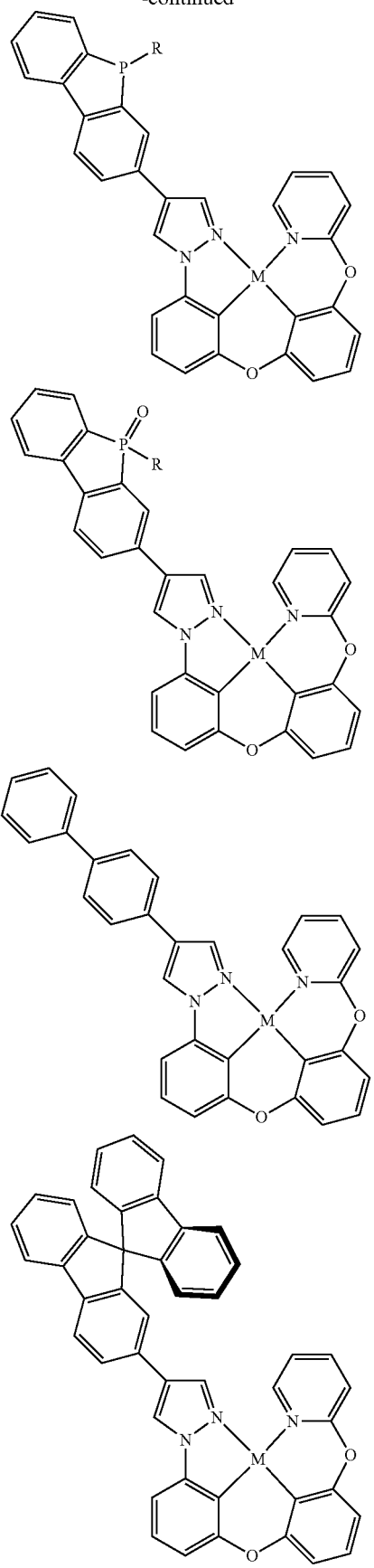

777
-continued
778
-continued
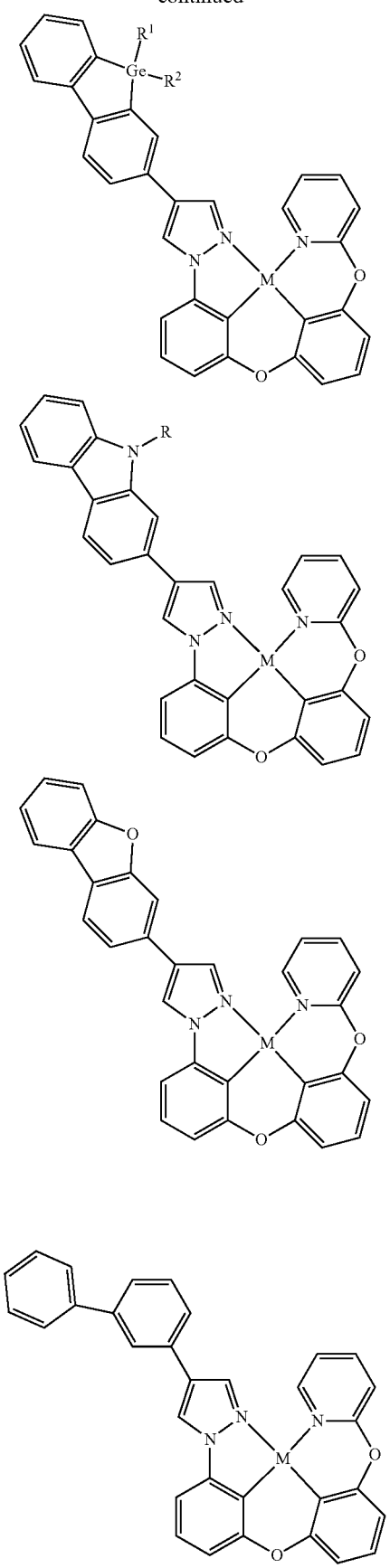
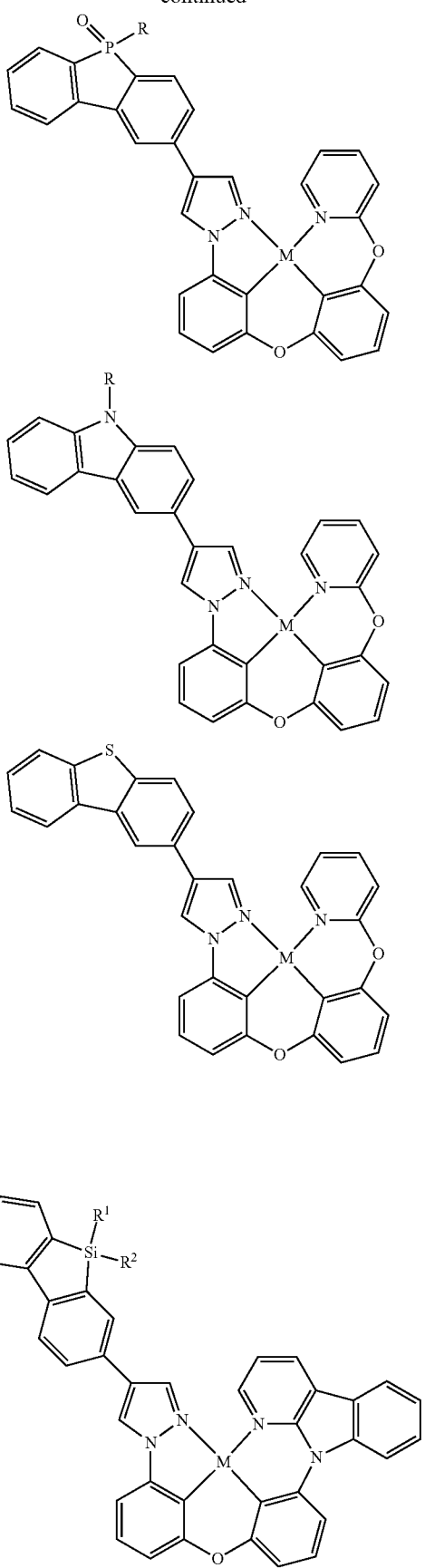

779
-continued
780
-continued
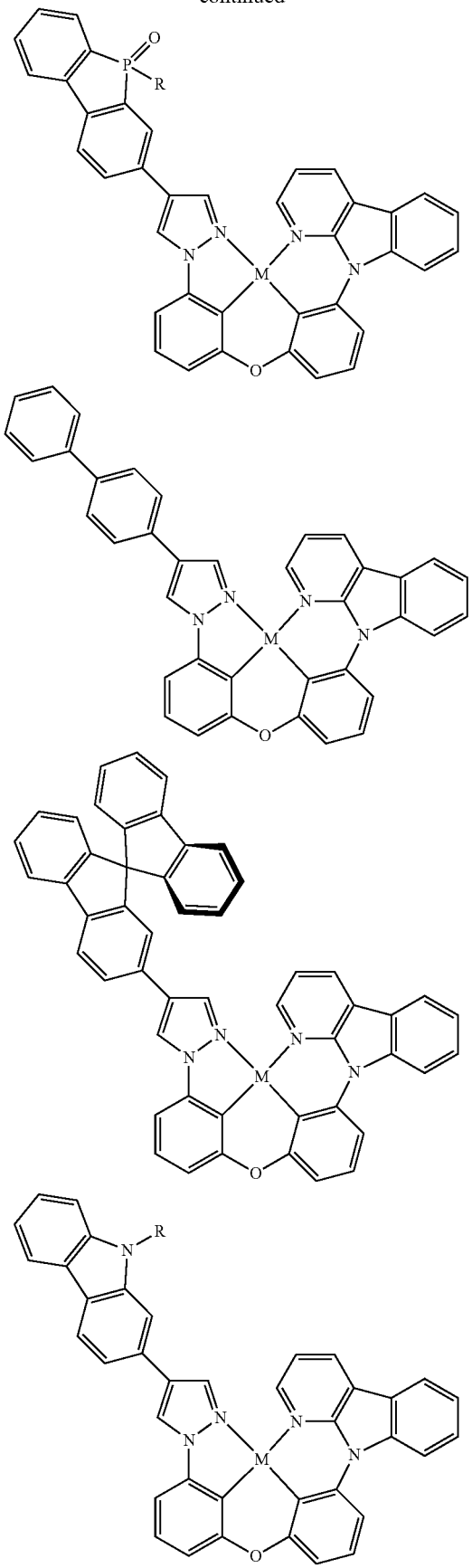
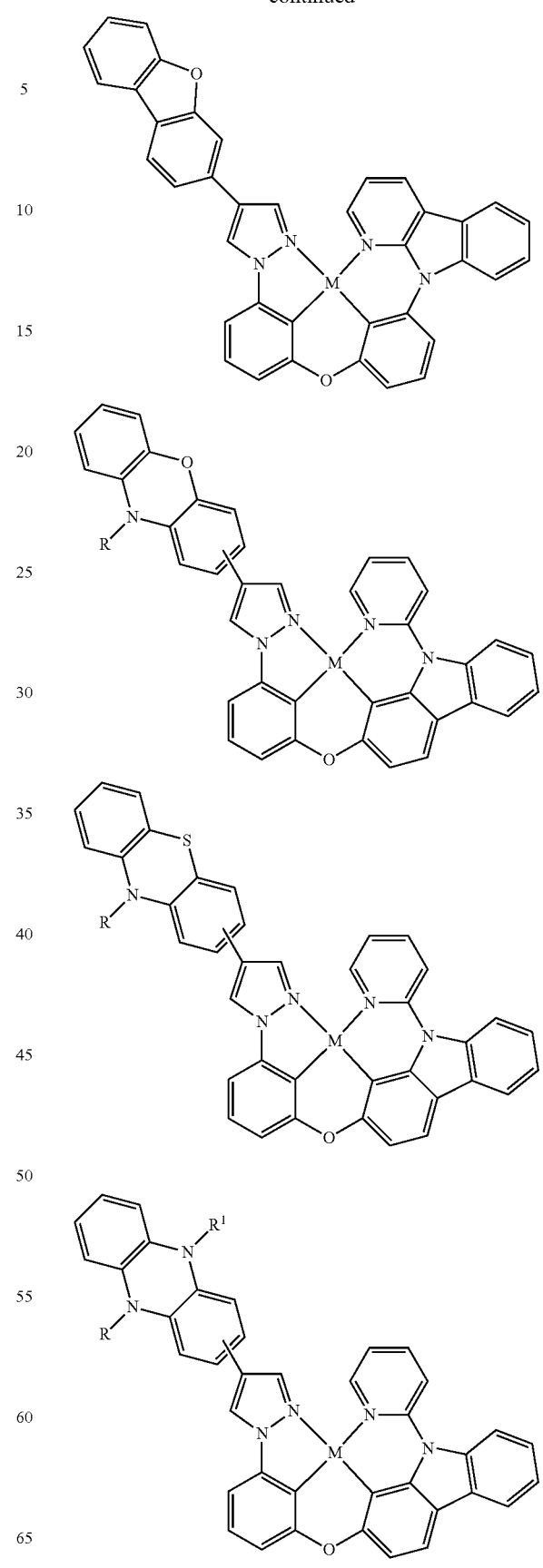

-continued
781
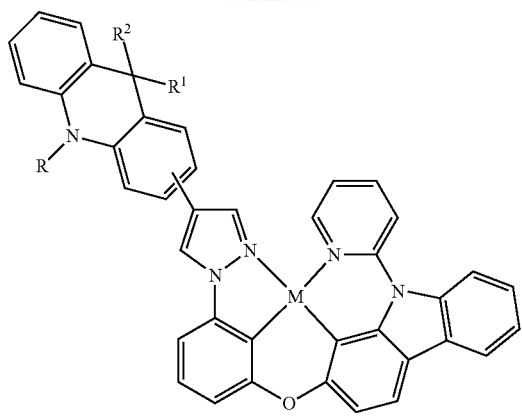
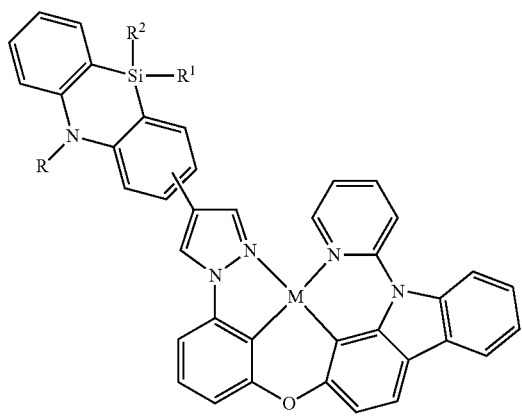
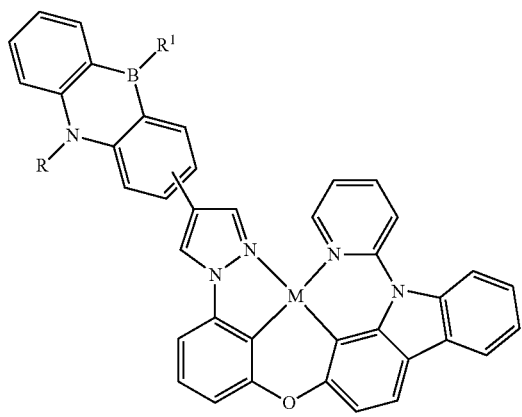
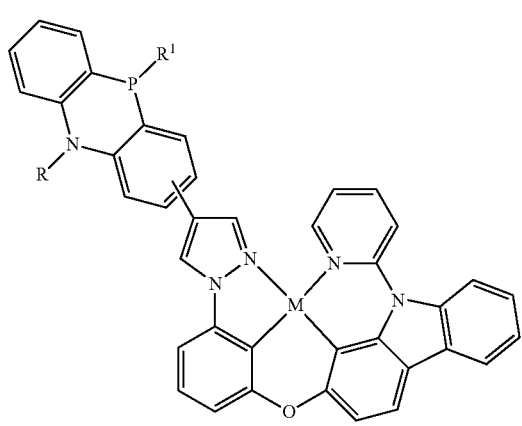
782
-continued
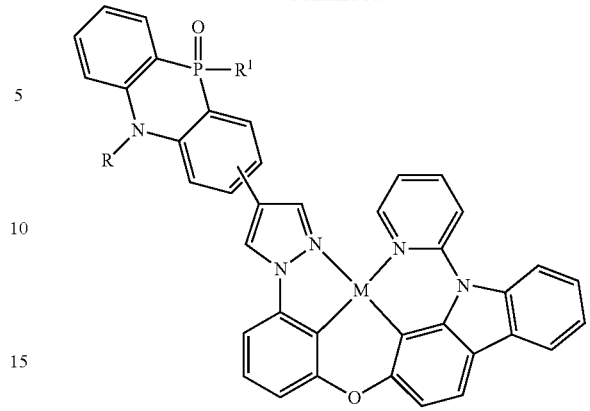
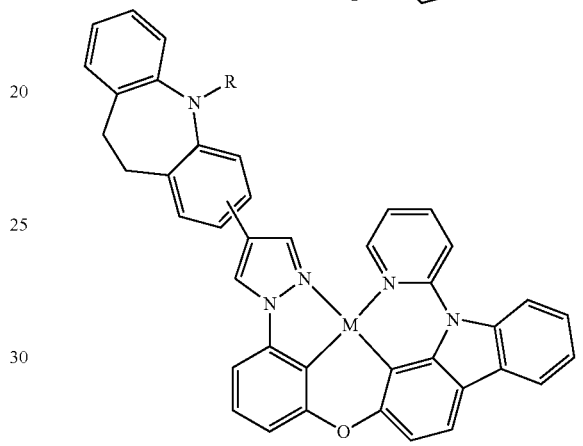
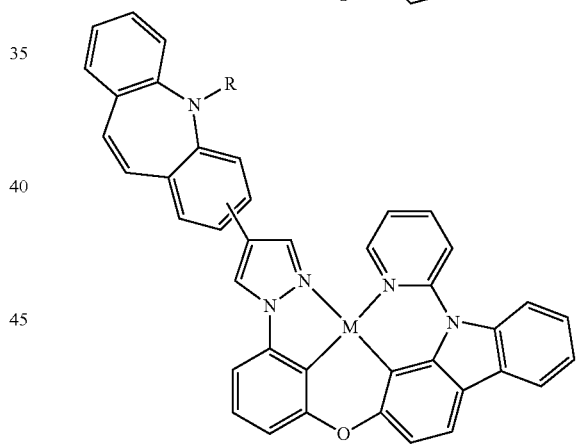
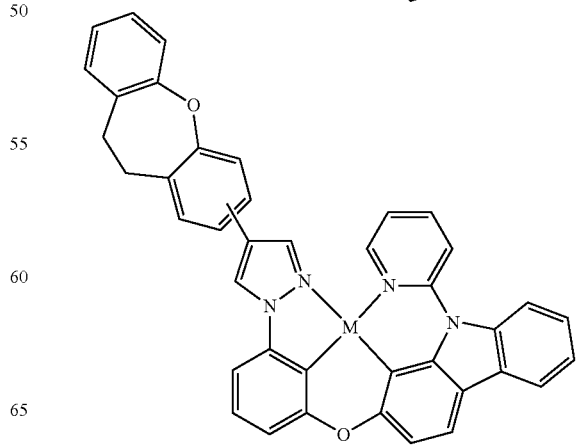

783
-continued
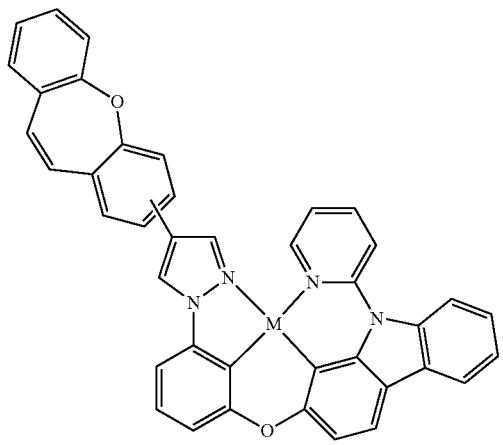
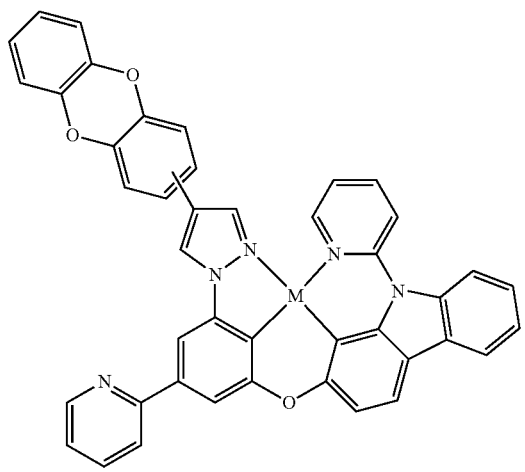
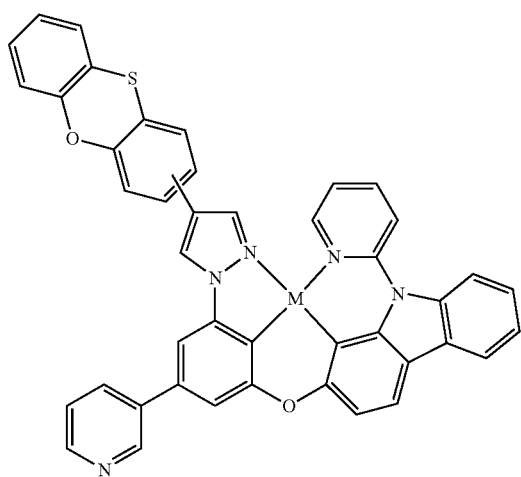
784
-continued
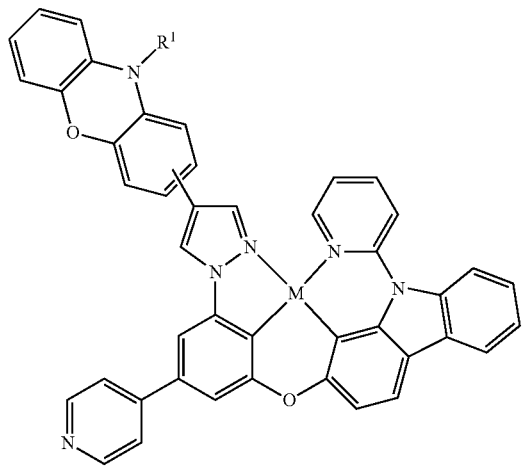
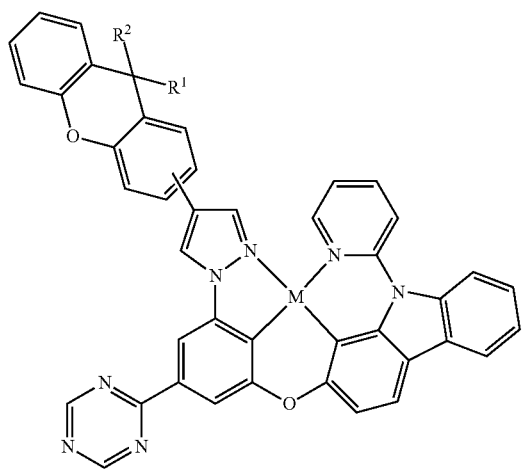
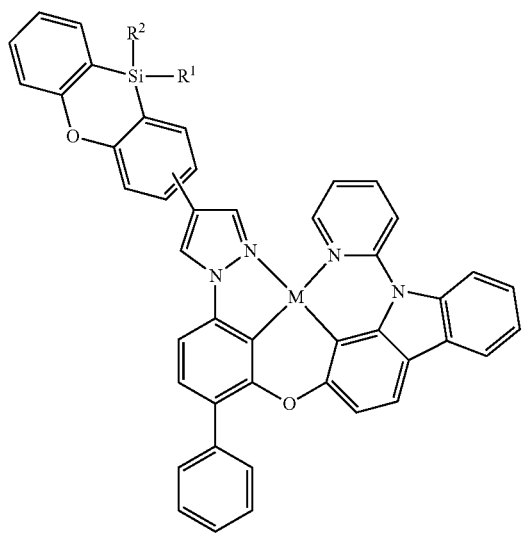

785
-continued
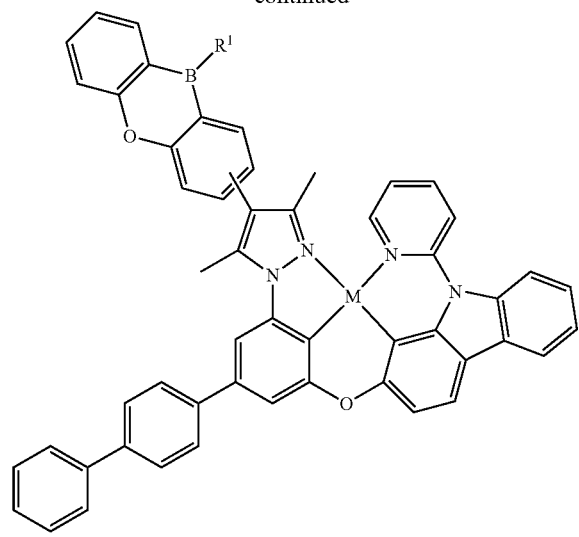
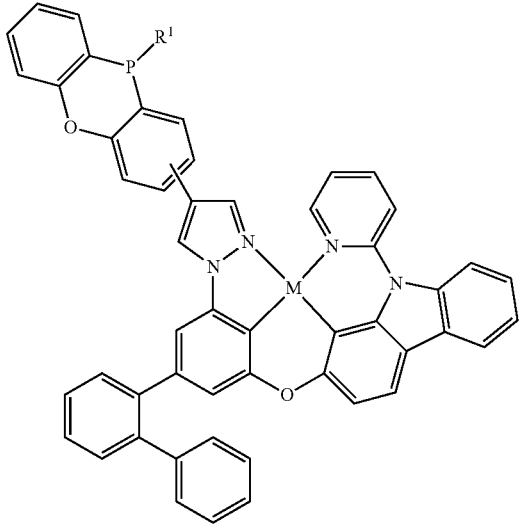
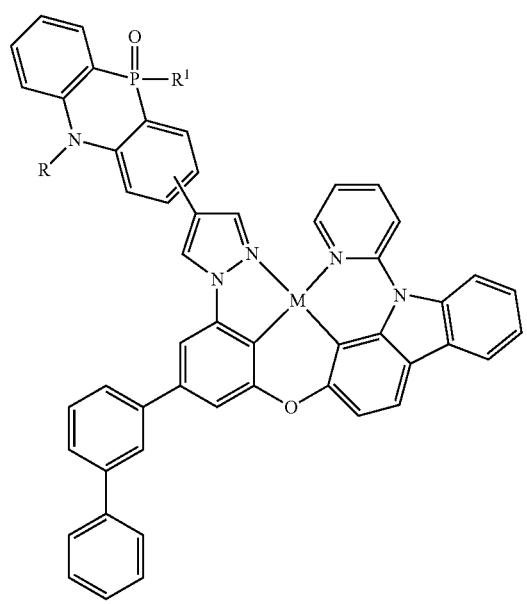
786
-continued
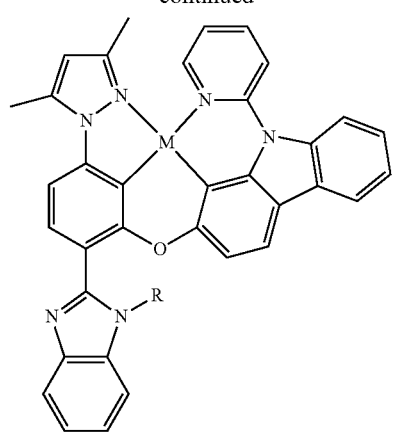
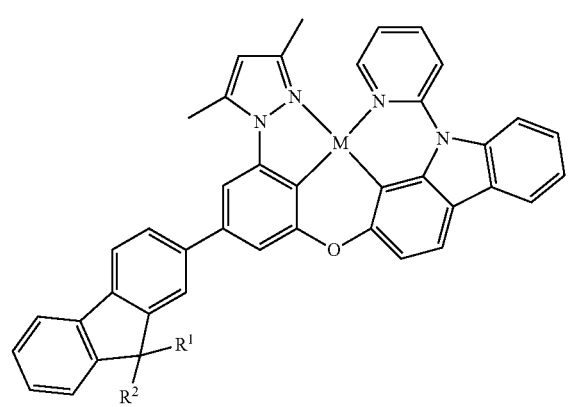
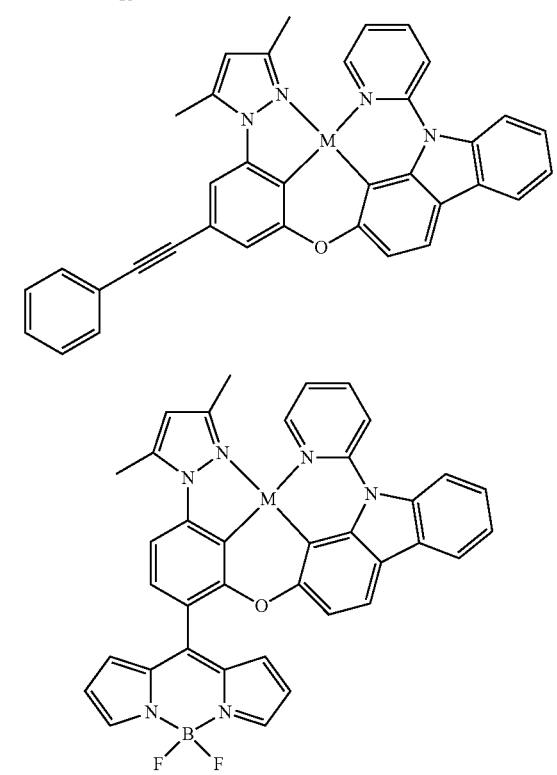

787
-continued
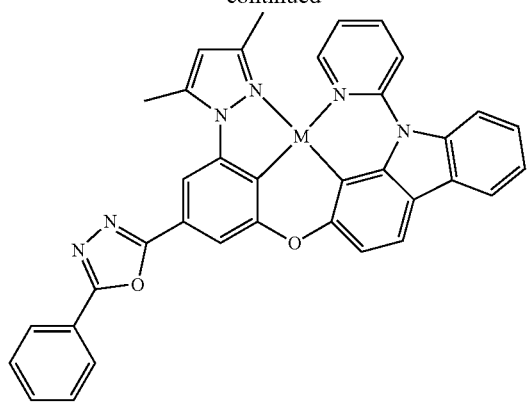
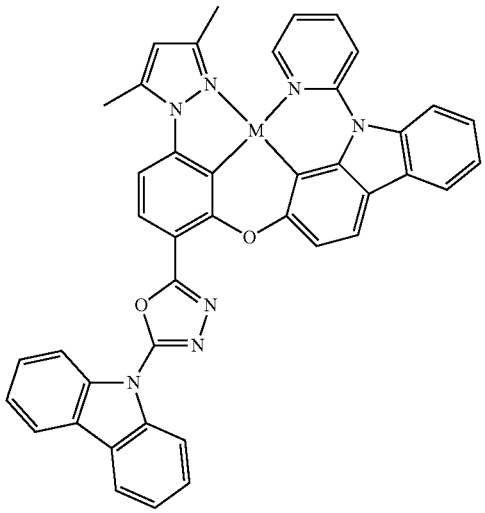
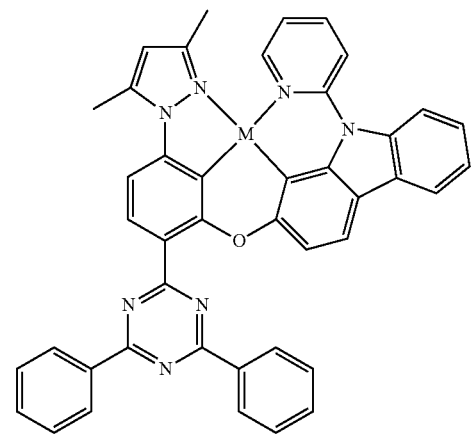
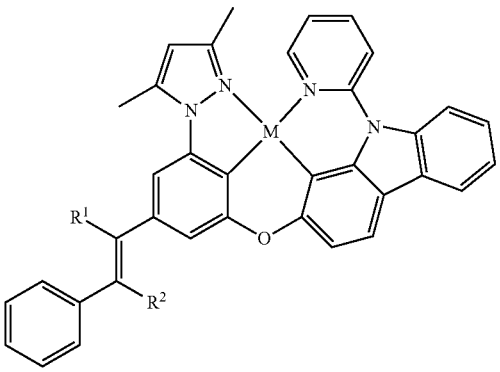
788
-continued
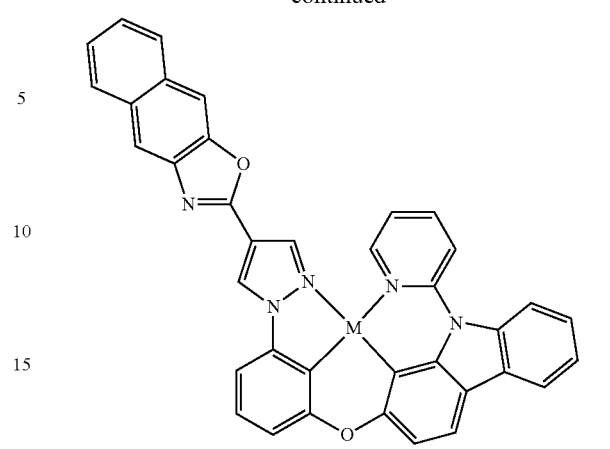
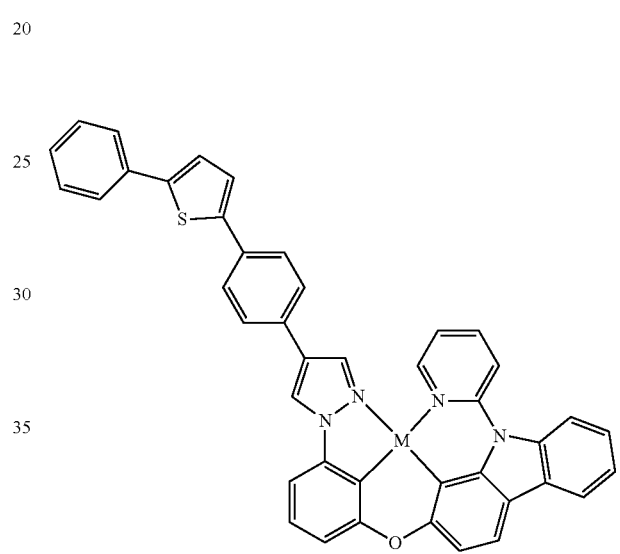
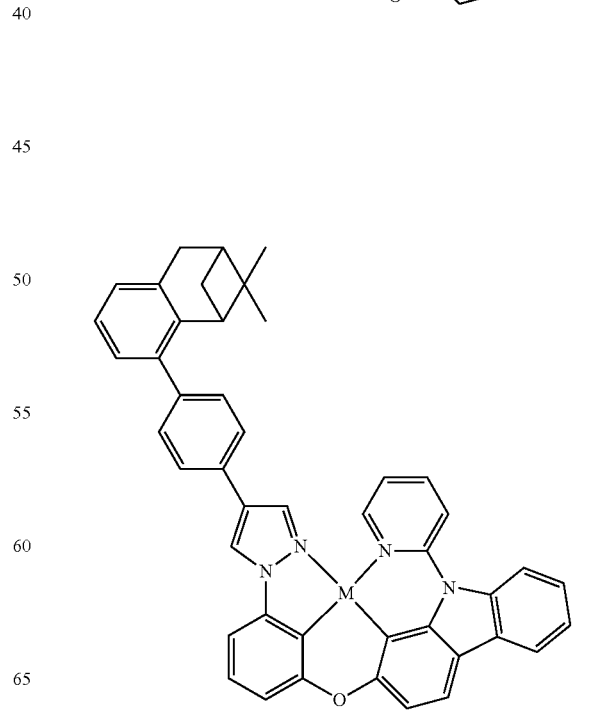

789
-continued
790
-continued
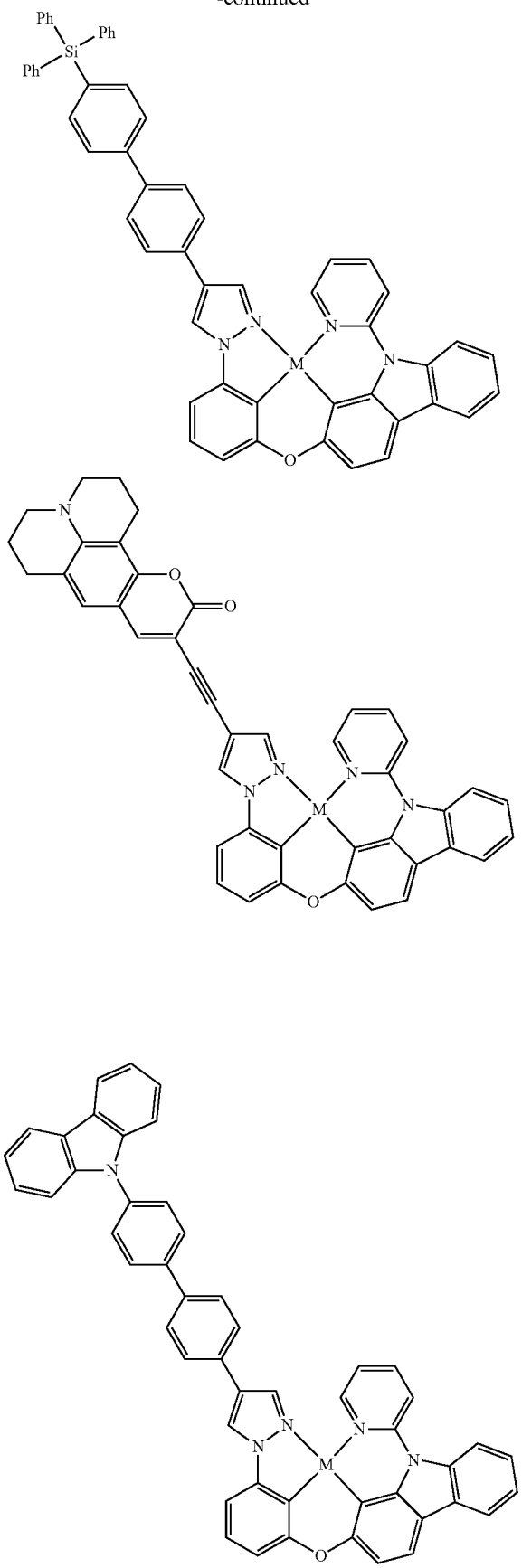
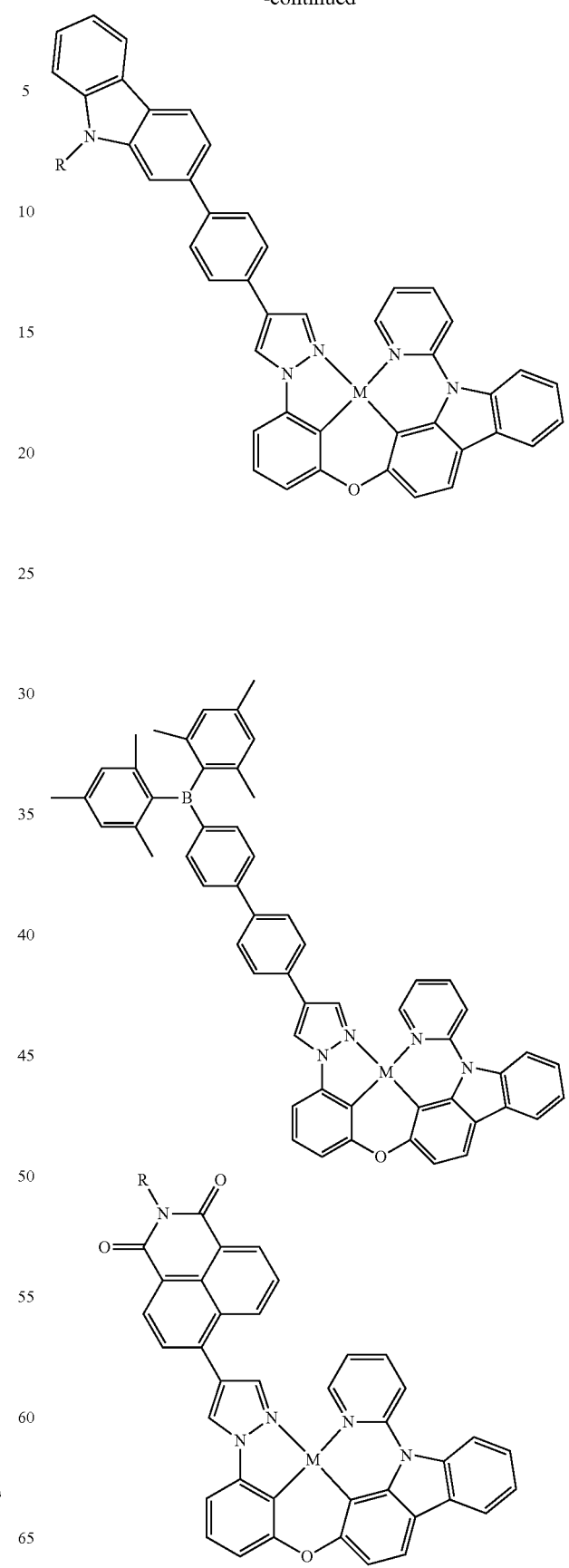

791
-continued
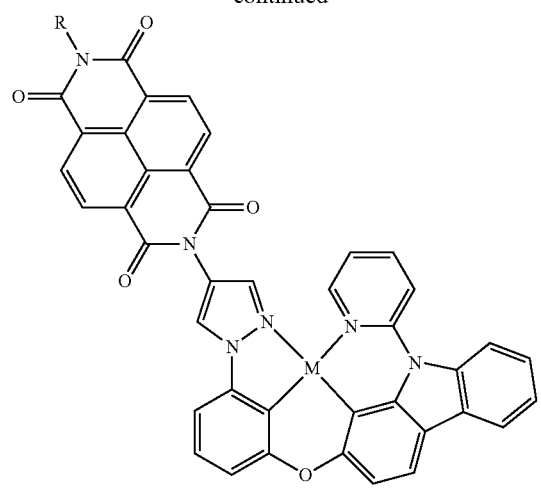
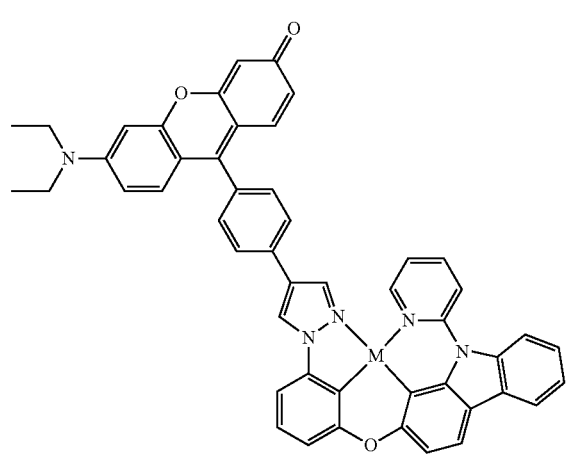
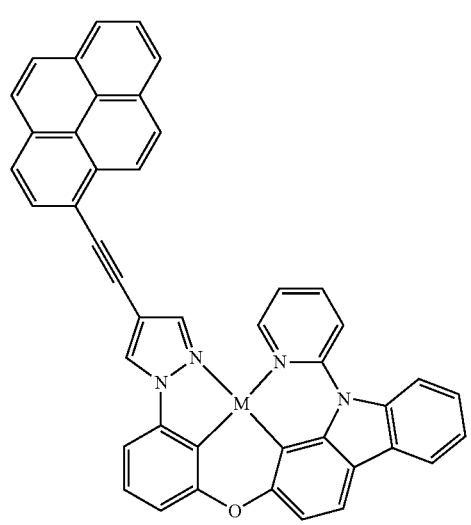
792
-continued
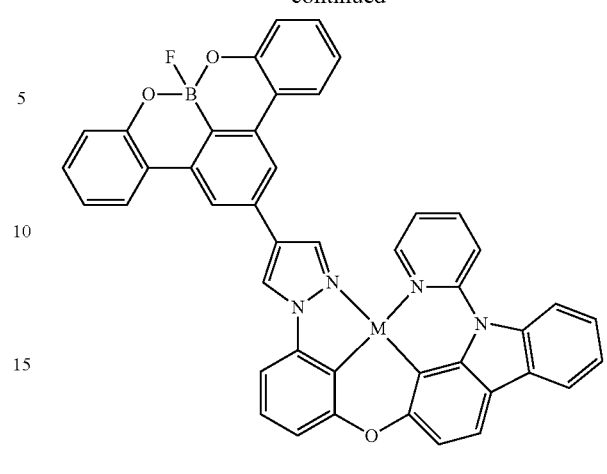
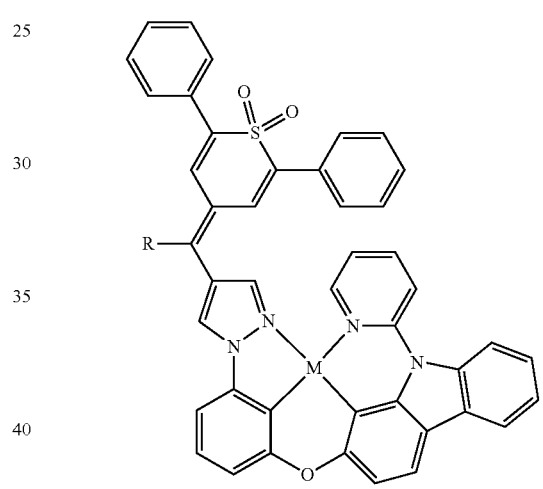
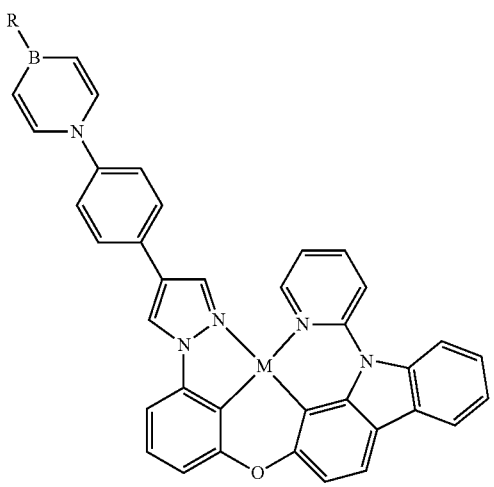

793
-continued
794
-continued
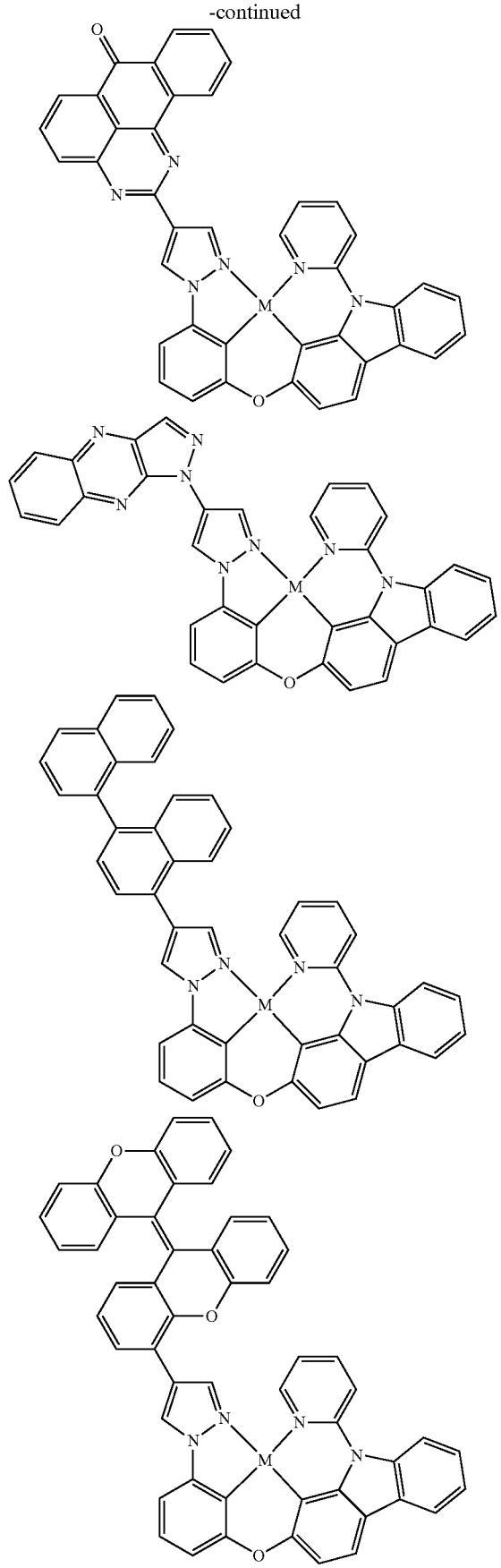
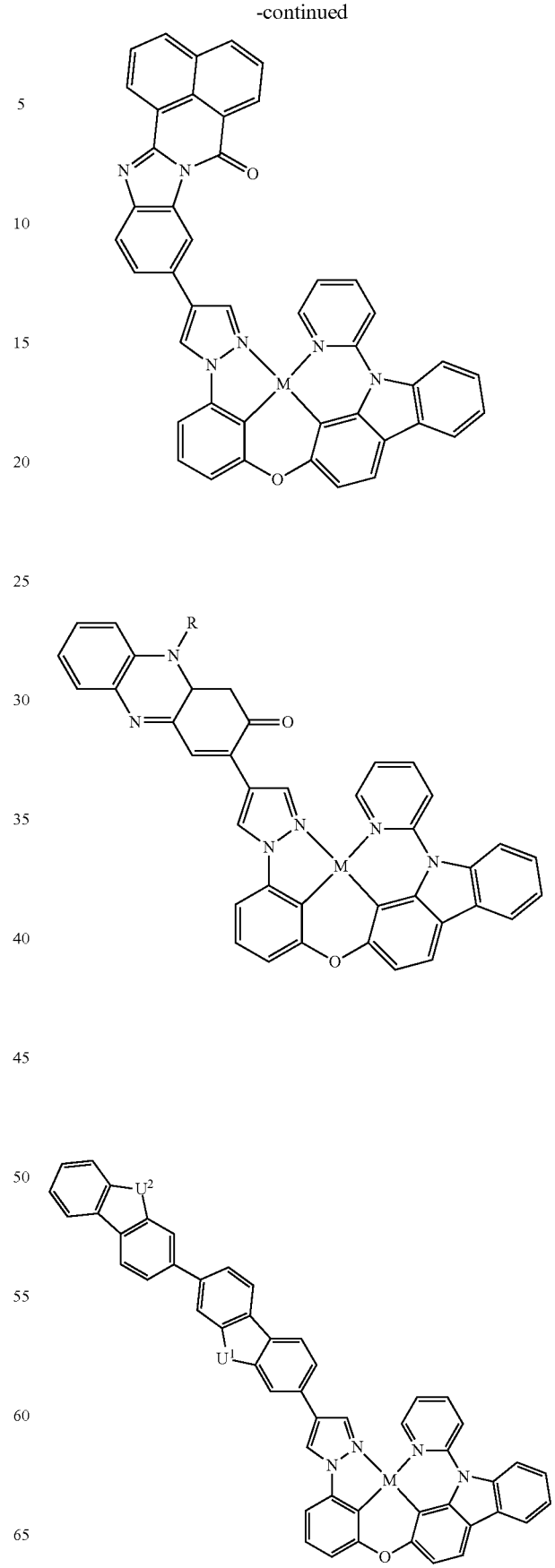

795
-continued
796
-continued
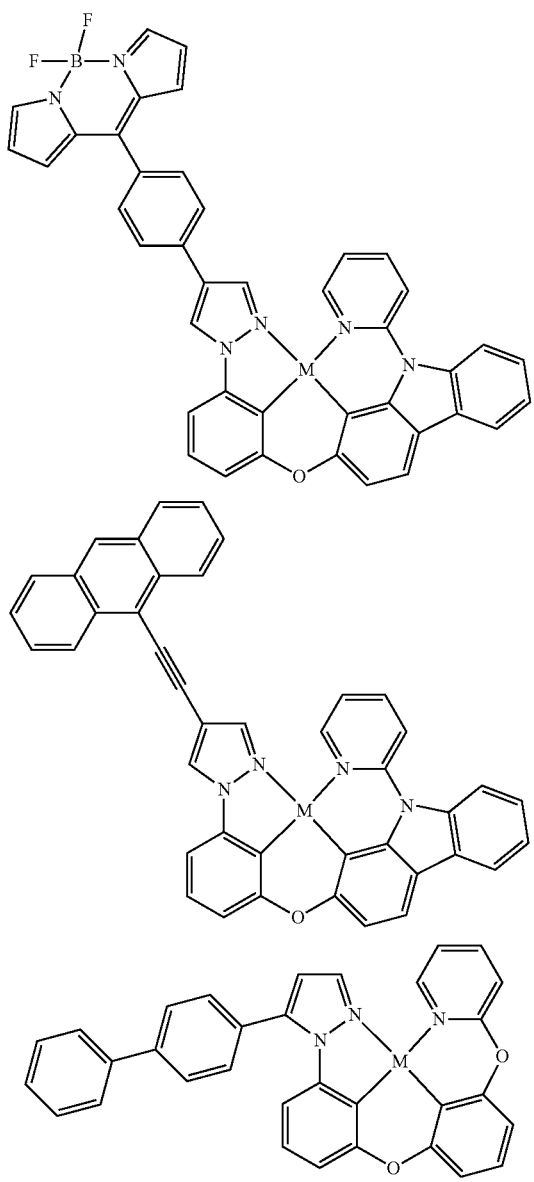
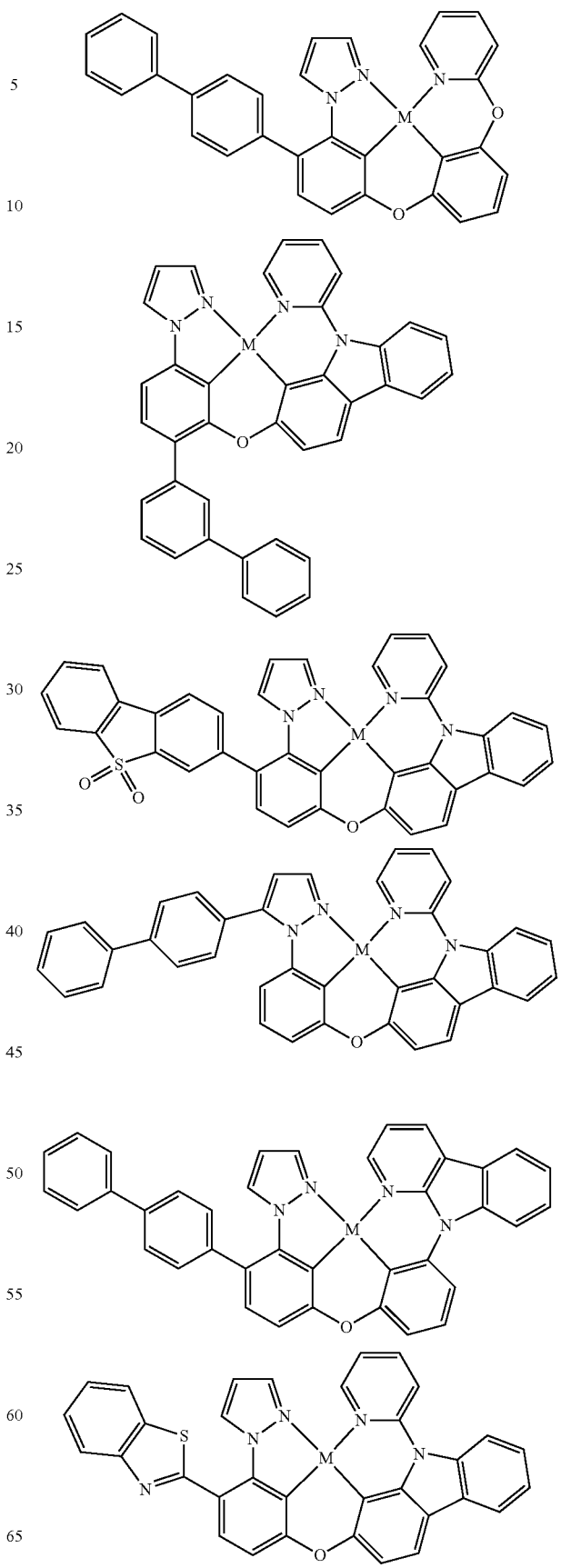

797
-continued
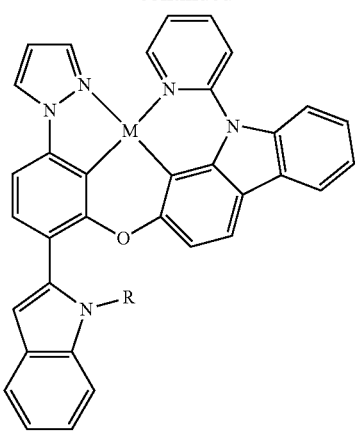
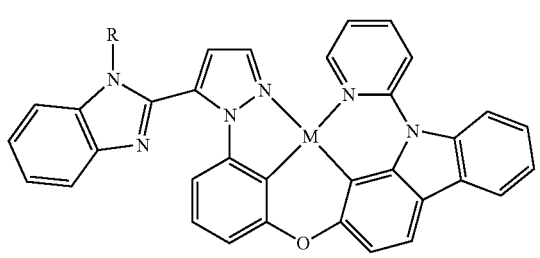
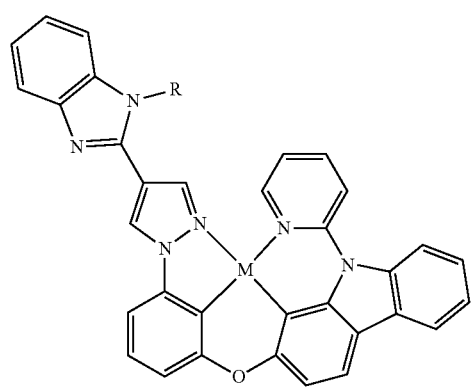
798
-continued
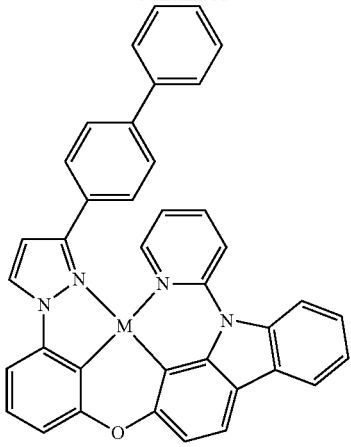
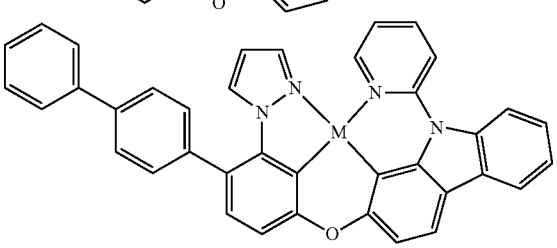
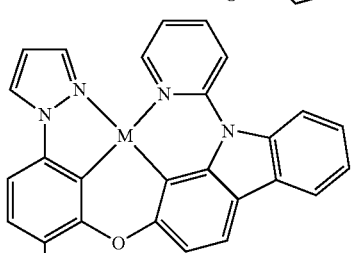
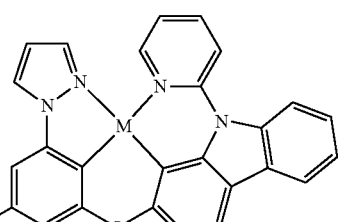

| 799 -continued | 800 -continued |
|---|---|
| 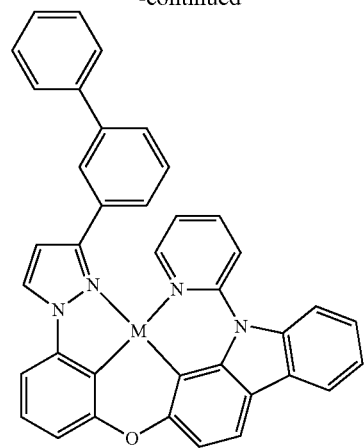 | 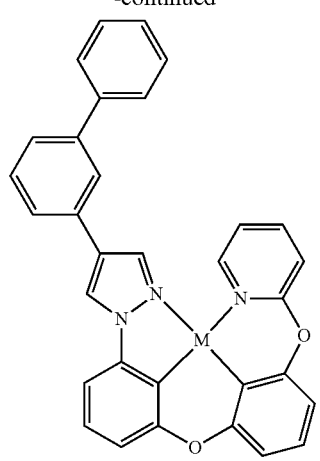 |
| 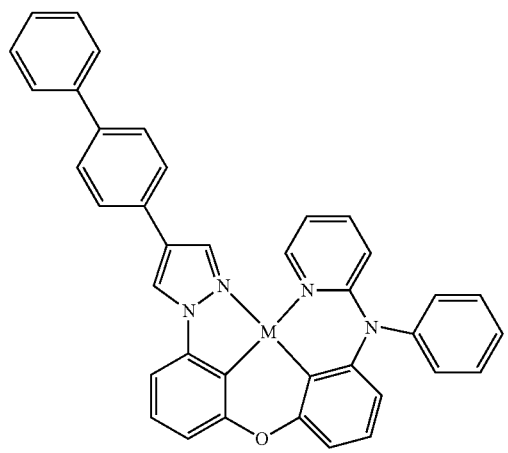 | 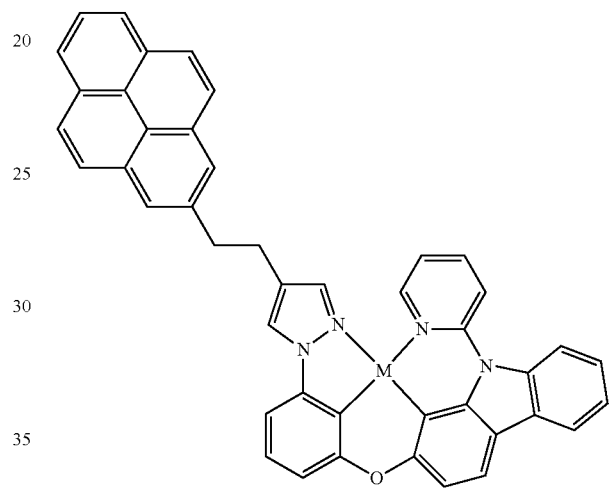 |
| 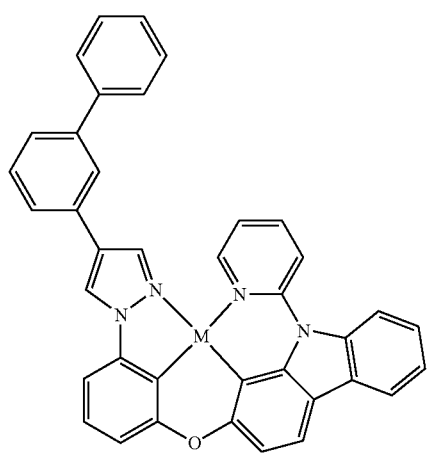 | 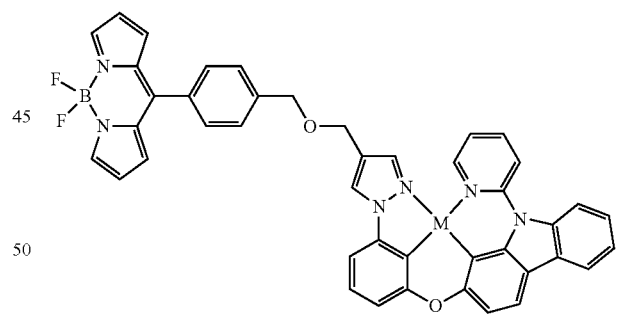 |
| | 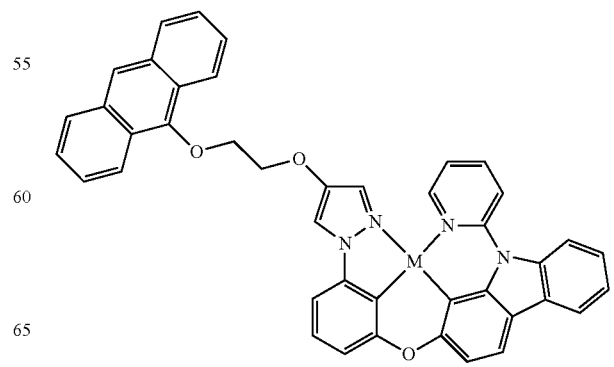 |

801
-continued
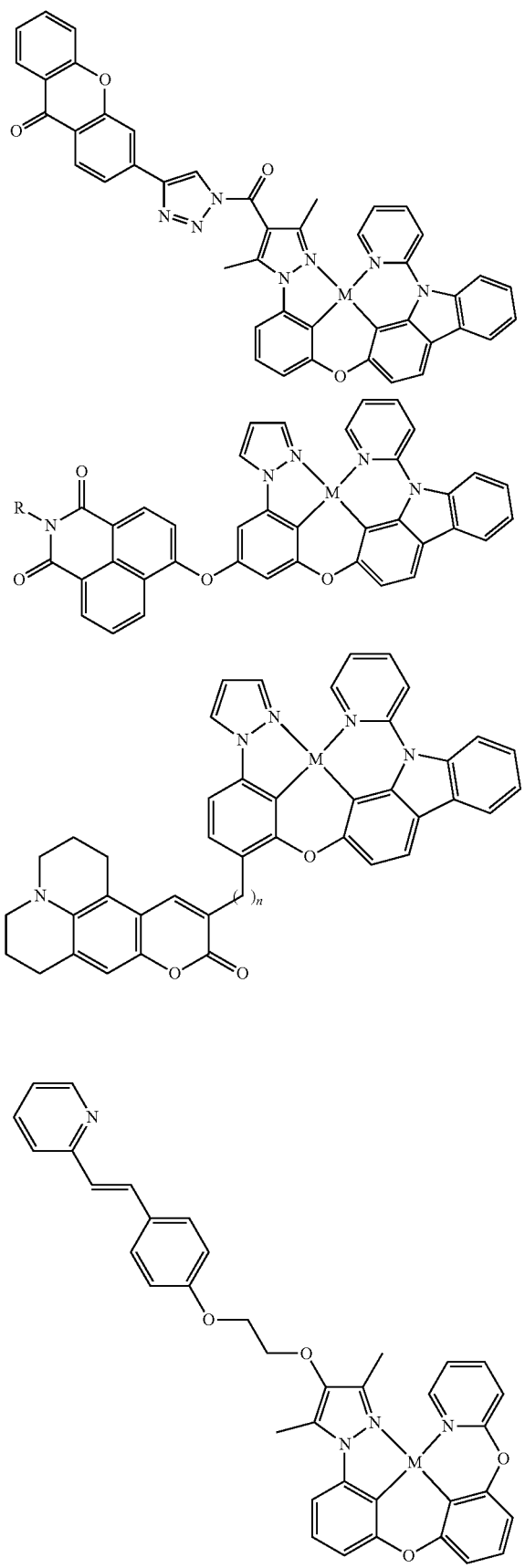
802
-continued
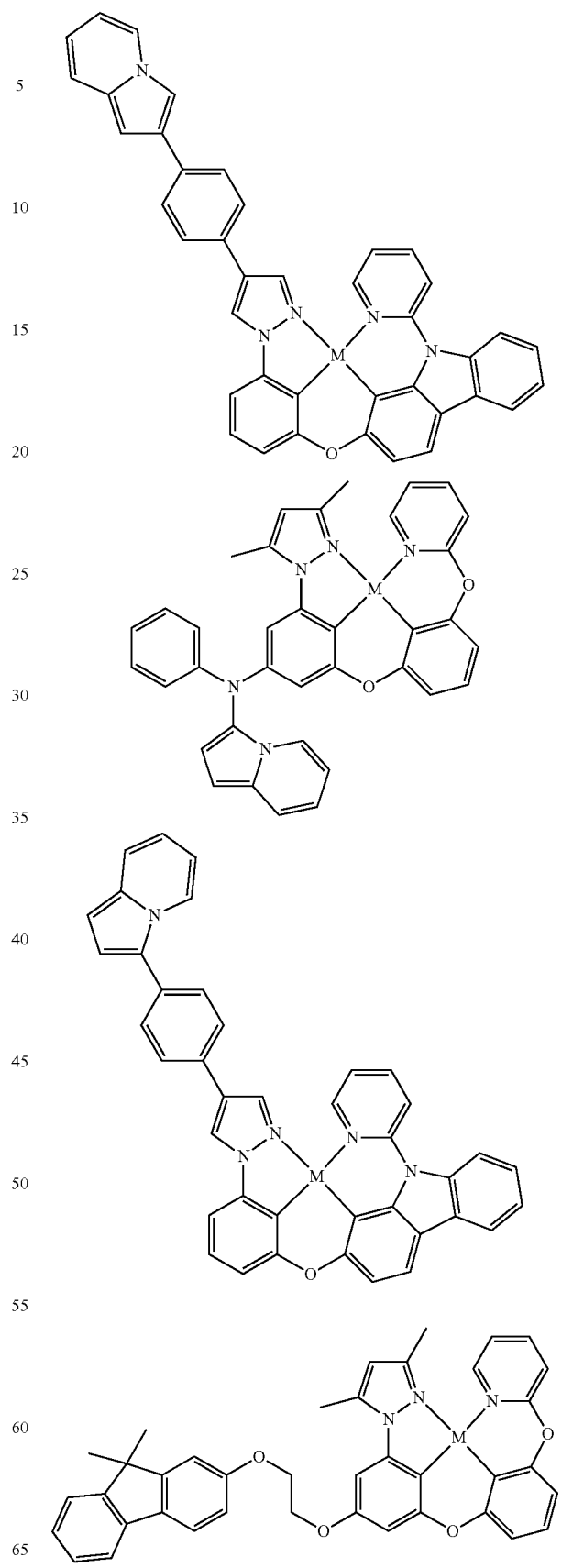

803
-continued
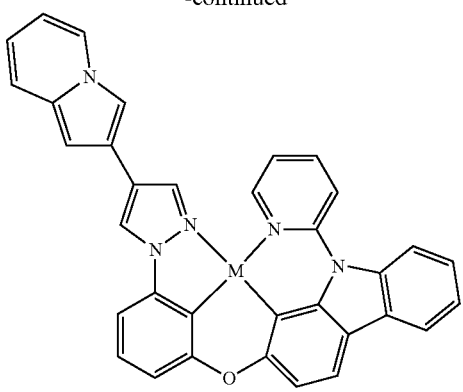
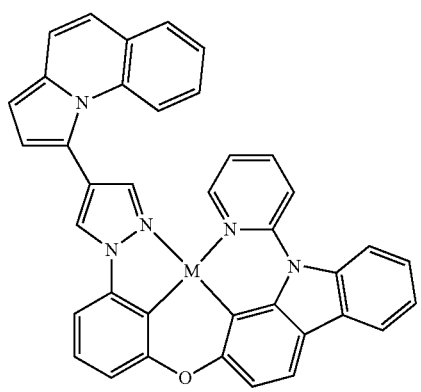
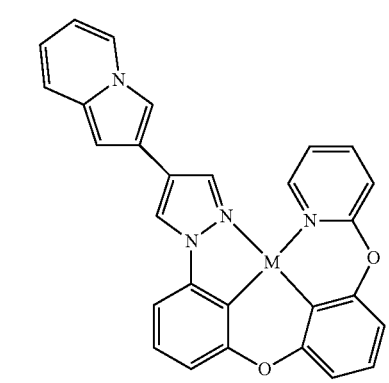
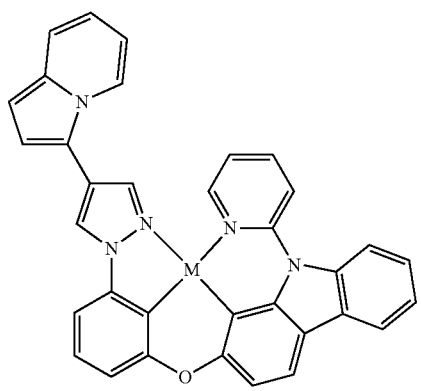
804
-continued
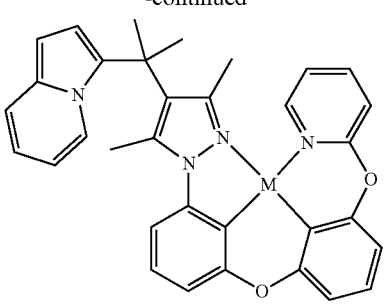
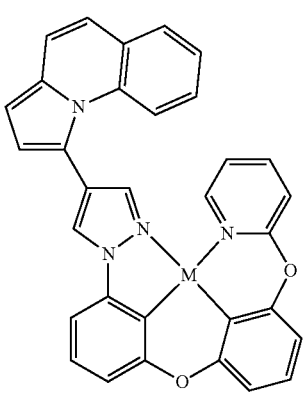
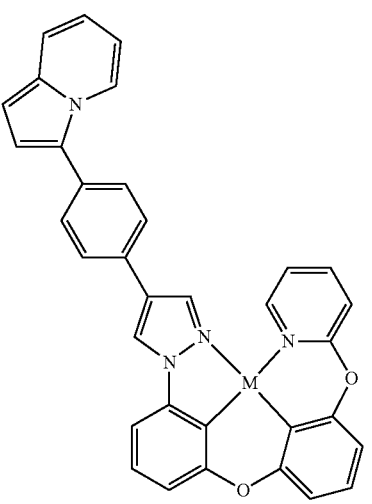
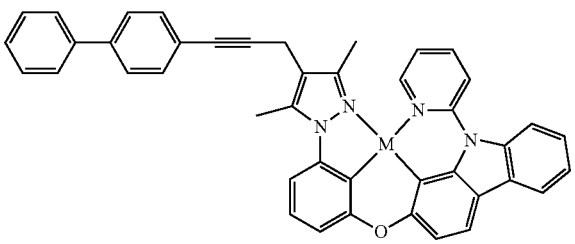

805
-continued
806
-continued
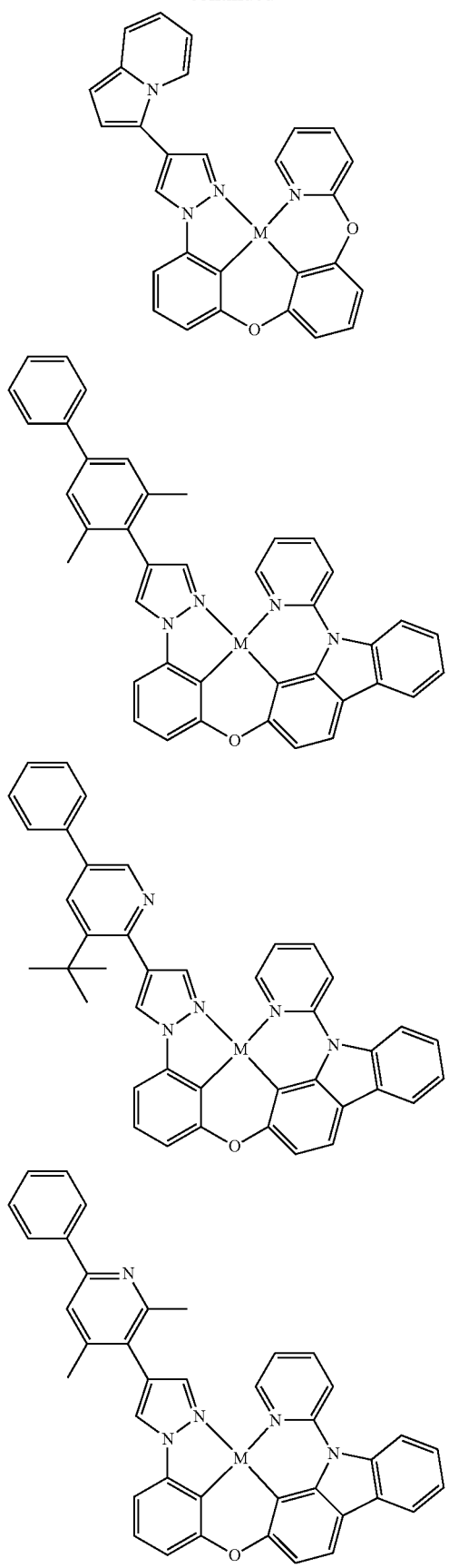
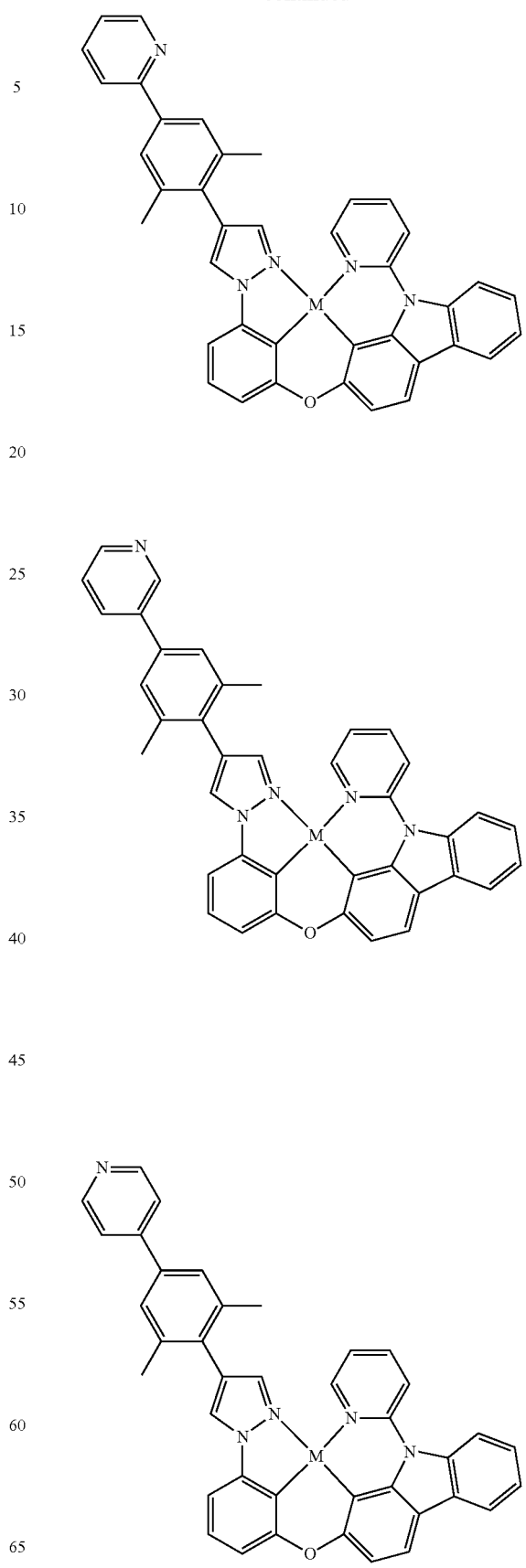

807
-continued
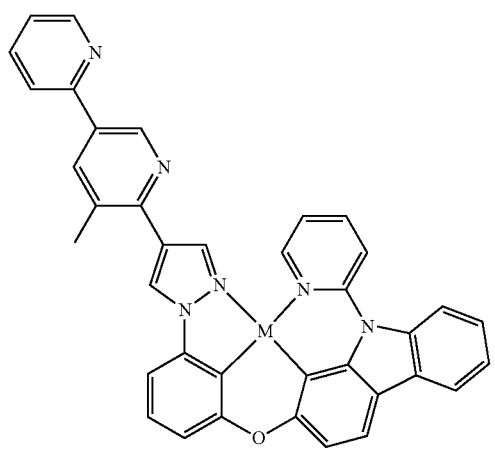
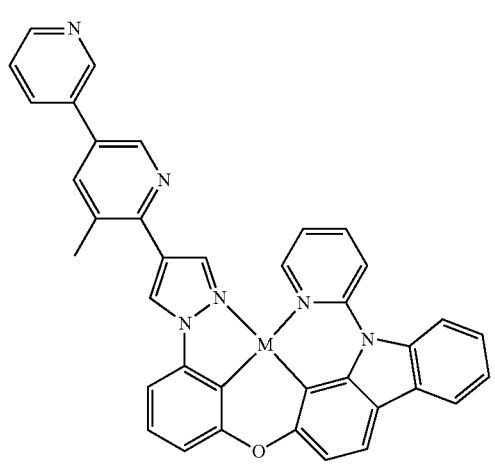
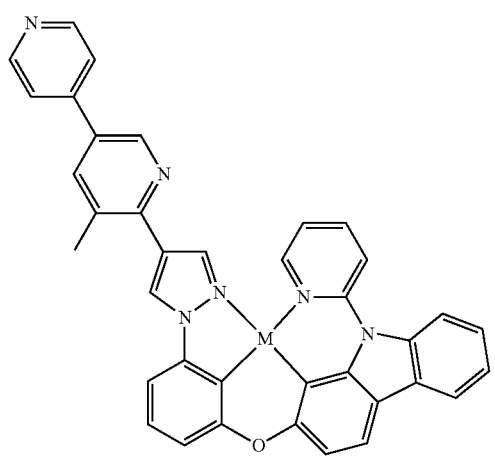
808
-continued
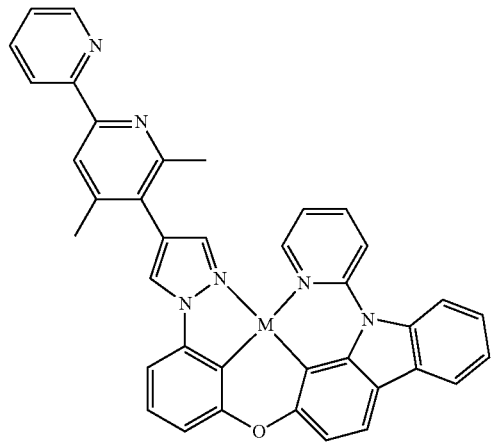
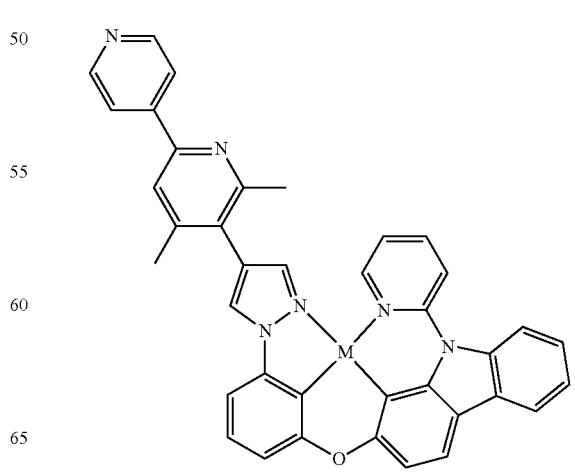

809
-continued
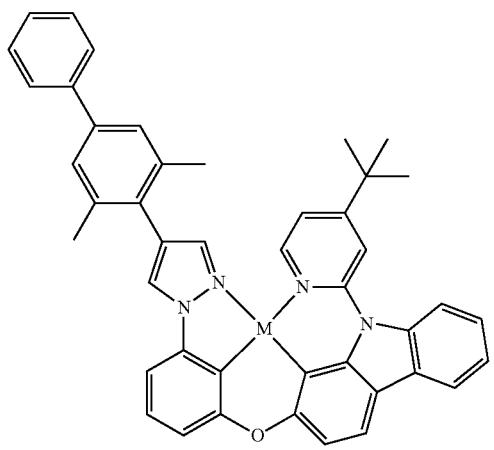
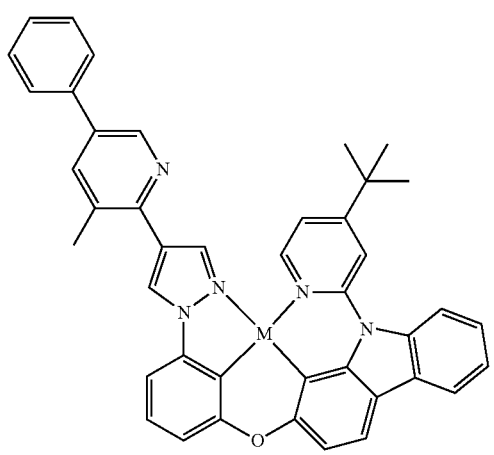
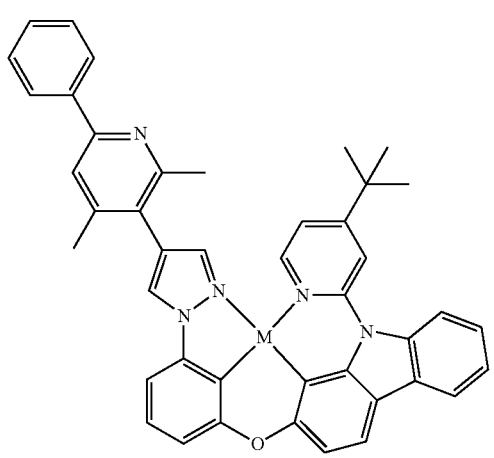
810
-continued
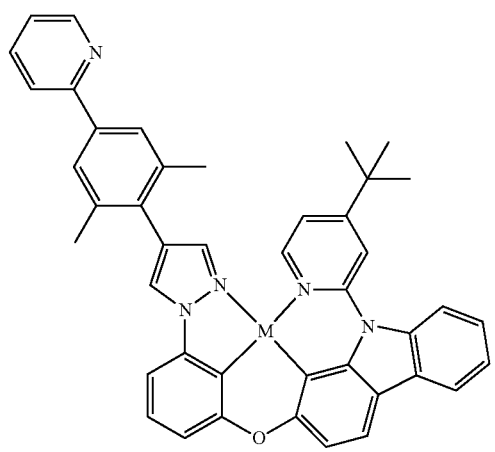
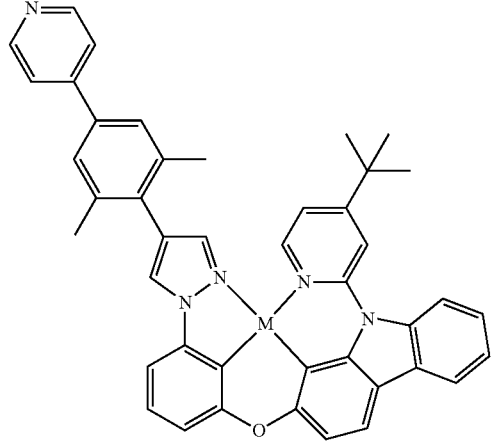

811
-continued
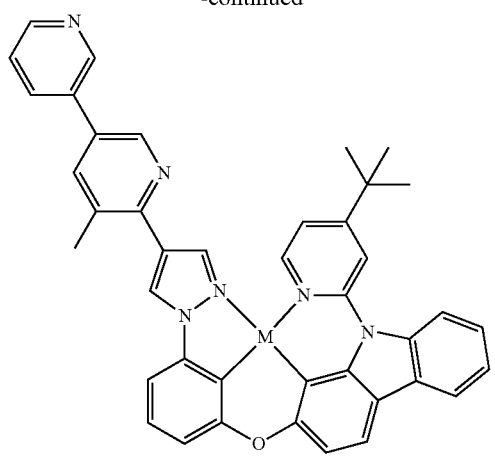
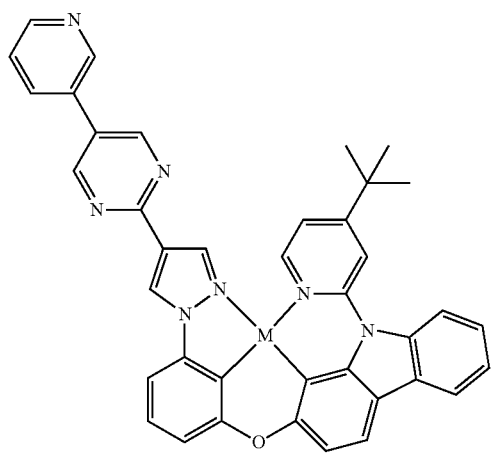
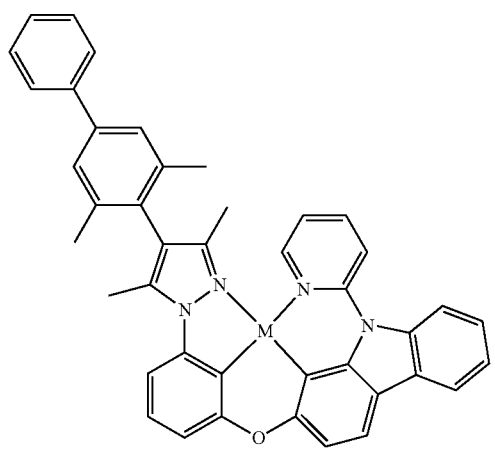
812
-continued
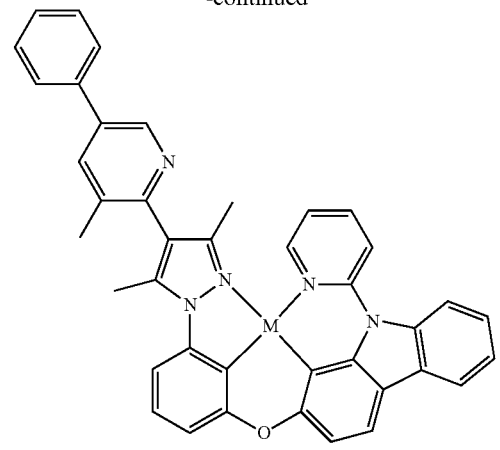
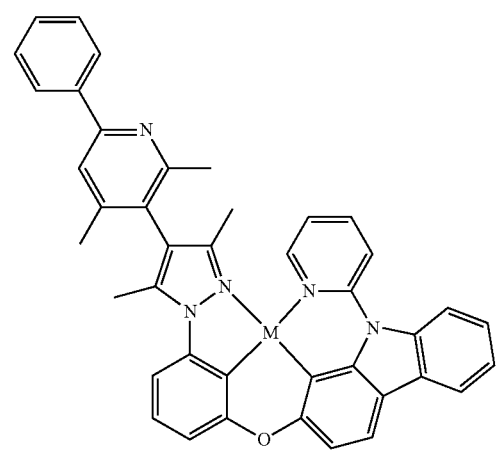
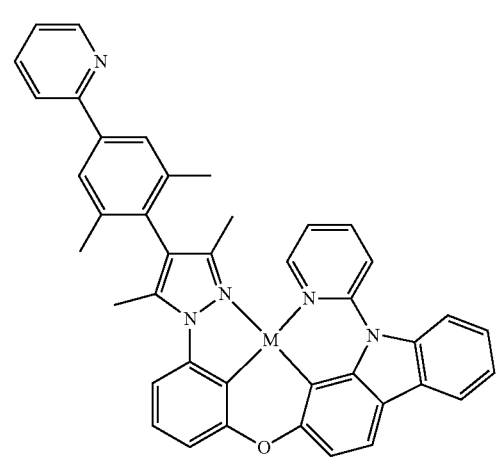

813
-continued
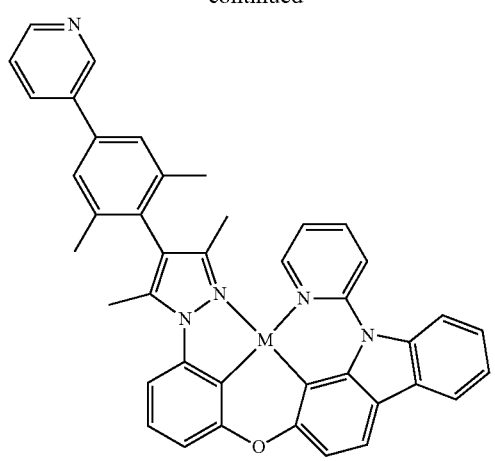
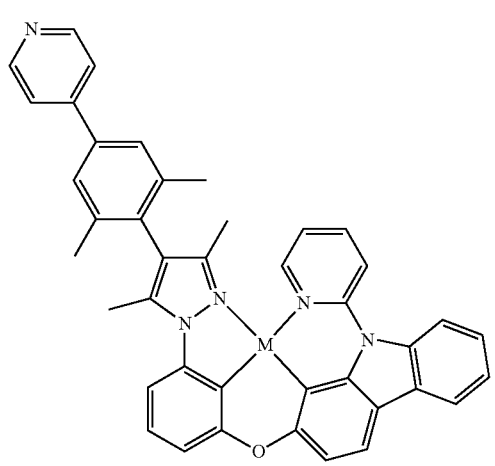
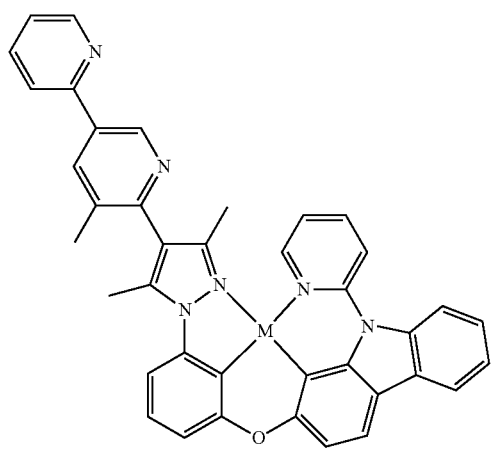
814
-continued
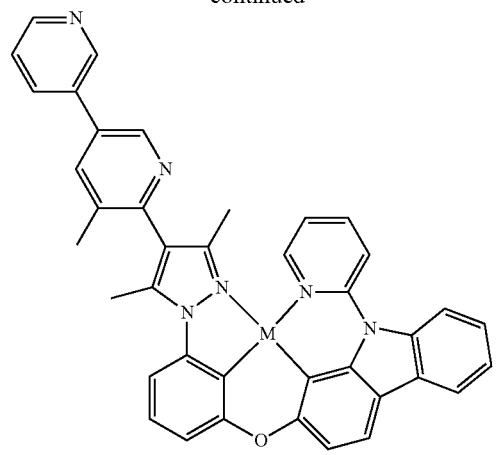
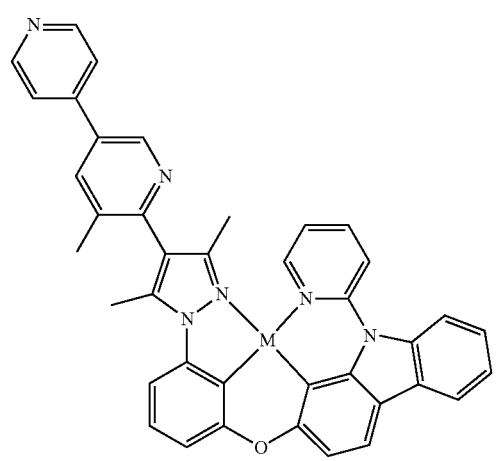
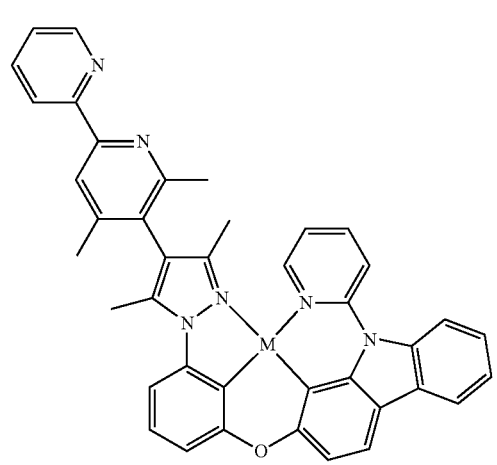

815
-continued
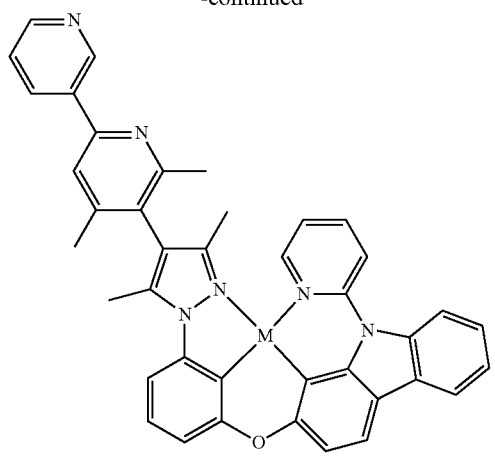
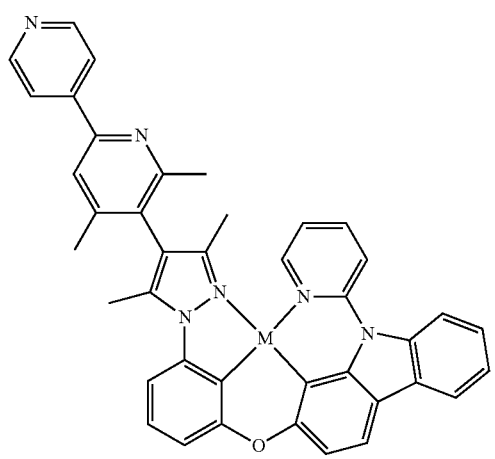
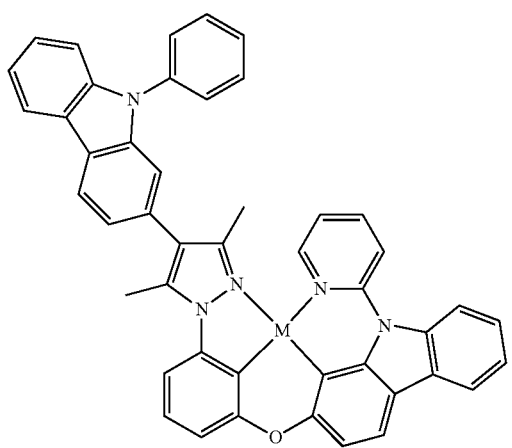
816
-continued
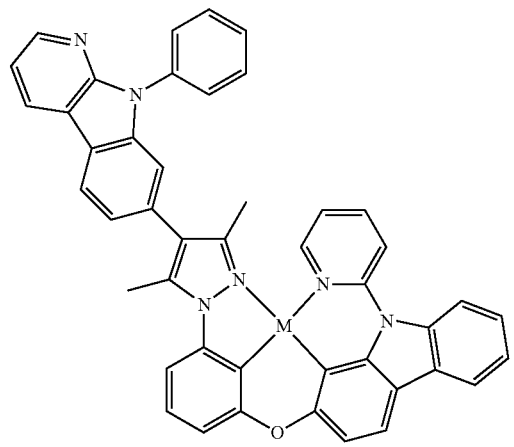
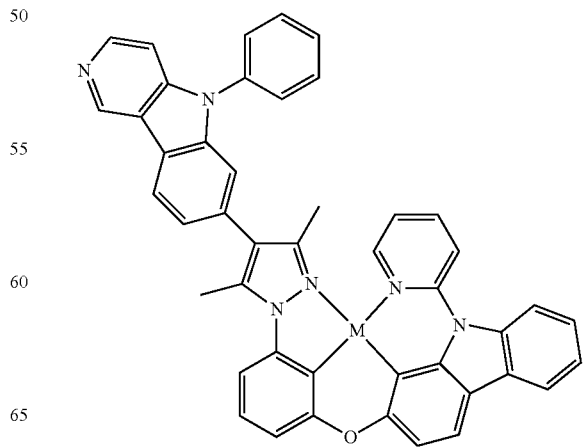

817
-continued
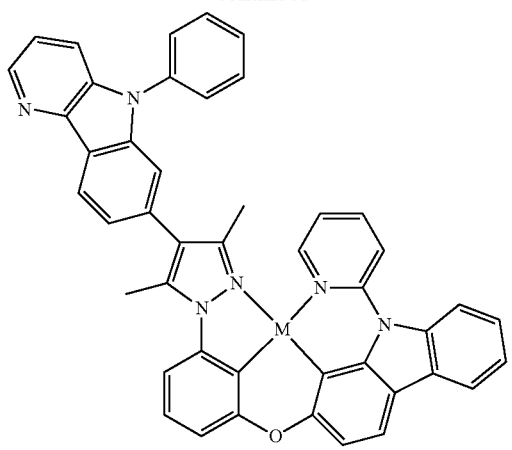
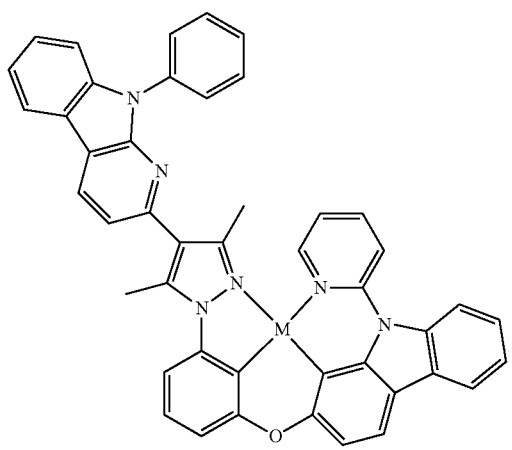
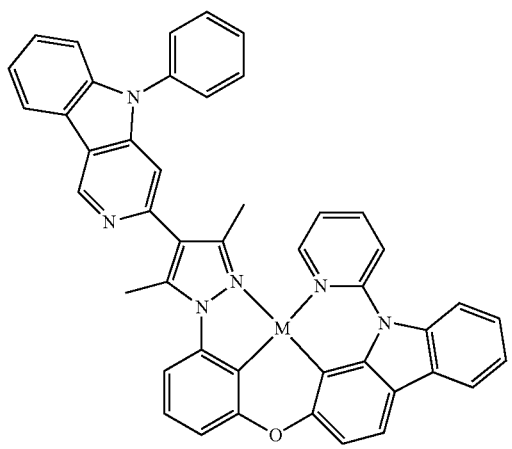
818
-continued
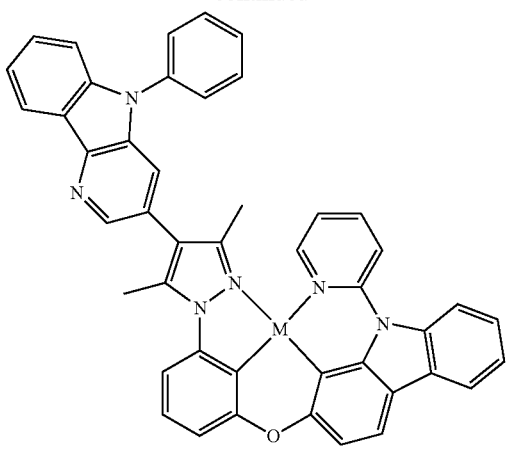
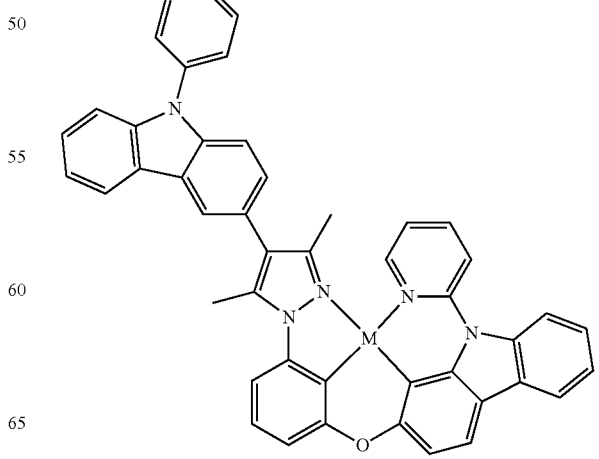

819
-continued
820
-continued
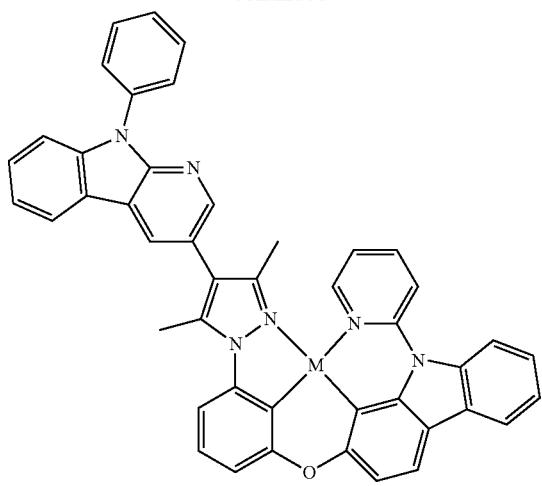
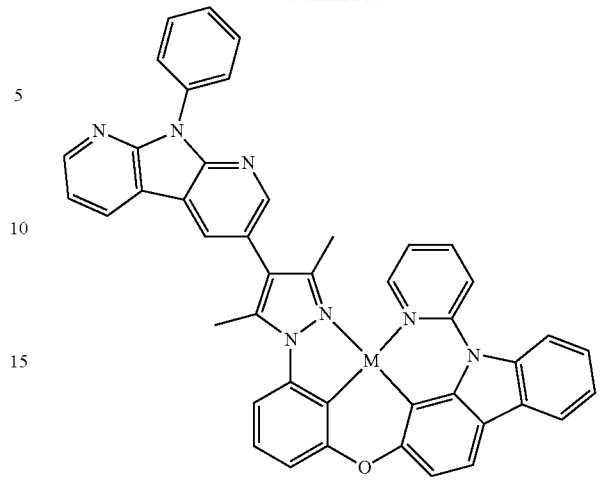
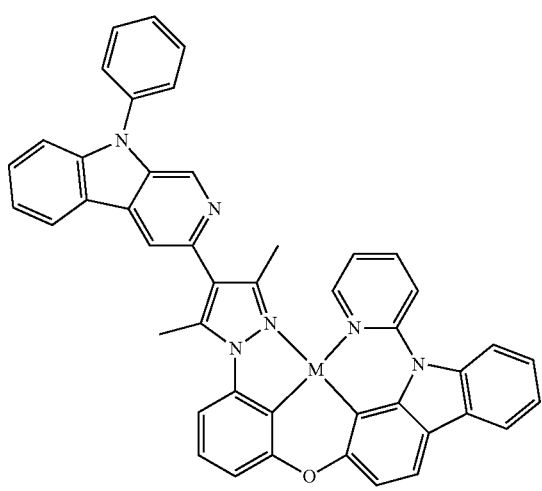
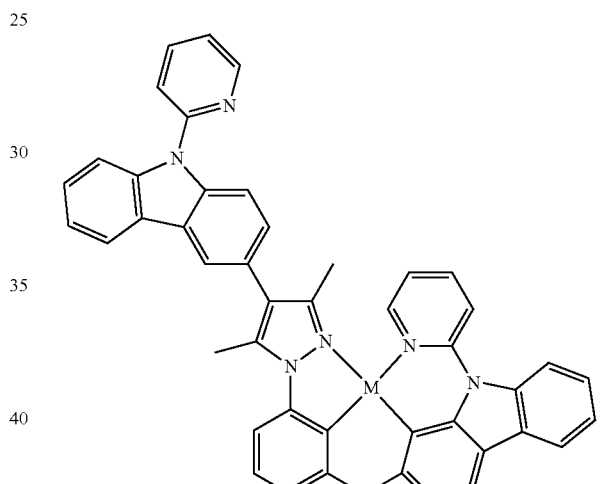
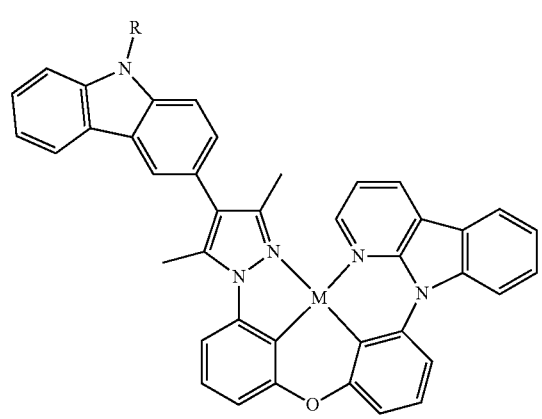
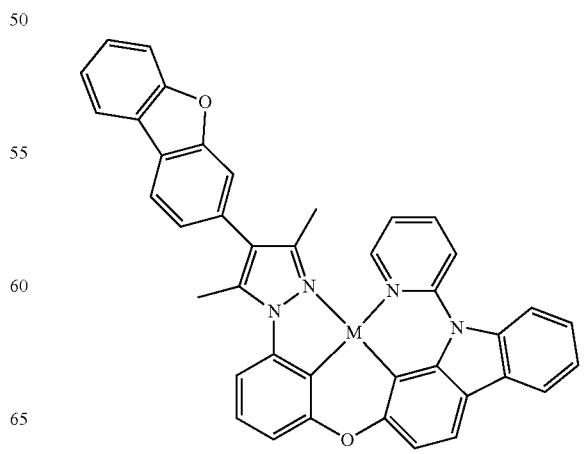

821
-continued
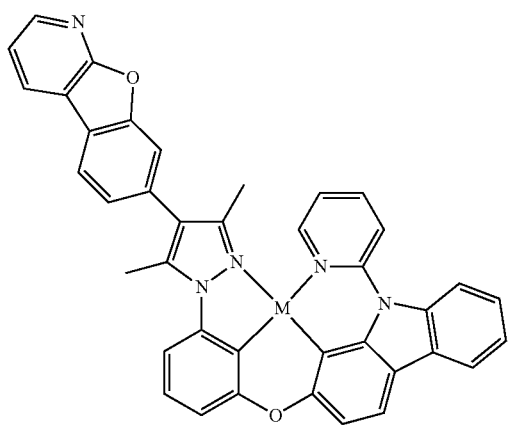
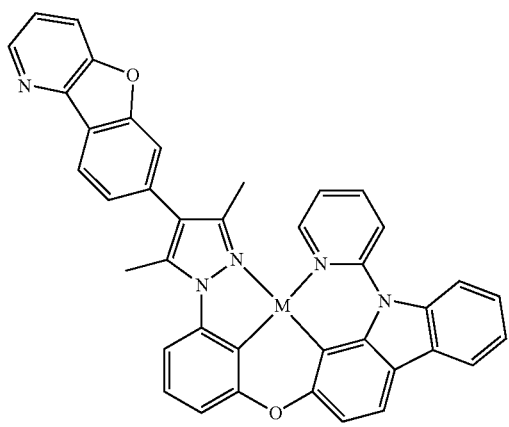
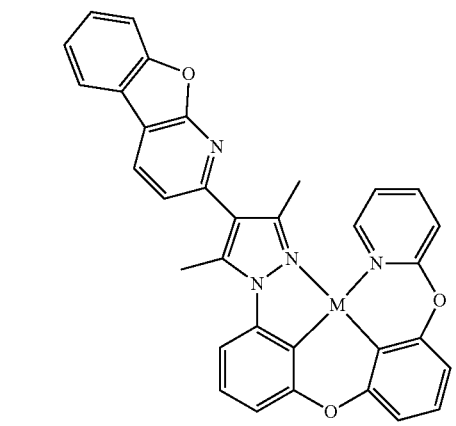
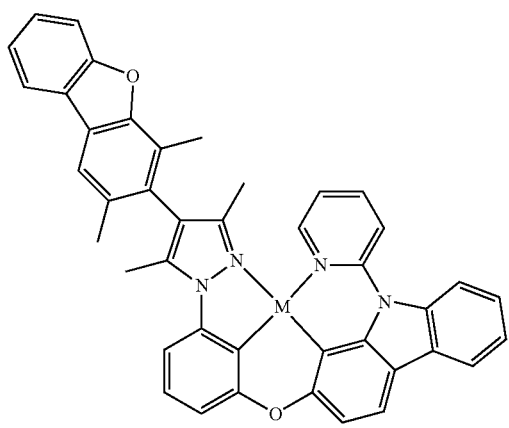
822
-continued
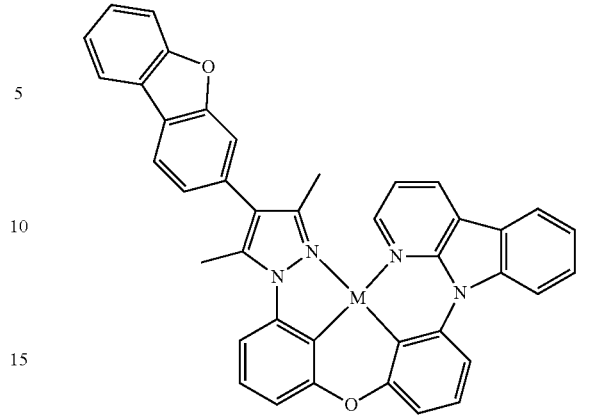
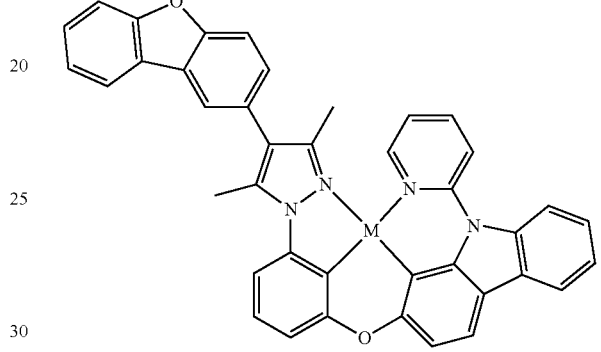
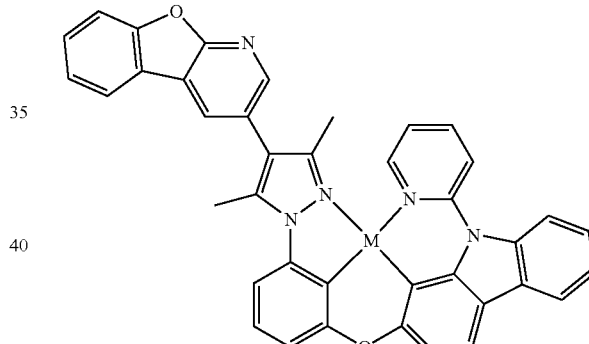
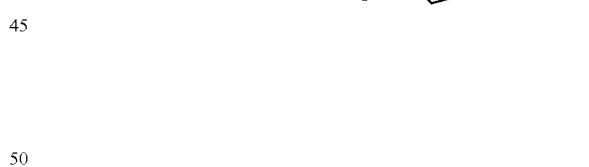
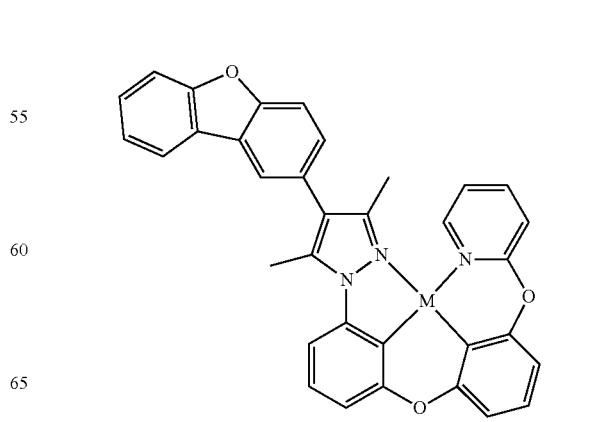

823
-continued
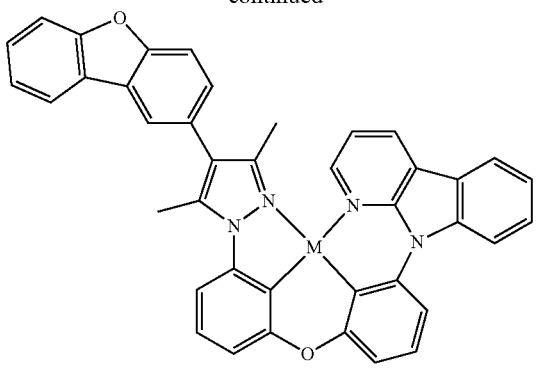
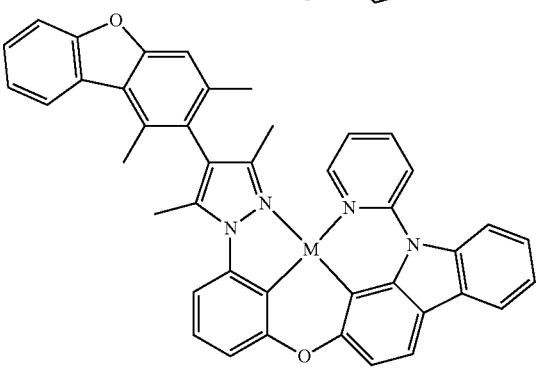
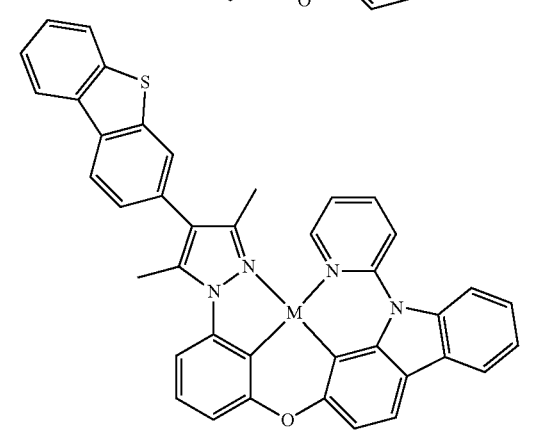
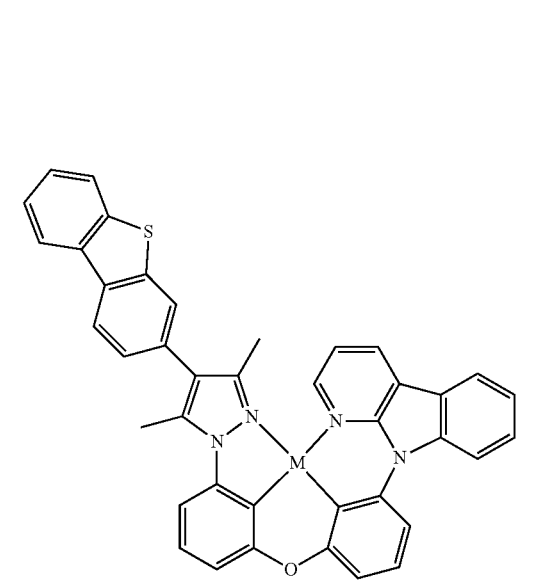
824
-continued
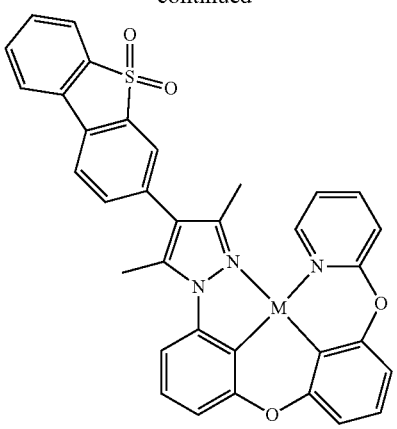
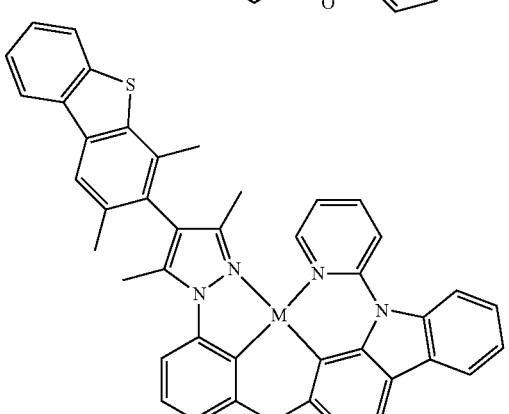
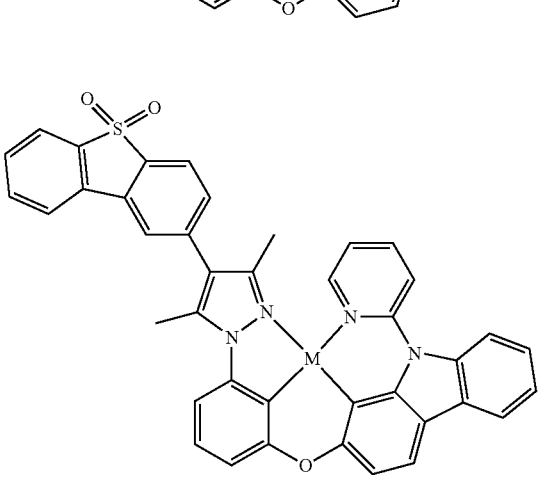
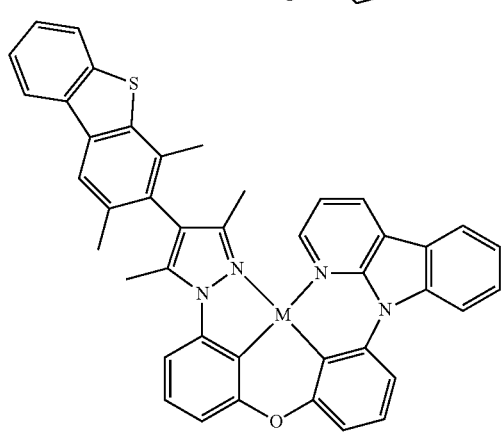

825
-continued
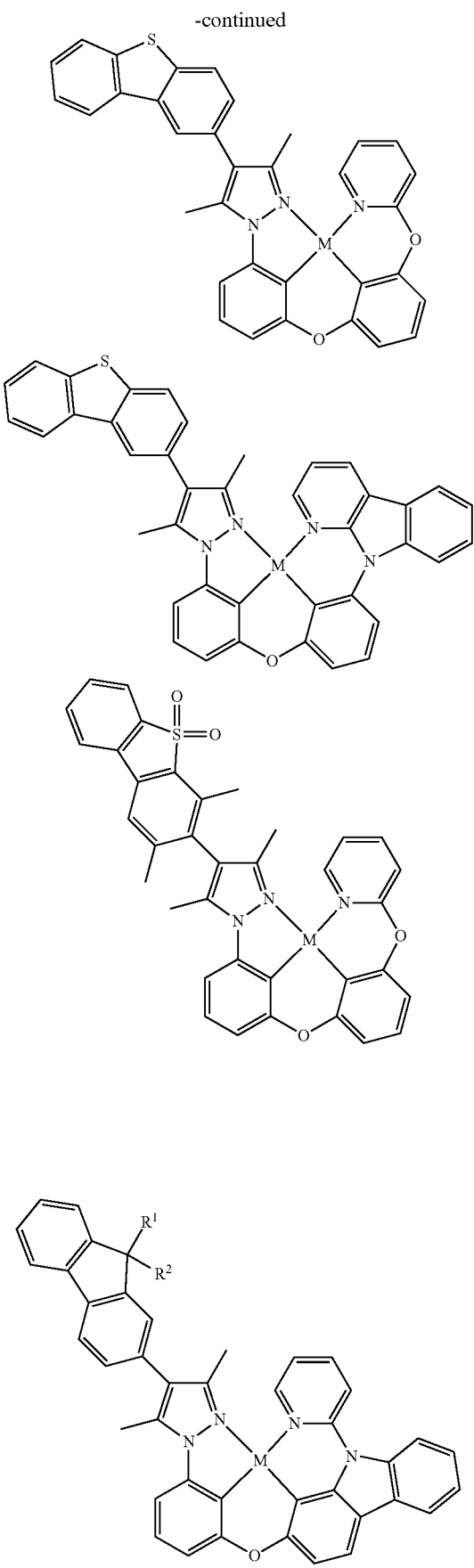
826
-continued
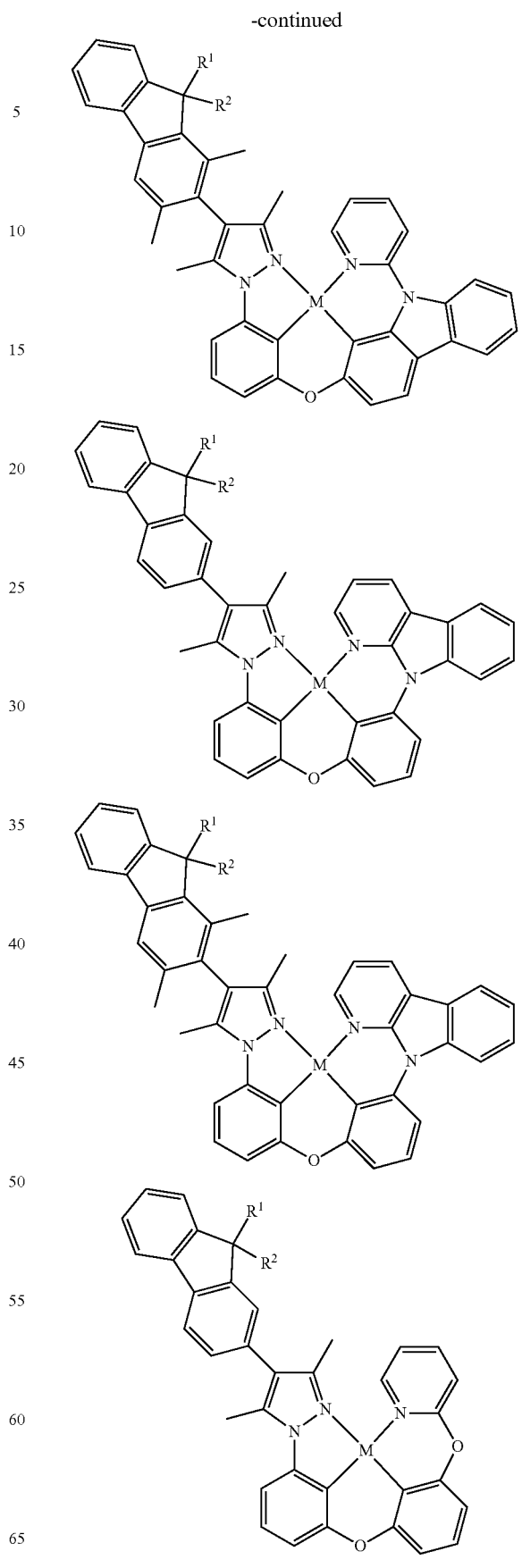

827
-continued
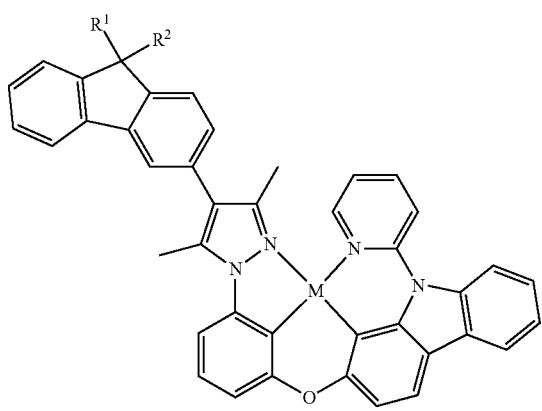
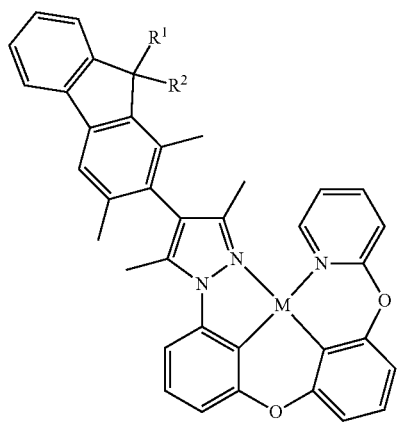
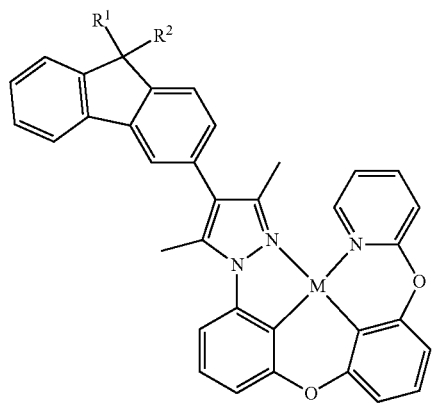
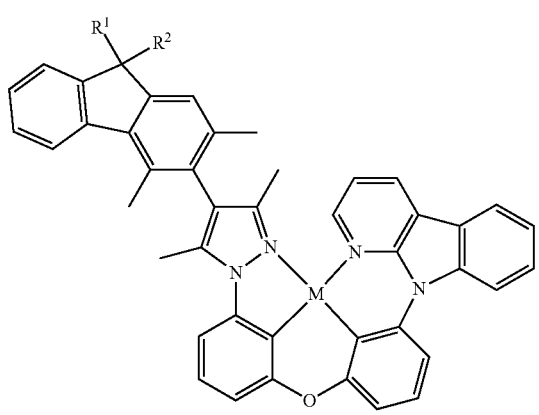
828
-continued
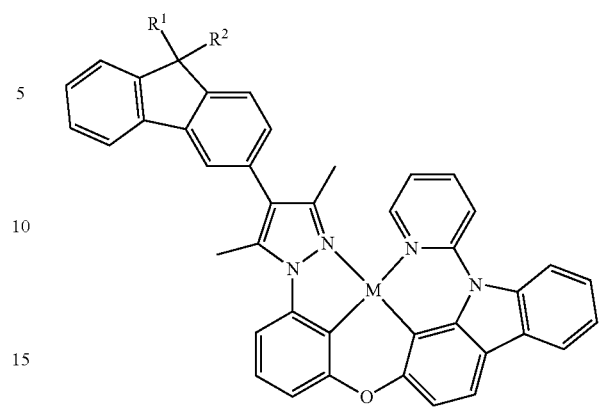
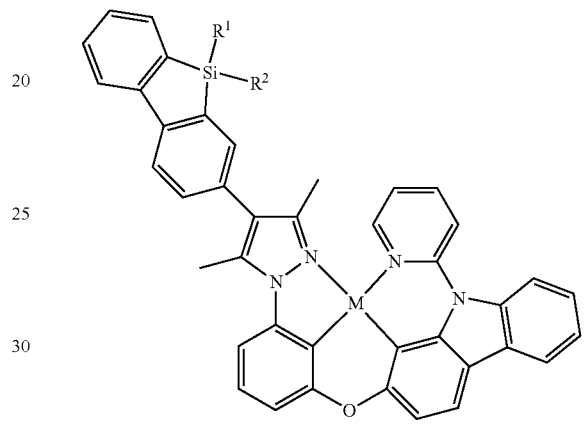
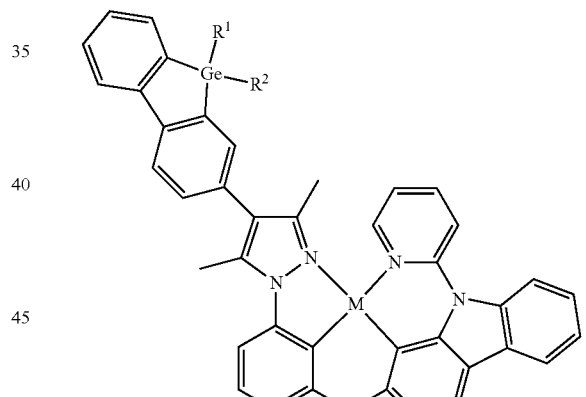
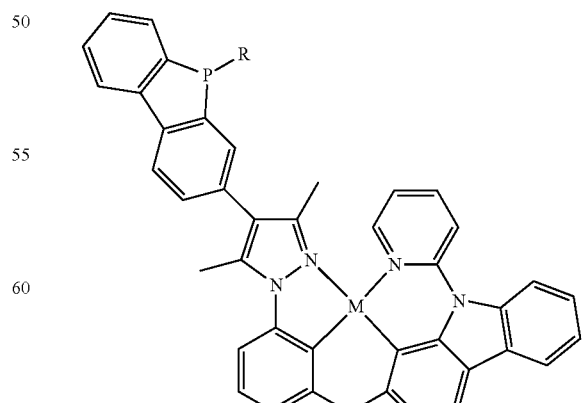

829
-continued
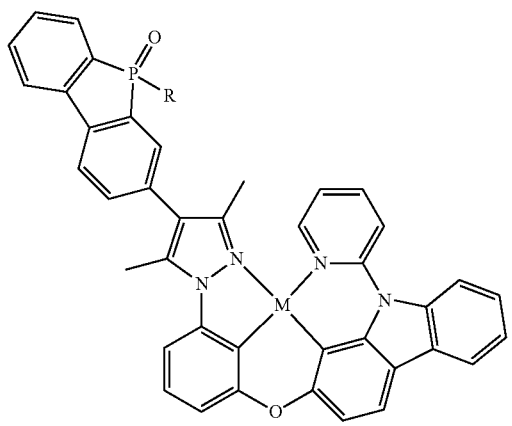
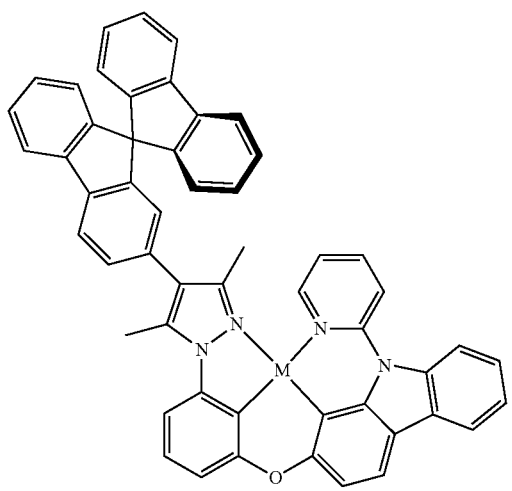
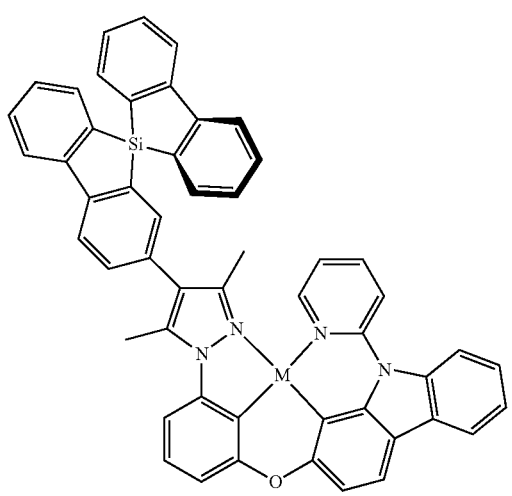
830
-continued
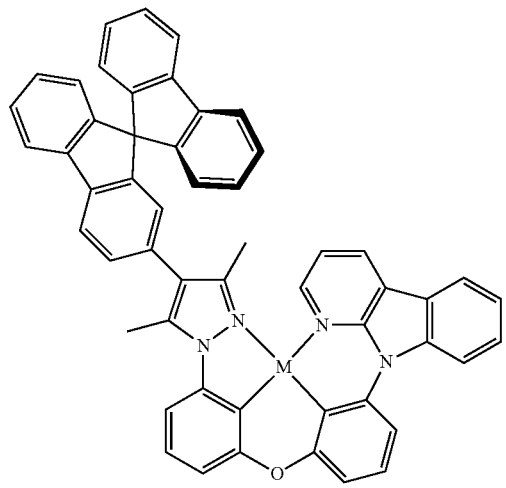
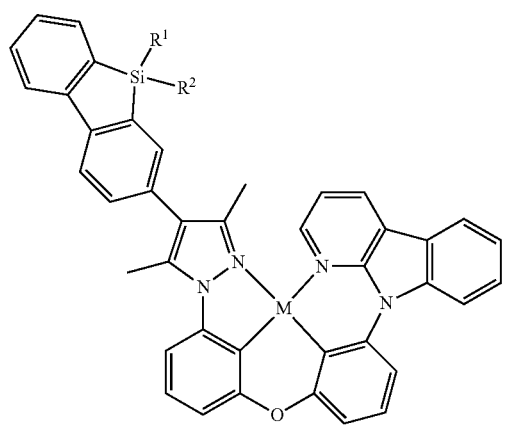

831
-continued
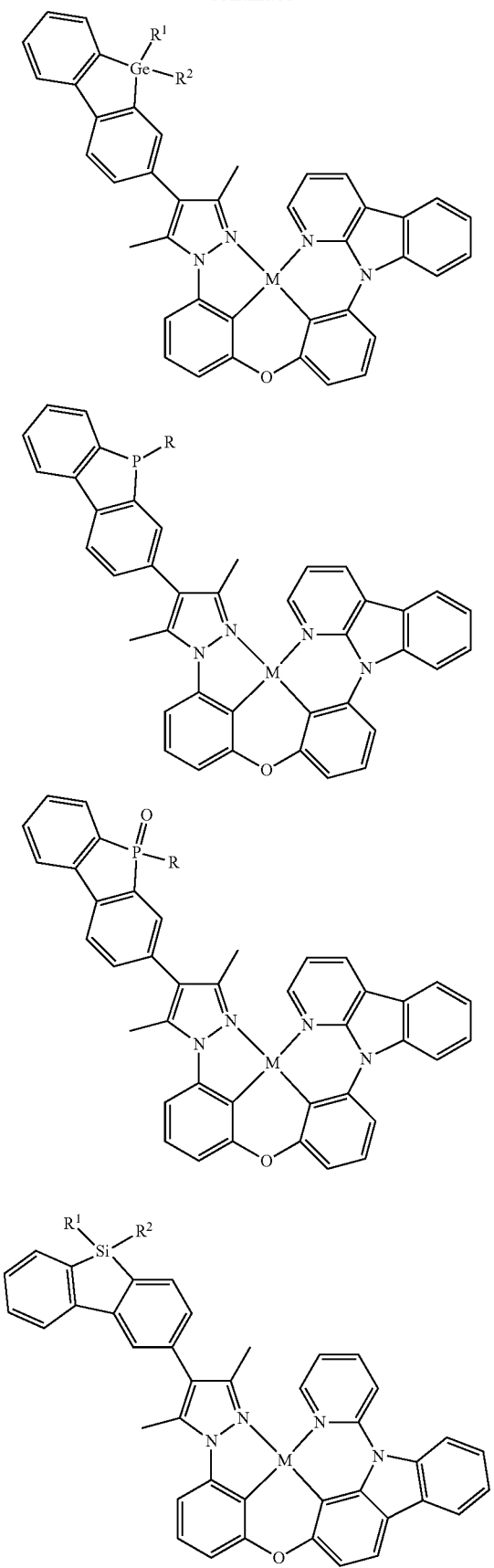
832
-continued
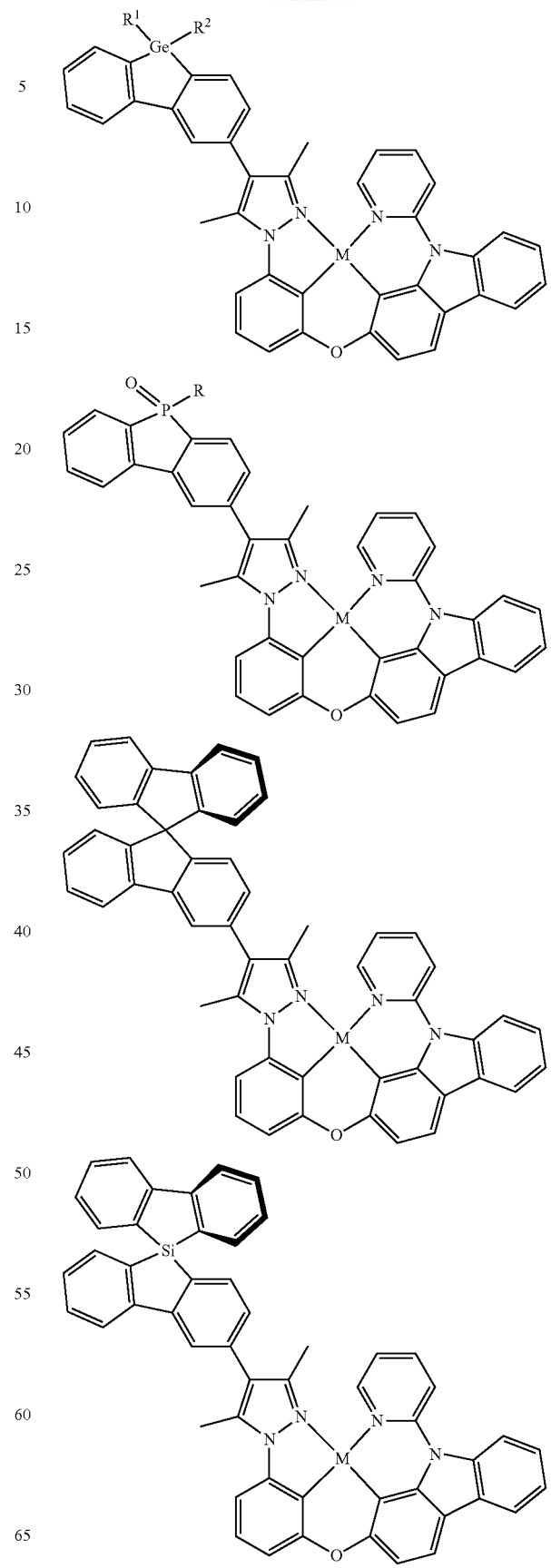

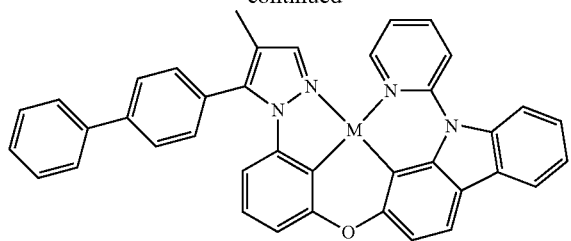
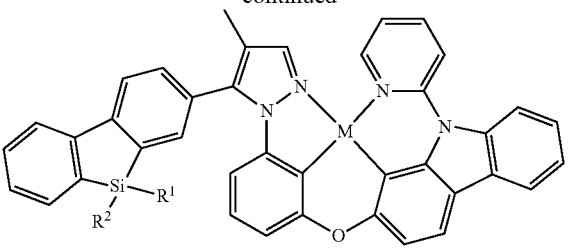

835
-continued
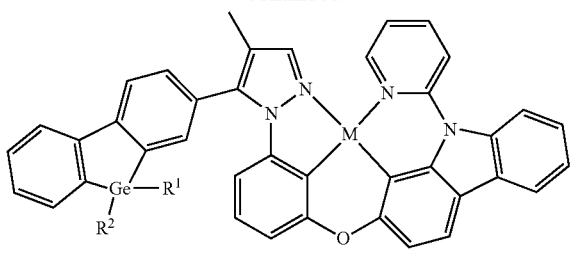
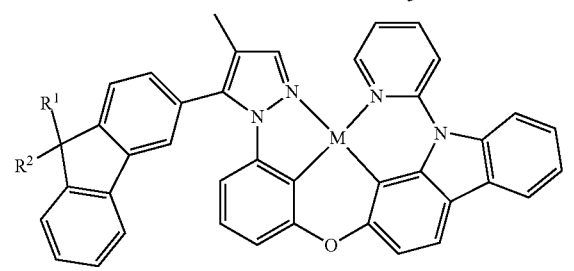
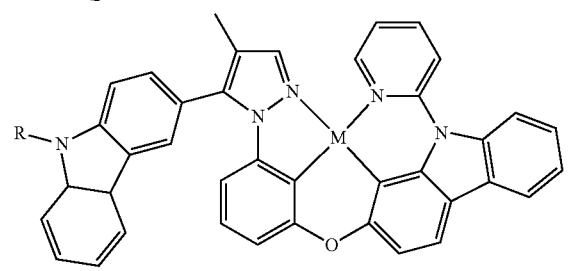
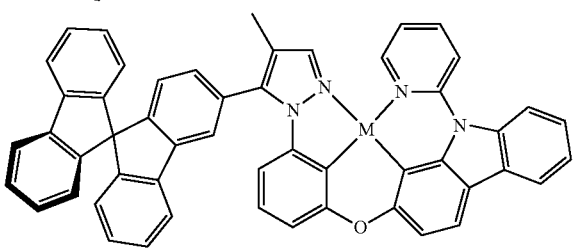
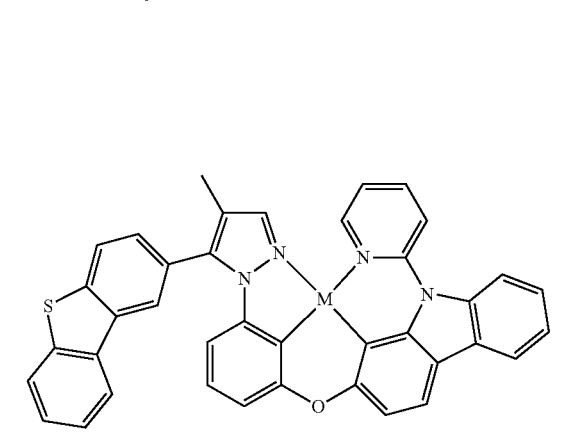
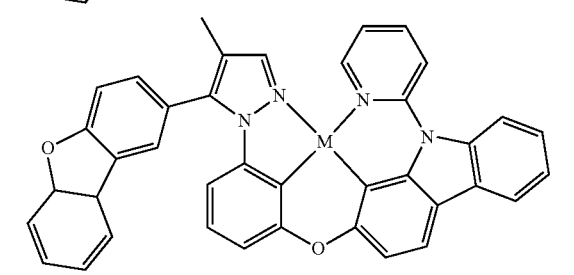
836
-continued
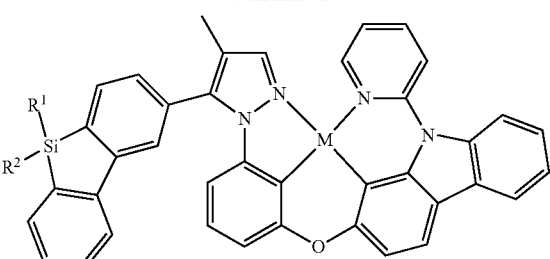
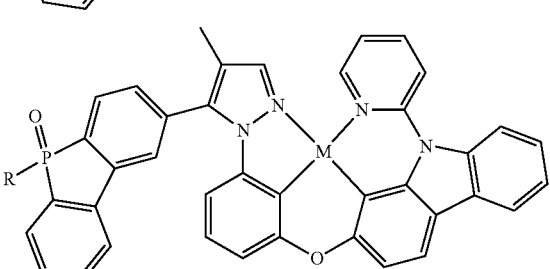
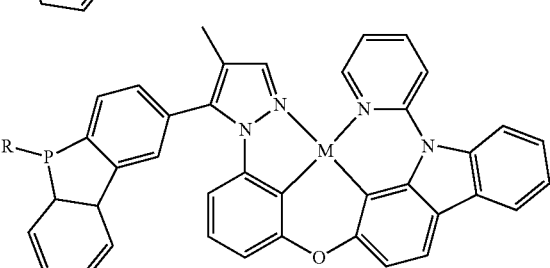
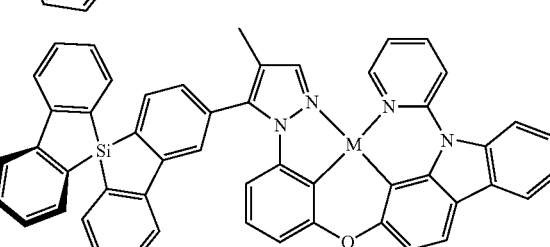
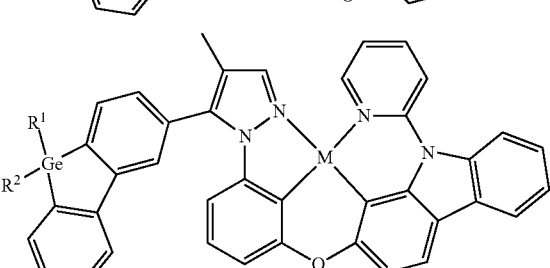
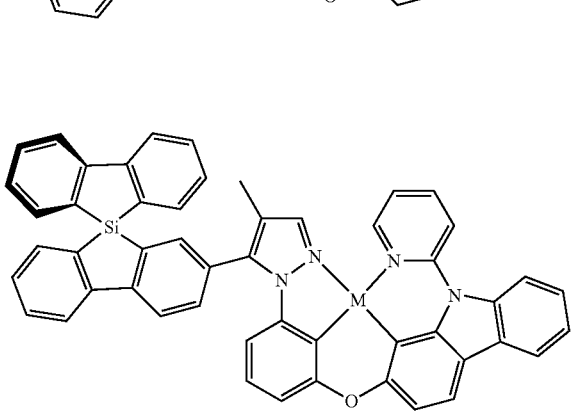

837
-continued
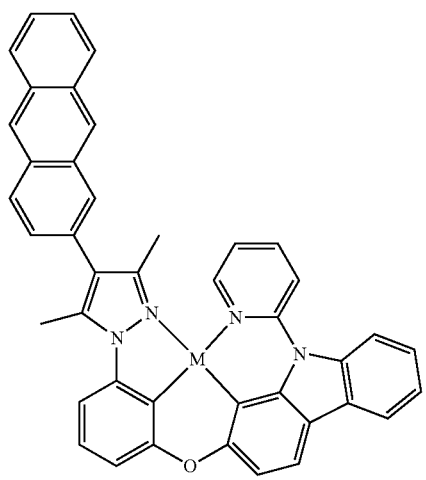
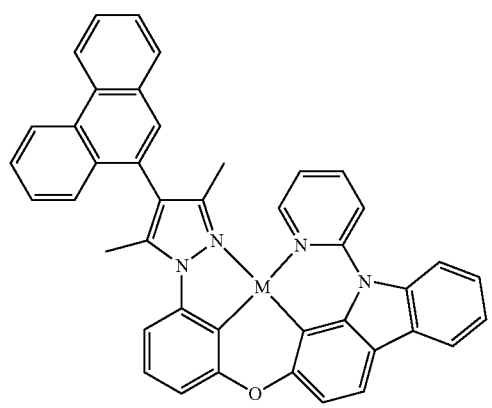
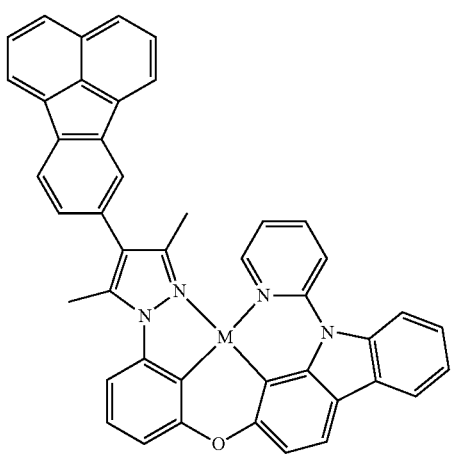
838
-continued
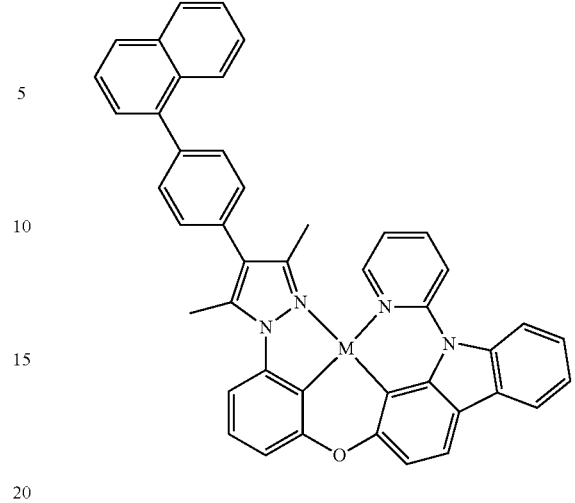
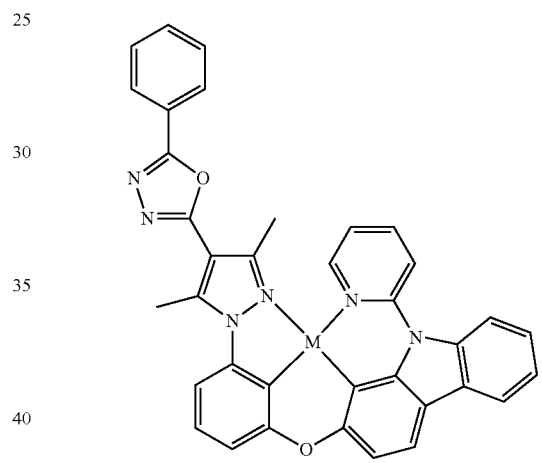
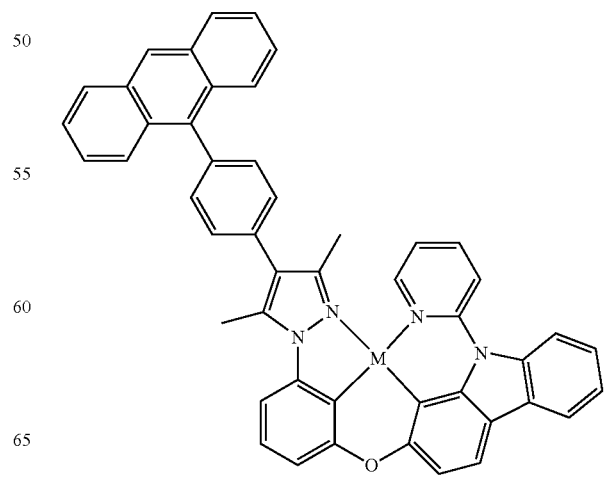

839
-continued
840
-continued
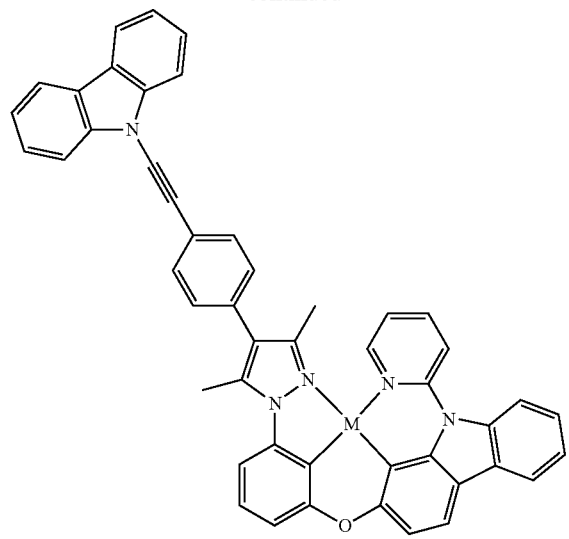
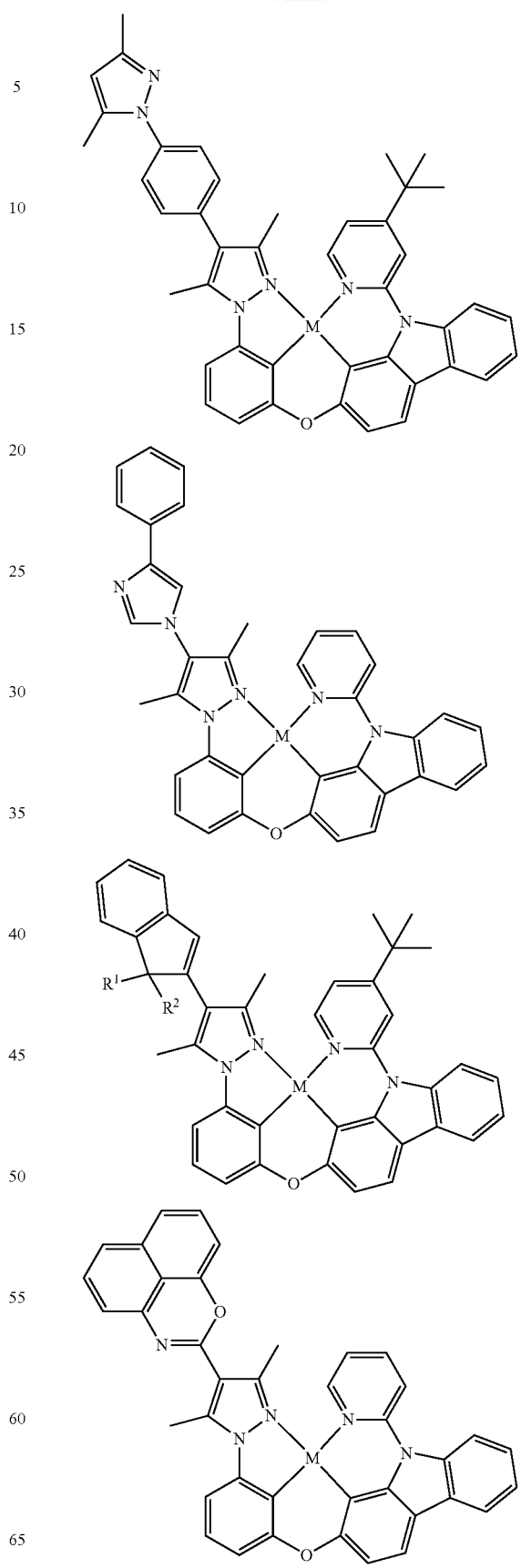

841
-continued
842
-continued
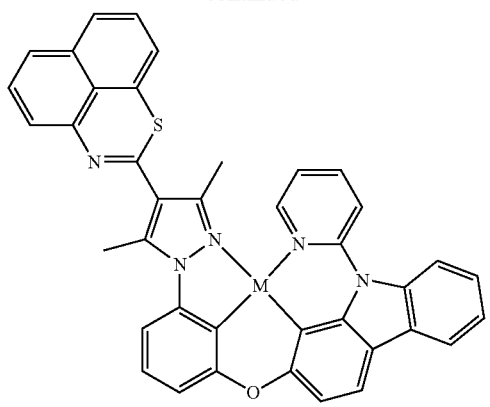
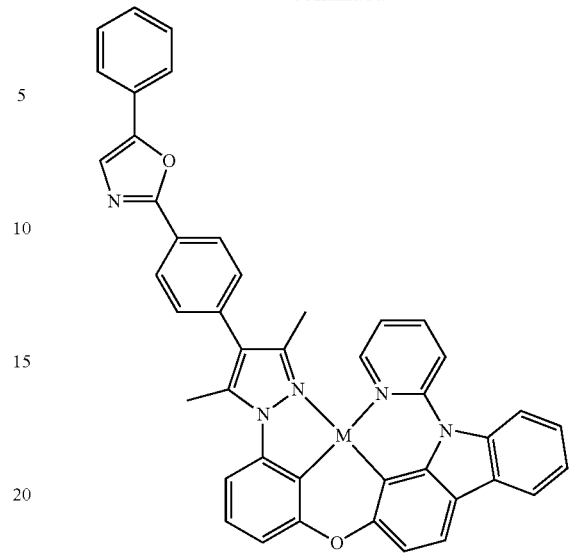
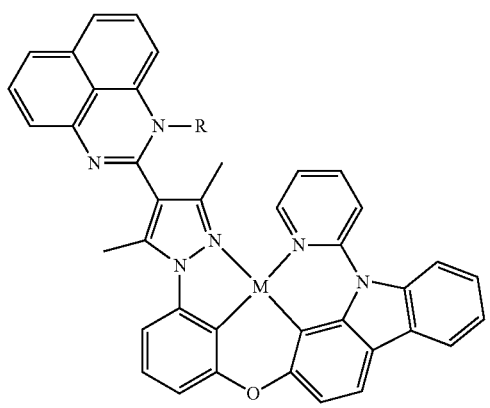
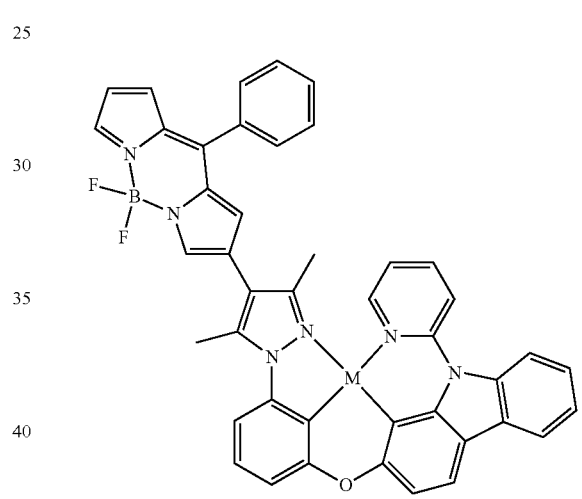
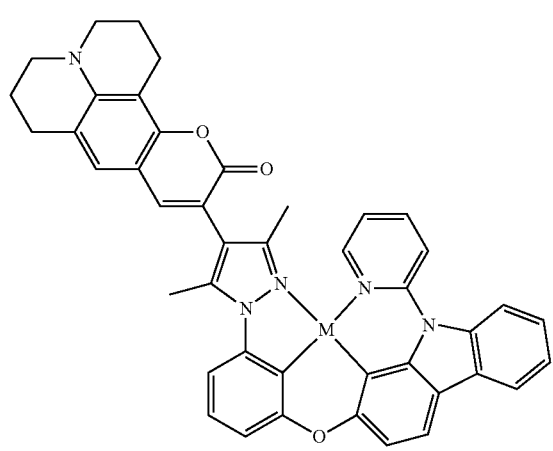
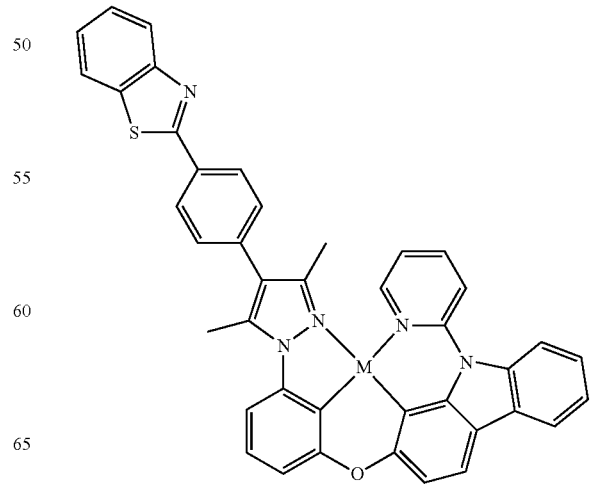

843
-continued
844
-continued
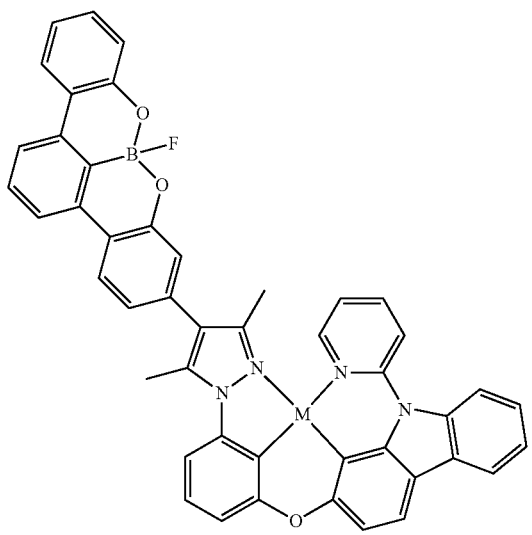
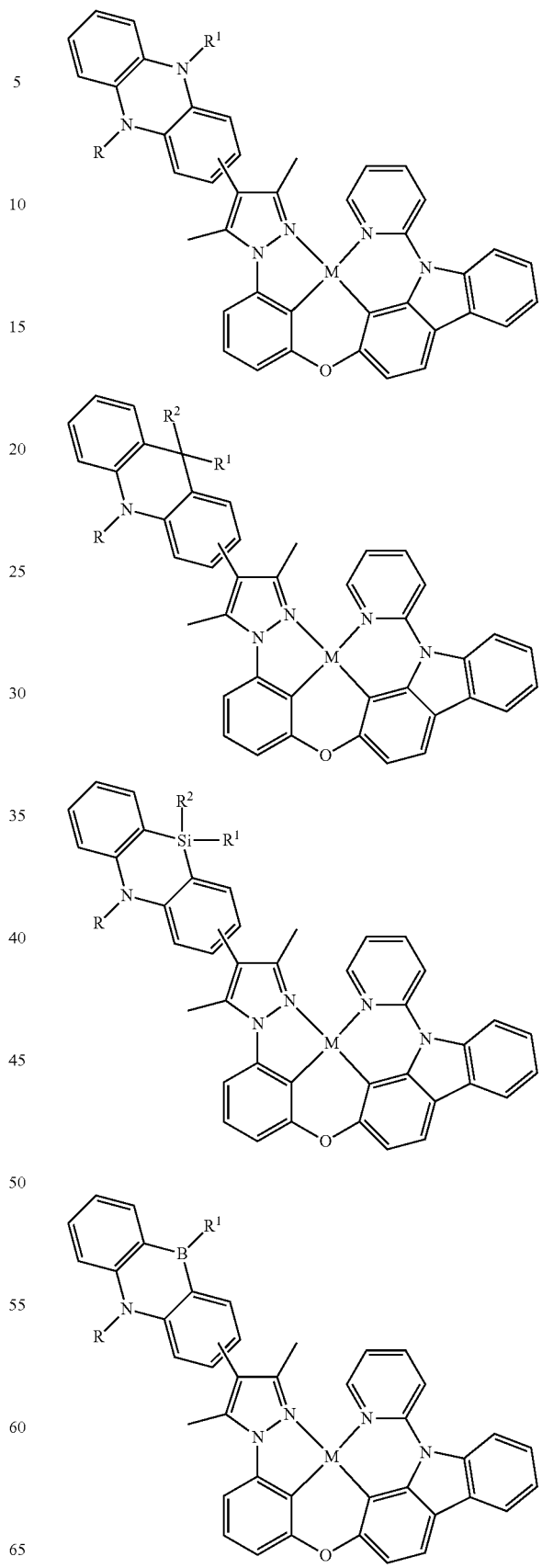

845
-continued
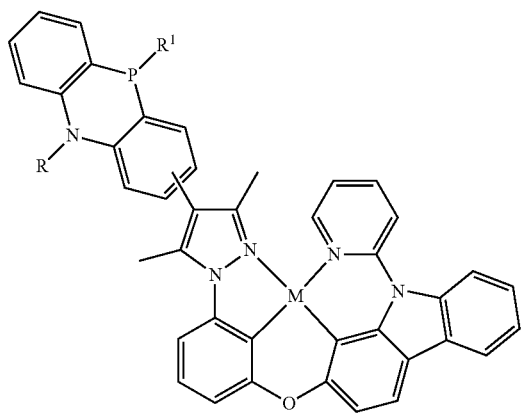
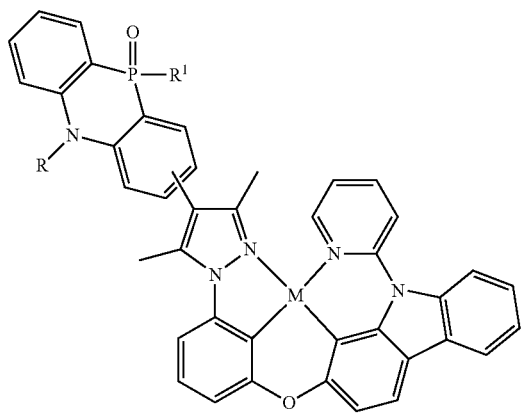
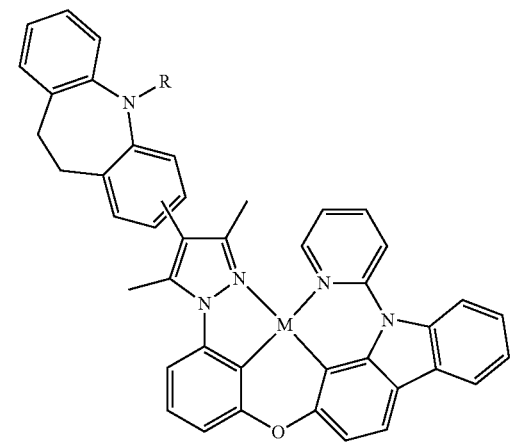
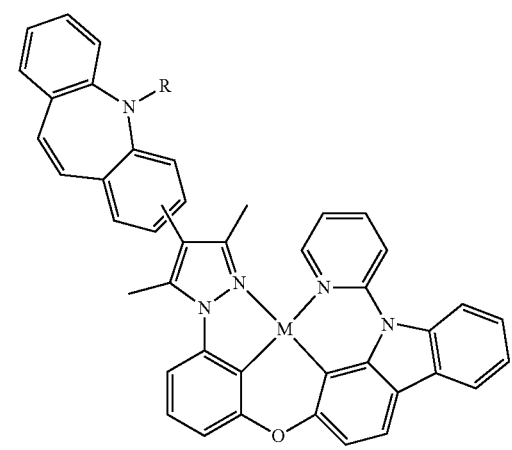
846
-continued
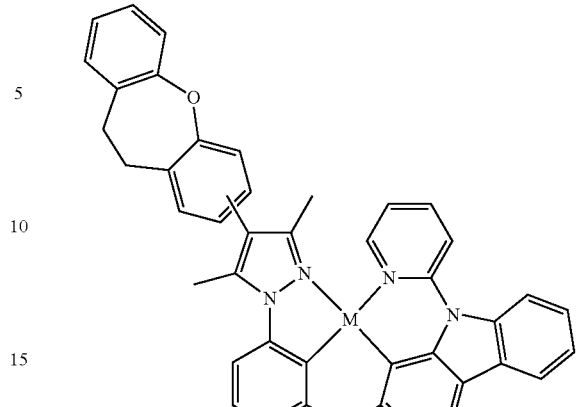
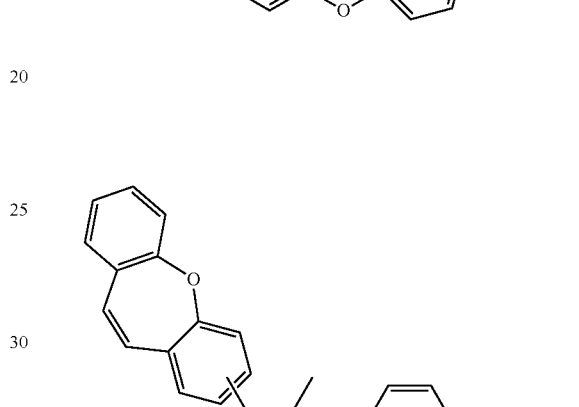
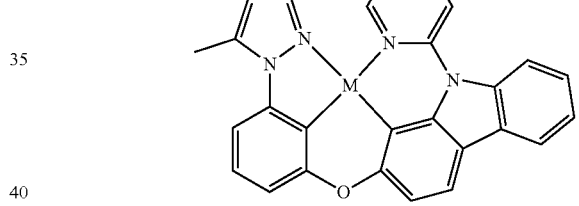
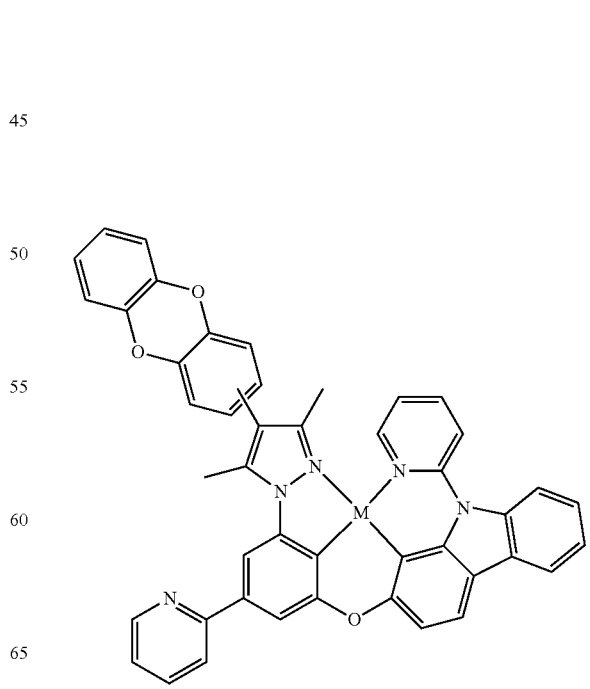

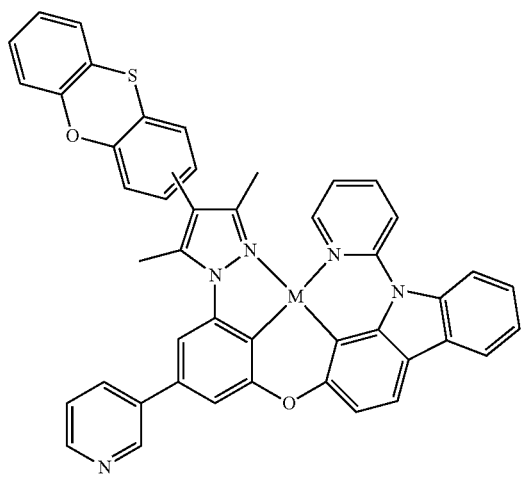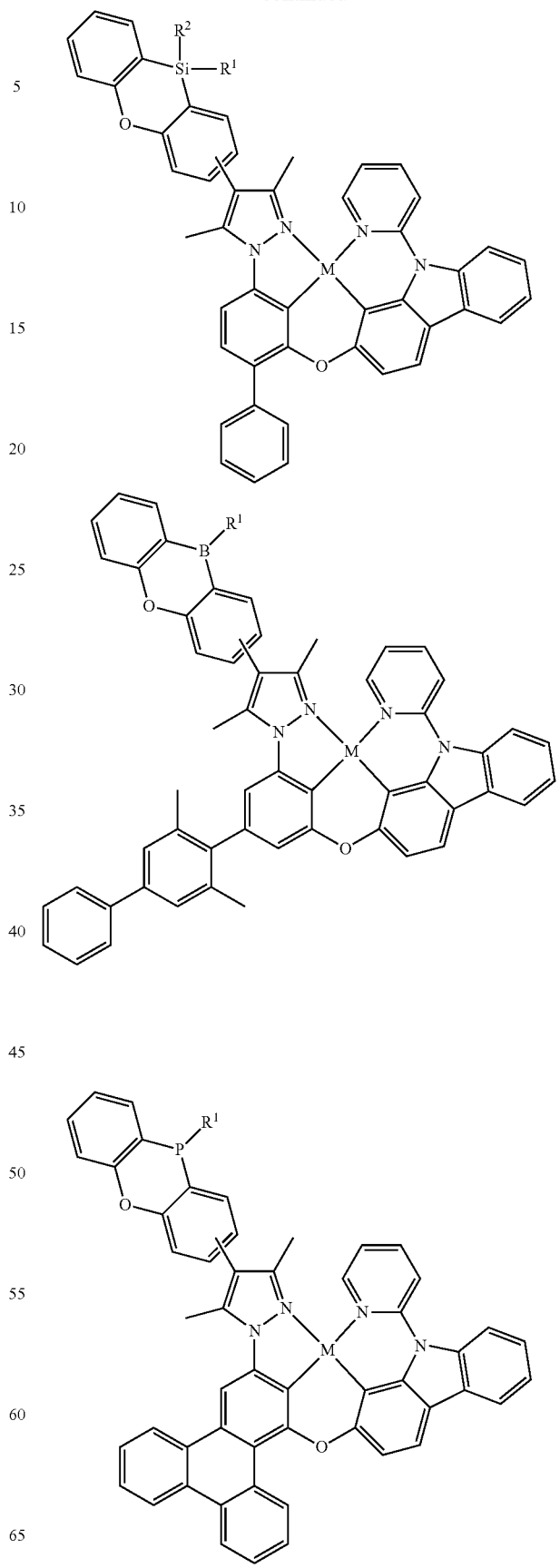

849
-continued
850
-continued
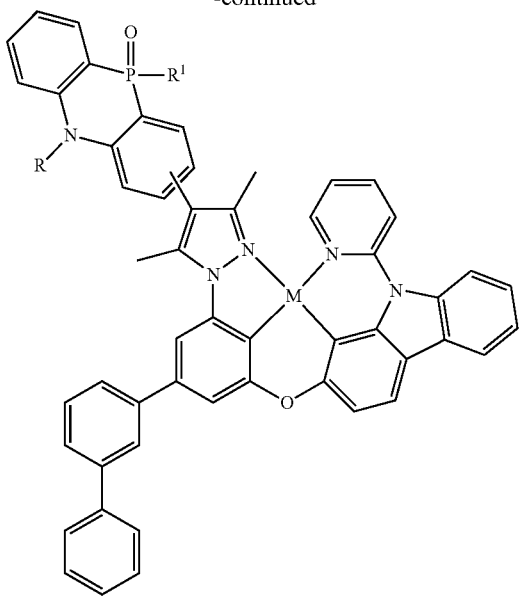
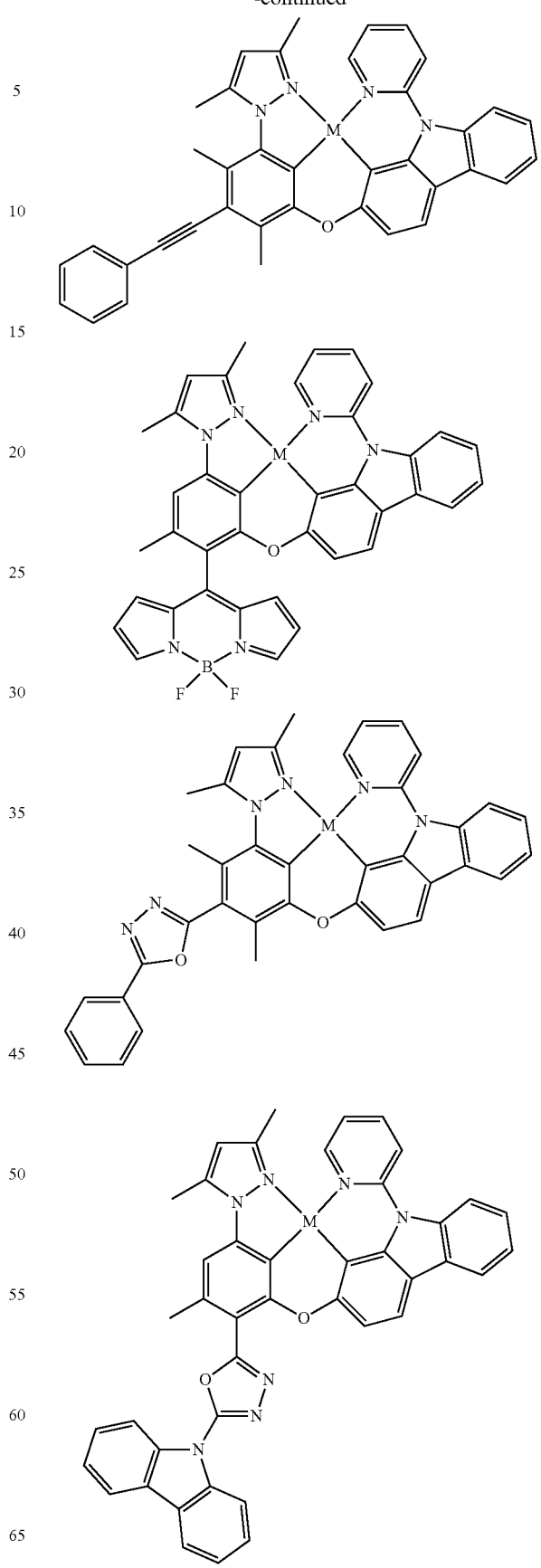

851
-continued
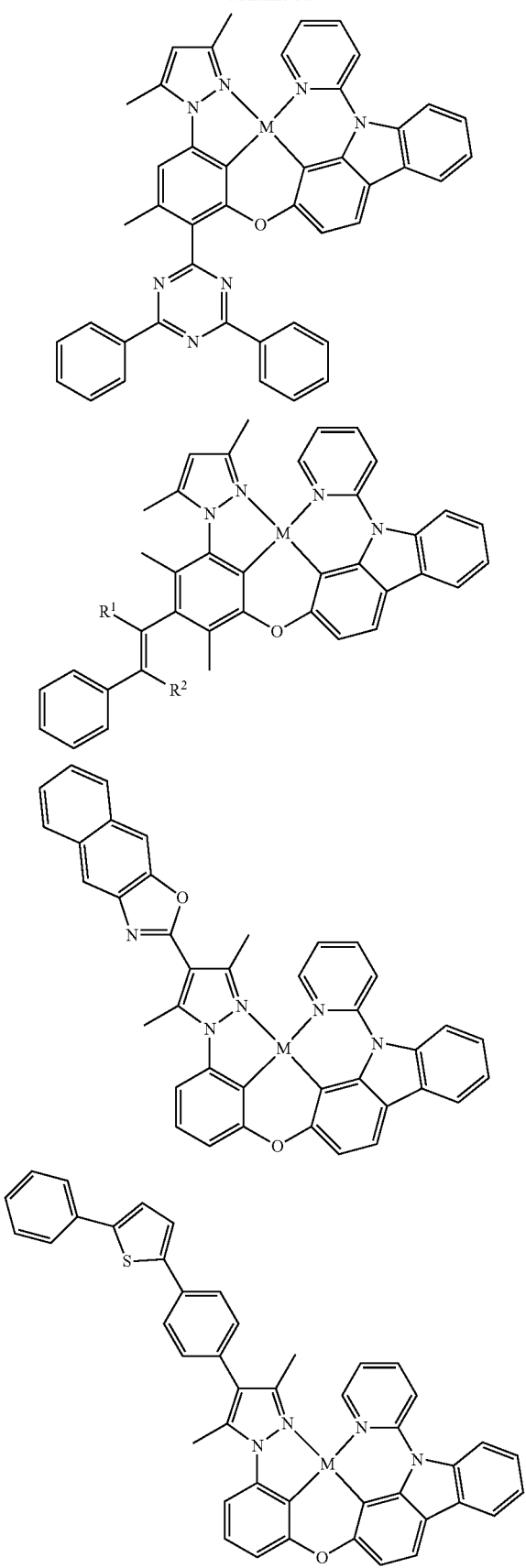
852
-continued
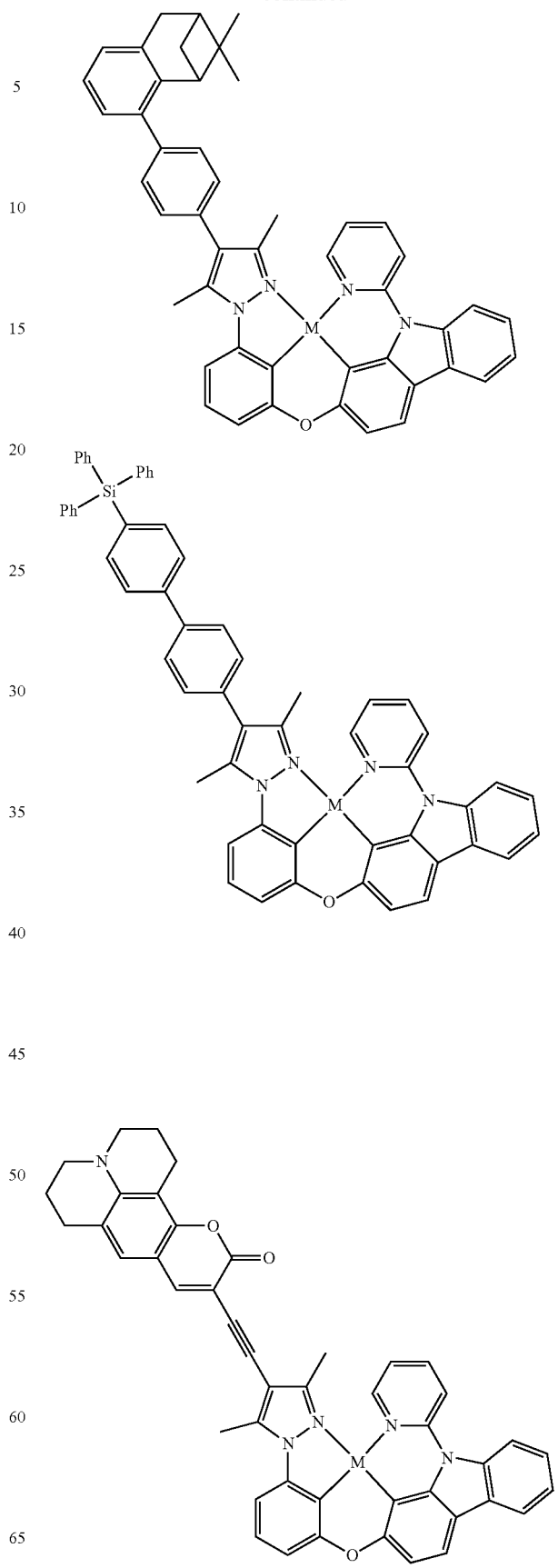

853
-continued
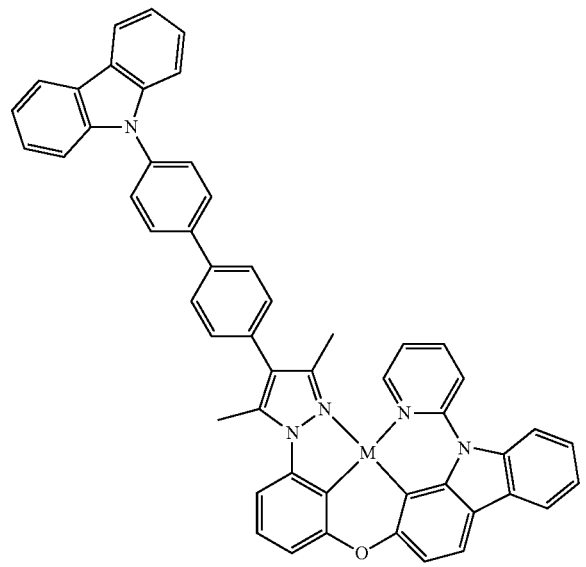
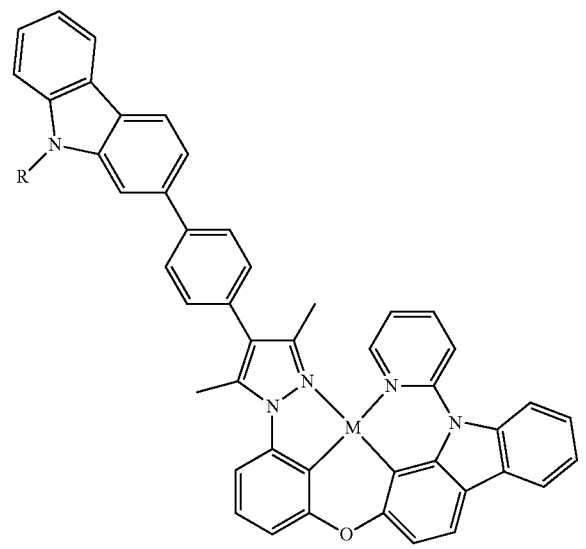
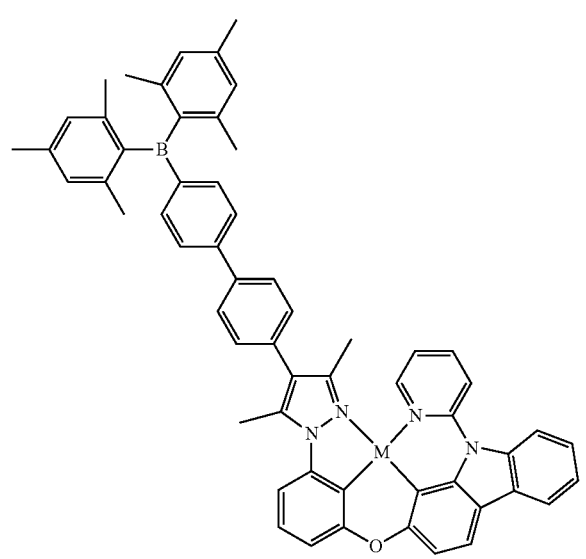
854
-continued
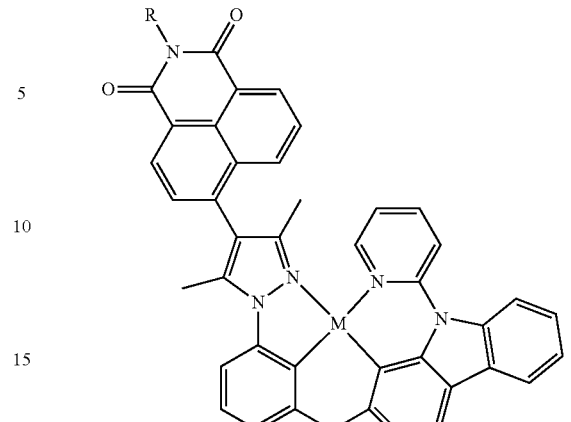
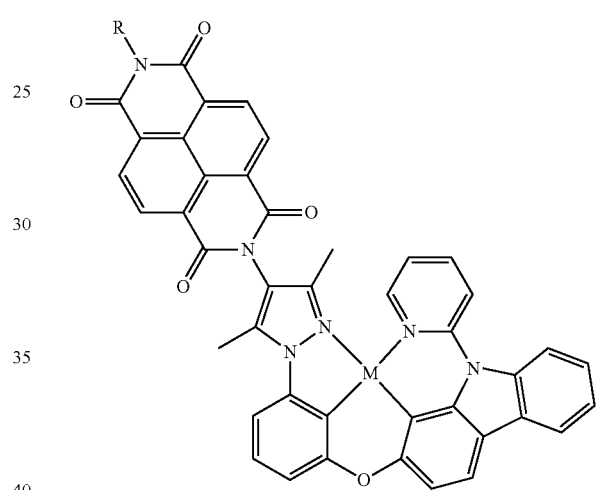
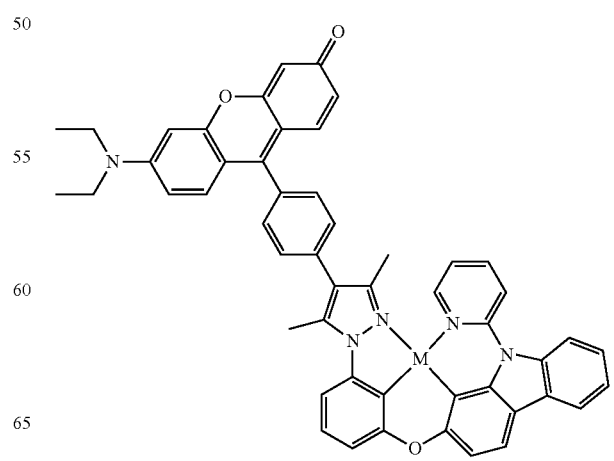

855
-continued
856
-continued
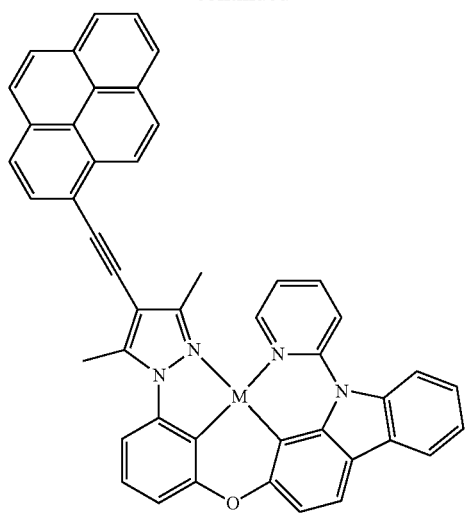
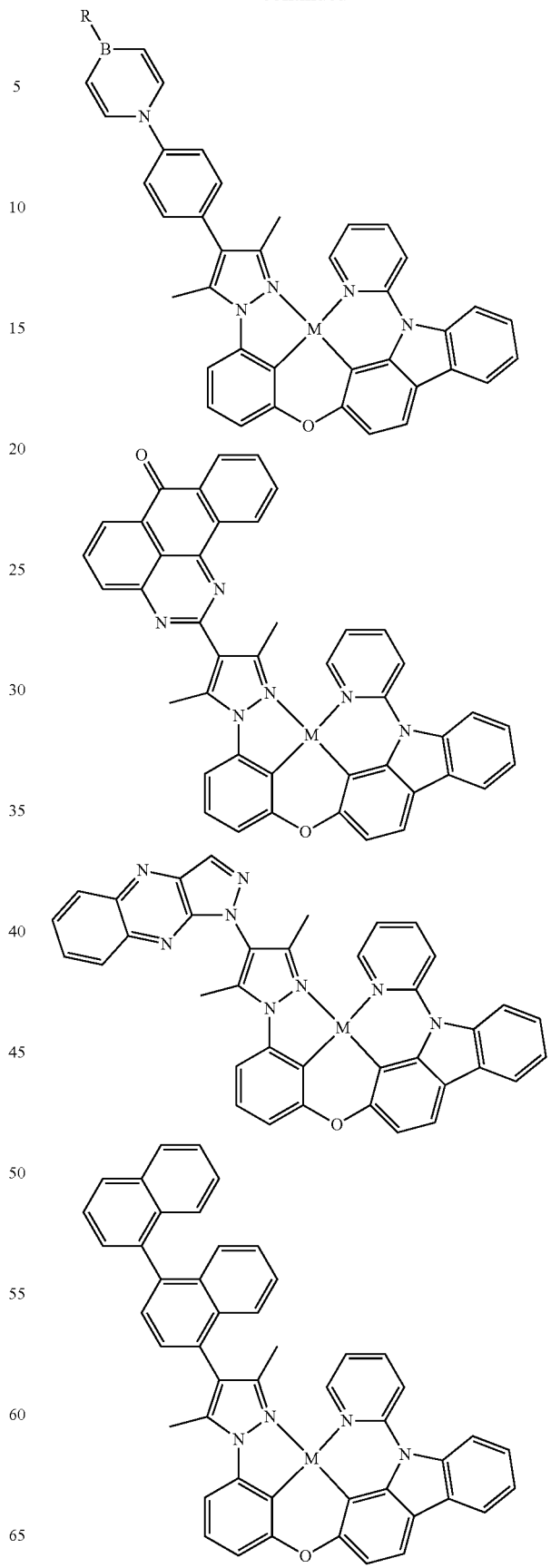

857
-continued
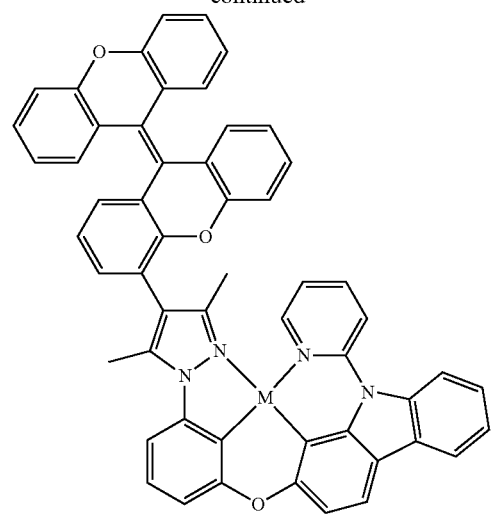
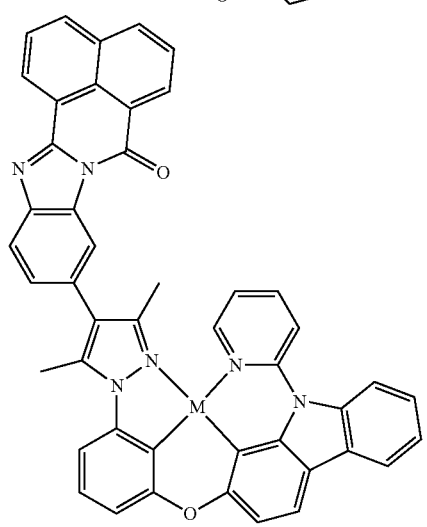
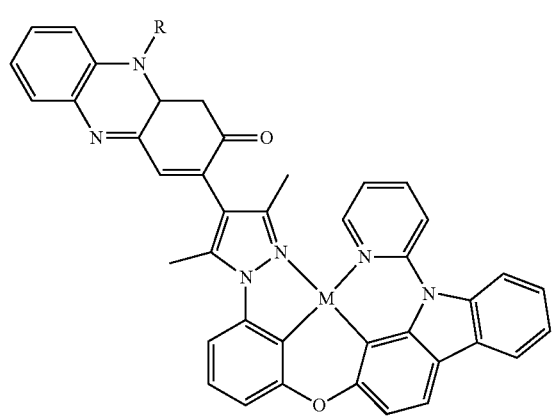
858
-continued
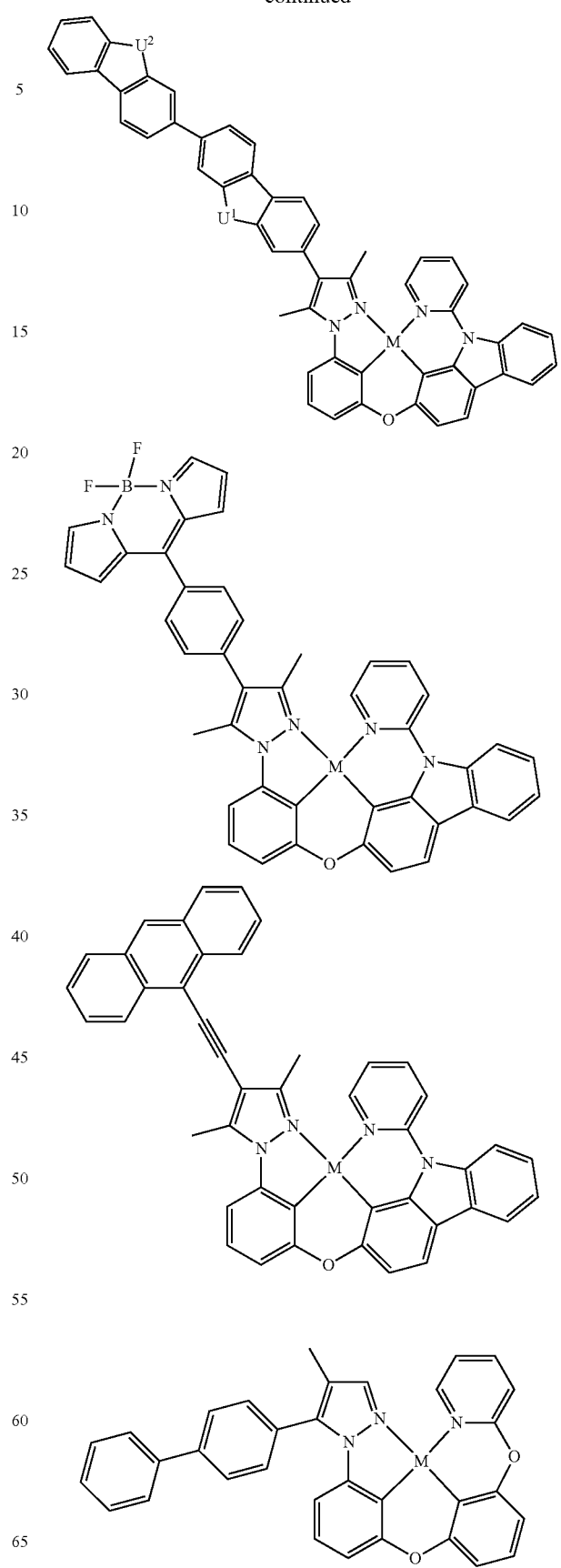

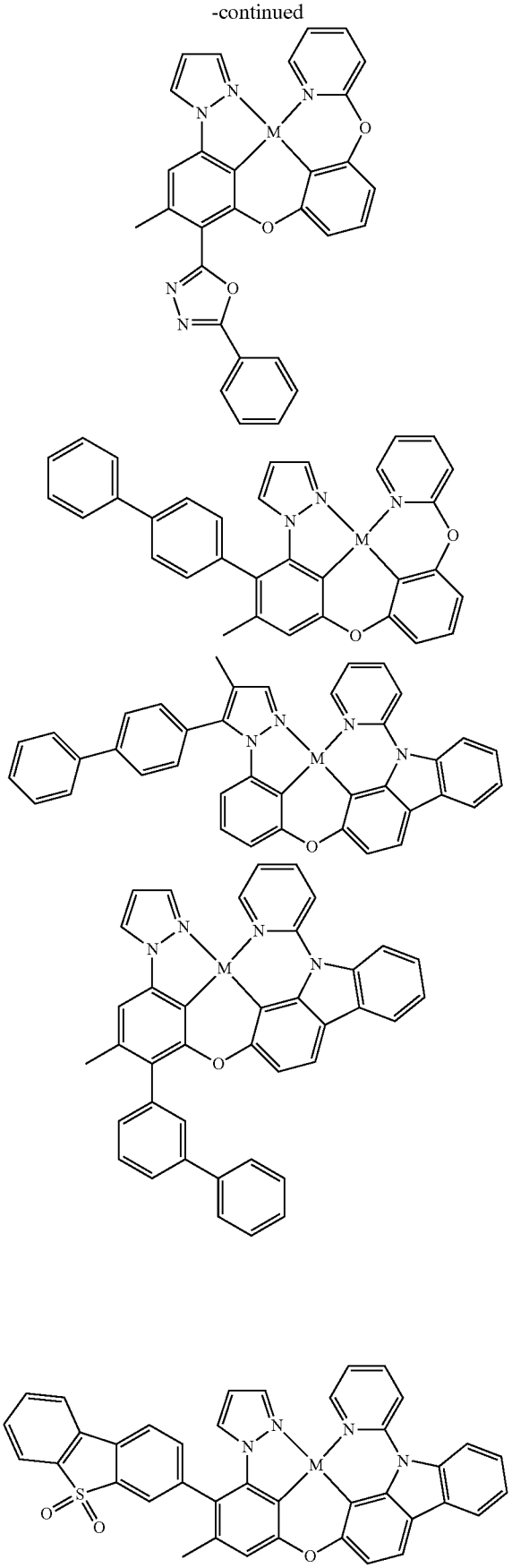

861
-continued
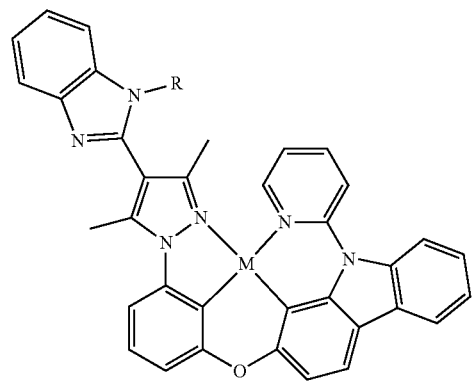
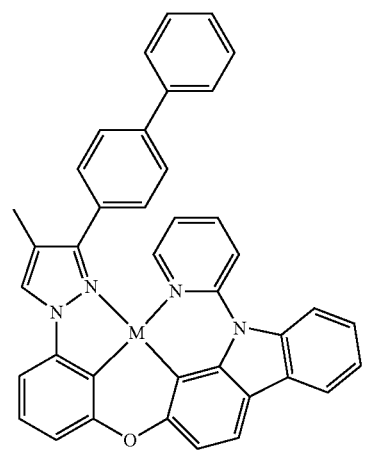
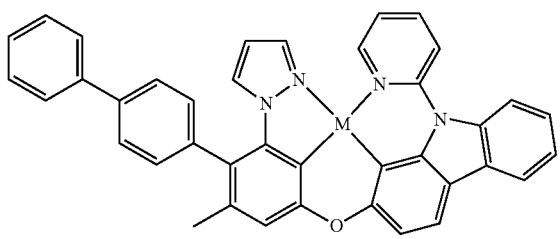
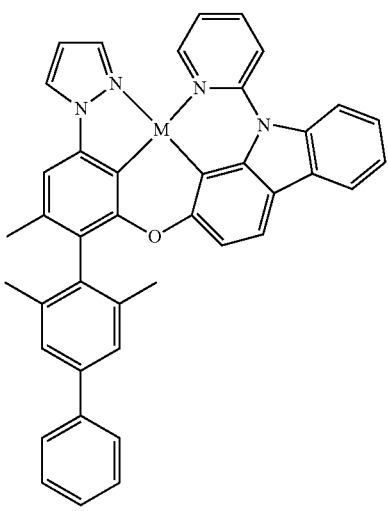
862
-continued
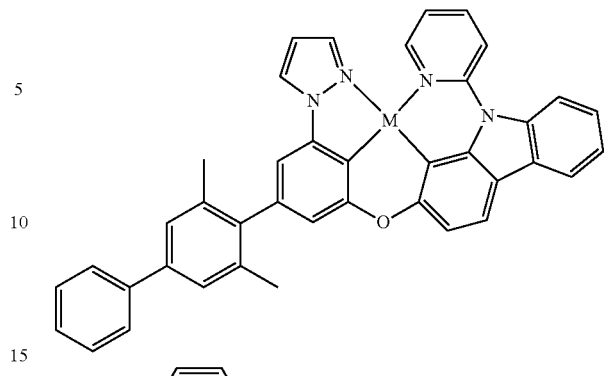
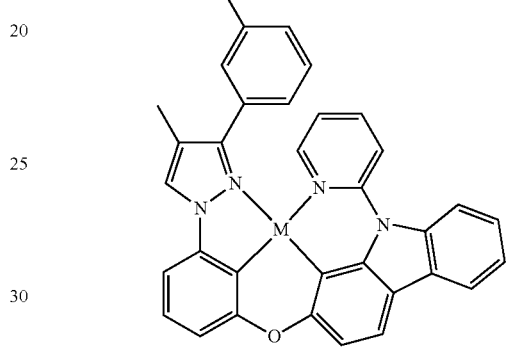
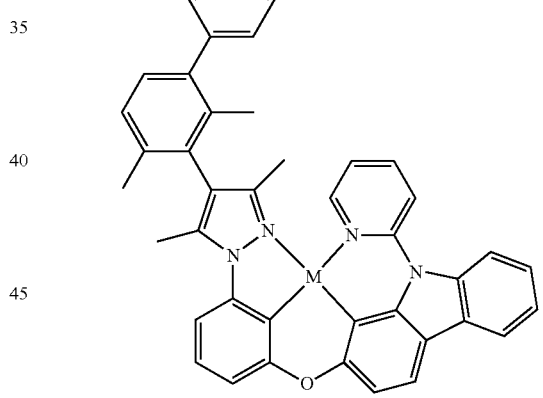
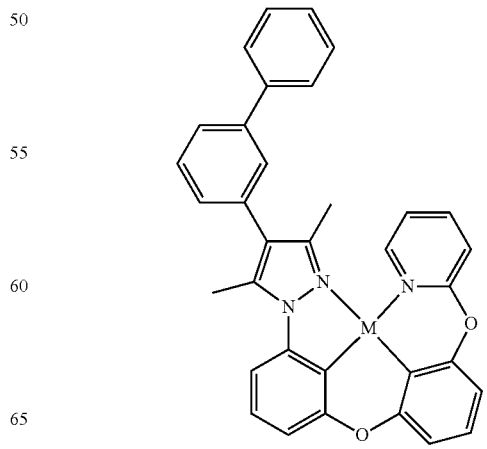

863
-continued
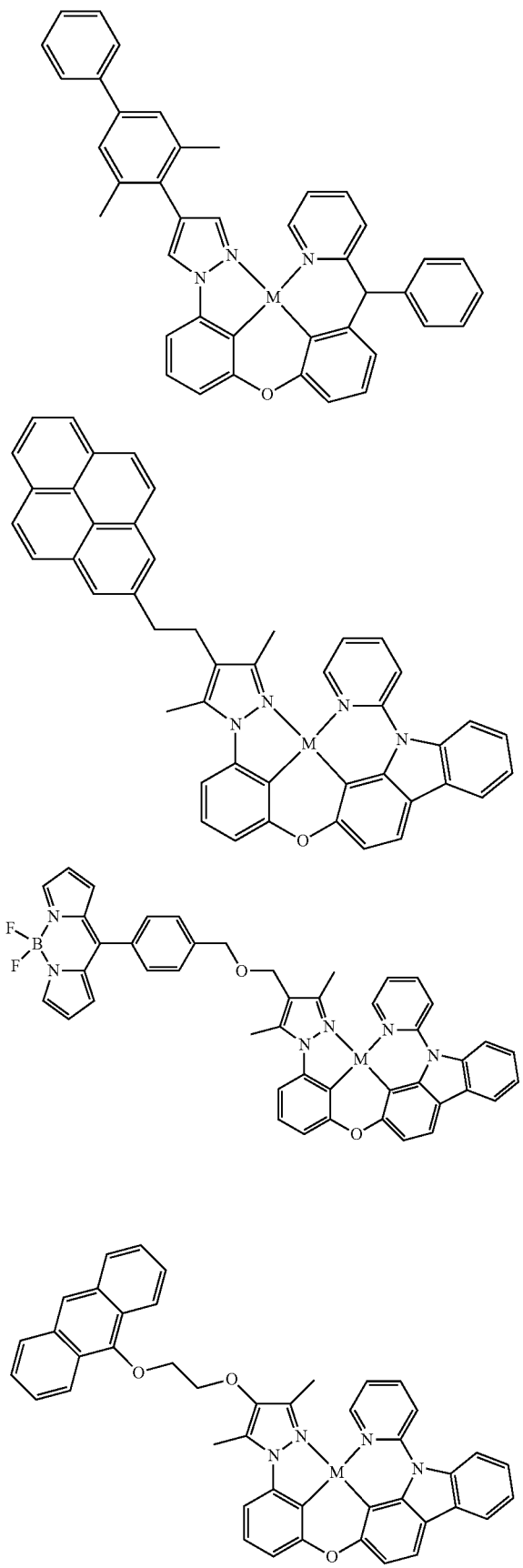
864
-continued
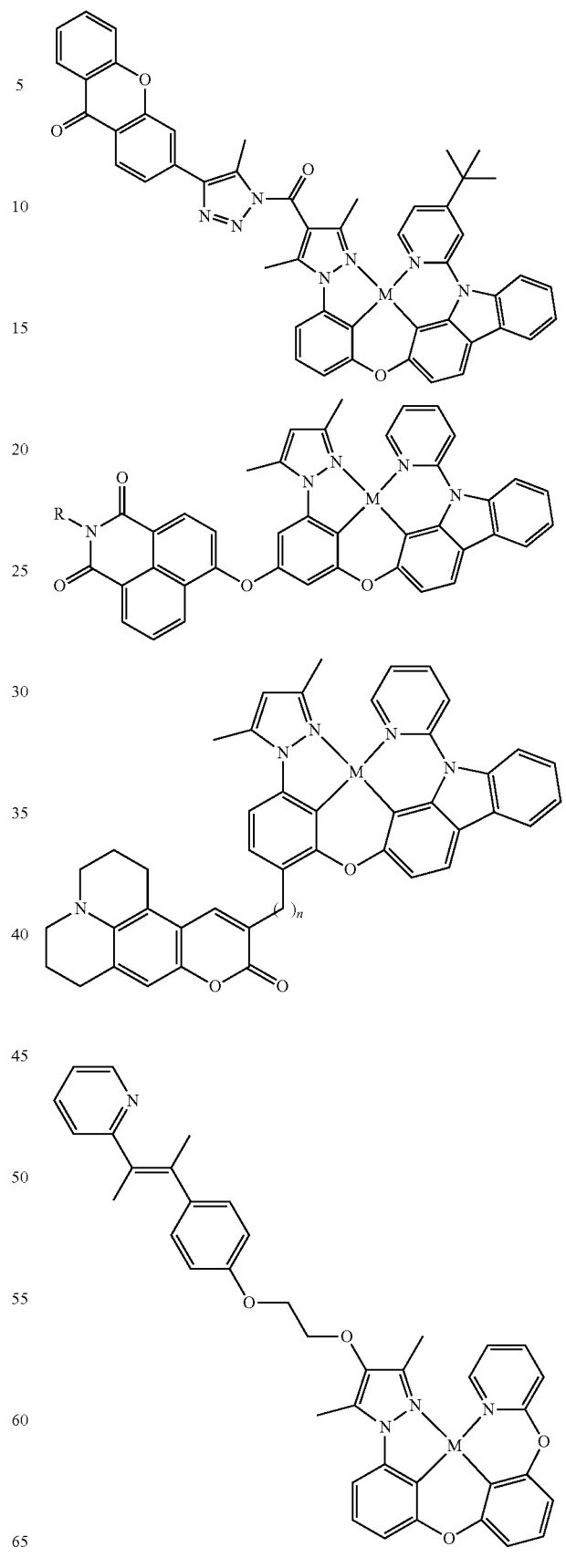

865
-continued
866
-continued
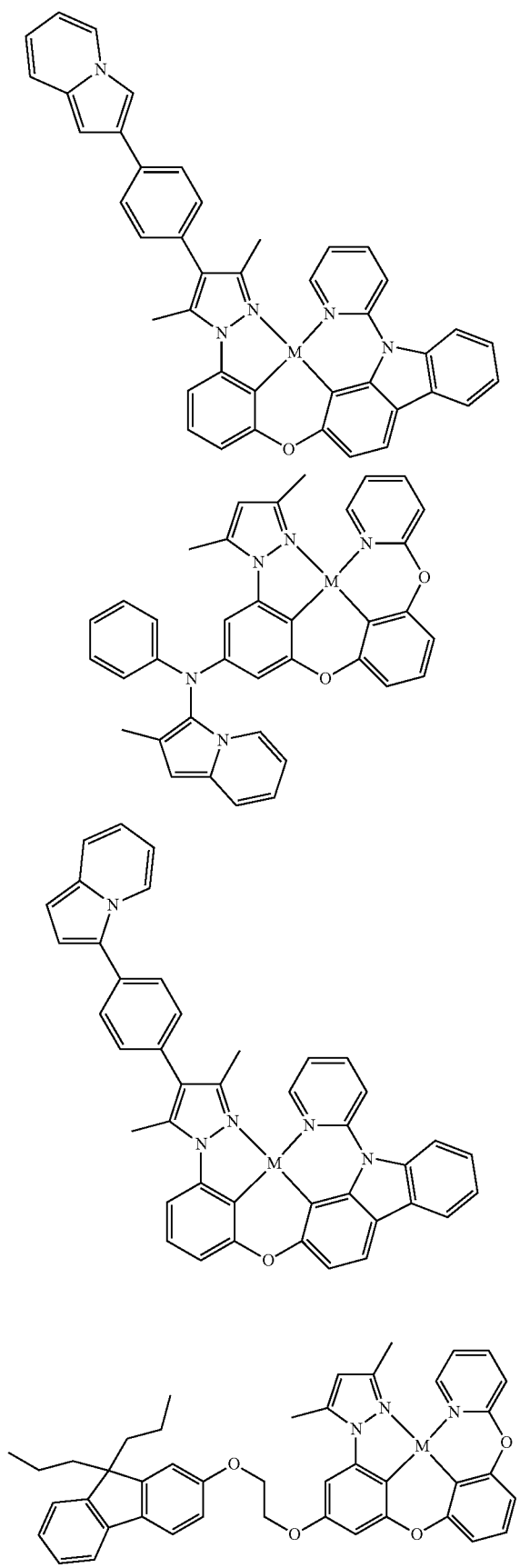
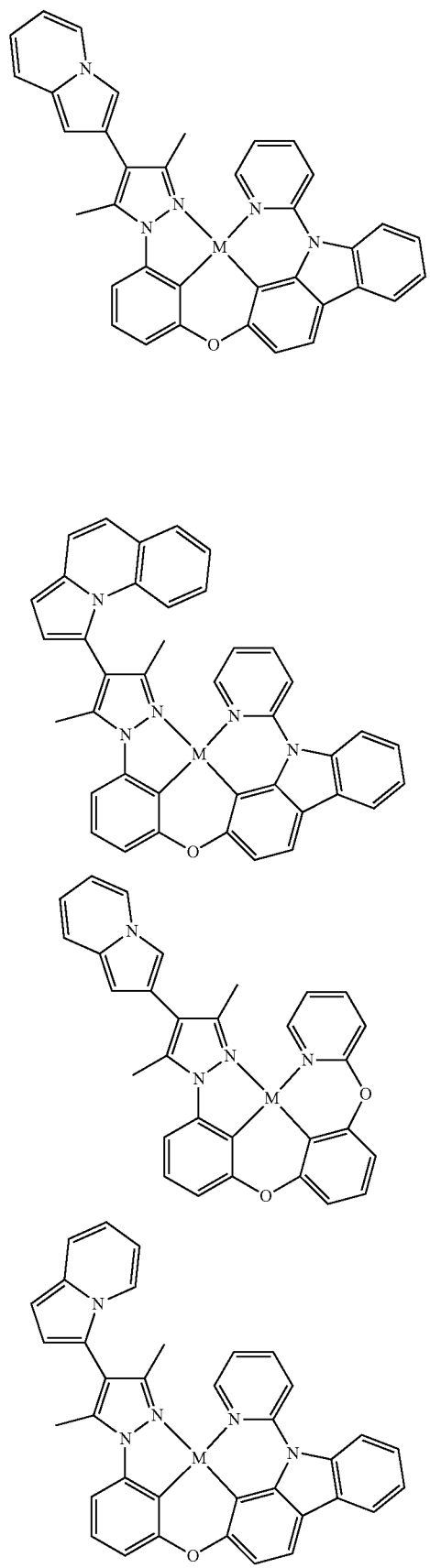

867
-continued
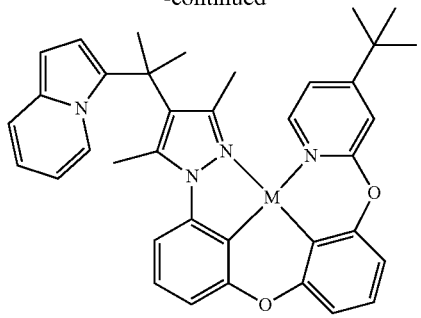
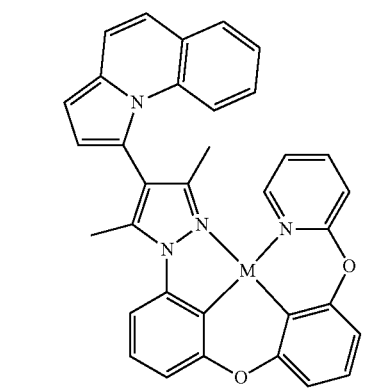
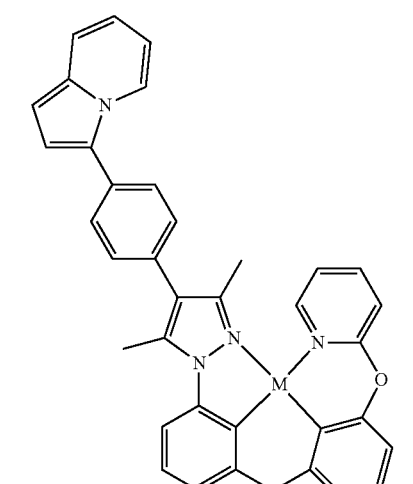
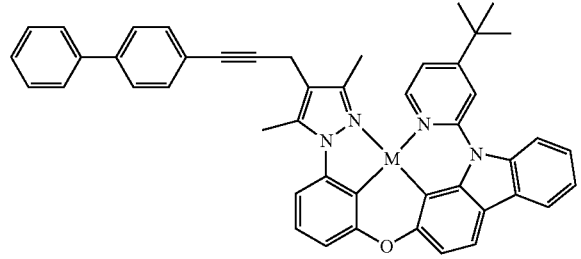
868
-continued
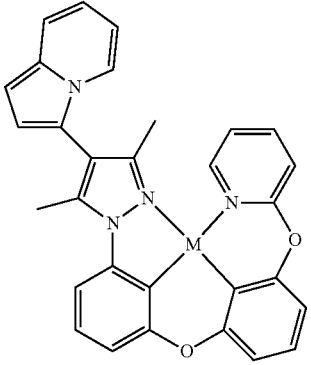
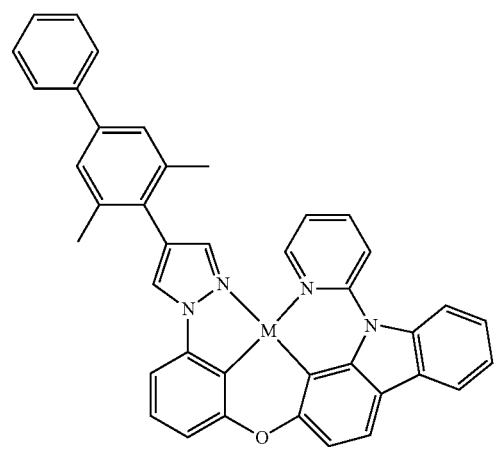
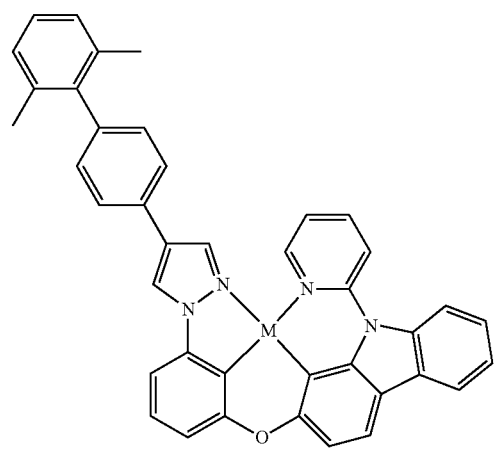
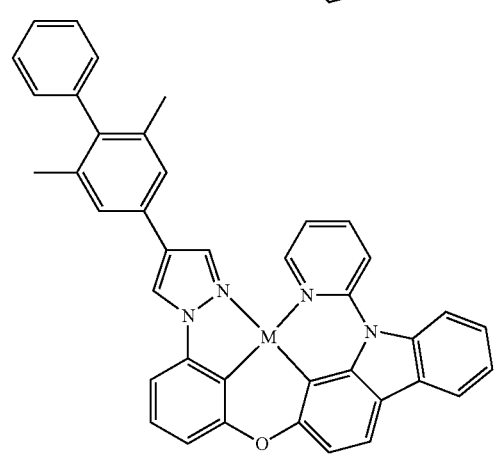

869
-continued
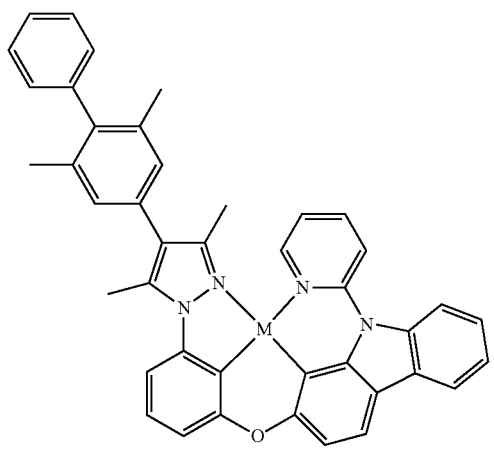
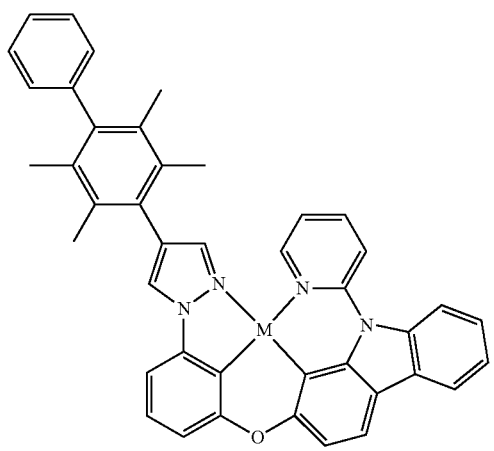
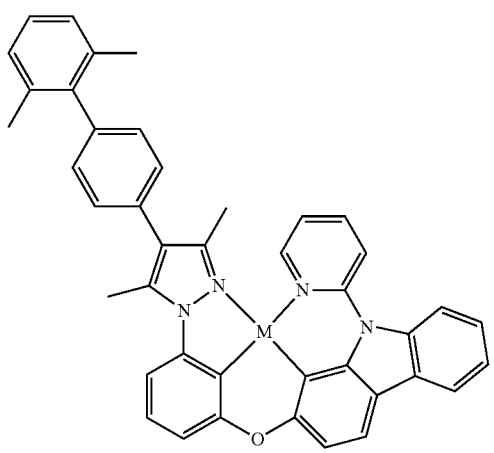
870
-continued
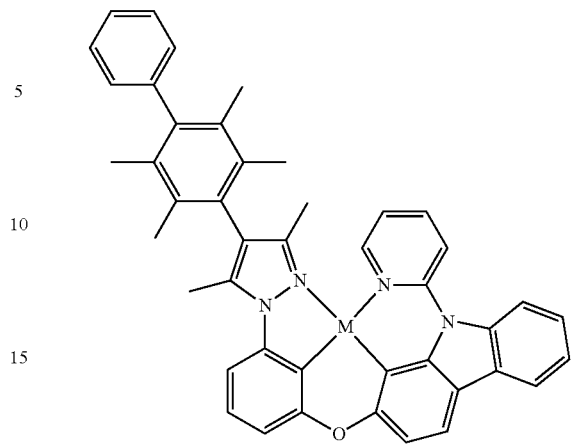
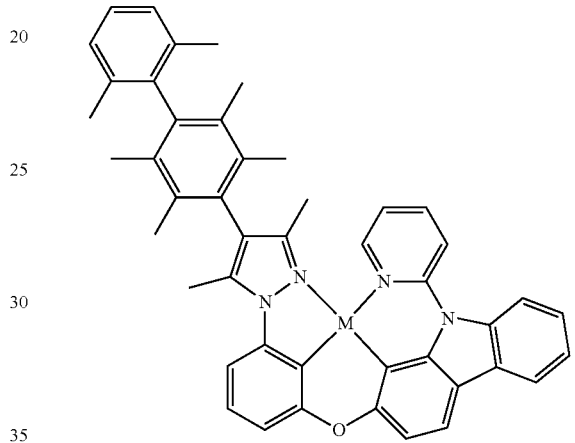
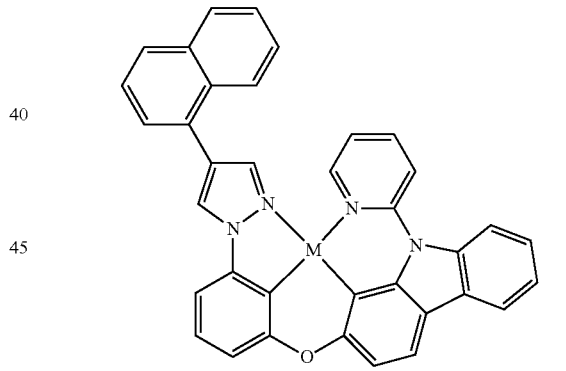
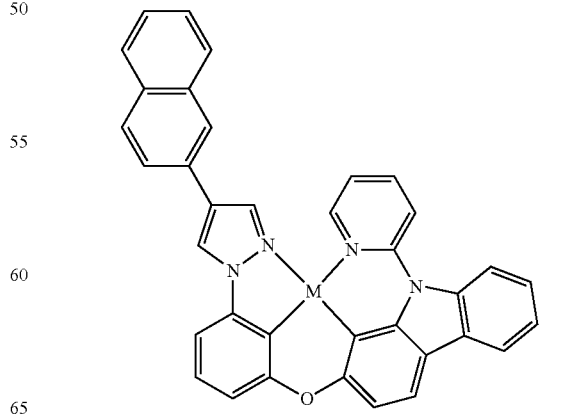

871
-continued
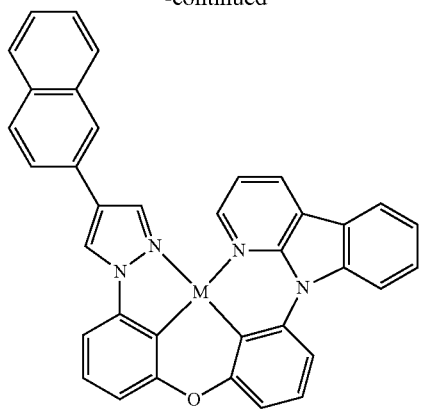
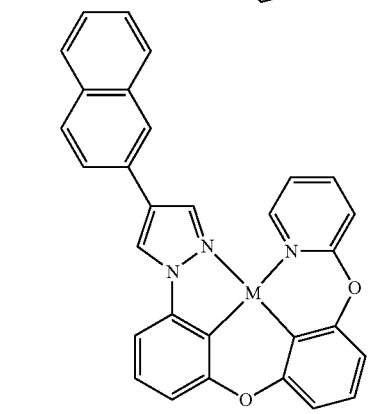
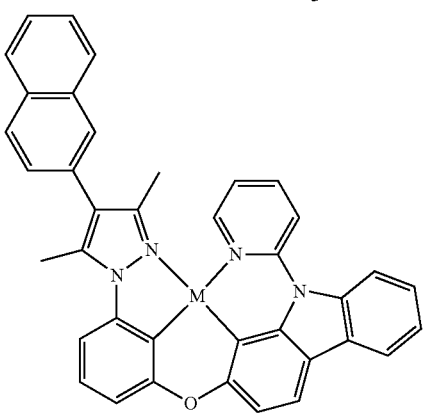
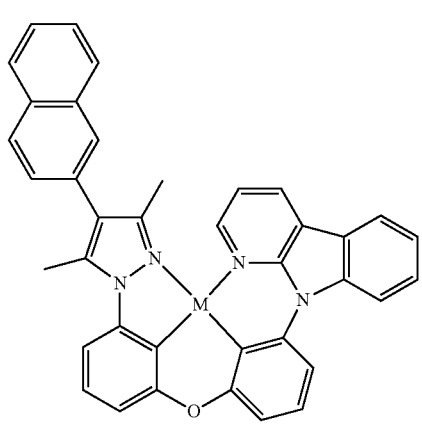
872
-continued
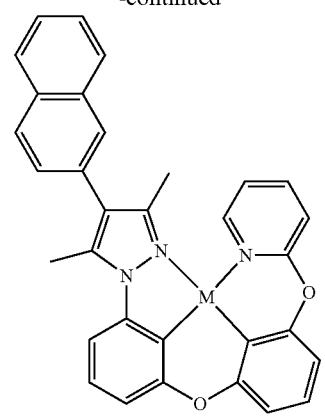
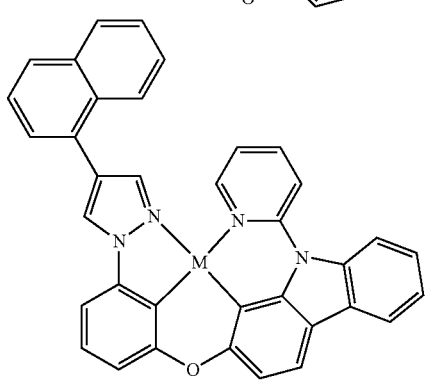
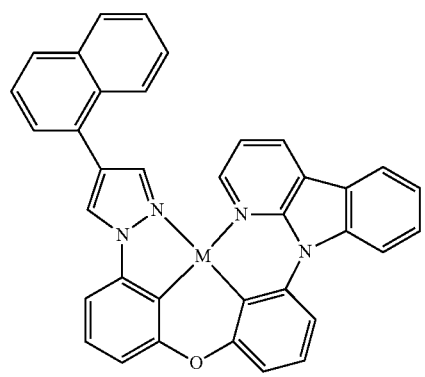
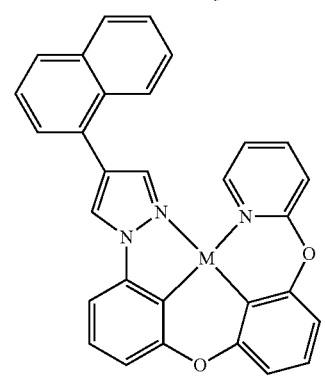

873
-continued
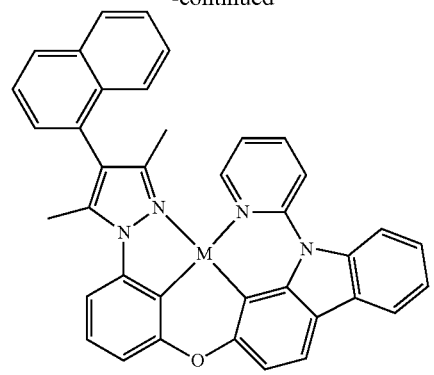
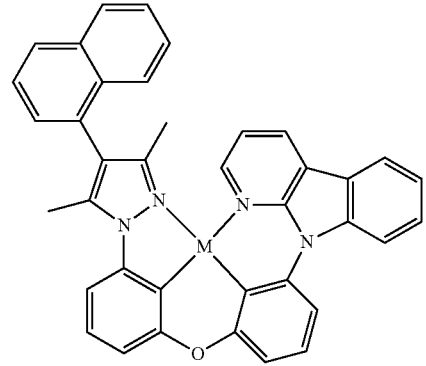
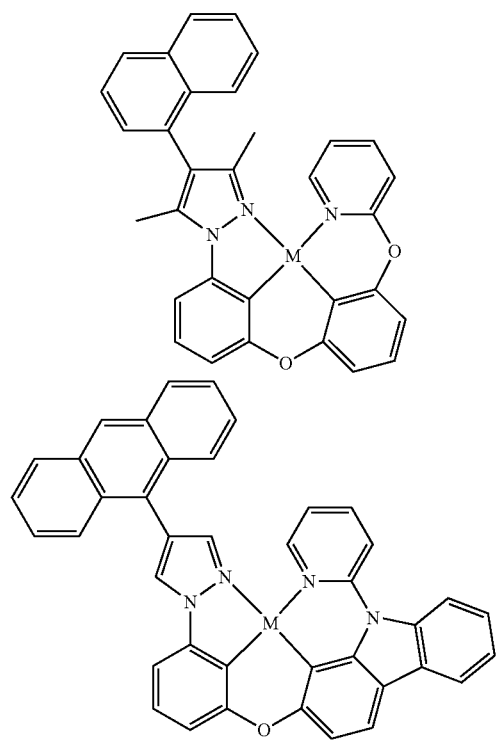
874
-continued
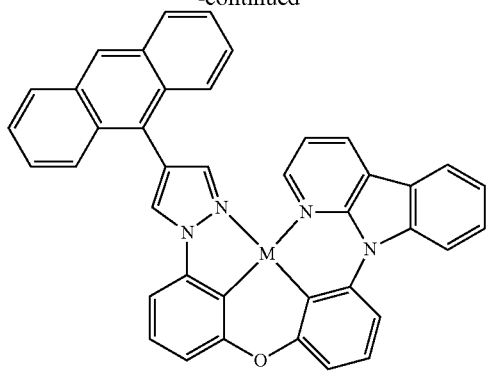
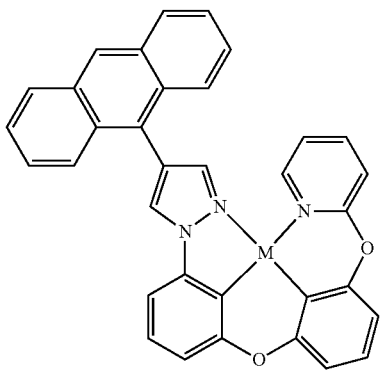
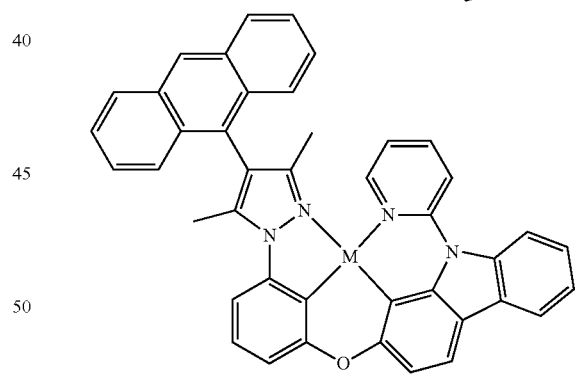
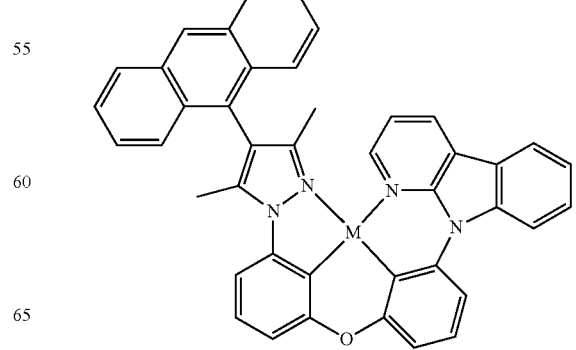

875
-continued
876
-continued
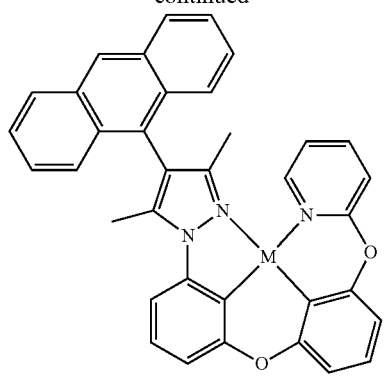
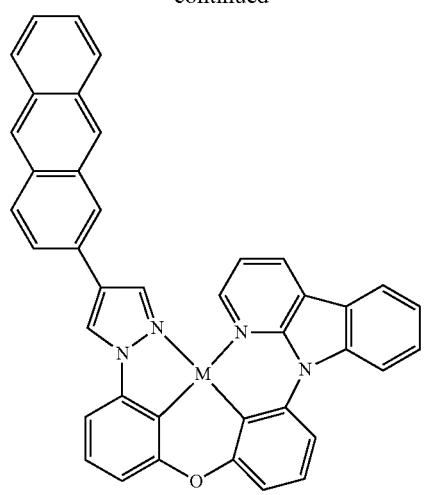
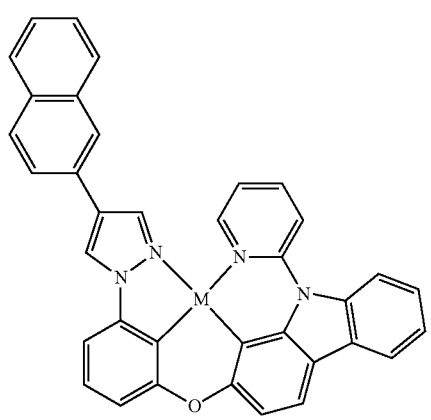
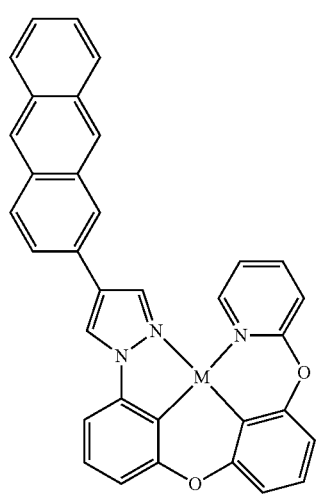
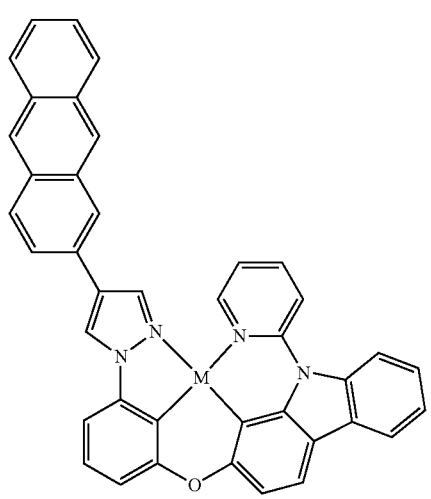
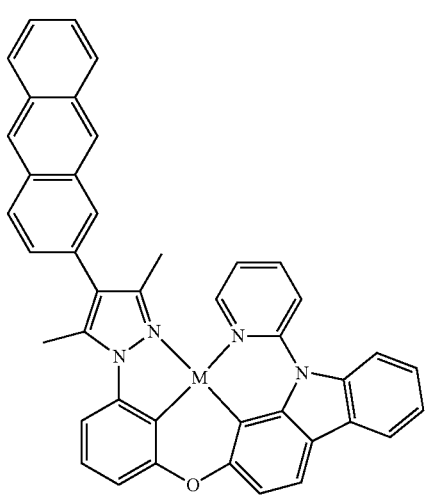

877
-continued
878
-continued
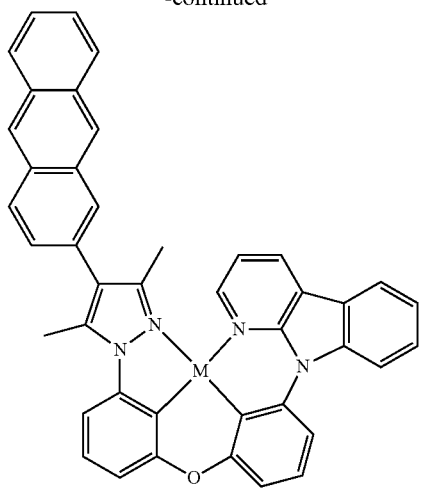
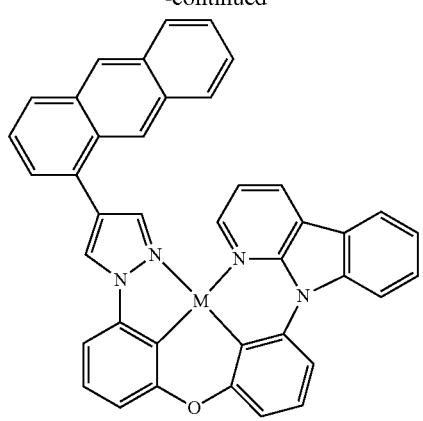
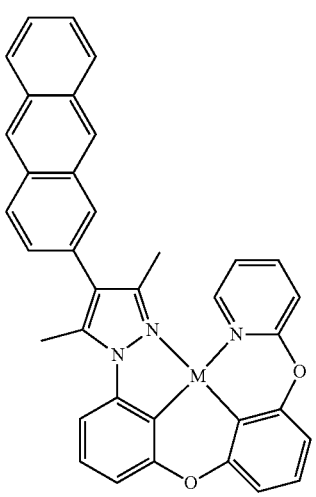
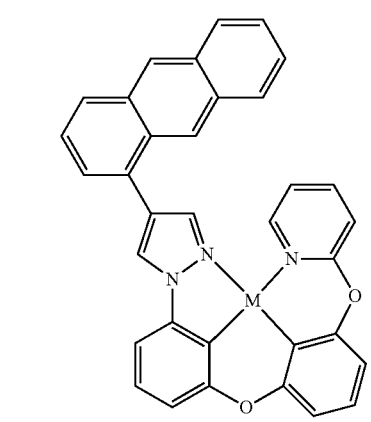
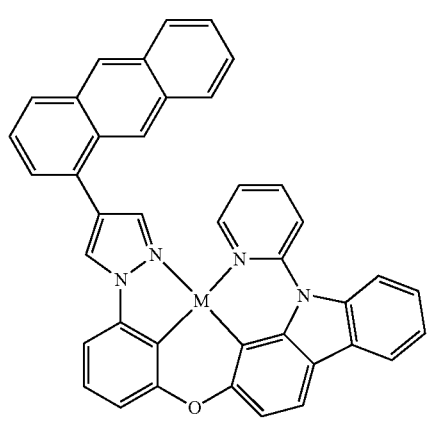
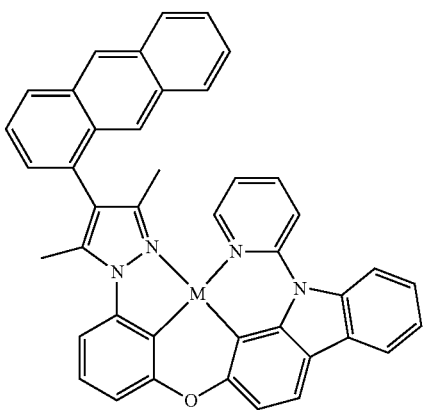
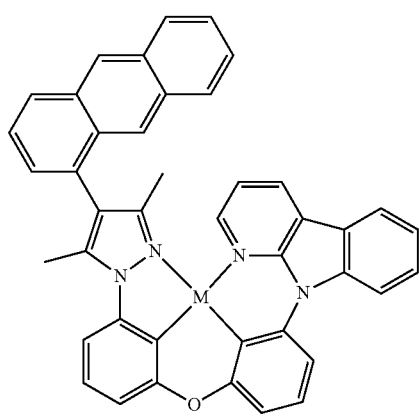

879
-continued
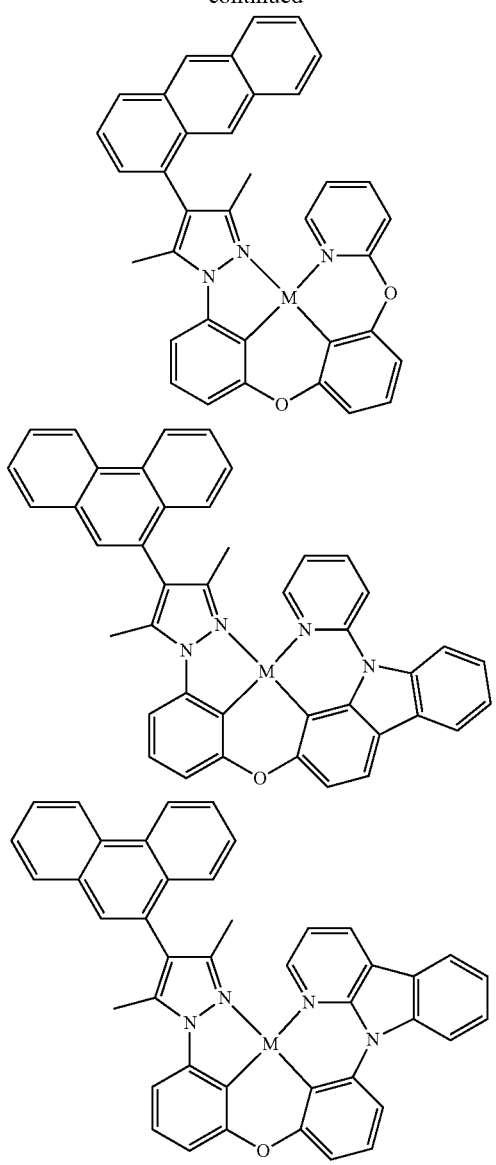
880
-continued
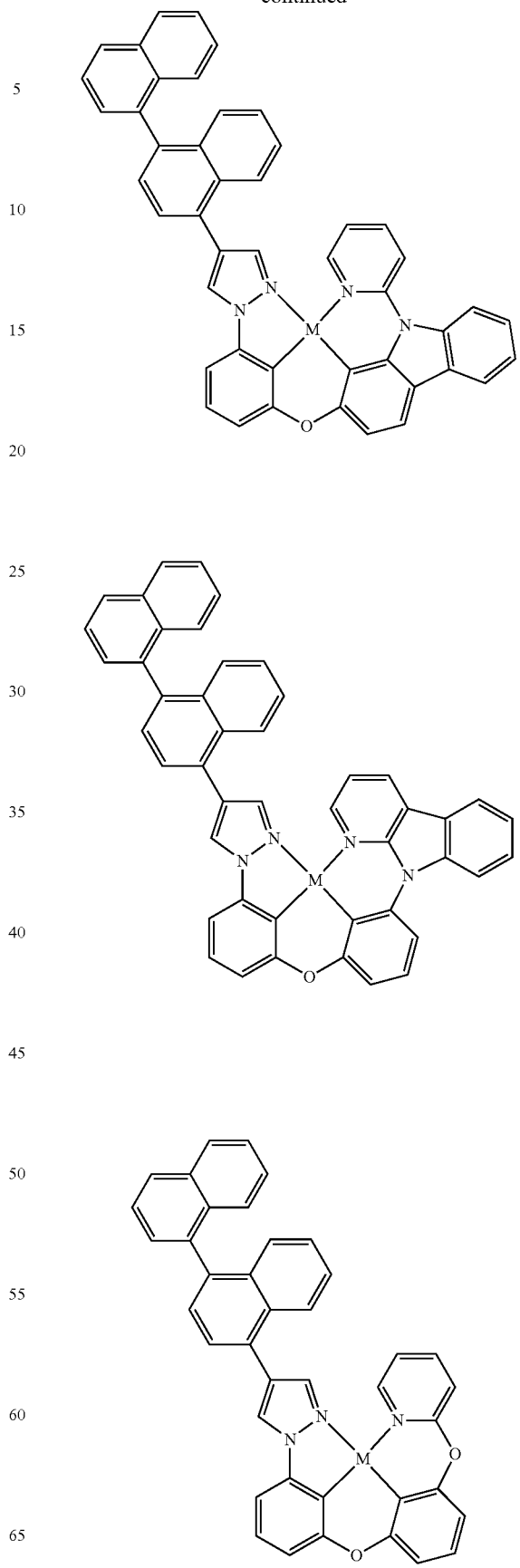

881
-continued
882
-continued
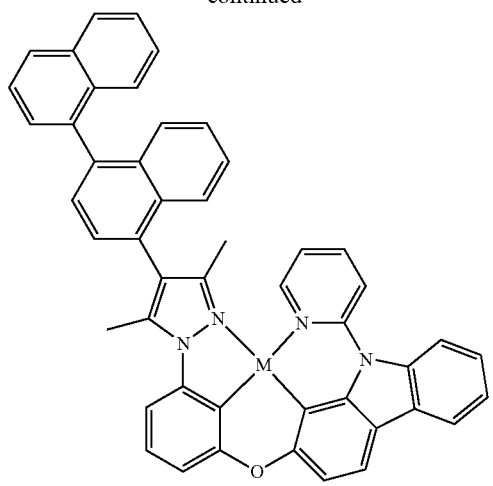
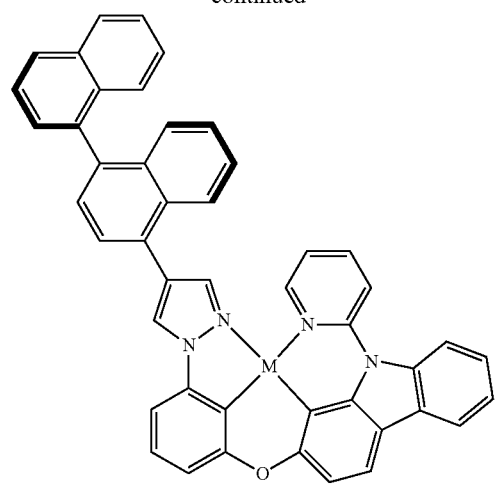
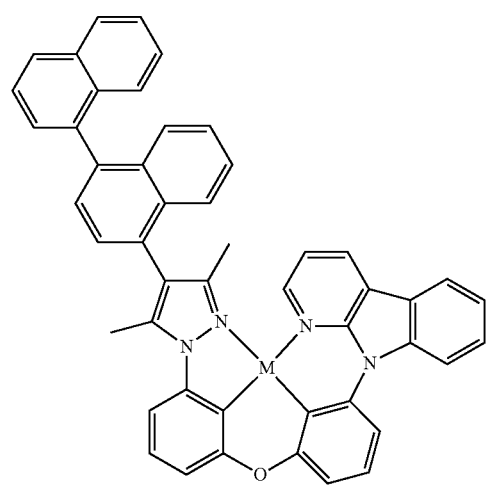
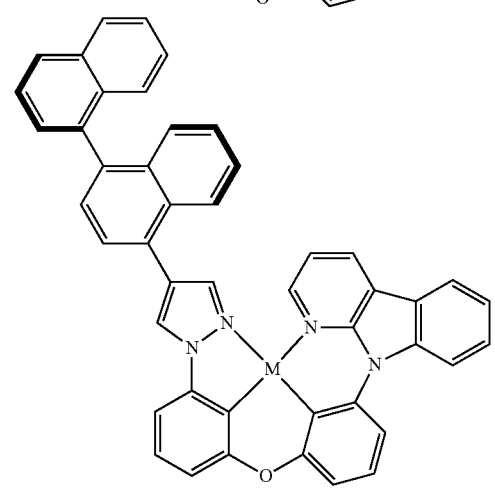
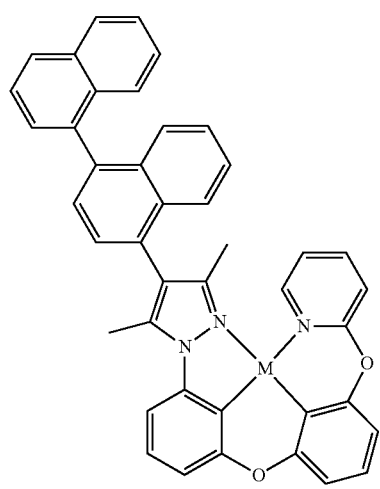
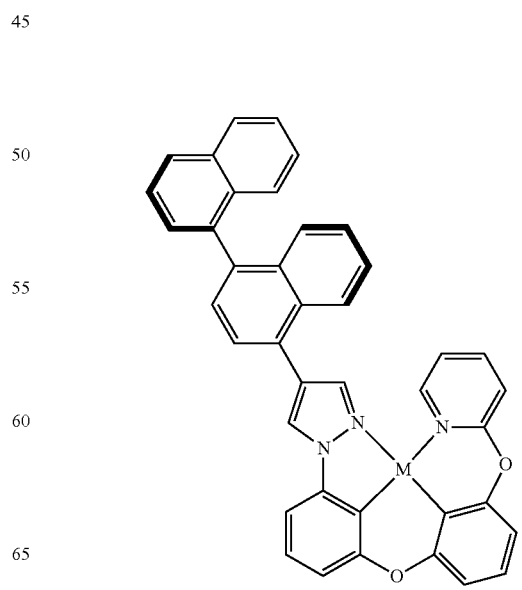

883
-continued
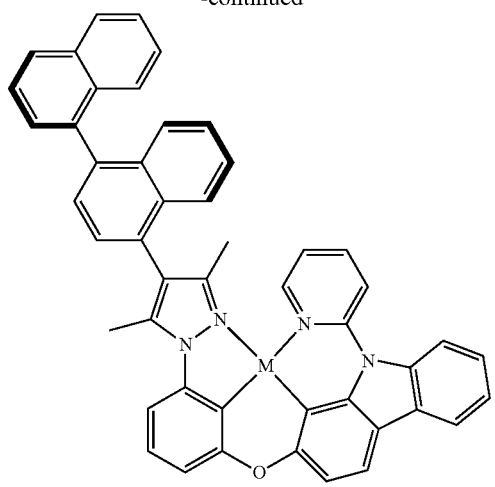
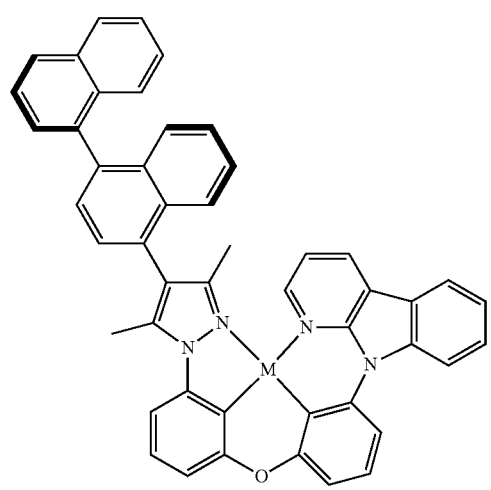
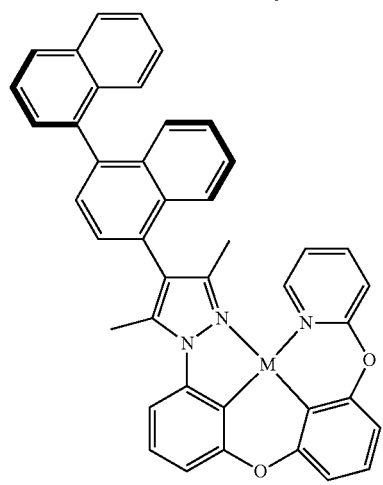
884
-continued
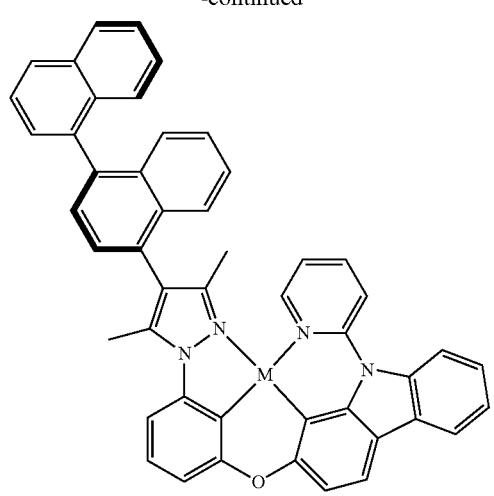
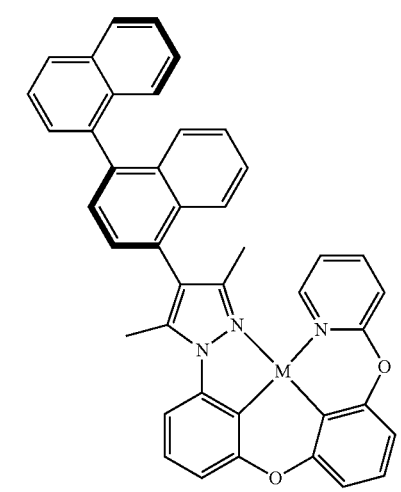

885
-continued

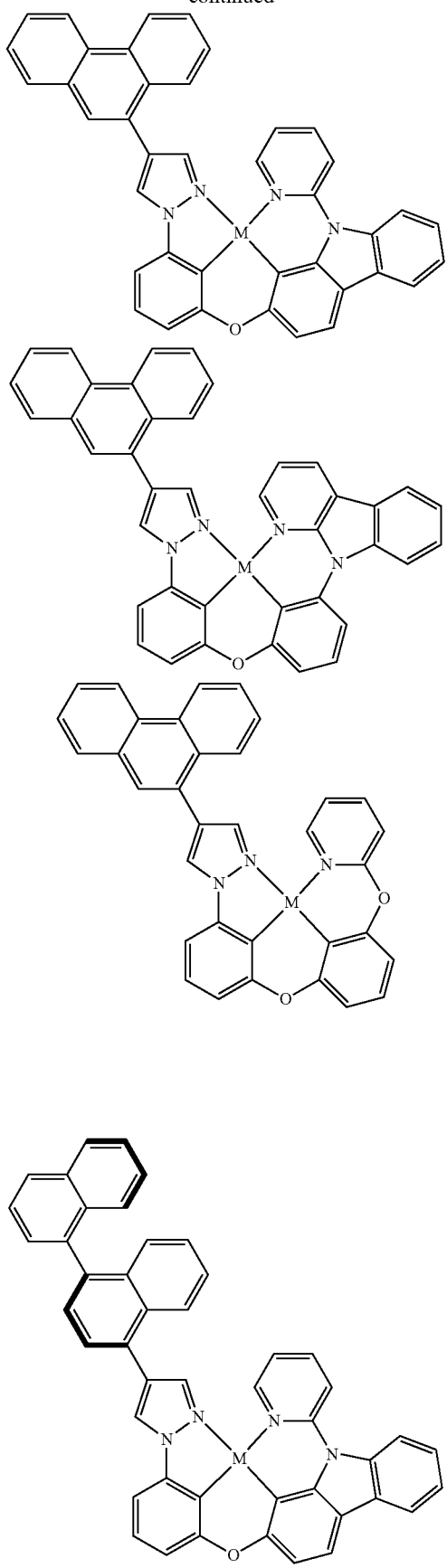

886
-continued

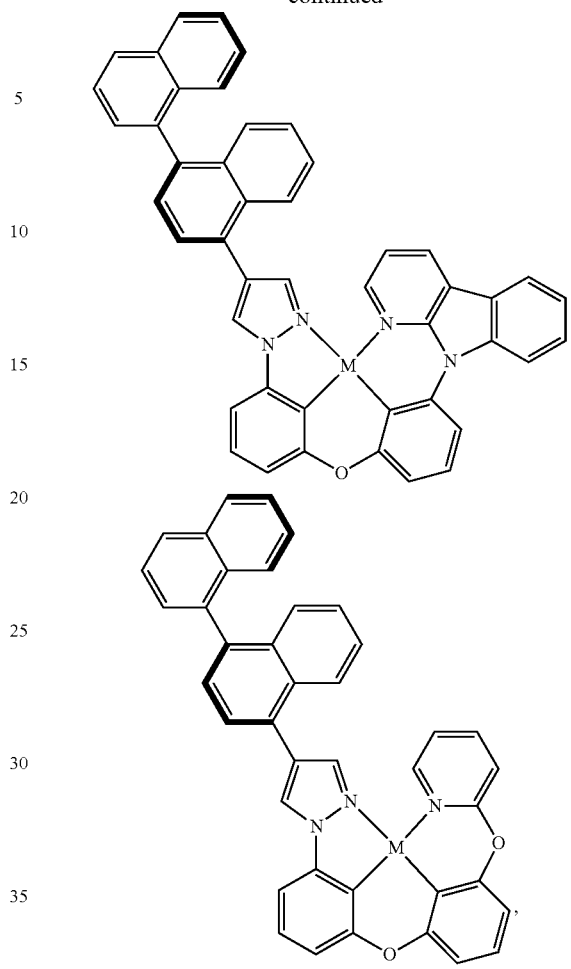

wherein:

M is platinum or palladium;

n is an integer; and each of R, R¹, and R² is independently hydrogen, deuterium, halogen, hydroxyl, thiol, nitro, cyano, nitrile, isonitrile, sulfinyl, mercapto, sulfo, carboxyl, hydrazino; substituted or unsubstituted aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

17. An emitter comprising the compound of claim 16, wherein the emitter is a delayed fluorescent emitter.

18. A light-emitting device comprising a compound of claim 16.

19. The light-emitting device of claim 18, wherein the compound demonstrates 100% internal quantum efficiency in the device settings.

20. A compound represented by one of the following structures:

887
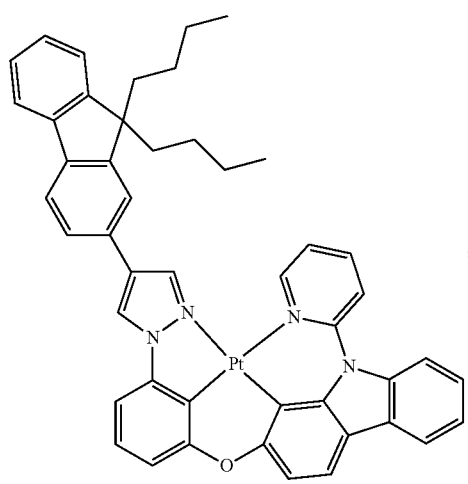
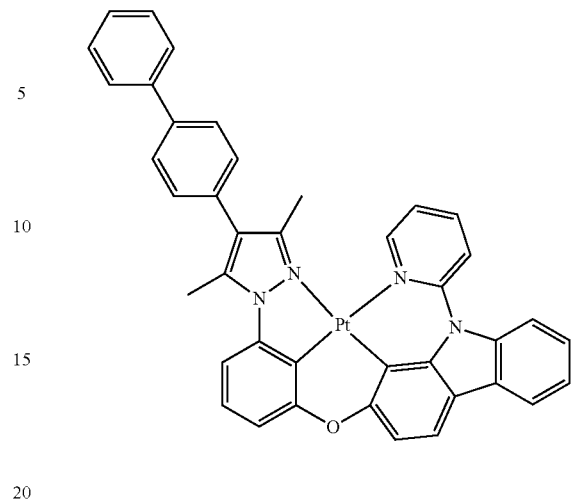
888
-continued
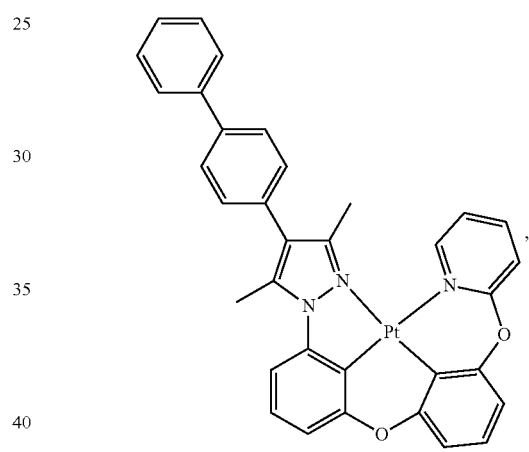
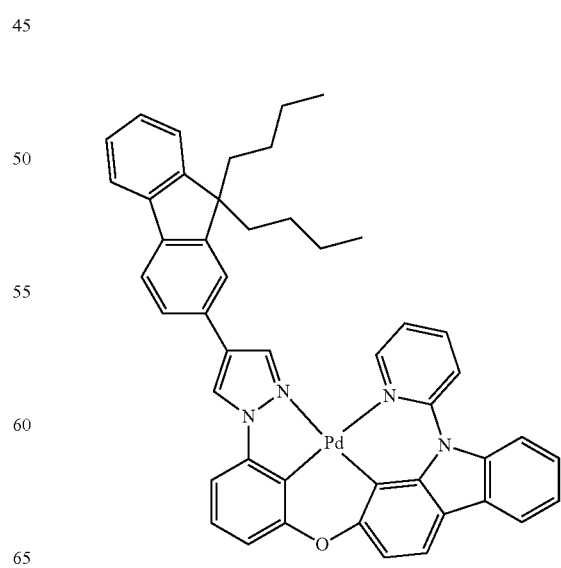

889
-continued
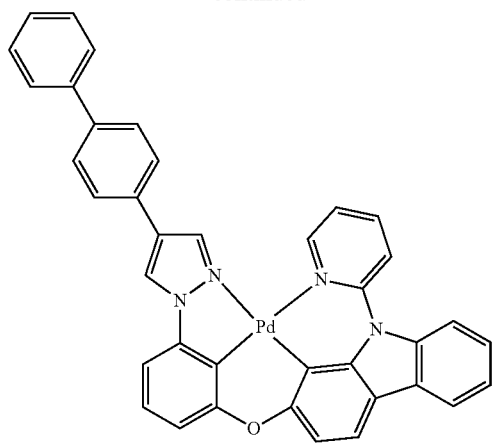
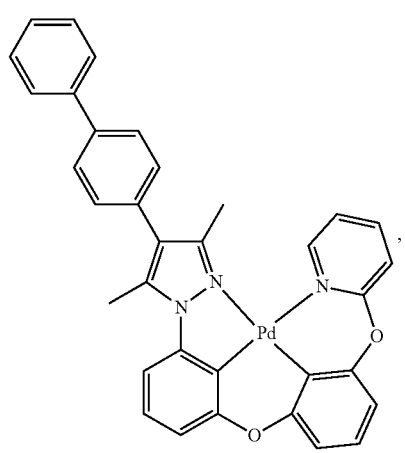
890
-continued
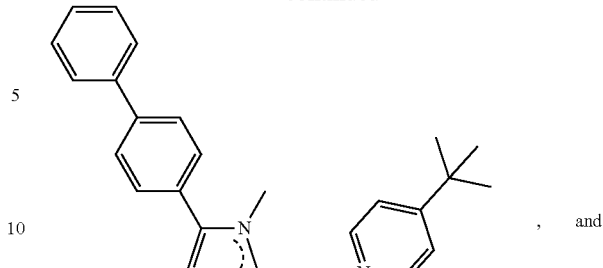
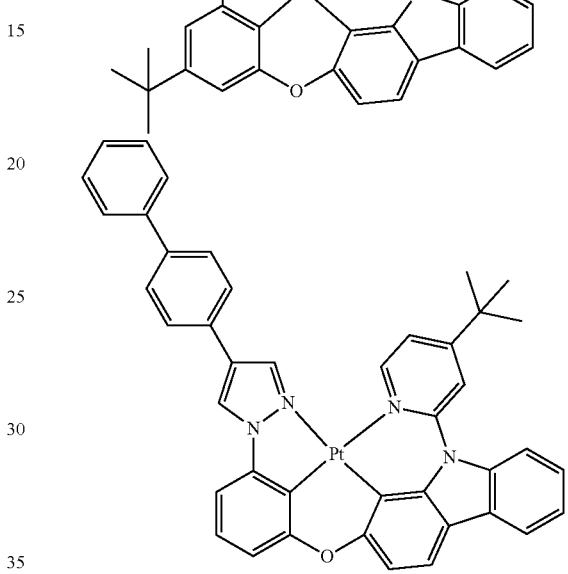
, and
* * * * *